US012540197B2

(12) United States Patent
Lee et al.

(10) Patent No.: US 12,540,197 B2
(45) Date of Patent: Feb. 3, 2026

(54) ANTI-TISSUE FACTOR ANTIBODIES AND ANTIBODY CONJUGATES, COMPOSITIONS COMPRISING ANTI-TISSUE FACTOR ANTIBODIES OR ANTIBODY CONJUGATES, AND METHODS OF MAKING AND USING ANTI-TISSUE FACTOR ANTIBODIES AND ANTIBODY CONJUGATES

(71) Applicant: SUTRO BIOPHARMA, INC., South San Francisco, CA (US)

(72) Inventors: Grace Jungeun Lee, Pacifica, CA (US); Amandeep Kaur Gakhal, San Mateo, CA (US); Daniel Calarese, Millbrae, CA (US); Junhao Yang, Palo Alto, CA (US); Krishna Bajjuri, Union City, CA (US); Xiaofan Li, Belmont, CA (US); Sihong Zhou, San Mateo, CA (US); Helena Kiefel, South San Francisco, CA (US); Robert Tian-Xuan Yuan, San Mateo, CA (US); Andrew James McGeehan, Mill Valley, CA (US); Miao Wen, Union City, CA (US); Gang Yin, South San Francisco, CA (US); Alice Yam, Belmont, CA (US)

(73) Assignee: SUTRO BIOPHARMA, INC., South San Francisco, CA (US)

( * ) Notice: Subject to any disclaimer, the term of this patent is extended or adjusted under 35 U.S.C. 154(b) by 0 days.

(21) Appl. No.: 18/914,023

(22) Filed: Oct. 11, 2024

(65) Prior Publication Data

US 2025/0122306 A1 Apr. 17, 2025

Related U.S. Application Data

(60) Provisional application No. 63/684,699, filed on Aug. 19, 2024, provisional application No. 63/590,343, filed on Oct. 13, 2023.

(51) Int. Cl.
*C07K 16/36* (2006.01)
*A61K 47/68* (2017.01)
*A61P 35/00* (2006.01)

(52) U.S. Cl.
CPC .......... *C07K 16/36* (2013.01); *A61K 47/6803* (2017.08); *A61K 47/6851* (2017.08);
(Continued)

(58) Field of Classification Search
None
See application file for complete search history.

(56) References Cited

U.S. PATENT DOCUMENTS

2013/0101608 A1* 4/2013 Satijn ...................... A61P 15/00 424/178.1
2024/0091365 A1 3/2024 Bajjuri et al.

FOREIGN PATENT DOCUMENTS

EP 4130036 A1 * 2/2023 .............. A61P 35/00
WO WO 2010/066803 A2 6/2010
(Continued)

OTHER PUBLICATIONS

International Search Report and Written Opinion dated May 20, 2025 for the PCT Application No. PCT/US2024/051143, 21 pages.
(Continued)

*Primary Examiner* — Karl J Puttlitz
(74) *Attorney, Agent, or Firm* — SQUIRE PATTON BOGGS (US)

(57) ABSTRACT

The present disclosure relates to antibodies and antibody conjugates that selectively bind to tissue factor and its isoforms and homologs, and compositions comprising the antibodies. Also provided are methods of using the antibodies and antibody conjugates, such as therapeutic and diagnostic methods.

40 Claims, 36 Drawing Sheets

Specification includes a Sequence Listing.

(52) U.S. Cl.
CPC .......... *A61P 35/00* (2018.01); *C07K 2317/24* (2013.01); *C07K 2317/732* (2013.01); *C07K 2317/92* (2013.01)

(56) References Cited

FOREIGN PATENT DOCUMENTS

| | | | |
|---|---|---|---|
| WO | WO 2016/123582 | A1 | 8/2016 |
| WO | WO 2018/036243 | A1 | 3/2018 |
| WO | WO 2019/102435 | A1 | 5/2019 |
| WO | WO 2024/015229 | A1 | 1/2024 |
| WO | WO 2024/054821 | A2 | 3/2024 |

OTHER PUBLICATIONS

Walsh et al., "Site-selective modification strategies in antibody-drug conjugates", Chemical Society Reviews, vol. 50, No. 2, Feb. 1, 2021 (Feb. 1, 2021), pp. 1305-1353, XP055815046, UK ISSN: 0306-0012, DOI: 10.1039/D0CS00310G.

* cited by examiner

SEQUENCE LISTING

```
Sequence total quantity: 3191
SEQ ID NO: 1           moltype = AA  length = 295
FEATURE                Location/Qualifiers
source                 1..295
                       mol_type = protein
                       organism = Homo sapiens
SEQUENCE: 1
METPAWPRVP RPETAVARTL LLGWVFAQVA GASGTTNTVA AYNLTWKSTN FKTILEWEPK  60
```

-continued

```
PVNQVYTVQI STKSGDWKSK CFYTTDTECD LTDEIVKDVK QTYLARVFSY PAGNVESTGS  120
AGEPLYENSP EFTPYLETNL GQPTIQSFEQ VGTKVNVTVE DERTLVRRNN TFLSLRDVFG  180
KDLIYTLYYW KSSSSGKKTA KTNTNEFLID VDKGENYCFS VQAVIPSRTV NRKSTDSPVE  240
CMGQEKGEFR EIFYIIGAVV FVVIILVIIL AISLHKCRKA GVGQSWKENS PLNVS       295

SEQ ID NO: 2           moltype = AA  length = 296
FEATURE                Location/Qualifiers
source                 1..296
                       mol_type = protein
                       organism = Macaca fascicularis
SEQUENCE: 2
METPAWPRVP RPETAVARTL LLGWVFAQVA GASGTTNTVA AYNLTWKSTN FKTILEWEPK  60
PINQVYTVQI STKSGDWKSK CFYTADTECD LTDEIVKDVK QTYLARVFSY PAGHVESTGS  120
TEEPPYENSP EFTPYLETNL GQPTIQSFEQ VGTKVNVTVQ DEWTLVRRND TFLSLRDVFG  180
KDLIYTLYYW KSSSSGKKTA KTNTNEFLID VDKGENYCFS VQAVIPSRRT ANRKSTDSPV  240
ECMGHEKGES REIFYIIGAV VFVVIILVII LAISLHKCKK ARVGRSWKEN SPLNVA      296

SEQ ID NO: 3           moltype =   length =
SEQUENCE: 3
000

SEQ ID NO: 4           moltype =   length =
SEQUENCE: 4
000

SEQ ID NO: 5           moltype =   length =
SEQUENCE: 5
000

SEQ ID NO: 6           moltype =   length =
SEQUENCE: 6
000

SEQ ID NO: 7           moltype =   length =
SEQUENCE: 7
000

SEQ ID NO: 8           moltype =   length =
SEQUENCE: 8
000

SEQ ID NO: 9           moltype =   length =
SEQUENCE: 9
000

SEQ ID NO: 10          moltype =   length =
SEQUENCE: 10
000

SEQ ID NO: 11          moltype =   length =
SEQUENCE: 11
000

SEQ ID NO: 12          moltype =   length =
SEQUENCE: 12
000

SEQ ID NO: 13          moltype =   length =
SEQUENCE: 13
000

SEQ ID NO: 14          moltype =   length =
SEQUENCE: 14
000

SEQ ID NO: 15          moltype =   length =
SEQUENCE: 15
000

SEQ ID NO: 16          moltype =   length =
SEQUENCE: 16
000

SEQ ID NO: 17          moltype =   length =
SEQUENCE: 17
000

SEQ ID NO: 18          moltype =   length =
SEQUENCE: 18
```

-continued

000

SEQ ID NO: 19 moltype = length =
SEQUENCE: 19
000

SEQ ID NO: 20 moltype = length =
SEQUENCE: 20
000

SEQ ID NO: 21 moltype = length =
SEQUENCE: 21
000

SEQ ID NO: 22 moltype = length =
SEQUENCE: 22
000

SEQ ID NO: 23 moltype = length =
SEQUENCE: 23
000

SEQ ID NO: 24 moltype = length =
SEQUENCE: 24
000

SEQ ID NO: 25 moltype = length =
SEQUENCE: 25
000

SEQ ID NO: 26 moltype = length =
SEQUENCE: 26
000

SEQ ID NO: 27 moltype = length =
SEQUENCE: 27
000

SEQ ID NO: 28 moltype = length =
SEQUENCE: 28
000

SEQ ID NO: 29 moltype = length =
SEQUENCE: 29
000

SEQ ID NO: 30 moltype = length =
SEQUENCE: 30
000

SEQ ID NO: 31 moltype = length =
SEQUENCE: 31
000

SEQ ID NO: 32 moltype = length =
SEQUENCE: 32
000

SEQ ID NO: 33 moltype = length =
SEQUENCE: 33
000

SEQ ID NO: 34 moltype = length =
SEQUENCE: 34
000

SEQ ID NO: 35 moltype = length =
SEQUENCE: 35
000

SEQ ID NO: 36 moltype = length =
SEQUENCE: 36
000

SEQ ID NO: 37 moltype = length =
SEQUENCE: 37
000

SEQ ID NO: 38 moltype = length =

SEQUENCE: 38
000

SEQ ID NO: 39 moltype = length =
SEQUENCE: 39
000

SEQ ID NO: 40 moltype = length =
SEQUENCE: 40
000

SEQ ID NO: 41 moltype = length =
SEQUENCE: 41
000

SEQ ID NO: 42 moltype = length =
SEQUENCE: 42
000

SEQ ID NO: 43 moltype = length =
SEQUENCE: 43
000

SEQ ID NO: 44 moltype = length =
SEQUENCE: 44
000

SEQ ID NO: 45 moltype = length =
SEQUENCE: 45
000

SEQ ID NO: 46 moltype = length =
SEQUENCE: 46
000

SEQ ID NO: 47 moltype = length =
SEQUENCE: 47
000

SEQ ID NO: 48 moltype = length =
SEQUENCE: 48
000

SEQ ID NO: 49 moltype = length =
SEQUENCE: 49
000

SEQ ID NO: 50 moltype = length =
SEQUENCE: 50
000

SEQ ID NO: 51 moltype = length =
SEQUENCE: 51
000

SEQ ID NO: 52 moltype = length =
SEQUENCE: 52
000

SEQ ID NO: 53 moltype = length =
SEQUENCE: 53
000

SEQ ID NO: 54 moltype = length =
SEQUENCE: 54
000

SEQ ID NO: 55 moltype = length =
SEQUENCE: 55
000

SEQ ID NO: 56 moltype = length =
SEQUENCE: 56
000

SEQ ID NO: 57 moltype = length =
SEQUENCE: 57
000

```
SEQ ID NO: 58          moltype =   length =
SEQUENCE: 58
000

SEQ ID NO: 59          moltype =   length =
SEQUENCE: 59
000

SEQ ID NO: 60          moltype =   length =
SEQUENCE: 60
000

SEQ ID NO: 61          moltype =   length =
SEQUENCE: 61
000

SEQ ID NO: 62          moltype =   length =
SEQUENCE: 62
000

SEQ ID NO: 63          moltype =   length =
SEQUENCE: 63
000

SEQ ID NO: 64          moltype =   length =
SEQUENCE: 64
000

SEQ ID NO: 65          moltype =   length =
SEQUENCE: 65
000

SEQ ID NO: 66          moltype =   length =
SEQUENCE: 66
000

SEQ ID NO: 67          moltype =   length =
SEQUENCE: 67
000

SEQ ID NO: 68          moltype =   length =
SEQUENCE: 68
000

SEQ ID NO: 69          moltype =   length =
SEQUENCE: 69
000

SEQ ID NO: 70          moltype =   length =
SEQUENCE: 70
000

SEQ ID NO: 71          moltype =   length =
SEQUENCE: 71
000

SEQ ID NO: 72          moltype =   length =
SEQUENCE: 72
000

SEQ ID NO: 73          moltype =   length =
SEQUENCE: 73
000

SEQ ID NO: 74          moltype =   length =
SEQUENCE: 74
000

SEQ ID NO: 75          moltype =   length =
SEQUENCE: 75
000

SEQ ID NO: 76          moltype =   length =
SEQUENCE: 76
000

SEQ ID NO: 77          moltype =   length =
SEQUENCE: 77
000
```

SEQ ID NO: 78 moltype = length =
SEQUENCE: 78
000

SEQ ID NO: 79 moltype = length =
SEQUENCE: 79
000

SEQ ID NO: 80 moltype = length =
SEQUENCE: 80
000

SEQ ID NO: 81 moltype = length =
SEQUENCE: 81
000

SEQ ID NO: 82 moltype = length =
SEQUENCE: 82
000

SEQ ID NO: 83 moltype = length =
SEQUENCE: 83
000

SEQ ID NO: 84 moltype = length =
SEQUENCE: 84
000

SEQ ID NO: 85 moltype = length =
SEQUENCE: 85
000

SEQ ID NO: 86 moltype = length =
SEQUENCE: 86
000

SEQ ID NO: 87 moltype = length =
SEQUENCE: 87
000

SEQ ID NO: 88 moltype = length =
SEQUENCE: 88
000

SEQ ID NO: 89 moltype = length =
SEQUENCE: 89
000

SEQ ID NO: 90 moltype = length =
SEQUENCE: 90
000

SEQ ID NO: 91 moltype = length =
SEQUENCE: 91
000

SEQ ID NO: 92 moltype = length =
SEQUENCE: 92
000

SEQ ID NO: 93 moltype = length =
SEQUENCE: 93
000

SEQ ID NO: 94 moltype = length =
SEQUENCE: 94
000

SEQ ID NO: 95 moltype = length =
SEQUENCE: 95
000

SEQ ID NO: 96 moltype = length =
SEQUENCE: 96
000

SEQ ID NO: 97 moltype = length =
SEQUENCE: 97

```
000

SEQ ID NO: 98          moltype =   length =
SEQUENCE: 98
000

SEQ ID NO: 99          moltype =   length =
SEQUENCE: 99
000

SEQ ID NO: 100         moltype =   length =
SEQUENCE: 100
000

SEQ ID NO: 101         moltype =   length =
SEQUENCE: 101
000

SEQ ID NO: 102         moltype =   length =
SEQUENCE: 102
000

SEQ ID NO: 103         moltype =   length =
SEQUENCE: 103
000

SEQ ID NO: 104         moltype =   length =
SEQUENCE: 104
000

SEQ ID NO: 105         moltype = AA  length = 7
FEATURE                Location/Qualifiers
REGION                 1..7
                       note = Synthetic
source                 1..7
                       mol_type = protein
                       organism = synthetic construct
SEQUENCE: 105
GFNISSY                                                  7

SEQ ID NO: 106         moltype =   length =
SEQUENCE: 106
000

SEQ ID NO: 107         moltype =   length =
SEQUENCE: 107
000

SEQ ID NO: 108         moltype =   length =
SEQUENCE: 108
000

SEQ ID NO: 109         moltype =   length =
SEQUENCE: 109
000

SEQ ID NO: 110         moltype =   length =
SEQUENCE: 110
000

SEQ ID NO: 111         moltype =   length =
SEQUENCE: 111
000

SEQ ID NO: 112         moltype =   length =
SEQUENCE: 112
000

SEQ ID NO: 113         moltype =   length =
SEQUENCE: 113
000

SEQ ID NO: 114         moltype = AA  length = 7
FEATURE                Location/Qualifiers
REGION                 1..7
                       note = Synthetic
source                 1..7
                       mol_type = protein
                       organism = synthetic construct
```

```
SEQUENCE: 114
GFNISDY                                                              7

SEQ ID NO: 115          moltype =   length =
SEQUENCE: 115
000

SEQ ID NO: 116          moltype =   length =
SEQUENCE: 116
000

SEQ ID NO: 117          moltype = AA  length = 7
FEATURE                 Location/Qualifiers
REGION                  1..7
                        note = Synthetic
source                  1..7
                        mol_type = protein
                        organism = synthetic construct
SEQUENCE: 117
GFNISDY                                                              7

SEQ ID NO: 118          moltype =   length =
SEQUENCE: 118
000

SEQ ID NO: 119          moltype =   length =
SEQUENCE: 119
000

SEQ ID NO: 120          moltype =   length =
SEQUENCE: 120
000

SEQ ID NO: 121          moltype =   length =
SEQUENCE: 121
000

SEQ ID NO: 122          moltype =   length =
SEQUENCE: 122
000

SEQ ID NO: 123          moltype =   length =
SEQUENCE: 123
000

SEQ ID NO: 124          moltype =   length =
SEQUENCE: 124
000

SEQ ID NO: 125          moltype =   length =
SEQUENCE: 125
000

SEQ ID NO: 126          moltype =   length =
SEQUENCE: 126
000

SEQ ID NO: 127          moltype =   length =
SEQUENCE: 127
000

SEQ ID NO: 128          moltype =   length =
SEQUENCE: 128
000

SEQ ID NO: 129          moltype = AA  length = 7
FEATURE                 Location/Qualifiers
REGION                  1..7
                        note = Synthetic
source                  1..7
                        mol_type = protein
                        organism = synthetic construct
SEQUENCE: 129
GFTISSY                                                              7

SEQ ID NO: 130          moltype = AA  length = 7
FEATURE                 Location/Qualifiers
REGION                  1..7
                        note = Synthetic
```

```
source                  1..7
                        mol_type = protein
                        organism = synthetic construct
SEQUENCE: 130
GFTISGY                                                                   7

SEQ ID NO: 131          moltype = AA  length = 7
FEATURE                 Location/Qualifiers
REGION                  1..7
                        note = Synthetic
source                  1..7
                        mol_type = protein
                        organism = synthetic construct
SEQUENCE: 131
GFTIPSY                                                                   7

SEQ ID NO: 132          moltype = AA  length = 7
FEATURE                 Location/Qualifiers
REGION                  1..7
                        note = Synthetic
source                  1..7
                        mol_type = protein
                        organism = synthetic construct
SEQUENCE: 132
GFTISGY                                                                   7

SEQ ID NO: 133          moltype = AA  length = 7
FEATURE                 Location/Qualifiers
REGION                  1..7
                        note = Synthetic
source                  1..7
                        mol_type = protein
                        organism = synthetic construct
SEQUENCE: 133
GFTIPDY                                                                   7

SEQ ID NO: 134          moltype = AA  length = 7
FEATURE                 Location/Qualifiers
REGION                  1..7
                        note = Synthetic
source                  1..7
                        mol_type = protein
                        organism = synthetic construct
SEQUENCE: 134
GFTISSY                                                                   7

SEQ ID NO: 135          moltype = AA  length = 7
FEATURE                 Location/Qualifiers
REGION                  1..7
                        note = Synthetic
source                  1..7
                        mol_type = protein
                        organism = synthetic construct
SEQUENCE: 135
GFTISSY                                                                   7

SEQ ID NO: 136          moltype = AA  length = 7
FEATURE                 Location/Qualifiers
REGION                  1..7
                        note = Synthetic
source                  1..7
                        mol_type = protein
                        organism = synthetic construct
SEQUENCE: 136
GFTLTGY                                                                   7

SEQ ID NO: 137          moltype = AA  length = 7
FEATURE                 Location/Qualifiers
REGION                  1..7
                        note = Synthetic
source                  1..7
                        mol_type = protein
                        organism = synthetic construct
SEQUENCE: 137
GFTIADY                                                                   7

SEQ ID NO: 138          moltype = AA  length = 7
FEATURE                 Location/Qualifiers
REGION                  1..7
```

```
                        note = Synthetic
source                  1..7
                        mol_type = protein
                        organism = synthetic construct
SEQUENCE: 138
GFTISSY                                                           7

SEQ ID NO: 139          moltype = AA  length = 7
FEATURE                 Location/Qualifiers
REGION                  1..7
                        note = Synthetic
source                  1..7
                        mol_type = protein
                        organism = synthetic construct
SEQUENCE: 139
GFTITDY                                                           7

SEQ ID NO: 140          moltype = AA  length = 7
FEATURE                 Location/Qualifiers
REGION                  1..7
                        note = Synthetic
source                  1..7
                        mol_type = protein
                        organism = synthetic construct
SEQUENCE: 140
GFTISGY                                                           7

SEQ ID NO: 141          moltype = AA  length = 7
FEATURE                 Location/Qualifiers
REGION                  1..7
                        note = Synthetic
source                  1..7
                        mol_type = protein
                        organism = synthetic construct
SEQUENCE: 141
GFTISDY                                                           7

SEQ ID NO: 142          moltype = AA  length = 7
FEATURE                 Location/Qualifiers
REGION                  1..7
                        note = Synthetic
source                  1..7
                        mol_type = protein
                        organism = synthetic construct
SEQUENCE: 142
GFTIADY                                                           7

SEQ ID NO: 143          moltype = AA  length = 7
FEATURE                 Location/Qualifiers
REGION                  1..7
                        note = Synthetic
source                  1..7
                        mol_type = protein
                        organism = synthetic construct
SEQUENCE: 143
GFTISEY                                                           7

SEQ ID NO: 144          moltype = AA  length = 7
FEATURE                 Location/Qualifiers
REGION                  1..7
                        note = Synthetic
source                  1..7
                        mol_type = protein
                        organism = synthetic construct
SEQUENCE: 144
GFTISGY                                                           7

SEQ ID NO: 145          moltype = AA  length = 7
FEATURE                 Location/Qualifiers
REGION                  1..7
                        note = Synthetic
source                  1..7
                        mol_type = protein
                        organism = synthetic construct
SEQUENCE: 145
GFTIPSY                                                           7

SEQ ID NO: 146          moltype = AA  length = 7
FEATURE                 Location/Qualifiers
```

```
REGION                  1..7
                        note = Synthetic
source                  1..7
                        mol_type = protein
                        organism = synthetic construct
SEQUENCE: 146
GFTIADY                                                                    7

SEQ ID NO: 147          moltype = AA  length = 7
FEATURE                 Location/Qualifiers
REGION                  1..7
                        note = Synthetic
source                  1..7
                        mol_type = protein
                        organism = synthetic construct
SEQUENCE: 147
GFTIPSY                                                                    7

SEQ ID NO: 148          moltype = AA  length = 7
FEATURE                 Location/Qualifiers
REGION                  1..7
                        note = Synthetic
source                  1..7
                        mol_type = protein
                        organism = synthetic construct
SEQUENCE: 148
GFTISQY                                                                    7

SEQ ID NO: 149          moltype = AA  length = 7
FEATURE                 Location/Qualifiers
REGION                  1..7
                        note = Synthetic
source                  1..7
                        mol_type = protein
                        organism = synthetic construct
SEQUENCE: 149
GFTIPAY                                                                    7

SEQ ID NO: 150          moltype = AA  length = 7
FEATURE                 Location/Qualifiers
REGION                  1..7
                        note = Synthetic
source                  1..7
                        mol_type = protein
                        organism = synthetic construct
SEQUENCE: 150
GFTIPAY                                                                    7

SEQ ID NO: 151          moltype = AA  length = 7
FEATURE                 Location/Qualifiers
REGION                  1..7
                        note = Synthetic
source                  1..7
                        mol_type = protein
                        organism = synthetic construct
SEQUENCE: 151
GFTIGSY                                                                    7

SEQ ID NO: 152          moltype = AA  length = 7
FEATURE                 Location/Qualifiers
REGION                  1..7
                        note = Synthetic
source                  1..7
                        mol_type = protein
                        organism = synthetic construct
SEQUENCE: 152
GFTISSY                                                                    7

SEQ ID NO: 153          moltype = AA  length = 7
FEATURE                 Location/Qualifiers
REGION                  1..7
                        note = Synthetic
source                  1..7
                        mol_type = protein
                        organism = synthetic construct
SEQUENCE: 153
GFTISGY                                                                    7

SEQ ID NO: 154          moltype = AA  length = 7
```

```
FEATURE                 Location/Qualifiers
REGION                  1..7
                        note = Synthetic
source                  1..7
                        mol_type = protein
                        organism = synthetic construct
SEQUENCE: 154
GFTIVSY                                                                     7

SEQ ID NO: 155          moltype = AA  length = 7
FEATURE                 Location/Qualifiers
REGION                  1..7
                        note = Synthetic
source                  1..7
                        mol_type = protein
                        organism = synthetic construct
SEQUENCE: 155
GFTISGY                                                                     7

SEQ ID NO: 156          moltype = AA  length = 7
FEATURE                 Location/Qualifiers
REGION                  1..7
                        note = Synthetic
source                  1..7
                        mol_type = protein
                        organism = synthetic construct
SEQUENCE: 156
GFTISGY                                                                     7

SEQ ID NO: 157          moltype = AA  length = 7
FEATURE                 Location/Qualifiers
REGION                  1..7
                        note = Synthetic
source                  1..7
                        mol_type = protein
                        organism = synthetic construct
SEQUENCE: 157
GFTISGY                                                                     7

SEQ ID NO: 158          moltype = AA  length = 7
FEATURE                 Location/Qualifiers
REGION                  1..7
                        note = Synthetic
source                  1..7
                        mol_type = protein
                        organism = synthetic construct
SEQUENCE: 158
GFTIPAY                                                                     7

SEQ ID NO: 159          moltype = AA  length = 7
FEATURE                 Location/Qualifiers
REGION                  1..7
                        note = Synthetic
source                  1..7
                        mol_type = protein
                        organism = synthetic construct
SEQUENCE: 159
GFTISDY                                                                     7

SEQ ID NO: 160          moltype = AA  length = 7
FEATURE                 Location/Qualifiers
REGION                  1..7
                        note = Synthetic
source                  1..7
                        mol_type = protein
                        organism = synthetic construct
SEQUENCE: 160
GFTISDY                                                                     7

SEQ ID NO: 161          moltype = AA  length = 7
FEATURE                 Location/Qualifiers
REGION                  1..7
                        note = Synthetic
source                  1..7
                        mol_type = protein
                        organism = synthetic construct
SEQUENCE: 161
GFTISQY                                                                     7
```

-continued

```
SEQ ID NO: 162          moltype = AA  length = 7
FEATURE                 Location/Qualifiers
REGION                  1..7
                        note = Synthetic
source                  1..7
                        mol_type = protein
                        organism = synthetic construct
SEQUENCE: 162
GFTIHEY                                                                7

SEQ ID NO: 163          moltype = AA  length = 7
FEATURE                 Location/Qualifiers
REGION                  1..7
                        note = Synthetic
source                  1..7
                        mol_type = protein
                        organism = synthetic construct
SEQUENCE: 163
GFTISDY                                                                7

SEQ ID NO: 164          moltype = AA  length = 7
FEATURE                 Location/Qualifiers
REGION                  1..7
                        note = Synthetic
source                  1..7
                        mol_type = protein
                        organism = synthetic construct
SEQUENCE: 164
GFTISQY                                                                7

SEQ ID NO: 165          moltype = AA  length = 7
FEATURE                 Location/Qualifiers
REGION                  1..7
                        note = Synthetic
source                  1..7
                        mol_type = protein
                        organism = synthetic construct
SEQUENCE: 165
GFTISDY                                                                7

SEQ ID NO: 166          moltype = AA  length = 7
FEATURE                 Location/Qualifiers
REGION                  1..7
                        note = Synthetic
source                  1..7
                        mol_type = protein
                        organism = synthetic construct
SEQUENCE: 166
GFAIANY                                                                7

SEQ ID NO: 167          moltype = AA  length = 7
FEATURE                 Location/Qualifiers
REGION                  1..7
                        note = Synthetic
source                  1..7
                        mol_type = protein
                        organism = synthetic construct
SEQUENCE: 167
GFTISDY                                                                7

SEQ ID NO: 168          moltype = AA  length = 7
FEATURE                 Location/Qualifiers
REGION                  1..7
                        note = Synthetic
source                  1..7
                        mol_type = protein
                        organism = synthetic construct
SEQUENCE: 168
GFTISDY                                                                7

SEQ ID NO: 169          moltype = AA  length = 7
FEATURE                 Location/Qualifiers
REGION                  1..7
                        note = Synthetic
source                  1..7
                        mol_type = protein
                        organism = synthetic construct
SEQUENCE: 169
GFTISDY                                                                7
```

```
SEQ ID NO: 170          moltype = AA  length = 7
FEATURE                 Location/Qualifiers
REGION                  1..7
                        note = Synthetic
source                  1..7
                        mol_type = protein
                        organism = synthetic construct
SEQUENCE: 170
GFTISGY                                                                    7

SEQ ID NO: 171          moltype = AA  length = 7
FEATURE                 Location/Qualifiers
REGION                  1..7
                        note = Synthetic
source                  1..7
                        mol_type = protein
                        organism = synthetic construct
SEQUENCE: 171
GFTISDY                                                                    7

SEQ ID NO: 172          moltype = AA  length = 7
FEATURE                 Location/Qualifiers
REGION                  1..7
                        note = Synthetic
source                  1..7
                        mol_type = protein
                        organism = synthetic construct
SEQUENCE: 172
GFTISDY                                                                    7

SEQ ID NO: 173          moltype = AA  length = 7
FEATURE                 Location/Qualifiers
REGION                  1..7
                        note = Synthetic
source                  1..7
                        mol_type = protein
                        organism = synthetic construct
SEQUENCE: 173
GFTISDY                                                                    7

SEQ ID NO: 174          moltype = AA  length = 7
FEATURE                 Location/Qualifiers
REGION                  1..7
                        note = Synthetic
source                  1..7
                        mol_type = protein
                        organism = synthetic construct
SEQUENCE: 174
GFTISDY                                                                    7

SEQ ID NO: 175          moltype = AA  length = 7
FEATURE                 Location/Qualifiers
REGION                  1..7
                        note = Synthetic
source                  1..7
                        mol_type = protein
                        organism = synthetic construct
SEQUENCE: 175
GFTISDY                                                                    7

SEQ ID NO: 176          moltype = AA  length = 7
FEATURE                 Location/Qualifiers
REGION                  1..7
                        note = Synthetic
source                  1..7
                        mol_type = protein
                        organism = synthetic construct
SEQUENCE: 176
GFTIPDY                                                                    7

SEQ ID NO: 177          moltype = AA  length = 7
FEATURE                 Location/Qualifiers
REGION                  1..7
                        note = Synthetic
source                  1..7
                        mol_type = protein
                        organism = synthetic construct
SEQUENCE: 177
```

```
GFTISGY                                                              7

SEQ ID NO: 178          moltype = AA  length = 7
FEATURE                 Location/Qualifiers
REGION                  1..7
                        note = Synthetic
source                  1..7
                        mol_type = protein
                        organism = synthetic construct
SEQUENCE: 178
GFTISGY                                                              7

SEQ ID NO: 179          moltype = AA  length = 7
FEATURE                 Location/Qualifiers
REGION                  1..7
                        note = Synthetic
source                  1..7
                        mol_type = protein
                        organism = synthetic construct
SEQUENCE: 179
GFTISQY                                                              7

SEQ ID NO: 180          moltype = AA  length = 7
FEATURE                 Location/Qualifiers
REGION                  1..7
                        note = Synthetic
source                  1..7
                        mol_type = protein
                        organism = synthetic construct
SEQUENCE: 180
GFTITDY                                                              7

SEQ ID NO: 181          moltype = AA  length = 7
FEATURE                 Location/Qualifiers
REGION                  1..7
                        note = Synthetic
source                  1..7
                        mol_type = protein
                        organism = synthetic construct
SEQUENCE: 181
GFTISQY                                                              7

SEQ ID NO: 182          moltype = AA  length = 7
FEATURE                 Location/Qualifiers
REGION                  1..7
                        note = Synthetic
source                  1..7
                        mol_type = protein
                        organism = synthetic construct
SEQUENCE: 182
GFTISDY                                                              7

SEQ ID NO: 183          moltype = AA  length = 7
FEATURE                 Location/Qualifiers
REGION                  1..7
                        note = Synthetic
source                  1..7
                        mol_type = protein
                        organism = synthetic construct
SEQUENCE: 183
GFTISYY                                                              7

SEQ ID NO: 184          moltype = AA  length = 7
FEATURE                 Location/Qualifiers
REGION                  1..7
                        note = Synthetic
source                  1..7
                        mol_type = protein
                        organism = synthetic construct
SEQUENCE: 184
GFTISDY                                                              7

SEQ ID NO: 185          moltype = AA  length = 7
FEATURE                 Location/Qualifiers
REGION                  1..7
                        note = Synthetic
source                  1..7
                        mol_type = protein
                        organism = synthetic construct
```

```
SEQUENCE: 185
GFTIGVY                                                     7

SEQ ID NO: 186          moltype = AA  length = 7
FEATURE                 Location/Qualifiers
REGION                  1..7
                        note = Synthetic
source                  1..7
                        mol_type = protein
                        organism = synthetic construct
SEQUENCE: 186
GFTISDY                                                     7

SEQ ID NO: 187          moltype = AA  length = 7
FEATURE                 Location/Qualifiers
REGION                  1..7
                        note = Synthetic
source                  1..7
                        mol_type = protein
                        organism = synthetic construct
SEQUENCE: 187
GFTISDY                                                     7

SEQ ID NO: 188          moltype = AA  length = 7
FEATURE                 Location/Qualifiers
REGION                  1..7
                        note = Synthetic
source                  1..7
                        mol_type = protein
                        organism = synthetic construct
SEQUENCE: 188
GFTINDY                                                     7

SEQ ID NO: 189          moltype = AA  length = 7
FEATURE                 Location/Qualifiers
REGION                  1..7
                        note = Synthetic
source                  1..7
                        mol_type = protein
                        organism = synthetic construct
SEQUENCE: 189
GFTISIY                                                     7

SEQ ID NO: 190          moltype = AA  length = 7
FEATURE                 Location/Qualifiers
REGION                  1..7
                        note = Synthetic
source                  1..7
                        mol_type = protein
                        organism = synthetic construct
SEQUENCE: 190
GFTISDY                                                     7

SEQ ID NO: 191          moltype = AA  length = 7
FEATURE                 Location/Qualifiers
REGION                  1..7
                        note = Synthetic
source                  1..7
                        mol_type = protein
                        organism = synthetic construct
SEQUENCE: 191
GFTIAYY                                                     7

SEQ ID NO: 192          moltype = AA  length = 7
FEATURE                 Location/Qualifiers
REGION                  1..7
                        note = Synthetic
source                  1..7
                        mol_type = protein
                        organism = synthetic construct
SEQUENCE: 192
GFTIHDY                                                     7

SEQ ID NO: 193          moltype = AA  length = 7
FEATURE                 Location/Qualifiers
REGION                  1..7
                        note = Synthetic
source                  1..7
                        mol_type = protein
```

```
                        organism = synthetic construct
SEQUENCE: 193
GFTISDY                                                                    7

SEQ ID NO: 194          moltype = AA  length = 7
FEATURE                 Location/Qualifiers
REGION                  1..7
                        note = Synthetic
source                  1..7
                        mol_type = protein
                        organism = synthetic construct
SEQUENCE: 194
GFTISGY                                                                    7

SEQ ID NO: 195          moltype = AA  length = 7
FEATURE                 Location/Qualifiers
REGION                  1..7
                        note = Synthetic
source                  1..7
                        mol_type = protein
                        organism = synthetic construct
SEQUENCE: 195
GFTIFDY                                                                    7

SEQ ID NO: 196          moltype = AA  length = 7
FEATURE                 Location/Qualifiers
REGION                  1..7
                        note = Synthetic
source                  1..7
                        mol_type = protein
                        organism = synthetic construct
SEQUENCE: 196
GFTISYY                                                                    7

SEQ ID NO: 197          moltype = AA  length = 7
FEATURE                 Location/Qualifiers
REGION                  1..7
                        note = Synthetic
source                  1..7
                        mol_type = protein
                        organism = synthetic construct
SEQUENCE: 197
GFTINNY                                                                    7

SEQ ID NO: 198          moltype = AA  length = 7
FEATURE                 Location/Qualifiers
REGION                  1..7
                        note = Synthetic
source                  1..7
                        mol_type = protein
                        organism = synthetic construct
SEQUENCE: 198
GFTTRDY                                                                    7

SEQ ID NO: 199          moltype = AA  length = 7
FEATURE                 Location/Qualifiers
REGION                  1..7
                        note = Synthetic
source                  1..7
                        mol_type = protein
                        organism = synthetic construct
SEQUENCE: 199
GFTIAYY                                                                    7

SEQ ID NO: 200          moltype = AA  length = 7
FEATURE                 Location/Qualifiers
REGION                  1..7
                        note = Synthetic
source                  1..7
                        mol_type = protein
                        organism = synthetic construct
SEQUENCE: 200
GFTISDY                                                                    7

SEQ ID NO: 201          moltype = AA  length = 7
FEATURE                 Location/Qualifiers
REGION                  1..7
                        note = Synthetic
source                  1..7
```

```
                        mol_type = protein
                        organism = synthetic construct
SEQUENCE: 201
GFTISDY                                                7

SEQ ID NO: 202          moltype = AA  length = 7
FEATURE                 Location/Qualifiers
REGION                  1..7
                        note = Synthetic
source                  1..7
                        mol_type = protein
                        organism = synthetic construct
SEQUENCE: 202
GFTIGGY                                                7

SEQ ID NO: 203          moltype = AA  length = 7
FEATURE                 Location/Qualifiers
REGION                  1..7
                        note = Synthetic
source                  1..7
                        mol_type = protein
                        organism = synthetic construct
SEQUENCE: 203
GFTISDY                                                7

SEQ ID NO: 204          moltype = AA  length = 7
FEATURE                 Location/Qualifiers
REGION                  1..7
                        note = Synthetic
source                  1..7
                        mol_type = protein
                        organism = synthetic construct
SEQUENCE: 204
GFTIPDY                                                7

SEQ ID NO: 205          moltype = AA  length = 7
FEATURE                 Location/Qualifiers
REGION                  1..7
                        note = Synthetic
source                  1..7
                        mol_type = protein
                        organism = synthetic construct
SEQUENCE: 205
GFTIYDY                                                7

SEQ ID NO: 206          moltype = AA  length = 7
FEATURE                 Location/Qualifiers
REGION                  1..7
                        note = Synthetic
source                  1..7
                        mol_type = protein
                        organism = synthetic construct
SEQUENCE: 206
GFTIFDY                                                7

SEQ ID NO: 207          moltype = AA  length = 7
FEATURE                 Location/Qualifiers
REGION                  1..7
                        note = Synthetic
source                  1..7
                        mol_type = protein
                        organism = synthetic construct
SEQUENCE: 207
GFTIFDY                                                7

SEQ ID NO: 208          moltype = AA  length = 7
FEATURE                 Location/Qualifiers
REGION                  1..7
                        note = Synthetic
source                  1..7
                        mol_type = protein
                        organism = synthetic construct
SEQUENCE: 208
GFTIYDY                                                7

SEQ ID NO: 209          moltype = AA  length = 7
FEATURE                 Location/Qualifiers
REGION                  1..7
                        note = Synthetic
```

```
source                  1..7
                        mol_type = protein
                        organism = synthetic construct
SEQUENCE: 209
GFTISHY                                                                     7

SEQ ID NO: 210          moltype = AA  length = 7
FEATURE                 Location/Qualifiers
REGION                  1..7
                        note = Synthetic
source                  1..7
                        mol_type = protein
                        organism = synthetic construct
SEQUENCE: 210
GFTISDY                                                                     7

SEQ ID NO: 211          moltype = AA  length = 7
FEATURE                 Location/Qualifiers
REGION                  1..7
                        note = Synthetic
source                  1..7
                        mol_type = protein
                        organism = synthetic construct
SEQUENCE: 211
GFTIAAY                                                                     7

SEQ ID NO: 212          moltype = AA  length = 7
FEATURE                 Location/Qualifiers
REGION                  1..7
                        note = Synthetic
source                  1..7
                        mol_type = protein
                        organism = synthetic construct
SEQUENCE: 212
GFNIAYY                                                                     7

SEQ ID NO: 213          moltype = AA  length = 7
FEATURE                 Location/Qualifiers
REGION                  1..7
                        note = Synthetic
source                  1..7
                        mol_type = protein
                        organism = synthetic construct
SEQUENCE: 213
GFTISDY                                                                     7

SEQ ID NO: 214          moltype = AA  length = 7
FEATURE                 Location/Qualifiers
REGION                  1..7
                        note = Synthetic
source                  1..7
                        mol_type = protein
                        organism = synthetic construct
SEQUENCE: 214
GFTISDY                                                                     7

SEQ ID NO: 215          moltype = AA  length = 7
FEATURE                 Location/Qualifiers
REGION                  1..7
                        note = Synthetic
source                  1..7
                        mol_type = protein
                        organism = synthetic construct
SEQUENCE: 215
GFTISDY                                                                     7

SEQ ID NO: 216          moltype = AA  length = 7
FEATURE                 Location/Qualifiers
REGION                  1..7
                        note = Synthetic
source                  1..7
                        mol_type = protein
                        organism = synthetic construct
SEQUENCE: 216
GFTISSY                                                                     7

SEQ ID NO: 217          moltype =   length =
SEQUENCE: 217
000
```

-continued

```
SEQ ID NO: 218          moltype = AA  length = 7
FEATURE                 Location/Qualifiers
REGION                  1..7
                        note = Synthetic
source                  1..7
                        mol_type = protein
                        organism = synthetic construct
SEQUENCE: 218
GFSISSY                                                                      7

SEQ ID NO: 219          moltype =   length =
SEQUENCE: 219
000

SEQ ID NO: 220          moltype =   length =
SEQUENCE: 220
000

SEQ ID NO: 221          moltype =   length =
SEQUENCE: 221
000

SEQ ID NO: 222          moltype =   length =
SEQUENCE: 222
000

SEQ ID NO: 223          moltype =   length =
SEQUENCE: 223
000

SEQ ID NO: 224          moltype = AA  length = 7
FEATURE                 Location/Qualifiers
REGION                  1..7
                        note = Synthetic
source                  1..7
                        mol_type = protein
                        organism = synthetic construct
SEQUENCE: 224
GFSLSYY                                                                      7

SEQ ID NO: 225          moltype =   length =
SEQUENCE: 225
000

SEQ ID NO: 226          moltype =   length =
SEQUENCE: 226
000

SEQ ID NO: 227          moltype =   length =
SEQUENCE: 227
000

SEQ ID NO: 228          moltype =   length =
SEQUENCE: 228
000

SEQ ID NO: 229          moltype = AA  length = 7
FEATURE                 Location/Qualifiers
REGION                  1..7
                        note = Synthetic
source                  1..7
                        mol_type = protein
                        organism = synthetic construct
SEQUENCE: 229
GFSLSYY                                                                      7

SEQ ID NO: 230          moltype =   length =
SEQUENCE: 230
000

SEQ ID NO: 231          moltype =   length =
SEQUENCE: 231
000

SEQ ID NO: 232          moltype =   length =
SEQUENCE: 232
000
```

```
SEQ ID NO: 233          moltype =   length =
SEQUENCE: 233
000

SEQ ID NO: 234          moltype =   length =
SEQUENCE: 234
000

SEQ ID NO: 235          moltype = AA  length = 7
FEATURE                 Location/Qualifiers
REGION                  1..7
                        note = Synthetic
source                  1..7
                        mol_type = protein
                        organism = synthetic construct
SEQUENCE: 235
GFSISSY                                                     7

SEQ ID NO: 236          moltype =   length =
SEQUENCE: 236
000

SEQ ID NO: 237          moltype = AA  length = 7
FEATURE                 Location/Qualifiers
REGION                  1..7
                        note = Synthetic
source                  1..7
                        mol_type = protein
                        organism = synthetic construct
SEQUENCE: 237
GFSISSY                                                     7

SEQ ID NO: 238          moltype = AA  length = 7
FEATURE                 Location/Qualifiers
REGION                  1..7
                        note = Synthetic
source                  1..7
                        mol_type = protein
                        organism = synthetic construct
SEQUENCE: 238
GFSISSY                                                     7

SEQ ID NO: 239          moltype =   length =
SEQUENCE: 239
000

SEQ ID NO: 240          moltype =   length =
SEQUENCE: 240
000

SEQ ID NO: 241          moltype =   length =
SEQUENCE: 241
000

SEQ ID NO: 242          moltype =   length =
SEQUENCE: 242
000

SEQ ID NO: 243          moltype =   length =
SEQUENCE: 243
000

SEQ ID NO: 244          moltype =   length =
SEQUENCE: 244
000

SEQ ID NO: 245          moltype =   length =
SEQUENCE: 245
000

SEQ ID NO: 246          moltype =   length =
SEQUENCE: 246
000

SEQ ID NO: 247          moltype =   length =
SEQUENCE: 247
000

SEQ ID NO: 248          moltype =   length =
```

SEQUENCE: 248
000

SEQ ID NO: 249 moltype = length =
SEQUENCE: 249
000

SEQ ID NO: 250 moltype = length =
SEQUENCE: 250
000

SEQ ID NO: 251 moltype = length =
SEQUENCE: 251
000

SEQ ID NO: 252 moltype = length =
SEQUENCE: 252
000

SEQ ID NO: 253 moltype = length =
SEQUENCE: 253
000

SEQ ID NO: 254 moltype = length =
SEQUENCE: 254
000

SEQ ID NO: 255 moltype = length =
SEQUENCE: 255
000

SEQ ID NO: 256 moltype = length =
SEQUENCE: 256
000

SEQ ID NO: 257 moltype = length =
SEQUENCE: 257
000

SEQ ID NO: 258 moltype = length =
SEQUENCE: 258
000

SEQ ID NO: 259 moltype = length =
SEQUENCE: 259
000

SEQ ID NO: 260 moltype = length =
SEQUENCE: 260
000

SEQ ID NO: 261 moltype = length =
SEQUENCE: 261
000

SEQ ID NO: 262 moltype = length =
SEQUENCE: 262
000

SEQ ID NO: 263 moltype = length =
SEQUENCE: 263
000

SEQ ID NO: 264 moltype = length =
SEQUENCE: 264
000

SEQ ID NO: 265 moltype = length =
SEQUENCE: 265
000

SEQ ID NO: 266 moltype = length =
SEQUENCE: 266
000

SEQ ID NO: 267 moltype = length =
SEQUENCE: 267
000

-continued

SEQ ID NO: 268 moltype = length =
SEQUENCE: 268
000

SEQ ID NO: 269 moltype = length =
SEQUENCE: 269
000

SEQ ID NO: 270 moltype = length =
SEQUENCE: 270
000

SEQ ID NO: 271 moltype = length =
SEQUENCE: 271
000

SEQ ID NO: 272 moltype = length =
SEQUENCE: 272
000

SEQ ID NO: 273 moltype = length =
SEQUENCE: 273
000

SEQ ID NO: 274 moltype = length =
SEQUENCE: 274
000

SEQ ID NO: 275 moltype = length =
SEQUENCE: 275
000

SEQ ID NO: 276 moltype = length =
SEQUENCE: 276
000

SEQ ID NO: 277 moltype = length =
SEQUENCE: 277
000

SEQ ID NO: 278 moltype = length =
SEQUENCE: 278
000

SEQ ID NO: 279 moltype = length =
SEQUENCE: 279
000

SEQ ID NO: 280 moltype = length =
SEQUENCE: 280
000

SEQ ID NO: 281 moltype = length =
SEQUENCE: 281
000

SEQ ID NO: 282 moltype = length =
SEQUENCE: 282
000

SEQ ID NO: 283 moltype = length =
SEQUENCE: 283
000

SEQ ID NO: 284 moltype = length =
SEQUENCE: 284
000

SEQ ID NO: 285 moltype = length =
SEQUENCE: 285
000

SEQ ID NO: 286 moltype = length =
SEQUENCE: 286
000

SEQ ID NO: 287 moltype = length =
SEQUENCE: 287
000

-continued

SEQ ID NO: 288 moltype = length =
SEQUENCE: 288
000

SEQ ID NO: 289 moltype = length =
SEQUENCE: 289
000

SEQ ID NO: 290 moltype = length =
SEQUENCE: 290
000

SEQ ID NO: 291 moltype = length =
SEQUENCE: 291
000

SEQ ID NO: 292 moltype = length =
SEQUENCE: 292
000

SEQ ID NO: 293 moltype = length =
SEQUENCE: 293
000

SEQ ID NO: 294 moltype = length =
SEQUENCE: 294
000

SEQ ID NO: 295 moltype = length =
SEQUENCE: 295
000

SEQ ID NO: 296 moltype = length =
SEQUENCE: 296
000

SEQ ID NO: 297 moltype = length =
SEQUENCE: 297
000

SEQ ID NO: 298 moltype = length =
SEQUENCE: 298
000

SEQ ID NO: 299 moltype = length =
SEQUENCE: 299
000

SEQ ID NO: 300 moltype = length =
SEQUENCE: 300
000

SEQ ID NO: 301 moltype = length =
SEQUENCE: 301
000

SEQ ID NO: 302 moltype = length =
SEQUENCE: 302
000

SEQ ID NO: 303 moltype = length =
SEQUENCE: 303
000

SEQ ID NO: 304 moltype = length =
SEQUENCE: 304
000

SEQ ID NO: 305 moltype = length =
SEQUENCE: 305
000

SEQ ID NO: 306 moltype = length =
SEQUENCE: 306
000

SEQ ID NO: 307 moltype = length =
SEQUENCE: 307

000

SEQ ID NO: 308 moltype = length =
SEQUENCE: 308
000

SEQ ID NO: 309 moltype = length =
SEQUENCE: 309
000

SEQ ID NO: 310 moltype = length =
SEQUENCE: 310
000

SEQ ID NO: 311 moltype = length =
SEQUENCE: 311
000

SEQ ID NO: 312 moltype = length =
SEQUENCE: 312
000

SEQ ID NO: 313 moltype = length =
SEQUENCE: 313
000

SEQ ID NO: 314 moltype = length =
SEQUENCE: 314
000

SEQ ID NO: 315 moltype = length =
SEQUENCE: 315
000

SEQ ID NO: 316 moltype = length =
SEQUENCE: 316
000

SEQ ID NO: 317 moltype = length =
SEQUENCE: 317
000

SEQ ID NO: 318 moltype = length =
SEQUENCE: 318
000

SEQ ID NO: 319 moltype = length =
SEQUENCE: 319
000

SEQ ID NO: 320 moltype = length =
SEQUENCE: 320
000

SEQ ID NO: 321 moltype = length =
SEQUENCE: 321
000

SEQ ID NO: 322 moltype = length =
SEQUENCE: 322
000

SEQ ID NO: 323 moltype = length =
SEQUENCE: 323
000

SEQ ID NO: 324 moltype = length =
SEQUENCE: 324
000

SEQ ID NO: 325 moltype = length =
SEQUENCE: 325
000

SEQ ID NO: 326 moltype = length =
SEQUENCE: 326
000

SEQ ID NO: 327 moltype = length =

```
SEQUENCE: 327
000

SEQ ID NO: 328        moltype =   length =
SEQUENCE: 328
000

SEQ ID NO: 329        moltype =   length =
SEQUENCE: 329
000

SEQ ID NO: 330        moltype =   length =
SEQUENCE: 330
000

SEQ ID NO: 331        moltype =   length =
SEQUENCE: 331
000

SEQ ID NO: 332        moltype =   length =
SEQUENCE: 332
000

SEQ ID NO: 333        moltype =   length =
SEQUENCE: 333
000

SEQ ID NO: 334        moltype =   length =
SEQUENCE: 334
000

SEQ ID NO: 335        moltype =   length =
SEQUENCE: 335
000

SEQ ID NO: 336        moltype =   length =
SEQUENCE: 336
000

SEQ ID NO: 337        moltype =   length =
SEQUENCE: 337
000

SEQ ID NO: 338        moltype =   length =
SEQUENCE: 338
000

SEQ ID NO: 339        moltype =   length =
SEQUENCE: 339
000

SEQ ID NO: 340        moltype =   length =
SEQUENCE: 340
000

SEQ ID NO: 341        moltype =   length =
SEQUENCE: 341
000

SEQ ID NO: 342        moltype =   length =
SEQUENCE: 342
000

SEQ ID NO: 343        moltype =   length =
SEQUENCE: 343
000

SEQ ID NO: 344        moltype =   length =
SEQUENCE: 344
000

SEQ ID NO: 345        moltype =   length =
SEQUENCE: 345
000

SEQ ID NO: 346        moltype =   length =
SEQUENCE: 346
000
```

-continued

SEQ ID NO: 347 moltype = length =
SEQUENCE: 347
000

SEQ ID NO: 348 moltype = length =
SEQUENCE: 348
000

SEQ ID NO: 349 moltype = length =
SEQUENCE: 349
000

SEQ ID NO: 350 moltype = length =
SEQUENCE: 350
000

SEQ ID NO: 351 moltype = length =
SEQUENCE: 351
000

SEQ ID NO: 352 moltype = length =
SEQUENCE: 352
000

SEQ ID NO: 353 moltype = length =
SEQUENCE: 353
000

SEQ ID NO: 354 moltype = length =
SEQUENCE: 354
000

SEQ ID NO: 355 moltype = length =
SEQUENCE: 355
000

SEQ ID NO: 356 moltype = length =
SEQUENCE: 356
000

SEQ ID NO: 357 moltype = length =
SEQUENCE: 357
000

SEQ ID NO: 358 moltype = length =
SEQUENCE: 358
000

SEQ ID NO: 359 moltype = length =
SEQUENCE: 359
000

SEQ ID NO: 360 moltype = length =
SEQUENCE: 360
000

SEQ ID NO: 361 moltype = length =
SEQUENCE: 361
000

SEQ ID NO: 362 moltype = length =
SEQUENCE: 362
000

SEQ ID NO: 363 moltype = length =
SEQUENCE: 363
000

SEQ ID NO: 364 moltype = length =
SEQUENCE: 364
000

SEQ ID NO: 365 moltype = length =
SEQUENCE: 365
000

SEQ ID NO: 366 moltype = length =
SEQUENCE: 366
000

SEQ ID NO: 367 moltype = length =
SEQUENCE: 367
000

SEQ ID NO: 368 moltype = length =
SEQUENCE: 368
000

SEQ ID NO: 369 moltype = length =
SEQUENCE: 369
000

SEQ ID NO: 370 moltype = length =
SEQUENCE: 370
000

SEQ ID NO: 371 moltype = length =
SEQUENCE: 371
000

SEQ ID NO: 372 moltype = length =
SEQUENCE: 372
000

SEQ ID NO: 373 moltype = length =
SEQUENCE: 373
000

SEQ ID NO: 374 moltype = length =
SEQUENCE: 374
000

SEQ ID NO: 375 moltype = length =
SEQUENCE: 375
000

SEQ ID NO: 376 moltype = length =
SEQUENCE: 376
000

SEQ ID NO: 377 moltype = length =
SEQUENCE: 377
000

SEQ ID NO: 378 moltype = length =
SEQUENCE: 378
000

SEQ ID NO: 379 moltype = length =
SEQUENCE: 379
000

SEQ ID NO: 380 moltype = length =
SEQUENCE: 380
000

SEQ ID NO: 381 moltype = length =
SEQUENCE: 381
000

SEQ ID NO: 382 moltype = length =
SEQUENCE: 382
000

SEQ ID NO: 383 moltype = length =
SEQUENCE: 383
000

SEQ ID NO: 384 moltype = length =
SEQUENCE: 384
000

SEQ ID NO: 385 moltype = length =
SEQUENCE: 385
000

SEQ ID NO: 386 moltype = length =
SEQUENCE: 386

-continued

000

SEQ ID NO: 387 moltype = length =
SEQUENCE: 387
000

SEQ ID NO: 388 moltype = length =
SEQUENCE: 388
000

SEQ ID NO: 389 moltype = length =
SEQUENCE: 389
000

SEQ ID NO: 390 moltype = length =
SEQUENCE: 390
000

SEQ ID NO: 391 moltype = length =
SEQUENCE: 391
000

SEQ ID NO: 392 moltype = length =
SEQUENCE: 392
000

SEQ ID NO: 393 moltype = length =
SEQUENCE: 393
000

SEQ ID NO: 394 moltype = length =
SEQUENCE: 394
000

SEQ ID NO: 395 moltype = length =
SEQUENCE: 395
000

SEQ ID NO: 396 moltype = length =
SEQUENCE: 396
000

SEQ ID NO: 397 moltype = length =
SEQUENCE: 397
000

SEQ ID NO: 398 moltype = length =
SEQUENCE: 398
000

SEQ ID NO: 399 moltype = length =
SEQUENCE: 399
000

SEQ ID NO: 400 moltype = length =
SEQUENCE: 400
000

SEQ ID NO: 401 moltype = length =
SEQUENCE: 401
000

SEQ ID NO: 402 moltype = length =
SEQUENCE: 402
000

SEQ ID NO: 403 moltype = length =
SEQUENCE: 403
000

SEQ ID NO: 404 moltype = length =
SEQUENCE: 404
000

SEQ ID NO: 405 moltype = length =
SEQUENCE: 405
000

SEQ ID NO: 406 moltype = length =

SEQUENCE: 406
000

SEQ ID NO: 407 moltype = length =
SEQUENCE: 407
000

SEQ ID NO: 408 moltype = length =
SEQUENCE: 408
000

SEQ ID NO: 409 moltype = length =
SEQUENCE: 409
000

SEQ ID NO: 410 moltype = length =
SEQUENCE: 410
000

SEQ ID NO: 411 moltype = length =
SEQUENCE: 411
000

SEQ ID NO: 412 moltype = length =
SEQUENCE: 412
000

SEQ ID NO: 413 moltype = length =
SEQUENCE: 413
000

SEQ ID NO: 414 moltype = length =
SEQUENCE: 414
000

SEQ ID NO: 415 moltype = length =
SEQUENCE: 415
000

SEQ ID NO: 416 moltype = length =
SEQUENCE: 416
000

SEQ ID NO: 417 moltype = length =
SEQUENCE: 417
000

SEQ ID NO: 418 moltype = length =
SEQUENCE: 418
000

SEQ ID NO: 419 moltype = length =
SEQUENCE: 419
000

SEQ ID NO: 420 moltype = length =
SEQUENCE: 420
000

SEQ ID NO: 421 moltype = length =
SEQUENCE: 421
000

SEQ ID NO: 422 moltype = length =
SEQUENCE: 422
000

SEQ ID NO: 423 moltype = length =
SEQUENCE: 423
000

SEQ ID NO: 424 moltype = length =
SEQUENCE: 424
000

SEQ ID NO: 425 moltype = length =
SEQUENCE: 425
000

-continued

```
SEQ ID NO: 426          moltype =   length =
SEQUENCE: 426
000

SEQ ID NO: 427          moltype =   length =
SEQUENCE: 427
000

SEQ ID NO: 428          moltype =   length =
SEQUENCE: 428
000

SEQ ID NO: 429          moltype =   length =
SEQUENCE: 429
000

SEQ ID NO: 430          moltype = AA  length = 5
FEATURE                 Location/Qualifiers
REGION                  1..5
                        note = Synthetic
source                  1..5
                        mol_type = protein
                        organism = synthetic construct
SEQUENCE: 430
SYWIH                                                                5

SEQ ID NO: 431          moltype =   length =
SEQUENCE: 431
000

SEQ ID NO: 432          moltype =   length =
SEQUENCE: 432
000

SEQ ID NO: 433          moltype =   length =
SEQUENCE: 433
000

SEQ ID NO: 434          moltype =   length =
SEQUENCE: 434
000

SEQ ID NO: 435          moltype =   length =
SEQUENCE: 435
000

SEQ ID NO: 436          moltype =   length =
SEQUENCE: 436
000

SEQ ID NO: 437          moltype =   length =
SEQUENCE: 437
000

SEQ ID NO: 438          moltype =   length =
SEQUENCE: 438
000

SEQ ID NO: 439          moltype = AA  length = 5
FEATURE                 Location/Qualifiers
REGION                  1..5
                        note = Synthetic
source                  1..5
                        mol_type = protein
                        organism = synthetic construct
SEQUENCE: 439
DYWIH                                                                5

SEQ ID NO: 440          moltype =   length =
SEQUENCE: 440
000

SEQ ID NO: 441          moltype =   length =
SEQUENCE: 441
000

SEQ ID NO: 442          moltype = AA  length = 5
FEATURE                 Location/Qualifiers
REGION                  1..5
```

```
                        note = Synthetic
source                  1..5
                        mol_type = protein
                        organism = synthetic construct
SEQUENCE: 442
DYNIH                                                       5

SEQ ID NO: 443          moltype =   length =
SEQUENCE: 443
000

SEQ ID NO: 444          moltype =   length =
SEQUENCE: 444
000

SEQ ID NO: 445          moltype =   length =
SEQUENCE: 445
000

SEQ ID NO: 446          moltype =   length =
SEQUENCE: 446
000

SEQ ID NO: 447          moltype =   length =
SEQUENCE: 447
000

SEQ ID NO: 448          moltype =   length =
SEQUENCE: 448
000

SEQ ID NO: 449          moltype =   length =
SEQUENCE: 449
000

SEQ ID NO: 450          moltype =   length =
SEQUENCE: 450
000

SEQ ID NO: 451          moltype =   length =
SEQUENCE: 451
000

SEQ ID NO: 452          moltype =   length =
SEQUENCE: 452
000

SEQ ID NO: 453          moltype =   length =
SEQUENCE: 453
000

SEQ ID NO: 454          moltype = AA  length = 5
FEATURE                 Location/Qualifiers
REGION                  1..5
                        note = Synthetic
source                  1..5
                        mol_type = protein
                        organism = synthetic construct
SEQUENCE: 454
SYWIH                                                       5

SEQ ID NO: 455          moltype = AA  length = 5
FEATURE                 Location/Qualifiers
REGION                  1..5
                        note = Synthetic
source                  1..5
                        mol_type = protein
                        organism = synthetic construct
SEQUENCE: 455
GYIIH                                                       5

SEQ ID NO: 456          moltype = AA  length = 5
FEATURE                 Location/Qualifiers
REGION                  1..5
                        note = Synthetic
source                  1..5
                        mol_type = protein
                        organism = synthetic construct
SEQUENCE: 456
```

```
SYWIH                                                            5

SEQ ID NO: 457          moltype = AA  length = 5
FEATURE                 Location/Qualifiers
REGION                  1..5
                        note = Synthetic
source                  1..5
                        mol_type = protein
                        organism = synthetic construct
SEQUENCE: 457
GYWIH                                                            5

SEQ ID NO: 458          moltype = AA  length = 5
FEATURE                 Location/Qualifiers
REGION                  1..5
                        note = Synthetic
source                  1..5
                        mol_type = protein
                        organism = synthetic construct
SEQUENCE: 458
DYWIH                                                            5

SEQ ID NO: 459          moltype = AA  length = 5
FEATURE                 Location/Qualifiers
REGION                  1..5
                        note = Synthetic
source                  1..5
                        mol_type = protein
                        organism = synthetic construct
SEQUENCE: 459
SYWIH                                                            5

SEQ ID NO: 460          moltype = AA  length = 5
FEATURE                 Location/Qualifiers
REGION                  1..5
                        note = Synthetic
source                  1..5
                        mol_type = protein
                        organism = synthetic construct
SEQUENCE: 460
SYWIH                                                            5

SEQ ID NO: 461          moltype = AA  length = 5
FEATURE                 Location/Qualifiers
REGION                  1..5
                        note = Synthetic
source                  1..5
                        mol_type = protein
                        organism = synthetic construct
SEQUENCE: 461
GYWIH                                                            5

SEQ ID NO: 462          moltype = AA  length = 5
FEATURE                 Location/Qualifiers
REGION                  1..5
                        note = Synthetic
source                  1..5
                        mol_type = protein
                        organism = synthetic construct
SEQUENCE: 462
DYWIH                                                            5

SEQ ID NO: 463          moltype = AA  length = 5
FEATURE                 Location/Qualifiers
REGION                  1..5
                        note = Synthetic
source                  1..5
                        mol_type = protein
                        organism = synthetic construct
SEQUENCE: 463
SYWIH                                                            5

SEQ ID NO: 464          moltype = AA  length = 5
FEATURE                 Location/Qualifiers
REGION                  1..5
                        note = Synthetic
source                  1..5
                        mol_type = protein
                        organism = synthetic construct
```

```
SEQUENCE: 464
DYVIH                                                                  5

SEQ ID NO: 465          moltype = AA  length = 5
FEATURE                 Location/Qualifiers
REGION                  1..5
                        note = Synthetic
source                  1..5
                        mol_type = protein
                        organism = synthetic construct
SEQUENCE: 465
GYWIH                                                                  5

SEQ ID NO: 466          moltype = AA  length = 5
FEATURE                 Location/Qualifiers
REGION                  1..5
                        note = Synthetic
source                  1..5
                        mol_type = protein
                        organism = synthetic construct
SEQUENCE: 466
DYWIH                                                                  5

SEQ ID NO: 467          moltype = AA  length = 5
FEATURE                 Location/Qualifiers
REGION                  1..5
                        note = Synthetic
source                  1..5
                        mol_type = protein
                        organism = synthetic construct
SEQUENCE: 467
DYWIH                                                                  5

SEQ ID NO: 468          moltype = AA  length = 5
FEATURE                 Location/Qualifiers
REGION                  1..5
                        note = Synthetic
source                  1..5
                        mol_type = protein
                        organism = synthetic construct
SEQUENCE: 468
EYWIH                                                                  5

SEQ ID NO: 469          moltype = AA  length = 5
FEATURE                 Location/Qualifiers
REGION                  1..5
                        note = Synthetic
source                  1..5
                        mol_type = protein
                        organism = synthetic construct
SEQUENCE: 469
GYWIH                                                                  5

SEQ ID NO: 470          moltype = AA  length = 5
FEATURE                 Location/Qualifiers
REGION                  1..5
                        note = Synthetic
source                  1..5
                        mol_type = protein
                        organism = synthetic construct
SEQUENCE: 470
SYWIH                                                                  5

SEQ ID NO: 471          moltype = AA  length = 5
FEATURE                 Location/Qualifiers
REGION                  1..5
                        note = Synthetic
source                  1..5
                        mol_type = protein
                        organism = synthetic construct
SEQUENCE: 471
DYWIH                                                                  5

SEQ ID NO: 472          moltype = AA  length = 5
FEATURE                 Location/Qualifiers
REGION                  1..5
                        note = Synthetic
source                  1..5
                        mol_type = protein
```

```
                        organism = synthetic construct
SEQUENCE: 472
SYWIH                                                                        5

SEQ ID NO: 473          moltype = AA  length = 5
FEATURE                 Location/Qualifiers
REGION                  1..5
                        note = Synthetic
source                  1..5
                        mol_type = protein
                        organism = synthetic construct
SEQUENCE: 473
QYWIH                                                                        5

SEQ ID NO: 474          moltype = AA  length = 5
FEATURE                 Location/Qualifiers
REGION                  1..5
                        note = Synthetic
source                  1..5
                        mol_type = protein
                        organism = synthetic construct
SEQUENCE: 474
AYWIH                                                                        5

SEQ ID NO: 475          moltype = AA  length = 5
FEATURE                 Location/Qualifiers
REGION                  1..5
                        note = Synthetic
source                  1..5
                        mol_type = protein
                        organism = synthetic construct
SEQUENCE: 475
AYWIH                                                                        5

SEQ ID NO: 476          moltype = AA  length = 5
FEATURE                 Location/Qualifiers
REGION                  1..5
                        note = Synthetic
source                  1..5
                        mol_type = protein
                        organism = synthetic construct
SEQUENCE: 476
SYWIH                                                                        5

SEQ ID NO: 477          moltype = AA  length = 5
FEATURE                 Location/Qualifiers
REGION                  1..5
                        note = Synthetic
source                  1..5
                        mol_type = protein
                        organism = synthetic construct
SEQUENCE: 477
SYWIH                                                                        5

SEQ ID NO: 478          moltype = AA  length = 5
FEATURE                 Location/Qualifiers
REGION                  1..5
                        note = Synthetic
source                  1..5
                        mol_type = protein
                        organism = synthetic construct
SEQUENCE: 478
GYWIH                                                                        5

SEQ ID NO: 479          moltype = AA  length = 5
FEATURE                 Location/Qualifiers
REGION                  1..5
                        note = Synthetic
source                  1..5
                        mol_type = protein
                        organism = synthetic construct
SEQUENCE: 479
SYWIH                                                                        5

SEQ ID NO: 480          moltype = AA  length = 5
FEATURE                 Location/Qualifiers
REGION                  1..5
                        note = Synthetic
source                  1..5
```

```
                        mol_type = protein
                        organism = synthetic construct
SEQUENCE: 480
GYWIH                                                                    5

SEQ ID NO: 481          moltype = AA  length = 5
FEATURE                 Location/Qualifiers
REGION                  1..5
                        note = Synthetic
source                  1..5
                        mol_type = protein
                        organism = synthetic construct
SEQUENCE: 481
GYWIH                                                                    5

SEQ ID NO: 482          moltype = AA  length = 5
FEATURE                 Location/Qualifiers
REGION                  1..5
                        note = Synthetic
source                  1..5
                        mol_type = protein
                        organism = synthetic construct
SEQUENCE: 482
GYWIH                                                                    5

SEQ ID NO: 483          moltype = AA  length = 5
FEATURE                 Location/Qualifiers
REGION                  1..5
                        note = Synthetic
source                  1..5
                        mol_type = protein
                        organism = synthetic construct
SEQUENCE: 483
AYWIH                                                                    5

SEQ ID NO: 484          moltype = AA  length = 5
FEATURE                 Location/Qualifiers
REGION                  1..5
                        note = Synthetic
source                  1..5
                        mol_type = protein
                        organism = synthetic construct
SEQUENCE: 484
DYIIH                                                                    5

SEQ ID NO: 485          moltype = AA  length = 5
FEATURE                 Location/Qualifiers
REGION                  1..5
                        note = Synthetic
source                  1..5
                        mol_type = protein
                        organism = synthetic construct
SEQUENCE: 485
DYWIH                                                                    5

SEQ ID NO: 486          moltype = AA  length = 5
FEATURE                 Location/Qualifiers
REGION                  1..5
                        note = Synthetic
source                  1..5
                        mol_type = protein
                        organism = synthetic construct
SEQUENCE: 486
QYWIH                                                                    5

SEQ ID NO: 487          moltype = AA  length = 5
FEATURE                 Location/Qualifiers
REGION                  1..5
                        note = Synthetic
source                  1..5
                        mol_type = protein
                        organism = synthetic construct
SEQUENCE: 487
EYWIH                                                                    5

SEQ ID NO: 488          moltype = AA  length = 5
FEATURE                 Location/Qualifiers
REGION                  1..5
                        note = Synthetic
```

```
source                  1..5
                        mol_type = protein
                        organism = synthetic construct
SEQUENCE: 488
DYWIH                                                                     5

SEQ ID NO: 489          moltype = AA  length = 5
FEATURE                 Location/Qualifiers
REGION                  1..5
                        note = Synthetic
source                  1..5
                        mol_type = protein
                        organism = synthetic construct
SEQUENCE: 489
QYWIH                                                                     5

SEQ ID NO: 490          moltype = AA  length = 5
FEATURE                 Location/Qualifiers
REGION                  1..5
                        note = Synthetic
source                  1..5
                        mol_type = protein
                        organism = synthetic construct
SEQUENCE: 490
DYWIH                                                                     5

SEQ ID NO: 491          moltype = AA  length = 5
FEATURE                 Location/Qualifiers
REGION                  1..5
                        note = Synthetic
source                  1..5
                        mol_type = protein
                        organism = synthetic construct
SEQUENCE: 491
NYWIH                                                                     5

SEQ ID NO: 492          moltype = AA  length = 5
FEATURE                 Location/Qualifiers
REGION                  1..5
                        note = Synthetic
source                  1..5
                        mol_type = protein
                        organism = synthetic construct
SEQUENCE: 492
DYWIH                                                                     5

SEQ ID NO: 493          moltype = AA  length = 5
FEATURE                 Location/Qualifiers
REGION                  1..5
                        note = Synthetic
source                  1..5
                        mol_type = protein
                        organism = synthetic construct
SEQUENCE: 493
DYWIH                                                                     5

SEQ ID NO: 494          moltype = AA  length = 5
FEATURE                 Location/Qualifiers
REGION                  1..5
                        note = Synthetic
source                  1..5
                        mol_type = protein
                        organism = synthetic construct
SEQUENCE: 494
DYWIH                                                                     5

SEQ ID NO: 495          moltype = AA  length = 5
FEATURE                 Location/Qualifiers
REGION                  1..5
                        note = Synthetic
source                  1..5
                        mol_type = protein
                        organism = synthetic construct
SEQUENCE: 495
GYWIH                                                                     5

SEQ ID NO: 496          moltype = AA  length = 5
FEATURE                 Location/Qualifiers
REGION                  1..5
```

```
                        note = Synthetic
source                  1..5
                        mol_type = protein
                        organism = synthetic construct
SEQUENCE: 496
DYWIH                                                             5

SEQ ID NO: 497          moltype = AA  length = 5
FEATURE                 Location/Qualifiers
REGION                  1..5
                        note = Synthetic
source                  1..5
                        mol_type = protein
                        organism = synthetic construct
SEQUENCE: 497
DYWIH                                                             5

SEQ ID NO: 498          moltype = AA  length = 5
FEATURE                 Location/Qualifiers
REGION                  1..5
                        note = Synthetic
source                  1..5
                        mol_type = protein
                        organism = synthetic construct
SEQUENCE: 498
DYWIH                                                             5

SEQ ID NO: 499          moltype = AA  length = 5
FEATURE                 Location/Qualifiers
REGION                  1..5
                        note = Synthetic
source                  1..5
                        mol_type = protein
                        organism = synthetic construct
SEQUENCE: 499
DYVIH                                                             5

SEQ ID NO: 500          moltype = AA  length = 5
FEATURE                 Location/Qualifiers
REGION                  1..5
                        note = Synthetic
source                  1..5
                        mol_type = protein
                        organism = synthetic construct
SEQUENCE: 500
DYWIH                                                             5

SEQ ID NO: 501          moltype = AA  length = 5
FEATURE                 Location/Qualifiers
REGION                  1..5
                        note = Synthetic
source                  1..5
                        mol_type = protein
                        organism = synthetic construct
SEQUENCE: 501
DYWIH                                                             5

SEQ ID NO: 502          moltype = AA  length = 5
FEATURE                 Location/Qualifiers
REGION                  1..5
                        note = Synthetic
source                  1..5
                        mol_type = protein
                        organism = synthetic construct
SEQUENCE: 502
GYWIH                                                             5

SEQ ID NO: 503          moltype = AA  length = 5
FEATURE                 Location/Qualifiers
REGION                  1..5
                        note = Synthetic
source                  1..5
                        mol_type = protein
                        organism = synthetic construct
SEQUENCE: 503
GYIIH                                                             5

SEQ ID NO: 504          moltype = AA  length = 5
FEATURE                 Location/Qualifiers
```

```
REGION                  1..5
                        note = Synthetic
source                  1..5
                        mol_type = protein
                        organism = synthetic construct
SEQUENCE: 504
QYWIH                                                                5

SEQ ID NO: 505          moltype = AA  length = 5
FEATURE                 Location/Qualifiers
REGION                  1..5
                        note = Synthetic
source                  1..5
                        mol_type = protein
                        organism = synthetic construct
SEQUENCE: 505
DYWIH                                                                5

SEQ ID NO: 506          moltype = AA  length = 5
FEATURE                 Location/Qualifiers
REGION                  1..5
                        note = Synthetic
source                  1..5
                        mol_type = protein
                        organism = synthetic construct
SEQUENCE: 506
QYWIH                                                                5

SEQ ID NO: 507          moltype = AA  length = 5
FEATURE                 Location/Qualifiers
REGION                  1..5
                        note = Synthetic
source                  1..5
                        mol_type = protein
                        organism = synthetic construct
SEQUENCE: 507
DYWIH                                                                5

SEQ ID NO: 508          moltype = AA  length = 5
FEATURE                 Location/Qualifiers
REGION                  1..5
                        note = Synthetic
source                  1..5
                        mol_type = protein
                        organism = synthetic construct
SEQUENCE: 508
YYIIH                                                                5

SEQ ID NO: 509          moltype = AA  length = 5
FEATURE                 Location/Qualifiers
REGION                  1..5
                        note = Synthetic
source                  1..5
                        mol_type = protein
                        organism = synthetic construct
SEQUENCE: 509
DYWIH                                                                5

SEQ ID NO: 510          moltype = AA  length = 5
FEATURE                 Location/Qualifiers
REGION                  1..5
                        note = Synthetic
source                  1..5
                        mol_type = protein
                        organism = synthetic construct
SEQUENCE: 510
VYIIH                                                                5

SEQ ID NO: 511          moltype = AA  length = 5
FEATURE                 Location/Qualifiers
REGION                  1..5
                        note = Synthetic
source                  1..5
                        mol_type = protein
                        organism = synthetic construct
SEQUENCE: 511
DYWIH                                                                5

SEQ ID NO: 512          moltype = AA  length = 5
```

-continued

```
FEATURE                 Location/Qualifiers
REGION                  1..5
                        note = Synthetic
source                  1..5
                        mol_type = protein
                        organism = synthetic construct
SEQUENCE: 512
DYWIH                                                                5

SEQ ID NO: 513          moltype = AA  length = 5
FEATURE                 Location/Qualifiers
REGION                  1..5
                        note = Synthetic
source                  1..5
                        mol_type = protein
                        organism = synthetic construct
SEQUENCE: 513
DYVIH                                                                5

SEQ ID NO: 514          moltype = AA  length = 5
FEATURE                 Location/Qualifiers
REGION                  1..5
                        note = Synthetic
source                  1..5
                        mol_type = protein
                        organism = synthetic construct
SEQUENCE: 514
IYTIH                                                                5

SEQ ID NO: 515          moltype = AA  length = 5
FEATURE                 Location/Qualifiers
REGION                  1..5
                        note = Synthetic
source                  1..5
                        mol_type = protein
                        organism = synthetic construct
SEQUENCE: 515
DYTIH                                                                5

SEQ ID NO: 516          moltype = AA  length = 5
FEATURE                 Location/Qualifiers
REGION                  1..5
                        note = Synthetic
source                  1..5
                        mol_type = protein
                        organism = synthetic construct
SEQUENCE: 516
YYIIH                                                                5

SEQ ID NO: 517          moltype = AA  length = 5
FEATURE                 Location/Qualifiers
REGION                  1..5
                        note = Synthetic
source                  1..5
                        mol_type = protein
                        organism = synthetic construct
SEQUENCE: 517
DYVIH                                                                5

SEQ ID NO: 518          moltype = AA  length = 5
FEATURE                 Location/Qualifiers
REGION                  1..5
                        note = Synthetic
source                  1..5
                        mol_type = protein
                        organism = synthetic construct
SEQUENCE: 518
DYVIH                                                                5

SEQ ID NO: 519          moltype = AA  length = 5
FEATURE                 Location/Qualifiers
REGION                  1..5
                        note = Synthetic
source                  1..5
                        mol_type = protein
                        organism = synthetic construct
SEQUENCE: 519
GYIIH                                                                5
```

```
SEQ ID NO: 520          moltype = AA  length = 5
FEATURE                 Location/Qualifiers
REGION                  1..5
                        note = Synthetic
source                  1..5
                        mol_type = protein
                        organism = synthetic construct
SEQUENCE: 520
DYTIH                                                                5

SEQ ID NO: 521          moltype = AA  length = 5
FEATURE                 Location/Qualifiers
REGION                  1..5
                        note = Synthetic
source                  1..5
                        mol_type = protein
                        organism = synthetic construct
SEQUENCE: 521
YYIIH                                                                5

SEQ ID NO: 522          moltype = AA  length = 5
FEATURE                 Location/Qualifiers
REGION                  1..5
                        note = Synthetic
source                  1..5
                        mol_type = protein
                        organism = synthetic construct
SEQUENCE: 522
NYIIH                                                                5

SEQ ID NO: 523          moltype = AA  length = 5
FEATURE                 Location/Qualifiers
REGION                  1..5
                        note = Synthetic
source                  1..5
                        mol_type = protein
                        organism = synthetic construct
SEQUENCE: 523
DYVIH                                                                5

SEQ ID NO: 524          moltype = AA  length = 5
FEATURE                 Location/Qualifiers
REGION                  1..5
                        note = Synthetic
source                  1..5
                        mol_type = protein
                        organism = synthetic construct
SEQUENCE: 524
YYVIH                                                                5

SEQ ID NO: 525          moltype = AA  length = 5
FEATURE                 Location/Qualifiers
REGION                  1..5
                        note = Synthetic
source                  1..5
                        mol_type = protein
                        organism = synthetic construct
SEQUENCE: 525
DYIIH                                                                5

SEQ ID NO: 526          moltype = AA  length = 5
FEATURE                 Location/Qualifiers
REGION                  1..5
                        note = Synthetic
source                  1..5
                        mol_type = protein
                        organism = synthetic construct
SEQUENCE: 526
DYVIH                                                                5

SEQ ID NO: 527          moltype = AA  length = 5
FEATURE                 Location/Qualifiers
REGION                  1..5
                        note = Synthetic
source                  1..5
                        mol_type = protein
                        organism = synthetic construct
SEQUENCE: 527
GYIIH                                                                5
```

```
SEQ ID NO: 528          moltype = AA  length = 5
FEATURE                 Location/Qualifiers
REGION                  1..5
                        note = Synthetic
source                  1..5
                        mol_type = protein
                        organism = synthetic construct
SEQUENCE: 528
DYIIH                                                              5

SEQ ID NO: 529          moltype = AA  length = 5
FEATURE                 Location/Qualifiers
REGION                  1..5
                        note = Synthetic
source                  1..5
                        mol_type = protein
                        organism = synthetic construct
SEQUENCE: 529
DYIIH                                                              5

SEQ ID NO: 530          moltype = AA  length = 5
FEATURE                 Location/Qualifiers
REGION                  1..5
                        note = Synthetic
source                  1..5
                        mol_type = protein
                        organism = synthetic construct
SEQUENCE: 530
DYIIH                                                              5

SEQ ID NO: 531          moltype = AA  length = 5
FEATURE                 Location/Qualifiers
REGION                  1..5
                        note = Synthetic
source                  1..5
                        mol_type = protein
                        organism = synthetic construct
SEQUENCE: 531
DYIIH                                                              5

SEQ ID NO: 532          moltype = AA  length = 5
FEATURE                 Location/Qualifiers
REGION                  1..5
                        note = Synthetic
source                  1..5
                        mol_type = protein
                        organism = synthetic construct
SEQUENCE: 532
DYIIH                                                              5

SEQ ID NO: 533          moltype = AA  length = 5
FEATURE                 Location/Qualifiers
REGION                  1..5
                        note = Synthetic
source                  1..5
                        mol_type = protein
                        organism = synthetic construct
SEQUENCE: 533
DYIIH                                                              5

SEQ ID NO: 534          moltype = AA  length = 5
FEATURE                 Location/Qualifiers
REGION                  1..5
                        note = Synthetic
source                  1..5
                        mol_type = protein
                        organism = synthetic construct
SEQUENCE: 534
HYIIH                                                              5

SEQ ID NO: 535          moltype = AA  length = 5
FEATURE                 Location/Qualifiers
REGION                  1..5
                        note = Synthetic
source                  1..5
                        mol_type = protein
                        organism = synthetic construct
SEQUENCE: 535
```

```
DYTIH                                                      5

SEQ ID NO: 536          moltype = AA  length = 5
FEATURE                 Location/Qualifiers
REGION                  1..5
                        note = Synthetic
source                  1..5
                        mol_type = protein
                        organism = synthetic construct
SEQUENCE: 536
AYIIH                                                      5

SEQ ID NO: 537          moltype = AA  length = 5
FEATURE                 Location/Qualifiers
REGION                  1..5
                        note = Synthetic
source                  1..5
                        mol_type = protein
                        organism = synthetic construct
SEQUENCE: 537
YYTIH                                                      5

SEQ ID NO: 538          moltype = AA  length = 5
FEATURE                 Location/Qualifiers
REGION                  1..5
                        note = Synthetic
source                  1..5
                        mol_type = protein
                        organism = synthetic construct
SEQUENCE: 538
DYVIH                                                      5

SEQ ID NO: 539          moltype = AA  length = 5
FEATURE                 Location/Qualifiers
REGION                  1..5
                        note = Synthetic
source                  1..5
                        mol_type = protein
                        organism = synthetic construct
SEQUENCE: 539
DYVIH                                                      5

SEQ ID NO: 540          moltype = AA  length = 5
FEATURE                 Location/Qualifiers
REGION                  1..5
                        note = Synthetic
source                  1..5
                        mol_type = protein
                        organism = synthetic construct
SEQUENCE: 540
DYVIH                                                      5

SEQ ID NO: 541          moltype = AA  length = 5
FEATURE                 Location/Qualifiers
REGION                  1..5
                        note = Synthetic
source                  1..5
                        mol_type = protein
                        organism = synthetic construct
SEQUENCE: 541
SYIIH                                                      5

SEQ ID NO: 542          moltype =   length =
SEQUENCE: 542
000

SEQ ID NO: 543          moltype = AA  length = 5
FEATURE                 Location/Qualifiers
REGION                  1..5
                        note = Synthetic
source                  1..5
                        mol_type = protein
                        organism = synthetic construct
SEQUENCE: 543
SYDMS                                                      5

SEQ ID NO: 544          moltype =   length =
SEQUENCE: 544
000
```

```
SEQ ID NO: 545         moltype =   length =
SEQUENCE: 545
000

SEQ ID NO: 546         moltype =   length =
SEQUENCE: 546
000

SEQ ID NO: 547         moltype =   length =
SEQUENCE: 547
000

SEQ ID NO: 548         moltype =   length =
SEQUENCE: 548
000

SEQ ID NO: 549         moltype = AA  length = 5
FEATURE                Location/Qualifiers
REGION                 1..5
                       note = Synthetic
source                 1..5
                       mol_type = protein
                       organism = synthetic construct
SEQUENCE: 549
YYGVS                                                        5

SEQ ID NO: 550         moltype =   length =
SEQUENCE: 550
000

SEQ ID NO: 551         moltype =   length =
SEQUENCE: 551
000

SEQ ID NO: 552         moltype =   length =
SEQUENCE: 552
000

SEQ ID NO: 553         moltype =   length =
SEQUENCE: 553
000

SEQ ID NO: 554         moltype = AA  length = 5
FEATURE                Location/Qualifiers
REGION                 1..5
                       note = Synthetic
source                 1..5
                       mol_type = protein
                       organism = synthetic construct
SEQUENCE: 554
YYGVS                                                        5

SEQ ID NO: 555         moltype =   length =
SEQUENCE: 555
000

SEQ ID NO: 556         moltype =   length =
SEQUENCE: 556
000

SEQ ID NO: 557         moltype =   length =
SEQUENCE: 557
000

SEQ ID NO: 558         moltype =   length =
SEQUENCE: 558
000

SEQ ID NO: 559         moltype =   length =
SEQUENCE: 559
000

SEQ ID NO: 560         moltype = AA  length = 5
FEATURE                Location/Qualifiers
REGION                 1..5
                       note = Synthetic
source                 1..5
                       mol_type = protein
```

```
                        organism = synthetic construct
SEQUENCE: 560
SYDMS                                                                5

SEQ ID NO: 561          moltype =   length =
SEQUENCE: 561
000

SEQ ID NO: 562          moltype = AA  length = 5
FEATURE                 Location/Qualifiers
REGION                  1..5
                        note = Synthetic
source                  1..5
                        mol_type = protein
                        organism = synthetic construct
SEQUENCE: 562
SYDMS                                                                5

SEQ ID NO: 563          moltype = AA  length = 5
FEATURE                 Location/Qualifiers
REGION                  1..5
                        note = Synthetic
source                  1..5
                        mol_type = protein
                        organism = synthetic construct
SEQUENCE: 563
SYDMS                                                                5

SEQ ID NO: 564          moltype =   length =
SEQUENCE: 564
000

SEQ ID NO: 565          moltype =   length =
SEQUENCE: 565
000

SEQ ID NO: 566          moltype =   length =
SEQUENCE: 566
000

SEQ ID NO: 567          moltype =   length =
SEQUENCE: 567
000

SEQ ID NO: 568          moltype =   length =
SEQUENCE: 568
000

SEQ ID NO: 569          moltype =   length =
SEQUENCE: 569
000

SEQ ID NO: 570          moltype =   length =
SEQUENCE: 570
000

SEQ ID NO: 571          moltype =   length =
SEQUENCE: 571
000

SEQ ID NO: 572          moltype =   length =
SEQUENCE: 572
000

SEQ ID NO: 573          moltype =   length =
SEQUENCE: 573
000

SEQ ID NO: 574          moltype =   length =
SEQUENCE: 574
000

SEQ ID NO: 575          moltype =   length =
SEQUENCE: 575
000

SEQ ID NO: 576          moltype =   length =
SEQUENCE: 576
000
```

-continued

SEQ ID NO: 577 moltype = length =
SEQUENCE: 577
000

SEQ ID NO: 578 moltype = length =
SEQUENCE: 578
000

SEQ ID NO: 579 moltype = length =
SEQUENCE: 579
000

SEQ ID NO: 580 moltype = length =
SEQUENCE: 580
000

SEQ ID NO: 581 moltype = length =
SEQUENCE: 581
000

SEQ ID NO: 582 moltype = length =
SEQUENCE: 582
000

SEQ ID NO: 583 moltype = length =
SEQUENCE: 583
000

SEQ ID NO: 584 moltype = length =
SEQUENCE: 584
000

SEQ ID NO: 585 moltype = length =
SEQUENCE: 585
000

SEQ ID NO: 586 moltype = length =
SEQUENCE: 586
000

SEQ ID NO: 587 moltype = length =
SEQUENCE: 587
000

SEQ ID NO: 588 moltype = length =
SEQUENCE: 588
000

SEQ ID NO: 589 moltype = length =
SEQUENCE: 589
000

SEQ ID NO: 590 moltype = length =
SEQUENCE: 590
000

SEQ ID NO: 591 moltype = length =
SEQUENCE: 591
000

SEQ ID NO: 592 moltype = length =
SEQUENCE: 592
000

SEQ ID NO: 593 moltype = length =
SEQUENCE: 593
000

SEQ ID NO: 594 moltype = length =
SEQUENCE: 594
000

SEQ ID NO: 595 moltype = length =
SEQUENCE: 595
000

SEQ ID NO: 596 moltype = length =
SEQUENCE: 596

-continued

000

SEQ ID NO: 597 moltype = length =
SEQUENCE: 597
000

SEQ ID NO: 598 moltype = length =
SEQUENCE: 598
000

SEQ ID NO: 599 moltype = length =
SEQUENCE: 599
000

SEQ ID NO: 600 moltype = length =
SEQUENCE: 600
000

SEQ ID NO: 601 moltype = length =
SEQUENCE: 601
000

SEQ ID NO: 602 moltype = length =
SEQUENCE: 602
000

SEQ ID NO: 603 moltype = length =
SEQUENCE: 603
000

SEQ ID NO: 604 moltype = length =
SEQUENCE: 604
000

SEQ ID NO: 605 moltype = length =
SEQUENCE: 605
000

SEQ ID NO: 606 moltype = length =
SEQUENCE: 606
000

SEQ ID NO: 607 moltype = length =
SEQUENCE: 607
000

SEQ ID NO: 608 moltype = length =
SEQUENCE: 608
000

SEQ ID NO: 609 moltype = length =
SEQUENCE: 609
000

SEQ ID NO: 610 moltype = length =
SEQUENCE: 610
000

SEQ ID NO: 611 moltype = length =
SEQUENCE: 611
000

SEQ ID NO: 612 moltype = length =
SEQUENCE: 612
000

SEQ ID NO: 613 moltype = length =
SEQUENCE: 613
000

SEQ ID NO: 614 moltype = length =
SEQUENCE: 614
000

SEQ ID NO: 615 moltype = length =
SEQUENCE: 615
000

SEQ ID NO: 616 moltype = length =

SEQUENCE: 616
000

SEQ ID NO: 617 moltype = length =
SEQUENCE: 617
000

SEQ ID NO: 618 moltype = length =
SEQUENCE: 618
000

SEQ ID NO: 619 moltype = length =
SEQUENCE: 619
000

SEQ ID NO: 620 moltype = length =
SEQUENCE: 620
000

SEQ ID NO: 621 moltype = length =
SEQUENCE: 621
000

SEQ ID NO: 622 moltype = length =
SEQUENCE: 622
000

SEQ ID NO: 623 moltype = length =
SEQUENCE: 623
000

SEQ ID NO: 624 moltype = length =
SEQUENCE: 624
000

SEQ ID NO: 625 moltype = length =
SEQUENCE: 625
000

SEQ ID NO: 626 moltype = length =
SEQUENCE: 626
000

SEQ ID NO: 627 moltype = length =
SEQUENCE: 627
000

SEQ ID NO: 628 moltype = length =
SEQUENCE: 628
000

SEQ ID NO: 629 moltype = length =
SEQUENCE: 629
000

SEQ ID NO: 630 moltype = length =
SEQUENCE: 630
000

SEQ ID NO: 631 moltype = length =
SEQUENCE: 631
000

SEQ ID NO: 632 moltype = length =
SEQUENCE: 632
000

SEQ ID NO: 633 moltype = length =
SEQUENCE: 633
000

SEQ ID NO: 634 moltype = length =
SEQUENCE: 634
000

SEQ ID NO: 635 moltype = length =
SEQUENCE: 635
000

-continued

SEQ ID NO: 636 moltype = length =
SEQUENCE: 636
000

SEQ ID NO: 637 moltype = length =
SEQUENCE: 637
000

SEQ ID NO: 638 moltype = length =
SEQUENCE: 638
000

SEQ ID NO: 639 moltype = length =
SEQUENCE: 639
000

SEQ ID NO: 640 moltype = length =
SEQUENCE: 640
000

SEQ ID NO: 641 moltype = length =
SEQUENCE: 641
000

SEQ ID NO: 642 moltype = length =
SEQUENCE: 642
000

SEQ ID NO: 643 moltype = length =
SEQUENCE: 643
000

SEQ ID NO: 644 moltype = length =
SEQUENCE: 644
000

SEQ ID NO: 645 moltype = length =
SEQUENCE: 645
000

SEQ ID NO: 646 moltype = length =
SEQUENCE: 646
000

SEQ ID NO: 647 moltype = length =
SEQUENCE: 647
000

SEQ ID NO: 648 moltype = length =
SEQUENCE: 648
000

SEQ ID NO: 649 moltype = length =
SEQUENCE: 649
000

SEQ ID NO: 650 moltype = length =
SEQUENCE: 650
000

SEQ ID NO: 651 moltype = length =
SEQUENCE: 651
000

SEQ ID NO: 652 moltype = length =
SEQUENCE: 652
000

SEQ ID NO: 653 moltype = length =
SEQUENCE: 653
000

SEQ ID NO: 654 moltype = length =
SEQUENCE: 654
000

SEQ ID NO: 655 moltype = length =
SEQUENCE: 655
000

SEQ ID NO: 656 moltype = length =
SEQUENCE: 656
000

SEQ ID NO: 657 moltype = length =
SEQUENCE: 657
000

SEQ ID NO: 658 moltype = length =
SEQUENCE: 658
000

SEQ ID NO: 659 moltype = length =
SEQUENCE: 659
000

SEQ ID NO: 660 moltype = length =
SEQUENCE: 660
000

SEQ ID NO: 661 moltype = length =
SEQUENCE: 661
000

SEQ ID NO: 662 moltype = length =
SEQUENCE: 662
000

SEQ ID NO: 663 moltype = length =
SEQUENCE: 663
000

SEQ ID NO: 664 moltype = length =
SEQUENCE: 664
000

SEQ ID NO: 665 moltype = length =
SEQUENCE: 665
000

SEQ ID NO: 666 moltype = length =
SEQUENCE: 666
000

SEQ ID NO: 667 moltype = length =
SEQUENCE: 667
000

SEQ ID NO: 668 moltype = length =
SEQUENCE: 668
000

SEQ ID NO: 669 moltype = length =
SEQUENCE: 669
000

SEQ ID NO: 670 moltype = length =
SEQUENCE: 670
000

SEQ ID NO: 671 moltype = length =
SEQUENCE: 671
000

SEQ ID NO: 672 moltype = length =
SEQUENCE: 672
000

SEQ ID NO: 673 moltype = length =
SEQUENCE: 673
000

SEQ ID NO: 674 moltype = length =
SEQUENCE: 674
000

SEQ ID NO: 675 moltype = length =
SEQUENCE: 675

000

SEQ ID NO: 676 moltype = length =
SEQUENCE: 676
000

SEQ ID NO: 677 moltype = length =
SEQUENCE: 677
000

SEQ ID NO: 678 moltype = length =
SEQUENCE: 678
000

SEQ ID NO: 679 moltype = length =
SEQUENCE: 679
000

SEQ ID NO: 680 moltype = length =
SEQUENCE: 680
000

SEQ ID NO: 681 moltype = length =
SEQUENCE: 681
000

SEQ ID NO: 682 moltype = length =
SEQUENCE: 682
000

SEQ ID NO: 683 moltype = length =
SEQUENCE: 683
000

SEQ ID NO: 684 moltype = length =
SEQUENCE: 684
000

SEQ ID NO: 685 moltype = length =
SEQUENCE: 685
000

SEQ ID NO: 686 moltype = length =
SEQUENCE: 686
000

SEQ ID NO: 687 moltype = length =
SEQUENCE: 687
000

SEQ ID NO: 688 moltype = length =
SEQUENCE: 688
000

SEQ ID NO: 689 moltype = length =
SEQUENCE: 689
000

SEQ ID NO: 690 moltype = length =
SEQUENCE: 690
000

SEQ ID NO: 691 moltype = length =
SEQUENCE: 691
000

SEQ ID NO: 692 moltype = length =
SEQUENCE: 692
000

SEQ ID NO: 693 moltype = length =
SEQUENCE: 693
000

SEQ ID NO: 694 moltype = length =
SEQUENCE: 694
000

SEQ ID NO: 695 moltype = length =

SEQUENCE: 695
000

SEQ ID NO: 696 moltype = length =
SEQUENCE: 696
000

SEQ ID NO: 697 moltype = length =
SEQUENCE: 697
000

SEQ ID NO: 698 moltype = length =
SEQUENCE: 698
000

SEQ ID NO: 699 moltype = length =
SEQUENCE: 699
000

SEQ ID NO: 700 moltype = length =
SEQUENCE: 700
000

SEQ ID NO: 701 moltype = length =
SEQUENCE: 701
000

SEQ ID NO: 702 moltype = length =
SEQUENCE: 702
000

SEQ ID NO: 703 moltype = length =
SEQUENCE: 703
000

SEQ ID NO: 704 moltype = length =
SEQUENCE: 704
000

SEQ ID NO: 705 moltype = length =
SEQUENCE: 705
000

SEQ ID NO: 706 moltype = length =
SEQUENCE: 706
000

SEQ ID NO: 707 moltype = length =
SEQUENCE: 707
000

SEQ ID NO: 708 moltype = length =
SEQUENCE: 708
000

SEQ ID NO: 709 moltype = length =
SEQUENCE: 709
000

SEQ ID NO: 710 moltype = length =
SEQUENCE: 710
000

SEQ ID NO: 711 moltype = length =
SEQUENCE: 711
000

SEQ ID NO: 712 moltype = length =
SEQUENCE: 712
000

SEQ ID NO: 713 moltype = length =
SEQUENCE: 713
000

SEQ ID NO: 714 moltype = length =
SEQUENCE: 714
000

-continued

SEQ ID NO: 715 moltype = length =
SEQUENCE: 715
000

SEQ ID NO: 716 moltype = length =
SEQUENCE: 716
000

SEQ ID NO: 717 moltype = length =
SEQUENCE: 717
000

SEQ ID NO: 718 moltype = length =
SEQUENCE: 718
000

SEQ ID NO: 719 moltype = length =
SEQUENCE: 719
000

SEQ ID NO: 720 moltype = length =
SEQUENCE: 720
000

SEQ ID NO: 721 moltype = length =
SEQUENCE: 721
000

SEQ ID NO: 722 moltype = length =
SEQUENCE: 722
000

SEQ ID NO: 723 moltype = length =
SEQUENCE: 723
000

SEQ ID NO: 724 moltype = length =
SEQUENCE: 724
000

SEQ ID NO: 725 moltype = length =
SEQUENCE: 725
000

SEQ ID NO: 726 moltype = length =
SEQUENCE: 726
000

SEQ ID NO: 727 moltype = length =
SEQUENCE: 727
000

SEQ ID NO: 728 moltype = length =
SEQUENCE: 728
000

SEQ ID NO: 729 moltype = length =
SEQUENCE: 729
000

SEQ ID NO: 730 moltype = length =
SEQUENCE: 730
000

SEQ ID NO: 731 moltype = length =
SEQUENCE: 731
000

SEQ ID NO: 732 moltype = length =
SEQUENCE: 732
000

SEQ ID NO: 733 moltype = length =
SEQUENCE: 733
000

SEQ ID NO: 734 moltype = length =
SEQUENCE: 734
000

SEQ ID NO: 735 moltype = length =
SEQUENCE: 735
000

SEQ ID NO: 736 moltype = length =
SEQUENCE: 736
000

SEQ ID NO: 737 moltype = length =
SEQUENCE: 737
000

SEQ ID NO: 738 moltype = length =
SEQUENCE: 738
000

SEQ ID NO: 739 moltype = length =
SEQUENCE: 739
000

SEQ ID NO: 740 moltype = length =
SEQUENCE: 740
000

SEQ ID NO: 741 moltype = length =
SEQUENCE: 741
000

SEQ ID NO: 742 moltype = length =
SEQUENCE: 742
000

SEQ ID NO: 743 moltype = length =
SEQUENCE: 743
000

SEQ ID NO: 744 moltype = length =
SEQUENCE: 744
000

SEQ ID NO: 745 moltype = length =
SEQUENCE: 745
000

SEQ ID NO: 746 moltype = length =
SEQUENCE: 746
000

SEQ ID NO: 747 moltype = length =
SEQUENCE: 747
000

SEQ ID NO: 748 moltype = length =
SEQUENCE: 748
000

SEQ ID NO: 749 moltype = length =
SEQUENCE: 749
000

SEQ ID NO: 750 moltype = length =
SEQUENCE: 750
000

SEQ ID NO: 751 moltype = length =
SEQUENCE: 751
000

SEQ ID NO: 752 moltype = length =
SEQUENCE: 752
000

SEQ ID NO: 753 moltype = length =
SEQUENCE: 753
000

SEQ ID NO: 754 moltype = length =
SEQUENCE: 754

```
000

SEQ ID NO: 755          moltype = AA  length = 6
FEATURE                 Location/Qualifiers
REGION                  1..6
                        note = Synthetic
source                  1..6
                        mol_type = protein
                        organism = synthetic construct
SEQUENCE: 755
DPYSGS                                                            6

SEQ ID NO: 756          moltype =   length =
SEQUENCE: 756
000

SEQ ID NO: 757          moltype =   length =
SEQUENCE: 757
000

SEQ ID NO: 758          moltype =   length =
SEQUENCE: 758
000

SEQ ID NO: 759          moltype =   length =
SEQUENCE: 759
000

SEQ ID NO: 760          moltype =   length =
SEQUENCE: 760
000

SEQ ID NO: 761          moltype =   length =
SEQUENCE: 761
000

SEQ ID NO: 762          moltype =   length =
SEQUENCE: 762
000

SEQ ID NO: 763          moltype =   length =
SEQUENCE: 763
000

SEQ ID NO: 764          moltype = AA  length = 6
FEATURE                 Location/Qualifiers
REGION                  1..6
                        note = Synthetic
source                  1..6
                        mol_type = protein
                        organism = synthetic construct
SEQUENCE: 764
DPYNGY                                                            6

SEQ ID NO: 765          moltype =   length =
SEQUENCE: 765
000

SEQ ID NO: 766          moltype =   length =
SEQUENCE: 766
000

SEQ ID NO: 767          moltype = AA  length = 6
FEATURE                 Location/Qualifiers
REGION                  1..6
                        note = Synthetic
source                  1..6
                        mol_type = protein
                        organism = synthetic construct
SEQUENCE: 767
DPSNGY                                                            6

SEQ ID NO: 768          moltype =   length =
SEQUENCE: 768
000

SEQ ID NO: 769          moltype =   length =
SEQUENCE: 769
000
```

-continued

```
SEQ ID NO: 770          moltype =   length =
SEQUENCE: 770
000

SEQ ID NO: 771          moltype =   length =
SEQUENCE: 771
000

SEQ ID NO: 772          moltype =   length =
SEQUENCE: 772
000

SEQ ID NO: 773          moltype =   length =
SEQUENCE: 773
000

SEQ ID NO: 774          moltype =   length =
SEQUENCE: 774
000

SEQ ID NO: 775          moltype =   length =
SEQUENCE: 775
000

SEQ ID NO: 776          moltype =   length =
SEQUENCE: 776
000

SEQ ID NO: 777          moltype =   length =
SEQUENCE: 777
000

SEQ ID NO: 778          moltype =   length =
SEQUENCE: 778
000

SEQ ID NO: 779          moltype = AA  length = 6
FEATURE                 Location/Qualifiers
REGION                  1..6
                        note = Synthetic
source                  1..6
                        mol_type = protein
                        organism = synthetic construct
SEQUENCE: 779
DPYNGA                                                                  6

SEQ ID NO: 780          moltype = AA  length = 6
FEATURE                 Location/Qualifiers
REGION                  1..6
                        note = Synthetic
source                  1..6
                        mol_type = protein
                        organism = synthetic construct
SEQUENCE: 780
DPSNGY                                                                  6

SEQ ID NO: 781          moltype = AA  length = 6
FEATURE                 Location/Qualifiers
REGION                  1..6
                        note = Synthetic
source                  1..6
                        mol_type = protein
                        organism = synthetic construct
SEQUENCE: 781
DPANGA                                                                  6

SEQ ID NO: 782          moltype = AA  length = 6
FEATURE                 Location/Qualifiers
REGION                  1..6
                        note = Synthetic
source                  1..6
                        mol_type = protein
                        organism = synthetic construct
SEQUENCE: 782
DPYNGA                                                                  6

SEQ ID NO: 783          moltype = AA  length = 6
FEATURE                 Location/Qualifiers
```

```
REGION                1..6
                      note = Synthetic
source                1..6
                      mol_type = protein
                      organism = synthetic construct
SEQUENCE: 783
DPYNGY                                                           6

SEQ ID NO: 784        moltype = AA  length = 6
FEATURE               Location/Qualifiers
REGION                1..6
                      note = Synthetic
source                1..6
                      mol_type = protein
                      organism = synthetic construct
SEQUENCE: 784
DPFNGA                                                           6

SEQ ID NO: 785        moltype = AA  length = 6
FEATURE               Location/Qualifiers
REGION                1..6
                      note = Synthetic
source                1..6
                      mol_type = protein
                      organism = synthetic construct
SEQUENCE: 785
DPYNGA                                                           6

SEQ ID NO: 786        moltype = AA  length = 6
FEATURE               Location/Qualifiers
REGION                1..6
                      note = Synthetic
source                1..6
                      mol_type = protein
                      organism = synthetic construct
SEQUENCE: 786
DPYNGA                                                           6

SEQ ID NO: 787        moltype = AA  length = 6
FEATURE               Location/Qualifiers
REGION                1..6
                      note = Synthetic
source                1..6
                      mol_type = protein
                      organism = synthetic construct
SEQUENCE: 787
DPYNGA                                                           6

SEQ ID NO: 788        moltype = AA  length = 6
FEATURE               Location/Qualifiers
REGION                1..6
                      note = Synthetic
source                1..6
                      mol_type = protein
                      organism = synthetic construct
SEQUENCE: 788
DPYNGA                                                           6

SEQ ID NO: 789        moltype = AA  length = 6
FEATURE               Location/Qualifiers
REGION                1..6
                      note = Synthetic
source                1..6
                      mol_type = protein
                      organism = synthetic construct
SEQUENCE: 789
DPSNGY                                                           6

SEQ ID NO: 790        moltype = AA  length = 6
FEATURE               Location/Qualifiers
REGION                1..6
                      note = Synthetic
source                1..6
                      mol_type = protein
                      organism = synthetic construct
SEQUENCE: 790
DPYNGA                                                           6

SEQ ID NO: 791        moltype = AA  length = 6
```

-continued

```
FEATURE                 Location/Qualifiers
REGION                  1..6
                        note = Synthetic
source                  1..6
                        mol_type = protein
                        organism = synthetic construct
SEQUENCE: 791
DPYNGA                                                                      6

SEQ ID NO: 792          moltype = AA  length = 6
FEATURE                 Location/Qualifiers
REGION                  1..6
                        note = Synthetic
source                  1..6
                        mol_type = protein
                        organism = synthetic construct
SEQUENCE: 792
DPYNGA                                                                      6

SEQ ID NO: 793          moltype = AA  length = 6
FEATURE                 Location/Qualifiers
REGION                  1..6
                        note = Synthetic
source                  1..6
                        mol_type = protein
                        organism = synthetic construct
SEQUENCE: 793
DPYNGY                                                                      6

SEQ ID NO: 794          moltype = AA  length = 6
FEATURE                 Location/Qualifiers
REGION                  1..6
                        note = Synthetic
source                  1..6
                        mol_type = protein
                        organism = synthetic construct
SEQUENCE: 794
DPYNGA                                                                      6

SEQ ID NO: 795          moltype = AA  length = 6
FEATURE                 Location/Qualifiers
REGION                  1..6
                        note = Synthetic
source                  1..6
                        mol_type = protein
                        organism = synthetic construct
SEQUENCE: 795
DPYNGA                                                                      6

SEQ ID NO: 796          moltype = AA  length = 6
FEATURE                 Location/Qualifiers
REGION                  1..6
                        note = Synthetic
source                  1..6
                        mol_type = protein
                        organism = synthetic construct
SEQUENCE: 796
DPYNGY                                                                      6

SEQ ID NO: 797          moltype = AA  length = 6
FEATURE                 Location/Qualifiers
REGION                  1..6
                        note = Synthetic
source                  1..6
                        mol_type = protein
                        organism = synthetic construct
SEQUENCE: 797
DPYNGY                                                                      6

SEQ ID NO: 798          moltype = AA  length = 6
FEATURE                 Location/Qualifiers
REGION                  1..6
                        note = Synthetic
source                  1..6
                        mol_type = protein
                        organism = synthetic construct
SEQUENCE: 798
DPYNGY                                                                      6
```

-continued

```
SEQ ID NO: 799          moltype = AA  length = 6
FEATURE                 Location/Qualifiers
REGION                  1..6
                        note = Synthetic
source                  1..6
                        mol_type = protein
                        organism = synthetic construct
SEQUENCE: 799
DPYNGS                                                                  6

SEQ ID NO: 800          moltype = AA  length = 6
FEATURE                 Location/Qualifiers
REGION                  1..6
                        note = Synthetic
source                  1..6
                        mol_type = protein
                        organism = synthetic construct
SEQUENCE: 800
DPSNGY                                                                  6

SEQ ID NO: 801          moltype = AA  length = 6
FEATURE                 Location/Qualifiers
REGION                  1..6
                        note = Synthetic
source                  1..6
                        mol_type = protein
                        organism = synthetic construct
SEQUENCE: 801
DPSNGY                                                                  6

SEQ ID NO: 802          moltype = AA  length = 6
FEATURE                 Location/Qualifiers
REGION                  1..6
                        note = Synthetic
source                  1..6
                        mol_type = protein
                        organism = synthetic construct
SEQUENCE: 802
DPYNGA                                                                  6

SEQ ID NO: 803          moltype = AA  length = 6
FEATURE                 Location/Qualifiers
REGION                  1..6
                        note = Synthetic
source                  1..6
                        mol_type = protein
                        organism = synthetic construct
SEQUENCE: 803
DPYNGA                                                                  6

SEQ ID NO: 804          moltype = AA  length = 6
FEATURE                 Location/Qualifiers
REGION                  1..6
                        note = Synthetic
source                  1..6
                        mol_type = protein
                        organism = synthetic construct
SEQUENCE: 804
DPYNGA                                                                  6

SEQ ID NO: 805          moltype = AA  length = 6
FEATURE                 Location/Qualifiers
REGION                  1..6
                        note = Synthetic
source                  1..6
                        mol_type = protein
                        organism = synthetic construct
SEQUENCE: 805
DPYNGA                                                                  6

SEQ ID NO: 806          moltype = AA  length = 6
FEATURE                 Location/Qualifiers
REGION                  1..6
                        note = Synthetic
source                  1..6
                        mol_type = protein
                        organism = synthetic construct
SEQUENCE: 806
DPYNGA                                                                  6
```

```
SEQ ID NO: 807          moltype = AA  length = 6
FEATURE                 Location/Qualifiers
REGION                  1..6
                        note = Synthetic
source                  1..6
                        mol_type = protein
                        organism = synthetic construct
SEQUENCE: 807
DPYNGA                                                            6

SEQ ID NO: 808          moltype = AA  length = 6
FEATURE                 Location/Qualifiers
REGION                  1..6
                        note = Synthetic
source                  1..6
                        mol_type = protein
                        organism = synthetic construct
SEQUENCE: 808
DPYNGS                                                            6

SEQ ID NO: 809          moltype = AA  length = 6
FEATURE                 Location/Qualifiers
REGION                  1..6
                        note = Synthetic
source                  1..6
                        mol_type = protein
                        organism = synthetic construct
SEQUENCE: 809
DPSNGY                                                            6

SEQ ID NO: 810          moltype = AA  length = 6
FEATURE                 Location/Qualifiers
REGION                  1..6
                        note = Synthetic
source                  1..6
                        mol_type = protein
                        organism = synthetic construct
SEQUENCE: 810
DPYNGY                                                            6

SEQ ID NO: 811          moltype = AA  length = 6
FEATURE                 Location/Qualifiers
REGION                  1..6
                        note = Synthetic
source                  1..6
                        mol_type = protein
                        organism = synthetic construct
SEQUENCE: 811
DPYNGY                                                            6

SEQ ID NO: 812          moltype = AA  length = 6
FEATURE                 Location/Qualifiers
REGION                  1..6
                        note = Synthetic
source                  1..6
                        mol_type = protein
                        organism = synthetic construct
SEQUENCE: 812
DPANGF                                                            6

SEQ ID NO: 813          moltype = AA  length = 6
FEATURE                 Location/Qualifiers
REGION                  1..6
                        note = Synthetic
source                  1..6
                        mol_type = protein
                        organism = synthetic construct
SEQUENCE: 813
DPYNGY                                                            6

SEQ ID NO: 814          moltype = AA  length = 6
FEATURE                 Location/Qualifiers
REGION                  1..6
                        note = Synthetic
source                  1..6
                        mol_type = protein
                        organism = synthetic construct
SEQUENCE: 814
```

```
DPYNGY                                                          6

SEQ ID NO: 815          moltype = AA  length = 6
FEATURE                 Location/Qualifiers
REGION                  1..6
                        note = Synthetic
source                  1..6
                        mol_type = protein
                        organism = synthetic construct
SEQUENCE: 815
DPYNGY                                                          6

SEQ ID NO: 816          moltype = AA  length = 6
FEATURE                 Location/Qualifiers
REGION                  1..6
                        note = Synthetic
source                  1..6
                        mol_type = protein
                        organism = synthetic construct
SEQUENCE: 816
DPYNGY                                                          6

SEQ ID NO: 817          moltype = AA  length = 6
FEATURE                 Location/Qualifiers
REGION                  1..6
                        note = Synthetic
source                  1..6
                        mol_type = protein
                        organism = synthetic construct
SEQUENCE: 817
DPQNGW                                                          6

SEQ ID NO: 818          moltype = AA  length = 6
FEATURE                 Location/Qualifiers
REGION                  1..6
                        note = Synthetic
source                  1..6
                        mol_type = protein
                        organism = synthetic construct
SEQUENCE: 818
DPSNGY                                                          6

SEQ ID NO: 819          moltype = AA  length = 6
FEATURE                 Location/Qualifiers
REGION                  1..6
                        note = Synthetic
source                  1..6
                        mol_type = protein
                        organism = synthetic construct
SEQUENCE: 819
DPYNGY                                                          6

SEQ ID NO: 820          moltype = AA  length = 6
FEATURE                 Location/Qualifiers
REGION                  1..6
                        note = Synthetic
source                  1..6
                        mol_type = protein
                        organism = synthetic construct
SEQUENCE: 820
DPANGF                                                          6

SEQ ID NO: 821          moltype = AA  length = 6
FEATURE                 Location/Qualifiers
REGION                  1..6
                        note = Synthetic
source                  1..6
                        mol_type = protein
                        organism = synthetic construct
SEQUENCE: 821
DPKNGY                                                          6

SEQ ID NO: 822          moltype = AA  length = 6
FEATURE                 Location/Qualifiers
REGION                  1..6
                        note = Synthetic
source                  1..6
                        mol_type = protein
                        organism = synthetic construct
```

```
SEQUENCE: 822
DPYNGY                                                              6

SEQ ID NO: 823          moltype = AA  length = 6
FEATURE                 Location/Qualifiers
REGION                  1..6
                        note = Synthetic
source                  1..6
                        mol_type = protein
                        organism = synthetic construct
SEQUENCE: 823
DPSNGY                                                              6

SEQ ID NO: 824          moltype = AA  length = 6
FEATURE                 Location/Qualifiers
REGION                  1..6
                        note = Synthetic
source                  1..6
                        mol_type = protein
                        organism = synthetic construct
SEQUENCE: 824
DPSNGY                                                              6

SEQ ID NO: 825          moltype = AA  length = 6
FEATURE                 Location/Qualifiers
REGION                  1..6
                        note = Synthetic
source                  1..6
                        mol_type = protein
                        organism = synthetic construct
SEQUENCE: 825
DPQNGW                                                              6

SEQ ID NO: 826          moltype = AA  length = 6
FEATURE                 Location/Qualifiers
REGION                  1..6
                        note = Synthetic
source                  1..6
                        mol_type = protein
                        organism = synthetic construct
SEQUENCE: 826
DPYSGS                                                              6

SEQ ID NO: 827          moltype = AA  length = 6
FEATURE                 Location/Qualifiers
REGION                  1..6
                        note = Synthetic
source                  1..6
                        mol_type = protein
                        organism = synthetic construct
SEQUENCE: 827
DPANGF                                                              6

SEQ ID NO: 828          moltype = AA  length = 6
FEATURE                 Location/Qualifiers
REGION                  1..6
                        note = Synthetic
source                  1..6
                        mol_type = protein
                        organism = synthetic construct
SEQUENCE: 828
DPSNGY                                                              6

SEQ ID NO: 829          moltype = AA  length = 6
FEATURE                 Location/Qualifiers
REGION                  1..6
                        note = Synthetic
source                  1..6
                        mol_type = protein
                        organism = synthetic construct
SEQUENCE: 829
DPYNGY                                                              6

SEQ ID NO: 830          moltype = AA  length = 6
FEATURE                 Location/Qualifiers
REGION                  1..6
                        note = Synthetic
source                  1..6
                        mol_type = protein
```

```
                         organism = synthetic construct
SEQUENCE: 830
DPYNGY                                                                     6

SEQ ID NO: 831           moltype = AA  length = 6
FEATURE                  Location/Qualifiers
REGION                   1..6
                         note = Synthetic
source                   1..6
                         mol_type = protein
                         organism = synthetic construct
SEQUENCE: 831
DPYNGY                                                                     6

SEQ ID NO: 832           moltype = AA  length = 6
FEATURE                  Location/Qualifiers
REGION                   1..6
                         note = Synthetic
source                   1..6
                         mol_type = protein
                         organism = synthetic construct
SEQUENCE: 832
DPANGY                                                                     6

SEQ ID NO: 833           moltype = AA  length = 6
FEATURE                  Location/Qualifiers
REGION                   1..6
                         note = Synthetic
source                   1..6
                         mol_type = protein
                         organism = synthetic construct
SEQUENCE: 833
DPSNGY                                                                     6

SEQ ID NO: 834           moltype = AA  length = 6
FEATURE                  Location/Qualifiers
REGION                   1..6
                         note = Synthetic
source                   1..6
                         mol_type = protein
                         organism = synthetic construct
SEQUENCE: 834
DPYNGY                                                                     6

SEQ ID NO: 835           moltype = AA  length = 6
FEATURE                  Location/Qualifiers
REGION                   1..6
                         note = Synthetic
source                   1..6
                         mol_type = protein
                         organism = synthetic construct
SEQUENCE: 835
DPSNGY                                                                     6

SEQ ID NO: 836           moltype = AA  length = 6
FEATURE                  Location/Qualifiers
REGION                   1..6
                         note = Synthetic
source                   1..6
                         mol_type = protein
                         organism = synthetic construct
SEQUENCE: 836
DPYNGY                                                                     6

SEQ ID NO: 837           moltype = AA  length = 6
FEATURE                  Location/Qualifiers
REGION                   1..6
                         note = Synthetic
source                   1..6
                         mol_type = protein
                         organism = synthetic construct
SEQUENCE: 837
DPYNGF                                                                     6

SEQ ID NO: 838           moltype = AA  length = 6
FEATURE                  Location/Qualifiers
REGION                   1..6
                         note = Synthetic
source                   1..6
```

```
                        mol_type = protein
                        organism = synthetic construct
SEQUENCE: 838
DPSNGY                                                              6

SEQ ID NO: 839          moltype = AA  length = 6
FEATURE                 Location/Qualifiers
REGION                  1..6
                        note = Synthetic
source                  1..6
                        mol_type = protein
                        organism = synthetic construct
SEQUENCE: 839
DPSNGY                                                              6

SEQ ID NO: 840          moltype = AA  length = 6
FEATURE                 Location/Qualifiers
REGION                  1..6
                        note = Synthetic
source                  1..6
                        mol_type = protein
                        organism = synthetic construct
SEQUENCE: 840
DPSNGY                                                              6

SEQ ID NO: 841          moltype = AA  length = 6
FEATURE                 Location/Qualifiers
REGION                  1..6
                        note = Synthetic
source                  1..6
                        mol_type = protein
                        organism = synthetic construct
SEQUENCE: 841
DPSNGY                                                              6

SEQ ID NO: 842          moltype = AA  length = 6
FEATURE                 Location/Qualifiers
REGION                  1..6
                        note = Synthetic
source                  1..6
                        mol_type = protein
                        organism = synthetic construct
SEQUENCE: 842
DPSNGY                                                              6

SEQ ID NO: 843          moltype = AA  length = 6
FEATURE                 Location/Qualifiers
REGION                  1..6
                        note = Synthetic
source                  1..6
                        mol_type = protein
                        organism = synthetic construct
SEQUENCE: 843
DPSNGY                                                              6

SEQ ID NO: 844          moltype = AA  length = 6
FEATURE                 Location/Qualifiers
REGION                  1..6
                        note = Synthetic
source                  1..6
                        mol_type = protein
                        organism = synthetic construct
SEQUENCE: 844
DPSNGY                                                              6

SEQ ID NO: 845          moltype = AA  length = 6
FEATURE                 Location/Qualifiers
REGION                  1..6
                        note = Synthetic
source                  1..6
                        mol_type = protein
                        organism = synthetic construct
SEQUENCE: 845
DPSNGY                                                              6

SEQ ID NO: 846          moltype = AA  length = 6
FEATURE                 Location/Qualifiers
REGION                  1..6
                        note = Synthetic
```

```
source                  1..6
                        mol_type = protein
                        organism = synthetic construct
SEQUENCE: 846
DPSNGY                                                                  6

SEQ ID NO: 847          moltype = AA  length = 6
FEATURE                 Location/Qualifiers
REGION                  1..6
                        note = Synthetic
source                  1..6
                        mol_type = protein
                        organism = synthetic construct
SEQUENCE: 847
DPSNGY                                                                  6

SEQ ID NO: 848          moltype = AA  length = 6
FEATURE                 Location/Qualifiers
REGION                  1..6
                        note = Synthetic
source                  1..6
                        mol_type = protein
                        organism = synthetic construct
SEQUENCE: 848
DPSNGY                                                                  6

SEQ ID NO: 849          moltype = AA  length = 6
FEATURE                 Location/Qualifiers
REGION                  1..6
                        note = Synthetic
source                  1..6
                        mol_type = protein
                        organism = synthetic construct
SEQUENCE: 849
DPSNGY                                                                  6

SEQ ID NO: 850          moltype = AA  length = 6
FEATURE                 Location/Qualifiers
REGION                  1..6
                        note = Synthetic
source                  1..6
                        mol_type = protein
                        organism = synthetic construct
SEQUENCE: 850
DPSNGY                                                                  6

SEQ ID NO: 851          moltype = AA  length = 6
FEATURE                 Location/Qualifiers
REGION                  1..6
                        note = Synthetic
source                  1..6
                        mol_type = protein
                        organism = synthetic construct
SEQUENCE: 851
DPSNGY                                                                  6

SEQ ID NO: 852          moltype = AA  length = 6
FEATURE                 Location/Qualifiers
REGION                  1..6
                        note = Synthetic
source                  1..6
                        mol_type = protein
                        organism = synthetic construct
SEQUENCE: 852
DPSNGY                                                                  6

SEQ ID NO: 853          moltype = AA  length = 6
FEATURE                 Location/Qualifiers
REGION                  1..6
                        note = Synthetic
source                  1..6
                        mol_type = protein
                        organism = synthetic construct
SEQUENCE: 853
DPSNGY                                                                  6

SEQ ID NO: 854          moltype = AA  length = 6
FEATURE                 Location/Qualifiers
REGION                  1..6
```

```
                        note = Synthetic
source                  1..6
                        mol_type = protein
                        organism = synthetic construct
SEQUENCE: 854
DPSNGY                                                              6

SEQ ID NO: 855          moltype = AA  length = 6
FEATURE                 Location/Qualifiers
REGION                  1..6
                        note = Synthetic
source                  1..6
                        mol_type = protein
                        organism = synthetic construct
SEQUENCE: 855
DPSNGY                                                              6

SEQ ID NO: 856          moltype = AA  length = 6
FEATURE                 Location/Qualifiers
REGION                  1..6
                        note = Synthetic
source                  1..6
                        mol_type = protein
                        organism = synthetic construct
SEQUENCE: 856
DPSNGY                                                              6

SEQ ID NO: 857          moltype = AA  length = 6
FEATURE                 Location/Qualifiers
REGION                  1..6
                        note = Synthetic
source                  1..6
                        mol_type = protein
                        organism = synthetic construct
SEQUENCE: 857
DPSNGY                                                              6

SEQ ID NO: 858          moltype = AA  length = 6
FEATURE                 Location/Qualifiers
REGION                  1..6
                        note = Synthetic
source                  1..6
                        mol_type = protein
                        organism = synthetic construct
SEQUENCE: 858
DPSNGY                                                              6

SEQ ID NO: 859          moltype = AA  length = 6
FEATURE                 Location/Qualifiers
REGION                  1..6
                        note = Synthetic
source                  1..6
                        mol_type = protein
                        organism = synthetic construct
SEQUENCE: 859
DPSNGY                                                              6

SEQ ID NO: 860          moltype = AA  length = 6
FEATURE                 Location/Qualifiers
REGION                  1..6
                        note = Synthetic
source                  1..6
                        mol_type = protein
                        organism = synthetic construct
SEQUENCE: 860
DPSNGY                                                              6

SEQ ID NO: 861          moltype = AA  length = 6
FEATURE                 Location/Qualifiers
REGION                  1..6
                        note = Synthetic
source                  1..6
                        mol_type = protein
                        organism = synthetic construct
SEQUENCE: 861
DPSNGY                                                              6

SEQ ID NO: 862          moltype = AA  length = 6
FEATURE                 Location/Qualifiers
```

```
REGION                  1..6
                        note = Synthetic
source                  1..6
                        mol_type = protein
                        organism = synthetic construct
SEQUENCE: 862
DPSNGY                                                                6

SEQ ID NO: 863          moltype = AA  length = 6
FEATURE                 Location/Qualifiers
REGION                  1..6
                        note = Synthetic
source                  1..6
                        mol_type = protein
                        organism = synthetic construct
SEQUENCE: 863
DPSNGY                                                                6

SEQ ID NO: 864          moltype = AA  length = 6
FEATURE                 Location/Qualifiers
REGION                  1..6
                        note = Synthetic
source                  1..6
                        mol_type = protein
                        organism = synthetic construct
SEQUENCE: 864
DPSNGY                                                                6

SEQ ID NO: 865          moltype = AA  length = 6
FEATURE                 Location/Qualifiers
REGION                  1..6
                        note = Synthetic
source                  1..6
                        mol_type = protein
                        organism = synthetic construct
SEQUENCE: 865
DPSNGF                                                                6

SEQ ID NO: 866          moltype = AA  length = 6
FEATURE                 Location/Qualifiers
REGION                  1..6
                        note = Synthetic
source                  1..6
                        mol_type = protein
                        organism = synthetic construct
SEQUENCE: 866
DPSNGY                                                                6

SEQ ID NO: 867          moltype =   length =
SEQUENCE: 867
000

SEQ ID NO: 868          moltype = AA  length = 6
FEATURE                 Location/Qualifiers
REGION                  1..6
                        note = Synthetic
source                  1..6
                        mol_type = protein
                        organism = synthetic construct
SEQUENCE: 868
IGSNGR                                                                6

SEQ ID NO: 869          moltype =   length =
SEQUENCE: 869
000

SEQ ID NO: 870          moltype =   length =
SEQUENCE: 870
000

SEQ ID NO: 871          moltype =   length =
SEQUENCE: 871
000

SEQ ID NO: 872          moltype =   length =
SEQUENCE: 872
000

SEQ ID NO: 873          moltype =   length =
```

-continued

```
SEQUENCE: 873
000

SEQ ID NO: 874          moltype = AA  length = 5
FEATURE                 Location/Qualifiers
REGION                  1..5
                        note = Synthetic
source                  1..5
                        mol_type = protein
                        organism = synthetic construct
SEQUENCE: 874
DSSGR                                                                5

SEQ ID NO: 875          moltype =   length =
SEQUENCE: 875
000

SEQ ID NO: 876          moltype =   length =
SEQUENCE: 876
000

SEQ ID NO: 877          moltype =   length =
SEQUENCE: 877
000

SEQ ID NO: 878          moltype =   length =
SEQUENCE: 878
000

SEQ ID NO: 879          moltype = AA  length = 5
FEATURE                 Location/Qualifiers
REGION                  1..5
                        note = Synthetic
source                  1..5
                        mol_type = protein
                        organism = synthetic construct
SEQUENCE: 879
DSSGR                                                                5

SEQ ID NO: 880          moltype =   length =
SEQUENCE: 880
000

SEQ ID NO: 881          moltype =   length =
SEQUENCE: 881
000

SEQ ID NO: 882          moltype =   length =
SEQUENCE: 882
000

SEQ ID NO: 883          moltype =   length =
SEQUENCE: 883
000

SEQ ID NO: 884          moltype =   length =
SEQUENCE: 884
000

SEQ ID NO: 885          moltype = AA  length = 6
FEATURE                 Location/Qualifiers
REGION                  1..6
                        note = Synthetic
source                  1..6
                        mol_type = protein
                        organism = synthetic construct
SEQUENCE: 885
IGSNGR                                                               6

SEQ ID NO: 886          moltype =   length =
SEQUENCE: 886
000

SEQ ID NO: 887          moltype = AA  length = 6
FEATURE                 Location/Qualifiers
REGION                  1..6
                        note = Synthetic
source                  1..6
                        mol_type = protein
```

-continued

```
                        organism = synthetic construct
SEQUENCE: 887
IGSNGR                                                                   6

SEQ ID NO: 888          moltype = AA  length = 6
FEATURE                 Location/Qualifiers
REGION                  1..6
                        note = Synthetic
source                  1..6
                        mol_type = protein
                        organism = synthetic construct
SEQUENCE: 888
IGSNGR                                                                   6

SEQ ID NO: 889          moltype =   length =
SEQUENCE: 889
000

SEQ ID NO: 890          moltype =   length =
SEQUENCE: 890
000

SEQ ID NO: 891          moltype =   length =
SEQUENCE: 891
000

SEQ ID NO: 892          moltype =   length =
SEQUENCE: 892
000

SEQ ID NO: 893          moltype =   length =
SEQUENCE: 893
000

SEQ ID NO: 894          moltype =   length =
SEQUENCE: 894
000

SEQ ID NO: 895          moltype =   length =
SEQUENCE: 895
000

SEQ ID NO: 896          moltype =   length =
SEQUENCE: 896
000

SEQ ID NO: 897          moltype =   length =
SEQUENCE: 897
000

SEQ ID NO: 898          moltype =   length =
SEQUENCE: 898
000

SEQ ID NO: 899          moltype =   length =
SEQUENCE: 899
000

SEQ ID NO: 900          moltype =   length =
SEQUENCE: 900
000

SEQ ID NO: 901          moltype =   length =
SEQUENCE: 901
000

SEQ ID NO: 902          moltype =   length =
SEQUENCE: 902
000

SEQ ID NO: 903          moltype =   length =
SEQUENCE: 903
000

SEQ ID NO: 904          moltype =   length =
SEQUENCE: 904
000

SEQ ID NO: 905          moltype =   length =
```

SEQUENCE: 905
000

SEQ ID NO: 906 moltype = length =
SEQUENCE: 906
000

SEQ ID NO: 907 moltype = length =
SEQUENCE: 907
000

SEQ ID NO: 908 moltype = length =
SEQUENCE: 908
000

SEQ ID NO: 909 moltype = length =
SEQUENCE: 909
000

SEQ ID NO: 910 moltype = length =
SEQUENCE: 910
000

SEQ ID NO: 911 moltype = length =
SEQUENCE: 911
000

SEQ ID NO: 912 moltype = length =
SEQUENCE: 912
000

SEQ ID NO: 913 moltype = length =
SEQUENCE: 913
000

SEQ ID NO: 914 moltype = length =
SEQUENCE: 914
000

SEQ ID NO: 915 moltype = length =
SEQUENCE: 915
000

SEQ ID NO: 916 moltype = length =
SEQUENCE: 916
000

SEQ ID NO: 917 moltype = length =
SEQUENCE: 917
000

SEQ ID NO: 918 moltype = length =
SEQUENCE: 918
000

SEQ ID NO: 919 moltype = length =
SEQUENCE: 919
000

SEQ ID NO: 920 moltype = length =
SEQUENCE: 920
000

SEQ ID NO: 921 moltype = length =
SEQUENCE: 921
000

SEQ ID NO: 922 moltype = length =
SEQUENCE: 922
000

SEQ ID NO: 923 moltype = length =
SEQUENCE: 923
000

SEQ ID NO: 924 moltype = length =
SEQUENCE: 924
000

SEQ ID NO: 925 moltype = length =
SEQUENCE: 925
000

SEQ ID NO: 926 moltype = length =
SEQUENCE: 926
000

SEQ ID NO: 927 moltype = length =
SEQUENCE: 927
000

SEQ ID NO: 928 moltype = length =
SEQUENCE: 928
000

SEQ ID NO: 929 moltype = length =
SEQUENCE: 929
000

SEQ ID NO: 930 moltype = length =
SEQUENCE: 930
000

SEQ ID NO: 931 moltype = length =
SEQUENCE: 931
000

SEQ ID NO: 932 moltype = length =
SEQUENCE: 932
000

SEQ ID NO: 933 moltype = length =
SEQUENCE: 933
000

SEQ ID NO: 934 moltype = length =
SEQUENCE: 934
000

SEQ ID NO: 935 moltype = length =
SEQUENCE: 935
000

SEQ ID NO: 936 moltype = length =
SEQUENCE: 936
000

SEQ ID NO: 937 moltype = length =
SEQUENCE: 937
000

SEQ ID NO: 938 moltype = length =
SEQUENCE: 938
000

SEQ ID NO: 939 moltype = length =
SEQUENCE: 939
000

SEQ ID NO: 940 moltype = length =
SEQUENCE: 940
000

SEQ ID NO: 941 moltype = length =
SEQUENCE: 941
000

SEQ ID NO: 942 moltype = length =
SEQUENCE: 942
000

SEQ ID NO: 943 moltype = length =
SEQUENCE: 943
000

SEQ ID NO: 944 moltype = length =
SEQUENCE: 944
000

SEQ ID NO: 945 moltype = length =
SEQUENCE: 945
000

SEQ ID NO: 946 moltype = length =
SEQUENCE: 946
000

SEQ ID NO: 947 moltype = length =
SEQUENCE: 947
000

SEQ ID NO: 948 moltype = length =
SEQUENCE: 948
000

SEQ ID NO: 949 moltype = length =
SEQUENCE: 949
000

SEQ ID NO: 950 moltype = length =
SEQUENCE: 950
000

SEQ ID NO: 951 moltype = length =
SEQUENCE: 951
000

SEQ ID NO: 952 moltype = length =
SEQUENCE: 952
000

SEQ ID NO: 953 moltype = length =
SEQUENCE: 953
000

SEQ ID NO: 954 moltype = length =
SEQUENCE: 954
000

SEQ ID NO: 955 moltype = length =
SEQUENCE: 955
000

SEQ ID NO: 956 moltype = length =
SEQUENCE: 956
000

SEQ ID NO: 957 moltype = length =
SEQUENCE: 957
000

SEQ ID NO: 958 moltype = length =
SEQUENCE: 958
000

SEQ ID NO: 959 moltype = length =
SEQUENCE: 959
000

SEQ ID NO: 960 moltype = length =
SEQUENCE: 960
000

SEQ ID NO: 961 moltype = length =
SEQUENCE: 961
000

SEQ ID NO: 962 moltype = length =
SEQUENCE: 962
000

SEQ ID NO: 963 moltype = length =
SEQUENCE: 963
000

SEQ ID NO: 964 moltype = length =
SEQUENCE: 964

000

SEQ ID NO: 965 moltype = length =
SEQUENCE: 965
000

SEQ ID NO: 966 moltype = length =
SEQUENCE: 966
000

SEQ ID NO: 967 moltype = length =
SEQUENCE: 967
000

SEQ ID NO: 968 moltype = length =
SEQUENCE: 968
000

SEQ ID NO: 969 moltype = length =
SEQUENCE: 969
000

SEQ ID NO: 970 moltype = length =
SEQUENCE: 970
000

SEQ ID NO: 971 moltype = length =
SEQUENCE: 971
000

SEQ ID NO: 972 moltype = length =
SEQUENCE: 972
000

SEQ ID NO: 973 moltype = length =
SEQUENCE: 973
000

SEQ ID NO: 974 moltype = length =
SEQUENCE: 974
000

SEQ ID NO: 975 moltype = length =
SEQUENCE: 975
000

SEQ ID NO: 976 moltype = length =
SEQUENCE: 976
000

SEQ ID NO: 977 moltype = length =
SEQUENCE: 977
000

SEQ ID NO: 978 moltype = length =
SEQUENCE: 978
000

SEQ ID NO: 979 moltype = length =
SEQUENCE: 979
000

SEQ ID NO: 980 moltype = length =
SEQUENCE: 980
000

SEQ ID NO: 981 moltype = length =
SEQUENCE: 981
000

SEQ ID NO: 982 moltype = length =
SEQUENCE: 982
000

SEQ ID NO: 983 moltype = length =
SEQUENCE: 983
000

SEQ ID NO: 984 moltype = length =

```
SEQUENCE: 984
000

SEQ ID NO: 985        moltype =   length =
SEQUENCE: 985
000

SEQ ID NO: 986        moltype =   length =
SEQUENCE: 986
000

SEQ ID NO: 987        moltype =   length =
SEQUENCE: 987
000

SEQ ID NO: 988        moltype =   length =
SEQUENCE: 988
000

SEQ ID NO: 989        moltype =   length =
SEQUENCE: 989
000

SEQ ID NO: 990        moltype =   length =
SEQUENCE: 990
000

SEQ ID NO: 991        moltype =   length =
SEQUENCE: 991
000

SEQ ID NO: 992        moltype =   length =
SEQUENCE: 992
000

SEQ ID NO: 993        moltype =   length =
SEQUENCE: 993
000

SEQ ID NO: 994        moltype =   length =
SEQUENCE: 994
000

SEQ ID NO: 995        moltype =   length =
SEQUENCE: 995
000

SEQ ID NO: 996        moltype =   length =
SEQUENCE: 996
000

SEQ ID NO: 997        moltype =   length =
SEQUENCE: 997
000

SEQ ID NO: 998        moltype =   length =
SEQUENCE: 998
000

SEQ ID NO: 999        moltype =   length =
SEQUENCE: 999
000

SEQ ID NO: 1000       moltype =   length =
SEQUENCE: 1000
000

SEQ ID NO: 1001       moltype =   length =
SEQUENCE: 1001
000

SEQ ID NO: 1002       moltype =   length =
SEQUENCE: 1002
000

SEQ ID NO: 1003       moltype =   length =
SEQUENCE: 1003
000
```

-continued

SEQ ID NO: 1004 moltype = length =
SEQUENCE: 1004
000

SEQ ID NO: 1005 moltype = length =
SEQUENCE: 1005
000

SEQ ID NO: 1006 moltype = length =
SEQUENCE: 1006
000

SEQ ID NO: 1007 moltype = length =
SEQUENCE: 1007
000

SEQ ID NO: 1008 moltype = length =
SEQUENCE: 1008
000

SEQ ID NO: 1009 moltype = length =
SEQUENCE: 1009
000

SEQ ID NO: 1010 moltype = length =
SEQUENCE: 1010
000

SEQ ID NO: 1011 moltype = length =
SEQUENCE: 1011
000

SEQ ID NO: 1012 moltype = length =
SEQUENCE: 1012
000

SEQ ID NO: 1013 moltype = length =
SEQUENCE: 1013
000

SEQ ID NO: 1014 moltype = length =
SEQUENCE: 1014
000

SEQ ID NO: 1015 moltype = length =
SEQUENCE: 1015
000

SEQ ID NO: 1016 moltype = length =
SEQUENCE: 1016
000

SEQ ID NO: 1017 moltype = length =
SEQUENCE: 1017
000

SEQ ID NO: 1018 moltype = length =
SEQUENCE: 1018
000

SEQ ID NO: 1019 moltype = length =
SEQUENCE: 1019
000

SEQ ID NO: 1020 moltype = length =
SEQUENCE: 1020
000

SEQ ID NO: 1021 moltype = length =
SEQUENCE: 1021
000

SEQ ID NO: 1022 moltype = length =
SEQUENCE: 1022
000

SEQ ID NO: 1023 moltype = length =
SEQUENCE: 1023
000

-continued

SEQ ID NO: 1024 moltype = length =
SEQUENCE: 1024
000

SEQ ID NO: 1025 moltype = length =
SEQUENCE: 1025
000

SEQ ID NO: 1026 moltype = length =
SEQUENCE: 1026
000

SEQ ID NO: 1027 moltype = length =
SEQUENCE: 1027
000

SEQ ID NO: 1028 moltype = length =
SEQUENCE: 1028
000

SEQ ID NO: 1029 moltype = length =
SEQUENCE: 1029
000

SEQ ID NO: 1030 moltype = length =
SEQUENCE: 1030
000

SEQ ID NO: 1031 moltype = length =
SEQUENCE: 1031
000

SEQ ID NO: 1032 moltype = length =
SEQUENCE: 1032
000

SEQ ID NO: 1033 moltype = length =
SEQUENCE: 1033
000

SEQ ID NO: 1034 moltype = length =
SEQUENCE: 1034
000

SEQ ID NO: 1035 moltype = length =
SEQUENCE: 1035
000

SEQ ID NO: 1036 moltype = length =
SEQUENCE: 1036
000

SEQ ID NO: 1037 moltype = length =
SEQUENCE: 1037
000

SEQ ID NO: 1038 moltype = length =
SEQUENCE: 1038
000

SEQ ID NO: 1039 moltype = length =
SEQUENCE: 1039
000

SEQ ID NO: 1040 moltype = length =
SEQUENCE: 1040
000

SEQ ID NO: 1041 moltype = length =
SEQUENCE: 1041
000

SEQ ID NO: 1042 moltype = length =
SEQUENCE: 1042
000

SEQ ID NO: 1043 moltype = length =
SEQUENCE: 1043

-continued

000

SEQ ID NO: 1044 moltype = length =
SEQUENCE: 1044
000

SEQ ID NO: 1045 moltype = length =
SEQUENCE: 1045
000

SEQ ID NO: 1046 moltype = length =
SEQUENCE: 1046
000

SEQ ID NO: 1047 moltype = length =
SEQUENCE: 1047
000

SEQ ID NO: 1048 moltype = length =
SEQUENCE: 1048
000

SEQ ID NO: 1049 moltype = length =
SEQUENCE: 1049
000

SEQ ID NO: 1050 moltype = length =
SEQUENCE: 1050
000

SEQ ID NO: 1051 moltype = length =
SEQUENCE: 1051
000

SEQ ID NO: 1052 moltype = length =
SEQUENCE: 1052
000

SEQ ID NO: 1053 moltype = length =
SEQUENCE: 1053
000

SEQ ID NO: 1054 moltype = length =
SEQUENCE: 1054
000

SEQ ID NO: 1055 moltype = length =
SEQUENCE: 1055
000

SEQ ID NO: 1056 moltype = length =
SEQUENCE: 1056
000

SEQ ID NO: 1057 moltype = length =
SEQUENCE: 1057
000

SEQ ID NO: 1058 moltype = length =
SEQUENCE: 1058
000

SEQ ID NO: 1059 moltype = length =
SEQUENCE: 1059
000

SEQ ID NO: 1060 moltype = length =
SEQUENCE: 1060
000

SEQ ID NO: 1061 moltype = length =
SEQUENCE: 1061
000

SEQ ID NO: 1062 moltype = length =
SEQUENCE: 1062
000

SEQ ID NO: 1063 moltype = length =

SEQUENCE: 1063
000

SEQ ID NO: 1064 moltype = length =
SEQUENCE: 1064
000

SEQ ID NO: 1065 moltype = length =
SEQUENCE: 1065
000

SEQ ID NO: 1066 moltype = length =
SEQUENCE: 1066
000

SEQ ID NO: 1067 moltype = length =
SEQUENCE: 1067
000

SEQ ID NO: 1068 moltype = length =
SEQUENCE: 1068
000

SEQ ID NO: 1069 moltype = length =
SEQUENCE: 1069
000

SEQ ID NO: 1070 moltype = length =
SEQUENCE: 1070
000

SEQ ID NO: 1071 moltype = length =
SEQUENCE: 1071
000

SEQ ID NO: 1072 moltype = length =
SEQUENCE: 1072
000

SEQ ID NO: 1073 moltype = length =
SEQUENCE: 1073
000

SEQ ID NO: 1074 moltype = length =
SEQUENCE: 1074
000

SEQ ID NO: 1075 moltype = length =
SEQUENCE: 1075
000

SEQ ID NO: 1076 moltype = length =
SEQUENCE: 1076
000

SEQ ID NO: 1077 moltype = length =
SEQUENCE: 1077
000

SEQ ID NO: 1078 moltype = length =
SEQUENCE: 1078
000

SEQ ID NO: 1079 moltype = length =
SEQUENCE: 1079
000

SEQ ID NO: 1080 moltype = AA length = 17
FEATURE Location/Qualifiers
REGION 1..17
note = Synthetic
source 1..17
mol_type = protein
organism = synthetic construct
SEQUENCE: 1080
YIDPYSGSTY YADSVKG 17

SEQ ID NO: 1081 moltype = length =
SEQUENCE: 1081

```
000

SEQ ID NO: 1082        moltype =   length =
SEQUENCE: 1082
000

SEQ ID NO: 1083        moltype =   length =
SEQUENCE: 1083
000

SEQ ID NO: 1084        moltype =   length =
SEQUENCE: 1084
000

SEQ ID NO: 1085        moltype =   length =
SEQUENCE: 1085
000

SEQ ID NO: 1086        moltype =   length =
SEQUENCE: 1086
000

SEQ ID NO: 1087        moltype =   length =
SEQUENCE: 1087
000

SEQ ID NO: 1088        moltype =   length =
SEQUENCE: 1088
000

SEQ ID NO: 1089        moltype = AA  length = 17
FEATURE                Location/Qualifiers
REGION                 1..17
                       note = Synthetic
source                 1..17
                       mol_type = protein
                       organism = synthetic construct
SEQUENCE: 1089
FIDPYNGYTN YADSVKG                                            17

SEQ ID NO: 1090        moltype =   length =
SEQUENCE: 1090
000

SEQ ID NO: 1091        moltype =   length =
SEQUENCE: 1091
000

SEQ ID NO: 1092        moltype = AA  length = 17
FEATURE                Location/Qualifiers
REGION                 1..17
                       note = Synthetic
source                 1..17
                       mol_type = protein
                       organism = synthetic construct
SEQUENCE: 1092
YIDPSNGYTY YADSVKG                                            17

SEQ ID NO: 1093        moltype =   length =
SEQUENCE: 1093
000

SEQ ID NO: 1094        moltype =   length =
SEQUENCE: 1094
000

SEQ ID NO: 1095        moltype =   length =
SEQUENCE: 1095
000

SEQ ID NO: 1096        moltype =   length =
SEQUENCE: 1096
000

SEQ ID NO: 1097        moltype =   length =
SEQUENCE: 1097
000

SEQ ID NO: 1098        moltype =   length =
```

```
SEQUENCE: 1098
000

SEQ ID NO: 1099        moltype =   length =
SEQUENCE: 1099
000

SEQ ID NO: 1100        moltype =   length =
SEQUENCE: 1100
000

SEQ ID NO: 1101        moltype =   length =
SEQUENCE: 1101
000

SEQ ID NO: 1102        moltype =   length =
SEQUENCE: 1102
000

SEQ ID NO: 1103        moltype =   length =
SEQUENCE: 1103
000

SEQ ID NO: 1104        moltype = AA  length = 17
FEATURE                Location/Qualifiers
REGION                 1..17
                       note = Synthetic
source                 1..17
                       mol_type = protein
                       organism = synthetic construct
SEQUENCE: 1104
YIDPYNGATY YADSVKG                                              17

SEQ ID NO: 1105        moltype = AA  length = 17
FEATURE                Location/Qualifiers
REGION                 1..17
                       note = Synthetic
source                 1..17
                       mol_type = protein
                       organism = synthetic construct
SEQUENCE: 1105
YIDPSNGYTY YADSVKG                                              17

SEQ ID NO: 1106        moltype = AA  length = 17
FEATURE                Location/Qualifiers
REGION                 1..17
                       note = Synthetic
source                 1..17
                       mol_type = protein
                       organism = synthetic construct
SEQUENCE: 1106
YIDPANGATY YADSVKG                                              17

SEQ ID NO: 1107        moltype = AA  length = 17
FEATURE                Location/Qualifiers
REGION                 1..17
                       note = Synthetic
source                 1..17
                       mol_type = protein
                       organism = synthetic construct
SEQUENCE: 1107
YIDPYNGATY YADSVKG                                              17

SEQ ID NO: 1108        moltype = AA  length = 17
FEATURE                Location/Qualifiers
REGION                 1..17
                       note = Synthetic
source                 1..17
                       mol_type = protein
                       organism = synthetic construct
SEQUENCE: 1108
FIDPYNGYTN YADPVKS                                              17

SEQ ID NO: 1109        moltype = AA  length = 17
FEATURE                Location/Qualifiers
REGION                 1..17
                       note = Synthetic
source                 1..17
                       mol_type = protein
```

```
                        organism = synthetic construct
SEQUENCE: 1109
YIDPFNGATY YADSVKG                                                 17

SEQ ID NO: 1110         moltype = AA  length = 17
FEATURE                 Location/Qualifiers
REGION                  1..17
                        note = Synthetic
source                  1..17
                        mol_type = protein
                        organism = synthetic construct
SEQUENCE: 1110
YIDPYNGATY YADSVKG                                                 17

SEQ ID NO: 1111         moltype = AA  length = 17
FEATURE                 Location/Qualifiers
REGION                  1..17
                        note = Synthetic
source                  1..17
                        mol_type = protein
                        organism = synthetic construct
SEQUENCE: 1111
YIDPYNGATY YADSVKG                                                 17

SEQ ID NO: 1112         moltype = AA  length = 17
FEATURE                 Location/Qualifiers
REGION                  1..17
                        note = Synthetic
source                  1..17
                        mol_type = protein
                        organism = synthetic construct
SEQUENCE: 1112
YIDPYNGATY YADSVKG                                                 17

SEQ ID NO: 1113         moltype = AA  length = 17
FEATURE                 Location/Qualifiers
REGION                  1..17
                        note = Synthetic
source                  1..17
                        mol_type = protein
                        organism = synthetic construct
SEQUENCE: 1113
YIDPYNGATY YADSVKG                                                 17

SEQ ID NO: 1114         moltype = AA  length = 17
FEATURE                 Location/Qualifiers
REGION                  1..17
                        note = Synthetic
source                  1..17
                        mol_type = protein
                        organism = synthetic construct
SEQUENCE: 1114
YIDPSNGYTY YADSVKG                                                 17

SEQ ID NO: 1115         moltype = AA  length = 17
FEATURE                 Location/Qualifiers
REGION                  1..17
                        note = Synthetic
source                  1..17
                        mol_type = protein
                        organism = synthetic construct
SEQUENCE: 1115
YIDPYNGATY YADSVKG                                                 17

SEQ ID NO: 1116         moltype = AA  length = 17
FEATURE                 Location/Qualifiers
REGION                  1..17
                        note = Synthetic
source                  1..17
                        mol_type = protein
                        organism = synthetic construct
SEQUENCE: 1116
YIDPYNGATY YADSVKG                                                 17

SEQ ID NO: 1117         moltype = AA  length = 17
FEATURE                 Location/Qualifiers
REGION                  1..17
                        note = Synthetic
source                  1..17
```

```
                        mol_type = protein
                        organism = synthetic construct
SEQUENCE: 1117
YIDPYNGATY YADSVKG                                                   17

SEQ ID NO: 1118         moltype = AA  length = 17
FEATURE                 Location/Qualifiers
REGION                  1..17
                        note = Synthetic
source                  1..17
                        mol_type = protein
                        organism = synthetic construct
SEQUENCE: 1118
FIDPYNGYTG YADSVRG                                                   17

SEQ ID NO: 1119         moltype = AA  length = 17
FEATURE                 Location/Qualifiers
REGION                  1..17
                        note = Synthetic
source                  1..17
                        mol_type = protein
                        organism = synthetic construct
SEQUENCE: 1119
YIDPYNGATY YADSVKG                                                   17

SEQ ID NO: 1120         moltype = AA  length = 17
FEATURE                 Location/Qualifiers
REGION                  1..17
                        note = Synthetic
source                  1..17
                        mol_type = protein
                        organism = synthetic construct
SEQUENCE: 1120
YIDPYNGATY YADSVKG                                                   17

SEQ ID NO: 1121         moltype = AA  length = 17
FEATURE                 Location/Qualifiers
REGION                  1..17
                        note = Synthetic
source                  1..17
                        mol_type = protein
                        organism = synthetic construct
SEQUENCE: 1121
FIDPYNGYTG YADSVKG                                                   17

SEQ ID NO: 1122         moltype = AA  length = 17
FEATURE                 Location/Qualifiers
REGION                  1..17
                        note = Synthetic
source                  1..17
                        mol_type = protein
                        organism = synthetic construct
SEQUENCE: 1122
YIDPYNGYTY YADSVKG                                                   17

SEQ ID NO: 1123         moltype = AA  length = 17
FEATURE                 Location/Qualifiers
REGION                  1..17
                        note = Synthetic
source                  1..17
                        mol_type = protein
                        organism = synthetic construct
SEQUENCE: 1123
FIDPYNGYTN YADSVKG                                                   17

SEQ ID NO: 1124         moltype = AA  length = 17
FEATURE                 Location/Qualifiers
REGION                  1..17
                        note = Synthetic
source                  1..17
                        mol_type = protein
                        organism = synthetic construct
SEQUENCE: 1124
YIDPYNGSTY YADSVKG                                                   17

SEQ ID NO: 1125         moltype = AA  length = 17
FEATURE                 Location/Qualifiers
REGION                  1..17
                        note = Synthetic
```

```
source                  1..17
                        mol_type = protein
                        organism = synthetic construct
SEQUENCE: 1125
YIDPSNGYTY YADSVKG                                                   17

SEQ ID NO: 1126         moltype = AA  length = 17
FEATURE                 Location/Qualifiers
REGION                  1..17
                        note = Synthetic
source                  1..17
                        mol_type = protein
                        organism = synthetic construct
SEQUENCE: 1126
YIDPSNGYTY YADSVKG                                                   17

SEQ ID NO: 1127         moltype = AA  length = 17
FEATURE                 Location/Qualifiers
REGION                  1..17
                        note = Synthetic
source                  1..17
                        mol_type = protein
                        organism = synthetic construct
SEQUENCE: 1127
YIDPYNGATY YADSVKG                                                   17

SEQ ID NO: 1128         moltype = AA  length = 17
FEATURE                 Location/Qualifiers
REGION                  1..17
                        note = Synthetic
source                  1..17
                        mol_type = protein
                        organism = synthetic construct
SEQUENCE: 1128
YIDPYNGATY YADSVKG                                                   17

SEQ ID NO: 1129         moltype = AA  length = 17
FEATURE                 Location/Qualifiers
REGION                  1..17
                        note = Synthetic
source                  1..17
                        mol_type = protein
                        organism = synthetic construct
SEQUENCE: 1129
YIDPYNGATY YADSVKG                                                   17

SEQ ID NO: 1130         moltype = AA  length = 17
FEATURE                 Location/Qualifiers
REGION                  1..17
                        note = Synthetic
source                  1..17
                        mol_type = protein
                        organism = synthetic construct
SEQUENCE: 1130
YIDPYNGATY YADSVKG                                                   17

SEQ ID NO: 1131         moltype = AA  length = 17
FEATURE                 Location/Qualifiers
REGION                  1..17
                        note = Synthetic
source                  1..17
                        mol_type = protein
                        organism = synthetic construct
SEQUENCE: 1131
YIDPYNGATF YADSVKG                                                   17

SEQ ID NO: 1132         moltype = AA  length = 17
FEATURE                 Location/Qualifiers
REGION                  1..17
                        note = Synthetic
source                  1..17
                        mol_type = protein
                        organism = synthetic construct
SEQUENCE: 1132
YIDPYNGATY YADSVKG                                                   17

SEQ ID NO: 1133         moltype = AA  length = 17
FEATURE                 Location/Qualifiers
REGION                  1..17
```

```
                        note = Synthetic
source                  1..17
                        mol_type = protein
                        organism = synthetic construct
SEQUENCE: 1133
YIDPYNGSTY HADSVKG                                                17

SEQ ID NO: 1134         moltype = AA  length = 17
FEATURE                 Location/Qualifiers
REGION                  1..17
                        note = Synthetic
source                  1..17
                        mol_type = protein
                        organism = synthetic construct
SEQUENCE: 1134
YIDPSNGYTY HADSVKG                                                17

SEQ ID NO: 1135         moltype = AA  length = 17
FEATURE                 Location/Qualifiers
REGION                  1..17
                        note = Synthetic
source                  1..17
                        mol_type = protein
                        organism = synthetic construct
SEQUENCE: 1135
YIDPYNGYTY YADSVNG                                                17

SEQ ID NO: 1136         moltype = AA  length = 17
FEATURE                 Location/Qualifiers
REGION                  1..17
                        note = Synthetic
source                  1..17
                        mol_type = protein
                        organism = synthetic construct
SEQUENCE: 1136
YIDPYNGYTY YADSVKG                                                17

SEQ ID NO: 1137         moltype = AA  length = 17
FEATURE                 Location/Qualifiers
REGION                  1..17
                        note = Synthetic
source                  1..17
                        mol_type = protein
                        organism = synthetic construct
SEQUENCE: 1137
YIDPANGFTY YADSVKG                                                17

SEQ ID NO: 1138         moltype = AA  length = 17
FEATURE                 Location/Qualifiers
REGION                  1..17
                        note = Synthetic
source                  1..17
                        mol_type = protein
                        organism = synthetic construct
SEQUENCE: 1138
YIDPYNGYTY YADSVKG                                                17

SEQ ID NO: 1139         moltype = AA  length = 17
FEATURE                 Location/Qualifiers
REGION                  1..17
                        note = Synthetic
source                  1..17
                        mol_type = protein
                        organism = synthetic construct
SEQUENCE: 1139
YIDPYNGYTY YADSVKG                                                17

SEQ ID NO: 1140         moltype = AA  length = 17
FEATURE                 Location/Qualifiers
REGION                  1..17
                        note = Synthetic
source                  1..17
                        mol_type = protein
                        organism = synthetic construct
SEQUENCE: 1140
FIDPYNGYTY HADSVEG                                                17

SEQ ID NO: 1141         moltype = AA  length = 17
FEATURE                 Location/Qualifiers
```

```
REGION                  1..17
                        note = Synthetic
source                  1..17
                        mol_type = protein
                        organism = synthetic construct
SEQUENCE: 1141
YIDPYNGYTY YADSVKG                                                   17

SEQ ID NO: 1142         moltype = AA  length = 17
FEATURE                 Location/Qualifiers
REGION                  1..17
                        note = Synthetic
source                  1..17
                        mol_type = protein
                        organism = synthetic construct
SEQUENCE: 1142
YIDPQNGWTY YADSVKG                                                   17

SEQ ID NO: 1143         moltype = AA  length = 17
FEATURE                 Location/Qualifiers
REGION                  1..17
                        note = Synthetic
source                  1..17
                        mol_type = protein
                        organism = synthetic construct
SEQUENCE: 1143
YIDPSNGYTY YADSVKG                                                   17

SEQ ID NO: 1144         moltype = AA  length = 17
FEATURE                 Location/Qualifiers
REGION                  1..17
                        note = Synthetic
source                  1..17
                        mol_type = protein
                        organism = synthetic construct
SEQUENCE: 1144
YIDPYNGYTY YADSVKG                                                   17

SEQ ID NO: 1145         moltype = AA  length = 17
FEATURE                 Location/Qualifiers
REGION                  1..17
                        note = Synthetic
source                  1..17
                        mol_type = protein
                        organism = synthetic construct
SEQUENCE: 1145
YIDPANGFTY YADSVKG                                                   17

SEQ ID NO: 1146         moltype = AA  length = 17
FEATURE                 Location/Qualifiers
REGION                  1..17
                        note = Synthetic
source                  1..17
                        mol_type = protein
                        organism = synthetic construct
SEQUENCE: 1146
FIDPKNGYTY YADSVKG                                                   17

SEQ ID NO: 1147         moltype = AA  length = 17
FEATURE                 Location/Qualifiers
REGION                  1..17
                        note = Synthetic
source                  1..17
                        mol_type = protein
                        organism = synthetic construct
SEQUENCE: 1147
YIDPYNGYTY YADSVKG                                                   17

SEQ ID NO: 1148         moltype = AA  length = 17
FEATURE                 Location/Qualifiers
REGION                  1..17
                        note = Synthetic
source                  1..17
                        mol_type = protein
                        organism = synthetic construct
SEQUENCE: 1148
YIDPSNGYTY YADSVKG                                                   17

SEQ ID NO: 1149         moltype = AA  length = 17
```

```
FEATURE                 Location/Qualifiers
REGION                  1..17
                        note = Synthetic
source                  1..17
                        mol_type = protein
                        organism = synthetic construct
SEQUENCE: 1149
YIDPSNGYTY YADPVKG                                                      17

SEQ ID NO: 1150         moltype = AA  length = 17
FEATURE                 Location/Qualifiers
REGION                  1..17
                        note = Synthetic
source                  1..17
                        mol_type = protein
                        organism = synthetic construct
SEQUENCE: 1150
YIDPQNGWTY YADSVKG                                                      17

SEQ ID NO: 1151         moltype = AA  length = 17
FEATURE                 Location/Qualifiers
REGION                  1..17
                        note = Synthetic
source                  1..17
                        mol_type = protein
                        organism = synthetic construct
SEQUENCE: 1151
YIDPYSGSTF YADSVKG                                                      17

SEQ ID NO: 1152         moltype = AA  length = 17
FEATURE                 Location/Qualifiers
REGION                  1..17
                        note = Synthetic
source                  1..17
                        mol_type = protein
                        organism = synthetic construct
SEQUENCE: 1152
YIDPANGFTY YADSVKG                                                      17

SEQ ID NO: 1153         moltype = AA  length = 17
FEATURE                 Location/Qualifiers
REGION                  1..17
                        note = Synthetic
source                  1..17
                        mol_type = protein
                        organism = synthetic construct
SEQUENCE: 1153
YIDPSNGYTY HADSVKG                                                      17

SEQ ID NO: 1154         moltype = AA  length = 17
FEATURE                 Location/Qualifiers
REGION                  1..17
                        note = Synthetic
source                  1..17
                        mol_type = protein
                        organism = synthetic construct
SEQUENCE: 1154
YIDPYNGYTY YADSVKG                                                      17

SEQ ID NO: 1155         moltype = AA  length = 17
FEATURE                 Location/Qualifiers
REGION                  1..17
                        note = Synthetic
source                  1..17
                        mol_type = protein
                        organism = synthetic construct
SEQUENCE: 1155
YIDPYNGYTY YADSVKG                                                      17

SEQ ID NO: 1156         moltype = AA  length = 17
FEATURE                 Location/Qualifiers
REGION                  1..17
                        note = Synthetic
source                  1..17
                        mol_type = protein
                        organism = synthetic construct
SEQUENCE: 1156
YIDPYNGYTY YADSVKG                                                      17
```

-continued

```
SEQ ID NO: 1157         moltype = AA  length = 17
FEATURE                 Location/Qualifiers
REGION                  1..17
                        note = Synthetic
source                  1..17
                        mol_type = protein
                        organism = synthetic construct
SEQUENCE: 1157
YIDPANGYTY YADSVKG                                                 17

SEQ ID NO: 1158         moltype = AA  length = 17
FEATURE                 Location/Qualifiers
REGION                  1..17
                        note = Synthetic
source                  1..17
                        mol_type = protein
                        organism = synthetic construct
SEQUENCE: 1158
YIDPSNGYTY YADSVKG                                                 17

SEQ ID NO: 1159         moltype = AA  length = 17
FEATURE                 Location/Qualifiers
REGION                  1..17
                        note = Synthetic
source                  1..17
                        mol_type = protein
                        organism = synthetic construct
SEQUENCE: 1159
YIDPYNGYTY YADSVRG                                                 17

SEQ ID NO: 1160         moltype = AA  length = 17
FEATURE                 Location/Qualifiers
REGION                  1..17
                        note = Synthetic
source                  1..17
                        mol_type = protein
                        organism = synthetic construct
SEQUENCE: 1160
YIDPSNGYTY YADSVKG                                                 17

SEQ ID NO: 1161         moltype = AA  length = 17
FEATURE                 Location/Qualifiers
REGION                  1..17
                        note = Synthetic
source                  1..17
                        mol_type = protein
                        organism = synthetic construct
SEQUENCE: 1161
YIDPYNGYTY YADSVKG                                                 17

SEQ ID NO: 1162         moltype = AA  length = 17
FEATURE                 Location/Qualifiers
REGION                  1..17
                        note = Synthetic
source                  1..17
                        mol_type = protein
                        organism = synthetic construct
SEQUENCE: 1162
YIDPYNGFTY YADSVKG                                                 17

SEQ ID NO: 1163         moltype = AA  length = 17
FEATURE                 Location/Qualifiers
REGION                  1..17
                        note = Synthetic
source                  1..17
                        mol_type = protein
                        organism = synthetic construct
SEQUENCE: 1163
YIDPSNGYTY YADSVKG                                                 17

SEQ ID NO: 1164         moltype = AA  length = 17
FEATURE                 Location/Qualifiers
REGION                  1..17
                        note = Synthetic
source                  1..17
                        mol_type = protein
                        organism = synthetic construct
SEQUENCE: 1164
YIDPSNGYTY YADSVKG                                                 17
```

```
SEQ ID NO: 1165         moltype = AA  length = 17
FEATURE                 Location/Qualifiers
REGION                  1..17
                        note = Synthetic
source                  1..17
                        mol_type = protein
                        organism = synthetic construct
SEQUENCE: 1165
YIDPSNGYTY HADSVKG                                                  17

SEQ ID NO: 1166         moltype = AA  length = 17
FEATURE                 Location/Qualifiers
REGION                  1..17
                        note = Synthetic
source                  1..17
                        mol_type = protein
                        organism = synthetic construct
SEQUENCE: 1166
YIDPSNGYTY YADSVKG                                                  17

SEQ ID NO: 1167         moltype = AA  length = 17
FEATURE                 Location/Qualifiers
REGION                  1..17
                        note = Synthetic
source                  1..17
                        mol_type = protein
                        organism = synthetic construct
SEQUENCE: 1167
YIDPSNGYTY YADSVKG                                                  17

SEQ ID NO: 1168         moltype = AA  length = 17
FEATURE                 Location/Qualifiers
REGION                  1..17
                        note = Synthetic
source                  1..17
                        mol_type = protein
                        organism = synthetic construct
SEQUENCE: 1168
YIDPSNGYTY YADSVKG                                                  17

SEQ ID NO: 1169         moltype = AA  length = 17
FEATURE                 Location/Qualifiers
REGION                  1..17
                        note = Synthetic
source                  1..17
                        mol_type = protein
                        organism = synthetic construct
SEQUENCE: 1169
YIDPSNGYTF YADSVKG                                                  17

SEQ ID NO: 1170         moltype = AA  length = 17
FEATURE                 Location/Qualifiers
REGION                  1..17
                        note = Synthetic
source                  1..17
                        mol_type = protein
                        organism = synthetic construct
SEQUENCE: 1170
YIDPSNGYTF YADSVKG                                                  17

SEQ ID NO: 1171         moltype = AA  length = 17
FEATURE                 Location/Qualifiers
REGION                  1..17
                        note = Synthetic
source                  1..17
                        mol_type = protein
                        organism = synthetic construct
SEQUENCE: 1171
YIDPSNGYTY YADSVKG                                                  17

SEQ ID NO: 1172         moltype = AA  length = 17
FEATURE                 Location/Qualifiers
REGION                  1..17
                        note = Synthetic
source                  1..17
                        mol_type = protein
                        organism = synthetic construct
SEQUENCE: 1172
```

```
YIDPSNGYTY YADSVKG                                              17

SEQ ID NO: 1173         moltype = AA  length = 17
FEATURE                 Location/Qualifiers
REGION                  1..17
                        note = Synthetic
source                  1..17
                        mol_type = protein
                        organism = synthetic construct
SEQUENCE: 1173
YIDPSNGYTY YADSVKG                                              17

SEQ ID NO: 1174         moltype = AA  length = 17
FEATURE                 Location/Qualifiers
REGION                  1..17
                        note = Synthetic
source                  1..17
                        mol_type = protein
                        organism = synthetic construct
SEQUENCE: 1174
YIDPSNGYTY YADSVKG                                              17

SEQ ID NO: 1175         moltype = AA  length = 17
FEATURE                 Location/Qualifiers
REGION                  1..17
                        note = Synthetic
source                  1..17
                        mol_type = protein
                        organism = synthetic construct
SEQUENCE: 1175
YIDPSNGYTY YADSVKG                                              17

SEQ ID NO: 1176         moltype = AA  length = 17
FEATURE                 Location/Qualifiers
REGION                  1..17
                        note = Synthetic
source                  1..17
                        mol_type = protein
                        organism = synthetic construct
SEQUENCE: 1176
YIDPSNGYTY YADSVKG                                              17

SEQ ID NO: 1177         moltype = AA  length = 17
FEATURE                 Location/Qualifiers
REGION                  1..17
                        note = Synthetic
source                  1..17
                        mol_type = protein
                        organism = synthetic construct
SEQUENCE: 1177
YIDPSNGYTY YADSVKG                                              17

SEQ ID NO: 1178         moltype = AA  length = 17
FEATURE                 Location/Qualifiers
REGION                  1..17
                        note = Synthetic
source                  1..17
                        mol_type = protein
                        organism = synthetic construct
SEQUENCE: 1178
YIDPSNGYTY YADSVKG                                              17

SEQ ID NO: 1179         moltype = AA  length = 17
FEATURE                 Location/Qualifiers
REGION                  1..17
                        note = Synthetic
source                  1..17
                        mol_type = protein
                        organism = synthetic construct
SEQUENCE: 1179
YIDPSNGYTY YADSVKG                                              17

SEQ ID NO: 1180         moltype = AA  length = 17
FEATURE                 Location/Qualifiers
REGION                  1..17
                        note = Synthetic
source                  1..17
                        mol_type = protein
                        organism = synthetic construct
```

```
SEQUENCE: 1180
YIDPSNGYTD YADSVKG                                              17

SEQ ID NO: 1181         moltype = AA  length = 17
FEATURE                 Location/Qualifiers
REGION                  1..17
                        note = Synthetic
source                  1..17
                        mol_type = protein
                        organism = synthetic construct
SEQUENCE: 1181
YIDPSNGYTY YADSVKG                                              17

SEQ ID NO: 1182         moltype = AA  length = 17
FEATURE                 Location/Qualifiers
REGION                  1..17
                        note = Synthetic
source                  1..17
                        mol_type = protein
                        organism = synthetic construct
SEQUENCE: 1182
YIDPSNGYTY YADSVKG                                              17

SEQ ID NO: 1183         moltype = AA  length = 17
FEATURE                 Location/Qualifiers
REGION                  1..17
                        note = Synthetic
source                  1..17
                        mol_type = protein
                        organism = synthetic construct
SEQUENCE: 1183
YIDPSNGYTY HADSVKG                                              17

SEQ ID NO: 1184         moltype = AA  length = 17
FEATURE                 Location/Qualifiers
REGION                  1..17
                        note = Synthetic
source                  1..17
                        mol_type = protein
                        organism = synthetic construct
SEQUENCE: 1184
YIDPSNGYTY YADSVKG                                              17

SEQ ID NO: 1185         moltype = AA  length = 17
FEATURE                 Location/Qualifiers
REGION                  1..17
                        note = Synthetic
source                  1..17
                        mol_type = protein
                        organism = synthetic construct
SEQUENCE: 1185
YIDPSNGYTY YADSVKG                                              17

SEQ ID NO: 1186         moltype = AA  length = 17
FEATURE                 Location/Qualifiers
REGION                  1..17
                        note = Synthetic
source                  1..17
                        mol_type = protein
                        organism = synthetic construct
SEQUENCE: 1186
YIDPSNGYTY YADSVKG                                              17

SEQ ID NO: 1187         moltype = AA  length = 17
FEATURE                 Location/Qualifiers
REGION                  1..17
                        note = Synthetic
source                  1..17
                        mol_type = protein
                        organism = synthetic construct
SEQUENCE: 1187
YIDPSNGYTY YADSVKG                                              17

SEQ ID NO: 1188         moltype = AA  length = 17
FEATURE                 Location/Qualifiers
REGION                  1..17
                        note = Synthetic
source                  1..17
                        mol_type = protein
```

```
                        organism = synthetic construct
SEQUENCE: 1188
YIDPSNGYTF YADSVKG                                                   17

SEQ ID NO: 1189         moltype = AA  length = 17
FEATURE                 Location/Qualifiers
REGION                  1..17
                        note = Synthetic
source                  1..17
                        mol_type = protein
                        organism = synthetic construct
SEQUENCE: 1189
YIDPSNGYTY YADSVKG                                                   17

SEQ ID NO: 1190         moltype = AA  length = 17
FEATURE                 Location/Qualifiers
REGION                  1..17
                        note = Synthetic
source                  1..17
                        mol_type = protein
                        organism = synthetic construct
SEQUENCE: 1190
YIDPSNGFTY YADSVKG                                                   17

SEQ ID NO: 1191         moltype = AA  length = 17
FEATURE                 Location/Qualifiers
REGION                  1..17
                        note = Synthetic
source                  1..17
                        mol_type = protein
                        organism = synthetic construct
SEQUENCE: 1191
YIDPSNGYTY YADSVKG                                                   17

SEQ ID NO: 1192         moltype =   length =
SEQUENCE: 1192
000

SEQ ID NO: 1193         moltype = AA  length = 16
FEATURE                 Location/Qualifiers
REGION                  1..16
                        note = Synthetic
source                  1..16
                        mol_type = protein
                        organism = synthetic construct
SEQUENCE: 1193
IIGSNGRTYY PNWAKS                                                    16

SEQ ID NO: 1194         moltype =   length =
SEQUENCE: 1194
000

SEQ ID NO: 1195         moltype =   length =
SEQUENCE: 1195
000

SEQ ID NO: 1196         moltype =   length =
SEQUENCE: 1196
000

SEQ ID NO: 1197         moltype =   length =
SEQUENCE: 1197
000

SEQ ID NO: 1198         moltype =   length =
SEQUENCE: 1198
000

SEQ ID NO: 1199         moltype = AA  length = 16
FEATURE                 Location/Qualifiers
REGION                  1..16
                        note = Synthetic
source                  1..16
                        mol_type = protein
                        organism = synthetic construct
SEQUENCE: 1199
TIDSSGRTYY ASWANG                                                    16

SEQ ID NO: 1200         moltype =   length =
```

SEQUENCE: 1200
000

SEQ ID NO: 1201 moltype = length =
SEQUENCE: 1201
000

SEQ ID NO: 1202 moltype = length =
SEQUENCE: 1202
000

SEQ ID NO: 1203 moltype = length =
SEQUENCE: 1203
000

SEQ ID NO: 1204 moltype = AA length = 16
FEATURE Location/Qualifiers
REGION 1..16
note = Synthetic
source 1..16
mol_type = protein
organism = synthetic construct
SEQUENCE: 1204
TIDSSGRTYY NPSLKS 16

SEQ ID NO: 1205 moltype = length =
SEQUENCE: 1205
000

SEQ ID NO: 1206 moltype = length =
SEQUENCE: 1206
000

SEQ ID NO: 1207 moltype = length =
SEQUENCE: 1207
000

SEQ ID NO: 1208 moltype = length =
SEQUENCE: 1208
000

SEQ ID NO: 1209 moltype = length =
SEQUENCE: 1209
000

SEQ ID NO: 1210 moltype = AA length = 16
FEATURE Location/Qualifiers
REGION 1..16
note = Synthetic
source 1..16
mol_type = protein
organism = synthetic construct
SEQUENCE: 1210
IIGSNGRTYY PDSVKG 16

SEQ ID NO: 1211 moltype = length =
SEQUENCE: 1211
000

SEQ ID NO: 1212 moltype = AA length = 16
FEATURE Location/Qualifiers
REGION 1..16
note = Synthetic
source 1..16
mol_type = protein
organism = synthetic construct
SEQUENCE: 1212
IIGSNGRTYY PDSVKG 16

SEQ ID NO: 1213 moltype = AA length = 16
FEATURE Location/Qualifiers
REGION 1..16
note = Synthetic
source 1..16
mol_type = protein
organism = synthetic construct
SEQUENCE: 1213
IIGSNGRTYY ADSVKG 16

-continued

SEQ ID NO: 1214 moltype = length =
SEQUENCE: 1214
000

SEQ ID NO: 1215 moltype = length =
SEQUENCE: 1215
000

SEQ ID NO: 1216 moltype = length =
SEQUENCE: 1216
000

SEQ ID NO: 1217 moltype = length =
SEQUENCE: 1217
000

SEQ ID NO: 1218 moltype = length =
SEQUENCE: 1218
000

SEQ ID NO: 1219 moltype = length =
SEQUENCE: 1219
000

SEQ ID NO: 1220 moltype = length =
SEQUENCE: 1220
000

SEQ ID NO: 1221 moltype = length =
SEQUENCE: 1221
000

SEQ ID NO: 1222 moltype = length =
SEQUENCE: 1222
000

SEQ ID NO: 1223 moltype = length =
SEQUENCE: 1223
000

SEQ ID NO: 1224 moltype = length =
SEQUENCE: 1224
000

SEQ ID NO: 1225 moltype = length =
SEQUENCE: 1225
000

SEQ ID NO: 1226 moltype = length =
SEQUENCE: 1226
000

SEQ ID NO: 1227 moltype = length =
SEQUENCE: 1227
000

SEQ ID NO: 1228 moltype = length =
SEQUENCE: 1228
000

SEQ ID NO: 1229 moltype = length =
SEQUENCE: 1229
000

SEQ ID NO: 1230 moltype = length =
SEQUENCE: 1230
000

SEQ ID NO: 1231 moltype = length =
SEQUENCE: 1231
000

SEQ ID NO: 1232 moltype = length =
SEQUENCE: 1232
000

SEQ ID NO: 1233 moltype = length =
SEQUENCE: 1233
000

-continued

SEQ ID NO: 1234 moltype = length =
SEQUENCE: 1234
000

SEQ ID NO: 1235 moltype = length =
SEQUENCE: 1235
000

SEQ ID NO: 1236 moltype = length =
SEQUENCE: 1236
000

SEQ ID NO: 1237 moltype = length =
SEQUENCE: 1237
000

SEQ ID NO: 1238 moltype = length =
SEQUENCE: 1238
000

SEQ ID NO: 1239 moltype = length =
SEQUENCE: 1239
000

SEQ ID NO: 1240 moltype = length =
SEQUENCE: 1240
000

SEQ ID NO: 1241 moltype = length =
SEQUENCE: 1241
000

SEQ ID NO: 1242 moltype = length =
SEQUENCE: 1242
000

SEQ ID NO: 1243 moltype = length =
SEQUENCE: 1243
000

SEQ ID NO: 1244 moltype = length =
SEQUENCE: 1244
000

SEQ ID NO: 1245 moltype = length =
SEQUENCE: 1245
000

SEQ ID NO: 1246 moltype = length =
SEQUENCE: 1246
000

SEQ ID NO: 1247 moltype = length =
SEQUENCE: 1247
000

SEQ ID NO: 1248 moltype = length =
SEQUENCE: 1248
000

SEQ ID NO: 1249 moltype = length =
SEQUENCE: 1249
000

SEQ ID NO: 1250 moltype = length =
SEQUENCE: 1250
000

SEQ ID NO: 1251 moltype = length =
SEQUENCE: 1251
000

SEQ ID NO: 1252 moltype = length =
SEQUENCE: 1252
000

SEQ ID NO: 1253 moltype = length =
SEQUENCE: 1253

-continued

000

SEQ ID NO: 1254 moltype = length =
SEQUENCE: 1254
000

SEQ ID NO: 1255 moltype = length =
SEQUENCE: 1255
000

SEQ ID NO: 1256 moltype = length =
SEQUENCE: 1256
000

SEQ ID NO: 1257 moltype = length =
SEQUENCE: 1257
000

SEQ ID NO: 1258 moltype = length =
SEQUENCE: 1258
000

SEQ ID NO: 1259 moltype = length =
SEQUENCE: 1259
000

SEQ ID NO: 1260 moltype = length =
SEQUENCE: 1260
000

SEQ ID NO: 1261 moltype = length =
SEQUENCE: 1261
000

SEQ ID NO: 1262 moltype = length =
SEQUENCE: 1262
000

SEQ ID NO: 1263 moltype = length =
SEQUENCE: 1263
000

SEQ ID NO: 1264 moltype = length =
SEQUENCE: 1264
000

SEQ ID NO: 1265 moltype = length =
SEQUENCE: 1265
000

SEQ ID NO: 1266 moltype = length =
SEQUENCE: 1266
000

SEQ ID NO: 1267 moltype = length =
SEQUENCE: 1267
000

SEQ ID NO: 1268 moltype = length =
SEQUENCE: 1268
000

SEQ ID NO: 1269 moltype = length =
SEQUENCE: 1269
000

SEQ ID NO: 1270 moltype = length =
SEQUENCE: 1270
000

SEQ ID NO: 1271 moltype = length =
SEQUENCE: 1271
000

SEQ ID NO: 1272 moltype = length =
SEQUENCE: 1272
000

SEQ ID NO: 1273 moltype = length =

-continued

SEQUENCE: 1273
000

SEQ ID NO: 1274 moltype = length =
SEQUENCE: 1274
000

SEQ ID NO: 1275 moltype = length =
SEQUENCE: 1275
000

SEQ ID NO: 1276 moltype = length =
SEQUENCE: 1276
000

SEQ ID NO: 1277 moltype = length =
SEQUENCE: 1277
000

SEQ ID NO: 1278 moltype = length =
SEQUENCE: 1278
000

SEQ ID NO: 1279 moltype = length =
SEQUENCE: 1279
000

SEQ ID NO: 1280 moltype = length =
SEQUENCE: 1280
000

SEQ ID NO: 1281 moltype = length =
SEQUENCE: 1281
000

SEQ ID NO: 1282 moltype = length =
SEQUENCE: 1282
000

SEQ ID NO: 1283 moltype = length =
SEQUENCE: 1283
000

SEQ ID NO: 1284 moltype = length =
SEQUENCE: 1284
000

SEQ ID NO: 1285 moltype = length =
SEQUENCE: 1285
000

SEQ ID NO: 1286 moltype = length =
SEQUENCE: 1286
000

SEQ ID NO: 1287 moltype = length =
SEQUENCE: 1287
000

SEQ ID NO: 1288 moltype = length =
SEQUENCE: 1288
000

SEQ ID NO: 1289 moltype = length =
SEQUENCE: 1289
000

SEQ ID NO: 1290 moltype = length =
SEQUENCE: 1290
000

SEQ ID NO: 1291 moltype = length =
SEQUENCE: 1291
000

SEQ ID NO: 1292 moltype = length =
SEQUENCE: 1292
000

-continued

SEQ ID NO: 1293 moltype = length =
SEQUENCE: 1293
000

SEQ ID NO: 1294 moltype = length =
SEQUENCE: 1294
000

SEQ ID NO: 1295 moltype = length =
SEQUENCE: 1295
000

SEQ ID NO: 1296 moltype = length =
SEQUENCE: 1296
000

SEQ ID NO: 1297 moltype = length =
SEQUENCE: 1297
000

SEQ ID NO: 1298 moltype = length =
SEQUENCE: 1298
000

SEQ ID NO: 1299 moltype = length =
SEQUENCE: 1299
000

SEQ ID NO: 1300 moltype = length =
SEQUENCE: 1300
000

SEQ ID NO: 1301 moltype = length =
SEQUENCE: 1301
000

SEQ ID NO: 1302 moltype = length =
SEQUENCE: 1302
000

SEQ ID NO: 1303 moltype = length =
SEQUENCE: 1303
000

SEQ ID NO: 1304 moltype = length =
SEQUENCE: 1304
000

SEQ ID NO: 1305 moltype = length =
SEQUENCE: 1305
000

SEQ ID NO: 1306 moltype = length =
SEQUENCE: 1306
000

SEQ ID NO: 1307 moltype = length =
SEQUENCE: 1307
000

SEQ ID NO: 1308 moltype = length =
SEQUENCE: 1308
000

SEQ ID NO: 1309 moltype = length =
SEQUENCE: 1309
000

SEQ ID NO: 1310 moltype = length =
SEQUENCE: 1310
000

SEQ ID NO: 1311 moltype = length =
SEQUENCE: 1311
000

SEQ ID NO: 1312 moltype = length =
SEQUENCE: 1312
000

SEQ ID NO: 1313 moltype = length =
SEQUENCE: 1313
000

SEQ ID NO: 1314 moltype = length =
SEQUENCE: 1314
000

SEQ ID NO: 1315 moltype = length =
SEQUENCE: 1315
000

SEQ ID NO: 1316 moltype = length =
SEQUENCE: 1316
000

SEQ ID NO: 1317 moltype = length =
SEQUENCE: 1317
000

SEQ ID NO: 1318 moltype = length =
SEQUENCE: 1318
000

SEQ ID NO: 1319 moltype = length =
SEQUENCE: 1319
000

SEQ ID NO: 1320 moltype = length =
SEQUENCE: 1320
000

SEQ ID NO: 1321 moltype = length =
SEQUENCE: 1321
000

SEQ ID NO: 1322 moltype = length =
SEQUENCE: 1322
000

SEQ ID NO: 1323 moltype = length =
SEQUENCE: 1323
000

SEQ ID NO: 1324 moltype = length =
SEQUENCE: 1324
000

SEQ ID NO: 1325 moltype = length =
SEQUENCE: 1325
000

SEQ ID NO: 1326 moltype = length =
SEQUENCE: 1326
000

SEQ ID NO: 1327 moltype = length =
SEQUENCE: 1327
000

SEQ ID NO: 1328 moltype = length =
SEQUENCE: 1328
000

SEQ ID NO: 1329 moltype = length =
SEQUENCE: 1329
000

SEQ ID NO: 1330 moltype = length =
SEQUENCE: 1330
000

SEQ ID NO: 1331 moltype = length =
SEQUENCE: 1331
000

SEQ ID NO: 1332 moltype = length =
SEQUENCE: 1332

000

SEQ ID NO: 1333 moltype = length =
SEQUENCE: 1333
000

SEQ ID NO: 1334 moltype = length =
SEQUENCE: 1334
000

SEQ ID NO: 1335 moltype = length =
SEQUENCE: 1335
000

SEQ ID NO: 1336 moltype = length =
SEQUENCE: 1336
000

SEQ ID NO: 1337 moltype = length =
SEQUENCE: 1337
000

SEQ ID NO: 1338 moltype = length =
SEQUENCE: 1338
000

SEQ ID NO: 1339 moltype = length =
SEQUENCE: 1339
000

SEQ ID NO: 1340 moltype = length =
SEQUENCE: 1340
000

SEQ ID NO: 1341 moltype = length =
SEQUENCE: 1341
000

SEQ ID NO: 1342 moltype = length =
SEQUENCE: 1342
000

SEQ ID NO: 1343 moltype = length =
SEQUENCE: 1343
000

SEQ ID NO: 1344 moltype = length =
SEQUENCE: 1344
000

SEQ ID NO: 1345 moltype = length =
SEQUENCE: 1345
000

SEQ ID NO: 1346 moltype = length =
SEQUENCE: 1346
000

SEQ ID NO: 1347 moltype = length =
SEQUENCE: 1347
000

SEQ ID NO: 1348 moltype = length =
SEQUENCE: 1348
000

SEQ ID NO: 1349 moltype = length =
SEQUENCE: 1349
000

SEQ ID NO: 1350 moltype = length =
SEQUENCE: 1350
000

SEQ ID NO: 1351 moltype = length =
SEQUENCE: 1351
000

SEQ ID NO: 1352 moltype = length =

-continued

SEQUENCE: 1352
000

SEQ ID NO: 1353 moltype = length =
SEQUENCE: 1353
000

SEQ ID NO: 1354 moltype = length =
SEQUENCE: 1354
000

SEQ ID NO: 1355 moltype = length =
SEQUENCE: 1355
000

SEQ ID NO: 1356 moltype = length =
SEQUENCE: 1356
000

SEQ ID NO: 1357 moltype = length =
SEQUENCE: 1357
000

SEQ ID NO: 1358 moltype = length =
SEQUENCE: 1358
000

SEQ ID NO: 1359 moltype = length =
SEQUENCE: 1359
000

SEQ ID NO: 1360 moltype = length =
SEQUENCE: 1360
000

SEQ ID NO: 1361 moltype = length =
SEQUENCE: 1361
000

SEQ ID NO: 1362 moltype = length =
SEQUENCE: 1362
000

SEQ ID NO: 1363 moltype = length =
SEQUENCE: 1363
000

SEQ ID NO: 1364 moltype = length =
SEQUENCE: 1364
000

SEQ ID NO: 1365 moltype = length =
SEQUENCE: 1365
000

SEQ ID NO: 1366 moltype = length =
SEQUENCE: 1366
000

SEQ ID NO: 1367 moltype = length =
SEQUENCE: 1367
000

SEQ ID NO: 1368 moltype = length =
SEQUENCE: 1368
000

SEQ ID NO: 1369 moltype = length =
SEQUENCE: 1369
000

SEQ ID NO: 1370 moltype = length =
SEQUENCE: 1370
000

SEQ ID NO: 1371 moltype = length =
SEQUENCE: 1371
000

-continued

SEQ ID NO: 1372 moltype = length =
SEQUENCE: 1372
000

SEQ ID NO: 1373 moltype = length =
SEQUENCE: 1373
000

SEQ ID NO: 1374 moltype = length =
SEQUENCE: 1374
000

SEQ ID NO: 1375 moltype = length =
SEQUENCE: 1375
000

SEQ ID NO: 1376 moltype = length =
SEQUENCE: 1376
000

SEQ ID NO: 1377 moltype = length =
SEQUENCE: 1377
000

SEQ ID NO: 1378 moltype = length =
SEQUENCE: 1378
000

SEQ ID NO: 1379 moltype = length =
SEQUENCE: 1379
000

SEQ ID NO: 1380 moltype = length =
SEQUENCE: 1380
000

SEQ ID NO: 1381 moltype = length =
SEQUENCE: 1381
000

SEQ ID NO: 1382 moltype = length =
SEQUENCE: 1382
000

SEQ ID NO: 1383 moltype = length =
SEQUENCE: 1383
000

SEQ ID NO: 1384 moltype = length =
SEQUENCE: 1384
000

SEQ ID NO: 1385 moltype = length =
SEQUENCE: 1385
000

SEQ ID NO: 1386 moltype = length =
SEQUENCE: 1386
000

SEQ ID NO: 1387 moltype = length =
SEQUENCE: 1387
000

SEQ ID NO: 1388 moltype = length =
SEQUENCE: 1388
000

SEQ ID NO: 1389 moltype = length =
SEQUENCE: 1389
000

SEQ ID NO: 1390 moltype = length =
SEQUENCE: 1390
000

SEQ ID NO: 1391 moltype = length =
SEQUENCE: 1391
000

SEQ ID NO: 1392 moltype = length =
SEQUENCE: 1392
000

SEQ ID NO: 1393 moltype = length =
SEQUENCE: 1393
000

SEQ ID NO: 1394 moltype = length =
SEQUENCE: 1394
000

SEQ ID NO: 1395 moltype = length =
SEQUENCE: 1395
000

SEQ ID NO: 1396 moltype = length =
SEQUENCE: 1396
000

SEQ ID NO: 1397 moltype = length =
SEQUENCE: 1397
000

SEQ ID NO: 1398 moltype = length =
SEQUENCE: 1398
000

SEQ ID NO: 1399 moltype = length =
SEQUENCE: 1399
000

SEQ ID NO: 1400 moltype = length =
SEQUENCE: 1400
000

SEQ ID NO: 1401 moltype = length =
SEQUENCE: 1401
000

SEQ ID NO: 1402 moltype = length =
SEQUENCE: 1402
000

SEQ ID NO: 1403 moltype = length =
SEQUENCE: 1403
000

SEQ ID NO: 1404 moltype = length =
SEQUENCE: 1404
000

SEQ ID NO: 1405 moltype = AA length = 9
FEATURE Location/Qualifiers
REGION 1..9
note = Synthetic
source 1..9
mol_type = protein
organism = synthetic construct
SEQUENCE: 1405
SDYYYVDEY 9

SEQ ID NO: 1406 moltype = length =
SEQUENCE: 1406
000

SEQ ID NO: 1407 moltype = length =
SEQUENCE: 1407
000

SEQ ID NO: 1408 moltype = length =
SEQUENCE: 1408
000

SEQ ID NO: 1409 moltype = length =
SEQUENCE: 1409
000

```
SEQ ID NO: 1410        moltype =   length =
SEQUENCE: 1410
000

SEQ ID NO: 1411        moltype =   length =
SEQUENCE: 1411
000

SEQ ID NO: 1412        moltype =   length =
SEQUENCE: 1412
000

SEQ ID NO: 1413        moltype =   length =
SEQUENCE: 1413
000

SEQ ID NO: 1414        moltype = AA  length = 8
FEATURE                Location/Qualifiers
REGION                 1..8
                       note = Synthetic
source                 1..8
                       mol_type = protein
                       organism = synthetic construct
SEQUENCE: 1414
GYGSWPDY                                                    8

SEQ ID NO: 1415        moltype =   length =
SEQUENCE: 1415
000

SEQ ID NO: 1416        moltype =   length =
SEQUENCE: 1416
000

SEQ ID NO: 1417        moltype = AA  length = 8
FEATURE                Location/Qualifiers
REGION                 1..8
                       note = Synthetic
source                 1..8
                       mol_type = protein
                       organism = synthetic construct
SEQUENCE: 1417
DDQSVSSP                                                    8

SEQ ID NO: 1418        moltype =   length =
SEQUENCE: 1418
000

SEQ ID NO: 1419        moltype =   length =
SEQUENCE: 1419
000

SEQ ID NO: 1420        moltype =   length =
SEQUENCE: 1420
000

SEQ ID NO: 1421        moltype =   length =
SEQUENCE: 1421
000

SEQ ID NO: 1422        moltype =   length =
SEQUENCE: 1422
000

SEQ ID NO: 1423        moltype =   length =
SEQUENCE: 1423
000

SEQ ID NO: 1424        moltype =   length =
SEQUENCE: 1424
000

SEQ ID NO: 1425        moltype =   length =
SEQUENCE: 1425
000

SEQ ID NO: 1426        moltype =   length =
SEQUENCE: 1426
000
```

```
SEQ ID NO: 1427        moltype =   length =
SEQUENCE: 1427
000

SEQ ID NO: 1428        moltype =   length =
SEQUENCE: 1428
000

SEQ ID NO: 1429        moltype = AA  length = 12
FEATURE                Location/Qualifiers
REGION                 1..12
                       note = Synthetic
source                 1..12
                       mol_type = protein
                       organism = synthetic construct
SEQUENCE: 1429
ADYYYVDEYF DY                                                  12

SEQ ID NO: 1430        moltype = AA  length = 11
FEATURE                Location/Qualifiers
REGION                 1..11
                       note = Synthetic
source                 1..11
                       mol_type = protein
                       organism = synthetic construct
SEQUENCE: 1430
DDQSLSSPFD Y                                                   11

SEQ ID NO: 1431        moltype = AA  length = 12
FEATURE                Location/Qualifiers
REGION                 1..12
                       note = Synthetic
source                 1..12
                       mol_type = protein
                       organism = synthetic construct
SEQUENCE: 1431
ADYFYVDEYL DY                                                  12

SEQ ID NO: 1432        moltype = AA  length = 12
FEATURE                Location/Qualifiers
REGION                 1..12
                       note = Synthetic
source                 1..12
                       mol_type = protein
                       organism = synthetic construct
SEQUENCE: 1432
ADYFYIDEYW DY                                                  12

SEQ ID NO: 1433        moltype = AA  length = 12
FEATURE                Location/Qualifiers
REGION                 1..12
                       note = Synthetic
source                 1..12
                       mol_type = protein
                       organism = synthetic construct
SEQUENCE: 1433
ADYYYVDEYW DY                                                  12

SEQ ID NO: 1434        moltype = AA  length = 12
FEATURE                Location/Qualifiers
REGION                 1..12
                       note = Synthetic
source                 1..12
                       mol_type = protein
                       organism = synthetic construct
SEQUENCE: 1434
ADYYYVDEYW DY                                                  12

SEQ ID NO: 1435        moltype = AA  length = 12
FEATURE                Location/Qualifiers
REGION                 1..12
                       note = Synthetic
source                 1..12
                       mol_type = protein
                       organism = synthetic construct
SEQUENCE: 1435
SDYYYVDEFF DY                                                  12
```

```
SEQ ID NO: 1436         moltype = AA  length = 12
FEATURE                 Location/Qualifiers
REGION                  1..12
                        note = Synthetic
source                  1..12
                        mol_type = protein
                        organism = synthetic construct
SEQUENCE: 1436
ADYYYVDEYW DY                                                      12

SEQ ID NO: 1437         moltype = AA  length = 12
FEATURE                 Location/Qualifiers
REGION                  1..12
                        note = Synthetic
source                  1..12
                        mol_type = protein
                        organism = synthetic construct
SEQUENCE: 1437
ADYYYVDEYW DY                                                      12

SEQ ID NO: 1438         moltype = AA  length = 12
FEATURE                 Location/Qualifiers
REGION                  1..12
                        note = Synthetic
source                  1..12
                        mol_type = protein
                        organism = synthetic construct
SEQUENCE: 1438
ADYYYVDEYL DY                                                      12

SEQ ID NO: 1439         moltype = AA  length = 11
FEATURE                 Location/Qualifiers
REGION                  1..11
                        note = Synthetic
source                  1..11
                        mol_type = protein
                        organism = synthetic construct
SEQUENCE: 1439
DDQSFTSPFD Y                                                       11

SEQ ID NO: 1440         moltype = AA  length = 12
FEATURE                 Location/Qualifiers
REGION                  1..12
                        note = Synthetic
source                  1..12
                        mol_type = protein
                        organism = synthetic construct
SEQUENCE: 1440
ADYYYVDEYL DY                                                      12

SEQ ID NO: 1441         moltype = AA  length = 12
FEATURE                 Location/Qualifiers
REGION                  1..12
                        note = Synthetic
source                  1..12
                        mol_type = protein
                        organism = synthetic construct
SEQUENCE: 1441
ADYYYVDEYW DY                                                      12

SEQ ID NO: 1442         moltype = AA  length = 12
FEATURE                 Location/Qualifiers
REGION                  1..12
                        note = Synthetic
source                  1..12
                        mol_type = protein
                        organism = synthetic construct
SEQUENCE: 1442
ADYYYVDEYW DY                                                      12

SEQ ID NO: 1443         moltype = AA  length = 12
FEATURE                 Location/Qualifiers
REGION                  1..12
                        note = Synthetic
source                  1..12
                        mol_type = protein
                        organism = synthetic construct
SEQUENCE: 1443
ADYYYVDEYW DY                                                      12
```

```
SEQ ID NO: 1444         moltype = AA  length = 12
FEATURE                 Location/Qualifiers
REGION                  1..12
                        note = Synthetic
source                  1..12
                        mol_type = protein
                        organism = synthetic construct
SEQUENCE: 1444
ADYYGVDEFL DY                                                        12

SEQ ID NO: 1445         moltype = AA  length = 12
FEATURE                 Location/Qualifiers
REGION                  1..12
                        note = Synthetic
source                  1..12
                        mol_type = protein
                        organism = synthetic construct
SEQUENCE: 1445
ADYHGVDEYW DY                                                        12

SEQ ID NO: 1446         moltype = AA  length = 12
FEATURE                 Location/Qualifiers
REGION                  1..12
                        note = Synthetic
source                  1..12
                        mol_type = protein
                        organism = synthetic construct
SEQUENCE: 1446
ADYHGVDEYW DY                                                        12

SEQ ID NO: 1447         moltype = AA  length = 12
FEATURE                 Location/Qualifiers
REGION                  1..12
                        note = Synthetic
source                  1..12
                        mol_type = protein
                        organism = synthetic construct
SEQUENCE: 1447
ADYYYVDEYF DY                                                        12

SEQ ID NO: 1448         moltype = AA  length = 12
FEATURE                 Location/Qualifiers
REGION                  1..12
                        note = Synthetic
source                  1..12
                        mol_type = protein
                        organism = synthetic construct
SEQUENCE: 1448
ADYYYVDEYW DY                                                        12

SEQ ID NO: 1449         moltype = AA  length = 12
FEATURE                 Location/Qualifiers
REGION                  1..12
                        note = Synthetic
source                  1..12
                        mol_type = protein
                        organism = synthetic construct
SEQUENCE: 1449
ADYYYVDEYW DY                                                        12

SEQ ID NO: 1450         moltype = AA  length = 12
FEATURE                 Location/Qualifiers
REGION                  1..12
                        note = Synthetic
source                  1..12
                        mol_type = protein
                        organism = synthetic construct
SEQUENCE: 1450
ADYHGVDEYW DY                                                        12

SEQ ID NO: 1451         moltype = AA  length = 12
FEATURE                 Location/Qualifiers
REGION                  1..12
                        note = Synthetic
source                  1..12
                        mol_type = protein
                        organism = synthetic construct
SEQUENCE: 1451
```

-continued

```
ADYYYVDEYW DY                                                        12

SEQ ID NO: 1452         moltype = AA  length = 12
FEATURE                 Location/Qualifiers
REGION                  1..12
                        note = Synthetic
source                  1..12
                        mol_type = protein
                        organism = synthetic construct
SEQUENCE: 1452
ADYYYVDEYW DY                                                        12

SEQ ID NO: 1453         moltype = AA  length = 12
FEATURE                 Location/Qualifiers
REGION                  1..12
                        note = Synthetic
source                  1..12
                        mol_type = protein
                        organism = synthetic construct
SEQUENCE: 1453
ADYYYVDEYW DY                                                        12

SEQ ID NO: 1454         moltype = AA  length = 12
FEATURE                 Location/Qualifiers
REGION                  1..12
                        note = Synthetic
source                  1..12
                        mol_type = protein
                        organism = synthetic construct
SEQUENCE: 1454
ADYYYVDEYW DY                                                        12

SEQ ID NO: 1455         moltype = AA  length = 12
FEATURE                 Location/Qualifiers
REGION                  1..12
                        note = Synthetic
source                  1..12
                        mol_type = protein
                        organism = synthetic construct
SEQUENCE: 1455
ADYHGVDEYW DY                                                        12

SEQ ID NO: 1456         moltype = AA  length = 12
FEATURE                 Location/Qualifiers
REGION                  1..12
                        note = Synthetic
source                  1..12
                        mol_type = protein
                        organism = synthetic construct
SEQUENCE: 1456
ADYYYVDEYW DY                                                        12

SEQ ID NO: 1457         moltype = AA  length = 12
FEATURE                 Location/Qualifiers
REGION                  1..12
                        note = Synthetic
source                  1..12
                        mol_type = protein
                        organism = synthetic construct
SEQUENCE: 1457
ADYYYVDEYF DY                                                        12

SEQ ID NO: 1458         moltype = AA  length = 12
FEATURE                 Location/Qualifiers
REGION                  1..12
                        note = Synthetic
source                  1..12
                        mol_type = protein
                        organism = synthetic construct
SEQUENCE: 1458
ADYYYVDEYW DY                                                        12

SEQ ID NO: 1459         moltype = AA  length = 11
FEATURE                 Location/Qualifiers
REGION                  1..11
                        note = Synthetic
source                  1..11
                        mol_type = protein
                        organism = synthetic construct
```

-continued

```
SEQUENCE: 1459
DDQSFSSPFD Y                                                        11

SEQ ID NO: 1460        moltype = AA  length = 11
FEATURE                Location/Qualifiers
REGION                 1..11
                       note = Synthetic
source                 1..11
                       mol_type = protein
                       organism = synthetic construct
SEQUENCE: 1460
DYGSYLVSLD Y                                                        11

SEQ ID NO: 1461        moltype = AA  length = 11
FEATURE                Location/Qualifiers
REGION                 1..11
                       note = Synthetic
source                 1..11
                       mol_type = protein
                       organism = synthetic construct
SEQUENCE: 1461
DYGSWRIRLD Y                                                        11

SEQ ID NO: 1462        moltype = AA  length = 11
FEATURE                Location/Qualifiers
REGION                 1..11
                       note = Synthetic
source                 1..11
                       mol_type = protein
                       organism = synthetic construct
SEQUENCE: 1462
DYGSLQVFLD Y                                                        11

SEQ ID NO: 1463        moltype = AA  length = 11
FEATURE                Location/Qualifiers
REGION                 1..11
                       note = Synthetic
source                 1..11
                       mol_type = protein
                       organism = synthetic construct
SEQUENCE: 1463
DYGSLQVFID H                                                        11

SEQ ID NO: 1464        moltype = AA  length = 11
FEATURE                Location/Qualifiers
REGION                 1..11
                       note = Synthetic
source                 1..11
                       mol_type = protein
                       organism = synthetic construct
SEQUENCE: 1464
DYGSLQVQLD Y                                                        11

SEQ ID NO: 1465        moltype = AA  length = 11
FEATURE                Location/Qualifiers
REGION                 1..11
                       note = Synthetic
source                 1..11
                       mol_type = protein
                       organism = synthetic construct
SEQUENCE: 1465
DYGSLQVQLD Y                                                        11

SEQ ID NO: 1466        moltype = AA  length = 11
FEATURE                Location/Qualifiers
REGION                 1..11
                       note = Synthetic
source                 1..11
                       mol_type = protein
                       organism = synthetic construct
SEQUENCE: 1466
DYGSLEVSLD Y                                                        11

SEQ ID NO: 1467        moltype = AA  length = 11
FEATURE                Location/Qualifiers
REGION                 1..11
                       note = Synthetic
source                 1..11
                       mol_type = protein
```

```
                        organism = synthetic construct
SEQUENCE: 1467
DYGSLTINLD Y                                                      11

SEQ ID NO: 1468         moltype = AA  length = 11
FEATURE                 Location/Qualifiers
REGION                  1..11
                        note = Synthetic
source                  1..11
                        mol_type = protein
                        organism = synthetic construct
SEQUENCE: 1468
DYGSLEVSLD Y                                                      11

SEQ ID NO: 1469         moltype = AA  length = 11
FEATURE                 Location/Qualifiers
REGION                  1..11
                        note = Synthetic
source                  1..11
                        mol_type = protein
                        organism = synthetic construct
SEQUENCE: 1469
DYGSLEVSLD Y                                                      11

SEQ ID NO: 1470         moltype = AA  length = 11
FEATURE                 Location/Qualifiers
REGION                  1..11
                        note = Synthetic
source                  1..11
                        mol_type = protein
                        organism = synthetic construct
SEQUENCE: 1470
DYGSIQVFLD Y                                                      11

SEQ ID NO: 1471         moltype = AA  length = 11
FEATURE                 Location/Qualifiers
REGION                  1..11
                        note = Synthetic
source                  1..11
                        mol_type = protein
                        organism = synthetic construct
SEQUENCE: 1471
DYGSLQVFID Y                                                      11

SEQ ID NO: 1472         moltype = AA  length = 11
FEATURE                 Location/Qualifiers
REGION                  1..11
                        note = Synthetic
source                  1..11
                        mol_type = protein
                        organism = synthetic construct
SEQUENCE: 1472
DYGSLQVQLD Y                                                      11

SEQ ID NO: 1473         moltype = AA  length = 11
FEATURE                 Location/Qualifiers
REGION                  1..11
                        note = Synthetic
source                  1..11
                        mol_type = protein
                        organism = synthetic construct
SEQUENCE: 1473
DYGSLQVFID Y                                                      11

SEQ ID NO: 1474         moltype = AA  length = 11
FEATURE                 Location/Qualifiers
REGION                  1..11
                        note = Synthetic
source                  1..11
                        mol_type = protein
                        organism = synthetic construct
SEQUENCE: 1474
DPQSFYIAFD Y                                                      11

SEQ ID NO: 1475         moltype = AA  length = 11
FEATURE                 Location/Qualifiers
REGION                  1..11
                        note = Synthetic
source                  1..11
```

```
                         mol_type = protein
                         organism = synthetic construct
SEQUENCE: 1475
DYGSLEVSLD Y                                                      11

SEQ ID NO: 1476          moltype = AA  length = 12
FEATURE                  Location/Qualifiers
REGION                   1..12
                         note = Synthetic
source                   1..12
                         mol_type = protein
                         organism = synthetic construct
SEQUENCE: 1476
ADYYYVDEYL DY                                                     12

SEQ ID NO: 1477          moltype = AA  length = 11
FEATURE                  Location/Qualifiers
REGION                   1..11
                         note = Synthetic
source                   1..11
                         mol_type = protein
                         organism = synthetic construct
SEQUENCE: 1477
DYGSVRVFLD Y                                                      11

SEQ ID NO: 1478          moltype = AA  length = 11
FEATURE                  Location/Qualifiers
REGION                   1..11
                         note = Synthetic
source                   1..11
                         mol_type = protein
                         organism = synthetic construct
SEQUENCE: 1478
DDQSVSSPFD Y                                                      11

SEQ ID NO: 1479          moltype = AA  length = 11
FEATURE                  Location/Qualifiers
REGION                   1..11
                         note = Synthetic
source                   1..11
                         mol_type = protein
                         organism = synthetic construct
SEQUENCE: 1479
DYGSLRVSLD Y                                                      11

SEQ ID NO: 1480          moltype = AA  length = 11
FEATURE                  Location/Qualifiers
REGION                   1..11
                         note = Synthetic
source                   1..11
                         mol_type = protein
                         organism = synthetic construct
SEQUENCE: 1480
DYGSLQVFID Y                                                      11

SEQ ID NO: 1481          moltype = AA  length = 11
FEATURE                  Location/Qualifiers
REGION                   1..11
                         note = Synthetic
source                   1..11
                         mol_type = protein
                         organism = synthetic construct
SEQUENCE: 1481
DYGSFRVQLD Y                                                      11

SEQ ID NO: 1482          moltype = AA  length = 11
FEATURE                  Location/Qualifiers
REGION                   1..11
                         note = Synthetic
source                   1..11
                         mol_type = protein
                         organism = synthetic construct
SEQUENCE: 1482
DYGSLHVQLD Y                                                      11

SEQ ID NO: 1483          moltype = AA  length = 11
FEATURE                  Location/Qualifiers
REGION                   1..11
                         note = Synthetic
```

```
source                  1..11
                        mol_type = protein
                        organism = synthetic construct
SEQUENCE: 1483
DVQSVSGEFD Y                                                  11

SEQ ID NO: 1484         moltype = AA  length = 11
FEATURE                 Location/Qualifiers
REGION                  1..11
                        note = Synthetic
source                  1..11
                        mol_type = protein
                        organism = synthetic construct
SEQUENCE: 1484
DYGSLQVFID Y                                                  11

SEQ ID NO: 1485         moltype = AA  length = 11
FEATURE                 Location/Qualifiers
REGION                  1..11
                        note = Synthetic
source                  1..11
                        mol_type = protein
                        organism = synthetic construct
SEQUENCE: 1485
DDQSVSSPFD Y                                                  11

SEQ ID NO: 1486         moltype = AA  length = 11
FEATURE                 Location/Qualifiers
REGION                  1..11
                        note = Synthetic
source                  1..11
                        mol_type = protein
                        organism = synthetic construct
SEQUENCE: 1486
DYGSLQVFID Y                                                  11

SEQ ID NO: 1487         moltype = AA  length = 11
FEATURE                 Location/Qualifiers
REGION                  1..11
                        note = Synthetic
source                  1..11
                        mol_type = protein
                        organism = synthetic construct
SEQUENCE: 1487
DYGSLQVFID Y                                                  11

SEQ ID NO: 1488         moltype = AA  length = 11
FEATURE                 Location/Qualifiers
REGION                  1..11
                        note = Synthetic
source                  1..11
                        mol_type = protein
                        organism = synthetic construct
SEQUENCE: 1488
DDQSLSSPFD Y                                                  11

SEQ ID NO: 1489         moltype = AA  length = 11
FEATURE                 Location/Qualifiers
REGION                  1..11
                        note = Synthetic
source                  1..11
                        mol_type = protein
                        organism = synthetic construct
SEQUENCE: 1489
DPQSISSPFD Y                                                  11

SEQ ID NO: 1490         moltype = AA  length = 11
FEATURE                 Location/Qualifiers
REGION                  1..11
                        note = Synthetic
source                  1..11
                        mol_type = protein
                        organism = synthetic construct
SEQUENCE: 1490
DPQSVSSPFD Y                                                  11

SEQ ID NO: 1491         moltype = AA  length = 11
FEATURE                 Location/Qualifiers
REGION                  1..11
```

```
                        note = Synthetic
source                  1..11
                        mol_type = protein
                        organism = synthetic construct
SEQUENCE: 1491
DDQSLSSPFD Y                                                        11

SEQ ID NO: 1492         moltype = AA  length = 11
FEATURE                 Location/Qualifiers
REGION                  1..11
                        note = Synthetic
source                  1..11
                        mol_type = protein
                        organism = synthetic construct
SEQUENCE: 1492
DDQSISSPLD Y                                                        11

SEQ ID NO: 1493         moltype = AA  length = 11
FEATURE                 Location/Qualifiers
REGION                  1..11
                        note = Synthetic
source                  1..11
                        mol_type = protein
                        organism = synthetic construct
SEQUENCE: 1493
DPQSLFYPFD Y                                                        11

SEQ ID NO: 1494         moltype = AA  length = 11
FEATURE                 Location/Qualifiers
REGION                  1..11
                        note = Synthetic
source                  1..11
                        mol_type = protein
                        organism = synthetic construct
SEQUENCE: 1494
DDQSLSSPFD Y                                                        11

SEQ ID NO: 1495         moltype = AA  length = 11
FEATURE                 Location/Qualifiers
REGION                  1..11
                        note = Synthetic
source                  1..11
                        mol_type = protein
                        organism = synthetic construct
SEQUENCE: 1495
DIQSVSGEFD Y                                                        11

SEQ ID NO: 1496         moltype = AA  length = 11
FEATURE                 Location/Qualifiers
REGION                  1..11
                        note = Synthetic
source                  1..11
                        mol_type = protein
                        organism = synthetic construct
SEQUENCE: 1496
DDQSVSSPFE Y                                                        11

SEQ ID NO: 1497         moltype = AA  length = 11
FEATURE                 Location/Qualifiers
REGION                  1..11
                        note = Synthetic
source                  1..11
                        mol_type = protein
                        organism = synthetic construct
SEQUENCE: 1497
DPQSLSSPFD Y                                                        11

SEQ ID NO: 1498         moltype = AA  length = 11
FEATURE                 Location/Qualifiers
REGION                  1..11
                        note = Synthetic
source                  1..11
                        mol_type = protein
                        organism = synthetic construct
SEQUENCE: 1498
DPQSLSSPFD Y                                                        11

SEQ ID NO: 1499         moltype = AA  length = 11
FEATURE                 Location/Qualifiers
```

```
REGION                1..11
                      note = Synthetic
source                1..11
                      mol_type = protein
                      organism = synthetic construct
SEQUENCE: 1499
DDQSLSSPFD Y                                                    11

SEQ ID NO: 1500       moltype = AA  length = 11
FEATURE               Location/Qualifiers
REGION                1..11
                      note = Synthetic
source                1..11
                      mol_type = protein
                      organism = synthetic construct
SEQUENCE: 1500
DDQSLSSPFD Y                                                    11

SEQ ID NO: 1501       moltype = AA  length = 11
FEATURE               Location/Qualifiers
REGION                1..11
                      note = Synthetic
source                1..11
                      mol_type = protein
                      organism = synthetic construct
SEQUENCE: 1501
DPQSLTSPFD Y                                                    11

SEQ ID NO: 1502       moltype = AA  length = 11
FEATURE               Location/Qualifiers
REGION                1..11
                      note = Synthetic
source                1..11
                      mol_type = protein
                      organism = synthetic construct
SEQUENCE: 1502
DIQSVSGEFD Y                                                    11

SEQ ID NO: 1503       moltype = AA  length = 11
FEATURE               Location/Qualifiers
REGION                1..11
                      note = Synthetic
source                1..11
                      mol_type = protein
                      organism = synthetic construct
SEQUENCE: 1503
DPQSLTSPFD Y                                                    11

SEQ ID NO: 1504       moltype = AA  length = 11
FEATURE               Location/Qualifiers
REGION                1..11
                      note = Synthetic
source                1..11
                      mol_type = protein
                      organism = synthetic construct
SEQUENCE: 1504
DIQSVSGEFD Y                                                    11

SEQ ID NO: 1505       moltype = AA  length = 11
FEATURE               Location/Qualifiers
REGION                1..11
                      note = Synthetic
source                1..11
                      mol_type = protein
                      organism = synthetic construct
SEQUENCE: 1505
DIQSVSGEFD Y                                                    11

SEQ ID NO: 1506       moltype = AA  length = 11
FEATURE               Location/Qualifiers
REGION                1..11
                      note = Synthetic
source                1..11
                      mol_type = protein
                      organism = synthetic construct
SEQUENCE: 1506
DPQSVGSEFD Y                                                    11

SEQ ID NO: 1507       moltype = AA  length = 11
```

```
FEATURE                 Location/Qualifiers
REGION                  1..11
                        note = Synthetic
source                  1..11
                        mol_type = protein
                        organism = synthetic construct
SEQUENCE: 1507
DIQSVSGEFD Y                                                        11

SEQ ID NO: 1508         moltype = AA  length = 11
FEATURE                 Location/Qualifiers
REGION                  1..11
                        note = Synthetic
source                  1..11
                        mol_type = protein
                        organism = synthetic construct
SEQUENCE: 1508
DPQSLSSPFD Y                                                        11

SEQ ID NO: 1509         moltype = AA  length = 11
FEATURE                 Location/Qualifiers
REGION                  1..11
                        note = Synthetic
source                  1..11
                        mol_type = protein
                        organism = synthetic construct
SEQUENCE: 1509
DIQSVSGEFD Y                                                        11

SEQ ID NO: 1510         moltype = AA  length = 11
FEATURE                 Location/Qualifiers
REGION                  1..11
                        note = Synthetic
source                  1..11
                        mol_type = protein
                        organism = synthetic construct
SEQUENCE: 1510
DIQSVSGEFD Y                                                        11

SEQ ID NO: 1511         moltype = AA  length = 11
FEATURE                 Location/Qualifiers
REGION                  1..11
                        note = Synthetic
source                  1..11
                        mol_type = protein
                        organism = synthetic construct
SEQUENCE: 1511
DDQSFSSPFD Y                                                        11

SEQ ID NO: 1512         moltype = AA  length = 11
FEATURE                 Location/Qualifiers
REGION                  1..11
                        note = Synthetic
source                  1..11
                        mol_type = protein
                        organism = synthetic construct
SEQUENCE: 1512
DPQSFSSPFD Y                                                        11

SEQ ID NO: 1513         moltype = AA  length = 11
FEATURE                 Location/Qualifiers
REGION                  1..11
                        note = Synthetic
source                  1..11
                        mol_type = protein
                        organism = synthetic construct
SEQUENCE: 1513
DPQSLSSPFD Y                                                        11

SEQ ID NO: 1514         moltype = AA  length = 11
FEATURE                 Location/Qualifiers
REGION                  1..11
                        note = Synthetic
source                  1..11
                        mol_type = protein
                        organism = synthetic construct
SEQUENCE: 1514
DDQSISSPLD Y                                                        11
```

-continued

```
SEQ ID NO: 1515        moltype = AA  length = 11
FEATURE                Location/Qualifiers
REGION                 1..11
                       note = Synthetic
source                 1..11
                       mol_type = protein
                       organism = synthetic construct
SEQUENCE: 1515
DIQSVSGEFD Y                                                  11

SEQ ID NO: 1516        moltype = AA  length = 11
FEATURE                Location/Qualifiers
REGION                 1..11
                       note = Synthetic
source                 1..11
                       mol_type = protein
                       organism = synthetic construct
SEQUENCE: 1516
DPQTLTSPFD Y                                                  11

SEQ ID NO: 1517        moltype =   length =
SEQUENCE: 1517
000

SEQ ID NO: 1518        moltype = AA  length = 9
FEATURE                Location/Qualifiers
REGION                 1..9
                       note = Synthetic
source                 1..9
                       mol_type = protein
                       organism = synthetic construct
SEQUENCE: 1518
GLYDGTGNI                                                     9

SEQ ID NO: 1519        moltype =   length =
SEQUENCE: 1519
000

SEQ ID NO: 1520        moltype =   length =
SEQUENCE: 1520
000

SEQ ID NO: 1521        moltype =   length =
SEQUENCE: 1521
000

SEQ ID NO: 1522        moltype =   length =
SEQUENCE: 1522
000

SEQ ID NO: 1523        moltype =   length =
SEQUENCE: 1523
000

SEQ ID NO: 1524        moltype = AA  length = 12
FEATURE                Location/Qualifiers
REGION                 1..12
                       note = Synthetic
source                 1..12
                       mol_type = protein
                       organism = synthetic construct
SEQUENCE: 1524
DFYGWNSGAL DI                                                 12

SEQ ID NO: 1525        moltype =   length =
SEQUENCE: 1525
000

SEQ ID NO: 1526        moltype =   length =
SEQUENCE: 1526
000

SEQ ID NO: 1527        moltype =   length =
SEQUENCE: 1527
000

SEQ ID NO: 1528        moltype =   length =
SEQUENCE: 1528
000
```

```
SEQ ID NO: 1529         moltype = AA  length = 12
FEATURE                 Location/Qualifiers
REGION                  1..12
                        note = Synthetic
source                  1..12
                        mol_type = protein
                        organism = synthetic construct
SEQUENCE: 1529
DFYGWNSGAL DI                                                         12

SEQ ID NO: 1530         moltype =   length =
SEQUENCE: 1530
000

SEQ ID NO: 1531         moltype =   length =
SEQUENCE: 1531
000

SEQ ID NO: 1532         moltype =   length =
SEQUENCE: 1532
000

SEQ ID NO: 1533         moltype =   length =
SEQUENCE: 1533
000

SEQ ID NO: 1534         moltype =   length =
SEQUENCE: 1534
000

SEQ ID NO: 1535         moltype = AA  length = 9
FEATURE                 Location/Qualifiers
REGION                  1..9
                        note = Synthetic
source                  1..9
                        mol_type = protein
                        organism = synthetic construct
SEQUENCE: 1535
GLYDGTGNI                                                             9

SEQ ID NO: 1536         moltype =   length =
SEQUENCE: 1536
000

SEQ ID NO: 1537         moltype = AA  length = 9
FEATURE                 Location/Qualifiers
REGION                  1..9
                        note = Synthetic
source                  1..9
                        mol_type = protein
                        organism = synthetic construct
SEQUENCE: 1537
GLYDGTGNI                                                             9

SEQ ID NO: 1538         moltype = AA  length = 9
FEATURE                 Location/Qualifiers
REGION                  1..9
                        note = Synthetic
source                  1..9
                        mol_type = protein
                        organism = synthetic construct
SEQUENCE: 1538
GLYDGTGNI                                                             9

SEQ ID NO: 1539         moltype =   length =
SEQUENCE: 1539
000

SEQ ID NO: 1540         moltype =   length =
SEQUENCE: 1540
000

SEQ ID NO: 1541         moltype =   length =
SEQUENCE: 1541
000

SEQ ID NO: 1542         moltype =   length =
SEQUENCE: 1542
```

000

SEQ ID NO: 1543 moltype = length =
SEQUENCE: 1543
000

SEQ ID NO: 1544 moltype = length =
SEQUENCE: 1544
000

SEQ ID NO: 1545 moltype = length =
SEQUENCE: 1545
000

SEQ ID NO: 1546 moltype = length =
SEQUENCE: 1546
000

SEQ ID NO: 1547 moltype = length =
SEQUENCE: 1547
000

SEQ ID NO: 1548 moltype = length =
SEQUENCE: 1548
000

SEQ ID NO: 1549 moltype = length =
SEQUENCE: 1549
000

SEQ ID NO: 1550 moltype = length =
SEQUENCE: 1550
000

SEQ ID NO: 1551 moltype = length =
SEQUENCE: 1551
000

SEQ ID NO: 1552 moltype = length =
SEQUENCE: 1552
000

SEQ ID NO: 1553 moltype = length =
SEQUENCE: 1553
000

SEQ ID NO: 1554 moltype = length =
SEQUENCE: 1554
000

SEQ ID NO: 1555 moltype = length =
SEQUENCE: 1555
000

SEQ ID NO: 1556 moltype = length =
SEQUENCE: 1556
000

SEQ ID NO: 1557 moltype = length =
SEQUENCE: 1557
000

SEQ ID NO: 1558 moltype = length =
SEQUENCE: 1558
000

SEQ ID NO: 1559 moltype = length =
SEQUENCE: 1559
000

SEQ ID NO: 1560 moltype = length =
SEQUENCE: 1560
000

SEQ ID NO: 1561 moltype = length =
SEQUENCE: 1561
000

SEQ ID NO: 1562 moltype = length =

SEQUENCE: 1562
000

SEQ ID NO: 1563 moltype = length =
SEQUENCE: 1563
000

SEQ ID NO: 1564 moltype = length =
SEQUENCE: 1564
000

SEQ ID NO: 1565 moltype = length =
SEQUENCE: 1565
000

SEQ ID NO: 1566 moltype = length =
SEQUENCE: 1566
000

SEQ ID NO: 1567 moltype = length =
SEQUENCE: 1567
000

SEQ ID NO: 1568 moltype = length =
SEQUENCE: 1568
000

SEQ ID NO: 1569 moltype = length =
SEQUENCE: 1569
000

SEQ ID NO: 1570 moltype = length =
SEQUENCE: 1570
000

SEQ ID NO: 1571 moltype = length =
SEQUENCE: 1571
000

SEQ ID NO: 1572 moltype = length =
SEQUENCE: 1572
000

SEQ ID NO: 1573 moltype = length =
SEQUENCE: 1573
000

SEQ ID NO: 1574 moltype = length =
SEQUENCE: 1574
000

SEQ ID NO: 1575 moltype = length =
SEQUENCE: 1575
000

SEQ ID NO: 1576 moltype = length =
SEQUENCE: 1576
000

SEQ ID NO: 1577 moltype = length =
SEQUENCE: 1577
000

SEQ ID NO: 1578 moltype = length =
SEQUENCE: 1578
000

SEQ ID NO: 1579 moltype = length =
SEQUENCE: 1579
000

SEQ ID NO: 1580 moltype = length =
SEQUENCE: 1580
000

SEQ ID NO: 1581 moltype = length =
SEQUENCE: 1581
000

-continued

SEQ ID NO: 1582 moltype = length =
SEQUENCE: 1582
000

SEQ ID NO: 1583 moltype = length =
SEQUENCE: 1583
000

SEQ ID NO: 1584 moltype = length =
SEQUENCE: 1584
000

SEQ ID NO: 1585 moltype = length =
SEQUENCE: 1585
000

SEQ ID NO: 1586 moltype = length =
SEQUENCE: 1586
000

SEQ ID NO: 1587 moltype = length =
SEQUENCE: 1587
000

SEQ ID NO: 1588 moltype = length =
SEQUENCE: 1588
000

SEQ ID NO: 1589 moltype = length =
SEQUENCE: 1589
000

SEQ ID NO: 1590 moltype = length =
SEQUENCE: 1590
000

SEQ ID NO: 1591 moltype = length =
SEQUENCE: 1591
000

SEQ ID NO: 1592 moltype = length =
SEQUENCE: 1592
000

SEQ ID NO: 1593 moltype = length =
SEQUENCE: 1593
000

SEQ ID NO: 1594 moltype = length =
SEQUENCE: 1594
000

SEQ ID NO: 1595 moltype = length =
SEQUENCE: 1595
000

SEQ ID NO: 1596 moltype = length =
SEQUENCE: 1596
000

SEQ ID NO: 1597 moltype = length =
SEQUENCE: 1597
000

SEQ ID NO: 1598 moltype = length =
SEQUENCE: 1598
000

SEQ ID NO: 1599 moltype = length =
SEQUENCE: 1599
000

SEQ ID NO: 1600 moltype = length =
SEQUENCE: 1600
000

SEQ ID NO: 1601 moltype = length =
SEQUENCE: 1601
000

SEQ ID NO: 1602 moltype = length =
SEQUENCE: 1602
000

SEQ ID NO: 1603 moltype = length =
SEQUENCE: 1603
000

SEQ ID NO: 1604 moltype = length =
SEQUENCE: 1604
000

SEQ ID NO: 1605 moltype = length =
SEQUENCE: 1605
000

SEQ ID NO: 1606 moltype = length =
SEQUENCE: 1606
000

SEQ ID NO: 1607 moltype = length =
SEQUENCE: 1607
000

SEQ ID NO: 1608 moltype = length =
SEQUENCE: 1608
000

SEQ ID NO: 1609 moltype = length =
SEQUENCE: 1609
000

SEQ ID NO: 1610 moltype = length =
SEQUENCE: 1610
000

SEQ ID NO: 1611 moltype = length =
SEQUENCE: 1611
000

SEQ ID NO: 1612 moltype = length =
SEQUENCE: 1612
000

SEQ ID NO: 1613 moltype = length =
SEQUENCE: 1613
000

SEQ ID NO: 1614 moltype = length =
SEQUENCE: 1614
000

SEQ ID NO: 1615 moltype = length =
SEQUENCE: 1615
000

SEQ ID NO: 1616 moltype = length =
SEQUENCE: 1616
000

SEQ ID NO: 1617 moltype = length =
SEQUENCE: 1617
000

SEQ ID NO: 1618 moltype = length =
SEQUENCE: 1618
000

SEQ ID NO: 1619 moltype = length =
SEQUENCE: 1619
000

SEQ ID NO: 1620 moltype = length =
SEQUENCE: 1620
000

SEQ ID NO: 1621 moltype = length =
SEQUENCE: 1621

000

SEQ ID NO: 1622 moltype = length =
SEQUENCE: 1622
000

SEQ ID NO: 1623 moltype = length =
SEQUENCE: 1623
000

SEQ ID NO: 1624 moltype = length =
SEQUENCE: 1624
000

SEQ ID NO: 1625 moltype = length =
SEQUENCE: 1625
000

SEQ ID NO: 1626 moltype = length =
SEQUENCE: 1626
000

SEQ ID NO: 1627 moltype = length =
SEQUENCE: 1627
000

SEQ ID NO: 1628 moltype = length =
SEQUENCE: 1628
000

SEQ ID NO: 1629 moltype = length =
SEQUENCE: 1629
000

SEQ ID NO: 1630 moltype = length =
SEQUENCE: 1630
000

SEQ ID NO: 1631 moltype = length =
SEQUENCE: 1631
000

SEQ ID NO: 1632 moltype = length =
SEQUENCE: 1632
000

SEQ ID NO: 1633 moltype = length =
SEQUENCE: 1633
000

SEQ ID NO: 1634 moltype = length =
SEQUENCE: 1634
000

SEQ ID NO: 1635 moltype = length =
SEQUENCE: 1635
000

SEQ ID NO: 1636 moltype = length =
SEQUENCE: 1636
000

SEQ ID NO: 1637 moltype = length =
SEQUENCE: 1637
000

SEQ ID NO: 1638 moltype = length =
SEQUENCE: 1638
000

SEQ ID NO: 1639 moltype = length =
SEQUENCE: 1639
000

SEQ ID NO: 1640 moltype = length =
SEQUENCE: 1640
000

SEQ ID NO: 1641 moltype = length =

-continued

```
SEQUENCE: 1641
000

SEQ ID NO: 1642        moltype =   length =
SEQUENCE: 1642
000

SEQ ID NO: 1643        moltype =   length =
SEQUENCE: 1643
000

SEQ ID NO: 1644        moltype =   length =
SEQUENCE: 1644
000

SEQ ID NO: 1645        moltype =   length =
SEQUENCE: 1645
000

SEQ ID NO: 1646        moltype =   length =
SEQUENCE: 1646
000

SEQ ID NO: 1647        moltype =   length =
SEQUENCE: 1647
000

SEQ ID NO: 1648        moltype =   length =
SEQUENCE: 1648
000

SEQ ID NO: 1649        moltype =   length =
SEQUENCE: 1649
000

SEQ ID NO: 1650        moltype =   length =
SEQUENCE: 1650
000

SEQ ID NO: 1651        moltype =   length =
SEQUENCE: 1651
000

SEQ ID NO: 1652        moltype =   length =
SEQUENCE: 1652
000

SEQ ID NO: 1653        moltype =   length =
SEQUENCE: 1653
000

SEQ ID NO: 1654        moltype =   length =
SEQUENCE: 1654
000

SEQ ID NO: 1655        moltype =   length =
SEQUENCE: 1655
000

SEQ ID NO: 1656        moltype =   length =
SEQUENCE: 1656
000

SEQ ID NO: 1657        moltype =   length =
SEQUENCE: 1657
000

SEQ ID NO: 1658        moltype =   length =
SEQUENCE: 1658
000

SEQ ID NO: 1659        moltype =   length =
SEQUENCE: 1659
000

SEQ ID NO: 1660        moltype =   length =
SEQUENCE: 1660
000
```

SEQ ID NO: 1661 moltype = length =
SEQUENCE: 1661
000

SEQ ID NO: 1662 moltype = length =
SEQUENCE: 1662
000

SEQ ID NO: 1663 moltype = length =
SEQUENCE: 1663
000

SEQ ID NO: 1664 moltype = length =
SEQUENCE: 1664
000

SEQ ID NO: 1665 moltype = length =
SEQUENCE: 1665
000

SEQ ID NO: 1666 moltype = length =
SEQUENCE: 1666
000

SEQ ID NO: 1667 moltype = length =
SEQUENCE: 1667
000

SEQ ID NO: 1668 moltype = length =
SEQUENCE: 1668
000

SEQ ID NO: 1669 moltype = length =
SEQUENCE: 1669
000

SEQ ID NO: 1670 moltype = length =
SEQUENCE: 1670
000

SEQ ID NO: 1671 moltype = length =
SEQUENCE: 1671
000

SEQ ID NO: 1672 moltype = length =
SEQUENCE: 1672
000

SEQ ID NO: 1673 moltype = length =
SEQUENCE: 1673
000

SEQ ID NO: 1674 moltype = length =
SEQUENCE: 1674
000

SEQ ID NO: 1675 moltype = length =
SEQUENCE: 1675
000

SEQ ID NO: 1676 moltype = length =
SEQUENCE: 1676
000

SEQ ID NO: 1677 moltype = length =
SEQUENCE: 1677
000

SEQ ID NO: 1678 moltype = length =
SEQUENCE: 1678
000

SEQ ID NO: 1679 moltype = length =
SEQUENCE: 1679
000

SEQ ID NO: 1680 moltype = length =
SEQUENCE: 1680
000

SEQ ID NO: 1681 moltype = length =
SEQUENCE: 1681
000

SEQ ID NO: 1682 moltype = length =
SEQUENCE: 1682
000

SEQ ID NO: 1683 moltype = length =
SEQUENCE: 1683
000

SEQ ID NO: 1684 moltype = length =
SEQUENCE: 1684
000

SEQ ID NO: 1685 moltype = length =
SEQUENCE: 1685
000

SEQ ID NO: 1686 moltype = length =
SEQUENCE: 1686
000

SEQ ID NO: 1687 moltype = length =
SEQUENCE: 1687
000

SEQ ID NO: 1688 moltype = length =
SEQUENCE: 1688
000

SEQ ID NO: 1689 moltype = length =
SEQUENCE: 1689
000

SEQ ID NO: 1690 moltype = length =
SEQUENCE: 1690
000

SEQ ID NO: 1691 moltype = length =
SEQUENCE: 1691
000

SEQ ID NO: 1692 moltype = length =
SEQUENCE: 1692
000

SEQ ID NO: 1693 moltype = length =
SEQUENCE: 1693
000

SEQ ID NO: 1694 moltype = length =
SEQUENCE: 1694
000

SEQ ID NO: 1695 moltype = length =
SEQUENCE: 1695
000

SEQ ID NO: 1696 moltype = length =
SEQUENCE: 1696
000

SEQ ID NO: 1697 moltype = length =
SEQUENCE: 1697
000

SEQ ID NO: 1698 moltype = length =
SEQUENCE: 1698
000

SEQ ID NO: 1699 moltype = length =
SEQUENCE: 1699
000

SEQ ID NO: 1700 moltype = length =
SEQUENCE: 1700

-continued

000

SEQ ID NO: 1701 moltype = length =
SEQUENCE: 1701
000

SEQ ID NO: 1702 moltype = length =
SEQUENCE: 1702
000

SEQ ID NO: 1703 moltype = length =
SEQUENCE: 1703
000

SEQ ID NO: 1704 moltype = length =
SEQUENCE: 1704
000

SEQ ID NO: 1705 moltype = length =
SEQUENCE: 1705
000

SEQ ID NO: 1706 moltype = length =
SEQUENCE: 1706
000

SEQ ID NO: 1707 moltype = length =
SEQUENCE: 1707
000

SEQ ID NO: 1708 moltype = length =
SEQUENCE: 1708
000

SEQ ID NO: 1709 moltype = length =
SEQUENCE: 1709
000

SEQ ID NO: 1710 moltype = length =
SEQUENCE: 1710
000

SEQ ID NO: 1711 moltype = length =
SEQUENCE: 1711
000

SEQ ID NO: 1712 moltype = length =
SEQUENCE: 1712
000

SEQ ID NO: 1713 moltype = length =
SEQUENCE: 1713
000

SEQ ID NO: 1714 moltype = length =
SEQUENCE: 1714
000

SEQ ID NO: 1715 moltype = length =
SEQUENCE: 1715
000

SEQ ID NO: 1716 moltype = length =
SEQUENCE: 1716
000

SEQ ID NO: 1717 moltype = length =
SEQUENCE: 1717
000

SEQ ID NO: 1718 moltype = length =
SEQUENCE: 1718
000

SEQ ID NO: 1719 moltype = length =
SEQUENCE: 1719
000

SEQ ID NO: 1720 moltype = length =

```
SEQUENCE: 1720
000

SEQ ID NO: 1721        moltype =   length =
SEQUENCE: 1721
000

SEQ ID NO: 1722        moltype =   length =
SEQUENCE: 1722
000

SEQ ID NO: 1723        moltype =   length =
SEQUENCE: 1723
000

SEQ ID NO: 1724        moltype =   length =
SEQUENCE: 1724
000

SEQ ID NO: 1725        moltype =   length =
SEQUENCE: 1725
000

SEQ ID NO: 1726        moltype =   length =
SEQUENCE: 1726
000

SEQ ID NO: 1727        moltype =   length =
SEQUENCE: 1727
000

SEQ ID NO: 1728        moltype =   length =
SEQUENCE: 1728
000

SEQ ID NO: 1729        moltype =   length =
SEQUENCE: 1729
000

SEQ ID NO: 1730        moltype = AA  length = 12
FEATURE                Location/Qualifiers
REGION                 1..12
                       note = Synthetic
source                 1..12
                       mol_type = protein
                       organism = synthetic construct
SEQUENCE: 1730
SDYYYVDEYM DY                                                       12

SEQ ID NO: 1731        moltype =   length =
SEQUENCE: 1731
000

SEQ ID NO: 1732        moltype =   length =
SEQUENCE: 1732
000

SEQ ID NO: 1733        moltype =   length =
SEQUENCE: 1733
000

SEQ ID NO: 1734        moltype =   length =
SEQUENCE: 1734
000

SEQ ID NO: 1735        moltype =   length =
SEQUENCE: 1735
000

SEQ ID NO: 1736        moltype =   length =
SEQUENCE: 1736
000

SEQ ID NO: 1737        moltype =   length =
SEQUENCE: 1737
000

SEQ ID NO: 1738        moltype =   length =
SEQUENCE: 1738
```

-continued

```
000

SEQ ID NO: 1739        moltype = AA  length = 11
FEATURE                Location/Qualifiers
REGION                 1..11
                       note = Synthetic
source                 1..11
                       mol_type = protein
                       organism = synthetic construct
SEQUENCE: 1739
GYGSWPDYLD Y                                                      11

SEQ ID NO: 1740        moltype =   length =
SEQUENCE: 1740
000

SEQ ID NO: 1741        moltype =   length =
SEQUENCE: 1741
000

SEQ ID NO: 1742        moltype = AA  length = 11
FEATURE                Location/Qualifiers
REGION                 1..11
                       note = Synthetic
source                 1..11
                       mol_type = protein
                       organism = synthetic construct
SEQUENCE: 1742
DDQSVSSPFD Y                                                      11

SEQ ID NO: 1743        moltype =   length =
SEQUENCE: 1743
000

SEQ ID NO: 1744        moltype =   length =
SEQUENCE: 1744
000

SEQ ID NO: 1745        moltype =   length =
SEQUENCE: 1745
000

SEQ ID NO: 1746        moltype =   length =
SEQUENCE: 1746
000

SEQ ID NO: 1747        moltype =   length =
SEQUENCE: 1747
000

SEQ ID NO: 1748        moltype =   length =
SEQUENCE: 1748
000

SEQ ID NO: 1749        moltype =   length =
SEQUENCE: 1749
000

SEQ ID NO: 1750        moltype =   length =
SEQUENCE: 1750
000

SEQ ID NO: 1751        moltype =   length =
SEQUENCE: 1751
000

SEQ ID NO: 1752        moltype =   length =
SEQUENCE: 1752
000

SEQ ID NO: 1753        moltype =   length =
SEQUENCE: 1753
000

SEQ ID NO: 1754        moltype = AA  length = 12
FEATURE                Location/Qualifiers
REGION                 1..12
                       note = Synthetic
source                 1..12
```

```
                         mol_type = protein
                         organism = synthetic construct
SEQUENCE: 1754
ADYYYVDEYF DY                                                     12

SEQ ID NO: 1755          moltype = AA  length = 11
FEATURE                  Location/Qualifiers
REGION                   1..11
                         note = Synthetic
source                   1..11
                         mol_type = protein
                         organism = synthetic construct
SEQUENCE: 1755
DDQSLSSPFD Y                                                      11

SEQ ID NO: 1756          moltype = AA  length = 12
FEATURE                  Location/Qualifiers
REGION                   1..12
                         note = Synthetic
source                   1..12
                         mol_type = protein
                         organism = synthetic construct
SEQUENCE: 1756
ADYFYVDEYL DY                                                     12

SEQ ID NO: 1757          moltype = AA  length = 12
FEATURE                  Location/Qualifiers
REGION                   1..12
                         note = Synthetic
source                   1..12
                         mol_type = protein
                         organism = synthetic construct
SEQUENCE: 1757
ADYFYIDEYW DY                                                     12

SEQ ID NO: 1758          moltype = AA  length = 12
FEATURE                  Location/Qualifiers
REGION                   1..12
                         note = Synthetic
source                   1..12
                         mol_type = protein
                         organism = synthetic construct
SEQUENCE: 1758
ADYYYVDEYW DY                                                     12

SEQ ID NO: 1759          moltype = AA  length = 12
FEATURE                  Location/Qualifiers
REGION                   1..12
                         note = Synthetic
source                   1..12
                         mol_type = protein
                         organism = synthetic construct
SEQUENCE: 1759
ADYYYVDEYW DY                                                     12

SEQ ID NO: 1760          moltype = AA  length = 12
FEATURE                  Location/Qualifiers
REGION                   1..12
                         note = Synthetic
source                   1..12
                         mol_type = protein
                         organism = synthetic construct
SEQUENCE: 1760
SDYYYVDEFF DY                                                     12

SEQ ID NO: 1761          moltype = AA  length = 12
FEATURE                  Location/Qualifiers
REGION                   1..12
                         note = Synthetic
source                   1..12
                         mol_type = protein
                         organism = synthetic construct
SEQUENCE: 1761
ADYYYVDEYW DY                                                     12

SEQ ID NO: 1762          moltype = AA  length = 12
FEATURE                  Location/Qualifiers
REGION                   1..12
                         note = Synthetic
```

```
source                  1..12
                        mol_type = protein
                        organism = synthetic construct
SEQUENCE: 1762
ADYYYVDEYW DY                                                    12

SEQ ID NO: 1763         moltype = AA  length = 12
FEATURE                 Location/Qualifiers
REGION                  1..12
                        note = Synthetic
source                  1..12
                        mol_type = protein
                        organism = synthetic construct
SEQUENCE: 1763
ADYYYVDEYL DY                                                    12

SEQ ID NO: 1764         moltype = AA  length = 11
FEATURE                 Location/Qualifiers
REGION                  1..11
                        note = Synthetic
source                  1..11
                        mol_type = protein
                        organism = synthetic construct
SEQUENCE: 1764
DDQSFTSPFD Y                                                     11

SEQ ID NO: 1765         moltype = AA  length = 12
FEATURE                 Location/Qualifiers
REGION                  1..12
                        note = Synthetic
source                  1..12
                        mol_type = protein
                        organism = synthetic construct
SEQUENCE: 1765
ADYYYVDEYL DY                                                    12

SEQ ID NO: 1766         moltype = AA  length = 12
FEATURE                 Location/Qualifiers
REGION                  1..12
                        note = Synthetic
source                  1..12
                        mol_type = protein
                        organism = synthetic construct
SEQUENCE: 1766
ADYYYVDEYW DY                                                    12

SEQ ID NO: 1767         moltype = AA  length = 12
FEATURE                 Location/Qualifiers
REGION                  1..12
                        note = Synthetic
source                  1..12
                        mol_type = protein
                        organism = synthetic construct
SEQUENCE: 1767
ADYYYVDEYW DY                                                    12

SEQ ID NO: 1768         moltype = AA  length = 12
FEATURE                 Location/Qualifiers
REGION                  1..12
                        note = Synthetic
source                  1..12
                        mol_type = protein
                        organism = synthetic construct
SEQUENCE: 1768
ADYYYVDEYW DY                                                    12

SEQ ID NO: 1769         moltype = AA  length = 12
FEATURE                 Location/Qualifiers
REGION                  1..12
                        note = Synthetic
source                  1..12
                        mol_type = protein
                        organism = synthetic construct
SEQUENCE: 1769
ADYYGVDEFL DY                                                    12

SEQ ID NO: 1770         moltype = AA  length = 12
FEATURE                 Location/Qualifiers
REGION                  1..12
```

```
                        note = Synthetic
source                  1..12
                        mol_type = protein
                        organism = synthetic construct
SEQUENCE: 1770
ADYHGVDEYW DY                                                             12

SEQ ID NO: 1771         moltype = AA  length = 12
FEATURE                 Location/Qualifiers
REGION                  1..12
                        note = Synthetic
source                  1..12
                        mol_type = protein
                        organism = synthetic construct
SEQUENCE: 1771
ADYHGVDEYW DY                                                             12

SEQ ID NO: 1772         moltype = AA  length = 12
FEATURE                 Location/Qualifiers
REGION                  1..12
                        note = Synthetic
source                  1..12
                        mol_type = protein
                        organism = synthetic construct
SEQUENCE: 1772
ADYYYVDEYF DY                                                             12

SEQ ID NO: 1773         moltype = AA  length = 12
FEATURE                 Location/Qualifiers
REGION                  1..12
                        note = Synthetic
source                  1..12
                        mol_type = protein
                        organism = synthetic construct
SEQUENCE: 1773
ADYYYVDEYW DY                                                             12

SEQ ID NO: 1774         moltype = AA  length = 12
FEATURE                 Location/Qualifiers
REGION                  1..12
                        note = Synthetic
source                  1..12
                        mol_type = protein
                        organism = synthetic construct
SEQUENCE: 1774
ADYYYVDEYW DY                                                             12

SEQ ID NO: 1775         moltype = AA  length = 12
FEATURE                 Location/Qualifiers
REGION                  1..12
                        note = Synthetic
source                  1..12
                        mol_type = protein
                        organism = synthetic construct
SEQUENCE: 1775
ADYHGVDEYW DY                                                             12

SEQ ID NO: 1776         moltype = AA  length = 12
FEATURE                 Location/Qualifiers
REGION                  1..12
                        note = Synthetic
source                  1..12
                        mol_type = protein
                        organism = synthetic construct
SEQUENCE: 1776
ADYYYVDEYW DY                                                             12

SEQ ID NO: 1777         moltype = AA  length = 12
FEATURE                 Location/Qualifiers
REGION                  1..12
                        note = Synthetic
source                  1..12
                        mol_type = protein
                        organism = synthetic construct
SEQUENCE: 1777
ADYYYVDEYW DY                                                             12

SEQ ID NO: 1778         moltype = AA  length = 12
FEATURE                 Location/Qualifiers
```

```
REGION                  1..12
                        note = Synthetic
source                  1..12
                        mol_type = protein
                        organism = synthetic construct
SEQUENCE: 1778
ADYYYVDEYW DY                                                             12

SEQ ID NO: 1779         moltype = AA  length = 12
FEATURE                 Location/Qualifiers
REGION                  1..12
                        note = Synthetic
source                  1..12
                        mol_type = protein
                        organism = synthetic construct
SEQUENCE: 1779
ADYYYVDEYW DY                                                             12

SEQ ID NO: 1780         moltype = AA  length = 12
FEATURE                 Location/Qualifiers
REGION                  1..12
                        note = Synthetic
source                  1..12
                        mol_type = protein
                        organism = synthetic construct
SEQUENCE: 1780
ADYHGVDEYW DY                                                             12

SEQ ID NO: 1781         moltype = AA  length = 12
FEATURE                 Location/Qualifiers
REGION                  1..12
                        note = Synthetic
source                  1..12
                        mol_type = protein
                        organism = synthetic construct
SEQUENCE: 1781
ADYYYVDEYW DY                                                             12

SEQ ID NO: 1782         moltype = AA  length = 12
FEATURE                 Location/Qualifiers
REGION                  1..12
                        note = Synthetic
source                  1..12
                        mol_type = protein
                        organism = synthetic construct
SEQUENCE: 1782
ADYYYVDEYF DY                                                             12

SEQ ID NO: 1783         moltype = AA  length = 12
FEATURE                 Location/Qualifiers
REGION                  1..12
                        note = Synthetic
source                  1..12
                        mol_type = protein
                        organism = synthetic construct
SEQUENCE: 1783
ADYYYVDEYW DY                                                             12

SEQ ID NO: 1784         moltype = AA  length = 11
FEATURE                 Location/Qualifiers
REGION                  1..11
                        note = Synthetic
source                  1..11
                        mol_type = protein
                        organism = synthetic construct
SEQUENCE: 1784
DDQSFSSPFD Y                                                              11

SEQ ID NO: 1785         moltype = AA  length = 11
FEATURE                 Location/Qualifiers
REGION                  1..11
                        note = Synthetic
source                  1..11
                        mol_type = protein
                        organism = synthetic construct
SEQUENCE: 1785
DYGSYLVSLD Y                                                              11

SEQ ID NO: 1786         moltype = AA  length = 11
```

```
FEATURE                 Location/Qualifiers
REGION                  1..11
                        note = Synthetic
source                  1..11
                        mol_type = protein
                        organism = synthetic construct
SEQUENCE: 1786
DYGSWRIRLD Y                                                       11

SEQ ID NO: 1787         moltype = AA  length = 11
FEATURE                 Location/Qualifiers
REGION                  1..11
                        note = Synthetic
source                  1..11
                        mol_type = protein
                        organism = synthetic construct
SEQUENCE: 1787
DYGSLQVFLD Y                                                       11

SEQ ID NO: 1788         moltype = AA  length = 11
FEATURE                 Location/Qualifiers
REGION                  1..11
                        note = Synthetic
source                  1..11
                        mol_type = protein
                        organism = synthetic construct
SEQUENCE: 1788
DYGSLQVFID H                                                       11

SEQ ID NO: 1789         moltype = AA  length = 11
FEATURE                 Location/Qualifiers
REGION                  1..11
                        note = Synthetic
source                  1..11
                        mol_type = protein
                        organism = synthetic construct
SEQUENCE: 1789
DYGSLQVQLD Y                                                       11

SEQ ID NO: 1790         moltype = AA  length = 11
FEATURE                 Location/Qualifiers
REGION                  1..11
                        note = Synthetic
source                  1..11
                        mol_type = protein
                        organism = synthetic construct
SEQUENCE: 1790
DYGSLQVQLD Y                                                       11

SEQ ID NO: 1791         moltype = AA  length = 11
FEATURE                 Location/Qualifiers
REGION                  1..11
                        note = Synthetic
source                  1..11
                        mol_type = protein
                        organism = synthetic construct
SEQUENCE: 1791
DYGSLEVSLD Y                                                       11

SEQ ID NO: 1792         moltype = AA  length = 11
FEATURE                 Location/Qualifiers
REGION                  1..11
                        note = Synthetic
source                  1..11
                        mol_type = protein
                        organism = synthetic construct
SEQUENCE: 1792
DYGSLTINLD Y                                                       11

SEQ ID NO: 1793         moltype = AA  length = 11
FEATURE                 Location/Qualifiers
REGION                  1..11
                        note = Synthetic
source                  1..11
                        mol_type = protein
                        organism = synthetic construct
SEQUENCE: 1793
DYGSLEVSLD Y                                                       11
```

```
SEQ ID NO: 1794         moltype = AA  length = 11
FEATURE                 Location/Qualifiers
REGION                  1..11
                        note = Synthetic
source                  1..11
                        mol_type = protein
                        organism = synthetic construct
SEQUENCE: 1794
DYGSLEVSLD Y                                                    11

SEQ ID NO: 1795         moltype = AA  length = 11
FEATURE                 Location/Qualifiers
REGION                  1..11
                        note = Synthetic
source                  1..11
                        mol_type = protein
                        organism = synthetic construct
SEQUENCE: 1795
DYGSIQVFLD Y                                                    11

SEQ ID NO: 1796         moltype = AA  length = 11
FEATURE                 Location/Qualifiers
REGION                  1..11
                        note = Synthetic
source                  1..11
                        mol_type = protein
                        organism = synthetic construct
SEQUENCE: 1796
DYGSLQVFID Y                                                    11

SEQ ID NO: 1797         moltype = AA  length = 11
FEATURE                 Location/Qualifiers
REGION                  1..11
                        note = Synthetic
source                  1..11
                        mol_type = protein
                        organism = synthetic construct
SEQUENCE: 1797
DYGSLQVQLD Y                                                    11

SEQ ID NO: 1798         moltype = AA  length = 11
FEATURE                 Location/Qualifiers
REGION                  1..11
                        note = Synthetic
source                  1..11
                        mol_type = protein
                        organism = synthetic construct
SEQUENCE: 1798
DYGSLQVFID Y                                                    11

SEQ ID NO: 1799         moltype = AA  length = 11
FEATURE                 Location/Qualifiers
REGION                  1..11
                        note = Synthetic
source                  1..11
                        mol_type = protein
                        organism = synthetic construct
SEQUENCE: 1799
DPQSFYIAFD Y                                                    11

SEQ ID NO: 1800         moltype = AA  length = 11
FEATURE                 Location/Qualifiers
REGION                  1..11
                        note = Synthetic
source                  1..11
                        mol_type = protein
                        organism = synthetic construct
SEQUENCE: 1800
DYGSLEVSLD Y                                                    11

SEQ ID NO: 1801         moltype = AA  length = 12
FEATURE                 Location/Qualifiers
REGION                  1..12
                        note = Synthetic
source                  1..12
                        mol_type = protein
                        organism = synthetic construct
SEQUENCE: 1801
ADYYYVDEYL DY                                                   12
```

```
SEQ ID NO: 1802         moltype = AA  length = 11
FEATURE                 Location/Qualifiers
REGION                  1..11
                        note = Synthetic
source                  1..11
                        mol_type = protein
                        organism = synthetic construct
SEQUENCE: 1802
DYGSVRVFLD Y                                                   11

SEQ ID NO: 1803         moltype = AA  length = 11
FEATURE                 Location/Qualifiers
REGION                  1..11
                        note = Synthetic
source                  1..11
                        mol_type = protein
                        organism = synthetic construct
SEQUENCE: 1803
DDQSVSSPFD Y                                                   11

SEQ ID NO: 1804         moltype = AA  length = 11
FEATURE                 Location/Qualifiers
REGION                  1..11
                        note = Synthetic
source                  1..11
                        mol_type = protein
                        organism = synthetic construct
SEQUENCE: 1804
DYGSLRVSLD Y                                                   11

SEQ ID NO: 1805         moltype = AA  length = 11
FEATURE                 Location/Qualifiers
REGION                  1..11
                        note = Synthetic
source                  1..11
                        mol_type = protein
                        organism = synthetic construct
SEQUENCE: 1805
DYGSLQVFID Y                                                   11

SEQ ID NO: 1806         moltype = AA  length = 11
FEATURE                 Location/Qualifiers
REGION                  1..11
                        note = Synthetic
source                  1..11
                        mol_type = protein
                        organism = synthetic construct
SEQUENCE: 1806
DYGSFRVQLD Y                                                   11

SEQ ID NO: 1807         moltype = AA  length = 11
FEATURE                 Location/Qualifiers
REGION                  1..11
                        note = Synthetic
source                  1..11
                        mol_type = protein
                        organism = synthetic construct
SEQUENCE: 1807
DYGSLHVQLD Y                                                   11

SEQ ID NO: 1808         moltype = AA  length = 11
FEATURE                 Location/Qualifiers
REGION                  1..11
                        note = Synthetic
source                  1..11
                        mol_type = protein
                        organism = synthetic construct
SEQUENCE: 1808
DVQSVSGEFD Y                                                   11

SEQ ID NO: 1809         moltype = AA  length = 11
FEATURE                 Location/Qualifiers
REGION                  1..11
                        note = Synthetic
source                  1..11
                        mol_type = protein
                        organism = synthetic construct
SEQUENCE: 1809
```

```
DYGSLQVFID Y                                                            11

SEQ ID NO: 1810        moltype = AA  length = 11
FEATURE                Location/Qualifiers
REGION                 1..11
                       note = Synthetic
source                 1..11
                       mol_type = protein
                       organism = synthetic construct
SEQUENCE: 1810
DDQSVSSPFD Y                                                            11

SEQ ID NO: 1811        moltype = AA  length = 11
FEATURE                Location/Qualifiers
REGION                 1..11
                       note = Synthetic
source                 1..11
                       mol_type = protein
                       organism = synthetic construct
SEQUENCE: 1811
DYGSLQVFID Y                                                            11

SEQ ID NO: 1812        moltype = AA  length = 11
FEATURE                Location/Qualifiers
REGION                 1..11
                       note = Synthetic
source                 1..11
                       mol_type = protein
                       organism = synthetic construct
SEQUENCE: 1812
DYGSLQVFID Y                                                            11

SEQ ID NO: 1813        moltype = AA  length = 11
FEATURE                Location/Qualifiers
REGION                 1..11
                       note = Synthetic
source                 1..11
                       mol_type = protein
                       organism = synthetic construct
SEQUENCE: 1813
DDQSLSSPFD Y                                                            11

SEQ ID NO: 1814        moltype = AA  length = 11
FEATURE                Location/Qualifiers
REGION                 1..11
                       note = Synthetic
source                 1..11
                       mol_type = protein
                       organism = synthetic construct
SEQUENCE: 1814
DPQSISSPFD Y                                                            11

SEQ ID NO: 1815        moltype = AA  length = 11
FEATURE                Location/Qualifiers
REGION                 1..11
                       note = Synthetic
source                 1..11
                       mol_type = protein
                       organism = synthetic construct
SEQUENCE: 1815
DPQSVSSPFD Y                                                            11

SEQ ID NO: 1816        moltype = AA  length = 11
FEATURE                Location/Qualifiers
REGION                 1..11
                       note = Synthetic
source                 1..11
                       mol_type = protein
                       organism = synthetic construct
SEQUENCE: 1816
DDQSLSSPFD Y                                                            11

SEQ ID NO: 1817        moltype = AA  length = 11
FEATURE                Location/Qualifiers
REGION                 1..11
                       note = Synthetic
source                 1..11
                       mol_type = protein
                       organism = synthetic construct
```

```
SEQUENCE: 1817
DDQSISSPLD Y                                                    11

SEQ ID NO: 1818        moltype = AA  length = 11
FEATURE                Location/Qualifiers
REGION                 1..11
                       note = Synthetic
source                 1..11
                       mol_type = protein
                       organism = synthetic construct
SEQUENCE: 1818
DPQSLFYPFD Y                                                    11

SEQ ID NO: 1819        moltype = AA  length = 11
FEATURE                Location/Qualifiers
REGION                 1..11
                       note = Synthetic
source                 1..11
                       mol_type = protein
                       organism = synthetic construct
SEQUENCE: 1819
DDQSLSSPFD Y                                                    11

SEQ ID NO: 1820        moltype = AA  length = 11
FEATURE                Location/Qualifiers
REGION                 1..11
                       note = Synthetic
source                 1..11
                       mol_type = protein
                       organism = synthetic construct
SEQUENCE: 1820
DIQSVSGEFD Y                                                    11

SEQ ID NO: 1821        moltype = AA  length = 11
FEATURE                Location/Qualifiers
REGION                 1..11
                       note = Synthetic
source                 1..11
                       mol_type = protein
                       organism = synthetic construct
SEQUENCE: 1821
DDQSVSSPFE Y                                                    11

SEQ ID NO: 1822        moltype = AA  length = 11
FEATURE                Location/Qualifiers
REGION                 1..11
                       note = Synthetic
source                 1..11
                       mol_type = protein
                       organism = synthetic construct
SEQUENCE: 1822
DPQSLSSPFD Y                                                    11

SEQ ID NO: 1823        moltype = AA  length = 11
FEATURE                Location/Qualifiers
REGION                 1..11
                       note = Synthetic
source                 1..11
                       mol_type = protein
                       organism = synthetic construct
SEQUENCE: 1823
DPQSLSSPFD Y                                                    11

SEQ ID NO: 1824        moltype = AA  length = 11
FEATURE                Location/Qualifiers
REGION                 1..11
                       note = Synthetic
source                 1..11
                       mol_type = protein
                       organism = synthetic construct
SEQUENCE: 1824
DDQSLSSPFD Y                                                    11

SEQ ID NO: 1825        moltype = AA  length = 11
FEATURE                Location/Qualifiers
REGION                 1..11
                       note = Synthetic
source                 1..11
                       mol_type = protein
```

```
                        organism = synthetic construct
SEQUENCE: 1825
DDQSLSSPFD Y                                                11

SEQ ID NO: 1826         moltype = AA  length = 11
FEATURE                 Location/Qualifiers
REGION                  1..11
                        note = Synthetic
source                  1..11
                        mol_type = protein
                        organism = synthetic construct
SEQUENCE: 1826
DPQSLTSPFD Y                                                11

SEQ ID NO: 1827         moltype = AA  length = 11
FEATURE                 Location/Qualifiers
REGION                  1..11
                        note = Synthetic
source                  1..11
                        mol_type = protein
                        organism = synthetic construct
SEQUENCE: 1827
DIQSVSGEFD Y                                                11

SEQ ID NO: 1828         moltype = AA  length = 11
FEATURE                 Location/Qualifiers
REGION                  1..11
                        note = Synthetic
source                  1..11
                        mol_type = protein
                        organism = synthetic construct
SEQUENCE: 1828
DPQSLTSPFD Y                                                11

SEQ ID NO: 1829         moltype = AA  length = 11
FEATURE                 Location/Qualifiers
REGION                  1..11
                        note = Synthetic
source                  1..11
                        mol_type = protein
                        organism = synthetic construct
SEQUENCE: 1829
DIQSVSGEFD Y                                                11

SEQ ID NO: 1830         moltype = AA  length = 11
FEATURE                 Location/Qualifiers
REGION                  1..11
                        note = Synthetic
source                  1..11
                        mol_type = protein
                        organism = synthetic construct
SEQUENCE: 1830
DIQSVSGEFD Y                                                11

SEQ ID NO: 1831         moltype = AA  length = 11
FEATURE                 Location/Qualifiers
REGION                  1..11
                        note = Synthetic
source                  1..11
                        mol_type = protein
                        organism = synthetic construct
SEQUENCE: 1831
DPQSVGSEFD Y                                                11

SEQ ID NO: 1832         moltype = AA  length = 11
FEATURE                 Location/Qualifiers
REGION                  1..11
                        note = Synthetic
source                  1..11
                        mol_type = protein
                        organism = synthetic construct
SEQUENCE: 1832
DIQSVSGEFD Y                                                11

SEQ ID NO: 1833         moltype = AA  length = 11
FEATURE                 Location/Qualifiers
REGION                  1..11
                        note = Synthetic
source                  1..11
```

```
                          mol_type = protein
                          organism = synthetic construct
SEQUENCE: 1833
DPQSLSSPFD Y                                                  11

SEQ ID NO: 1834           moltype = AA  length = 11
FEATURE                   Location/Qualifiers
REGION                    1..11
                          note = Synthetic
source                    1..11
                          mol_type = protein
                          organism = synthetic construct
SEQUENCE: 1834
DIQSVSGEFD Y                                                  11

SEQ ID NO: 1835           moltype = AA  length = 11
FEATURE                   Location/Qualifiers
REGION                    1..11
                          note = Synthetic
source                    1..11
                          mol_type = protein
                          organism = synthetic construct
SEQUENCE: 1835
DIQSVSGEFD Y                                                  11

SEQ ID NO: 1836           moltype = AA  length = 11
FEATURE                   Location/Qualifiers
REGION                    1..11
                          note = Synthetic
source                    1..11
                          mol_type = protein
                          organism = synthetic construct
SEQUENCE: 1836
DDQSFSSPFD Y                                                  11

SEQ ID NO: 1837           moltype = AA  length = 11
FEATURE                   Location/Qualifiers
REGION                    1..11
                          note = Synthetic
source                    1..11
                          mol_type = protein
                          organism = synthetic construct
SEQUENCE: 1837
DPQSFSSPFD Y                                                  11

SEQ ID NO: 1838           moltype = AA  length = 11
FEATURE                   Location/Qualifiers
REGION                    1..11
                          note = Synthetic
source                    1..11
                          mol_type = protein
                          organism = synthetic construct
SEQUENCE: 1838
DPQSLSSPFD Y                                                  11

SEQ ID NO: 1839           moltype = AA  length = 11
FEATURE                   Location/Qualifiers
REGION                    1..11
                          note = Synthetic
source                    1..11
                          mol_type = protein
                          organism = synthetic construct
SEQUENCE: 1839
DDQSISSPLD Y                                                  11

SEQ ID NO: 1840           moltype = AA  length = 11
FEATURE                   Location/Qualifiers
REGION                    1..11
                          note = Synthetic
source                    1..11
                          mol_type = protein
                          organism = synthetic construct
SEQUENCE: 1840
DIQSVSGEFD Y                                                  11

SEQ ID NO: 1841           moltype = AA  length = 11
FEATURE                   Location/Qualifiers
REGION                    1..11
                          note = Synthetic
```

```
source                 1..11
                       mol_type = protein
                       organism = synthetic construct
SEQUENCE: 1841
DPQTLTSPFD Y                                                   11

SEQ ID NO: 1842        moltype =   length =
SEQUENCE: 1842
000

SEQ ID NO: 1843        moltype = AA  length = 9
FEATURE                Location/Qualifiers
REGION                 1..9
                       note = Synthetic
source                 1..9
                       mol_type = protein
                       organism = synthetic construct
SEQUENCE: 1843
GLYDGTGNI                                                      9

SEQ ID NO: 1844        moltype =   length =
SEQUENCE: 1844
000

SEQ ID NO: 1845        moltype =   length =
SEQUENCE: 1845
000

SEQ ID NO: 1846        moltype =   length =
SEQUENCE: 1846
000

SEQ ID NO: 1847        moltype =   length =
SEQUENCE: 1847
000

SEQ ID NO: 1848        moltype =   length =
SEQUENCE: 1848
000

SEQ ID NO: 1849        moltype = AA  length = 4
FEATURE                Location/Qualifiers
REGION                 1..4
                       note = Synthetic
source                 1..4
                       mol_type = protein
                       organism = synthetic construct
SEQUENCE: 1849
DFYG                                                           4

SEQ ID NO: 1850        moltype =   length =
SEQUENCE: 1850
000

SEQ ID NO: 1851        moltype =   length =
SEQUENCE: 1851
000

SEQ ID NO: 1852        moltype =   length =
SEQUENCE: 1852
000

SEQ ID NO: 1853        moltype =   length =
SEQUENCE: 1853
000

SEQ ID NO: 1854        moltype = AA  length = 12
FEATURE                Location/Qualifiers
REGION                 1..12
                       note = Synthetic
source                 1..12
                       mol_type = protein
                       organism = synthetic construct
SEQUENCE: 1854
DFYGWNSGAL DI                                                  12

SEQ ID NO: 1855        moltype =   length =
SEQUENCE: 1855
000
```

```
SEQ ID NO: 1856        moltype =   length =
SEQUENCE: 1856
000

SEQ ID NO: 1857        moltype =   length =
SEQUENCE: 1857
000

SEQ ID NO: 1858        moltype =   length =
SEQUENCE: 1858
000

SEQ ID NO: 1859        moltype =   length =
SEQUENCE: 1859
000

SEQ ID NO: 1860        moltype = AA  length = 9
FEATURE                Location/Qualifiers
REGION                 1..9
                       note = Synthetic
source                 1..9
                       mol_type = protein
                       organism = synthetic construct
SEQUENCE: 1860
GLYDGTGNI                                                  9

SEQ ID NO: 1861        moltype =   length =
SEQUENCE: 1861
000

SEQ ID NO: 1862        moltype = AA  length = 9
FEATURE                Location/Qualifiers
REGION                 1..9
                       note = Synthetic
source                 1..9
                       mol_type = protein
                       organism = synthetic construct
SEQUENCE: 1862
GLYDGTGNI                                                  9

SEQ ID NO: 1863        moltype = AA  length = 9
FEATURE                Location/Qualifiers
REGION                 1..9
                       note = Synthetic
source                 1..9
                       mol_type = protein
                       organism = synthetic construct
SEQUENCE: 1863
GLYDGTGNI                                                  9

SEQ ID NO: 1864        moltype =   length =
SEQUENCE: 1864
000

SEQ ID NO: 1865        moltype =   length =
SEQUENCE: 1865
000

SEQ ID NO: 1866        moltype =   length =
SEQUENCE: 1866
000

SEQ ID NO: 1867        moltype =   length =
SEQUENCE: 1867
000

SEQ ID NO: 1868        moltype =   length =
SEQUENCE: 1868
000

SEQ ID NO: 1869        moltype =   length =
SEQUENCE: 1869
000

SEQ ID NO: 1870        moltype =   length =
SEQUENCE: 1870
000
```

-continued

SEQ ID NO: 1871 moltype = length =
SEQUENCE: 1871
000

SEQ ID NO: 1872 moltype = length =
SEQUENCE: 1872
000

SEQ ID NO: 1873 moltype = length =
SEQUENCE: 1873
000

SEQ ID NO: 1874 moltype = length =
SEQUENCE: 1874
000

SEQ ID NO: 1875 moltype = length =
SEQUENCE: 1875
000

SEQ ID NO: 1876 moltype = length =
SEQUENCE: 1876
000

SEQ ID NO: 1877 moltype = length =
SEQUENCE: 1877
000

SEQ ID NO: 1878 moltype = length =
SEQUENCE: 1878
000

SEQ ID NO: 1879 moltype = length =
SEQUENCE: 1879
000

SEQ ID NO: 1880 moltype = length =
SEQUENCE: 1880
000

SEQ ID NO: 1881 moltype = length =
SEQUENCE: 1881
000

SEQ ID NO: 1882 moltype = length =
SEQUENCE: 1882
000

SEQ ID NO: 1883 moltype = length =
SEQUENCE: 1883
000

SEQ ID NO: 1884 moltype = length =
SEQUENCE: 1884
000

SEQ ID NO: 1885 moltype = length =
SEQUENCE: 1885
000

SEQ ID NO: 1886 moltype = length =
SEQUENCE: 1886
000

SEQ ID NO: 1887 moltype = length =
SEQUENCE: 1887
000

SEQ ID NO: 1888 moltype = length =
SEQUENCE: 1888
000

SEQ ID NO: 1889 moltype = length =
SEQUENCE: 1889
000

SEQ ID NO: 1890 moltype = length =
SEQUENCE: 1890
000

-continued

SEQ ID NO: 1891 moltype = length =
SEQUENCE: 1891
000

SEQ ID NO: 1892 moltype = length =
SEQUENCE: 1892
000

SEQ ID NO: 1893 moltype = length =
SEQUENCE: 1893
000

SEQ ID NO: 1894 moltype = length =
SEQUENCE: 1894
000

SEQ ID NO: 1895 moltype = length =
SEQUENCE: 1895
000

SEQ ID NO: 1896 moltype = length =
SEQUENCE: 1896
000

SEQ ID NO: 1897 moltype = length =
SEQUENCE: 1897
000

SEQ ID NO: 1898 moltype = length =
SEQUENCE: 1898
000

SEQ ID NO: 1899 moltype = length =
SEQUENCE: 1899
000

SEQ ID NO: 1900 moltype = length =
SEQUENCE: 1900
000

SEQ ID NO: 1901 moltype = length =
SEQUENCE: 1901
000

SEQ ID NO: 1902 moltype = length =
SEQUENCE: 1902
000

SEQ ID NO: 1903 moltype = length =
SEQUENCE: 1903
000

SEQ ID NO: 1904 moltype = length =
SEQUENCE: 1904
000

SEQ ID NO: 1905 moltype = length =
SEQUENCE: 1905
000

SEQ ID NO: 1906 moltype = length =
SEQUENCE: 1906
000

SEQ ID NO: 1907 moltype = length =
SEQUENCE: 1907
000

SEQ ID NO: 1908 moltype = length =
SEQUENCE: 1908
000

SEQ ID NO: 1909 moltype = length =
SEQUENCE: 1909
000

SEQ ID NO: 1910 moltype = length =
SEQUENCE: 1910

-continued

000

SEQ ID NO: 1911 moltype = length =
SEQUENCE: 1911
000

SEQ ID NO: 1912 moltype = length =
SEQUENCE: 1912
000

SEQ ID NO: 1913 moltype = length =
SEQUENCE: 1913
000

SEQ ID NO: 1914 moltype = length =
SEQUENCE: 1914
000

SEQ ID NO: 1915 moltype = length =
SEQUENCE: 1915
000

SEQ ID NO: 1916 moltype = length =
SEQUENCE: 1916
000

SEQ ID NO: 1917 moltype = length =
SEQUENCE: 1917
000

SEQ ID NO: 1918 moltype = length =
SEQUENCE: 1918
000

SEQ ID NO: 1919 moltype = length =
SEQUENCE: 1919
000

SEQ ID NO: 1920 moltype = length =
SEQUENCE: 1920
000

SEQ ID NO: 1921 moltype = length =
SEQUENCE: 1921
000

SEQ ID NO: 1922 moltype = length =
SEQUENCE: 1922
000

SEQ ID NO: 1923 moltype = length =
SEQUENCE: 1923
000

SEQ ID NO: 1924 moltype = length =
SEQUENCE: 1924
000

SEQ ID NO: 1925 moltype = length =
SEQUENCE: 1925
000

SEQ ID NO: 1926 moltype = length =
SEQUENCE: 1926
000

SEQ ID NO: 1927 moltype = length =
SEQUENCE: 1927
000

SEQ ID NO: 1928 moltype = length =
SEQUENCE: 1928
000

SEQ ID NO: 1929 moltype = length =
SEQUENCE: 1929
000

SEQ ID NO: 1930 moltype = length =

SEQUENCE: 1930
000

SEQ ID NO: 1931 moltype = length =
SEQUENCE: 1931
000

SEQ ID NO: 1932 moltype = length =
SEQUENCE: 1932
000

SEQ ID NO: 1933 moltype = length =
SEQUENCE: 1933
000

SEQ ID NO: 1934 moltype = length =
SEQUENCE: 1934
000

SEQ ID NO: 1935 moltype = length =
SEQUENCE: 1935
000

SEQ ID NO: 1936 moltype = length =
SEQUENCE: 1936
000

SEQ ID NO: 1937 moltype = length =
SEQUENCE: 1937
000

SEQ ID NO: 1938 moltype = length =
SEQUENCE: 1938
000

SEQ ID NO: 1939 moltype = length =
SEQUENCE: 1939
000

SEQ ID NO: 1940 moltype = length =
SEQUENCE: 1940
000

SEQ ID NO: 1941 moltype = length =
SEQUENCE: 1941
000

SEQ ID NO: 1942 moltype = length =
SEQUENCE: 1942
000

SEQ ID NO: 1943 moltype = length =
SEQUENCE: 1943
000

SEQ ID NO: 1944 moltype = length =
SEQUENCE: 1944
000

SEQ ID NO: 1945 moltype = length =
SEQUENCE: 1945
000

SEQ ID NO: 1946 moltype = length =
SEQUENCE: 1946
000

SEQ ID NO: 1947 moltype = length =
SEQUENCE: 1947
000

SEQ ID NO: 1948 moltype = length =
SEQUENCE: 1948
000

SEQ ID NO: 1949 moltype = length =
SEQUENCE: 1949
000

-continued

```
SEQ ID NO: 1950        moltype =   length =
SEQUENCE: 1950
000

SEQ ID NO: 1951        moltype =   length =
SEQUENCE: 1951
000

SEQ ID NO: 1952        moltype =   length =
SEQUENCE: 1952
000

SEQ ID NO: 1953        moltype =   length =
SEQUENCE: 1953
000

SEQ ID NO: 1954        moltype = AA  length = 13
FEATURE                Location/Qualifiers
REGION                 1..13
                       note = Synthetic
source                 1..13
                       mol_type = protein
                       organism = synthetic construct
SEQUENCE: 1954
QASQSVYGNN WLS                                                    13

SEQ ID NO: 1955        moltype =   length =
SEQUENCE: 1955
000

SEQ ID NO: 1956        moltype =   length =
SEQUENCE: 1956
000

SEQ ID NO: 1957        moltype =   length =
SEQUENCE: 1957
000

SEQ ID NO: 1958        moltype =   length =
SEQUENCE: 1958
000

SEQ ID NO: 1959        moltype =   length =
SEQUENCE: 1959
000

SEQ ID NO: 1960        moltype = AA  length = 13
FEATURE                Location/Qualifiers
REGION                 1..13
                       note = Synthetic
source                 1..13
                       mol_type = protein
                       organism = synthetic construct
SEQUENCE: 1960
QASQSVYSNK YLS                                                    13

SEQ ID NO: 1961        moltype =   length =
SEQUENCE: 1961
000

SEQ ID NO: 1962        moltype =   length =
SEQUENCE: 1962
000

SEQ ID NO: 1963        moltype =   length =
SEQUENCE: 1963
000

SEQ ID NO: 1964        moltype =   length =
SEQUENCE: 1964
000

SEQ ID NO: 1965        moltype = AA  length = 13
FEATURE                Location/Qualifiers
REGION                 1..13
                       note = Synthetic
source                 1..13
                       mol_type = protein
                       organism = synthetic construct
```

```
SEQUENCE: 1965
RASQSVYSNK YLS                                               13

SEQ ID NO: 1966        moltype =   length =
SEQUENCE: 1966
000

SEQ ID NO: 1967        moltype =   length =
SEQUENCE: 1967
000

SEQ ID NO: 1968        moltype =   length =
SEQUENCE: 1968
000

SEQ ID NO: 1969        moltype =   length =
SEQUENCE: 1969
000

SEQ ID NO: 1970        moltype =   length =
SEQUENCE: 1970
000

SEQ ID NO: 1971        moltype = AA  length = 13
FEATURE                Location/Qualifiers
REGION                 1..13
                       note = Synthetic
source                 1..13
                       mol_type = protein
                       organism = synthetic construct
SEQUENCE: 1971
RASQSVYGNN WLS                                               13

SEQ ID NO: 1972        moltype =   length =
SEQUENCE: 1972
000

SEQ ID NO: 1973        moltype = AA  length = 13
FEATURE                Location/Qualifiers
REGION                 1..13
                       note = Synthetic
source                 1..13
                       mol_type = protein
                       organism = synthetic construct
SEQUENCE: 1973
RASQSVYGNN WLS                                               13

SEQ ID NO: 1974        moltype = AA  length = 13
FEATURE                Location/Qualifiers
REGION                 1..13
                       note = Synthetic
source                 1..13
                       mol_type = protein
                       organism = synthetic construct
SEQUENCE: 1974
QASQSVYGNN WLS                                               13

SEQ ID NO: 1975        moltype =   length =
SEQUENCE: 1975
000

SEQ ID NO: 1976        moltype =   length =
SEQUENCE: 1976
000

SEQ ID NO: 1977        moltype =   length =
SEQUENCE: 1977
000

SEQ ID NO: 1978        moltype =   length =
SEQUENCE: 1978
000

SEQ ID NO: 1979        moltype =   length =
SEQUENCE: 1979
000

SEQ ID NO: 1980        moltype =   length =
SEQUENCE: 1980
```

000

SEQ ID NO: 1981 moltype = length =
SEQUENCE: 1981
000

SEQ ID NO: 1982 moltype = length =
SEQUENCE: 1982
000

SEQ ID NO: 1983 moltype = length =
SEQUENCE: 1983
000

SEQ ID NO: 1984 moltype = length =
SEQUENCE: 1984
000

SEQ ID NO: 1985 moltype = length =
SEQUENCE: 1985
000

SEQ ID NO: 1986 moltype = length =
SEQUENCE: 1986
000

SEQ ID NO: 1987 moltype = length =
SEQUENCE: 1987
000

SEQ ID NO: 1988 moltype = length =
SEQUENCE: 1988
000

SEQ ID NO: 1989 moltype = length =
SEQUENCE: 1989
000

SEQ ID NO: 1990 moltype = length =
SEQUENCE: 1990
000

SEQ ID NO: 1991 moltype = length =
SEQUENCE: 1991
000

SEQ ID NO: 1992 moltype = length =
SEQUENCE: 1992
000

SEQ ID NO: 1993 moltype = length =
SEQUENCE: 1993
000

SEQ ID NO: 1994 moltype = length =
SEQUENCE: 1994
000

SEQ ID NO: 1995 moltype = length =
SEQUENCE: 1995
000

SEQ ID NO: 1996 moltype = length =
SEQUENCE: 1996
000

SEQ ID NO: 1997 moltype = length =
SEQUENCE: 1997
000

SEQ ID NO: 1998 moltype = length =
SEQUENCE: 1998
000

SEQ ID NO: 1999 moltype = length =
SEQUENCE: 1999
000

SEQ ID NO: 2000 moltype = length =

-continued

SEQUENCE: 2000
000

SEQ ID NO: 2001 moltype = length =
SEQUENCE: 2001
000

SEQ ID NO: 2002 moltype = length =
SEQUENCE: 2002
000

SEQ ID NO: 2003 moltype = length =
SEQUENCE: 2003
000

SEQ ID NO: 2004 moltype = length =
SEQUENCE: 2004
000

SEQ ID NO: 2005 moltype = length =
SEQUENCE: 2005
000

SEQ ID NO: 2006 moltype = length =
SEQUENCE: 2006
000

SEQ ID NO: 2007 moltype = length =
SEQUENCE: 2007
000

SEQ ID NO: 2008 moltype = length =
SEQUENCE: 2008
000

SEQ ID NO: 2009 moltype = length =
SEQUENCE: 2009
000

SEQ ID NO: 2010 moltype = length =
SEQUENCE: 2010
000

SEQ ID NO: 2011 moltype = length =
SEQUENCE: 2011
000

SEQ ID NO: 2012 moltype = length =
SEQUENCE: 2012
000

SEQ ID NO: 2013 moltype = length =
SEQUENCE: 2013
000

SEQ ID NO: 2014 moltype = length =
SEQUENCE: 2014
000

SEQ ID NO: 2015 moltype = length =
SEQUENCE: 2015
000

SEQ ID NO: 2016 moltype = length =
SEQUENCE: 2016
000

SEQ ID NO: 2017 moltype = length =
SEQUENCE: 2017
000

SEQ ID NO: 2018 moltype = length =
SEQUENCE: 2018
000

SEQ ID NO: 2019 moltype = length =
SEQUENCE: 2019
000

-continued

SEQ ID NO: 2020 moltype = length =
SEQUENCE: 2020
000

SEQ ID NO: 2021 moltype = length =
SEQUENCE: 2021
000

SEQ ID NO: 2022 moltype = length =
SEQUENCE: 2022
000

SEQ ID NO: 2023 moltype = length =
SEQUENCE: 2023
000

SEQ ID NO: 2024 moltype = length =
SEQUENCE: 2024
000

SEQ ID NO: 2025 moltype = length =
SEQUENCE: 2025
000

SEQ ID NO: 2026 moltype = length =
SEQUENCE: 2026
000

SEQ ID NO: 2027 moltype = length =
SEQUENCE: 2027
000

SEQ ID NO: 2028 moltype = length =
SEQUENCE: 2028
000

SEQ ID NO: 2029 moltype = length =
SEQUENCE: 2029
000

SEQ ID NO: 2030 moltype = length =
SEQUENCE: 2030
000

SEQ ID NO: 2031 moltype = length =
SEQUENCE: 2031
000

SEQ ID NO: 2032 moltype = length =
SEQUENCE: 2032
000

SEQ ID NO: 2033 moltype = length =
SEQUENCE: 2033
000

SEQ ID NO: 2034 moltype = length =
SEQUENCE: 2034
000

SEQ ID NO: 2035 moltype = length =
SEQUENCE: 2035
000

SEQ ID NO: 2036 moltype = length =
SEQUENCE: 2036
000

SEQ ID NO: 2037 moltype = length =
SEQUENCE: 2037
000

SEQ ID NO: 2038 moltype = length =
SEQUENCE: 2038
000

SEQ ID NO: 2039 moltype = length =
SEQUENCE: 2039
000

SEQ ID NO: 2040 moltype = length =
SEQUENCE: 2040
000

SEQ ID NO: 2041 moltype = length =
SEQUENCE: 2041
000

SEQ ID NO: 2042 moltype = length =
SEQUENCE: 2042
000

SEQ ID NO: 2043 moltype = length =
SEQUENCE: 2043
000

SEQ ID NO: 2044 moltype = length =
SEQUENCE: 2044
000

SEQ ID NO: 2045 moltype = length =
SEQUENCE: 2045
000

SEQ ID NO: 2046 moltype = length =
SEQUENCE: 2046
000

SEQ ID NO: 2047 moltype = length =
SEQUENCE: 2047
000

SEQ ID NO: 2048 moltype = length =
SEQUENCE: 2048
000

SEQ ID NO: 2049 moltype = length =
SEQUENCE: 2049
000

SEQ ID NO: 2050 moltype = length =
SEQUENCE: 2050
000

SEQ ID NO: 2051 moltype = length =
SEQUENCE: 2051
000

SEQ ID NO: 2052 moltype = length =
SEQUENCE: 2052
000

SEQ ID NO: 2053 moltype = length =
SEQUENCE: 2053
000

SEQ ID NO: 2054 moltype = length =
SEQUENCE: 2054
000

SEQ ID NO: 2055 moltype = length =
SEQUENCE: 2055
000

SEQ ID NO: 2056 moltype = length =
SEQUENCE: 2056
000

SEQ ID NO: 2057 moltype = length =
SEQUENCE: 2057
000

SEQ ID NO: 2058 moltype = length =
SEQUENCE: 2058
000

SEQ ID NO: 2059 moltype = length =
SEQUENCE: 2059

000

SEQ ID NO: 2060 moltype = length =
SEQUENCE: 2060
000

SEQ ID NO: 2061 moltype = length =
SEQUENCE: 2061
000

SEQ ID NO: 2062 moltype = length =
SEQUENCE: 2062
000

SEQ ID NO: 2063 moltype = length =
SEQUENCE: 2063
000

SEQ ID NO: 2064 moltype = AA length = 11
FEATURE Location/Qualifiers
REGION 1..11
note = Synthetic
source 1..11
mol_type = protein
organism = synthetic construct
SEQUENCE: 2064
RASQDVNTAV A 11

SEQ ID NO: 2065 moltype = length =
SEQUENCE: 2065
000

SEQ ID NO: 2066 moltype = AA length = 13
FEATURE Location/Qualifiers
REGION 1..13
note = Synthetic
source 1..13
mol_type = protein
organism = synthetic construct
SEQUENCE: 2066
QASQSVYGNN WLS 13

SEQ ID NO: 2067 moltype = length =
SEQUENCE: 2067
000

SEQ ID NO: 2068 moltype = length =
SEQUENCE: 2068
000

SEQ ID NO: 2069 moltype = length =
SEQUENCE: 2069
000

SEQ ID NO: 2070 moltype = length =
SEQUENCE: 2070
000

SEQ ID NO: 2071 moltype = length =
SEQUENCE: 2071
000

SEQ ID NO: 2072 moltype = AA length = 13
FEATURE Location/Qualifiers
REGION 1..13
note = Synthetic
source 1..13
mol_type = protein
organism = synthetic construct
SEQUENCE: 2072
QASQSVYSNK YLS 13

SEQ ID NO: 2073 moltype = length =
SEQUENCE: 2073
000

SEQ ID NO: 2074 moltype = length =
SEQUENCE: 2074
000

```
SEQ ID NO: 2075        moltype =   length =
SEQUENCE: 2075
000

SEQ ID NO: 2076        moltype =   length =
SEQUENCE: 2076
000

SEQ ID NO: 2077        moltype = AA  length = 13
FEATURE                Location/Qualifiers
REGION                 1..13
                       note = Synthetic
source                 1..13
                       mol_type = protein
                       organism = synthetic construct
SEQUENCE: 2077
RASQSVYSNK YLS                                                     13

SEQ ID NO: 2078        moltype =   length =
SEQUENCE: 2078
000

SEQ ID NO: 2079        moltype =   length =
SEQUENCE: 2079
000

SEQ ID NO: 2080        moltype =   length =
SEQUENCE: 2080
000

SEQ ID NO: 2081        moltype =   length =
SEQUENCE: 2081
000

SEQ ID NO: 2082        moltype =   length =
SEQUENCE: 2082
000

SEQ ID NO: 2083        moltype = AA  length = 13
FEATURE                Location/Qualifiers
REGION                 1..13
                       note = Synthetic
source                 1..13
                       mol_type = protein
                       organism = synthetic construct
SEQUENCE: 2083
RASQSVYGNN WLS                                                     13

SEQ ID NO: 2084        moltype =   length =
SEQUENCE: 2084
000

SEQ ID NO: 2085        moltype = AA  length = 13
FEATURE                Location/Qualifiers
REGION                 1..13
                       note = Synthetic
source                 1..13
                       mol_type = protein
                       organism = synthetic construct
SEQUENCE: 2085
RASQSVYGNN WLS                                                     13

SEQ ID NO: 2086        moltype = AA  length = 13
FEATURE                Location/Qualifiers
REGION                 1..13
                       note = Synthetic
source                 1..13
                       mol_type = protein
                       organism = synthetic construct
SEQUENCE: 2086
QASQSVYGNN WLS                                                     13

SEQ ID NO: 2087        moltype =   length =
SEQUENCE: 2087
000

SEQ ID NO: 2088        moltype =   length =
SEQUENCE: 2088
```

000

SEQ ID NO: 2089 moltype = length =
SEQUENCE: 2089
000

SEQ ID NO: 2090 moltype = length =
SEQUENCE: 2090
000

SEQ ID NO: 2091 moltype = length =
SEQUENCE: 2091
000

SEQ ID NO: 2092 moltype = length =
SEQUENCE: 2092
000

SEQ ID NO: 2093 moltype = length =
SEQUENCE: 2093
000

SEQ ID NO: 2094 moltype = length =
SEQUENCE: 2094
000

SEQ ID NO: 2095 moltype = length =
SEQUENCE: 2095
000

SEQ ID NO: 2096 moltype = length =
SEQUENCE: 2096
000

SEQ ID NO: 2097 moltype = length =
SEQUENCE: 2097
000

SEQ ID NO: 2098 moltype = length =
SEQUENCE: 2098
000

SEQ ID NO: 2099 moltype = length =
SEQUENCE: 2099
000

SEQ ID NO: 2100 moltype = length =
SEQUENCE: 2100
000

SEQ ID NO: 2101 moltype = length =
SEQUENCE: 2101
000

SEQ ID NO: 2102 moltype = length =
SEQUENCE: 2102
000

SEQ ID NO: 2103 moltype = length =
SEQUENCE: 2103
000

SEQ ID NO: 2104 moltype = length =
SEQUENCE: 2104
000

SEQ ID NO: 2105 moltype = length =
SEQUENCE: 2105
000

SEQ ID NO: 2106 moltype = length =
SEQUENCE: 2106
000

SEQ ID NO: 2107 moltype = length =
SEQUENCE: 2107
000

SEQ ID NO: 2108 moltype = length =

SEQUENCE: 2108
000

SEQ ID NO: 2109 moltype = length =
SEQUENCE: 2109
000

SEQ ID NO: 2110 moltype = length =
SEQUENCE: 2110
000

SEQ ID NO: 2111 moltype = length =
SEQUENCE: 2111
000

SEQ ID NO: 2112 moltype = length =
SEQUENCE: 2112
000

SEQ ID NO: 2113 moltype = length =
SEQUENCE: 2113
000

SEQ ID NO: 2114 moltype = length =
SEQUENCE: 2114
000

SEQ ID NO: 2115 moltype = length =
SEQUENCE: 2115
000

SEQ ID NO: 2116 moltype = length =
SEQUENCE: 2116
000

SEQ ID NO: 2117 moltype = length =
SEQUENCE: 2117
000

SEQ ID NO: 2118 moltype = length =
SEQUENCE: 2118
000

SEQ ID NO: 2119 moltype = length =
SEQUENCE: 2119
000

SEQ ID NO: 2120 moltype = length =
SEQUENCE: 2120
000

SEQ ID NO: 2121 moltype = length =
SEQUENCE: 2121
000

SEQ ID NO: 2122 moltype = length =
SEQUENCE: 2122
000

SEQ ID NO: 2123 moltype = length =
SEQUENCE: 2123
000

SEQ ID NO: 2124 moltype = length =
SEQUENCE: 2124
000

SEQ ID NO: 2125 moltype = length =
SEQUENCE: 2125
000

SEQ ID NO: 2126 moltype = length =
SEQUENCE: 2126
000

SEQ ID NO: 2127 moltype = length =
SEQUENCE: 2127
000

-continued

SEQ ID NO: 2128 moltype = length =
SEQUENCE: 2128
000

SEQ ID NO: 2129 moltype = length =
SEQUENCE: 2129
000

SEQ ID NO: 2130 moltype = length =
SEQUENCE: 2130
000

SEQ ID NO: 2131 moltype = length =
SEQUENCE: 2131
000

SEQ ID NO: 2132 moltype = length =
SEQUENCE: 2132
000

SEQ ID NO: 2133 moltype = length =
SEQUENCE: 2133
000

SEQ ID NO: 2134 moltype = length =
SEQUENCE: 2134
000

SEQ ID NO: 2135 moltype = length =
SEQUENCE: 2135
000

SEQ ID NO: 2136 moltype = length =
SEQUENCE: 2136
000

SEQ ID NO: 2137 moltype = length =
SEQUENCE: 2137
000

SEQ ID NO: 2138 moltype = length =
SEQUENCE: 2138
000

SEQ ID NO: 2139 moltype = length =
SEQUENCE: 2139
000

SEQ ID NO: 2140 moltype = length =
SEQUENCE: 2140
000

SEQ ID NO: 2141 moltype = length =
SEQUENCE: 2141
000

SEQ ID NO: 2142 moltype = length =
SEQUENCE: 2142
000

SEQ ID NO: 2143 moltype = length =
SEQUENCE: 2143
000

SEQ ID NO: 2144 moltype = length =
SEQUENCE: 2144
000

SEQ ID NO: 2145 moltype = length =
SEQUENCE: 2145
000

SEQ ID NO: 2146 moltype = length =
SEQUENCE: 2146
000

SEQ ID NO: 2147 moltype = length =
SEQUENCE: 2147
000

SEQ ID NO: 2148 moltype = length =
SEQUENCE: 2148
000

SEQ ID NO: 2149 moltype = length =
SEQUENCE: 2149
000

SEQ ID NO: 2150 moltype = length =
SEQUENCE: 2150
000

SEQ ID NO: 2151 moltype = length =
SEQUENCE: 2151
000

SEQ ID NO: 2152 moltype = length =
SEQUENCE: 2152
000

SEQ ID NO: 2153 moltype = length =
SEQUENCE: 2153
000

SEQ ID NO: 2154 moltype = length =
SEQUENCE: 2154
000

SEQ ID NO: 2155 moltype = length =
SEQUENCE: 2155
000

SEQ ID NO: 2156 moltype = length =
SEQUENCE: 2156
000

SEQ ID NO: 2157 moltype = length =
SEQUENCE: 2157
000

SEQ ID NO: 2158 moltype = length =
SEQUENCE: 2158
000

SEQ ID NO: 2159 moltype = length =
SEQUENCE: 2159
000

SEQ ID NO: 2160 moltype = length =
SEQUENCE: 2160
000

SEQ ID NO: 2161 moltype = length =
SEQUENCE: 2161
000

SEQ ID NO: 2162 moltype = length =
SEQUENCE: 2162
000

SEQ ID NO: 2163 moltype = length =
SEQUENCE: 2163
000

SEQ ID NO: 2164 moltype = length =
SEQUENCE: 2164
000

SEQ ID NO: 2165 moltype = length =
SEQUENCE: 2165
000

SEQ ID NO: 2166 moltype = length =
SEQUENCE: 2166
000

SEQ ID NO: 2167 moltype = length =
SEQUENCE: 2167

```
000

SEQ ID NO: 2168        moltype =   length =
SEQUENCE: 2168
000

SEQ ID NO: 2169        moltype =   length =
SEQUENCE: 2169
000

SEQ ID NO: 2170        moltype =   length =
SEQUENCE: 2170
000

SEQ ID NO: 2171        moltype =   length =
SEQUENCE: 2171
000

SEQ ID NO: 2172        moltype =   length =
SEQUENCE: 2172
000

SEQ ID NO: 2173        moltype =   length =
SEQUENCE: 2173
000

SEQ ID NO: 2174        moltype =   length =
SEQUENCE: 2174
000

SEQ ID NO: 2175        moltype =   length =
SEQUENCE: 2175
000

SEQ ID NO: 2176        moltype = AA  length = 11
FEATURE                Location/Qualifiers
REGION                 1..11
                       note = Synthetic
source                 1..11
                       mol_type = protein
                       organism = synthetic construct
SEQUENCE: 2176
RASQDVNTAV A                                                      11

SEQ ID NO: 2177        moltype =   length =
SEQUENCE: 2177
000

SEQ ID NO: 2178        moltype = AA  length = 7
FEATURE                Location/Qualifiers
REGION                 1..7
                       note = Synthetic
source                 1..7
                       mol_type = protein
                       organism = synthetic construct
SEQUENCE: 2178
GASKLAS                                                           7

SEQ ID NO: 2179        moltype =   length =
SEQUENCE: 2179
000

SEQ ID NO: 2180        moltype =   length =
SEQUENCE: 2180
000

SEQ ID NO: 2181        moltype =   length =
SEQUENCE: 2181
000

SEQ ID NO: 2182        moltype =   length =
SEQUENCE: 2182
000

SEQ ID NO: 2183        moltype =   length =
SEQUENCE: 2183
000

SEQ ID NO: 2184        moltype = AA  length = 7
```

```
FEATURE                 Location/Qualifiers
REGION                  1..7
                        note = Synthetic
source                  1..7
                        mol_type = protein
                        organism = synthetic construct
SEQUENCE: 2184
KASTLAS                                                                     7

SEQ ID NO: 2185         moltype =   length =
SEQUENCE: 2185
000

SEQ ID NO: 2186         moltype =   length =
SEQUENCE: 2186
000

SEQ ID NO: 2187         moltype =   length =
SEQUENCE: 2187
000

SEQ ID NO: 2188         moltype =   length =
SEQUENCE: 2188
000

SEQ ID NO: 2189         moltype = AA  length = 7
FEATURE                 Location/Qualifiers
REGION                  1..7
                        note = Synthetic
source                  1..7
                        mol_type = protein
                        organism = synthetic construct
SEQUENCE: 2189
KASTLAS                                                                     7

SEQ ID NO: 2190         moltype =   length =
SEQUENCE: 2190
000

SEQ ID NO: 2191         moltype =   length =
SEQUENCE: 2191
000

SEQ ID NO: 2192         moltype =   length =
SEQUENCE: 2192
000

SEQ ID NO: 2193         moltype =   length =
SEQUENCE: 2193
000

SEQ ID NO: 2194         moltype =   length =
SEQUENCE: 2194
000

SEQ ID NO: 2195         moltype = AA  length = 7
FEATURE                 Location/Qualifiers
REGION                  1..7
                        note = Synthetic
source                  1..7
                        mol_type = protein
                        organism = synthetic construct
SEQUENCE: 2195
GASKLAS                                                                     7

SEQ ID NO: 2196         moltype =   length =
SEQUENCE: 2196
000

SEQ ID NO: 2197         moltype = AA  length = 7
FEATURE                 Location/Qualifiers
REGION                  1..7
                        note = Synthetic
source                  1..7
                        mol_type = protein
                        organism = synthetic construct
SEQUENCE: 2197
GASKLAT                                                                     7
```

```
SEQ ID NO: 2198         moltype = AA  length = 7
FEATURE                 Location/Qualifiers
REGION                  1..7
                        note = Synthetic
source                  1..7
                        mol_type = protein
                        organism = synthetic construct
SEQUENCE: 2198
GASKLAS                                                                    7

SEQ ID NO: 2199         moltype =   length =
SEQUENCE: 2199
000

SEQ ID NO: 2200         moltype =   length =
SEQUENCE: 2200
000

SEQ ID NO: 2201         moltype =   length =
SEQUENCE: 2201
000

SEQ ID NO: 2202         moltype =   length =
SEQUENCE: 2202
000

SEQ ID NO: 2203         moltype =   length =
SEQUENCE: 2203
000

SEQ ID NO: 2204         moltype =   length =
SEQUENCE: 2204
000

SEQ ID NO: 2205         moltype =   length =
SEQUENCE: 2205
000

SEQ ID NO: 2206         moltype =   length =
SEQUENCE: 2206
000

SEQ ID NO: 2207         moltype =   length =
SEQUENCE: 2207
000

SEQ ID NO: 2208         moltype =   length =
SEQUENCE: 2208
000

SEQ ID NO: 2209         moltype =   length =
SEQUENCE: 2209
000

SEQ ID NO: 2210         moltype =   length =
SEQUENCE: 2210
000

SEQ ID NO: 2211         moltype =   length =
SEQUENCE: 2211
000

SEQ ID NO: 2212         moltype =   length =
SEQUENCE: 2212
000

SEQ ID NO: 2213         moltype =   length =
SEQUENCE: 2213
000

SEQ ID NO: 2214         moltype =   length =
SEQUENCE: 2214
000

SEQ ID NO: 2215         moltype =   length =
SEQUENCE: 2215
000

SEQ ID NO: 2216         moltype =   length =
```

SEQUENCE: 2216
000

SEQ ID NO: 2217 moltype = length =
SEQUENCE: 2217
000

SEQ ID NO: 2218 moltype = length =
SEQUENCE: 2218
000

SEQ ID NO: 2219 moltype = length =
SEQUENCE: 2219
000

SEQ ID NO: 2220 moltype = length =
SEQUENCE: 2220
000

SEQ ID NO: 2221 moltype = length =
SEQUENCE: 2221
000

SEQ ID NO: 2222 moltype = length =
SEQUENCE: 2222
000

SEQ ID NO: 2223 moltype = length =
SEQUENCE: 2223
000

SEQ ID NO: 2224 moltype = length =
SEQUENCE: 2224
000

SEQ ID NO: 2225 moltype = length =
SEQUENCE: 2225
000

SEQ ID NO: 2226 moltype = length =
SEQUENCE: 2226
000

SEQ ID NO: 2227 moltype = length =
SEQUENCE: 2227
000

SEQ ID NO: 2228 moltype = length =
SEQUENCE: 2228
000

SEQ ID NO: 2229 moltype = length =
SEQUENCE: 2229
000

SEQ ID NO: 2230 moltype = length =
SEQUENCE: 2230
000

SEQ ID NO: 2231 moltype = length =
SEQUENCE: 2231
000

SEQ ID NO: 2232 moltype = length =
SEQUENCE: 2232
000

SEQ ID NO: 2233 moltype = length =
SEQUENCE: 2233
000

SEQ ID NO: 2234 moltype = length =
SEQUENCE: 2234
000

SEQ ID NO: 2235 moltype = length =
SEQUENCE: 2235
000

-continued

SEQ ID NO: 2236 moltype = length =
SEQUENCE: 2236
000

SEQ ID NO: 2237 moltype = length =
SEQUENCE: 2237
000

SEQ ID NO: 2238 moltype = length =
SEQUENCE: 2238
000

SEQ ID NO: 2239 moltype = length =
SEQUENCE: 2239
000

SEQ ID NO: 2240 moltype = length =
SEQUENCE: 2240
000

SEQ ID NO: 2241 moltype = length =
SEQUENCE: 2241
000

SEQ ID NO: 2242 moltype = length =
SEQUENCE: 2242
000

SEQ ID NO: 2243 moltype = length =
SEQUENCE: 2243
000

SEQ ID NO: 2244 moltype = length =
SEQUENCE: 2244
000

SEQ ID NO: 2245 moltype = length =
SEQUENCE: 2245
000

SEQ ID NO: 2246 moltype = length =
SEQUENCE: 2246
000

SEQ ID NO: 2247 moltype = length =
SEQUENCE: 2247
000

SEQ ID NO: 2248 moltype = length =
SEQUENCE: 2248
000

SEQ ID NO: 2249 moltype = length =
SEQUENCE: 2249
000

SEQ ID NO: 2250 moltype = length =
SEQUENCE: 2250
000

SEQ ID NO: 2251 moltype = length =
SEQUENCE: 2251
000

SEQ ID NO: 2252 moltype = length =
SEQUENCE: 2252
000

SEQ ID NO: 2253 moltype = length =
SEQUENCE: 2253
000

SEQ ID NO: 2254 moltype = length =
SEQUENCE: 2254
000

SEQ ID NO: 2255 moltype = length =
SEQUENCE: 2255
000

-continued

SEQ ID NO: 2256 moltype = length =
SEQUENCE: 2256
000

SEQ ID NO: 2257 moltype = length =
SEQUENCE: 2257
000

SEQ ID NO: 2258 moltype = length =
SEQUENCE: 2258
000

SEQ ID NO: 2259 moltype = length =
SEQUENCE: 2259
000

SEQ ID NO: 2260 moltype = length =
SEQUENCE: 2260
000

SEQ ID NO: 2261 moltype = length =
SEQUENCE: 2261
000

SEQ ID NO: 2262 moltype = length =
SEQUENCE: 2262
000

SEQ ID NO: 2263 moltype = length =
SEQUENCE: 2263
000

SEQ ID NO: 2264 moltype = length =
SEQUENCE: 2264
000

SEQ ID NO: 2265 moltype = length =
SEQUENCE: 2265
000

SEQ ID NO: 2266 moltype = length =
SEQUENCE: 2266
000

SEQ ID NO: 2267 moltype = length =
SEQUENCE: 2267
000

SEQ ID NO: 2268 moltype = length =
SEQUENCE: 2268
000

SEQ ID NO: 2269 moltype = length =
SEQUENCE: 2269
000

SEQ ID NO: 2270 moltype = length =
SEQUENCE: 2270
000

SEQ ID NO: 2271 moltype = length =
SEQUENCE: 2271
000

SEQ ID NO: 2272 moltype = length =
SEQUENCE: 2272
000

SEQ ID NO: 2273 moltype = length =
SEQUENCE: 2273
000

SEQ ID NO: 2274 moltype = length =
SEQUENCE: 2274
000

SEQ ID NO: 2275 moltype = length =
SEQUENCE: 2275

```
000

SEQ ID NO: 2276        moltype =   length =
SEQUENCE: 2276
000

SEQ ID NO: 2277        moltype =   length =
SEQUENCE: 2277
000

SEQ ID NO: 2278        moltype =   length =
SEQUENCE: 2278
000

SEQ ID NO: 2279        moltype =   length =
SEQUENCE: 2279
000

SEQ ID NO: 2280        moltype =   length =
SEQUENCE: 2280
000

SEQ ID NO: 2281        moltype =   length =
SEQUENCE: 2281
000

SEQ ID NO: 2282        moltype =   length =
SEQUENCE: 2282
000

SEQ ID NO: 2283        moltype =   length =
SEQUENCE: 2283
000

SEQ ID NO: 2284        moltype =   length =
SEQUENCE: 2284
000

SEQ ID NO: 2285        moltype =   length =
SEQUENCE: 2285
000

SEQ ID NO: 2286        moltype =   length =
SEQUENCE: 2286
000

SEQ ID NO: 2287        moltype =   length =
SEQUENCE: 2287
000

SEQ ID NO: 2288        moltype = AA  length = 7
FEATURE                Location/Qualifiers
REGION                 1..7
                       note = Synthetic
source                 1..7
                       mol_type = protein
                       organism = synthetic construct
SEQUENCE: 2288
SASFLYS                                                                7

SEQ ID NO: 2289        moltype =   length =
SEQUENCE: 2289
000

SEQ ID NO: 2290        moltype = AA  length = 7
FEATURE                Location/Qualifiers
REGION                 1..7
                       note = Synthetic
source                 1..7
                       mol_type = protein
                       organism = synthetic construct
SEQUENCE: 2290
GASKLAS                                                                7

SEQ ID NO: 2291        moltype =   length =
SEQUENCE: 2291
000

SEQ ID NO: 2292        moltype =   length =
```

SEQUENCE: 2292
000

SEQ ID NO: 2293 moltype = length =
SEQUENCE: 2293
000

SEQ ID NO: 2294 moltype = length =
SEQUENCE: 2294
000

SEQ ID NO: 2295 moltype = length =
SEQUENCE: 2295
000

SEQ ID NO: 2296 moltype = AA length = 7
FEATURE Location/Qualifiers
REGION 1..7
note = Synthetic
source 1..7
mol_type = protein
organism = synthetic construct
SEQUENCE: 2296
KASTLAS 7

SEQ ID NO: 2297 moltype = length =
SEQUENCE: 2297
000

SEQ ID NO: 2298 moltype = length =
SEQUENCE: 2298
000

SEQ ID NO: 2299 moltype = length =
SEQUENCE: 2299
000

SEQ ID NO: 2300 moltype = length =
SEQUENCE: 2300
000

SEQ ID NO: 2301 moltype = AA length = 7
FEATURE Location/Qualifiers
REGION 1..7
note = Synthetic
source 1..7
mol_type = protein
organism = synthetic construct
SEQUENCE: 2301
KASTLAS 7

SEQ ID NO: 2302 moltype = length =
SEQUENCE: 2302
000

SEQ ID NO: 2303 moltype = length =
SEQUENCE: 2303
000

SEQ ID NO: 2304 moltype = length =
SEQUENCE: 2304
000

SEQ ID NO: 2305 moltype = length =
SEQUENCE: 2305
000

SEQ ID NO: 2306 moltype = length =
SEQUENCE: 2306
000

SEQ ID NO: 2307 moltype = AA length = 7
FEATURE Location/Qualifiers
REGION 1..7
note = Synthetic
source 1..7
mol_type = protein
organism = synthetic construct
SEQUENCE: 2307

```
GASKLAS                                                                 7

SEQ ID NO: 2308       moltype =   length =
SEQUENCE: 2308
000

SEQ ID NO: 2309       moltype = AA  length = 7
FEATURE               Location/Qualifiers
REGION                1..7
                      note = Synthetic
source                1..7
                      mol_type = protein
                      organism = synthetic construct
SEQUENCE: 2309
GASKLAT                                                                 7

SEQ ID NO: 2310       moltype = AA  length = 7
FEATURE               Location/Qualifiers
REGION                1..7
                      note = Synthetic
source                1..7
                      mol_type = protein
                      organism = synthetic construct
SEQUENCE: 2310
GASKLAS                                                                 7

SEQ ID NO: 2311       moltype =   length =
SEQUENCE: 2311
000

SEQ ID NO: 2312       moltype =   length =
SEQUENCE: 2312
000

SEQ ID NO: 2313       moltype =   length =
SEQUENCE: 2313
000

SEQ ID NO: 2314       moltype =   length =
SEQUENCE: 2314
000

SEQ ID NO: 2315       moltype =   length =
SEQUENCE: 2315
000

SEQ ID NO: 2316       moltype =   length =
SEQUENCE: 2316
000

SEQ ID NO: 2317       moltype =   length =
SEQUENCE: 2317
000

SEQ ID NO: 2318       moltype =   length =
SEQUENCE: 2318
000

SEQ ID NO: 2319       moltype =   length =
SEQUENCE: 2319
000

SEQ ID NO: 2320       moltype =   length =
SEQUENCE: 2320
000

SEQ ID NO: 2321       moltype =   length =
SEQUENCE: 2321
000

SEQ ID NO: 2322       moltype =   length =
SEQUENCE: 2322
000

SEQ ID NO: 2323       moltype =   length =
SEQUENCE: 2323
000

SEQ ID NO: 2324       moltype =   length =
```

-continued

SEQUENCE: 2324
000

SEQ ID NO: 2325 moltype = length =
SEQUENCE: 2325
000

SEQ ID NO: 2326 moltype = length =
SEQUENCE: 2326
000

SEQ ID NO: 2327 moltype = length =
SEQUENCE: 2327
000

SEQ ID NO: 2328 moltype = length =
SEQUENCE: 2328
000

SEQ ID NO: 2329 moltype = length =
SEQUENCE: 2329
000

SEQ ID NO: 2330 moltype = length =
SEQUENCE: 2330
000

SEQ ID NO: 2331 moltype = length =
SEQUENCE: 2331
000

SEQ ID NO: 2332 moltype = length =
SEQUENCE: 2332
000

SEQ ID NO: 2333 moltype = length =
SEQUENCE: 2333
000

SEQ ID NO: 2334 moltype = length =
SEQUENCE: 2334
000

SEQ ID NO: 2335 moltype = length =
SEQUENCE: 2335
000

SEQ ID NO: 2336 moltype = length =
SEQUENCE: 2336
000

SEQ ID NO: 2337 moltype = length =
SEQUENCE: 2337
000

SEQ ID NO: 2338 moltype = length =
SEQUENCE: 2338
000

SEQ ID NO: 2339 moltype = length =
SEQUENCE: 2339
000

SEQ ID NO: 2340 moltype = length =
SEQUENCE: 2340
000

SEQ ID NO: 2341 moltype = length =
SEQUENCE: 2341
000

SEQ ID NO: 2342 moltype = length =
SEQUENCE: 2342
000

SEQ ID NO: 2343 moltype = length =
SEQUENCE: 2343
000

-continued

SEQ ID NO: 2344 moltype = length =
SEQUENCE: 2344
000

SEQ ID NO: 2345 moltype = length =
SEQUENCE: 2345
000

SEQ ID NO: 2346 moltype = length =
SEQUENCE: 2346
000

SEQ ID NO: 2347 moltype = length =
SEQUENCE: 2347
000

SEQ ID NO: 2348 moltype = length =
SEQUENCE: 2348
000

SEQ ID NO: 2349 moltype = length =
SEQUENCE: 2349
000

SEQ ID NO: 2350 moltype = length =
SEQUENCE: 2350
000

SEQ ID NO: 2351 moltype = length =
SEQUENCE: 2351
000

SEQ ID NO: 2352 moltype = length =
SEQUENCE: 2352
000

SEQ ID NO: 2353 moltype = length =
SEQUENCE: 2353
000

SEQ ID NO: 2354 moltype = length =
SEQUENCE: 2354
000

SEQ ID NO: 2355 moltype = length =
SEQUENCE: 2355
000

SEQ ID NO: 2356 moltype = length =
SEQUENCE: 2356
000

SEQ ID NO: 2357 moltype = length =
SEQUENCE: 2357
000

SEQ ID NO: 2358 moltype = length =
SEQUENCE: 2358
000

SEQ ID NO: 2359 moltype = length =
SEQUENCE: 2359
000

SEQ ID NO: 2360 moltype = length =
SEQUENCE: 2360
000

SEQ ID NO: 2361 moltype = length =
SEQUENCE: 2361
000

SEQ ID NO: 2362 moltype = length =
SEQUENCE: 2362
000

SEQ ID NO: 2363 moltype = length =
SEQUENCE: 2363
000

SEQ ID NO: 2364 moltype = length =
SEQUENCE: 2364
000

SEQ ID NO: 2365 moltype = length =
SEQUENCE: 2365
000

SEQ ID NO: 2366 moltype = length =
SEQUENCE: 2366
000

SEQ ID NO: 2367 moltype = length =
SEQUENCE: 2367
000

SEQ ID NO: 2368 moltype = length =
SEQUENCE: 2368
000

SEQ ID NO: 2369 moltype = length =
SEQUENCE: 2369
000

SEQ ID NO: 2370 moltype = length =
SEQUENCE: 2370
000

SEQ ID NO: 2371 moltype = length =
SEQUENCE: 2371
000

SEQ ID NO: 2372 moltype = length =
SEQUENCE: 2372
000

SEQ ID NO: 2373 moltype = length =
SEQUENCE: 2373
000

SEQ ID NO: 2374 moltype = length =
SEQUENCE: 2374
000

SEQ ID NO: 2375 moltype = length =
SEQUENCE: 2375
000

SEQ ID NO: 2376 moltype = length =
SEQUENCE: 2376
000

SEQ ID NO: 2377 moltype = length =
SEQUENCE: 2377
000

SEQ ID NO: 2378 moltype = length =
SEQUENCE: 2378
000

SEQ ID NO: 2379 moltype = length =
SEQUENCE: 2379
000

SEQ ID NO: 2380 moltype = length =
SEQUENCE: 2380
000

SEQ ID NO: 2381 moltype = length =
SEQUENCE: 2381
000

SEQ ID NO: 2382 moltype = length =
SEQUENCE: 2382
000

SEQ ID NO: 2383 moltype = length =
SEQUENCE: 2383

```
000

SEQ ID NO: 2384        moltype =   length =
SEQUENCE: 2384
000

SEQ ID NO: 2385        moltype =   length =
SEQUENCE: 2385
000

SEQ ID NO: 2386        moltype =   length =
SEQUENCE: 2386
000

SEQ ID NO: 2387        moltype =   length =
SEQUENCE: 2387
000

SEQ ID NO: 2388        moltype =   length =
SEQUENCE: 2388
000

SEQ ID NO: 2389        moltype =   length =
SEQUENCE: 2389
000

SEQ ID NO: 2390        moltype =   length =
SEQUENCE: 2390
000

SEQ ID NO: 2391        moltype =   length =
SEQUENCE: 2391
000

SEQ ID NO: 2392        moltype =   length =
SEQUENCE: 2392
000

SEQ ID NO: 2393        moltype =   length =
SEQUENCE: 2393
000

SEQ ID NO: 2394        moltype =   length =
SEQUENCE: 2394
000

SEQ ID NO: 2395        moltype =   length =
SEQUENCE: 2395
000

SEQ ID NO: 2396        moltype =   length =
SEQUENCE: 2396
000

SEQ ID NO: 2397        moltype =   length =
SEQUENCE: 2397
000

SEQ ID NO: 2398        moltype =   length =
SEQUENCE: 2398
000

SEQ ID NO: 2399        moltype =   length =
SEQUENCE: 2399
000

SEQ ID NO: 2400        moltype = AA  length = 7
FEATURE                Location/Qualifiers
REGION                 1..7
                       note = Synthetic
source                 1..7
                       mol_type = protein
                       organism = synthetic construct
SEQUENCE: 2400
SASFLYS                                                        7

SEQ ID NO: 2401        moltype =   length =
SEQUENCE: 2401
000
```

-continued

```
SEQ ID NO: 2402        moltype = AA  length = 12
FEATURE                Location/Qualifiers
REGION                 1..12
                       note = Synthetic
source                 1..12
                       mol_type = protein
                       organism = synthetic construct
SEQUENCE: 2402
QGTYYSGDWY FA                                                     12

SEQ ID NO: 2403        moltype =   length =
SEQUENCE: 2403
000

SEQ ID NO: 2404        moltype =   length =
SEQUENCE: 2404
000

SEQ ID NO: 2405        moltype =   length =
SEQUENCE: 2405
000

SEQ ID NO: 2406        moltype =   length =
SEQUENCE: 2406
000

SEQ ID NO: 2407        moltype =   length =
SEQUENCE: 2407
000

SEQ ID NO: 2408        moltype = AA  length = 11
FEATURE                Location/Qualifiers
REGION                 1..11
                       note = Synthetic
source                 1..11
                       mol_type = protein
                       organism = synthetic construct
SEQUENCE: 2408
AAAYSDDSDT A                                                      11

SEQ ID NO: 2409        moltype =   length =
SEQUENCE: 2409
000

SEQ ID NO: 2410        moltype =   length =
SEQUENCE: 2410
000

SEQ ID NO: 2411        moltype =   length =
SEQUENCE: 2411
000

SEQ ID NO: 2412        moltype =   length =
SEQUENCE: 2412
000

SEQ ID NO: 2413        moltype = AA  length = 11
FEATURE                Location/Qualifiers
REGION                 1..11
                       note = Synthetic
source                 1..11
                       mol_type = protein
                       organism = synthetic construct
SEQUENCE: 2413
AAAYSDDSDT A                                                      11

SEQ ID NO: 2414        moltype =   length =
SEQUENCE: 2414
000

SEQ ID NO: 2415        moltype =   length =
SEQUENCE: 2415
000

SEQ ID NO: 2416        moltype =   length =
SEQUENCE: 2416
000
```

```
SEQ ID NO: 2417        moltype =   length =
SEQUENCE: 2417
000

SEQ ID NO: 2418        moltype =   length =
SEQUENCE: 2418
000

SEQ ID NO: 2419        moltype = AA  length = 12
FEATURE                Location/Qualifiers
REGION                 1..12
                       note = Synthetic
source                 1..12
                       mol_type = protein
                       organism = synthetic construct
SEQUENCE: 2419
QGTYYSGDWY FA                                                         12

SEQ ID NO: 2420        moltype =   length =
SEQUENCE: 2420
000

SEQ ID NO: 2421        moltype = AA  length = 12
FEATURE                Location/Qualifiers
REGION                 1..12
                       note = Synthetic
source                 1..12
                       mol_type = protein
                       organism = synthetic construct
SEQUENCE: 2421
QGTYYSGDWY FA                                                         12

SEQ ID NO: 2422        moltype = AA  length = 12
FEATURE                Location/Qualifiers
REGION                 1..12
                       note = Synthetic
source                 1..12
                       mol_type = protein
                       organism = synthetic construct
SEQUENCE: 2422
QGTYYSGDWY FA                                                         12

SEQ ID NO: 2423        moltype =   length =
SEQUENCE: 2423
000

SEQ ID NO: 2424        moltype =   length =
SEQUENCE: 2424
000

SEQ ID NO: 2425        moltype =   length =
SEQUENCE: 2425
000

SEQ ID NO: 2426        moltype =   length =
SEQUENCE: 2426
000

SEQ ID NO: 2427        moltype =   length =
SEQUENCE: 2427
000

SEQ ID NO: 2428        moltype =   length =
SEQUENCE: 2428
000

SEQ ID NO: 2429        moltype =   length =
SEQUENCE: 2429
000

SEQ ID NO: 2430        moltype =   length =
SEQUENCE: 2430
000

SEQ ID NO: 2431        moltype =   length =
SEQUENCE: 2431
000

SEQ ID NO: 2432        moltype =   length =
```

SEQUENCE: 2432
000

SEQ ID NO: 2433 moltype = length =
SEQUENCE: 2433
000

SEQ ID NO: 2434 moltype = length =
SEQUENCE: 2434
000

SEQ ID NO: 2435 moltype = length =
SEQUENCE: 2435
000

SEQ ID NO: 2436 moltype = length =
SEQUENCE: 2436
000

SEQ ID NO: 2437 moltype = length =
SEQUENCE: 2437
000

SEQ ID NO: 2438 moltype = length =
SEQUENCE: 2438
000

SEQ ID NO: 2439 moltype = length =
SEQUENCE: 2439
000

SEQ ID NO: 2440 moltype = length =
SEQUENCE: 2440
000

SEQ ID NO: 2441 moltype = length =
SEQUENCE: 2441
000

SEQ ID NO: 2442 moltype = length =
SEQUENCE: 2442
000

SEQ ID NO: 2443 moltype = length =
SEQUENCE: 2443
000

SEQ ID NO: 2444 moltype = length =
SEQUENCE: 2444
000

SEQ ID NO: 2445 moltype = length =
SEQUENCE: 2445
000

SEQ ID NO: 2446 moltype = length =
SEQUENCE: 2446
000

SEQ ID NO: 2447 moltype = length =
SEQUENCE: 2447
000

SEQ ID NO: 2448 moltype = length =
SEQUENCE: 2448
000

SEQ ID NO: 2449 moltype = length =
SEQUENCE: 2449
000

SEQ ID NO: 2450 moltype = length =
SEQUENCE: 2450
000

SEQ ID NO: 2451 moltype = length =
SEQUENCE: 2451
000

-continued

SEQ ID NO: 2452 moltype = length =
SEQUENCE: 2452
000

SEQ ID NO: 2453 moltype = length =
SEQUENCE: 2453
000

SEQ ID NO: 2454 moltype = length =
SEQUENCE: 2454
000

SEQ ID NO: 2455 moltype = length =
SEQUENCE: 2455
000

SEQ ID NO: 2456 moltype = length =
SEQUENCE: 2456
000

SEQ ID NO: 2457 moltype = length =
SEQUENCE: 2457
000

SEQ ID NO: 2458 moltype = length =
SEQUENCE: 2458
000

SEQ ID NO: 2459 moltype = length =
SEQUENCE: 2459
000

SEQ ID NO: 2460 moltype = length =
SEQUENCE: 2460
000

SEQ ID NO: 2461 moltype = length =
SEQUENCE: 2461
000

SEQ ID NO: 2462 moltype = length =
SEQUENCE: 2462
000

SEQ ID NO: 2463 moltype = length =
SEQUENCE: 2463
000

SEQ ID NO: 2464 moltype = length =
SEQUENCE: 2464
000

SEQ ID NO: 2465 moltype = length =
SEQUENCE: 2465
000

SEQ ID NO: 2466 moltype = length =
SEQUENCE: 2466
000

SEQ ID NO: 2467 moltype = length =
SEQUENCE: 2467
000

SEQ ID NO: 2468 moltype = length =
SEQUENCE: 2468
000

SEQ ID NO: 2469 moltype = length =
SEQUENCE: 2469
000

SEQ ID NO: 2470 moltype = length =
SEQUENCE: 2470
000

SEQ ID NO: 2471 moltype = length =
SEQUENCE: 2471
000

-continued

SEQ ID NO: 2472 moltype = length =
SEQUENCE: 2472
000

SEQ ID NO: 2473 moltype = length =
SEQUENCE: 2473
000

SEQ ID NO: 2474 moltype = length =
SEQUENCE: 2474
000

SEQ ID NO: 2475 moltype = length =
SEQUENCE: 2475
000

SEQ ID NO: 2476 moltype = length =
SEQUENCE: 2476
000

SEQ ID NO: 2477 moltype = length =
SEQUENCE: 2477
000

SEQ ID NO: 2478 moltype = length =
SEQUENCE: 2478
000

SEQ ID NO: 2479 moltype = length =
SEQUENCE: 2479
000

SEQ ID NO: 2480 moltype = length =
SEQUENCE: 2480
000

SEQ ID NO: 2481 moltype = length =
SEQUENCE: 2481
000

SEQ ID NO: 2482 moltype = length =
SEQUENCE: 2482
000

SEQ ID NO: 2483 moltype = length =
SEQUENCE: 2483
000

SEQ ID NO: 2484 moltype = length =
SEQUENCE: 2484
000

SEQ ID NO: 2485 moltype = length =
SEQUENCE: 2485
000

SEQ ID NO: 2486 moltype = length =
SEQUENCE: 2486
000

SEQ ID NO: 2487 moltype = length =
SEQUENCE: 2487
000

SEQ ID NO: 2488 moltype = length =
SEQUENCE: 2488
000

SEQ ID NO: 2489 moltype = length =
SEQUENCE: 2489
000

SEQ ID NO: 2490 moltype = length =
SEQUENCE: 2490
000

SEQ ID NO: 2491 moltype = length =
SEQUENCE: 2491

-continued

000

SEQ ID NO: 2492 moltype = length =
SEQUENCE: 2492
000

SEQ ID NO: 2493 moltype = length =
SEQUENCE: 2493
000

SEQ ID NO: 2494 moltype = length =
SEQUENCE: 2494
000

SEQ ID NO: 2495 moltype = length =
SEQUENCE: 2495
000

SEQ ID NO: 2496 moltype = length =
SEQUENCE: 2496
000

SEQ ID NO: 2497 moltype = length =
SEQUENCE: 2497
000

SEQ ID NO: 2498 moltype = length =
SEQUENCE: 2498
000

SEQ ID NO: 2499 moltype = length =
SEQUENCE: 2499
000

SEQ ID NO: 2500 moltype = length =
SEQUENCE: 2500
000

SEQ ID NO: 2501 moltype = length =
SEQUENCE: 2501
000

SEQ ID NO: 2502 moltype = length =
SEQUENCE: 2502
000

SEQ ID NO: 2503 moltype = length =
SEQUENCE: 2503
000

SEQ ID NO: 2504 moltype = length =
SEQUENCE: 2504
000

SEQ ID NO: 2505 moltype = length =
SEQUENCE: 2505
000

SEQ ID NO: 2506 moltype = length =
SEQUENCE: 2506
000

SEQ ID NO: 2507 moltype = length =
SEQUENCE: 2507
000

SEQ ID NO: 2508 moltype = length =
SEQUENCE: 2508
000

SEQ ID NO: 2509 moltype = length =
SEQUENCE: 2509
000

SEQ ID NO: 2510 moltype = length =
SEQUENCE: 2510
000

SEQ ID NO: 2511 moltype = length =

```
SEQUENCE: 2511
000

SEQ ID NO: 2512        moltype = AA  length = 9
FEATURE                Location/Qualifiers
REGION                 1..9
                       note = Synthetic
source                 1..9
                       mol_type = protein
                       organism = synthetic construct
SEQUENCE: 2512
QQHYTTPPT                                                   9

SEQ ID NO: 2513        moltype =   length =
SEQUENCE: 2513
000

SEQ ID NO: 2514        moltype = AA  length = 12
FEATURE                Location/Qualifiers
REGION                 1..12
                       note = Synthetic
source                 1..12
                       mol_type = protein
                       organism = synthetic construct
SEQUENCE: 2514
QGTYYSGDWY FA                                               12

SEQ ID NO: 2515        moltype =   length =
SEQUENCE: 2515
000

SEQ ID NO: 2516        moltype =   length =
SEQUENCE: 2516
000

SEQ ID NO: 2517        moltype =   length =
SEQUENCE: 2517
000

SEQ ID NO: 2518        moltype =   length =
SEQUENCE: 2518
000

SEQ ID NO: 2519        moltype =   length =
SEQUENCE: 2519
000

SEQ ID NO: 2520        moltype = AA  length = 11
FEATURE                Location/Qualifiers
REGION                 1..11
                       note = Synthetic
source                 1..11
                       mol_type = protein
                       organism = synthetic construct
SEQUENCE: 2520
AAAYSDDSDT A                                                11

SEQ ID NO: 2521        moltype =   length =
SEQUENCE: 2521
000

SEQ ID NO: 2522        moltype =   length =
SEQUENCE: 2522
000

SEQ ID NO: 2523        moltype =   length =
SEQUENCE: 2523
000

SEQ ID NO: 2524        moltype =   length =
SEQUENCE: 2524
000

SEQ ID NO: 2525        moltype = AA  length = 11
FEATURE                Location/Qualifiers
REGION                 1..11
                       note = Synthetic
source                 1..11
                       mol_type = protein
```

```
                        organism = synthetic construct
SEQUENCE: 2525
AAAYSDDSDT A                                                    11

SEQ ID NO: 2526         moltype =   length =
SEQUENCE: 2526
000

SEQ ID NO: 2527         moltype =   length =
SEQUENCE: 2527
000

SEQ ID NO: 2528         moltype =   length =
SEQUENCE: 2528
000

SEQ ID NO: 2529         moltype =   length =
SEQUENCE: 2529
000

SEQ ID NO: 2530         moltype =   length =
SEQUENCE: 2530
000

SEQ ID NO: 2531         moltype = AA  length = 12
FEATURE                 Location/Qualifiers
REGION                  1..12
                        note = Synthetic
source                  1..12
                        mol_type = protein
                        organism = synthetic construct
SEQUENCE: 2531
QGTYYSGDWY FA                                                   12

SEQ ID NO: 2532         moltype =   length =
SEQUENCE: 2532
000

SEQ ID NO: 2533         moltype = AA  length = 12
FEATURE                 Location/Qualifiers
REGION                  1..12
                        note = Synthetic
source                  1..12
                        mol_type = protein
                        organism = synthetic construct
SEQUENCE: 2533
QGTYYSGDWY FA                                                   12

SEQ ID NO: 2534         moltype = AA  length = 12
FEATURE                 Location/Qualifiers
REGION                  1..12
                        note = Synthetic
source                  1..12
                        mol_type = protein
                        organism = synthetic construct
SEQUENCE: 2534
QGTYYSGDWY FA                                                   12

SEQ ID NO: 2535         moltype =   length =
SEQUENCE: 2535
000

SEQ ID NO: 2536         moltype =   length =
SEQUENCE: 2536
000

SEQ ID NO: 2537         moltype =   length =
SEQUENCE: 2537
000

SEQ ID NO: 2538         moltype =   length =
SEQUENCE: 2538
000

SEQ ID NO: 2539         moltype =   length =
SEQUENCE: 2539
000

SEQ ID NO: 2540         moltype =   length =
```

SEQUENCE: 2540
000

SEQ ID NO: 2541 moltype = length =
SEQUENCE: 2541
000

SEQ ID NO: 2542 moltype = length =
SEQUENCE: 2542
000

SEQ ID NO: 2543 moltype = length =
SEQUENCE: 2543
000

SEQ ID NO: 2544 moltype = length =
SEQUENCE: 2544
000

SEQ ID NO: 2545 moltype = length =
SEQUENCE: 2545
000

SEQ ID NO: 2546 moltype = length =
SEQUENCE: 2546
000

SEQ ID NO: 2547 moltype = length =
SEQUENCE: 2547
000

SEQ ID NO: 2548 moltype = length =
SEQUENCE: 2548
000

SEQ ID NO: 2549 moltype = length =
SEQUENCE: 2549
000

SEQ ID NO: 2550 moltype = length =
SEQUENCE: 2550
000

SEQ ID NO: 2551 moltype = length =
SEQUENCE: 2551
000

SEQ ID NO: 2552 moltype = length =
SEQUENCE: 2552
000

SEQ ID NO: 2553 moltype = length =
SEQUENCE: 2553
000

SEQ ID NO: 2554 moltype = length =
SEQUENCE: 2554
000

SEQ ID NO: 2555 moltype = length =
SEQUENCE: 2555
000

SEQ ID NO: 2556 moltype = length =
SEQUENCE: 2556
000

SEQ ID NO: 2557 moltype = length =
SEQUENCE: 2557
000

SEQ ID NO: 2558 moltype = length =
SEQUENCE: 2558
000

SEQ ID NO: 2559 moltype = length =
SEQUENCE: 2559
000

-continued

SEQ ID NO: 2560 moltype = length =
SEQUENCE: 2560
000

SEQ ID NO: 2561 moltype = length =
SEQUENCE: 2561
000

SEQ ID NO: 2562 moltype = length =
SEQUENCE: 2562
000

SEQ ID NO: 2563 moltype = length =
SEQUENCE: 2563
000

SEQ ID NO: 2564 moltype = length =
SEQUENCE: 2564
000

SEQ ID NO: 2565 moltype = length =
SEQUENCE: 2565
000

SEQ ID NO: 2566 moltype = length =
SEQUENCE: 2566
000

SEQ ID NO: 2567 moltype = length =
SEQUENCE: 2567
000

SEQ ID NO: 2568 moltype = length =
SEQUENCE: 2568
000

SEQ ID NO: 2569 moltype = length =
SEQUENCE: 2569
000

SEQ ID NO: 2570 moltype = length =
SEQUENCE: 2570
000

SEQ ID NO: 2571 moltype = length =
SEQUENCE: 2571
000

SEQ ID NO: 2572 moltype = length =
SEQUENCE: 2572
000

SEQ ID NO: 2573 moltype = length =
SEQUENCE: 2573
000

SEQ ID NO: 2574 moltype = length =
SEQUENCE: 2574
000

SEQ ID NO: 2575 moltype = length =
SEQUENCE: 2575
000

SEQ ID NO: 2576 moltype = length =
SEQUENCE: 2576
000

SEQ ID NO: 2577 moltype = length =
SEQUENCE: 2577
000

SEQ ID NO: 2578 moltype = length =
SEQUENCE: 2578
000

SEQ ID NO: 2579 moltype = length =
SEQUENCE: 2579
000

SEQ ID NO: 2580 moltype = length =
SEQUENCE: 2580
000

SEQ ID NO: 2581 moltype = length =
SEQUENCE: 2581
000

SEQ ID NO: 2582 moltype = length =
SEQUENCE: 2582
000

SEQ ID NO: 2583 moltype = length =
SEQUENCE: 2583
000

SEQ ID NO: 2584 moltype = length =
SEQUENCE: 2584
000

SEQ ID NO: 2585 moltype = length =
SEQUENCE: 2585
000

SEQ ID NO: 2586 moltype = length =
SEQUENCE: 2586
000

SEQ ID NO: 2587 moltype = length =
SEQUENCE: 2587
000

SEQ ID NO: 2588 moltype = length =
SEQUENCE: 2588
000

SEQ ID NO: 2589 moltype = length =
SEQUENCE: 2589
000

SEQ ID NO: 2590 moltype = length =
SEQUENCE: 2590
000

SEQ ID NO: 2591 moltype = length =
SEQUENCE: 2591
000

SEQ ID NO: 2592 moltype = length =
SEQUENCE: 2592
000

SEQ ID NO: 2593 moltype = length =
SEQUENCE: 2593
000

SEQ ID NO: 2594 moltype = length =
SEQUENCE: 2594
000

SEQ ID NO: 2595 moltype = length =
SEQUENCE: 2595
000

SEQ ID NO: 2596 moltype = length =
SEQUENCE: 2596
000

SEQ ID NO: 2597 moltype = length =
SEQUENCE: 2597
000

SEQ ID NO: 2598 moltype = length =
SEQUENCE: 2598
000

SEQ ID NO: 2599 moltype = length =
SEQUENCE: 2599

000

SEQ ID NO: 2600 moltype = length =
SEQUENCE: 2600
000

SEQ ID NO: 2601 moltype = length =
SEQUENCE: 2601
000

SEQ ID NO: 2602 moltype = length =
SEQUENCE: 2602
000

SEQ ID NO: 2603 moltype = length =
SEQUENCE: 2603
000

SEQ ID NO: 2604 moltype = length =
SEQUENCE: 2604
000

SEQ ID NO: 2605 moltype = length =
SEQUENCE: 2605
000

SEQ ID NO: 2606 moltype = length =
SEQUENCE: 2606
000

SEQ ID NO: 2607 moltype = length =
SEQUENCE: 2607
000

SEQ ID NO: 2608 moltype = length =
SEQUENCE: 2608
000

SEQ ID NO: 2609 moltype = length =
SEQUENCE: 2609
000

SEQ ID NO: 2610 moltype = length =
SEQUENCE: 2610
000

SEQ ID NO: 2611 moltype = length =
SEQUENCE: 2611
000

SEQ ID NO: 2612 moltype = length =
SEQUENCE: 2612
000

SEQ ID NO: 2613 moltype = length =
SEQUENCE: 2613
000

SEQ ID NO: 2614 moltype = length =
SEQUENCE: 2614
000

SEQ ID NO: 2615 moltype = length =
SEQUENCE: 2615
000

SEQ ID NO: 2616 moltype = length =
SEQUENCE: 2616
000

SEQ ID NO: 2617 moltype = length =
SEQUENCE: 2617
000

SEQ ID NO: 2618 moltype = length =
SEQUENCE: 2618
000

SEQ ID NO: 2619 moltype = length =

SEQUENCE: 2619
000

SEQ ID NO: 2620 moltype = length =
SEQUENCE: 2620
000

SEQ ID NO: 2621 moltype = length =
SEQUENCE: 2621
000

SEQ ID NO: 2622 moltype = length =
SEQUENCE: 2622
000

SEQ ID NO: 2623 moltype = length =
SEQUENCE: 2623
000

SEQ ID NO: 2624 moltype = AA length = 9
FEATURE Location/Qualifiers
REGION 1..9
note = Synthetic
source 1..9
mol_type = protein
organism = synthetic construct
SEQUENCE: 2624
QQHYTTPPT 9

SEQ ID NO: 2625 moltype = length =
SEQUENCE: 2625
000

SEQ ID NO: 2626 moltype = length =
SEQUENCE: 2626
000

SEQ ID NO: 2627 moltype = length =
SEQUENCE: 2627
000

SEQ ID NO: 2628 moltype = length =
SEQUENCE: 2628
000

SEQ ID NO: 2629 moltype = length =
SEQUENCE: 2629
000

SEQ ID NO: 2630 moltype = length =
SEQUENCE: 2630
000

SEQ ID NO: 2631 moltype = length =
SEQUENCE: 2631
000

SEQ ID NO: 2632 moltype = length =
SEQUENCE: 2632
000

SEQ ID NO: 2633 moltype = length =
SEQUENCE: 2633
000

SEQ ID NO: 2634 moltype = length =
SEQUENCE: 2634
000

SEQ ID NO: 2635 moltype = length =
SEQUENCE: 2635
000

SEQ ID NO: 2636 moltype = length =
SEQUENCE: 2636
000

SEQ ID NO: 2637 moltype = length =
SEQUENCE: 2637

000

SEQ ID NO: 2638 moltype = length =
SEQUENCE: 2638
000

SEQ ID NO: 2639 moltype = length =
SEQUENCE: 2639
000

SEQ ID NO: 2640 moltype = length =
SEQUENCE: 2640
000

SEQ ID NO: 2641 moltype = length =
SEQUENCE: 2641
000

SEQ ID NO: 2642 moltype = length =
SEQUENCE: 2642
000

SEQ ID NO: 2643 moltype = length =
SEQUENCE: 2643
000

SEQ ID NO: 2644 moltype = length =
SEQUENCE: 2644
000

SEQ ID NO: 2645 moltype = length =
SEQUENCE: 2645
000

SEQ ID NO: 2646 moltype = length =
SEQUENCE: 2646
000

SEQ ID NO: 2647 moltype = length =
SEQUENCE: 2647
000

SEQ ID NO: 2648 moltype = length =
SEQUENCE: 2648
000

SEQ ID NO: 2649 moltype = length =
SEQUENCE: 2649
000

SEQ ID NO: 2650 moltype = length =
SEQUENCE: 2650
000

SEQ ID NO: 2651 moltype = length =
SEQUENCE: 2651
000

SEQ ID NO: 2652 moltype = length =
SEQUENCE: 2652
000

SEQ ID NO: 2653 moltype = length =
SEQUENCE: 2653
000

SEQ ID NO: 2654 moltype = length =
SEQUENCE: 2654
000

SEQ ID NO: 2655 moltype = length =
SEQUENCE: 2655
000

SEQ ID NO: 2656 moltype = length =
SEQUENCE: 2656
000

SEQ ID NO: 2657 moltype = length =

-continued

SEQUENCE: 2657
000

SEQ ID NO: 2658 moltype = length =
SEQUENCE: 2658
000

SEQ ID NO: 2659 moltype = length =
SEQUENCE: 2659
000

SEQ ID NO: 2660 moltype = length =
SEQUENCE: 2660
000

SEQ ID NO: 2661 moltype = length =
SEQUENCE: 2661
000

SEQ ID NO: 2662 moltype = length =
SEQUENCE: 2662
000

SEQ ID NO: 2663 moltype = length =
SEQUENCE: 2663
000

SEQ ID NO: 2664 moltype = length =
SEQUENCE: 2664
000

SEQ ID NO: 2665 moltype = length =
SEQUENCE: 2665
000

SEQ ID NO: 2666 moltype = length =
SEQUENCE: 2666
000

SEQ ID NO: 2667 moltype = length =
SEQUENCE: 2667
000

SEQ ID NO: 2668 moltype = length =
SEQUENCE: 2668
000

SEQ ID NO: 2669 moltype = length =
SEQUENCE: 2669
000

SEQ ID NO: 2670 moltype = length =
SEQUENCE: 2670
000

SEQ ID NO: 2671 moltype = length =
SEQUENCE: 2671
000

SEQ ID NO: 2672 moltype = length =
SEQUENCE: 2672
000

SEQ ID NO: 2673 moltype = length =
SEQUENCE: 2673
000

SEQ ID NO: 2674 moltype = length =
SEQUENCE: 2674
000

SEQ ID NO: 2675 moltype = length =
SEQUENCE: 2675
000

SEQ ID NO: 2676 moltype = length =
SEQUENCE: 2676
000

-continued

SEQ ID NO: 2677 moltype = length =
SEQUENCE: 2677
000

SEQ ID NO: 2678 moltype = length =
SEQUENCE: 2678
000

SEQ ID NO: 2679 moltype = length =
SEQUENCE: 2679
000

SEQ ID NO: 2680 moltype = length =
SEQUENCE: 2680
000

SEQ ID NO: 2681 moltype = length =
SEQUENCE: 2681
000

SEQ ID NO: 2682 moltype = length =
SEQUENCE: 2682
000

SEQ ID NO: 2683 moltype = length =
SEQUENCE: 2683
000

SEQ ID NO: 2684 moltype = length =
SEQUENCE: 2684
000

SEQ ID NO: 2685 moltype = length =
SEQUENCE: 2685
000

SEQ ID NO: 2686 moltype = length =
SEQUENCE: 2686
000

SEQ ID NO: 2687 moltype = length =
SEQUENCE: 2687
000

SEQ ID NO: 2688 moltype = length =
SEQUENCE: 2688
000

SEQ ID NO: 2689 moltype = length =
SEQUENCE: 2689
000

SEQ ID NO: 2690 moltype = length =
SEQUENCE: 2690
000

SEQ ID NO: 2691 moltype = length =
SEQUENCE: 2691
000

SEQ ID NO: 2692 moltype = length =
SEQUENCE: 2692
000

SEQ ID NO: 2693 moltype = length =
SEQUENCE: 2693
000

SEQ ID NO: 2694 moltype = length =
SEQUENCE: 2694
000

SEQ ID NO: 2695 moltype = length =
SEQUENCE: 2695
000

SEQ ID NO: 2696 moltype = length =
SEQUENCE: 2696
000

-continued

SEQ ID NO: 2697 moltype = length =
SEQUENCE: 2697
000

SEQ ID NO: 2698 moltype = length =
SEQUENCE: 2698
000

SEQ ID NO: 2699 moltype = length =
SEQUENCE: 2699
000

SEQ ID NO: 2700 moltype = length =
SEQUENCE: 2700
000

SEQ ID NO: 2701 moltype = length =
SEQUENCE: 2701
000

SEQ ID NO: 2702 moltype = length =
SEQUENCE: 2702
000

SEQ ID NO: 2703 moltype = length =
SEQUENCE: 2703
000

SEQ ID NO: 2704 moltype = length =
SEQUENCE: 2704
000

SEQ ID NO: 2705 moltype = length =
SEQUENCE: 2705
000

SEQ ID NO: 2706 moltype = length =
SEQUENCE: 2706
000

SEQ ID NO: 2707 moltype = length =
SEQUENCE: 2707
000

SEQ ID NO: 2708 moltype = length =
SEQUENCE: 2708
000

SEQ ID NO: 2709 moltype = length =
SEQUENCE: 2709
000

SEQ ID NO: 2710 moltype = length =
SEQUENCE: 2710
000

SEQ ID NO: 2711 moltype = length =
SEQUENCE: 2711
000

SEQ ID NO: 2712 moltype = length =
SEQUENCE: 2712
000

SEQ ID NO: 2713 moltype = length =
SEQUENCE: 2713
000

SEQ ID NO: 2714 moltype = length =
SEQUENCE: 2714
000

SEQ ID NO: 2715 moltype = length =
SEQUENCE: 2715
000

SEQ ID NO: 2716 moltype = length =
SEQUENCE: 2716

```
000

SEQ ID NO: 2717        moltype =   length =
SEQUENCE: 2717
000

SEQ ID NO: 2718        moltype =   length =
SEQUENCE: 2718
000

SEQ ID NO: 2719        moltype =   length =
SEQUENCE: 2719
000

SEQ ID NO: 2720        moltype =   length =
SEQUENCE: 2720
000

SEQ ID NO: 2721        moltype =   length =
SEQUENCE: 2721
000

SEQ ID NO: 2722        moltype =   length =
SEQUENCE: 2722
000

SEQ ID NO: 2723        moltype =   length =
SEQUENCE: 2723
000

SEQ ID NO: 2724        moltype =   length =
SEQUENCE: 2724
000

SEQ ID NO: 2725        moltype =   length =
SEQUENCE: 2725
000

SEQ ID NO: 2726        moltype =   length =
SEQUENCE: 2726
000

SEQ ID NO: 2727        moltype = AA  length = 123
FEATURE                Location/Qualifiers
REGION                 1..123
                       note = Synthetic
source                 1..123
                       mol_type = protein
                       organism = synthetic construct
SEQUENCE: 2727
MAEVQLVESG GGLVQPGGSL RLSCAASGFN ISSYWIHWVR QAPGKGLEWV GYIDPYSGST  60
YYADSVKGRF TISADTSKNT AYLQMNSLRA EDTAVYYCAR SDYYYVDEYM DYWGQGTLVT  120
VSS                                                               123

SEQ ID NO: 2728        moltype =   length =
SEQUENCE: 2728
000

SEQ ID NO: 2729        moltype =   length =
SEQUENCE: 2729
000

SEQ ID NO: 2730        moltype =   length =
SEQUENCE: 2730
000

SEQ ID NO: 2731        moltype =   length =
SEQUENCE: 2731
000

SEQ ID NO: 2732        moltype =   length =
SEQUENCE: 2732
000

SEQ ID NO: 2733        moltype =   length =
SEQUENCE: 2733
000

SEQ ID NO: 2734        moltype =   length =
```

-continued

```
SEQUENCE: 2734
000

SEQ ID NO: 2735        moltype =   length =
SEQUENCE: 2735
000

SEQ ID NO: 2736        moltype = AA  length = 122
FEATURE                Location/Qualifiers
REGION                 1..122
                       note = Synthetic
source                 1..122
                       mol_type = protein
                       organism = synthetic construct
SEQUENCE: 2736
MAEVQLVESG GGLVQPGGSL RLSCAASGFN ISDYWIHWVR QAPGKGLEWV GFIDPYNGYT  60
NYADSVKGRF TISADTSKNT AYLQMNSLRA EDTAVYYCAR GYGSWPDYLD YWGQGTLVTV  120
SS                                                                122

SEQ ID NO: 2737        moltype =   length =
SEQUENCE: 2737
000

SEQ ID NO: 2738        moltype =   length =
SEQUENCE: 2738
000

SEQ ID NO: 2739        moltype = AA  length = 122
FEATURE                Location/Qualifiers
REGION                 1..122
                       note = Synthetic
source                 1..122
                       mol_type = protein
                       organism = synthetic construct
SEQUENCE: 2739
MAEVQLVESG GGLVQPGGSL RLSCAASGFN ISDYNIHWVR QAPGKGLEWV GYIDPSNGYT  60
YYADSVKGRF TISADTSKNT AYLQMNSLRA EDTAVYYCAR DDQSVSSPFD YWGQGTLVTV  120
SS                                                                122

SEQ ID NO: 2740        moltype =   length =
SEQUENCE: 2740
000

SEQ ID NO: 2741        moltype =   length =
SEQUENCE: 2741
000

SEQ ID NO: 2742        moltype =   length =
SEQUENCE: 2742
000

SEQ ID NO: 2743        moltype =   length =
SEQUENCE: 2743
000

SEQ ID NO: 2744        moltype =   length =
SEQUENCE: 2744
000

SEQ ID NO: 2745        moltype =   length =
SEQUENCE: 2745
000

SEQ ID NO: 2746        moltype =   length =
SEQUENCE: 2746
000

SEQ ID NO: 2747        moltype =   length =
SEQUENCE: 2747
000

SEQ ID NO: 2748        moltype =   length =
SEQUENCE: 2748
000

SEQ ID NO: 2749        moltype =   length =
SEQUENCE: 2749
000
```

```
SEQ ID NO: 2750        moltype =   length =
SEQUENCE: 2750
000

SEQ ID NO: 2751        moltype = AA  length = 122
FEATURE                Location/Qualifiers
REGION                 1..122
                       note = Synthetic
source                 1..122
                       mol_type = protein
                       organism = synthetic construct
SEQUENCE: 2751
MEVQLVESGG GLVQPGGSLR LSCAASGFTI SSYWIHWVRQ APGKGLKWVG YIDPYNGATY  60
YADSVKGRFT ISADTSKNTA YLQMNSLRAE DTAVYYCARA DYYYVDEYFD YWGQGTLVTV  120
SS                                                                 122

SEQ ID NO: 2752        moltype = AA  length = 121
FEATURE                Location/Qualifiers
REGION                 1..121
                       note = Synthetic
source                 1..121
                       mol_type = protein
                       organism = synthetic construct
SEQUENCE: 2752
MEVQLVESGG GLVQPGGSLR LSCAASGFTI SGYIIHWVRQ APGKGLEWVG YIDPSNGYTY  60
YADSVKGRFT ISADTSKNTA YLQMNSLRAE DTAVYYCARD DQSLSSPFDY WGQGTLVTVS  120
S                                                                  121

SEQ ID NO: 2753        moltype = AA  length = 122
FEATURE                Location/Qualifiers
REGION                 1..122
                       note = Synthetic
source                 1..122
                       mol_type = protein
                       organism = synthetic construct
SEQUENCE: 2753
MEVQLVESGG GLVQPGGSLR LSCAASGFTI PSYWIHWVRQ APGKGLEWVG YIDPANGATY  60
YADSVKGRFT ISADTSKNTA YLQMNSLRAE DTAVYYCARA DYFYVDEYLD YWGQGTLVTV  120
SS                                                                 122

SEQ ID NO: 2754        moltype = AA  length = 122
FEATURE                Location/Qualifiers
REGION                 1..122
                       note = Synthetic
source                 1..122
                       mol_type = protein
                       organism = synthetic construct
SEQUENCE: 2754
MEVQLVESGG GLVQPGGSLR LSCAASGFTI SGYWIHWVRQ APGKGLEWVG YIDPYNGATY  60
YADSVKGRFT ISADTSKNAA YLQMNSLRAE DTAVYYCARA DYFYIDEYWD YWGQGTLVTV  120
SS                                                                 122

SEQ ID NO: 2755        moltype = AA  length = 122
FEATURE                Location/Qualifiers
REGION                 1..122
                       note = Synthetic
source                 1..122
                       mol_type = protein
                       organism = synthetic construct
SEQUENCE: 2755
MEVQLVESGG GLVQPGGSLR LSCAASGFTI PDYWIHWVRQ APGKGLEWVG FIDPYNGYTN  60
YADPVKSRFT ISADTSKNTA YLQMNSLRAE DTAVYYCARA DYYYVDEYWD YWGQGTLVTV  120
SS                                                                 122

SEQ ID NO: 2756        moltype = AA  length = 122
FEATURE                Location/Qualifiers
REGION                 1..122
                       note = Synthetic
source                 1..122
                       mol_type = protein
                       organism = synthetic construct
SEQUENCE: 2756
MEVQLVESGG GLVQPGGSLR LSCAASGFTI SSYWIHWVRQ APGKGLEWVG YIDPFNGATY  60
YADSVKGRFT ISADTSKNTA YLQMNSLRAE DTAVYYCARA DYYYVDEYWD YWGQGTLVTV  120
SS                                                                 122

SEQ ID NO: 2757        moltype = AA  length = 122
FEATURE                Location/Qualifiers
REGION                 1..122
```

```
                        note = Synthetic
source                  1..122
                        mol_type = protein
                        organism = synthetic construct
SEQUENCE: 2757
MEVQLVESGG GLVQPGGSLR LSCAASGFTI SSYWIHWVRQ APGKGLEWVG YIDPYNGATY  60
YADSVKGRFT ISADTSKNTA YLQMNSLRAE DTAVYYCARS DYYYVDEFFD YWGQGTLVTV  120
SS                                                                122

SEQ ID NO: 2758         moltype = AA  length = 122
FEATURE                 Location/Qualifiers
REGION                  1..122
                        note = Synthetic
source                  1..122
                        mol_type = protein
                        organism = synthetic construct
SEQUENCE: 2758
MEVQLVESGG GLVQPGGSLR LSCAASGFTL TGYWIHWVRQ APGKGLEWVG YIDPYNGATY  60
YADSVKGRFT ISADTSKNTA YLQMNSLRAE DTAVYYCARA DYYYVDEYWD YWGQGTLVTV  120
SS                                                                122

SEQ ID NO: 2759         moltype = AA  length = 122
FEATURE                 Location/Qualifiers
REGION                  1..122
                        note = Synthetic
source                  1..122
                        mol_type = protein
                        organism = synthetic construct
SEQUENCE: 2759
MEVQLVESGG GLVQPGGSLR LSCAASGFTI ADYWIHWVRQ APGKGLEWVG YIDPYNGATY  60
YADSVKGRFT ISADTSKNTA YLQMNSLRAE DTAVYYCARA DYYYVDEYWD YWGQGTLVTV  120
SS                                                                122

SEQ ID NO: 2760         moltype = AA  length = 122
FEATURE                 Location/Qualifiers
REGION                  1..122
                        note = Synthetic
source                  1..122
                        mol_type = protein
                        organism = synthetic construct
SEQUENCE: 2760
MEVQLVESGG GLVQPGGALR LSCAASGFTI SSYWIHWVRQ APGKGLEWVG YIDPYNGATY  60
YADSVKGRFT ISADTSKNTA YLQMNSLRAE DTAVYYCARA DYYYVDEYLD YWGQGTLVTV  120
SS                                                                122

SEQ ID NO: 2761         moltype = AA  length = 121
FEATURE                 Location/Qualifiers
REGION                  1..121
                        note = Synthetic
source                  1..121
                        mol_type = protein
                        organism = synthetic construct
SEQUENCE: 2761
MEVQLVESGG GLVQPGGSLR LSCAASGFTI TDYVIHWVRQ APGKGLEWVG YIDPSNGYTY  60
YADSVKGRFT ISADTSKNTA YLQMNSLRAE DTAVYYCARD DQSFTSPFDY WGQGTLVTVS  120
S                                                                 121

SEQ ID NO: 2762         moltype = AA  length = 122
FEATURE                 Location/Qualifiers
REGION                  1..122
                        note = Synthetic
source                  1..122
                        mol_type = protein
                        organism = synthetic construct
SEQUENCE: 2762
MEVQLVESGG GLVQPGGSLR LSCAASGFTI SGYWIHWVRQ APGKGLEWVG YIDPYNGATY  60
YADSVKGRFT ISADTSKNTA YLQMNSLRAE DTAVYYCARA DYYYVDEYLD YWGQGTLVTV  120
SS                                                                122

SEQ ID NO: 2763         moltype = AA  length = 122
FEATURE                 Location/Qualifiers
REGION                  1..122
                        note = Synthetic
source                  1..122
                        mol_type = protein
                        organism = synthetic construct
SEQUENCE: 2763
MEVQLVESGG GSVQPGGSLR LSCAASGFTI SDYWIHWVRQ APGKGLEWVG YIDPYNGATY  60
YADSVKGRFT ISADTSKNTA YLQMNSLRAE DTAVYYCARA DYYYVDEYWD YWGQGTLVTV  120
```

-continued

```
SS                                                                   122

SEQ ID NO: 2764        moltype = AA  length = 122
FEATURE                Location/Qualifiers
REGION                 1..122
                       note = Synthetic
source                 1..122
                       mol_type = protein
                       organism = synthetic construct
SEQUENCE: 2764
MEVQLVESGG GLVQPGGSLR LSCSASGFTI ADYWIHWVRQ APGKGLEWVG YIDPYNGATY  60
YADSVKGRFT ISADTSKNTA YLQMNSLRAE DTAVYYCARA DYYYVDEYWD YWGQGTLVTV  120
SS                                                                   122

SEQ ID NO: 2765        moltype = AA  length = 122
FEATURE                Location/Qualifiers
REGION                 1..122
                       note = Synthetic
source                 1..122
                       mol_type = protein
                       organism = synthetic construct
SEQUENCE: 2765
MEVQLVESGG GLVQPGGSLR LSCAASGFTI SEYWIHWVRQ APGKGLEWVG FIDPYNGYTG  60
YADSVRGRFT ISADTSKNTA YLQMNSLRAE DTAVYYCARA DYYYVDEYWD YWGQGTLVTV  120
SS                                                                   122

SEQ ID NO: 2766        moltype = AA  length = 122
FEATURE                Location/Qualifiers
REGION                 1..122
                       note = Synthetic
source                 1..122
                       mol_type = protein
                       organism = synthetic construct
SEQUENCE: 2766
MEVQLVESGG GLVQPGGSLR LSCAASGFTI SGYWIHWVRQ APGKGLEWVG YIDPYNGATY  60
YADSVKGRFT ISADTSKNTA YLQMNSLRAE DTAVYYCARA DYYGVDEFLD YWGQGTLVTV  120
SS                                                                   122

SEQ ID NO: 2767        moltype = AA  length = 122
FEATURE                Location/Qualifiers
REGION                 1..122
                       note = Synthetic
source                 1..122
                       mol_type = protein
                       organism = synthetic construct
SEQUENCE: 2767
MEVQLVESGG GLVQPGGSLR LSCAASGFTI PSYWIHWVRQ APGKGLEWVG YIDPYNGATY  60
YADSVKGRFT ISADTSKNTA YLQMNSLRAE DTAVYYCARA DYHGVDEYWD YWGQGTLVTV  120
SS                                                                   122

SEQ ID NO: 2768        moltype = AA  length = 122
FEATURE                Location/Qualifiers
REGION                 1..122
                       note = Synthetic
source                 1..122
                       mol_type = protein
                       organism = synthetic construct
SEQUENCE: 2768
MEVQLVESGG GLVQPGGSLR LSCAASGFTI ADYWIHWVRQ APGKGLEWVG FIDPYNGYTG  60
YADSVKGRFT ISADNSKNTA YLQMNSLRAE DTAVYYCARA DYHGVDEYWD YWGQGTLVTV  120
SS                                                                   122

SEQ ID NO: 2769        moltype = AA  length = 122
FEATURE                Location/Qualifiers
REGION                 1..122
                       note = Synthetic
source                 1..122
                       mol_type = protein
                       organism = synthetic construct
SEQUENCE: 2769
MEVQLVESGG GLVQPGGSLR LSCAASGFTI PSYWIHWVRQ APGKGLEWVG YIDPYNGYTY  60
YADSVKGRFT ISADTSKNTA YLQMNSLRAE DTAVYYCARA DYYYVDEYFD YWGQGTLVTV  120
SS                                                                   122

SEQ ID NO: 2770        moltype = AA  length = 122
FEATURE                Location/Qualifiers
REGION                 1..122
                       note = Synthetic
source                 1..122
```

```
                         mol_type = protein
                         organism = synthetic construct
SEQUENCE: 2770
MEVQLVESGG GLVQPGGSLR LSCAASGFTI SQYWIHWVRQ APGKGLEWVG FIDPYNGYTN  60
YADSVKGRFT ISADTSENTA YLQMNSLRAE DTAVYYCARA DYYYVDEYWD YWGQGTLVTV  120
SS                                                                 122

SEQ ID NO: 2771          moltype = AA  length = 122
FEATURE                  Location/Qualifiers
REGION                   1..122
                         note = Synthetic
source                   1..122
                         mol_type = protein
                         organism = synthetic construct
SEQUENCE: 2771
MEVQLVESGG GLVQPGGSLR LSCAASGFTI PAYWIHWVRQ APGKGLEWVG YIDPYNGSTY  60
YADSVKGRFT ISADTSKNTA YLQMNSLRAE DTAVYYCARA DYYYVDEYWD YWGQGTLVTV  120
SS                                                                 122

SEQ ID NO: 2772          moltype = AA  length = 122
FEATURE                  Location/Qualifiers
REGION                   1..122
                         note = Synthetic
source                   1..122
                         mol_type = protein
                         organism = synthetic construct
SEQUENCE: 2772
MEVQLVESGG GLVQPGGSLR LSCAASGFTI PAYWIHWVRQ APGKGLEWVG YIDPSNGYTY  60
YADSVKGRFT ISADASKNTA YLQMNSLRAE DTAAYYCARA DYHGVDEYWD YWGQGTLVTV  120
SS                                                                 122

SEQ ID NO: 2773          moltype = AA  length = 122
FEATURE                  Location/Qualifiers
REGION                   1..122
                         note = Synthetic
source                   1..122
                         mol_type = protein
                         organism = synthetic construct
SEQUENCE: 2773
MEVQLVESGG GLVQPGGSLR LSCAASGFTI GSYWIHWVRQ APGKGLEWVG YIDPSNGYTY  60
YADSVKGRFT ISADTSKNTA YLQMNSLRAE DTAVYYCARA DYYYVDEYWD YWGQGTLVTV  120
SS                                                                 122

SEQ ID NO: 2774          moltype = AA  length = 122
FEATURE                  Location/Qualifiers
REGION                   1..122
                         note = Synthetic
source                   1..122
                         mol_type = protein
                         organism = synthetic construct
SEQUENCE: 2774
MEVQLVESGG GLVQPGGSLR LSCAASGFTI SSYWIHWVRQ APGKGLEWVG YIDPYNGATY  60
YADSVKGRFT ISADTSKNTA YLQMNSLRAE DTAVYYCARA DYYYVDEYWD YWGQGTLVTV  120
SS                                                                 122

SEQ ID NO: 2775          moltype = AA  length = 122
FEATURE                  Location/Qualifiers
REGION                   1..122
                         note = Synthetic
source                   1..122
                         mol_type = protein
                         organism = synthetic construct
SEQUENCE: 2775
MEVQLVESGG GLVQPGGSLR LSCAASGFTI SGYWIHWVRQ APGKGLEWVG YIDPYNGATY  60
YADSVKGRFT ISADTSKNTA YLQMNSLRAE DTAVYYCARA DYYYVDEYWD YWGQGTLVTV  120
SS                                                                 122

SEQ ID NO: 2776          moltype = AA  length = 122
FEATURE                  Location/Qualifiers
REGION                   1..122
                         note = Synthetic
source                   1..122
                         mol_type = protein
                         organism = synthetic construct
SEQUENCE: 2776
MEVQLVESGG GLVQPGGSLR LSCAASGFTI VSYWIHWVRQ APGKGLEWVG YIDPYNGATY  60
YADSVKGRFT ISADTSKNTA YLQMNSLRAE DTAVYYCARA DYYYVDEYWD YWGQGTLVTV  120
SS                                                                 122
```

```
SEQ ID NO: 2777        moltype = AA  length = 122
FEATURE                Location/Qualifiers
REGION                 1..122
                       note = Synthetic
source                 1..122
                       mol_type = protein
                       organism = synthetic construct
SEQUENCE: 2777
MEVQLVESGG GLVQPGGSLR LSCAASGFTI SGYWIHWVRQ APGKGLEWVG YIDPYNGATY  60
YADSVKGRFT ISADTPKNTA YLQMNSLRAE DTAVYYCARA DYHGVDEYWD YWGQGTLVTV  120
SS                                                                122

SEQ ID NO: 2778        moltype = AA  length = 122
FEATURE                Location/Qualifiers
REGION                 1..122
                       note = Synthetic
source                 1..122
                       mol_type = protein
                       organism = synthetic construct
SEQUENCE: 2778
MEVQLVESGG GLVQPGGSLR LSCAASGFTI SGYWIHWVRQ APGKGLEWVG YIDPYNGATF  60
YADSVKGRFT ISADTSKNTA YLQMNSLRAE DTAVYYCARA DYYYVDEYWD YWGQGTLVTV  120
SS                                                                122

SEQ ID NO: 2779        moltype = AA  length = 122
FEATURE                Location/Qualifiers
REGION                 1..122
                       note = Synthetic
source                 1..122
                       mol_type = protein
                       organism = synthetic construct
SEQUENCE: 2779
MEVQLVESGG GLVQPGGSLR LSCAASGFTI SGYWIHWVRQ APGKGLEWVG YIDPYNGATY  60
YADSVKGRFT ISADTSKNTA YLQMNSLRAE DTAVYYCARA DYYYVDEYFD YWGQGTLVTV  120
SS                                                                122

SEQ ID NO: 2780        moltype = AA  length = 122
FEATURE                Location/Qualifiers
REGION                 1..122
                       note = Synthetic
source                 1..122
                       mol_type = protein
                       organism = synthetic construct
SEQUENCE: 2780
MEVQLVESGG GLVQPGGSLR LSCAASGFTI PAYWIHWVRQ APGKGLEWVG YIDPYNGSTY  60
HADSVKGRFT ISADTSKNTA YLQMNSLRAE DTAVYYCARA DYYYVDEYWD YWGQGTLVTV  120
SS                                                                122

SEQ ID NO: 2781        moltype = AA  length = 121
FEATURE                Location/Qualifiers
REGION                 1..121
                       note = Synthetic
source                 1..121
                       mol_type = protein
                       organism = synthetic construct
SEQUENCE: 2781
MEVQLVESGG GLVQPGGSLR LSCAASGFTI SDYIIHWVRQ APGKGLEWVG YIDPSNGYTY  60
HADSVKGRFT ISADTSKNTA YLQMNSLRAE DTAVYYCARD DQSFSSPFDY WGQGTLVTVS  120
S                                                                 121

SEQ ID NO: 2782        moltype = AA  length = 121
FEATURE                Location/Qualifiers
REGION                 1..121
                       note = Synthetic
source                 1..121
                       mol_type = protein
                       organism = synthetic construct
SEQUENCE: 2782
MEVQLVESGG GLVQPGGSLR LSCAASGFTI SDYWIHWVRQ APGKGLEWVG YIDPYNGYTY  60
YADSVNGRFT ISADTSKNTA YLQMNSLRAE DTAVYYCARD YGSYLVSLDY WGQGTLVTVS  120
S                                                                 121

SEQ ID NO: 2783        moltype = AA  length = 121
FEATURE                Location/Qualifiers
REGION                 1..121
                       note = Synthetic
source                 1..121
                       mol_type = protein
                       organism = synthetic construct
```

-continued

```
SEQUENCE: 2783
MEVQLVESGG GLVQPGGSLR LSCAASGFTI SQYWIHWVRQ APGKGLEWVG YIDPYNGYTY  60
YADSVKGRFT ISADTSKNTA YLQMNSLRAE DTAVYYCARD YGSWRIRLDY WGQGTLVTVS  120
S                                                                  121

SEQ ID NO: 2784        moltype = AA  length = 121
FEATURE                Location/Qualifiers
REGION                 1..121
                       note = Synthetic
source                 1..121
                       mol_type = protein
                       organism = synthetic construct
SEQUENCE: 2784
MEVQLVESGG GLVQPGGSLR LSCAASGFTI HEYWIHWVRQ APGKGLEWVG YIDPANGFTY  60
YADSVKGRFT ISADTSKNTA YLQMNSLRAE DTAVYYCARD YGSLQVFLDY WGQGTLVTVS  120
S                                                                  121

SEQ ID NO: 2785        moltype = AA  length = 121
FEATURE                Location/Qualifiers
REGION                 1..121
                       note = Synthetic
source                 1..121
                       mol_type = protein
                       organism = synthetic construct
SEQUENCE: 2785
MEVQLVESGG GLVQPGGSLR LSCAASGFTI SDYWIHWVRQ APGKGLEWVG YIDPYNGYTY  60
YADSVKGRFT ISADTSKNTA YLQMNSLRAE DTAVYYCARD YGSLQVFIDH WGQGTLVTVS  120
S                                                                  121

SEQ ID NO: 2786        moltype = AA  length = 121
FEATURE                Location/Qualifiers
REGION                 1..121
                       note = Synthetic
source                 1..121
                       mol_type = protein
                       organism = synthetic construct
SEQUENCE: 2786
MEVQLVESGG GLVQPGGSLR LSCAASGFTI SQYWIHWVRQ APGKGLEWVG YIDPYNGYTY  60
YADSVKGRFT ISADTSKNTA YLQMNSLRAE DTAVYYCARD YGSLQVQLDY WGQGTLVTVS  120
S                                                                  121

SEQ ID NO: 2787        moltype = AA  length = 121
FEATURE                Location/Qualifiers
REGION                 1..121
                       note = Synthetic
source                 1..121
                       mol_type = protein
                       organism = synthetic construct
SEQUENCE: 2787
MEVQLVESGG GLVQPGGSLR LSCAASGFTI SDYWIHWVRQ APGKGLEWVG FIDPYNGYTY  60
HADSVEGRFT ISADTSKNTA YLQMNSLRAE DTAVYYCARD YGSLQVQLDY WGQGTLVTVS  120
S                                                                  121

SEQ ID NO: 2788        moltype = AA  length = 121
FEATURE                Location/Qualifiers
REGION                 1..121
                       note = Synthetic
source                 1..121
                       mol_type = protein
                       organism = synthetic construct
SEQUENCE: 2788
MEVQLVESGG GLVQPGGSLR LSCAASGFAI ANYWIHWVRQ APGKGLEWVG YIDPYNGYTY  60
YADSVKGRFT ISADTSKNTA YLQMNSLRAE DTAVYYCARD YGSLEVSLDY WGQGTLVTVS  120
S                                                                  121

SEQ ID NO: 2789        moltype = AA  length = 121
FEATURE                Location/Qualifiers
REGION                 1..121
                       note = Synthetic
source                 1..121
                       mol_type = protein
                       organism = synthetic construct
SEQUENCE: 2789
MEVQLVESGG GLVQPGGSLR LSCAASGFTI SDYWIHWVRQ APGKGLEWVG YIDPQNGWTY  60
YADSVKGRFT ISADTSKNTA YLQMNSLRAE DTAVYYCARD YGSLTINLDY WGQGTLVTVS  120
S                                                                  121

SEQ ID NO: 2790        moltype = AA  length = 121
FEATURE                Location/Qualifiers
```

```
REGION                  1..121
                        note = Synthetic
source                  1..121
                        mol_type = protein
                        organism = synthetic construct
SEQUENCE: 2790
MEVQLVESGG GLVQPGGSLR LSCAASGFTI SDYWIHWVRQ APGKGLEWVG YIDPSNGYTY  60
YADSVKGRFT ISADTSRNTA YLQMNSLRAE DTAVYYCARD YGSLEVSLDY WGQGTLVTVS  120
S                                                                  121

SEQ ID NO: 2791         moltype = AA  length = 121
FEATURE                 Location/Qualifiers
REGION                  1..121
                        note = Synthetic
source                  1..121
                        mol_type = protein
                        organism = synthetic construct
SEQUENCE: 2791
MEVQLVESGG GLVQPGGSLR LSCAASGFTI SDYWIHWVRQ APGKGLEWVG YIDPYNGYTY  60
YADSVKGRFT ISADTSKNTA YLQMNSLRAE DTAVYYCARD YGSLEVSLDY WGQGTLVTVS  120
S                                                                  121

SEQ ID NO: 2792         moltype = AA  length = 121
FEATURE                 Location/Qualifiers
REGION                  1..121
                        note = Synthetic
source                  1..121
                        mol_type = protein
                        organism = synthetic construct
SEQUENCE: 2792
MEVQLVESGG GLVQPGGSLR LSCAASGFTI SGYWIHWVRQ APGKGLEWVG YIDPANGFTY  60
YADSVKGRFT ISADTSKNTA YLQMNSLRAE DTAVYYCARD YGSIQVFLDY WGQGTLVTVS  120
S                                                                  121

SEQ ID NO: 2793         moltype = AA  length = 121
FEATURE                 Location/Qualifiers
REGION                  1..121
                        note = Synthetic
source                  1..121
                        mol_type = protein
                        organism = synthetic construct
SEQUENCE: 2793
MEVQLVESGG GLVQPGGSLR LSCAASGFTI SDYWIHWVRQ APGKGLEWVG FIDPKNGYTY  60
YADSVKGRFT ISAGTSKNTA YLQMNSLRAE DTAVYYCARD YGSLQVFIDY WGQGTLVTVS  120
S                                                                  121

SEQ ID NO: 2794         moltype = AA  length = 121
FEATURE                 Location/Qualifiers
REGION                  1..121
                        note = Synthetic
source                  1..121
                        mol_type = protein
                        organism = synthetic construct
SEQUENCE: 2794
MEVQLVESGG GLVQPGGSLR LSCAASGFTI SDYWIHWVRQ APGKGLEWVG YIDPYNGYTY  60
YADSVKGRFT ISADTSKNTA YLQMNPLRAE DTAVYYCARD YGSLQVQLDY WGQGTLVTVS  120
S                                                                  121

SEQ ID NO: 2795         moltype = AA  length = 121
FEATURE                 Location/Qualifiers
REGION                  1..121
                        note = Synthetic
source                  1..121
                        mol_type = protein
                        organism = synthetic construct
SEQUENCE: 2795
MEVQLVESGG GLVQPGGSLR LSCAASGFTI SDYWIHWVRQ APGKGLEWVG YIDPSNGYTY  60
YADSVKGRFT ISADTSKNTA YLQMNSLRAE DTAVYYCARD YGSLQVFIDY WGQGTLVTVS  120
S                                                                  121

SEQ ID NO: 2796         moltype = AA  length = 121
FEATURE                 Location/Qualifiers
REGION                  1..121
                        note = Synthetic
source                  1..121
                        mol_type = protein
                        organism = synthetic construct
SEQUENCE: 2796
MEVQLVESGG GLVQPGGSLR LSCAASGFTI SDYVIHWVRQ APGKGLEWVG YIDPSNGYTY  60
```

-continued

```
YADPVKGRFT ISADTSKNTA YLQMNSLRAE DTAVYYCARD PQSFYIAFDY WGQGTLVTVS  120
S                                                                  121

SEQ ID NO: 2797        moltype = AA  length = 121
FEATURE                Location/Qualifiers
REGION                 1..121
                       note = Synthetic
source                 1..121
                       mol_type = protein
                       organism = synthetic construct
SEQUENCE: 2797
MEVQLVESGG GLVQPGGSLR LSCAASGFTI SDYWIHWVRQ APGKGLEWVG YIDPQNGWTY  60
YADSVKGRFT ISADTSKNTA YLQMNSLRAE DTAVYYCARD YGSLEVSLDY WGQGTLVTVS  120
S                                                                  121

SEQ ID NO: 2798        moltype = AA  length = 122
FEATURE                Location/Qualifiers
REGION                 1..122
                       note = Synthetic
source                 1..122
                       mol_type = protein
                       organism = synthetic construct
SEQUENCE: 2798
MEVQLVESGG GLVQPGGSLR LSCAASGFTI PDYWIHWVRQ APGKGLEWVG YIDPYSGSTF  60
YADSVKGRFT ISADTSKNTA YLQMNSLRAE DTAVYYCARA DYYYVDEYLD YWGQGTLVTV  120
SS                                                                 122

SEQ ID NO: 2799        moltype = AA  length = 121
FEATURE                Location/Qualifiers
REGION                 1..121
                       note = Synthetic
source                 1..121
                       mol_type = protein
                       organism = synthetic construct
SEQUENCE: 2799
MEVQLVESGG GLVQPGGSLR LSCAASGFTI SGYWIHWVRQ APGKGLEWVG YIDPANGFTY  60
YADSVKGRFT ISADTSKNTA YLQMNSLRAE DTAVYYCARD YGSVRVFLDY WGQGTLVTVS  120
S                                                                  121

SEQ ID NO: 2800        moltype = AA  length = 121
FEATURE                Location/Qualifiers
REGION                 1..121
                       note = Synthetic
source                 1..121
                       mol_type = protein
                       organism = synthetic construct
SEQUENCE: 2800
MEVQLVESGG GLVQPGGSLR LSCAASGFTI SGYIIHWVRQ APGKGLEWVG YIDPSNGYTY  60
HADSVKGRFT ISADTSKNTA YLQMNSLRAE DTAVYYCARD DQSVSSPFDY WGQGTLVTVS  120
S                                                                  121

SEQ ID NO: 2801        moltype = AA  length = 121
FEATURE                Location/Qualifiers
REGION                 1..121
                       note = Synthetic
source                 1..121
                       mol_type = protein
                       organism = synthetic construct
SEQUENCE: 2801
MEVQLVESGG GLVQPGGSLR LSCAASGFTI SQYWIHWVRQ APGKGLEWVG YIDPYNGYTY  60
YADSVKGRFT ISADTSKNTA YLQMNSLRAE DTAVYYCARD YGSLRVSLDY WGQGTLVTVS  120
S                                                                  121

SEQ ID NO: 2802        moltype = AA  length = 121
FEATURE                Location/Qualifiers
REGION                 1..121
                       note = Synthetic
source                 1..121
                       mol_type = protein
                       organism = synthetic construct
SEQUENCE: 2802
MEVQLVESGG GLVQPGGSLR LSCAASGFTI TDYWIHWVRQ APGKGLEWVG YIDPYNGYTY  60
YADSVKGRFT ISADTSKNTA YLQMNSLRAE DTAVYYCARD YGSLQVFIDY WGQGTLVTVS  120
S                                                                  121

SEQ ID NO: 2803        moltype = AA  length = 121
FEATURE                Location/Qualifiers
REGION                 1..121
                       note = Synthetic
```

```
source                  1..121
                        mol_type = protein
                        organism = synthetic construct
SEQUENCE: 2803
MEVQLVESGG GLVQPGGSLR LSCAASGFTI SQYWIHWVRQ APGKGLEWVG YIDPYNGYTY  60
YADSVKGRFT ISADTSKNTA HLQMNSLRAE DTAVYYCARD YGSFRVQLDY WGQGTLVTVS  120
S                                                                  121

SEQ ID NO: 2804         moltype = AA  length = 121
FEATURE                 Location/Qualifiers
REGION                  1..121
                        note = Synthetic
source                  1..121
                        mol_type = protein
                        organism = synthetic construct
SEQUENCE: 2804
MEVQLVESGG GLVQPGGSLR LSCAASGFTI SDYWIHWVRQ APGKGLEWVG YIDPANGYTY  60
YADSVKGRFT ISADTSKNTA YLQMNSLRAE DTAVYYCARD YGSLHVQLDY WGQGTLVTVS  120
S                                                                  121

SEQ ID NO: 2805         moltype = AA  length = 121
FEATURE                 Location/Qualifiers
REGION                  1..121
                        note = Synthetic
source                  1..121
                        mol_type = protein
                        organism = synthetic construct
SEQUENCE: 2805
MEVQLVESGG GLVQPGGSLR LSCAASGFTI SYYIIHWVRQ APGKGLEWVG YIDPSNGYTY  60
YADSVKGRFT ISADTSKNTA YLQMNSLRAE DTAVYYCARD VQSVSGEFDY WGQGTLVTVS  120
S                                                                  121

SEQ ID NO: 2806         moltype = AA  length = 121
FEATURE                 Location/Qualifiers
REGION                  1..121
                        note = Synthetic
source                  1..121
                        mol_type = protein
                        organism = synthetic construct
SEQUENCE: 2806
MEVQLVESGG GLVQPGGSLR LSCAASGFTI SDYWIHWVRQ APGKGLEWVG YIDPYNGYTY  60
YADSVRGRFT ISADTSKNTA YLQMNSLRAE DTAVYYCARD YGSLQVFIDY WGQGTLVTVS  120
S                                                                  121

SEQ ID NO: 2807         moltype = AA  length = 121
FEATURE                 Location/Qualifiers
REGION                  1..121
                        note = Synthetic
source                  1..121
                        mol_type = protein
                        organism = synthetic construct
SEQUENCE: 2807
MEVQLVESGG GLVQPGGSLR LACAASGFTI GVYIIHWVRQ APGKGLEWVG YIDPSNGYTY  60
YADSVKGRFT ISADTSKNTA YLQMNSLRAE DTAVYYCARD DQSVSSPFDY WGQGTLVTVS  120
S                                                                  121

SEQ ID NO: 2808         moltype = AA  length = 121
FEATURE                 Location/Qualifiers
REGION                  1..121
                        note = Synthetic
source                  1..121
                        mol_type = protein
                        organism = synthetic construct
SEQUENCE: 2808
MEVQLVESGG GLVQPGGSLR LSCAASGFTI SDYWIHWVRQ APGKGLEWVG YIDPYNGYTY  60
YADSVKGRFT ISAGTSKNTA YLQMNSLRAE DTAVYYCARD YGSLQVFIDY WGQGTLVTVS  120
S                                                                  121

SEQ ID NO: 2809         moltype = AA  length = 121
FEATURE                 Location/Qualifiers
REGION                  1..121
                        note = Synthetic
source                  1..121
                        mol_type = protein
                        organism = synthetic construct
SEQUENCE: 2809
MEVQLVESGG GLVQPGGSLR LSCAASGFTI SDYWIHWVRQ APGKGLEWVG YIDPYNGFTY  60
YADSVKGRFT ISADTSKNTA YLQMNSLRAE DTAVYYCARD YGSLQVFIDY WGQGTLVTVS  120
S                                                                  121
```

```
SEQ ID NO: 2810        moltype = AA  length = 121
FEATURE                Location/Qualifiers
REGION                 1..121
                       note = Synthetic
source                 1..121
                       mol_type = protein
                       organism = synthetic construct
SEQUENCE: 2810
MEVQLVESGG GLVQPGGSLR LSCAASGFTI NDYVIHWVRQ APGKGLEWVG YIDPSNGYTY  60
YADSVKGRFT ISADTSKNTA YLQMNSLRAE DTAVYYCARD DQSLSSPFDY WGQGTLVTVS  120
S                                                                  121

SEQ ID NO: 2811        moltype = AA  length = 121
FEATURE                Location/Qualifiers
REGION                 1..121
                       note = Synthetic
source                 1..121
                       mol_type = protein
                       organism = synthetic construct
SEQUENCE: 2811
MEVQLVESGG GLVQPGGSLR LSCAASGFTI SIYTIHWVRQ APGKGLEWVG YIDPSNGYTY  60
YADSVKGRLT ISADTSKNTA YLQMNSLRAE DTAVYYCARD PQSISSPFDY WGQGTLVTVS  120
S                                                                  121

SEQ ID NO: 2812        moltype = AA  length = 121
FEATURE                Location/Qualifiers
REGION                 1..121
                       note = Synthetic
source                 1..121
                       mol_type = protein
                       organism = synthetic construct
SEQUENCE: 2812
MEVQLVESGG GLVQPGGSLR LSCAASGFTI SDYTIHWVRQ APGKGLEWVG YIDPSNGYTY  60
HADSVKGRFT ISADTSKNTA YLQMNSLRAE DTAVYYCARD PQSVSSPFDY WGQGTLVTVS  120
S                                                                  121

SEQ ID NO: 2813        moltype = AA  length = 121
FEATURE                Location/Qualifiers
REGION                 1..121
                       note = Synthetic
source                 1..121
                       mol_type = protein
                       organism = synthetic construct
SEQUENCE: 2813
MEVQLVESGG GLVQPGGSLR LSCAASGFTI AYYIIHWVRQ APGKGLEWVG YIDPSNGYTY  60
YADSVKGRFT ISADTSKNTA YLQMNSLRAE DTAVYYCARD DQSLSSPFDY WGQGTLVTVS  120
S                                                                  121

SEQ ID NO: 2814        moltype = AA  length = 121
FEATURE                Location/Qualifiers
REGION                 1..121
                       note = Synthetic
source                 1..121
                       mol_type = protein
                       organism = synthetic construct
SEQUENCE: 2814
MEVQLVESGG GLVQPGGSLR LSCAASGFTI HDYVIHWVRQ APGKGLEWVG YIDPSNGYTY  60
YADSVKGRFT ISADTSKNTA YLQMNSLRAE DTAVYYCARD DQSISSPLDY WGQGTLVTVS  120
S                                                                  121

SEQ ID NO: 2815        moltype = AA  length = 121
FEATURE                Location/Qualifiers
REGION                 1..121
                       note = Synthetic
source                 1..121
                       mol_type = protein
                       organism = synthetic construct
SEQUENCE: 2815
MEVQLVESGG GLVQPGGSLR LSCAASGFTI SDYVIHWVRQ APGKGLEWVG YIDPSNGYTY  60
YADSVKGRFT ISADTSKNTA YLQMNSLRAE DTAVYYCARD PQSLFYPFDY WGQGTLVTVS  120
S                                                                  121

SEQ ID NO: 2816        moltype = AA  length = 121
FEATURE                Location/Qualifiers
REGION                 1..121
                       note = Synthetic
source                 1..121
                       mol_type = protein
```

```
                        organism = synthetic construct
SEQUENCE: 2816
MEVQLVESGG GLVQPGGSLR LSCAASGFTI SGYIIHWVRQ APGKGLEWVG YIDPSNGYTF  60
YADSVKGRFT ISADTSKNTA YLRMNSLRAE DTAVYYCARD DQSLSSPFDY WGQGTLVTVS  120
S                                                                  121

SEQ ID NO: 2817         moltype = AA  length = 121
FEATURE                 Location/Qualifiers
REGION                  1..121
                        note = Synthetic
source                  1..121
                        mol_type = protein
                        organism = synthetic construct
SEQUENCE: 2817
MEVQLVESGG GLVQPGGSLR LSCAASGFTI FDYTIHWVRQ APGKGLEWVG YIDPSNGYTF  60
YADSVKGRFT ISADTSKNTA YLQVNSLRAE DTAVYYCARD IQSVSGEFDY WGQGTLVTVS  120
S                                                                  121

SEQ ID NO: 2818         moltype = AA  length = 121
FEATURE                 Location/Qualifiers
REGION                  1..121
                        note = Synthetic
source                  1..121
                        mol_type = protein
                        organism = synthetic construct
SEQUENCE: 2818
MEVQLVESGG DLVRPGGSLR LSCAASGFTI SYYIIHWVRQ APGKGLEWVG YIDPSNGYTY  60
YADSVKGRFT ISADTSKNTA YLQMNSLRAE DTAVYYCARD DQSVSSPFEY WGQGTLVTVS  120
S                                                                  121

SEQ ID NO: 2819         moltype = AA  length = 121
FEATURE                 Location/Qualifiers
REGION                  1..121
                        note = Synthetic
source                  1..121
                        mol_type = protein
                        organism = synthetic construct
SEQUENCE: 2819
MEVQLVESGG GLVQPGGSLR LSCAASGFTI NNYIIHWVRQ APGKGLEWVG YIDPSNGYTY  60
YADSVKGRFT ISADTSKNTA YLQMNSLRAE DTAVYYCARD PQSLSSPFDY WGQGTLVTVS  120
S                                                                  121

SEQ ID NO: 2820         moltype = AA  length = 121
FEATURE                 Location/Qualifiers
REGION                  1..121
                        note = Synthetic
source                  1..121
                        mol_type = protein
                        organism = synthetic construct
SEQUENCE: 2820
MEVQLVESGG GLVQPGGSLR LSCAASGFTT RDYVIHWVRQ APGKGLEWVG YIDPSNGYTY  60
YADSVKGRFT ISADTSKNTA YLQMNSLRAE DTAVYYCARD PQSLSSPFDY WGQGTLVTVS  120
S                                                                  121

SEQ ID NO: 2821         moltype = AA  length = 121
FEATURE                 Location/Qualifiers
REGION                  1..121
                        note = Synthetic
source                  1..121
                        mol_type = protein
                        organism = synthetic construct
SEQUENCE: 2821
MEVQLVESGG GLVQPGGLLR LSCAASGFTI AYYVIHWVRQ APGKGLEWVG YIDPSNGYTY  60
YADSVKGRFT ISADTSKNTA YLQMNSLRAE DTAVYYCARD DQSLSSPFDY WGQGTLVTVS  120
S                                                                  121

SEQ ID NO: 2822         moltype = AA  length = 121
FEATURE                 Location/Qualifiers
REGION                  1..121
                        note = Synthetic
source                  1..121
                        mol_type = protein
                        organism = synthetic construct
SEQUENCE: 2822
MEVQLVESGG GLVQPGGSLR LSCAASGFTI SDYIIHWVRQ APGKGLEWVG YIDPSNGYTY  60
YADSVKGRFT ISADTSKNTA YLQMNSLRAE DTAVYYCARD DQSLSSPFDY WGQGTLVTVS  120
S                                                                  121

SEQ ID NO: 2823         moltype = AA  length = 121
```

-continued

```
FEATURE                 Location/Qualifiers
REGION                  1..121
                        note = Synthetic
source                  1..121
                        mol_type = protein
                        organism = synthetic construct
SEQUENCE: 2823
MEVQLVESGG GLVQPGGSLR LSCAASGFTI SDYVIHWVRQ APGKGLEWVG YIDPSNGYTY  60
YADSVKGRFT ISADTSKNTA YLQMNSLRAE DTAVYYCARD PQSLTSPFDY WGQGTLVTVS  120
S                                                                   121

SEQ ID NO: 2824         moltype = AA  length = 121
FEATURE                 Location/Qualifiers
REGION                  1..121
                        note = Synthetic
source                  1..121
                        mol_type = protein
                        organism = synthetic construct
SEQUENCE: 2824
MEVQLVESGG GLVQLGGSLR LSCAASGFTI GGYIIHWVRQ APGKGLEWVG YIDPSNGYTY  60
YADSVKGRFT ISADTSKNTA YLQMNSLRAE DTAVYYCARD IQSVSGEFDY WGQGTLVTVS  120
S                                                                   121

SEQ ID NO: 2825         moltype = AA  length = 121
FEATURE                 Location/Qualifiers
REGION                  1..121
                        note = Synthetic
source                  1..121
                        mol_type = protein
                        organism = synthetic construct
SEQUENCE: 2825
MEVQLVESGG GLVQPGGSLR LSCAASGFTI SDYIIHWVRQ APGKGLEWVG YIDPSNGYTY  60
YADSVKGRFT ISADTSKNTA YLQMNSLRAE DTAVYYCARD PQSLTSPFDY WGQGTLVTVS  120
S                                                                   121

SEQ ID NO: 2826         moltype = AA  length = 121
FEATURE                 Location/Qualifiers
REGION                  1..121
                        note = Synthetic
source                  1..121
                        mol_type = protein
                        organism = synthetic construct
SEQUENCE: 2826
MEVQLVESGG GLVQPGGSLR LSCAASGFTI PDYIIHWVRQ APGKGLEWVG YIDPSNGYTY  60
YADSVKGRFT ISADTSKNTA YLQMNSLRAE DTAVYYCARD IQSVSGEFDY WGQGTLVTVS  120
S                                                                   121

SEQ ID NO: 2827         moltype = AA  length = 121
FEATURE                 Location/Qualifiers
REGION                  1..121
                        note = Synthetic
source                  1..121
                        mol_type = protein
                        organism = synthetic construct
SEQUENCE: 2827
MEVQLVESGG GLVQPGGSSR LSCAASGFTI YDYIIHWVRQ APGKGLEWVG YIDPSNGYTD  60
YADSVKGRFT ISADTSKNTA YLQMNSLRAE DTAVYYCARD IQSVSGEFDY WGQGTLVTVS  120
S                                                                   121

SEQ ID NO: 2828         moltype = AA  length = 121
FEATURE                 Location/Qualifiers
REGION                  1..121
                        note = Synthetic
source                  1..121
                        mol_type = protein
                        organism = synthetic construct
SEQUENCE: 2828
MEVQLVESGG GLVQPGGSLR LSCAASGFTI FDYIIHWVRQ APGKGLEWVG YIDPSNGYTY  60
YADSVKGRFT ISADTSKNTA YLQMNSLRAE DTAVYYCARD PQSVGSEFDY WGQGTLVTVS  120
S                                                                   121

SEQ ID NO: 2829         moltype = AA  length = 121
FEATURE                 Location/Qualifiers
REGION                  1..121
                        note = Synthetic
source                  1..121
                        mol_type = protein
                        organism = synthetic construct
SEQUENCE: 2829
```

-continued

```
MEVQLVESGG GLVQPGGSLR LSCAASGFTI FDYIIHWVRQ APGKGLEWVG YIDPSNGYTY  60
YADSVKGRFT ISADTSKNTA YLQMNSLRAE DTAVYYCARD IQSVSGEFDY WGQGTLVTVS  120
S                                                                 121

SEQ ID NO: 2830         moltype = AA  length = 121
FEATURE                 Location/Qualifiers
REGION                  1..121
                        note = Synthetic
source                  1..121
                        mol_type = protein
                        organism = synthetic construct
SEQUENCE: 2830
MEVQLVESGG GLVQPGGSLR LSCAASGFTI YDYIIHWVRQ APGKGLEWVG YIDPSNGYTY  60
HADSVKGRFT ISADTSKNTA YLQMNSLRAE DTAVYYCARD PQSLSSPFDY WGQGTLVTVS  120
S                                                                 121

SEQ ID NO: 2831         moltype = AA  length = 121
FEATURE                 Location/Qualifiers
REGION                  1..121
                        note = Synthetic
source                  1..121
                        mol_type = protein
                        organism = synthetic construct
SEQUENCE: 2831
MEVQLVESGG GLVQPGGSLR LSCAASGFTI SHYIIHWVRQ APGKGLEWVG YIDPSNGYTY  60
YADSVKGRFT ISADTSKNTA YLQMNSLRAE DTAVYYCARD IQSVSGEFDY WGQGTLVTVS  120
S                                                                 121

SEQ ID NO: 2832         moltype = AA  length = 121
FEATURE                 Location/Qualifiers
REGION                  1..121
                        note = Synthetic
source                  1..121
                        mol_type = protein
                        organism = synthetic construct
SEQUENCE: 2832
MEVQLVESGG GLVQPGGSLR LSCAASGFTI SDYTIHWVRQ APGKGLEWVG YIDPSNGYTY  60
YADSVKGRFT ISADTSKNTA YLQMNSLRAE DTAVYYCARD IQSVSGEFDY WGQGTLVTVS  120
S                                                                 121

SEQ ID NO: 2833         moltype = AA  length = 121
FEATURE                 Location/Qualifiers
REGION                  1..121
                        note = Synthetic
source                  1..121
                        mol_type = protein
                        organism = synthetic construct
SEQUENCE: 2833
MEVQLVESGG GLVQPGGSLR LSCAASGFTI AAYIIHWVRQ APGKGLEWVG YIDPSNGYTY  60
YADSVKGRFT ISADTSKNTA YLQMNSLRAE DTAVYYCARD DQSFSSPFDY WGQGTLVTVS  120
S                                                                 121

SEQ ID NO: 2834         moltype = AA  length = 121
FEATURE                 Location/Qualifiers
REGION                  1..121
                        note = Synthetic
source                  1..121
                        mol_type = protein
                        organism = synthetic construct
SEQUENCE: 2834
MEVQLVESGG GLVQPGGSLR LSCAASGFNI AYYTIHWVRQ APGKGLEWVG YIDPSNGYTY  60
YADSVKGRFT ISADTSKNTA YLQMNSLRAE DTAVYYCARD PQSFSSPFDY WGQGTLVTVS  120
S                                                                 121

SEQ ID NO: 2835         moltype = AA  length = 121
FEATURE                 Location/Qualifiers
REGION                  1..121
                        note = Synthetic
source                  1..121
                        mol_type = protein
                        organism = synthetic construct
SEQUENCE: 2835
MEVQLVESGG GLVQPGGSLR LSCAASGFTI SDYVIHWVRQ APGKGLEWVG YIDPSNGYTF  60
YADSVKGRFT ISADTPKNTA YLQMNSLRAK DTAVYYCARD PQSLSSPFDY WGQGTLVTVS  120
S                                                                 121

SEQ ID NO: 2836         moltype = AA  length = 121
FEATURE                 Location/Qualifiers
REGION                  1..121
```

```
                         note = Synthetic
source                   1..121
                         mol_type = protein
                         organism = synthetic construct
SEQUENCE: 2836
MEVQLVESGG GLVQPGGSLR LSCAASGFTI SDYVIHWVRQ APGKGLEWVG YIDPSNGYTY  60
YADSVKGRFT ISADTSKNTA YLQMNSLRAE DTAVYYCARD DQSISSPLDY WGQGTLVTVS  120
S                                                                   121

SEQ ID NO: 2837          moltype = AA  length = 121
FEATURE                  Location/Qualifiers
REGION                   1..121
                         note = Synthetic
source                   1..121
                         mol_type = protein
                         organism = synthetic construct
SEQUENCE: 2837
MEVQLVESGG GLVQPGGSLR LSCAASGFTI SDYVIHWVRQ APGKGLEWVG YIDPSNGFTY  60
YADSVKGRFT ISADTSKNTA YLQTNSLRAE DTAVYYCARD IQSVSGEFDY WGQGTLVTVS  120
S                                                                   121

SEQ ID NO: 2838          moltype = AA  length = 121
FEATURE                  Location/Qualifiers
REGION                   1..121
                         note = Synthetic
source                   1..121
                         mol_type = protein
                         organism = synthetic construct
SEQUENCE: 2838
MEVQLVESGG GLVQPGGSLR LSCAASGFTI SSYIIHWVRQ APGKGPEWVG YIDPSNGYTY  60
YADSVKGRFT ISADTSKNTA YLQMNSLRAE DTAVYYCARD PQTLTSPFDY WGQGTLVTVS  120
S                                                                   121

SEQ ID NO: 2839          moltype =   length =
SEQUENCE: 2839
000

SEQ ID NO: 2840          moltype = AA  length = 116
FEATURE                  Location/Qualifiers
REGION                   1..116
                         note = Synthetic
source                   1..116
                         mol_type = protein
                         organism = synthetic construct
SEQUENCE: 2840
QSVEESEGGL FKPADTLTLT CTASGFSISS YDMSWVRQAP GNGLEWIGII GSNGRTYYPN  60
WAKSRSTITR NTNENTVTLK MTSLTAADTA TYFCARGLYD GTGNIWGPGT LVTVSS      116

SEQ ID NO: 2841          moltype =   length =
SEQUENCE: 2841
000

SEQ ID NO: 2842          moltype =   length =
SEQUENCE: 2842
000

SEQ ID NO: 2843          moltype =   length =
SEQUENCE: 2843
000

SEQ ID NO: 2844          moltype =   length =
SEQUENCE: 2844
000

SEQ ID NO: 2845          moltype =   length =
SEQUENCE: 2845
000

SEQ ID NO: 2846          moltype = AA  length = 119
FEATURE                  Location/Qualifiers
REGION                   1..119
                         note = Synthetic
source                   1..119
                         mol_type = protein
                         organism = synthetic construct
SEQUENCE: 2846
QSVEESEGGL FKPTDTLTLT CTVSGFSLSY YGVSWVRQAP GNGLEWIGTI DSSGRTYYAS  60
WANGRFTISN DNAPNTVSLQ VNSLAADTA TYFCARDFYG WNSGALDIWG PGTLVTVSS   119
```

```
SEQ ID NO: 2847        moltype =   length =
SEQUENCE: 2847
000

SEQ ID NO: 2848        moltype =   length =
SEQUENCE: 2848
000

SEQ ID NO: 2849        moltype =   length =
SEQUENCE: 2849
000

SEQ ID NO: 2850        moltype =   length =
SEQUENCE: 2850
000

SEQ ID NO: 2851        moltype = AA  length = 121
FEATURE                Location/Qualifiers
REGION                 1..121
                       note = Synthetic
source                 1..121
                       mol_type = protein
                       organism = synthetic construct
SEQUENCE: 2851
MQVQVQESGP GLVKPPGTLS LTCAVSGFSL SSYYGVSWVRQ PPGKGLEWIG TIDSSGRTYY  60
NPSLKSRVTI SNDNAPNTVS LKLSSVTAAD TAVYYCARDF YGWNSGALDI WGQGTLVTVS  120
S                                                                  121

SEQ ID NO: 2852        moltype =   length =
SEQUENCE: 2852
000

SEQ ID NO: 2853        moltype =   length =
SEQUENCE: 2853
000

SEQ ID NO: 2854        moltype =   length =
SEQUENCE: 2854
000

SEQ ID NO: 2855        moltype =   length =
SEQUENCE: 2855
000

SEQ ID NO: 2856        moltype =   length =
SEQUENCE: 2856
000

SEQ ID NO: 2857        moltype = AA  length = 118
FEATURE                Location/Qualifiers
REGION                 1..118
                       note = Synthetic
source                 1..118
                       mol_type = protein
                       organism = synthetic construct
SEQUENCE: 2857
MEVQLVESGG GLVQPGGSLR LSCAASGFSI SSYDMSWVRQ APGKGLEWIG IIGSNGRTYY  60
PDSVKGRFTI SRDNSKNTVT LQMNSLRAED TAVYYCARGL YDGTGNIWGQ GTLVTVSS    118

SEQ ID NO: 2858        moltype =   length =
SEQUENCE: 2858
000

SEQ ID NO: 2859        moltype = AA  length = 118
FEATURE                Location/Qualifiers
REGION                 1..118
                       note = Synthetic
source                 1..118
                       mol_type = protein
                       organism = synthetic construct
SEQUENCE: 2859
MEVQLVESGG GLVQPGGSLR LSCAASGFSI SSYDMSWVRQ APGKGLEWIG IIGSNGRTYY  60
PDSVKGRFTI SRDNSKNTVT LQMNSLRAED TAVYYCARGL YDGTGNIWGQ GTLVTVSS    118

SEQ ID NO: 2860        moltype = AA  length = 118
FEATURE                Location/Qualifiers
REGION                 1..118
                       note = Synthetic
source                 1..118
```

mol_type = protein
organism = synthetic construct
SEQUENCE: 2860
MQVQVVESGG GLVKPGGSLR LSCAASGFSI SSYDMSWIRQ APGKGLEWIG IIGSNGRTYY 60
ADSVKGRFTI SRNTNENTVY LQMNSLRAED TAVYYCARGL YDGTGNIWGQ GTLVTVSS 118

SEQ ID NO: 2861 moltype = length =
SEQUENCE: 2861
000

SEQ ID NO: 2862 moltype = length =
SEQUENCE: 2862
000

SEQ ID NO: 2863 moltype = length =
SEQUENCE: 2863
000

SEQ ID NO: 2864 moltype = length =
SEQUENCE: 2864
000

SEQ ID NO: 2865 moltype = length =
SEQUENCE: 2865
000

SEQ ID NO: 2866 moltype = length =
SEQUENCE: 2866
000

SEQ ID NO: 2867 moltype = length =
SEQUENCE: 2867
000

SEQ ID NO: 2868 moltype = length =
SEQUENCE: 2868
000

SEQ ID NO: 2869 moltype = length =
SEQUENCE: 2869
000

SEQ ID NO: 2870 moltype = length =
SEQUENCE: 2870
000

SEQ ID NO: 2871 moltype = length =
SEQUENCE: 2871
000

SEQ ID NO: 2872 moltype = length =
SEQUENCE: 2872
000

SEQ ID NO: 2873 moltype = length =
SEQUENCE: 2873
000

SEQ ID NO: 2874 moltype = length =
SEQUENCE: 2874
000

SEQ ID NO: 2875 moltype = length =
SEQUENCE: 2875
000

SEQ ID NO: 2876 moltype = length =
SEQUENCE: 2876
000

SEQ ID NO: 2877 moltype = length =
SEQUENCE: 2877
000

SEQ ID NO: 2878 moltype = length =
SEQUENCE: 2878
000

SEQ ID NO: 2879 moltype = length =

SEQUENCE: 2879
000

SEQ ID NO: 2880 moltype = length =
SEQUENCE: 2880
000

SEQ ID NO: 2881 moltype = length =
SEQUENCE: 2881
000

SEQ ID NO: 2882 moltype = length =
SEQUENCE: 2882
000

SEQ ID NO: 2883 moltype = length =
SEQUENCE: 2883
000

SEQ ID NO: 2884 moltype = length =
SEQUENCE: 2884
000

SEQ ID NO: 2885 moltype = length =
SEQUENCE: 2885
000

SEQ ID NO: 2886 moltype = length =
SEQUENCE: 2886
000

SEQ ID NO: 2887 moltype = length =
SEQUENCE: 2887
000

SEQ ID NO: 2888 moltype = length =
SEQUENCE: 2888
000

SEQ ID NO: 2889 moltype = length =
SEQUENCE: 2889
000

SEQ ID NO: 2890 moltype = length =
SEQUENCE: 2890
000

SEQ ID NO: 2891 moltype = length =
SEQUENCE: 2891
000

SEQ ID NO: 2892 moltype = length =
SEQUENCE: 2892
000

SEQ ID NO: 2893 moltype = length =
SEQUENCE: 2893
000

SEQ ID NO: 2894 moltype = length =
SEQUENCE: 2894
000

SEQ ID NO: 2895 moltype = length =
SEQUENCE: 2895
000

SEQ ID NO: 2896 moltype = length =
SEQUENCE: 2896
000

SEQ ID NO: 2897 moltype = length =
SEQUENCE: 2897
000

SEQ ID NO: 2898 moltype = length =
SEQUENCE: 2898
000

-continued

SEQ ID NO: 2899 moltype = length =
SEQUENCE: 2899
000

SEQ ID NO: 2900 moltype = length =
SEQUENCE: 2900
000

SEQ ID NO: 2901 moltype = length =
SEQUENCE: 2901
000

SEQ ID NO: 2902 moltype = length =
SEQUENCE: 2902
000

SEQ ID NO: 2903 moltype = length =
SEQUENCE: 2903
000

SEQ ID NO: 2904 moltype = length =
SEQUENCE: 2904
000

SEQ ID NO: 2905 moltype = length =
SEQUENCE: 2905
000

SEQ ID NO: 2906 moltype = length =
SEQUENCE: 2906
000

SEQ ID NO: 2907 moltype = length =
SEQUENCE: 2907
000

SEQ ID NO: 2908 moltype = length =
SEQUENCE: 2908
000

SEQ ID NO: 2909 moltype = length =
SEQUENCE: 2909
000

SEQ ID NO: 2910 moltype = length =
SEQUENCE: 2910
000

SEQ ID NO: 2911 moltype = length =
SEQUENCE: 2911
000

SEQ ID NO: 2912 moltype = length =
SEQUENCE: 2912
000

SEQ ID NO: 2913 moltype = length =
SEQUENCE: 2913
000

SEQ ID NO: 2914 moltype = length =
SEQUENCE: 2914
000

SEQ ID NO: 2915 moltype = length =
SEQUENCE: 2915
000

SEQ ID NO: 2916 moltype = length =
SEQUENCE: 2916
000

SEQ ID NO: 2917 moltype = length =
SEQUENCE: 2917
000

SEQ ID NO: 2918 moltype = length =
SEQUENCE: 2918
000

SEQ ID NO: 2919 moltype = length =
SEQUENCE: 2919
000

SEQ ID NO: 2920 moltype = length =
SEQUENCE: 2920
000

SEQ ID NO: 2921 moltype = length =
SEQUENCE: 2921
000

SEQ ID NO: 2922 moltype = length =
SEQUENCE: 2922
000

SEQ ID NO: 2923 moltype = length =
SEQUENCE: 2923
000

SEQ ID NO: 2924 moltype = length =
SEQUENCE: 2924
000

SEQ ID NO: 2925 moltype = length =
SEQUENCE: 2925
000

SEQ ID NO: 2926 moltype = length =
SEQUENCE: 2926
000

SEQ ID NO: 2927 moltype = length =
SEQUENCE: 2927
000

SEQ ID NO: 2928 moltype = length =
SEQUENCE: 2928
000

SEQ ID NO: 2929 moltype = length =
SEQUENCE: 2929
000

SEQ ID NO: 2930 moltype = length =
SEQUENCE: 2930
000

SEQ ID NO: 2931 moltype = length =
SEQUENCE: 2931
000

SEQ ID NO: 2932 moltype = length =
SEQUENCE: 2932
000

SEQ ID NO: 2933 moltype = length =
SEQUENCE: 2933
000

SEQ ID NO: 2934 moltype = length =
SEQUENCE: 2934
000

SEQ ID NO: 2935 moltype = length =
SEQUENCE: 2935
000

SEQ ID NO: 2936 moltype = length =
SEQUENCE: 2936
000

SEQ ID NO: 2937 moltype = length =
SEQUENCE: 2937
000

SEQ ID NO: 2938 moltype = length =
SEQUENCE: 2938

000

SEQ ID NO: 2939 moltype = length =
SEQUENCE: 2939
000

SEQ ID NO: 2940 moltype = length =
SEQUENCE: 2940
000

SEQ ID NO: 2941 moltype = length =
SEQUENCE: 2941
000

SEQ ID NO: 2942 moltype = length =
SEQUENCE: 2942
000

SEQ ID NO: 2943 moltype = length =
SEQUENCE: 2943
000

SEQ ID NO: 2944 moltype = length =
SEQUENCE: 2944
000

SEQ ID NO: 2945 moltype = length =
SEQUENCE: 2945
000

SEQ ID NO: 2946 moltype = length =
SEQUENCE: 2946
000

SEQ ID NO: 2947 moltype = length =
SEQUENCE: 2947
000

SEQ ID NO: 2948 moltype = length =
SEQUENCE: 2948
000

SEQ ID NO: 2949 moltype = length =
SEQUENCE: 2949
000

SEQ ID NO: 2950 moltype = length =
SEQUENCE: 2950
000

SEQ ID NO: 2951 moltype = AA length = 112
FEATURE Location/Qualifiers
REGION 1..112
note = Synthetic
source 1..112
mol_type = protein
organism = synthetic construct
SEQUENCE: 2951
ELVMTQTPSP VSAAVGSTVT ISCQASQSVY GNNWLSWFQQ KPGQPPKLLI YGASKLASGV 60
SSRFKGSGSG TQFTLTISGV QCDDAATYYC QGTYYSGDWY FAFGGGTELE IL 112

SEQ ID NO: 2952 moltype = length =
SEQUENCE: 2952
000

SEQ ID NO: 2953 moltype = length =
SEQUENCE: 2953
000

SEQ ID NO: 2954 moltype = length =
SEQUENCE: 2954
000

SEQ ID NO: 2955 moltype = length =
SEQUENCE: 2955
000

SEQ ID NO: 2956 moltype = length =
SEQUENCE: 2956

```
000

SEQ ID NO: 2957        moltype = AA  length = 111
FEATURE                Location/Qualifiers
REGION                 1..111
                       note = Synthetic
source                 1..111
                       mol_type = protein
                       organism = synthetic construct
SEQUENCE: 2957
ELDLTQTASP VSAAVGGTVT INCQASQSVY SNKYLSWYQQ KPGQPPKLLI YKASTLASGV  60
PSRFSGSGFG TEFTLTISDV QCDDAATYYC AAAYSDDSDT AFGGGTKVVV E           111

SEQ ID NO: 2958        moltype =   length =
SEQUENCE: 2958
000

SEQ ID NO: 2959        moltype =   length =
SEQUENCE: 2959
000

SEQ ID NO: 2960        moltype =   length =
SEQUENCE: 2960
000

SEQ ID NO: 2961        moltype =   length =
SEQUENCE: 2961
000

SEQ ID NO: 2962        moltype = AA  length = 112
FEATURE                Location/Qualifiers
REGION                 1..112
                       note = Synthetic
source                 1..112
                       mol_type = protein
                       organism = synthetic construct
SEQUENCE: 2962
MDLQLTQSPS TLSASVGDRV TITCRASQSV YSNKYLSWYQ QKPGKAPKLL IYKASTLASG  60
VPSRFSGSGS GTEFTLTISS LQPDDFATYY CAAAYSDDSD TAFGQGTKVE IK          112

SEQ ID NO: 2963        moltype =   length =
SEQUENCE: 2963
000

SEQ ID NO: 2964        moltype =   length =
SEQUENCE: 2964
000

SEQ ID NO: 2965        moltype =   length =
SEQUENCE: 2965
000

SEQ ID NO: 2966        moltype =   length =
SEQUENCE: 2966
000

SEQ ID NO: 2967        moltype =   length =
SEQUENCE: 2967
000

SEQ ID NO: 2968        moltype = AA  length = 113
FEATURE                Location/Qualifiers
REGION                 1..113
                       note = Synthetic
source                 1..113
                       mol_type = protein
                       organism = synthetic construct
SEQUENCE: 2968
MDLQMTQSPS SLSASVGDRV TITCRASQSV YGNNWLSWYQ QKPGKAPKLL IYGASKLASG  60
VPSRFSGSGS GTQFTLTISS LQPEDFATYY CQGTYYSGDW YFAFGQGTKV EIK         113

SEQ ID NO: 2969        moltype =   length =
SEQUENCE: 2969
000

SEQ ID NO: 2970        moltype = AA  length = 113
FEATURE                Location/Qualifiers
REGION                 1..113
                       note = Synthetic
```

-continued

```
source                  1..113
                        mol_type = protein
                        organism = synthetic construct
SEQUENCE: 2970
MELVMTQSPP TLSLSPGERV TLSCRASQSV YGNNWLSWYQ QKPGQAPRLL IYGASKLATS  60
IPARFSGSGS GTQFTLTISS LQPEDFAVYY CQGTYYSGDW YFAFGQGTKV EIK         113

SEQ ID NO: 2971         moltype = AA  length = 113
FEATURE                 Location/Qualifiers
REGION                  1..113
                        note = Synthetic
source                  1..113
                        mol_type = protein
                        organism = synthetic construct
SEQUENCE: 2971
MDIQMTQSPS SLSASVGDRV TITCQASQSV YGNNWLSWYQ QKPGKAPKLL IYGASKLASG  60
VPSRFSGSGS GTDFTLTISS LQPEDFATYY CQGTYYSGDW YFAFGGGTKV EIK         113

SEQ ID NO: 2972         moltype =   length =
SEQUENCE: 2972
000

SEQ ID NO: 2973         moltype =   length =
SEQUENCE: 2973
000

SEQ ID NO: 2974         moltype =   length =
SEQUENCE: 2974
000

SEQ ID NO: 2975         moltype =   length =
SEQUENCE: 2975
000

SEQ ID NO: 2976         moltype =   length =
SEQUENCE: 2976
000

SEQ ID NO: 2977         moltype =   length =
SEQUENCE: 2977
000

SEQ ID NO: 2978         moltype =   length =
SEQUENCE: 2978
000

SEQ ID NO: 2979         moltype =   length =
SEQUENCE: 2979
000

SEQ ID NO: 2980         moltype =   length =
SEQUENCE: 2980
000

SEQ ID NO: 2981         moltype =   length =
SEQUENCE: 2981
000

SEQ ID NO: 2982         moltype =   length =
SEQUENCE: 2982
000

SEQ ID NO: 2983         moltype =   length =
SEQUENCE: 2983
000

SEQ ID NO: 2984         moltype =   length =
SEQUENCE: 2984
000

SEQ ID NO: 2985         moltype =   length =
SEQUENCE: 2985
000

SEQ ID NO: 2986         moltype =   length =
SEQUENCE: 2986
000

SEQ ID NO: 2987         moltype =   length =
```

-continued

SEQUENCE: 2987
000

SEQ ID NO: 2988 moltype = length =
SEQUENCE: 2988
000

SEQ ID NO: 2989 moltype = length =
SEQUENCE: 2989
000

SEQ ID NO: 2990 moltype = length =
SEQUENCE: 2990
000

SEQ ID NO: 2991 moltype = length =
SEQUENCE: 2991
000

SEQ ID NO: 2992 moltype = length =
SEQUENCE: 2992
000

SEQ ID NO: 2993 moltype = length =
SEQUENCE: 2993
000

SEQ ID NO: 2994 moltype = length =
SEQUENCE: 2994
000

SEQ ID NO: 2995 moltype = length =
SEQUENCE: 2995
000

SEQ ID NO: 2996 moltype = length =
SEQUENCE: 2996
000

SEQ ID NO: 2997 moltype = length =
SEQUENCE: 2997
000

SEQ ID NO: 2998 moltype = length =
SEQUENCE: 2998
000

SEQ ID NO: 2999 moltype = length =
SEQUENCE: 2999
000

SEQ ID NO: 3000 moltype = length =
SEQUENCE: 3000
000

SEQ ID NO: 3001 moltype = length =
SEQUENCE: 3001
000

SEQ ID NO: 3002 moltype = length =
SEQUENCE: 3002
000

SEQ ID NO: 3003 moltype = length =
SEQUENCE: 3003
000

SEQ ID NO: 3004 moltype = length =
SEQUENCE: 3004
000

SEQ ID NO: 3005 moltype = length =
SEQUENCE: 3005
000

SEQ ID NO: 3006 moltype = length =
SEQUENCE: 3006
000

-continued

SEQ ID NO: 3007 moltype = length =
SEQUENCE: 3007
000

SEQ ID NO: 3008 moltype = length =
SEQUENCE: 3008
000

SEQ ID NO: 3009 moltype = length =
SEQUENCE: 3009
000

SEQ ID NO: 3010 moltype = length =
SEQUENCE: 3010
000

SEQ ID NO: 3011 moltype = length =
SEQUENCE: 3011
000

SEQ ID NO: 3012 moltype = length =
SEQUENCE: 3012
000

SEQ ID NO: 3013 moltype = length =
SEQUENCE: 3013
000

SEQ ID NO: 3014 moltype = length =
SEQUENCE: 3014
000

SEQ ID NO: 3015 moltype = length =
SEQUENCE: 3015
000

SEQ ID NO: 3016 moltype = length =
SEQUENCE: 3016
000

SEQ ID NO: 3017 moltype = length =
SEQUENCE: 3017
000

SEQ ID NO: 3018 moltype = length =
SEQUENCE: 3018
000

SEQ ID NO: 3019 moltype = length =
SEQUENCE: 3019
000

SEQ ID NO: 3020 moltype = length =
SEQUENCE: 3020
000

SEQ ID NO: 3021 moltype = length =
SEQUENCE: 3021
000

SEQ ID NO: 3022 moltype = length =
SEQUENCE: 3022
000

SEQ ID NO: 3023 moltype = length =
SEQUENCE: 3023
000

SEQ ID NO: 3024 moltype = length =
SEQUENCE: 3024
000

SEQ ID NO: 3025 moltype = length =
SEQUENCE: 3025
000

SEQ ID NO: 3026 moltype = length =
SEQUENCE: 3026
000

SEQ ID NO: 3027 moltype = length =
SEQUENCE: 3027
000

SEQ ID NO: 3028 moltype = length =
SEQUENCE: 3028
000

SEQ ID NO: 3029 moltype = length =
SEQUENCE: 3029
000

SEQ ID NO: 3030 moltype = length =
SEQUENCE: 3030
000

SEQ ID NO: 3031 moltype = length =
SEQUENCE: 3031
000

SEQ ID NO: 3032 moltype = length =
SEQUENCE: 3032
000

SEQ ID NO: 3033 moltype = length =
SEQUENCE: 3033
000

SEQ ID NO: 3034 moltype = length =
SEQUENCE: 3034
000

SEQ ID NO: 3035 moltype = length =
SEQUENCE: 3035
000

SEQ ID NO: 3036 moltype = length =
SEQUENCE: 3036
000

SEQ ID NO: 3037 moltype = length =
SEQUENCE: 3037
000

SEQ ID NO: 3038 moltype = length =
SEQUENCE: 3038
000

SEQ ID NO: 3039 moltype = length =
SEQUENCE: 3039
000

SEQ ID NO: 3040 moltype = length =
SEQUENCE: 3040
000

SEQ ID NO: 3041 moltype = length =
SEQUENCE: 3041
000

SEQ ID NO: 3042 moltype = length =
SEQUENCE: 3042
000

SEQ ID NO: 3043 moltype = length =
SEQUENCE: 3043
000

SEQ ID NO: 3044 moltype = length =
SEQUENCE: 3044
000

SEQ ID NO: 3045 moltype = length =
SEQUENCE: 3045
000

SEQ ID NO: 3046 moltype = length =
SEQUENCE: 3046

```
000

SEQ ID NO: 3047        moltype =   length =
SEQUENCE: 3047
000

SEQ ID NO: 3048        moltype =   length =
SEQUENCE: 3048
000

SEQ ID NO: 3049        moltype =   length =
SEQUENCE: 3049
000

SEQ ID NO: 3050        moltype =   length =
SEQUENCE: 3050
000

SEQ ID NO: 3051        moltype =   length =
SEQUENCE: 3051
000

SEQ ID NO: 3052        moltype =   length =
SEQUENCE: 3052
000

SEQ ID NO: 3053        moltype =   length =
SEQUENCE: 3053
000

SEQ ID NO: 3054        moltype =   length =
SEQUENCE: 3054
000

SEQ ID NO: 3055        moltype =   length =
SEQUENCE: 3055
000

SEQ ID NO: 3056        moltype =   length =
SEQUENCE: 3056
000

SEQ ID NO: 3057        moltype =   length =
SEQUENCE: 3057
000

SEQ ID NO: 3058        moltype =   length =
SEQUENCE: 3058
000

SEQ ID NO: 3059        moltype =   length =
SEQUENCE: 3059
000

SEQ ID NO: 3060        moltype =   length =
SEQUENCE: 3060
000

SEQ ID NO: 3061        moltype = AA  length = 107
FEATURE                Location/Qualifiers
REGION                 1..107
                       note = Synthetic
source                 1..107
                       mol_type = protein
                       organism = synthetic construct
SEQUENCE: 3061
DIQMTQSPSS LSASVGDRVT ITCRASQDVN TAVAWYQQKP GKAPKLLIYS ASFLYSGVPS  60
RFSGSRSGTD FTLTISSLQP EDFATYYCQQ HYTTPPTFGQ GTKVEIK                107

SEQ ID NO: 3062        moltype = AA  length = 330
FEATURE                Location/Qualifiers
source                 1..330
                       mol_type = protein
                       organism = Homo sapiens
SEQUENCE: 3062
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
```

-continued

```
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 3063        moltype = AA  length = 107
FEATURE                Location/Qualifiers
source                 1..107
                       mol_type = protein
                       organism = Homo sapiens
SEQUENCE: 3063
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC                107

SEQ ID NO: 3064        moltype = AA  length = 323
FEATURE                Location/Qualifiers
source                 1..323
                       mol_type = protein
                       organism = Mus musculus
SEQUENCE: 3064
AKTTPPSVYP LAPGSAAQTN SMVTLGCLVK GYFPEPVTVT WNSGSLSSGV HTFPAVLQSD  60
LYTLSSSVTV PSSTWPSETV TCNVAHPASS TKVDKKIVPR DCGCKPCICT VPEVSSVFIF  120
PPKPKDVLTI TLTPKVTCVV VDISKDDPEV QFSWFVDDVE VHTAQTQPRE EQFNSTFRSV  180
SELPIMHQDW LNGKEFKCRV NSAAFPAPIE KTISKTKGRP KAPQVYTIPP PKEQMAKDKV  240
SLTCMITDFF PEDITVEWQW NGQPAENYKN TQPIMDTDGS YFVYSKLNVQ KSNWEAGNTF  300
TCSVLHEGLH NHHTEKSLSH SPG                                          323

SEQ ID NO: 3065        moltype = AA  length = 107
FEATURE                Location/Qualifiers
source                 1..107
                       mol_type = protein
                       organism = Mus musculus
SEQUENCE: 3065
RADAAPTVSI FPPSSEQLTS GGASVVCFLN NFYPKDINVK WKIDGSERQN GVLNSWTDQD  60
SKDSTYSMSS TLTLTKDEYE RHNSYTCEAT HKTSTSPIVK SFNRNEC                107

SEQ ID NO: 3066        moltype = AA  length = 108
FEATURE                Location/Qualifiers
REGION                 1..108
                       note = Synthetic
source                 1..108
                       mol_type = protein
                       organism = synthetic construct
SEQUENCE: 3066
HMTVAAPSVF IFPPSDEQLK SGTASVVCLL NNFYPREAKV QWKVDNALQS GNSQESVTEQ  60
DSKDSTYSLS STLTLSKADY EKHKVYACEV THQGLSSPVT KSFNRGEC               108

SEQ ID NO: 3067        moltype = AA  length = 106
FEATURE                Location/Qualifiers
REGION                 1..106
                       note = Synthetic
source                 1..106
                       mol_type = protein
                       organism = synthetic construct
SEQUENCE: 3067
GQPKAAPSVT LFPPSSEELQ ANKATLVCLI SDFYPGAVTV AWKADSSPVK AGVETTTPSK  60
QSNNKYAASS YLSLTPEQWK SHRSYSCQVT HEGSTVEKTV APTECS                 106

SEQ ID NO: 3068        moltype = AA  length = 241
FEATURE                Location/Qualifiers
REGION                 1..241
                       note = Synthetic
source                 1..241
                       mol_type = protein
                       organism = synthetic construct
SEQUENCE: 3068
DKTHTCPPCS APELLGGSSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGKGSG DYKDDDDKGS  240
G                                                                  241

SEQ ID NO: 3069        moltype = AA  length = 20
FEATURE                Location/Qualifiers
REGION                 1..20
                       note = Synthetic
source                 1..20
                       mol_type = protein
                       organism = synthetic construct
SEQUENCE: 3069
GSGDYKDDDD KGSGHHHHHH                                              20
```

```
SEQ ID NO: 3070        moltype = AA  length = 15
FEATURE                Location/Qualifiers
REGION                 1..15
                       note = Synthetic
source                 1..15
                       mol_type = protein
                       organism = synthetic construct
SEQUENCE: 3070
GGGGSGGGGS GGGGS                                                   15

SEQ ID NO: 3071        moltype = AA  length = 11
FEATURE                Location/Qualifiers
REGION                 1..11
                       note = Synthetic
source                 1..11
                       mol_type = protein
                       organism = synthetic construct
SEQUENCE: 3071
AAGSDQEPKS S                                                       11

SEQ ID NO: 3072        moltype =   length =
SEQUENCE: 3072
000

SEQ ID NO: 3073        moltype = AA  length = 249
FEATURE                Location/Qualifiers
REGION                 1..249
                       note = Synthetic
source                 1..249
                       mol_type = protein
                       organism = synthetic construct
SEQUENCE: 3073
MSKNKQSVEE SEGGLFKPAD TLTLTCTASG FSISSYDMSW VRQAPGNGLE WIGIIGSNGR  60
TYYPNWAKSR STITRNTNEN TVTLKMTSLT AADTATYFCA RGLYDGTGNI WGPGTLVTVS  120
SGGGGSGGGG SGGGGSELVM TQTPSPVSAA VGSTVTISCQ ASQSVYGNNW LSWFQQKPGQ  180
PPKLLIYGAS KLASGVSSRF KGSGSGTQFT LTISGVQCDD AATYYCQGTY YSGDWYFAFG  240
GGTELEILA                                                          249

SEQ ID NO: 3074        moltype =   length =
SEQUENCE: 3074
000

SEQ ID NO: 3075        moltype =   length =
SEQUENCE: 3075
000

SEQ ID NO: 3076        moltype =   length =
SEQUENCE: 3076
000

SEQ ID NO: 3077        moltype =   length =
SEQUENCE: 3077
000

SEQ ID NO: 3078        moltype =   length =
SEQUENCE: 3078
000

SEQ ID NO: 3079        moltype = AA  length = 251
FEATURE                Location/Qualifiers
REGION                 1..251
                       note = Synthetic
source                 1..251
                       mol_type = protein
                       organism = synthetic construct
SEQUENCE: 3079
MSKNKQSVEE SEGGLFKPTD TLTLTCTVSG FSLSYYGVSW VRQAPGNGLE WIGTIDSSGR  60
TYYASWANGR FTISNDNAPN TVSLQVNSLA AADTATYFCA RDFYGWNSGA LDIWGPGTLV  120
TVSSGGGGSG GGGSGGGGSE LDLTQTASPV SAAVGGTVTI NCQASQSVYS NKYLSWYQQK  180
PGQPPKLLIY KASTLASGVP SRFSGSGFGT EFTLTISDVQ CDDAATYYCA AAYSDDSDTA  240
FGGGTKVVVE A                                                       251

SEQ ID NO: 3080        moltype =   length =
SEQUENCE: 3080
000

SEQ ID NO: 3081        moltype =   length =
SEQUENCE: 3081
```

000

SEQ ID NO: 3082 moltype = length =
SEQUENCE: 3082
000

SEQ ID NO: 3083 moltype = length =
SEQUENCE: 3083
000

SEQ ID NO: 3084 moltype = length =
SEQUENCE: 3084
000

SEQ ID NO: 3085 moltype = length =
SEQUENCE: 3085
000

SEQ ID NO: 3086 moltype = length =
SEQUENCE: 3086
000

SEQ ID NO: 3087 moltype = length =
SEQUENCE: 3087
000

SEQ ID NO: 3088 moltype = length =
SEQUENCE: 3088
000

SEQ ID NO: 3089 moltype = length =
SEQUENCE: 3089
000

SEQ ID NO: 3090 moltype = length =
SEQUENCE: 3090
000

SEQ ID NO: 3091 moltype = length =
SEQUENCE: 3091
000

SEQ ID NO: 3092 moltype = length =
SEQUENCE: 3092
000

SEQ ID NO: 3093 moltype = length =
SEQUENCE: 3093
000

SEQ ID NO: 3094 moltype = length =
SEQUENCE: 3094
000

SEQ ID NO: 3095 moltype = length =
SEQUENCE: 3095
000

SEQ ID NO: 3096 moltype = length =
SEQUENCE: 3096
000

SEQ ID NO: 3097 moltype = length =
SEQUENCE: 3097
000

SEQ ID NO: 3098 moltype = length =
SEQUENCE: 3098
000

SEQ ID NO: 3099 moltype = length =
SEQUENCE: 3099
000

SEQ ID NO: 3100 moltype = length =
SEQUENCE: 3100
000

SEQ ID NO: 3101 moltype = length =

SEQUENCE: 3101
000

SEQ ID NO: 3102 moltype = length =
SEQUENCE: 3102
000

SEQ ID NO: 3103 moltype = length =
SEQUENCE: 3103
000

SEQ ID NO: 3104 moltype = length =
SEQUENCE: 3104
000

SEQ ID NO: 3105 moltype = length =
SEQUENCE: 3105
000

SEQ ID NO: 3106 moltype = length =
SEQUENCE: 3106
000

SEQ ID NO: 3107 moltype = length =
SEQUENCE: 3107
000

SEQ ID NO: 3108 moltype = length =
SEQUENCE: 3108
000

SEQ ID NO: 3109 moltype = length =
SEQUENCE: 3109
000

SEQ ID NO: 3110 moltype = length =
SEQUENCE: 3110
000

SEQ ID NO: 3111 moltype = length =
SEQUENCE: 3111
000

SEQ ID NO: 3112 moltype = length =
SEQUENCE: 3112
000

SEQ ID NO: 3113 moltype = length =
SEQUENCE: 3113
000

SEQ ID NO: 3114 moltype = length =
SEQUENCE: 3114
000

SEQ ID NO: 3115 moltype = length =
SEQUENCE: 3115
000

SEQ ID NO: 3116 moltype = length =
SEQUENCE: 3116
000

SEQ ID NO: 3117 moltype = length =
SEQUENCE: 3117
000

SEQ ID NO: 3118 moltype = length =
SEQUENCE: 3118
000

SEQ ID NO: 3119 moltype = length =
SEQUENCE: 3119
000

SEQ ID NO: 3120 moltype = length =
SEQUENCE: 3120
000

-continued

SEQ ID NO: 3121 moltype = length =
SEQUENCE: 3121
000

SEQ ID NO: 3122 moltype = length =
SEQUENCE: 3122
000

SEQ ID NO: 3123 moltype = length =
SEQUENCE: 3123
000

SEQ ID NO: 3124 moltype = length =
SEQUENCE: 3124
000

SEQ ID NO: 3125 moltype = length =
SEQUENCE: 3125
000

SEQ ID NO: 3126 moltype = length =
SEQUENCE: 3126
000

SEQ ID NO: 3127 moltype = length =
SEQUENCE: 3127
000

SEQ ID NO: 3128 moltype = length =
SEQUENCE: 3128
000

SEQ ID NO: 3129 moltype = length =
SEQUENCE: 3129
000

SEQ ID NO: 3130 moltype = length =
SEQUENCE: 3130
000

SEQ ID NO: 3131 moltype = length =
SEQUENCE: 3131
000

SEQ ID NO: 3132 moltype = length =
SEQUENCE: 3132
000

SEQ ID NO: 3133 moltype = length =
SEQUENCE: 3133
000

SEQ ID NO: 3134 moltype = length =
SEQUENCE: 3134
000

SEQ ID NO: 3135 moltype = length =
SEQUENCE: 3135
000

SEQ ID NO: 3136 moltype = length =
SEQUENCE: 3136
000

SEQ ID NO: 3137 moltype = length =
SEQUENCE: 3137
000

SEQ ID NO: 3138 moltype = length =
SEQUENCE: 3138
000

SEQ ID NO: 3139 moltype = length =
SEQUENCE: 3139
000

SEQ ID NO: 3140 moltype = length =
SEQUENCE: 3140
000

SEQ ID NO: 3141 moltype = length =
SEQUENCE: 3141
000

SEQ ID NO: 3142 moltype = length =
SEQUENCE: 3142
000

SEQ ID NO: 3143 moltype = length =
SEQUENCE: 3143
000

SEQ ID NO: 3144 moltype = length =
SEQUENCE: 3144
000

SEQ ID NO: 3145 moltype = length =
SEQUENCE: 3145
000

SEQ ID NO: 3146 moltype = length =
SEQUENCE: 3146
000

SEQ ID NO: 3147 moltype = length =
SEQUENCE: 3147
000

SEQ ID NO: 3148 moltype = length =
SEQUENCE: 3148
000

SEQ ID NO: 3149 moltype = length =
SEQUENCE: 3149
000

SEQ ID NO: 3150 moltype = length =
SEQUENCE: 3150
000

SEQ ID NO: 3151 moltype = length =
SEQUENCE: 3151
000

SEQ ID NO: 3152 moltype = length =
SEQUENCE: 3152
000

SEQ ID NO: 3153 moltype = length =
SEQUENCE: 3153
000

SEQ ID NO: 3154 moltype = length =
SEQUENCE: 3154
000

SEQ ID NO: 3155 moltype = length =
SEQUENCE: 3155
000

SEQ ID NO: 3156 moltype = length =
SEQUENCE: 3156
000

SEQ ID NO: 3157 moltype = length =
SEQUENCE: 3157
000

SEQ ID NO: 3158 moltype = length =
SEQUENCE: 3158
000

SEQ ID NO: 3159 moltype = length =
SEQUENCE: 3159
000

SEQ ID NO: 3160 moltype = AA length = 294
FEATURE Location/Qualifiers

```
source                  1..294
                        mol_type = protein
                        organism = Mus musculus
SEQUENCE: 3160
MAILVRPRLL AALAPTFLGC LLLQVIAGAG IPEKAFNLTW ISTDFKTILE WQPKPTNYTY  60
TVQISDRSRN WKNKCFSTTD TECDLTDEIV KDVTWAYEAK VLSVPRRNSV HGDGDQLVIH  120
GEEPPFTNAP KFLPYRDTNL GQPVIQQFEQ DGRKLNVVVK DSLTLVRKNG TFLTLRQVFG  180
KDLGYIITYR KGSSTGKKTN ITNTNEFSID VEEGVSYCFF VQAMIFSRKT NQNSPGSSTV  240
CTEQWKSFLG ETLIIVGAVV LLATIFIILL SISLCKRRKN RAGQKGKNTP SRLA        294

SEQ ID NO: 3161         moltype = AA  length = 238
FEATURE                 Location/Qualifiers
source                  1..238
                        mol_type = protein
                        organism = Homo sapiens
SEQUENCE: 3161
METPAWPRVP RPETAVARTL LLGWVFAQVA GASGTTNTVA AYNLTWKSTN FKTILEWEPK  60
PVNQVYTVQI STKSGDWKSK CFYTTDTECD LTDEIVKDVK QTYLARVFSY PAGNVESTGS  120
AGEPLYENSP EFTPYLETNL GQPTIQSFEQ VGTKVNVTVE DERTLVRRNN TFLSLRDVFG  180
KDLIYTLYYW KSSSSGKKYS TSLELWYLWS SSLSSSWLYL YTSVERQEWG RAGRRTPH    238

SEQ ID NO: 3162         moltype = AA  length = 294
FEATURE                 Location/Qualifiers
source                  1..294
                        mol_type = protein
                        organism = Mus musculus
SEQUENCE: 3162
MAILVRPRLL AALAPTFLGC LLLQVTAGAG IPEKAFNLTW ISTDFKTILE WQPKPTNYTY  60
TVQISDRSRN WKNKCFSTTD TECDLTDEIV KDVTWAYEAK VLSVPRRNSV HGDGDQLVIH  120
GEEPPFTNAP KFLPYRDTNL GQPVIQQFEQ DGRKLNVVVK DSLTLVRKNG TFLTLRQVFG  180
KDLGYIITYR KGSSTGKKTN ITNTNEFSID VEEGVSYCFF VQAMIFSRKT NQNSPGSSTV  240
CTEQWKSFLG ETLIIVGAVV LLATIFIILL SISLCKRRKN RAGQKGKNTP SRLA        294

SEQ ID NO: 3163         moltype = AA  length = 450
FEATURE                 Location/Qualifiers
REGION                  1..450
                        note = Synthetic
source                  1..450
                        mol_type = protein
                        organism = synthetic construct
SEQUENCE: 3163
MEVQLVESGG GLVQPGGSLR LSCAASGFNI SSYWIHWVRQ APGKGLEWVG YIDPYSGSTY  60
YADSVKGRFT ISADTSKNTA YLQMNSLRAE DTAVYYCARS DYYYVDEYMD YWGQGTLVTV  120
SSASTKGPSV FPLAPSSKST SGGTAALGCL VKDYFPEPVT VSWNSGALTS GVHTFPAVLQ  180
SSGLSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFLY SKLTVDKSRW  420
QQGNVFSCSV MHEALHNHYT QKSLSLSPGK                                  450

SEQ ID NO: 3164         moltype = AA  length = 449
FEATURE                 Location/Qualifiers
REGION                  1..449
                        note = Synthetic
source                  1..449
                        mol_type = protein
                        organism = synthetic construct
SEQUENCE: 3164
MEVQLVESGG GLVQPGGSLR LSCAASGFNI SDYWIHWVRQ APGKGLEWVG FIDPYNGYTN  60
YADSVKGRFT ISADTSKNTA YLQMNSLRAE DTAVYYCARG YGSWPDYLDY WGQGTLVTVS  120
SASTKGPSVF PLAPSSKSTS GGTAALGCLV KDYFPEPVTV SWNSGALTSG VHTFPAVLQS  180
SGLSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFLYS KLTVDKSRWQ  420
QGNVFSCSVM HEALHNHYTQ KSLSLSPGK                                   449

SEQ ID NO: 3165         moltype = AA  length = 449
FEATURE                 Location/Qualifiers
REGION                  1..449
                        note = Synthetic
source                  1..449
                        mol_type = protein
                        organism = synthetic construct
SEQUENCE: 3165
MEVQLVESGG GLVQPGGSLR LSCAASGFNI SDYNIHWVRQ APGKGLEWVG YIDPSNGYTY  60
YADSVKGRFT ISADTSKNTA YLQMNSLRAE DTAVYYCARD DQSVSSPFDY WGQGTLVTVS  120
SASTKGPSVF PLAPSSKSTS GGTAALGCLV KDYFPEPVTV SWNSGALTSG VHTFPAVLQS  180
SGLSLSSVVT VPSSSLGTQT YICNVNHKPS NTKVDKKVEP KSCDKTHTCP PCPAPELLGG  240
```

-continued

```
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFLYS KLTVDKSRWQ  420
QGNVFSCSVM HEALHNHYTQ KSLSLSPGK                                    449

SEQ ID NO: 3166        moltype =   length =
SEQUENCE: 3166
000

SEQ ID NO: 3167        moltype =   length =
SEQUENCE: 3167
000

SEQ ID NO: 3168        moltype = AA  length = 449
FEATURE                Location/Qualifiers
REGION                 1..449
                       note = Synthetic
source                 1..449
                       mol_type = protein
                       organism = synthetic construct
SEQUENCE: 3168
MEVQLVESGG GLVQPGGSLR LSCAASGFTI SGYIIHWVRQ APGKGLEWVG YIDPSNGYTY  60
YADSVKGRFT ISADTSKNTA YLQMNSLRAE DTAVYYCARD DQSLSSPFDY WGQGTLVTVS  120
SASTKGPSVF PLAPSSKSTS GGTAALGCLV KDYFPEPVTV SWNSGALTSG VHTFPAVLQS  180
SGLSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFLYS KLTVDKSRWQ  420
QGNVFSCSVM HEALHNHYTQ KSLSLSPGK                                    449

SEQ ID NO: 3169        moltype = AA  length = 446
FEATURE                Location/Qualifiers
REGION                 1..446
                       note = Synthetic
source                 1..446
                       mol_type = protein
                       organism = synthetic construct
SEQUENCE: 3169
MEVQLVESGG GLVQPGGSLR LSCAASGFSI SSYDMSWVRQ APGKGLEWIG IIGSNGRTYY  60
PDSVKGRFTI SRDNSKNTVT LQMNSLRAED TAVYYCARGL YDGTGNIWGQ GTLVTVSSAS  120
TKGPSVFPLA PSSKSTSGGT AALGCLVKDY FPEPVTVSWN SGALTSGVHT FPAVLQSSGL  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSREEMTK  360
NQVSLTCLVK GFYPSDIAVE WESNGQPENN YKTTPPVLDS DGSFLYSKLT VDKSRWQQGN  420
VFSCSVMHEA LHNHYTQKSL SLSPGK                                       446

SEQ ID NO: 3170        moltype = AA  length = 449
FEATURE                Location/Qualifiers
REGION                 1..449
                       note = Synthetic
source                 1..449
                       mol_type = protein
                       organism = synthetic construct
SEQUENCE: 3170
MEVQLVESGG GLVQPGGSLR LSCAASGFTI SQYWIHWVRQ APGKGLEWVG YIDPYNGYTY  60
YADSVKGRFT ISADTSKNTA YLQMNSLRAE DTAVYYCARD YGSWRIRLDY WGQGTLVTVS  120
SASTKGPSVF PLAPSSKSTS GGTAALGCLV KDYFPEPVTV SWNSGALTSG VHTFPAVLQS  180
SGLSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFLYS KLTVDKSRWQ  420
QGNVFSCSVM HEALHNHYTQ KSLSLSPGK                                    449

SEQ ID NO: 3171        moltype = AA  length = 449
FEATURE                Location/Qualifiers
REGION                 1..449
                       note = Synthetic
source                 1..449
                       mol_type = protein
                       organism = synthetic construct
SEQUENCE: 3171
MEVQLVESGG GLVQPGGSLR LSCAASGFTI SIYTIHWVRQ APGKGLEWVG YIDPSNGYTY  60
YADSVKGRLT ISADTSKNTA YLQMNSLRAE DTAVYYCARD PQSISSPFDY WGQGTLVTVS  120
SASTKGPSVF PLAPSSKSTS GGTAALGCLV KDYFPEPVTV SWNSGALTSG VHTFPAVLQS  180
SGLSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFLYS KLTVDKSRWQ  420
```

-continued

```
QGNVFSCSVM HEALHNHYTQ KSLSLSPGK                                449

SEQ ID NO: 3172        moltype = AA  length = 449
FEATURE                Location/Qualifiers
REGION                 1..449
                       note = Synthetic
source                 1..449
                       mol_type = protein
                       organism = synthetic construct
SEQUENCE: 3172
MEVQLVESGG GLVQPGGSLR LSCAASGFTI HDYVIHWVRQ APGKGLEWVG YIDPSNGYTY  60
YADSVKGRFT ISADTSKNTA YLQMNSLRAE DTAVYYCARD DQSISSPLDY WGQGTLVTVS  120
SASTKGPSVF PLAPSSKSTS GGTAALGCLV KDYFPEPVTV SWNSGALTSG VHTFPAVLQS  180
SGLSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFLYS KLTVDKSRWQ  420
QGNVFSCSVM HEALHNHYTQ KSLSLSPGK                                449

SEQ ID NO: 3173        moltype = AA  length = 449
FEATURE                Location/Qualifiers
REGION                 1..449
                       note = Synthetic
source                 1..449
                       mol_type = protein
                       organism = synthetic construct
SEQUENCE: 3173
MEVQLVESGG GLVQPGGSLR LSCAASGFTI AAYIIHWVRQ APGKGLEWVG YIDPSNGYTY  60
YADSVKGRFT ISADTSKNTA YLQMNSLRAE DTAVYYCARD DQSFSSPFDY WGQGTLVTVS  120
SASTKGPSVF PLAPSSKSTS GGTAALGCLV KDYFPEPVTV SWNSGALTSG VHTFPAVLQS  180
SGLSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFLYS KLTVDKSRWQ  420
QGNVFSCSVM HEALHNHYTQ KSLSLSPGK                                449

SEQ ID NO: 3174        moltype = AA  length = 449
FEATURE                Location/Qualifiers
REGION                 1..449
                       note = Synthetic
source                 1..449
                       mol_type = protein
                       organism = synthetic construct
SEQUENCE: 3174
MEVQLVESGG GLVQPGGSLR LSCAASGFTI SDYVIHWVRQ APGKGLEWVG YIDPSNGYTY  60
YADSVKGRFT ISADTSKNTA YLQMNSLRAE DTAVYYCARD DQSISSPLDY WGQGTLVTVS  120
SASTKGPSVF PLAPSSKSTS GGTAALGCLV KDYFPEPVTV SWNSGALTSG VHTFPAVLQS  180
SGLSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFLYS KLTVDKSRWQ  420
QGNVFSCSVM HEALHNHYTQ KSLSLSPGK                                449

SEQ ID NO: 3175        moltype = AA  length = 446
FEATURE                Location/Qualifiers
REGION                 1..446
                       note = Synthetic
source                 1..446
                       mol_type = protein
                       organism = synthetic construct
SEQUENCE: 3175
MQVQVVESGG GLVKPGGSLR LSCAASGFSI SSYDMSWIRQ APGKGLEWIG IIGSNGRTYY  60
ADSVKGRFTI SRNTNENTVY LQMNSLRAED TAVYYCARGL YDGTGNIWGQ GTLVTVSSAS  120
TKGPSVFPLA PSSKSTSGGT AALGCLVKDY FPEPVTVSWN SGALTSGVHT FPAVLQSSGL  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSREEMTK  360
NQVSLTCLVK GFYPSDIAVE WESNGQPENN YKTTPPVLDS DGSFLYSKLT VDKSRWQQGN  420
VFSCSVMHEA LHNHYTQKSL SLSPGK                                   446

SEQ ID NO: 3176        moltype = AA  length = 449
FEATURE                Location/Qualifiers
REGION                 1..449
                       note = Synthetic
source                 1..449
                       mol_type = protein
                       organism = synthetic construct
SEQUENCE: 3176
MQVQVQESGP GLVKPPGTLS LTCAVSGFSL SYYGVSWVRQ PPGKGLEWIG TIDSSGRTYY  60
```

-continued

```
NPSLKSRVTI SNDNAPNTVS LKLSSVTAAD TAVYYCARDF YGWNSGALDI WGQGTLVTVS  120
SASTKGPSVF PLAPSSKSTS GGTAALGCLV KDYFPEPVTV SWNSGALTSG VHTFPAVLQS  180
SGLSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFLYS KLTVDKSRWQ  420
QGNVFSCSVM HEALHNHYTQ KSLSLSPGK                                  449

SEQ ID NO: 3177        moltype = AA  length = 448
FEATURE                Location/Qualifiers
REGION                 1..448
                       note = Synthetic
source                 1..448
                       mol_type = protein
                       organism = synthetic construct
SEQUENCE: 3177
MEVQLVESGG GLVQPGGSLR LSCAASGFTI SGYIIHWVRQ APGKGLEWVG YIDPSNGYTY  60
YADSVKGRFT ISADTSKNTA YLQMNSLRAE DTAVYYCARD DQSLSSPFDY WGQGTLVTVS  120
SASTKGPSVF PLAPSSKSTS GGTAALGCLV KDYFPEPVTV SWNSGALTSG VHTFPAVLQS  180
SGLSLSSVVT VPSSSLGTQT YICNVNHKPS NTKVDKKVEP KSCDKTHTCP PCPAPELLGG  240
PSVLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFLYSK LTVDKSRWQQ  420
GNVFSCSVMH EALHNHYTQK SLSLSPGK                                   448

SEQ ID NO: 3178        moltype = AA  length = 449
FEATURE                Location/Qualifiers
REGION                 1..449
                       note = Synthetic
source                 1..449
                       mol_type = protein
                       organism = synthetic construct
SEQUENCE: 3178
MEVQLVESGG GLVQPGGSLR LSCAASGFTI SGYIIHWVRQ APGKGLEWVG YIDPSNGYTY  60
YADSVKGRFT ISADTSKNTA YLQMNSLRAE DTAVYYCARD DQSLSSPFDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFLYS KLTVDKSRWQ  420
QGNVFSCSVM HEALHNHYTQ KSLSLSPGK                                  449

SEQ ID NO: 3179        moltype = AA  length = 215
FEATURE                Location/Qualifiers
REGION                 1..215
                       note = Synthetic
source                 1..215
                       mol_type = protein
                       organism = synthetic construct
SEQUENCE: 3179
MDIQMTQSPS SLSASVGDRV TITCRASQDV NTAVAWYQQK PGKAPKLLIY SASFLYSGVP  60
SRFSGSRSGT DFTLTISSLQ PEDFATYYCQ QHYTTPPTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGEC                            215

SEQ ID NO: 3180        moltype = AA  length = 220
FEATURE                Location/Qualifiers
REGION                 1..220
                       note = Synthetic
source                 1..220
                       mol_type = protein
                       organism = synthetic construct
SEQUENCE: 3180
MELVMTQSPP TLSLSPGERV TLSCRASQSV YGNNWLSWYQ QKPGQAPRLL IYGASKLATS  60
IPARFSGSGS GTQFTLTISS LQPEDFAVYY CQGTYYSGDW YFAFGQGTKV EIKRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                       220

SEQ ID NO: 3181        moltype = AA  length = 220
FEATURE                Location/Qualifiers
REGION                 1..220
                       note = Synthetic
source                 1..220
                       mol_type = protein
                       organism = synthetic construct
SEQUENCE: 3181
MDLQMTQSPS SLSASVGDRV TITCRASQSV YGNNWLSWYQ QKPGKAPKLL IYGASKLASG  60
VPSRFSGSGS GTQFTLTISS LQPEDFATYY CQGTYYSGDW YFAFGQGTKV EIKRTVAAPS  120
VFIFPPSDEQ LKSGTASVVC LLNNFYPREA KVQWKVDNAL QSGNSQESVT EQDSKDSTYS  180
```

```
LSSTLTLSKA DYEKHKVYAC EVTHQGLSSP VTKSFNRGEC                        220

SEQ ID NO: 3182        moltype = AA  length = 220
FEATURE                Location/Qualifiers
REGION                 1..220
                       note = Synthetic
source                 1..220
                       mol_type = protein
                       organism = synthetic construct
SEQUENCE: 3182
MDIQMTQSPS SLSASVGDRV TITCQASQSV YGNNWLSWYQ QKPGKAPKLL IYGASKLASG  60
VPSRFSGSGS GTDFTLTISS LQPEDFATYY CQGTYYSGDW YFAFGGGTKV EIKRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                        220

SEQ ID NO: 3183        moltype = AA  length = 219
FEATURE                Location/Qualifiers
REGION                 1..219
                       note = Synthetic
source                 1..219
                       mol_type = protein
                       organism = synthetic construct
SEQUENCE: 3183
MDLQLTQSPS TLSASVGDRV TITCRASQSV YSNKYLSWYQ QKPGKAPKLL IYKASTLASG  60
VPSRFSGSGS GTEFTLTISS LQPDDFATYY CAAAYSDDSD TAFGQGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 3184        moltype = AA  length = 213
FEATURE                Location/Qualifiers
REGION                 1..213
                       note = Synthetic
source                 1..213
                       mol_type = protein
                       organism = synthetic construct
SEQUENCE: 3184
MDIQMTQSPS SLSASVGDRV TITCRASQDV NTAVAWYQQK PGAPKLLIYS ASFLYSGVPS  60
RFSGSRSGTD FTLTISSLQP EDFATYYCQQ HYTTPPTFGQ GTKVEIKRTV AAPSVFIFPP  120
SDEQLKSGTA SVVCLLNNFY PREAKVQWKV DNALQSGNSQ SVTEQDSKDS TYSLSSTLTL  180
SKADYEKHKV YACEVTHQGL SSPVTKSFNR GEC                               213

SEQ ID NO: 3185        moltype = AA  length = 214
FEATURE                Location/Qualifiers
REGION                 1..214
                       note = Synthetic
source                 1..214
                       mol_type = protein
                       organism = synthetic construct
SEQUENCE: 3185
MDIQMTQSPS SLSASVGDRV TITCRASQDV NTAVAWYQQK PGAPKLLIYS ASFLYSGVPS  60
RFSGSRSGTD FTLTISSLQP EDFATYYCQQ HYTTPPTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 3186        moltype = AA  length = 449
FEATURE                Location/Qualifiers
REGION                 1..449
                       note = Synthetic
source                 1..449
                       mol_type = protein
                       organism = synthetic construct
SEQUENCE: 3186
MEVQLVESGG GLVQPGGSLR LSCAASGFTI SQYWIHWVRQ APGKGLEWVG YIDPYNGYTY  60
YADSVKGRFT ISADTSKNTA YLQMNSLRAE DTAVYYCARD YGSWRIRLDY WGQGTLVTVS  120
SASTKGPSVF PLAPSSKSTS GGTAALGCLV KDYFPEPVTV SWNSGALTSG VHTFPAVLQS  180
SGLSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFLYS KLTVDKSRWQ  420
QGNVFSCSVM HEALHNHYTQ KSLSLSPGK                                    449

SEQ ID NO: 3187        moltype = AA  length = 449
FEATURE                Location/Qualifiers
REGION                 1..449
                       note = Synthetic
source                 1..449
                       mol_type = protein
                       organism = synthetic construct
SEQUENCE: 3187
```

```
MEVQLVESGG GLVQPGGSLR LSCAASGFTI SIYTIHWVRQ APGKGLEWVG YIDPSNGYTY  60
YADSVKGRLT ISADTSKNTA YLQMNSLRAE DTAVYYCARD PQSISSPFDY WGQGTLVTVS  120
SASTKGPSVF PLAPSSKSTS GGTAALGCLV KDYFPEPVTV SWNSGALTSG VHTFPAVLQS  180
SGLSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFLYS KLTVDKSRWQ  420
QGNVFSCSVM HEALHNHYTQ KSLSLSPGK                                  449

SEQ ID NO: 3188        moltype = AA  length = 449
FEATURE                Location/Qualifiers
REGION                 1..449
                       note = Synthetic
source                 1..449
                       mol_type = protein
                       organism = synthetic construct
SEQUENCE: 3188
MEVQLVESGG GLVQPGGSLR LSCAASGFTI HDYVIHWVRQ APGKGLEWVG YIDPSNGYTY  60
YADSVKGRFT ISADTSKNTA YLQMNSLRAE DTAVYYCARD DQSISSPLDY WGQGTLVTVS  120
SASTKGPSVF PLAPSSKSTS GGTAALGCLV KDYFPEPVTV SWNSGALTSG VHTFPAVLQS  180
SGLSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFLYS KLTVDKSRWQ  420
QGNVFSCSVM HEALHNHYTQ KSLSLSPGK                                  449

SEQ ID NO: 3189        moltype = AA  length = 449
FEATURE                Location/Qualifiers
REGION                 1..449
                       note = Synthetic
source                 1..449
                       mol_type = protein
                       organism = synthetic construct
SEQUENCE: 3189
MEVQLVESGG GLVQPGGSLR LSCAASGFTI AAYIIHWVRQ APGKGLEWVG YIDPSNGYTY  60
YADSVKGRFT ISADTSKNTA YLQMNSLRAE DTAVYYCARD DQSFSSPFDY WGQGTLVTVS  120
SASTKGPSVF PLAPSSKSTS GGTAALGCLV KDYFPEPVTV SWNSGALTSG VHTFPAVLQS  180
SGLSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFLYS KLTVDKSRWQ  420
QGNVFSCSVM HEALHNHYTQ KSLSLSPGK                                  449

SEQ ID NO: 3190        moltype = AA  length = 449
FEATURE                Location/Qualifiers
REGION                 1..449
                       note = Synthetic
source                 1..449
                       mol_type = protein
                       organism = synthetic construct
SEQUENCE: 3190
MEVQLVESGG GLVQPGGSLR LSCAASGFTI SDYVIHWVRQ APGKGLEWVG YIDPSNGYTY  60
YADSVKGRFT ISADTSKNTA YLQMNSLRAE DTAVYYCARD DQSISSPLDY WGQGTLVTVS  120
SASTKGPSVF PLAPSSKSTS GGTAALGCLV KDYFPEPVTV SWNSGALTSG VHTFPAVLQS  180
SGLSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFLYS KLTVDKSRWQ  420
QGNVFSCSVM HEALHNHYTQ KSLSLSPGK                                  449

SEQ ID NO: 3191        moltype = AA  length = 447
FEATURE                Location/Qualifiers
REGION                 1..447
                       note = Synthetic
source                 1..447
                       mol_type = protein
                       organism = synthetic construct
SEQUENCE: 3191
MEVQLVESGG GLVQPGGSLR LSCAASGFTI SGYIIHWVRQ APGKGLEWVG YIDPSNGYTY  60
YADSVKGRFT ISADTSKNTA YLQMNSLRAE DTAVYYCARD DQSLSSPFDY WGQGTLVTVS  120
SASTKGPSVF PLAPSSKSTS GGTAALGCLV KDYFPEPVTV SWNSGALTSG VHTFPAVLQS  180
SGLSLSSVVT VPSSSLGTQT YICNVNHKPS NTKVDKKVEP KSCDKTHTCP PCPAPELLGG  240
PSVLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNKTTPPVLD SDGSFLYSKL TVDKSRWQQG  420
NVFSCSVMHE ALHNHYTQKS LSLSPGK                                    447
```

ANTI-TISSUE FACTOR ANTIBODIES AND ANTIBODY CONJUGATES, COMPOSITIONS COMPRISING ANTI-TISSUE FACTOR ANTIBODIES OR ANTIBODY CONJUGATES, AND METHODS OF MAKING AND USING ANTI-TISSUE FACTOR ANTIBODIES AND ANTIBODY CONJUGATES

CROSS-REFERENCE TO RELATED APPLICATIONS

This application claims the benefit of U.S. Provisional Application No. 63/590,343, filed Oct. 13, 2023, and U.S. Provisional Application No. 63/684,699, filed Aug. 19, 2024. Each of these applications are incorporated for all purposes in their entirety.

REFERENCE TO ELECTRONIC SEQUENCE LISTING

The application contains a Sequence Listing which has been submitted electronically in .XML format and is hereby incorporated by reference in its entirety. Said .XML copy, created on Oct. 7, 2024, is named "108843.00506.xml" and is 1,460,613 bytes in size. The sequence listing contained in this .XML file is part of the specification and is hereby incorporated by reference herein in its entirety.

FIELD OF THE INVENTION

The present disclosure generally relates to antibodies and antibody conjugates with binding specificity for tissue factor and compositions comprising the antibodies or antibody conjugates, including pharmaceutical compositions, diagnostic compositions, and kits. Also provided are methods of making anti-tissue factor antibodies and antibody conjugates, and methods of using anti-tissue factor antibodies and antibody conjugates, for example, for therapeutic purposes, diagnostic purposes, and research purposes.

BACKGROUND

Tissue factor (TF), also known as CD142, is a cellular membrane glycoprotein. Tissue factor is sometimes referred to as Coagulation Factor III because it is the primary initiator of blood coagulation, where complexation of Factor VIIa and tissue factor (TF:FVIIa complex) activates the coagulation protease cascade. Mackman, et al., 2004, *Atherosclerosis, Thrombosis, and Vascular Biology* 24:1015-1022. TF is expressed in the subendothelium. When endothelium is damaged, tissue factor combines with circulating factor VII to activate factor X. Activated factor X initiates the coagulation cascade, allowing clot formation.

Aberrant expression of TF plays a role in thrombosis in disease, including sepsis, atherosclerosis, and cancer. TF has also been implicated in inflammation, angiogenesis, metastasis, and cell migration. Mackman, et al., 2004, *Atherosclerosis, Thrombosis, and Vascular Biology* 24:1015-1022. TF is broadly expressed across multiple solid tumor indications.

Accordingly, there is a need for improved methods of modulating the activity of TF and the downstream signaling coagulation processes activated by TF. Moreover, given the implication of TF in thrombosis, there is a need for improved therapeutics that specifically target cells and tissues that express TF. Antibody conjugates to TF could be used to deliver therapeutic or diagnostic payload moieties to target cells expressing TF for the treatment or diagnosis of such diseases.

SUMMARY

Provided herein are antibodies that selectively bind tissue factor (TF). In some embodiments, the antibodies bind human TF. In some embodiments, the antibodies also bind homologs of human TF. In some aspects, the homologs include a cynomolgus monkey homolog.

Also provided herein are antibody conjugates that selectively bind TF. The antibody conjugates comprise an antibody that binds TF linked to one or more payload moieties. The antibody can be linked to the payload directly by a covalent bond or indirectly by way of a linker. TF antibodies are described in detail herein, as are useful payload moieties, and useful linkers.

In some embodiments, the antibodies or antibody conjugates comprise an illustrative CDR, $V_H$, $V_L$, HC, or LC sequence provided in this disclosure, or a variant thereof. In some aspects, the variant is a variant with one or more conservative amino acid substitutions. In some aspects, the variant has sequence identity to the illustrative sequence or sequences.

In another aspect, provided are compositions comprising the antibodies or antibody conjugates. In some embodiments, the compositions are pharmaceutical compositions. In some embodiments, the pharmaceutical composition is for parenteral administration. Any suitable pharmaceutical composition may be used. In some embodiments, the pharmaceutical composition is a composition for parenteral administration. In a further aspect, provided herein are kits comprising the antibodies or antibody conjugates or pharmaceutical compositions.

This disclosure also provides methods of using the anti-TF antibodies or antibody conjugates provided herein. In some embodiments, the methods are methods of delivering one or more payload moieties to a target cell or tissue expressing TF. In some embodiments, the method is a method of treatment. In some embodiments, the method is a diagnostic method. In some embodiments, the method is an analytical method. In some embodiments, the method is a method of purifying and/or quantifying TF.

In some embodiments, the antibodies, antibody conjugates, or pharmaceutical compositions thereof are used to treat a disease or condition. In some aspects, the disease or condition is a TF-expressing malignancy. In some aspects, the disease or condition is selected from a cancer, autoimmune disease, and infection.

In some embodiments, the antibodies or antibody conjugates bind human TF. In some embodiments, the antibodies or antibody conjugates also bind homologs of human TF. In some aspects, the antibodies or antibody conjugates also bind homologs of cynomolgus monkey and/or mouse TF.

These and other embodiments of the invention along with many of its features are described in more detail in conjunction with the text below and attached figures.

BRIEF DESCRIPTION OF THE FIGURES

FIG. 7C provides a scatter plot of individual tumor volumes on day 35 post treatment, when control tumors reached the study endpoint. Arrows represent dosing days. Statistical analysis was performed on tumor volumes on day 35 using one-way ANOVA with Dunnett's multiple comparisons test versus the vehicle group. A probability of less than 5% ($p<0.05$) was considered significant. ****=$p<0.0001$. All graphs are presented as individual values or mean±SEM.

(FIG. 8B) Scatter plot of individual tumor volumes on day 17 post treatment, when control tumors reached the study endpoint. Arrows represent dosing days. Statistical analysis was performed on tumor volumes on day 17 using one-way ANOVA with Dunnett's multiple comparisons test versus the vehicle group. A probability of less than 5% ($p<0.05$) was considered significant. ****=$p<0.0001$. All graphs are presented as individual values or mean±SEM.

(FIG. 9B) Scatter plot of individual tumor volumes on day 18 post treatment, when control tumors reached the study endpoint. Arrows represent dosing days. Statistical analysis was performed on tumor volumes on day 18 using one-way ANOVA with Dunnett's multiple comparisons test versus the vehicle group. A probability of less than 5% ($p<0.05$) was considered significant. ****=$p<0.0001$. All graphs are presented as individual values or mean±SEM.

(FIG. 10B) Scatter plot of individual tumor volumes on day 42 post treatment, when control tumors reached the study endpoint. Arrows represent dosing days. Statistical analysis was performed on tumor volumes on day 42 using one-way ANOVA with Dunnett's multiple comparisons test versus the vehicle group. A probability of less than 5% ($p<0.05$) was considered significant. **=$p<0.0001$. All graphs are presented as individual values or mean±SEM. (FIG. 10C) MDA-MB-231 tumor growth curves in response to treatment with two weekly i.v. doses (qwx2) of a TF-targeted ADC at doses ranging from 0.25 mg/kg to 1 mg/kg. (FIG. 10D) Scatter plot of individual tumor volumes on day 41 post treatment, when control tumors reached the study endpoint. Arrows represent dosing days. Statistical analysis was performed on tumor volumes on day 41 using one-way ANOVA with Dunnett's multiple comparisons test versus the vehicle group. A probability of less than 5% ($p<0.05$) was considered significant. **=$p<0.0001$. All graphs are presented as individual values or mean±SEM.

(FIG. 11B) Scatter plot of individual tumor volumes on day 24 post treatment, when control tumors reached the study endpoint. Arrows represent dosing days. Statistical analysis was performed on tumor volumes on day 24 using one-way ANOVA with Dunnett's multiple comparisons test versus the vehicle group. A probability of less than 5% ($p<0.05$) was considered significant. *=$p<0.001$; =$p<0.0001$. All graphs are presented as individual values or mean±SEM. (FIG. 11C) H1975 tumor growth curves in response to treatment with a single i.v. dose of TF-targeted ADCs at doses ranging from 0.125 mg/kg to 1 mg/kg. (FIG. 11D) Scatter plot of individual tumor volumes on day 25 post treatment, when control tumors reached the study endpoint. Statistical analysis was performed on tumor volumes on day 25 using one-way ANOVA with Dunnett's multiple comparisons test versus the vehicle group. A probability of less than 5% ($p<0.05$) was considered significant. =$p<0.01$; ****=$p<0.0001$. All graphs are presented as individual values or mean±SEM.

(FIG. 12B) Scatter plot of individual tumor volumes on day 21 post treatment, when control tumors reached the study endpoint. Arrow represents dosing day. Statistical analysis was performed on tumor volumes on day 21 using one-way ANOVA with Dunnett's multiple comparisons test versus the vehicle group. A probability of less than 5% ($p<0.05$) was considered significant. =$p<0.0001$. All graphs are presented as individual values or mean±SEM. (FIG. 12C) Detroit562 tumor growth curves in response to treatment with a single i.v. dose of TF-targeted ADCs at doses ranging from 0.25 mg/kg to 2 mg/kg. (FIG. 12D) Scatter plot of individual tumor volumes on day 21 post treatment, when control tumors reached the study endpoint. Statistical analysis was performed on tumor volumes on day 21 using one-way ANOVA with Dunnett's multiple comparisons test versus the vehicle group. A probability of less than 5% ($p<0.05$) was considered significant. **=$p<0.0001$. All graphs are presented as individual values or mean±SEM.

(FIG. 13B) Scatter plot of individual tumor volumes on day 21 post treatment, when control tumors reached the study endpoint. Statistical analysis was performed on tumor volumes on day 21 using one-way ANOVA with Dunnett's multiple comparisons test versus the vehicle group. A probability of less than 5% ($p<0.05$) was considered significant. ****=$p<0.0001$. All graphs are presented as individual values or mean±SEM.

(FIG. 14B) Scatter plot of individual tumor volumes on day 6 post treatment, when control tumors reached the study endpoint. Arrows represent dosing days. Statistical analysis was performed on tumor volumes on day 6 using one-way ANOVA with Dunnett's multiple comparisons test versus the vehicle group. A probability of less than 5% ($p<0.05$) was considered significant. =$p<0.01$; =$p<0.0001$. All graphs are presented as individual values or mean±SEM. (FIG. 14C) MC38-hTF tumor growth curves in response to treatment with a single i.v. dose of Conjugate 35 at 5 mg/kg, multiple i.p. doses of anti-PD-1 at 10 mg/kg, or combination treatment. Number of complete responses (CRs) are designated to the right of the tumor growth curves. (FIG. 14D) Scatter plot of individual tumor volumes on day 8 post treatment, when control tumors reached the study endpoint. Arrows represent dosing days. Statistical analysis was performed on tumor volumes on day 8 using one-way ANOVA with Dunnett's multiple comparisons test versus the vehicle group. A probability of less than 5% ($p<0.05$) was considered significant. **=$p<0.0001$. All graphs are presented as individual values or mean±SEM.

(FIG. 15B) Scatter plot of individual tumor volumes on day 37 post treatment, when control tumors reached the study endpoint. Arrow represents dosing day. Statistical analysis was performed on tumor volumes on day 37 using one-way ANOVA with Dunnett's multiple comparisons test versus the vehicle group. A probability of less than 5% ($p<0.05$) was considered significant. **=$p<0.01$; **=$p<0.001$. All graphs are presented as individual values or mean±SEM.

DETAILED DESCRIPTION OF THE EMBODIMENTS

1. Definitions

Figure 1A:
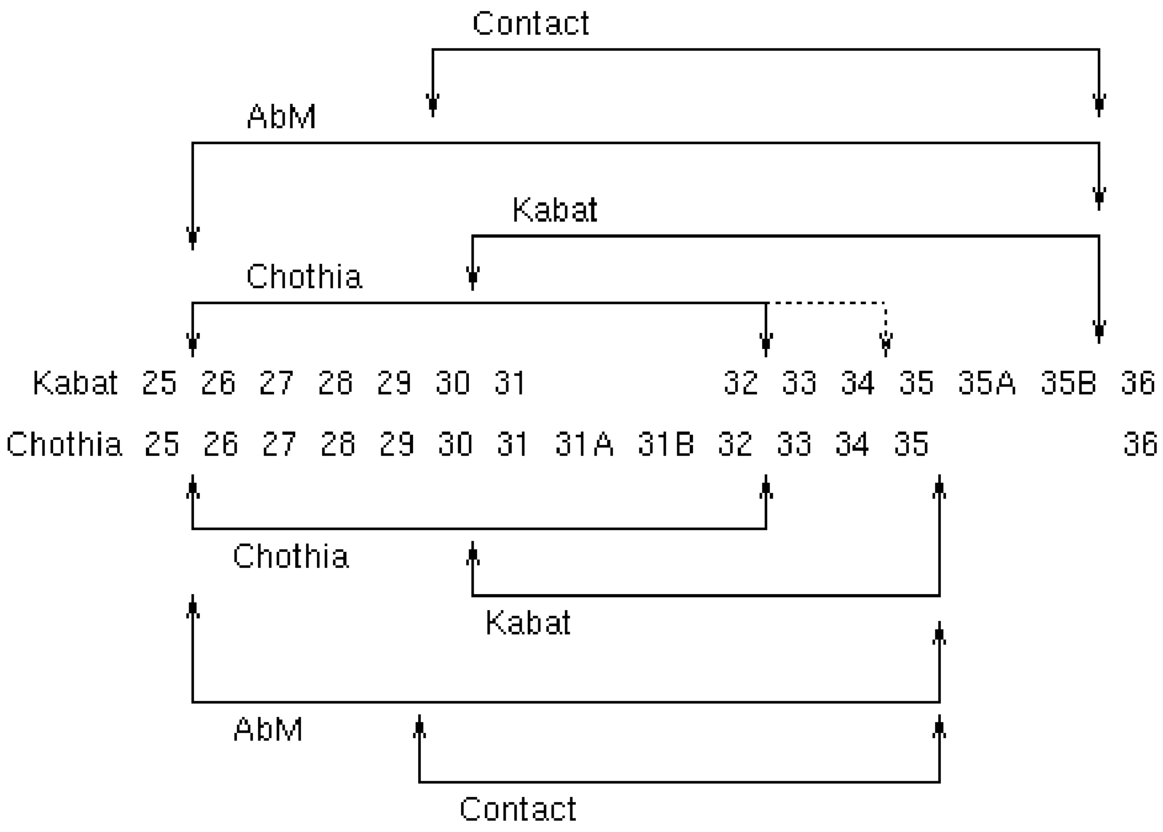
FIG. 1A provides a comparison of the Kabat and Chothia numbering systems for CDR-H1. Adapted from Martin A. C. R. (2010). Protein Sequence and Structure Analysis of Antibody Variable Domains. In R. Kontermann & S. Dübel (Eds.), *Antibody Engineering* vol. 2 (pp. 33-51). Springer-Verlag, Berlin Heidelberg.
Figure 1B:
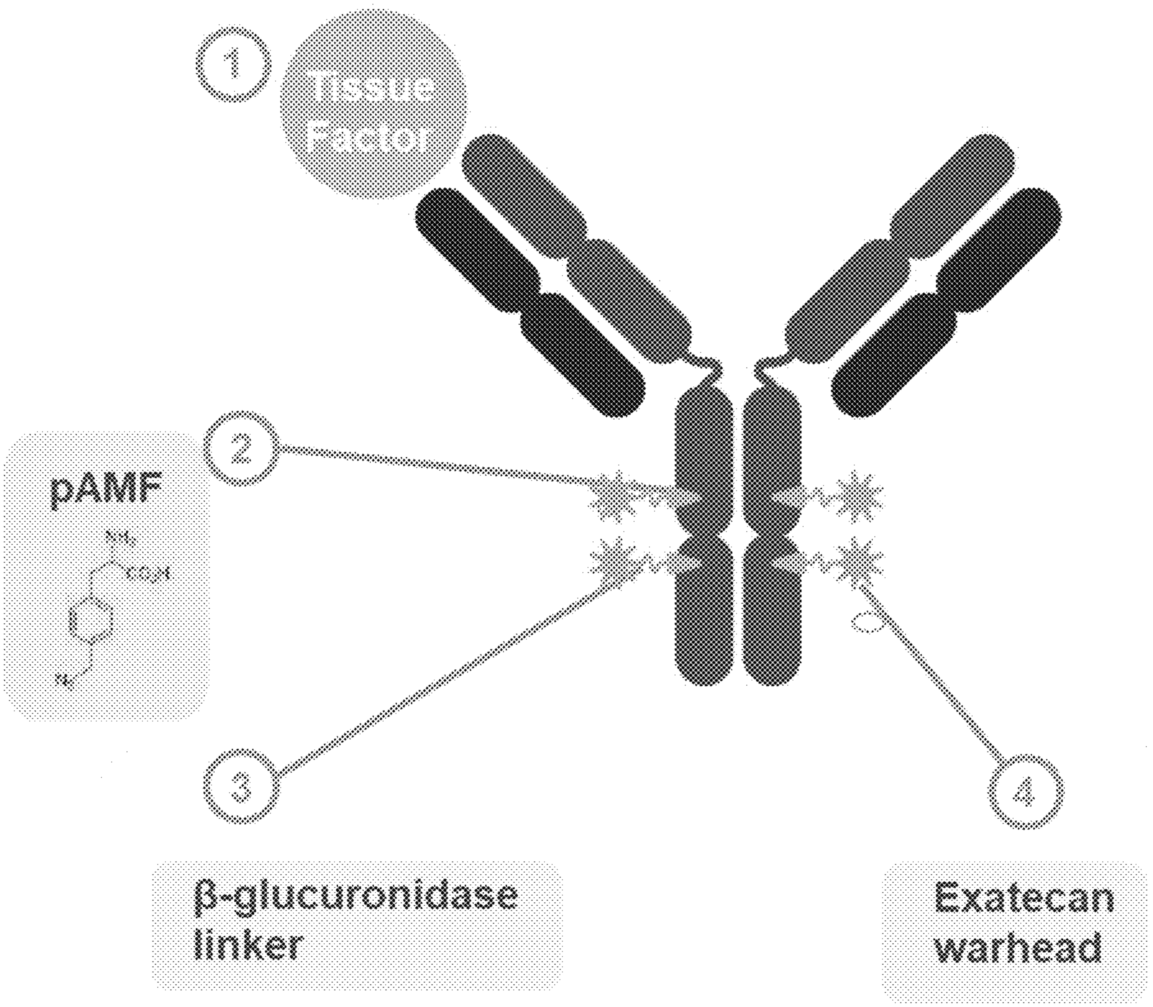
FIG. 1B provides a general schematic design for a representative antibody conjugate of the present disclosure where 1 is TF, 2 is a non-natural amino acid (pAMF), 3 is a β-glucuronidase linker and 4 is an exatecan payload.
Figure 2:
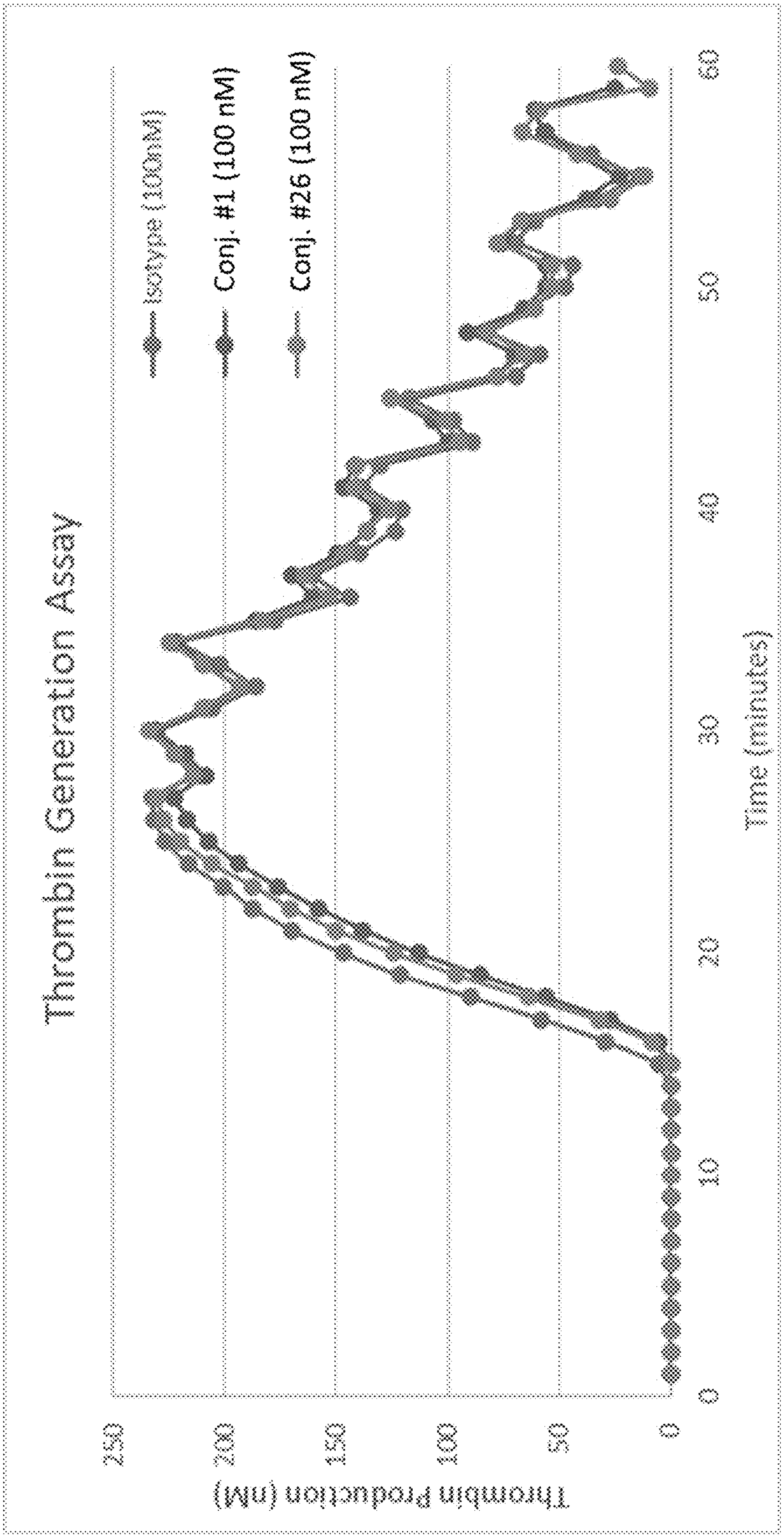
FIG. 2 provides thrombin production data for Conjugate 1 and Conjugate 26.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., *Molecular Cloning: A Laboratory Manual* 2nd ed. (1989) Cold Spring Harbor Laboratory Press, Cold Spring Harbor, NY. As appropriate, procedures involving the use of commercially available kits and reagents are generally carried out in accordance with manufacturer-defined protocols and conditions unless otherwise noted.

As used herein, the singular forms "a," "an," and "the" include the plural referents unless the context clearly indicates otherwise.

The term "about" indicates and encompasses an indicated value and a range above and below that value. In certain embodiments, the term "about" indicates the designated value ±10%, ±5%, or ±1%. In certain embodiments, the term "about" indicates the designated value ±one standard deviation of that value.

The term "combinations thereof" includes every possible combination of elements to which the term refers to. For example, a sentence stating "A, B, C, and combinations thereof" includes the following combinations: (1) A, (2) A and B, (3) A, B and C, (4) A and C, (5) B, (6) B and C, and (7) C.

The terms "tissue factor," "TF," and "TF antigen" are used interchangeably herein. Unless specified otherwise, the terms include any variants, isoforms and species homologs of human tissue factor that are naturally expressed by cells, or that are expressed by cells transfected with a tissue factor gene. Tissue factor proteins include, for example, human tissue factor (SEQ ID NO: 1). In some embodiments, tissue factor proteins include cynomolgus monkey tissue factor (SEQ ID NO: 2). In some embodiments, tissue factor proteins include murine tissue factor (SEQ ID NO: 3160). In some embodiments, tissue factor proteins include human tissue factor isoform 2 precursor (SEQ ID NO: 3161). In some embodiments, tissue factor proteins include murine tissue factor precursor (SEQ ID NO: 3162).

The term "immunoglobulin" refers to a class of structurally related proteins generally comprising two pairs of polypeptide chains: one pair of light (L) chains and one pair of heavy (H) chains. In an "intact immunoglobulin," all four of these chains are interconnected by disulfide bonds. The structure of immunoglobulins has been well characterized. See, e.g., Paul, *Fundamental Immunology* 7th ed., Ch. 5 (2013) *Lippincott Williams & Wilkins*, Philadelphia, PA. Briefly, each heavy chain typically comprises a heavy chain variable region ($V_H$) and a heavy chain constant region ($C_H$). The heavy chain constant region typically comprises three domains, abbreviated $C_{H1}$, $C_{H2}$, and $C_{H3}$. Each light chain typically comprises a light chain variable region ($V_L$) and a light chain constant region. The light chain constant region typically comprises one domain, abbreviated $C_L$.

The term "antibody" describes a type of immunoglobulin molecule and is used herein in its broadest sense. An antibody specifically includes intact antibodies (e.g., intact immunoglobulins), and antibody fragments. Antibodies comprise at least one antigen-binding domain. One example of an antigen-binding domain is an antigen binding domain formed by a $V_H$-$V_L$ dimer. A "tissue factor antibody," "anti-tissue factor antibody," "tissue factor Ab," "tissue factor-specific antibody" or "anti-tissue factor Ab" or the equivalent is an antibody, as described herein, which binds specifically to the antigen tissue factor. In some embodiments, the antibody binds the extracellular domain of tissue factor.

The $V_H$ and $V_L$ regions may be further subdivided into regions of hypervariability ("hypervariable regions (HVRs);" also called "complementarity determining regions" (CDRs)) interspersed with regions that are more conserved. The more conserved regions are called framework regions (FRs). Each $V_H$ and $V_L$ generally comprises three CDRs and four FRs, arranged in the following order (from N-terminus to C-terminus): FR1-CDR1-FR2-CDR2-FR3-CDR3-FR4. The CDRs are involved in antigen binding, and influence antigen specificity and binding affinity of the antibody. See Kabat et al., *Sequences of Proteins of Immunological Interest* 5th ed. (1991) Public Health Service, National Institutes of Health, Bethesda, MD, incorporated by reference in its entirety.

The light chain from any vertebrate species can be assigned to one of two types, called kappa and lambda, based on the sequence of the constant domain.

The heavy chain from any vertebrate species can be assigned to one of five different classes (or isotypes): IgA, IgD, IgE, IgG, and IgM. These classes are also designated α, δ, ε, γ, and μ, respectively. The IgG and IgA classes are further divided into subclasses on the basis of differences in sequence and function. Humans express the following subclasses: IgG1, IgG2, IgG3, IgG4, IgA1, and IgA2.

The amino acid sequence boundaries of a CDR can be determined by one of skill in the art using any of a number of known numbering schemes, including those described by Kabat et al., supra ("Kabat" numbering scheme); Al-Lazikani et al., 1997, *J. Mol. Biol.,* 273:927-948 ("Chothia" numbering scheme); MacCallum et al., 1996, *J. Mol. Biol.* 262:732-745 ("Contact" numbering scheme); Lefranc et al., *Dev. Comp. Immunol.,* 2003, 27:55-77 ("IMGT" numbering scheme); and Honegge and Plückthun, *J. Mol. Biol.,* 2001, 309:657-70 ("AHo" numbering scheme), each of which is incorporated by reference in its entirety.

Table 1 provides the positions of CDR-L1, CDR-L2, CDR-L3, CDR-H1, CDR-H2, and CDR-H3 as identified by the Kabat and Chothia schemes. For CDR-H1, residue numbering is provided using both the Kabat and Chothia numbering schemes.

TABLE 1

Residues in CDRs according to Kabat and Chothia numbering schemes.

| CDR | Kabat | Chothia |
|---|---|---|
| L1 | L24-L34 | L24-L34 |
| L2 | L50-L56 | L50-L56 |
| L3 | L89-L97 | L89-L97 |
| H1 (Kabat Numbering) | H31-H35B | H26-H32 or H34* |
| H1 (Chothia Numbering) | H31-H35 | H26-H32 |
| H2 | H50-H65 | H52-H56 |
| H3 | H95-H102 | H95-H102 |

*The C-terminus of CDR-H1, when numbered using the Kabat numbering convention, varies between H32 and H34, depending on the length of the CDR, as illustrated in FIG. 1A.

Unless otherwise specified, the numbering scheme used for identification of a particular CDR herein is the Kabat/Chothia numbering scheme. Where the residues encompassed by these two numbering schemes diverge (e.g., CDR-H1 and/or CDR-H2), the numbering scheme is specified as either Kabat or Chothia. For convenience, CDR-H3 is sometimes referred to herein as either Kabat or Chothia. However, this is not intended to imply differences in sequence where they do not exist, and one of skill in the art can readily confirm whether the sequences are the same or different by examining the sequences.

CDRs may be assigned, for example, using antibody numbering software, such as Abnum, available at http://www.bioinf.org.uk/abs/abnum/, and described in Abhinandan and Martin, *Immunology,* 2008, 45:3832-3839, incorporated by reference in its entirety.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

An "antibody fragment" comprises a portion of an intact antibody, such as the antigen binding or variable region of an intact antibody. Antibody fragments include, for example, Fv fragments, Fab fragments, $F(ab')_2$ fragments, Fab' fragments, scFv (sFv) fragments, and scFv-Fc fragments.

"Fv" fragments comprise a non-covalently-linked dimer of one heavy chain variable domain and one light chain variable domain.

"Fab" fragments comprise, in addition to the heavy and light chain variable domains, the constant domain of the light chain and the first constant domain ($C_{H1}$) of the heavy chain. Fab fragments may be generated, for example, by recombinant methods or by papain digestion of a full-length antibody.

"$F(ab')_2$" fragments contain two Fab' fragments joined, near the hinge region, by disulfide bonds. $F(ab')_2$ fragments may be generated, for example, by recombinant methods or by pepsin digestion of an intact antibody. The F(ab') fragments can be dissociated, for example, by treatment with ß-mercaptoethanol.

"Single-chain Fv" or "sFv" or "scFv" antibody fragments comprise a $V_H$ domain and a $V_L$ domain in a single polypeptide chain. The $V_H$ and $V_L$ are generally linked by a peptide linker. See Plückthun A. (1994). In some embodiments, the linker is SEQ ID NO: 3071. Antibodies from *Escherichia coli*. In Rosenberg M. & Moore G. P. (Eds.), *The Pharmacology of Monoclonal Antibodies* vol. 113 (pp. 269-315). Springer-Verlag, New York, incorporated by reference in its entirety.

"scFv-Fc" fragments comprise an scFv attached to an Fc domain. For example, an Fc domain may be attached to the C-terminus of the scFv. The Fc domain may follow the $V_H$ or $V_L$, depending on the orientation of the variable domains in the scFv (i.e., $V_H$-$V_L$ or $V_L$-$V_H$). Any suitable Fc domain known in the art or described herein may be used. In some cases, the Fc domain comprises an IgG1 Fc domain. In some embodiments, the IgG1 Fc domain comprises SEQ ID NO: 3062, or a portion thereof, or SEQ ID NO: 3068. SEQ ID NO: 3062 provides the sequence of $C_{H1}$, $C_{H2}$, and $C_{H3}$ of the human IgG1 constant region. In some embodiments, the constant region can comprise sequences selected from SEQ ID NOs: 3062, 3063, 3064, and 3065. SEQ ID NO: 3068 provides the sequence of the constant region used in the illustrative scFv-Fc antibodies provided herein. In some embodiments, the sequence of the constant region can be linked to the scFv by a linker such as, by way of example, but not limitation, the linker of SEQ ID NO: 3071. In some embodiments, the linker can be N-terminal to the sequence of SEQ ID NO: 3068. In some embodiments, the constant region can further include a FlagHis Tag, such as that of SEQ ID NO: 3069 which can, by way of example but not limitation, be C-terminal to the Fc sequence.

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

The term "chimeric antibody" refers to an antibody in which a portion of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human immunoglobulin (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies may also comprise residues that are not found in either the recipient antibody or the donor antibody. Such modifications may be made to further refine antibody function. For further details, see Jones et al., *Nature,* 1986, 321:522-525; Riechmann et al., *Nature,* 1988, 332:323-329; and Presta, *Curr. Op. Struct. Biol.,* 1992, 2:593-596, each of which is incorporated by reference in its entirety.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

An "isolated antibody" is one that has been separated and/or recovered from a component of its natural environment. Components of the natural environment may include enzymes, hormones, and other proteinaceous or nonproteinaceous materials. In some embodiments, an isolated antibody is purified to a degree sufficient to obtain at least 15 residues of N-terminal or internal amino acid sequence, for example by use of a spinning cup sequenator. In some embodiments, an isolated antibody is purified to homogeneity by gel electrophoresis (e.g., SDS-PAGE) under reducing or nonreducing conditions, with detection by Coomassie blue or silver stain. An isolated antibody includes an antibody in situ within recombinant cells, since at least one component of the antibody's natural environment is not present. In some aspects, an isolated antibody is prepared by at least one purification step.

In some embodiments, an isolated antibody is purified to at least 80%, 85%, 90%, 95%, or 99% by weight. In some embodiments, an isolated antibody is purified to at least 80%, 85%, 90%, 95%, or 99% by volume. In some embodiments, an isolated antibody is provided as a solution comprising at least 85%, 90%, 95%, 98%, 99% to 100% by weight. In some embodiments, an isolated antibody is provided as a solution comprising at least 85%, 90%, 95%, 98%, 99% to 100% by volume.

The term "non-natural amino acid" refers to an amino acid that is not a proteinogenic amino acid, or a post-translationally modified variant thereof. In particular, the term refers to an amino acid that is not one of the 20 common amino acids or pyrrolysine or selenocysteine, or post-translationally modified variants thereof.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity, which reflects a 1:1 interaction between members of a binding pair (e.g., antibody and antigen). The affinity of a molecule X for its partner Y can be represented by the dissociation constant ($K_D$). Affinity can be measured by common methods known in the art, including those described herein. Affinity can be determined, for example, using surface plasmon resonance (SPR) technology, such as a Biacore® instrument. In some embodiments, the affinity is determined at 25° C.

With regard to the binding of an antibody to a target molecule, the terms "specific binding," "specifically binds to," "specific for," "selectively binds," and "selective for" a particular antigen (e.g., a polypeptide target) or an epitope on a particular antigen mean binding that is measurably different from a non-specific or non-selective interaction. Specific binding can be measured, for example, by determining binding of a molecule compared to binding of a control molecule. Specific binding can also be determined by competition with a control molecule that mimics the antibody binding site on the target. In that case, specific binding is indicated if the binding of the antibody to the target is competitively inhibited by the control molecule.

The term "$k_d$" ($sec^{-1}$), as used herein, refers to the dissociation rate constant of a particular antibody-antigen interaction. This value is also referred to as the $k_{off}$ value.

The term "$k_a$" ($M^{-1}\times sec^{-1}$), as used herein, refers to the association rate constant of a particular antibody-antigen interaction. This value is also referred to as the $k_{on}$ value.

The term "$K_D$" (M), as used herein, refers to the dissociation equilibrium constant of a particular antibody-antigen interaction. $K_D=k_d/k_a$.

The term "$K_A$" ($M^{-1}$), as used herein, refers to the association equilibrium constant of a particular antibody-antigen interaction. $K_A=k_a/k_d$.

An "affinity matured" antibody is one with one or more alterations in one or more CDRs or FRs that result in an improvement in the affinity of the antibody for its antigen, compared to a parent antibody which does not possess the alteration(s). In one embodiment, an affinity matured antibody has nanomolar or picomolar affinity for the target antigen. Affinity matured antibodies may be produced using a variety of methods known in the art. For example, Marks et al. (*Bio/Technology,* 1992, 10:779-783, incorporated by reference in its entirety) describes affinity maturation by $V_H$ and $V_L$ domain shuffling. Random mutagenesis of CDR and/or framework residues is described by, for example, Barbas et al. (*Proc. Nat. Acad. Sci. U.S.A.,* 1994, 91:3809-3813); Schier et al., *Gene,* 1995, 169:147-155; Yelton et al., *J. Immunol.,* 1995, 155:1994-2004; Jackson et al., *J. Immunol.,* 1995, 154:3310-33199; and Hawkins et al, *J. Mol. Biol.,* 1992, 226:889-896, each of which is incorporated by reference in its entirety.

When used herein in the context of two or more antibodies, the term "competes with" or "cross-competes with" indicates that the two or more antibodies compete for binding to an antigen (e.g., TF). In one exemplary assay, TF is coated on a plate and allowed to bind a first antibody, after which a second, labeled antibody is added. If the presence of the first antibody reduces binding of the second antibody, then the antibodies compete. In another exemplary assay, a first antibody is coated on a plate and allowed to bind the antigen, and then the second antibody is added. The term "competes with" also includes combinations of antibodies where one antibody reduces binding of another antibody, but where no competition is observed when the antibodies are added in the reverse order. However, in some embodiments, the first and second antibodies inhibit binding of each other, regardless of the order in which they are added. In some embodiments, one antibody reduces binding of another antibody to its antigen by at least 50%, at least 60%, at least 70%, at least 80%, or at least 90%.

The term "epitope" means a portion of an antigen capable of specific binding to an antibody. Epitopes frequently consist of surface-accessible amino acid residues and/or sugar side chains and may have specific three-dimensional structural characteristics, as well as specific charge characteristics. Conformational and non-conformational epitopes are distinguished in that the binding to the former but not the latter is lost in the presence of denaturing solvents. An epitope may comprise amino acid residues that are directly involved in the binding, and other amino acid residues, which are not directly involved in the binding. The epitope to which an antibody binds can be determined using known techniques for epitope determination such as, for example, testing for antibody binding to TF variants with different point-mutations, or to chimeric TF variants as described further in the Examples provided herein.

Percent "identity" between a polypeptide sequence and a reference sequence, is defined as the percentage of amino acid residues in the polypeptide sequence that are identical to the amino acid residues in the reference sequence, after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, MEGALIGN (DNASTAR), CLUSTALW, CLUSTAL OMEGA, or MUSCLE software. Those skilled in the art can determine appropriate parameters for aligning sequences, including any algorithms needed to achieve maximal alignment over the full length of the sequences being compared.

A "conservative substitution" or a "conservative amino acid substitution," refers to the substitution of an amino acid with a chemically or functionally similar amino acid. Conservative substitution tables providing similar amino acids are well known in the art. Polypeptide sequences having such substitutions are known as "conservatively modified variants." Such conservatively modified variants are in addition to and do not exclude polymorphic variants, interspecies homologs, and alleles. By way of example, the groups of amino acids provided in Tables 2-4 are, in some embodiments, considered conservative substitutions for one another.

TABLE 2

Selected groups of amino acids that are considered conservative substitutions for one another, in certain embodiments.

| | |
|---|---|
| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |
| Alcohol Group-Containing Residues | S and T |
| Aliphatic Residues | I, L, V, and M |
| Cycloalkenyl-associated Residues | F, H, W, and Y |
| Hydrophobic Residues | A, C, F, G, H, I, L, M, R, T, V, W, and Y |
| Negatively Charged Residues | D and E |
| Polar Residues | C, D, E, H, K, N, Q, R, S, and T |
| Positively Charged Residues | H, K, and R |

TABLE 2-continued

Selected groups of amino acids that are considered conservative substitutions for one another, in certain embodiments.

| | |
|---|---|
| Small Residues | A, C, D, G, N, P, S, T, and V |
| Very Small Residues | A, G, and S |
| Residues Involved in Turn Formation | A, C, D, E, G, H, K, N, Q, R, S, P, and T |
| Flexible Residues | Q, T, K, S, G, P, D, E, and R |

TABLE 3

Additional selected groups of amino acids that are considered conservative substitutions for one another, in certain embodiments.

| | |
|---|---|
| Group 1 | A, S, and T |
| Group 2 | D and E |
| Group 3 | N and Q |
| Group 4 | R and K |
| Group 5 | I, L, and M |
| Group 6 | F, Y, and W |

TABLE 4

Further selected groups of amino acids that are considered conservative substitutions for one another, in certain embodiments.

| | |
|---|---|
| Group A | A and G |
| Group B | D and E |
| Group C | N and Q |
| Group D | R, K, and H |
| Group E | I, L, M, V |
| Group F | F, Y, and W |
| Group G | S and T |
| Group H | C and M |

Additional conservative substitutions may be found, for example, in Creighton, *Proteins: Structures and Molecular Properties* 2nd ed. (1993) W. H. Freeman & Co., New York, NY. An antibody generated by making one or more conservative substitutions of amino acid residues in a parent antibody is referred to as a "conservatively modified variant."

The term "payload" refers to a molecular moiety that can be conjugated to an antibody. In particular embodiments, payloads are selected from the group consisting of therapeutic moieties and labelling moieties.

"Triple negative breast cancer" (TNBC) refers to a breast cancer characterized as estrogen receptor-negative, progesterone receptor-negative and human epidermal growth factor receptor-2-negative (HER2-negative). The TNBC can be BRCA1/2 wildtype or BRCA1/2 mutated. The determination of negative status of the estrogen, progesterone, and Her2/neu expression is readily determined by one of skill in the art, e.g., in accordance with the current accepted guidelines. For example, guidelines set forth by the American Society of Clinical Oncology (ASCO) and the College of American Pathologists (CAP) are widely accepted. The ASCO/CAP recommends testing by immunohistochemistry (IHC) or in situ hybridization (ISH) techniques. Further, a cancer is Her2 negative if a single test (or all tests) performed on a tumor specimen show: (a) IHC negative, IHC 1+ or IHC 0, or (b) ISH negative using single-probe ISH or dual-probe ISH. One of skill in the art would recognize that the triple negative cancer described herein does not include any cancer having an apparent histopathologic discordance as observed by the pathologist. Wolff, A C et al. *J Clin Oncol.* 2013 Nov. 1: 31 (31): 3997-4013. Cancer is ERnegative or PR-negative if <1% of tumor cell nuclei are immunoreactive in the presence of evidence that the sample can express ER or PR (positive intrinsic controls are seen).

As used herein, the term "inhibits growth" (e.g., referring to cells, such as tumor cells) is intended to include any measurable decrease in cell growth (e.g., tumor cell growth) when contacted with a TF antibody or antibody conjugate described herein, as compared to the growth of the same cells not in contact with a TF antibody. In some embodiments, growth may be inhibited by at least about 10%, 20%, 30%, 40%, 50%, 60%, 70%, 80%, 90%, 99%, or 100%. The decrease in cell growth can occur by a variety of mechanisms, including but not limited to antibody internalization, apoptosis, necrosis, and/or effector function-mediated activity.

In some chemical structures illustrated herein, certain substituents, chemical groups, and atoms are depicted with a curvy/wavy line (e.g.,  )

that intersects a bond or bonds to indicate the atom through which the substituents, chemical groups, and atoms are bonded. For example, in some structures, such as but not limited to

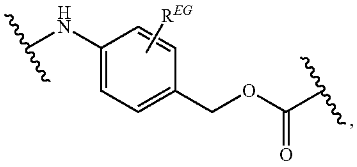,

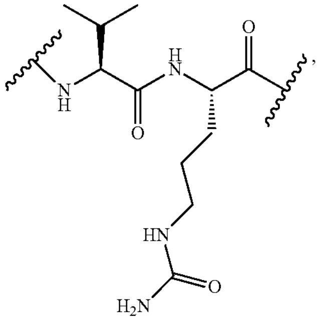, or 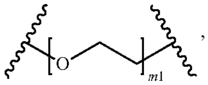, this curvy/wavy line indicates the atoms in the backbone of a conjugate or linker-payload to which the illustrated chemical entity is bonded. In some structures, such as but not limited to

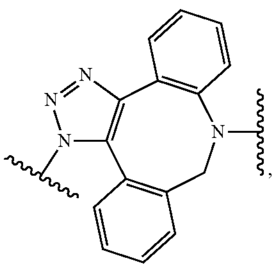 [SMILES: *N1Cc2ccccc2-c2c(nnn2*)-c2ccccc21], this curvy/wavy line indicates the atoms in the antibody or antibody fragment as well as the atoms in the backbone of a conjugate or linker-payload to which the illustrated chemical entity is bonded.

Spiro compounds depicted with overlapping rings indicate that the rings can bond at any vertex. For instance, in the spiro group

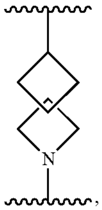, the two rings can bond at any of the three available vertex atoms in either ring.

When referring to the compounds provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise.

"Alkoxy" and "alkoxyl," refer to the group —OR" where R" is alkyl or cycloalkyl. Alkoxy groups include, in certain embodiments, methoxy, ethoxy, n-propoxy, isopropoxy, n-butoxy, tert-butoxy, sec-butoxy, n-pentoxy, n-hexoxy, 1,2-dimethylbutoxy, and the like.

The term "alkoxyamine," as used herein, refers to the group -alkylene-O—$NH_2$, wherein alkylene is as defined herein. In some embodiments, alkoxyamine groups can react with aldehydes to form oxime residues. Examples of alkoxyamine groups include —$CH_2CH_2$—O—$NH_2$, —$CH_2$—O—$NH_2$, and —O—$NH_2$.

The term "alkyl," as used herein, unless otherwise specified, refers to a saturated straight or branched hydrocarbon. In certain embodiments, the alkyl group is a primary, secondary, or tertiary hydrocarbon. In certain embodiments, the alkyl group includes one to ten carbon atoms (i.e., $C_1$ to $C_{10}$ alkyl). In certain embodiments, the alkyl is a lower alkyl, for example, $C_{1-6}$alkyl, and the like. In certain embodiments, the alkyl group is selected from the group consisting of methyl, ethyl, propyl, isopropyl, butyl, isobutyl, sec-butyl, t-butyl, pentyl, isopentyl, neopentyl, hexyl, isohexyl, 3-methylpentyl, 2,2-dimethylbutyl, and 2,3-dimethylbutyl. In certain embodiments, "substituted alkyl" refers to an alkyl substituted with, for example, one, two, or three groups independently selected from a halogen (e.g., fluoro (F), chloro (Cl), bromo (Br), or iodo (I)), alkyl, —CN, —$NO_2$, amido, —C(O)—, —C(S)—, ester, carbamate, alkenyl, alkynyl, cycloalkyl, heterocycloalkyl, dialkylamino, haloalkyl, hydroxyl, amino, alkylamino, and alkoxy. In some embodiments, alkyl is unsubstituted.

The term "alkylene," as used herein, unless otherwise specified, refers to a divalent alkyl group, as defined herein. "Substituted alkylene" refers to an alkylene group substituted as described herein for alkyl. In some embodiments, alkylene is unsubstituted.

"Alkenyl" refers to an olefinically unsaturated hydrocarbon group, in certain embodiments, having up to about eleven carbon atoms or from two to six carbon atoms (e.g., "lower alkenyl"), which can be straight-chained or branched, and having at least one or from one to two sites of olefinic unsaturation. "Substituted alkenyl" refers to an alkenyl group substituted as described herein for alkyl.

"Alkenylene" refers to a divalent alkenyl as defined herein. Lower alkenylene is, for example, $C_2$-$C_6$-alkenylene.

"Alkynyl" refers to acetylenically unsaturated hydrocarbon groups, in certain embodiments, having up to about eleven carbon atoms or from two to six carbon atoms (e.g., "lower alkynyl"), which can be straight-chained or branched, and having at least one or from one to two sites of acetylenic unsaturation. Non-limiting examples of alkynyl groups include acetylene (—C≡CH), propargyl (—$CH_2$C≡CH), and the like. "Substituted alkynyl" refers to an alkynyl group substituted as described herein for alkyl.

"Alkynylene" refers to a divalent alkynyl as defined herein. Lower alkynylene is, for example, $C_2$-$C_6$-alkynylene.

"Amino" refers to —$NH_2$.

The term "alkylamino," as used herein, and unless otherwise specified, refers to the group —NHR" where R" is, for example, $C_{1-10}$alkyl, $C_{2-10}$ alkenyl, $C_{2-10}$ alkynyl, $C_{3-12}$ carbocycle, 3- to 12-membered heterocycle, $C_{1-10}$ haloalkyl, and the like as defined herein. In certain embodiments, alkylamino is $C_{1-6}$alkylamino.

The term "dialkylamino," as used herein, and unless otherwise specified, refers to the group —NR"R" where each R" is independently $C_{1-10}$alkyl, as defined herein. In certain embodiments, dialkylamino is, for example, di-$C_{1-6}$ alkylamino, $C_{2-10}$ alkenyl, $C_{2-10}$ alkynyl, $C_{3-12}$ carbocycle, 3- to 12-membered heterocycle, $C_{1-10}$ haloalkyl, and the like.

The term "aryl," as used herein, and unless otherwise specified, refers to phenyl, biphenyl, or naphthyl. The term includes both substituted and unsubstituted moieties. An aryl group can be substituted with any described moiety including, but not limited to, one or more moieties (e.g., in some embodiments one, two, or three moieties) selected from the group consisting of halogen (e.g., fluoro (F), chloro (Cl), bromo (Br), or iodo (I)), alkyl, haloalkyl, hydroxyl, amino, alkylamino, arylamino, alkoxy, aryloxy, nitro, cyano, sulfonic acid, sulfate, phosphonic acid, phosphate, and phosphonate, wherein each moiety is independently either unprotected, or protected as necessary, as would be appreciated by those skilled in the art (see, e.g., Greene, et al., *Protective Groups in Organic Synthesis*, John Wiley and Sons, Second Edition, 1991); and wherein the aryl in the arylamino and aryloxy substituents are not further substituted.

The term "arylamino," as used herein, and unless otherwise specified, refers to an —NR'R" group where R' is hydrogen or $C_1$-$C_6$-alkyl; and R" is aryl, as defined herein.

The term "arylene," as used herein, and unless otherwise specified, refers to a divalent aryl group, as defined herein.

The term "aryloxy," as used herein, and unless otherwise specified, refers to an —OR group where R is aryl, as defined herein.

"Alkarylene" refers to an arylene group, as defined herein, wherein the aryl ring is substituted with one or two alkyl groups. "Substituted alkarylene" refers to an alkarylene, as defined herein, where the arylene group is further substituted, as defined herein for aryl.

"Aralkylene" refers to a —$CH_2$-arylene-, -arylene-$CH_2$—, or —$CH_2$-arylene-$CH_2$— group, where arylene is as defined herein. "Substituted aralkylene" refers to an aralkylene, as defined herein, where the aralkylene group is substituted, as defined herein for aryl.

"Carboxyl" or "carboxy" refers to —C(O)OH or —COOH.

The term "cycloalkyl" as used herein, unless otherwise specified, refers to a saturated cyclic hydrocarbon. In certain embodiments, the cycloalkyl group may be saturated, and/or bridged, and/or non-bridged, and/or a fused bicyclic group and/or a spirocyclic bicyclic group. In certain embodiments, the cycloalkyl group includes three to ten carbon atoms (i.e., $C_3$ to $C_{10}$ cycloalkyl). In some embodiments, the cycloalkyl has from three to fifteen carbons ($C_{3-15}$), from three to ten carbons ($C_{3-10}$), from three to seven carbons ($C_{3-7}$), or from three to six carbons ($C_3$-$C_6$) (i.e., "lower cycloalkyl"). In certain embodiments, the cycloalkyl group is cyclopropyl, cyclobutyl, cyclopentyl, cyclohexyl, cyclohexylmethyl, cycloheptyl, bicyclo[2.1.1]hexyl, bicyclo[2.2.1]heptyl, decalinyl, or adamantyl. Exemplary "cycloalkyl" or "carbocycles" include cyclopentyl, cyclohexyl, cyclohexenyl, adamantyl, phenyl, indanyl, and naphthyl. "Cycloalkyl" or "carbocycle" includes 3- to 10-membered monocyclic rings, 6- to 12-membered bicyclic rings, and 6- to 12-membered bridged rings. Each ring of a bicyclic cycloalkyl or carbocycle may be selected from saturated, unsaturated, and aromatic rings. A bicyclic cycloalkyl or carbocycle includes any combination of saturated, unsaturated and aromatic bicyclic rings, as valence permits. A bicyclic cycloalkyl or carbocycle includes any combination of ring sizes such as 4-5 fused ring systems, 5-5 fused ring systems, 5-6 fused ring systems, 6-6 fused ring systems, 5-7 fused ring systems, 6-7 fused ring systems, 5-8 fused ring systems, and 6-8 fused ring systems. Non-limiting examples of bridged bicyclic cycloalkyl or carbocycle groups include, but are not limited to, bicyclo[1.1.1]pentyl, bicyclo[2.1.1]hexyl, bicyclo[2.1.1]hexyl, bicyclo[3.1.1]heptyl, bicyclo[2.2.1]heptyl, bicyclo[3.2.1]octyl, bicyclo[2.2.2]octyl, bicyclo[3.3.1]nonyl, bicyclo[3.3.2]decyl, and 2-oxabicyclo[2.2.2]octyl. Non-limiting examples of spirocyclic cycloalkyl or carbocycle groups include, but are not limited to, spiro[3.3]heptyl, spiro[3.4]octyl, spiro[3.5]nonyl, spiro[3.6]decyl, spiro[4.4]nonyl, spiro[4.5]decyl, spiro[5.5]undecyl, spiro[5.6]dodecyl, and spiro[5.7]tridecyl.

The term "bicyclic ring system" includes 6-12 (e.g., 8-12 or 9-, 10-, or 11-) membered structures that form two rings, wherein the two rings have at least one atom in common (e.g., two atoms in common). Bicyclic rings can be fused, bridged, or spirocyclic. Bicyclic ring systems include bicycloaliphatics (e.g., bicycloalkyl or bicycloalkenyl), bicycloheteroaliphatics, bicyclic aryls, and bicyclic heteroaryls.

The term "bridged bicyclic ring system" refers to a bicyclic heterocyclicalipahtic ring system or bicyclic cycloaliphatic ring system in which the rings are bridged. Examples of bridged bicyclic ring systems include, but are not limited to, adamantanyl, norbornanyl, bicyclo[1.1.1]pentyl, bicyclo[2.1.1]hexyl, bicyclo[2.1.1]hexyl, bicyclo[3.1.1]heptyl, bicyclo[2.2.1]heptyl, bicyclo[3.2.1]octyl, bicyclo[2.2.2]octyl, bicyclo[3.3.1]nonyl, bicyclo[3.3.2]decyl, 2-oxabicyclo[2.2.2]octyl, 6-azabicyclo[3.1.1]heptyl, 6-azabicyclo[3.1.1]heptyl, 1-azabicyclo[2.2.1]heptyl, 2-azabicyclo[2.2.1]heptyl, 7-azabicyclo[2.2.1]heptyl, 1-azabicyclo[2.2.2]octyl, 3-azabicyclo[3.2.1]octyl, and 2-oxabicyclo[3.1.1]heptyl, 2,6-dioxa-tricyclo[3.3.1.$0^{3,7}$]nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl) carbonylamino, arylcarbonylamino, aralkylcarbonylamino, (heterocycloalkyl) carbonylamino, (heterocycloalkylalkyl) carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

The term "spiro bicyclic ring system" refers to a bicyclic heterocyclicalipahtic ring system or bicyclic cycloaliphatic ring system in which 2 or 3 rings are linked together by one common atom. Spiro compounds depicted with overlapping rings indicate that the rings can bond at any vertex. For instance, in the spiro group

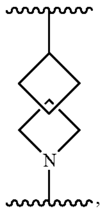, the two rings can bond at any of the three available vertex atoms in either ring.

The term "cycloalkylene," as used herein refers to a divalent cycloalkyl group, as defined herein. In certain embodiments, the cycloalkylene group is cyclopropylene

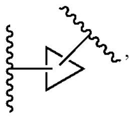, cyclobutylene

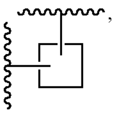, cyclopentylene

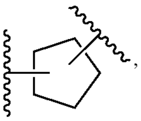, cyclohexylene

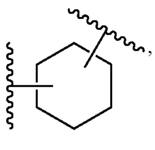, cycloheptylene

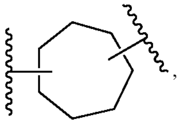, and the like. Lower cycloalkylene refers to a $C_3$-$C_6$-cycloalkylene.

The term "cycloalkylalkyl," as used herein, unless otherwise specified, refers to an alkyl group, as defined herein, substituted with one or two cycloalkyl, as defined herein.

The term "ester," as used herein, refers to —C(O)OR or —COOR where R is alkyl, as defined herein.

The term "fluorene" as used herein refers to

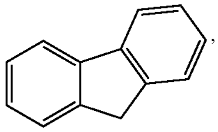 [SMILES: c1ccc2c(c1)Cc1ccccc1-2 ; ","], wherein any one or more carbons bearing one or more hydrogens can be substituted with a chemical functional group as described herein.

The term "haloalkyl" refers to an alkyl group, as defined herein, substituted with one or more halogen atoms (e.g., in some embodiments one, two, three, four, or five) which are independently selected.

The term "heteroalkyl" refers to an alkyl, as defined herein, in which one or more carbon atoms are replaced by heteroatoms. As used herein, "heteroalkenyl" refers to an alkenyl, as defined herein, in which one or more carbon atoms are replaced by heteroatoms. As used herein, "heteroalkynyl" refers to an alkynyl, as defined herein, in which one or more carbon atoms are replaced by heteroatoms. Suitable heteroatoms include, but are not limited to, nitrogen (N), oxygen (O), and sulfur(S) atoms. Heteroalkyl, heteroalkenyl, and heteroalkynyl are optionally substituted. Examples of heteroalkyl moieties include, but are not limited to, aminoalkyl, sulfonylalkyl, and sulfinylalkyl. Examples of heteroalkyl moieties also include, but are not limited to, methylamino, methylsulfonyl, and methylsulfinyl. "Substituted heteroalkyl" refers to heteroalkyl substituted with one, two, or three groups independently selected from halogen (e.g., fluoro (F), chloro (Cl), bromo (Br), or iodo (I)), alkyl, haloalkyl, hydroxyl, amino, alkylamino, and alkoxy. In some embodiments, a heteroalkyl group may comprise one, two, three, or four heteroatoms. Those of skill in the art will recognize that a 4-membered heteroalkyl may generally comprise one or two heteroatoms, a 5- or 6-membered heteroalkyl may generally comprise one, two, or three heteroatoms, and a 7- to 10-membered heteroalkyl may generally comprise one, two, three, or four heteroatoms.

The term "heteroalkylene," as used herein, refers to a divalent heteroalkyl, as defined herein. "Substituted heteroalkylene" refers to a divalent heteroalkyl, as defined herein, substituted as described for heteroalkyl.

The term "heterocycloalkyl" refers to a monovalent, monocyclic, or multicyclic non-aromatic ring system, wherein one or more of the ring atoms are heteroatoms independently selected from oxygen (O), sulfur(S), and nitrogen (N) (e.g., where the nitrogen or sulfur atoms may be optionally oxidized, and the nitrogen atoms may be optionally quaternized) and the remaining ring atoms of the non-aromatic ring are carbon atoms. In certain embodiments, heterocycloalkyl is a monovalent, monocyclic, or multicyclic fully-saturated ring system. In certain embodiments, the heterocycloalkyl group has from three to twenty, from three to fifteen, from three to ten, from three to eight, from four to seven, from four to eleven, or from five to six ring atoms. The heterocycloalkyl may be attached to a core structure at any heteroatom or carbon atom which results in the creation of a stable compound. In certain embodiments, the heterocycloalkyl is a monocyclic, bicyclic, tricyclic, or tetracyclic ring system, which may include a fused, and/or bridged bicyclic group, and/or a spirocyclic bicyclic group ring system and in which the nitrogen or sulfur atoms may be optionally oxidized, and/or the nitrogen atoms may be optionally quaternized. In some embodiments, heterocycloalkyl radicals include, but are not limited to, 2,5-diazabicyclo[2.2.2]octanyl, decahydroisoquinolinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocycloalkyl may also be optionally substituted as described herein. In certain embodiments, heterocycloalkyl is substituted with one, two, or three groups independently selected from halogen (e.g., fluoro (F), chloro (Cl), bromo (Br), or iodo (I)), alkyl, haloalkyl, hydroxyl, amino, alkylamino, and alkoxy. In some embodiments, a heterocycloalkyl group may comprise one, two, three, or four heteroatoms. Those of skill in the art will recognize that a 4-membered heterocycloalkyl may generally comprise one or two heteroatoms, a 5- or 6-membered heterocycloalkyl may generally comprise one, two, or three heteroatoms, and a 7- to 10-membered heterocycloalkyl may generally comprise one, two, three, or four heteroatoms. In some embodiments, "heterocycloalkyl" or "heterocycle" radicals include, but are not limited to, 2,5-diazabicyclo[2.2.2]octanyl, decahydroisoquinolinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. Non-limiting examples of bridged heterocycloalkyl or heterocycle groups include, but are not limited to, 6-azabicyclo[3.1.1]heptyl, 6-azabicyclo[3.1.1]heptyl, 1-azabicyclo[2.2.1]heptyl, 2-azabicyclo[2.2.1]heptyl, 7-azabicyclo[2.2.1]heptyl, 1-azabicyclo[2.2.2]octyl, 3-azabicyclo[3.2.1]octyl, and 2-oxabicyclo[3.1.1]heptyl, 2,6-dioxa-tricyclo[3.3.1.0$^{3,7}$]nonyl. Non-limiting examples of spirocyclic heterocycloalkyl or heterocycle groups include, but are not limited to, 2,8-diazaspiro[4.5]decyl; 2,7-diazaspiro[3.5]nonyl; 3,9-diazaspiro[5.5]undecyl; 3-azaspiro[5.5]undecyl; 2-oxa-6-azaspiro[3.4]octyl; 2-oxa-9-azaspiro[5.5]undecyl; 3-oxa-9-azaspiro[5.5]undecyl; 7-azaspiro[3.5]nonyl; 2-azaspiro[3.5]nonyl; 7-oxaspiro[3.5]nonyl; and, 2-oxaspiro[3.5]nonyl.

"Heterocycloalkylene" refers to a divalent heterocycloalkyl as defined herein.

The term "heteroaryl" refers to a monovalent, monocyclic aromatic group and/or multicyclic aromatic group, wherein at least one aromatic ring contains one or more heteroatoms independently selected from oxygen, sulfur, and nitrogen within the ring. Each ring of a heteroaryl group can contain one or two oxygen atoms, one or two sulfur atoms, and/or one to four nitrogen atoms, provided that the total number of heteroatoms in each ring is four or less and each ring contains at least one carbon atom. In certain embodiments, the heteroaryl has from five to twenty, from five to fifteen, or from five to ten ring atoms. A heteroaryl may be attached to the rest of the molecule via a nitrogen or a carbon atom. In some embodiments, monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, triazolyl, thiadiazolyl, thiazolyl, thienyl, tetrazolyl, and triazinyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, heteroaryl may also be optionally substituted as described herein. "Substituted heteroaryl" is a heteroaryl substituted as defined for aryl.

The term "heteroarylene" refers to a divalent heteroaryl group, as defined herein. "Substituted heteroarylene" is a heteroarylene substituted as defined for aryl.

The term "protecting group," as used herein, and unless otherwise specified, refers to a group that is added to an oxygen, nitrogen, or phosphorus atom to prevent further reaction at the (protected) oxygen, nitrogen, or phosphorus, or for other purposes. A wide variety of oxygen and nitrogen protecting groups are known to those skilled in the art of organic synthesis (see, e.g., Greene, et al., *Protective Groups in Organic Synthesis*, John Wiley and Sons, Fourth Edition, 2006, which is incorporated herein by reference in its entirety).

"Pharmaceutically acceptable salt" refers to any salt of a compound provided herein which retains its biological properties and which is not toxic or otherwise undesirable for pharmaceutical use. Such salts may be derived from a variety of organic and inorganic counter-ions well known in the art. Such salts include, but are not limited to (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, glutamic, hydroxynaphthoic, salicylic, stearic, cyclohexylsulfamic, quinic, and muconic acids, and the like; or (2) salts formed when an acidic proton present in the parent compound either (a) is replaced by a metal ion, for example, an alkali metal ion, an alkaline earth ion, or an aluminum ion, or alkali metal or alkaline earth metal hydroxides, such as sodium, potassium, calcium, magnesium, aluminum, lithium, zinc, and barium hydroxide, or ammonia; or (b) coordinates with an organic base, such as aliphatic, alicyclic, or aromatic organic amines, including, without limitation, ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, procaine, N-benzylphenethylamine, N-methylglucamine piperazine, tris(hydroxymethyl)-aminomethane, tetramethylammonium hydroxide, and the like.

Pharmaceutically acceptable salts further include, by way of example and without limitation, sodium, potassium, calcium, magnesium, ammonium, and tetraalkylammonium salts, and the like, and when the compound contains a basic functionality, salts of non-toxic organic or inorganic acids, such as hydrohalides, for example, hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, glutamate, hydroxynaphthoate, salicylate, stearate, cyclohexylsulfamate, quinate, muconate, and the like.

The term "substantially free of" or "substantially in the absence of" with respect to a composition refers to a composition that includes at least 85% or 90% by weight, in certain embodiments 95%, 98%, 99%, or 100% by weight; or in certain embodiments, 95%, 98%, 99%, or 100% of the designated enantiomer or diastereomer of a compound. In certain embodiments, in the methods and compounds provided herein, the compounds are substantially free of one of two enantiomers. In certain embodiments, in the methods and compounds provided herein, the compounds are substantially free of one of two diastereomers. In certain embodiments, in the methods and compounds provided herein, the compounds are substantially free of enantiomers (i.e., the compounds are not a racemic or 50:50 mixture of compounds).

Similarly, the term "isolated" with respect to a composition refers to a composition that includes at least 85%, 90%, 95%, 98%, or 99% to 100% by weight, of the compound, the remainder comprising other chemical species, enantiomers, or diastereomers.

"Solvate" refers to a compound provided herein, or a salt thereof, that further includes a stoichiometric or non-stoichiometric amount of solvent bound by non-covalent intermolecular forces. Where the solvent is water, the solvate is a hydrate.

"Isotopic composition" refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as hydrogen (H), the position is understood to have hydrogen at its natural isotopic composition.

"Isotopic enrichment" refers to the percentage of incorporation of an amount of a specific isotope at a given atom in a molecule in the place of that atom's natural isotopic abundance. For example, deuterium (D) enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

"Isotopically enriched" refers to an atom having an isotopic composition other than the natural isotopic composition of that atom. "Isotopically enriched" may also refer to a compound containing at least one atom having an isotopic composition other than the natural isotopic composition of that atom.

As used herein, "alkyl," "alkylene," "alkylamino," "dialkylamino," "cycloalkyl," "aryl," "arylene," "alkoxy," "amino," "carboxyl," "heterocycloalkyl," "heteroaryl," "heteroarylene," "carboxyl," and "amino acid" groups optionally comprise deuterium (D) at one or more positions where hydrogen (H) atoms are present, and wherein the deuterium composition of the atom or atoms is other than the natural isotopic composition.

Also as used herein, "alkyl," "alkylene," "alkylamino," "dialkylamino," "cycloalkyl," "aryl," "arylene," "alkoxy," "amino," "carboxyl," "heterocycloalkyl," "heteroaryl," "heteroarylene," "carboxyl," and "amino acid" groups optionally comprise carbon-13 ($^{13}C$) at an amount other than the natural isotopic composition.

The term "macromolecule" or "macromolecular moiety" refers to a protein, peptide, antibody, nucleic acid, carbohydrate, or other large molecule composed of polymerized monomers. They include peptides of two or more residues, or ten or more residues. In certain embodiments, a macromolecule is at least 1000 Da in mass. In certain embodiments, a macromolecule has at least 1000 atoms. In certain embodiments, a macromolecule can be modified. For instance, a protein, peptide, or antibody can be modified with one or more carbohydrates and/or small molecule therapeutic compounds.

The term "amino acid" refers to the twenty common naturally occurring amino acids. Naturally occurring amino acids include alanine (Ala; A), arginine (Arg; R), asparagine (Asn; N), aspartic acid (Asp; D), cysteine (Cys; C); glutamic acid (Glu; E), glutamine (Gln; Q), Glycine (Gly; G); histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V), and the less common pyrrolysine and selenocysteine. Natural amino acids also include citrulline. Naturally encoded amino acids include post-translational variants of the twenty-two naturally occurring amino acids such as prenylated amino acids, isoprenylated amino acids, myrisoylated amino acids, palmitoylated amino acids, N-linked glycosylated amino acids, O-linked glycosylated amino acids, phosphorylated amino acids, and acylated amino acids. The term "amino acid" also includes non-natural (or unnatural) or synthetic α-, β-, γ-, or δ-amino acids, and includes, but is not limited to, amino acids found in proteins, i.e., glycine, alanine, valine, leucine, isoleucine, methionine, phenylalanine, tryptophan, proline, serine, threonine, cysteine, tyrosine, asparagine, glutamine, aspartate, glutamate, lysine, arginine, and histidine. In certain embodiments, the amino acid is in the L-configuration. In certain embodiments, the amino acid is in the D-configuration. Alternatively, the amino acid can be a derivative of alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleucinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl, or β-histidinyl. Unnatural amino acids are not proteinogenic amino acids, or post-translationally modified variants thereof. In particular, the term unnatural amino acid refers to an amino acid that is not one of the twenty common amino acids or pyrrolysine or selenocysteine, or post-translationally modified variants thereof.

The term "conjugate" or "antibody conjugate" refers to a compound or drug moiety described herein linked to one or more macromolecular moieties. The macromolecular moiety is as defined herein or is any macromolecule deemed suitable to the person of skill in the art. The compound or drug moiety can be any compound or drug moiety described herein. The compound or drug moiety can be directly linked to the macromolecular moiety via a covalent bond, or the compound or drug moiety can be linked to the macromolecular moiety indirectly via a linker. Typically, the linker is covalently bonded to the macromolecular moiety and also covalently bonded to the compound or drug moiety.

"pAMF," "pAMF residue," or "pAMF mutation" refers to a variant phenylalanine residue (i.e., para-azidomethyl-L-phenylalanine) added or substituted into a polypeptide.

The term "linker" refers to a molecular moiety that is capable of forming at least two covalent bonds. Typically, a linker is capable of forming at least one covalent bond to a macromolecular moiety and at least another covalent bond to a compound or drug moiety. In certain embodiments, a linker can form more than one covalent bond to a macromolecular moiety. In certain embodiments, a linker can form more than one covalent bond to a compound or drug moiety or can form covalent bonds to more than one compound or drug moiety. After a linker forms a bond to a macromolecular moiety, or a compound or drug moiety, or both, the remaining structure (i.e. the residue of the linker ("linker residue") after one or more covalent bonds are formed) may still be referred to as a "linker" herein. The term "linker precursor" refers to a linker having one or more reactive groups capable of forming a covalent bond with a macromolecule, or compound or drug moiety, or both. A person of ordinary skill in the art, given the context of how the term linker is used, would understand whether "linker" means linker precursor with one reactive group, a linker precursor with more than one reactive groups, a linker residue which is covalently bonded to the macromolecule, a linker residue which is covalently bonded to a compound or drug moiety, and/or a linker residue which is covalently bonded to the macromolecule and is covalently bonded to a compound or drug moiety. In some embodiments, the linker is a cleavable linker. For example, a cleavable linker can be one that is released by a bio-labile or enzymatic function, which may or may not be engineered. In some embodiments, the linker is a non-cleavable linker. For example, a non-cleavable linker can be one that is released upon degradation of the macromolecular moiety.

As used herein, term "$EC_{50}$" refers to a dosage, concentration, or amount of a particular test compound that elicits a dose-dependent response at 50% of maximal expression of a particular response that is induced, provoked, or potentiated by the particular test compound.

As used herein, and unless otherwise specified, the term "$IC_{50}$" refers to an amount, concentration, or dosage of a particular test compound that achieves a 50% inhibition of a maximal response in an assay that measures such response.

As used herein, the terms "subject" and "patient" are used interchangeably. The terms "subject" and "subjects" refer to an animal, such as a mammal including a non-primate (e.g., a cow, pig, horse, cat, dog, rat, mouse, camel, avian, goat, and sheep) and a primate (e.g., a monkey, such as a cynomolgous monkey, a chimpanzee, and a human), and in certain embodiments, a human. In certain embodiments, the subject is a farm animal (e.g., a horse, a cow, a pig, etc.) or a pet (e.g., a dog or a cat). In certain embodiments, the subject is a human. In some embodiments, the subject has a disease that can be treated or diagnosed with an antibody or antibody conjugate provided herein. In some embodiments, the disease is gastric carcinoma, colorectal carcinoma, renal cell carcinoma, cervical carcinoma, non-small cell lung carcinoma, ovarian cancer, breast cancer, triple-negative breast cancer, endometrial cancer, prostate cancer, and/or a cancer of epithelial origin.

As used herein, the terms "therapeutic agent" and "therapeutic agents" refer to any agent(s) which can be used in the treatment or prevention of a disorder or one or more symptoms thereof. In certain embodiments, the term "therapeutic agent" includes an antibody or antibody conjugate provided herein. In certain embodiments, a therapeutic agent is an agent which is known to be useful for, or has been or is currently being used for the treatment or prevention of a disorder or one or more symptoms thereof.

"Treating" or "treatment" of any disease or disorder refers, in certain embodiments, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying or preventing the onset of the disease or disorder, or delaying or preventing recurrence of the disease or disorder. In yet another embodiment, "treating" or "treatment" includes the reduction or elimination of either the disease or disorder, or retarding the progression of the disease or disorder or of one or more symptoms of the disease or disorder, or reducing the severity of the disease or disorder or of one or more symptoms of the disease or disorder.

As used herein, the terms "prophylactic agent" and "prophylactic agents" as used refer to any agent(s) which can be used in the prevention of a disorder or one or more symptoms thereof. In certain embodiments, the term "prophylactic agent" includes a compound, drug moiety, or conjugate provided herein. In certain other embodiments, the term "prophylactic agent" does not refer a compound, drug moiety, or conjugate provided herein. For example, a prophylactic agent is an agent which is known to be useful for, or has been or is currently being used to prevent or impede the onset, development, progression, and/or severity of a disorder.

As used herein, the phrase "prophylactically effective amount" refers to the amount of a therapy (e.g., prophylactic agent) which is sufficient to result in the prevention or reduction of the development, recurrence, or onset of one or more symptoms associated with a disorder or to enhance or improve the prophylactic effect(s) of another therapy (e.g., another prophylactic agent).

In some chemical structures illustrated herein, certain substituents, chemical groups, and atoms are depicted with a curvy/wavy/wiggly line (e.g.,  or )

that intersects a bond or bonds to indicate the atom through which the substituents, chemical groups, and atoms are bonded. For example, in some structures, such as but not limited to,

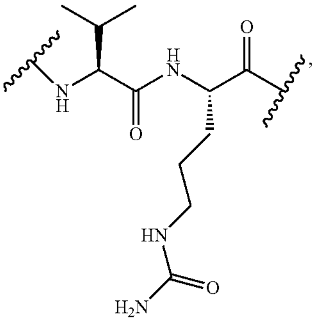 or 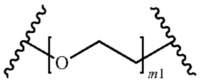, this curvy/wavy/wiggly line indicates the atoms in the backbone of a conjugate, compound, or drug moiety structure to which the illustrated chemical entity is bonded. In some structures, such as but not limited to

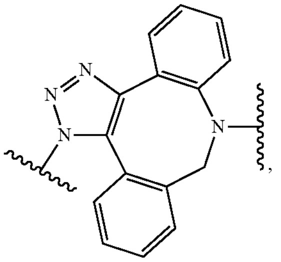 [SMILES: *N1Cc2ccccc2-c2c(nnn2*)-c2ccccc21], this curvy/wavy/wiggly line indicates the atoms in the macromolecule as well as the atoms in the backbone of a conjugate, compound, or drug moiety structure to which the illustrated chemical entity is bonded.

As used herein, illustrations showing substituents bonded to a cyclic group (e.g., aromatic, heteroaromatic, fused ring, and saturated or unsaturated cycloalkyl or heterocycloalkyl) through a bond between ring atoms are meant to indicate, unless specified otherwise, that the cyclic group may be substituted with that substituent at any ring position in the cyclic group or on any ring in the fused ring group, according to techniques set forth herein or which are known in the field to which the instant disclosure pertains. For example, the group,

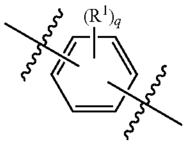 or 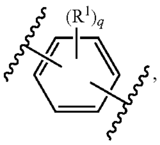, wherein subscript q is an integer from zero to four and in which the positions of substituent $R^1$ are described generically, i.e., not directly attached to any vertex of the bond line structure, i.e., specific ring carbon atom, includes the following, non-limiting examples of groups in which the substituent $R^1$ is bonded to a specific ring carbon atom:

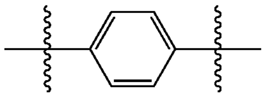, 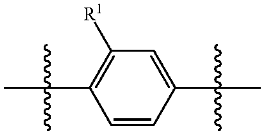,

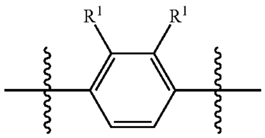, 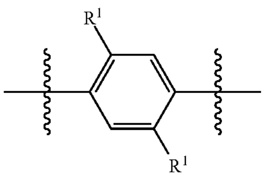,

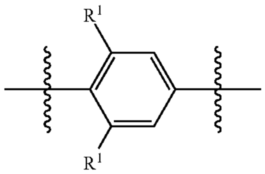, 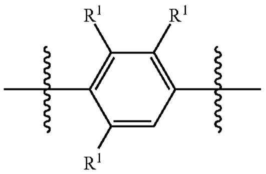,

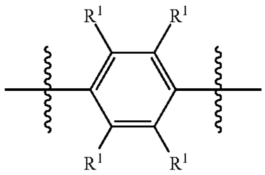, 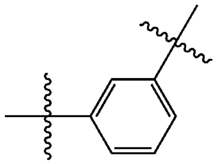,

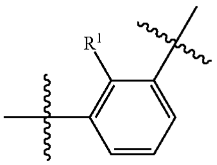, 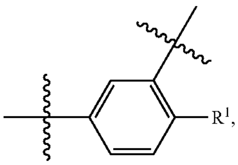,

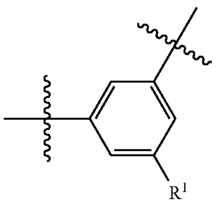, 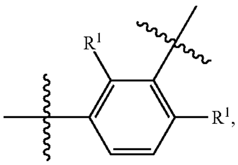,

-continued

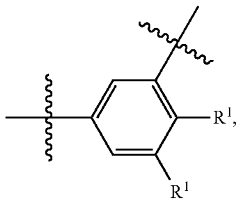
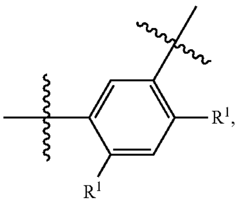
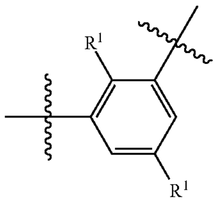
,
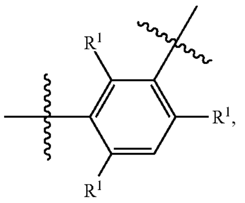
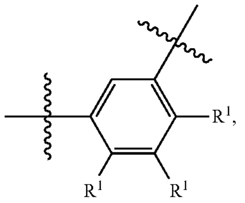
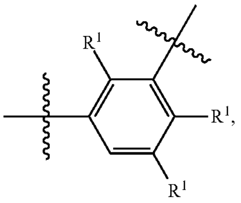
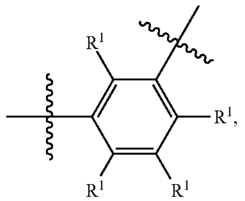
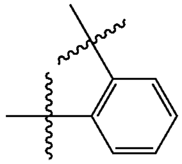
,
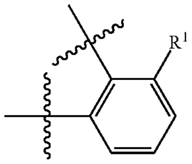
,
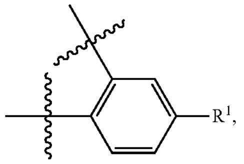
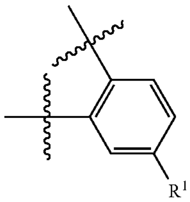
,
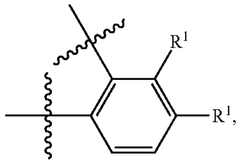
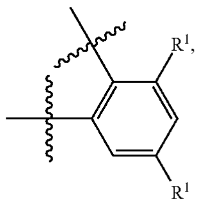
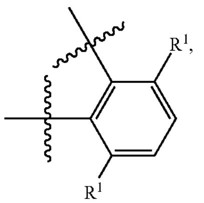
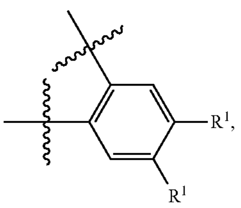
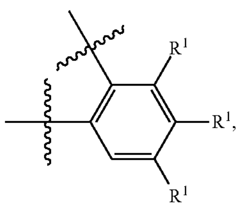

-continued

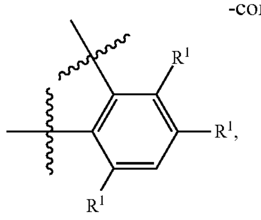
and
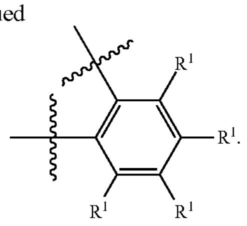

The term “carbocycle” as used herein, unless otherwise specified, refers to a saturated, unsaturated, or aromatic ring in which atom of the ring is carbon. In certain embodiments, the carbocycle group may be saturated, and/or bridged, and/or non-bridged, and/or a fused bicyclic group, and/or a spirocyclic bicyclic group. In certain embodiments, the carbocycle group includes three to ten carbon atoms (i.e., $C_3$ to $C_{10}$ carbocycle). In some embodiments, the carbocycle has from three to fifteen carbons ($C_{3-15}$), from three to ten carbons ($C_{3-10}$), from three to seven carbons ($C_{3-7}$), or from three to six carbons ($C_3$-$C_6$). In certain embodiments, the carbocycle group is cyclopropyl, cyclobutyl, cyclopentyl, cyclohexyl, cyclohexylmethyl, cycloheptyl, bicyclo[2.1.1]hexyl, bicyclo[2.2.1]heptyl, decalinyl, or adamantyl.

The term “heterocycle” refers to a saturated, unsaturated or aromatic ring comprising one or more heteroatoms. Exemplary heteroatoms include N, O, Si, P, B, and S atoms where the nitrogen or sulfur atoms may be optionally oxidized, and the nitrogen atoms may be optionally quaternized and the remaining ring atoms of the non-aromatic ring are carbon atoms. Heterocycles include 3- to 10-membered monocyclic rings, 6- to 12-membered bicyclic rings, and 6- to 12-membered bridged rings. In certain embodiments, heterocycle is a monovalent, monocyclic, or multicyclic fully-saturated ring system. In certain embodiments, the heterocycloalkyl or “heterocycle” group may be unsaturated, and/or bridged, and/or non-bridged, and/or a fused bicyclic group, and/or a spirocyclic bicyclic group.

The term “site-specific” refers to a modification of a polypeptide at a predetermined sequence location in the polypeptide. The modification is at a single, predictable residue of the polypeptide with little or no variation. In particular embodiments, a modified amino acid is introduced at that sequence location, for instance recombinantly or synthetically. Similarly, a moiety can be “site-specifically” linked to a residue at a particular sequence location in the polypeptide. In certain embodiments, a polypeptide can comprise more than one site-specific modification.

As used herein, the term “therapeutically effective amount” or “effective amount” refers to an amount of an antibody, antibody conjugate, or composition that when administered to a subject is effective to treat a disease or disorder. In some embodiments, a therapeutically effective amount or effective amount refers to an amount of an antibody, antibody conjugate, or composition that when administered to a subject is effective to prevent or ameliorate a disease or the progression of the disease, or result in amelioration of symptoms. A “therapeutically effective amount” can vary depending on, inter alia, the compound, the disease or disorder and its severity, and the age, weight, etc., of the subject to be treated.

As used herein, the term “subject” means a mammalian subject. Exemplary subjects include, but are not limited to humans, monkeys, dogs, cats, mice, rats, cows, horses, camels, avians, goats, and sheep. In certain embodiments, the subject is a human. In some embodiments, the subject has a disease that can be treated or diagnosed with an antibody provided herein. In some embodiments, the disease is gastric carcinoma, colorectal carcinoma, renal cell carcinoma, cervical carcinoma, non-small cell lung carcinoma, ovarian cancer, prostate cancer, and/or a cancer of epithelial origin.

2. Antibodies and Antibody Specificity

The present disclosure provides antibodies as described here that selectively bind to TF. Provided herein are antibodies that selectively bind human TF. In some aspects, the antibody selectively binds to the extracellular domain of human TF.

Also provided herein are conjugates that comprise antibodies that selectively bind human TF. In some aspects, the antibody of the conjugate selectively binds to the extracellular domain of human TF.

In some embodiments, the antibody binds to a homolog of human TF. In some aspects, the antibody binds to a homolog of human TF from a species selected from monkeys, mice, dogs, cats, rats, cows, horses, goats and sheep. In some aspects, the homolog is a cynomolgus monkey homolog.

In some embodiments, the antibody has one or more CDRs having particular lengths, in terms of the number of amino acid residues. In some embodiments, the Chothia CDR-H1 of the antibody is 6, 7, or 8 residues in length. In some embodiments, the Kabat CDR-H1 of the antibody is 4, 5, or 6 residues in length. In some embodiments, the Chothia CDR-H2 of the antibody is 5, 6, or 7 residues in length. In some embodiments, the Kabat CDR-H2 of the antibody is 16, 17, or 18 residues in length. In some embodiments, the Kabat/Chothia CDR-H3 of the antibody is 7, 8, 9, 10, 11, 12, or 13 residues in length.

In some aspects, the Kabat/Chothia CDR-L1 of the antibody is 10, 11, 12, 13, 14, 15, or 16 residues in length. In some aspects, the Kabat/Chothia CDR-L2 of the antibody is 6, 7, or 8 residues in length. In some aspects, the Kabat/Chothia CDR-L3 of the antibody is 8, 9, or 10 residues in length.

In some embodiments, the antibody comprises a light chain. In some aspects, the light chain is a kappa light chain. In some aspects, the light chain is a lambda light chain.

In some embodiments, the antibody comprises a heavy chain. In some aspects, the heavy chain is an IgA. In some aspects, the heavy chain is an IgD. In some aspects, the heavy chain is an IgE. In some aspects, the heavy chain is an IgG. In some aspects, the heavy chain is an IgM. In some aspects, the heavy chain is an IgG1. In some aspects, the heavy chain is an IgG2. In some aspects, the heavy chain is an IgG3. In some aspects, the heavy chain is an IgG4. In some aspects, the heavy chain is an IgA1. In some aspects, the heavy chain is an IgA2.

In some embodiments, the antibody is an antibody fragment. In some aspects, the antibody fragment is an Fv fragment. In some aspects, the antibody fragment is a Fab fragment. In some aspects, the antibody fragment is a $F(ab')_2$ fragment. In some aspects, the antibody fragment is a Fab' fragment. In some aspects, the antibody fragment is an scFv (sFv) fragment. In some aspects, the antibody fragment is an scFv-Fc fragment.

In some embodiments, the scFv-Fc fragment comprises a constant region wherein the constant region comprises SEQ ID NO: 3068. The constant region in SEQ ID NO: 3068 differs from the human IgG1 constant region of SEQ ID NO: 3062 in several respects. First, the sequence in SEQ ID NO: 3068 comprises the linker AAGSDQEPKSS (SEQ ID NO: 3071). SEQ ID NO: 3068 also does not comprise the CH1 domain of the IgG1 constant region. SEQ ID NO: 3068 further comprises a C220S (EU numbering system) mutation, which removes an unpaired cysteine reside that is not needed when the light chain constant region is not present (e.g., in an scFv-Fc format). SEQ ID NO: 3068 further comprises two, optional, P to S mutations (P230S and P238S by the EU numbering system). Either or both of these serine residues can be reverted to the naturally occurring proline residues. Finally, SEQ ID NO: 3068 comprises an aspartic acid (D) residue at EU position 356 and a leucine (L) residue at EU position 358. In contrast, SEQ ID NO: 3062 comprises glutamic acid (E) in EU position 356 and methionine (M) in EU position 358. In some embodiments, the antibodies provided herein comprise constant regions comprising D356/L358, E356/M358, D356/M358, or E356/L358 (EU numbering). However, a skilled person will recognize that the antibodies provide herein may comprise any suitable constant region and that the constant region sequences provided herein are for illustrative purposes.

In some embodiments, the antibody is a monoclonal antibody. In some embodiments, the antibody is a polyclonal antibody.

In some embodiments, the antibody is a chimeric antibody. In some embodiments, the antibody is a humanized antibody. In some embodiments, the antibody is a human antibody.

In some embodiments, the antibody is an affinity matured antibody. In some aspects, the antibody is an affinity matured antibody derived from an illustrative sequence provided in this disclosure.

The antibodies provided herein may be useful for the treatment of a variety of diseases and conditions including cancers. In some embodiments, the antibodies provided herein may be useful for the treatment of cancers of solid tumors. For example, the antibodies provided herein can be useful for the treatment of colorectal cancer.

2.2 $V_H$ Sequences Comprising Illustrative CDRs

In some embodiments, the antibody comprises a $V_H$ sequence comprising one or more CDR-H sequences comprising, consisting of, or consisting essentially of one or more illustrative CDR-H sequences provided in this disclosure, and variants thereof. In some embodiments, the CDR-H sequences comprise, consist of, or consist essentially of one or more CDR-H sequences provided in a $V_H$ sequence selected from SEQ ID NOs: 2625-2949.

2.2.1. $V_H$ Sequences Comprising Illustrative Kabat CDRs

In some embodiments, the antibody comprises a $V_H$ sequence comprising one or more Kabat CDR-H sequences comprising, consisting of, or consisting essentially of one or more illustrative Kabat CDR-H sequences provided in this disclosure, and variants thereof.

2.2.1.1. Kabat CDR-H1+Kabat CDR-H2+Kabat CDR-H3

In some embodiments, the antibody comprises a $V_H$ sequence comprising a Kabat CDR-H1 sequence comprising, consisting of, or consisting essentially of a sequence selected from SEQ ID NOs: 430, 439, 442, 454-541, 543, 549, 554, 560, 562, and 563, a Kabat CDR-H2 sequence comprising, consisting of, or consisting essentially of a sequence selected from SEQ ID NOs: 1080, 1089, 1092, 1104-1191, 1193, 1199, 1204, 1200, 1212, and 1213, and a Kabat CDR-H3 sequence comprising, consisting of, or consisting essentially of a sequence selected from SEQ ID NOs: 1730, 1739, 1742, 1754-1841, 1843, 1849, 1854, 1860, 1862, and 1863. In some aspects, the Kabat CDR-H1 sequence, Kabat CDR-H2 sequence, and Kabat CDR-H3 sequence are all from a single illustrative $V_H$ sequence provided in this disclosure. For example, in some aspects, the Kabat CDR-H1, Kabat CDR-H2, and Kabat CDR-H3 are all from a single illustrative $V_H$ sequence selected from SEQ ID NOs: 2727, 2736, 2739, 2751-2838, 2840, 2846, 2851, 2857, 2859, and 2860.

2.2.1.2. Variants of $V_H$ Sequences Comprising Illustrative Kabat CDRs

In some embodiments, the $V_H$ sequences provided herein comprise a variant of an illustrative Kabat CDR-H3, CDR-H2, and/or CDR-H1 sequence provided in this disclosure.

In some aspects, the Kabat CDR-H3 sequence comprises, consists of, or consists essentially of a variant of an illustrative Kabat CDR-H3 sequence provided in this disclosure. In some aspects, the Kabat CDR-H3 sequence comprises, consists of, or consists essentially of a sequence having at least 70%, 75%, 80%, 85%, 90%, 95%, 96%, 97%, 98%, or 99% identity with any of the illustrative Kabat CDR-H3 sequences provided in this disclosure. In some aspects, the Kabat CDR-H3 sequence comprises, consists of, or consists essentially of any of the illustrative Kabat CDR-H3 sequences provided in this disclosure, with 1, 2, or 3 amino acid substitutions. In some aspects, the amino acid substitutions are conservative amino acid substitutions.

In some aspects, the Kabat CDR-H2 sequence comprises, consists of, or consists essentially of a variant of an illustrative Kabat CDR-H2 sequence provided in this disclosure. In some aspects, the Kabat CDR-H2 sequence comprises, consists of, or consists essentially of a sequence having at least 70%, 75%, 80%, 85%, 90%, 95%, 96%, 97%, 98%, or 99% identity with any of the illustrative Kabat CDR-H2 sequences provided in this disclosure. In some aspects, the Kabat CDR-H2 sequence comprises, consists of, or consists essentially of any of the illustrative Kabat CDR-H2 sequences provided in this disclosure, with 1, 2, or 3 amino acid substitutions. In some aspects, the amino acid substitutions are conservative amino acid substitutions.

In some aspects, the Kabat CDR-H1 sequence comprises, consists of, or consists essentially of a variant of an illustrative Kabat CDR-H1 sequence provided in this disclosure. In some aspects, the Kabat CDR-H1 sequence comprises, consists of, or consists essentially of a sequence having at least 70%, 75%, 80%, 85%, 90%, 95%, 96%, 97%, 98%, or 99% identity with any of the illustrative Kabat CDR-H1 sequences provided in this disclosure. In some aspects, the Kabat CDR-H1 sequence comprises, consists of, or consists essentially of any of the illustrative Kabat CDR-H1 sequences provided in this disclosure, with 1, 2, or 3 amino acid substitutions. In some aspects, the amino acid substitutions are conservative amino acid substitutions.

2.2.2. $V_H$ Sequences Comprising Illustrative Chothia CDRs

In some embodiments, the antibody comprises a $V_H$ sequence comprising one or more Chothia CDR-H sequences comprising, consisting of, or consisting essentially of one or more illustrative Chothia CDR-H sequences provided in this disclosure, and variants thereof.

2.2.2.1. Chothia CDR-H1+Chothia CDR-H2+Chothia CDR-H3

In some embodiments, the antibody comprises a $V_H$ sequence comprising a Chothia CDR-H1 sequence comprising, consisting of, or consisting essentially of a sequence selected from SEQ ID NOs: 105, 114, 117, 129-216, 218, 224, 229, 235, 237, and 238, a Chothia CDR-H2 sequence comprising, consisting of, or consisting essentially of a sequence selected from SEQ ID NOs: 755, 764, 767, 779-866, 868, 874, 879, 885, 887, and 888, and a Chothia CDR-H3 sequence comprising, consisting of, or consisting essentially of a sequence selected from SEQ ID NOs: 1405, 1414, 1417, 1429-1516, 1518, 1524, 1529, 1535, 1537, and 1538. In some aspects, the Chothia CDR-H1 sequence, Chothia CDR-H2 sequence, and Chothia CDR-H3 sequence are all from a single illustrative $V_H$ sequence provided in this disclosure. For example, in some aspects, the Chothia CDR-H1, Chothia CDR-H2, and Chothia CDR-H3 are all from a single illustrative $V_H$ sequence selected from SEQ ID NOs: 2727, 2736, 2739, 2751-2838, 2840, 2846, 2851, 2857, 2859, and 2860.

2.2.2.2. Variants of $V_H$ Sequences Comprising Illustrative Chothia CDRs

In some embodiments, the $V_H$ sequences provided herein comprise a variant of an illustrative Chothia CDR-H3, CDR-H2, and/or CDR-H1 sequence provided in this disclosure.

In some aspects, the Chothia CDR-H3 sequence comprises, consists of, or consists essentially of a variant of an illustrative Chothia CDR-H3 sequence provided in this disclosure. In some aspects, the Chothia CDR-H3 sequence comprises, consists of, or consists essentially of a sequence having at least 70%, 75%, 80%, 85%, 90%, 95%, 96%, 97%, 98%, or 99% identity with any of the illustrative Chothia CDR-H3 sequences provided in this disclosure. In some aspects, the Chothia CDR-H3 sequence comprises, consists of, or consists essentially of any of the illustrative Chothia CDR-H3 sequences provided in this disclosure, with 1, 2, or 3 amino acid substitutions. In some aspects, the amino acid substitutions are conservative amino acid substitutions.

In some aspects, the Chothia CDR-H2 sequence comprises, consists of, or consists essentially of a variant of an illustrative Chothia CDR-H2 sequence provided in this disclosure. In some aspects, the Chothia CDR-H2 sequence comprises, consists of, or consists essentially of a sequence having at least 70%, 75%, 80%, 85%, 90%, 95%, 96%, 97%, 98%, or 99% identity with any of the illustrative Chothia CDR-H2 sequences provided in this disclosure. In some aspects, the Chothia CDR-H2 sequence comprises, consists of, or consists essentially of any of the illustrative Chothia CDR-H2 sequences provided in this disclosure, with 1, 2, or 3 amino acid substitutions. In some aspects, the amino acid substitutions are conservative amino acid substitutions.

In some aspects, the Chothia CDR-H1 sequence comprises, consists of, or consists essentially of a variant of an illustrative Chothia CDR-H1 sequence provided in this disclosure. In some aspects, the Chothia CDR-H1 sequence comprises, consists of, or consists essentially of a sequence having at least 70%, 75%, 80%, 85%, 90%, 95%, 96%, 97%, 98%, or 99% identity with any of the illustrative Chothia CDR-H1 sequences provided in this disclosure. In some aspects, the Chothia CDR-H1 sequence comprises, consists of, or consists essentially of any of the illustrative Chothia CDR-H1 sequences provided in this disclosure, with 1, 2, or 3 amino acid substitutions. In some aspects, the amino acid substitutions are conservative amino acid substitutions.

2.3. $V_H$ Sequences

In some embodiments, the antibody comprises, consists of, or consists essentially of a $V_H$ sequence of an scFv sequence provided in SEQ ID NOs: 3073 and 3079. In some embodiments, the antibody comprises, consists of, or consists essentially of a $V_H$ sequence provided in SEQ ID NOs.: 2727, 2736, 2739, 2751-2838, 2840, 2846, 2851, 2857, 2859, and 2860.

In some embodiments, the antibody comprises a $V_H$ sequence comprising, consisting of, or consisting essentially of a sequence selected from SEQ ID NOs: 2727, 2736, 2739, 2751-2838, 2840, 2846, 2851, 2857, 2859, and 2860.

In some aspects, the antibody comprises a $V_H$ sequence comprising, consisting of, or consisting essentially of SEQ ID NO:2727. In some aspects, the antibody comprises a $V_H$ sequence comprising, consisting of, or consisting essentially of SEQ ID NO:2736. In some aspects, the antibody comprises a $V_H$ sequence comprising, consisting of, or consisting essentially of SEQ ID NO:2739.

In some aspects, the antibody comprises a $V_H$ sequence comprising, consisting of, or consisting essentially of SEQ ID NO:2751. In some aspects, the antibody comprises a $V_H$ sequence comprising, consisting of, or consisting essentially of SEQ ID NO:2752. In some aspects, the antibody comprises a $V_H$ sequence comprising, consisting of, or consisting essentially of SEQ ID NO:2753. In some aspects, the antibody comprises a $V_H$ sequence comprising, consisting of, or consisting essentially of SEQ ID NO:2754. In some aspects, the antibody comprises a $V_H$ sequence comprising, consisting of, or consisting essentially of SEQ ID NO: 2755. In some aspects, the antibody comprises a $V_H$ sequence comprising, consisting of, or consisting essentially of SEQ ID NO:2756. In some aspects, the antibody comprises a $V_H$ sequence comprising, consisting of, or consisting essentially of SEQ ID NO:2757. In some aspects, the antibody comprises a $V_H$ sequence comprising, consisting of, or consisting essentially of SEQ ID NO:2758. In some aspects, the antibody comprises a $V_H$ sequence comprising, consisting of, or consisting essentially of SEQ ID NO:2759. In some aspects, the antibody comprises a $V_H$ sequence comprising, consisting of, or consisting essentially of SEQ ID NO: 2760. In some aspects, the antibody comprises a $V_H$ sequence comprising, consisting of, or consisting essentially of SEQ ID NO:2761. In some aspects, the antibody comprises a $V_H$ sequence comprising, consisting of, or consisting essentially of SEQ ID NO:2762. In some aspects, the antibody comprises a $V_H$ sequence comprising, consisting of, or consisting essentially of SEQ ID NO:2763. In some aspects, the antibody comprises a $V_H$ sequence comprising, consisting of, or consisting essentially of SEQ ID NO:2764. In some aspects, the antibody comprises a $V_H$ sequence comprising, consisting of, or consisting essentially of SEQ ID NO: 2765. In some aspects, the antibody comprises a $V_H$ sequence comprising, consisting of, or consisting essentially of SEQ ID NO:2766. In some aspects, the antibody comprises a $V_H$ sequence comprising, consisting of, or consisting essentially of SEQ ID NO:2767. In some aspects, the antibody comprises a $V_H$ sequence comprising, consisting of, or consisting essentially of SEQ ID NO:2768. In some aspects, the antibody comprises a $V_H$ sequence comprising, consisting of, or consisting essentially of SEQ ID NO:2769. In some aspects, the antibody comprises a $V_H$ sequence comprising, consisting of, or consisting essentially of SEQ ID NO: 2770. In some aspects, the antibody comprises a $V_H$ sequence comprising, consisting of, or consisting essentially of SEQ ID NO:2771. In some aspects, the antibody comprises a $V_H$ sequence comprising, consisting of, or consisting essentially of SEQ ID NO:2772. In some aspects, the antibody comprises a $V_H$ sequence comprising, consisting of, or consisting essentially of SEQ ID NO:2773. In some aspects, the antibody comprises a $V_H$ sequence comprising, consisting of, or consisting essentially of SEQ ID NO:2774. In some aspects, the antibody comprises a $V_H$ sequence comprising, consisting of, or consisting essentially of SEQ ID NO: 2775. In some aspects, the antibody comprises a $V_H$ sequence comprising, consisting of, or consisting essentially of SEQ ID NO:2776. In some aspects, the antibody comprises a $V_H$ sequence comprising, consisting of, or consisting essentially of SEQ ID NO:2777. In some aspects, the antibody comprises a $V_H$ sequence comprising, consisting of, or consisting essentially of SEQ ID NO:2778. In some aspects, the antibody comprises a $V_H$ sequence comprising, consisting of, or consisting essentially of SEQ ID NO:2779. In some aspects, the antibody comprises a $V_H$ sequence comprising, consisting of, or consisting essentially of SEQ ID NO: 2780. In some aspects, the antibody comprises a $V_H$ sequence comprising, consisting of, or consisting essentially of SEQ ID NO:2781. In some aspects, the antibody comprises a $V_H$ sequence comprising, consisting of, or consisting essentially of SEQ ID NO:2782. In some aspects, the antibody comprises a $V_H$ sequence comprising, consisting of, or consisting essentially of SEQ ID NO:2783. In some aspects, the antibody comprises a $V_H$ sequence comprising, consisting of, or consisting essentially of SEQ ID NO:2784. In some aspects, the antibody comprises a $V_H$ sequence comprising, consisting of, or consisting essentially of SEQ ID NO: 2785. In some aspects, the antibody comprises a $V_H$ sequence comprising, consisting of, or consisting essentially of SEQ ID NO:2786. In some aspects, the antibody comprises a $V_H$ sequence comprising, consisting of, or consisting essentially of SEQ ID NO:2787. In some aspects, the antibody comprises a $V_H$ sequence comprising, consisting of, or consisting essentially of SEQ ID NO:2788. In some aspects, the antibody comprises a $V_H$ sequence comprising, consisting of, or consisting essentially of SEQ ID NO:2789. In some aspects, the antibody comprises a $V_H$ sequence comprising, consisting of, or consisting essentially of SEQ ID NO: 2790. In some aspects, the antibody comprises a $V_H$ sequence comprising, consisting of, or consisting essentially of SEQ ID NO:2791. In some aspects, the antibody comprises a $V_H$ sequence comprising, consisting of, or consisting essentially of SEQ ID NO:2792. In some aspects, the antibody comprises a $V_H$ sequence comprising, consisting of, or consisting essentially of SEQ ID NO:2793. In some aspects, the antibody comprises a $V_H$ sequence comprising, consisting of, or consisting essentially of SEQ ID NO:2794. In some aspects, the antibody comprises a $V_H$ sequence comprising, consisting of, or consisting essentially of SEQ ID NO: 2795. In some aspects, the antibody comprises a $V_H$ sequence comprising, consisting of, or consisting essentially of SEQ ID NO:2796. In some aspects, the antibody comprises a $V_H$ sequence comprising, consisting of, or consisting essentially of SEQ ID NO:2797. In some aspects, the antibody comprises a $V_H$ sequence comprising, consisting of, or consisting essentially of SEQ ID NO:2798. In some aspects, the antibody comprises a $V_H$ sequence comprising, consisting of, or consisting essentially of SEQ ID NO:2799. In some aspects, the antibody comprises a $V_H$ sequence comprising, consisting of, or consisting essentially of SEQ ID NO: 2800. In some aspects, the antibody comprises a $V_H$ sequence comprising, consisting of, or consisting essentially of SEQ ID NO:2801. In some aspects, the antibody comprises a $V_H$ sequence comprising, consisting of, or consisting essentially of SEQ ID NO:2802. In some aspects, the antibody comprises a $V_H$ sequence comprising, consisting of, or consisting essentially of SEQ ID NO:2803. In some aspects, the antibody comprises a $V_H$ sequence comprising, consisting of, or consisting essentially of SEQ ID NO:2804. In some aspects, the antibody comprises a $V_H$ sequence comprising, consisting of, or consisting essentially of SEQ ID NO: 2805. In some aspects, the antibody comprises a $V_H$ sequence comprising, consisting of, or consisting essentially of SEQ ID NO:2806. In some aspects, the antibody comprises a $V_H$ sequence comprising, consisting of, or consisting essentially of SEQ ID NO:2807. In some aspects, the antibody comprises a $V_H$ sequence comprising, consisting of, or consisting essentially of SEQ ID NO:2808. In some aspects, the antibody comprises a $V_H$ sequence comprising, consisting of, or consisting essentially of SEQ ID NO:2809. In some aspects, the antibody comprises a $V_H$ sequence comprising, consisting of, or consisting essentially of SEQ ID NO: 2810. In some aspects, the antibody comprises a $V_H$ sequence comprising, consisting of, or consisting essentially of SEQ ID NO:2811. In some aspects, the antibody comprises a $V_H$ sequence comprising, consisting of, or consisting essentially of SEQ ID NO:2812. In some aspects, the antibody comprises a $V_H$ sequence comprising, consisting of, or consisting essentially of SEQ ID NO:2813. In some aspects, the antibody comprises a $V_H$ sequence comprising, consisting of, or consisting essentially of SEQ ID NO:2814. In some aspects, the antibody comprises a $V_H$ sequence comprising, consisting of, or consisting essentially of SEQ ID NO: 2815. In some aspects, the antibody comprises a $V_H$ sequence comprising, consisting of, or consisting essentially of SEQ ID NO:2816. In some aspects, the antibody comprises a $V_H$ sequence comprising, consisting of, or consisting essentially of SEQ ID NO:2817. In some aspects, the antibody comprises a $V_H$ sequence comprising, consisting of, or consisting essentially of SEQ ID NO:2818. In some aspects, the antibody comprises a $V_H$ sequence comprising, consisting of, or consisting essentially of SEQ ID NO:2819. In some aspects, the antibody comprises a $V_H$ sequence comprising, consisting of, or consisting essentially of SEQ ID NO: 2820. In some aspects, the antibody comprises a $V_H$ sequence comprising, consisting of, or consisting essentially of SEQ ID NO:2821. In some aspects, the antibody comprises a $V_H$ sequence comprising, consisting of, or consisting essentially of SEQ ID NO:2822. In some aspects, the antibody comprises a $V_H$ sequence comprising, consisting of, or consisting essentially of SEQ ID NO:2823. In some aspects, the antibody comprises a $V_H$ sequence comprising, consisting of, or consisting essentially of SEQ ID NO:2824.

In some aspects, the antibody comprises a $V_H$ sequence comprising, consisting of, or consisting essentially of SEQ ID NO:2825. In some aspects, the antibody comprises a $V_H$ sequence comprising, consisting of, or consisting essentially of SEQ ID NO:2826. In some aspects, the antibody comprises a $V_H$ sequence comprising, consisting of, or consisting essentially of SEQ ID NO:2827. In some aspects, the antibody comprises a $V_H$ sequence comprising, consisting of, or consisting essentially of SEQ ID NO:2828. In some aspects, the antibody comprises a $V_H$ sequence comprising, consisting of, or consisting essentially of SEQ ID NO: 2829. In some aspects, the antibody comprises a $V_H$ sequence comprising, consisting of, or consisting essentially of SEQ ID NO:2830. In some aspects, the antibody comprises a $V_H$ sequence comprising, consisting of, or consisting essentially of SEQ ID NO:2831. In some aspects, the antibody comprises a $V_H$ sequence comprising, consisting of, or consisting essentially of SEQ ID NO:2832. In some aspects, the antibody comprises a $V_H$ sequence comprising, consisting of, or consisting essentially of SEQ ID NO:2833. In some aspects, the antibody comprises a $V_H$ sequence comprising, consisting of, or consisting essentially of SEQ ID NO: 2834. In some aspects, the antibody comprises a $V_H$ sequence comprising, consisting of, or consisting essentially of SEQ ID NO:2835. In some aspects, the antibody comprises a $V_H$ sequence comprising, consisting of, or consisting essentially of SEQ ID NO:2836. In some aspects, the antibody comprises a $V_H$ sequence comprising, consisting of, or consisting essentially of SEQ ID NO:2837. In some aspects, the antibody comprises a $V_H$ sequence comprising, consisting of, or consisting essentially of SEQ ID NO:2838.

In some aspects, the antibody comprises a $V_H$ sequence comprising, consisting of, or consisting essentially of SEQ ID NO:2840. In some aspects, the antibody comprises a $V_H$ sequence comprising, consisting of, or consisting essentially of SEQ ID NO:2846. In some aspects, the antibody comprises a $V_H$ sequence comprising, consisting of, or consisting essentially of SEQ ID NO:2851. In some aspects, the antibody comprises a $V_H$ sequence comprising, consisting of, or consisting essentially of SEQ ID NO:2857. In some aspects, the antibody comprises a $V_H$ sequence comprising, consisting of, or consisting essentially of SEQ ID NO: 2859. In some aspects, the antibody comprises a $V_H$ sequence comprising, consisting of, or consisting essentially of SEQ ID NO:2860.

2.3.1. Variants of $V_H$ Sequences

In some embodiments, the $V_H$ sequences provided herein comprise, consist of, or consist essentially of a variant of an illustrative $V_H$ sequence provided in this disclosure.

In some aspects, the $V_H$ sequence comprises, consists of, or consists essentially of a variant of an illustrative $V_H$ sequence provided in this disclosure. In some aspects, the $V_H$ sequence comprises, consists of, or consists essentially of a sequence having at least 85%, 90%, 95%, 96%, 97%, 98%, 99%, or 99.5% identity with any of the illustrative $V_H$ sequences provided in this disclosure.

In some embodiments, the $V_H$ sequence comprises, consists of, or consists essentially of any of the illustrative $V_H$ sequences provided in this disclosure having 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

2.4. $V_L$ Sequences Comprising Illustrative CDRs

In some embodiments, the antibody comprises a $V_L$ sequence comprising one or more CDR-L sequences comprising, consisting of, or consisting essentially of one or more illustrative CDR-L sequences provided in this disclosure, and variants thereof.

2.4.1. $V_L$ Sequences Comprising Illustrative Kabat CDRs

In some embodiments, the antibody comprises a $V_L$ sequence comprising one or more Kabat CDR-L sequences comprising, consisting of, or consisting essentially of one or more illustrative Kabat CDR-L sequences provided in this disclosure, and variants thereof.

2.4.1.1. Kabat CDR-L1+Kabat CDR-L2+Kabat CDR-L3

In some embodiments, the antibody comprises a $V_L$ sequence comprising a Kabat CDR-L1 sequence comprising, consisting of, or consisting essentially of a sequence selected from SEQ ID NOs: 2066, 2072, 2077, 2083, 2085, 2086, and 2176, a Kabat CDR-L2 sequence comprising, consisting of, or consisting essentially of a sequence selected from SEQ ID NOs: 2290, 2296, 2301, 2307, 2309, 2310, and 2400, and a Kabat CDR-L3 sequence comprising, consisting of, or consisting essentially of a sequence selected from SEQ ID NOs: 2514, 2520, 2525, 2531, 2533, 2534, and 2624. In some aspects, the Kabat CDR-L1 sequence, Kabat CDR-L2 sequence, and Kabat CDR-L3 sequence are all from a single illustrative $V_L$ sequence provided in this disclosure. For example, in some aspects, the Kabat CDR-L1, Kabat CDR-L2, and Kabat CDR-L3 are all from a single illustrative $V_L$ sequence selected from SEQ ID NOs: 2951, 2957, 2962, 2968, 2970, 2971, and 3061.

2.4.1.2. Variants of $V_L$ Sequences Comprising Illustrative Kabat CDRs

In some embodiments, the $V_L$ sequences provided herein comprise a variant of an illustrative Kabat CDR-L3, CDR-L2, and/or CDR-L1 sequence provided in this disclosure.

In some aspects, the Kabat CDR-L3 sequence comprises, consists of, or consists essentially of a variant of an illustrative Kabat CDR-L3 sequence provided in this disclosure. In some aspects, the Kabat CDR-L3 sequence comprises, consists of, or consists essentially of a sequence having at least 70%, 75%, 80%, 85%, 90%, 95%, 96%, 97%, 98%, or 99% identity with any of the illustrative Kabat CDR-L3 sequences provided in this disclosure. In some aspects, the Kabat CDR-L3 sequence comprises, consists of, or consists essentially of any of the illustrative Kabat CDR-L3 sequences provided in this disclosure, with 1, 2, or 3 amino acid substitutions. In some aspects, the amino acid substitutions are conservative amino acid substitutions.

In some aspects, the Kabat CDR-L2 sequence comprises, consists of, or consists essentially of a variant of an illustrative Kabat CDR-L2 sequence provided in this disclosure. In some aspects, the Kabat CDR-L2 sequence comprises, consists of, or consists essentially of a sequence having at least 70%, 75%, 80%, 85%, 90%, 95%, 96%, 97%, 98%, or 99% identity with any of the illustrative Kabat CDR-L2 sequences provided in this disclosure. In some aspects, the Kabat CDR-L2 sequence comprises, consists of, or consists essentially of any of the illustrative Kabat CDR-L2 sequences provided in this disclosure, with 1, 2, or 3 amino acid substitutions. In some aspects, the amino acid substitutions are conservative amino acid substitutions.

In some aspects, the Kabat CDR-L1 sequence comprises, consists of, or consists essentially of a variant of an illustrative Kabat CDR-L1 sequence provided in this disclosure. In some aspects, the Kabat CDR-L1 sequence comprises, consists of, or consists essentially of a sequence having at least 70%, 75%, 80%, 85%, 90%, 95%, 96%, 97%, 98%, or 99% identity with any of the illustrative Kabat CDR-L1 sequences provided in this disclosure. In some aspects, the Kabat CDR-L1 sequence comprises, consists of, or consists essentially of any of the illustrative Kabat CDR-L1 sequences provided in this disclosure, with 1, 2, or 3 amino acid substitutions. In some aspects, the amino acid substitutions are conservative amino acid substitutions.

2.4.2. $V_L$ Sequences Comprising Illustrative Chothia CDRs

In some embodiments, the antibody comprises a $V_L$ sequence comprising one or more Chothia CDR-L sequences comprising, consisting of, or consisting essentially of one or more illustrative Chothia CDR-L sequences provided in this disclosure, and variants thereof.

2.4.2.1. Chothia CDR-L1+Chothia CDR-L2+Chothia CDR-L3

In some embodiments, the antibody comprises a $V_L$ sequence comprising a Chothia CDR-L1 sequence comprising, consisting of, or consisting essentially of a sequence selected from SEQ ID NOs: 1954, 1960, 1965, 1971, 1973, 1974 and 2064, a Chothia CDR-L2 sequence comprising, consisting of, or consisting essentially of a sequence selected from SEQ ID NOs: 2178, 2184, 2189, 2195, 2197, 2198, and 2288, and a Chothia CDR-L3 sequence comprising, consisting of, or consisting essentially of a sequence selected from SEQ ID NOs: 2402, 2408, 2413, 2419, 2421, 2422, and 2512. In some aspects, the Chothia CDR-L1 sequence, Chothia CDR-L2 sequence, and Chothia CDR-L3 sequence are all from a single illustrative $V_L$ sequence provided in this disclosure. For example, in some aspects, the Chothia CDR-L1, Chothia CDR-L2, and Chothia CDR-L3 are all from a single illustrative $V_L$ sequence selected from SEQ ID NOs: 2951, 2957, 2962, 2968, 2970, 2971, and 3061.

2.4.2.2. Variants of $V_L$ Sequences Comprising Illustrative Chothia CDRs

In some embodiments, the $V_H$ sequences provided herein comprise a variant of an illustrative Chothia CDR-L3, CDR-L2, and/or CDR-L1 sequence provided in this disclosure.

In some aspects, the Chothia CDR-L3 sequence comprises, consists of, or consists essentially of a variant of an illustrative Chothia CDR-L3 sequence provided in this disclosure. In some aspects, the Chothia CDR-L3 sequence comprises, consists of, or consists essentially of a sequence having at least 70%, 75%, 80%, 85%, 90%, 95%, 96%, 97%, 98%, or 99% identity with any of the illustrative Chothia CDR-L3 sequences provided in this disclosure. In some aspects, the Chothia CDR-L3 sequence comprises, consists of, or consists essentially of any of the illustrative Chothia CDR-L3 sequences provided in this disclosure, with 1, 2, or 3 amino acid substitutions. In some aspects, the amino acid substitutions are conservative amino acid substitutions.

In some aspects, the Chothia CDR-L2 sequence comprises, consists of, or consists essentially of a variant of an illustrative Chothia CDR-L2 sequence provided in this disclosure. In some aspects, the Chothia CDR-L2 sequence comprises, consists of, or consists essentially of a sequence having at least 70%, 75%, 80%, 85%, 90%, 95%, 96%, 97%, 98%, or 99% identity with any of the illustrative Chothia CDR-L2 sequences provided in this disclosure. In some aspects, the Chothia CDR-L2 sequence comprises, consists of, or consists essentially of any of the illustrative Chothia CDR-L2 sequences provided in this disclosure, with 1, 2, or 3 amino acid substitutions. In some aspects, the amino acid substitutions are conservative amino acid substitutions.

In some aspects, the Chothia CDR-L1 sequence comprises, consists of, or consists essentially of a variant of an illustrative Chothia CDR-L1 sequence provided in this disclosure. In some aspects, the Chothia CDR-L1 sequence comprises, consists of, or consists essentially of a sequence having at least 70%, 75%, 80%, 85%, 90%, 95%, 96%, 97%, 98%, or 99% identity with any of the illustrative Chothia CDR-L1 sequences provided in this disclosure.

In some aspects, the Chothia CDR-L1 sequence comprises, consists of, or consists essentially of any of the illustrative Chothia CDR-L1 sequences provided in this disclosure, with 1, 2, or 3 amino acid substitutions. In some aspects, the amino acid substitutions are conservative amino acid substitutions.

2.5. $V_L$ Sequences

In some embodiments, the antibody comprises, consists of, or consists essentially of a $V_L$ sequence of an scFv sequence provided in SEQ ID NOs.: 3073 and 3079. In some embodiments, the antibody comprises, consists of, or consists essentially of a $V_L$ sequence provided in SEQ ID NOs.: 2951, 2957, 2962, 2968, 2970, 2971, and 3061.

In some embodiments, the antibody comprises a $V_L$ sequence comprising, consisting of, or consisting essentially of a sequence selected from SEQ ID NOs: 2951, 2957, 2962, 2968, 2970, 2971, and 3061.

In some aspects, the antibody comprises a $V_L$ sequence comprising, consisting of, or consisting essentially of SEQ ID NO:2951. In some aspects, the antibody comprises a $V_L$ sequence comprising, consisting of, or consisting essentially of SEQ ID NO:2957. In some aspects, the antibody comprises a $V_L$ sequence comprising, consisting of, or consisting essentially of SEQ ID NO:2962. In some aspects, the antibody comprises a $V_L$ sequence comprising, consisting of, or consisting essentially of SEQ ID NO:2968. In some aspects, the antibody comprises a $V_L$ sequence comprising, consisting of, or consisting essentially of SEQ ID NO: 2970. In some aspects, the antibody comprises a $V_L$ sequence comprising, consisting of, or consisting essentially of SEQ ID NO:2971. In some aspects, the antibody comprises a $V_L$ sequence comprising, consisting of, or consisting essentially of SEQ ID NO:3061.

2.5.1. Variants of $V_L$ Sequences

In some embodiments, the $V_L$ sequences provided herein comprise, consist of, or consist essentially of a variant of an illustrative $V_L$ sequence provided in this disclosure.

In some aspects, the $V_L$ sequence comprises, consists of, or consists essentially of a variant of an illustrative $V_L$ sequence provided in this disclosure. In some aspects, the $V_L$ sequence comprises, consists of, or consists essentially of a sequence having at least 85%, 90%, 95%, 96%, 97%, 98%, 99%, or 99.5% identity with any of the illustrative $V_L$ sequences provided in this disclosure.

In some embodiments, the $V_L$ sequence comprises, consists of, or consists essentially of any of the illustrative $V_L$ sequences provided in this disclosure having 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

2.6. Pairs 2.6.1. $V_H$-$V_L$ Pairs

In some embodiments, the antibody comprises a $V_H$ sequence and a $V_L$ sequence.

In some aspects, the $V_H$ sequence is a $V_H$ sequence comprising, consisting of, or consisting essentially of SEQ ID NOs: 2727, 2736, 2739, 2751-2838, 2840, 2846, 2851, 2857, 2859, and 2860, and the $V_L$ sequence is a $V_L$ sequence comprising, consisting of, or consisting essentially of SEQ ID NOs: 2951, 2957, 2962, 2968, 2970, 2971, and 3061.

In some embodiments, the antibody comprises a $V_H$/$V_L$ pair together comprising, consisting of, or consisting essentially of the sequences of any pair selected from the group consisting of SEQ ID NOs: 2727/3061, 2736/3061, 2739/3061, 2751/3061, 2752/3061, 2753/3061, 2754/3061, 2755/3061, 2756/3061, 2757/3061, 2758/3061, 2759/3061, 2760/3061, 2761/3061, 2762/3061, 2763/3061, 2764/3061, 2765/3061, 2766/3061, 2767/3061, 2768/3061, 2769/3061, 2770/3061, 2771/3061, 2772/3061, 2773/3061, 2774/3061, 2775/3061, 2776/3061, 2777/3061, 2778/3061, 2779/3061, 2780/3061, 2781/3061, 2782/3061, 2783/3061, 2784/3061, 2785/3061, 2786/3061, 2787/3061, 2788/3061, 2789/3061, 2790/3061, 2791/3061, 2792/3061, 2793/3061, 2794/3061, 2795/3061, 2796/3061, 2797/3061, 2798/3061, 2799/3061, 2800/3061, 2801/3061, 2802/3061, 2803/3061, 2804/3061, 2805/3061, 2806/3061, 2807/3061, 2808/3061, 2809/3061, 2810/3061, 2811/3061, 2812/3061, 2813/3061, 2814/3061, 2815/3061, 2816/3061, 2817/3061, 2818/3061, 2819/3061, 2820/3061, 2821/3061, 2822/3061, 2823/3061, 2824/3061, 2825/3061, 2826/3061, 2827/3061, 2828/3061, 2829/3061, 2830/3061, 2831/3061, 2832/3061, 2833/3061, 2834/3061, 2835/3061, 2836/3061, 2837/3061, 2838/3061, 2840/2951, 2846/2957, 2851/2962, 2857/2968, 2859/2970, and 2860/2971.

In some aspects, the antibody comprises a $V_H$/$V_L$ pair together comprising, consisting of, or consisting essentially of the sequences of any pair as shown in the Table 5 below:

TABLE 5

$V_H$/$V_L$ pairs.

| Antibody | $V_H$ Sequence (SEQ ID NO) | VL Sequence (SEQ ID NO) |
|---|---|---|
| SRP2799-A05 | 2727 | 3061 |
| SRP2799-B03 | 2736 | 3061 |
| SRP2799-B06 | 2739 | 3061 |
| SRP2900-A01 | 2751 | 3061 |
| SRP2900-A02 | 2752 | 3061 |
| SRP2900-A03 | 2753 | 3061 |
| SRP2900-A04 | 2754 | 3061 |
| SRP2900-A05 | 2755 | 3061 |
| SRP2900-A06 | 2756 | 3061 |
| SRP2900-A07 | 2757 | 3061 |
| SRP2900-A08 | 2758 | 3061 |
| SRP2900-A09 | 2759 | 3061 |
| SRP2900-A10 | 2760 | 3061 |
| SRP2900-A11 | 2761 | 3061 |
| SRP2900-B01 | 2762 | 3061 |
| SRP2900-B02 | 2763 | 3061 |
| SRP2900-B03 | 2764 | 3061 |
| SRP2900-B04 | 2765 | 3061 |
| SRP2900-B05 | 2766 | 3061 |
| SRP2900-B06 | 2767 | 3061 |
| SRP2900-B07 | 2768 | 3061 |
| SRP2900-B08 | 2769 | 3061 |
| SRP2900-B09 | 2770 | 3061 |
| SRP2900-B10 | 2771 | 3061 |
| SRP2900-B11 | 2772 | 3061 |
| SRP2900-C01 | 2773 | 3061 |
| SRP2900-C02 | 2774 | 3061 |
| SRP2900-C03 | 2775 | 3061 |
| SRP2900-C04 | 2776 | 3061 |
| SRP2900-C05 | 2777 | 3061 |
| SRP2900-C06 | 2778 | 3061 |
| SRP2900-C07 | 2779 | 3061 |
| SRP2900-C08 | 2780 | 3061 |
| SRP2900-C09 | 2781 | 3061 |
| SRP2900-C10 | 2782 | 3061 |
| SRP2900-C11 | 2783 | 3061 |
| SRP2900-D01 | 2784 | 3061 |
| SRP2900-D02 | 2785 | 3061 |
| SRP2900-D03 | 2786 | 3061 |
| SRP2900-D04 | 2787 | 3061 |
| SRP2900-D05 | 2788 | 3061 |
| SRP2900-D06 | 2789 | 3061 |
| SRP2900-D07 | 2790 | 3061 |
| SRP2900-D08 | 2791 | 3061 |
| SRP2900-D09 | 2792 | 3061 |
| SRP2900-D10 | 2793 | 3061 |
| SRP2900-D11 | 2794 | 3061 |
| SRP2900-E01 | 2795 | 3061 |
| SRP2900-E02 | 2796 | 3061 |
| SRP2900-E03 | 2797 | 3061 |
| SRP2900-E04 | 2798 | 3061 |
| SRP2900-E05 | 2799 | 3061 |
| SRP2900-E06 | 2800 | 3061 |
| SRP2900-E07 | 2801 | 3061 |
| SRP2900-E08 | 2802 | 3061 |
| SRP2900-E09 | 2803 | 3061 |
| SRP2900-E10 | 2804 | 3061 |
| SRP2900-E11 | 2805 | 3061 |
| SRP2900-F01 | 2806 | 3061 |
| SRP2900-F02 | 2807 | 3061 |
| SRP2900-F03 | 2808 | 3061 |
| SRP2900-F04 | 2809 | 3061 |
| SRP2900-F05 | 2810 | 3061 |
| SRP2900-F06 | 2811 | 3061 |
| SRP2900-F07 | 2812 | 3061 |
| SRP2900-F08 | 2813 | 3061 |
| SRP2900-F09 | 2814 | 3061 |
| SRP2900-F10 | 2815 | 3061 |
| SRP2900-F11 | 2816 | 3061 |
| SRP2900-G01 | 2817 | 3061 |
| SRP2900-G02 | 2818 | 3061 |
| SRP2900-G03 | 2819 | 3061 |
| SRP2900-G04 | 2820 | 3061 |
| SRP2900-G05 | 2821 | 3061 |
| SRP2900-G06 | 2822 | 3061 |

TABLE 5-continued

| $V_H/V_L$ pairs. | | |
|---|---|---|
| Antibody | $V_H$ Sequence (SEQ ID NO) | VL Sequence (SEQ ID NO) |
| SRP2900-G07 | 2823 | 3061 |
| SRP2900-G08 | 2824 | 3061 |
| SRP2900-G09 | 2825 | 3061 |
| SRP2900-G10 | 2826 | 3061 |
| SRP2900-G11 | 2827 | 3061 |
| SRP2900-H01 | 2828 | 3061 |
| SRP2900-H02 | 2829 | 3061 |
| SRP2900-H03 | 2830 | 3061 |
| SRP2900-H04 | 2831 | 3061 |
| SRP2900-H05 | 2832 | 3061 |
| SRP2900-H06 | 2833 | 3061 |
| SRP2900-H07 | 2834 | 3061 |
| SRP2900-H08 | 2835 | 3061 |
| SRP2900-H09 | 2836 | 3061 |
| SRP2900-H10 | 2837 | 3061 |
| SRP2900-H11 | 2838 | 3061 |
| SRP2842-B01 | 2840 | 2951 |
| SRP2842-G04 | 2846 | 2957 |
| SRP2901-B05 | 2851 | 2962 |
| SRP2901-D03 | 2857 | 2968 |
| SRP2901-E03 | 2859 | 2970 |
| SRP2901-F01 | 2860 | 2971 |

2.6.1.1. Variants of $V_H$-$V_L$ Pairs

In some embodiments, the $V_H$-$V_L$ pairs provided herein comprise a variant of an illustrative $V_H$ and/or $V_L$ sequence provided in this disclosure.

In some aspects, the $V_H$ sequence comprises, consists of, or consists essentially of a variant of an illustrative $V_H$ sequence provided in this disclosure. In some aspects, the $V_H$ sequence comprises, consists of, or consists essentially of a sequence having at least 85%, 90%, 95%, 96%, 97%, 98%, 99%, or 99.5% identity with any of the illustrative $V_H$ sequences provided in this disclosure.

In some embodiments, the $V_H$ sequence comprises, consists of, or consists essentially of any of the illustrative $V_H$ sequences provided in this disclosure having 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

In some aspects, the $V_L$ sequence comprises, consists of, or consists essentially of a variant of an illustrative $V_L$ sequence provided in this disclosure. In some aspects, the $V_L$ sequence comprises, consists of, or consists essentially of a sequence having at least 85%, 90%, 95%, 96%, 97%, 98%, 99%, or 99.5% identity with any of the illustrative $V_L$ sequences provided in this disclosure.

In some embodiments, the $V_L$ sequence comprises, consists of, or consists essentially of any of the illustrative $V_L$ sequences provided in this disclosure having 20 or fewer, 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer, or 1 or fewer amino acid substitutions. In some aspects, the amino acid substitutions are conservative amino acid substitutions.

2.7. Antibodies Comprising all Six CDRs

In some embodiments, the antibody comprises a CDR-H1 sequence, a CDR-H2 sequence, a CDR-H3 sequence, a CDR-L1 sequence, and a CDR-L3 sequence. In some aspects, the CDR sequences are part of a $V_H$ (for CDR-H) or $V_L$ (for CDR-L).

In some aspects, the CDR-H1 sequence is a Chothia CDR-H1 sequence comprising, consisting of, or consisting essentially of SEQ ID NOs: 105, 114, 117, 129-216, 218, 224, 229, 235, 237, and 238; the CDR-H2 sequence is a Chothia CDR-H2 sequence comprising, consisting of, or consisting essentially of SEQ ID NOs: 755, 764, 767, 779-866, 868, 874, 879, 885, 887, and 888; the CDR-H3 sequence is a Chothia CDR-H3 sequence comprising, consisting of, or consisting essentially of SEQ ID NOs: 1405, 1414, 1417, 1429-1516, 1518, 1524, 1529, 1535, 1537, and 1538; the CDR-L1 sequence is a Chothia CDR-L1 sequence comprising, consisting of, or consisting essentially of SEQ ID NOs: 1954, 1960, 1965, 1971, 1973, 1974 and 2064; the CDR-L2 sequence is a Chothia CDR-L2 sequence comprising, consisting of, or consisting essentially of SEQ ID NOs: 2178, 2184, 2189, 2195, 2197, 2198, and 2288; and the CDR-L3 sequence is a Chothia CDR-L3 sequence comprising, consisting of, or consisting essentially of SEQ ID NOs: 2402, 2408, 2413, 2419, 2421, 2422, and 2512.

In some aspects, the CDR-H1 sequence is a Kabat CDR-H1 sequence comprising, consisting of, or consisting essentially of SEQ ID NOs: 430, 439, 442, 454-541, 543, 549, 554, 560, 562, and 563; the CDR-H2 sequence is a Kabat CDR-H2 sequence comprising, consisting of, or consisting essentially of SEQ ID NOs: 1080, 1089, 1092, 1104-1191, 1193, 1199, 1204, 1200, 1212, and 1213; the CDR-H3 sequence is a Kabat CDR-H3 sequence comprising, consisting of, or consisting essentially of SEQ ID NOs: 1730, 1739, 1742, 1754-1841, 1843, 1849, 1854, 1860, 1862, and 1863; the CDR-L1 sequence is a Kabat CDR-L1 sequence comprising, consisting of, or consisting essentially of SEQ ID NOs: 2066, 2072, 2077, 2083, 2085, 2086, and 2176; the CDR-L2 sequence is a Kabat CDR-L2 sequence comprising, consisting of, or consisting essentially of SEQ ID NOs: 2290, 2296, 2301, 2307, 2309, 2310, and 2400; and the CDR-L3 sequence is a Kabat CDR-L3 sequence comprising, consisting of, or consisting essentially of SEQ ID NOs: 2514, 2520, 2525, 2531, 2533, 2534, and 2624.

In some aspects, the antibody comprises three heavy chain CDRs from a $V_H$ sequence selected from SEQ ID NOs: 2727, 2736, 2739, 2751-2838, 2840, 2846, 2851, 2857, 2859, and 2860, or variants thereof, and three light chain CDRs from a $V_L$ sequence selected from SEQ ID NOs: 2951, 2957, 2962, 2968, 2970, 2971, and 3061, or variants thereof. The CDRs can be according to any CDR scheme known to the person of skill. In certain embodiments, the CDRs are Kabat CDRs. In certain embodiments, the CDRs are Chothia CDRs.

In some embodiments, the antibody comprises three heavy chain CDRs, or variants thereof, and three light chain CDRs, or variants thereof, from a $V_H$/$V_L$ pair selected from the group consisting of the group consisting of SEQ ID NOs: 2727/3061, 2736/3061, 2739/3061, 2751/3061, 2752/3061, 2753/3061, 2754/3061, 2755/3061, 2756/3061, 2757/3061, 2758/3061, 2759/3061, 2760/3061, 2761/3061, 2762/3061, 2763/3061, 2764/3061, 2765/3061, 2766/3061, 2767/3061, 2768/3061, 2769/3061, 2770/3061, 2771/3061, 2772/3061, 2773/3061, 2774/3061, 2775/3061, 2776/3061, 2777/3061, 2778/3061, 2779/3061, 2780/3061, 2781/3061, 2782/3061, 2783/3061, 2784/3061, 2785/3061, 2786/3061, 2787/3061, 2788/3061, 2789/3061, 2790/3061, 2791/3061, 2792/3061, 2793/3061, 2794/3061, 2795/3061, 2796/3061, 2797/3061, 2798/3061, 2799/3061, 2800/3061, 2801/3061, 2802/3061, 2803/3061, 2804/3061, 2805/3061, 2806/3061, 2807/3061, 2808/3061, 2809/3061, 2810/3061, 2811/3061, 2812/3061, 2813/3061, 2814/3061, 2815/3061, 2816/3061, 2817/3061, 2818/3061, 2819/3061, 2820/3061, 2821/3061, 2822/3061, 2823/3061, 2824/3061, 2825/3061, 2826/3061, 2827/3061, 2828/3061, 2829/3061, 2830/3061, 2831/3061, 2832/3061, 2833/3061, 2834/3061, 2835/3061, 2836/3061, 2837/3061, 2838/3061, 2840/2951, 2846/2957, 2851/2962, 2857/2968, 2859/2970, and 2860/2971.

In some embodiments, the antibody comprises three heavy chain CDRs, or variants thereof, and three light chain CDRs, or variants thereof, from a $V_H/V_L$ pair selected from the group consisting of the group consisting of SEQ ID NOs: 2727/3061, 2736/3061, and 2739/3061. In some embodiments, the antibody comprises three heavy chain CDRs, or variants thereof, and three light chain CDRs, or variants thereof, from the $V_H/V_L$ pair of SEQ ID NOs: 2752/3061.

The CDRs can be according to any CDR scheme known to the person of skill. In certain embodiments, the CDRs are Kabat CDRs. In certain embodiments, the CDRs are Chothia CDRs. In certain embodiments, the antibody further comprises the framework regions of the $V_H/V_L$ pair.

2.7.1. Variants of Antibodies Comprising all Six CDRs

In some embodiments, the CDR-H1, CDR-H2, CDR-H3, CDR-L1, CDR-L2, and CDR-L3 provided herein comprise a variant of an illustrative CDR-H1, CDR-H2, CDR-H3, CDR-L1, CDR-L2, and/or CDR-L3 sequence provided in this disclosure.

In some aspects, the CDR-H1 sequence comprises, consists of, or consists essentially of a variant of an illustrative Chothia or Kabat CDR-H1 sequence provided in this disclosure. In some aspects, the CDR-H1 sequence comprises, consists of, or consists essentially of a sequence having at least 70%, 75%, 80%, 85%, 90%, 95%, 96%, 97%, 98%, or 99% identity with any of the illustrative Chothia or Kabat CDR-H1 sequences provided in this disclosure. In some aspects, the CDR-H1 sequence comprises, consists of, or consists essentially of any of the illustrative Chothia or Kabat CDR-H1 sequences provided in this disclosure, with 1, 2, or 3 amino acid substitutions. In some aspects, the amino acid substitutions are conservative amino acid substitutions.

In some aspects, the CDR-H2 sequence comprises, consists of, or consists essentially of a variant of an illustrative Chothia or Kabat CDR-H2 sequence provided in this disclosure. In some aspects, the CDR-H2 sequence comprises, consists of, or consists essentially of a sequence having at least 70%, 75%, 80%, 85%, 90%, 95%, 96%, 97%, 98%, or 99% identity with any of the illustrative Chothia or Kabat CDR-H2 sequences provided in this disclosure. In some aspects, the CDR-H2 sequence comprises, consists of, or consists essentially of any of the illustrative Chothia or Kabat CDR-H2 sequences provided in this disclosure, with 1, 2, or 3 amino acid substitutions. In some aspects, the amino acid substitutions are conservative amino acid substitutions.

In some aspects, the CDR-H3 sequence comprises, consists of, or consists essentially of a variant of an illustrative CDR-H3 sequence provided in this disclosure. In some aspects, the CDR-H3 sequence comprises, consists of, or consists essentially of a sequence having at least 70%, 75%, 80%, 85%, 90%, 95%, 96%, 97%, 98%, or 99% identity with any of the illustrative CDR-H3 sequences provided in this disclosure. In some aspects, the CDR-H3 sequence comprises, consists of, or consists essentially of any of the illustrative CDR-H3 sequences provided in this disclosure, with 1, 2, or 3 amino acid substitutions. In some aspects, the amino acid substitutions are conservative amino acid substitutions.

In some aspects, the CDR-L1 sequence comprises, consists of, or consists essentially of a variant of an illustrative CDR-L1 sequence provided in this disclosure. In some aspects, the CDR-L1 sequence comprises, consists of, or consists essentially of a sequence having at least 70%, 75%, 80%, 85%, 90%, 95%, 96%, 97%, 98%, or 99% identity with any of the illustrative CDR-L1 sequences provided in this disclosure. In some aspects, the CDR-L1 sequence comprises, consists of, or consists essentially of any of the illustrative CDR-L1 sequences provided in this disclosure, with 1, 2, or 3 amino acid substitutions. In some aspects, the amino acid substitutions are conservative amino acid substitutions.

In some aspects, the CDR-L2 sequence comprises, consists of, or consists essentially of a variant of an illustrative CDR-L2 sequence provided in this disclosure. In some aspects, the CDR-L2 sequence comprises, consists of, or consists essentially of a sequence having at least 70%, 75%, 80%, 85%, 90%, 95%, 96%, 97%, 98%, or 99% identity with any of the illustrative CDR-L2 sequences provided in this disclosure. In some aspects, the CDR-L2 sequence comprises, consists of, or consists essentially of any of the illustrative CDR-L2 sequences provided in this disclosure, with 1, 2, or 3 amino acid substitutions. In some aspects, the amino acid substitutions are conservative amino acid substitutions.

In some aspects, the CDR-L3 sequence comprises, consists of, or consists essentially of a variant of an illustrative CDR-L3 sequence provided in this disclosure. In some aspects, the CDR-L3 sequence comprises, consists of, or consists essentially of a sequence having at least 70%, 75%, 80%, 85%, 90%, 95%, 96%, 97%, 98%, or 99% identity with any of the illustrative CDR-L3 sequences provided in this disclosure. In some aspects, the CDR-L3 sequence comprises, consists of, or consists essentially of any of the illustrative CDR-L3 sequences provided in this disclosure, with 1, 2, or 3 amino acid substitutions. In some aspects, the amino acid substitutions are conservative amino acid substitutions.

3. Conjugates

Provided herein are conjugates of antibodies to TF. The conjugates comprise an antibody to TF covalently linked directly or indirectly, via a linker, to a payload. In some embodiments, the conjugate comprises an antibody that specifically binds to TF linked site-specifically to at least one payload moiety, and the antibody comprises one or more non-natural amino acids. In certain embodiments, the antibody is linked to one payload. In further embodiments, the antibody is linked to more than one payload. In certain embodiments, the antibody is linked to two, three, four, five, six, seven, eight, nine, ten, or more payloads.

The payload can be any payload deemed useful by the practitioner of skill. In certain embodiments, the payload is a therapeutic moiety. In certain embodiments, the payload is a diagnostic moiety, e.g., a label. Useful payloads are described in the sections and examples below.

The linker can be any linker capable of forming at least one bond to the antibody and at least one bond to a payload. Useful linkers are described the sections and examples below.

In the conjugates provided herein, the antibody can be any antibody with binding specificity for TF. The TF can be from any species. In certain embodiments, the TF is a vertebrate TF. In certain embodiments, the TF is a mammalian TF. In certain embodiments, the TF is human TF. In certain embodiments, the TF is mouse TF. In certain embodiments, the TF is cynomolgus TF.

In certain embodiments, the antibody to TF competes with an antibody described herein for binding. In certain embodiments, the antibody to TF binds to the same epitope as an antibody described herein.

The antibody is typically a protein comprising multiple polypeptide chains. In certain embodiments, the antibody is a heterotetramer comprising two identical light (L) chains and two identical heavy (H) chains. Each light chain can be linked to a heavy chain by one covalent disulfide bond. Each heavy chain can be linked to the other heavy chain by one or more covalent disulfide bonds. Each heavy chain and each light chain can also have one or more intrachain disulfide bonds. As is known to those of skill in the art, each heavy chain typically comprises a variable domain ($V_H$) followed by a number of constant domains. Each light chain typically comprises a variable domain at one end ($V_L$) and a constant domain. As is known to those of skill in the art, antibodies typically have selective affinity for their target molecules, i.e., antigens.

The antibodies provided herein can have any antibody form known to those of skill in the art. They can be full-length, or fragments. Exemplary full-length antibodies include IgA, IgA1, IgA2, IgD, IgE, IgG, IgG1, IgG2, IgG3, IgG4, IgM, etc. Exemplary fragments include Fv, Fab, Fc, scFv, scFv-Fc, and etc.

In certain embodiments, the antibody of the conjugate comprises one, two, three, four, five, or six of the CDR sequences described herein. In certain embodiments, the antibody of the conjugate comprises a heavy chain variable domain ($V_H$) described herein. In certain embodiments, the antibody of the conjugate comprises a light chain variable domain ($V_L$) described herein. In certain embodiments, the antibody of the conjugate comprises a heavy chain variable domain ($V_H$) described herein and a light chain variable domain ($V_L$) described herein. In certain embodiments, the antibody of the conjugate comprises a paired heavy chain variable domain and a light chain variable domain described herein ($V_H$-$V_L$ pair). In certain embodiments, the antibody of the conjugate comprises a heavy chain (HC) described herein. In certain embodiments, the antibody of the conjugate comprises a light chain (LC) described herein. In certain embodiments, the antibody of the conjugate comprises a heavy chain (HC) described herein and a light chain (LC) described herein. In certain embodiments, the antibody of the conjugate comprises a paired heavy chain and a light chain described herein (HC-LC pair). In certain embodiments, the antibody of the conjugate comprises a heavy chain (HC) described herein. In certain embodiments, the antibody of the conjugate comprises a light chain (LC) described herein. In certain embodiments, the antibody of the conjugate comprises a heavy chain (HC) described herein and a light chain (LC) described herein. In certain embodiments, the antibody of the conjugate comprises a paired heavy chain and a light chain described herein (HC-LC pair).

In certain embodiments, the antibody of the conjugate comprises any of the amino acid sequences of the antibodies described above. In certain embodiments, the antibody comprises any of the amino acid sequences above with up to 10 amino acid substitutions. In certain embodiments, the antibody comprises any of the amino acid sequences above with up to 9 amino acid substitutions. In certain embodiments, the antibody comprises any of the amino acid sequences above with up to 8 amino acid substitutions. In certain embodiments, the antibody comprises any of the amino acid sequences above with up to 7 amino acid substitutions. In certain embodiments, the antibody comprises any of the amino acid sequences above with up to 6 amino acid substitutions. In certain embodiments, the antibody comprises any of the amino acid sequences above with up to 5 amino acid substitutions. In certain embodiments, the antibody comprises any of the amino acid sequences above with up to 4 amino acid substitutions. In certain embodiments, the antibody comprises any of the amino acid sequences above with up to 3 amino acid substitutions. In certain embodiments, the antibody comprises any of the amino acid sequences above with up to 2 amino acid substitutions. In certain embodiments, the antibody comprises any of the amino acid sequences above with up to 1 conservative amino acid substitution. In some embodiments, the amino acid substitutions are conservative amino acid substitutions. For example, in certain embodiments, the antibody comprises any of the amino acid sequences above with up to 10 conservative amino acid substitutions. In certain embodiments, the antibody comprises any of the amino acid sequences above with up to 9 conservative amino acid substitutions. In certain embodiments, the antibody comprises any of the amino acid sequences above with up to 8 conservative amino acid substitutions. In certain embodiments, the antibody comprises any of the amino acid sequences above with up to 7 conservative amino acid substitutions. In certain embodiments, the antibody comprises any of the amino acid sequences above with up to 6 conservative amino acid substitutions. In certain embodiments, the antibody comprises any of the amino acid sequences above with up to 5 conservative amino acid substitutions. In certain embodiments, the antibody comprises any of the amino acid sequences above with up to 4 conservative amino acid substitutions. In certain embodiments, the antibody comprises any of the amino acid sequences above with up to 3 conservative amino acid substitutions. In certain embodiments, the antibody comprises any of the amino acid sequences above with up to 2 conservative amino acid substitutions. In certain embodiments, the antibody comprises any of the amino acid sequences above with up to 1 conservative amino acid substitution.

In certain embodiments, the antibody conjugate can be formed from an antibody that comprises one or more reactive groups. In certain embodiments, the antibody conjugate can be formed from an antibody comprising all naturally encoded amino acids. Those of skill in the art will recognize that several naturally encoded amino acids include reactive groups capable of conjugation to a payload or to a linker. These reactive groups include cysteine side chains, lysine side chains, and amino-terminal groups. In these embodiments, the antibody conjugate can comprise a payload or linker linked to the residue of an antibody reactive group. In these embodiments, the payload precursor or linker precursor comprises a reactive group capable of forming a bond with an antibody reactive group. Typical reactive groups include maleimide groups, activated carbonates (including but not limited to, p-nitrophenyl ester), activated esters (including but not limited to, N-hydroxysuccinimide, p-nitrophenyl ester, and aldehydes). Particularly useful reactive groups include maleimide and succinimide, for instance N-hydroxysuccinimide, for forming bonds to cysteine and lysine side chains. Additional reactive groups include alkynes, for example strained alkynes, and azides, for forming bonds to non-natural amino acids incorporated in antibody polypeptide chains. Further reactive groups are described in the sections and examples below.

In certain embodiments, the antibody comprises one or more modified amino acids having a reactive group, as described herein. Typically, the modified amino acid is not a naturally encoded amino acid. These modified amino acids can comprise a reactive group useful for forming a covalent bond to a linker precursor or to a payload precursor. One of skill in the art can use the reactive group to link the polypeptide to any molecular entity capable of forming a covalent bond to the modified amino acid. Thus, provided herein are conjugates comprising an antibody comprising a modified amino acid residue linked to a payload directly or indirectly via a linker. Exemplary modified amino acids are described in the sections below. Generally, the modified amino acids have reactive groups capable of forming bonds to linkers or payloads with complementary reactive groups.

The non-natural amino acids are positioned at select locations in a polypeptide chain of the antibody. These locations were identified as providing optimum sites for substitution with the non-natural amino acids. Each site is capable of bearing a non-natural amino acid with optimum structure, function and/or methods for producing the antibody.

In certain embodiments, a site-specific position for substitution provides an antibody that is stable. Stability can be measured by any technique apparent to those of skill in the art.

In certain embodiments, a site-specific position for substitution provides an antibody that has optimal functional properties. For instance, the antibody can show little or no loss of binding affinity for its target antigen compared to an antibody without the site-specific non-natural amino acid. In certain embodiments, the antibody can show enhanced binding compared to an antibody without the site-specific non-natural amino acid.

In certain embodiments, a site-specific position for substitution provides an antibody that can be made advantageously. For instance, in certain embodiments, the antibody shows advantageous properties in its methods of synthesis, discussed below. In certain embodiments, the antibody can show little or no loss in yield in production compared to an antibody without the site-specific non-natural amino acid. In certain embodiments, the antibody can show enhanced yield in production compared to an antibody without the site-specific non-natural amino acid. In certain embodiments, the antibody can show little or no loss of tRNA suppression compared to an antibody without the site-specific non-natural amino acid. In certain embodiments, the antibody can show enhanced tRNA suppression in production compared to an antibody without the site-specific non-natural amino acid.

In certain embodiments, a site-specific position for substitution provides an antibody that has advantageous solubility. In certain embodiments, the antibody can show little or no loss in solubility compared to an antibody without the site-specific non-natural amino acid. In certain embodiments, the antibody can show enhanced solubility compared to an antibody without the site-specific non-natural amino acid.

In certain embodiments, a site-specific position for substitution provides an antibody that has advantageous expression. In certain embodiments, the antibody can show little or no loss in expression compared to an antibody without the site-specific non-natural amino acid. In certain embodiments, the antibody can show enhanced expression compared to an antibody without the site-specific non-natural amino acid.

In certain embodiments, a site-specific position for substitution provides an antibody that has advantageous folding. In certain embodiments, the antibody can show little or no loss in proper folding compared to an antibody without the site-specific non-natural amino acid. In certain embodiments, the antibody can show enhanced folding compared to an antibody without the site-specific non-natural amino acid.

In certain embodiments, a site-specific position for substitution provides an antibody that is capable of advantageous conjugation. As described below, several non-natural amino acids have side chains or functional groups that facilitate conjugation of the antibody to a second agent, either directly or via a linker. In certain embodiments, the antibody can show enhanced conjugation efficiency compared to an antibody without the same or other non-natural amino acids at other positions. In certain embodiments, the antibody can show enhanced conjugation yield compared to an antibody without the same or other non-natural amino acids at other positions. In certain embodiments, the antibody can show enhanced conjugation specificity compared to an antibody without the same or other non-natural amino acids at other positions.

The one or more non-natural amino acids are located at selected site-specific positions in at least one polypeptide chain of the antibody. The polypeptide chain can be any polypeptide chain of the antibody without limitation, including either light chain or either heavy chain. The site-specific position can be in any domain of the antibody, including any variable domain and any constant domain.

In certain embodiments, the antibodies provided herein comprise one non-natural amino acid at a site-specific position. In certain embodiments, the antibodies provided herein comprise two non-natural amino acids at site-specific positions. In certain embodiments, the antibodies provided herein comprise three non-natural amino acids at site-specific positions. In certain embodiments, the antibodies provided herein comprise more than three non-natural amino acids at site-specific positions. In certain embodiments, the antibodies provided herein comprise four non-natural amino acids at site-specific positions.

In certain embodiments, the antibodies provided herein comprise one or more non-natural amino acids each at a position selected from the group consisting of heavy chain or light chain residues HC-F404, HC-K121, HC-Y180, HC-F241, HC-221, HC-Y391, LC-T22, LC-S7, LC-N152, LC-K42, LC-E161, LC-D170, HC-S136, HC-S25, HC-A40, HC-S119, HC-S190, HC-K222, HC-R19, HC-Y52, or HC-S70 according to the Kabat or Chothia or EU numbering scheme, or a post-translationally modified variant thereof. In certain embodiments, the antibodies provided herein comprise one or more non-natural amino acids each at a position selected from the group consisting of heavy chain or light chain residues HC-F404, HC-Y180, HC-F241, HC-Y391, LC-K42, and LC-E161, according to the Kabat or Chothia or EU numbering scheme, or a post-translationally modified variant thereof. In certain embodiments, the antibodies provided herein comprise one or more non-natural amino acids each at a position selected from the group consisting of heavy chain or light chain residues HC-F404, HC-Y180, LC-K42, and LC-E161, according to the Kabat or Chothia or EU numbering scheme, or a post-translationally modified variant thereof. In certain embodiments, the antibodies provided herein comprise one or more non-natural amino acids each at a position selected from the group consisting of heavy chain or light chain residues HC-F404, HC-Y180, HC-Y391, HC-F241, and LC-K42, according to the Kabat or Chothia or EU numbering scheme, or a post-translationally modified variant thereof. In certain embodiments, the antibodies provided herein comprise a non-natural amino acid at position HC-F404 according to the Kabat or Chothia or EU numbering scheme, or a post-translationally modified variant thereof. In certain embodiments, the antibodies provided herein comprise a non-natural amino acid at position HC-Y180, according to the Kabat or Chothia or EU numbering scheme, or a post-translationally modified variant thereof. In certain embodiments, the antibodies provided herein comprise non-natural amino acids at positions HC-F404 and HC-Y180, according to the Kabat or Chothia or EU numbering scheme, or a post-translationally modified variant thereof. In certain embodiments, the antibodies provided herein comprise a non-natural amino acid at position HC-F241 according to the Kabat or Chothia or EU numbering scheme, or a post-translationally modified variant thereof. In certain embodiments, the antibodies provided herein comprise a non-natural amino acid at position LC-K42 according to the Kabat or Chothia or EU numbering scheme, or a post-translationally modified variant thereof. In certain embodiments, the antibodies provided herein comprise a non-natural amino acid at position LC-E161 according to the Kabat or Chothia or EU numbering scheme, or a post-translationally modified variant thereof. In certain embodiments, the antibodies provided herein comprise non-natural amino acids at positions HC-F404, HC-Y180, and LC-K42, according to the Kabat or Chothia or EU numbering scheme, or a post-translationally modified variant thereof. In certain embodiments, the antibodies provided herein comprise non-natural amino acids at positions HC-F404, HC-Y180, LC-K42, and LC-E161, according to the Kabat or Chothia or EU numbering scheme, or a post-translationally modified variant thereof. In certain embodiments, the antibodies provided herein comprise non-natural amino acids at positions HC-F404, HC-Y180, and HC-F241, according to the Kabat or Chothia or EU numbering scheme, or a post-translationally modified variant thereof. In certain embodiments, the antibodies provided herein comprise non-natural amino acids at positions HC-F404, HC-Y180, HC-F241, and LC-K42, according to the Kabat or Chothia or EU numbering scheme, or a post-translationally modified variant thereof. In certain embodiments, the antibodies provided herein comprise non-natural amino acids at positions HC-F404, HC-Y180, HC-F241, and LC-K42, according to the Kabat or Chothia or EU numbering scheme, or a post-translationally modified variant thereof. In certain embodiments, the antibodies provided herein comprise non-natural amino acids at positions HC-F241 and HC-F404, according to the Kabat or Chothia or EU numbering scheme, or a post-translationally modified variant thereof. In certain embodiments, the antibodies provided herein comprise non-natural amino acids at positions HC-Y180, HC-F404, LC-K42 and LC-E161, according to the Kabat or Chothia or EU numbering scheme, or a post-translationally modified variant thereof. In certain embodiments, the antibodies provided herein comprise non-natural amino acids at positions HC-Y180, HC-F241, HC-F404 and HC-Y391, according to the Kabat or Chothia or EU numbering scheme, or a post-translationally modified variant thereof. In these designations, HC indicates a heavy chain residue, and LC indicates a light chain residue.

In some aspects, the present disclosure provides antibody conjugates according to the following formula:

$$\text{COMP}\!\mathrel{+}\!\!\left[\text{LINK-PAY}\right]_{n2}$$

or a pharmaceutically acceptable salt, solvate, stereoisomer, regioisomer, or tautomer thereof, wherein:

COMP is a residue of an anti-Tissue Factor antibody;

i. PAY is a payload moiety;

ii. LINK is a linker; and iii. n2 is an integer from 1 to 10, iv. wherein COMP comprises one or more non-natural amino acids.

In certain embodiments, provided herein are conjugates according to Formula (C1) or (C2):

(C1)

$$\text{COMP}\!+\!\left[\text{R}-\text{W}^5-\text{SG}-\text{W}^4-\text{HP}-\text{W}^3-\text{RT}-\text{W}^2-\underset{}{\overset{\displaystyle\text{RT}\atop|}{\text{EG}}}-\text{W}^1-\text{SG}-\text{PAY}\right]_{n2}$$

(C2)

$$\text{COMP}\!+\!\left[\text{R}-\text{W}^5-\text{SG}-\text{W}^4-\text{HP}-\text{W}^3-\text{RT}-\text{W}^2-\text{RT}-\text{W}^1-\text{SG}-\text{PAY}\right]_{n2}$$

or a pharmaceutically acceptable salt, solvate, stereoisomer, regioisomer, or tautomer thereof, wherein:

COMP is a residue of an anti-Tissue Factor antibody;

PAY is a payload moiety;

$W^1$, $W^2$, $W^3$, $W^4$, and $W^5$ are each independently a single bond, absent, or a divalent attaching group;

EG is absent, or an eliminator group;

each RT is a release trigger group, in the backbone of Formula (C1) or (C2) or bonded to EG, wherein each RT is optional;

HP is a single bond, absent, or a divalent hydrophilic group;

each SG is a single bond, absent, or a divalent spacer group;

R is hydrogen, a terminal conjugating group, or a divalent residue of a terminal conjugating group; and n2 is an integer from 1 to 10.

In some embodiments, a conjugate according to Formula (C1) or (C2) comprises n2 number of linked PAY moieties, wherein n2 is an integer from 1 to 10. In some embodiments, n2 is 2. In some embodiments, n2 is 3. In some embodiments, n2 is 4. In some embodiments, n2 is 5. In some embodiments, n2 is 6. In some embodiments, n2 is 7. In some embodiments, n2 is 8. In some embodiments, n2 is 10.

1. Attaching Groups

Attaching groups facilitate incorporation of eliminator groups, release trigger groups, hydrophobic groups, spacer groups, and/or conjugating groups into a compound. Useful attaching groups are known to, and are apparent to, those of skill in the art. Examples of useful attaching groups are provided herein. In certain embodiments, attaching groups are designated $W^1$, $W^2$, $W^3$, W4, or $W^5$. In certain embodiments, an attaching group can comprise a divalent ketone, divalent ester, divalent ether, divalent amide, divalent amine, alkylene, arylene, sulfide, disulfide, carbonylene, or a combination thereof. In certain embodiments an attaching group can comprise —C(O)—, —O—, —C(O)NH—, —C(O)NH-alkyl-, —OC(O)NH—, —SC(O)NH—, —NH—, —NH-alkyl-, $—N(CH_3)CH_2CH_2N(CH_3)—$, —S—, —S—S—, $—OCH_2CH_2O—$, or the reverse (e.g. —NHC(O)—) thereof, or a combination thereof.

2. Eliminator Groups

Eliminator groups facilitate separation of a biologically active portion of a compound or conjugate described herein from the remainder of the compound or conjugate in vivo and/or in vitro. Eliminator groups can also facilitate separation of a biologically active portion of a compound or conjugate described herein in conjunction with a release trigger group. For example, the eliminator group and the release trigger group can react in a Releasing Reaction to release a biologically active portion of a compound or conjugate described herein from the compound or conjugate in vivo and/or in vitro. Upon initiation of the Releasing Reaction by the release trigger, the eliminator group cleaves the biologically active moiety, or a prodrug form of the biologically active moiety, and forms a stable, non-toxic entity that has no further effect on the activity of the biologically active moiety.

In certain embodiments, the eliminator group is designated EG herein. Useful eliminator groups include those described herein. In certain embodiments, the eliminator group is:

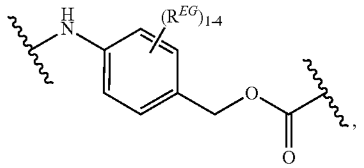

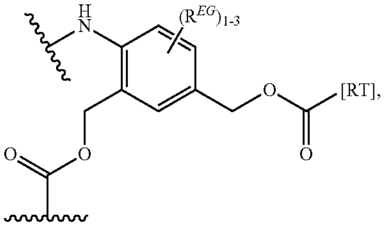

or

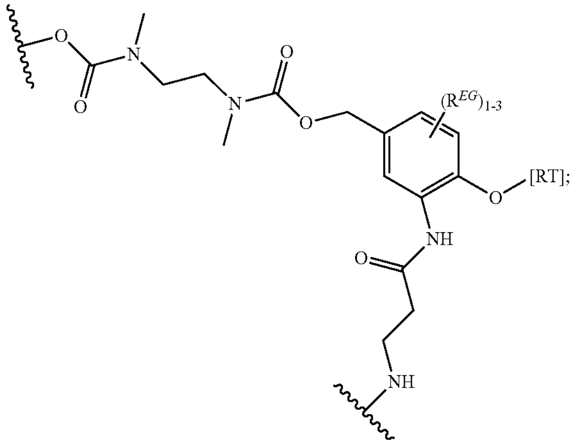

wherein $R^{EG}$ is selected from the group consisting of hydrogen, alkyl, biphenyl, —$CF_3$, —$NO_2$, —CN, fluoro, bromo, chloro, alkoxyl, alkylamino, dialkylamino, alkyl-C(O)O—, alkylamino-C(O)— and dialkylaminoC(O)—. In each structure, the phenyl ring can be bound to one, two, three, or in some cases, four $R^{EG}$ groups. In the second and third structures, those of skill will recognize that EG is bonded to an RT that is not within the backbone of formula (C1) as indicated in the above description of formula (C1). In some embodiments, $R^{EG}$ is selected from the group consisting of hydrogen, alkyl, biphenyl, —$CF_3$, alkoxyl, alkylamino, dialkylamino, alkyl-C(O)O—, alkylamino-C(O)— and dialkylaminoC(O)—. In further embodiments, $R^{EG}$ is selected from the group consisting of hydrogen, —$NO_2$, —CN, fluoro, bromo, and chloro. In certain embodiments, the eliminator group is

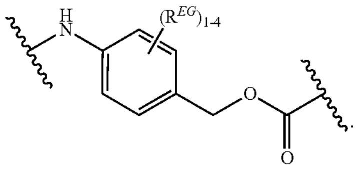

In certain embodiments, the eliminator group is

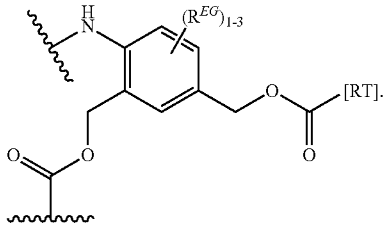

In certain embodiments, the eliminator group is

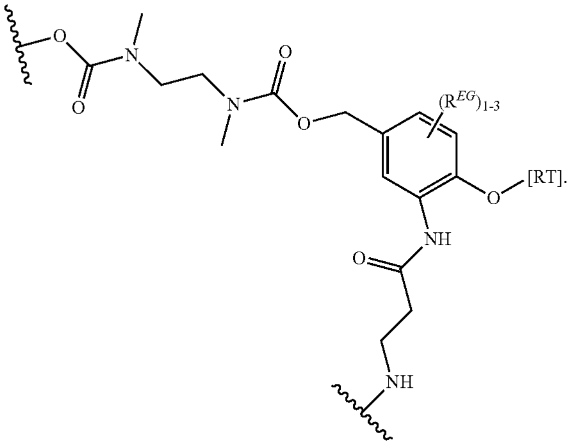

In some embodiments, provided herein is a conjugate according to Formula (C1) or (C2) or a pharmaceutically acceptable salt, solvate, stereoisomer, or tautomer thereof; wherein EG comprises phenylene, carboxylene, amine, or a combination thereof. In some embodiments, the eliminator group is:

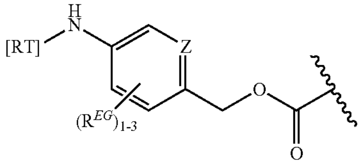

-continued

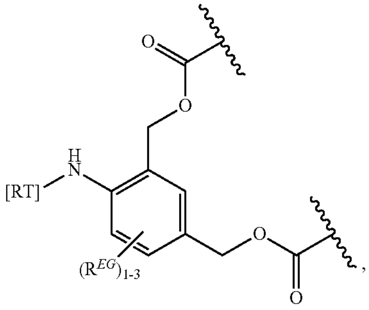

, or

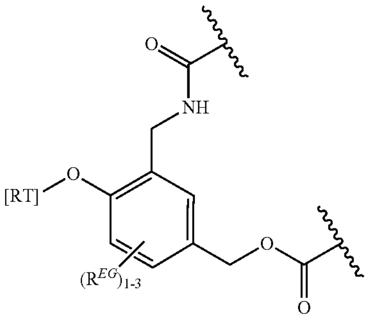

, wherein Z may be CH or N, $R^{EG}$ is selected from the group consisting of hydrogen, alkyl, biphenyl, —$CF_3$, —$NO_2$, —CN, fluoro, bromo, chloro, alkoxyl, alkylamino, dialkylamino, alkyl-C(O)O—, alkylamino-C(O)— and dialkylaminoC(O)—. In each structure, the phenyl ring can be bound to one, two, three, or in some cases, four $R^{EG}$ groups. In the first and second structures, those of skill will recognize that EG is bonded to an RT that is not within the backbone of formula (C1) as indicated in the above description of formula (C1). In some embodiments, $R^{EG}$ is selected from the group consisting of hydrogen, alkyl, biphenyl, —$CF_3$, alkoxyl, alkylamino, dialkylamino, alkyl-C(O)O—, alkylamino-C(O)— and dialkylaminoC(O)—. In further embodiments, $R^{EG}$ is selected from the group consisting of hydrogen, —$NO_2$, —CN, fluoro, bromo, and chloro. In some embodiments, each $R^{EG}$ in the EG is hydrogen. In certain embodiments, the eliminator group is

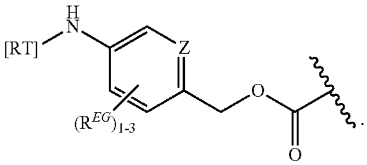

.

In certain embodiments, the eliminator group is

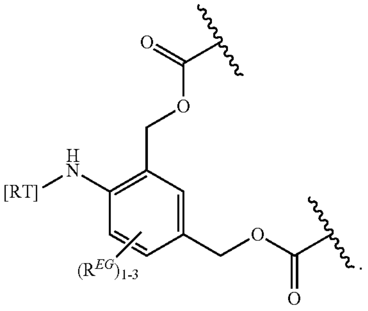

.

In certain embodiments, the eliminator group is

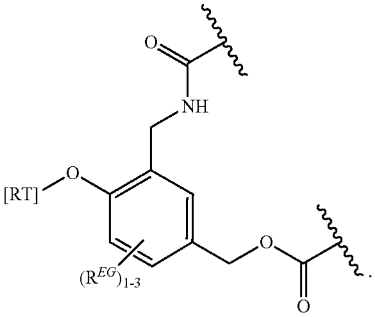

.

3. Release Trigger Groups

Release trigger groups facilitate separation of a biologically active portion of a compound or conjugate described herein from the remainder of the compound or conjugate in vivo and/or in vitro. Release trigger groups can also facilitate separation of a biologically active portion of a compound or conjugate described herein in conjunction with an eliminator group. For example, the eliminator group and the release trigger group can react in a Releasing Reaction to release a biologically active portion of a compound or conjugate described herein from the compound or conjugate in vivo and/or in vitro. In certain embodiments, the release trigger can act through a biologically-driven reaction with high tumor:nontumor specificity, such as the proteolytic action of an enzyme overexpressed in a tumor environment.

In certain embodiments, the release trigger group is designated RT herein. In certain embodiments, RT is divalent and bonded within the backbone of formula (C1). In other embodiments, RT is monovalent and bonded to EG as depicted above. Useful release trigger groups include those described herein. In certain embodiments, the release trigger group comprises a residue of a natural or non-natural amino acid or residue of a sugar ring. In certain embodiments, the release trigger group is:

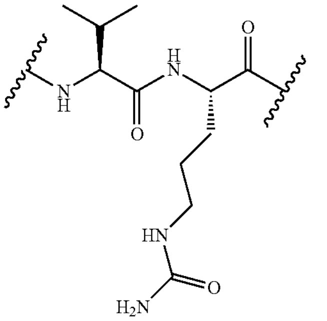

or

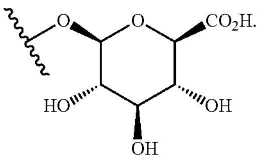

Those skilled in the art will recognize that the first structure is divalent and can be bonded within the backbone of Formula (C1) or as depicted in Formula (C2), and that the second structure is monovalent and can be bonded to EG as depicted in formula (C1) above. In certain embodiments, the release trigger group is

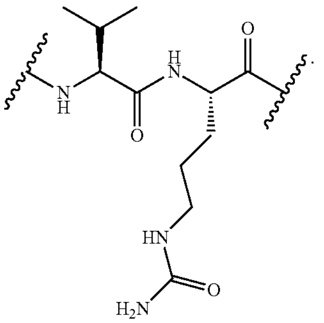 [SMILES: *N[C@H](C(=O)N[C@@H](CCCNC(N)=O)C(*)=O)C(C)C]

In certain embodiments, the release trigger group is

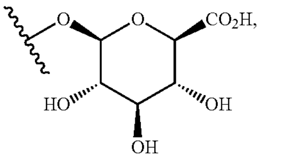

In some embodiments, the release trigger group is a protease-cleavable $R_1$-Val-X peptide having the structure of:

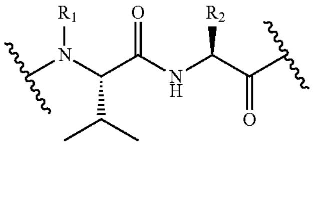

wherein $R_1$ is H or

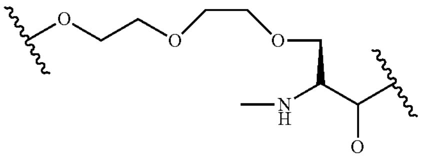

and $R_2$ is $CH_3$, $CH_2CH_2CO_2H$, or $(CH_2)_3NHCONH_2$; a legumain-cleavable Ala-Ala-Asn or Ala-Ala-Asp peptide having the structure of:

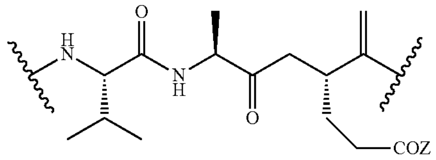

where Z is OH or $NH_2$; or a β-glucuronidase-cleavable β-glucuronide having the structure of:

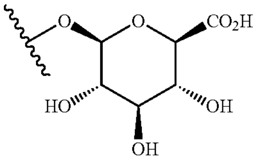 [SMILES: *O[C@H]1O[C@@H](C(=O)O)[C@H](O)[C@@H](O)[C@@H]1O]

or a Val-Lys-Gly peptide having the structure of:

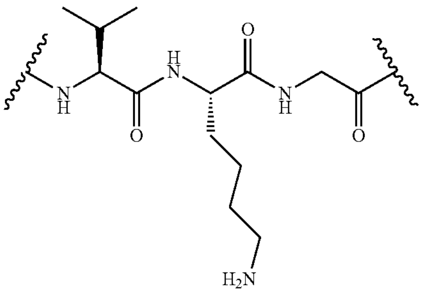 [SMILES: *N[C@H](C(=O)N[C@@H](CCCCN)C(=O)NCC(*)=O)C(C)C]

Those of skill will recognize that

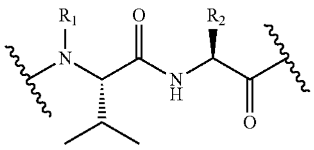

and

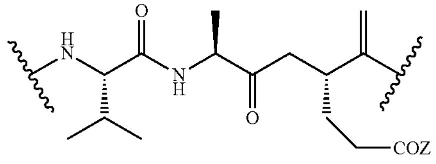

are divalent structures and can be bonded within the backbone of Formula (C1) or as depicted in Formula (C2). The structure

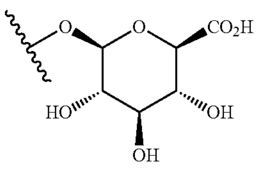 [SMILES: *O[C@H]1O[C@@H](C(=O)O)[C@H](O)[C@@H](O)[C@@H]1O]

is monovalent and can be bonded to EG as depicted in formula (C1) above.

In certain embodiments, the release trigger is selected from the group consisting of Val-Lys-Gly, Val-Ala-Asp, Ala-Ala-Ala, Val-Lys, Gly-Gly-Gly, Val-Ala, Gly-Gly-Phe-Gly, Val-Cit, Val-Cit, Val-Glu, Ala-Ala-Asn, and Gly. In certain embodiments, the release trigger further comprises a non-natural amino acid. In certain embodiments, the non-natural amino acid is according to

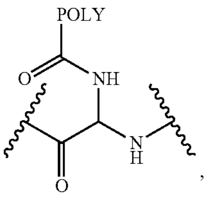

, where POLY is a polymer, for instance a hydrophilic polymer. In certain embodiments, the non-natural amino acid is according to

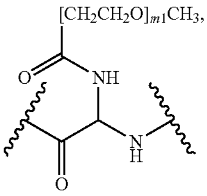

where m1 is an integer from 1 to 25, for instance 8, 9, 10, 11, 12, 13, 14, 15, 20, or 25.

4. Hydrophilic Groups

Hydrophilic groups facilitate increasing the hydrophilicity of the compounds described herein. It is believed that increased hydrophilicity allows for greater solubility in aqueous solutions, such as aqueous solutions found in biological systems. Hydrophilic groups can also function as spacer groups, which are described in further detail herein.

In certain embodiments, the hydrophilic group is designated HP herein. Useful hydrophilic groups include those described herein. In certain embodiments, the hydrophilic group is a divalent poly(ethylene glycol). In certain embodiments, the hydrophilic group is a divalent poly(ethylene glycol) according to the formula:

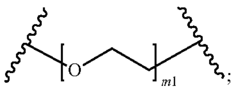

;

wherein m1 is an integer from 1 to 13, optionally 1 to 4, optionally 2 to 4, or optionally 4 to 8. In certain embodiments, m1 is 4. In certain embodiments, m1 is 12. In certain embodiments, m1 is 13.

In some embodiments, the hydrophilic group is a divalent poly(ethylene glycol) having the following formula:

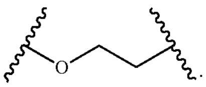

.

In some other embodiments, the hydrophilic group is a divalent poly(ethylene glycol) having the following formula:

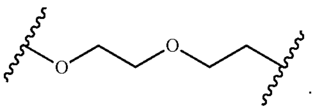

.

In other embodiments, the hydrophilic group is a divalent poly(ethylene glycol) having the following formula:

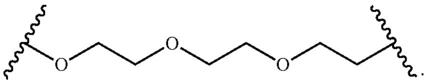 [SMILES: *CCOCCOCCO*]

.

In other embodiments, the hydrophilic group is a divalent poly(ethylene glycol) having the following formula:

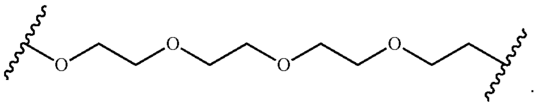 [SMILES: *CCOCCOCCOCCO*]

.

In some embodiments, the hydrophilic group is sulfonic acid. In some embodiments, the hydrophilic group is the side chain of cysteic acid. In some embodiments, the hydrophilic group can bear a chain-presented sulfonic acid having the formula:

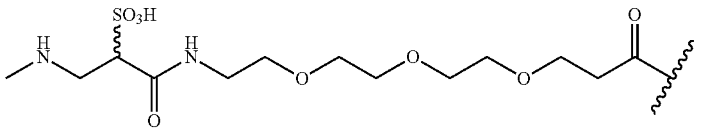

or

-continued

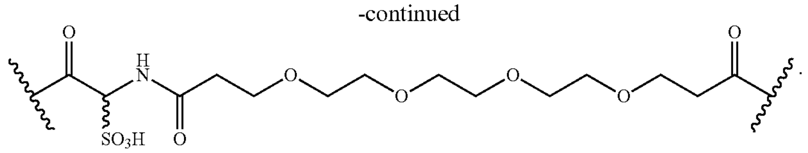

(a) In certain embodiments, the hydrophilic group is the side chain of a non-natural amino acid according to

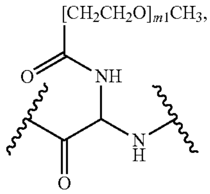

where m1 is an integer from 1 to 25, for instance 8, 9, 10, 11, 12, 13, 14, 15, 20, or 25.

5. Spacer Groups

Spacer groups facilitate spacing of the conjugating group from the other groups of the compounds described herein. This spacing can lead to more efficient conjugation of the compounds described herein to an antibody as well as more efficient cleavage of the active catabolite. The spacer group can also stabilize the conjugating group and lead to improved overall antibody-drug conjugate properties.

In certain embodiments, the spacer group is designated SP herein. Useful spacer groups include those described herein. In certain embodiments, the spacer group is:

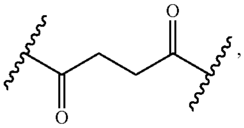

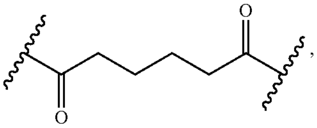

or

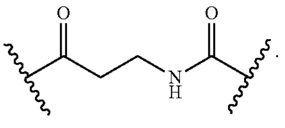

In certain embodiments, the spacer group, $W^4$, and the hydrophilic group combine to form a divalent poly(ethylene glycol) according to the formula:

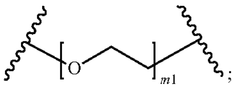

wherein m1 is an integer from 1 to 13, optionally 1 to 4, optionally 2 to 4, or optionally 4 to 8.

In some embodiments, the SP is

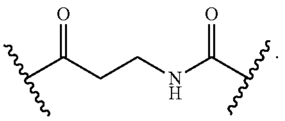 [SMILES: *C(=O)CCNC(*)=O]

In some embodiments, the divalent poly(ethylene glycol) has the following formula:

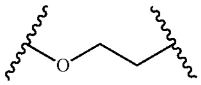

In some other embodiments, the divalent poly(ethylene glycol) has the following formula:

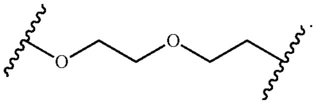 [SMILES: *CCOCCO*]

In other embodiments, the divalent poly(ethylene glycol) has the following formula:

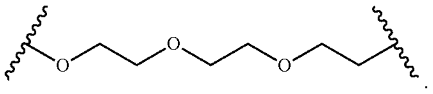 [SMILES: *CCOCCOCCO*]

In other embodiments, the divalent poly(ethylene glycol) has the following formula:

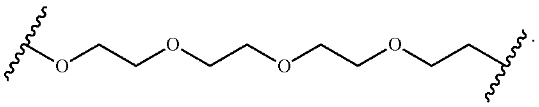 [SMILES: *CCOCCOCCOCCO*]

In some embodiments, the spacer group can bear a chain-presented sulfonic acid having the formula:

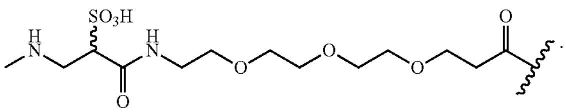 [SMILES: *C(=O)CCOCCOCCOCCNC(=O)C(CNC)S(=O)(=O)O]

In some embodiments, the spacer group is a diamine. In some embodiments, the spacer group is according to

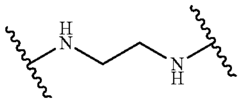.

In some embodiments, the spacer group comprises fused rings or spiro rings. In some embodiments, the spacer group is according to

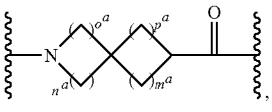, where each $n^a$, $m^a$, $o^a$, and $p^a$ is an integer independently selected from 1, 2, 3, 4, and 5. In some embodiments, the spacer group is according to

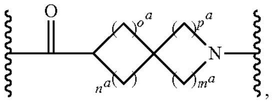, where each $n^a$, $m^a$, $o^a$, and $p^a$ is an integer independently selected from 1, 2, 3, 4, and 5. In some embodiments, the spacer group is selected from the group consisting of:

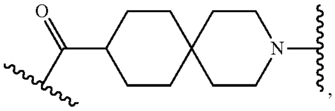,

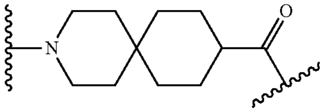

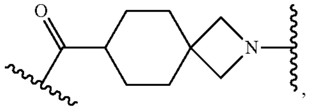,

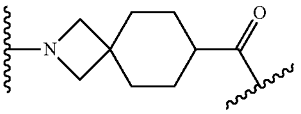

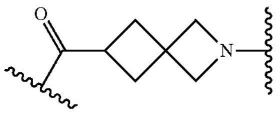, 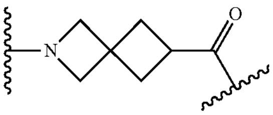

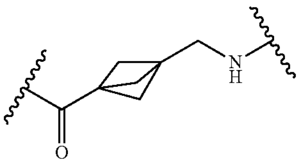, and

-continued

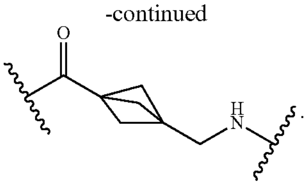.

6. Conjugating Groups and Residues Thereof

Conjugating groups facilitate conjugation of the payloads described herein to a second compound, such as an antibody described herein. In certain embodiments, the conjugating group is designated R herein. Conjugating groups can react via any suitable reaction mechanism known to those of skill in the art. In certain embodiments, a conjugating group reacts through a [3+2]alkyne-azide cycloaddition reaction, inverse-electron demand Diels-Alder ligation reaction, thiol-electrophile reaction, or carbonyl-oxyamine reaction, as described in detail herein. In certain embodiments, the conjugating group comprises an alkyne, strained alkyne, tetrazine, thiol, para-acetyl-phenylalanine residue, oxyamine, maleimide, or azide. In certain embodiments, the conjugating group is:

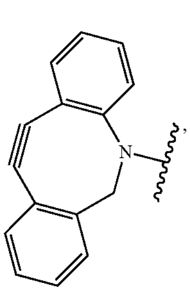, 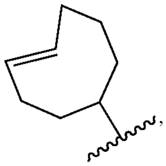,

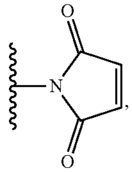, 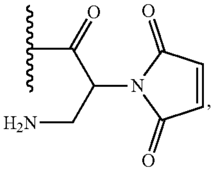,

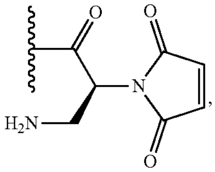, 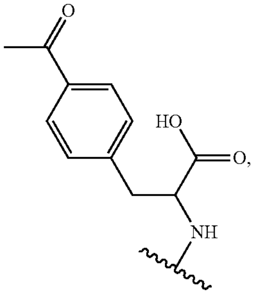,

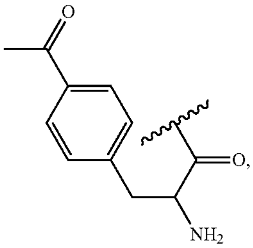, 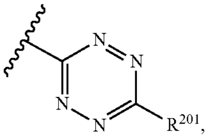,

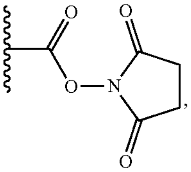, 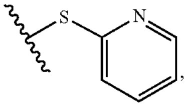,

-continued

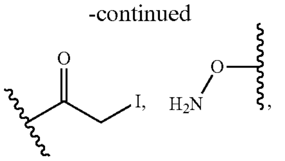

—$N_3$, or —SH; wherein $R^{201}$ is lower alkyl. In an embodiment, $R^{201}$ is methyl, ethyl, or propyl. In an embodiment, $R^{201}$ is methyl. Additional conjugating groups are described in, for example, U.S. Patent Publication No. 2014/0356385, U.S. Patent Publication No. 2013/0189287, U.S. Patent Publication No. 2013/0251783, U.S. Pat. Nos. 8,703,936, 9,145,361, 9,222,940, and 8,431,558.

After conjugation, a divalent residue of the conjugating group is formed and is bonded to the residue of an antibody. The structure of the divalent residue is determined by the type of conjugation reaction employed to form the conjugate.

In certain embodiments when a conjugate is formed through a [3+2]alkyne-azide cycloaddition reaction, the divalent residue of the conjugating group comprises a triazole ring or fused cyclic group comprising a triazole ring. In certain embodiment when a conjugate is formed through a strain-promoted [3+2] alkyne-azide cycloaddition (SPAAC) reaction, the divalent residue of the conjugating group is:

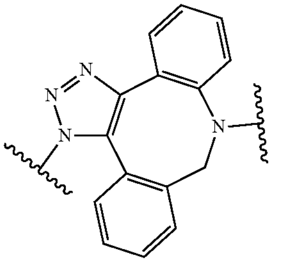

and/or

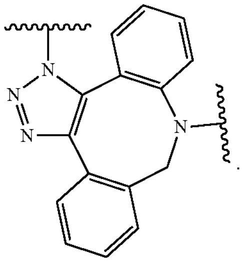

In certain embodiments when a conjugate is formed through a tetrazine inverse electron demand Diels-Alder ligation reaction, the divalent residue of the conjugating group comprises a fused bicyclic ring having at least two adjacent nitrogen atoms in the ring. In certain embodiments when a conjugate is formed through a tetrazine inverse electron demand Diels-Alder ligation reaction, the divalent residue of the conjugating group is:

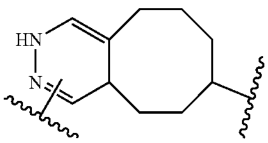

or

-continued

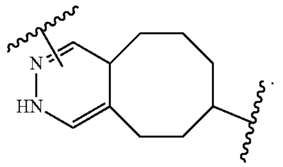

In certain embodiments when a conjugate is formed through a thiol-maleimide reaction, the divalent residue of the conjugating group comprises succinimidylene and a sulfur linkage. In certain embodiments when a conjugate is formed through a thiol-maleimide reaction, the divalent residue of the conjugating group is:

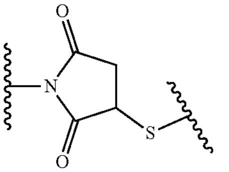

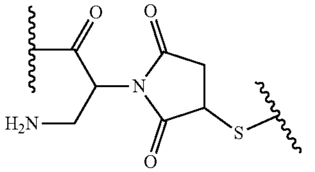

or

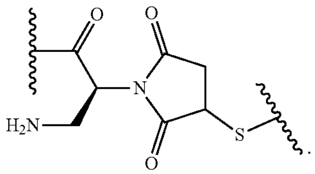

In certain embodiments, a conjugate is formed through a thiol-N-hydroxysuccinimide reaction using the following group:

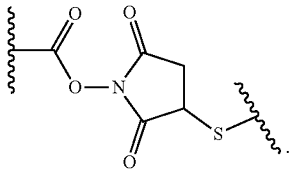 [SMILES: *SC1CC(=O)N(OC(*)=O)C1=O]

The reaction involved for formation of the conjugate comprises the following step:

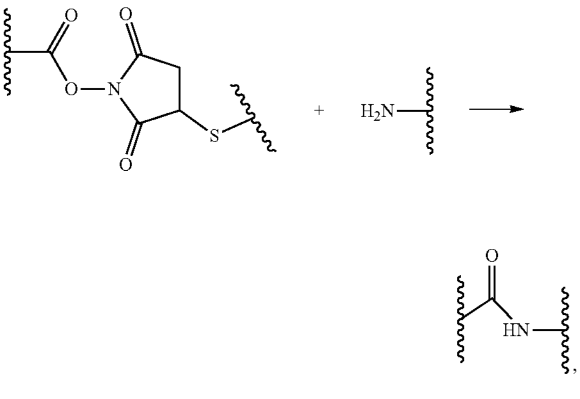

and the resulting divalent residue of the conjugating group is:

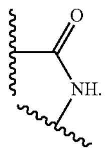 [SMILES: *NC(*)=O]

In certain embodiments when a conjugate is formed through a carbonyl-oxyamine reaction, the divalent residue of the conjugating group comprises a divalent residue of a non-natural amino acid. In certain embodiments when a conjugate is formed through a carbonyl-oxyamine reaction, the divalent residue of the conjugating group is:

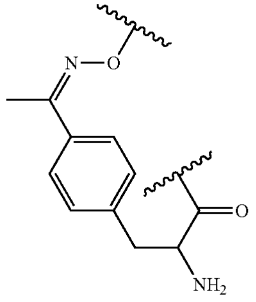

or

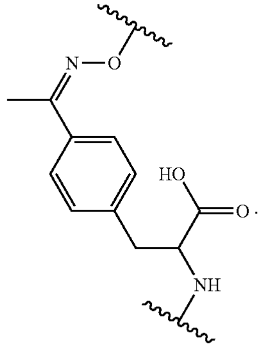

In certain embodiments when a conjugate is formed through a carbonyl-oxyamine reaction, the divalent residue of the conjugating group comprises an oxime linkage. In certain embodiments when a conjugate is formed through a carbonyl-oxyamine reaction, the divalent residue of the conjugating group is:

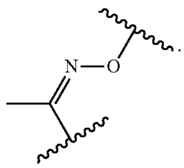 [SMILES: *O/N=C(\*)C]

In an embodiment, provided herein is a conjugate according to Formula (C1) or (C2), or a pharmaceutically acceptable salt, solvate, stereoisomer, or tautomer thereof; wherein R comprises a triazole ring. In an embodiment, provided herein is a conjugate according to Formula (C1) or (C2), or a pharmaceutically acceptable salt, solvate, stereoisomer, or tautomer thereof; wherein R is a triazole ring or fused cyclic group comprising a triazole ring. In an embodiment, provided herein is a conjugate according to Formula (C1) or (C2), or a pharmaceutically acceptable salt, solvate, stereoisomer, or tautomer thereof; wherein R is:

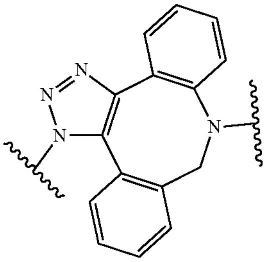

or

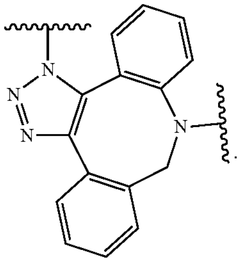

In an embodiment, provided herein is a conjugate according to Formula (C1) or (C2), or a pharmaceutically acceptable salt, solvate, stereoisomer, or tautomer thereof; wherein R comprises a fused bicyclic ring having at least two adjacent nitrogen atoms in the ring. In an embodiment, provided herein is a conjugate according to Formula (C1) or (C2), or a pharmaceutically acceptable salt, solvate, stereoisomer, or tautomer thereof; wherein R is:

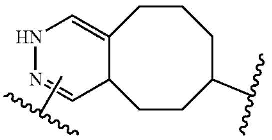

or

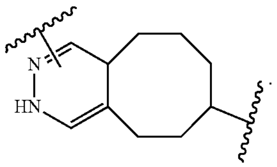

In an embodiment, provided herein is a conjugate according to Formula (C1) or (C2), or a pharmaceutically acceptable salt, solvate, stereoisomer, or tautomer thereof; wherein R comprises a sulfur linkage. In an embodiment, provided herein is a conjugate according to Formula (C1) or (C2), or a pharmaceutically acceptable salt, solvate, stereoisomer, or tautomer thereof; wherein R is:

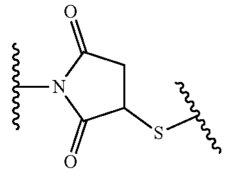

,

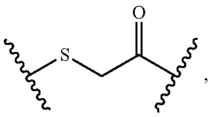

,

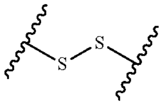

,

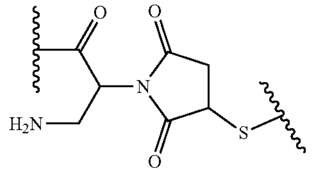

or

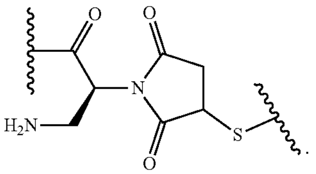

In an embodiment, provided herein is a conjugate according to Formula (C1) or (C2), or a pharmaceutically acceptable salt, solvate, stereoisomer, or tautomer thereof; wherein R comprises a divalent residue of a non-natural amino acid. In an embodiment, provided herein is a conjugate according to Formula (C1) or (C2), or a pharmaceutically acceptable salt, solvate, stereoisomer, or tautomer thereof; wherein R is:

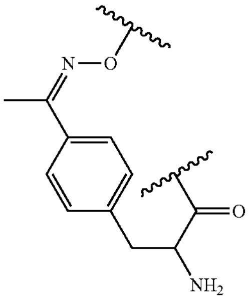

or

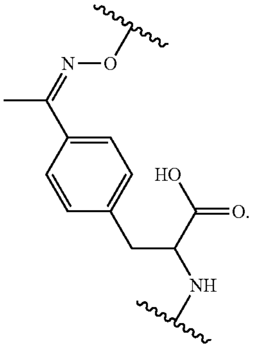

In an embodiment, provided herein is a conjugate according to Formula (C1) or (C2), or a pharmaceutically acceptable salt, solvate, stereoisomer, or tautomer thereof; wherein comprises an amide linkage. In an embodiment, provided herein is a conjugate according to Formula (C1) or (C2), or a pharmaceutically acceptable salt, solvate, stereoisomer, or tautomer thereof; wherein R is:

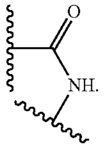 [SMILES: *NC(*)=O]

In an embodiment, provided herein is a conjugate according to Formula (C1) or (C2), or a pharmaceutically acceptable salt, solvate, stereoisomer, or tautomer thereof; wherein comprises an oxime linkage. In an embodiment, provided herein is a conjugate according to Formula (C1) or (C2), or a pharmaceutically acceptable salt, solvate, stereoisomer, or tautomer thereof; wherein R is:

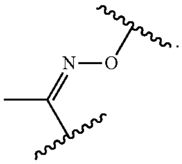 [SMILES: *O/N=C(\*)C]

In an embodiment, provided herein is a conjugate according to Formula (C1) or (C2), or a pharmaceutically acceptable salt, solvate, stereoisomer, or tautomer thereof; wherein R is:

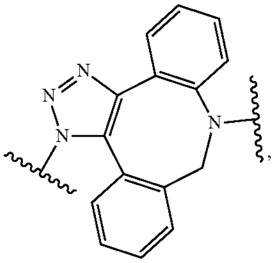

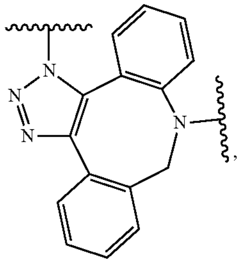

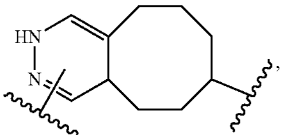

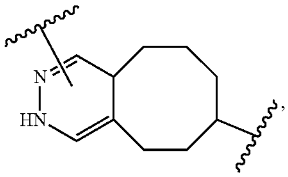

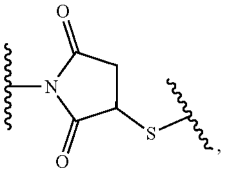

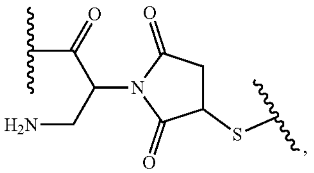

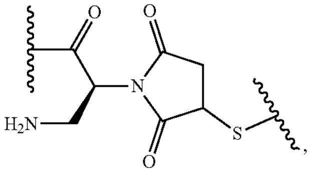

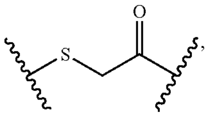

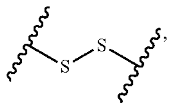

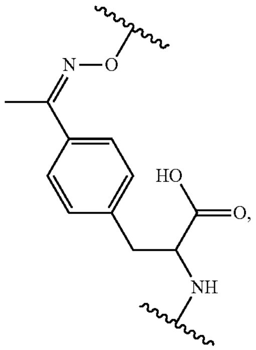

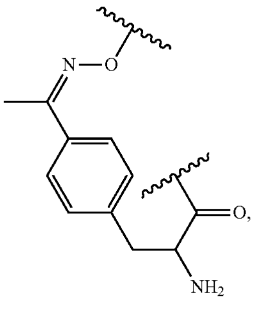

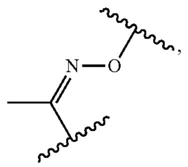

or

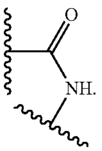

In an embodiment, provided herein is a compound according to Formula (C1) or (C2), or a pharmaceutically acceptable salt, solvate, stereoisomer, or tautomer thereof;

wherein COMP is a residue of any compound known to be useful for conjugation to a payload, described herein, and an optional linker, described herein. In an embodiment, provided herein is a compound according to Formula (C1) or (C2), or a pharmaceutically acceptable salt, solvate, stereoisomer, or tautomer thereof; wherein COMP is a residue of an antibody chain.

In an aspect, provided herein is an antibody conjugate comprising payload, described herein, and an optional linker, described herein, linked to an anti-Tissue Factor antibody, wherein COMP is a residue of the antibody. In an embodiment, provided herein is an antibody conjugate according to Formula (C1) or (C2), or a pharmaceutically acceptable salt, solvate, stereoisomer, or tautomer thereof, wherein: COMP is a residue of the antibody; and R comprises a triazole ring or fused cyclic group comprising a triazole ring. In an embodiment, provided herein is an antibody conjugate according to Formula (C1) or (C2), or a pharmaceutically acceptable salt, solvate, stereoisomer, or tautomer thereof, wherein: COMP is a residue of the antibody; and R is:

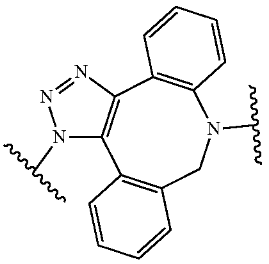

or

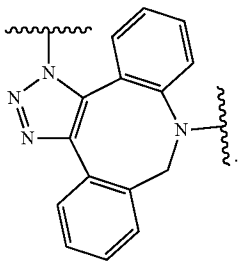

In an embodiment, provided herein is an antibody conjugate according to Formula (C1) or (C2), or a pharmaceutically acceptable salt, solvate, stereoisomer, or tautomer thereof, wherein: COMP is a residue of the antibody; and R comprises a fused bicyclic ring, wherein the fused bicyclic ring has at least two adjacent nitrogen atoms in the ring. In an embodiment, provided herein is an antibody conjugate according to Formula (C1) or (C2), or a pharmaceutically acceptable salt, solvate, stereoisomer, or tautomer thereof, wherein: COMP is a residue of the antibody; and R is:

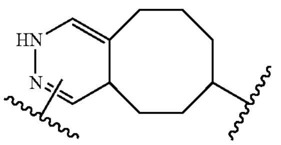

or

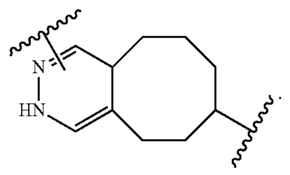

In an embodiment, provided herein is an antibody conjugate according to Formula (C1) or (C2), or a pharmaceutically acceptable salt, solvate, stereoisomer, or tautomer thereof, wherein: COMP is a residue of the polypeptide; and R comprises a sulfur linkage. In an embodiment, provided herein is an antibody conjugate according to Formula (C1) or (C2), or a pharmaceutically acceptable salt, solvate, stereoisomer, or tautomer thereof, wherein: COMP is a residue of the polypeptide; and R is:

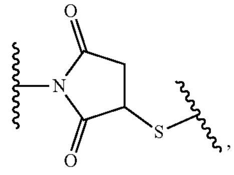

,

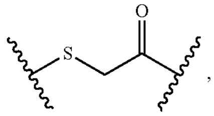

,

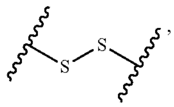

,

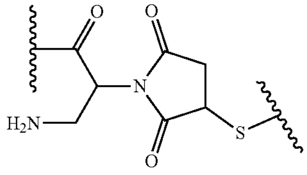

, or

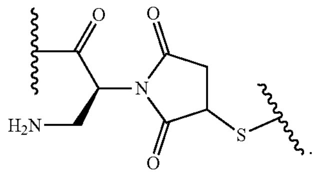

In an embodiment, provided herein is an antibody conjugate according to Formula (C1) or (C2), or a pharmaceutically acceptable salt, solvate, stereoisomer, or tautomer thereof, wherein: COMP is a residue of the polypeptide; and R comprises a divalent residue of a non-natural amino acid. In an embodiment, provided herein is an antibody conjugate according to Formula (C1) or (C2), or a pharmaceutically acceptable salt, solvate, stereoisomer, or tautomer thereof, wherein: COMP is a residue of the polypeptide; and R is:

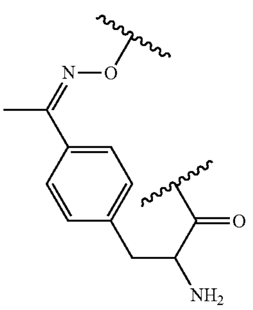

or

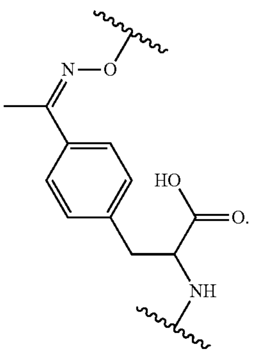

In an embodiment, provided herein is an antibody conjugate according to Formula (C1) or (C2), or a pharmaceutically acceptable salt, solvate, stereoisomer, or tautomer thereof, wherein: COMP is a residue of the polypeptide; and R comprises an amide linkage. In an embodiment, provided herein is an antibody conjugate according to Formula (C1) or (C2), or a pharmaceutically acceptable salt, solvate, stereoisomer, or tautomer thereof, wherein: COMP is a residue of the polypeptide; and R is:

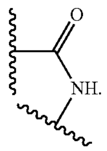 [SMILES: *NC(*)=O]

In an embodiment, provided herein is an antibody conjugate according to Formula (C1) or (C2), or a pharmaceutically acceptable salt, solvate, stereoisomer, or tautomer thereof, wherein: COMP is a residue of the polypeptide; and R comprises an amide linkage. In an embodiment, provided herein is an antibody conjugate according to Formula (C1) or (C2), or a pharmaceutically acceptable salt, solvate, stereoisomer, or tautomer thereof, wherein: COMP is a residue of the polypeptide; and R is:

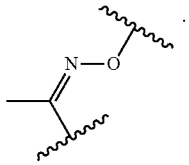 [SMILES: *O/N=C(\*)C]

In an aspect, provided herein is an antibody conjugate comprising a payload, described herein, and an optional linker, described herein, linked to an antibody according to Formula (C1) or (C2), or a pharmaceutically acceptable salt, solvate, stereoisomer, or tautomer thereof, wherein COMP is a residue of the antibody. In an embodiment, provided herein is an antibody conjugate according to Formula (C1) or (C2), or a pharmaceutically acceptable salt, solvate, stereoisomer, or tautomer thereof, wherein: COMP is a residue of the antibody; and R comprises a triazole ring or fused cyclic group comprising a triazole ring. In an embodiment, provided herein is an antibody conjugate according to Formula (C1) or (C2), or a pharmaceutically acceptable salt, solvate, stereoisomer, or tautomer thereof, wherein: COMP is a residue of the antibody; and R is:

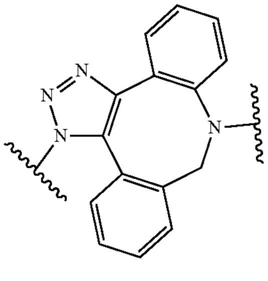
or
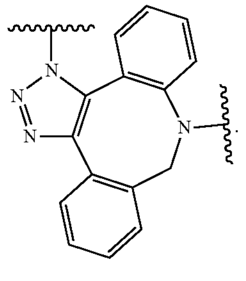

In an embodiment, provided herein is an antibody conjugate according to Formula (C1) or (C2), or a pharmaceutically acceptable salt, solvate, stereoisomer, or tautomer thereof, wherein: COMP is a residue of the antibody; and R comprises a fused bicyclic ring, wherein the fused bicyclic ring has at least two adjacent nitrogen atoms in the ring. In an embodiment, provided herein is an antibody conjugate according to Formula (C1) or (C2), or a pharmaceutically acceptable salt, solvate, stereoisomer, or tautomer thereof, wherein: COMP is a residue of the antibody; and R is:

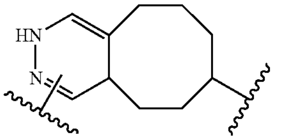
or
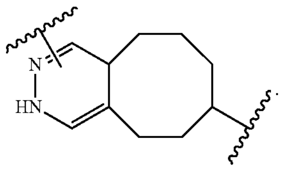

In an embodiment, provided herein is an antibody conjugate according to Formula (C1) or (C2), or a pharmaceutically acceptable salt, solvate, stereoisomer, or tautomer thereof, wherein: COMP is a residue of the antibody; and R comprises a sulfur linkage. In an embodiment, provided herein is an antibody conjugate according to Formula (C1) or (C2), or a pharmaceutically acceptable salt, solvate, stereoisomer, or tautomer thereof, wherein: COMP is a residue of the antibody; and R is:

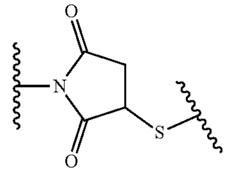
,
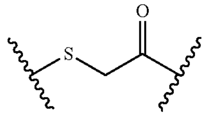
,
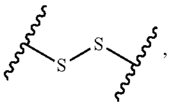
,
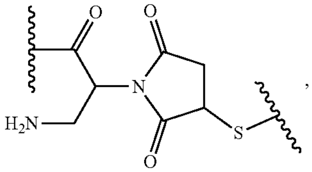
, or
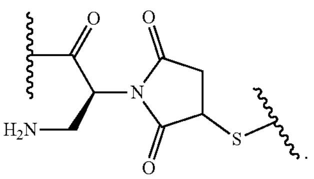

In an embodiment, provided herein is an antibody conjugate according to Formula (C1) or (C2), or a pharmaceutically acceptable salt, solvate, stereoisomer, or tautomer thereof, wherein: COMP is a residue of the antibody; and R comprises a divalent residue of a non-natural amino acid. In an embodiment, provided herein is an antibody conjugate according to Formula (C1) or (C2), or a pharmaceutically acceptable salt, solvate, stereoisomer, or tautomer thereof, wherein: COMP is a residue of the antibody; and R is:

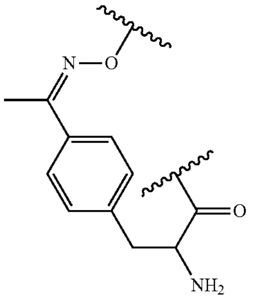

or

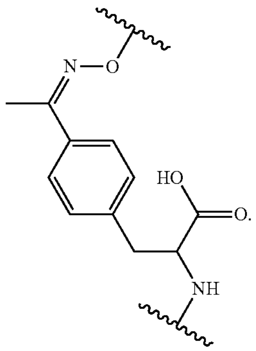

In an embodiment, provided herein is an antibody conjugate according to Formula (C1) or (C2), or a pharmaceutically acceptable salt, solvate, stereoisomer, or tautomer thereof, wherein: COMP is a residue of the antibody; and R comprises an amide linkage. In an embodiment, provided herein is an antibody conjugate according to Formula (C1) or (C2), or a pharmaceutically acceptable salt, solvate, stereoisomer, or tautomer thereof, wherein: COMP is a residue of the antibody; and R is:

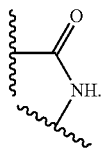 [SMILES: *NC(*)=O]

In an embodiment, provided herein is an antibody conjugate according to Formula (C1) or (C2), or a pharmaceutically acceptable salt, solvate, stereoisomer, or tautomer thereof, wherein: COMP is a residue of the antibody; and R comprises an oxime linkage. In an embodiment, provided herein is an antibody conjugate according to Formula (C1) or (C2), or a pharmaceutically acceptable salt, solvate, stereoisomer, or tautomer thereof, wherein: COMP is a residue of the antibody; and R is:

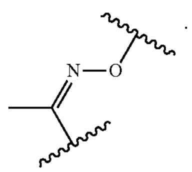 [SMILES: *O/N=C(\*)C]

In an aspect, provided herein is an antibody conjugate comprising a payload, described herein, and an optional linker, described herein, linked to an antibody chain according to Formula (C1) or (C2), or a pharmaceutically acceptable salt, solvate, stereoisomer, or tautomer thereof, wherein COMP is a residue of the antibody chain. In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R comprises a triazole ring or fused cyclic group comprising a triazole ring. In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R is:

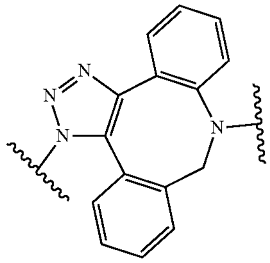

or

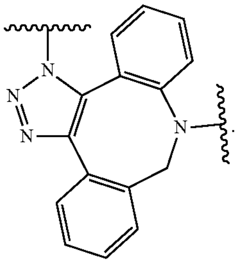

In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R comprises a fused bicyclic ring, wherein the fused bicyclic ring has at least two adjacent nitrogen atoms in the ring. In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R is:

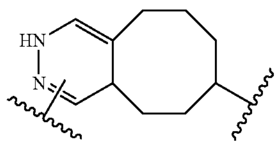

or

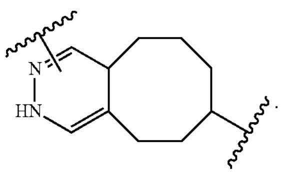

In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R comprises a sulfur linkage. In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R is:

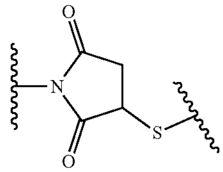

,

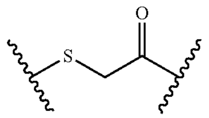

,

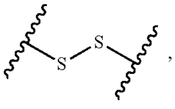

,

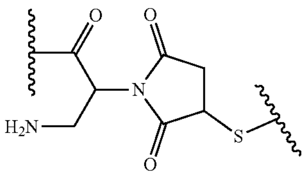

, or

-continued

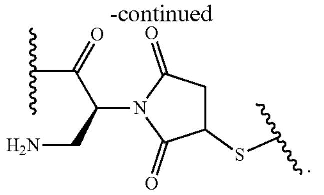

In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R comprises a divalent residue of a non-natural amino acid. In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R is:

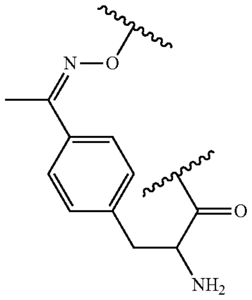

or

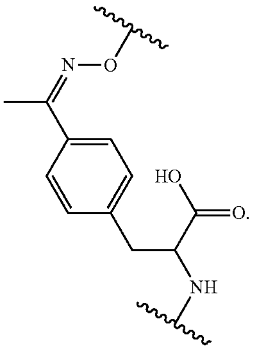

In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R comprises an amide linkage. In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R is:

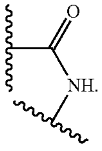

In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R comprises an amide linkage. In an embodiment, provided herein is an antibody conjugate according to Formula (C1) or (C2), or a pharmaceutically acceptable salt, solvate, stereoisomer, or tautomer thereof, wherein: COMP is a residue of the antibody chain; and R is:

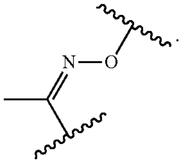 [SMILES: *O/N=C(\*)C]

(b) Conjugates

In an embodiment, provided herein is a conjugate according to any of the following formulas, where COMP indicates a residue of the anti-Tissue Factor antibody and PAY indicates a payload moiety:

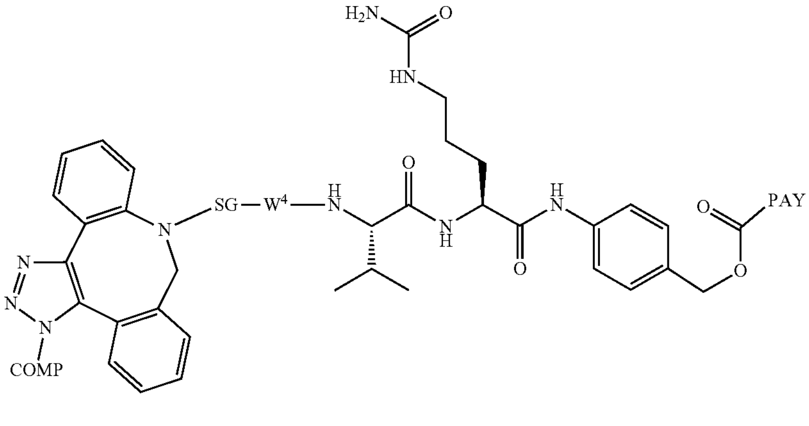

-continued
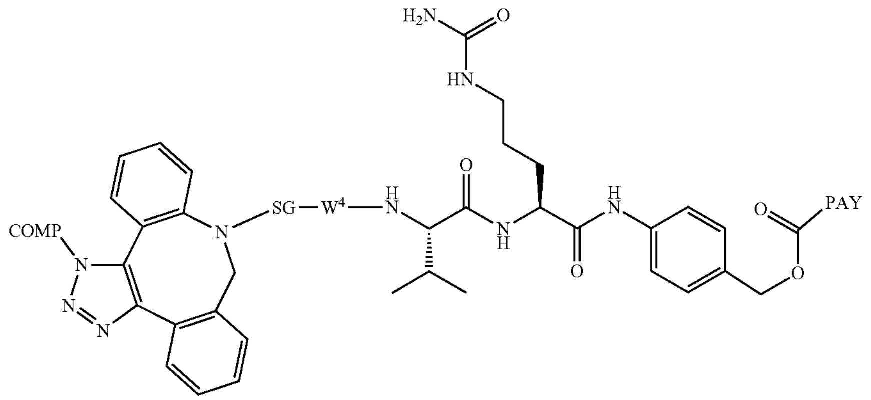
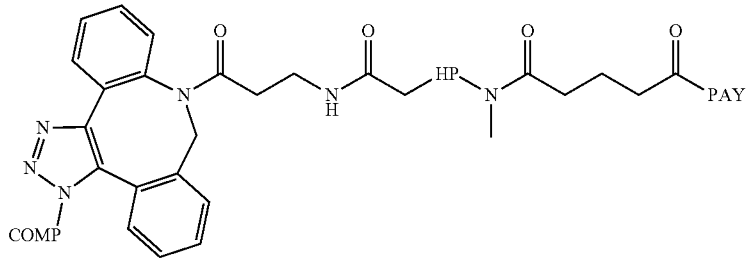
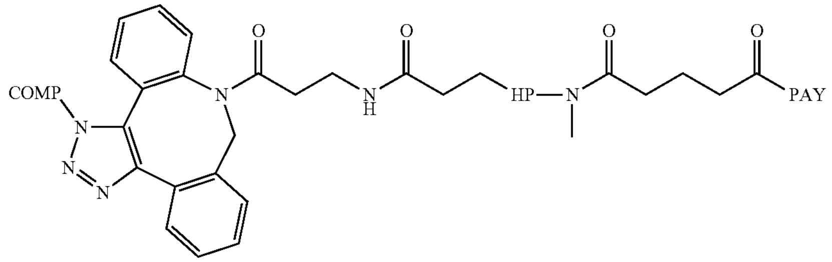
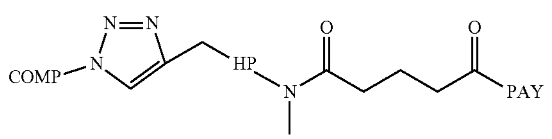
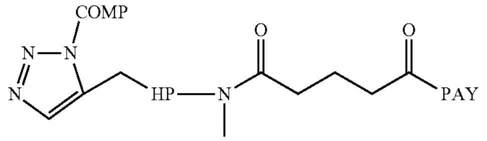
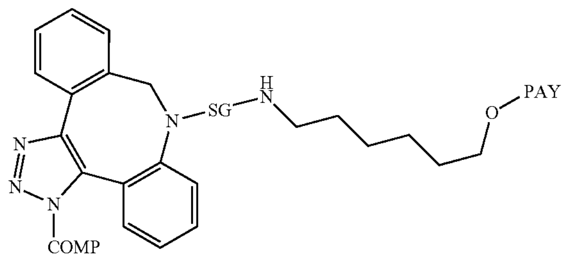
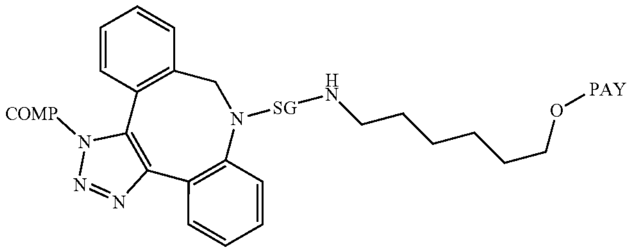
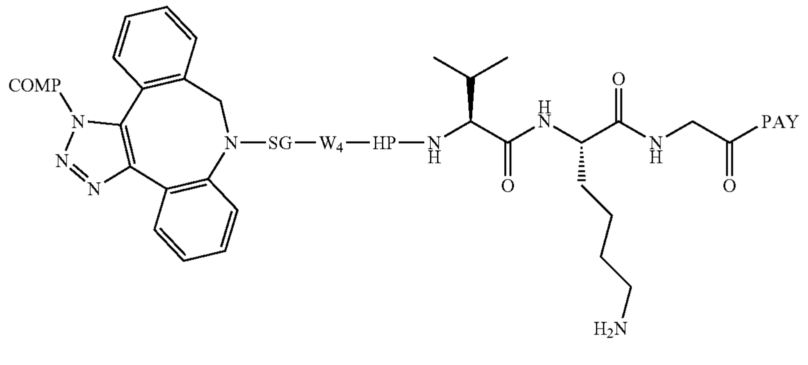

-continued
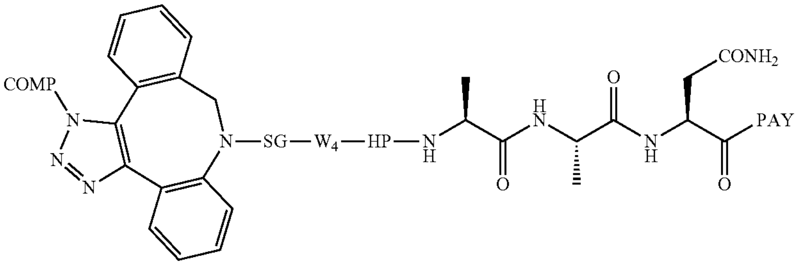
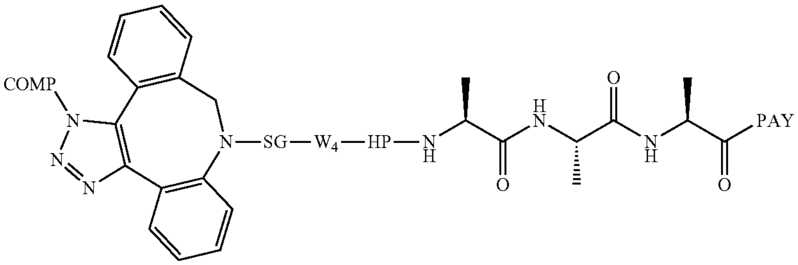
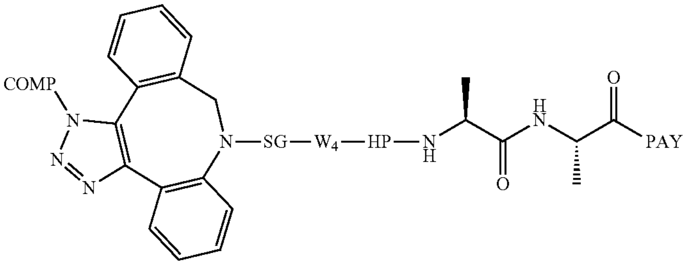
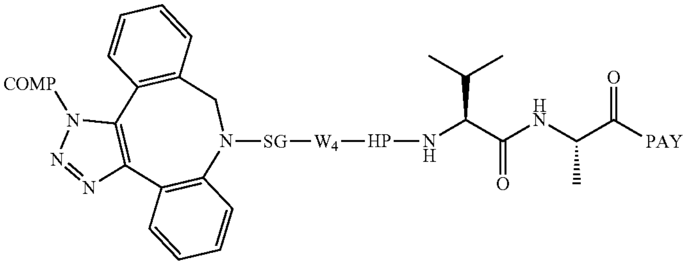
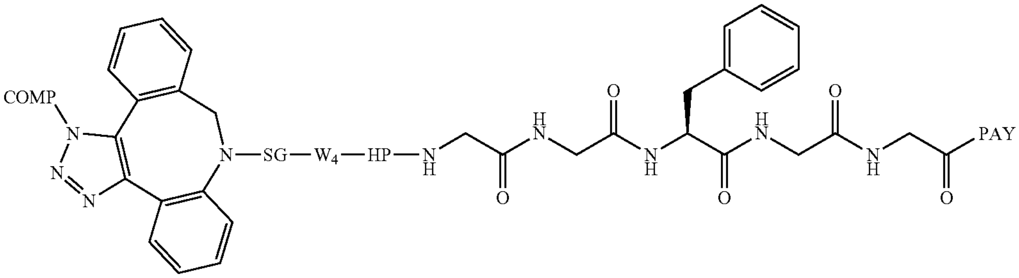
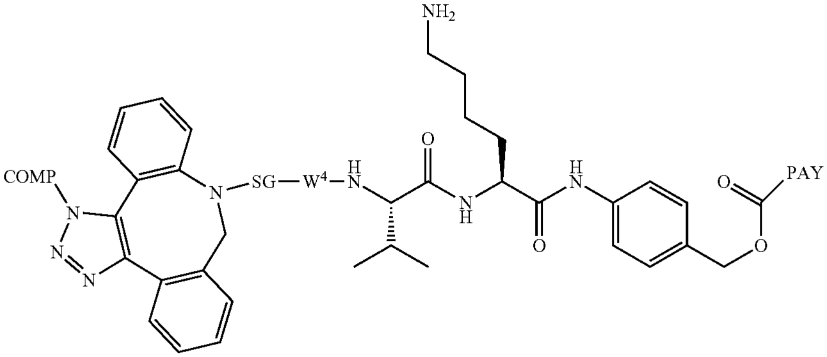

-continued

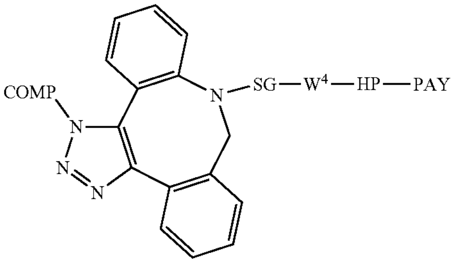

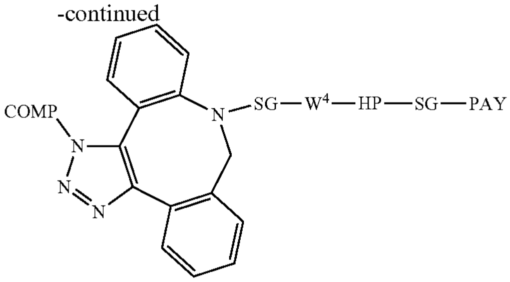

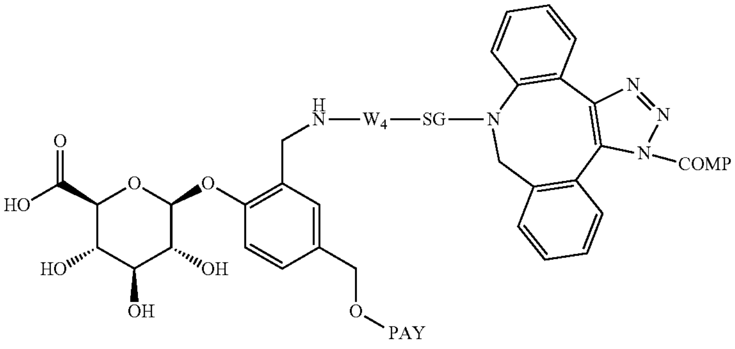

In an embodiment, provided herein is a conjugate according to any of the following formulas, where COMP indicates a residue of the anti-Tissue Factor antibody and PAY indicates a payload moiety:

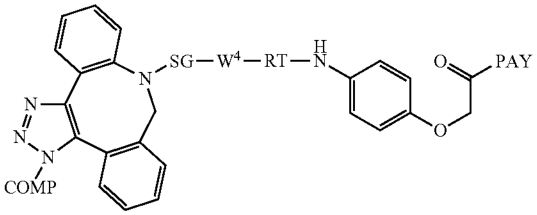

or

-continued

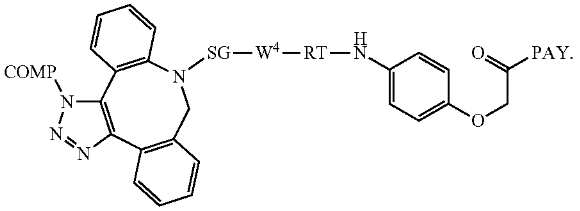

In an embodiment, provided herein is a conjugate according to any of the following formulas, where COMP indicates a residue of the anti-Tissue Factor antibody and PAY indicates a payload moiety:

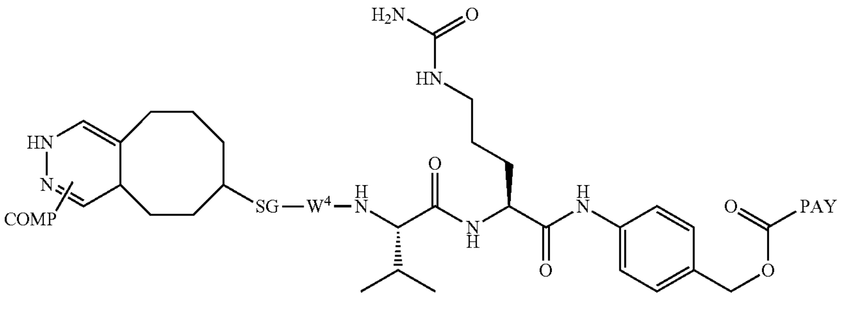

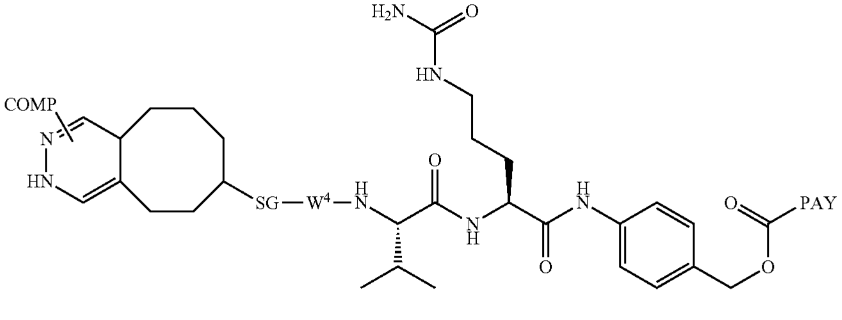

-continued
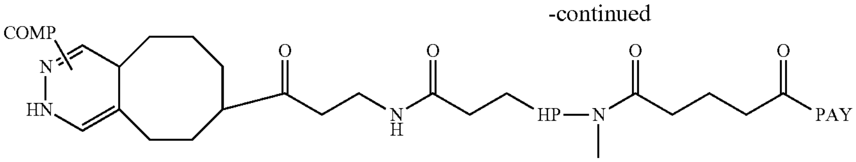
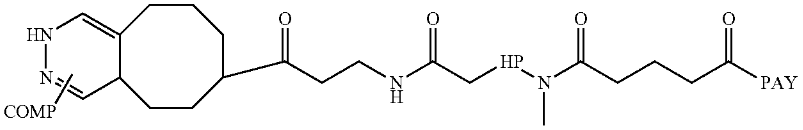
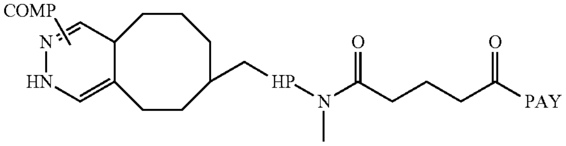
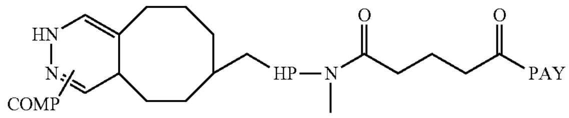
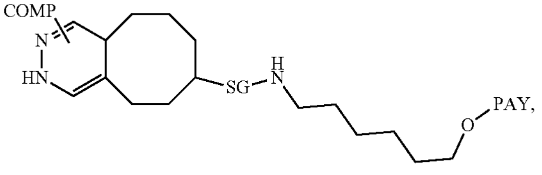
or
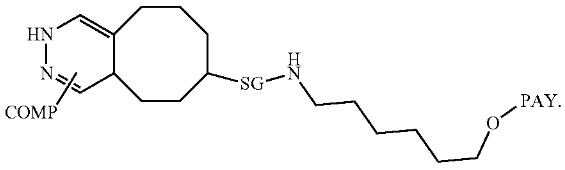
In an embodiment, provided herein is a conjugate according to any of Formulas 101a-104b, where COMP indicates a residue of the anti-Tissue Factor antibody and PAY indicates a payload moiety:
(101a)
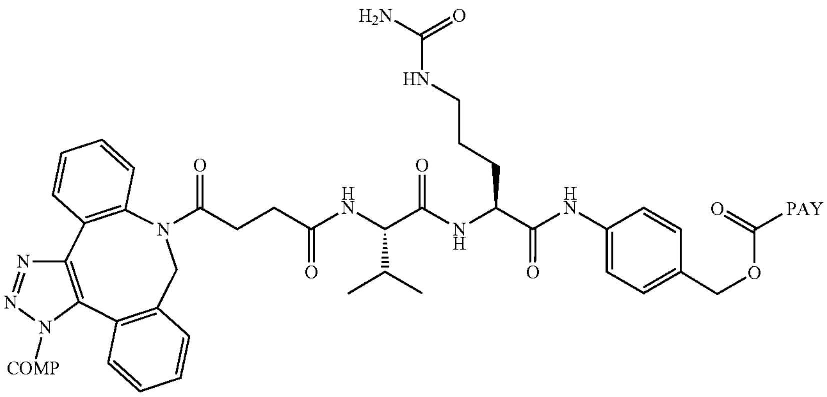
(101b)
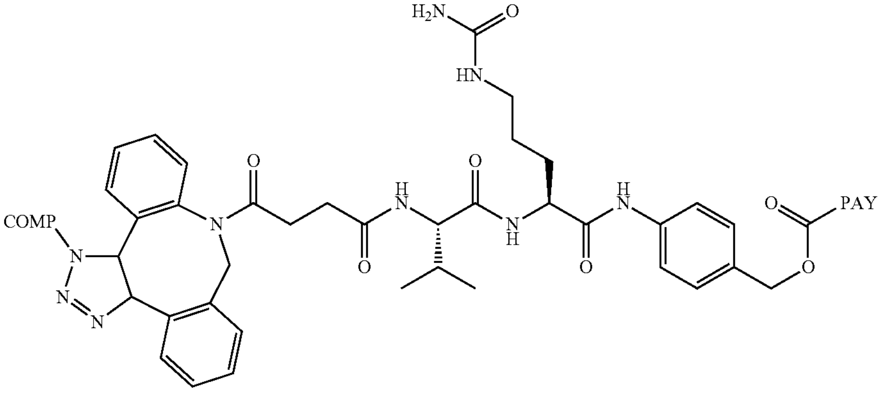

-continued (102a)

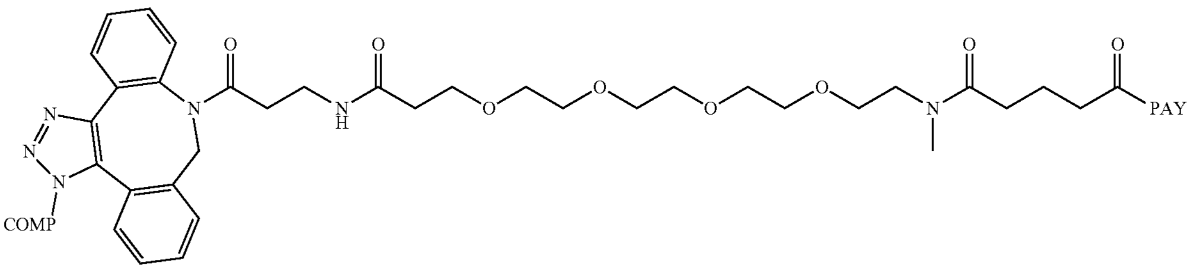

(102b)

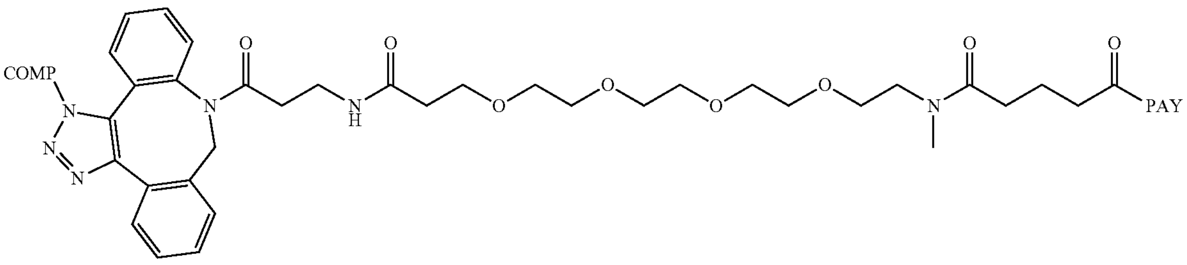

(103a)

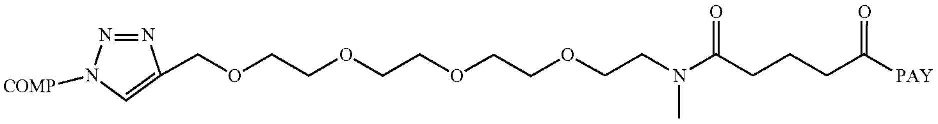

(103b)

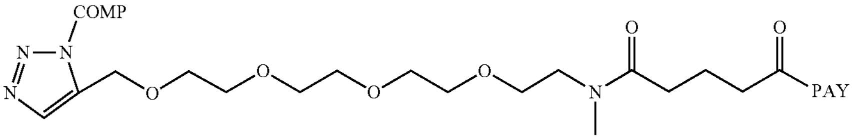

(104a)

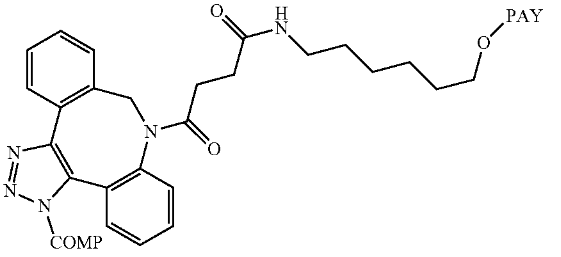

(104b)

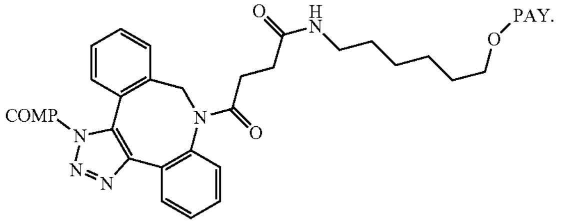

In any of the foregoing embodiments, the conjugate comprises n2 number of PAY moieties, wherein n2 is an integer from 1 to 10. In some embodiments, n2 is 2. In some embodiments, n2 is 3. In some embodiments, n2 is 4. In some embodiments, n2 is 5. In some embodiments, n2 is 6. In some embodiments, n2 is 7. In some embodiments, n2 is 8. In some embodiments, n2 is 9. In some embodiments, n2 is 10.

In some embodiments, provided herein are anti-Tissue Factor conjugates comprising a modified hemiasterlin and linker as described, for example, in PCT Publication No. WO 2016/123582. For example, the conjugate can have a structure comprising any of Formulas 1000-1000b, 1001-1001b, 1002-1002b, and I-XIXb-2, 101-111b, or 1-8b as described in PCT Publication No. WO 2016/123582. Examples of conjugates comprising a modified hemiasterlin and linker are provided below.

In some embodiments, provided is a conjugate of Formula (I)

(I)

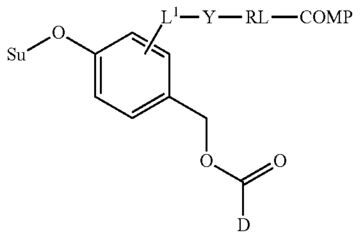

or a pharmaceutically acceptable salt thereof, wherein

COMP is a residue of an anti-Tissue Factor antibody provided herein;

$L^1$ is $—C_{1-6}$ alkylene-;

Y is $—X^1—C_{1-6}$ alkylene-$[X^1—C_{1-6}$ alkylene$]_n$-$[X^1]_p—$, $—X^1—C_{2-6}$ alkenylene-$[X^1—C_{2-6}$ alkenylene$]_n$-

$[X^1]_p$—, —$X^1$—$C_{2-6}$ alkynylene-[$X^1$—$C_{2-6}$ alkynylene]$_n$-[$X^1$]$_p$—, wherein at least one alkylene, alkenylene or alkynylene in Y is substituted with one or more substituents selected from $R^{50}$; and wherein the alkylene, alkenylene, or alkynylene in Y is optionally substituted with one or more substituents selected from $R^{51}$;

$R^{50}$ is —$C_{1-6}$ alkylene-$X^2$—[$C_{1-6}$ alkylene]$_m$-POLY, —$C_{2-6}$ alkenylene-$X^2$—[$C_{2-6}$ alkenylene]$_m$-POLY, or —$C_{2-6}$ alkynylene-$X^2$—[$C_{2-6}$ alkynylene]$_m$-POLY, wherein each alkylene, alkenylene or alkynylene of $R^{50}$ is optionally substituted with one or more substituents selected from halogen, —CN, —$NO_2$, —OH, —$N(R^{10})_2$, —$C(O)N(R^{10})_2$, —C(O)—, —C(S)—, —$C(O)OCH_2C_6H_5$, —$NHC(O)OCH_2C_6H_5$, $C_{1-10}$ alkyl, $C_{2-10}$ alkenyl, $C_{2-10}$ alkynyl, $C_{3-12}$ carbocycle, 3- to 12-membered heterocycle, and $C_{1-10}$ haloalkyl;

$R^{51}$ is independently selected from halogen, —CN, —$NO_2$, —OH, —$N(R^{10})_2$, —$C(O)N(R^{10})_2$, —C(O)—, —C(S)—, —$C(O)OCH_2C_6H_5$, —$NHC(O)OCH_2C_6H_5$, $C_{1-10}$ alkyl, $C_{2-10}$ alkenyl, $C_{2-10}$ alkynyl, $C_{3-12}$ carbocycle, 3- to 12-membered heterocycle, and $C_{1-10}$ haloalkyl;

$X^1$ and $X^2$ are independently selected from —C(O)— and —$N(R^{10})C(O)$—;

$R^{10}$ is independently selected at each occurrence from hydrogen, $C_{1-10}$ alkyl, $C_{2-10}$ alkenyl, $C_{2-10}$ alkynyl, $C_{3-12}$ carbocycle, 3- to 12-membered heterocycle, and $C_{1-10}$ haloalkyl;

POLY is a water-soluble polymer;

n is an integer selected from zero, one, two, and three;

m is an integer selected from zero and one;

p is an integer selected from zero and one;

Su is a hexose form of a monosaccharide;

D is a drug moiety; and

RL is a reactive group residue.

In some embodiments, provided is a conjugate of Formula (II)

(II)

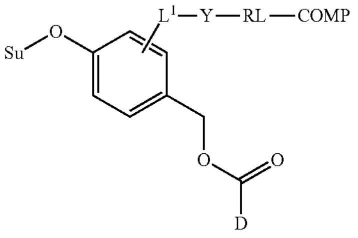

or a pharmaceutically acceptable salt thereof, wherein

COMP is a residue of an anti-Tissue Factor antibody provided herein;

$L^1$ is —$C_{1-6}$ alkylene-;

Y is —$X^1$—$C_{1-6}$ alkylene-[$X^1$—$C_{1-6}$ alkylene]$_n$-$X^1$—, —$X^1$—$C_{2-6}$ alkenylene-[$X^1$—$C_{2-6}$ alkenylene]$_n$-$X^1$—, —$X^1$—$C_{2-6}$ alkynylene-[$X^1$—$C_{2-6}$ alkynylene]$_n$-$X^1$—, wherein at least one alkylene, alkenylene or alkynylene in Y is substituted with one or more substituents selected from $R^{50}$;

$R^{50}$ is —$C_{1-6}$ alkylene-$X^2$—[$C_{1-6}$ alkylene]$_m$-POLY, —$C_{2-6}$ alkenylene-$X^2$—[$C_{2-6}$ alkenylene]$_m$-POLY, or —$C_{2-6}$ alkynylene-$X^2$—[$C_{2-6}$ alkynylene]$_m$-POLY, wherein each alkylene, alkenylene or alkynylene of $R^{50}$ is optionally substituted with one or more substituents selected from halogen, —CN, —$NO_2$, —OH, —$N(R^{10})_2$, —$C(O)N(R^{10})_2$, —C(O)—, —C(S)—, —$C(O)OCH_2C_6H_5$, —$NHC(O)OCH_2C_6H_5$, $C_{1-10}$ alkyl, $C_{2-10}$ alkenyl, $C_{2-10}$ alkynyl, $C_{3-12}$ carbocycle, 3- to 12-membered heterocycle, and $C_{1-10}$ haloalkyl;

$X^1$ and $X^2$ are independently selected from —C(O)— and —$N(R^{10})C(O)$—;

$R^{10}$ is independently selected at each occurrence from hydrogen, $C_{1-10}$ alkyl, $C_{2-10}$ alkenyl, $C_{2-10}$ alkynyl, $C_{3-12}$ carbocycle, 3- to 12-membered heterocycle, and $C_{1-10}$ haloalkyl;

POLY is a water-soluble polymer;

n is an integer selected from zero, one, two, and three;

m is an integer selected from zero and one;

Su is a hexose form of a monosaccharide;

D is a drug moiety; and

RL is a reactive group residue.

In some embodiments, provided is a conjugate of Formula (IIA)

(IIA)

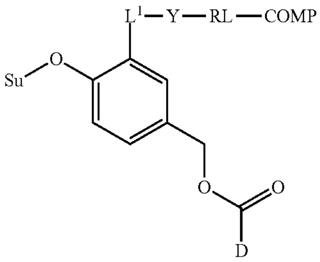

or a pharmaceutically acceptable salt thereof.

In some embodiments, the compound of Formula (II) is according to Formula (IIB)

(IIB)

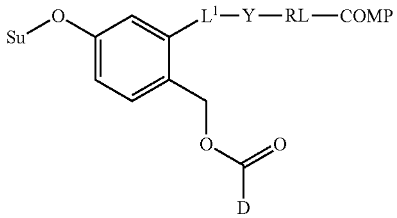

or a pharmaceutically acceptable salt thereof.

In some embodiments of Formula (I), (II), (IIA), or (IIB), $L^1$ is —$C_{1-3}$ alkylene-. In some embodiments, $L^1$ is —$CH_2$—. In some embodiments of Formula (I), (II), (IIA), or (IIB), $L^1$ is —$CH_2CH_2$—. In some embodiments, $L^1$ is —$CH_2CH_2CH_2$—.

In some embodiments of Formula (I), including any of the foregoing, p is 0. In some embodiments of Formula (I), including any of the foregoing, p is 1.

In some embodiments of Formula (I), (II), (IIA), or (IIB), including any of the foregoing, Y is —$X^1$—$C_{1-6}$ alkylene-[$X^1$—$C_{1-6}$ alkylene]$_n$-$X^1$—, wherein at least one alkylene in Y is substituted with one or more substituents selected from $R^{50}$. In some embodiments of Formula (I), (II), (IIA), or (IIB), including any of the foregoing, Y is —$X^1$—$C_{1-6}$ alkylene-[$X^1$—$C_{1-6}$ alkylene]$_n$-, wherein at least one alkylene in Y is substituted with one or more substituents selected from $R^{50}$. In some embodiments of Formula (I), (II), (IIA), or (IIB), including any of the foregoing, Y is —$X^1$—$C_{2-6}$ alkenylene-[$X^1$—$C_{2-6}$ alkenylene]$_n$-$X^1$— wherein at least one alkenylene in Y is substituted with one or more substituents selected from $R^{50}$. In some embodiments of Formula (I), (II), (IIA), or (IIB), including any of the foregoing, Y is —$X^1$—$C_{2-6}$ alkenylene-[$X^1$—$C_{2-6}$ alkenylene]$_n$- wherein at least one alkenylene in Y is substituted with one or more substituents selected from $R^{50}$. In some embodiments of Formula (I), (II), (IIA), or (IIB), including any of the foregoing, Y is —$X^1$—$C_{2-6}$ alkynylene-[$X^1$—$C_{2-6}$ alkynylene]$_n$-$X^1$— wherein at least one alkynylene in Y is substituted with one or more substituents selected from $R^{50}$. In some embodiments of Formula (I), (II), (IIA), or (IIB), including any of the foregoing, Y is —$X^1$—$C_{2-6}$ alkynylene-[$X^1$—$C_{2-6}$ alkynylene]$_n$- wherein at least one alkynylene in Y is substituted with one or more substituents selected from $R^{50}$. In some embodiments of Formula (I), (II), (IIA), or (IIB), including any of the foregoing, n is zero. In some embodiments of Formula (I), (II), (IIA), or (IIB), n is one. In some embodiments of Formula (I), (II), (IIA), or (IIB), including any of the foregoing, n is two. In some embodiments, including any of the foregoing, n is three.

In certain embodiments of Formula (I), (II), (IIA), or (IIB), including any of the foregoing, Y is —$X^1$—$C_{1-4}$ alkylene-[$X^1$—$C_{1-4}$ alkylene]$_n$-$X^1$—, wherein at least one alkylene in Y is substituted with one or more substituents selected from $R^{50}$. In some embodiments of Formula (I), (II), (IIA), or (IIB), including any of the foregoing, n is zero. In some embodiments of Formula (I), (II), (IIA), or (IIB), including any of the foregoing, n is one. In some embodiments of Formula (I), (II), (IIA), or (IIB), including any of the foregoing, n is two. In some embodiments of Formula (I), (II), (IIA), or (IIB), including any of the foregoing, n is three.

In certain embodiments of Formula (I), (II), (IIA), or (IIB), including any of the foregoing, Y is —$X^1$—$C_{1-4}$ alkylene-$X^1$—$C_{1-4}$ alkylene-$X^1$—$C_{1-4}$ alkylene-$X^1$—$C_{1-4}$ alkylene-$X^1$—, wherein at least one alkylene in Y is substituted with one or more substituents selected from $R^{50}$. In certain embodiments of Formula (I), (II), (IIA), or (IIB), including any of the foregoing, Y is —$X^1$—$C_{1-4}$ alkylene-$X^1$—$C_{1-4}$ alkylene-$X^1$—$C_{1-4}$ alkylene-$X^1$—, wherein at least one alkylene in Y is substituted with one or more substituents selected from $R^{50}$. In certain embodiments of Formula (I), (II), (IIA), or (IIB), including any of the foregoing, Y is —$X^1$—$C_{1-4}$ alkylene-$X^1$—$C_{1-4}$ alkylene-$X^1$—, wherein at least one alkylene in Y is substituted with one or more substituents selected from $R^{50}$.

In certain embodiments of Formula (I), (II), (IIA), or (IIB), including any of the foregoing, $R^{50}$ is —$C_{1-6}$ alkylene-$X^2$—[$C_{1-6}$ alkylene]$_m$-POLY, wherein each alkylene of $R^{50}$ is optionally substituted with one or more substituents selected from halogen, —CN, —$NO_2$, —OH, —$N(R^{10})_2$, —$C(O)N(R^{10})_2$, —C(O)—, —C(S)—, —$C(O)OCH_2C_6H_5$, —$NHC(O)OCH_2C_6H_5$, $C_{1-10}$ alkyl, $C_{2-10}$ alkenyl, $C_{2-10}$ alkynyl, $C_{3-12}$ carbocycle, 3- to 12-membered heterocycle, and $C_{1-10}$ haloalkyl. In some embodiments of Formula (I), (II), (IIA), or (IIB), including any of the foregoing, $R^{50}$ is —$C_{1-4}$ alkylene-$X^2$—[$C_{1-4}$ alkylene]$_m$-POLY, wherein each alkylene of $R^{50}$ is optionally substituted with one or more substituents selected from halogen, —CN, —$NO_2$, —OH, —$N(R^{10})_2$, —$C(O)N(R^{10})_2$, —C(O)—, —C(S)—, —$C(O)OCH_2C_6H_5$, —$NHC(O)OCH_2C_6H_5$, $C_{1-10}$ alkyl, $C_{2-10}$ alkenyl, $C_{2-10}$ alkynyl, $C_{3-12}$ carbocycle, 3- to 12-membered heterocycle, and $C_{1-10}$ haloalkyl. In some embodiments of Formula (I), (II), (IIA), or (IIB), including any of the foregoing, each alkylene of $R^{50}$ is optionally substituted with one or more substituents selected from halogen, —OH, —$N(R^{10})_2$, —$C(O)N(R^{10})_2$, —C(O)—, $C_{1-10}$ alkyl, $C_{2-10}$ alkenyl, $C_{2-10}$ alkynyl, $C_{3-12}$ carbocycle, 3- to 12-membered heterocycle, and $C_{1-10}$ haloalkyl. In some embodiments of Formula (I), (II), (IIA), or (IIB), including any of the foregoing, m is zero. In some embodiments of Formula (I), (II), (IIA), or (IIB), including any of the foregoing, m is one.

In certain embodiments of Formula (I), (II), (IIA), or (IIB), including any of the foregoing, $R^{50}$ is —$C_{2-6}$ alkenylene-$X^2$—[$C_{2-6}$ alkenylene]$_m$-POLY, wherein each alkenylene of $R^{50}$ is optionally substituted with one or more substituents selected from halogen, —CN, —$NO_2$, —OH, —$N(R^{10})_2$, —$C(O)N(R^{10})_2$, —C(O)—, —C(S)—, —$C(O)OCH_2C_6H_5$, —$NHC(O)OCH_2C_6H_5$, $C_{1-10}$ alkyl, $C_{2-10}$ alkenyl, $C_{2-10}$ alkynyl, $C_{3-12}$ carbocycle, 3- to 12-membered heterocycle, and $C_{1-10}$ haloalkyl. In some embodiments of Formula (I), (II), (IIA), or (IIB), including any of the foregoing, m is zero. In some embodiments of Formula (I), (II), (IIA), or (IIB), including any of the foregoing, m is one.

In certain embodiments of Formula (I), (II), (IIA), or (IIB), including any of the foregoing, $R^{50}$ is —$C_{2-6}$ alkynylene-$X^2$—[$C_{2-6}$ alkynylene]$_m$-POLY, wherein each alkynylene of $R^{50}$ is optionally substituted with one or more substituents selected from halogen, —CN, —$NO_2$, —OH, —$N(R^{10})_2$, —$C(O)N(R^{10})_2$, —C(O)—, —C(S)—, —$C(O)OCH_2C_6H_5$, —$NHC(O)OCH_2C_6H_5$, $C_{1-10}$ alkyl, $C_{2-10}$ alkenyl, $C_{2-10}$ alkynyl, $C_{3-12}$ carbocycle, 3- to 12-membered heterocycle, and $C_{1-10}$ haloalkyl. In come embodiments of Formula (I), (II), (IIA), or (IIB), including any of the foregoing, m is zero. In some embodiments of Formula (I), (II), (IIA), or (IIB), including any of the foregoing, m is one.

In certain embodiments of Formula (I), (II), (IIA), or (IIB), including any of the foregoing, POLY is polyethylene glycol (PEG), methoxypolyethylene glycol (mPEG), poly(propylene glycol) (PPG), copolymers of ethylene glycol and propylene glycol, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazolines (POZ), poly(N-acryloylmorpholine), polysarcosine, or a combination thereof. In some embodiments of Formula (I), (II), (IIA), or (IIB), including any of the foregoing, POLY is polyethylene glycol (PEG). In some embodiments of Formula (I), (II), (IIA), or (IIB), including any of the foregoing, POLY is methoxypolyethylene glycol (mPEG). In some embodiments of Formula (I), (II), (IIA), or (IIB), including any of the foregoing, POLY is poly(propylene glycol) (PPG). In some embodiments, POLY is copolymers of ethylene glycol and propylene glycol. In some embodiments of Formula (I), (II), (IIA), or (IIB), including any of the foregoing, POLY is poly(oxyethylated polyol). In some embodiments of Formula (I), (II), (IIA), or (IIB), including any of the foregoing, POLY is poly(olefinic alcohol). In some embodiments, POLY is poly(vinylpyrrolidone). In some embodiments of Formula (I), (II), (IIA), or (IIB), including any of the foregoing, POLY is poly(hydroxyalkylmethacrylamide). In some embodiments of Formula (I), (II), (IIA), or (IIB), including any of the foregoing, POLY is poly(hydroxyalkylmethacrylate). In some embodiments of Formula (I), (II), (IIA), or (IIB), including any of the foregoing, POLY is poly(saccharides). In some embodiments of Formula (I), (II), (IIA), or (IIB), including any of the foregoing, POLY is poly(α-hydroxy acid). In some embodiments of Formula (I), (II), (IIA), or (IIB), including any of the foregoing, POLY is poly(vinyl alcohol). In some embodiments of Formula (I), (II), (IIA), or (IIB), including any of the foregoing, POLY is polyphosphazene. In some embodiments of Formula (I), (II), (IIA), or (IIB), including any of the foregoing, POLY is polyoxazolines (POZ). In some embodiments of Formula (I), (II), (IIA), or (IIB), including any of the foregoing, POLY is poly(N-acryloylmorpholine). In some embodiments of Formula (I), (II), (IIA), or (IIB), including any of the foregoing, POLY is polysarcosine. In some embodiments of Formula (I), (II), (IIA), or (IIB), including any of the foregoing, POLY is a nonpeptidic, water-soluble polymer. In certain embodiments of Formula (I), (II), (IIA), or (IIB), including any of the foregoing, POLY includes a polyethylene glycol (PEG) or methoxypolyethylene glycol (mPEG). In certain embodiments of Formula (I), (II), (IIA), or (IIB), including any of the foregoing, POLY is

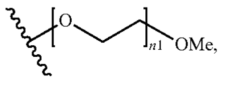

wherein  represents attachment to the remainder of the compound, and wherein n1 is an integer from one to twenty. In certain embodiments of Formula (I), (II), (IIA), or (IIB), including any of the foregoing, n1 is an integer between five to fifteen. In some embodiments of Formula (I), (II), (IIA), or (IIB), including any of the foregoing, n1 is one. In some embodiments of Formula (I), (II), (IIA), or (IIB), including any of the foregoing, n1 is two. In some embodiments of Formula (I), (II), (IIA), or (IIB), including any of the foregoing, n1 is three. In some embodiments of Formula (I), (II), (IIA), or (IIB), including any of the foregoing, n1 is four. In some embodiments of Formula (II), (IIA), or (IIB), including any of the foregoing, n1 is five. In some embodiments of Formula (I), (II), (IIA), or (IIB), including any of the foregoing, n1 is six. In some embodiment of Formula (I), (II), (IIA), or (IIB) s, n1 is seven. In some embodiments of Formula (I), (II), (IIA), or (IIB), including any of the foregoing, n1 is eight. In some embodiments of Formula (I), (II), (IIA), or (IIB), including any of the foregoing, n1 is nine. In some embodiments of Formula (I), (II), (IIA), or (IIB), including any of the foregoing, n1 is ten. In some embodiments of Formula (I), (II), (IIA), or (IIB), including any of the foregoing, n1 is eleven. In some embodiments of Formula (I), (II), (IIA), or (IIB), including any of the foregoing, n1 is twelve. In some embodiments of Formula (I), (II), (IIA), or (IIB), including any of the foregoing, n1 is thirteen. In some embodiments of Formula (I), (II), (IIA), or (IIB), including any of the foregoing, n1 is fourteen. In some embodiments of Formula (I), (II), (IIA), or (IIB), including any of the foregoing, n1 is fifteen. In some embodiments of Formula (I), (II), (IIA), or (IIB), including any of the foregoing, n1 is sixteen. In some embodiments of Formula (I), (II), (IIA), or (IIB), including any of the foregoing, n1 is seventeen. In some embodiments of Formula (I), (II), (IIA), or (IIB), n1 is eighteen. In some embodiments of Formula (I), (II), (IIA), or (IIB), including any of the foregoing, n1 is nineteen. In some embodiments of Formula (II), (IIA), or (IIB), including any of the foregoing, n1 is twenty. In some embodiments of Formula (I), (II), (IIA), or (IIB), including any of the foregoing, n1 is twenty-one. In some embodiments of Formula (I), (II), (IIA), or (IIB), including any of the foregoing, n1 is twenty-two. In some embodiments of Formula (I), (II), (IIA), or (IIB), including any of the foregoing, n1 is twenty-three. In some embodiments of Formula (I), (II), (IIA), or (IIB), including any of the foregoing, n1 is twenty-four. In some embodiments of Formula (I), (II), (IIA), or (IIB), including any of the foregoing, n1 is twenty-five. In some embodiments of Formula (I), (II), (IIA), or (IIB), including any of the foregoing, n1 is twenty-six. In some embodiments of Formula (I), (II), (IIA), or (IIB), including any of the foregoing, n1 is twenty-seven. In some embodiments of Formula (I), (II), (IIA), or (IIB), including any of the foregoing, n1 is twenty-eight. In some embodiments of Formula (I), (II), (IIA), or (IIB), including any of the foregoing, n1 is twenty-nine. In some embodiments of Formula (I), (II), (IIA), or (IIB), including any of the foregoing, n1 is thirty.

In certain embodiments, RL includes an alkyne, cyclooctyne, a strained alkene, a tetrazine, an amine, methylcyclopropene, a thiol, a para-acetyl-phenylalanine residue, an oxyamine, a maleimide, or an azide. In some embodiments, RL includes an alkyne. In some embodiments, RL includes an cyclooctyne. In some embodiments, RL includes a strained alkene. In some embodiments, RL includes a tetrazine. In some embodiments, RL includes an amine. In some embodiments, RL includes an methylcyclopropene. In some embodiments, RL includes a thiol. In some embodiments, RL includes a para-acetyl-phenylalanine residue. In some embodiments, RL includes an oxyamine. In some embodiments, RL includes a maleimide. In some embodiments, RL includes an azide. In certain embodiments, RL is selected from the group consisting of

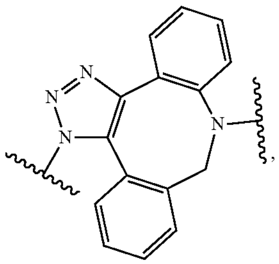,

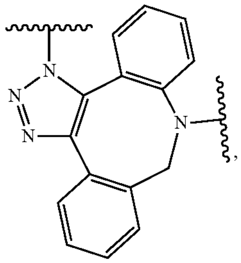,

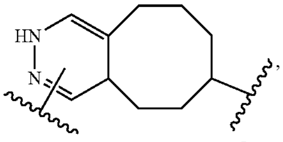,

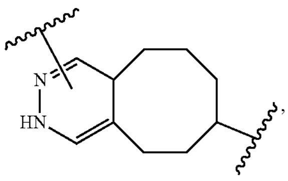,

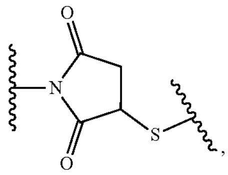,

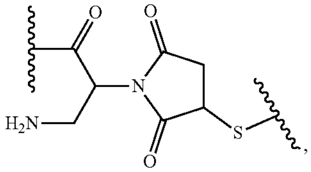,

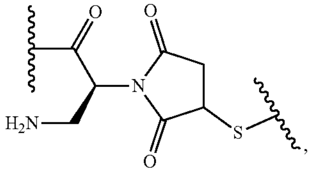,

-continued

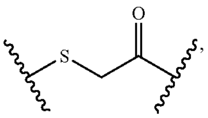

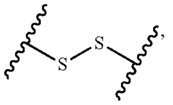

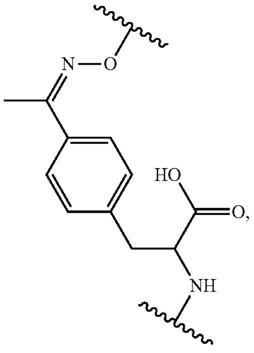

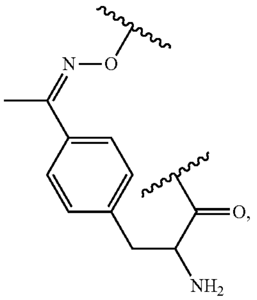

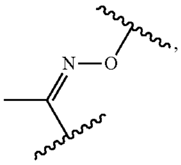

and

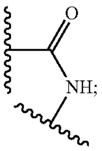

(c) and represents attachment to the remainder of the compound. In some embodiments, RL is

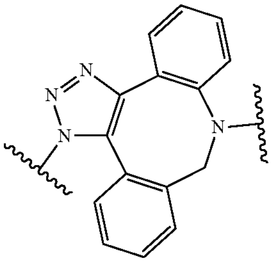

or

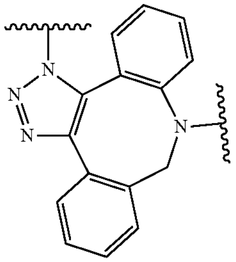

and represents attachment to the remainder of the compound. In one some embodiments, RL is

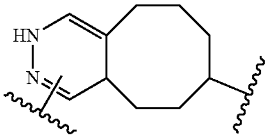

or

-continued

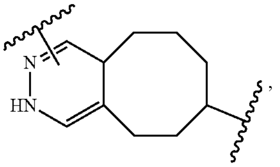

and represents attachment to the remainder of the compound. In some embodiments, RL is

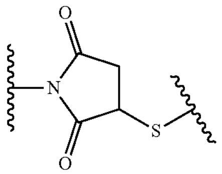 [SMILES: *SC1CC(=O)N(*)C1=O]

and represents attachment to the remainder of the compound. In some embodiments, RL is

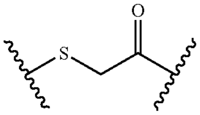 [SMILES: *SCC(*)=O]

and represents attachment to the remainder of the compound. In some embodiments, RL is

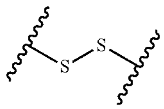 [SMILES: *SS*]

and represents attachment to the remainder of the compound. In some embodiments, RL is

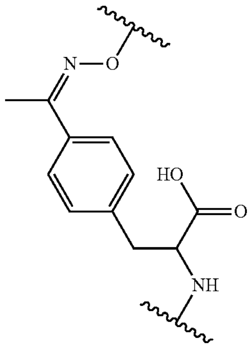

or

-continued

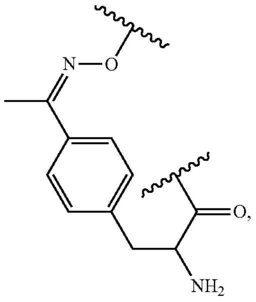

wherein represents attachment to the remainder of the compound. In some embodiments, RL is

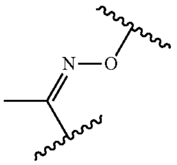 [SMILES: *O/N=C(\*)C]

and represents attachment to the remainder of the compound. In some embodiments, RL is

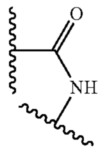

and represents attachment to the remainder of the compound. In some embodiments, RL is

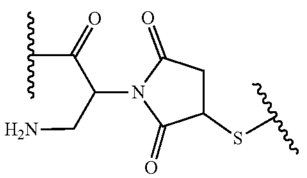

or

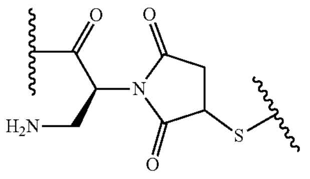

and represents attachment to the remainder of the compound. In some embodiments, Su is a sugar moiety. In some embodiments, Su is a hexose form of a monosaccharide. Su may be a glucuronic acid or mannose residue. In certain embodiments, Su is

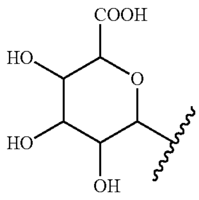

wherein represents attachment to the remainder of the compound. In certain embodiments, Su is

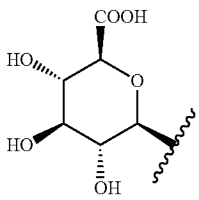

wherein represents attachment to the remainder of the compound.

In one aspect, provided herein is a conjugate of Formula (III):

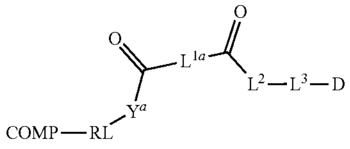

(III)

or a pharmaceutically acceptable salt and/or regioisomer thereof;

wherein $L^{1a}$ is selected from

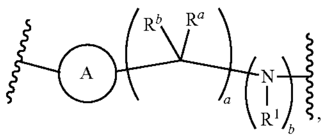

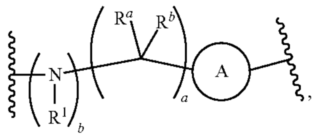

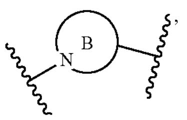

, and

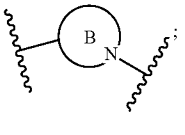

;

Ring A is an optionally substituted bridged, fused, or spirocyclic bicyclic carbocycle, or an optionally substituted bridged, fused, or spirocyclic bicyclic heterocycle, wherein the carbocycle or the heterocycle of Ring A are optionally substituted with one or more substituents selected from alkyl, alkenyl, alkynyl, cycloalkyl, halogen, alkoxy, —CN, —$NO_2$, —OH, —$N(R^2R^3)_2$, —C(O)—, —C(O)N($R^2R^3$)$_2$, —C(O)O$R^2$, aminoalkyl, hydroxyalkyl, haloalkyl, aryl, arylalkyl, heteroaryl, and heteroarylalkyl;

Ring B is an optionally substituted N-linked bridged, fused, or spirocyclic bicyclic heterocycle, wherein Ring B is optionally substituted with one or more substituents selected from alkyl, alkenyl, alkynyl, cycloalkyl, halogen, alkoxy, —CN, —$NO_2$, —OH, —N($R^2R^3$)$_2$, —C(O)—, —C(O)N($R^2R^3$)$_2$, —C(O)O$R^2$, aminoalkyl, hydroxyalkyl, haloalkyl, aryl, arylalkyl, heteroaryl, and heteroarylalkyl;

$R^a$ and $R^b$ are independently selected from hydrogen, alkyl, alkenyl, alkynyl, cycloalkyl, halogen, alkoxy, —CN, —$NO_2$, —OH, —N($R^2R^3$)$_2$, —C(O)N($R^2R^3$)$_2$, —C(O)O$R^2$, aminoalkyl, hydroxyalkyl, haloalkyl, aryl, arylalkyl, heteroaryl, and heteroarylalkyl;

a is an integer independently selected from 0, 1, 2, 3, 4, 5, and 6;

$R^1$ is hydrogen or alkyl optionally substituted with one or more substituents selected from cycloalkyl, halogen, alkoxy, —CN, —$NO_2$, —OH, —N($R^2R^3$)$_2$, —C(O)N($R^2R^3$)$_2$, —C(O)O$R_2$, aryl, and heteroaryl;

$R^2$ and $R^3$ are independently selected from hydrogen, alkyl, cycloalkyl, aryl, arylalkyl, heteroaryl, and heteroarylalkyl;

$Y^a$ is *—C(O)—($CR^aR^b$)$_c$—NH— or *—C(O)—($CR^aR^b$)$_c$—, wherein * represents where $Y^a$ is bound to RL;

c is an integer selected from 1, 2, 3, 4, 5, or 6;

RL is a reactive group residue;

$L^2$ is absent or a linker comprising a hydrophilic polymer residue;

$L^3$ is absent, —C(O)-AA-, —C(O)-AA-Z—($CR^aR^b$)$_a$—Z—($CR^aR^b$)$_a$—C(O)—, —C(O)—Z—($CR^aR^b$)$_a$—C(O)—Z-$L^4$-OC(O)—, —Z-AA-, -AA-, —C(O)—, —C(O)-AA-Z—($CR^aR^b$)$_a$—, -AA-C(O)—, —C(O)—($CR^aR^b$)$_a$—Z—($CR^aR^b$)—Z-AA-C(O)—, —C(O)O-$L^4$-Z—C(O)—($CR^aR^b$)$_a$—Z—C(O)—, -AA-Z—, or —($CR^aR^b$)$_a$—Z-AA-C(O)—;

Z is selected from —N$R^2$— and —O—;

AA is an amino acid residue or a peptide residue;

$L^4$ is

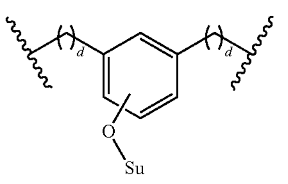

wherein Su is a hexose form of a monosaccharide;

d is an integer independently selected from 1, 2, and 3;

D is a drug moiety;

COMP is a residue of a Tissue Factor antibody; and

 represents attachment to the remainder of the compound.

In certain embodiments, the compound of Formula (III) is a compound of Formula (IIIA):

(IIIA)

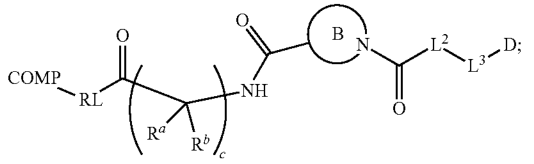

or a pharmaceutically acceptable salt and/or regioisomer thereof;

wherein integer c, RL, $R^a$, $R^b$, Ring B, $L^2$, $L^3$, D, and COMP are as defined herein.

In certain embodiments, the compound of Formula (IIIA) is selected from the following:

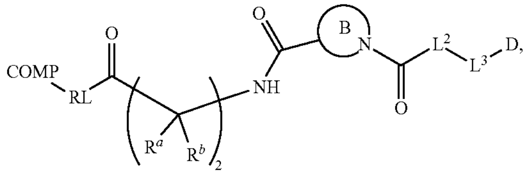

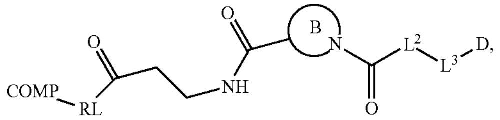

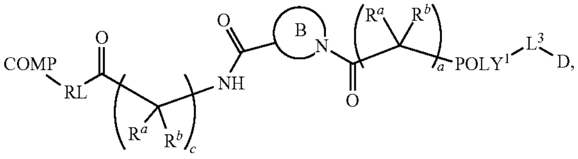

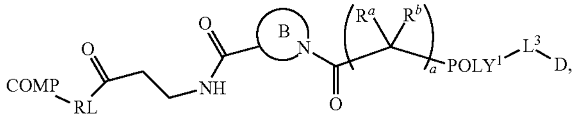

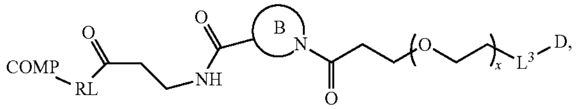

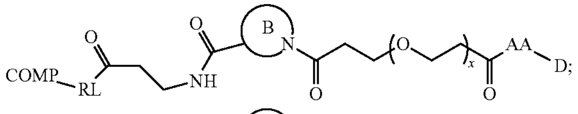

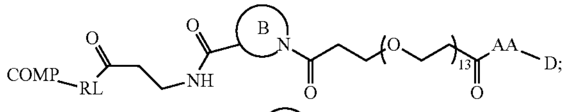

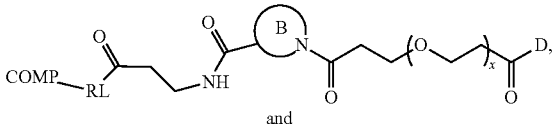

and

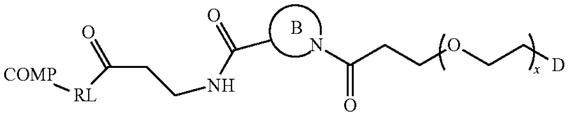

or a pharmaceutically acceptable salt and/or regioisomer thereof.

In certain embodiments, the compound of Formula (III) is a compound of Formula (IIIB):

(IIIB)

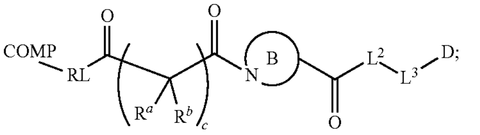

or a pharmaceutically acceptable salt and/or regioisomer thereof;

wherein integer c, RL, $R^a$, $R^b$, Ring B, $L^2$, $L^3$, D, and COMP are as defined herein.

In certain embodiments, the compound of Formula (IIIB) is selected from the following:

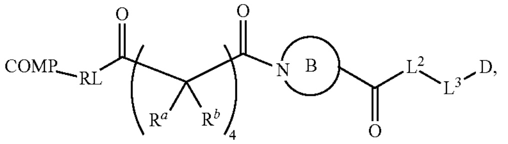

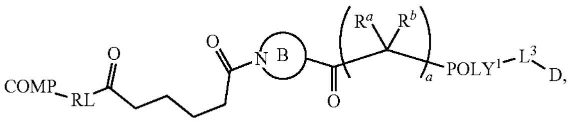

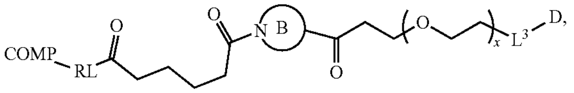

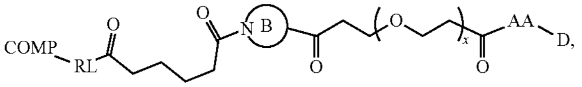

and

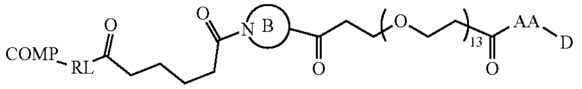

or a pharmaceutically acceptable salt and/or regioisomer thereof.

In certain embodiments, the compound of Formula (III) is a compound of Formula (IIIC):

(IIIC)

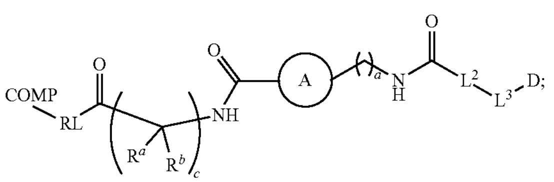

or a pharmaceutically acceptable salt and/or regioisomer thereof;

wherein integer a, integer c, RL, $R^a$, $R^b$, Ring A, $L^2$, $L^3$, D, and COMP are as defined herein.

In certain embodiments, the compound of Formula (IIIC) is selected from the following:

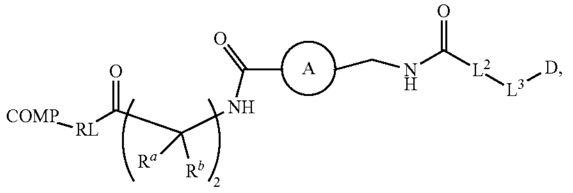

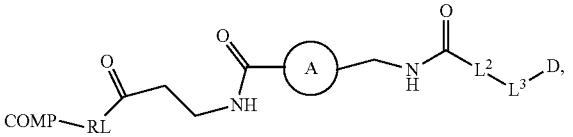

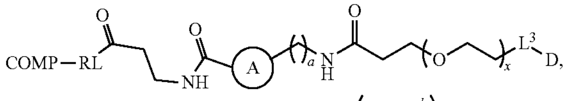

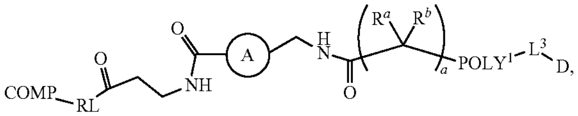

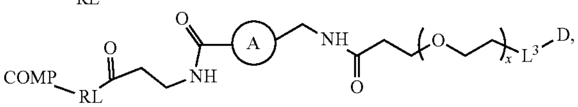

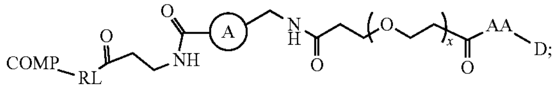

and

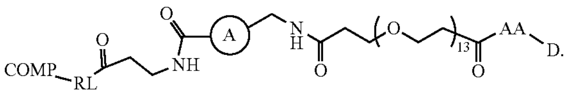

Or a pharmaceutically acceptable salt and/or regioisomer thereof.

In certain embodiments, the compound of Formula (III) is a compound of Formula (IIID):

(IIID)

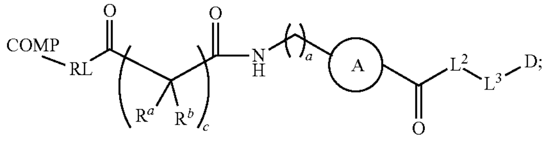

or a pharmaceutically acceptable salt and/or regioisomer thereof;

wherein integer a, integer c, RL, $R^a$, $R^b$, Ring A, $L^2$, $L^3$, D, and COMP are as defined herein.

In certain embodiments, the compound of Formula (IIID) is selected from the following:

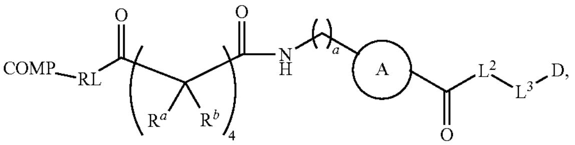

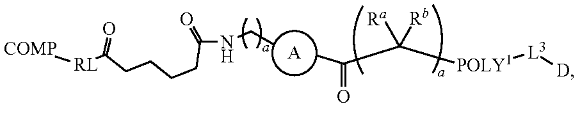

-continued

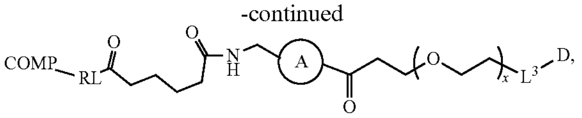

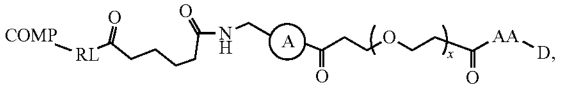

and

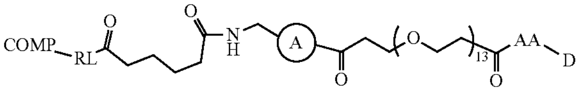

or a pharmaceutically acceptable salt and/or regioisomer thereof.

In certain embodiments, the compound of Formula (III) is a compound of Formula (IIIE):

(IIIE)

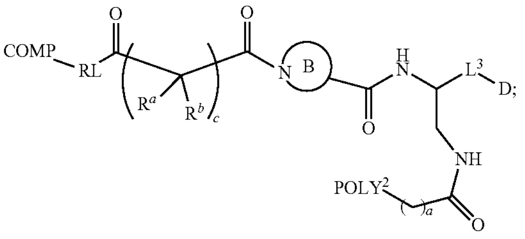

or a pharmaceutically acceptable salt and/or regioisomer thereof;

wherein integer a, integer c, RL, $R^a$, $R^b$, Ring B, $L^3$, $POLY^2$, D, and COMP are as defined herein.

In certain embodiments, the compound of Formula (IIIE) is selected from the following:

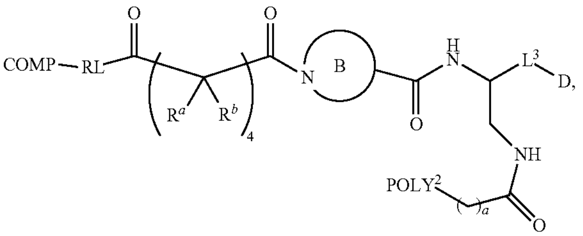

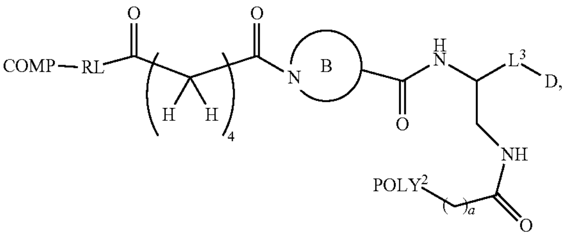

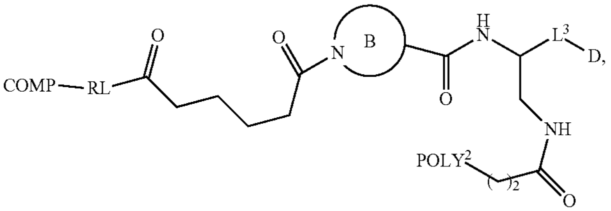

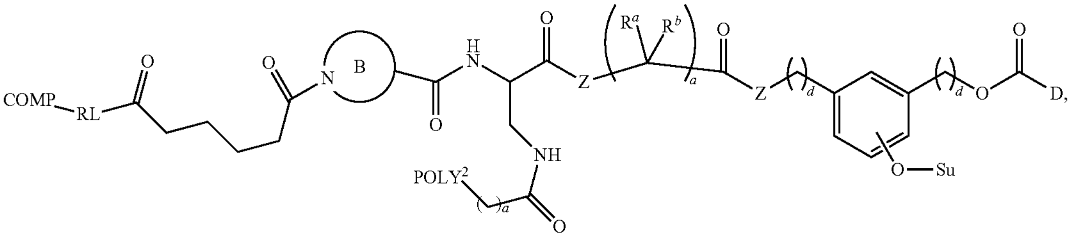

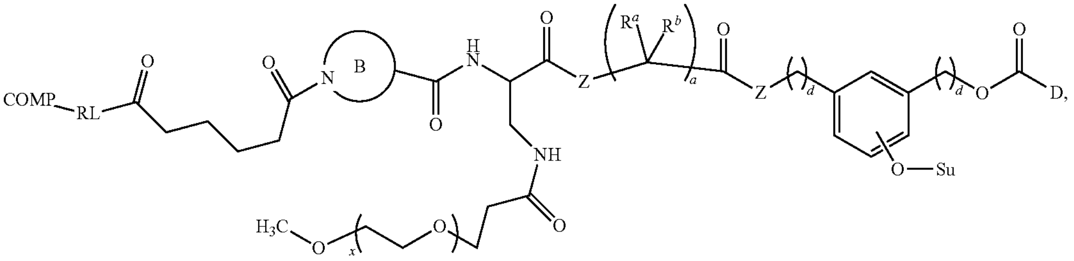

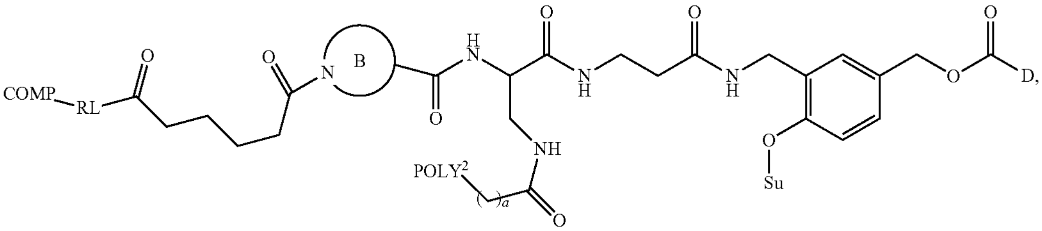

-continued

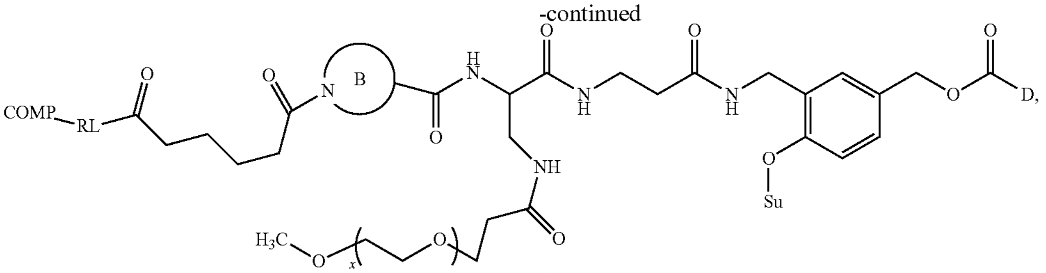

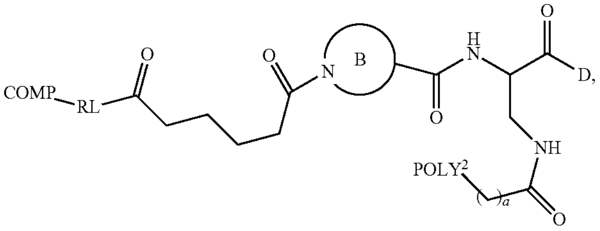

and

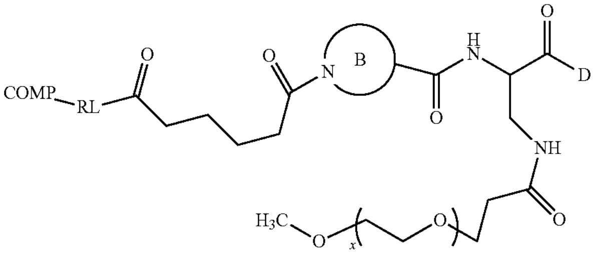

or a pharmaceutically acceptable salt and/or regioisomer thereof.

In certain embodiments, the compound of Formula (III) is a compound of Formula (IIIF):

(IIIF)

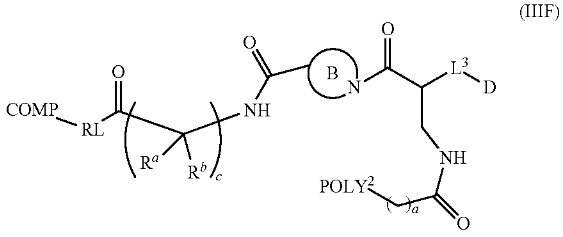

or a pharmaceutically acceptable salt and/or regioisomer thereof;

wherein integer a, integer c, RL, $R^a$, $R^b$, Ring B, $L^3$, $POLY^2$, D, and COMP are as defined herein.

In certain embodiments, the compound of Formula (IIIF) is selected from the following:

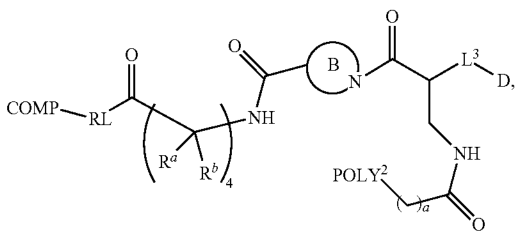

-continued

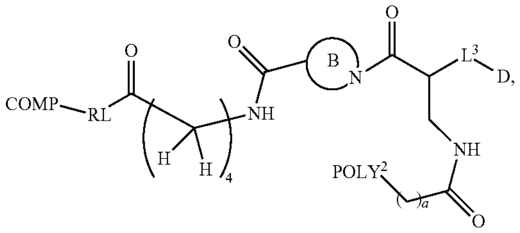

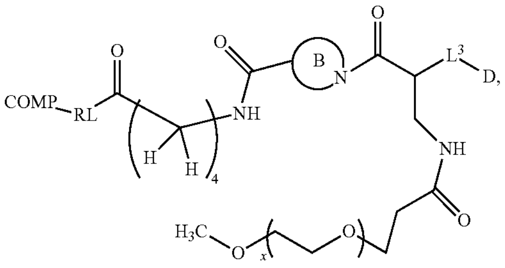

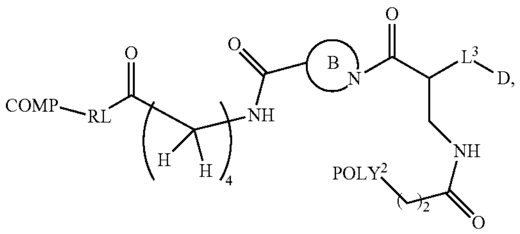

-continued

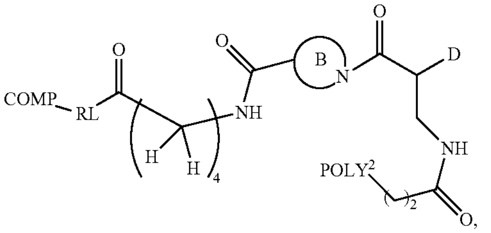

and

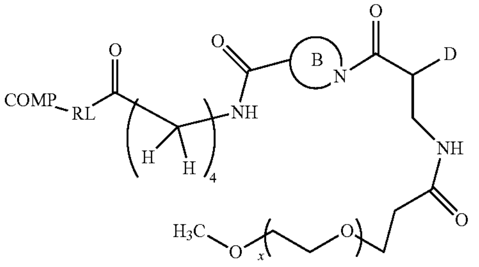

or a pharmaceutically acceptable salt and/or regioisomer thereof.

In certain embodiments, the compound of Formula (III) is a compound of Formula (IIIG):

(IIIG)

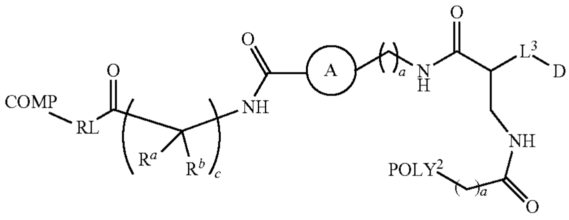

or a pharmaceutically acceptable salt and/or regioisomer thereof;

wherein integer a, integer c, RL, $R^a$, $R^b$, Ring A, $L^3$, $POLY^2$, D, and COMP are as defined herein.

In certain embodiments, the compound of Formula (IIIG) is selected from the following:

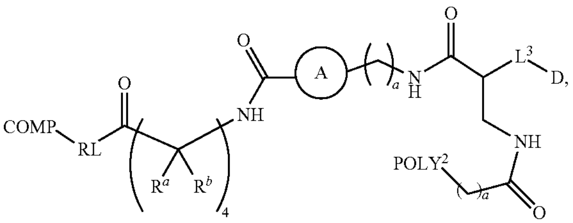

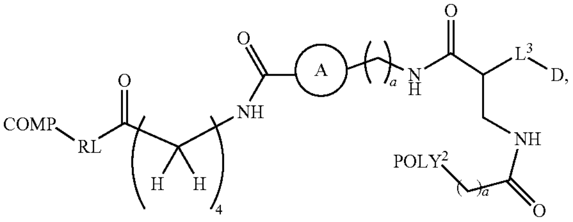

-continued

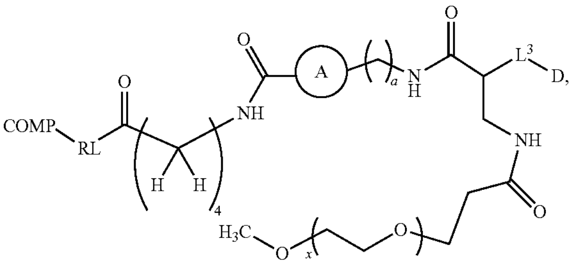

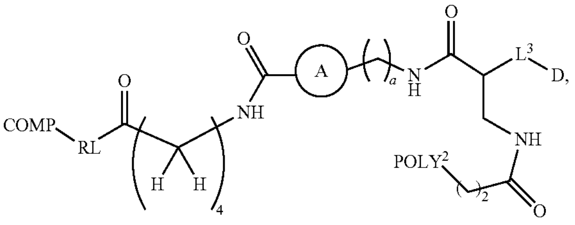

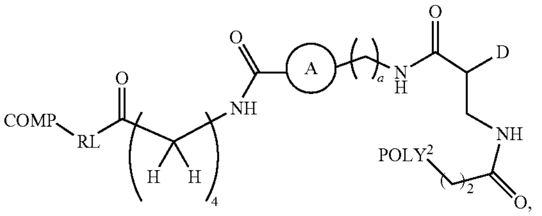

and

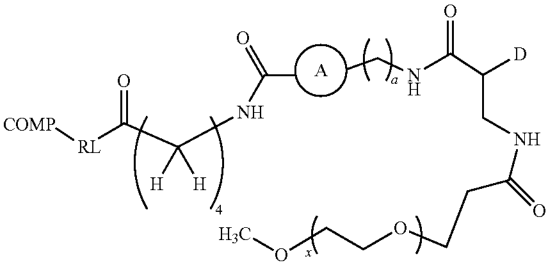

or a pharmaceutically acceptable salt and/or regioisomer thereof.

In certain embodiments, the compound of Formula (III) is a compound of Formula (IIIH):

(IIIH)

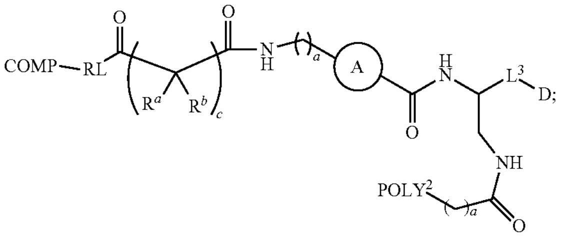

or a pharmaceutically acceptable salt and/or regioisomer thereof;

wherein integer a, integer c, RL, $R^a$, $R^b$, Ring A, $L^3$, $POLY^2$, D, and COMP are as defined herein.

In certain embodiments, the compound of Formula (IIIH) is selected from the following:

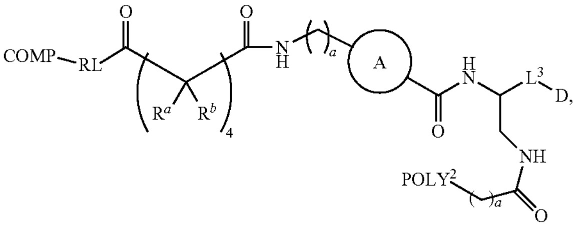

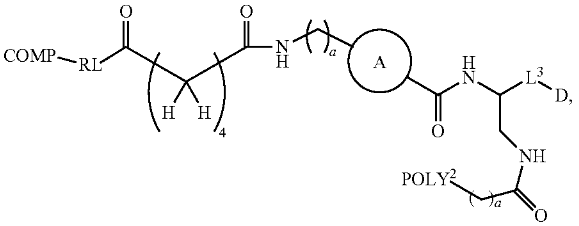

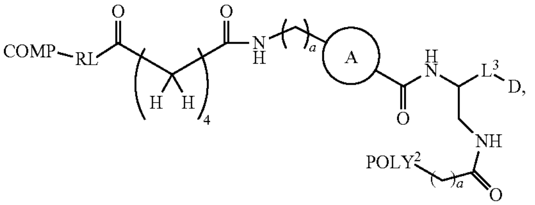

and

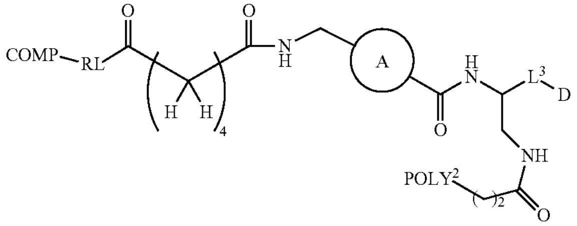

or a pharmaceutically acceptable salt and/or regioisomer thereof.

In one aspect, provided herein is a conjugate of Formula (V):

(V)

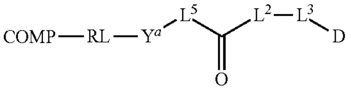

or a pharmaceutically acceptable salt and/or regioisomer thereof;

wherein $L^5$ is a linker comprising an unnatural amino acid; and

RL, COMP, $Y^a$, $L^2$, $L^3$, and D are as defined herein.

In certain embodiments, the compound of Formula (V) is a compound of Formula (VA):

(VA)

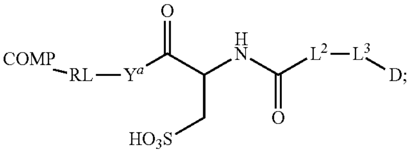

or a pharmaceutically acceptable salt and/or regioisomer thereof;

wherein RL, COMP, $Y^a$, $L^2$, $L^3$, and D are as defined herein.

In certain embodiments, the compound of Formula (V) is a compound of Formula (VB):

(VB)

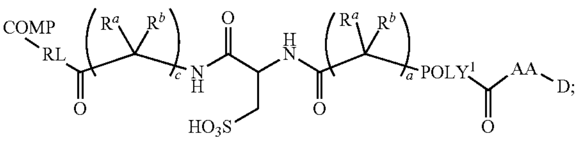

or a pharmaceutically acceptable salt and/or regioisomer thereof;

wherein integer a, integer c, RL, COMP, $R^a$, $R^b$, $POLY^1$, AA, and D are as defined herein.

In certain embodiments, the compound of Formula (VB) is a compound of the formula:

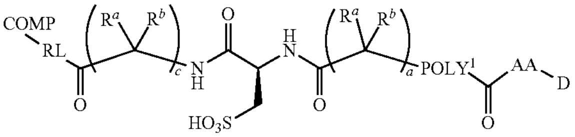

or a pharmaceutically acceptable salt and/or regioisomer thereof.

In certain embodiments of Formula (III)-(VB), including any of the foregoing, $L^{1a}$ is

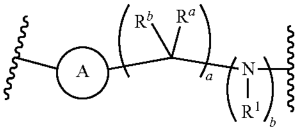

or

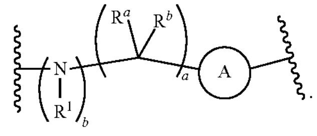

In certain embodiments of Formula (III)-(VB), including any of the foregoing, $L^{1a}$ is

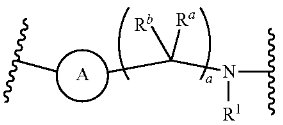

or

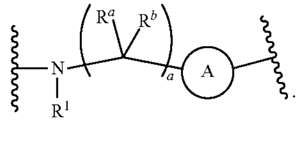

In certain embodiments of Formula (III)-(VB), including any of the foregoing, $L^{1a}$ is

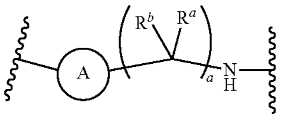

or

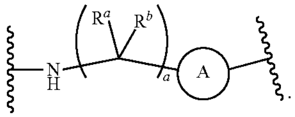

In certain embodiments of Formula (III)-(VB), including any of the foregoing, $L^{1a}$ is

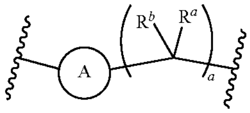

or

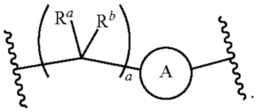

In certain embodiments of Formula (III)-(VB), including any of the foregoing, $L^{1a}$ is

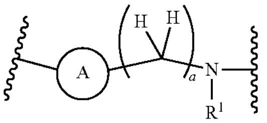

or

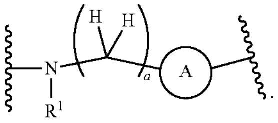

In certain embodiments of Formula (III)-(VB), including any of the foregoing, $L^{1a}$ is

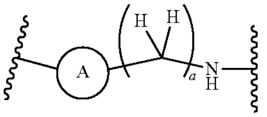

or

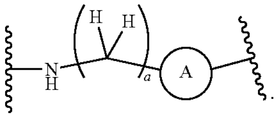

In certain embodiments of Formula (III)-(VB), including any of the foregoing, $L^{1a}$ is

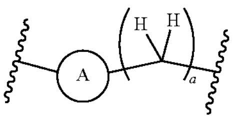

or

-continued

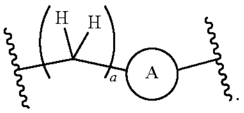

In certain embodiments of Formula (III)-(VB), including any of the foregoing, $L^{1a}$ is

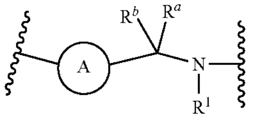

or

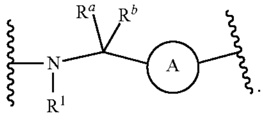

In certain embodiments of Formula (III)-(VB), including any of the foregoing, $L^{1a}$ is

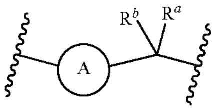

or

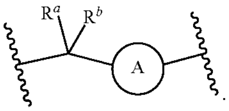

In certain embodiments of Formula (III)-(VB), including any of the foregoing, $L^{1a}$ is

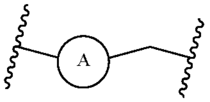

or

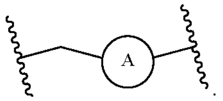

In certain embodiments of Formula (III)-(VB), including any of the foregoing, $L^{1a}$ is

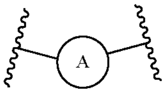

or

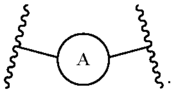

In certain embodiments of Formula (III)-(VB), including any of the foregoing, $L^{1a}$ is

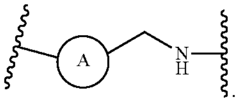

In certain embodiments of Formula (III)-(VB), including any of the foregoing, $L^{1a}$ is

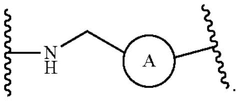

In certain embodiments of Formula (III)-(VB), including any of the foregoing, $L^{1a}$ is

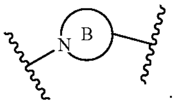

In certain embodiments of Formula (III)-(VB), including any of the foregoing, $L^{1a}$ is

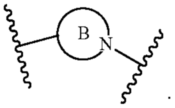

In certain embodiments of Formula (III)-(VB), including any of the foregoing, Ring B of $L^{1a}$ is an optionally substituted 5- to 12-membered N-linked bridged, fused, or spirocyclic bicyclic heterocycle containing 1, 2, or 3 heteroatoms independently selected from N, O, and S including the N to which the ring is attached, wherein Ring B is optionally substituted with one or more substituents selected from alkyl, alkenyl, alkynyl, cycloalkyl, halogen, alkoxy, —CN, —$NO_2$, —OH, —$N(R^2R^3)_2$, —C(O)—, —$C(O)N(R^2R^3)_2$, —$C(O)OR^2$, aminoalkyl, hydroxyalkyl, haloalkyl, aryl, arylalkyl, heteroaryl, and heteroarylalkyl. In certain embodiments of Formula (III)-(VB), including any of the foregoing, Ring B of $L^{1a}$ is an optionally substituted 5- to 12-membered N-linked spirocyclic bicyclic heterocycle containing 1, 2, or 3 heteroatoms independently selected from N, O, and S including the N to which the ring is attached.

In certain embodiments of Formula (III)-(VB), including any of the foregoing, Ring B of $L^{1a}$ is selected from

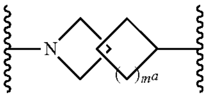,
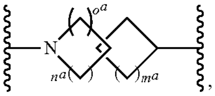,
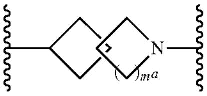, and
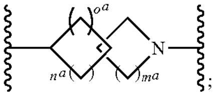;

wherein $m^a$ is an integer selected from 1, 2, 3, 4, and 5; and each of $n^a$ and $o^a$ is an integer independently selected from 1, 2, and 3.

In certain embodiments of Formula (III)-(VB), including any of the foregoing, Ring B of $L^{1a}$ is

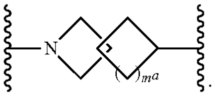

In certain embodiments of Formula (III)-(VB),

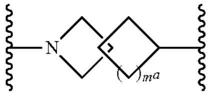

is selected from

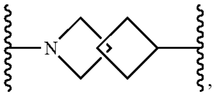,
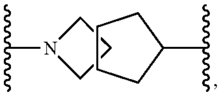,
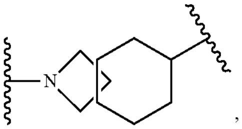,
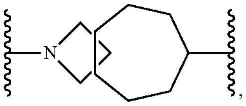, and
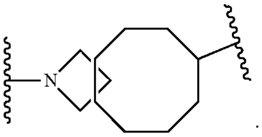

In certain embodiments of Formula (III)-(VB),

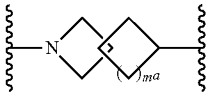

is selected from

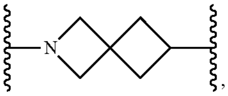,
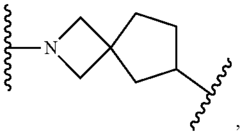,
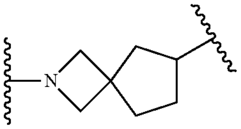,
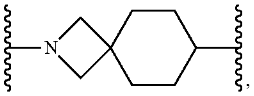,
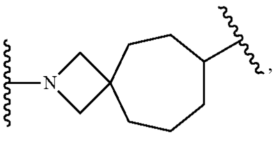,
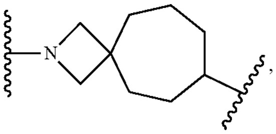, and

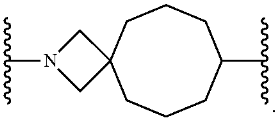

In certain embodiments of Formula (III)-(VB), Ring B of $L^{1a}$ is

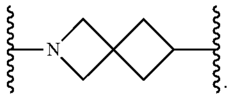 [SMILES: *C1CC2(C1)CN(*)C2]

In certain embodiments, Ring B is

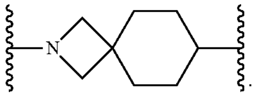

In certain embodiments of Formula (III)-(VB), including any of the foregoing, Ring B of $L^{1a}$ is

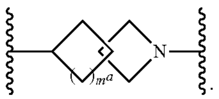

In certain embodiments of Formula (III)-(VB),

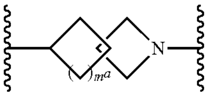

is selected from

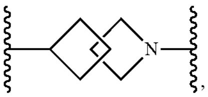

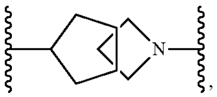

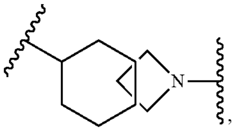

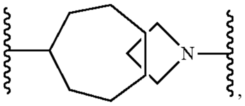

and

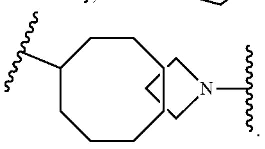

In certain embodiments of Formula (III)-(VB),

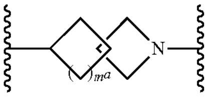

is selected from

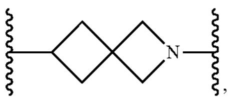

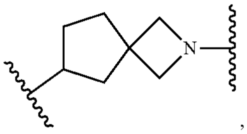

-continued

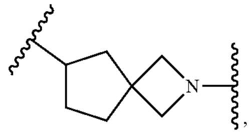

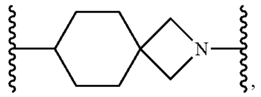

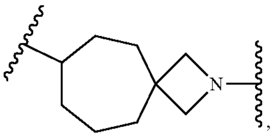

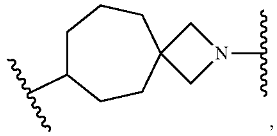

and

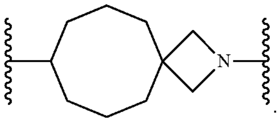

In certain embodiments of Formula (III)-(VB), Ring B of $L^{1a}$ is

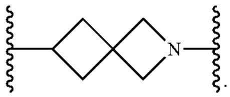 [SMILES: *C1CC2(C1)CN(*)C2]

In certain embodiments of Formula (III)-(VB), Ring B of $L^{1a}$ is

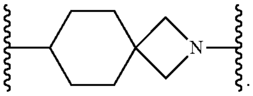 [SMILES: *C1CCC2(CC1)CN(*)C2]

In certain embodiments of Formula (III)-(VB), including any of the foregoing, Ring B of $L^{1a}$ is

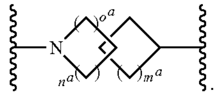

In certain embodiments of Formula (III)-(VB),

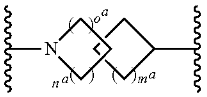

is

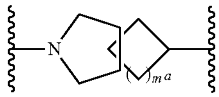

wherein $m^a$ is 1, 2, or 3. In certain embodiments of Formula (III)-(VB),

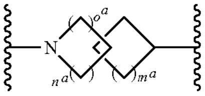

is

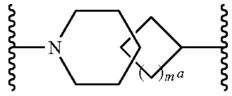

wherein $m^a$ is 1, 2, or 3. In certain embodiments of Formula (III)-(VB),

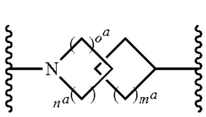
is
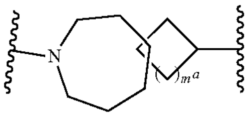

wherein $m^a$ is 1, 2, or 3. In certain embodiments of Formula (III)-(VB),

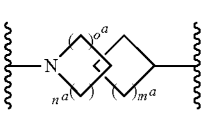
is
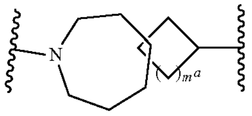

wherein $m^a$ is 1, 2, or 3.

In certain embodiments of Formula (III)-(VB),

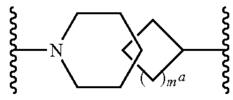
is
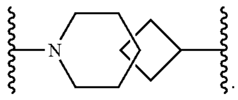

In certain embodiments of Formula (III)-(VB),

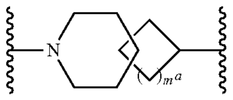
is
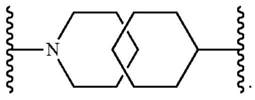

In certain embodiments of Formula (III)-(VB),

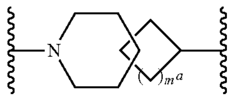
is
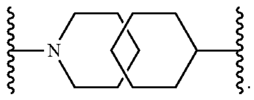

In certain embodiments of Formula (III)-(VB),

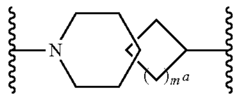
is
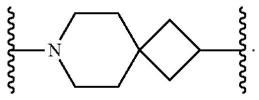

In certain embodiments of Formula (III)-(VB),

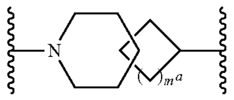
is
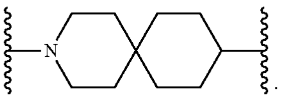

In certain embodiments of Formula (III)-(VB), including any of the foregoing, Ring B of $L^{1a}$ is

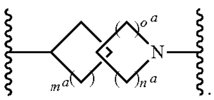

In certain embodiments of Formula (III)-(VB),

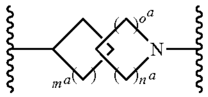
is
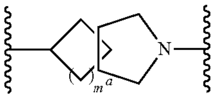

wherein $m^a$ is 1, 2, or 3. In certain embodiments of Formula (III)-(VB),

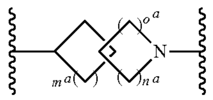
is
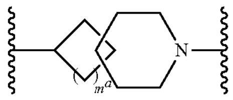

wherein $m^a$ is 1, 2, or 3. In certain embodiments of Formula (III)-(VB),

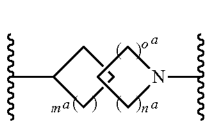
is
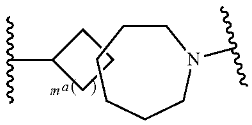

wherein $m^a$ is 1, 2, or 3. In certain embodiments of Formula (III)-(VB),

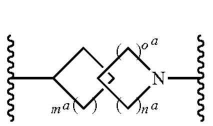
is
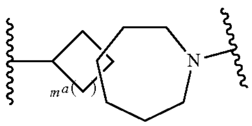

wherein $m^a$ is 1, 2, or 3.

In certain embodiments of Formula (III)-(VB),

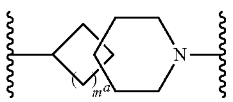
is
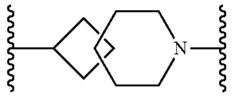

In certain embodiments of Formula (III)-(VB),

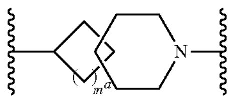
is
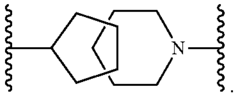

In certain embodiments of Formula (III)-(VB),

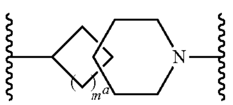
is
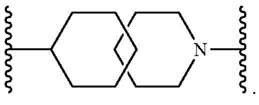

In certain embodiments,

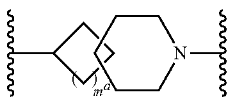 is 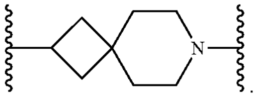.

In certain embodiments of Formula (III)-(VB),

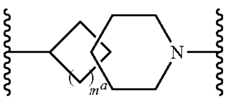 is 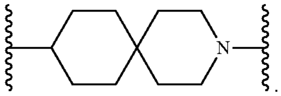.

In certain embodiments of Formula (III)-(VB), including any of the foregoing, Ring B of $L^{1a}$ is

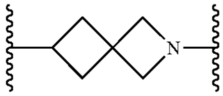, 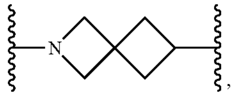,

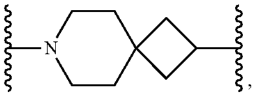, 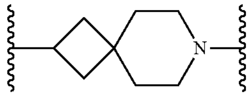,

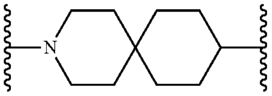 or

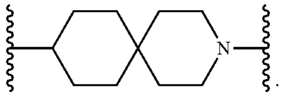.

In certain embodiments of Formula (III)-(VB), including any of the foregoing, Ring B of $L^{1a}$ is selected from

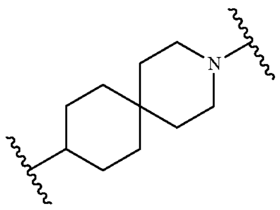, 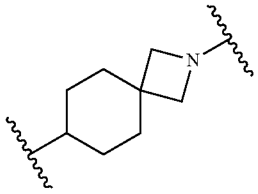,

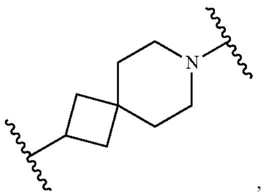, and 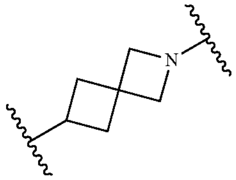.

In certain embodiments of Formula (III)-(VB), including any of the foregoing, Ring B of $L^{1a}$ is selected from

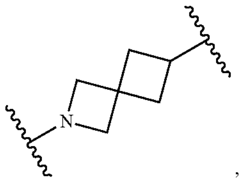, 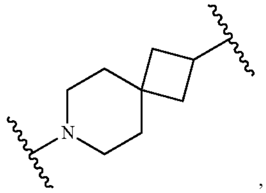, and

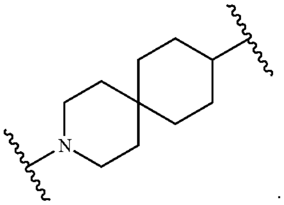.

In certain embodiments of Formula (III)-(VB), including any of the foregoing, $L^{1a}$ is selected from

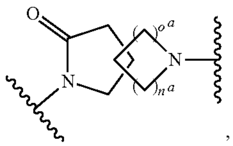, 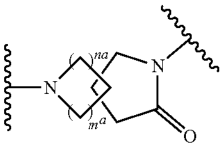, and

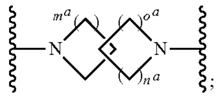;

wherein $m^a$ is an integer selected from 1, 2, 3, 4, and 5; and each of $n^a$ and $o^a$ is an integer independently selected from 1, 2, and 3.

In certain embodiments of Formula (III)-(VB), including any of the foregoing, $L^{1a}$ is selected from

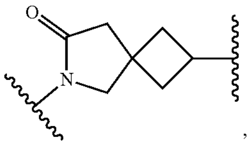, 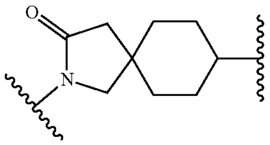,

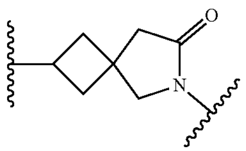, and

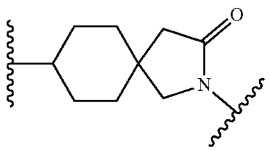.

In certain embodiments of Formula (III)-(VB), including any of the foregoing, Ring B of $L^{1a}$ is selected from

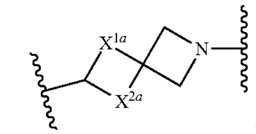, 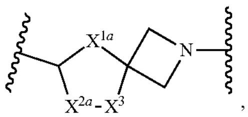, 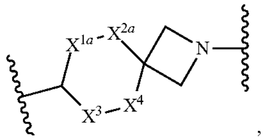, 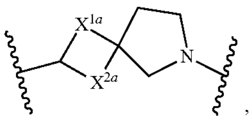, 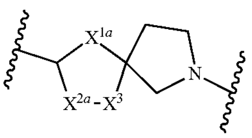, 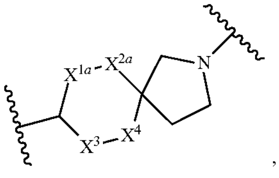, 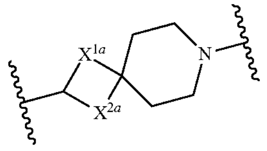, 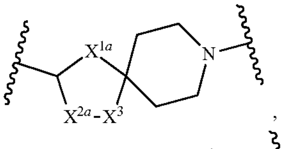, and 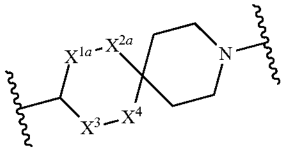;

wherein $X^{1a}$, $X^{2a}$, $X^3$, and $X^4$ are independently selected from —$C(R^4)_2$—, —NH—, —O—, and —S— wherein when $X^{1a}$, $X^{2a}$, and $X^3$ are present, at least one of $X^{1a}$—$X^3$ is —$C(R^4)_2$— and when $X^{1a}$, $X^{2a}$, $X^3$, and $X^4$ are present, at least two of $X^{1a}$—$X^4$ are —$C(R^4)_2$—; and $R^4$ is independently selected from hydrogen, $C_{1-6}$ alkyl, $C_{2-6}$ alkenyl, $C_{2-6}$ alkynyl, $C_{3-12}$ cycloalkyl, halogen, alkoxy, —CN, —$NO_2$, —OH, —$N(R^2R^3)_2$, —C(O)$N(R^2R^3)_2$, —C(O)$OR^2$, aminoalkyl, hydroxyalkyl, haloalkyl, aryl, arylalkyl, heteroaryl, and heteroarylalkyl; or two $R^4$ groups on the same carbon are taken together to form an oxo group In certain embodiments of Formula (III)-(VB), including any of the foregoing, Ring B of $L^{1a}$ is selected from

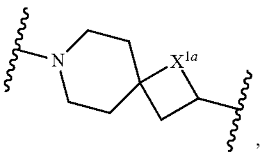, 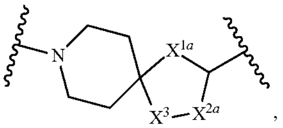, 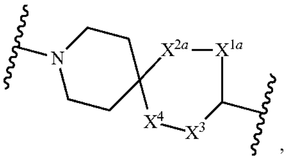, 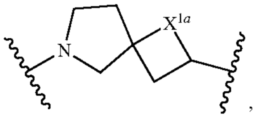,

-continued

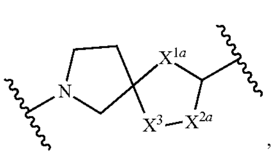, 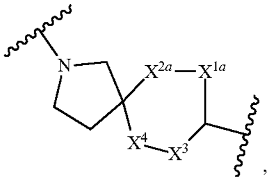, 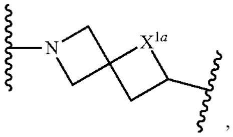, 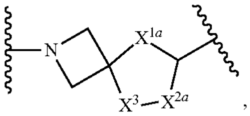, and 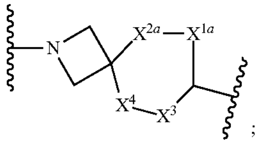;

wherein $X^{1a}$, $X^{2a}$, $X^3$, and $X^4$ are independently selected from —$C(R^4)_2$—, —NH—, —O—, and —S— wherein when $X^{1a}$, $X^{2a}$, and $X^3$ are present, at least one of $X^{1a}$—$X^3$ is —$C(R^4)_2$— and when $X^{1a}$, $X^{2a}$, $X^3$, and $X^4$ are present, at least two of $X^{1a}$—$X^4$ are —$C(R^4)_2$—; and $R^4$ is independently selected from hydrogen, $C_{1-6}$ alkyl, $C_{2-6}$ alkenyl, $C_{2-6}$ alkynyl, $C_{3-12}$ cycloalkyl, halogen, alkoxy, —CN, —$NO_2$, —OH, —$N(R^2R^3)_2$, —C(O)$N(R^2R^3)_2$, —C(O)$OR^2$, aminoalkyl, hydroxyalkyl, haloalkyl, aryl, arylalkyl, heteroaryl, and heteroarylalkyl; or two $R^4$ groups on the same carbon are taken together to form an oxo group.

In certain embodiments of Formula (III)-(VB), including any of the foregoing, Ring A of $L^{1a}$ is an optionally substituted bridged, fused, or spirocyclic bicyclic carbocycle, wherein the carbocycle or the heterocycle of Ring A are optionally substituted with one or more substituents selected from alkyl, alkenyl, alkynyl, cycloalkyl, halogen, alkoxy, —CN, —$NO_2$, —OH, —$N(R^2R^3)_2$, —C(O)—, —C(O)N$(R^2R^3)_2$, —C(O)$OR^2$, aminoalkyl, hydroxyalkyl, haloalkyl, aryl, arylalkyl, heteroaryl, and heteroarylalkyl. In certain embodiments, including any of the foregoing, Ring A of $L^{1a}$ is an optionally substituted $C_{4-12}$ bridged, fused, or spirocyclic bicyclic carbocycle. In certain embodiments of Formula (III)-(VB), including any of the foregoing, Ring A of $L^{1a}$ is an optionally substituted $C_{4-12}$ bridged bicyclic carbocycle. In certain embodiments of Formula (III)-(VB), including any of the foregoing, Ring A of $L^{1a}$ is an optionally substituted $C_{4-8}$ bridged bicyclic carbocycle.

In certain embodiments of Formula (III)-(VB), including any of the foregoing, Ring A of $L^{1a}$ is selected from

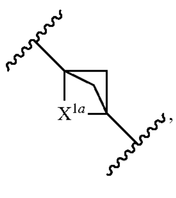, 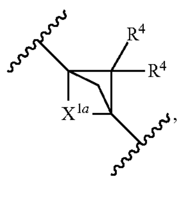,

-continued

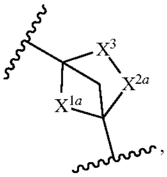,

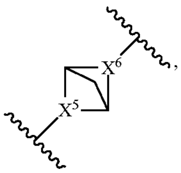,

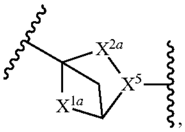, 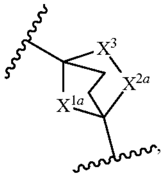, 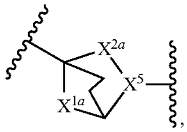,

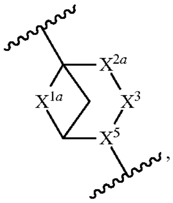, 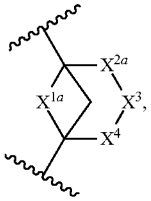, 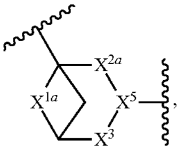,

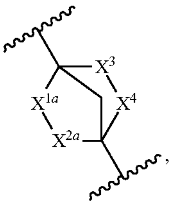, and 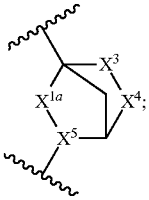;

wherein $X^{1a}$, $X^{2a}$, $X^3$, and $X^4$ are independently selected from —$C(R^4)_2$—, —NH—, —O—, and —S— wherein when $X^{1a}$, $X^{2a}$, and $X^3$ are present, at least one of $X^{1a}$—$X^3$ is —$C(R^4)_2$— and when $X^{1a}$, $X^{2a}$, $X^3$, and $X^4$ are present, at least two of $X^{1a}$—$X^4$ are —$C(R^4)_2$—;

$X^5$ is $CR^4$ or N; and $R^4$ is independently selected from hydrogen, $C_{1-6}$ alkyl, $C_{2-6}$ alkenyl, $C_{2-6}$ alkynyl, $C_{3-12}$ cycloalkyl, halogen, alkoxy, —CN, —$NO_2$, —OH, —$N(R^2R^3)_2$, —C(O)N$(R^2R^3)_2$, —C(O)$OR^2$, aminoalkyl, hydroxyalkyl, haloalkyl, aryl, arylalkyl, heteroaryl, and heteroarylalkyl; or two $R^4$ groups on the same carbon are taken together to form an oxo group.

In certain embodiments of Formula (III)-(VB), including any of the foregoing, Ring A of $L^{1a}$ is selected from

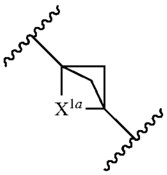, 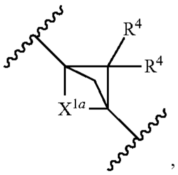, 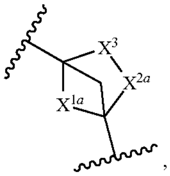,

-continued

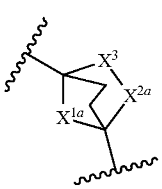, and 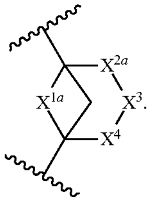.

In certain embodiments of Formula (III)-(VB), including any of the foregoing, Ring A of $L^{1a}$ is selected from

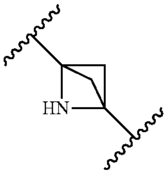, 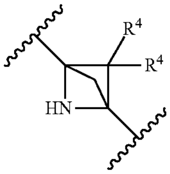, 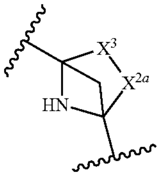,

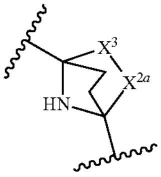, and 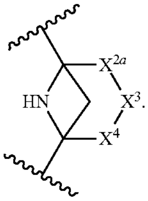.

In certain embodiments of Formula (III)-(VB), including any of the foregoing, Ring A of $L^{1a}$ is selected from

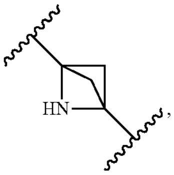, 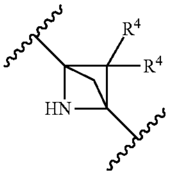,

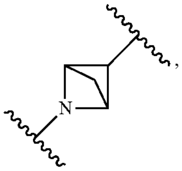, 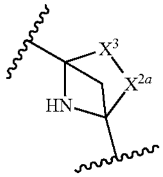,

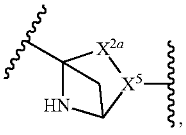, 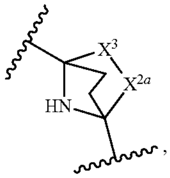, 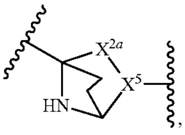,

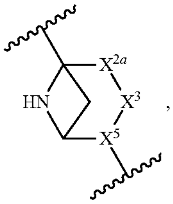, 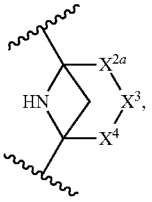, 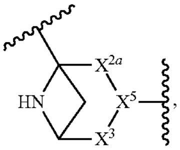,

-continued

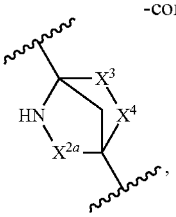, and 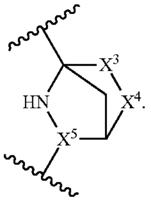.

In certain embodiments of Formula (III)-(VB), including any of the foregoing, Ring A of $L^{1a}$ is selected from

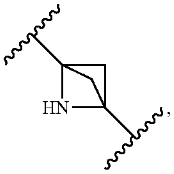, 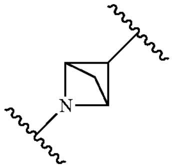,

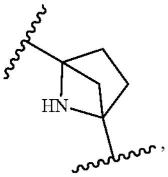, 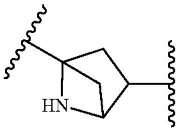,

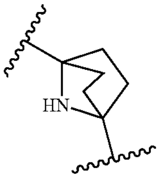, 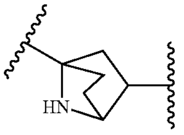,

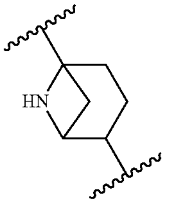, 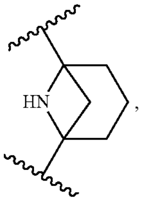, 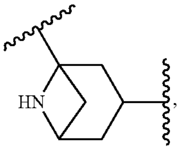,

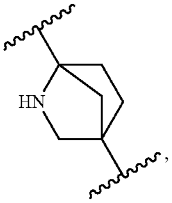, and 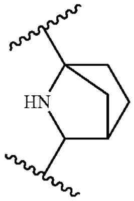.

In certain embodiments of Formula (III)-(VB), including any of the foregoing, Ring A of $L^{1a}$ is

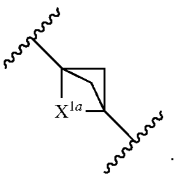.

In certain embodiments of Formula (III)-(VB), including any of the foregoing, Ring A of $L^{1a}$ is

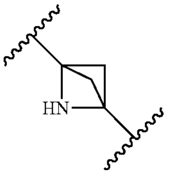.

In certain embodiments of Formula (III)-(VB), including any of the foregoing, $X^{1a}$, $X^{2a}$, $X^3$, and/or $X^4$ is —$C(R^4)_2$—. In certain embodiments of Formula (III)-(VB), including any of the foregoing, $X^{1a}$ and $X^{2a}$ are —$C(R^4)_2$—. In certain embodiments of Formula (III)-(VB), including any of the foregoing, $X^{1a}$, $X^{2a}$, and $X^3$ are —$C(R^4)_2$—. In certain embodiments of Formula (III)-(VB), including any of the foregoing, $X^{1a}$, $X^{2a}$, $X^3$, and $X^4$ are —$C(R^4)_2$—. In certain embodiments of Formula (III)-(VB), including any of the foregoing, $X^{1a}$ is —NH—. In certain embodiments of Formula (III)-(VB), including any of the foregoing, $X^{2a}$ is NH—. In certain embodiments of Formula (III)-(VB), including any of the foregoing, $X^3$ is —NH—. In certain embodiments of Formula (III)-(VB), including any of the foregoing, $X^4$ is NH—. In certain embodiments, including any of the foregoing, $X^{1a}$ is —O—. In certain embodiments of Formula (III)-(VB), including any of the foregoing, $X^{2a}$ is —O—. In certain embodiments of Formula (III)-(VB), including any of the foregoing, $X^3$ is —O—. In certain embodiments of Formula (III)-(VB), including any of the foregoing, $X^4$ is —O—.

In certain embodiments of Formula (III)-(VB), including any of the foregoing, $L^{1a}$ is (d)

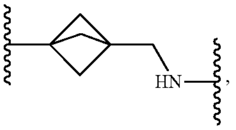,

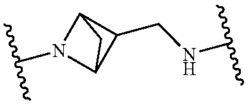, or 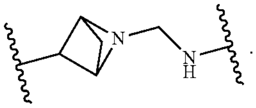 [SMILES: *NCN1C2CC1C2*].

In certain embodiments, $L^{1a}$ is

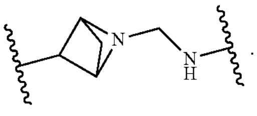.

In certain embodiments, including any of the foregoing, a is 0. In certain embodiments, including any of the foregoing, a is 1. In certain embodiments, including any of the foregoing, a is 2. In certain embodiments, including any of the foregoing, a is 3. In certain embodiments, including any of the foregoing, a is 4. In certain embodiments, including any of the foregoing, a is 5. In certain embodiments, including any of the foregoing, a is 6.

In certain embodiments of Formula (III)-(VB), b is 0. In certain embodiments, b is 1.

In certain embodiments of Formula (III)-(VB), b is 0 and a is 0. In certain embodiments of Formula (III)-(VB), b is 0 and a is 1. In certain embodiments of Formula (III)-(VB), b is 0 and a is 2. In certain embodiments of Formula (III)-(VB), b is 0 and a is 3. In certain embodiments of Formula (III)-(VB), b is 0 and a is 4. In certain embodiments of Formula (III)-(VB), b is 0 and a is 5. In certain embodiments of Formula (III)-(VB), b is 0 and a is 6. In certain embodiments of Formula (III)-(VB), b is 1 and a is 1. In certain embodiments of Formula (III)-(VB), b is 1 and a is 2. In certain embodiments of Formula (III)-(VB), b is 1 and a is 3. In certain embodiments of Formula (III)-(VB), b is 1 and a is 4. In certain embodiments of Formula (III)-(VB), b is 1 and a is 5. In certain embodiments of Formula (III)-(VB), b is 1 and a is 6.

In certain embodiments of Formula (III)-(VB), including any of the foregoing, $R^1$ is hydrogen. In certain embodiments of Formula (III)-(VB), including any of the foregoing, $R^1$ is unsubstituted alkyl. In certain embodiments of Formula (III)-(VB), including any of the foregoing, $R^1$ is methyl. In certain embodiments of Formula (III)-(VB), including any of the foregoing, $R^1$ is alkyl optionally substituted with one or more substituent selected from cycloalkyl, halogen, alkoxy, —CN, —$NO_2$, and —OH.

In certain embodiments of Formula (III)—(IVB), $L^5$ is a linker that comprises at least one amino acid selected from sulfoalanine, hydroxyproline (Hyp), beta-alanine, citrulline (Cit), ornithine (Orn), norleucine (Nle), 3-nitrotyrosine, nitroarginine, pyroglutamic acid (Pyr), naphtylalanine (Nal), 2,4-diaminobutyric acid (DAB), methionine sulfoxide, and methionine sulfone. In certain embodiments of Formula (III)—(IVB), $L^5$ is a linker that comprises

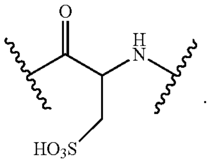 [SMILES: *NC(CS(=O)(=O)O)C(*)=O]

In certain embodiments of Formula (III)—(IVB), $L^5$ is a linker that comprises

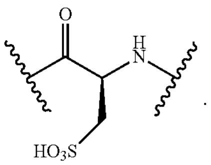 [SMILES: *N[C@@H](CS(=O)(=O)O)C(*)=O]

In certain embodiments of Formula (III)—(IVB), $L^5$ is

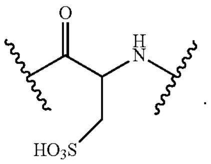 [SMILES: *NC(CS(=O)(=O)O)C(*)=O]

In certain embodiments of Formula (III)—(IVB), $L^5$ is

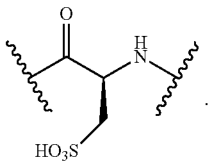 [SMILES: *N[C@@H](CS(=O)(=O)O)C(*)=O]

In certain embodiments, including any of the foregoing, $R^a$ is hydrogen and $R^b$ is selected from hydrogen, alkyl, alkenyl, alkynyl, cycloalkyl, halogen, alkoxy, —CN, —$NO_2$, —OH, —$N(R^2R^3)_2$, —$C(O)N(R^2R^3)_2$, —$C(O)OR^2$, aminoalkyl, hydroxyalkyl, haloalkyl, aryl, arylalkyl, heteroaryl, and heteroarylalkyl. In certain embodiments, including any of the foregoing, $R^a$ is hydrogen and $R^b$ is selected from hydrogen, alkyl, alkenyl, alkynyl, cycloalkyl, halogen, alkoxy, —CN, —$NO_2$, —OH, —$NH_2$, —C(O)$NH_2$, —C(O)OH, aminoalkyl, hydroxyalkyl, haloalkyl, aryl, arylalkyl, heteroaryl, and heteroarylalkyl. In certain embodiments, including any of the foregoing, $R^a$ is hydrogen and $R^b$ is selected from hydrogen, alkyl, halogen, alkoxy, —CN, —$NO_2$, —OH, —$NH_2$, —C(O)$NH_2$, and —C(O)OH. In certain embodiments, including any of the foregoing, $R^a$ and $R^b$ are both hydrogen.

In certain embodiments of Formula (III)-(VB), including any of the foregoing, $R^a$ is hydrogen; $R^b$ is selected from hydrogen, alkyl, halogen, alkoxy, —CN, —$NO_2$, —OH, —$NH_2$, —C(O)$NH_2$, and —C(O)OH; $R^1$ is hydrogen; a is 1; and b is 1. In certain embodiments of Formula (III)-(VB), including any of the foregoing, $R^a$ is hydrogen; $R^b$ is selected from hydrogen, alkyl, halogen, alkoxy, —CN, —$NO_2$, —OH, —$NH_2$, —C(O)$NH_2$, and —C(O)OH; $R^1$ is hydrogen; a is 2; and b is 1. In certain embodiments of Formula (III)-(VB), including any of the foregoing, $R^a$ is hydrogen; $R^b$ is selected from hydrogen, alkyl, halogen, alkoxy, —CN, —$NO_2$, —OH, —$NH_2$, —C(O)$NH_2$, and —C(O)OH; $R^1$ is hydrogen; a is 3; and b is 1.

In certain embodiments of Formula (III)-(VB), including any of the foregoing, $R^a$ is hydrogen; $R^b$ is selected from hydrogen, alkyl, halogen, alkoxy, —CN, —$NO_2$, —OH, —$NH_2$, —C(O)$NH_2$, and —C(O)OH; a is 1; and b is 0. In certain embodiments of Formula (III)-(VB), including any of the foregoing, $R^a$ is hydrogen; $R^b$ is selected from hydrogen, alkyl, halogen, alkoxy, —CN, —$NO_2$, —OH, —$NH_2$, —C(O)$NH_2$, and —C(O)OH; a is 2, and b is 0. In certain embodiments of Formula (III)-(VB), including any of the foregoing, $R^a$ is hydrogen; $R^b$ is selected from hydrogen, alkyl, halogen, alkoxy, —CN, —$NO_2$, —OH, —$NH_2$, —C(O)$NH_2$, and —C(O)OH; a is 3, and b is 0.

In certain embodiments of Formula (III)-(VB), including any of the foregoing, $R^a$ is hydrogen; $R^b$ is selected from hydrogen, alkyl, halogen, alkoxy, —CN, —$NO_2$, —OH, —$NH_2$, —C(O)$NH_2$, and —C(O)OH; $R^1$ is methyl; a is 1; and b is 1. In certain embodiments of Formula (III)-(VB), including any of the foregoing, $R^a$ is hydrogen; $R^b$ is selected from hydrogen, alkyl, halogen, alkoxy, —CN, —$NO_2$, —OH, —$NH_2$, —C(O)$NH_2$, and —C(O)OH; $R^1$ is methyl; a is 2; and b is 1. In certain embodiments of Formula (III)-(VB), including any of the foregoing, $R^a$ is hydrogen; $R^b$ is selected from hydrogen, alkyl, halogen, alkoxy, —CN, —$NO_2$, —OH, —$NH_2$, —C(O)$NH_2$, and —C(O)OH; $R^1$ is methyl; a is 3, and b is 1.

In certain embodiments, including any of the foregoing of Formula (III)-(VB), $R^a$ and $R^b$ are both hydrogen; $R^1$ is hydrogen; a is 1, and b is 1. In certain embodiments of Formula (III)-(VB), including any of the foregoing, $R^a$ and $R^b$ are both hydrogen; $R^1$ is hydrogen; a is 2, and b is 1. In certain embodiments of Formula (III)-(VB), including any of the foregoing, $R^a$ and $R^b$ are both hydrogen; $R^1$ is hydrogen; a is 3, and b is 1. In certain embodiments of Formula (III)-(VB), including any of the foregoing, $R^a$ and $R^b$ are both hydrogen; $R^1$ is hydrogen; a is 4, and b is 1. In certain embodiments of Formula (III)-(VB), including any of the foregoing, $R^a$ and $R^b$ are both hydrogen; $R^1$ is hydrogen; a is 5, and b is 1. In certain embodiments of Formula (III)-(VB), including any of the foregoing, $R^a$ and $R^b$ are both hydrogen; $R^1$ is hydrogen; a is 6, and b is 1

In certain embodiments of Formula (III)-(VB), including any of the foregoing, $R^a$ and $R^b$ are both hydrogen; a is 1; and b is 0. In certain embodiments of Formula (III)-(VB), including any of the foregoing, $R^a$ and $R^b$ are both hydrogen; a is 2; and b is 0. In certain embodiments of Formula (III)-(VB), including any of the foregoing, $R^a$ and $R^b$ are both hydrogen; a is 3; and b is 0. In certain embodiments of Formula (III)-(VB), including any of the foregoing, $R^a$ and $R^b$ are both hydrogen; a is 4; and b is 0. In certain embodiments of Formula (III)-(VB), including any of the foregoing, $R^a$ and $R^b$ are both hydrogen; a is 5; and b is 0. In certain embodiments of Formula (III)-(VB), including any of the foregoing, $R^a$ and $R^b$ are both hydrogen; a is 6; and b is 0.

In certain embodiments of Formula (III)-(VB), including any of the foregoing, $R^a$ and $R^b$ are both hydrogen; $R^1$ is methyl; a is 1; and b is 0. In certain embodiments of Formula (III)-(VB), including any of the foregoing, $R^a$ and $R^b$ are both hydrogen; $R^1$ is methyl; a is 2; and b is 0. In certain embodiments of Formula (III)-(VB), including any of the foregoing, $R^a$ and $R^b$ are both hydrogen; $R^1$ is methyl; a is 3; and b is 0. In certain embodiments of Formula (III)-(VB), including any of the foregoing, $R^a$ and $R^b$ are both hydrogen; $R^1$ is methyl; a is 4; and b is 0. In certain embodiments of Formula (III)-(VB), including any of the foregoing, $R^a$ and $R^b$ are both hydrogen; $R^1$ is methyl; a is 5; and b is 0. In certain embodiments of Formula (III)-(VB), including any of the foregoing, $R^a$ and $R^b$ are both hydrogen; $R^1$ is methyl; a is 6; and b is 0.

In certain embodiments of Formula (III)—(IVB), including any of the foregoing, $R^a$ is hydrogen; $R^b$ is selected from hydrogen, alkyl, halogen, alkoxy, —CN, —$NO_2$, —OH, —$NH_2$, —C(O)$NH_2$, and —C(O)OH; a is 1; and c is 1. In certain embodiments of Formula (III)—(IVB), including any of the foregoing, $R^a$ is hydrogen; $R^b$ is selected from hydrogen, alkyl, halogen, alkoxy, —CN, —$NO_2$, —OH, —$NH_2$, —C(O)$NH_2$, and —C(O)OH; a is 2; and c is 1. In certain embodiments of Formula (III)—(IVB), including any of the foregoing, $R^a$ is hydrogen; $R^b$ is selected from hydrogen, alkyl, halogen, alkoxy, —CN, —$NO_2$, —OH, —$NH_2$, —C(O)$NH_2$, and —C(O)OH; a is 3; and c is 1.

In certain embodiments of Formula (III)—(IVB), including any of the foregoing, $Y^a$ is *—C(O)—$(CR^aR^b)_c$—NH— wherein * represents where $Y^a$ is bound to RL. In certain embodiments of Formula (III)—(IVB), including any of the foregoing, $Y^a$ is *—C(O)—$(CH_2)_c$—NH—. In certain embodiments of Formula (III)—(IVB), including any of the foregoing, $Y^a$ is *—C(O)—$(CH_2)$—NH—. In certain embodiments, including any of the foregoing, $Y^a$ is *—C(O)—$(CH_2)_2$—NH—. In certain embodiments of Formula (III)—(IVB), including any of the foregoing, $Y^a$ is *—C(O)—$(CH_2)_3$—NH—. In certain embodiments of Formula (III)—(IVB), including any of the foregoing, $Y^a$ is *—C(O)—$(CH_2)_4$—NH—. In certain embodiments of Formula (III)—(IVB), including any of the foregoing, $Y^a$ is *—C(O)—$(CH_2)_5$—NH—. In certain embodiments of Formula (III)—(IVB), including any of the foregoing, $Y^a$ is *—C(O)—$(CH_2)_6$—NH—.

In certain embodiments of Formula (III)—(IVB), including any of the foregoing, $Y^a$ is *—C(O)—$(CR^aR^b)$—NH—. In certain embodiments of Formula (III)—(IVB), including any of the foregoing, $Y^a$ is *—C(O)—$(CR^aR^b)_2$—NH—. In certain embodiments of Formula (III)—(IVB), including any of the foregoing, $Y^a$ is *—C(O)—$(CR^aR^b)_3$—NH—. In certain embodiments of Formula (III)—(IVB), including any of the foregoing, $Y^a$ is *—C(O)—$(CR^aR^b)_4$—NH—. In certain embodiments of Formula (III)—(IVB), including any of the foregoing, $Y^a$ is *—C(O)—$(CR^aR^b)_5$—NH—. In certain embodiments of Formula (III)—(IVB), including any of the foregoing, $Y^a$ is *—C(O)—$(CR^aR^b)_6$—NH—.

In certain embodiments of Formula (III)—(IVB), including any of the foregoing, $Y^a$ is *—C(O)—$(CR^aR^b)_c$—NH— wherein $R^a$ is hydrogen and $R^b$ is selected from hydrogen, alkyl, alkenyl, alkynyl, cycloalkyl, halogen, alkoxy, —CN, —$NO_2$, —OH, —$N(R^2R^3)_2$, —C(O)$N(R^2R^3)_2$, —C(O)$OR^2$, aminoalkyl, hydroxyalkyl, haloalkyl, aryl, arylalkyl, heteroaryl, and heteroarylalkyl. In certain embodiments of Formula (III)—(IVB), including any of the foregoing, $Y^a$ is *—C(O)—$(CR^aR^b)_2$—NH—, *—C(O)—$(CR^aR^b)_3$—NH—, or *—C(O)—$(CR^aR^b)_4$—NH— wherein $R^a$ is hydrogen and $R^b$ is selected from hydrogen, alkyl, alkenyl, alkynyl, cycloalkyl, halogen, alkoxy, —CN, —$NO_2$, —OH, —$N(R^2R^3)_2$, —C(O)$N(R^2R^3)_2$, —C(O)$OR^2$, aminoalkyl, hydroxyalkyl, haloalkyl, aryl, arylalkyl, heteroaryl, and heteroarylalkyl.

In certain embodiments of Formula (III)—(IVB), including any of the foregoing, $Y^a$ is *—C(O)—$(CR^aR^b)_c$— wherein * represents where $Y^a$ is bound to RL. In certain embodiments of Formula (III)—(IVB), including any of the foregoing, $Y^a$ is *—C(O)—$(CH_2)_c$—. In certain embodiments of Formula (III)—(IVB), including any of the foregoing, $Y^a$ is *—C(O)—$(CH_2)$—. In certain embodiments of Formula (III)—(IVB), including any of the foregoing, $Y^a$ is *—C(O)—$(CH_2)_2$—. In certain embodiments of Formula (III)—(IVB), including any of the foregoing, $Y^a$ is *—C(O)—$(CH_2)_3$—. In certain embodiments of Formula (III)—(IVB), including any of the foregoing, $Y^a$ is *—C(O)—$(CH_2)_4$—. In certain embodiments of Formula (III)—(IVB), including any of the foregoing of Formula (III)—(IVB), $Y^a$ is *—C(O)—$(CH_2)_5$—. In certain embodiments, including any of the foregoing, $Y^a$ is *—C(O)—$(CH_2)_6$—.

In certain embodiments, including any of the foregoing of Formula (III)—(IVB), $Y^a$ is *—C(O)—$(CR^aR^b)$—. In certain embodiments of Formula (III)—(IVB), including any of the foregoing, $Y^a$ is *—C(O)—$(CR^aR^b)_2$—. In certain embodiments of Formula (III)—(IVB), including any of the foregoing, $Y^a$ is *—C(O)—$(CR^aR^b)_3$—. In certain embodiments of Formula (III)—(IVB), including any of the foregoing, $Y^a$ is *—C(O)—$(CR^aR^b)_4$—. In certain embodiments of Formula (III)—(IVB), including any of the foregoing, $Y^a$ is *—C(O)—$(CR^aR^b)_5$—. In certain embodiments of Formula (III)—(IVB), including any of the foregoing, $Y^a$ is *—C(O)—$(CR^aR^b)_6$—.

In certain embodiments of Formula (III)—(IVB), including any of the foregoing, $Y^a$ is *—C(O)—$(CR^aR^b)_c$— wherein $R^a$ is hydrogen and $R^b$ is selected from hydrogen, alkyl, alkenyl, alkynyl, cycloalkyl, halogen, alkoxy, —CN, —$NO_2$, —OH, —$N(R^2R^3)_2$, —C(O)$N(R^2R^3)_2$, —C(O)$OR^2$, aminoalkyl, hydroxyalkyl, haloalkyl, aryl, arylalkyl, heteroaryl, and heteroarylalkyl. In certain embodiments of Formula (III)—(IVB), including any of the foregoing, $Y^a$ is

*—C(O)—$(CR^aR^b)_2$—, *—C(O)—$(CR^aR^b)_3$—, or *—C(O)—$(CR^aR^b)_4$— wherein $R^a$ is hydrogen and $R^b$ is selected from hydrogen, alkyl, alkenyl, alkynyl, cycloalkyl, halogen, alkoxy, —CN, —$NO_2$, —OH, —$N(R^2R^3)_2$, —C(O)N$(R^2R^3)_2$, —C(O)$OR^2$, aminoalkyl, hydroxyalkyl, haloalkyl, aryl, arylalkyl, heteroaryl, and heteroarylalkyl.

In certain embodiments of Formula (III)—(IVB), including any of the foregoing, $Y^a$ is *—C(O)—$(CH_2)_2$—NH— or *—C(O)—$(CH_2)_4$—.

In certain embodiments of Formula (III)—(IVB), including any of the foregoing, $L^2$ is absent. In certain embodiments of Formula (III)—(IVB), including any of the foregoing, $L^2$ is a linker comprising a hydrophilic polymer residue.

In certain embodiments of Formula (III)—(IVB), including any of the foregoing, $L^2$ is —$(CR^aR^b)_a$-$POLY^1$-. In certain embodiments of Formula (III)—(IVB), including any of the foregoing, $L^2$ is —$CH_2$-$POLY^1$-. In certain embodiments of Formula (III)—(IVB), including any of the foregoing, $L^2$ is —$(CH_2)_2$-$POLY^1$-. In certain embodiments of Formula (III)—(IVB), including any of the foregoing, $L^2$ is —$(CH_2)_3$-$POLY^1$-. In certain embodiments of Formula (III)—(IVB), including any of the foregoing, $L^2$ is —$(CH_2)_4$-$POLY^1$-. In certain embodiments of Formula (III)—(IVB), including any of the foregoing, $L^2$ is —$(CH_2)_5$-$POLY^1$-. In certain embodiments of Formula (III)—(IVB), including any of the foregoing, $L^2$ is —$(CH_2)_6$-$POLY^1$-. In certain embodiments of Formula (III)—(IVB), including any of the foregoing, $L^2$ is —$CR^aR^b$-$POLY^1$-. In certain embodiments of Formula (III)—(IVB), including any of the foregoing, $L^2$ is —$(CR^aR^b)_2$-$POLY^1$-. In certain embodiments, including any of the foregoing, $L^2$ is —$(CR^aR^b)_3$-$POLY^1$-. In certain embodiments of Formula (III)—(IVB), including any of the foregoing, $L^2$ is —$(CR^aR^b)_4$-$POLY^1$-.

In certain embodiments of Formula (III)—(IVB), including any of the foregoing, $L^2$ is -$POLY^1$-.

In certain embodiments of Formula (III)—(IVB), including any of the foregoing, $L^2$ is —$(CR^aR^b)_a$-$POLY^1$-$(CR^aR^b)_a$—. In certain embodiments of Formula (III)—(IVB), including any of the foregoing, $L^2$ is —$(CR^aR^b)_2$-$POLY^1$-$(CR^aR^b)_a$— wherein a is independently selected from 0, 1, 2, 3, 4, 5, or 6. In certain embodiments of Formula (III)—(IVB), including any of the foregoing, $L^2$ is —$(CH_2)_a$-$POLY^1$-$(CH_2)_a$— wherein a is independently selected from 0, 1, 2, 3, 4, 5, or 6. In certain embodiments of Formula (III)—(IVB), including any of the foregoing, $L^2$ is —$(CH_2)_a$-$POLY^1$-$(CR^aR^b)_a$— wherein a is selected from 1, 2, 3, 4, 5, or 6. In certain embodiments of Formula (III)—(IVB), including any of the foregoing, $L^2$ is —$(CR^aR^b)_a$-$POLY^1$-$(CH_2)_a$— wherein a is independently selected from 0, 1, 2, 3, 4, 5, or 6.

In certain embodiments of Formula (III)—(IVB), including any of the foregoing, $POLY^1$ is a diavalent residue of a nonpeptidic, hydrophilic polymer. In certain embodiments of Formula (III)—(IVB), $POLY^1$ is a diavalent residue of polyethylene glycol (PEG), poly(propylene glycol) (PPG), copolymers of ethylene glycol and propylene glycol, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazolines (POZ), poly(N-acryloylmorpholine), polysarcosine, or a combination thereof. In certain embodiments of Formula (III)—(IVB), including any of the foregoing, $POLY^1$ is a divalent residue of polyethylene glycol (PEG), poly(propylene glycol) (PPG), or a copolymer of ethylene glycol and propylene glycol.

In certain embodiments of Formula (III)—(IVB), including any of the foregoing, $POLY^1$ is a diavalent residue of polyethylene glycol (PEG). In certain embodiments of Formula (III)—(IVB), including any of the foregoing, $POLY^1$ is a diavalent residue of poly(propylene glycol) (PPG). In certain embodiments of Formula (III)—(IVB), including any of the foregoing, $POLY^1$ is a diavalent residue of copolymers of ethylene glycol and propylene glycol. In certain embodiments of Formula (III)—(IVB), including any of the foregoing, $POLY^1$ is a diavalent residue of poly(oxyethylated polyol). In certain embodiments of Formula (III)—(IVB), including any of the foregoing, $POLY^1$ is a diavalent residue of poly(olefinic alcohol). In certain embodiments of Formula (III)—(IVB), including any of the foregoing, $POLY^1$ is a diavalent residue of poly(vinylpyrrolidone). In certain embodiments of Formula (III)—(IVB), including any of the foregoing, $POLY^1$ is a diavalent residue of poly(hydroxyalkylmethacrylamide). In certain embodiments of Formula (III)—(IVB), including any of the foregoing, $POLY^1$ is a diavalent residue of poly(hydroxyalkylmethacrylate). In certain embodiments of Formula (III)—(IVB), including any of the foregoing, $POLY^1$ is a diavalent residue of poly(saccharides). In certain embodiments of Formula (III)—(IVB), including any of the foregoing, $POLY^1$ is a diavalent residue of poly(α-hydroxy acid). In certain embodiments of Formula (III)—(IVB), including any of the foregoing, $POLY^1$ is a diavalent residue of poly(vinyl alcohol). In certain embodiments of Formula (III)—(IVB), including any of the foregoing, $POLY^1$ is a diavalent residue of polyphosphazene. In certain embodiments of Formula (III)—(IVB), including any of the foregoing, $POLY^1$ is a diavalent residue of polyoxazolines (POZ). In certain embodiments of Formula (III)—(IVB), including any of the foregoing, $POLY^1$ is a diavalent residue of poly(N-acryloylmorpholine). In certain embodiments of Formula (III)—(IVB), including any of the foregoing, $POLY^1$ is a diavalent residue of polysarcosine.

In certain embodiments of Formula (III)—(IVB), including any of the foregoing, $POLY^1$ is

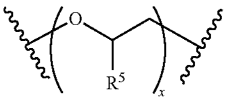

, wherein $R^5$ is hydrogen or methyl, x is an integer from 1 to 100, inclusive, and represents attachment to the remainder of the compound or conjugate. In certain embodiments of Formula (III)—(IVB), including any of the foregoing, x is an integer between 1 to 25. In certain embodiments of Formula (III)—(IVB), including any of the foregoing, x is an integer between 5 to 15. In some embodiments of Formula (III)—(IVB), including any of the foregoing, x is 1. In some embodiments of Formula (III)—(IVB), including any of the foregoing, x is 2. In some embodiments of Formula (III)—(IVB), including any of the foregoing, x is 3. In some embodiments of Formula (III)—(IVB), including any of the foregoing, x is 4. In some embodiments of Formula (III)—(IVB), including any of the foregoing, x is 5. In some embodiments of Formula (III)—(IVB), including any of the foregoing, x is 6. In some embodiments of Formula (III)—(IVB), including any of the foregoing, x is 7. In some embodiments of Formula (III)—(IVB), including any of the foregoing, x is 8. In some embodiments of Formula (III)—(IVB), including any of the foregoing, x is 9.

In some embodiments of Formula (III)—(IVB), including any of the foregoing, x is 10. In some embodiments of Formula (III)—(IVB), including any of the foregoing, x is 11. In some embodiments of Formula (III)—(IVB), including any of the foregoing, x is 12. In some embodiments of Formula (III)—(IVB), including any of the foregoing, x is 13. In some embodiments of Formula (III)—(IVB), including any of the foregoing, x is 14. In some embodiments of Formula (III)—(IVB), including any of the foregoing, x is 15. In some embodiments of Formula (III)—(IVB), including any of the foregoing, x is 16. In some embodiments of Formula (III)—(IVB), including any of the foregoing, x is 17. In some embodiments, including any of the foregoing, x is 18. In some embodiments of Formula (III)—(IVB), including any of the foregoing, x is 19. In some embodiments of Formula (III)—(IVB), including any of the foregoing, x is 20. In certain embodiments of Formula (III)—(IVB), including any of the foregoing, x is an integer between 25 and 50. In certain embodiments of Formula (III)—(IVB), including any of the foregoing, x is an integer between 35 and 45. In certain embodiments of Formula (III)—(IVB), including any of the foregoing, x is an integer between 50 and 75. In certain embodiments of Formula (III)—(IVB), including any of the foregoing, x is an integer between 55 and 65. In certain embodiments of Formula (III)—(IVB), including any of the foregoing, x is an integer between 75 and 100. In certain embodiments of Formula (III)—(IVB), including any of the foregoing, x is an integer between 85 and 95. In certain embodiments of Formula (III)—(IVB), including any of the foregoing, x is an integer in the range of 1 and 25, 20 and 45, 40 and 65, 60 and 85, 70 and 95, or 75 and 100.

In some embodiments of Formula (III)—(IVB), including any of the foregoing, $R^5$ is hydrogen. In some embodiments, including any of the foregoing, $R^5$ is methyl.

In certain embodiments of Formula (III)—(IVB), including any of the foregoing, $L^2$ is —$(CR^aR^b)_a$-$POLY^1$- wherein $POLY^1$ is

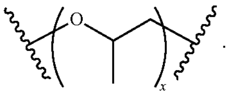

In certain embodiments of Formula (III)—(IVB), including any of the foregoing, $L^2$ is —$(CR^aR^b)_a$-$POLY^1$- wherein $POLY^1$ is

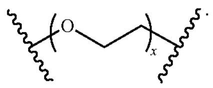

In certain embodiments of Formula (III)—(IVB), including any of the foregoing, $L^2$ is —$(CH_2)_a$-$POLY^1$- wherein $POLY^1$ is

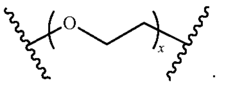

In certain embodiments of Formula (III)—(IVB), including any of the foregoing, $L^2$ is —$(CH_2)_2$-$POLY^1$- wherein $POLY^1$ is

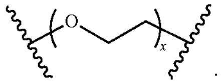

In certain embodiments of Formula (III)—(IVB), including any of the foregoing, $L^2$ is —$(CR^aR^b)_a$-$POLY^1$- wherein $POLY^1$ is

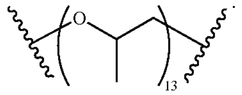

In certain embodiments of Formula (III)—(IVB), including any of the foregoing, $L^2$ is —$(CR^aR^b)_a$-$POLY^1$- wherein $POLY^1$ is

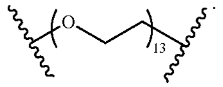

In certain embodiments of Formula (III)—(IVB), including any of the foregoing, $L^2$ is —$(CH_2)_2$-$POLY^1$- wherein $POLY^1$ is

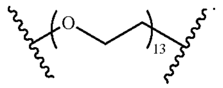

In certain embodiments of Formula (III)—(IVB), including any of the foregoing, $L^2$ is —$(CH_2)_2$-$POLY^1$- wherein $POLY^1$ is

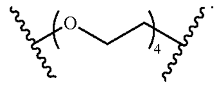

In certain embodiments of Formula (III)—(IVB), including any of the foregoing, $L^2$ is —$(CH_2)_2$-$POLY^1$- wherein $POLY^1$ is

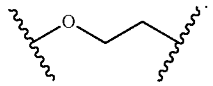 [SMILES: *CCO*]

In certain embodiments of Formula (III)—(IVB), including any of the foregoing, $L^2$ is

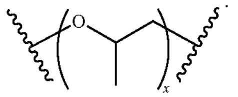

In certain embodiments, including any of the foregoing, $L^2$ is

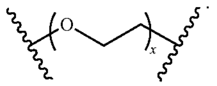

In certain embodiments of Formula (III)—(IVB), including any of the foregoing, $L^2$ is

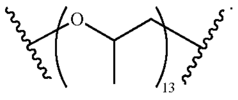

In certain embodiments of Formula (III)—(IVB), including any of the foregoing, $L^2$ is

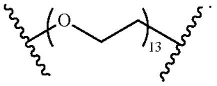

In certain embodiments of Formula (III)—(IVB), including any of the foregoing, $L^2$ is $—(CR^aR^b)$, $-POLY^1-(CR^aR^b)_a—$ wherein $POLY^1$ is

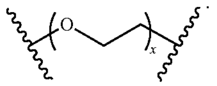

In certain embodiments of Formula (III)—(IVB), including any of the foregoing, $L^2$ is $—(CR^aR^b)_a-POLY^1-(CR^aR^b)_a—$ wherein $POLY^1$ is

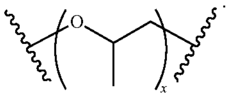

In certain embodiments of Formula (III)—(IVB), including any of the foregoing, $L^2$ is $—(CR^aR^b)_2-POLY^1-(CR^aR^b)_a—$ wherein $POLY^1$ is

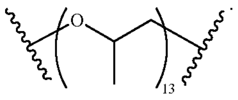

In certain embodiments of Formula (III)—(IVB), including any of the foregoing, $L^2$ is $—(CR^aR^b)_a-POLY^1-(CR^aR^b)_a—$ wherein $POLY^1$ is

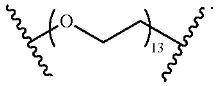

In certain embodiments of Formula (III)—(IVB), including any of the foregoing, $L^2$ is selected from

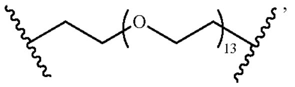

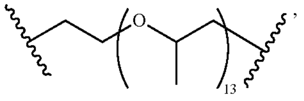

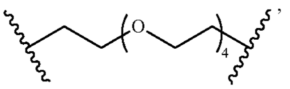

and

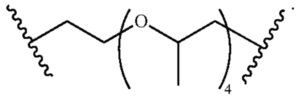

In certain embodiments of Formula (III)—(IVB), including any of the foregoing, $L^2$ is

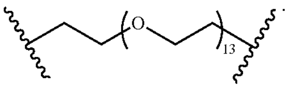

In certain embodiments of Formula (III)—(IVB), including any of the foregoing, $L^2$ is

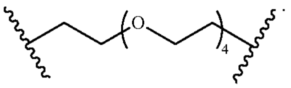

In certain embodiments of Formula (III)—(IVB), including any of the foregoing, $L^2$ is

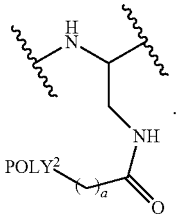

In certain embodiments of Formula (III)—(IVB), including any of the foregoing, $L^2$ is

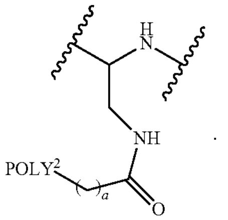

In certain embodiments of Formula (III)—(IVB), including any of the foregoing, $L^2$ is

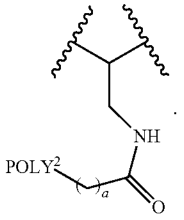

In certain embodiments of Formula (III)—(IVB), including any of the foregoing, $L^2$ is

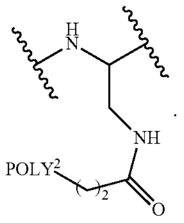

In certain embodiments of Formula (III)—(IVB), including any of the foregoing, $L^2$ is

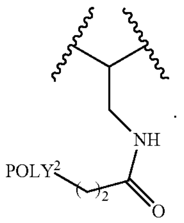

In certain embodiments of Formula (III)—(IVB), including any of the foregoing, $POLY^2$ is a residue of a nonpeptidic, hydrophilic polymer. In certain embodiments of Formula (III)—(IVB), $POLY^2$ is a residue of polyethylene glycol (PEG), methoxypolyethylene glycol (mPEG), poly (propylene glycol) (PPG), copolymers of ethylene glycol and propylene glycol, poly(oxyethylated polyol), poly (olefinic alcohol), poly(vinylpyrrolidone), poly(hydroxyalkylmethacrylamide), poly(hydroxyalkylmethacrylate), poly (saccharides), poly(α-hydroxy acid), poly(vinyl alcohol), polyphosphazene, polyoxazolines (POZ), poly(N-acryloylmorpholine), polysarcosine, or a combination thereof. In certain embodiments of Formula (III)—(IVB), including any of the foregoing, $POLY^2$ is a residue of polyethylene glycol (PEG), methoxypolyethylene glycol (mPEG), poly (propylene glycol) (PPG), or a copolymer of ethylene glycol and propylene glycol. In certain embodiments of Formula (III)—(IVB), including any of the foregoing, $POLY^2$ is a residue of methoxypolyethylene glycol (mPEG).

In certain embodiments of Formula (III)—(IVB), including any of the foregoing, $POLY^2$ is a residue of polyethylene glycol (PEG). In certain embodiments of Formula (III)—(IVB), including any of the foregoing, $POLY^2$ is a residue of poly(propylene glycol) (PPG). In certain embodiments, including any of the foregoing, $POLY^2$ is a residue of copolymers of ethylene glycol and propylene glycol. In certain embodiments of Formula (III)—(IVB), including any of the foregoing, $POLY^2$ is a residue of poly(oxyethylated polyol). In certain embodiments of Formula (III)—(IVB), including any of the foregoing, $POLY^2$ is a residue of poly(olefinic alcohol). In certain embodiments of Formula (III)—(IVB), including any of the foregoing, $POLY^2$ is a residue of poly(vinylpyrrolidone). In certain embodiments of Formula (III)—(IVB), including any of the foregoing, $POLY^2$ is a residue of poly(hydroxyalkylmethacrylamide). In certain embodiments of Formula (III)—(IVB), including any of the foregoing, $POLY^2$ is a residue of poly(hydroxyalkylmethacrylate). In certain embodiments of Formula (III)—(IVB), including any of the foregoing, $POLY^2$ is a residue of poly(saccharides). In certain embodiments of Formula (III)—(IVB), including any of the foregoing, $POLY^2$ is a residue of poly(α-hydroxy acid). In certain embodiments of Formula (III)—(IVB), including any of the foregoing, $POLY^2$ is a residue of poly(vinyl alcohol). In certain embodiments of Formula (III)—(IVB), including any of the foregoing, $POLY^2$ is a residue of polyphosphazene. In certain embodiments of Formula (III)—(IVB), including any of the foregoing, $POLY^2$ is a residue of polyoxazolines (POZ). In certain embodiments of Formula (III)—(IVB), including any of the foregoing, $POLY^2$ is a residue of poly(N-acryloylmorpholine). In certain embodiments of Formula (III)—(IVB), including any of the foregoing, $POLY^2$ is a residue of polysarcosine.

In certain embodiments of Formula (III)—(IVB), including any of the foregoing, $POLY^2$ is

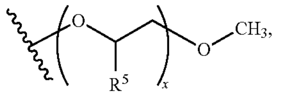

wherein $R^5$ is hydrogen or methyl, x is an integer from 1 to 100, inclusive, and  represents attachment to the remainder of the compound or conjugate. In certain embodiments of Formula (III)—(IVB), including any of the foregoing, x is an integer between 1 to 25. In certain embodiments of Formula (III)—(IVB), including any of the foregoing, x is an integer between 5 to 15. In some embodiments of Formula (III)—(IVB), including any of the foregoing, x is 1. In some embodiments of Formula (III)—(IVB), including any of the foregoing, x is 2. In some embodiments of Formula (III)—(IVB), including any of the foregoing, x is 3. In some embodiments of Formula (III)—(IVB), including any of the foregoing, x is 4. In some embodiments of Formula (III)—(IVB), including any of the foregoing, x is 5. In some embodiments of Formula (III)—(IVB), including any of the foregoing, x is 6. In some embodiments, including any of the foregoing, x is 7. In some embodiments of Formula (III)—(IVB), including any of the foregoing, x is 8. In some embodiments of Formula (III)—(IVB), including any of the foregoing, x is 9. In some embodiments of Formula (III)—(IVB), including any of the foregoing, x is 10. In some embodiments of Formula (III)—(IVB), including any of the foregoing, x is 11. In some embodiments of Formula (III)—(IVB), including any of the foregoing, x is 12. In some embodiments of Formula (III)—(IVB), including any of the foregoing, x is 13. In some embodiments of Formula (III)—(IVB), including any of the foregoing, x is 14. In some embodiments of Formula (III)—(IVB), including any of the foregoing, x is 15. In some embodiments of Formula (III)—(IVB), including any of the foregoing, x is 16. In some embodiments of Formula (III)—(IVB), including any of the foregoing of Formula (III)—(IVB), x is 17. In some embodiments, including any of the foregoing of Formula (III)—(IVB), x is 18. In some embodiments of Formula (III)—(IVB), including any of the foregoing, x is 19. In some embodiments of Formula (III)—(IVB), including any of the foregoing, x is 20. In certain embodiments of Formula (III)—(IVB), including any of the foregoing, x is an integer between 25 and 50. In certain embodiments of Formula (III)—(IVB), including any of the foregoing, x is an integer between 35 and 45. In certain embodiments of Formula (III)—(IVB), including any of the foregoing, x is an integer between 50 and 75. In certain embodiments of Formula (III)—(IVB), including any of the foregoing, x is an integer between 55 and 65. In certain embodiments of Formula (III)—(IVB), including any of the foregoing, x is an integer between 75 and 100. In certain embodiments of Formula (III)—(IVB), including any of the foregoing, x is an integer between 85 and 95. In certain embodiments of Formula (III)—(IVB), including any of the foregoing, x is an integer in the range of 1 and 25, 20 and 45, 40 and 65, 60 and 85, 70 and 95, or 75 and 100.

In some embodiments of Formula (III)—(IVB), including any of the foregoing, $R^5$ is hydrogen. In some embodiments of Formula (III)—(IVB), including any of the foregoing, $R^5$ is methyl.

In certain embodiments of Formula (III)—(IVB), including any of the foregoing, $L^2$ is selected from the group consisting of

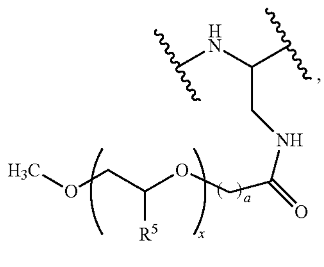

,

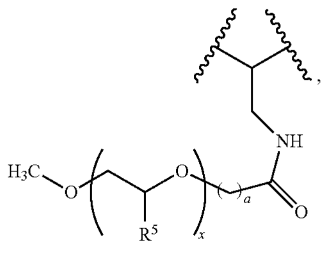

,

-continued

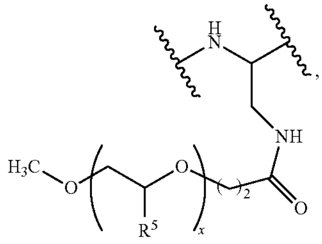

,

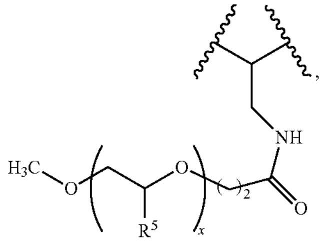

,

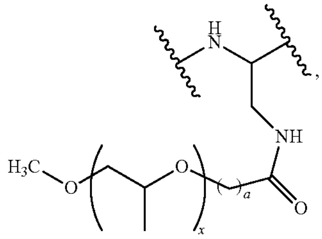

,

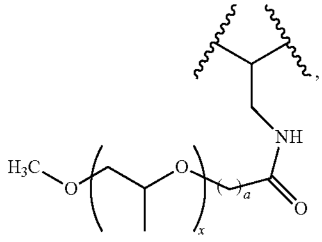

,

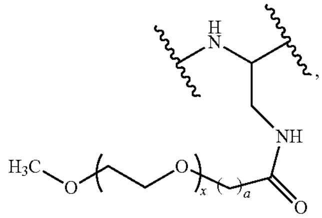

, and

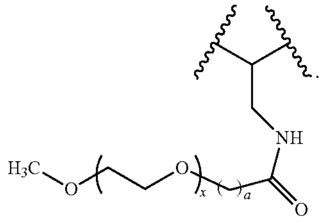

.

In certain embodiments of Formula (III)—(IVB), including any of the foregoing, $L^2$ is selected from the group consisting of

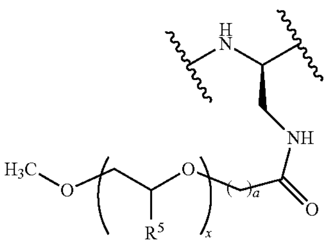
,

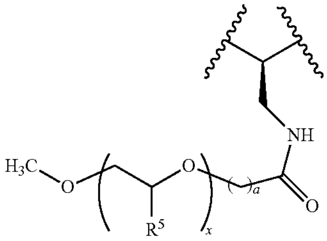
,

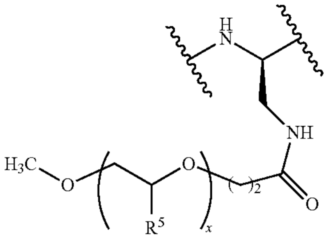
,

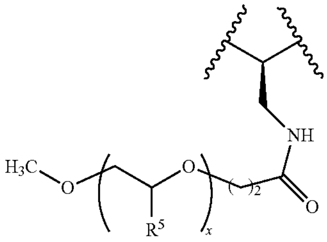
,

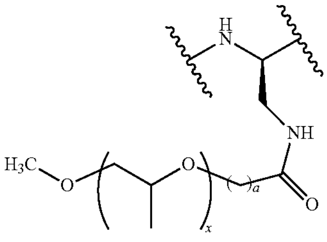
,

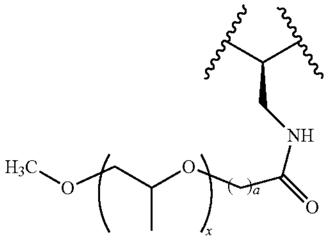
,

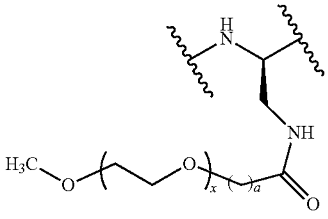
, and

-continued

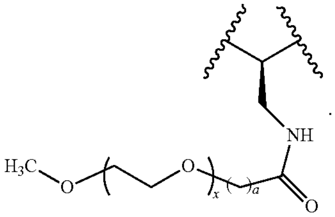
.

In certain embodiments of Formula (III)—(IVB), including any of the foregoing, $L^2$ is

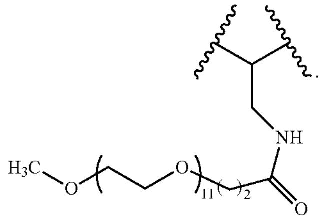
.

In certain embodiments of Formula (III)—(IVB), including any of the foregoing, $L^2$ is

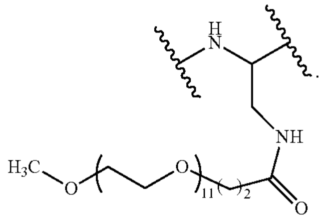
.

In certain embodiments of Formula (III)—(IVB), including any of the foregoing, $L^2$ is

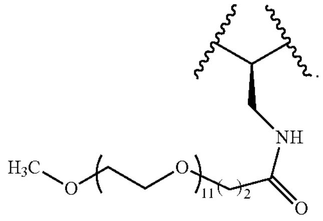
.

In certain embodiments of Formula (III)—(IVB), including any of the foregoing, $L^2$ is

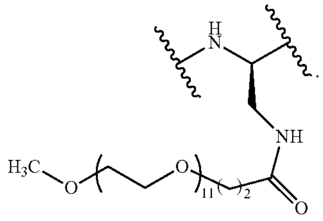
.

In certain embodiments of Formula (III)—(IVB), including any of the foregoing, $L^3$ is —C(O)-AA-.

In certain embodiments of Formula (III)—(IVB), including any of the foregoing, $L^3$ is —C(O)-AA-Z—$(CR^aR^b)_a$—Z—$(CR^aR^b)_a$—C(O)—. In certain embodiments of Formula (III)—(IVB), including any of the foregoing, $L^3$ is —C(O)-AA-$NR^2$—$(CR^aR^b)_a$—$NR^2$—$(CR^aR^b)_a$—C(O)—. In certain embodiments of Formula (III)—(IVB), including any of the foregoing, $L^3$ is —C(O)-AA-NH—$(CR^aR^b)_a$—NH—$(CR^aR^b)_a$—C(O)—. In certain embodiments of Formula (III)—(IVB), including any of the foregoing, $L^3$ is —C(O)-AA-NH—$(CH_2)_a$—NH—$(CH_2)_a$—C(O)—. In certain embodiments of Formula (III)—(IVB), including any of the foregoing, $L^3$ is —C(O)-AA-NH—$(CH_2)_a$—NH—$(CH_2)_a$—C(O)— wherein a is selected from 1, 2, and 3. In certain embodiments, including any of the foregoing, $L^3$ is —C(O)-AA-NH—$CH_2$—NH—$CH_2$—C(O)—

In certain embodiments of Formula (III)—(IVB), including any of the foregoing, $L^3$ is —C(O)-AA-Z—$(CR^aR^b)$ a. In certain embodiments, including any of the foregoing, $L^3$ is —C(O)-AA-$NR^2$—$(CH_2)$ a. In certain embodiments of Formula (III)—(IVB), including any of the foregoing, $L^3$ is —C(O)-AA-NH—$(CH_2)_2$.

In certain embodiments of Formula (III)—(IVB), including any of the foregoing, $L^3$ is -AA-. In certain embodiments, including any of the foregoing, $L^3$ is

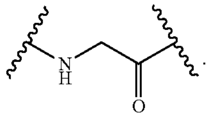 [SMILES: *NCC(*)=O].

In certain embodiments of Formula (III)—(IVB), including any of the foregoing, -AA- is an amino acid residue. In certain embodiments of Formula (III)—(IVB), including any of the foregoing, -AA- is a peptide residue. In certain embodiments of Formula (III)—(IVB), including any of the foregoing, -AA- is a dipeptide residue, a tripeptide residue, a tetrapeptide residue, or a pentapeptide residue. In certain embodiments of Formula (III)—(IVB), including any of the foregoing, -AA- comprises at least one amino acid residue selected from alanine, glycine, valine, and asparagine. In certain embodiments of Formula (III)—(IVB), including any of the foregoing, -AA- comprises at least one amino acid residue selected from alanine and glycine. In certain embodiments of Formula (III)—(IVB), including any of the foregoing, -AA- is selected from the group consisting of

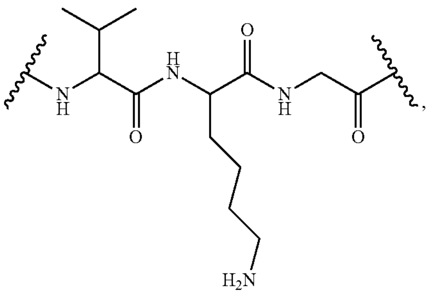,

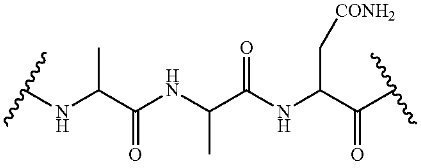,

-continued

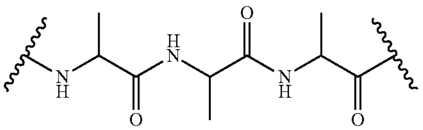,

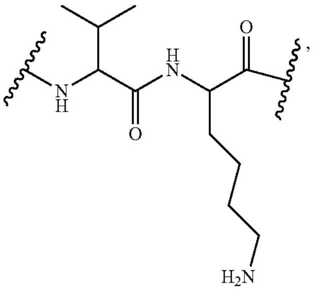,

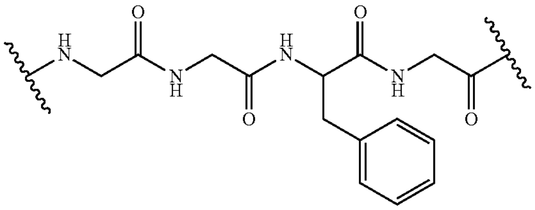,

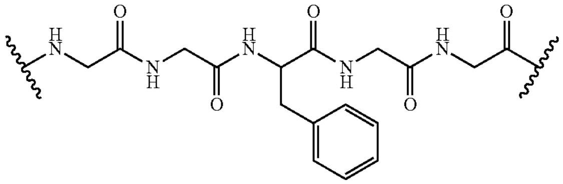,

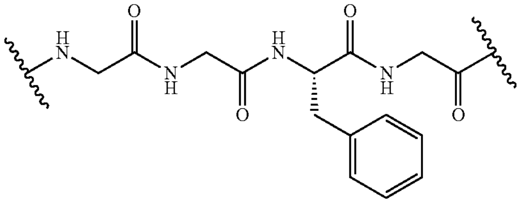, and

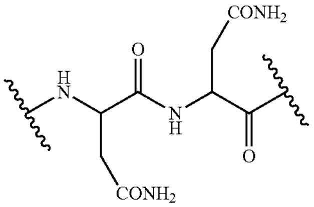.

In certain embodiments of Formula (III)—(IVB), including any of the foregoing, -AA- is selected from the group consisting of

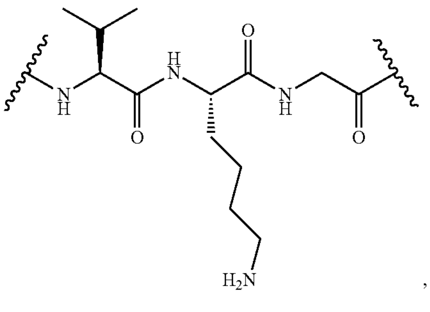,

-continued

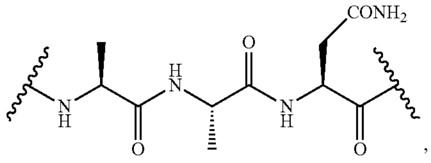

,

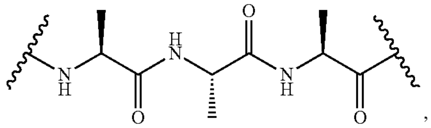

,

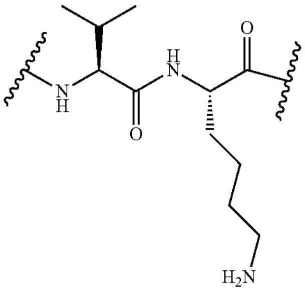

,

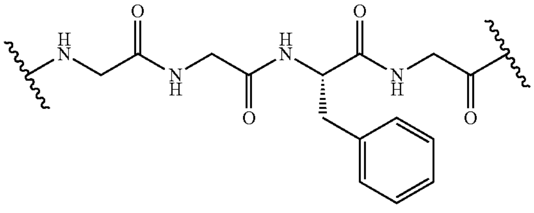

,

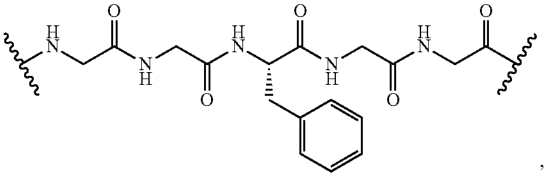

,

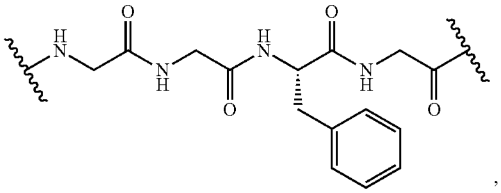

, and

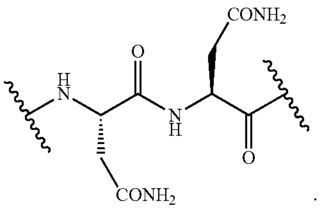

.

In certain embodiments of Formula (III)—(IVB), including any of the foregoing, $L^3$ is —C(O)—.

In certain embodiments of Formula (III)—(IVB), including any of the foregoing, $L^3$ is —C(O)—Z—$(CR^aR^b)_a$—C(O)—Z-$L^4$-OC(O)— wherein $L^4$ is

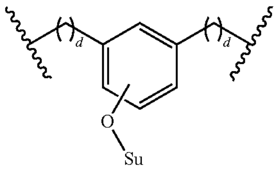

and Su is a hexose form of a monosaccharide and d is an integer independently selected from 1, 2, and 3. In certain embodiments of Formula (III)—(IVB), including any of the foregoing, $L^3$ is —C(O)—$NR^2$—$(CR^aR^b)_a$—C(O)—$NR^2$-$L^4$-OC(O)—. In certain embodiments of Formula (III)—(IVB), including any of the foregoing, $L^3$ is —C(O)—$NR^2$—$(CH_2)_2$—C(O)—$NR^2$-$L^4$-OC(O)—. In certain embodiments of Formula (III)—(IVB), including any of the foregoing, $L^3$ is —C(O)—NH—$(CR^aR^b)_a$—C(O)—NH-$L^4$-OC(O)—. In certain embodiments of Formula (III)—(IVB), including any of the foregoing, $L^3$ is —C(O)—NH—$(CH_2)_2$—C(O)—NH-$L^4$-OC(O)—.

In certain embodiments of Formula (III)—(IVB), including any of the foregoing, $L^4$ is

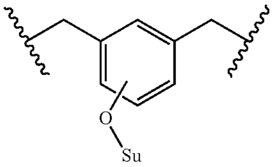

.

In certain embodiments of Formula (III)—(IVB), including any of the foregoing, $L^4$ is

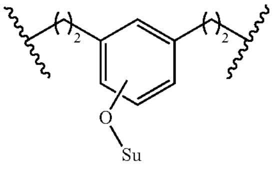

.

In certain embodiments of Formula (III)—(IVB), including any of the foregoing, $L^4$ is

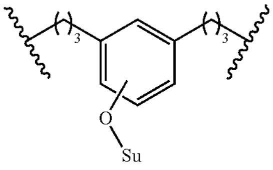

.

In some embodiments of Formula (III)—(IVB), including any of the foregoing, Su is a sugar moiety. In some embodiments, Su is a hexose form of a monosaccharide. Su may be a glucuronic acid or mannose residue. In certain embodiments of Formula (III)—(IVB), including any of the foregoing, Su is

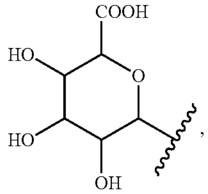 [SMILES: *C1OC(C(=O)O)C(O)C(O)C1O]

, wherein  represents attachment to the remainder of the compound. In certain embodiments of Formula (III)—(IVB), including any of the foregoing, Su is

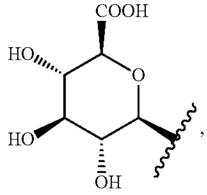 [SMILES: *[C@@H]1O[C@H](C(=O)O)[C@@H](O)[C@H](O)[C@H]1O]

, wherein  represents attachment to the remainder of the compound.

In certain embodiments of Formula (III)—(IVB), including any of the foregoing, $L^4$ is

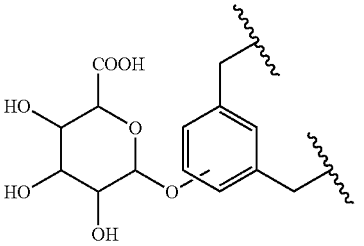

or

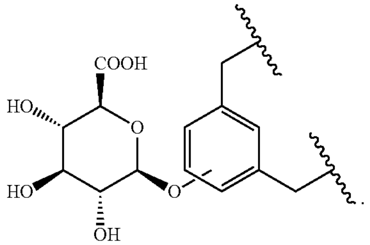

.

In certain embodiments of Formula (III)—(IVB), including any of the foregoing, $L^3$ is —C(O)—NH—$(CH_2)_2$—C(O)—NH-$L^4$-OC(O)— wherein $L^4$ is

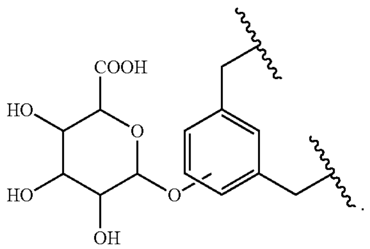

.

In certain embodiments of Formula (III)—(IVB), including any of the foregoing, $L^3$ is —C(O)—NH—$(CH_2)_2$—C(O)—NH-$L^4$-OC(O)— wherein $L^4$ is

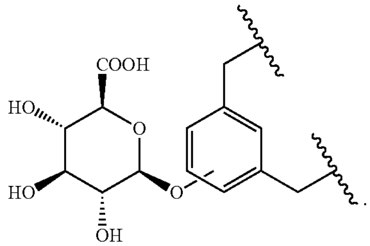

.

In certain embodiments of Formula (III)—(IVB), including any of the foregoing, $L^2$ is —$(CR^aR^b)_a$-$POLY^1$- and $L^3$ is —C(O)-AA-. In certain embodiments of Formula (III)—(IVB), including any of the foregoing, $L^2$ is —$(CR^aR^b)_a$-$POLY^1$-; $L^3$ is —C(O)-AA-; and, $POLY^1$ is

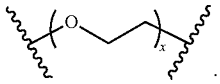

.

In certain embodiments of Formula (III)—(IVB), including any of the foregoing, $L^2$ is —$(CH_2)_a$-$POLY^1$-; $L^3$ is —C(O)-AA-; $POLY^1$ is

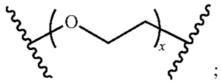

;

and x is an integer between 10 and 15. In certain embodiments of Formula (III)—(IVB), including any of the foregoing, $L^2$ is —$(CH_2)_2$-$POLY^1$-; $L^3$ is —C(O)-AA-; and, $POLY^1$ is

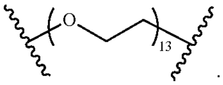

.

In certain embodiments of Formula (III)—(IVB), including any of the foregoing, $L^2$ is —$(CH_2)_2$-$POLY^1$-; $L^3$ is —C(O)-AA-; $POLY^1$ is

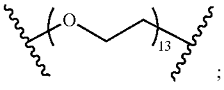

;

and AA is a dipeptide residue, a tripeptide residue, a tetrapeptide residue, or a pentapeptide residue.

In certain embodiments of Formula (III)—(IVB), including any of the foregoing, $L^2$ is —$(CR^aR^b)_a$-$POLY^1$- and $L^3$ is —C(O)-AA-Z—$(CR^aR^b)_a$—Z—$(CR^aR^b)_a$—C(O)—. In certain embodiments of Formula (III)—(IVB), including any of the foregoing. $L^2$ is —$(CR^aR^b)$, -$POLY^1$-; $L^3$ is —C(O)-AA-Z—$(CR^aR^b)_a$—Z—$(CR^aR^b)_a$—C(O)—; $POLY^1$ is

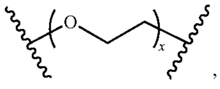, and Z is —NH—. In certain embodiments of Formula (III)—(IVB), including any of the foregoing, $L^2$ is: —$(CH_2)_a$-$POLY^1$-; $L^3$ is —C(O)-AA-NH—$(CH_2)_a$—NH—$(CH_2)_a$—C(O)—; $POLY^1$ is

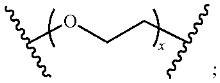;

and x is an integer between 10 and 15. In certain embodiments of Formula (III)—(IVB), including any of the foregoing, $L^2$ is —$(CH_2)_2$-$POLY^1$-; $L^3$ is —C(O)-AA-NH—$CH_2$—NH—$CH_2$—C(O)—; and, $POLY^1$ is

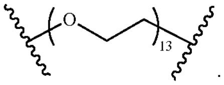.

In certain embodiments of Formula (III)—(IVB), including any of the foregoing, $L^2$ is —$(CH_2)_2$-$POLY^1$-; $L^3$ is —C(O)-AA-NH—$CH_2$—NH—$CH_2$—C(O)—; $POLY^1$ is

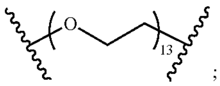;

and AA is a dipeptide residue, a tripeptide residue, a tetrapeptide residue, or a pentapeptide residue.

In certain embodiments of Formula (III)—(IVB), including any of the foregoing, $L^2$ is —$(CR^aR^b)_a$-$POLY^1$- and $L^3$ is —C(O). In certain embodiments of Formula (III)—(IVB), including any of the foregoing, $L^2$ is —$(CR^aR^b)_a$-$POLY^1$-; $L^3$ is —C(O); and, $POLY^1$ is

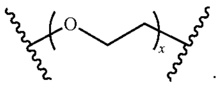.

In certain embodiments of Formula (III)—(IVB), including any of the foregoing, $L^2$ is —$(CH_2)_a$-$POLY^1$-; $L^3$ is —C(O); $POLY^1$ is

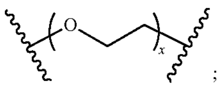;

and x is an integer between 10 and 15. In certain embodiments of Formula (III)—(IVB), including any of the foregoing, $L^2$ is —$(CH_2)_2$-POLY'-; $L^3$ is —C(O); and, $POLY^1$ is

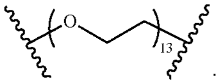.

In certain embodiments of Formula (III)—(IVB), including any of the foregoing, $L^2$ is —$(CH_2)_2$-$POLY^1$-; $L^3$ is —C(O); $POLY^1$ is

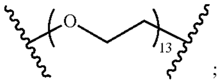;

and AA is a dipeptide residue, a tripeptide residue, a tetrapeptide residue, or a pentapeptide residue.

In certain embodiments of Formula (III)—(IVB), including any of the foregoing, $L^2$ is —$(CR^aR^b)_a$-$POLY^1$- and $L^3$ is absent. In certain embodiments of Formula (III)—(IVB), including any of the foregoing, $L^2$ is —$(CR^aR^b)_a$-$POLY^1$-; $L^3$ is absent; and, $POLY^1$ is

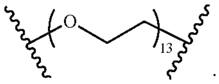.

In certain embodiments of Formula (III)—(IVB), including any of the foregoing, $L^2$ is —$(CH_2)_a$-$POLY^1$-; $L^3$ is absent; $POLY^1$ is

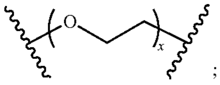;

and x is an integer between 10 and 15. In certain embodiments of Formula (III)—(IVB), including any of the foregoing, $L^2$ is —$(CH_2)_2$-$POLY^1$-; $L^3$ is absent; and, $POLY^1$ is

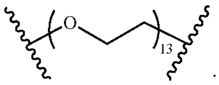.

In certain embodiments of Formula (III)—(IVB), including any of the foregoing, $L^2$ is —$(CH_2)_2$-$POLY^1$-; $L^3$ is absent; $POLY^1$ is

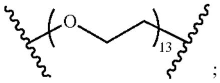;

and AA is a dipeptide residue, a tripeptide residue, a tetrapeptide residue, or a pentapeptide residue.

In certain embodiments of Formula (III)—(IVB), including any of the foregoing, $L^2$ is —$(CR^aR^b)_a$-$POLY^1$- and $L^3$ is —C(O)-AA-Z—$(CR^aR^b)_a$—. In certain embodiments of Formula (III)—(IVB), including any of the foregoing, $L^2$ is —$(CR^aR^b)_a$-$POLY^1$; $L^3$ is —C(O)-AA-Z—$(CR^aR^b)_a$—; and, $POLY^1$ is

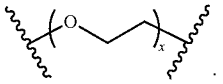

In certain embodiments of Formula (III)—(IVB), including any of the foregoing, $L^2$ is $—(CH_2)_a$-POLY$^1$-; —C(O)-AA-$NR^2$—$(CR^aR^b)_a$—; POLY$^1$ is

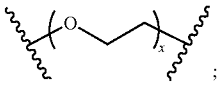

and x is an integer between 10 and 15. In certain embodiments of Formula (III)—(IVB), including any of the foregoing, $L^2$ is $—(CH_2)_2$-POLY$^1$-; $L^3$ is —C(O)-AA-NH—$(CR^aR^b)_a$—; and, POLY$^1$ is

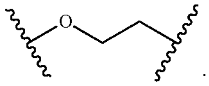 [SMILES: *CCO*]

In certain embodiments of Formula (III)—(IVB), including any of the foregoing, $L^2$ is $—(CH_2)_2$-POLY$^1$-; $L^3$ is —C(O)-AA-NH—$(CR^aR^b)_a$—; POLY$^1$ is

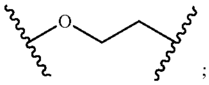 [SMILES: *CCO*]

and AA is a dipeptide residue, a tripeptide residue, a tetrapeptide residue, or a pentapeptide residue.

Non-limiting examples of -$L^2$-$L^3$-include:

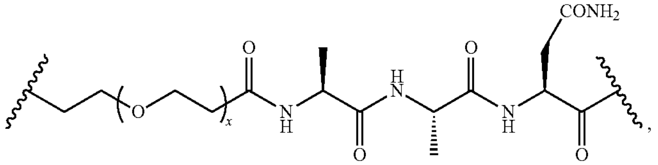

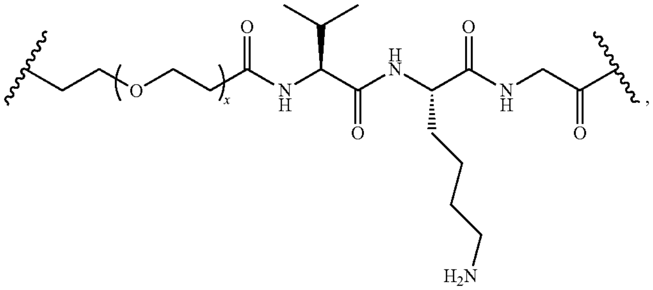

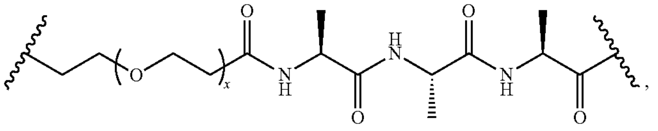

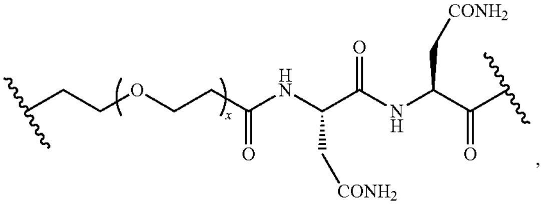

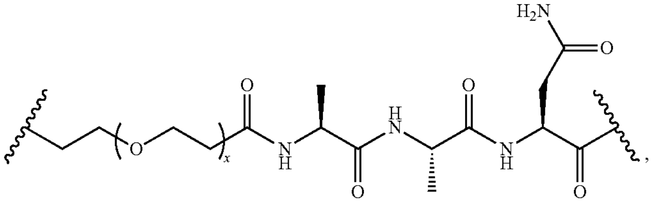

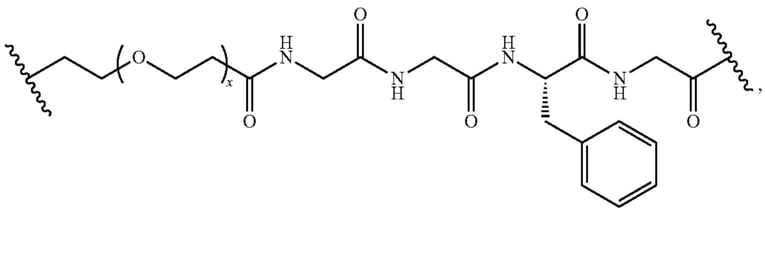

-continued
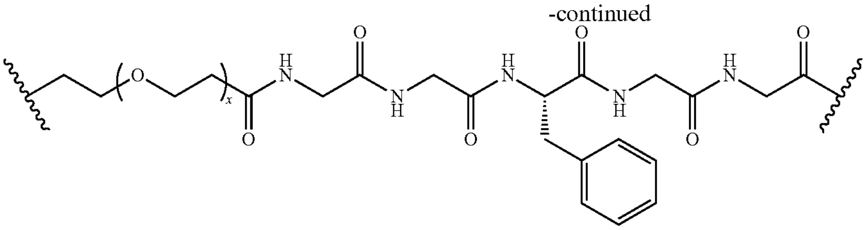,
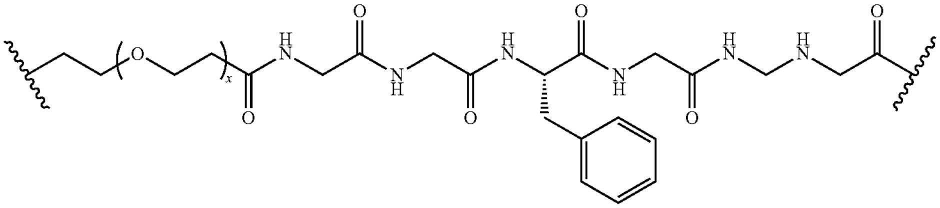,
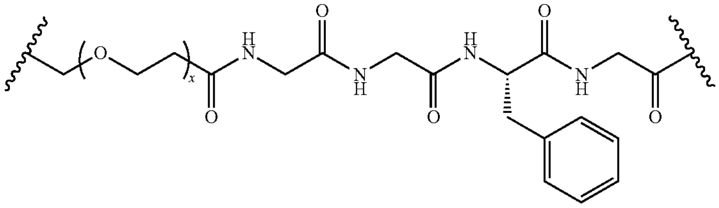,
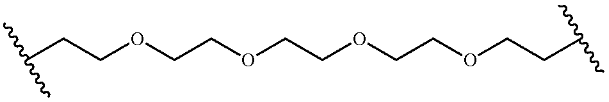
and
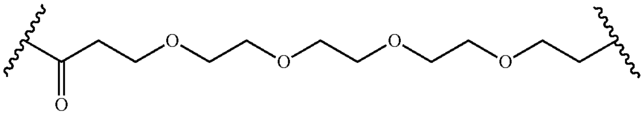
Additional non-limiting examples of -$L^2$-$L^3$-include:
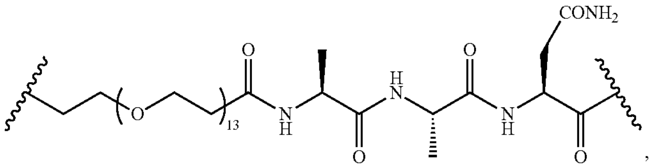,
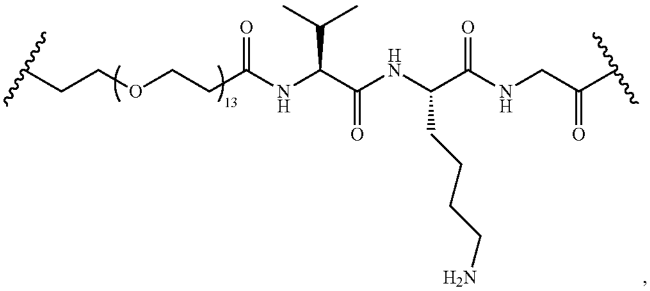,
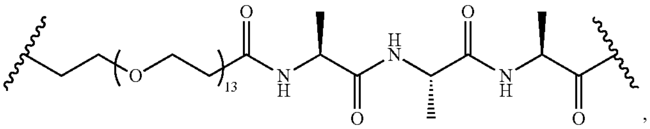,
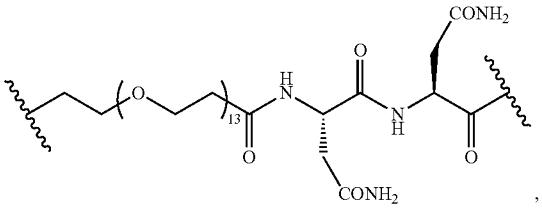, -continued

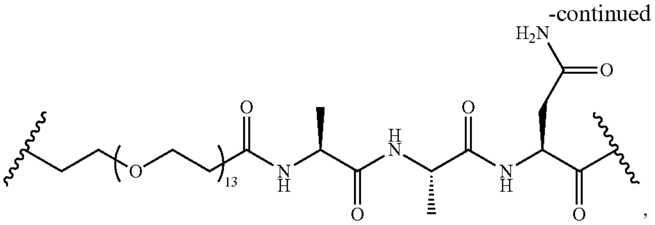

,

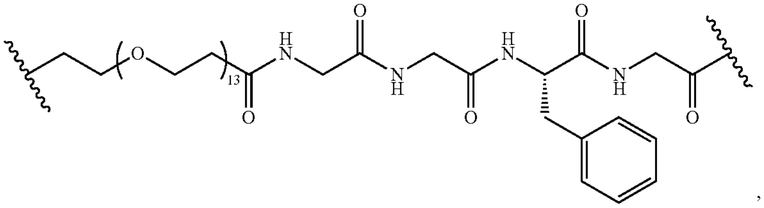

,

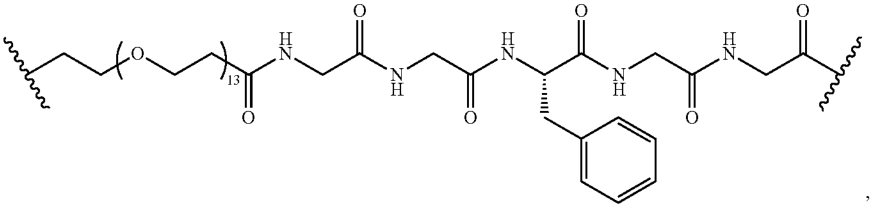

,

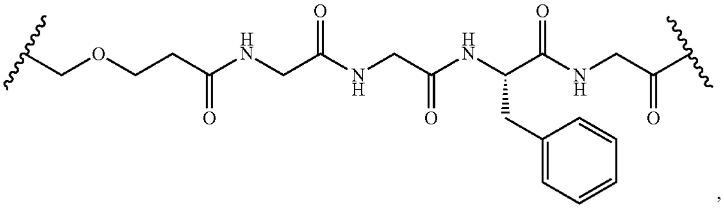

, and

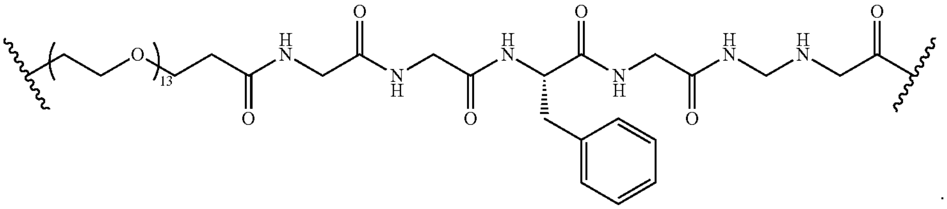

.

In certain embodiments of Formula (III)—(IVB), including any of the foregoing, $L^2$ is

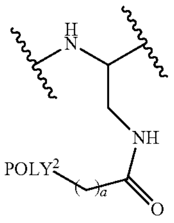

and $L^3$ is —C(O)—Z—$(CR^aR^b)_a$—C(O)—Z-$L^4$-OC(O)— wherein $L^4$ is

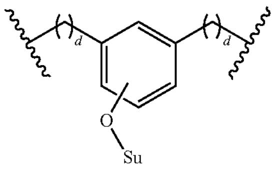

and Su is a hexose form of a monosaccharide and d is an integer independently selected from 1, 2, and 3. In certain embodiments of Formula (III)—(IVB), including any of the foregoing, $L^2$ is

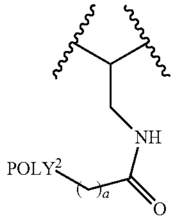

and $L^3$ is —C(O)—Z—$(CR^aR^b)_a$—C(O)—Z-$L^4$-OC(O)—.

In certain embodiments of Formula (III)—(IVB), including any of the foregoing, $L^2$ is

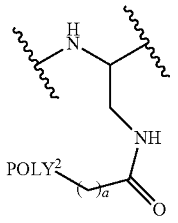

and $L^3$ is —C(O). In certain embodiments, including any of the foregoing, $L^2$ is

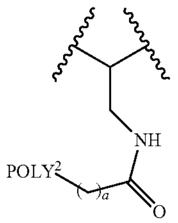

and $L^3$ is absent.

In certain embodiments of Formula (III)—(IVB), including any of the foregoing, $L^2$ is selected from the group consisting of

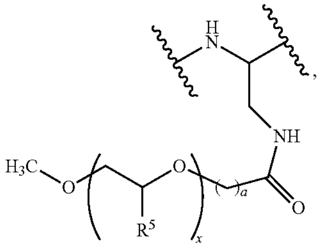

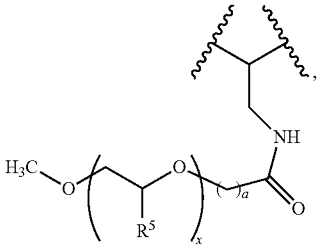

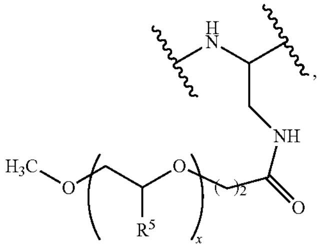

-continued

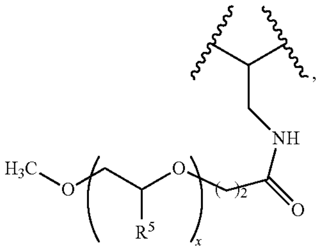

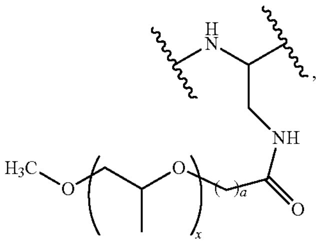

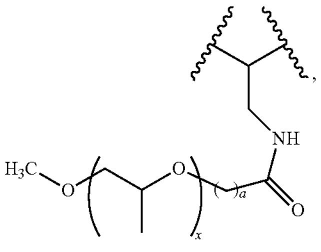

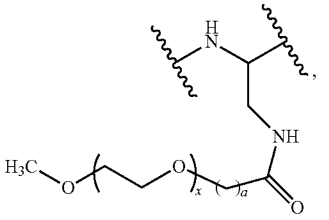

and

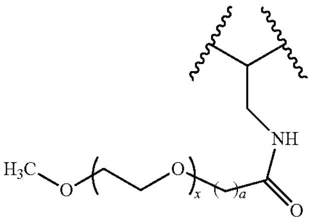

and $L^3$ is —C(O)—NH—$(CR^aR^b)_a$—C(O)—NH-$L^4$-OC(O)—.

In certain embodiments of Formula (III)—(IVB), including any of the foregoing, $L^2$ is selected from the group consisting of

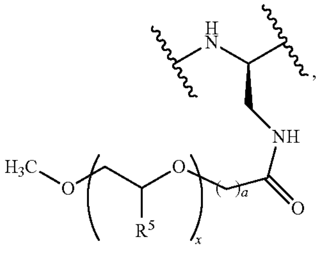

-continued
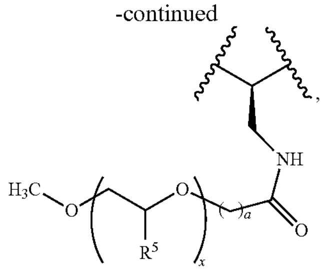,
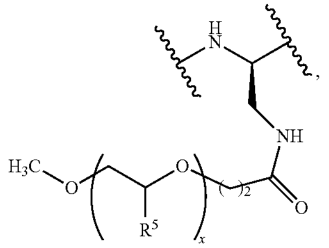,
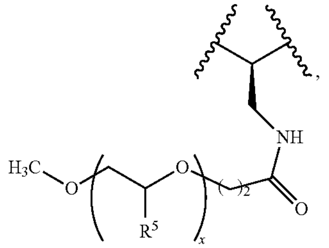,
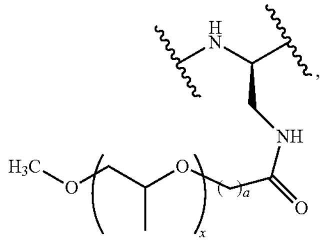,
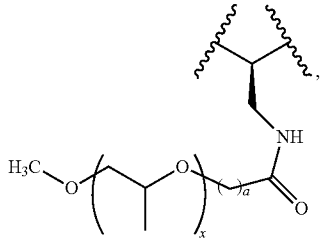,
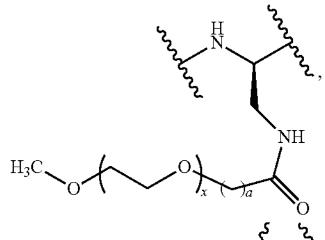, and
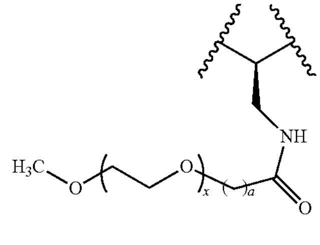
and $L^3$ is —C(O)—NH—$(CR^aR^b)_a$—C(O)—NH-$L^4$-OC(O)—.
In certain embodiments of Formula (III)—(IVB), including any of the foregoing, $L^2$ is selected from the group consisting of
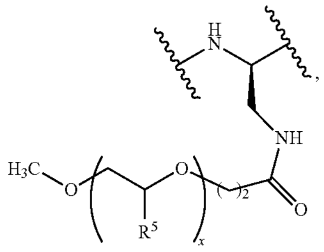,
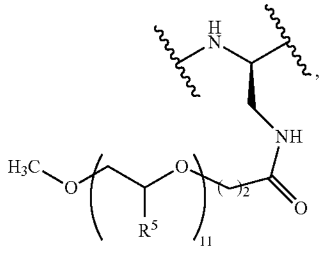,
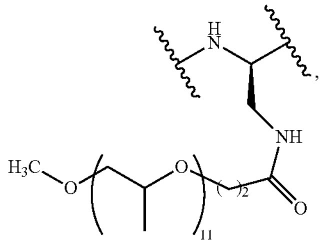, and
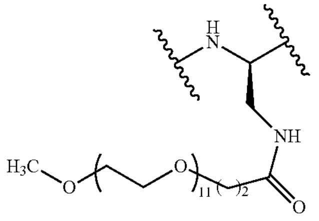
and $L^3$ is —C(O)—NH—$(CH_2)_2$—C(O)—NH-$L^4$-OC(O)— wherein $L^4$ is
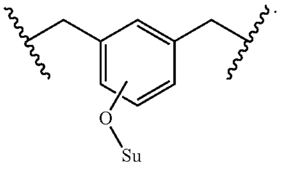.
In certain embodiments of Formula (III)—(IVB), including any of the foregoing, $L^2$ is selected from the group consisting of

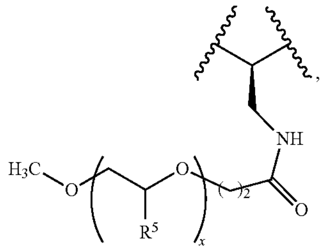

,

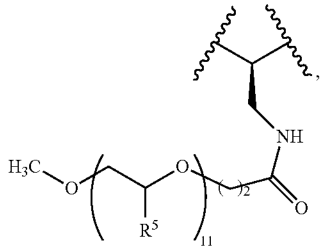

,

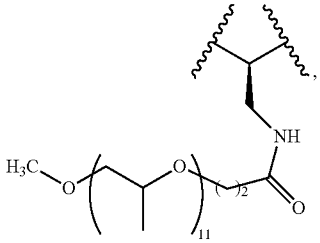

, and

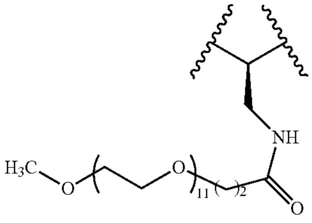

and $L^3$ is —C(O).

In certain embodiments, including any of the foregoing, D is a cytotoxic payload selected from a tubulin inhibitor, a DNA topoisomerase I inhibitor, and a DNA topoisomerase II inhibitor. In some embodiments, including any of the foregoing, D is a tubulin inhibitor. In some embodiments, including any of the foregoing, D is a DNA topoisomerase I inhibitor. In some embodiments, including any of the foregoing, D is a DNA topoisomerase I inhibitor selected from the group consisting of irinotecan, SN-38, topotecan, exatecan. In some embodiments, including any of the foregoing, D is irinotecan. In some embodiments, including any of the foregoing, D is SN-38. In some embodiments, including any of the foregoing, D is topotecan. In some embodiments, including any of the foregoing, D is exatecan. In some embodiments, including any of the foregoing, D is a DNA topoisomerase II inhibitor. In some embodiments, including any of the foregoing, D is a DNA topoisomerase II inhibitor selected from the group consisting of etoposide, teniposide, and tafluposide. In some embodiments, including any of the foregoing, D is etoposide. In some embodiments, including any of the foregoing, D is teniposide. In some embodiments, including any of the foregoing, D is tafluposide. In some embodiments, including any of the foregoing, D is selected from the group consisting of hemiasterlins, camptothecins, and anthracyclines. Anthracyclines may include PNU-159682 and EDA PNU-159682 derivatives. In some embodiments, including any of the foregoing, D is an anthracycline selected from the group consisting of daunorubicin, doxorubicin, epirubicin, idarubicin, mitoxantrone, and valrubicin. In some embodiments, including any of the foregoing, D is daunorubicin. In some embodiments, including any of the foregoing, D is doxorubicin. In some embodiments, including any of the foregoing, D is epirubicin. In some embodiments, including any of the foregoing, D is idarubicin. In some embodiments, including any of the foregoing, D is mitoxantrone. In some embodiments, including any of the foregoing, D is valrubicin. In some embodiments, including any of the foregoing, D is a hemiasterlin. In some embodiments, including any of the foregoing, D is a camptothecin. In some embodiments, including any of the foregoing, D is an anthracycline. In some embodiments, including any of the foregoing, D is PNU-159682. In some embodiments, including any of the foregoing, D is an EDA PNU compound. In some embodiments, including any of the foregoing, D is an EDA PNU-159682 derivative. In some embodiments, including any of the foregoing, D is hemiasterlin, exatecan, PNU-159682, or an EDA PNU-159682 derivative. In some embodiments, including any of the foregoing, D is hemiasterlin. In some embodiments, including any of the foregoing, D is exatecan. In some embodiments, including any of the foregoing, D is of PNU-159682. In some embodiments, including any of the foregoing, D is EDA PNU-159682 compound or derivative.

In some embodiments, including any of the foregoing, D is an alkylating agent. In some embodiments, including any of the foregoing, D is a bifunctional alkylator. In some embodiments, including any of the foregoing, D is a bifunctional alkylator selected from the group consisting of cyclophosphamide, mechlorethamine, chlorambucil, and melphalan. In some embodiments, including any of the foregoing, D is cyclophosphamide. In some embodiments, including any of the foregoing, D is mechlorethamine. In some embodiments, including any of the foregoing, D is chlorambucil. In some embodiments, including any of the foregoing, D is melphalan. In some embodiments, including any of the foregoing, D is a monofunctional alkylator. In some embodiments, including any of the foregoing, D is a monofunctional alkylator selected from the group consisting of dacarbazine, nitrosourea, and temozolomide. In some embodiments, including any of the foregoing, D is dacarbazine. In some embodiments, including any of the foregoing, D is nitrosourea. In some embodiments, including any of the foregoing, D is temozolomide. In some embodiments, including any of the foregoing, D is a cytoskeletal disruptor (e.g., a taxane). In some embodiments, including any of the foregoing, D is a cytoskeletal disruptor selected from the group consisting of paclitaxel, docetaxel, abraxane, and taxotere. In some embodiments, including any of the foregoing, D is paclitaxel. In some embodiments, including any of the foregoing, D is docetaxel. In some embodiments, including any of the foregoing, D is abraxane. In some embodiments, including any of the foregoing, D is taxotere. In some embodiments, including any of the foregoing, D is an epothilone. In some embodiments, including any of the foregoing, D is an epothilone selected from the group consisting of epothilone A, epothilone B, epothilone C, epothilone D, and ixabepilone. In some embodiments, including any of the foregoing, D is epothilone A. In some embodiments, including any of the foregoing, D is epothilone B. In some embodiments, including any of the foregoing, D is epothilone C. In some embodiments, including any of the foregoing, D is epothilone D. In some embodiments, including any of the foregoing, D is ixabepilone. In some embodiments, including any of the foregoing, D is a histone deacetylase inhibitor. In some embodiments, including any of the foregoing, D is a histone deacetylase inhibitor selected from the group consisting of vorinostat and romidepsin. In some embodiments, including any of the foregoing, D is vorinostat. In some embodiments, including any of the foregoing, D is romidepsin. In some embodiments, including any of the foregoing, D is a kinase inhibitor. In some embodiments, including any of the foregoing, D is a kinase inhibitor selected from the group consisting of bortezomib, erlotinib, gefitinib, imatinib, vemurafenib, and vismodegib. In some embodiments, including any of the foregoing, D is bortezomib. In some embodiments, including any of the foregoing, D is erlotinib. In some embodiments, including any of the foregoing, D is gefitinib. In some embodiments, including any of the foregoing, D is imatinib. In some embodiments, including any of the foregoing, D is vemurafenib. In some embodiments, including any of the foregoing, D is vismodegib. In some embodiments, including any of the foregoing, D is a nucleotide analog and/or precursor analog. In some embodiments, including any of the foregoing, D is a nucleotide analog and/or precursor analog selected from the group consisting of azacitidine, azathioprine, capecitabine, cytarabine, doxifluridine, fluorouracil, gemcitabine, hydroxyurea, mercaptopurine, methotrexate, and tioguanine (formerly thioguanine). In some embodiments, including any of the foregoing, D is azacitidine. In some embodiments, including any of the foregoing, D is azathioprine. In some embodiments, including any of the foregoing, D is capecitabine. In some embodiments, including any of the foregoing, D is cytarabine. In some embodiments, including any of the foregoing, D is doxifluridine. In some embodiments, including any of the foregoing, D is fluorouracil. In some embodiments, including any of the foregoing, D is gemcitabine. In some embodiments, including any of the foregoing, D is hydroxyurea. In some embodiments, including any of the foregoing, D is mercaptopurine. In some embodiments, including any of the foregoing, D is methotrexate. In some embodiments, including any of the foregoing, D is tioguanine (formerly thioguanine). In some embodiments, including any of the foregoing, D is a peptide antibiotic. In some embodiments, including any of the foregoing, D is a peptide antibiotic selected from the group consisting of bleomycin and actinomycin. In some embodiments, including any of the foregoing, D is bleomycin. In some embodiments, including any of the foregoing, D is actinomycin. In some embodiments, including any of the foregoing, D is a platinum-based agent. In some embodiments, including any of the foregoing, D is a platinum-based agent selected from the group consisting of carboplatin, cisplatin, and oxaliplatin. In some embodiments, including any of the foregoing, D is carboplatin. In some embodiments, including any of the foregoing, D is cisplatin. In some embodiments, including any of the foregoing, D is oxaliplatin. In some embodiments, including any of the foregoing, D is a retinoid. In some embodiments, including any of the foregoing, D is a retinoid selected from the group consisting of tretinoin, alitretinoin, and bexarotene. In some embodiments, including any of the foregoing, D is tretinoin. In some embodiments, including any of the foregoing, D is alitretinoin. In some embodiments, including any of the foregoing, D is bexarotene. In some embodiments, including any of the foregoing, D is a vinca alkaloid and derivatives thereof. In some embodiments, including any of the foregoing, D is a vinca alkaloid and derivatives thereof selected from the group consisting of vinblastine, vincristine, vindesine, vinorelbine. In some embodiments, including any of the foregoing, D is a residue of vinblastine. In some embodiments, including any of the foregoing, D is vincristine. In some embodiments, including any of the foregoing, D is vindesine.

In any of the foregoing embodiments, the conjugate comprises n2 number of linker-payloads, wherein n2 is an integer from 1 to 10. In some embodiments, n2 is 2. In some embodiments, n2 is 3. In some embodiments, n2 is 4. In some embodiments, n2 is 5. In some embodiments, n2 is 6. In some embodiments, n2 is 7. In some embodiments, n2 is 8. In some embodiments, n2 is 9. In some embodiments, n2 is 10.

In some embodiments, provided herein are anti-Tissue Factor conjugates having the structure of any of Conjugates A-E in the table below. In some embodiments, n2 is an integer from 1 to 8. In some embodiments, n2 is 2. In some embodiments, n2 is 4. In some embodiments, n2 is 6. In some embodiments, n2 is 8. The present disclosure encompasses each and every regioisomer of the conjugate structures depicted below.

A

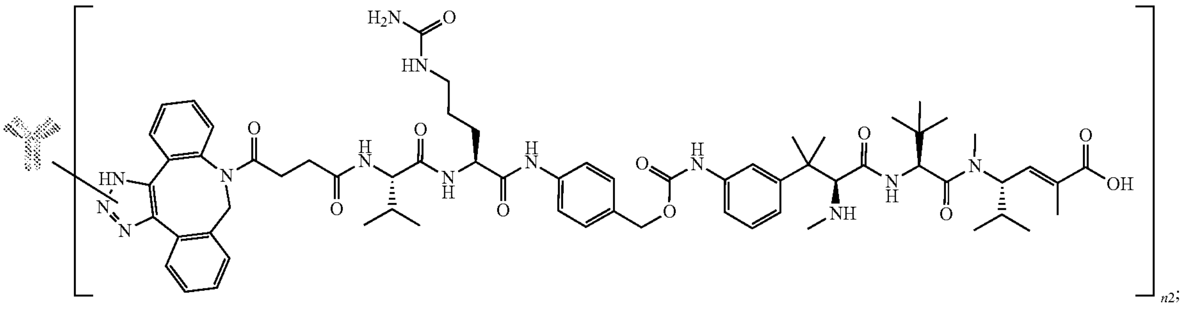

-continued
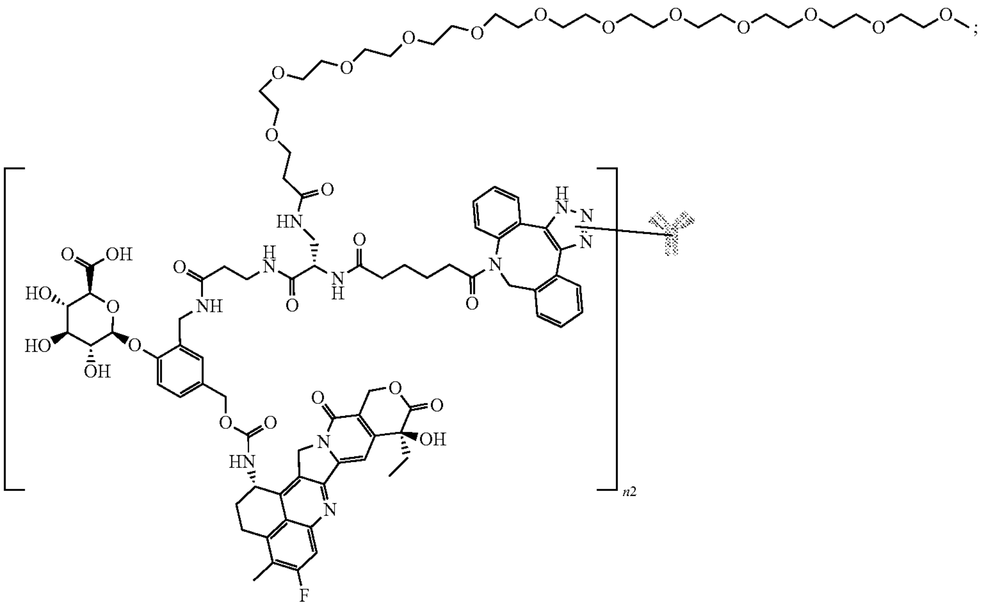
B
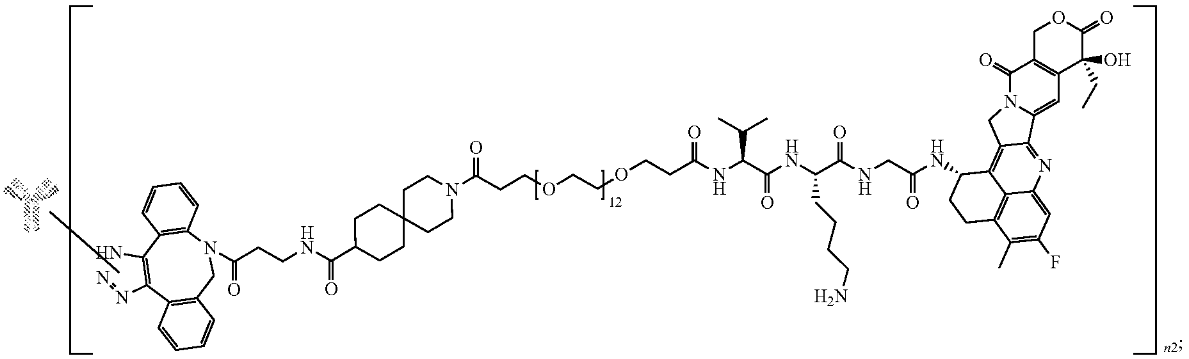
C
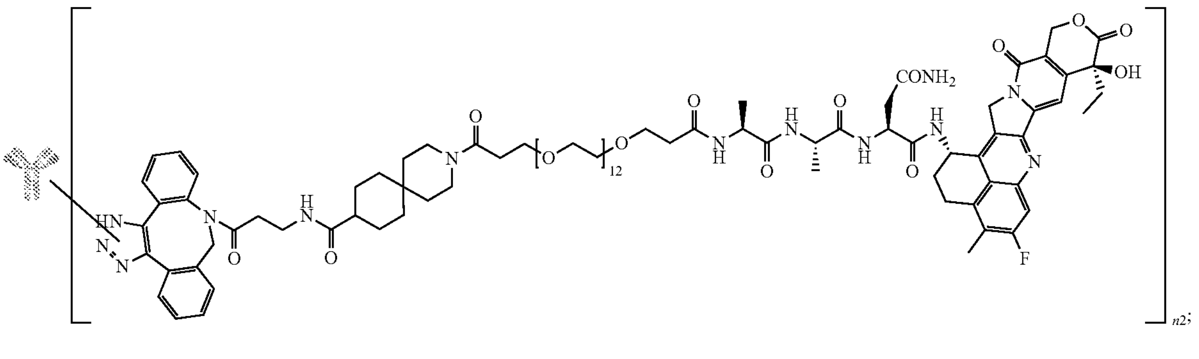
D

-continued

E

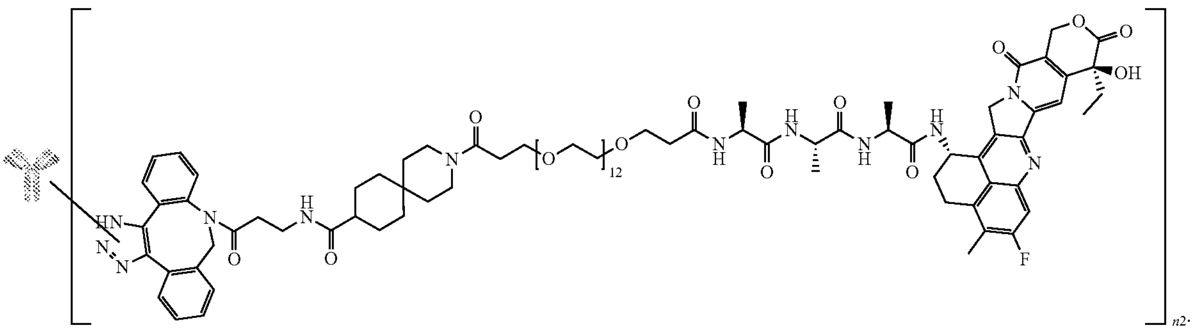

In some embodiments, provided herein are anti-Tissue Factor conjugates having the structure of any of Conjugates A1-E1 in the table below. In some embodiments, n2 is an integer from 1 to 8. In some embodiments, n2 is 2. In some embodiments, n2 is 4. In some embodiments, n2 is 6. In some embodiments, n2 is 8. The present disclosure encompasses each and every regioisomer of the conjugate structures depicted below.

A1

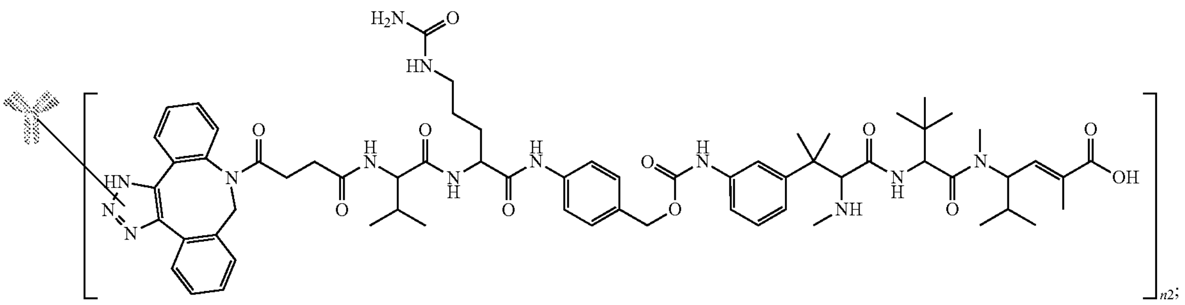

B1

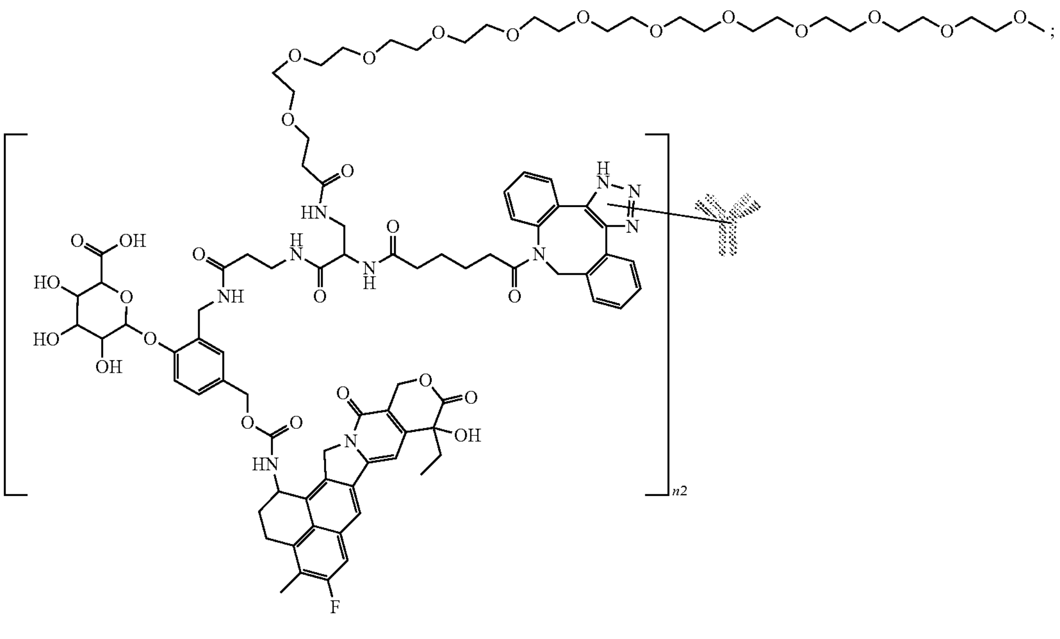

-continued

C1

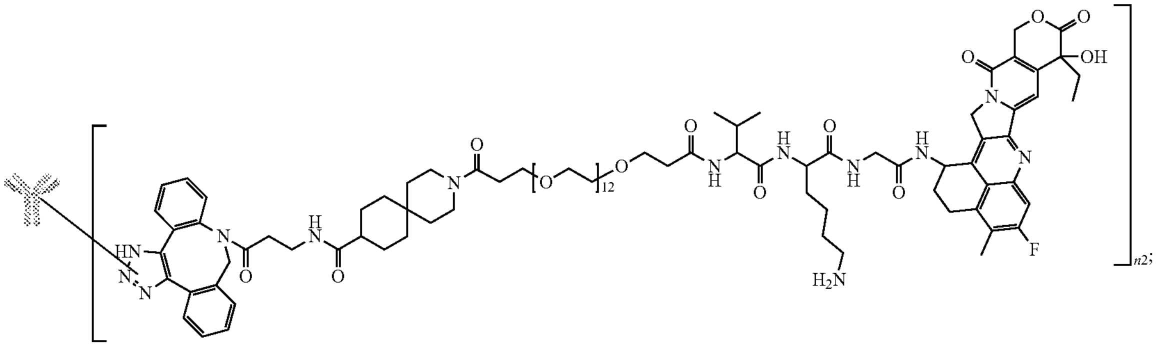

D1

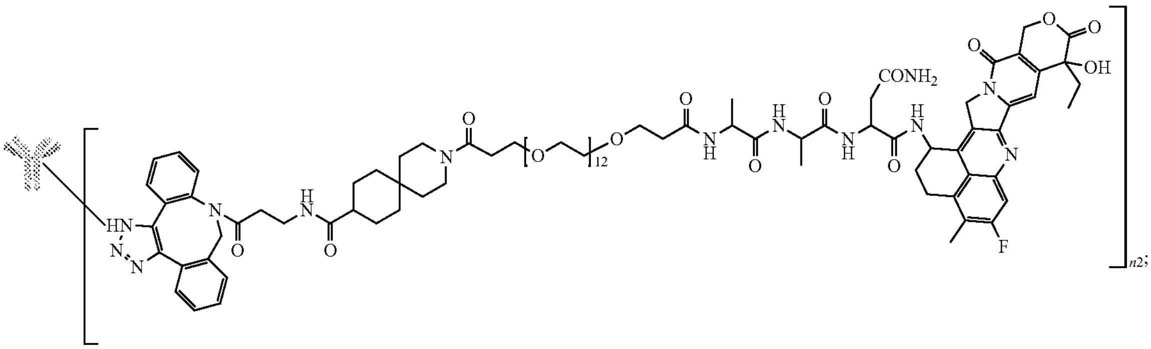

E1

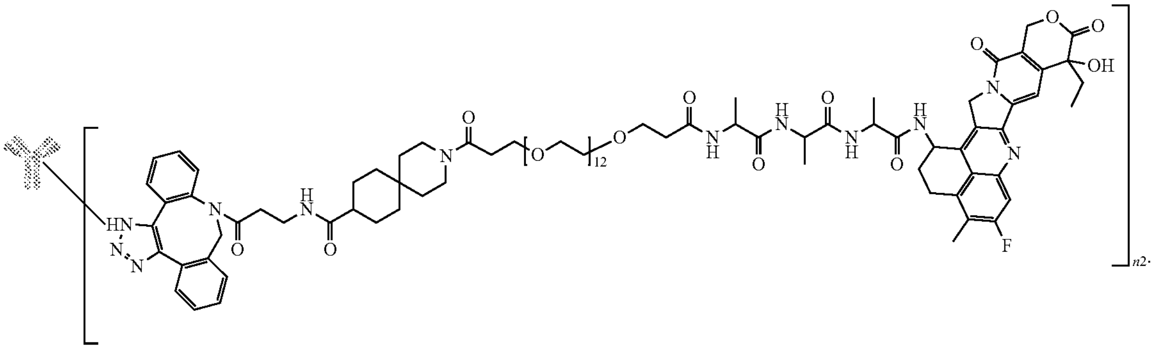

It should be understood that in certain embodiments, other linker payloads and conjugation structures are provided such as those discussed in International Patent Application No. PCT/US2023/023688, filed Jun. 27, 2023 entitled β-Glucuronide Linker-Payloads, Protein Conjugates Thereof, And Methods Thereof as well as U.S. Provisional Application No. 61/516,579, filed Jul. 31, 2023, entitled STING Agonist Compounds and Conjugates, each of which is incorporated herein by reference in its entirety. In some embodiments provided herein are anti-Tissue Factor conjugates comprising an antibody described herein linked to one or more linker-payloads as described in PCT Application PCT/US2023/26338, PCT/US/2020/031052, PCT/US/2018/051364, PCT/US2018/051322, PCT/US2017/015501, PCT/US2017/015503, and PCT/US2016/015844, each of which are incorporated by reference in its entirety.

In any of the foregoing embodiments wherein the anti-Tissue Factor conjugate has a structure according to any one of Conjugates A-E, the bracketed structure can be covalently bonded to one or more non-natural amino acids of the antibody, wherein the one or more non-natural amino acids are located at sites selected from the group consisting of: HC-F404, HC-Y180, HC-F241, LC-K42, and LC-E161, according to the Kabat or EU numbering scheme of Kabat. In some embodiments, the bracketed structure is covalently bonded to one or more non-natural amino acids at site HC-F404 of the antibody. In some embodiments, the bracketed structure is covalently bonded to one or more non-natural amino acids at site HC-Y180 of the antibody. In some embodiments, the bracketed structure is covalently bonded to one or more non-natural amino acids at site HC-F241 of the antibody. In some embodiments, the bracketed structure is covalently bonded to one or more non-natural amino acids at site LC-K42 of the antibody. In some embodiments, the bracketed structure is covalently bonded to one or more non-natural amino acids at site LC-E161 of the antibody. In some embodiments, the bracketed structures are covalently bonded to non-natural amino acids at sites HC-F404 and HC-Y180 of the antibody. In some embodiments, the bracketed structures are covalently bonded to non-natural amino acids at sites HC-F404, HC-Y180, and LC-K42 of the antibody. In some embodiments, the bracketed structures are covalently bonded to non-natural amino acids at sites HC-F404, HC-Y180, LC-K42, and LC-E161 of the antibody. In some embodiments, the bracketed structures are covalently bonded to non-natural amino acids at sites HC-F404, HC-Y180, and HC-F241 of the antibody. In some embodiments, the bracketed structures are covalently bonded to non-natural amino acids at sites HC-F404, HC-Y180, HC-F241, and LC-K42 of the antibody. In some embodiments, the bracketed structures are covalently bonded to non-natural amino acids at sites HC-F404 and HC-F241.

In particular embodiments, provided herein are anti-Tissue Factor conjugates according to any of the conjugates described herein wherein COMP indicates a residue of the non-natural amino acid according to Formula (30), below. In particular embodiments, provided herein are anti-Tissue Factor conjugates according to any of the conjugates described herein wherein COMP indicates a residue of the non-natural amino acid according to Formula (30), below, at heavy chain position 404 according to the EU numbering system. In particular embodiments, provided herein are anti-Tissue Factor conjugates according to any of the conjugates described herein wherein COMP indicates a residue of the non-natural amino acid according to Formula (30), below, at heavy chain position 180 according to the EU numbering system. In particular embodiments, provided herein are anti-Tissue Factor conjugates according to any of the conjugates described herein wherein COMP indicates a residue of the non-natural amino acid according to Formula (30), below, at heavy chain position 241 according to the EU numbering system. In particular embodiments, provided herein are anti-Tissue Factor conjugates according to any of the conjugates described herein wherein COMP indicates a residue of the non-natural amino acid according to Formula (30), below, at heavy chain position 222 according to the EU numbering system. In particular embodiments, provided herein are anti-Tissue Factor conjugates according to any of the conjugates described herein wherein COMP indicates a residue of the non-natural amino acid according to Formula (30), below, at light chain position 7 according to the Kabat or Chothia numbering system. In particular embodiments, provided herein are anti-Tissue Factor conjugates according to any of the conjugates described herein wherein COMP indicates a residue of the non-natural amino acid according to Formula (30), below, at light chain position 42 according to the Kabat or Chothia numbering system. In certain embodiments, PAY is selected from the group consisting of maytansine, hemiasterlin, amanitin, camptothecin, exatecan, exatecan derivative (DXd), SN-38, anthracycline, PNU-159682, PNU derivative (PNU-EDA), pyrrolobenzodiazepine (PBD), MMAF, and MMAE. In certain embodiments, PAY is maytansine. In certain embodiments, PAY is hemiasterlin. In certain embodiments, PAY is amanitin. In certain embodiments, PAY is exatecan. In certain embodiments, PAY is exatecan derivative Dxd. In certain embodiments, PAY is anthracycline. In certain embodiments, PAY is PNU-159682. In certain embodiments, PAY is PNU derivative (PNU-EDA). In certain embodiments, PAY is pyrrolobenzodiazepine. In certain embodiments, PAY is MMAF. In certain embodiments, PAY is MMAE.

(30)

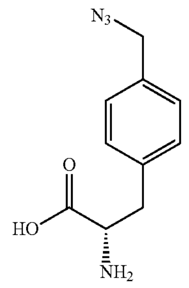

In particular embodiments, provided herein are anti-Tissue Factor conjugates according to any of the conjugates described herein wherein COMP indicates a residue of the non-natural amino acid according to Formula (56), below. In particular embodiments, provided herein are anti-Tissue Factor conjugates according to any of the conjugates described herein wherein COMP indicates a residue of the non-natural amino acid according to Formula (56), below, at heavy chain position 404 according to the EU numbering system. In particular embodiments, provided herein are anti-Tissue Factor conjugates according to any of the conjugates described herein wherein COMP indicates a residue of the non-natural amino acid according to Formula (56), below, at heavy chain position 180 according to the EU numbering system. In particular embodiments, provided herein are anti-Tissue Factor conjugates according to any of the conjugates described herein wherein COMP indicates a residue of the non-natural amino acid according to Formula (56), below, at heavy chain position 241 according to the EU numbering system. In particular embodiments, provided herein are anti-Tissue Factor conjugates according to any of the conjugates described herein wherein COMP indicates a residue of the non-natural amino acid according to Formula (56), below, at heavy chain position 222 according to the EU numbering system. In particular embodiments, provided herein are anti-Tissue Factor conjugates according to any of the conjugates described herein wherein COMP indicates a residue of the non-natural amino acid according to Formula (56), below, at light chain position 7 according to the Kabat or Chothia numbering system. In particular embodiments, provided herein are anti-Tissue Factor conjugates according to any of the conjugates described herein wherein COMP indicates a residue of the non-natural amino acid according to Formula (56), below, at light chain position 42 according to the Kabat or Chothia numbering system. In certain embodiments, PAY is selected from the group consisting of maytansine, hemiasterlin, amanitin, camptothecin, exatecan, exatecan derivative (DXd), SN-38, anthracycline, PNU-159682, PNU derivative (PNU-EDA), pyrrolobenzodiazepine (PBD), MMAF, and MMAE. In certain embodiments, PAY is maytansine. In certain embodiments, PAY is hemiasterlin. In certain embodiments, PAY is amanitin. In certain embodiments, PAY is exatecan. In certain embodiments, PAY is exatecan derivative (Dxd). In certain embodiments, PAY is deruxtecan. In certain embodiments, PAY is anthracycline. In certain embodiments, PAY is PNU-159682. In certain embodiments, PAY is PNU derivative (PNU-EDA). In certain embodiments, PAY is pyrrolobenzodiazepine. In certain embodiments, PAY is MMAF. In certain embodiments, PAY is MMAE.

(56)

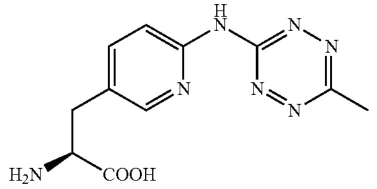

In particular embodiments, provided herein are anti-Tissue Factor conjugates according to any of the conjugates described herein wherein COMP indicates a non-natural amino acid residue of para-azido-L-phenylalanine. In particular embodiments, provided herein are anti-Tissue Factor conjugates according to any of the conjugates described herein wherein COMP indicates the non-natural amino acid residue para-azido-phenylalanine at heavy chain position 404 according to the EU numbering system. In particular embodiments, provided herein are anti-Tissue Factor conjugates according to any of the conjugates described herein wherein COMP indicates a non-natural amino acid residue of para-azido-L-phenylalanine at heavy chain position 180 according to the EU numbering system. In particular embodiments, provided herein anti-Tissue Factor conjugates according to any of the conjugates described herein wherein COMP indicates a non-natural amino acid residue para-azido-L-phenylalanine at heavy chain position 241 according to the EU numbering system. In particular embodiments, provided herein are anti-Tissue Factor conjugates according to any of the conjugates described herein wherein COMP indicates a non-natural amino acid residue para-azido-L-phenylalanine at heavy chain position 222 according to the EU numbering system. In particular embodiments, provided herein are anti-Tissue Factor conjugates according to any of the conjugates described herein wherein COMP indicates a non-natural amino acid residue para-azido-L-phenylalanine at light chain position 7 according to the Kabat or Chothia numbering system. In particular embodiments, provided herein are anti-Tissue Factor conjugates according to any of the conjugates described herein wherein COMP indicates a non-natural amino acid residue para-azido-L-phenylalanine at light chain position 42 according to the Kabat or Chothia numbering system. In certain embodiments, PAY is selected from the group consisting of maytansine, hemiasterlin, amanitin, camptothecin, exatecan, exatecan derivative (DXd), SN-38, anthracycline, PNU-159682, pyrrolobenzodiazepine (PBD), MMAF, and MMAE. In certain embodiments, PAY is maytansine. In certain embodiments, PAY is hemiasterlin. In certain embodiments, PAY is amanitin. In certain embodiments, PAY is exatecan. In certain embodiments, PAY is exatecan derivative (Dxd). In certain embodiments, PAY is anthracycline. In certain embodiments, PAY is PNU-159682. In certain embodiments, PAY is PNU derivative (PNU-EDA). In certain embodiments, PAY is pyrrolobenzodiazepine. In certain embodiments, PAY is MMAF. In certain embodiments, PAY is MMAE.

It is expected without being bound to theory that the antibody conjugates of the present disclosure can avoid Factor X inhibition and bleeding issues by selection of an antibody that does not interfere with Tissue Factor binding to coagulation factors. The exatecan payload is believed to inhibit TOPO-1 causing DNA disruption which elicits potent tumor cell killing, bystander activity and immunogenic cell death.

In some embodiments, an antibody conjugate of the present disclosure can include (a) an antibody comprising: (1) a $V_H$ comprising: a CDR-H1 comprising at least one of SEQ ID NOs: 130 and 455; a CDR-H2 comprising at least one of SEQ ID NOs: 780 and 1105; and a CDR-H3 comprising at least one of SEQ ID NOs: 1430 and 1755; and a $V_L$ comprising: a CDR-L1 comprising SEQ ID NO: 2064; a CDR-L2 comprising SEQ ID NO: 2288; and a CDR-L3 comprising SEQ ID NO; 2512; (2) a $V_H$ comprising: a CDR-H1 comprising at least one of SEQ ID NOs: 161 and 486; a CDR-H2 comprising at least one of SEQ ID NOs: 811 and 1136; and a CDR-H3 comprising at least one of SEQ ID NOs: 1461 and 1786; and a $V_L$ comprising: a CDR-L1 comprising SEQ ID NO: 2064; a CDR-L2 comprising SEQ ID NO: 2288; and a CDR-L3 comprising SEQ ID NO; 2512; (3) a $V_H$ comprising: a CDR-H1 comprising at least one of SEQ ID NOs: 189 and 514; a CDR-H2 comprising at least one of SEQ ID NOs: 839 and 1164; and a CDR-H3 comprising at least one of SEQ ID NOs: 1489 and 1814; and a $V_L$ comprising: a CDR-L1 comprising SEQ ID NO: 2064; a CDR-L2 comprising SEQ ID NO: 2288; and a CDR-L3 comprising SEQ ID NO; 2512; (4) a $V_H$ comprising: a CDR-H1 comprising at least one of SEQ ID NOs: 192 and 517; a CDR-H2 comprising at least one of SEQ ID NOs: 842 and 1167; and a CDR-H3 comprising at least one of SEQ ID NOs: 1492 and 1817; and a $V_L$ comprising: a CDR-L1 comprising SEQ ID NO: 2064; a CDR-L2 comprising SEQ ID NO: 2288; and a CDR-L3 comprising SEQ ID NO; 2512; (5) a $V_H$ comprising: a CDR-H1 comprising at least one of SEQ ID NOs: 211 and 536; a CDR-H2 comprising at least one of SEQ ID NOs: 861 and 1186; and a CDR-H3 comprising at least one of SEQ ID NOs: 1511 and 1836; and a $V_L$ comprising: a CDR-L1 comprising SEQ ID NO: 2064; a CDR-L2 comprising SEQ ID NO: 2288; and a CDR-L3 comprising SEQ ID NO; 2512; (6) a $V_H$ comprising: a CDR-H1 comprising at least one of SEQ ID NOs: 214 and 539; a CDR-H2 comprising at least one of SEQ ID NOs: 864 and 1189; and a CDR-H3 comprising at least one of SEQ ID NOs: 1514 and 1839; and a $V_L$ comprising: a CDR-L1 comprising SEQ ID NO: 2064; a CDR-L2 comprising SEQ ID NO: 2288; and a CDR-L3 comprising SEQ ID NO; 2512; (7) a $V_H$ comprising: a CDR-H1 comprising at least one of SEQ ID NOs: 218 and 543; a CDR-H2 comprising at least one of SEQ ID NOs: 868 and 1210; and a CDR-H3 comprising at least one of SEQ ID NOs: 1518 and 1843; and a $V_L$ comprising: a CDR-L1 comprising at least one of SEQ ID NOs: 1974 and 2086; a CDR-L2 comprising at least one of SEQ ID NOs: 2198 and 2310; and a CDR-L3 comprising at least one of SEQ ID NOs: 2422 and 2534; (8) a $V_H$ comprising: a CDR-H1 comprising at least one of SEQ ID NOs: 105 and 430; a CDR-H2 comprising at least one of SEQ ID NOs: 755 and 1080; and a CDR-H3 comprising at least one of SEQ ID NOs: 1405 and 1730; and a $V_L$ comprising: a CDR-L1 comprising SEQ ID NO: 2064; a CDR-L2 comprising SEQ ID NO: 2288; and a CDR-L3 comprising SEQ ID NO; 2512; (9) a $V_H$ comprising: a CDR-H1 comprising at least one of SEQ ID NOs: 114 and 439; a CDR-H2 comprising at least one of SEQ ID NOs: 764 and 1089; and a CDR-H3 comprising at least one of SEQ ID NOs: 1414 and 1739; and a $V_L$ comprising: a CDR-L1 comprising SEQ ID NO: 2064; a CDR-L2 comprising SEQ ID NO: 2288; and a CDR-L3 comprising SEQ ID NO; 2512; (10) a $V_H$ comprising: a CDR-H1 comprising at least one of SEQ ID NOs: 117 and 442; a CDR-H2 comprising at least one of SEQ ID NOs: 767 and 1092; and a CDR-H3 comprising at least one of SEQ ID NOs: 1417 and 1742; and a $V_L$ comprising: a CDR-L1 comprising SEQ ID NO: 2064;

a CDR-L2 comprising SEQ ID NO: 2288; and a CDR-L3 comprising SEQ ID NO; 2512; (b) para-azidomethylphenylalanine residues at antibody sites selected from the group consisting of HC180, HC241, HC404, LC42, LC161 and combinations thereof; and (c) a linker-payload selected from the group consisting of:
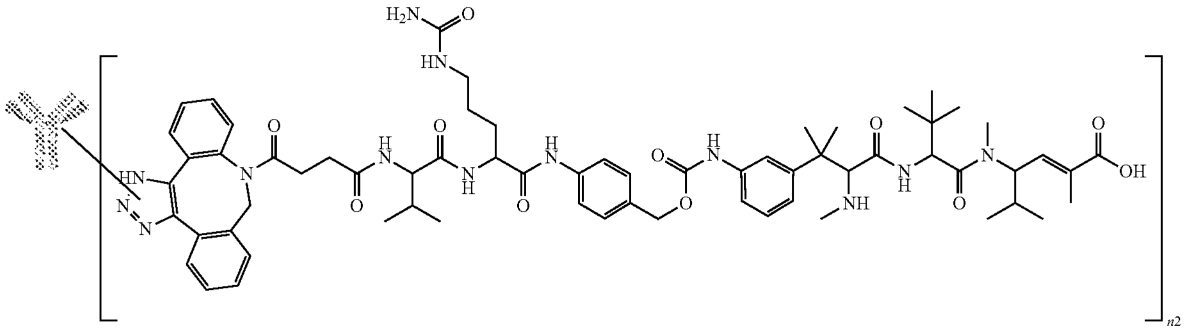
,
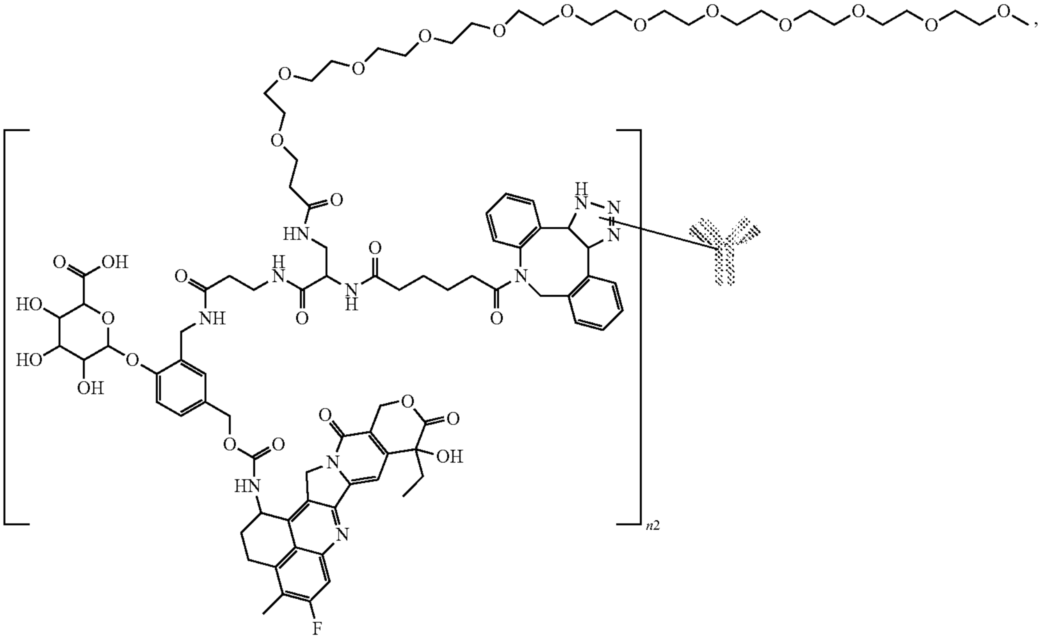
,
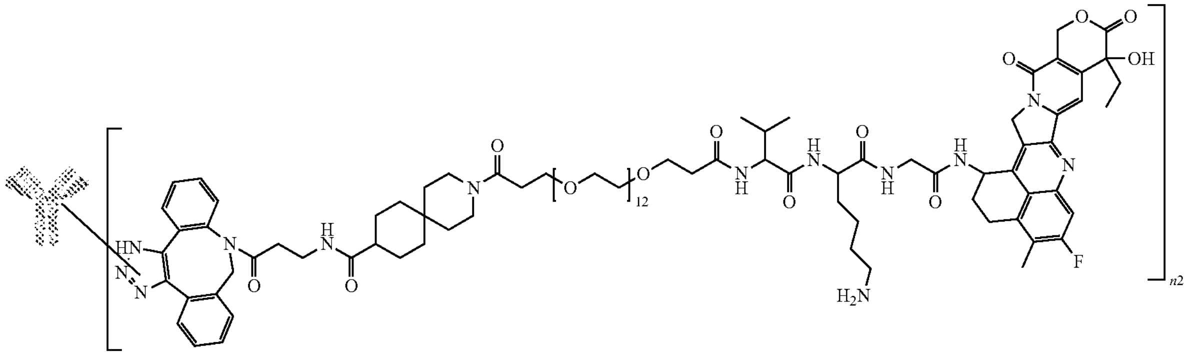
,
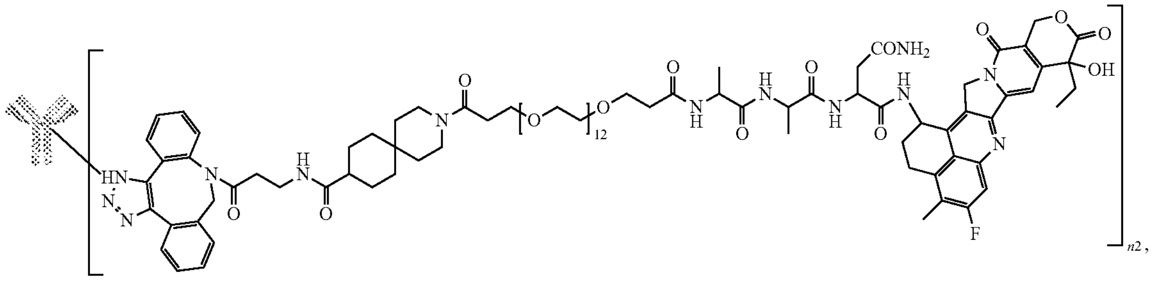
, and -continued

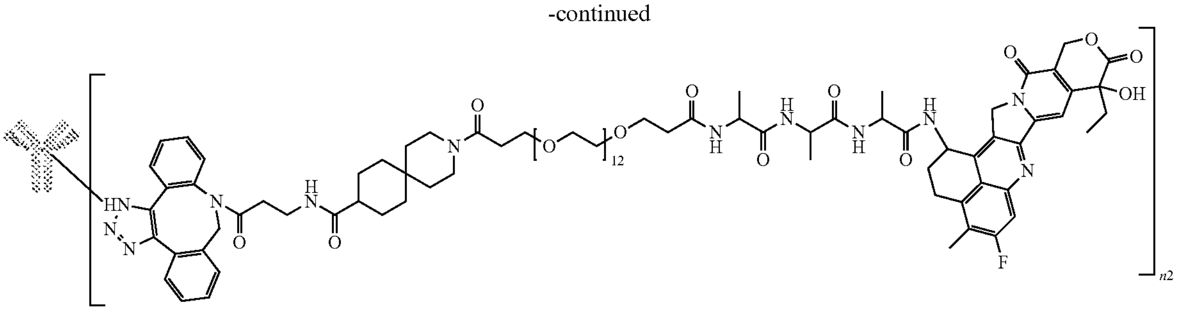

wherein n2 is 2, 4, 6, 8 or 10 and each linker-payload is bonded to one of the para-azidomethylphenylalanine residue side chains.

In some embodiments, an antibody conjugate of the present disclosure can include (a) an antibody comprising: (1) a $V_H$ comprising: a CDR-H1 comprising at least one of SEQ ID NOs: 130 and 455; a CDR-H2 comprising at least one of SEQ ID NOs: 780 and 1105; and a CDR-H3 comprising at least one of SEQ ID NOs: 1430 and 1755; and a $V_L$ comprising: a CDR-L1 comprising SEQ ID NO: 2064; a CDR-L2 comprising SEQ ID NO: 2288; and a CDR-L3 comprising SEQ ID NO; 2512; (2) a $V_H$ comprising: a CDR-H1 comprising at least one of SEQ ID NOs: 161 and 486; a CDR-H2 comprising at least one of SEQ ID NOs: 811 and 1136; and a CDR-H3 comprising at least one of SEQ ID NOs: 1461 and 1786; and a $V_L$ comprising: a CDR-L1 comprising SEQ ID NO: 2064; a CDR-L2 comprising SEQ ID NO: 2288; and a CDR-L3 comprising SEQ ID NO; 2512; (3) a $V_H$ comprising: a CDR-H1 comprising at least one of SEQ ID NOs: 189 and 514; a CDR-H2 comprising at least one of SEQ ID NOs: 839 and 1164; and a CDR-H3 comprising at least one of SEQ ID NOs: 1489 and 1814; and a $V_L$ comprising: a CDR-L1 comprising SEQ ID NO: 2064; a CDR-L2 comprising SEQ ID NO: 2288; and a CDR-L3 comprising SEQ ID NO; 2512; (4) a $V_H$ comprising: a CDR-H1 comprising at least one of SEQ ID NOs: 192 and 517; a CDR-H2 comprising at least one of SEQ ID NOs: 842 and 1167; and a CDR-H3 comprising at least one of SEQ ID NOs: 1492 and 1817; and a $V_L$ comprising: a CDR-L1 comprising SEQ ID NO: 2064; a CDR-L2 comprising SEQ ID NO: 2288; and a CDR-L3 comprising SEQ ID NO; 2512; (5) a $V_H$ comprising: a CDR-H1 comprising at least one of SEQ ID NOs: 211 and 536; a CDR-H2 comprising at least one of SEQ ID NOs: 861 and 1186; and a CDR-H3 comprising at least one of SEQ ID NOs: 1511 and 1836; and a $V_L$ comprising: a CDR-L1 comprising SEQ ID NO: 2064; a CDR-L2 comprising SEQ ID NO: 2288; and a CDR-L3 comprising SEQ ID NO; 2512; (6) a $V_H$ comprising: a CDR-H1 comprising at least one of SEQ ID NOs: 214 and 539; a CDR-H2 comprising at least one of SEQ ID NOs: 864 and 1189; and a CDR-H3 comprising at least one of SEQ ID NOs: 1514 and 1839; and a $V_L$ comprising: a CDR-L1 comprising SEQ ID NO: 2064; a CDR-L2 comprising SEQ ID NO: 2288; and a CDR-L3 comprising SEQ ID NO; 2512; (7) a $V_H$ comprising: a CDR-H1 comprising at least one of: SEQ ID NOs: 218 and 543; a CDR-H2 comprising at least one of SEQ ID NOs: 868 and 1210; and a CDR-H3 comprising at least one of SEQ ID NOs: 1518 and 1843; and a $V_L$ comprising: a CDR-L1 comprising at least one of SEQ ID NOs: 1974 and 2086; a CDR-L2 comprising at least one of SEQ ID NOs: 2198 and 2310; and a CDR-L3 comprising at least one of SEQ ID NOs: 2422 and 2534; (8) a $V_H$ comprising: a CDR-H1 comprising at least one of SEQ ID NOs: 105 and 430; a CDR-H2 comprising at least one of SEQ ID NOs: 755 and 1080; and a CDR-H3 comprising at least one of SEQ ID NOs: 1405 and 1730; and a $V_L$ comprising: a CDR-L1 comprising SEQ ID NO: 2064; a CDR-L2 comprising SEQ ID NO: 2288; and a CDR-L3 comprising SEQ ID NO; 2512; (9) a $V_H$ comprising: a CDR-H1 comprising at least one of SEQ ID NOs: 114 and 439; a CDR-H2 comprising at least one of SEQ ID NOs: 764 and 1089; and a CDR-H3 comprising at least one of SEQ ID NOs: 1414 and 1739; and a $V_L$ comprising: a CDR-L1 comprising SEQ ID NO: 2064; a CDR-L2 comprising SEQ ID NO: 2288; and a CDR-L3 comprising SEQ ID NO; 2512; (10) a $V_H$ comprising: a CDR-H1 comprising at least one of SEQ ID NOs: 117 and 442; a CDR-H2 comprising at least one of SEQ ID NOs: 767 and 1092; and a CDR-H3 comprising at least one of SEQ ID NOs: 1417 and 1742; and a $V_L$ comprising: a CDR-L1 comprising SEQ ID NO: 2064; a CDR-L2 comprising SEQ ID NO: 2288; and a CDR-L3 comprising SEQ ID NO; 2512; (b) para-azidomethylphenylalanine residues at antibody sites selected from the group consisting of HC180, HC241, HC404, LC42, LC161 and combinations thereof; and (c) a linker-payload selected from the group consisting of:

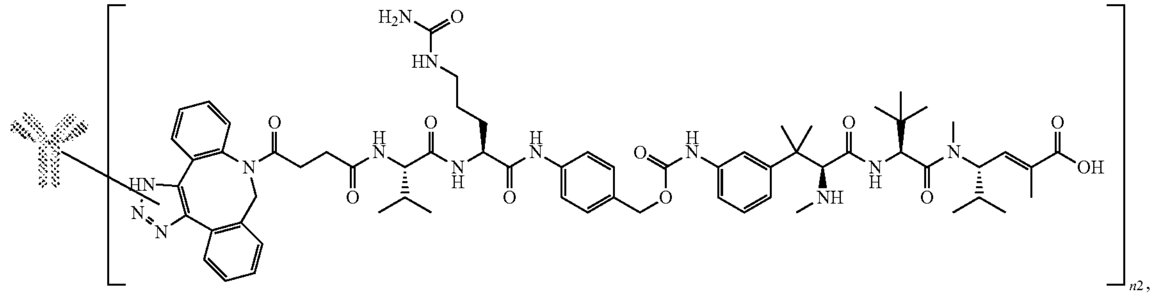

-continued
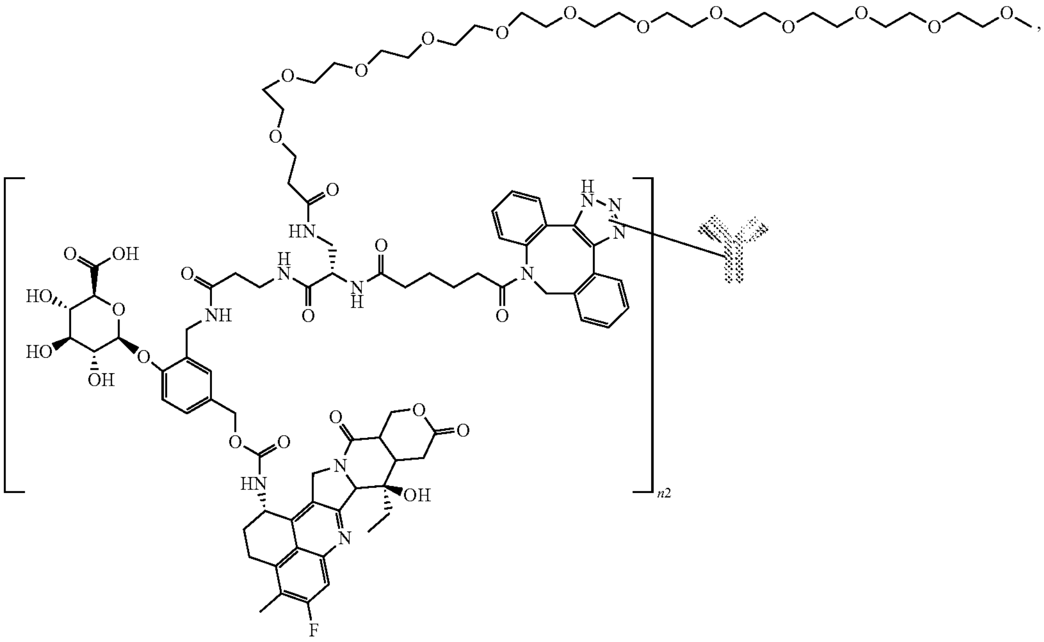
,
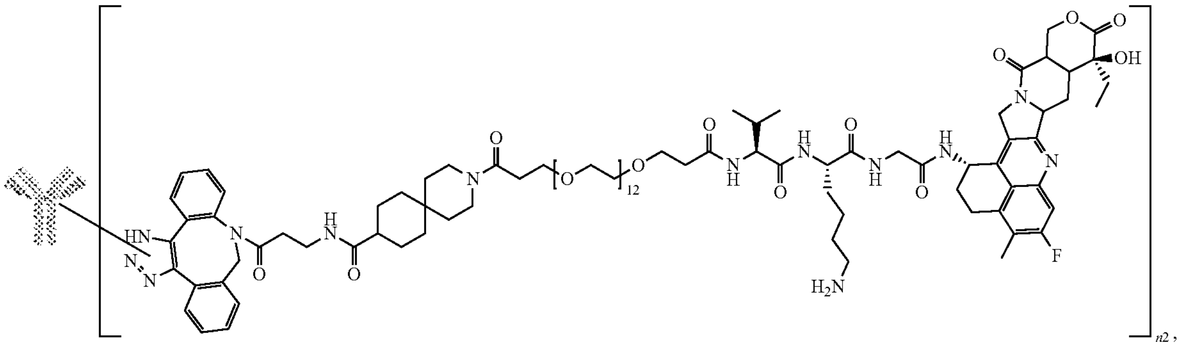
,
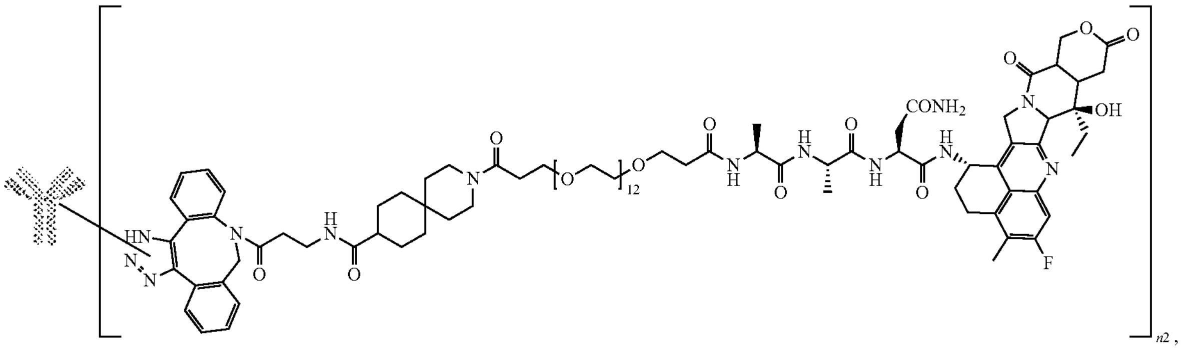
,
and

-continued

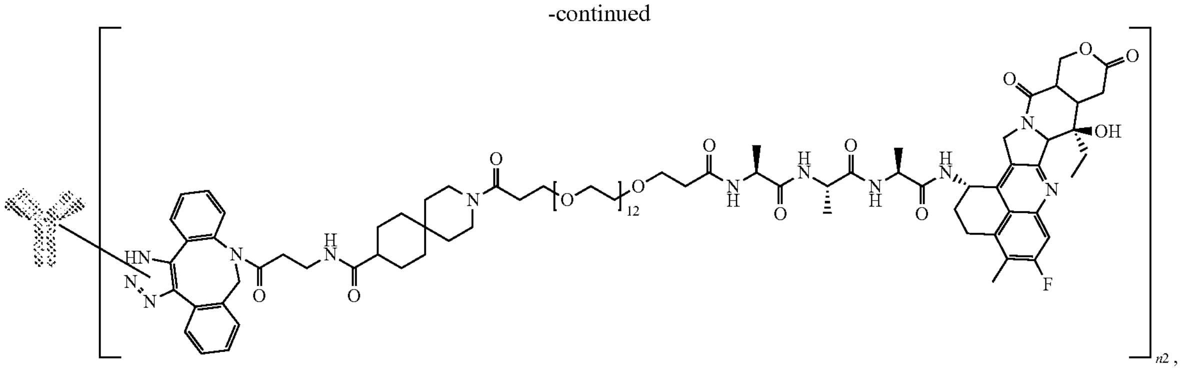

wherein n2 is 2, 4, 6, 8 or 10 and each linker-payload is bonded to one of the para-azidomethylphenylalanine residue side chains.

In some embodiments, an antibody conjugate is provided that comprises: (a) an antibody comprising a $V_H$ comprising: a CDR-H1 comprising at least one of SEQ ID NOs: 130 and 455; a CDR-H2 comprising at least one of SEQ ID NOs: 780 and 1105; and a CDR-H3 comprising at least one of SEQ ID NOs: 1430 and 1755; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites selected from the group consisting of HC180, HC241, HC404, LC42, LC161 and combinations thereof; and (c) a linker-payload selected from the group consisting of:

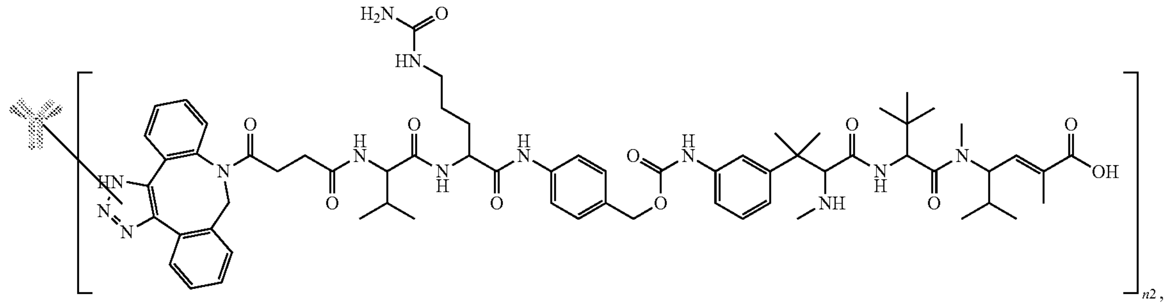

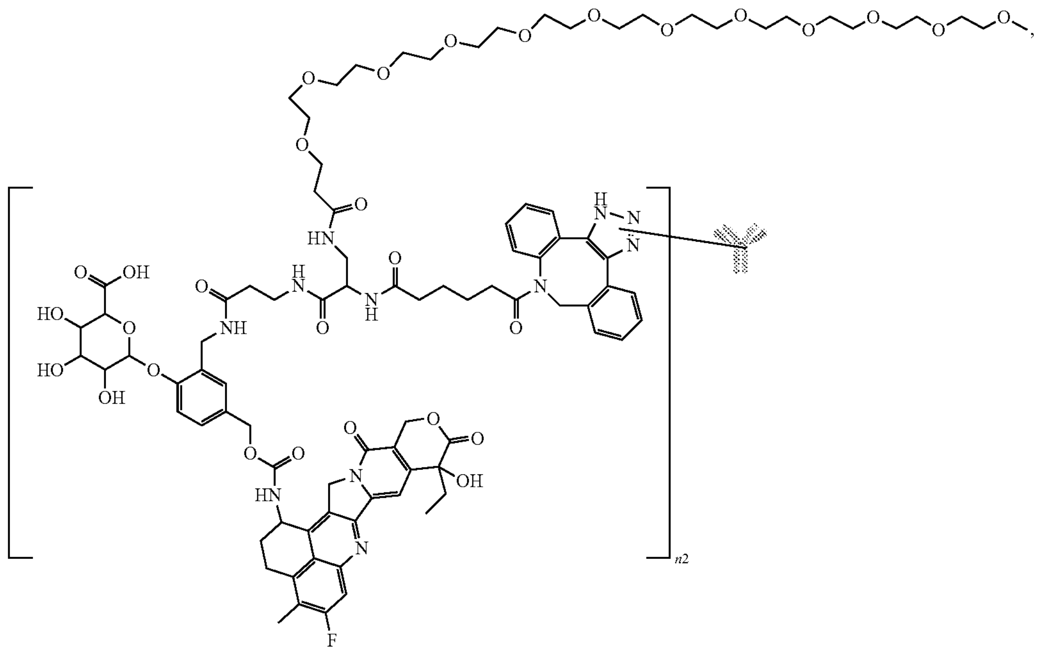

-continued

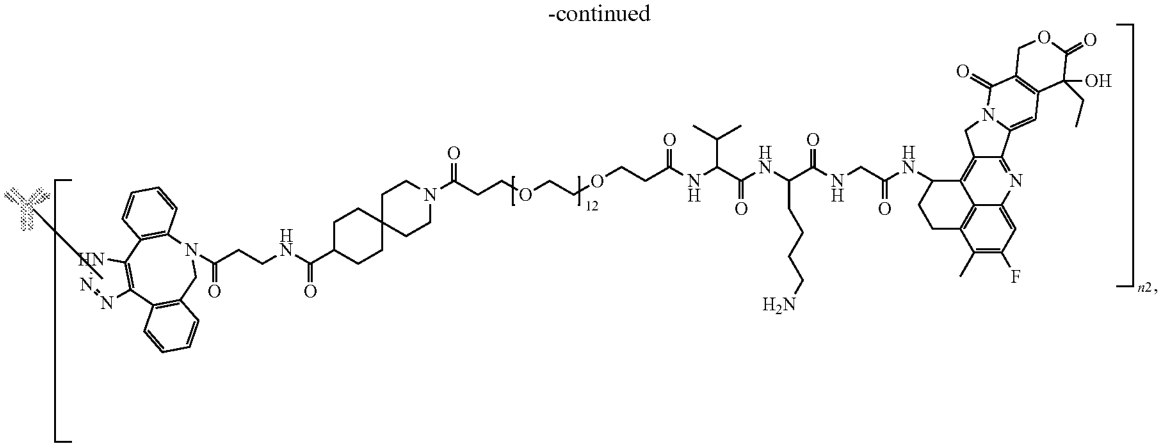

,

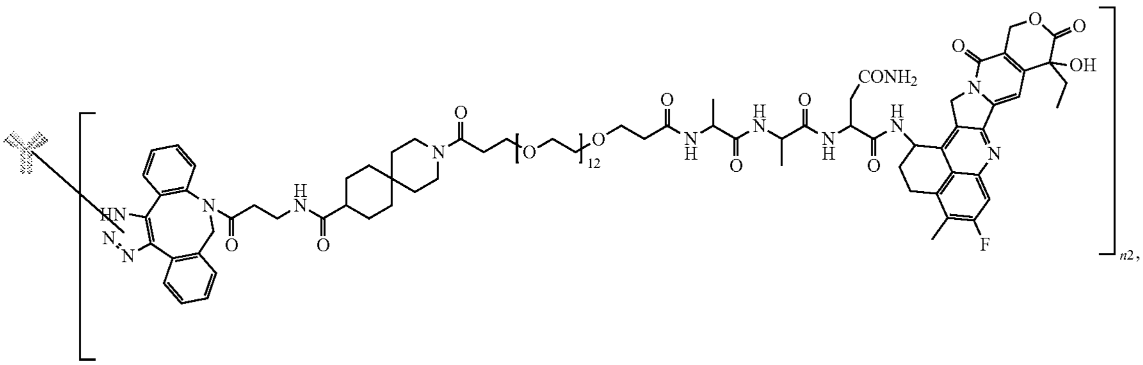

, and

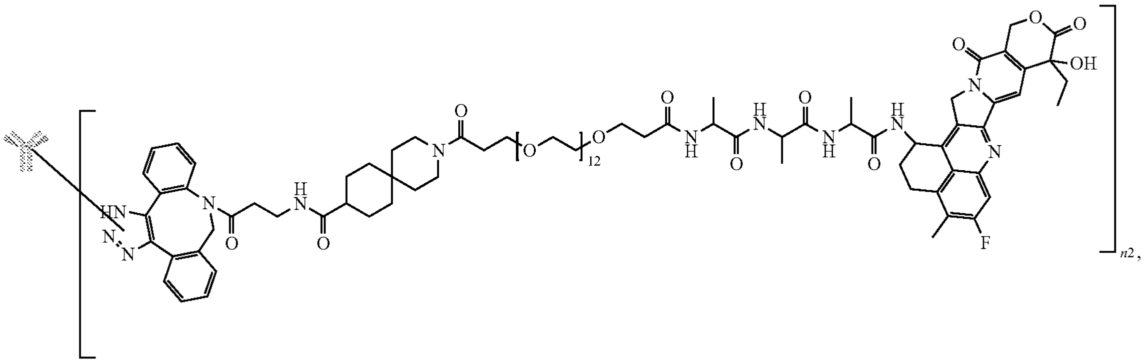

, wherein n2 is 2, 4, 6, 8 or 10 and each linker-payload is bonded to one of the para-azidomethylphenylalanine residue side chains.

In some embodiments, an antibody conjugate is provided that comprises: (a) an antibody comprising a $V_H$ comprising: a CDR-H1 comprising at least one of SEQ ID NOs: 130 and 455; a CDR-H2 comprising at least one of SEQ ID NOs: 780 and 1105; and a CDR-H3 comprising at least one of SEQ ID NOs: 1430 and 1755; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites selected from the group consisting of HC180, HC241, HC404, LC42, LC161 and combinations thereof; and (c) linker-payload selected from the group consisting of:

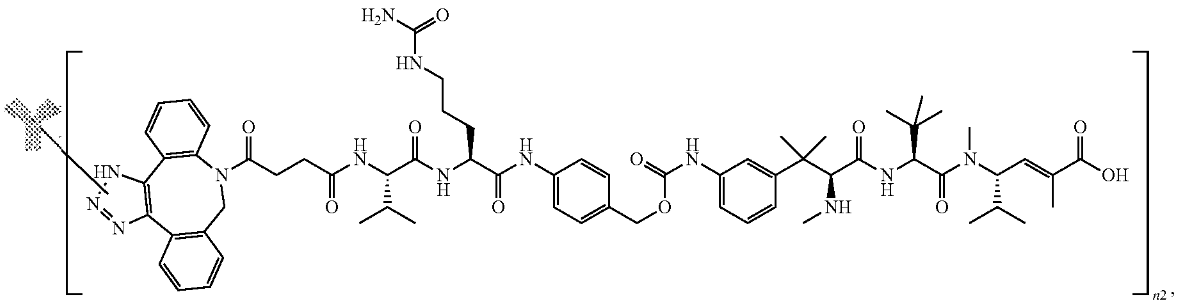
,
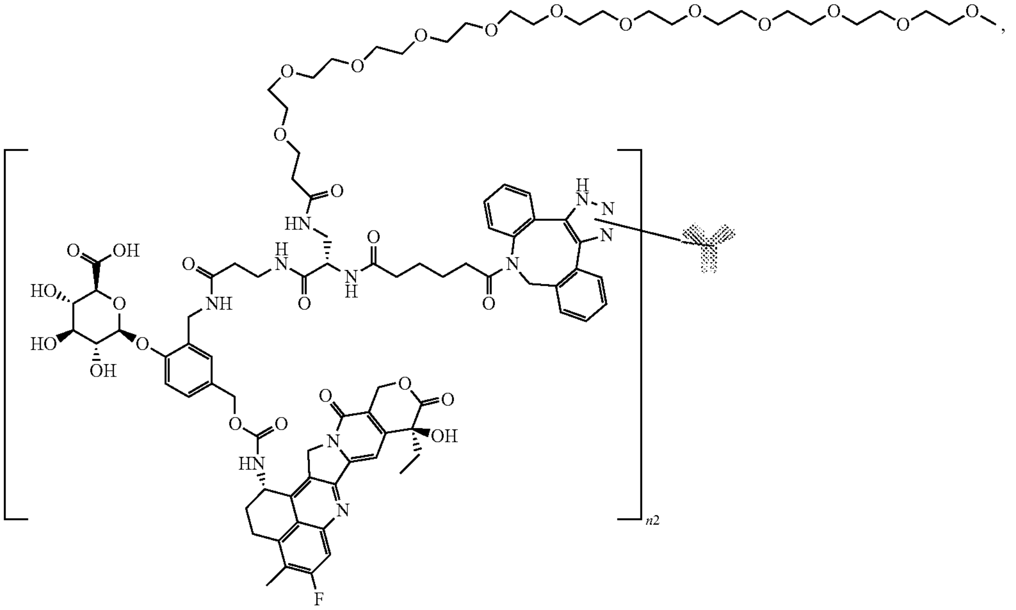
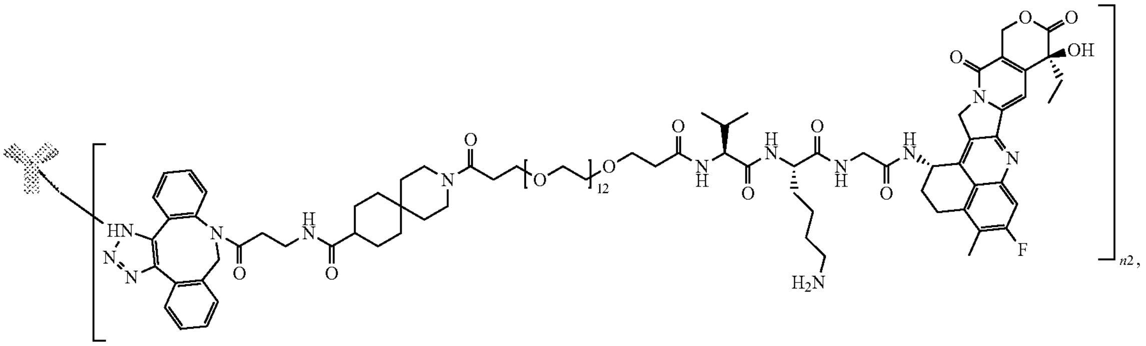
,
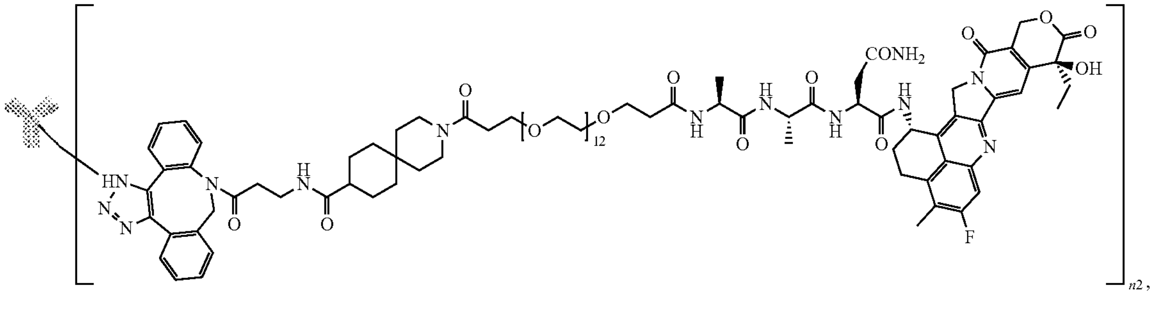
, and

-continued

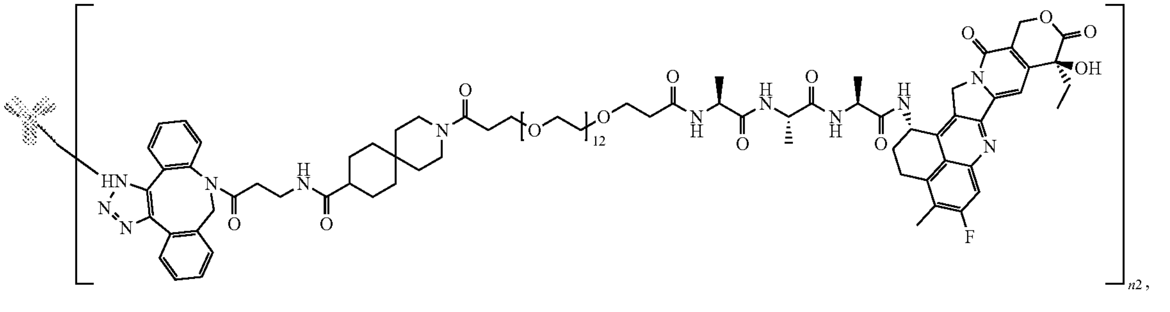

wherein n2 is 2, 4, 6, 8 or 10 and each linker-payload is bonded to one of the para-azidomethylphenylalanine residue side chains.

In some embodiments, an antibody conjugate is provided that comprises: (a) an antibody comprising a $V_H$ comprising: a CDR-H1 comprising at least one of SEQ ID NOs: 130 and 455; a CDR-H2 comprising at least one of SEQ ID NOs: 780 and 1105; and a CDR-H3 comprising at least one of SEQ ID NOs: 1430 and 1755; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC241 and HC404; and (c) a linker-payload, wherein n2 is 4 and each linker-payload is bonded to one of the para-azidomethylphenylalanine residue side chains:

In some embodiments, an antibody conjugate is provided that comprises: (a) an antibody comprising a $V_H$ comprising: a CDR-H1 comprising at least one of SEQ ID NOs: 130 and 455; a CDR-H2 comprising at least one of SEQ ID NOs: 780 and 1105; and a CDR-H3 comprising at least one of SEQ ID NOs: 1430 and 1755; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC241 and HC404; and (c) a linker-payload, wherein n2 is 4 and each linker-payload is bonded to one of the para-azidomethylphenylalanine residue side chains:

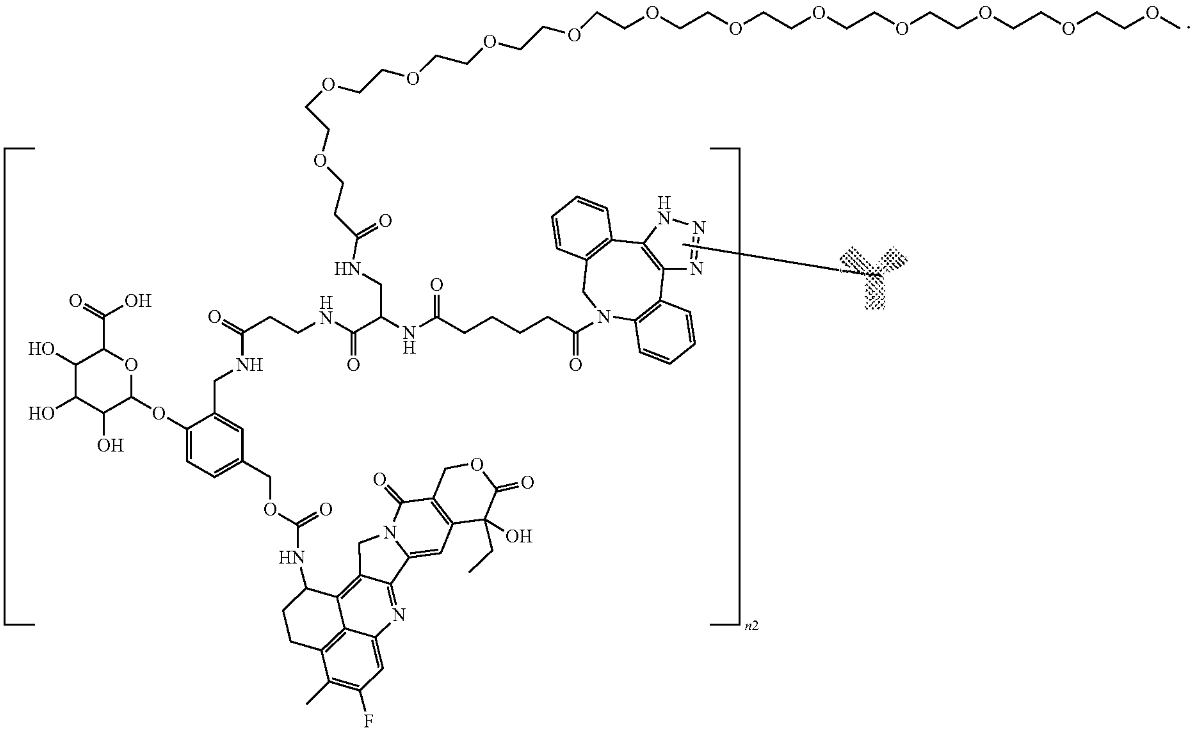

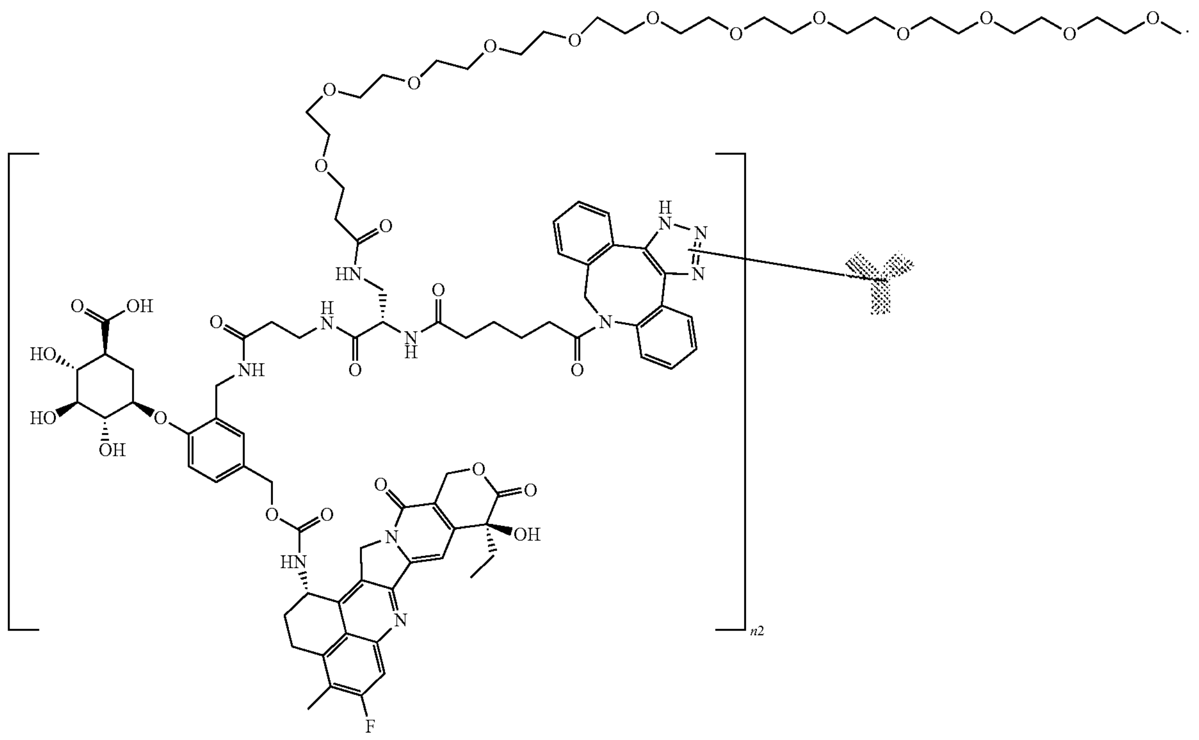

In some embodiments, an antibody conjugate is provided that comprises: (a) an antibody comprising a $V_H$ comprising: a CDR-H1 comprising at least one of SEQ ID NOs: 130 and 455; a CDR-H2 comprising at least one of SEQ ID NOs: 780 and 1105; and a CDR-H3 comprising at least one of SEQ ID NOs: 1430 and 1755; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC241, HC404, HC180, and HC391; and (c) a linker-payload, wherein n2 is 8 and each linker-payload is bonded to one of the para-azidomethylphenylalanine residue side chains:

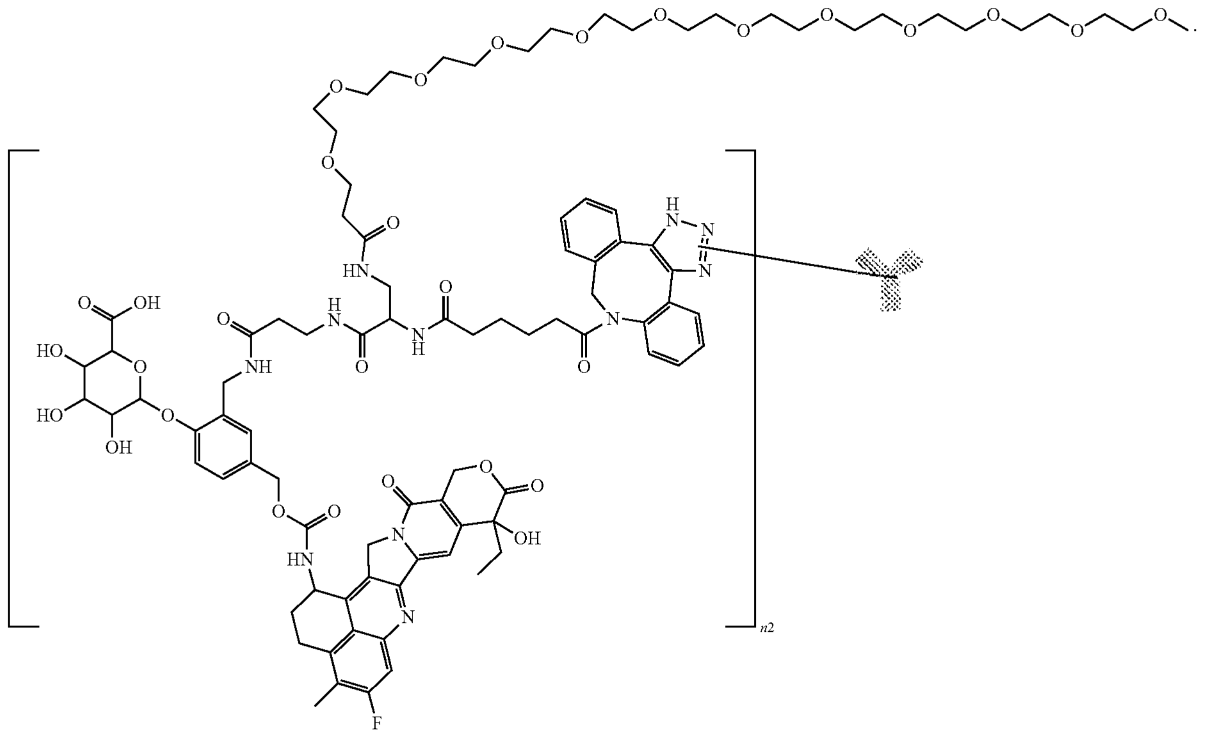

In some embodiments, an antibody conjugate is provided that comprises: (a) an antibody comprising a $V_H$ comprising: a CDR-H1 comprising at least one of SEQ ID NOs: 130 and 455; a CDR-H2 comprising at least one of SEQ ID NOs: 780 and 1105; and a CDR-H3 comprising at least one of SEQ ID NOs: 1430 and 1755; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180 and HC404; and (c) a linker-payload, wherein n2 is 4 and each linker-payload is bonded to one of the para-azidomethylphenylalanine residue side chains:

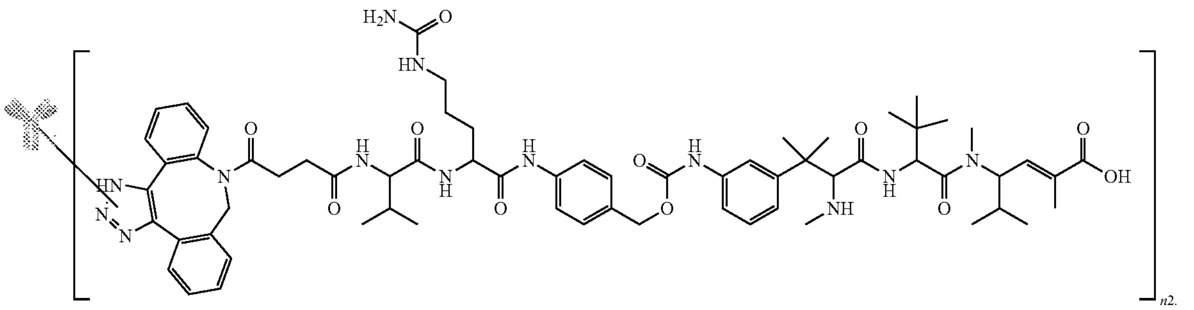

In some embodiments, an antibody conjugate is provided that comprises: (a) an antibody comprising a $V_H$ comprising: a CDR-H1 comprising at least one of SEQ ID NOs: 130 and 455; a CDR-H2 comprising at least one of SEQ ID NOs: 780 and 1105; and a CDR-H3 comprising at least one of SEQ ID NOs: 1430 and 1755; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180 and HC404; and (c) a linker-payload, wherein n2 is 4 and each linker-payload is bonded to one of the para-azidomethylphenylalanine residue side chains:

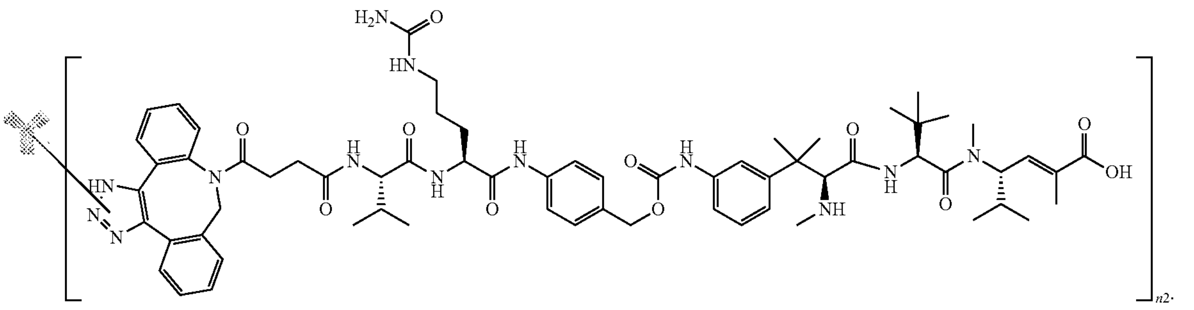

In some embodiments, an antibody conjugate is provided that comprises: (a) an antibody comprising a $V_H$ comprising: a CDR-H1 comprising at least one of SEQ ID NOs: 130 and 455; a CDR-H2 comprising at least one of SEQ ID NOs: 780 and 1105; and a CDR-H3 comprising at least one of SEQ ID NOs: 1430 and 1755; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC241 and HC404; and (c) a linker-payload, wherein n2 is 4 and each linker-payload is bonded to one of the para-azidomethylphenylalanine residue side chains:

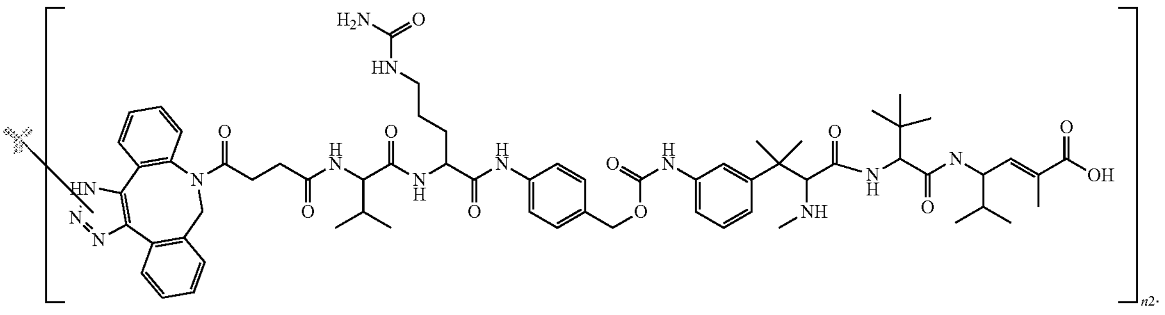

In some embodiments, an antibody conjugate is provided that comprises: (a) an antibody comprising a $V_H$ comprising: a CDR-H1 comprising at least one of SEQ ID NOs: 130 and 455; a CDR-H2 comprising at least one of SEQ ID NOs: 780 and 1105; and a CDR-H3 comprising at least one of SEQ ID NOs: 1430 and 1755; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC241 and HC404; and (c) a linker-payload, wherein n2 is 4 and each linker-payload is bonded to one of the para-azidomethylphenylalanine residue side chains:

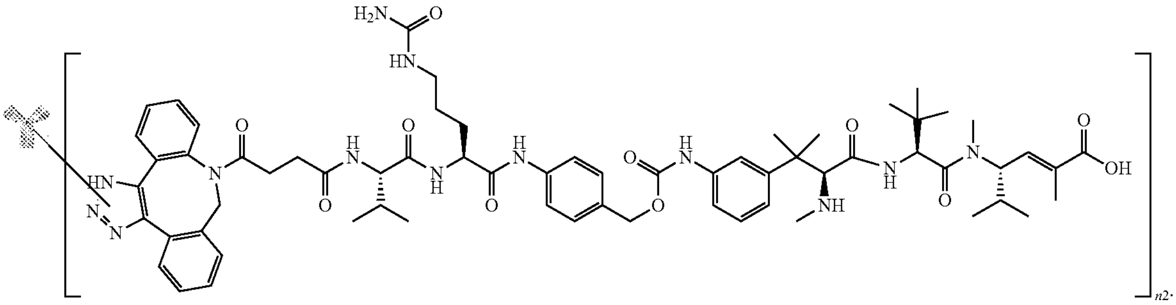

In some embodiments, an antibody conjugate is provided that comprises: (a) an antibody comprising a $V_H$ comprising: a CDR-H1 comprising at least one of SEQ ID NOs: 130 and 455; a CDR-H2 comprising at least one of SEQ ID NOs: 780 and 1105; and a CDR-H3 comprising at least one of SEQ ID NOs: 1430 and 1755; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180, HC404 and LC42; and (c) a linker-payload, wherein n2 is 6 and each linker-payload is bonded to one of the para-azidomethylphenylalanine residue side chains:

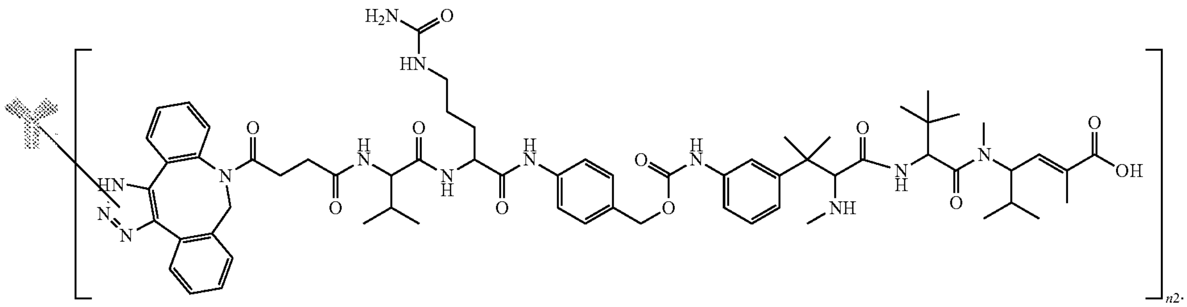

In some embodiments, an antibody conjugate is provided that comprises: (a) an antibody comprising a $V_H$ comprising: a CDR-H1 comprising at least one of SEQ ID NOs: 130 and 455; a CDR-H2 comprising at least one of SEQ ID NOs: 780 and 1105; and a CDR-H3 comprising at least one of SEQ ID NOs: 1430 and 1755; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180, HC404 and LC42; and (c) a linker-payload, wherein n2 is 6 and each linker-payload is bonded to one of the para-azidomethylphenylalanine residue side chains:

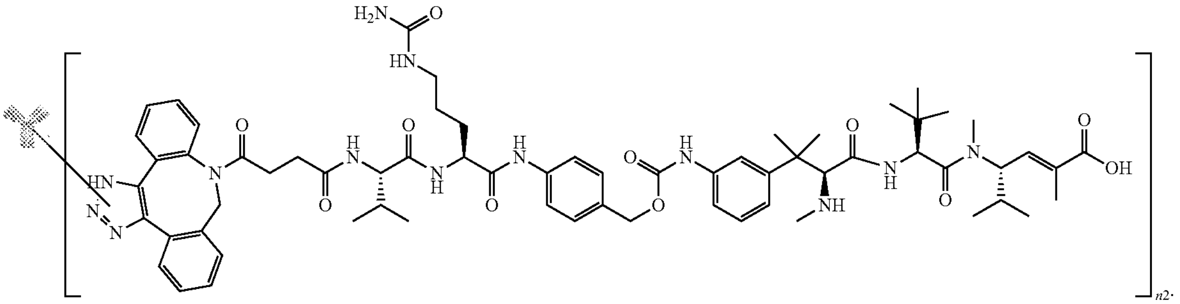

In some embodiments, an antibody conjugate is provided that comprises: (a) an antibody comprising a $V_H$ comprising: a CDR-H1 comprising at least one of SEQ ID NOs: 130 and 455; a CDR-H2 comprising at least one of SEQ ID NOs: 780 and 1105; and a CDR-H3 comprising at least one of SEQ ID NOs: 1430 and 1755; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180, HC241 and HC404; and (c) a linker-payload, wherein n2 is 6 and each linker-payload is bonded to one of the para-azidomethylphenylalanine residue side chains:

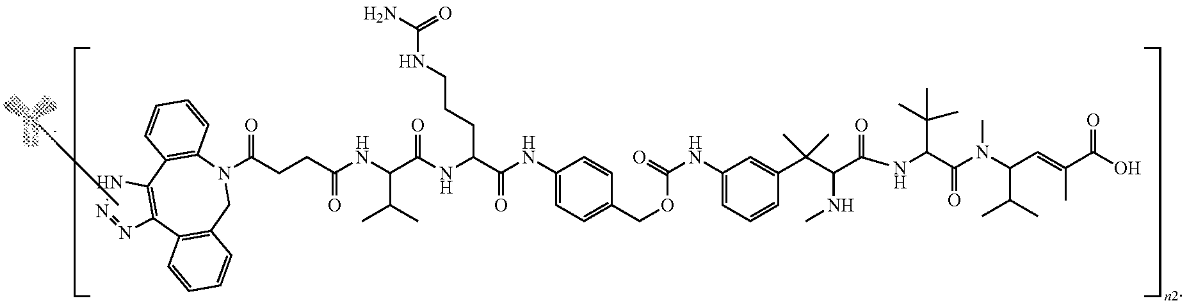

In some embodiments, an antibody conjugate is provided that comprises: (a) an antibody comprising a $V_H$ comprising: a CDR-H1 comprising at least one of SEQ ID NOs: 130 and 455; a CDR-H2 comprising at least one of SEQ ID NOs: 780 and 1105; and a CDR-H3 comprising at least one of SEQ ID NOs: 1430 and 1755; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180, HC241 and HC404; and (c) a linker-payload, wherein n2 is 6 and each linker-payload is bonded to one of the para-azidomethylphenylalanine residue side chains:

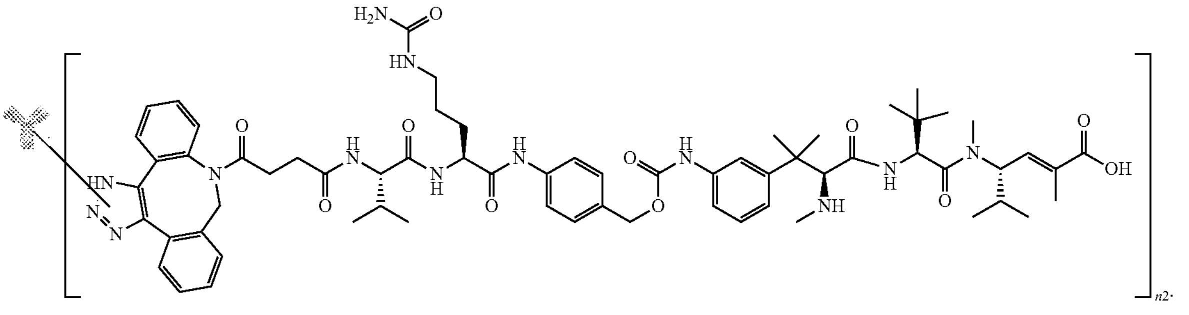

In some embodiments, an antibody conjugate is provided that comprises: (a) an antibody comprising a $V_H$ comprising: a CDR-H1 comprising at least one of SEQ ID NOs: 130 and 455; a CDR-H2 comprising at least one of SEQ ID NOs: 780 and 1105; and a CDR-H3 comprising at least one of SEQ ID NOs: 1430 and 1755; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180, HC404, LC42 and LC161; and (c) a linker-payload, wherein n2 is 8 and each linker-payload is bonded to one of the para-azidomethylphenylalanine residue side chains:

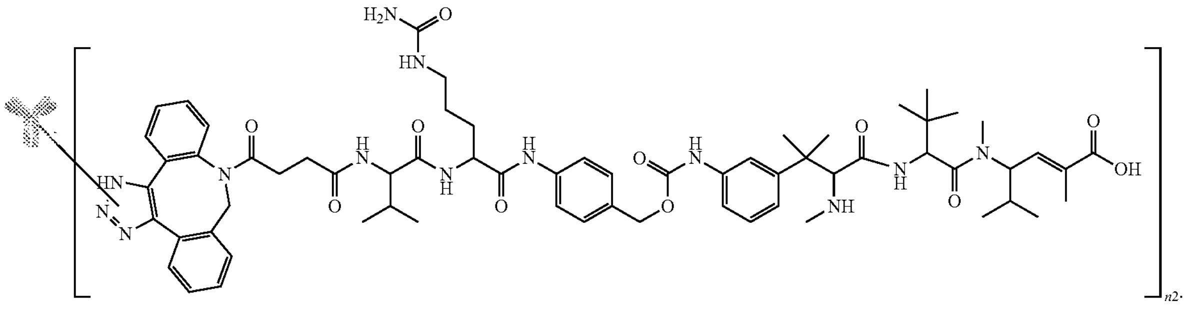

In some embodiments, an antibody conjugate is provided that comprises: (a) an antibody comprising a $V_H$ comprising: a CDR-H1 comprising at least one of SEQ ID NOs: 130 and 455; a CDR-H2 comprising at least one of SEQ ID NOs: 780 and 1105; and a CDR-H3 comprising at least one of SEQ ID NOs: 1430 and 1755; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180, HC404, LC42 and LC161; and (c) a linker-payload, wherein n2 is 8 and each linker-payload is bonded to one of the para-azidomethylphenylalanine residue side chains:

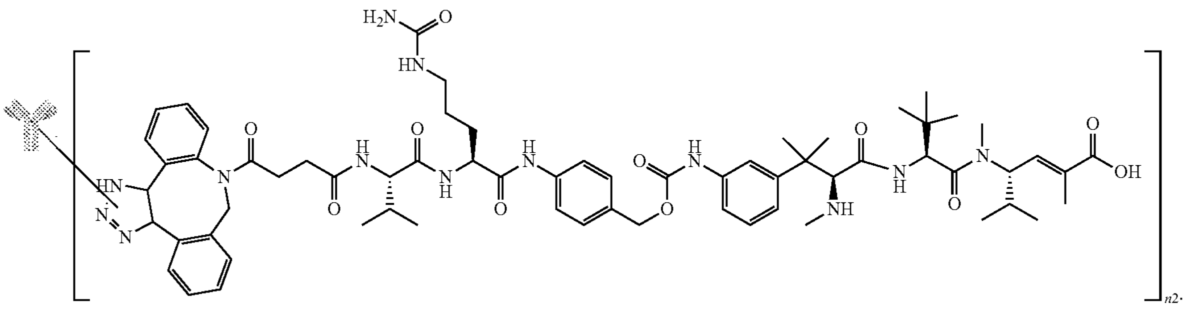

In some embodiments, an antibody conjugate is provided that comprises: (a) an antibody comprising a $V_H$ comprising: a CDR-H1 comprising at least one of SEQ ID NOs: 130 and 455; a CDR-H2 comprising at least one of SEQ ID NOs: 780 and 1105; and a CDR-H3 comprising at least one of SEQ ID NOs: 1430 and 1755; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180, HC241, HC404 and LC42; and (c) a linker-payload, wherein n2 is 8 and each linker-payload is bonded to one of the para-azidomethylphenylalanine residue side chains:

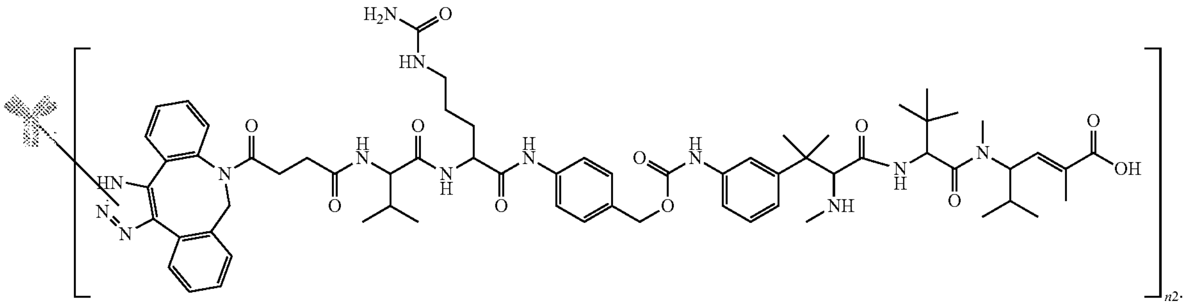

In some embodiments, an antibody conjugate is provided that comprises: (a) an antibody comprising a $V_H$ comprising: a CDR-H1 comprising at least one of SEQ ID NOs: 130 and 455; a CDR-H2 comprising at least one of SEQ ID NOs: 780 and 1105; and a CDR-H3 comprising at least one of SEQ ID NOs: 1430 and 1755; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180, HC241, HC404 and LC42; and (c) a linker-payload, wherein n2 is 8 and each linker-payload is bonded to one of the para-azidomethylphenylalanine residue side chains:

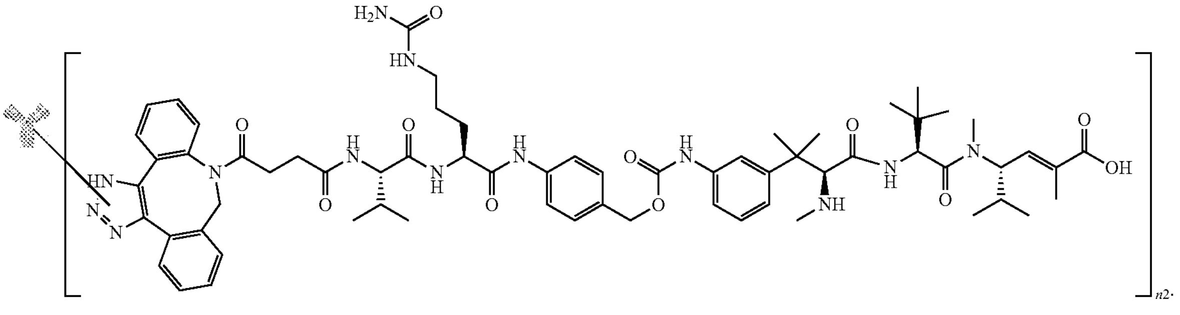

In some embodiments, an antibody conjugate is provided that comprises: (a) an antibody comprising a $V_H$ comprising: a CDR-H1 comprising at least one of SEQ ID NOs: 130 and 455; a CDR-H2 comprising at least one of SEQ ID NOs: 780 and 1105; and a CDR-H3 comprising at least one of SEQ ID NOs: 1430 and 1755; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180, HC241, HC404 and LC42; and (c) a linker-payload, wherein n2 is 8 and each linker-payload is bonded to one of the para-azidomethylphenylalanine residue side chains:

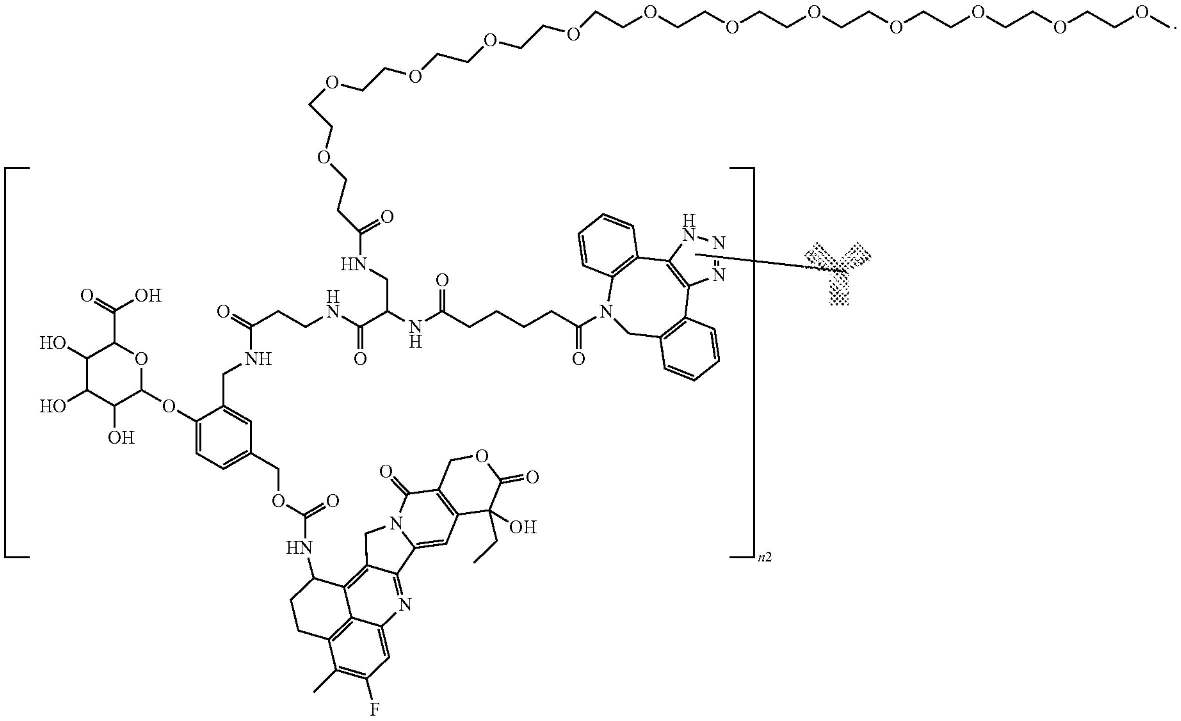

In some embodiments, an antibody conjugate is provided that comprises: (a) an antibody comprising a $V_H$ comprising: a CDR-H1 comprising at least one of SEQ ID NOs: 130 and 455; a CDR-H2 comprising at least one of SEQ ID NOs: 780 and 1105; and a CDR-H3 comprising at least one of SEQ ID NOs: 1430 and 1755; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180, HC241, HC404 and LC42; and (c) a linker-payload, wherein n2 is 8 and each linker-payload is bonded to one of the para-azidomethylphenylalanine residue side chains:

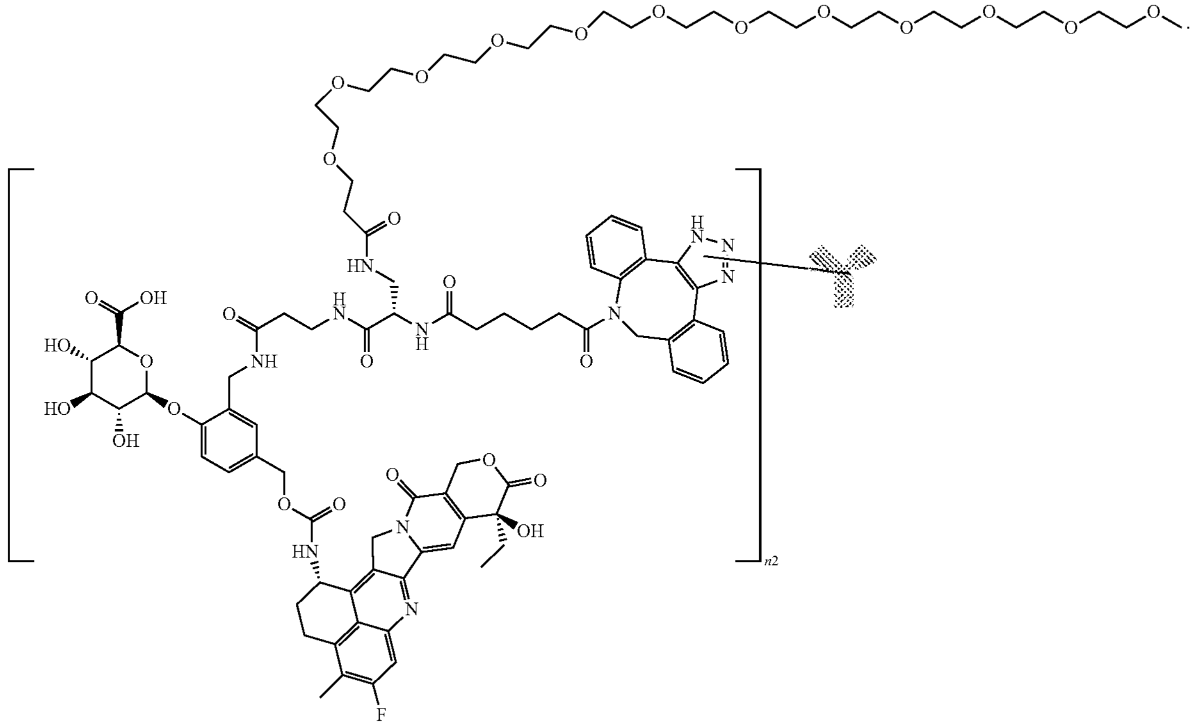

In some embodiments, an antibody conjugate is provided that comprises: (a) an antibody comprising a $V_H$ comprising: a CDR-H1 comprising at least one of SEQ ID NOs: 130 and 455; a CDR-H2 comprising at least one of SEQ ID NOs: 780 and 1105; and a CDR-H3 comprising at least one of SEQ ID NOs: 1430 and 1755; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180 and HC404; and (c) a linker-payload, wherein n2 is 4 and each linker-payload is bonded to one of the para-azidomethylphenylalanine residue side chains:

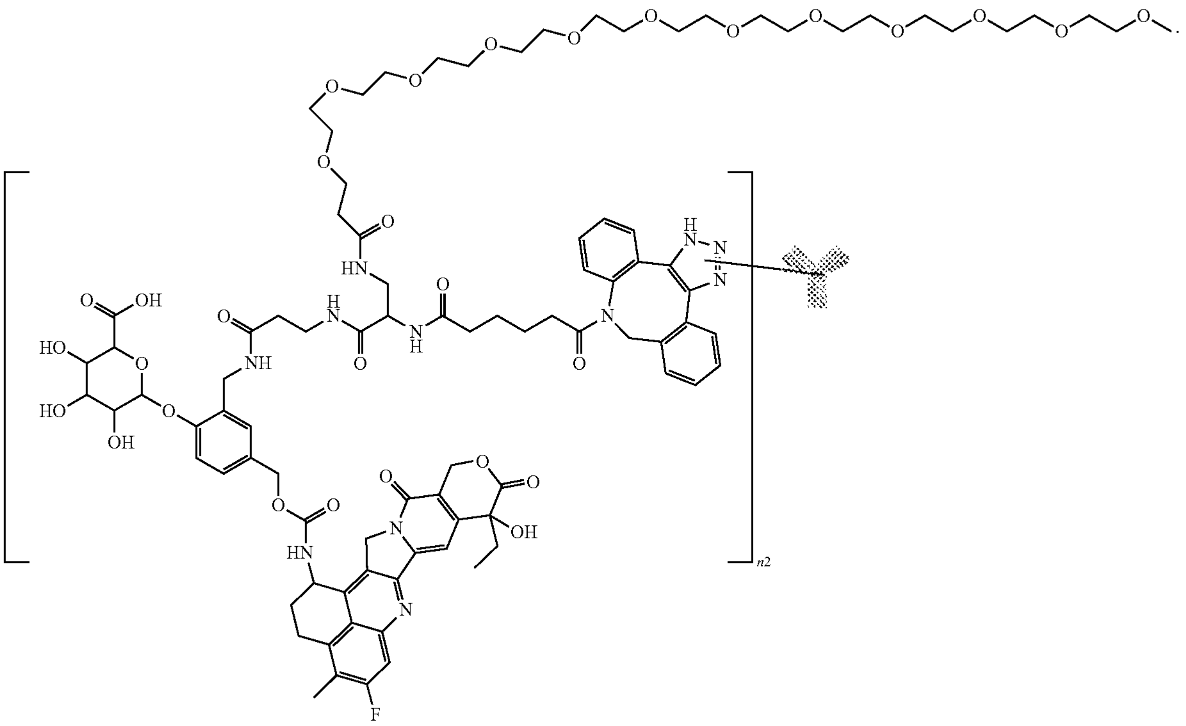

In some embodiments, an antibody conjugate is provided that comprises: (a) an antibody comprising a $V_H$ comprising: a CDR-H1 comprising at least one of SEQ ID NOs: 130 and 455; a CDR-H2 comprising at least one of SEQ ID NOs: 780 and 1105; and a CDR-H3 comprising at least one of SEQ ID NOs: 1430 and 1755; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180 and HC404; and (c) a linker-payload, wherein n2 is 4 and each linker-payload is bonded to one of the para-azidomethylphenylalanine residue side chains:

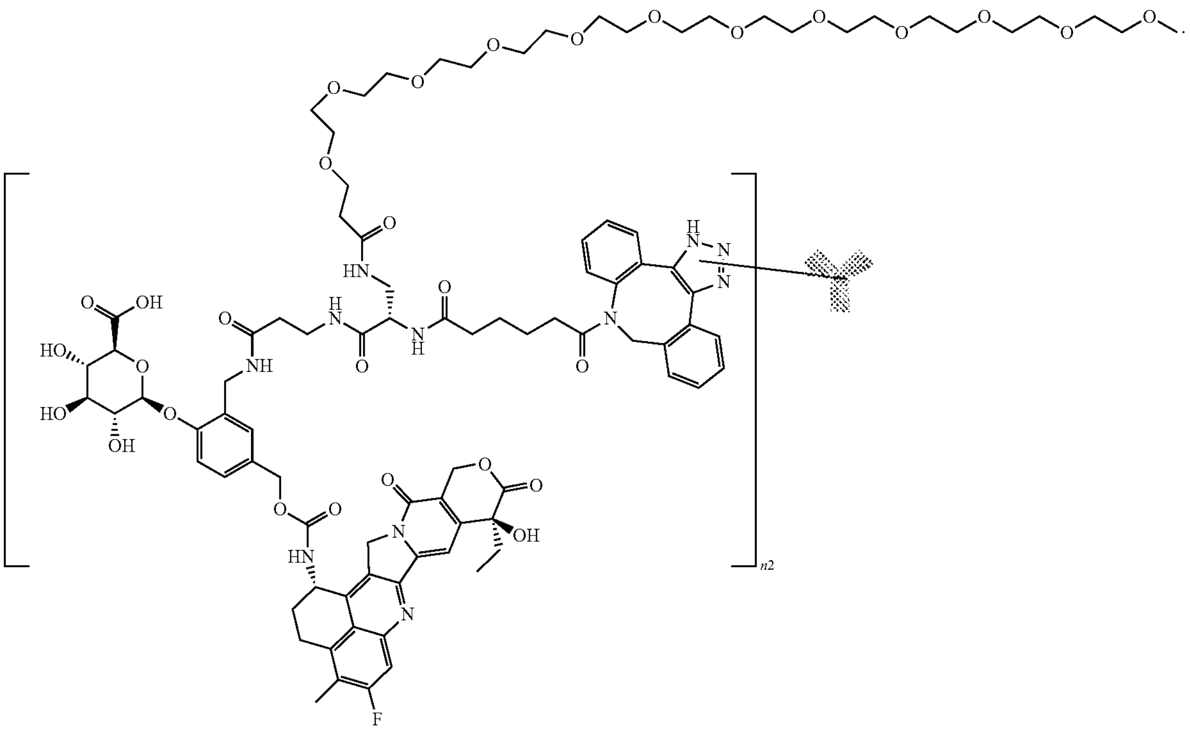

In some embodiments, an antibody conjugate is provided that comprises: (a) an antibody comprising a $V_H$ comprising: a CDR-H1 comprising at least one of SEQ ID NOs: 130 and 455; a CDR-H2 comprising at least one of SEQ ID NOs: 780 and 1105; and a CDR-H3 comprising at least one of SEQ ID NOs: 1430 and 1755; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180 and HC404; and (c) a linker-payload, wherein n2 is 4 and each linker-payload is bonded to one of the para-azidomethylphenylalanine residue side chains:

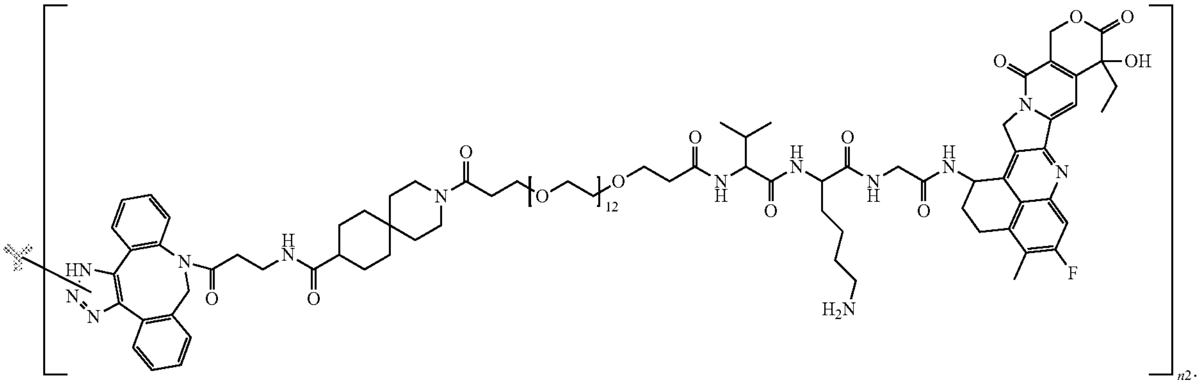

In some embodiments, an antibody conjugate is provided that comprises: (a) an antibody comprising a $V_H$ comprising: a CDR-H1 comprising at least one of SEQ ID NOs: 130 and 455; a CDR-H2 comprising at least one of SEQ ID NOs: 780 and 1105; and a CDR-H3 comprising at least one of SEQ ID NOs: 1430 and 1755; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180 and HC404; and (c) a linker-payload, wherein n2 is 4 and each linker-payload is bonded to one of the para-azidomethylphenylalanine residue side chains:

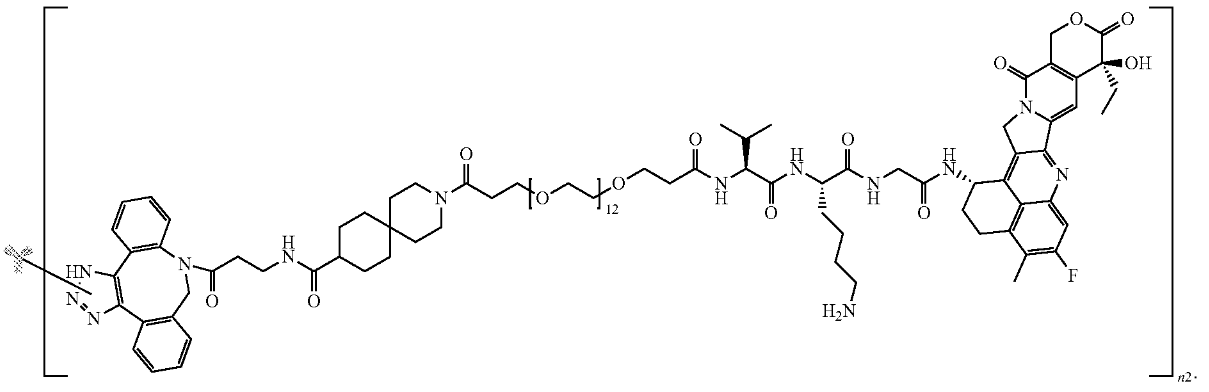

In some embodiments, an antibody conjugate is provided that comprises: (a) an antibody comprising a $V_H$ comprising: a CDR-H1 comprising at least one of SEQ ID NOs: 130 and 455; a CDR-H2 comprising at least one of SEQ ID NOs: 780 and 1105; and a CDR-H3 comprising at least one of SEQ ID NOs: 1430 and 1755; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180 and HC404; and (c) a linker-payload, wherein n2 is 4 and each linker-payload is bonded to one of the para-azidomethylphenylalanine residue side chains:

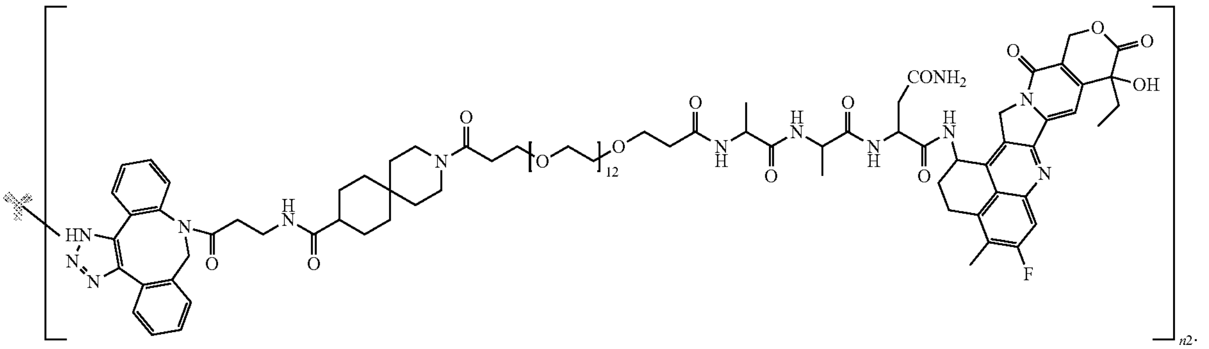

In some embodiments, an antibody conjugate is provided that comprises: (a) an antibody comprising a $V_H$ comprising: a CDR-H1 comprising at least one of SEQ ID NOs: 130 and 455; a CDR-H2 comprising at least one of SEQ ID NOs: 780 and 1105; and a CDR-H3 comprising at least one of SEQ ID NOs: 1430 and 1755; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180 and HC404; and (c) a linker-payload, wherein n2 is 4 and each linker-payload is bonded to one of the para-azidomethylphenylalanine residue side chains:

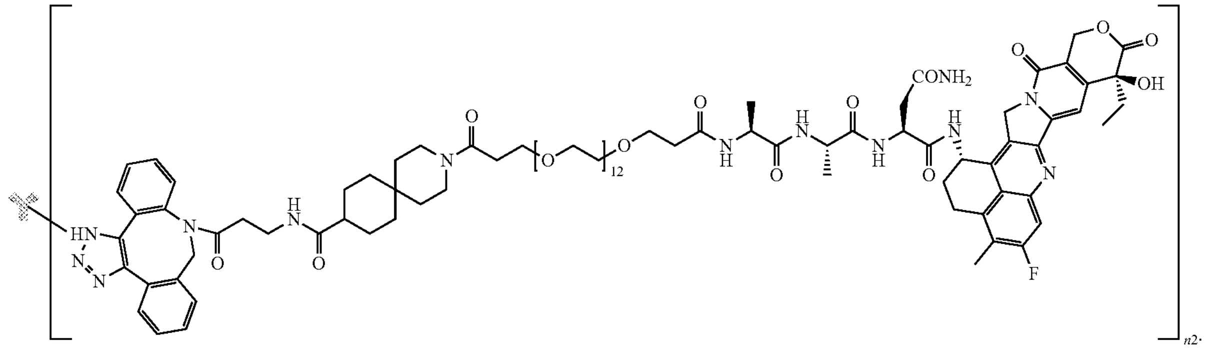

In some embodiments, an antibody conjugate is provided that comprises: (a) an antibody comprising a $V_H$ comprising: a CDR-H1 comprising at least one of SEQ ID NOs: 130 and 455; a CDR-H2 comprising at least one of SEQ ID NOs: 780 and 1105; and a CDR-H3 comprising at least one of SEQ ID NOs: 1430 and 1755; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180 and HC404; and (c) a linker-payload, wherein n2 is 4 and each linker-payload is bonded to one of the para-azidomethylphenylalanine residue side chains:

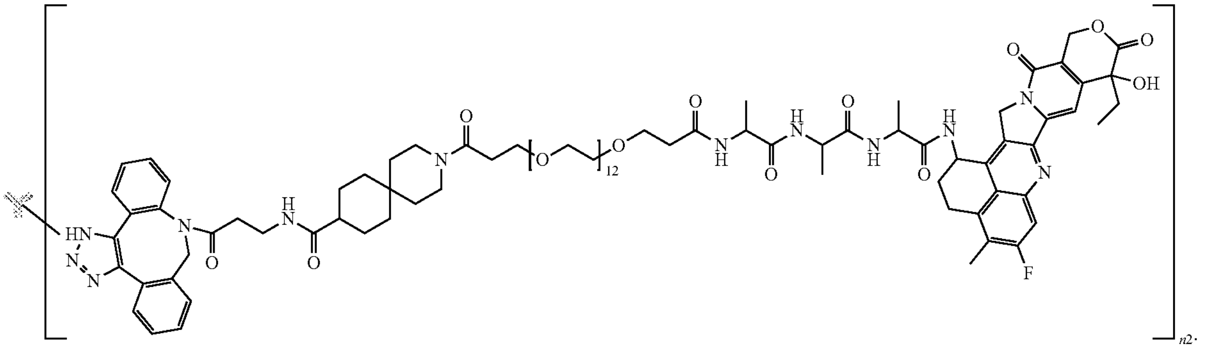

In some embodiments, an antibody conjugate is provided that comprises: (a) an antibody comprising a $V_H$ comprising: a CDR-H1 comprising at least one of SEQ ID NOs: 130 and 455; a CDR-H2 comprising at least one of SEQ ID NOs: 780 and 1105; and a CDR-H3 comprising at least one of SEQ ID NOs: 1430 and 1755; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180 and HC404; and (c) a linker-payload, wherein n2 is 4 and each linker-payload is bonded to one of the para-azidomethylphenylalanine residue side chains:

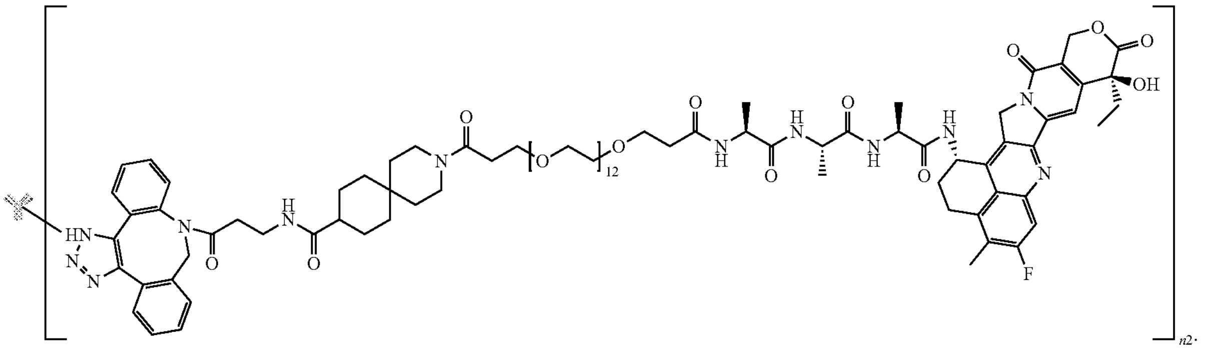

In some embodiments, the antibody of the antibody drug conjugate comprises the $V_H$/$V_L$ pair SEQ ID NOs: 2752/3061.

In some embodiments, the antibody of the antibody drug conjugate comprises the complementarity determining regions (CDRs) of a $V_H$ region selected from SEQ ID NOs: 2727, 2736, 2739, 2751-2838, 2840, 2846, 2851, 2857, and 2859-2860 and the CDRs of a $V_L$ region selected from SEQ ID NOs: 2951, 2957, 2962, 2968, 2970-2971, and 3061. In some embodiments, the antibody of the antibody conjugate comprises a $V_H$ region selected from SEQ ID NOs: 2727, 2736, 2739, 2751-2838, 2840, 2846, 2851, 2857, and 2859-2860 and a $V_L$ region selected from SEQ ID NOs: 2951, 2957, 2962, 2968, 2970-2971, and 3061. In some embodiments, the antibody of the antibody conjugate binds to the same epitope as a second antibody with a $V_H$ region selected from SEQ ID NOs: 2727, 2736, 2739, 2751-2838, 2840, 2846, 2851, 2857, and 2859-2860 and a $V_L$ region selected from SEQ ID NOs: 2951, 2957, 2962, 2968, 2970-2971, and 3061.

In some embodiments, an antibody conjugate is provided that comprises: (a) an antibody comprising a $V_H$ comprising: a CDR-H1 comprising at least one of SEQ ID NOs: 161 and 486; a CDR-H2 comprising at least one of SEQ ID NOs: 811 and 1136; and a CDR-H3 comprising at least one of SEQ ID NOs: 1461 and 1786; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180 and HC404; and (c) a linker-payload, wherein n2 is 4 and each linker-payload is bonded to one of the para-azidomethylphenylalanine residue side chains:

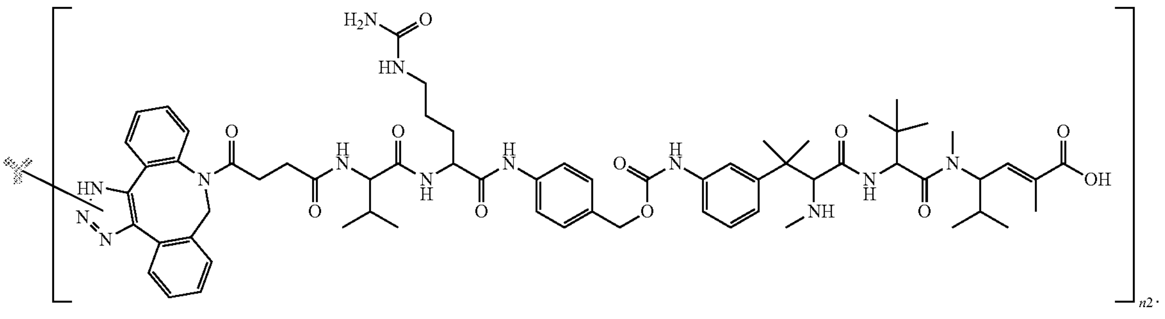

In some embodiments, the antibody of the antibody conjugate comprises the $V_H/V_L$ pair SEQ ID NOs: 2783/3061.

In some embodiments, an antibody conjugate is provided that comprises: (a) an antibody comprising a $V_H$ comprising: a CDR-H1 comprising at least one of SEQ ID NOs: 161 and 486; a CDR-H2 comprising at least one of SEQ ID NOs: 811 and 1136; and a CDR-H3 comprising at least one of SEQ ID NOs: 1461 and 1786; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180 and HC404; and (c) a linker-payload, wherein n2 is 4 and each linker-payload is bonded to one of the para-azidomethylphenylalanine residue side chains:

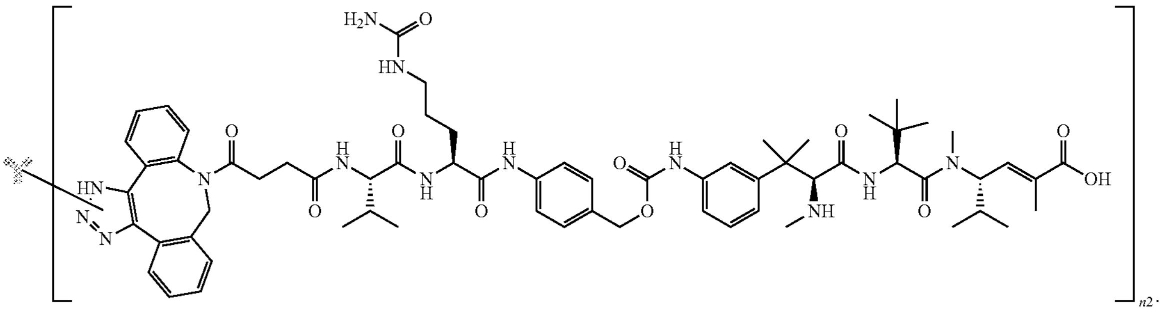

In some embodiments, the antibody of the antibody conjugate comprises the $V_H/V_L$ pair SEQ ID NOS: 2783/3061.

In some embodiments, an antibody conjugate is provided that comprises: (a) an antibody comprising a $V_H$ comprising: a CDR-H1 comprising at least one of SEQ ID NOs: 189 and 514; a CDR-H2 comprising at least one of SEQ ID NOs: 839 and 1164; and a CDR-H3 comprising at least one of SEQ ID NOs: 1489 and 1814; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180 and HC404; and (c) a linker-payload, wherein n2 is 4 and each linker-payload is bonded to one of the para-azidomethylphenylalanine residue side chains:

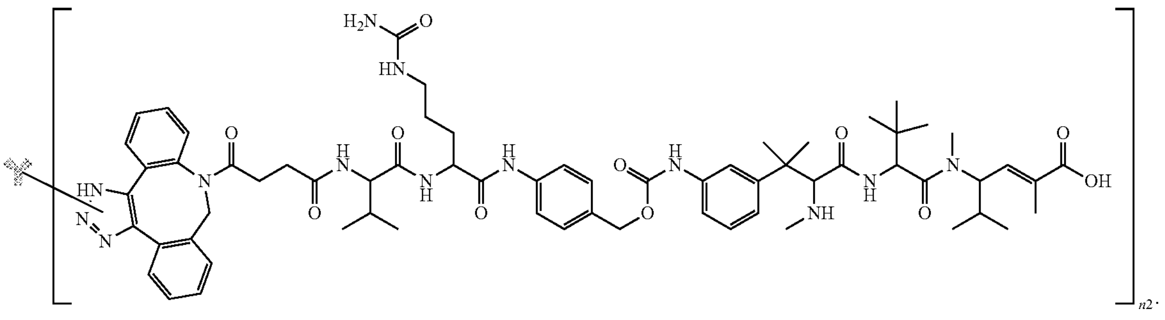

In some embodiments, the antibody of the antibody conjugate comprises the $V_H/V_L$ pair SEQ ID NOs: 2811/3061.

In some embodiments, an antibody conjugate is provided that comprises: (a) an antibody comprising a $V_H$ comprising: a CDR-H1 comprising at least one of SEQ ID NOs: 189 and 514; a CDR-H2 comprising at least one of SEQ ID NOs: 839 and 1164; and a CDR-H3 comprising at least one of SEQ ID NOs: 1489 and 1814; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180 and HC404; and (c) a linker-payload, wherein n2 is 4 and each linker-payload is bonded to one of the para-azidomethylphenylalanine residue side chains:

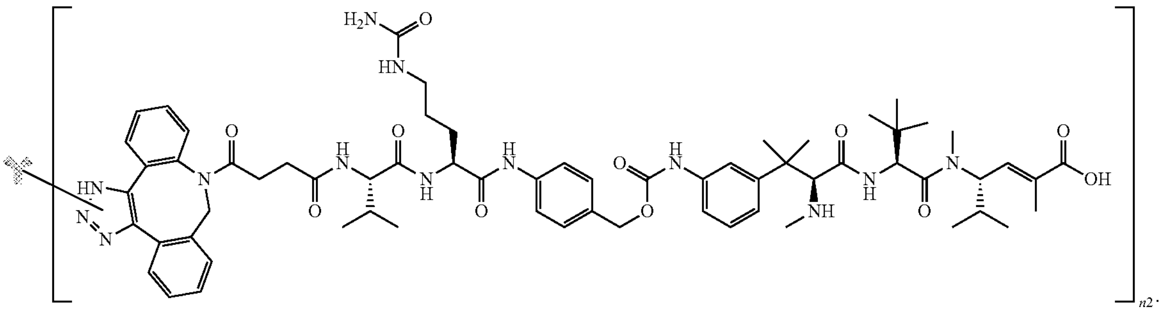

In some embodiments, the antibody of the antibody conjugate comprises the $V_H/V_L$ pair SEQ ID NOS: 2811/3061.

In some embodiments, an antibody conjugate is provided that comprises: (a) an antibody comprising a $V_H$ comprising: a CDR-H1 comprising at least one of SEQ ID NOs: 192 and 517; a CDR-H2 comprising at least one of SEQ ID NOs: 842 and 1167; and a CDR-H3 comprising at least one of SEQ ID NOs: 1492 and 1817; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180 and HC404; and (c) a linker-payload, wherein n2 is 4 and each linker-payload is bonded to one of the para-azidomethylphenylalanine residue side chains:

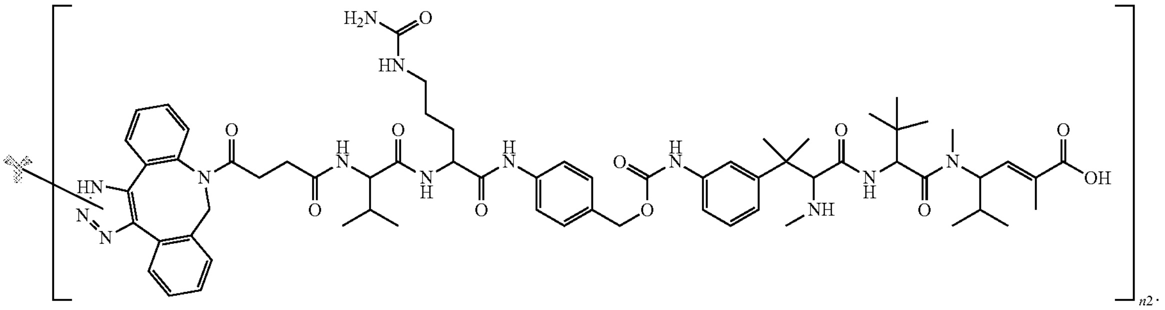

In some embodiments, the antibody of the antibody conjugate comprises the $V_H/V_L$ pair SEQ ID NOs: 2814/3061.

In some embodiments, an antibody conjugate is provided that comprises: (a) an antibody comprising a $V_H$ comprising: a CDR-H1 comprising at least one of SEQ ID NOs: 192 and 517; a CDR-H2 comprising at least one of SEQ ID NOs: 842 and 1167; and a CDR-H3 comprising at least one of SEQ ID NOs: 1492 and 1817; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180 and HC404; and (c) a linker-payload, wherein n2 is 4 and each linker-payload is bonded to one of the para-azidomethylphenylalanine residue side chains:

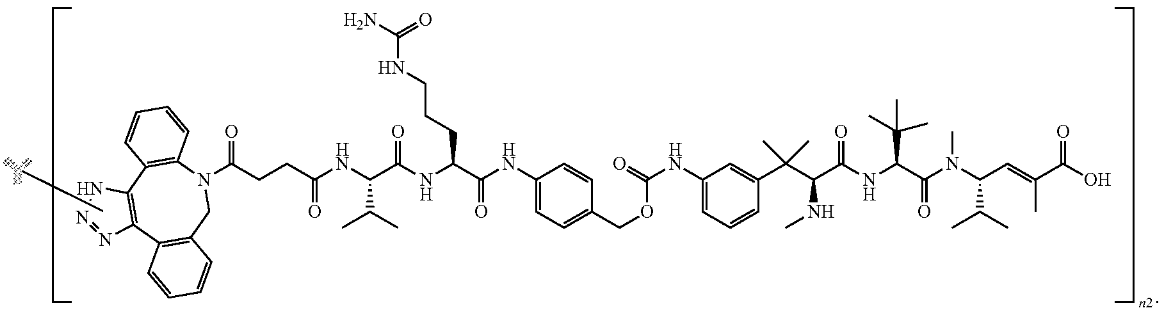

In some embodiments, the antibody of the antibody conjugate comprises the $V_H/V_L$ pair SEQ ID NOs: 2814/3061.

In some embodiments, an antibody conjugate is provided that comprises: (a) an antibody comprising a $V_H$ comprising: a CDR-H1 comprising at least one of SEQ ID NOs: 211 and 536; a CDR-H2 comprising at least one of SEQ ID NOs: 861 and 1186; and a CDR-H3 comprising at least one of SEQ ID NOs: 1511 and 1836; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180 and HC404; and (c) a linker-payload, wherein n2 is 4 and each linker-payload is bonded to one of the para-azidomethylphenylalanine residue side chains:

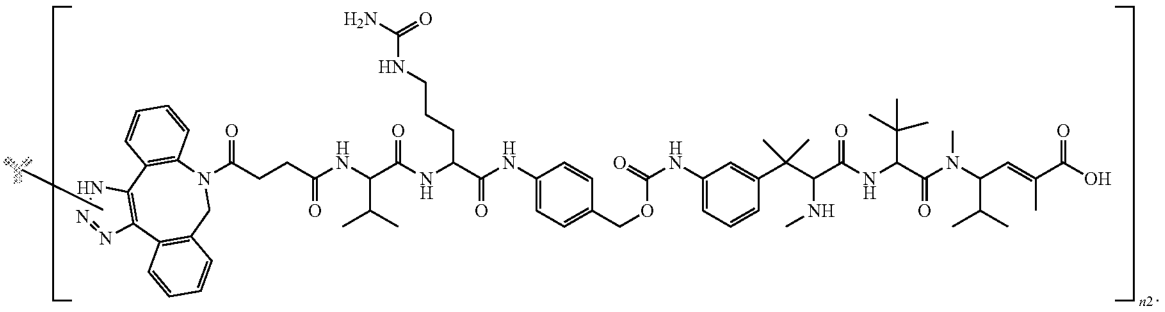

In some embodiments, the antibody of the antibody conjugate comprises the $V_H/V_L$ pair SEQ ID NOs: 2833/3061.

In some embodiments, an antibody conjugate is provided that comprises: (a) an antibody comprising a $V_H$ comprising: a CDR-H1 comprising at least one of SEQ ID NOs: 211 and 536; a CDR-H2 comprising at least one of SEQ ID NOs: 861 and 1186; and a CDR-H3 comprising at least one of SEQ ID NOs: 1511 and 1836; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180 and HC404; and (c) a linker-payload, wherein n2 is 4 and each linker-payload is bonded to one of the para-azidomethylphenylalanine residue side chains:

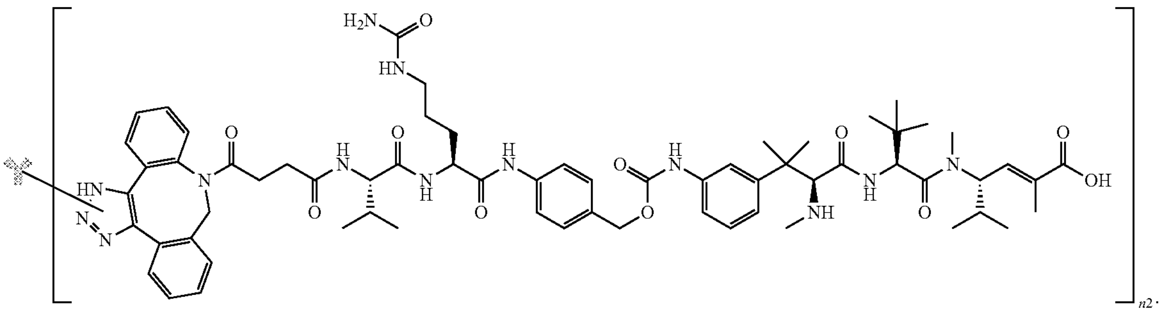

In some embodiments, the antibody of the antibody conjugate comprises the $V_H/V_L$ pair SEQ ID NOS: 2833/3061.

In some embodiments, an antibody conjugate is provided that comprises: (a) an antibody comprising a $V_H$ comprising: a CDR-H1 comprising at least one of SEQ ID NOs: 214 and 539; a CDR-H2 comprising at least one of SEQ ID NOs: 864 and 1189; and a CDR-H3 comprising at least one of SEQ ID NOs: 1514 and 1839; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180 and HC404; and (c) a linker-payload, wherein n2 is 4 and each linker-payload is bonded to one the para-azidomethylphenylalanine residue side chains:

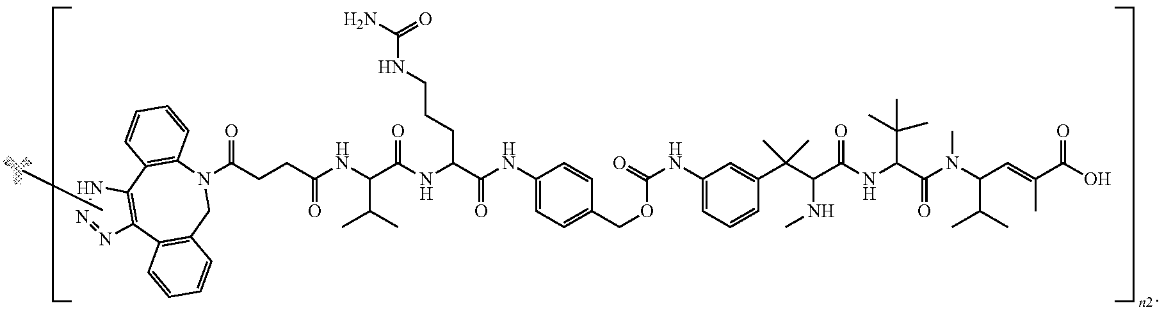

In some embodiments, the antibody of the antibody conjugate comprises the $V_H/V_L$ pair SEQ ID NOs: 2836/3061.

In some embodiments, an antibody conjugate is provided that comprises (a) an antibody comprising a $V_H$ comprising: a CDR-H1 comprising at least one of SEQ ID NOs: 214 and 539; a CDR-H2 comprising at least one of SEQ ID NOs: 864 and 1189; and a CDR-H3 comprising at least one of SEQ ID NOs: 1514 and 1839; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180 and HC404; and (c) a linker-payload, wherein n2 is 4 and each linker-payload is bonded to one of the para-azidomethylphenylalanine residue side chains:

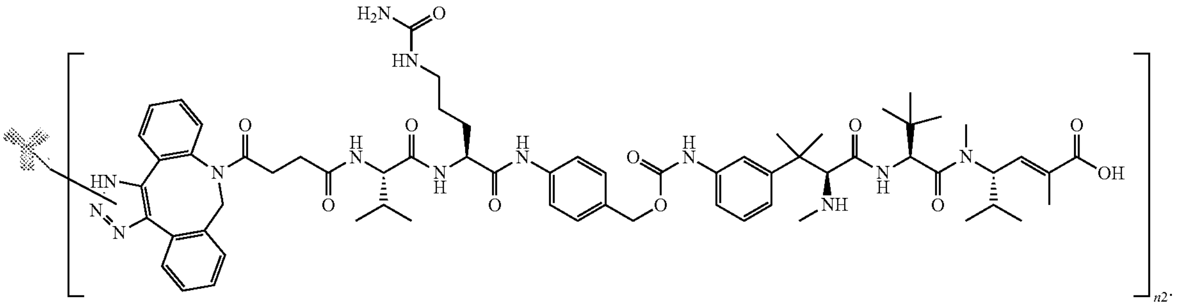

In some embodiments, the antibody of the antibody conjugate comprises the $V_H/V_L$ pair SEQ ID NOS: 2836/3061.

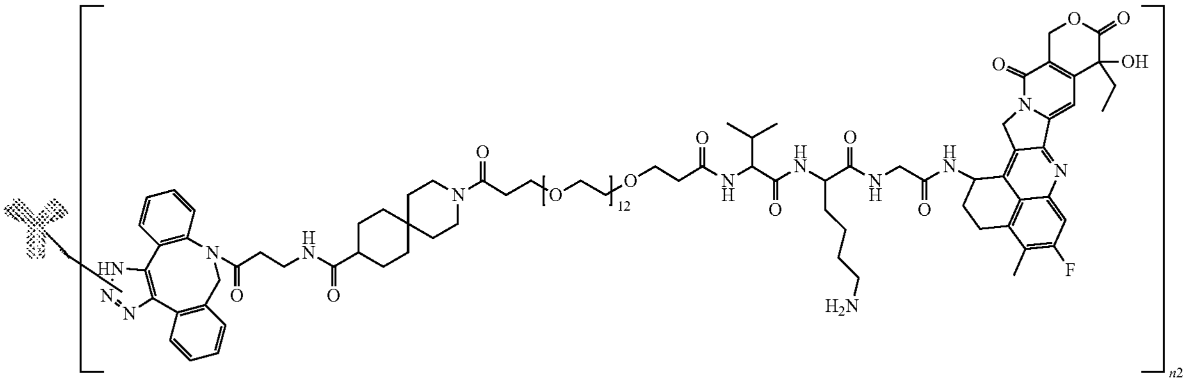
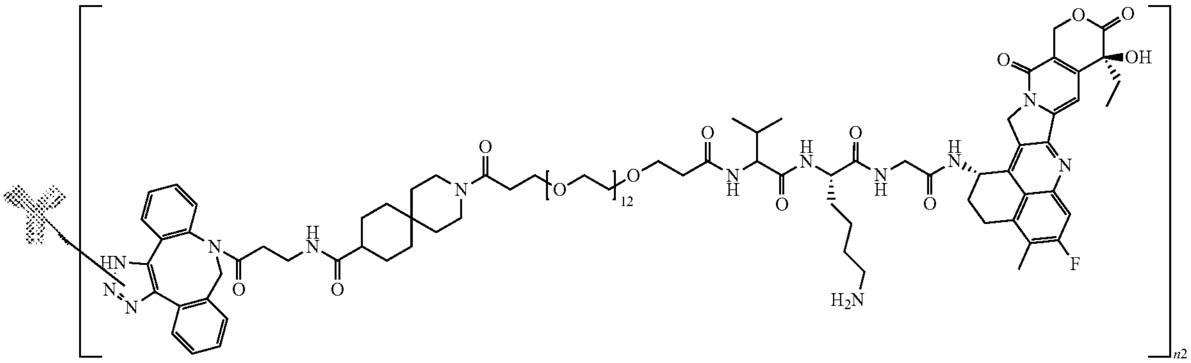
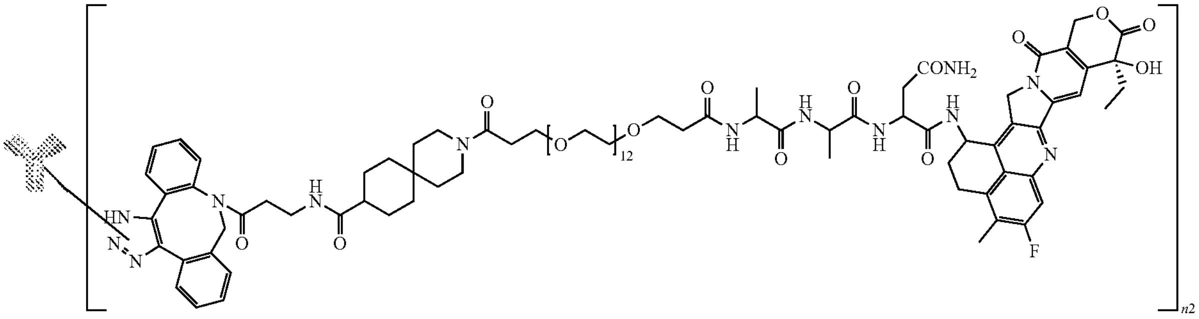
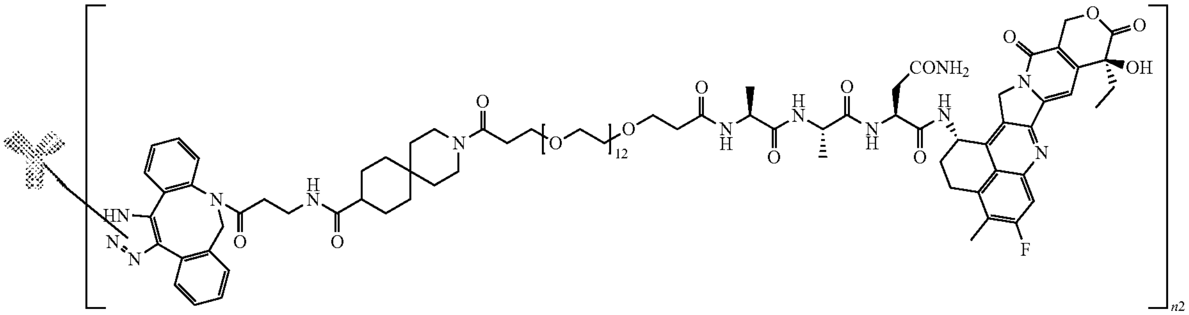
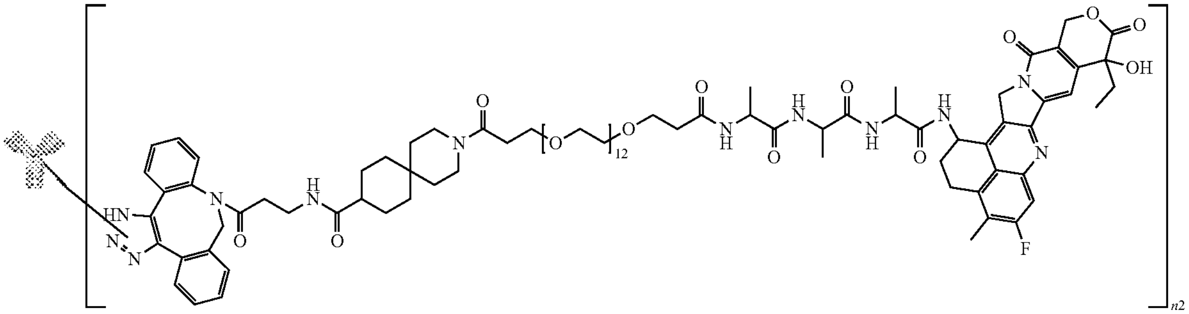

-continued
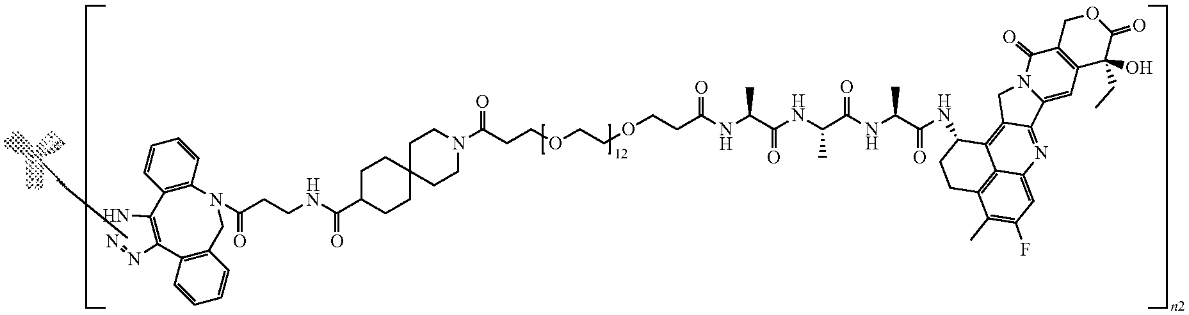
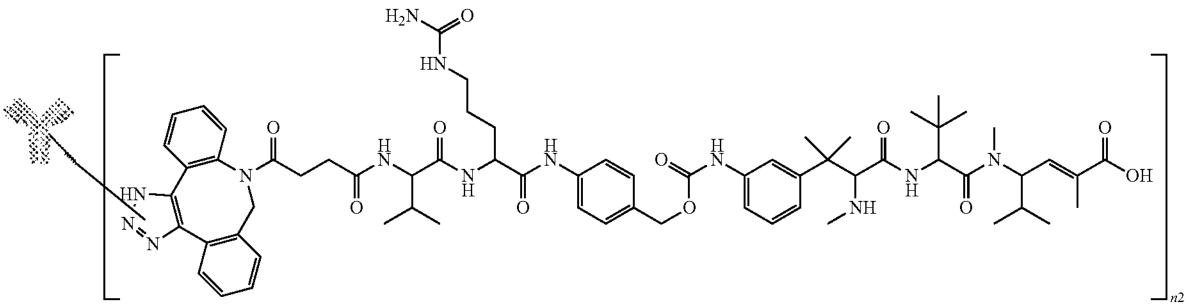
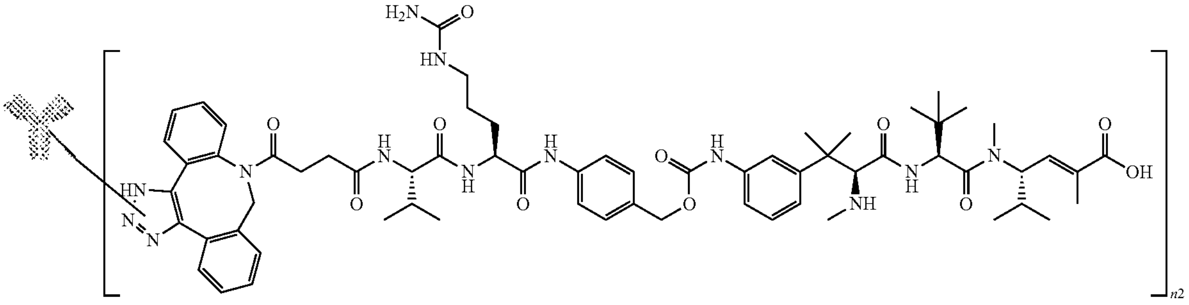
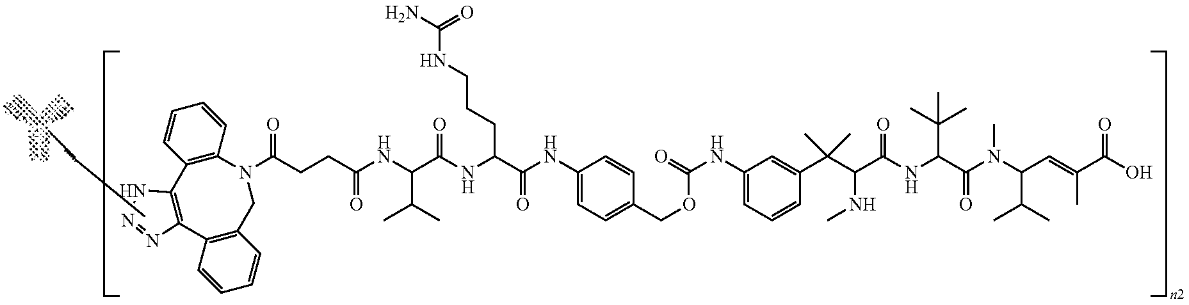
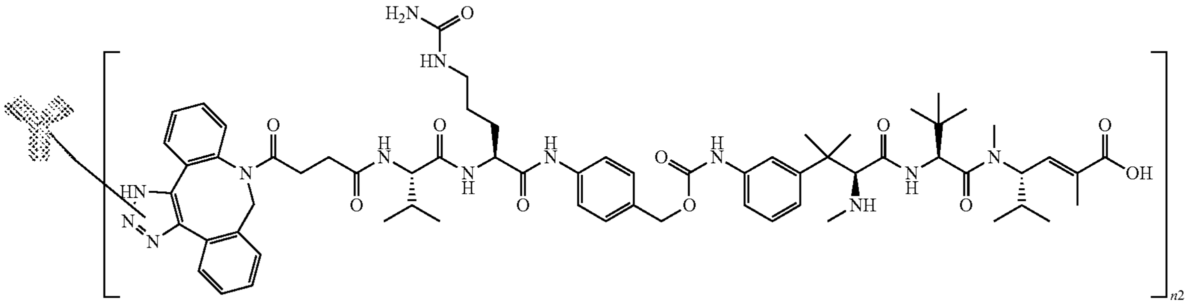

-continued

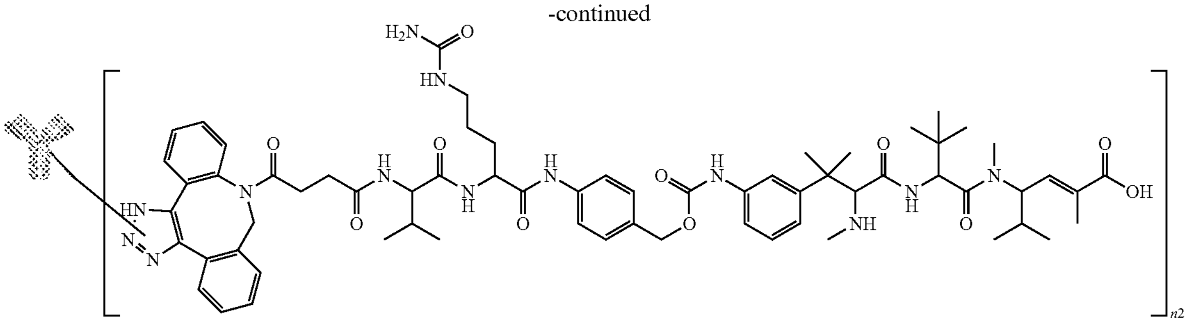

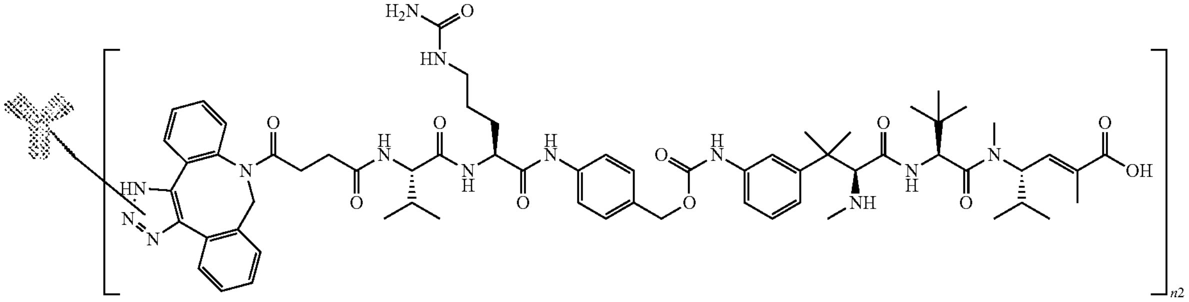

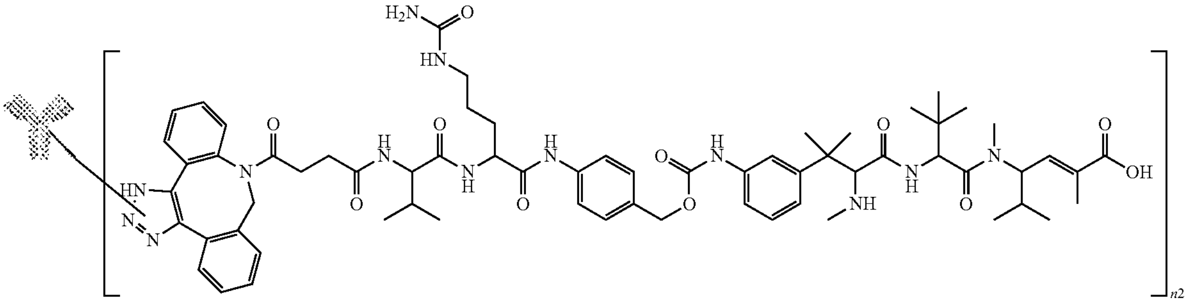

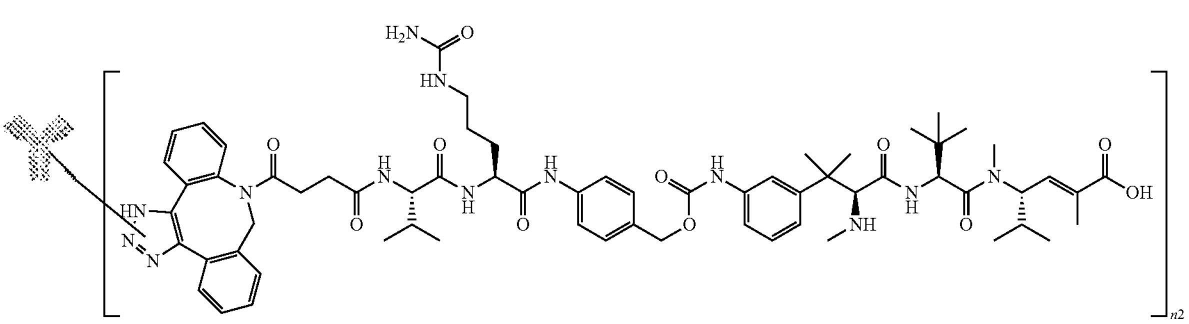

In some embodiments, an antibody conjugate is provided that comprises: (a) an antibody comprising a $V_H$ comprising: a CDR-H1 comprising at least one of SEQ ID NOs: 105 and 430; a CDR-H2 comprising at least one of SEQ ID NOs: 755 and 1080; and a CDR-H3 comprising at least one of SEQ ID NOs: 1405 and 1730; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180 and HC404; and (c) a linker-payload, wherein n2 is 4 and each linker-payload is bonded to one of the para-azidomethylphenylalanine residue side chains:

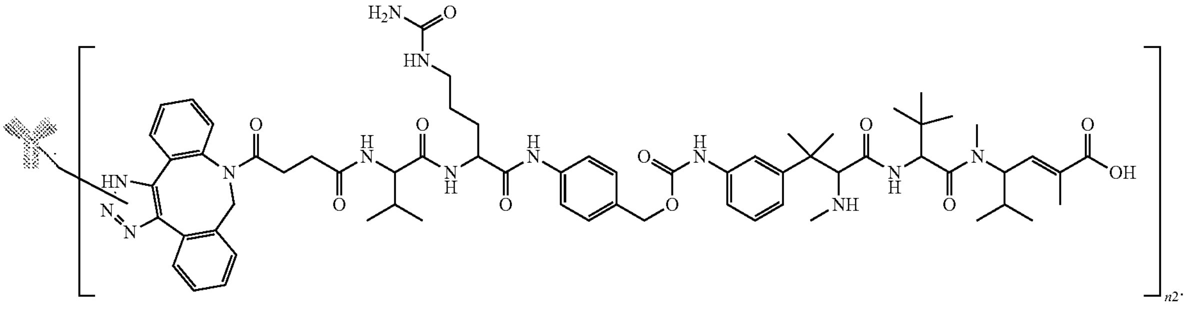

In some embodiments, the antibody of the antibody conjugate comprises the $V_H/V_L$ pair SEQ ID NOs: 2727/3061.

In some embodiments, an antibody conjugate is provided that comprises: (a) an antibody comprising a $V_H$ comprising: a CDR-H1 comprising at least one of SEQ ID NOs: 105 and 430; a CDR-H2 comprising at least one of SEQ ID NOs: 755 and 1080; and a CDR-H3 comprising at least one of SEQ ID NOs: 1405 and 1730; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180 and HC404; and (c) a linker-payload, wherein n2 is 4 and each linker-payload is bonded to one of the para-azidomethylphenylalanine residue side chains:

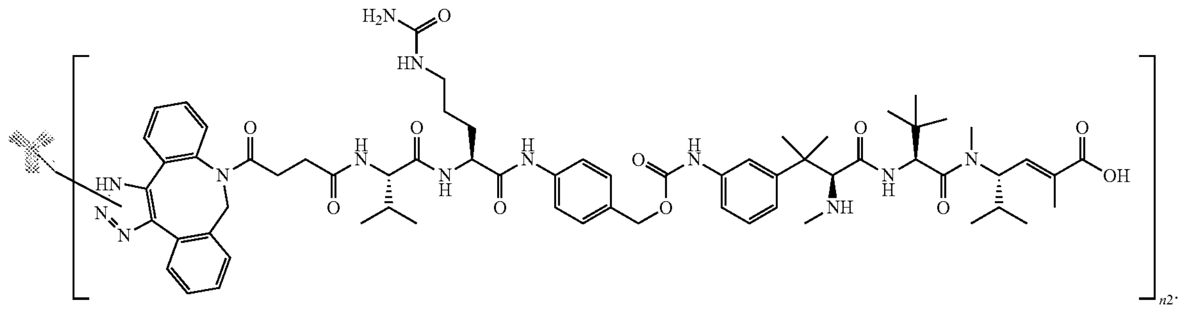

In some embodiments, the antibody of the antibody conjugate comprises the $V_H/V_L$ pair SEQ ID NOs: 2727/3061.

In some embodiments, an antibody conjugate is provided that comprises: (a) an antibody comprising a $V_H$ comprising: a CDR-H1 comprising at least one of SEQ ID NOs: 114 and 439; a CDR-H2 comprising at least one of SEQ ID NOs: 764 and 1089; and a CDR-H3 comprising at least one of SEQ ID NOs: 1414 and 1739; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180 and HC404; and (c) a linker-payload, wherein n2 is 4 and each linker-payload is bonded to one of the para-azidomethylphenylalanine residue side chains:

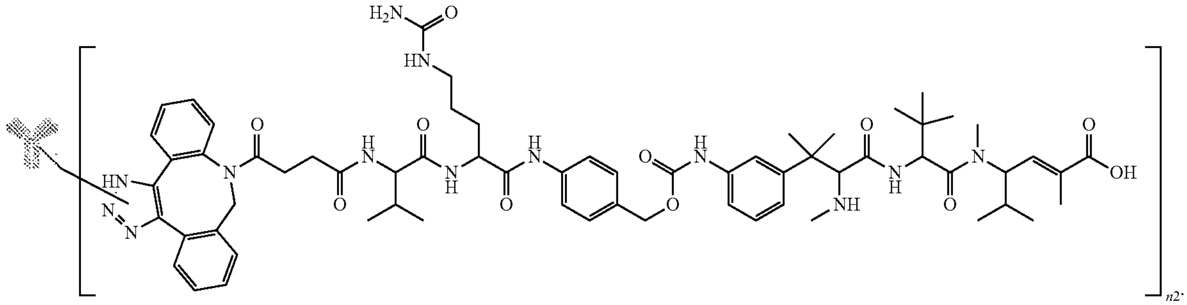

In some embodiments, the antibody of the antibody conjugate comprises the $V_H/V_L$ pair SEQ ID NOs: 2736/3061.

In some embodiments, an antibody conjugate is provided that comprises: (a) an antibody comprising a $V_H$ comprising: a CDR-H1 comprising at least one of SEQ ID NOs: 114 and 439; a CDR-H2 comprising at least one of SEQ ID NOs: 764 and 1089; and a CDR-H3 comprising at least one of SEQ ID NOs: 1414 and 1739; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180 and HC404; and (c) a linker-payload, wherein n2 is 4 and each linker-payload is bonded to one of the para-azidomethylphenylalanine residue side chains:

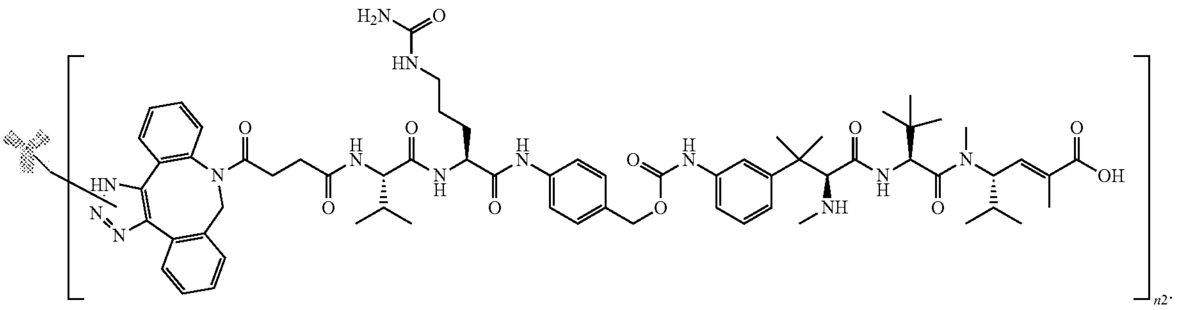

In some embodiments, the antibody of the antibody conjugate comprises the $V_H/V_L$ pair SEQ ID NOs: 2736/3061.

In some embodiments, an antibody conjugate is provided that comprises: (a) an antibody comprising a $V_H$ comprising: a CDR-H1 comprising at least one of SEQ ID NOs: 117 and 442; a CDR-H2 comprising at least one of SEQ ID NOs: 767 and 1092; and a CDR-H3 comprising at least one of SEQ ID NOs: 1417 and 1742; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180 and HC404; and (c) a linker-payload, wherein n2 is 4 and each linker-payload is bonded to one of the para-azidomethylphenylalanine residue side chains:

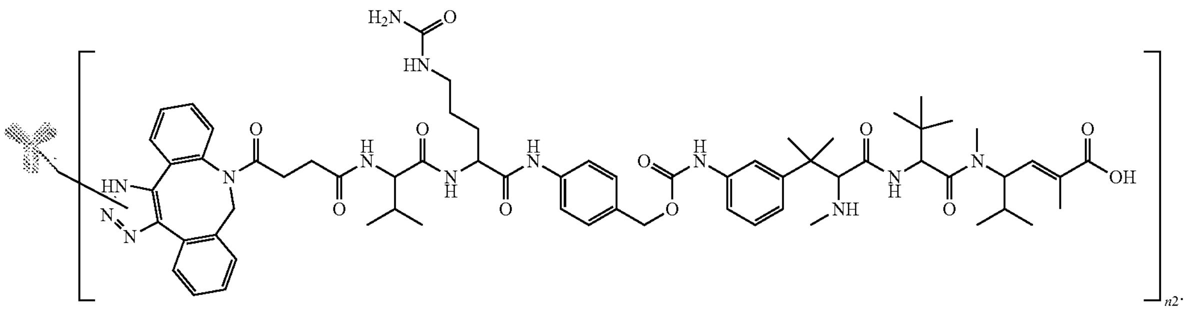

In some embodiments, the antibody of the antibody conjugate comprises the $V_H/V_L$ pair SEQ ID NOs: 2739/3061.

In some embodiments, an antibody conjugate is provided that comprises: (a) an antibody comprising a $V_H$ comprising: a CDR-H1 comprising at least one of SEQ ID NOs: 117 and 442; a CDR-H2 comprising at least one of SEQ ID NOs: 767 and 1092; and a CDR-H3 comprising at least one of SEQ ID NOs: 1417 and 1742; and a $V_L$ comprising: a CDR-L1 comprising SEQ ID NO: 2064; a CDR-L2 comprising SEQ ID NO: 2288; and a CDR-L3 comprising SEQ ID NO: 2512; (b) para-azidomethylphenylalanine residues at antibody sites HC180 and HC404; and (c) a linker-payload, wherein n2 is 4 and each linker-payload is bonded to one of the para-azidomethylphenylalanine residue side chains:

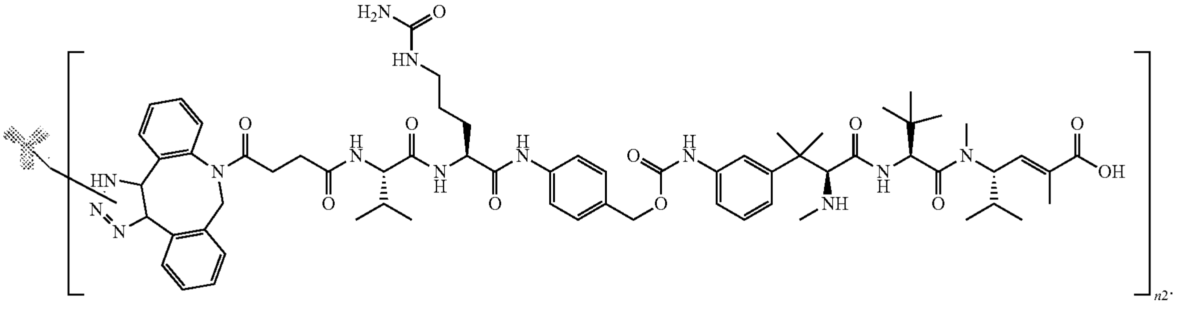
In some embodiments, the antibody of the antibody conjugate comprises the $V_H/V_L$ pair SEQ ID NOs: 2739/3061.
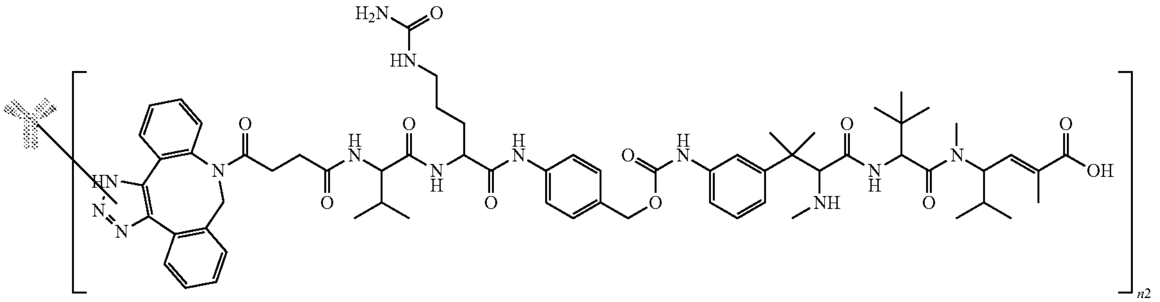
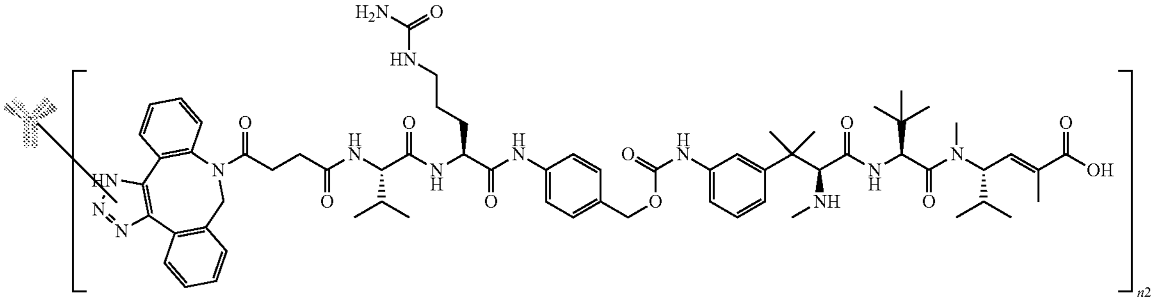
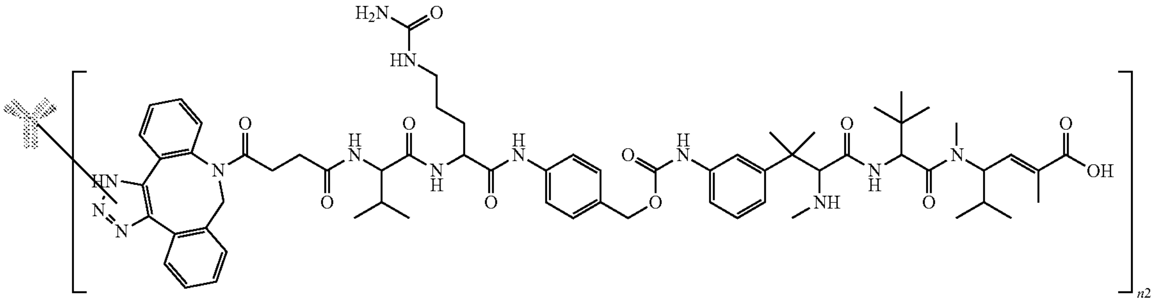
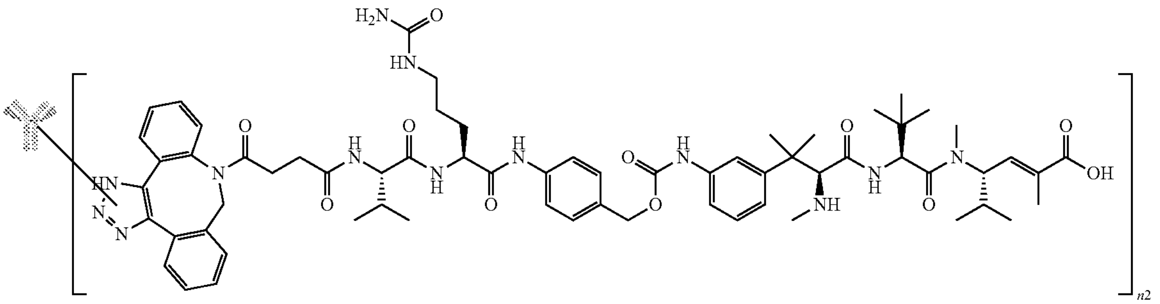

4.

Payloads

In addition to the payloads described above, the molecular payload can be any molecular entity that one of skill in the art might desire to conjugate to the polypeptide. In certain embodiments, the payload is a therapeutic moiety. In such embodiment, the antibody conjugate can be used to target the therapeutic moiety to its molecular target. In certain embodiments, the payload is a labeling moiety. In such embodiments, the antibody conjugate can be used to detect binding of the polypeptide to its target. In certain embodiments, the payload is a cytotoxic moiety. In such embodiments, the antibody conjugate can be used target the cytotoxic moiety to a diseased cell, for example a cancer cell, to initiate destruction or elimination of the cell. Conjugates comprising other molecular payloads apparent to those of skill in the art are within the scope of the conjugates described herein.

In certain embodiments, an antibody conjugate can have a payload selected from the group consisting of a label, a dye, a polymer, a water-soluble polymer, polyethylene glycol, a derivative of polyethylene glycol, a photocrosslinker, a cytotoxic compound, a radionuclide, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a peptide, a water-soluble dendrimer, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, or any combination thereof. In an embodiment, the payload is a label, a dye, a polymer, a cytotoxic compound, a radionuclide, a drug, an affinity label, a resin, a protein, a polypeptide, a polypeptide analog, an antibody, antibody fragment, a metal chelator, a cofactor, a fatty acid, a carbohydrate, a polynucleotide, a DNA, a RNA, a peptide, a fluorophore, or a carbon-linked sugar. In another embodiment, the payload is a label, a dye, a polymer, a drug, an antibody, antibody fragment, a DNA, an RNA, or a peptide.

Useful drug payloads include any cytotoxic or cytostatic agent. Useful classes of cytotoxic agents include, for example, antitubulin agents, auristatins, DNA minor groove binders, DNA replication inhibitors, alkylating agents (e.g., platinum complexes such as cis-platin, mono (platinum), bis (platinum) and tri-nuclear platinum complexes and carboplatin), anthracyclines, antibiotics, antifolates, antimetabolites, calmodulin inhibitors, chemotherapy sensitizers, duocarmycins, etoposides, fluorinated pyrimidines, ionophores, lexitropsins, maytansinoids, nitrosoureas, platinols, pore-forming compounds, purine antimetabolites, puromycins, radiation sensitizers, rapamycins, steroids, taxanes, topoisomerase inhibitors, vinca alkaloids, or the like.

Individual cytotoxic agents include, for example, an androgen, anthramycin (AMC), asparaginase, 5-azacytidine, azathioprine, bleomycin, busulfan, buthionine sulfoximine, calicheamicin, calicheamicin derivatives, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (formerly actinomycin), daunorubicin, decarbazine, DM1, DM4, docetaxel, doxorubicin, etoposide, an estrogen, 5-flurordeoxyuridine, 5-fluorouracil, gemcitabine, gramicidin D, hydroxyurea, idarubicin, ifosfamide, irinotecan, lomustine (CCNU), maytansine, mechlorethamine, melphalan, 6-mercaptopurine, methotrexate, mithramycin, mitomycin C, mitoxantrone, nitroimidazole, paclitaxel, palytoxin, plicamycin, procarbizine, rhizoxin, streptozotocin, tenoposide, 6-thioguanine, thioTEPA, topotecan, vinblastine, vincristine, vinorelbine, VP-16 and VM-26.

In some embodiments, suitable cytotoxic agents include, for example, DNA minor groove binders (e.g., enediynes and lexitropsins, a CBI compound; see also U.S. Pat. No. 6,130,237), duocarmycins, taxanes (e.g., paclitaxel and docetaxel), puromycins, vinca alkaloids, CC-1065, SN-38, topotecan, morpholino-doxorubicin, rhizoxin, cyanomorpholino-doxorubicin, echinomycin, combretastatin, netropsin, epothilone A and B, estramustine, cryptophycins, cemadotin, maytansinoids, discodermolide, eleutherobin, and mitoxantrone.

In some embodiments, the payload is an anti-tubulin agent. Examples of anti-tubulin agents include, but are not limited to, taxanes (e.g., Taxol® (paclitaxel), Taxotere® (docetaxel)), T67 (Tularik) and vinca alkyloids (e.g., vincristine, vinblastine, vindesine, and vinorelbine). Other antitubulin agents include, for example, baccatin derivatives, taxane analogs, epothilones (e.g., epothilone A and B), nocodazole, colchicine and colcimid, estramustine, cryptophycins, cemadotin, maytansinoids, combretastatins, discodermolide, and eleutherobin.

In certain embodiments, the cytotoxic agent is a maytansinoid, another group of anti-tubulin agents. For example, in specific embodiments, the maytansinoid can be maytansine or DM1 (ImmunoGen, Inc.; see also Chari et al., 1992, *Cancer Res.* 52:127-131).

In some embodiments, the payload is an auristatin, such as auristatin E or a derivative thereof. For example, the auristatin E derivative can be an ester formed between auristatin E and a keto acid. For example, auristatin E can be reacted with paraacetyl benzoic acid or benzoylvaleric acid to produce AEB and AEVB, respectively. Other typical auristatin derivatives include AFP (auristatin phenylalanine phenylenediamine), MMAF (monomethyl auristatin F), and MMAE (monomethyl auristatin E). The synthesis and structure of auristatin derivatives are described in U.S. Patent Application Publication Nos. 2003-0083263, 2005-0238649 and 2005-0009751; International Patent Publication No. WO 04/010957, International Patent Publication No. WO 02/088172, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414.

In some embodiments, the payload is a hemiasterlin. Hemiasterlins suitable for use in the antibody-drug conjugates described herein are described, for example, in International Patent Publication No. WO 2016/123582, which is incorporated herein by reference in its entirety.

In some embodiments, the payload is not a radioisotope. In some embodiments, the payload is not radioactive.

In some embodiments, the payload is an antimetabolite. The antimetabolite can be, for example, a purine antagonist (e.g., azothioprine or mycophenolate mofetil), a dihydrofolate reductase inhibitor (e.g., methotrexate), acyclovir, gangcyclovir, zidovudine, vidarabine, ribavarin, azidothymidine, cytidine arabinoside, amantadine, dideoxyuridine, iododeoxyuridine, poscarnet, or trifluridine.

In other embodiments, the payload is tacrolimus, cyclosporine, FU506 or rapamycin. In further embodiments, the Drug is aldesleukin, alemtuzumab, alitretinoin, allopurinol, altretamine, amifostine, anastrozole, arsenic trioxide, bexarotene, bexarotene, calusterone, capecitabine, celecoxib, cladribine, Darbepoetin alfa, Denileukin diftitox, dexrazoxane, dromostanolone propionate, epirubicin, Epoetin alfa, estramustine, exemestane, Filgrastim, floxuridine, fludarabine, fulvestrant, gemcitabine, gemtuzumab ozogamicin (MYLOTARG), goserelin, idarubicin, ifosfamide, imatinib mesylate, Interferon alfa-2a, irinotecan, letrozole, leucovorin, levamisole, meclorethamine or nitrogen mustard, megestrol, mesna, methotrexate, methoxsalen, mitomycin C, mitotane, nandrolone phenpropionate, oprelvekin, oxaliplatin, pamidronate, pegademase, pegaspargase, pegfilgrastim, pentostatin, pipobroman, a pladienolide, plicamycin, porfimer sodium, procarbazine, quinacrine, rasburicase, Rituximab, Sargramostim, streptozocin, tamoxifen, temozolomide, teniposide, testolactone, thioguanine, toremifene, Tositumomab, Trastuzumab (HERCEPTIN), tretinoin, uracil mustard, valrubicin, vinblastine, vincristine, vinorelbine or zoledronate.

Other useful drug payloads include chemical compounds useful in the treatment of cancer. Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB®, GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and: ranimnustine; antibiotics such as the enediyne antibiotics (e.g., calicheamicin, especially uncialamycin, calicheamicin gammall, and calicheamicin omegall (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pladienolide B, pteropterin, trimetrexate; purine analogs such as fludarabine, 6-mercaptopurine, thiamniprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine; and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Other useful payloads include: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4 (5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); (x) agents that act to regulate or inhibit activity of members of the poly(ADP-ribose) polymerase (PARP) family in tumors (e.g., Talazoparib (BMN-673), Iniparib (BSI 201), Veliparib (ABT-888), Olaparib (AZD-2281, trade name LYNPARZA™), Rucaparib (AG 014699), BGB-290, E7016, E7449, and CEP-9722); (xi) agents that act to regulate or inhibit activity of members of the histone deacetylase (HDAC) family in tumors (e.g., abexinostat, entinostat, gavinostat, 4SC-202, ACY-241, AR-42, CG200745, CHR-2845, CHR-3996, CXD101, MPTOE028, OBP-801, SHP-141, CUDC-101, KA2507, panobinostat, pracinostat, quisinostat, resminostat, ricolinostat); (xii) agents that act to regulate or inhibit activity of mitochondrial enzyme isocitrate dehydrogenase type 2 (IDH2) in tumors (e.g., enasidenib mesylate (CC-90007, AG-221 mesylate); and (xiii) pharmaceutically acceptable salts, acids and derivatives of any of the above. Other useful payloads include anti-angiogenic agents, including, e.g., MMP-2 (matrix-metalloproteinase 2) inhibitors, MMP-9 (matrix-metalloproteinase 9) inhibitors, COX-II (cyclooxygenase II) inhibitors, and VEGF receptor tyrosine kinase inhibitors. Examples of such useful matrix metalloproteinase inhibitors that can be used in combination with the present compounds/compositions are described in WO 96/33172, WO 96/27583, EP 818442, EP 1004578, WO 98/07697, WO 98/03516, WO 98/34918, WO 98/34915, WO 98/33768, WO 98/30566, EP 606,046, EP 931,788, WO 90/05719, WO 99/52910, WO 99/52889, WO 99/29667, WO 99/07675, EP 945864, U.S. Pat. Nos. 5,863,949, 5,861,510, and EP 780,386, all of which are incorporated herein in their entireties by reference. Examples of VEGF receptor tyrosine kinase inhibitors include 4-(4-bromo-2-fluoroanilino)-6-methoxy-7-(1-methylpiperidin-4-ylmethoxy) quinazoline (ZD6474; Example 2 within WO 01/32651), 4-(4-fluoro-2-methylindol-5-yloxy)-6-methoxy-7-(3-pyrrolidin-1-ylpropoxy) quinazoline (AZD2171; Example 240 within WO 00/47212), vatalanib (PTK787; WO 98/35985) and SU11248 (sunitinib; WO 01/60814), and compounds such as those disclosed in PCT Publication Nos. WO 97/22596, WO 97/30035, WO 97/32856, and WO 98/13354).

In certain embodiments, the payload is selected from the group consisting of maytansine, hemiasterlin, amanitin, exatecan, deruxtecan (DXd), anthracycline, PNU-159682, pyrrolobenzodiazepine (PBD), MMAF, and MMAE. In certain embodiments, the payload is maytansine. In certain embodiments, the payload is hemiasterlin. In certain embodiments, the payload is amanitin. In certain embodiments, the payload is hemiasterlin. In certain embodiments, the payload is amanitin. In certain embodiments, the payload is hemiasterlin. In certain embodiments, the payload is deruxtecan. In certain embodiments, the payload is hemiasterlin. In certain embodiments, the payload is anthracycline. In certain embodiments, the payload is hemiasterlin. In certain embodiments, the payload is PNU-159682. In certain embodiments, the payload is hemiasterlin. In certain embodiments, the payload is pyrrolobenzodiazepine. In certain embodiments, the payload is MMAF. In certain embodiments, the payload is MMAE.

In certain embodiments, the payload is an antibody or an antibody fragment. In certain embodiments, the payload antibody or fragment can be encoded by any of the immunoglobulin genes recognized by those of skill in the art. The immunoglobulin genes include, but are not limited to, the κ, λ, α, γ (IgG1, IgG2, IgG3, and IgG4), δ, ε and μ constant region genes, as well as the immunoglobulin variable region genes. The term includes full-length antibody and antibody fragments recognized by those of skill in the art, and variants thereof. Exemplary fragments include but are not limited to Fv, Fc, Fab, and $(Fab')_2$, single chain Fv (scFv), diabodies, triabodies, tetrabodies, bifunctional hybrid polypeptides, CDR1, CDR2, CDR3, combinations of CDR's, variable regions, framework regions, constant regions, and the like.

In certain embodiments, the payload is one or more water-soluble polymers. A wide variety of macromolecular polymers and other molecules can be linked to the polypeptides described herein to modulate biological properties of the polypeptide, and/or provide new biological properties to the polypeptide. These macromolecular polymers can be linked to the polypeptide via a naturally encoded amino acid, via a non-naturally encoded amino acid, or any functional substituent of a natural or modified amino acid, or any substituent or functional group added to a natural or modified amino acid. The molecular weight of the polymer may be of a wide range, including but not limited to, between about 100 Da and about 100,000 Da or more.

The polymer selected may be water soluble so that a protein to which it is attached does not precipitate in an aqueous environment, such as a physiological environment. The polymer may be branched or unbranched. Preferably, for therapeutic use of the end-product preparation, the polymer will be pharmaceutically acceptable.

In certain embodiments, the proportion of polyethylene glycol molecules to polypeptide molecules will vary, as will their concentrations in the reaction mixture. In general, the optimum ratio (in terms of efficiency of reaction in that there is minimal excess unreacted protein or polymer) may be determined by the molecular weight of the polyethylene glycol selected and on the number of available reactive groups available. As relates to molecular weight, typically the higher the molecular weight of the polymer, the fewer number of polymer molecules which may be attached to the protein. Similarly, branching of the polymer should be taken into account when optimizing these parameters. Generally, the higher the molecular weight (or the more branches) the higher the polymer:protein ratio.

The water-soluble polymer may be any structural form including but not limited to linear, forked or branched. Typically, the water soluble polymer is a poly(alkylene glycol), such as poly(ethylene glycol) (PEG), but other water soluble polymers can also be employed. By way of example, PEG is used to describe certain embodiments.

PEG is a well-known, water-soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented as linked to a polypeptide by the formula: $XO—(CH_2CH_2O)_n—CH_2CH_2—Y$ where n is 2 to 10,000, X is H or a terminal modification, including but not limited to, a $C_{1-4}$ alkyl, and Y is the attachment point to the polypeptide.

In some cases, a PEG terminates on one end with hydroxy or methoxy, i.e., X is H or $CH_3$ ("methoxy PEG"). Alternatively, the PEG can terminate with a reactive group, thereby forming a bifunctional polymer. Typical reactive groups can include those reactive groups that are commonly used to react with the functional groups found in the 20 common amino acids (including but not limited to, maleimide groups, activated carbonates (including but not limited to, p-nitrophenyl ester), activated esters (including but not limited to, N-hydroxysuccinimide, p-nitrophenyl ester, and aldehydes) as well as functional groups that are inert to the 20 common amino acids but that react specifically with complementary functional groups present in non-naturally encoded amino acids (including but not limited to, azide groups, alkyne groups). It is noted that the other end of the PEG, which is shown in the above formula by Y, will attach either directly or indirectly to a polypeptide via a naturally-occurring or non-naturally encoded amino acid. For instance, Y may be an amide, carbamate, or urea linkage to an amine group (including but not limited to, the epsilon amine of lysine or the N-terminus) of the polypeptide. Alternatively, Y may be a maleimide linkage to a thiol group (including but not limited to, the thiol group of cysteine). Alternatively, Y may be a linkage to a residue not commonly accessible via the 20 common amino acids. For example, an azide group on the PEG can be reacted with an alkyne group on the polypeptide to form a Huisgen [3+2] cycloaddition product. Alternatively, an alkyne group on the PEG can be reacted with an azide group present in a non-naturally encoded amino acid, such as the modified amino acids described herein, to form a similar product. In some embodiments, a strong nucleophile (including but not limited to, hydrazine, hydrazide, hydroxylamine, semicarbazide) can be reacted with an aldehyde or ketone group present in a non-naturally encoded amino acid to form a hydrazone, oxime or semicarbazone, as applicable, which in some cases can be further reduced by treatment with an appropriate reducing agent. Alternatively, the strong nucleophile can be incorporated into the polypeptide via a non-naturally encoded amino acid and used to react preferentially with a ketone or aldehyde group present in the water-soluble polymer.

Any molecular mass for a PEG can be used as practically desired, including but not limited to, from about 100 Daltons (Da) to 100,000 Da or more as desired (including but not limited to, sometimes 0.1-50 kDa or $10^{-40}$ kDa). Branched chain PEGs, including but not limited to, PEG molecules with each chain having a MW ranging from 1-100 kDa (including but not limited to, 1-50 kDa or 5-20 kDa) can also be used. A wide range of PEG molecules are described in, including but not limited to, the Shearwater Polymers, Inc. catalog, and the Nektar Therapeutics catalog, incorporated herein by reference.

Generally, at least one terminus of the PEG molecule is available for reaction with the antibody. For example, PEG derivatives bearing alkyne and azide moieties for reaction with amino acid side chains can be used to attach PEG to non-naturally encoded amino acids as described herein. If the non-naturally encoded amino acid comprises an azide, then the PEG will typically contain either an alkyne moiety to effect formation of the [3+2] cycloaddition product or an activated PEG species (i.e., ester, carbonate) containing a phosphine group to effect formation of the amide linkage. Alternatively, if the non-naturally encoded amino acid comprises an alkyne, then the PEG will typically contain an azide moiety to effect formation of the [3+2] Huisgen cycloaddition product. If the non-naturally encoded amino acid comprises a carbonyl group, the PEG will typically comprise a potent nucleophile (including but not limited to, a hydrazide, hydrazine, hydroxylamine, or semicarbazide functionality) in order to effect formation of corresponding hydrazone, oxime, and semicarbazone linkages, respectively. In other alternatives, a reverse of the orientation of the reactive groups described herein can be used, i.e., an azide moiety in the non-naturally encoded amino acid can be reacted with a PEG derivative containing an alkyne.

In some embodiments, the polypeptide variant with a PEG derivative contains a chemical functionality that is reactive with the chemical functionality present on the side chain of the non-naturally encoded amino acid.

In certain embodiments, the payload is an azide- or acetylene-containing polymer comprising a water-soluble polymer backbone having an average molecular weight from about 800 Da to about 100,000 Da. The polymer backbone of the water-soluble polymer can be poly(ethylene glycol). However, it should be understood that a wide variety of water soluble polymers including but not limited to poly (ethylene) glycol and other related polymers, including poly(dextran) and poly(propylene glycol), are also suitable for use and that the use of the term PEG or poly(ethylene glycol) is intended to encompass and include all such molecules. The term PEG includes, but is not limited to, poly(ethylene glycol) in any of its forms, including bifunctional PEG, multiarmed PEG, derivatized PEG, forked PEG, branched PEG, pendent PEG (i.e. PEG or related polymers having one or more functional groups pendent to the polymer backbone), or PEG with degradable linkages therein.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, glycerol oligomers, pentaerythritol and sorbitol. The central branch moiety can also be derived from several amino acids, such as lysine. The branched poly(ethylene glycol) can be represented in general form as $R(\text{-PEG-OH})_m$ in which R is derived from a core moiety, such as glycerol, glycerol oligomers, or pentaerythritol, and m represents the number of arms. Multi-armed PEG molecules, such as those described in U.S. Pat. Nos. 5,932,462 5,643,575; 5,229,490; 4,289,872; U.S. Pat. Appl. 2003/0143596; WO 96/21469; and WO 93/21259, each of which is incorporated by reference herein in its entirety, can also be used as the polymer backbone.

Branched PEG can also be in the form of a forked PEG represented by $PEG(\text{-YCHZ}_2)_n$, where Y is a linking group and Z is an activated terminal group linked to CH by a chain of atoms of defined length.

Yet another branched form, the pendant PEG, has reactive groups, such as carboxyl, along the PEG backbone rather than at the end of PEG chains.

In addition to these forms of PEG, the polymer can also be prepared with weak or degradable linkages in the backbone. For example, PEG can be prepared with ester linkages in the polymer backbone that are subject to hydrolysis. As shown herein, this hydrolysis results in cleavage of the polymer into fragments of lower molecular weight: $\text{-PEG-CO}_2\text{-PEG-}+H_2O \rightarrow \text{PEG-CO}_2H+\text{HO-PEG-}$It is understood by those skilled in the art that the term poly(ethylene glycol) or PEG represents or includes all the forms known in the art including but not limited to those disclosed herein.

Many other polymers are also suitable for use. In some embodiments, polymer backbones that are water-soluble, with from 2 to about 300 termini, are particularly suitable. Examples of suitable polymers include, but are not limited to, other poly(alkylene glycols), such as poly(propylene glycol) ("PPG"), copolymers thereof (including but not limited to copolymers of ethylene glycol and propylene glycol), terpolymers thereof, mixtures thereof, and the like. Although the molecular weight of each chain of the polymer backbone can vary, it is typically in the range of from about 800 Da to about 100,000 Da, often from about 6,000 Da to about 80,000 Da.

Those of ordinary skill in the art will recognize that the foregoing list for substantially water-soluble backbones is by no means exhaustive and is merely illustrative, and that all polymeric materials having the qualities described herein are contemplated as being suitable for use.

In some embodiments the polymer derivatives are "multi-functional", meaning that the polymer backbone has at least two termini, and possibly as many as about 300 termini, functionalized or activated with a functional group. Multi-functional polymer derivatives include, but are not limited to, linear polymers having two termini, each terminus being bonded to a functional group which may be the same or different.

In certain embodiments, the antibody conjugate can comprise one, two, three, four, five, six, seven, eight, nine, ten or more payloads per antibody. In certain embodiments, the antibody conjugate can comprise one payload per antibody. In certain embodiments, the antibody conjugate can comprise two payloads per antibody. In certain embodiments, the antibody conjugate can comprise four payloads per antibody. In certain embodiments, the antibody conjugate can comprise six payloads per antibody. In certain embodiments, the antibody conjugate can comprise eight payloads per antibody.

5. Linkers

In certain embodiments, the antibodies can be linked to the payloads with one or more linkers capable of reacting with an antibody amino acid and with a payload group. The one or more linkers can be any linkers apparent to those of skill in the art.

The term "linker" is used herein to refer to groups or bonds that normally are formed as the result of a chemical reaction and typically are covalent linkages.

Useful linkers include those described herein. In certain embodiments, the linker is any divalent or multivalent linker known to those of skill in the art. Useful divalent linkers include alkylene, substituted alkylene, heteroalkylene, substituted heteroalkylene, arylene, substituted arylene, heteroarlyene, and substituted heteroarylene. In certain embodiments, the linker is $C_{1-10}$ alkylene or $C_{1-10}$ heteroalkylene. In some embodiments, the $C_{1-10}$heteoalkylene is PEG.

In certain embodiments, the linker is hydrolytically stable. Hydrolytically stable linkages means that the linkages are substantially stable in water and do not react with water at useful pH values, including but not limited to, under physiological conditions for an extended period of time, perhaps even indefinitely. In certain embodiments, the linker is hydrolytically unstable. Hydrolytically unstable or degradable linkages mean that the linkages are degradable in water or in aqueous solutions, including for example, blood. Enzymatically unstable or degradable linkages mean that the linkage can be degraded by one or more enzymes.

As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent.

Other hydrolytically degradable linkages include, but are not limited to, carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. The length of the linker may be predetermined or selected depending upon a desired spatial relationship between the polypeptide and the molecule linked to it. In view of the large number of methods that have been reported for attaching a variety of radiodiagnostic compounds, radiotherapeutic compounds, drugs, toxins, and other agents to polypeptides one skilled in the art will be able to determine a suitable method for attaching a given agent to a polypeptide.

The linker may have a wide range of molecular weight or molecular length. Larger or smaller molecular weight linkers may be used to provide a desired spatial relationship or conformation between the polypeptide and the linked entity. Linkers having longer or shorter molecular length may also be used to provide a desired space or flexibility between the polypeptide and the linked entity. Similarly, a linker having a particular shape or conformation may be utilized to impart a particular shape or conformation to the polypeptide or the linked entity, either before or after the polypeptide reaches its target. The functional groups present on each end of the linker may be selected to modulate the release of a polypeptide or a payload under desired conditions. This optimization of the spatial relationship between the polypeptide and the linked entity may provide new, modulated, or desired properties to the molecule.

In some embodiments, provided herein are water-soluble bifunctional linkers that have a dumbbell structure that includes: a) an azide, an alkyne, a hydrazine, a hydrazide, a hydroxylamine, or a carbonyl-containing moiety on at least a first end of a polymer backbone; and b) at least a second functional group on a second end of the polymer backbone. The second functional group can be the same or different as the first functional group. The second functional group, in some embodiments, is not reactive with the first functional group. In some embodiments, water-soluble compounds that comprise at least one arm of a branched molecular structure are provided. For example, the branched molecular structure can be a dendritic structure.

In some embodiments, the linker is derived from a linker precursor selected from the group consisting of: N-succinimidyl-3-(2-pyridyldithio) propionate (SPDP), N-succinimidyl 4-(2-pyridyldithio) pentanoate (SPP), N-succinimidyl 4-(2-pyridyldithio) butanoate (SPDB), N-succinimidyl-4-(2-pyridyldithio)-2-sulfo-butanoate (sulfo-SPDB), N-succinimidyl iodoacetate (SIA), N-succinimidyl (4-iodoacetyl) aminobenzoate (SIAB), maleimide PEG NHS, N-succinimidyl 4-(maleimidomethyl) cyclohexanecarboxylate (SMCC), N-sulfosuccinimidyl 4-(maleimidomethyl) cyclohexanecarboxylate (sulfo-SMCC) or 2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1). In a specific embodiment, the linker is derived from the linker precursor N-succinimidyl 4-(maleimidomethyl) cyclohexanecarboxylate (SMCC).

In some embodiments, the linker is derived from a linker precursor selected from the group consisting of dipeptides, tripeptides, tetrapeptides, and pentapeptides. In such embodiments, the linker can be cleaved by a protease. Exemplary dipeptides include, but are not limited to, valine-citrulline (vc or val-cit), alanine-phenylalanine (af or ala-phe); phenylalanine-lysine (fk or phe-lys); phenylalanine-homolysine (phe-homolys); and N-methyl-valine-citrulline (Me-val-cit). Exemplary tripeptides include, but are not limited to, glycine-valine-citrulline (gly-val-cit), glycine-glycine-glycine (gly-gly-gly), and glycine-methoxyethoxyethyl) serine-valine (gly-val-citalanine OMESerValAla).

In some embodiments, a linker comprises a self-immolative spacer. In certain embodiments, the self-immolative spacer comprises p-aminobenzyl. In some embodiments, a p-aminobenzyl alcohol is attached to an amino acid unit via an amide bond, and a carbamate, methylcarbamate, or carbonate is made between the benzyl alcohol and the payload (Hamann et al. (2005) Expert Opin. Ther. Patents (2005) 15:1087-1103). In some embodiments, the linker comprises p-aminobenzyloxycarbonyl (PAB). Other examples of self-immolative spacers include, but are not limited to, aromatic compounds that are electronically similar to the PAB group, such as 2-aminoimidazol-5-methanol derivatives (U.S. Pat. No. 7,375,078; Hay et al. (1999) Bioorg. Med. Chem. Lett. 9:2237) and ortho- or para-aminobenzylacetals. In some embodiments, spacers can be used that undergo cyclization upon amide bond hydrolysis, such as substituted and unsubstituted 4-aminobutyric acid amides (Rodrigues et al. (1995) Chemistry Biology 2:223), appropriately substituted bicyclo[2.2.1] and bicyclo[2.2.2] ring systems (Storm et al. (1972) J. Amer. Chem. Soc. 94:5815) and 2-aminophenylpropionic acid amides (Amsberry, et al. (1990) J. Org. Chem. 55:5867). Linkage of a drug to the α-carbon of a glycine residue is another example of a self-immolative spacer that may be useful in conjugates (Kingsbury et al. (1984) J. Med. Chem. 27:1447).

In certain embodiments, linker precursors can be combined to form larger linkers. For instance, in certain embodiments, linkers comprise the dipeptide valine-citrulline and p-aminobenzyloxycarbonyl. These are also referenced as citValCit-PAB linkers.

In certain embodiments, the payloads can be linked to the linkers, referred to herein as a linker-payload, with one or more linker groups capable of reacting with an antibody amino acid group. The one or more linkers can be any linkers apparent to those of skill in the art or those set forth herein.

Additional linkers are disclosed herein, such as, for example, the linker precursors (A)-(L) described below.

6. Germline

In some embodiments, the antibody or antibody of the conjugate that specifically binds Tissue Factor is an antibody comprising a variable region that is encoded by a particular germline gene, or a variant thereof. The illustrative antibodies provided herein comprise variable regions that are encoded by the heavy chain variable region germline genes $V_H1$-18, $V_H3$-33, $V_H2$-5, $V_H2$-70, and $V_H4$-30-4. or variants thereof; and the light chain variable region germline genes Vκ1-5, Vκ3-11, Vκ2-20, Vκ1-33, and Vκ1-16, or variants thereof.

One of skill in the art would recognize that the CDR sequences provided herein may also be useful when combined with variable regions encoded by other variable region germline genes, or variants thereof. In particular, the CDR sequences provided herein may be useful when combined with variable regions encoded by variable region germline genes, or variants thereof, that are structurally similar to the variable region germline genes recited above. For example, in some embodiments, a CDR-H sequence provided herein may be combined with a variable region encoded by a variable region germline gene selected from the $V_H$ 1, $V_H$ 2, $V_H$ 3, or $V_H$ 4 families, or a variant thereof. In some embodiments, a CDR-L sequence provided herein may be combined with a variable region encoded by a variable region germline gene selected from the Vκ1, Vκ2, or Vκ3, or a variant thereof.

7. Affinity

In some embodiments, the affinity of the antibody for tissue factor as indicated by $K_D$, is less than about $10^{-5}$ M, less than about $10^{-6}$ M, less than about $10^{-7}$ M, less than about $10^{-8}$ M, less than about $10^{-9}$ M, less than about $10^{-10}$ M, less than about $10^{-11}$ M, or less than about $10^{-12}$ M. In some embodiments, the affinity of the antibody is between about $10^{-7}$ M and $10^{-11}$ M. In some embodiments, the affinity of the antibody is between about $10^{-7}$ M and $10^{-10}$ M. In some embodiments, the affinity of the antibody is between about $10^{-7}$ M and $10^{-9}$ M. In some embodiments, the affinity of the antibody is between about $10^{-7}$ M and $10^{-8}$ M. In some embodiments, the affinity of the antibody is between about $10^{-8}$ M and $10^{-11}$ M. In some embodiments, the affinity of the antibody is between about $10^{-8}$ M and $10^{-10}$ M. In some embodiments, the affinity of the antibody is between about $10^{-9}$ M and $10^{-11}$ M. In some embodiments, the affinity of the antibody is between about $10^{-10}$ M and $10^{-11}$ M.

In some embodiments, the affinity of the antibody for human tissue factor, as determined by surface plasmon resonance at 25° C., and as indicated by $K_D$, is from about $3.59\times10^{-9}$ M to about $1.91\times10^{-8}$ M. In some embodiments, the affinity of the antibody for human tissue factor is about $3.59\times10^{-9}$ M, about $3.71\times10^{-9}$ M, about $3.73\times10^{-9}$ M, about $4.52\times10^{-9}$ M, about $4.77\times10^{-9}$ M, about $5.42\times10^{-9}$ M, about $6.24\times10^{-9}$ M, about $7.30\times10^{-9}$ M, about $7.78\times10^{-9}$ M, about $7.81\times10^{-9}$ M, about $1.38\times10^{-8}$ M, about $1.74\times10^{-8}$ M, or about $1.91\times10^{-8}$ M.

In some embodiments, the affinity of the antibody for cynomolgus tissue factor, as determined by surface plasmon resonance at 25° C., and as indicated by $K_D$, is from about $2.55\times10^{-10}$ M to about $6.07\times10^{-8}$ M. In some embodiments, the affinity of the antibody for human tissue factor is about $2.55\times10^{-10}$ M, about $1.12\times10^{-9}$ M, about $1.19\times10^{-9}$ M, about $1.84\times10^{-9}$ M, about $2.61\times10^{-9}$ M, about $7.33\times10^{-9}$ M, about $1.56\times10^{-8}$ M, about $1.89\times10^{-8}$ M, about $2.01\times10^{-8}$ M, about $2.42\times10^{-8}$ M, about $2.99\times10^{-8}$ M, about $4.16\times10^{-8}$ M, or about $6.07\times10^{-8}$ M.

In some embodiments the antibody has a $k_a$ of at least about $10^4$ $M^{-1}\times sec^{-1}$. In some embodiments the antibody has a $k_a$ of at least about $10^5$ $M^{-1}\times sec^{-1}$. In some embodiments the antibody has a $k_a$ of at least about $10^6$ $M^{-1}\times sec^{-1}$. In some embodiments the antibody has a ka of between about $10^4$ $M^{-1}\times sec^{-1}$ and about $10^5$ $M^{-1}\times sec^{-1}$. In some embodiments the antibody has a $k_a$ of between about $10^5$ $M^{-1}\times sec^{-1}$ and about $10^6$ $M^{-1}\times sec^{-1}$.

In some embodiments the antibody has a $k_a$ when associating with human tissue factor, as determined by surface plasmon resonance at 25° C., of from about $5.4\times10^4$ $M^{-1}\times sec^{-1}$ to about $5.47\times10^5$ $M^{-1}\times sec^{-1}$. In some embodiments the antibody has a $k_a$ when associating with human tissue factor of about $5.4\times10^4$ $M^{-1}\times sec^{-1}$, about $5.72\times10^4$ $M^{-1}\times sec^{-1}$, about $6.25\times10^4$ $M^{-1}\times sec^{-1}$, about $7.12\times10^4$ $M^{-1}\times sec^{-1}$, about $1.88\times10^5$ $M^{-1}\times sec^{-1}$, about $3.03\times10^5$ $M^{-1}\times sec^{-1}$, about $3.11\times10^5$ $M^{-1}\times sec^{-1}$, about $3.62\times10^5$ $M^{-1}\times sec^{-1}$, about $4.03\times10^5$ $M^{-1}\times sec^{-1}$, about $4.87\times10^5$ M $1\times sec^{-1}$, about $5.4\times10^5$ $M^{-1}\times sec^{-1}$, or about $5.47\times10^5$ $M^{-1}\times sec^{-1}$.

In some embodiments the antibody has a $k_a$ when associating with cynomolgus tissue factor, as determined by surface plasmon resonance at 25° C., of from about $7.24\times10^4$ $M^{-1}\times sec^{-1}$ to about $1.21\times10^6$ $M^{-1}\times sec^{-1}$. In some embodiments the antibody has a $k_a$ when associating with cynomolgus tissue factor of about $7.24\times10^4$ $M^{-1}\times sec^{-1}$, about $8.08\times10^4$ $M^{-1}\times sec^{-1}$ 1, about $8.27\times10^4$ $M^{-1}\times sec^{-1}$, about $1.28\times10^5$ $M^{-1}\times sec^{-1}$, about $1.64\times10^5$ $M^{-1}\times sec^{-1}$, about $2.85\times10^5$ $M^{-1}\times sec^{-1}$, about $3.16\times10^5$ $M^{-1}\times sec^{-1}$, about $4.57\times10^5$ $M^{-1}\times sec^{-1}$, about $7.47\times10^5$ $M^{-1}\times sec^{-1}$, about $7.52\times10^5$ $M^{-1}\times sec^{-1}$, or about $1.21\times10^6$ $M^{-1}\times sec^{-1}$.

In some embodiments the antibody has a $k_d$ of about $10^{-5}$ $sec^{-1}$ or less. In some embodiments the antibody has a $k_d$ of about $10^{-4}$ $sec^{-1}$ or less. In some embodiments the antibody has a $k_d$ of about $10^{-3}$ $sec^{-1}$ or less. In some embodiments the antibody has a $k_d$ of between about $10^{-2}$ $sec^{-1}$ and about $10^{-5}$ $sec^{-1}$. In some embodiments the antibody has a $k_d$ of between about $10^{-2}$ $sec^{-1}$ and about $10^{-4}$ $sec^{-1}$. In some embodiments the antibody has a $k_d$ of between about $10^{-3}$ $sec^{-1}$ and about $10^{-5}$ $sec^{-1}$.

In some embodiments the antibody has a $k_d$ when dissociating from human tissue factor, as determined by surface plasmon resonance at 25° C., of from about $2.75\times10^{-4}$ $sec^{-1}$ to about $2.01\times10^{-2}$ $sec^{-1}$. In some embodiments the antibody has a $k_d$ when dissociating from human tissue factor of about $2.75\times10^{-4}$ $sec^{-1}$, about $2.99\times10^{-4}$ $sec^{-1}$, about $3.03\times10^{-4}$ $sec^{-1}$, about $3.61\times10^{-4}$ $sec^{-1}$, about $4.16\times10^{-4}$ $sec^{-1}$, about $4.18\times10^{-4}$ $sec^{-1}$, about $4.22\times10^{-4}$ $sec^{-1}$, about $4.39\times10^{-4}$ $sec^{-1}$, about $6.99\times10^{-4}$ $sec^{-1}$, about $5.11\times10^{-1}$ $sec^{-1}$, about $5.23\times10^{-4}$ $sec^{-1}$, about $5.28\times10^{-4}$ $sec^{-1}$, about $5.40\times10^{-4}$ $sec^{-1}$, about $6.04\times10^{-4}$ $sec^{-1}$, about $6.74\times10^{-4}$ $sec^{-1}$, about $6.78\times10^{-4}$ $sec^{-1}$, about $6.91\times10^{-4}$ $sec^{-1}$, about $6.95\times10^{-4}$ $sec^{-1}$, about $7.26\times10^{-4}$ $sec^{-1}$, about $7.27\times10^{-4}$ $sec^{-1}$, about $7.36\times10^{-4}$ $sec^{-1}$, about $7.85\times10^{-4}$ $sec^{-1}$, about $8.42\times10^{-4}$ $sec^{-1}$, about $8.65\times10^{-4}$ $sec^{-1}$, about $9.13\times10^{-4}$ $sec^{-1}$, about $9.78\times10^{-4}$ $sec^{-1}$, about $1.15\times10^{-3}$ $sec^{-1}$, about $1.16\times10^{-3}$ $sec^{-1}$, about $1.24\times10^{-3}$ $sec^{-1}$, about $1.29\times10^{-3}$ $sec^{-1}$, about $1.31\times10^{-3}$ $sec^{-1}$, about $1.39\times10^{-3}$ $sec^{-1}$, about $1.41\times10^{-3}$ $sec^{-1}$, about $1.44\times10^{-3}$ $sec^{-1}$, about $1.69\times10^{-3}$ $sec^{-1}$, about $1.82\times10^{-3}$ $sec^{-1}$, about $1.86\times10^{-3}$ $sec^{-1}$, about $1.96\times10^{-3}$ $sec^{-1}$, about $2.04\times10^{-3}$ $sec^{-1}$, about $2.05\times10^{-3}$ $sec^{-1}$, about $2.26\times10^{-3}$ $sec^{-1}$, about $2.27\times10^{-3}$ $sec^{-1}$, about $2.50\times10^{-3}$ $sec^{-1}$, about $2.74\times10^{-3}$ $sec^{-1}$, about $3.04\times10^{-3}$ $sec^{-1}$, about $3.13\times10^{-3}$ $sec^{-1}$, about $3.47\times10^{-3}$ $sec^{-1}$, about $4.15\times10^{-3}$ $sec^{-1}$, about $4.23\times10^{-3}$ $sec^{-1}$, about $4.26\times10^{-3}$ $sec^{-1}$, about $5.94\times10^{-3}$ $sec^{-1}$, about $7.74\times10^{-3}$ $sec^{-1}$, about $8.27\times10^{-3}$ $sec^{-1}$, about $1.22\times10^{-2}$ $sec^{-1}$, or about $2.01\times10^{-2}$ $sec^{-1}$.

In some embodiments, the antibody has a $k_d$ when dissociating from cynomolgus tissue factor, as determined by surface plasmon resonance at 25° C., of from about $3.09\times10^{-4}$ sec-1 to $3.93\times10^2$ $sec^{-1}$. In some embodiments, the antibody has a $k_d$ when dissociating from cynomolgus tissue factor of about $3.09\times10^{-4}$ $sec^{-1}$, about $4.32\times10^{-4}$ $sec^{-1}$, about $4.59\times10^{-4}$ $sec^{-1}$, about $5.14\times10^{-4}$ $sec^{-1}$, about $5.87\times10^{-4}$ $sec^{-1}$, about $6.05\times10^{-4}$ $sec^{-1}$, about $6.31\times10^{-4}$ $sec^{-1}$, about $6.46\times10^{-4}$ $sec^{-1}$, about $6.48\times10^{-4}$ $sec^{-1}$, about $6.65\times10^{-4}$ $sec^{-1}$, about $6.67\times10^{-4}$ $sec^{-1}$, about $6.89\times10^{-4}$ $sec^{-1}$, about $6.96\times10^{-4}$ $sec^{-1}$, about $7.43\times10^{-4}$ $sec^{-1}$, about $7.61\times10^{-4}$ $sec^{-1}$, about $7.82\times10^{-4}$ $sec^{-1}$, about $8.40\times10^{-4}$ $sec^{-1}$, about $8.43\times10^{-4}$ $sec^{-1}$, about $8.61\times10^{-4}$ $sec^{-1}$, about $8.72\times10^{-4}$ $sec^{-1}$, about $9.46\times10^{-4}$ $sec^{-1}$, about $9.91\times10^{-4}$ $sec^{-1}$, about $9.92\times10^{-4}$ $sec^{-1}$, about $1.07\times10^{-3}$ $sec^{-1}$, about $1.13\times10^{-3}$ $sec^{-1}$, about $1.15\times10^{-3}$ $sec^{-1}$, about $1.17\times10^{-3}$ $sec^{-1}$, about $1.18\times10^{-3}$ $sec^{-1}$, about $1.22\times10^{-3}$ $sec^{-1}$, about $1.25\times10^{-3}$ $sec^{-1}$, about $1.27\times10^{-3}$ $sec^{-1}$, about $1.30\times10^{-3}$ $sec^{-1}$, about $1.41\times10^{-3}$ $sec^{-1}$, about $1.42\times10^{-3}$ $sec^{-1}$, about $1.66\times10^{-3}$ $sec^{-1}$, about $1.69\times10^{-3}$ $sec^{-1}$, about $1.70\times10^{-3}$ $sec^{-1}$, about $1.82\times10^{-3}$ $sec^{-1}$, about $1.84\times10^{-3}$ $sec^{-1}$, about $1.87\times10^{-3}$ $sec^{-1}$, about $1.88\times10^{-3}$ $sec^{-1}$, about $1.95\times10^{-3}$ $sec^{-1}$, about $2.00\times10^{-3}$ $sec^{-1}$, about $2.15\times10^{-3}$ $sec^{-1}$, about $2.31\times10^{-3}$ $sec^{-1}$, about $2.41\times10^{-3}$ $sec^{-1}$, about $2.57\times10^{-3}$ $sec^{-1}$, about $3.03\times10^{-3}$ $sec^{-1}$, about $3.09\times10^{-3}$ $sec^{-1}$, about $3.14\times10^{-3}$ $sec^{-1}$, about $3.52\times10^{-3}$ $sec^{-1}$, about $4.20\times10^{-3}$ $sec^{-1}$, about $5.84\times10^{-3}$ $sec^{-1}$, about $5.96\times10^{-3}$ $sec^{-1}$, about $6.81\times10^{-3}$ $sec^{-1}$, about $7.29\times10^{-3}$ $sec^{-1}$, about $7.35\times10^{-3}$ $sec^{-1}$, about $7.82\times10^{-3}$ $sec^{-1}$, about $1.28\times10^{-2}$ $sec^{-1}$, about $1.30\times10^{-2}$ $sec^{-1}$, about $2.88\times10^{-2}$ $sec^{-1}$, about $3.37\times10^{-2}$ $sec^{-1}$, $6.98\times100$ $sec^{-1}$, about $1.43\times10^{-2}$ $sec^{-1}$, about $1.62\times10^{-2}$ $sec^{-1}$, about $2.41\times10^{-2}$ $sec^{-1}$, about $2.63\times10^{-2}$ $sec^{-1}$, about $3.55\times10^2$ $sec^{-1}$, or about $3.93\times10^{-2}$ $sec^{-1}$.

In some embodiments, the antibody conjugate has a $k_a$ when associating with human tissue factor of about $5.08\times10^5$ $M^{-1}\times sec^{-1}$ at a temperature of 25° C.

In some embodiments, the antibody conjugate has a $k_a$ when associating with cynomolgus tissue factor of about $5.82\times10^5$ $M^{-1}\times sec^{-1}$ to about $7.47\times10^5$ $M^{-1}\times sec^{-1}$ at a temperature of 25° C. In some embodiments, the antibody conjugate has a $k_a$ when associating with cynomolgus tissue factor of about $5.82\times10^5$ $M^{-1}\times sec^{-1}$ or about $7.47\times10^5$ $M^{-1}\times sec^{-1}$ at a temperature of 25° C.

In some embodiments, the antibody conjugate has a $k_d$ when dissociating from human tissue factor of about $1.89\times10^{-3}$ $sec^{-1}$ to about $2.09\times10^{-3}$ $sec^{-1}$ when dissociating from human TF at a temperature of 25° C. In some embodiments, the antibody conjugate has a $k_d$ when dissociating from human tissue factor of about $1.89\times10^{-3}$ $sec^{-1}$ or about $2.09\times10^{-3}$ $sec^{-1}$ when dissociating from human TF at a temperature of 25° C.

In some embodiments, the antibody conjugate has a $k_d$ when dissociating from cynomolgus tissue factor of about $8.92\times10^{-4}$ $sec^{-1}$ to about $1.03\times10^{-3}$ $sec^{-1}$ when dissociating from cynomolgus TF at a temperature of 25° C. In some embodiments, the antibody conjugate has a ka when dissociating from cynomolgus tissue factor of about $8.92\times10^{-4}$ $sec^{-1}$ or about $1.03\times10^{-3}$ $sec^{-1}$ when dissociating from cynomolgus TF at a temperature of 25° C.

In some embodiments, the antibody conjugate has an affinity to human tissue factor ($K_D$) of about $3.71\times10^{-9}$ M to about $4.11\times10^{-9}$ M when bound to human TF at a temperature of 25° C. In some embodiments, the antibody conjugate has a affinity to human tissue factor ($K_D$) of about $3.71\times10^{-9}$ M or about $4.11\times10^{-9}$ M when bound to human TF at a temperature of 25° C.

In some embodiments, the antibody conjugate has an affinity to cynomolgus tissue factor ($K_D$) of about $1.12\times10^{-9}$ M to about $1.77\times10^{-9}$ M when bound to human TF at a temperature of 25° C. In some embodiments, the antibody conjugate has an affinity to cynomolgus tissue factor ($K_D$) of about $1.12\times10^{-9}$ M, about $1.19\times10^{-9}$ M, or about $1.77\times10^{-9}$ M when bound to cynomolgus TF at a temperature of 25° C.

In some aspects, the $K_D$, $k_a$, and $k_d$ are determined at 25° C. In some embodiments, the $K_D$, $k_a$, and $k_d$ are determined by surface plasmon resonance. In some embodiments, the $K_D$, $k_a$, and $k_d$ are determined according to the methods described in the Examples provided herein.

8. Epitope Bins

In some embodiments, the antibody binds the same epitope as the scFv antibody provided in SEQ ID NOs: 3073 and 3079. In some embodiments, the antibody binds to a different epitope from the scFv antibody provided in SEQ ID NOs: 3073 and 3079. In some embodiments, the antibody binds the same epitope as an antibody encompassing any of SEQ ID NOs: 2727, 2736, 2739, 2751-2838, 2840, 2846, 2851, 2857, and 2859-2860. In some embodiments, the antibody binds the same epitope as an antibody comprising any of the $V_H$-$V_L$ pairs, above. In some embodiments, the antibody binds to part of the epitope bound by the scFv antibody provided in SEQ ID NOs: 3073 and 3079. In some embodiments, the antibody competes for epitope binding with the scFv antibody provided in SEQ ID NOs: 3073 and 3079. In some embodiments, the antibody does not compete for epitope binding with scFv antibody provided in SEQ ID NOs: 3073 and 3079. In some embodiments, the antibody competes for epitope binding with an antibody encompassing any of SEQ ID NOs: 2727, 2736, 2739, 2751 2838, 2840, 2846, 2851, 2857, and 2859-2860. In some embodiments, the antibody competes for epitope binding with an antibody comprising any of the $V_H$-$V_L$ pairs, above.

9. Glycosylation Variants

In certain embodiments, an antibody may be altered to increase, decrease or eliminate the extent to which it is glycosylated. Glycosylation of polypeptides is typically either "N-linked" or "O-linked."

"N-linked" glycosylation refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site.

"O-linked" glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition or deletion of N-linked glycosylation sites to the antibody may be accomplished by altering the amino acid sequence such that one or more of the above-described tripeptide sequences is created or removed. Addition or deletion of O-linked glycosylation sites may be accomplished by addition, deletion, or substitution of one or more serine or threonine residues in or to (as the case may be) the sequence of an antibody.

10. Fc Variants

In certain embodiments, amino acid modifications may be introduced into the Fc region of an antibody provided herein to generate an Fc region variant. In certain embodiments, the Fc region variant possesses some, but not all, effector functions. Such antibodies may be useful, for example, in applications in which the half-life of the antibody in vivo is important, yet certain effector functions are unnecessary or deleterious. Examples of effector functions include complement-dependent cytotoxicity (CDC) and antibody-directed complement-mediated cytotoxicity (ADCC). Numerous substitutions or substitutions or deletions with altered effector function are known in the art.

In some embodiments, the Fc comprises one or more modifications in at least one of the CH3 sequences. In some embodiments, the Fc comprises one or more modifications in at least one of the CH2 sequences. For example, the Fc can include one or modifications selected from the group consisting of: V262E, V262D, V262K, V262R, V262S, V264S, V303R, and V305R. In some embodiments, an Fc is a single polypeptide. In some embodiments, an Fc is multiple peptides, e.g., two polypeptides. Exemplary modifications in the Fc region are described, for example, in International Patent Application No. PCT/US2017/037545, filed Jun. 14, 2017.

An alteration in in CDC and/or ADCC activity can be confirmed using in vitro and/or in vivo assays. For example, Fc receptor (FcR) binding assays can be conducted to measure FcγR binding. The primary cells for mediating ADCC, NK cells, express FcγRIII only, whereas monocytes express FcγRI, FcγRII and FcγRIII. FcR expression on hematopoietic cells is summarized in Ravetch and Kinet, Ann. Rev. Immunol., 1991, 9:457-492, incorporated by reference in its entirety.

Non-limiting examples of in vitro assays to assess ADCC activity of a molecule of interest are provided in U.S. Pat. Nos. 5,500,362 and 5,821,337; Hellstrom et al., Proc. Natl. Acad. Sci. U.S.A., 1986, 83:7059-7063; Hellstrom et al., Proc. Natl. Acad. Sci. U.S.A., 1985, 82:1499-1502; and Bruggemann et al., J. Exp. Med., 1987, 166:1351-1361; each of which is incorporated by reference in its entirety. Useful effector cells for such assays include peripheral blood mononuclear cells (PBMC) and Natural Killer (NK) cells. Alternatively, or additionally, ADCC activity of the molecule of interest may be assessed in vivo, using an animal model such as that disclosed in Clynes et al. Proc. Natl. Acad. Sci. U.S.A., 1998, 95:652-656, incorporated by reference in its entirety.

C1q binding assays may also be carried out to confirm that the antibody is unable to bind C1q and hence lacks CDC activity. Examples of C1q binding assays include those described in WO 2006/029879 and WO 2005/100402, each of which is incorporated by reference in its entirety.

Complement activation assays include those described, for example, in Gazzano Santoro et al., J. Immunol. Methods, 1996, 202:163-171; Cragg et al., Blood, 2003, 101: 1045-1052; and Cragg and Glennie, Blood, 2004, 103:2738-2743; each of which is incorporated by reference in its entirety.

11. Modified Amino Acids

When the antibody conjugate comprises a modified amino acid, the modified amino acid can be any modified amino acid deemed suitable by the practitioner. In particular embodiments, the modified amino acid comprises a reactive group useful for forming a covalent bond to a linker precursor or to a payload precursor. In certain embodiments, the modified amino acid is a non-natural amino acid. In certain embodiments, the reactive group is selected from the group consisting of amino, carboxy, acetyl, hydrazino, hydrazido, semicarbazido, sulfanyl, azido and alkynyl. Modified amino acids are also described in, for example, WO 2013/185115 and WO 2015/006555, each of which is incorporated herein by reference in its entirety.

In certain embodiments, the amino acid residue is according to any of the following formulas:

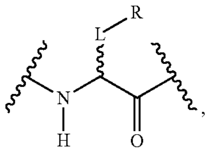,
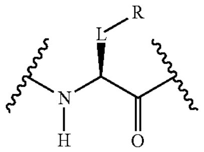
or
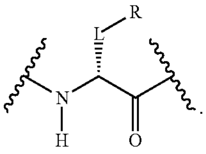.

Those of skill in the art will recognize that antibodies are generally comprised of L-amino acids However, with non-natural amino acids, the present methods and compositions provide the practitioner with the ability to use L-, D- or racemic non-natural amino acids at the site-specific positions. In certain embodiments, the non-natural amino acids described herein include D-versions of the natural amino acids and racemic versions of the natural amino acids.

In the above formulas, the wavy lines indicate bonds that connect to the remainder of the polypeptide chains of the antibodies. These non-natural amino acids can be incorporated into polypeptide chains just as natural amino acids are incorporated into the same polypeptide chains. In certain embodiments, the non-natural amino acids are incorporated into the polypeptide chain via amide bonds as indicated in the formulas.

In the above formulas, R designates any functional group without limitation, so long as the amino acid residue is not identical to a natural amino acid residue. In certain embodiments, R can be a hydrophobic group, a hydrophilic group, a polar group, an acidic group, a basic group, a chelating group, a reactive group, a therapeutic moiety or a labeling moiety. In certain embodiments, R is selected from the group consisting of $R^{1a}NR^{2a}R^{3a}$, $R^{1a}C(=O)R^{2a}$, $R^{1a}C(=O)OR^{2a}$, $R^{1a}N_3$, $R^{1a}C(\equiv CH)$. In these embodiments, $R^{1a}$ is selected from the group consisting of a bond, alkylene, heteroalkylene, arylene, heteroarylene. $R^{2a}$ and $R^{3a}$ are each independently selected from the group consisting of hydrogen, alkyl and heteroalkyl.

In some embodiments, the non-naturally encoded amino acids include side chain functional groups that react efficiently and selectively with functional groups not found in the 20 common amino acids (including but not limited to, azido, ketone, aldehyde and aminooxy groups) to form stable conjugates. For example, antigen-binding polypeptide that includes a non-naturally encoded amino acid containing an azido functional group can be reacted with a polymer (including but not limited to, poly(ethylene glycol) or, alternatively, a second polypeptide containing an alkyne moiety to form a stable conjugate resulting for the selective reaction of the azide and the alkyne functional groups to form a Huisgen [3+2] cycloaddition product.

Exemplary non-naturally encoded amino acids that may be suitable for use in the present invention and that are useful for reactions with water soluble polymers include, but are not limited to, those with carbonyl, aminooxy, hydrazine, hydrazide, semicarbazide, azide and alkyne reactive groups. In some embodiments, non-naturally encoded amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature-including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

Many of the non-naturally encoded amino acids provided herein are commercially available, e.g., from Sigma-Aldrich (St. Louis, Mo., USA), Novabiochem (a division of EMD Biosciences, Darmstadt, Germany), or Peptech (Burlington, Mass., USA). Those that are not commercially available are optionally synthesized as provided herein or using standard methods known to those of skill in the art. For organic synthesis techniques, see, e.g., Organic Chemistry by Fessendon and Fessendon, (1982, Second Edition, Willard Grant Press, Boston Mass.); Advanced Organic Chemistry by March (Third Edition, 1985, Wiley and Sons, New York); and Advanced Organic Chemistry by Carey and Sundberg (Third Edition, Parts A and B, 1990, Plenum Press, New York). See, also, U.S. Patent Application Publications 2003/0082575 and 2003/0108885, which is incorporated by reference herein. In addition to unnatural amino acids that contain unnatural side chains, unnatural amino acids that may be suitable for use in the present invention also optionally comprise modified backbone structures, including but not limited to, as illustrated by the structures of Formula II-1 and III-1:

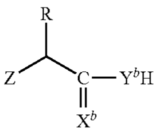
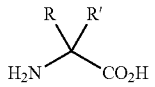

wherein Z typically comprises OH, $NH_2$, SH, NH—R', or S—R'; $X^b$ and $Y^b$, which can be the same or different, typically comprise S or O, and R and R', which are optionally the same or different, are typically selected from the same list of constituents for the R group described herein for the unnatural amino acids having Formula I-I as well as hydrogen. For example, unnatural amino acids of the invention optionally comprise substitutions in the amino or carboxyl group as illustrated by Formulas II-I and III-I. Unnatural amino acids of this type include, but are not limited to, α-hydroxy acids, α-thioacids, α-aminothiocarboxylates, including but not limited to, with side chains corresponding to the common twenty natural amino acids or unnatural side chains. In addition, substitutions at the α-carbon optionally include, but are not limited to, L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring proline analogues, P and y amino acids such as substituted β-alanine and γ-amino butyric acid.

Many unnatural amino acids are based on natural amino acids, such as tyrosine, glutamine, phenylalanine, and the like, and are suitable for use in the present invention. Tyrosine analogs include, but are not limited to, para-substituted tyrosines, ortho-substituted tyrosines, and meta substituted tyrosines, where the substituted tyrosine comprises, including but not limited to, a keto group (including but not limited to, an acetyl group), a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, an alkynyl group or the like. In addition, multiply substituted aryl rings are also contemplated. Glutamine analogs that may be suitable for use in the present invention include, but are not limited to, α-hydroxy derivatives, γ-substituted derivatives, cyclic derivatives, and amide substituted glutamine derivatives. Example phenylalanine analogs that may be suitable for use in the present invention include, but are not limited to, para-substituted phenylalanines, ortho-substituted phenyalanines, and meta-substituted phenylalanines, where the substituent comprises, including but not limited to, a hydroxy group, a methoxy group, a methyl group, an allyl group, an aldehyde, an azido, an iodo, a bromo, a keto group (including but not limited to, an acetyl group), a benzoyl, an alkynyl group, or the like. Specific examples of unnatural amino acids that may be suitable for use in the present invention include, but are not limited to, a p-acetyl-L-phenylalanine, an O-methyl-L-tyrosine, an L-3-(2-naphthyl) alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-azido-methyl-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, and a p-propargyloxy-phenylalanine, and the like. Examples of structures of a variety of unnatural amino acids that may be suitable for use in the present invention are provided in, for example, WO 2002/085923 entitled "In vivo incorporation of unnatural amino acids." See also Kiick et al., (2002) Incorporation of azides into recombinant proteins for chemoselective modification by the Staudinger ligation, PNAS 99:19-24, for additional methionine analogs.

Many of the unnatural amino acids suitable for use in the present invention are commercially available, e.g., from Sigma (USA) or Aldrich (Milwaukee, Wis., USA). Those that are not commercially available are optionally synthesized as provided herein or as provided in various publications or using standard methods known to those of skill in the art. For organic synthesis techniques, see, e.g., Organic Chemistry by Fessendon and Fessendon, (1982, Second Edition, Willard Grant Press, Boston Mass.); Advanced Organic Chemistry by March (Third Edition, 1985, Wiley and Sons, New York); and Advanced Organic Chemistry by Carey and Sundberg (Third Edition, Parts A and B, 1990, Plenum Press, New York). Additional publications describing the synthesis of unnatural amino acids include, e.g., WO 2002/085923 entitled "In vivo incorporation of Unnatural Amino Acids;" Matsoukas et al., (1995) J. Med. Chem., 38, 4660-4669; King, F. E. & Kidd, D. A. A. (1949) A New Synthesis of Glutamine and of γ-Dipeptides of Glutamic Acid from Phthylated Intermediates. J. Chem. Soc., 3315-3319; Friedman, O. M. & Chatterrji, R. (1959) Synthesis of Derivatives of Glutamine as Model Substrates for Anti-Tumor Agents. J. Am. Chem. Soc. 81, 3750-3752; Craig, J. C. et al. (1988) Absolute Configuration of the Enantiomers of 7-Chloro-4 [[4-(diethylamino)-1-methylbutyl]amino]quinoline (Chloroquine). J. Org. Chem. 53, 1167-1170; Azoulay, M., Vilmont, M. & Frappier, F. (1991) Glutamine analogues as Potential Antimalarials, Eur. J. Med. Chem. 26, 201-5; Koskinen, A. M. P. & Rapoport, H. (1989) Synthesis of 4-Substituted Prolines as Conformationally Constrained Amino Acid Analogues. J. Org. Chem. 54, 1859-1866; Christie, B. D. & Rapoport, H. (1985) Synthesis of Optically Pure Pipecolates from L-Asparagine. Application to the Total Synthesis of (+)-Apovincamine through Amino Acid Decarbonylation and Iminium Ion Cyclization. J. Org. Chem. 1989:1859-1866; Barton et al., (1987) Synthesis of Novel a-Amino-Acids and Derivatives Using Radical Chemistry: Synthesis of L- and D-a-Amino-Adipic Acids, L-a-aminopimelic Acid and Appropriate Unsaturated Derivatives. Tetrahedron Lett. 43:4297-4308; and, Subasinghe et al., (1992) Quisqualic acid analogues: synthesis of beta-heterocyclic 2-aminopropanoic acid derivatives and their activity at a novel quisqualate-sensitized site. J. Med. Chem. 35:4602-7. See also, patent applications entitled "Protein Arrays," filed Dec. 22, 2003, Ser. No. 10/744,899 and Ser. No. 60/435,821 filed on Dec. 22, 2002.

Amino acids with a carbonyl reactive group allow for a variety of reactions to link molecules (including but not limited to, PEG or other water soluble molecules) via nucleophilic addition or aldol condensation reactions among others.

Exemplary carbonyl-containing amino acids can be represented as follows:

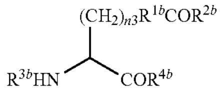

wherein n3 is 0-10; $R^{1b}$ is an alkyl, aryl, substituted alkyl, or substituted aryl; $R^{2b}$ is H, alkyl, aryl, substituted alkyl, and substituted aryl; and $R^{3b}$ is H, an amino acid, a polypeptide, or an amino terminus modification group, and $R^{4b}$ is H, an amino acid, a polypeptide, or a carboxy terminus modification group. In some embodiments, n3 is 1, $R^{1b}$ is phenyl and $R^{2b}$ is a simple alkyl (i.e., methyl, ethyl, or propyl) and the ketone moiety is positioned in the para position relative to the alkyl side chain. In some embodiments, n3 is 1, $R^{1b}$ is phenyl and $R^{2b}$ is a simple alkyl (i.e., methyl, ethyl, or propyl) and the ketone moiety is positioned in the meta position relative to the alkyl side chain.

In some examples, a non-naturally encoded amino acid bearing adjacent hydroxyl and amino groups can be incorporated into the polypeptide as a "masked" aldehyde functionality. For example, 5-hydroxylysine bears a hydroxyl group adjacent to the epsilon amine. Reaction conditions for generating the aldehyde typically involve addition of molar excess of sodium metaperiodate under mild conditions to avoid oxidation at other sites within the polypeptide. The pH of the oxidation reaction is typically about 7.0. A typical reaction involves the addition of about 1.5 molar excess of sodium meta periodate to a buffered solution of the polypeptide, followed by incubation for about 10 minutes in the dark. See, e.g. U.S. Pat. No. 6,423,685, which is incorporated by reference herein.

The carbonyl functionality can be reacted selectively with a hydrazine-, hydrazide-, hydroxylamine-, or semicarbazide-containing reagent under mild conditions in aqueous solution to form the corresponding hydrazone, oxime, or semicarbazone linkages, respectively, that are stable under physiological conditions. See, e.g., Jencks, W. P., J. Am. Chem. Soc. 81, 475-481 (1959); Shao, J. and Tam, J. P., J. Am. Chem. Soc. 117:3893-3899 (1995). Moreover, the unique reactivity of the carbonyl group allows for selective modification in the presence of the other amino acid side chains. See, e.g., Cornish, V. W., et al., J. Am. Chem. Soc.

118:8150-8151 (1996); Geoghegan, K. F. & Stroh, J. G., Bioconjug. Chem. 3:138-146 (1992); Mahal, L. K., et al., Science 276:1125-1128 (1997).

Non-naturally encoded amino acids containing a nucleophilic group, such as a hydrazine, hydrazide or semicarbazide, allow for reaction with a variety of electrophilic groups to form conjugates (including but not limited to, with PEG or other water soluble polymers).

Exemplary hydrazine, hydrazide or semicarbazide-containing amino acids can be represented as follows:

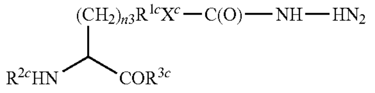

wherein n3 is 0-10; $R^{1c}$ is an alkyl, aryl, substituted alkyl, or substituted aryl or not present; $X^c$, is O, N, or S or not present; $R^{2c}$ is H, an amino acid, a polypeptide, or an amino terminus modification group, and $R^{3c}$ is H, an amino acid, a polypeptide, or a carboxy terminus modification group.

In some embodiments, n3 is 4, $R^{1c}$ is not present, and X is N. In some embodiments, n3 is 2, $R^{1c}$ is not present, and X is not present. In some embodiments, n3 is 1, $R^{1c}$ is phenyl, X is O, and the oxygen atom is positioned para to the aliphatic group on the aryl ring.

Hydrazide-, hydrazine-, and semicarbazide-containing amino acids are available from commercial sources. For instance, L-glutamate-γ-hydrazide is available from Sigma Chemical (St. Louis, Mo.). Other amino acids not available commercially can be prepared by one skilled in the art. See, e.g., U.S. Pat. No. 6,281,211, which is incorporated by reference herein.

Polypeptides containing non-naturally encoded amino acids that bear hydrazide, hydrazine or semicarbazide functionalities can be reacted efficiently and selectively with a variety of molecules that contain aldehydes or other functional groups with similar chemical reactivity. See, e.g., Shao, J. and Tam, J., J. Am. Chem. Soc. 117:3893-3899 (1995). The unique reactivity of hydrazide, hydrazine and semicarbazide functional groups makes them significantly more reactive toward aldehydes, ketones and other electrophilic groups as compared to the nucleophilic groups present on the 20 common amino acids (including but not limited to, the hydroxyl group of serine or threonine or the amino groups of lysine and the N-terminus).

Non-naturally encoded amino acids containing an aminooxy (also called a hydroxylamine) group allow for reaction with a variety of electrophilic groups to form conjugates (including but not limited to, with PEG or other water soluble polymers). Like hydrazines, hydrazides and semicarbazides, the enhanced nucleophilicity of the aminooxy group permits it to react efficiently and selectively with a variety of molecules that contain aldehydes or other functional groups with similar chemical reactivity. See, e.g., Shao, J. and Tam, J., J. Am. Chem. Soc. 117:3893-3899 (1995); H. Hang and C. Bertozzi, Acc. Chem. Res. 34:727-736 (2001). Whereas the result of reaction with a hydrazine group is the corresponding hydrazone, however, an oxime results generally from the reaction of an aminooxy group with a carbonyl-containing group such as a ketone.

Exemplary amino acids containing aminooxy groups can be represented as follows:

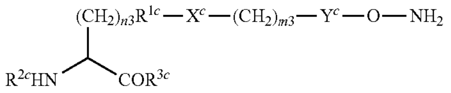

wherein n3 is 0-10; $R^{1c}$ is an alkyl, aryl, substituted alkyl, or substituted aryl or not present; $X^c$ is O, N, S or not present; m3 is 0-10; $Y^c$ is =C(O) or not present; $R^{2c}$ is H, an amino acid, a polypeptide, or an amino terminus modification group, and $R^{3c}$ is H, an amino acid, a polypeptide, or a carboxy terminus modification group. In some embodiments, n3 is 1, $R^{1a}$ is phenyl, $X^c$ is O, m is 1, and $Y^c$ is present. In some embodiments, n3 is 2, $R^{1c}$ and $X^c$ are not present, m3 is 0, and $Y^c$ is not present.

Aminooxy-containing amino acids can be prepared from readily available amino acid precursors (homoserine, serine and threonine). See, e.g., M. Carrasco and R. Brown, J. Org. Chem. 68:8853-8858 (2003). Certain aminooxy-containing amino acids, such as L-2-amino-4-(aminooxy) butyric acid), have been isolated from natural sources (Rosenthal, G. et al., Life Sci. 60:1635-1641 (1997). Other aminooxy-containing amino acids can be prepared by one skilled in the art.

The unique reactivity of azide and alkyne functional groups makes them extremely useful for the selective modification of polypeptides and other biological molecules. Organic azides, particularly aliphatic azides, and alkynes are generally stable toward common reactive chemical conditions. In particular, both the azide and the alkyne functional groups are inert toward the side chains (i.e., R groups) of the 20 common amino acids found in naturally-occurring polypeptides. When brought into close proximity, however, the "spring-loaded" nature of the azide and alkyne groups is revealed and they react selectively and efficiently via Huisgen [3+2] cycloaddition reaction to generate the corresponding triazole. See, e.g., Chin J., et al., Science 301:964-7 (2003); Wang, Q., et al., J. Am. Chem. Soc. 125, 3192-3193 (2003); Chin, J. W., et al., J. Am. Chem. Soc. 124:9026-9027 (2002).

Because the Huisgen cycloaddition reaction involves a selective cycloaddition reaction (see, e.g., Padwa, A., in COMPREHENSIVE ORGANIC SYNTHESIS, Vol. 4, (ed. Trost, B. M., 1991), p. 1069-1109; Huisgen, R. in 1,3-DIPOLAR CYCLOADDITION CHEMISTRY, (ed. Padwa, A., 1984), p. 1-176) rather than a nucleophilic substitution, the incorporation of non-naturally encoded amino acids bearing azide and alkyne-containing side chains permits the resultant polypeptides to be modified selectively at the position of the non-naturally encoded amino acid. Cycloaddition reaction involving azide or alkyne-containing antibody can be carried out at room temperature under aqueous conditions by the addition of Cu (II) (including but not limited to, in the form of a catalytic amount of $CuSO_4$) in the presence of a reducing agent for reducing Cu (II) to Cu (I), in situ, in catalytic amount. See, e.g., Wang, Q., et al., J. Am. Chem. Soc. 125, 3192-3193 (2003); Tornoe, C. W., et al., J. Org. Chem. 67:3057-3064 (2002); Rostovtsev, et al., Angew. Chem. Int. Ed. 41:2596-2599 (2002). Exemplary reducing agents include, including but not limited to, ascorbate, metallic copper, quinine, hydroquinone, vitamin K, glutathione, cysteine, $Fe^{2+}$, $Co^{2+}$, and an applied electric potential.

In some cases, where a Huisgen [3+2] cycloaddition reaction between an azide and an alkyne is desired, the antigen-binding polypeptide comprises a non-naturally encoded amino acid comprising an alkyne moiety and the water soluble polymer to be attached to the amino acid comprises an azide moiety. Alternatively, the converse reaction (i.e., with the azide moiety on the amino acid and the alkyne moiety present on the water soluble polymer) can also be performed.

The azide functional group can also be reacted selectively with a water soluble polymer containing an aryl ester and appropriately functionalized with an aryl phosphine moiety to generate an amide linkage. The aryl phosphine group reduces the azide in situ and the resulting amine then reacts efficiently with a proximal ester linkage to generate the corresponding amide. See, e.g., E. Saxon and C. Bertozzi, Science 287, 2007-2010 (2000). The azide-containing amino acid can be either an alkyl azide (including but not limited to, 2-amino-6-azido-1-hexanoic acid) or an aryl azide (p-azido-phenylalanine).

Exemplary water soluble polymers containing an aryl ester and a phosphine moiety can be represented as follows:

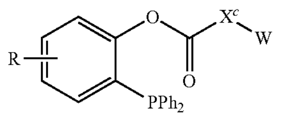

wherein $X^c$ can be O, N, S or not present, Ph is phenyl, W is a water soluble polymer and R can be H, alkyl, aryl, substituted alkyl and substituted aryl groups. Exemplary R groups include but are not limited to —$CH_2$, —$C(CH_3)_3$, —OR', —NR'R", —SR', -halogen, —C(O)R', —CONR'R", —$S(O)_2R'$, —$S(O)_2NR'R"$, —CN and —$NO_2$. R', R", R" and R" each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R" and R" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term “alkyl” is meant to include groups including carbon atoms bound to groups other than hydrogen groups, such as haloalkyl (including but not limited to, —$CF_3$ and —$CH_2CF_3$) and acyl (including but not limited to, —$C(O)CH_3$, —$C(O)CF_3$, —$C(O)CH_2OCH_3$, and the like).

The azide functional group can also be reacted selectively with a water soluble polymer containing a thioester and appropriately functionalized with an aryl phosphine moiety to generate an amide linkage. The aryl phosphine group reduces the azide in situ and the resulting amine then reacts efficiently with the thioester linkage to generate the corresponding amide. Exemplary water soluble polymers containing a thioester and a phosphine moiety can be represented as follows:

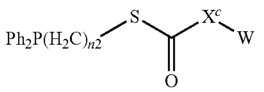

wherein n2 is 1-10; Xc can be O, N, S or not present, Ph is phenyl, and W is a water soluble polymer.

Exemplary alkyne-containing amino acids can be represented as follows:

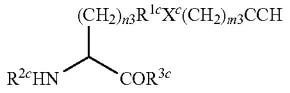

wherein n3 is 0-10; $R^{1c}$ is an alkyl, aryl, substituted alkyl, or substituted aryl or not present; $X^c$ is O, N, S or not present; m3 is 0-10, $R^{2c}$ is H, an amino acid, a polypeptide, or an amino terminus modification group, and $R^{3c}$ is H, an amino acid, a polypeptide, or a carboxy terminus modification group. In some embodiments, n3 is 1, $R^{1c}$ is phenyl, Xc is not present, m3 is 0 and the acetylene moiety is positioned in the para position relative to the alkyl side chain. In some embodiments, n3 is 1, $R^{1c}$ is phenyl, $X^c$ is O, m3 is 1 and the propargyloxy group is positioned in the para position relative to the alkyl side chain (i.e., O-propargyl-tyrosine). In some embodiments, n3 is 1, $R^{1c}$ and $X^c$ are not present and m3 is 0 (i.e., proparylglycine).

Alkyne-containing amino acids are commercially available. For example, propargylglycine is commercially available from Peptech (Burlington, Mass.). Alternatively, alkyne-containing amino acids can be prepared according to standard methods. For instance, p-propargyloxyphenylalanine can be synthesized, for example, as described in Deiters, A., et al., J. Am. Chem. Soc. 125:11782-11783 (2003), and 4-alkynyl-L-phenylalanine can be synthesized as described in Kayser, B., et al., Tetrahedron 53 (7): 2475-2484 (1997). Other alkyne-containing amino acids can be prepared by one skilled in the art.

Exemplary azide-containing amino acids can be represented as follows:

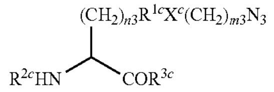

wherein n3 is 0-10; $R^{1c}$ is an alkyl, aryl, substituted alkyl, substituted aryl or not present; $X^c$ is O, N, S or not present; m3 is 0-10; $R^{2c}$ is H, an amino acid, a polypeptide, or an amino terminus modification group, and $R^{3c}$ is H, an amino acid, a polypeptide, or a carboxy terminus modification group. In some embodiments, n3 is 1, $R^{1c}$ is phenyl, $X^c$ is not present, m3 is 0 and the azide moiety is positioned para to the alkyl side chain. In some embodiments, n3 is 0-4 and $R^{1c}$ and $X^c$ are not present, and m3-0. In some embodiments, n3 is 1, $R^{1c}$ is phenyl, $X^c$ is O, m3 is 2 and the P-azidoethoxy moiety is positioned in the para position relative to the alkyl side chain.

Azide-containing amino acids are available from commercial sources. For instance, 4-azidophenylalanine can be obtained from Chem-Impex International, Inc. (Wood Dale, Ill.). For those azide-containing amino acids that are not commercially available, the azide group can be prepared relatively readily using standard methods known to those of skill in the art, including but not limited to, via displacement of a suitable leaving group (including but not limited to, halide, mesylate, tosylate) or via opening of a suitably protected lactone. See, e.g., Advanced Organic Chemistry by March (Third Edition, 1985, Wiley and Sons, New York).

The unique reactivity of beta-substituted aminothiol functional groups makes them extremely useful for the selective modification of polypeptides and other biological molecules that contain aldehyde groups via formation of the thiazolidine. See, e.g., J. Shao and J. Tam, J. Am. Chem. Soc. 1995, 117 (14) 3893-3899. In some embodiments, beta-substituted aminothiol amino acids can be incorporated into antibodies and then reacted with water soluble polymers comprising an aldehyde functionality. In some embodiments, a water soluble polymer, drug conjugate or other payload can be coupled to an antibody polypeptide comprising a beta-substituted aminothiol amino acid via formation of the thiazolidine.

Particular examples of useful non-natural amino acids include, but are not limited to, p-acetyl-L-phenylalanine, O-methyl-L-tyrosine, L-3-(2-naphthyl) alanine, 3-methyl-phenylalanine, O-4-allyl-L-tyrosine, 4-propyl-L-tyrosine, tri-O-acetyl-GlcNAc b-serine, L-Dopa, fluorinated phenylalanine, isopropyl-L-phenylalanine, p-azido-methyl-L-phenylalanine, p-azido-L-phenylalanine, p-acyl-L-phenylalanine, p-benzoyl-L-phenylalanine, L-phosphoserine, phosphonoserine, phosphonotyrosine, p-iodo-phenylalanine, p-bromophenylalanine, p-amino-L-phenylalanine, isopropyl-L-phenylalanine, and p-propargyloxy-phenylalanine. Further useful examples include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine.

In particular embodiments, the non-natural amino acids are selected from p-acetyl-phenylalanine, p-ethynyl-phenylalanine, p-propargyloxyphenylalanine, p-azido-methyl-phenylalanine, and p-azido-phenylalanine. One particularly useful non-natural amino acid is p-azido phenylalanine. This amino acid residue is known to those of skill in the art to facilitate Huisgen [3+2] cycloaddition reactions (so-called "click" chemistry reactions) with, for example, compounds bearing alkynyl groups. This reaction enables one of skill in the art to readily and rapidly conjugate to the antibody at the site-specific location of the non-natural amino acid.

In certain embodiments, the first reactive group is an alkynyl moiety (including but not limited to, in the unnatural amino acid p-propargyloxyphenylalanine, where the propargyl group is also sometimes referred to as an acetylene moiety) and the second reactive group is an azido moiety, and [3+2] cycloaddition chemistry can be used. In certain embodiments, the first reactive group is the azido moiety (including but not limited to, in the unnatural amino acid p-azido-L-phenylalanine) and the second reactive group is the alkynyl moiety.

In the above formulas, each L represents a divalent linker. The divalent linker can be any divalent linker known to those of skill in the art. Generally, the divalent linker is capable of forming covalent bonds to the functional moiety R and the cognate reactive group (e.g., alpha carbon) of the non-natural amino acid. Useful divalent linkers a bond, alkylene, substituted alkylene, heteroalkylene, substituted heteroalkylene, arylene, substituted arylene, heteroarlyene and substituted heteroarylene. In certain embodiments, L is $C_{1-10}$ alkylene or $C_{1-10}$ heteroalkylene.

The non-natural amino acids used in the methods and compositions described herein have at least one of the following four properties: (1) at least one functional group on the sidechain of the non-natural amino acid has at least one characteristics and/or activity and/or reactivity orthogonal to the chemical reactivity of the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine), or at least orthogonal to the chemical reactivity of the naturally occurring amino acids present in the polypeptide that includes the non-natural amino acid; (2) the introduced non-natural amino acids are substantially chemically inert toward the 20 common, genetically-encoded amino acids; (3) the non-natural amino acid can be stably incorporated into a polypeptide, preferably with the stability commensurate with the naturally-occurring amino acids or under typical physiological conditions, and further preferably such incorporation can occur via an in vivo system; and (4) the non-natural amino acid includes an oxime functional group or a functional group that can be transformed into an oxime group by reacting with a reagent, preferably under conditions that do not destroy the biological properties of the polypeptide that includes the non-natural amino acid (unless of course such a destruction of biological properties is the purpose of the modification/transformation), or where the transformation can occur under aqueous conditions at a pH between about 4 and about 8, or where the reactive site on the non-natural amino acid is an electrophilic site. Any number of non-natural amino acids can be introduced into the polypeptide. Non-natural amino acids may also include protected or masked oximes or protected or masked groups that can be transformed into an oxime group after deprotection of the protected group or unmasking of the masked group. Non-natural amino acids may also include protected or masked carbonyl or dicarbonyl groups, which can be transformed into a carbonyl or dicarbonyl group after deprotection of the protected group or unmasking of the masked group and thereby are available to react with hydroxylamines or oximes to form oxime groups.

In further embodiments, non-natural amino acids that may be used in the methods and compositions described herein include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or non-covalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, aldehyde-containing amino acids, amino acids comprising polyethylene glycol or other polyethers, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

In some embodiments, non-natural amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature-including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

The chemical moieties incorporated into antibodies via incorporation of non-natural amino acids offer a variety of advantages and manipulations of polypeptides. For example, the unique reactivity of a carbonyl or dicarbonyl functional group (including a keto- or aldehyde-functional group) allows selective modification of antibodies with any of a number of hydrazine- or hydroxylamine-containing reagents in vivo and in vitro. A heavy atom non-natural amino acid, for example, can be useful for phasing x-ray structure data. The site-specific introduction of heavy atoms using non-natural amino acids also provides selectivity and flexibility in choosing positions for heavy atoms. Photoreactive non-natural amino acids (including but not limited to, amino acids with benzophenone and arylazides (including but not limited to, phenylazide) side chains), for example, allow for efficient in vivo and in vitro photocrosslinking of polypeptides. Examples of photoreactive non-natural amino acids include, but are not limited to, p-azido-phenylalanine and p-benzoyl-phenylalanine. The antibodies with the photoreactive non-natural amino acids may then be crosslinked at will by excitation of the photoreactive group-providing temporal control. In a non-limiting example, the methyl group of a non-natural amino can be substituted with an isotopically labeled, including but not limited to, with a methyl group, as a probe of local structure and dynamics, including but not limited to, with the use of nuclear magnetic resonance and vibrational spectroscopy.

Amino acids with an electrophilic reactive group allow for a variety of reactions to link molecules via various chemical reactions, including, but not limited to, nucleophilic addition reactions. Such electrophilic reactive groups include a carbonyl- or dicarbonyl-group (including a keto- or aldehyde group), a carbonyl-like- or dicarbonyl-like-group (which has reactivity similar to a carbonyl- or dicarbonyl-group and is structurally similar to a carbonyl- or dicarbonyl-group), a masked carbonyl- or masked dicarbonyl-group (which can be readily converted into a carbonyl- or dicarbonyl-group), or a protected carbonyl- or protected dicarbonyl-group (which has reactivity similar to a carbonyl- or dicarbonyl-group upon deprotection). Such amino acids include amino acids having the structure of Formula (I-1):

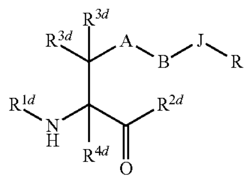

wherein: A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene), —S—, —S-(alkylene or substituted alkylene)-, —$S(O)_k$— where k is 1, 2, or 3, —$S(O)_k$(alkylene or substituted alkylene)-, —C(O)—, —$NS(O)_2$—, —$OS(O)_2$—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —$S(O)_k$N(R')—, —N(R')C(O)N(R')—, —N(R')C(S)N(R')—, —N(R')$S(O)_k$N(R')—, —N(R')—N═, —C(R')═N—, —C(R')═N—N(R')—, —C(R')═N—N═, —$C(R')_2$—N═N—, and —$C(R')_2$—N(R')—N(R')—, where each R' is independently H, alkyl, or substituted alkyl; J is

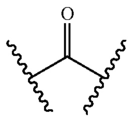,
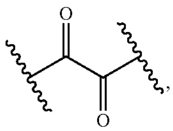,
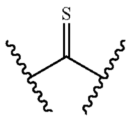,
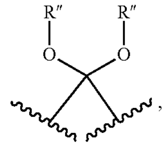,
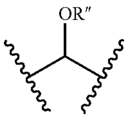,
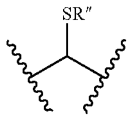,
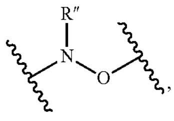, or
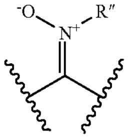;

R is H, alkyl, substituted alkyl, cycloalkyl, or substituted cycloalkyl; each R" is independently H, alkyl, substituted alkyl, or a protecting group, or when more than one R" group is present, two R" optionally form a heterocycloalkyl; $R^{1d}$ is H, an amino protecting group, resin, amino acid, polypeptide, or polynucleotide; and $R^{2d}$ is OH, an ester protecting group, resin, amino acid, polypeptide, or polynucleotide; each of $R^{3d}$ and $R^{4d}$ is independently H, halogen, lower alkyl, or substituted lower alkyl, or $R^{3d}$ and $R^{4d}$ or two $R^{3d}$ groups optionally form a cycloalkyl or a heterocycloalkyl; or the -A-B-J-R groups together form a bicyclic or tricyclic cycloalkyl or heterocycloalkyl comprising at least one carbonyl group, including a dicarbonyl group, protected carbonyl group, including a protected dicarbonyl group, or masked carbonyl group, including a masked dicarbonyl group; or the -J-R group together forms a monocyclic or bicyclic cycloalkyl or heterocycloalkyl comprising at least one carbonyl group, including a dicarbonyl group, protected carbonyl group, including a protected dicarbonyl group, or masked carbonyl group, including a masked dicarbonyl group; with a proviso that when A is phenylene and each $R^{3d}$ is H, B is present; and that when A is —$(CH_2)_4$— and each $R^{3d}$ is H, B is not —$NHC(O)(CH_2CH_2)$—; and that when A and B are absent and each $R^{3d}$ is H, R is not methyl. Such non-natural amino acids may be in the form of a salt, or may be incorporated into a non-natural amino acid polypeptide, polymer, polysaccharide, or a polynucleotide and optionally post translationally modified.

In certain embodiments, compounds of Formula (I-1) are stable in aqueous solution for at least 1 month under mildly acidic conditions. In certain embodiments, compounds of Formula (I-1) are stable for at least 2 weeks under mildly acidic conditions. In certain embodiments, compounds of Formula (I-1) are stable for at least 5 days under mildly acidic conditions. In certain embodiments, such acidic conditions are pH 2 to 8.

In certain embodiments of compounds of Formula (I-1), B is lower alkylene, substituted lower alkylene, —O-(alkylene or substituted alkylene)-, —C(R')=N—N(R')—, —N(R')CO—, —C(O)—, —C(R')=N—, —C(O) (alkylene or substituted alkylene)-, CON(R')-(alkylene or substituted alkylene)-, —S(alkylene or substituted alkylene)-, —S(O) (alkylene or substituted alkylene)-, or —$S(O)_2$ (alkylene or substituted alkylene)-. In certain embodiments of compounds of Formula (I-1), B is —$O(CH_2)$—, —CH=N—, —CH=N—NH—, —$NHCH_2$—, —NHCO—, —C(O)—, C(O)—$(CH_2)$—, —$CONH(CH_2)$—, —$SCH_2$—, —S(=O) $CH_2$, or —$S(O)_2CH_2$—. In certain embodiments of compounds of Formula (I-1), R is $C_{1-6}$ alkyl or cycloalkyl. In certain embodiments of compounds of Formula (I-1) R is —$CH_3$, —$CH(CH_3)_2$, or cyclopropyl. In certain embodiments of compounds of Formula (I-1), $R^{1d}$ is H, tert-butyloxycarbonyl (Boc), 9-Fluorenylmethoxycarbonyl (Fmoc), N-acetyl, tetrafluoroacetyl (TFA), or benzyloxycarbonyl (Cbz). In certain embodiments of compounds of Formula (I-1), $R^{1d}$ is a resin, amino acid, polypeptide, or polynucleotide. In certain embodiments of compounds of Formula (I-1), $R^{2d}$ is OH, O-methyl, O-ethyl, or O-t-butyl. In certain embodiments of compounds of Formula (I-1), $R^{2d}$ is a resin, amino acid, polypeptide, or polynucleotide. In certain embodiments of compounds of Formula (I-1), $R^{2d}$ is a polynucleotide. In certain embodiments of compounds of Formula (I-1), $R^{2d}$ is ribonucleic acid (RNA). In certain embodiments of compounds of Formula (I-1), $R^{2d}$ is tRNA. In certain embodiments of compounds of Formula (I-1), the tRNA specifically recognizes a selector codon. In certain embodiments of compounds of Formula (I-1) the selector codon is selected from the group consisting of an amber codon, ochre codon, opal codon, a unique codon, a rare codon, an unnatural codon, a five-base codon, and a four-base codon. In certain embodiments of compounds of Formula (I-1), $R^{2d}$ is a suppressor tRNA.

In certain embodiments of compounds of Formula (1-2),

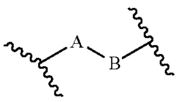

is selected from the group consisting of: (i) A is substituted lower alkylene, $C_4$-arylene, substituted arylene, heteroarylene, substituted heteroarylene, alkarylene, substituted alkarylene, aralkylene, or substituted aralkylene; B is optional, and when present is a divalent linker selected from the group consisting of lower alkylene, substituted lower alkylene, lower alkenylene, substituted lower alkenylene, —O—, —O-(alkylene or substituted alkylene)-, —S—, —S(O)—, —$S(O)_2$—, —$NS(O)_2$—, —$OS(O)_2$—, —C(O)—, —C(O)-(alkylene or substituted alkylene)-, —C(S)—, —N(R')—, —C(O)N(R')—, —CON(R')-(alkylene or substituted alkylene)-, —CSN(R')—, —N(R')CO-(alkylene or substituted alkylene)-, —N(R')C(O)O—, —N(R')C(S)—, —S(O)N(R'), —$S(O)_2$N(R'), —N(R')C(O)N(R')—, —N(R')C(S)N(R')—, —N(R')S(O)N(R')—, —N(R')$S(O)_2$N(R')—, —N(R')—N=, —C(R')=N—N(R')—, —C(R')=N—N=, —$C(R')_2$—N=N—, and —$C(R')_2$—N(R')—N(R')—; (ii) A is optional, and when present is substituted lower alkylene, C4-arylene, substituted arylene, heteroarylene, substituted heteroarylene, alkarylene, substituted alkarylene, aralkylene, or substituted aralkylene; B is a divalent linker selected from the group consisting of lower alkylene, substituted lower alkylene, lower alkenylene, substituted lower alkenylene, —O—, —O-(alkylene or substituted alkylene)-, —S—, —S(O)—, —$S(O)_2$—, —$NS(O)_2$—, —$OS(O)_2$—, —C(O)—, —C(O) (alkylene or substituted alkylene)-, —C(S)—, —N(R')—, —C(O)N(R')—, —CON(R')-(alkylene or substituted alkylene)-, —CSN(R')—, —N(R')CO-(alkylene or substituted alkylene)-, —N(R')C(O)O—, —N(R')C(S)—, —S(O)N(R'), —$S(O)_2$N(R'), —N(R')C(O)N(R')—, —N(R')C(S)N(R')—, —N(R')S(O)N(R')—, —N(R')$S(O)_2$N(R')—, —N(R')—N=, —C(R')=N—N(R')—, —C(R')=N—N=, —$C(R')_2$—N=N—, and —$C(R')_2$—N(R')—N(R')—; (iii) A is lower alkylene; B is optional, and when present is a divalent linker selected from the group consisting of lower alkylene, substituted lower alkylene, lower alkenylene, substituted lower alkenylene, —O—, —O-(alkylene or substituted alkylene)-, —S—, —S(O)—, —$S(O)_2$—, —$NS(O)_2$—, —$OS(O)_2$—, —C(O)—, —C(O) (alkylene or substituted alkylene)-, —C(S)—, —N(R')—, C(O)N(R')—, —CSN(R')—, —CON(R') (alkylene or substituted alkylene)-, —N(R')C(O)O—, —N(R')C(S)—, —S(O)N(R'), —$S(O)_2$N(R'), —N(R')C(O)N(R')—, —N(R')C(S)N(R')—, —N(R')S(O)N(R')—, —N(R')$S(O)_2$N(R')—, —N(R')—N=, —C(R')—N—N(R')—, —C(R')=N—N=, $C(R')_2$—N=N—, and —$C(R')_2$—N(R')—N(R')—; and (iv) A is phenylene; B is a divalent linker selected from the group consisting of lower alkylene, substituted lower alkylene, lower alkenylene, substituted lower alkenylene, —O—, —O-(alkylene or substituted alkylene)-, —S—, —S(O)—, —$S(O)_2$—, —$NS(O)_2$—, —$OS(O)_2$—, —C(O)—, —C(O)-(alkylene or substituted alkylene)-, —C(S)—, —N(R')—, —C(O)N(R')—, —CON(R')-(alkylene or substituted alkylene)-, —CSN(R')—, —N(R')CO-(alkylene or substituted alkylene)-, —N(R')C(O)O—, —N(R')C(S)—, —S(O)N(R'), —$S(O)_2$N(R'), —N(R')C(O)N(R')—, —N(R')C(S)N(R')—, —N(R')S(O)N(R')—, —N(R')$S(O)_2$N(R')—, —N(R')—N=, —C(R')'N—N(R')—, —C(R')=N—N=, —$C(R')_2$—N=N—, and —$C(R')_2$—N(R')—N(R')—; J is

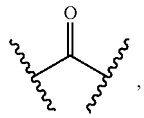 , 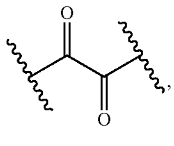 , 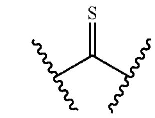 ,

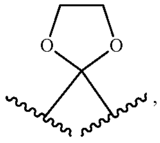 , 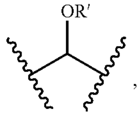 , 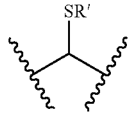 ,

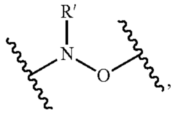 , or 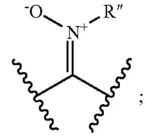 ;

each R' is independently H, alkyl, or substituted alkyl; $R^{1d}$ is optional, and when present, is H, an amino protecting group, resin, amino acid, polypeptide, or polynucleotide; and $R^{2d}$ is optional, and when present, is OH, an ester protecting group, resin, amino acid, polypeptide, or polynucleotide; and each $R^{3d}$ and $R^{4d}$ is independently H, halogen, lower alkyl, or substituted lower alkyl; and R is H, alkyl, substituted alkyl, cycloalkyl, or substituted cycloalkyl.

In certain embodiments, the non-natural amino acid can be according to formula XIX:

Formula XIX

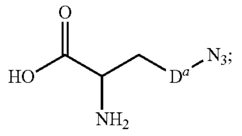

or a salt thereof, wherein: $D^a$ is —Ar—$W^{3a}$— or —$W^{1a}$—$Y^{1a}$—C(O)—$Y^{2a}$—$W^{2a}$—; Ar is

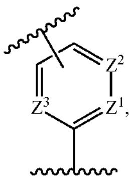
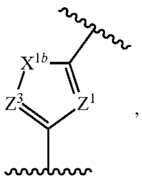
,
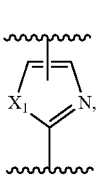
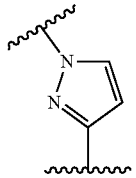
,
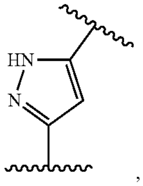
,
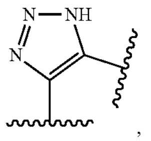
, or
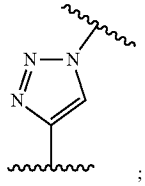
;

each of $W^{1a}$, $W^{2a}$, and $W^{3a}$ is independently a single bond or lower alkylene; each $X^{1b}$ is independently —NH—, —O—, or —S—; each $Y^{1a}$ is independently a single bond, —NH—, or —O—; each $Y^{2a}$ is independently a single bond, —NH—, —O—, or an N-linked or C-linked pyrrolidinylene; and one of $Z^1$, $Z^2$, and $Z^3$ is —N- and the others of $Z^1$, $Z^2$, and $Z^3$ are independently —CH—. In certain embodiments, the non-natural amino acid is according to formula XIXa:

Formula XIXa

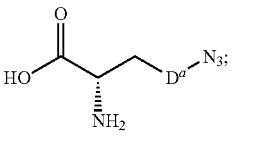

where $D^a$ is a defined in the context of formula XIX. In certain embodiments, the non-natural amino acid is according formula XIXb:

Formula XIXb

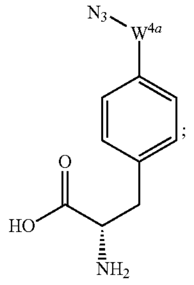

or a salt thereof, wherein $W^{4a}$ is $C_1$-$C_{10}$ alkylene. In a further embodiment, $W^{4a}$ is $C_1$-$C_5$ alkylene. In an embodiment, $W^{4a}$ is $C_1$-$C_3$ alkylene. In an embodiment, $W^{4a}$ is $C_1$ alkylene. In particular embodiments, the non-natural amino acid is selected from the group consisting of:

(1)

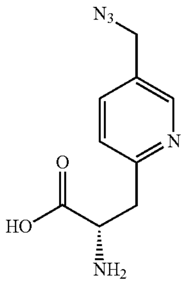

(2)

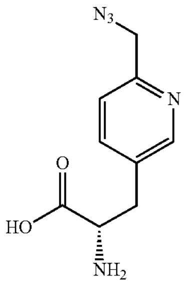

(3)

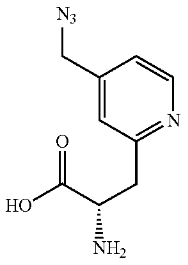

(4)

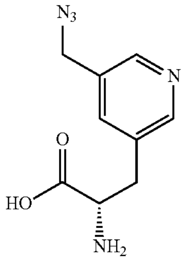

-continued
(5)
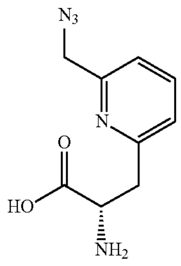
(6)
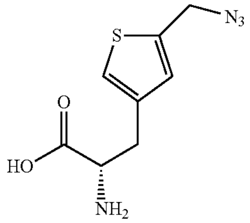
(7)
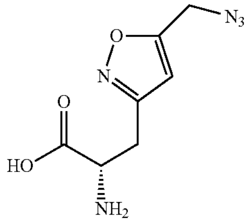
(8)
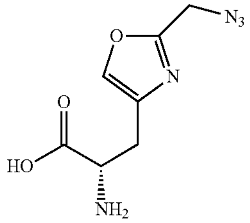
(9)
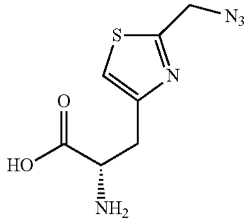
(10)
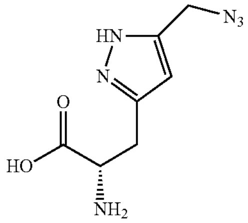
-continued
(11)
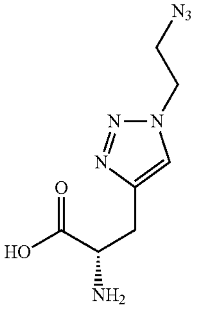
(12)
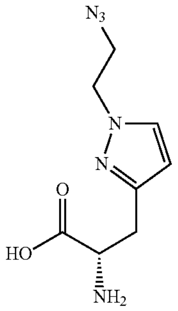
(13)
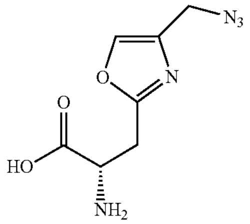
(14)
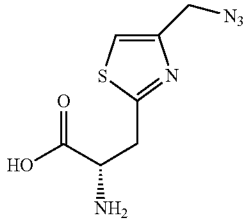
(15)
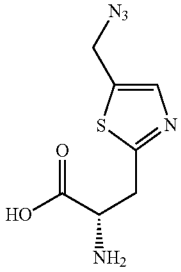

-continued
(16)
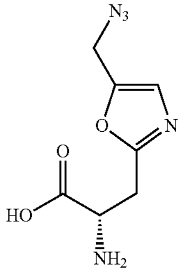
(17)
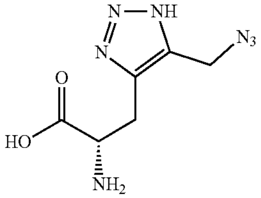
(18)
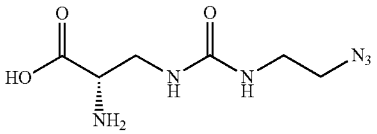
(19)
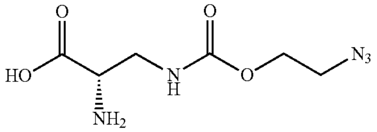
(20)
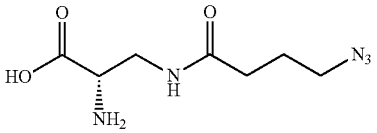
(21)
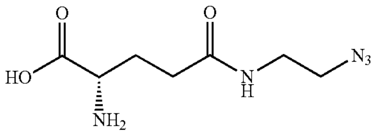
(22)
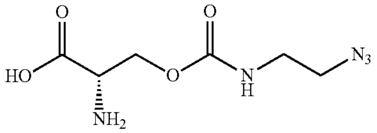
(23)
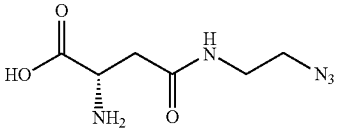
(24)
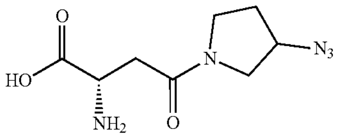
-continued
(25)
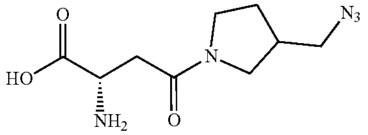
(26)
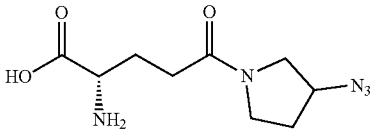
(27)
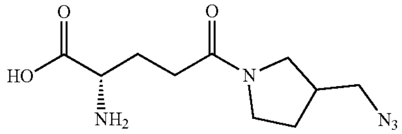
(28)
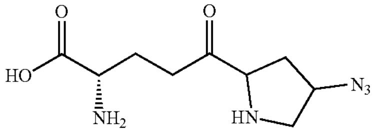
(29)
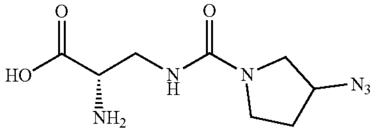
(30)
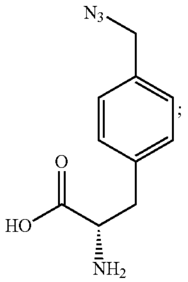
; and
(40)
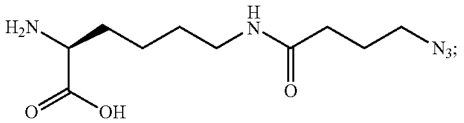
or a salt thereof. Such non-natural amino acids may be in the form of a salt, or may be incorporated into a non-natural amino acid polypeptide, polymer, polysaccharide, or a polynucleotide and optionally post translationally modified.
In certain embodiments, the modified amino acid is according to formula I:
Formula I
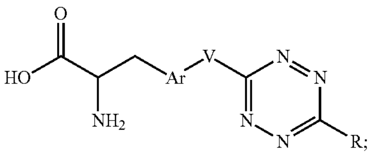

or a salt thereof, wherein Ar is:

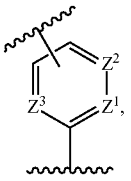, 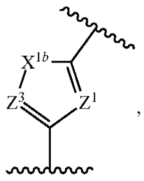, 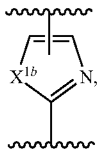

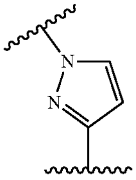, 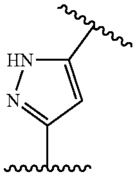, or 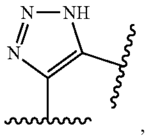,

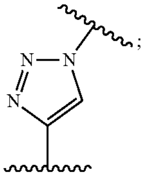

V is a single bond, lower alkylene, or —$W^{1a}$-$W^{2a}$-; one of $W^{1a}$ and $W^{2a}$ is absent or lower alkylene, and the other is —NH—, —O—, or —S—; each $X^1$b is independently-NH—, —O—, or —S—; one of $Z^1$, $Z^2$, and $Z^3$ is —CH— or —N— and the others of $Z^1$, $Z^2$, and $Z^3$ are each independently —CH—; and R is lower alkyl. In certain embodiments, when Ar is

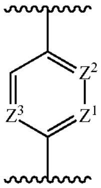

and V is —NH—, then one of $Z^1$, $Z^2$, and $Z^3$ is —N—. In certain embodiments, V is a single bond, —NH—, or —$CH_2$NH—.

In certain embodiments, Ar is

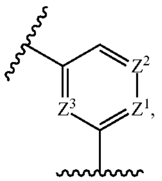 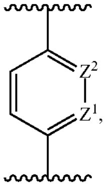 or 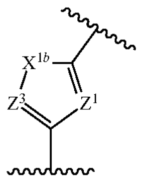

and $Z^1$, $Z^2$, $Z^3$ and $X^{1b}$ are as defined in the context of formula I. In certain embodiments according to this paragraph, V is —$W^{1a}$-$W^{2a}$-; one of $W^{1a}$ and $W^{2a}$ is absent or —$CH_2$—, and the other is —NH—, —O—, or —S—. In certain embodiments according to this paragraph, V is a single bond, —NH—, or —$CH_2$NH—. In certain embodiments according to this paragraph, $Z^1$ is N. In certain embodiments according to this paragraph, $Z^2$ is N. In certain embodiments according to this paragraph, $Z^3$ is N. In certain embodiments according to this paragraph, $Z^1$ is CH, $Z^3$ is CH and $X^{1b}$ is S.

In certain embodiments, Ar is

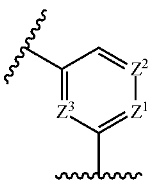 or 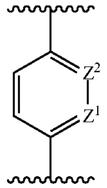

and $Z^1$, $Z^2$, and $Z^3$ are as defined in the context of formula I. In certain embodiments according to this paragraph, V is —$W^{1a}$-$W^{2a}$—; one of $W^{1a}$ and $W^{2a}$ is absent or —$CH_2$—, and the other is —NH—, —O—, or —S—. In certain embodiments according to this paragraph, V is a single bond, —NH—, or —$CH_2$NH—. In certain embodiments according to this paragraph, $Z^1$ is N. In certain embodiments according to this paragraph, $Z^2$ is N. In certain embodiments according to this paragraph, $Z^3$ is N.

In certain embodiments, Ar is

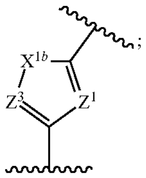

and $Z^1$, $Z^3$ and $X^1$ are as defined in the context of Formula I-1. In certain embodiments according to this paragraph, V is —$W^{1a}$-$W^{2a}$-; one of $W^{1a}$ and $W^{2a}$ is absent or —$CH_2$—, and the other is —NH—, —O—, or —S—. In certain embodiments according to this paragraph, V is a single bond, —NH—, or —$CH_2$NH—. In certain embodiments according to this paragraph, $Z^1$ is N. In certain embodiments according to this paragraph, $Z^3$ is N. In certain embodiments according to this paragraph, $Z^1$ is CH, $Z^3$ is CH and $X^{1b}$ is S.

In certain embodiments, the modified amino acid is according to Formula Ia:

Formula I-1a

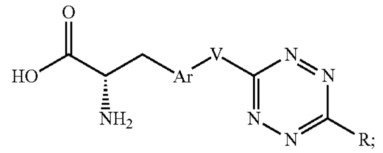

where Ar, V, and R are defined in the context of Formula I-1.

In an embodiment, compounds of either of Formulas I-1 and I-1a are provided wherein V is a single bond. In another embodiment, compounds of either of Formulas I-1 and I-la are provided wherein V is —NH—. In another embodiment, compounds of either of Formulas I-1 and I-1a are provided wherein V is —$CH_2$NH—.

In certain embodiments, the modified amino acid is according to Formula II-1:

Formula II-1

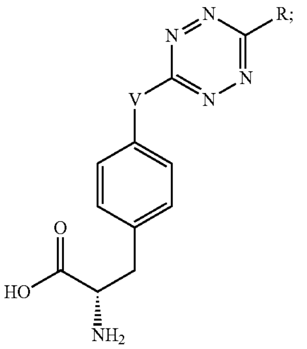

or a salt thereof, wherein V and R are as defined in Formula I-1. In certain embodiments according to this paragraph, V is —$W^{1a}$-$W^{2a}$-; one of $W^{1a}$ and $W^{2a}$ is absent or —$CH_2$—, and the other is —NH—, —O—, or —S—. In certain embodiments, V is a single bond, —NH—, or —$CH_2NH$—. In certain embodiments, V is a single bond or —$CH_2NH$—; and R is methyl.

In certain embodiments, the modified amino acid is according to Formula III-1:

Formula III-1

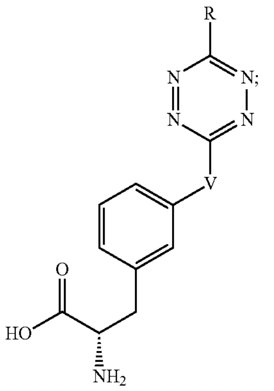

or a salt thereof, wherein V and R are as defined in Formula I-1. In certain embodiments according to this paragraph, V is —$W^{1a}$-$W^{2a}$-; one of $W^{1a}$ and $W^{2a}$ is absent or —$CH_2$—, and the other is —NH—, —O—, or —S—. In certain embodiments, V is a single bond, —NH—, or —$CH_2NH$—. In certain embodiments, V is a single bond, —NH—, or —$CH_2NH$—; and R is methyl.

In certain embodiments, the modified amino acid is according to Formula IV-1:

Formula IV-1

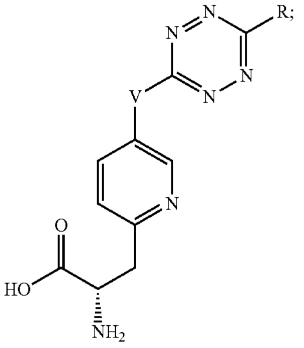

or a salt thereof, wherein V and R are as defined in Formula I-1. In certain embodiments according to this paragraph, V is —$W^{1a}$-$W^{2a}$-; one of $W^{1a}$ and $W^2$a is absent or —$CH_2$—, and the other is —NH—, —O—, or —S—. In certain embodiments, V is a single bond, —NH—, or —$CH_2NH$—. In certain embodiments, V is a single bond, —NH—, or —$CH_2NH$—; and R is methyl.

In certain embodiments, the modified amino acid is according to Formula V-1:

Formula V-1

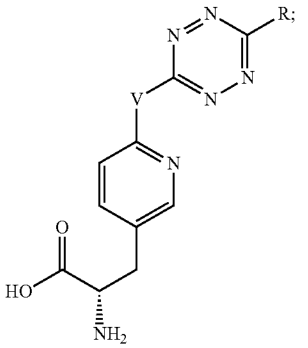

or a salt thereof, wherein V and R are as defined in Formula I. In certain embodiments according to this paragraph, V is —$W^{1a}$-$W^{2a}$-; one of $W^{1a}$ and $W^2$a is absent or —$CH_2$—, and the other is —NH—, —O—, or —S—. In certain embodiments, V is a single bond, —NH—, or —$CH_2NH$—. In certain embodiments, V is a single bond, —NH—, or —$CH_2NH$—; and R is methyl.

In certain embodiments, the modified amino acid is according to Formula VI-1:

Formula VI-1

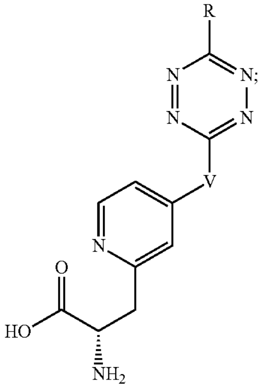

or a salt thereof, wherein V and R are as defined in Formula I. In certain embodiments according to this paragraph, V is —$W^{1a}$-$W^{2a}$—; one of $W^{1a}$ and $W^{2a}$ is absent or —$CH_2$—, and the other is —NH—, —O—, or —S—. In certain embodiments, V is a single bond, —NH—, or —$CH_2$NH—. In certain embodiments, V is a single bond, —NH—, or —$CH_2$NH—; and R is methyl.

In certain embodiments, the modified amino acid is according to Formula VII-1:

Formula VII

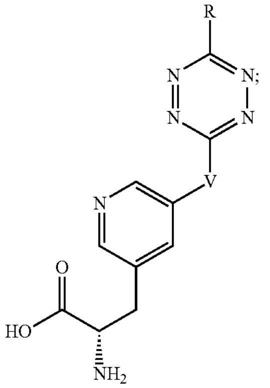

or a salt thereof, wherein V and R are as defined in Formula I. In certain embodiments according to this paragraph, V is —$W^{1a}$-$W^{2a}$-; one of $W^{1a}$ and $W^{2a}$ is absent or —$CH_2$—, and the other is —NH—, —O—, or —S—. In certain embodiments, V is a single bond, —NH—, or —$CH_2$NH—. In certain embodiments, V is a single bond, —NH—, or —$CH_2$NH—; and R is methyl.

In certain embodiments, the modified amino acid is according to Formula VIII-1:

Formula VIII-1

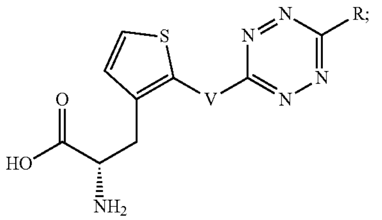

Or a salt thereof, wherein V and R are as defined in Formula I. In certain embodiments according to this paragraph, V is —$W^{1a}$-$W^{2a}$-; one of $W^{1a}$ and $W^{2a}$ is absent or —$CH_2$—, and the other is —NH—, —O—, or —S—. In certain embodiments, V is a single bond, —NH—, or —$CH_2$NH—. In certain embodiments, V is a single bond, —NH—, or —$CH_2$NH—; and R is methyl.

In certain embodiments, the modified amino acid is according to Formula IX-1:

Formula IX-1

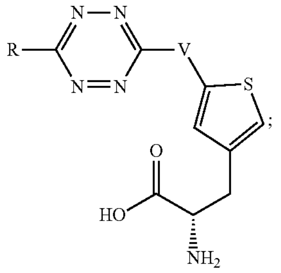

or a salt thereof, wherein V and R are as defined in Formula I-1. In certain embodiments according to this paragraph, V is —$W^{1a}$-$W^{2a}$-; one of $W^{1a}$ and $W^{2a}$ is absent or —$CH_2$—, and the other is —NH—, —O—, or —S—. In certain embodiments, V is a single bond, —NH—, or —$CH_2$NH—. In certain embodiments, V is a single bond, —NH—, or —$CH_2$NH—; and R is methyl.

In certain embodiments, the modified amino acid is according to any of formulas 51-62:

(51)

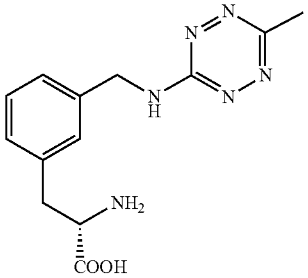

(52)

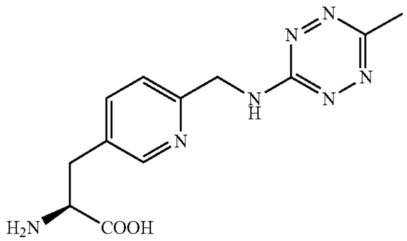

-continued (53)

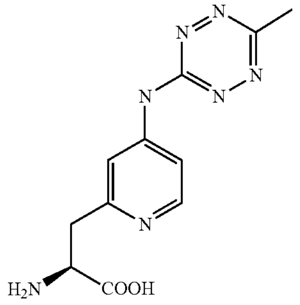

(54)

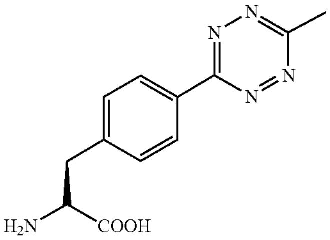

(55)

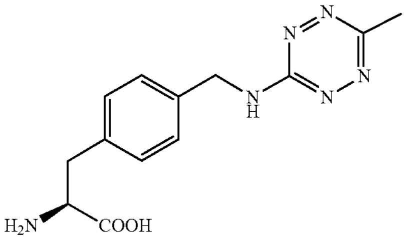

(56)

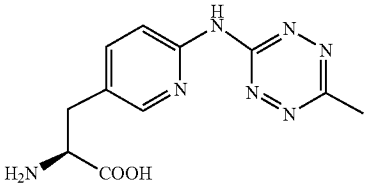

(57)

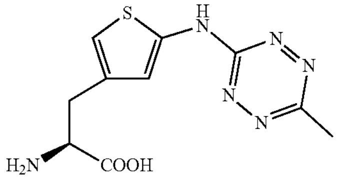

(58)

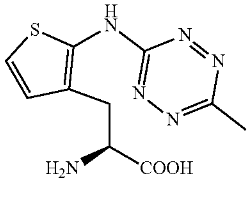

(59)

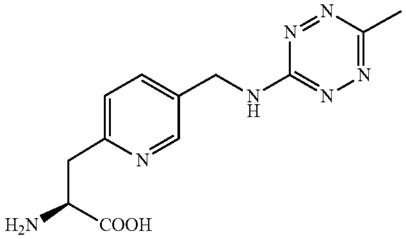

-continued (60)

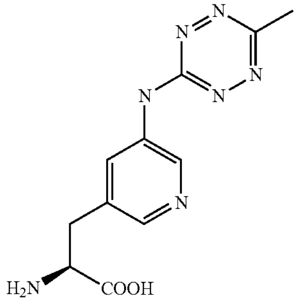

(61)

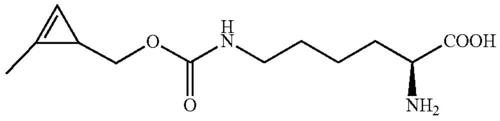

(62)

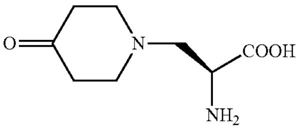

or a salt thereof.

In certain embodiments, the non-natural amino acid is selected from the group consisting of compounds 30, 53, 56, 59, 60, 61, and 62 above. In certain embodiments, the non-natural amino acid is compound 30. In certain embodiments, the non-natural amino acid is compound 56. In some embodiments, the non-natural amino acid is compound 61. In some embodiments, the non-natural amino acid is compound 62.

12. Preparation of Antibodies and Antibody Conjugates 12.1. Antigen Preparation

The tissue factor antigen to be used for isolation of the antibodies may be intact tissue factor or a fragment of tissue factor. The intact tissue factor, or fragment of tissue factor, may be in the form of an isolated protein or protein expressed by a cell. Other forms of tissue factor useful for generating antibodies will be apparent to those skilled in the art.

12.2. Monoclonal Antibodies

Monoclonal antibodies may be obtained, for example, using the hybridoma method first described by Kohler et al., *Nature,* 1975, 256:495-497 (incorporated by reference in its entirety), and/or by recombinant DNA methods (see e.g., U.S. Pat. No. 4,816,567, incorporated by reference in its entirety). Monoclonal antibodies may also be obtained, for example, using phage or yeast-based libraries. See e.g., U.S. Pat. Nos. 8,258,082 and 8,691,730, each of which is incorporated by reference in its entirety.

In the hybridoma method, a mouse or other appropriate host animal is immunized to elicit lymphocytes that produce or are capable of producing antibodies that will specifically bind to the protein used for immunization. Alternatively, lymphocytes may be immunized in vitro. Lymphocytes are then fused with myeloma cells using a suitable fusing agent, such as polyethylene glycol, to form a hybridoma cell. See Goding J. W., *Monoclonal Antibodies: Principles and Practice* 3rd ed. (1986) Academic Press, San Diego, CA, incorporated by reference in its entirety.

The hybridoma cells are seeded and grown in a suitable culture medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Useful myeloma cells are those that fuse efficiently, support stable high-level production of antibody by the selected antibody-producing cells, and are sensitive media conditions, such as the presence or absence of HAT medium. Among these, preferred myeloma cell lines are murine myeloma lines, such as those derived from MOP-21 and MC-11 mouse tumors (available from the Salk Institute Cell Distribution Center, San Diego, CA), and SP-2 or X63-Ag8-653 cells (available from the American Type Culture Collection, Rockville, MD). Human myeloma and mouse-human heteromyeloma cell lines also have been described for the production of human monoclonal antibodies. See e.g., Kozbor, *J. Immunol.,* 1984, 133:3001, incorporated by reference in its entirety.

After the identification of hybridoma cells that produce antibodies of the desired specificity, affinity, and/or biological activity, selected clones may be subcloned by limiting dilution procedures and grown by standard methods. See Goding, supra. Suitable culture media for this purpose include, for example, D-MEM or RPMI-1640 medium. In addition, the hybridoma cells may be grown in vivo as ascites tumors in an animal.

DNA encoding the monoclonal antibodies may be readily isolated and sequenced using conventional procedures (e.g., by using oligonucleotide probes that are capable of binding specifically to genes encoding the heavy and light chains of the monoclonal antibodies). Thus, the hybridoma cells can serve as a useful source of DNA encoding antibodies with the desired properties. Once isolated, the DNA may be placed into expression vectors, which are then transfected into host cells such as bacteria (e.g., *E. coli*), yeast (e.g., *Saccharomyces* or *Pichia* sp.), COS cells, Chinese hamster ovary (CHO) cells, or myeloma cells that do not otherwise produce antibody, to produce the monoclonal antibodies.

12.3. Humanized Antibodies

Humanized antibodies may be generated by replacing most, or all, of the structural portions of a non-human monoclonal antibody with corresponding human antibody sequences. Consequently, a hybrid molecule is generated in which only the antigen-specific variable, or CDR, is composed of non-human sequence. Methods to obtain humanized antibodies include those described in, for example, Winter and Milstein, *Nature,* 1991, 349:293-299; Rader et al., *Proc. Nat. Acad. Sci. U.S.A.,* 1998, 95:8910-8915; Steinberger et al., *J. Biol. Chem.,* 2000, 275:36073-36078; Queen et al., *Proc. Natl. Acad. Sci. U.S.A.,* 1989, 86:10029-10033; and U.S. Pat. Nos. 5,585,089, 5,693,761, 5,693,762, and 6,180,370; each of which is incorporated by reference in its entirety.

12.4. Human Antibodies

Human antibodies can be generated by a variety of techniques known in the art, for example by using transgenic animals (e.g., humanized mice). See, e.g., Jakobovits et al., *Proc. Natl. Acad. Sci. U.S.A.,* 1993, 90:2551; Jakobovits et al., *Nature,* 1993, 362:255-258; Bruggermann et al., *Year in Immuno.,* 1993, 7:33; and U.S. Pat. Nos. 5,591,669, 5,589,369 and 5,545,807; each of which is incorporated by reference in its entirety. Human antibodies can also be derived from phage-display libraries (see e.g., Hoogenboom et al., *J. Mol. Biol.,* 1991, 227:381-388; Marks et al., *J. Mol. Biol.,* 1991, 222:581-597; and U.S. Pat. Nos. 5,565,332 and 5,573,905; each of which is incorporated by reference in its entirety). Human antibodies may also be generated by in vitro activated B cells (see e.g., U.S. Pat. Nos. 5,567,610 and 5,229,275, each of which is incorporated by reference in its entirety). Human antibodies may also be derived from yeast-based libraries (see e.g., U.S. Pat. No. 8,691,730, incorporated by reference in its entirety).

12.5 Conjugation

The antibody conjugates can be prepared by standard techniques. In certain embodiments, an antibody is contacted with a payload precursor under conditions suitable for forming a bond from the antibody to the payload to form an antibody-payload conjugate. In certain embodiments, an antibody is contacted with a linker precursor under conditions suitable for forming a bond from the antibody to the linker. The resulting antibody-linker is contacted with a payload precursor under conditions suitable for forming a bond from the antibody-linker to the payload to form an antibody-linker-payload conjugate. In certain embodiments, a payload precursor is contacted with a linker precursor under conditions suitable for forming a bond from the payload to the linker. The resulting payload-linker is contacted with an antibody under conditions suitable for forming a bond from the payload-linker to the antibody to form an antibody-linker-payload conjugate. Suitable linkers for preparing the antibody conjugates are disclosed herein, and exemplary conditions for conjugation are described in the Examples below.

In some embodiments, an anti-Tissue Factor conjugate is prepared by contacting an anti-Tissue Factor antibody as disclosed herein with a linker precursor having a structure of any of LP1-LP5:

LP1

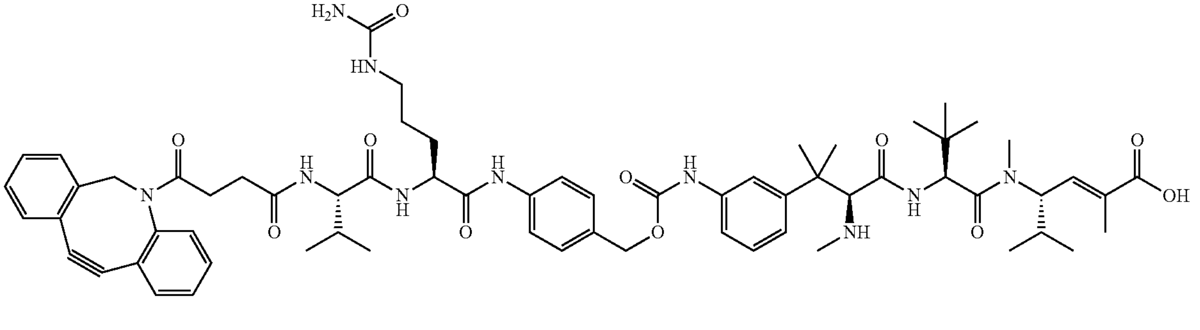

-continued
LP2
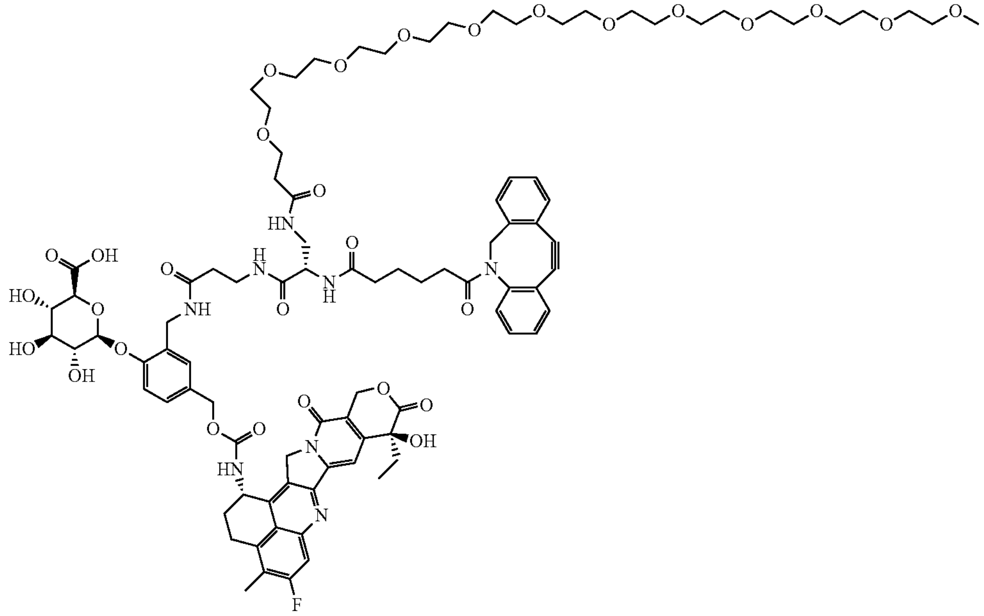
LP3
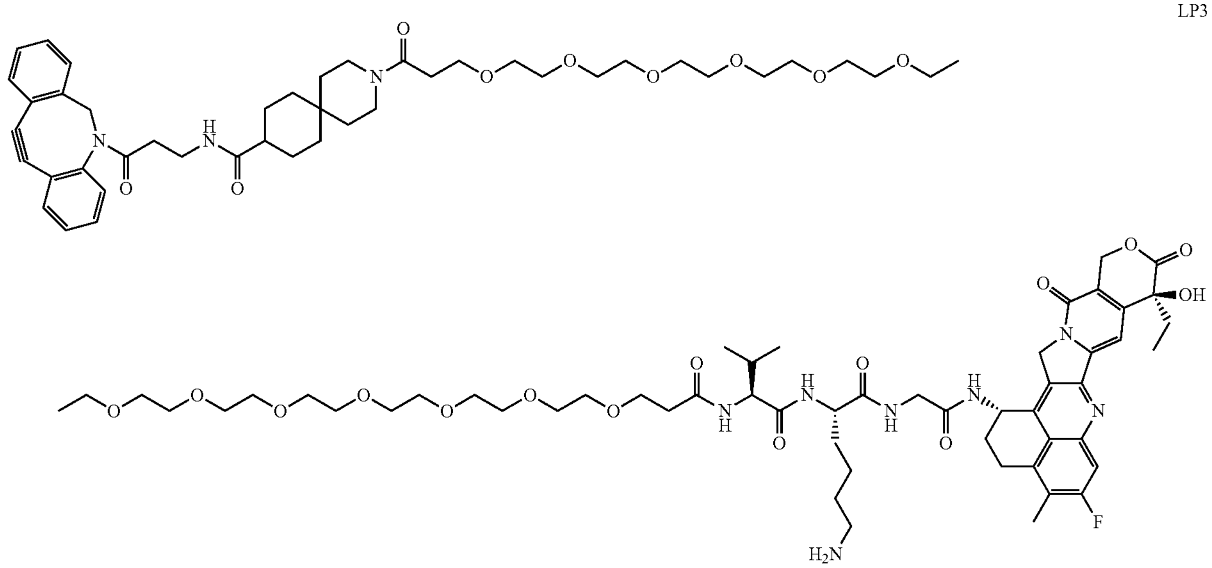
LP4
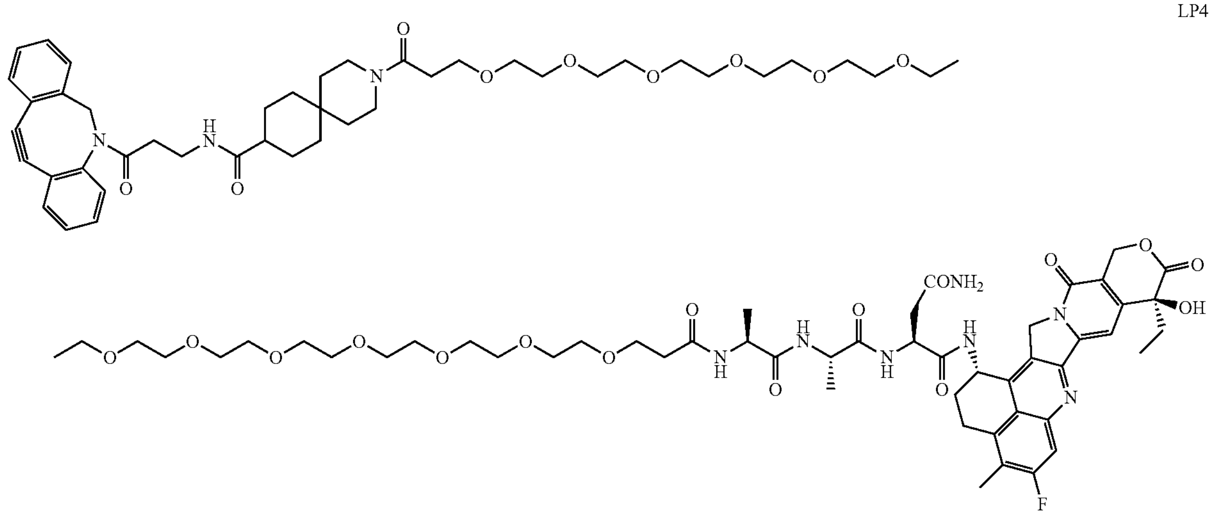

-continued
LP5
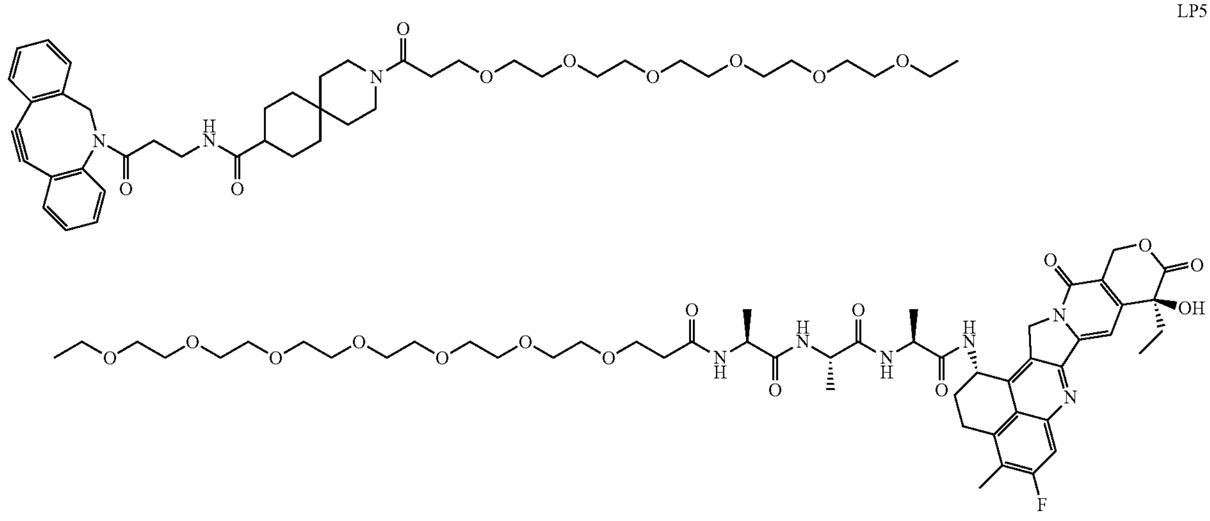
In some embodiments, an anti-Tissue Factor conjugate is prepared by contacting an anti-Tissue Factor antibody as disclosed herein with a linker precursor having a structure of any of LP1A-LP5A:
LP1A
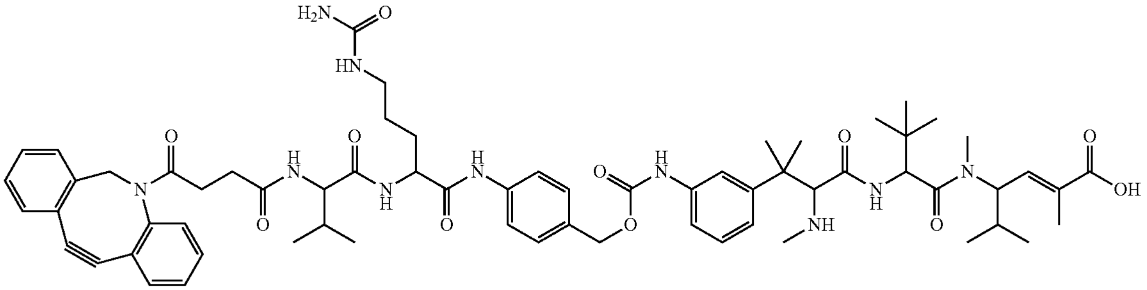
LP2A
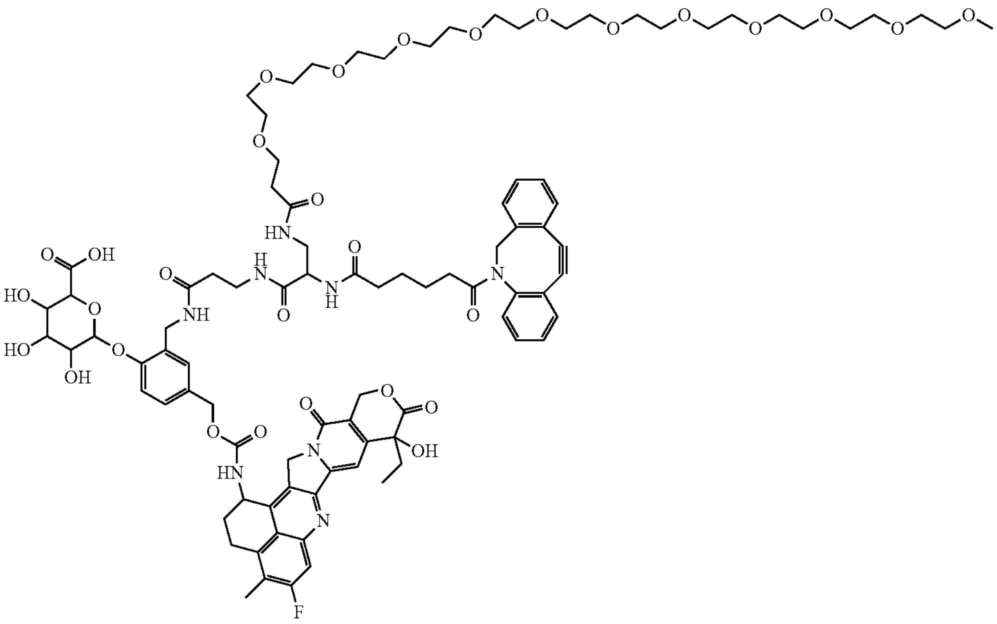

-continued
LP3A
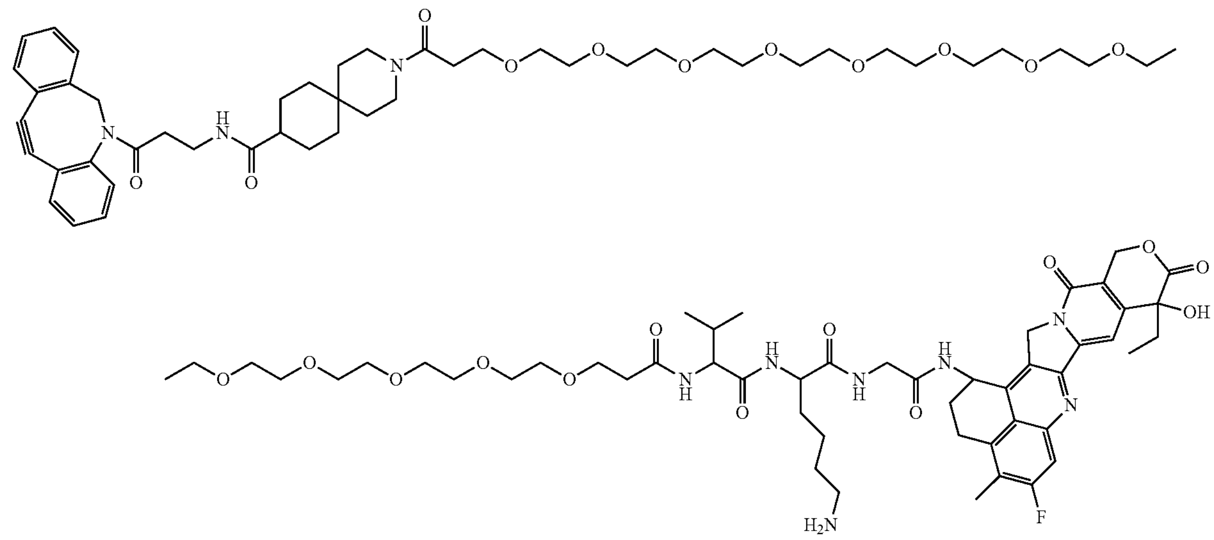
LP4A
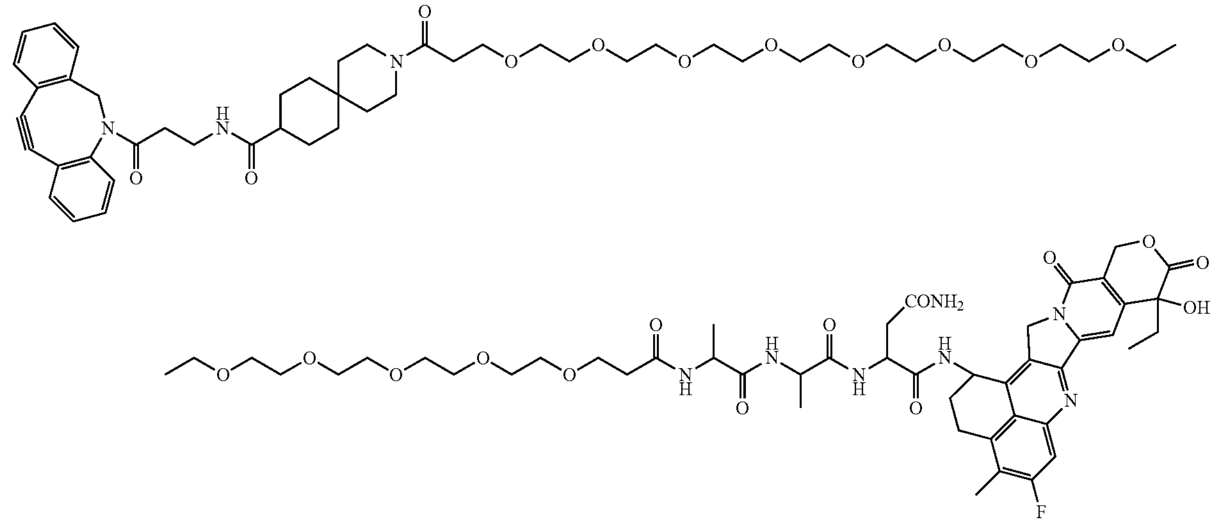
LP5A
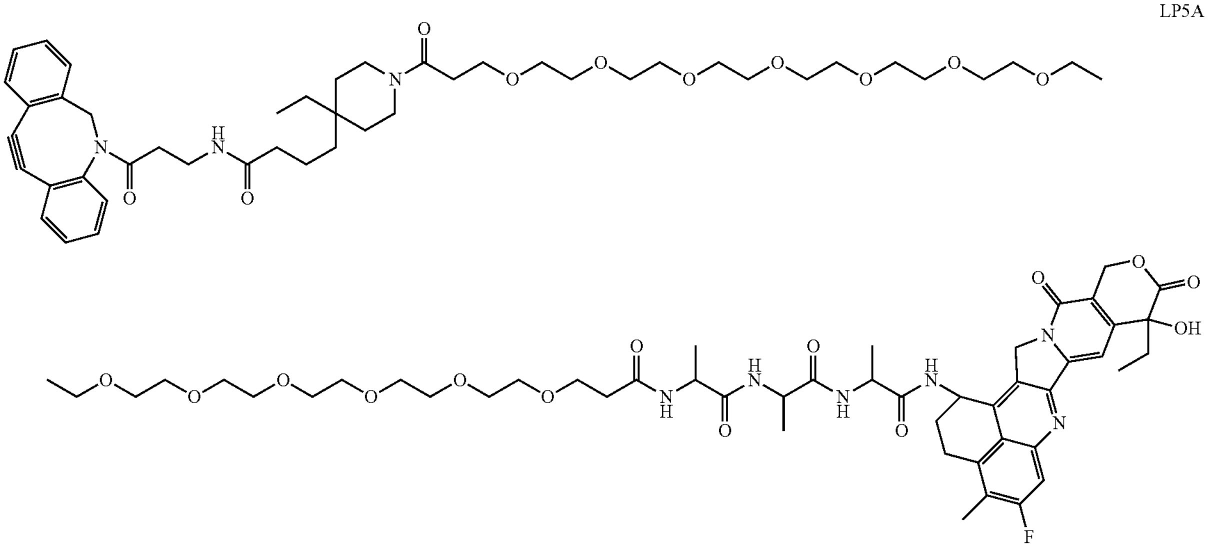

13. Vectors, Host Cells, and Recombinant Methods

The invention also provides isolated nucleic acids encoding anti-tissue factor antibodies, vectors and host cells comprising the nucleic acids, and recombinant techniques for the production of the antibodies.

For recombinant production of the antibody, the nucleic acid(s) encoding it may be isolated and inserted into a replicable vector for further cloning (i.e., amplification of the DNA) or expression. In some aspects, the nucleic acid may be produced by homologous recombination, for example as described in U.S. Pat. No. 5,204,244, incorporated by reference in its entirety.

Many different vectors are known in the art. The vector components generally include, but are not limited to, one or more of the following: a signal sequence, an origin of replication, one or more marker genes, an enhancer element, a promoter, and a transcription termination sequence, for example as described in U.S. Pat. No. 5,534,615, incorporated by reference in its entirety.

Illustrative examples of suitable host cells are provided below. These host cells are not meant to be limiting.

Suitable host cells include any prokaryotic (e.g., bacterial), lower eukaryotic (e.g., yeast), or higher eukaryotic (e.g., mammalian) cells. Suitable prokaryotes include eubacteria, such as Gram-negative or Gram-positive organisms, for example, Enterobacteriaceae such as *Escherichia* (*E. coli*), *Enterobacter, Erwinia, Klebsiella, Proteus, Salmonella* (*S. typhimurium*), *Serratia* (*S. marcescans*), *Shigella*, Bacilli (*B. subtilis* and *B. licheniformis*), *Pseudomonas* (*P. aeruginosa*), and *Streptomyces*. One useful *E. coli* cloning host is *E. coli* 294, although other strains such as *E. coli* B, *E. coli* X1776, and *E. coli* W311LP0 are suitable.

In addition to prokaryotes, eukaryotic microbes such as filamentous fungi or yeast are also suitable cloning or expression hosts for anti-tissue factor antibody-encoding vectors. *Saccharomyces cerevisiae*, or common baker's yeast, is a commonly used lower eukaryotic host microorganism. However, a number of other genera, species, and strains are available and useful, such as *Schizosaccharomyces pombe, Kluyveromyces* (*K. lactis, K. fragilis, K. bulgaricus K. wickeramii, K. waltii, K. drosophilarum, K. thermotolerans*, and *K. marxianus*), *Yarrowia, Pichia pastoris, Candida* (*C. albicans*), *Trichoderma* reesia, *Neurospora crassa, Schwanniomyces* (*S. occidentalis*), and filamentous fungi such as, for example *Penicillium, Tolypocladium*, and *Aspergillus* (*A. nidulans* and *A. niger*).

Useful mammalian host cells include COS-7 cells, HEK293 cells; baby hamster kidney (BHK) cells; Chinese hamster ovary (CHO); mouse sertoli cells; African green monkey kidney cells (VERO-76), and the like.

The host cells used to produce the anti-tissue factor antibody of this invention may be cultured in a variety of media. Commercially available media such as, for example, Ham's F10, Minimal Essential Medium (MEM), RPMI-1640, and Dulbecco's Modified Eagle's Medium (DMEM) are suitable for culturing the host cells. In addition, any of the media described in Ham et al., *Meth. Enz.*, 1979, 58:44; Barnes et al., *Anal. Biochem.*, 1980, 102:255; and U.S. Pat. Nos. 4,767,704, 4,657,866, 4,927,762, 4,560,655, and 5,122,469, or WO 90/03430 and WO 87/00195 may be used. Each of the foregoing references is incorporated by reference in its entirety.

Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics, trace elements (defined as inorganic compounds usually present at final concentrations in the micromolar range), and glucose or an equivalent energy source. Any other necessary supplements may also be included at appropriate concentrations that would be known to those skilled in the art.

The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. For example, Carter et al. (*Bio/Technology,* 1992, 10:163-167) describes a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation.

In some embodiments, the antibody is produced in a cell-free system. In some aspects, the cell-free system is an in vitro transcription and translation system as described in Yin et al., *mAbs,* 2012, 4:217-225, incorporated by reference in its entirety. In some aspects, the cell-free system utilizes a cell-free extract from a eukaryotic cell or from a prokaryotic cell. In some aspects, the prokaryotic cell is *E. coli*. Cell-free expression of the antibody may be useful, for example, where the antibody accumulates in a cell as an insoluble aggregate, or where yields from periplasmic expression are low.

Where the antibody is secreted into the medium, supernatants from such expression systems are generally first concentrated using a commercially available protein concentration filter, for example, an Amicon® or Millipore® Pellcon® ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a particularly useful purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.,* 1983, 62:1-13, incorporated by reference in its entirety). Protein G is useful for all mouse isotypes and for human γ3 (Guss et al., *EMBO J.,* 1986, 5:1567-1575, incorporated by reference in its entirety).

The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the BakerBond ABX® resin is useful for purification.

Other techniques for protein purification, such as fractionation on an ion-exchange column, ethanol precipitation, Reverse Phase HPLC, chromatography on silica, chromatography on heparin Sepharose®, chromatofocusing, SDS-PAGE, and ammonium sulfate precipitation are also available, and can be applied by one of skill in the art.

Following any preliminary purification step(s), the mixture comprising the antibody of interest and contaminants may be subjected to low pH hydrophobic interaction chromatography using an elution buffer at a pH between about 2.5 to about 4.5, generally performed at low salt concentrations (e.g., from about 0 to about 0.25 M salt).

14. Pharmaceutical Compositions and Methods of Administration

The antibodies or the antibody conjugates provided herein can be formulated into pharmaceutical compositions using methods available in the art and those disclosed herein. Any of the antibodies or the antibody conjugates provided herein can be provided in any appropriate pharmaceutical composition and be administered by any suitable route of administration. Suitable routes of administration include, but are not limited to, the inhalation, intraarterial, intradermal, intramuscular, intraperitoneal, intravenous, nasal, parenteral, pulmonary, and subcutaneous routes.

The methods provided herein encompass administering pharmaceutical compositions comprising at least one antibody or antibody conjugate provided herein and one or more compatible and pharmaceutically acceptable carriers. In this context, the term “pharmaceutically acceptable” means approved by a regulatory agency of the Federal or a state government or listed in the U.S. Pharmacopeia or other generally recognized pharmacopeia for use in animals, and more particularly in humans. The term “carrier” includes a diluent, adjuvant (e.g., Freund’s adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in Martin, E. W., *Remington’s Pharmaceutical Sciences*.

In clinical practice the pharmaceutical compositions, antibodies, or antibody conjugates provided herein may be administered by any route known in the art. Exemplary routes of administration include, but are not limited to, the inhalation, intraarterial, intradermal, intramuscular, intraperitoneal, intravenous, nasal, parenteral, pulmonary, and subcutaneous routes. In some embodiments, a pharmaceutical composition, antibody, or antibody conjugate provided herein is administered parenterally.

The compositions for parenteral administration can be emulsions or sterile solutions. Parenteral compositions may include, for example, propylene glycol, polyethylene glycol, vegetable oils, and injectable organic esters (e.g., ethyl oleate). These compositions can also contain wetting, isotonizing, emulsifying, dispersing and stabilizing agents. Sterilization can be carried out in several ways, for example using a bacteriological filter, by radiation or by heating. Parenteral compositions can also be prepared in the form of sterile solid compositions which can be dissolved at the time of use in sterile water or any other injectable sterile medium.

In some embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic antibody conjugates.

The pharmaceutical composition may comprise one or more pharmaceutical excipients. Any suitable pharmaceutical excipient may be used, and one of ordinary skill in the art is capable of selecting suitable pharmaceutical excipients. Non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific antibody in the dosage form. The composition or single unit dosage form, if desired, can also contain minor amounts of wetting or emulsifying agents, or pH buffering agents. Accordingly, the pharmaceutical excipients provided below are intended to be illustrative, and not limiting. Additional pharmaceutical excipients include, for example, those described in the *Handbook of Pharmaceutical Excipients*, Rowe et al. (Eds.) $6^{th}$ Ed. (2009), incorporated by reference in its entirety.

In some embodiments, the pharmaceutical composition comprises an anti-foaming agent. Any suitable anti-foaming agent may be used. In some aspects, the anti-foaming agent is selected from an alcohol, an ether, an oil, a wax, a silicone, a surfactant, and combinations thereof. In some aspects, the anti-foaming agent is selected from a mineral oil, a vegetable oil, ethylene bis stearamide, a paraffin wax, an ester wax, a fatty alcohol wax, a long chain fatty alcohol, a fatty acid soap, a fatty acid ester, a silicon glycol, a fluorosilicone, a polyethylene glycol-polypropylene glycol copolymer, polydimethylsiloxane-silicon dioxide, ether, octyl alcohol, capryl alcohol, sorbitan trioleate, ethyl alcohol, 2-ethyl-hexanol, dimethicone, oleyl alcohol, simethicone, and combinations thereof.

In some embodiments, the pharmaceutical composition comprises a co-solvent. Illustrative examples of co-solvents include ethanol, poly(ethylene) glycol, butylene glycol, dimethylacetamide, glycerin, and propylene glycol.

In some embodiments, the pharmaceutical composition comprises a buffer. Illustrative examples of buffers include acetate, borate, carbonate, lactate, malate, phosphate, citrate, hydroxide, diethanolamine, monoethanolamine, glycine, methionine, guar gum, and monosodium glutamate.

In some embodiments, the pharmaceutical composition comprises a carrier or filler. Illustrative examples of carriers or fillers include lactose, maltodextrin, mannitol, sorbitol, chitosan, stearic acid, xanthan gum, and guar gum.

In some embodiments, the pharmaceutical composition comprises a surfactant. Illustrative examples of surfactants include d-alpha tocopherol, benzalkonium chloride, benzethonium chloride, cetrimide, cetylpyridinium chloride, docusate sodium, glyceryl behenate, glyceryl monooleate, lauric acid, macrogol 15 hydroxystearate, myristyl alcohol, phospholipids, polyoxyethylene alkyl ethers, polyoxyethylene sorbitan fatty acid esters, polyoxyethylene stearates, polyoxylglycerides, sodium lauryl sulfate, sorbitan esters, and vitamin E polyethylene (glycol) succinate.

In some embodiments, the pharmaceutical composition comprises an anti-caking agent. Illustrative examples of anti-caking agents include calcium phosphate (tribasic), hydroxymethyl cellulose, hydroxypropyl cellulose, and magnesium oxide.

Other excipients that may be used with the pharmaceutical compositions include, for example, albumin, antioxidants, antibacterial agents, antifungal agents, bioabsorbable polymers, chelating agents, controlled release agents, diluents, dispersing agents, dissolution enhancers, emulsifying agents, gelling agents, ointment bases, penetration enhancers, preservatives, solubilizing agents, solvents, stabilizing agents, and sugars. Specific examples of each of these agents are described, for example, in the *Handbook of Pharmaceutical Excipients*, Rowe et al. (Eds.) $6^{th}$ Ed. (2009), The Pharmaceutical Press, incorporated by reference in its entirety.

In some embodiments, the pharmaceutical composition comprises a solvent. In some aspects, the solvent is saline solution, such as a sterile isotonic saline solution or dextrose solution. In some aspects, the solvent is water for injection.

In some embodiments, the pharmaceutical compositions are in a particulate form, such as a microparticle or a nanoparticle. Microparticles and nanoparticles may be formed from any suitable material, such as a polymer or a lipid. In some aspects, the microparticles or nanoparticles are micelles, liposomes, or polymersomes.

Further provided herein are anhydrous pharmaceutical compositions and dosage forms comprising an antibody or antibody conjugate, since, in some embodiments, water can facilitate the degradation of some antibodies.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition can be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Lactose-free compositions provided herein can comprise excipients that are well known in the art and are listed, for example, in the U.S. Pharmocopia (USP) SP (XXI)/NF (XVI). In general, lactose-free compositions comprise an active ingredient, a binder/filler, and a lubricant in pharmaceutically compatible and pharmaceutically acceptable amounts. Exemplary lactose-free dosage forms comprise an active ingredient, microcrystalline cellulose, pre gelatinized starch, and magnesium stearate.

Also provided are pharmaceutical compositions and dosage forms that comprise one or more excipients that reduce the rate by which an antibody or antibody-conjugate will decompose. Such excipients, which are referred to herein as "stabilizers," include, but are not limited to, antioxidants such as ascorbic acid, pH buffers, or salt buffers.

14.1. Parenteral Dosage Forms

In certain embodiments, provided are parenteral dosage forms. Parenteral dosage forms can be administered to subjects by various routes including, but not limited to, subcutaneous, intravenous (including bolus injection), intramuscular, and intraarterial. Because their administration typically bypasses subjects' natural defenses against contaminants, parenteral dosage forms are typically, sterile or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Excipients that increase the solubility of one or more of the antibodies disclosed herein can also be incorporated into the parenteral dosage forms.

14.2. Dosage and Unit Dosage Forms

In human therapeutics, the doctor will determine the posology which he considers most appropriate according to a preventive or curative treatment and according to the age, weight, condition and other factors specific to the subject to be treated.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic antibodies or antibody conjugates.

The amount of the antibody or antibody conjugate or composition which will be effective in the prevention or treatment of a disorder or one or more symptoms thereof will vary with the nature and severity of the disease or condition, and the route by which the antibody or antibody conjugate is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the antibody or antibody conjugate per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). In certain embodiment, the dosage of the antibody or antibody conjugate provided herein, based on weight of the antibody or antibody conjugate, administered to prevent, treat, manage, or ameliorate a disorder, or one or more symptoms thereof in a subject is between 0.1 mg/kg and 15 mg/kg of a subject's body weight. In another embodiment, the dosage of the composition or a composition provided herein administered to prevent, treat, manage, or ameliorate a disorder, or one or more symptoms thereof in a subject is between 0.1 mg and 200 mg.

The dose can be administered according to a suitable schedule. It may be necessary to use dosages of the antibody outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the antibodies provided herein are also encompassed by the herein described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiments, treatment or prevention can be initiated with one or more loading doses of an antibody or composition provided herein followed by one or more maintenance doses.

In certain embodiments, a dose of an antibody or composition provided herein can be administered to achieve a steady-state concentration of the antibody in blood or serum of the subject. The steady-state concentration can be determined by measurement according to techniques available to those of skill or can be based on the physical characteristics of the subject such as height, weight and age.

14.3 Combination Therapies and Formulations

In certain embodiments, provided are methods for treatment and/or compositions and therapeutic formulations comprising any of the antibodies or antibody conjugates provided herein in combination with one or more chemotherapeutic agents disclosed herein, and methods of treatment comprising administering such combinations to subjects in need thereof. Examples of chemotherapeutic agents include, but are not limited to, Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB®, GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially uncialamycin, calicheamicin gammall, and calicheamicin omegall (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pladienolide B, pteropterin, trimetrexate; purine analogs such as fludarabine, 6-mercaptopurine, thiamniprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

In certain embodiments, provided are methods for treatment and/or compositions and therapeutic formulations comprising any of the antibodies or antibody conjugates provided herein in combination with a checkpoint inhibitor, for example, a PD-1 inhibitor, PD-L1 inhibitor, PD-L2 inhibitor, CTLA-4 inhibitor, LAG-3 inhibitor, TIM-3 inhibitor, V-domain Ig suppressor of T-cell activation (VISTA) inhibitors, small molecule, peptide, nucleotide, or other inhibitor.

In certain embodiments, provided are methods for treatment and/or compositions and therapeutic formulations comprising any of the antibodies or antibody conjugates provided herein in combination with one or more PD-1 or PD-L1 inhibitors, and methods of treatment comprising administering such combinations to subjects in need thereof. In some embodiments, the one or more PD-1 or PD-L1 inhibitors comprise a small molecule blocker of the PD-1 or PD-L[1] pathway. In some embodiments, the one or more PD-1 or PD-L1 inhibitors comprise an antibody that inhibits PD-1 or PD-L1 activity. In some embodiments, the one or more PD-1 or PD-L1 inhibitors are selected from the group consisting of: CA-170, BMS-8, BMS-202, BMS-936558, CK-301, and AUNP12. In some embodiments, the one or more PD-1 or PD-L1 inhibitors are selected from the group consisting of: avelumab, nivolumab, pembrolizumab, atezolizumab, durvalumab, AMP-224 (GlaxoSmithKline), MEDI0680/AMP-514 (AstraZeneca), PDR001 (Novartis), cemiplimab, TSR-042 (Tesaro), Tizlelizumab/BGB-A317 (Beigene), CK-301 (Checkpoint Therapeutics), BMS-936559 (Bristol-Meyers Squibb), camrelizumab, sintilimab, toripalimab, genolimzumab, and A167 (Sichuan Kelun-Biotech Biopharmaceutical). In some embodiments, the one or more PD-1 or PD-L1 inhibitors are selected from the group consisting of: MGA012 (Incyte/MacroGenics), PF-06801591 (Pfizer/Merck KGaA), LY3300054 (Eli Lilly), FAZ053 (Novartis), PD-11 (Novartis), CX-072 (CytomX), BGB-A333 (Beigene), BI 754091 (Boehringer Ingelheim), JNJ-63723283 (Johnson and Johnson/Jannsen), AGEN2034 (Agenus), CA-327 (Curis), CX-188 (CytomX), STI-A1110 (Servier), JTX-4014 (Jounce), (LLY) AM0001 (Armo Biosciences), CBT-502 (CBT Pharmaceuticals), FS118 (F-Star/Merck KGaA), XmAb20717 (Xencor), XmAb23104 (Xencor), AB122 (Arcus Biosciences), KY1003 (Kymab), RXI-762 (RXi). In some embodiments, the one or more PD-1 or PD-L1 inhibitors are selected from the group consisting of: PRS-332 (Pieris Pharmaceuticals), ALPN-202 (Alpine Immune Science), TSR-075 (Tesaro/Anaptys Bio), MCLA-145 (Merus), MGD013 (Macrogenics), MGD019 (Macrogenics). An additional PD-1 inhibitor is Pidilizumab (CT-011). In some embodiments, the one or more PD-1 or PD-L1 inhibitors are selected from an anti-PD1 mono-specific or bi-specific antibody described in, for example, WO 2016/077397, WO 2018/156777, and International Application No. PCT/US2013/034213, filed May 23, 2018.

In some embodiments, the one or more PD-1 or PD-L1 inhibitors are selected from the group consisting of CA-170, BMS-8, BMS-202, BMS-936558, CK-301, AUNP12, avelumab, nivolumab, atezolizumab, pembrolizumab, durvalumab, AMP-224, MEDI0680/AMP-514, PDR001, cemiplimab, TSR-042, Tizlelizumab/BGB-A317, CK-301, BMS-936559, camrelizumab, sintilimab, toripalimab, genolimzumab, A167, MGA012, PF-06801591, LY3300054, FAZ053, PD-11, CX-072, BGB-A333, BI 754091, JNJ-63723283, AGEN2034, CA-327, CX-188, STI-A1110, JTX-4014, (LLY) AM0001, CBT-502, FS118, XmAb20717, XmAb23104, AB122, KY1003, RXI-762, PRS-33, ALPN-202, TSR-075, MCLA-145, MGD013, and MGD019.

In certain embodiments, provided are methods for treatment and/or compositions and therapeutic formulations comprising any of the antibodies or antibody conjugates provided herein in combination with one or more CTLA-4 inhibitors, and methods of treatment comprising administering such combinations to subjects in need thereof. CTLA-4 inhibitors include, but are not limited to, ipilimumab (Yervoy®), tremelimumab (AstraZeneca and MedImmune), AGEN1884 and AGEN2041 (Agenus).

In certain embodiments, provided are methods for treatment and/or compositions and therapeutic formulations comprising any of the antibodies or antibody conjugates provided herein in combination with one or more LAG-3 inhibitors, and methods of treatment comprising administering such combinations to subjects in need thereof. Examples of LAG-3 immune checkpoint inhibitors include, but are not limited to, BMS-986016 (Bristol-Myers Squibb), GSK2831781 (GaxoSmithKline), IMP321 (Prima BioMed), LAG525 (Novartis), and the dual PD-1 and LAG-3 inhibitor MGD013 (MacroGenics).

In certain embodiments, provided are methods for treatment and/or compositions and therapeutic formulations comprising any of the antibodies or antibody conjugates provided herein in combination with one or more TIM-3 inhibitors, and methods of treatment comprising administering such combinations to subjects in need thereof. A specific TIM-3 inhibitor includes, but is not limited to, TSR-022 (Tesaro).

Other immune checkpoint inhibitors for use in the invention described herein include, but are not limited to, B7-H3/CD276 immune checkpoint inhibitors such as MGA217; indoleamine 2,3-dioxygenase (IDO) immune checkpoint inhibitors such as Indoximod and INCB024360; killer immunoglobulin-like receptors (KIRs) immune checkpoint inhibitors such as Lirilumab (BMS-986015); and, carcinoembryonic antigen cell adhesion molecule (CEACAM) inhibitors (e.g., CEACAM-1, -3 and/or -5).

In certain embodiments, provided are methods for treatment and/or compositions or therapeutic formulations comprising any of the antibody conjugates provided herein in combination with a PARP inhibitor, including, but not limited to olaparib (AZD-2281, Lynparza®), rucaparib (AG 014699, Rubraca®), niraparib (Zejula®), talazoparib (BMN-673, Talzenna®), veliparib (ABT-888), fluzoparib (HS10160), Iniparib (BSI 201), BGB-290, E7016, E7449, and CEP-9722. In one embodiment, an antibody conjugate provided herein is administered in combination with olaparib, rucaparib, niraparib, or talazoparib. In one embodiment, an antibody conjugate provided herein is administered in combination with olaparib.

In certain embodiments, provided are methods for treatment and/or composition or therapeutic formulations comprising any of the antibody conjugates provided herein in combination with an ATR inhibitor, ATM inhibitor, Wee1 inhibitor, CHK1 inhibitor, NAMPT inhibitor, or a Topo2 inhibitor.

The agents administered in combination with the antibodies or antibody conjugates disclosed herein can be administered just prior to, sequentially, concurrent with, or shortly after the administration of the antibodies or antibody conjugates. In one embodiment, the agents administered in combination with the antibodies or antibody conjugates disclosed herein are administered sequentially after the administration of the antibody conjugates. In one embodiment, the agents administered in combination with the antibodies or antibody conjugates disclosed herein are administered concurrently after the administration of the antibody conjugates. For purposes of the present disclosure, such administration regimens are considered the administration of an antibody conjugate "in combination with" an additional therapeutically active component. Embodiments include pharmaceutical compositions in which an antibody conjugate disclosed herein is co-formulated with one or more of the chemotherapeutic agents, PD-1 inhibitors, PD-L1 inhibitors, or PARP inhibitors disclosed herein.

15. Therapeutic Applications.

For therapeutic applications, the antibodies or antibody conjugates of the invention are administered to a mammal, generally a human, in a pharmaceutically acceptable dosage form such as those known in the art and those discussed above. For example, the antibodies or antibody conjugates of the invention may be administered to a human intravenously as a bolus or by continuous infusion over a period of time, by intramuscular, intraperitoneal, intra-cerebrospinal, subcutaneous, intra-articular, intrasynovial, intrathecal, or intratumoral routes. The antibodies or antibody conjugates also are suitably administered by peritumoral, intralesional, or perilesional routes, to exert local as well as systemic therapeutic effects. The intraperitoneal route may be particularly useful, for example, in the treatment of ovarian tumors.

In some aspects, a method for reducing cell proliferation in a subject in need thereof can comprise administering to the subject an effective amount of an isolated antibody, antibody conjugate or pharmaceutical composition thereof of the present disclosure. In some aspects, an isolated antibody, antibody conjugate or pharmaceutical composition thereof of the present disclosure can be used for reducing cell proliferation in a subject in need thereof. In some aspects, an isolated antibody, antibody conjugate or pharmaceutical composition thereof of the present disclosure can be used for the preparation of a medicament for reducing cell proliferation in a subject in need thereof.

In some aspects, a method for treating or preventing a disease or condition in a subject in need thereof can comprise administering to the subject an effective amount of an isolated antibody, antibody conjugate or pharmaceutical composition thereof of the present disclosure. In some aspects, an isolated antibody, antibody conjugate or pharmaceutical composition thereof of the present disclosure can be used for treating or preventing a disease or condition in a subject in need thereof. In some aspects, an isolated antibody, antibody conjugate or pharmaceutical composition thereof of the present disclosure can be used for the preparation of a medicament for treating or preventing a disease or condition in a subject in need thereof.

The antibodies or antibody conjugates provided herein may be useful for the treatment of any disease or condition involving tissue factor. In some embodiments, the disease or condition is a disease or condition that can be diagnosed by overexpression of tissue factor. In some embodiments, the disease or condition is a disease or condition that can benefit from treatment with an anti-tissue factor antibody or antibody conjugate. In some embodiments, the disease or condition is cancer. In some embodiments, the disease or condition is a Tissue Factor-expressing cancer. In certain embodiments, the anti-TF antibody conjugates treat the disease or condition, for example cancer, by inducing DNA damage and/or cell death, or by activating anti-tumor immunity or protective immunity.

Any suitable cancer may be treated with the antibodies or antibody conjugates provided herein. Illustrative suitable cancers include, for example, acute lymphoblastic leukemia (ALL), acute myeloid leukemia (AML), adrenocortical carcinoma, anal cancer, appendix cancer, astrocytoma, basal cell carcinoma, brain tumor, bile duct cancer, bladder cancer, bone cancer, breast cancer, bronchial tumor, carcinoma of unknown primary origin, cardiac tumor, cervical cancer, chordoma, colon cancer, colorectal cancer, craniopharyngioma, ductal carcinoma, embryonal tumor, endometrial cancer, ependymoma, esophageal cancer, esthesioneuroblastoma, fibrous histiocytoma, Ewing sarcoma, eye cancer, germ cell tumor, gallbladder cancer, gastric cancer, gastrointestinal carcinoid tumor, gastrointestinal stromal tumor, gestational trophoblastic disease, glioma, head and neck cancer, hepatocellular cancer, histiocytosis, Hodgkin lymphoma, hypopharyngeal cancer, intraocular melanoma, islet cell tumor, Kaposi sarcoma, kidney cancer, Langerhans cell histiocytosis, laryngeal cancer, lip and oral cavity cancer, liver cancer, lobular carcinoma in situ, lung cancer, macroglobulinemia, malignant fibrous histiocytoma, melanoma, Merkel cell carcinoma, mesothelioma, metastatic squamous neck cancer with occult primary, head and neck squamous cell carcinoma, midline tract carcinoma involving NUT gene, mouth cancer, multiple endocrine neoplasia syndrome, multiple myeloma, mycosis fungoides, myelodysplastic syndrome, myelodysplastic/myeloproliferative neoplasm, nasal cavity and par nasal sinus cancer, nasopharyngeal cancer, neuroblastoma, non-small cell lung cancer, oropharyngeal cancer, osteosarcoma, ovarian cancer, pancreatic cancer, papillomatosis, paraganglioma, parathyroid cancer, penile cancer, pharyngeal cancer, pheochromocytomas, pituitary tumor, pleuropulmonary blastoma, primary central nervous system lymphoma, prostate cancer, rectal cancer, renal cell cancer, renal pelvis and ureter cancer, retinoblastoma, rhabdoid tumor, salivary gland cancer, Sezary syndrome, skin cancer, small cell lung cancer, small intestine cancer, soft tissue sarcoma, spinal cord tumor, stomach cancer, T-cell lymphoma, teratoid tumor, testicular cancer, throat cancer, thymoma and thymic carcinoma, thyroid cancer, urethral cancer, uterine cancer, vaginal cancer, vulvar cancer, and Wilms tumor.

In some embodiments, the disease to be treated with the antibodies or antibody conjugates provided herein is gastric cancer, colorectal cancer, renal cell carcinoma, cervical carcinoma, endometrial cancer, non-small cell lung carcinoma, ovarian cancer, prostate cancer, breast cancer, head and neck cancer, pancreatic cancer, mesothelioma, and/or a cancer of epithelial origin. In some embodiments, the disease is cervical cancer, head and neck squamous cell carcinoma, endometrial cancer, esophageal cancer, non-small cell lung cancer, or prostate cancer. In some embodiments, the disease or condition is a solid tumor cancer. In particular embodiments, the disease is colorectal cancer. In some embodiments, the disease is gastric cancer. In some embodiments, the disease is ovarian cancer. In some embodiments, the disease is breast cancer. In some embodiments, the disease is lung cancer. In some embodiments, the disease is non-small cell lung cancer. In some embodiments, the disease is head and neck cancer. In some embodiments, the disease is head and neck squamous cell carcinoma. In some embodiments, the disease is cervical cancer. In some embodiments, the disease is endometrial cancer. In some embodiments, the disease is prostate cancer. In some embodiments, the disease is esophageal cancer. In some embodiments, the disease is colon cancer. In some embodiments, the disease is pancreatic cancer. In some embodiments, the disease is mesothelioma.

16. Diagnostic Applications

In some embodiments, the antibodies or antibody conjugates provided herein are used in diagnostic applications. For example, an anti-tissue factor antibody or antibody conjugate may be useful in assays for tissue factor protein. In some aspects the antibody can be used to detect the expression of tissue factor in various cells and tissues. These assays may be useful, for example, in making a diagnosis and/or prognosis for a disease, such as a cancer.

In some aspects, a method of diagnosing a disease or condition in a subject in need thereof can comprise administering to the subject an effective amount of an isolated antibody, antibody conjugate or pharmaceutical composition thereof of the present disclosure.

In some diagnostic and prognostic applications, the antibody or antibody conjugate may be labeled with a detectable moiety. Suitable detectable moieties include, but are not limited to radioisotopes, fluorescent labels, and enzyme-substrate labels. In another embodiment, the anti-tissue factor antibody or antibody conjugate need not be labeled, and the presence of the antibody can be detected using a labeled antibody which specifically binds to the anti-tissue factor antibody.

17. Affinity Purification Reagents

The antibodies or antibody conjugates provided herein of the invention may be used as affinity purification agents. In this process, the antibodies or antibody conjugates may be immobilized on a solid phase such a resin or filter paper, using methods well known in the art. The immobilized antibody is contacted with a sample containing the tissue factor protein (or fragment thereof) to be purified, and thereafter the support is washed with a suitable solvent that will remove substantially all the material in the sample except the tissue factor protein, which is bound to the immobilized antibody. Finally, the support is washed with another suitable solvent, such as glycine buffer, pH 5.0 that will release the tissue factor protein from the antibody.

18. Kits

In some embodiments, an anti-tissue factor antibody or antibody conjugate provided herein is provided in the form of a kit, i.e., a packaged combination of reagents in predetermined amounts with instructions for performing a procedure. In some embodiments, the procedure is a diagnostic assay. In other embodiments, the procedure is a therapeutic procedure.

In some embodiments, the kit further comprises a solvent for the reconstitution of the anti-tissue factor antibody or antibody conjugate. In some embodiments, the anti-tissue factor antibody is provided in the form of a pharmaceutical composition.

EXAMPLES

Example 1: Generation and Primary Screening of Anti-TF Antibodies

Antibody Fab and scFv libraries were constructed using a standard overlap extension PCR protocol with mutagenic primers targeting complementary determining regions (CDRs). See Heckman and Pease, *Nat. Protoc.,* 2007, 2:924-932; Stafford et al., 2014, *Protein Eng. Des. Sel.* 27:97-109, both incorporated by reference in their entireties. After multiple rounds of selection, the DNA from RT-PCR output was cloned into an optimized vector for cell-free expression using standard molecular biology techniques. All constructs were HIS- and FLAG-tagged to streamline purification and testing during screening.

Selections for novel antibodies were performed using standard ribosome display protocols. See Dreier and Pluckthun, *Methods Mol. Biol.,* 2003, 687:283-306, Clifton, NJ; Hanes and Plückthun, *Proc. Natl. Acad. Sci. U.S.A.,* 1997, 94:4937-4942, both incorporated by reference in their entireties. Fab and scFv ribosome display selections were performed according to published protocols. See Stafford et al., 2014, *Protein Eng. Des. Sel.* 27:97-109; Hanes and Pluckthun, *Proc. Natl. Acad. Sci. U.S.A.,* 1997, 94:4937-4942; both incorporated by reference in their entireties. After multiple rounds of selection, the DNA from RT-PCR output was cloned into an optimized vector for cell-free expression using standard molecular biology techniques. See Yin et al., *mAbs,* 2012, 4:217-225, incorporated by reference in its entirety. All constructs were HIS- and FLAG-tagged to streamline purification and testing during screening.

Antibody Fab libraries were constructed using a trastuzumab Fab sequence codon optimized for XpressCF® in a modified, commercially available p3 phagemid vector (Antibody Design Labs). Briefly, the phagemid vector was modified to express Fab heavy chains as a C-terminal p3 fusion proteins and regulatory regions (start codons, restriction enzyme sites, periplasmic leader sequences) were optimized for Fab display levels. Libraries were constructed using standard overlap expression PCR protocols with mutagenic primers targeting heavy chain complementary determining regions (CDRs) and rescued through electroporation in M13-K07 infected SS320 *E. coli* cells. See, Heckman and Pease, *Nat. Protoc.,* 2007, 2:924-932; Rajan, S. & Sidhu, S. S., *Methods Enzymol.,* 2012, 502:3-23, both incorporated by reference in their entireties. Immune libraries were similarly constructed using standard overlap PCR protocols, with heavy and light variable genes amplified from total RNA extracted from splenocytes. See Barbas II, CF & Burton, DR, Phage Display: A Laboratory Manual (2001), Cold Spring Harbor Laboratory Press, incorporated by reference in its entirety. Library selections were performed using standard phage display protocols. See Marks, J. D. & Bradbury, A., *Methods Mol. Biol.,* 2004, 248:161-76; Rajan, S. & Sidhu, S. S., *Methods Enzymol.,* 2012, 502:3-23; Barbas II, CF & Burton, DR, *Phage Display: A Laboratory Manual* (2001), Cold Spring Harbor Laboratory Press, each of which is incorporated herein by reference in its entirety. Following multiple selection rounds, Fab heavy chain pools were transferred into cell-free expression vectors for expression as His6 and FLAG-tagged IgG1. Immune scFvs were transferred into cell-free expression vectors with a 4 residue SKNK peptide leader found to facilitate expression. Immune scFvs were expressed as scFv-Fc with Flag and His6 C-terminal tags.

Libraries of antibody variants generated by selection workflow were transformed into *E. coli* and grown on agar plates with antibiotic (kanamycin). Individual colonies were grown in liquid broth (TB+kanamycin), and used as a template for DNA amplification via rolling circle amplification (RCA). The variants were then expressed in cell-free protein synthesis reactions as described in Zawada et al., *Biotechnol. Bioeng.,* 2011, 108:1570-1578 and Cai, et al., *Biotechnol. Prg.,* 2015, 823-831, each of which is incorporated by reference in its entirety.

Briefly, cell-free extracts were treated with 50 μM iodoacetamide for 30 min at room temperature (20° C.) and added to a premix containing cell-free components (see Groff et al., *mAbs,* 2014, 6:671-678 and Cai et al., *Biotechnol. Prg.,* 2015, 823-831, each of which is incorporated by reference in its entirety) and 10% (v/v) RCA DNA template (approximately 10 μg/mL DNA) for HC variants of interest, in addition to 6 μg/mL Trastuzumab LC which is present for antibody assembly but is not varied in the library. Trastuzumab LC DNA was not added to CF reactions for scFvFc libraries. Sixty microliters of cell-free reactions were incubated at 30° C. for 12 hr on a shaker at 650 rpm in 96-well plates. Four hundred to one-thousand-two-hundred colonies were screened, depending on the predicted diversity of different selection campaigns.

Following synthesis, each reaction was diluted 1:50 into PBS (pH 7.4) with 0.1% Tween-20 and 0.2% bovine serum albumin. Diluted CF material was tested for TF binding via ELISA. Briefly, 1 μg/mL of human TF (Lake Pharma) or cynomolgus TF (Sino Bio #90885-C08H) or Neutravidin (NA) (ThermoFisher #31050) were coated to 384-well polystyrene plates overnight at 4° C. in 0.1M bicarbonate (pH 8.9) buffer before they were washed and blocked with 2% BSA in PBST (PBS, 0.1% Tween-20) for 1 hour at room temperature. The diluted CF material was applied to the ELISA plates for 1 hour at 30° C. Antibody binding was detected via HRP-conjugated anti-Flag antibody (Sigma) and detection with SuperSignal ELISA Pico Chemiluminescent Substrate (ThermoFisher #37069). Binding was reported as a ratio of TF ELISA signal over NA ELISA signal. The resulting antibodies are reported in Table 6, below.

The top leads from ELISA-based screening were cultured, and plasmid minipreps were performed using a QIAprep® 96 Turbo miniprep kit (Qiagen) according to the manufacturer's instructions. 7.5 μg/mL miniprepped HC DNA and 2.5 μg/mL of the trastuzumab LC was added to 4 mL cell-free reactions and incubated overnight for 12 hr at 30° C., at 650 rpm. In the case of IgG variants with a common Trastuzumab LC, 7.5 μg/mL of the HC variant DNA and 2.5 μg/mL of the common Trastuzumab LC were added to the reaction.

Antibodies from programs 2901 and 2842 did not have the common trastuzumab LC.

Expressed variants from clarified cell-free reactions were purified via Protein A purification using a semi-automated high throughput batch purification method. Briefly, purifications were performed in a 96-well plate format where 100 μL/well of Protein-A-Sepharose resin slurry (Invitrogen #101090) was equilibrated in phosphate buffered saline (PBS), incubated with 1 mL cell-free reaction for 30 minutes with mixing followed by two washes in PBS. Antibody variants were then eluted using 180 μL/well 0.1M glycine pH 2.0-2.5 (Santa Cruz Biotechnology), neutralized with 20 μL/well 1M Tris HCl pH 8.1, and buffer exchanged into PBS+10% sucrose using a 96-well Zeba plate (7 kD MWCO, ThermoFisher #89808). Purified antibodies were quantified via high throughput capillary electrophoresis using the LabChip GXII (Perkin Elmer) against a Herceptin standard curve, according to the manufacturer's instructions.

TABLE 6

Affinity Matured (2799) Antibodies

| Antibody | $V_H$ | SEQ ID NO. | $V_L$ | SEQ ID NO. |
|---|---|---|---|---|
| SRP2799-A05 (parent) | SRP2799-A05 (parent) | 2727 | Trastuzumab LC | 3061 |
| SRP2799-B03 (parent) | SRP2799-B03 (parent) | 2736 | Trastuzumab LC | 3061 |
| SRP2799-B06 (parent) | SRP2799-B06 (parent) | 2739 | Trastuzumab LC | 3061 |

Certain antibodies were generated by phage display selection in scFv format. The scFv candidates were reformatted to scFvFc format after selection and screened as scFvFcs. Selection and screening were carried out as described above.

Rabbit antibody leads SRP-2842-G04 and SRP-2842-B01 were selected for humanization.

Human germline framework sequences from preferred gene families (e.g., IGHV3, IGHV4 and IGHJ4) were used for "CDR-grafting" the heavy chain variable region of the selected rabbit lead antibodies. Some mutations were designed in the frameworks of "CDR-grafted" heavy chain variable region sequences. Similarly, preferred human germline framework sequences from kappa light chain families (e.g., IGKV1, IGKV3, IGKJ1 and IGKJ4) were used for "CDR-grafting" the light chain variable region of the selected rabbit lead antibodies. Some mutations were designed in the frameworks of "CDR-grafted" light chain variable region sequences.

Humanized heavy chain variable region and light chain variable region sequences were fused to human IGHG1 and IGKC constant region sequences respectively to construct full-length humanized antibody heavy chain and light chain sequences.

Rabbit scFv sequences correspond to clones with IDs starting with 2842 and humanized sequences are from clone IDs 2901.

Clones with IDs starting with 2900 are HC from phage display with common trastuzumab LC.

Example 2: Preparation of scFvs

A single-chain antibody is made in either the $V_HV_L$ or $V_LV_H$ orientation with a linker sequence between the $V_H$ and $V_L$ domains. Typically, scFv linkers are composed of $(GGGGS)_n$ repeats where n=3, 4, 5, or 6 for linkers of 15, 20, 25, or 30 residues respectively, such as $(GGGGS)_3$ (SEQ ID NO: 3070). For cell-free expression, an N-terminal Met is added, but for mammalian expression a leader peptide is added. On the C-terminal end of the scFv, an Fc sequence can be added to extend in vivo half-life or the scFv can be used directly. An optional linker sequence can be incorporated between the scFv and the Fc. An exemplary scFv-Fc linker sequence is AAGSDQEPKSS (SEQ ID NO: 3071). C-terminal affinity tags can optionally be added to facilitate purification and assay development. An exemplary affinity tag is a C-terminal FlagHis tag GSGDYKDDDDKGSGHHHHHH (SEQ ID NO: 3069). A stop codon is typically inserted at the end of the sequence. Exemplary scFv's of the present disclosure include SEQ ID NOs: 3073 and 3079, with an N-terminal Met residue, a SKNK peptide leader, a $V_H$ domain, a GGGGSGGGGSGGGGS (SEQ ID NO: 3070) linker, and a $V_L$ domain. Exemplary scFvFc's of the present disclosure include these scFv's further including an AAGSDQEPKSS (SEQ ID NO: 3071) linker, an Fc domain, a FlagHis tag, and a stop codon.

Exemplary scFv's embodiment are illustrated in SEQ ID NOs: 3073 and 3079.

Example 3: Melting Temperature, Affinity, and Kinetic Binding Analyses

A protein thermal shift assay was carried out by mixing the protein to be assayed with an environmentally sensitive dye (SYPRO Orange, Life Technologies #S-6650) and monitoring the fluorescence of the mixture in real time as it underwent controlled thermal denaturation. Protein solutions between 0.2-2 mg/mL were mixed at a 1:1 volumetric ratio with a solution of SYPRO Orange solution diluted 250-fold in PBS+10% sucrose. 10 μL aliquots of the protein-dye mixture were dispensed in quadruplicate in a 384-well microplate (Bio-Rad #MSP-3852). The plate was sealed with an optically clear sealing film (Bio-Rad #MSB-1001) and placed in a 384-well plate real-time thermocycler (Bio-Rad CFX384 Real Time System). The protein-dye mixture was heated from 25° C. to 95° C., at increments of 0.2° C. per cycle, allowing 3 seconds of equilibration at each temperature before taking a fluorescence measurement. At the end of the experiment, the transition melting temperatures (TM1 and TM2) were determined using the Bio-Rad CFX manager software. TM1 represents the melting temperature of the Fc domain. TM2 represents the melting temperature of the Fab domain. For scFvFc variants, typically only a single melting temperature was observed. Results are shown in Tables 7-11 below.

Anti-Fc polyclonal antibodies were immobilized onto a CM4 chip (Cytiva #BR100534) using amine coupling chemistry (Human Antibody Capture Kit, Cytiva #BR100839). The immobilization steps were carried out at a flow rate of 25 μL/min in 1×HBS-EP+buffer (Cytiva #BR100669). The sensor surfaces were activated for 7 min with a mixture of N-hydroxysuccinimide (NHS, 0.05 M) and 1-ethyl-3-(3-dimethylaminopropyl)-carbodiimide (EDC, 0.2 M). The anti-Fc polyclonal antibodies were injected over all 4 flow cells at a concentration of 25 μg/mL in 10 mM sodium acetate, pH 4.5, for 7 min. Ethanolamine (1 M, pH 8.5) was injected for 7 min to block any remaining activated groups. Approximately 6,000 response units (RU) of capture antibody was immobilized on each flow cell.

Off-rate and kinetic binding experiments were performed at 25° C. using 1×HBS-EP+buffer. Antibodies were injected over the anti-Fc surface at a concentration of 3 μg/mL for 12 seconds at a flow rate of 10 μL/min on flow cells 2, 3 and 4, followed by a buffer wash for 30 seconds at the same flow rate. Single point off-rate analysis was carried out using an antigen concentration of 100 nM. Detailed kinetic characterization of antibody samples was carried out with a range of antigen concentrations from about 1 to 100 nM and 1 injection of 0 nM antigen (for example, 100, 25, 12.5, 3.125, 0.781 and 0 nM). After capturing ligand (antibody) on the anti-Fc surface, the analyte (human TF, Lake Pharma; cynomolgus TF, Sino Bio #90885-$C_{08}$H; mouse TF, R&D Systems #3178-PA) was bound for 180 seconds, followed by a 420 second dissociation phase at a flow rate of 50 μL/min. Between each ligand capture and analyte binding cycle, regeneration was carried out using 2 injections of 10 mM glycine pH 2.0 for 30 seconds at 30 μL/min, followed by a 30 second buffer wash step.

The data were fit with the Biacore T200 Evaluation software, using a 1:1 Langmuir binding model. $K_D$ (affinity, nM) was determined as a ratio of the kinetic rate constants calculated from the fits of the association and dissociation phases.

Example 4: Flow Cytometry-Based Cell Binding Assay

HEK293T, BxPC3 cells (TF positive) and NCI-H1703 (TF negative) cells were obtained from ATCC (American Type Culture Collection) and maintained in DMEM:F12 (1:1), high glucose (Corning) supplemented with 10% heat-inactivated fetal bovine serum (ThermoScientific), 1× Penicillin/Streptomycin (Corning) and 2 mmol glutamax (Thermo Fisher Scientific). To generate cells that stably expressing human tissue factor (HEK293T-humanTF) or cynomolgus tissue factor (HEK293T-cynoTF), HEK293T cells were transfected with plasmid vectors that contain the corresponding protein sequence and stable clones were selected with puromycin.

For a fluorescence-activated cell sorting (FACS) cell-binding assay, cells were collected by Accutase and counted by the Vi-CELL Cell Viability Analyzersharvested and, then re-suspended in FACS buffer (DPBS buffer supplemented with 1% bovine serum albumin). A total of 200,000 cells in 100 μL were incubated on ice with 100 μL of anti-TF antibodies in each well of a 96-well plate. Cells were washed twice with ice-cold FACS buffer and then incubated on ice for 60 mins with 5 μg/mL Alexa 647-labeled donkey anti-human Fc antibody (Jackson ImmunoResearch). Unstained cells and cells stained with secondary antibody alone were used as controls. Cells were washed twice with FACS buffer and analyzed using a BD FACS Canto system. Geometric mean fluorescence intensities (MFI) were fitted using non-linear regression analysis with one site specific binding equation on GraphPad Prism (GraphPad Software; La Jolla, CA).

Example 5: Thrombin Generation Assay

Antibodies and antibody drug conjugates (ADC) as described below were assessed for inhibition of thrombin production using a Thrombin Generation Assay Kit (Technoclone #5006010). All kit reagents were prepared as described in the manufacturer's protocol. A thrombin calibration curve was generated using the kit's thrombin standard and thrombin generation in test samples was calculated using this standard curve. Antibodies were tested at 100 nM and dilutions were made using the kit's assay buffer. In each well of a black Maxisorp plate (NUNC #475515), 10 μL of the kit's RC reagent was incubated with 5 μL of the antibody dilution for 10 minutes at room temperature. 35 μL of the kit's human plasma was added to each well along with 50 μL of the thrombin fluorogenic substrate. The fluorescence at 360 nm/360 nm was read immediately, every minute for 60 minutes at 37° C. Relative fluorescence units were converted to thrombin concentration based on the calibration curve.

Example 6: Cell-Killing Analysis

The internalization ability of the lead antibodies was evaluated by an ADC cell killing assay on Tissue Factor positive BxPC3 cells. A total of 625 cells in a volume of 25 μL were seeded in each well of a 384-well flat bottom white polystyrene plate. Lead antibodies were formulated at 4-fold starting concentration in the cell culture medium and filtered through MultiScreenHTS 96-Well Filter Plates (Millipore; Billerica, Massachusetts). 12.5 μL of antibody was added into each treatment well, and 12.5 μL of anti-human Fc nanobody conjugated to SC236 was then added into each well at a fixed final concentration of 20 nM. Assay plates were cultured at 37° C. in a $CO_2$ incubator for 120 hrs before assay. For cell viability measurement, 30 μL of Cell Titer-Glo® reagent (Promega Corp. Madison, WI) was added into each well, and plates were processed as per product instructions. Relative luminescence was measured on an ENVISION® plate reader (Perkin-Elmer; Waltham, MA). Relative luminescence readings were converted to percent viability using untreated cells as controls. Data was fitted with non-linear regression analysis, using a log (inhibitor) vs. response-variable slope, 4 parameter fit with GraphPad Prism (GraphPad v 5.0, Software; San Diego, California).

Example 7: FX Conversion Assay

Antibodies were assessed for inhibition of FX activation using a Tissue Factor Activity Assay Kit (Abcam #ab108906). The kit's reagents were prepared as described in the manufacturer's protocol. Antibodies were tested at 10 nM, 100 nM, and 1000 nM. All dilutions were made in the sample dilution buffer provided in the kit. 10 μL of the tissue factor reagent was incubated with 10 μL of antibody at room temperature for 20 minutes. 10 μL each of the FVII reagent and the FX reagent were diluted with 40 μL of the kit's assay diluent and added to each well of the provided 96-well microplate. The pre-incubated TF+antibody was added to the FVII+FX mixture and incubated at 37° C. for 30 minutes. 20 μL of FXa substrate was added to each well. The absorbance at $OD_{405}$ was read immediately, every 5 minutes or 25 minutes while incubating at 37° C. The percent inhibition of FX conversion for 1000 nM antibody at the final timepoint was calculated relative to a no-antibody control.

Example 8: Characteristics of Illustrative Anti-TF Antibodies

Tables 7 through 20 show results obtained using the illustrative antibodies described herein.

Tables 7 through 8 show results for melting temperatures from affinity-matured antibodies from initial primary screen leads, from mouse immune library scFvFc candidates from the initial primary screen and for humanized rabbit antibodies.

Tables 9 through 13 show results obtained for single point off-rates for affinity-matured antibodies form initial primary screen leads, for scFvFc candidates for humanization as well as melting temperatures for rabbit immune library scFvFc candidates for humanization, for humanized rabbit antibodies, for affinity-matured antibodies and humanized rabbit antibodies, for mouse scFvFc variants, and for lead antibody/ADC candidates.

Tables 14 through 18 show results for cell binding and/or cell killing for illustrative antibodies of the disclosure.

Tables 19 through 20 show results for FX inhibition assays for illustrative antibodies of the disclosure.

TABLE 7

Melting Temperatures for Affinity-Matured Antibodies from Initial Primary Screen Leads

| Variant ID | DSF TM2 (° C.) |
|---|---|
| SRP2799-A05 (parent) | 81.4 |
| SRP2799-B03 (parent) | 82.1 |
| SRP2799-B06 (parent) | 85.7 |
| SRP2900-A01 | 78.1 |
| SRP2900-A02 | 83.6 |
| SRP2900-A03 | 77.2 |
| SRP2900-A04 | 78.8 |
| SRP2900-A06 | 81.5 |
| SRP2900-A07 | 81.9 |
| SRP2900-A08 | 80.3 |
| SRP2900-A09 | 82.2 |
| SRP2900-A10 | 79.4 |
| SRP2900-A11 | 82.3 |
| SRP2900-B01 | 79.8 |
| SRP2900-B02 | 80.3 |
| SRP2900-B03 | 81.6 |
| SRP2900-B04 | 82.5 |
| SRP2900-B05 | 81.9 |
| SRP2900-B06 | 80.3 |
| SRP2900-B07 | 85.5 |
| SRP2900-B08 | 75.4 |
| SRP2900-B09 | 82.8 |
| SRP2900-B10 | 76.2 |
| SRP2900-B11 | 78.2 |
| SRP2900-C01 | 82.1 |
| SRP2900-C02 | 80.4 |
| SRP2900-C03 | 80.8 |
| SRP2900-C04 | 81.3 |
| SRP2900-C05 | 82.7 |
| SRP2900-C06 | 80.7 |
| SRP2900-C07 | 79.3 |
| SRP2900-C09 | 81.6 |
| SRP2900-C10 | 81.7 |
| SRP2900-C11 | 82.4 |
| SRP2900-D01 | 84.2 |
| SRP2900-D02 | 82 |

TABLE 7-continued

Melting Temperatures for Affinity-Matured Antibodies from Initial Primary Screen Leads

| Variant ID | DSF TM2 (° C.) |
|---|---|
| SRP2900-D03 | 81.4 |
| SRP2900-D04 | 79.3 |
| SRP2900-D05 | 84 |
| SRP2900-D06 | 81 |
| SRP2900-D07 | 84.6 |
| SRP2900-D08 | 83.7 |
| SRP2900-D09 | 82.5 |
| SRP2900-D10 | 78.7 |
| SRP2900-D11 | 78.6 |
| SRP2900-E01 | 82.7 |
| SRP2900-E02 | 83.4 |
| SRP2900-E03 | 84.1 |
| SRP2900-E04 | 76.8 |
| SRP2900-E05 | 83 |
| SRP2900-E06 | 81.7 |
| SRP2900-E07 | 84.9 |
| SRP2900-E08 | 82 |
| SRP2900-E09 | 79.5 |
| SRP2900-E10 | 81.9 |
| SRP2900-E11 | 80.3 |
| SRP2900-F02 | 81.8 |
| SRP2900-F03 | 76.3 |
| SRP2900-F04 | 81.7 |
| SRP2900-F05 | 83.6 |
| SRP2900-F06 | 79.7 |
| SRP2900-F07 | 83.1 |
| SRP2900-F08 | 83.2 |
| SRP2900-F09 | 83.5 |
| SRP2900-F10 | 82.1 |
| SRP2900-F11 | 82.3 |
| SRP2900-G01 | 80.8 |
| SRP2900-G02 | 81.4 |
| SRP2900-G03 | 82.5 |
| SRP2900-G04 | 79.3 |
| SRP2900-G05 | 81.3 |
| SRP2900-G06 | 83.1 |
| SRP2900-G07 | 83 |
| SRP2900-G08 | 78.3 |
| SRP2900-G09 | 82.5 |
| SRP2900-G10 | 79 |
| SRP2900-G11 | 80.6 |
| SRP2900-H01 | 79.5 |
| SRP2900-H02 | 80.4 |
| SRP2900-H03 | 81.6 |
| SRP2900-H04 | 80.7 |
| SRP2900-H05 | 81.8 |
| SRP2900-H06 | 82 |
| SRP2900-H07 | 83.3 |
| SRP2900-H08 | 79.8 |
| SRP2900-H09 | 83.9 |
| SRP2900-H10 | 78.8 |
| SRP2900-H11 | 80.4 |

TABLE 8

Melting Temperatures for Humanized Rabbit Antibodies.

| Variant ID | DSF TM2 (° C.) |
|---|---|
| 2842-B01 HC1/LC1 | 87.3 |
| 2842-B01 HC1/LC2 | 82.4 |
| 2842-B01 HC1/LC3 | 87.6 |
| 2842-B01 HC2/LC1 | 86.3 |
| 2842-B01 HC2/LC3 | 87.6 |
| 2842-B01 HC3/LC1 | 86.5 |
| 2842-B01 HC3/LC2 | 81.5 |
| 2842-G04 HC1/LC2 | 80 |
| 2842-G04 HC2/LC1 | 80.4 |
| 2842-G04 HC2/LC2 | 80.2 |

TABLE 8-continued

| Melting Temperatures for Humanized Rabbit Antibodies. | |
|---|---|
| Variant ID | DSF TM2 (° C.) |
| 2842-G04 HC3/LC2 | 86.7 |
| 2842-G04 HC3/LC3 | 82.3 |

TABLE 9

Single point off-rates for affinity-matured antibodies from initial primary screen leads.

| Variant ID | Biacore human TF single point off-rate kinetics kd (1/s) | Biacore cynomolgus TF single point off-rate kinetics kd (1/s) |
|---|---|---|
| SRP2799-A05 (parent) | 3.04E−03 | 3.37E−02 |
| SRP2799-B03 (parent) | 4.15E−03 | 1.69E−03 |
| SRP2799-B06 (parent) | 8.27E−03 | 1.66E−03 |
| SRP2900-A02 | 1.16E−03 | 7.61E−04 |
| SRP2900-C01 | 1.83E−03 | 1.18E−03 |
| SRP2900-C11 | 8.42E−04 | 2.57E−03 |
| SRP2900-E02 | 5.28E−04 | 1.82E−03 |
| SRP2900-E06 | 9.78E−04 | 6.89E−04 |
| SRP2900-E07 | 5.11E−04 | 1.13E−03 |
| SRP2900-F02 | 2.74E−03 | 6.96E−04 |
| SRP2900-F06 | 4.23E−03 | 1.84E−03 |
| SRP2900-F08 | 1.31E−03 | 6.65E−04 |
| SRP2900-F09 | 1.39E−03 | 2.15E−03 |
| SRP2900-F11 | 2.04E−03 | 1.15E−03 |
| SRP2900-G02 | 4.15E−03 | 1.41E−03 |
| SRP2900-G03 | 6.99E−04 | 1.95E−03 |
| SRP2900-G05 | 1.15E−03 | 6.67E−04 |
| SRP2900-H06 | 3.47E−03 | 6.48E−04 |
| SRP2900-H07 | 2.05E−03 | 1.30E−03 |
| SRP2900-H09 | 1.69E−03 | 5.84E−03 |
| SRP2900-H11 | 2.50E−03 | 9.46E−04 |

TABLE 10

Rabbit immune library scFvFc candidates for humanization.

| Variant ID | Biacore human TF single point off-rate kinetics kd (1/s) | Biacore cynomolgus TF single point off-rate kinetics kd (1/s) | DSF TM (° C.) |
|---|---|---|---|
| 2842-B01 (scFvFc parent) | 3.03E−04 | 1.27E−03 | 58.3 |
| 2842-G04 (scFvFc parent) | 6.04E−04 | 1.41E−03 | 54.3 |

TABLE 11

Single point off-rates for humanized rabbit antibodies.

| Variant ID | Biacore human TF single point off-rate kinetics kd (1/s) | Biacore cynomolgus TF single point off-rate kinetics kd (1/s) |
|---|---|---|
| 2842-B01 HC1/LC1 | 7.27E−04 | 3.52E−03 |
| 2842-B01 HC1/LC2 | 6.91E−04 | 1.42E−03 |
| 2842-B01 HC1/LC3 | 5.40E−04 | 1.17E−03 |
| 2842-B01 HC2/LC1 | 5.23E−04 | 9.91E−04 |
| 2842-B01 HC2/LC3 | 7.26E−04 | 3.14E−03 |
| 2842-B01 HC3/LC1 | 4.16E−04 | 1.87E−03 |
| 2842-B01 HC3/LC2 | 3.61E−04 | 7.82E−04 |
| 2842-G04 HC2/LC1 | 6.78E−04 | 3.03E−03 |
| 2842-G04 HC2/LC2 | 7.36E−04 | 1.70E−03 |

TABLE 12

Biacore kinetics for affinity-matured antibodies and humanized rabbit antibodies.

| | | Biacore human TF kinetics | | | Biacore cynomolgus TF kinetics | | |
|---|---|---|---|---|---|---|---|
| mAb # | Variant ID | ka (1/Ms) | kd (1/s) | KD (M) | ka (1/Ms) | kd (1/s) | KD (M) |
| 36 | 2900-A02 | 3.03E+05 | 1.44E−03 | 4.77E−09 | 2.85E+05 | 7.43E−04 | 2.61E−09 |
| 42 | 2900-C11 | 1.88E+05 | 6.74E−04 | 3.59E−09 | 1.28E+05 | 3.09E−03 | 2.42E−08 |
| 43 | 2900-F06 | 3.11E+05 | 5.94E−03 | 1.91E−08 | 3.16E+05 | 2.31E−03 | 7.33E−09 |
| 44 | 2900-F09 | 3.62E+05 | 1.96E−03 | 5.42E−09 | 1.64E+05 | 3.09E−03 | 1.89E−08 |
| 45 | 2900-H06 | 5.47E+05 | 4.26E−03 | 7.78E−09 | 1.21E+06 | 3.09E−04 | 2.55E−10 |
| 46 | 2900-H09 | 3.62E+05 | 2.26E−03 | 6.24E−09 | 1.64E+05 | 6.81E−03 | 4.16E−08 |
| 37 | 2842-B01 HC3/LC2 | 5.72E+04 | 4.18E−04 | 7.30E−09 | 7.24E+04 | 1.13E−03 | 1.56E−08 |
| 47 | 2842-B01 HC3/LC1 | 5.40E+04 | 4.22E−04 | 7.81E−09 | 8.27E+04 | 1.66E−03 | 2.01E−08 |
| 48 | 2842-B01 HC1/LC3 | 7.12E+04 | 1.24E−03 | 1.74E−08 | 1.21E+05 | 7.35E−03 | 6.07E−08 |
| 49 | 2842-G04 HC2/LC2 | 6.25E+04 | 8.65E−04 | 1.38E−08 | 8.08E+04 | 2.41E−03 | 2.99E−08 |

TABLE 13

| Biacore kinetics for lead antibody/ADC. | | | | | | | |
|---|---|---|---|---|---|---|---|
| | | | | | Biacore cynomolgus TF kinetics | | |
| Conjugate | | Biacore human TF kinetics | | | ka | kd | |
| or mAb # | Description | ka (1/Ms) | kd (1/s) | KD (M) | (1/Ms) | (1/s) | KD (M) |
| mAb #41 | 2900-A02 F241/F404TAG | 4.87E+05 | 1.82E−03 | 3.73E−09 | 7.52E+05 | 8.43E−04 | 1.12E−09 |
| Conjugate 2 | 2900-A02 F241/F404 LP1 | 5.08E+05 | 1.89E−03 | 3.71E−09 | 7.47E+05 | 8.92E−04 | 1.19E−09 |

TABLE 14

| Cell Killing and Cell Binding Activity of Antibodies from SRP2799. | | | | | | |
|---|---|---|---|---|---|---|
| | | | BxPC3 Cell Killing | | BxPC3 Cell Binding | |
| Sample | Expression, IgG (ug/mL) | % monomer | EC50 (nM) | Span (%) | Kd (nM) | Bmax (MFI) |
| SRP2799-A05 | 2622 | 89 | 0.092 | 95 | 26.1 | 52703 |
| SRP2799-B03 | 1758 | 81 | 0.072 | 97 | 4.7 | 45417 |
| SRP2799-B06 | 1453 | 78 | 0.06 | 96 | 4.1 | 46326 |

TABLE 15

| Cell Killing Activity of Antibodies from SRP2842. | | | |
|---|---|---|---|
| | [scFv-Fc] | BxPC3 Cell Killing | |
| Sample | ug/mL | EC50 (nM) | Span (%) |
| SRP2842-B01 | 761 | 0.057 | 91.1 |
| SRP2842-G04 | 998 | 0.059 | 94.2 |
| Tisotumab | 4100 | 0.023 | 94.7 |

TABLE 16

| Cell Binding Activity of Antibodies from SRP2900 and SRP2842. | | | | | | | |
|---|---|---|---|---|---|---|---|
| | | HEK293T-human TF | | HEK293T-cyno TF | | HEK293T | |
| mAb # | Sample Name | Bmax (MFI) | Kd (nM) | Bmax (MFI) | Kd (nM) | Bmax (MFI) | Kd (nM) |
| 36 | 2900-A02 | 306977 | 1.2 | 443667 | 14 | 1503 | NC |
| 42 | 2900-C11 | 274969 | 0.8 | 426333 | 16 | 1525 | NC |
| 43 | 2900-F06 | 253290 | 1.7 | 419173 | 21 | 1401 | NC |
| 44 | 2900-F09 | 295588 | 0.9 | 428667 | 29 | 2046 | NC |
| 45 | 2900-H06 | 302074 | 1.3 | 441333 | 7.5 | 1732 | NC |
| 46 | 2900-H09 | 299871 | 0.93 | 482667 | 38 | 1253 | NC |
| 37 | 2842-B01__HC3/LC2 | 334235 | 3.9 | 493000 | 3.9 | 1062 | NC |
| 47 | 2842-B01__HC3/LC1 | 351065 | 3.3 | 500667 | 3.2 | 1285 | NC |
| 48 | 2842-B01__HC1/LC3 | 317623 | 2.3 | 485667 | 3.4 | 1232 | NC |
| 49 | 2842-G04__HC2/LC2 | 243765 | 1.4 | 464667 | 5.1 | 1366 | NC |

TABLE 17

| Cell Killing and Cell Binding Activity of Antibodies from SRP2901. | | | | | |
|---|---|---|---|---|---|
| | | BxPC3 Cell Killing | | BxPC3 Cell Binding | |
| Sample | [IgG] ug/mL | EC50 (nM) | Span (%) | Kd (nM) | Bmax (MFI) |
| SRP2901-B05 | 395 | 0.059 | 84 | 0.389 | 42810 |
| SRP2901-D03 | 456 | 0.184 | 77.4 | 0.344 | 29147 |
| SRP2901-E03 | 252 | 0.166 | 92.4 | 0.386 | 35248 |
| SRP2901-F01 | 593 | 0.364 | 87 | 0.61 | 25351 |
| SRP2842-B01 | 761 | 0.057 | 91.1 | 0.089 | 39002 |
| SRP2842-G04 | 998 | 0.059 | 94.2 | 0.058 | 34919 |

TABLE 18

| Cell Killing Activity of Antibodies from SRP2799, 2900 and 2916. | | | |
|---|---|---|---|
| | [IgG] | BxPC3 Cell Killing | |
| Sample | ug/mL | EC50 (nM) | Span (%) |
| SRP2799-A05 | 1243 | 0.054 | 98.92 |
| SRP2799-B03 | 1088 | 0.059 | 96.26 |

TABLE 18-continued

| Cell Killing Activity of Antibodies from SRP2799, 2900 and 2916. | | | |
|---|---|---|---|
| | [IgG] | BxPC3 Cell Killing | |
| Sample | ug/mL | EC50 (nM) | Span (%) |
| SRP2799-B06 | 1248 | 0.06 | 88.79 |
| SRP2900-A02 | 1286 | 0.08 | 84.59 |
| SRP2900-C11 | 775 | 0.057 | 85.14 |
| SRP2900-E07 | 787 | 0.174 | 81.95 |
| SRP2900-F02 | 1197 | 0.056 | 95.85 |
| SRP2900-F06 | 708 | 0.108 | 87.57 |
| SRP2900-F08 | 1157 | 0.057 | 93.67 |
| SRP2900-F09 | 1194 | 0.059 | 90.6 |
| SRP2900-F11 | 1293 | 0.069 | 90.07 |
| SRP2900-G02 | 1106 | 0.104 | 93.11 |
| SRP2900-G05 | 1179 | 0.059 | 95.94 |
| SRP2900-H06 | 1240 | 0.061 | 94.04 |
| SRP2900-H09 | 1199 | 0.035 | 88.18 |
| SRP2900-H11 | 991 | 0.067 | 90.92 |

TABLE 19

| Inhibition of FX Conversion by Affinity-Matured Antibodies from Initial Primary Screen Leads. | |
|---|---|
| Variant ID | FX conversion (% inhibition) |
| SRP2799-A05 (parent) | 1.12% |
| SRP2799-B03 (parent) | 2.41% |
| SRP2799-B06 (parent) | −1.01% |
| SRP2900-A01 | 36.97% |
| SRP2900-A02 | 0.21% |
| SRP2900-A03 | 26.28% |
| SRP2900-A04 | 38.58% |
| SRP2900-A06 | 36.84% |
| SRP2900-A07 | 28.44% |
| SRP2900-A08 | 41.86% |
| SRP2900-A09 | 46.87% |
| SRP2900-A11 | 31.74% |
| SRP2900-B01 | 38.70% |
| SRP2900-B02 | 26.97% |
| SRP2900-B03 | 44.14% |
| SRP2900-B04 | 46.27% |
| SRP2900-B05 | 35.51% |
| SRP2900-B06 | 28.16% |
| SRP2900-B07 | 42.25% |
| SRP2900-B08 | 43.33% |
| SRP2900-B09 | 35.02% |
| SRP2900-B10 | 33.33% |
| SRP2900-B11 | 22.38% |
| SRP2900-C01 | 16.43% |
| SRP2900-C02 | 29.56% |
| SRP2900-C04 | 36.70% |
| SRP2900-C05 | 35.67% |
| SRP2900-C07 | 41.57% |
| SRP2900-C10 | 42.07% |
| SRP2900-C11 | 12.44% |
| SRP2900-D01 | 32.68% |
| SRP2900-D02 | 32.11% |
| SRP2900-D03 | 37.37% |
| SRP2900-D04 | 45.95% |
| SRP2900-D05 | 33.58% |
| SRP2900-D06 | 46.18% |
| SRP2900-D07 | 47.42% |
| SRP2900-D08 | 44.87% |
| SRP2900-D09 | 30.02% |
| SRP2900-D10 | 36.95% |
| SRP2900-D11 | 51.41% |
| SRP2900-E01 | 40.44% |
| SRP2900-E02 | 17.72% |
| SRP2900-E03 | 48.68% |
| SRP2900-E04 | 25.91% |
| SRP2900-E05 | 23.50% |
| SRP2900-E06 | 18.71% |
| SRP2900-E07 | 15.61% |
| SRP2900-E08 | 45.79% |
| SRP2900-E09 | 32.16% |
| SRP2900-E10 | 50.72% |
| SRP2900-E11 | 39.94% |
| SRP2900-F02 | 0.23% |
| SRP2900-F04 | 47.26% |
| SRP2900-F05 | 25.11% |
| SRP2900-F06 | 1.72% |
| SRP2900-F07 | 30.27% |
| SRP2900-F08 | 9.78% |
| SRP2900-F09 | 5.23% |
| SRP2900-F10 | 32.52% |
| SRP2900-F11 | 6.38% |
| SRP2900-G01 | 25.06% |
| SRP2900-G02 | −0.11% |
| SRP2900-G03 | 20.01% |
| SRP2900-G04 | 31.24% |
| SRP2900-G05 | 12.05% |
| SRP2900-G06 | 21.37% |
| SRP2900-G07 | 38.31% |
| SRP2900-G08 | 38.93% |
| SRP2900-G09 | 30.43% |
| SRP2900-G10 | 48.66% |
| SRP2900-G11 | 40.85% |
| SRP2900-H01 | 30.48% |
| SRP2900-H02 | 40.42% |
| SRP2900-H03 | 40.81% |
| SRP2900-H04 | 36.26% |
| SRP2900-H05 | 36.24% |
| SRP2900-H06 | 4.04% |
| SRP2900-H07 | 13.54% |
| SRP2900-H08 | 32.22% |
| SRP2900-H09 | 4.48% |
| SRP2900-H10 | 45.40% |
| SRP2900-H11 | −3.63% |

TABLE 20

| Inhibition of FX Conversion by scFvFc Parents and Humanized Rabbit Antibodies. | |
|---|---|
| Variant ID | FX conversion (% inhibition) |
| 2842-B01 (scFvFc parent) | 2.54% |
| 2842-G04 (scFvFc parent) | 2.29% |
| 2842-B01 HC1/LC1 | −0.45% |
| 2842-B01 HC1/LC2 | −0.99% |
| 2842-B01 HC1/LC3 | 0.77% |
| 2842-B01 HC2/LC1 | −3.76% |
| 2842-B01 HC2/LC3 | −0.42% |
| 2842-B01 HC3/LC1 | −1.60% |
| 2842-B01 HC3/LC2 | −0.84% |
| 2842-G04 HC2/LC1 | −22.15% |
| 2842-G04 HC2/LC2 | 0.62% |

SYNTHETIC EXAMPLES

The present examples below describe the preparation and testing of the following linker-payloads, antibodies and conjugates.

Linker Payloads.

| LP No. | Linker payload description | Linker release mechanism |
|---|---|---|
| 1 | DBCO-Valcit-pAB-hemiasterlin | Cathepsin cleavable |

-continued

| LP No. | Linker payload description | Linker release mechanism |
|---|---|---|
| 2 | DBCO-β-Glucuronide-PEG12-Exatecan | β-Glucuronidase cleavable |
| 3 | DBCO-nnAA-PEG13-VKG-Exatecan | Cathepsin cleavable |
| 4 | DBCO-nnAA-PEG13-AAN-Exatecan | Legumain (LGMN) cleavable |

-continued

| LP No. | Linker payload description | Linker release mechanism |
|---|---|---|
| 5 | DBCO-nnAA-PEG13-AAA-Exatecan | Cathepsin cleavable |

Antibodies.

| mAb | Name | Conjugation site on HC | LC and/or Conjugation site | mAb |
|---|---|---|---|---|
| 36 | aTF_2900-A02_HC_Y180/F404TAG_SerOpt pAzMeF; Trastuzumab LC SerOpt | Y180/F404 (SEQ ID NO: 3168) | (SEQ ID NO: 3179) | 2900-A02 HC/trastuzumab LC |
| 37 | aTF_2842-B01_Hc3_Y180/F404TAG pAzMeF; aTF_2842-B01_Lc2 | Y180/F404 (SEQ ID NO: 3169) | (SEQ ID NO: 3180) | 2842-B01-Hc3/Lc2 |
| 38 | aTF_2900-A02_HC_Y180/F404TAG_SerOpt pAzMeF; trastuzumab LC SerOpt K42TAG/E161TAG/TCT162AGC pAzMeF | Y180/F404 (SEQ ID NO: 3168) | K42/E161 (SEQ ID NO: 3184) | 2900-A02 HC/trastuzumab LC |
| 39 | aTF_2900-A02_HC_Y180/F404TAG_SerOpt pAzMeF; trastuzumab LC SerOpt K42TAG pAzMeF | Y180/F404 (SEQ ID NO: 3168) | K42 (SEQ ID NO: 3185) | 2900-A02 HC/trastuzumab LC |
| 40 | aTF_2900-A02_HC_Y180/F241/F404TAG_SerOpt pAzMeF; trastuzumab LC SerOpt K42TAG pAzMeF | Y180/F241/F404 (SEQ ID NO: 3177) | K42 (SEQ ID NO: 3185) | 2900-A02 HC/trastuzumab LC |
| 41 | aTF_2900-A02_HC_F241/F404TAG_SerOpt pAzMeF; Trastuzumab LC SerOpt | F241/F404 (SEQ ID NO: 3178) | (SEQ ID NO: 3179) | 2900-A02 HC/trastuzumab LC |
| 42 | aTF_2900-C11_HC_Y180/F404TAG_SerOpt; Trastuzumab LC SerOpt | Y180/F404 (SEQ ID NO: 3186) | (SEQ ID NO: 3179) | 2900-A02 HC/trastuzumab LC |
| 43 | aTF_2900-F06_HC_Y180/F404TAG_SerOpt; Trastuzumab LC SerOpt | Y180/F404 (SEQ ID NO: 3187) | (SEQ ID NO: 3179) | 2900-F06 HC/trastuzumab LC |
| 44 | aTF_2900-F09_HC_Y180/F404TAG_SerOpt; Trastuzumab LC SerOpt | Y180/F404 (SEQ ID NO: 3188) | (SEQ ID NO: 3179) | 2900-F09 HC/trastuzumab LC |

-continued

| mAb | Name | Conjugation site on HC | LC and/or Conjugation site | mAb |
|---|---|---|---|---|
| 45 | aTF_2900-H06_HC_Y180/F404TAG_SerOpt; Trastuzumab LC SerOpt | Y180/F404 (SEQ ID NO: 3189) | (SEQ ID NO: 3179) | 2900-H06 HC/trastuzumab LC |
| 46 | aTF_2900-H09_HC_Y180/F404TAG_SerOpt; Trastuzumab LC SerOpt | Y180/F404 (SEQ ID NO: 3190) | (SEQ ID NO: 3179) | 2900-H09 HC/trastuzumab LC |
| 47 | aTF_2842-B01_HC3_Y180/F404TAG; aTF_2842-B01_LC1 | Y180/F404 (SEQ ID NO: 3169) | (SEQ ID NO: 3181) | |
| 48 | aTF_2842-B01_HC1_Y180/F404TAG; aTF_2842-B01_LC3 | Y180/F404 (SEQ ID NO: 3175) | (SEQ ID NO: 3182) | |
| 49 | aTF_2842-G04_HC2_Y180/F404TAG; aTF_2842-G04_LC2 | Y180/F404 (SEQ ID NO: 3176) | (SEQ ID NO: 3183) | |
| 50 | | Y180/F241/Y391/F404 (SEQ ID NO: 3191) | (SEQ ID NO: 3179) | |

Antibody-Drug Conjugates.

| Conjugate | Conjugation site on HC | Conjugation site on LC | mAb | LP |
|---|---|---|---|---|
| 1 | Y180/F404 (SEQ ID NO: 3168) | (SEQ ID NO: 3179) | 2900-A02 | LP1 |
| 2 | F241/F404 (SEQ ID NO: 3178) | (SEQ ID NO: 3179) | 2900-A02 | LP1 |
| 3 | Y180/F404 (SEQ ID NO: 3168) | K42 (SEQ ID NO: 3185) | 2900-A02 | LP1 |
| 4 | Y180/F241/F404 (SEQ ID NO: 3177) | (SEQ ID NO: 3179) | 2900-A02 | LP1 |
| 5 | Y180/F404 (SEQ ID NO: 3168) | K42/E161 (SEQ ID NO: 3184) | 2900-A02 | LP1 |
| 6 | Y180/F241/F404 (SEQ ID NO: 3177) | K42 (SEQ ID NO: 3185) | 2900-A02 | LP1 |
| 7 | F241/F404 (SEQ ID NO: 3178) | (SEQ ID NO: 3179) | 2900-A02 | LP2 |
| 8 | Y180/F241/F404 (SEQ ID NO: 3177) | K42 (SEQ ID NO: 3185) | 2900-A02 | LP2 |
| 9 | Y180/F404 (SEQ ID NO: 3168) | (SEQ ID NO: 3179) | 2900-A02 | LP2 |
| 10 | Y180/F404 (SEQ ID NO: 3168) | (SEQ ID NO: 3179) | 2900-A02 | LP3 |
| 11 | Y180/F404 (SEQ ID NO: 3168) | (SEQ ID NO: 3179) | 2900-A02 | LP4 |
| 12 | Y180/F404 (SEQ ID NO: 3168) | (SEQ ID NO: 3179) | 2900-A02 | LP5 |
| 18 | Y180/F404 (SEQ ID NO: 3169) | (SEQ ID NO: 3180) | 2842-B01 HC3/LC2 | LP3 |
| 19 | Y180/F404 (SEQ ID NO: 3169) | (SEQ ID NO: 3180) | 2842-B01 HC3/LC2 | LP4 |
| 20 | Y180/F404 (SEQ ID NO: 3169) | (SEQ ID NO: 3180) | 2842-B01 HC3/LC2 | LP5 |
| 21 | Y180/F404 (SEQ ID NO: 3170) | (SEQ ID NO: 3179) | 2900-C11 | LP1 |
| 22 | Y180/F404 (SEQ ID NO: 3171) | (SEQ ID NO: 3179) | 2900-F06 | LP1 |
| 23 | Y180/F404 (SEQ ID NO: 3172) | (SEQ ID NO: 3179) | 2900-F09 | LP1 |
| 24 | Y180/F404 (SEQ ID NO: 3173) | (SEQ ID NO: 3179) | 2900-H06 | LP1 |
| 25 | Y180/F404 (SEQ ID NO: 3174) | (SEQ ID NO: 3179) | 2900-H09 | LP1 |
| 26 | Y180/F404 (SEQ ID NO: 3169) | (SEQ ID NO: 3180) | 2842-B01 HC3/LC2 | LP1 |
| 27 | Y180/F404 (SEQ ID NO: 3169) | (SEQ ID NO: 3181) | 2842-B01 HC3/LC1 | LP1 |
| 28 | Y180/F404 (SEQ ID NO: 3175) | (SEQ ID NO: 3182) | 2842-B01 HC1/LC3 | LP1 |

-continued
| Conjugate | Conjugation site on HC | Conjugation site on LC | mAb | LP |
|---|---|---|---|---|
| 29 | Y180/F404 (SEQ ID NO: 3176) | (SEQ ID NO: 3183) | 2842-G04 HC2/LC2 | LP1 |
| 30 | Y180/F404 (SEQ ID No: 3163) | (SEQ ID NO: 3179) | 2799-A05 | LP1 |
| 31 | Y180/F404 (SEQ ID NO: 3164) | (SEQ ID NO: 3179) | 2799-B03 | LP1 |
| 32 | Y180/F404 (SEQ ID NO: 3165) | (SEQ ID NO: 3179) | 2799-B06 | LP1 |
| 35 | Y180/F241/ Y391/F404 (SEQ ID NO: 3191) | (SEQ ID NO: 3179) | 2900-A02 | LP2 |
Example 9: Syntenic Example LP1 (DBCO-Valcit-pAB-Hemiasterlin)
LP1
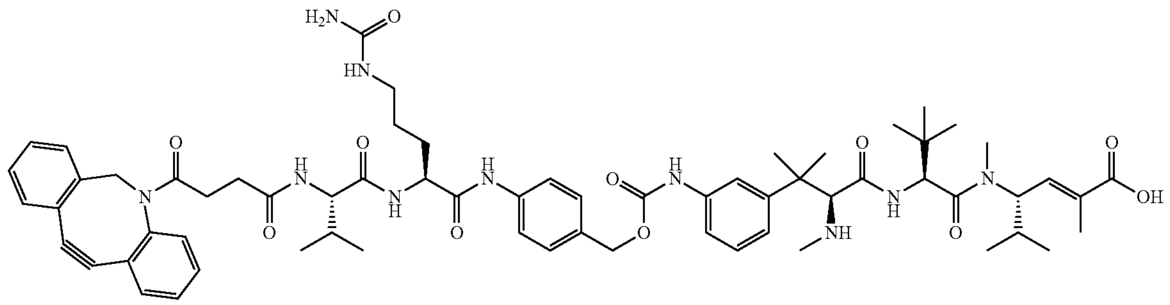
Scheme 1
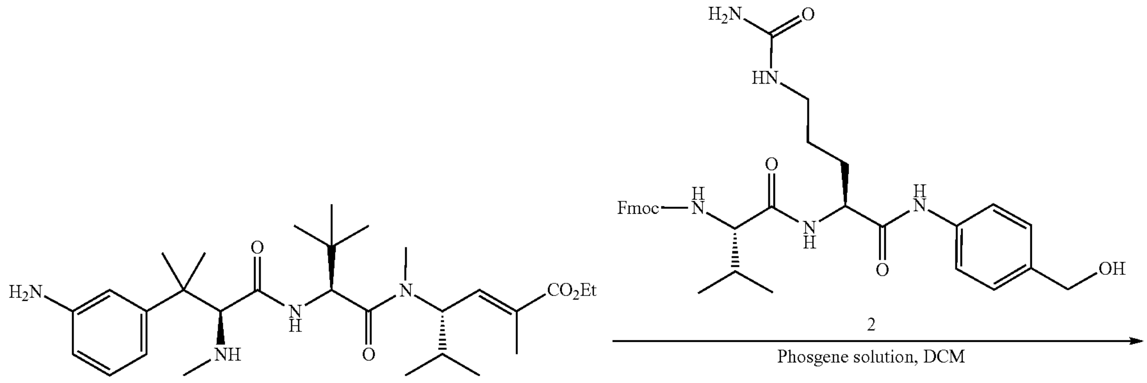
1
2
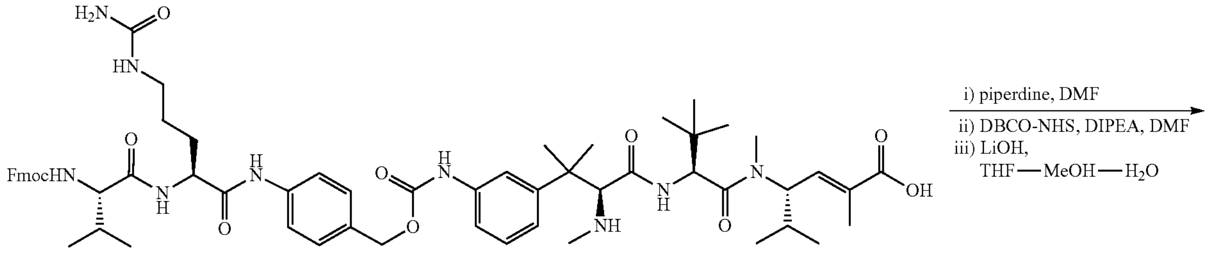
3

-continued
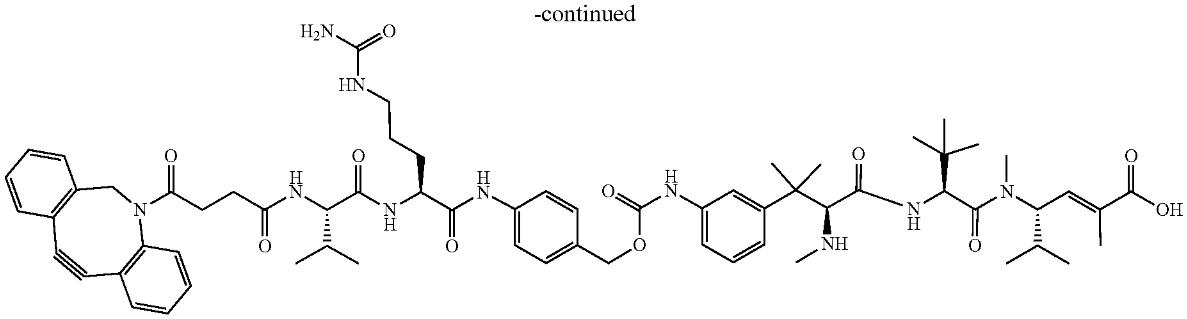
LP1
LP1 DBCO-Valcit-pAB-hemiasterlin Linker payload is synthesized as described in PCT/US2016/15844, WO 2020/252015 A1, the contents of which are hereby incorporated by reference in their entirety.
Example 10: Synthetic Example LP2 (DBCO-Beta-Glucuronide-PEG12-Exatecan) (Pegylated-DBCO-Beta-Glucuronidase Cleavable Exatecan Linker Payload)
LP2
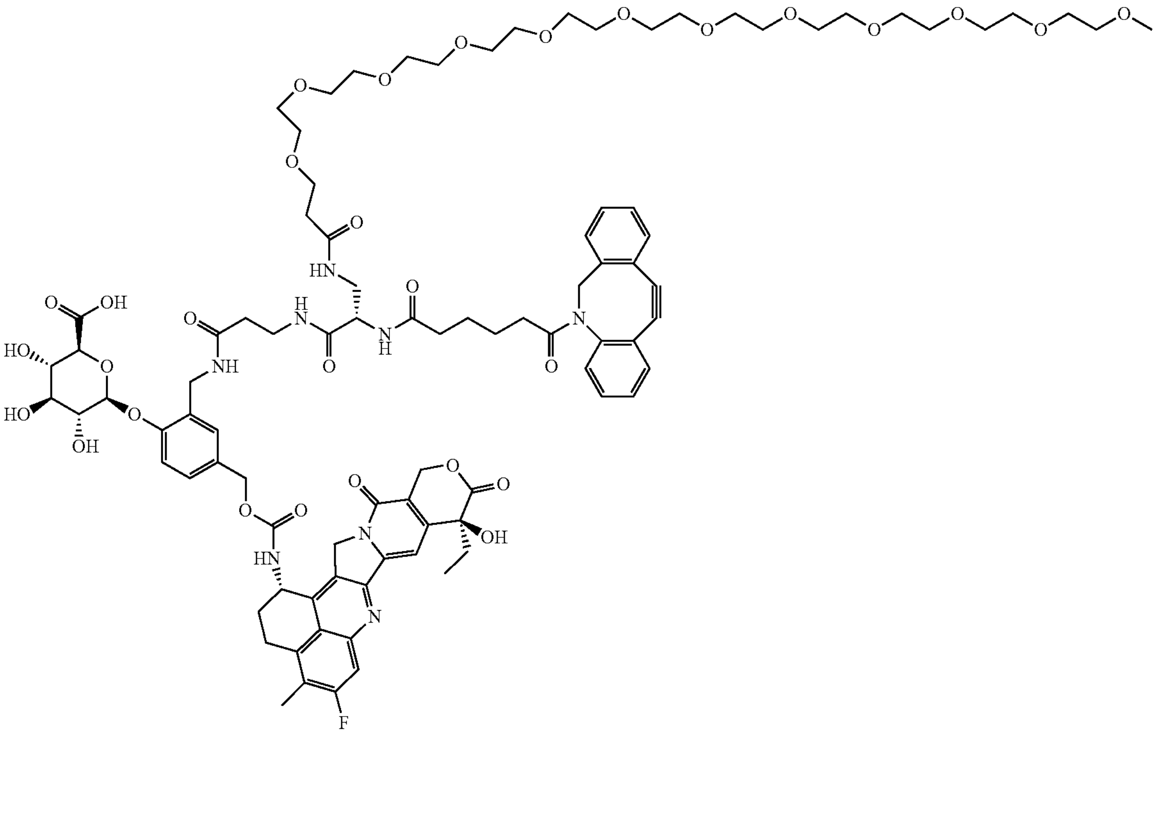

Scheme 2: Synthetic Scheme for β-Glu-Exatecan Benzylamine (Compound (19))
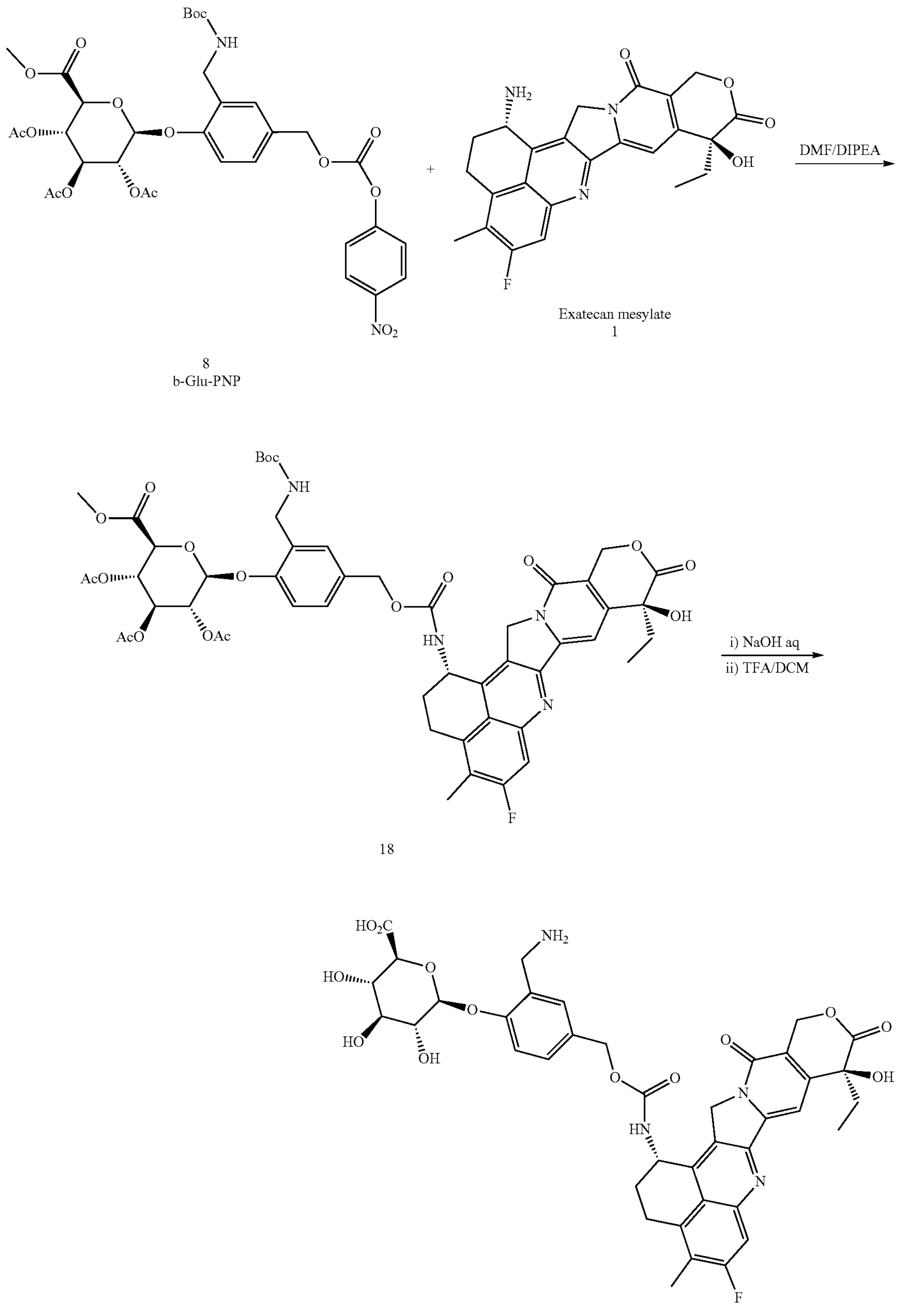
8
b-Glu-PNP
Exatecan mesylate
1
18
19

Synthetic Scheme for Compound DBCO-β-Glu-PEG12-Exatecan (LP2)
Scheme 3: Synthesis of β-Glu PNP linker (8)
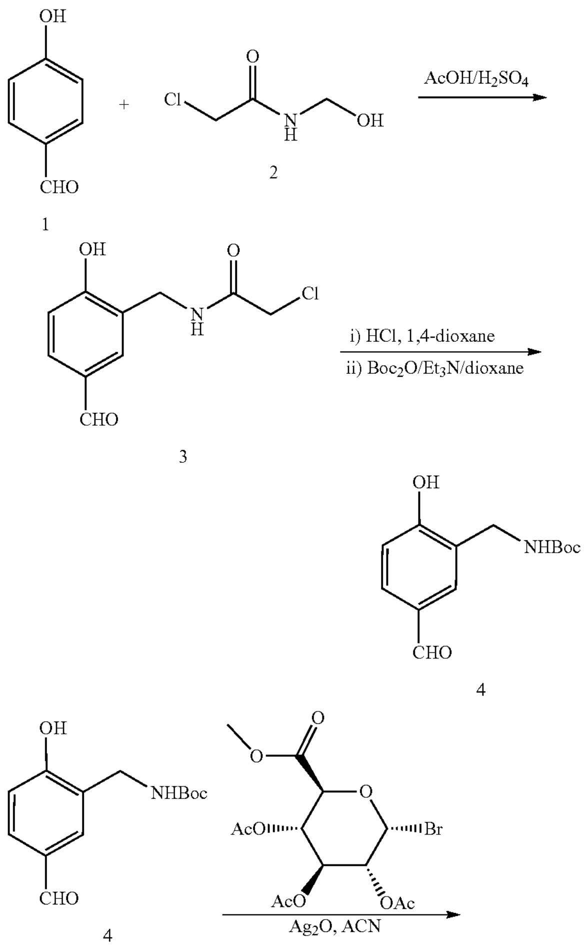
1 2 3 4 4
-continued
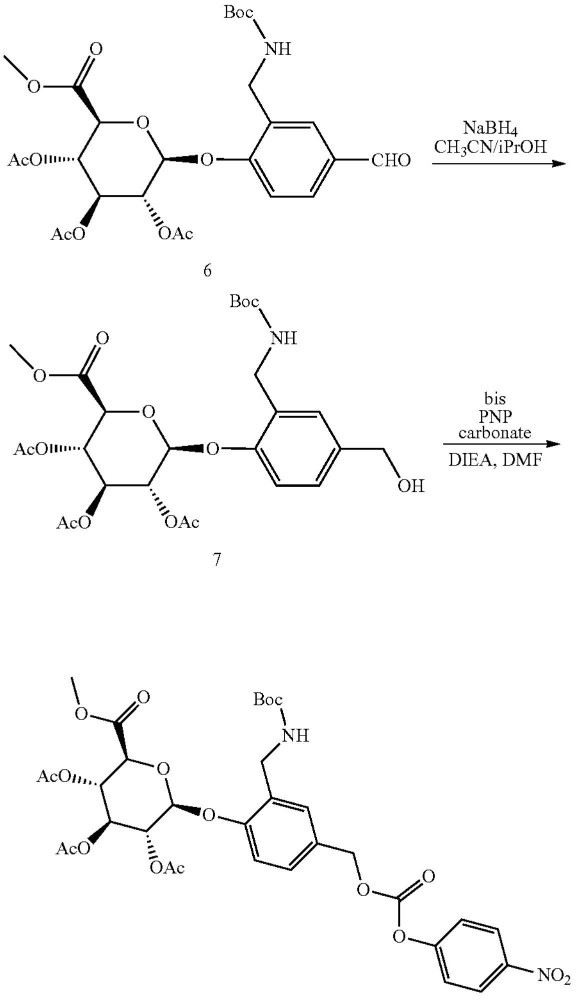
6 7 8
Scheme 4: Synthesis of m-PEG12-DBCO-PFP linker (16)
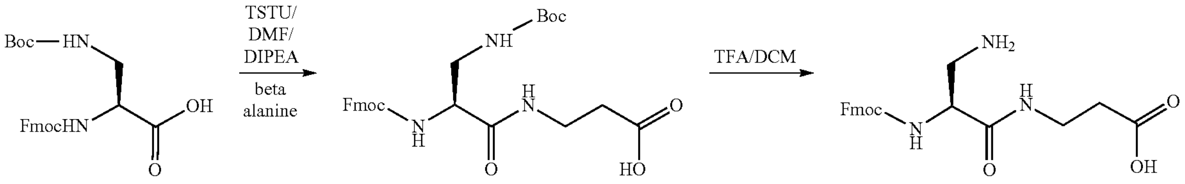
9 10 11
m-PEG12-Acid
12
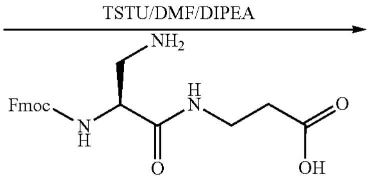
11

-continued
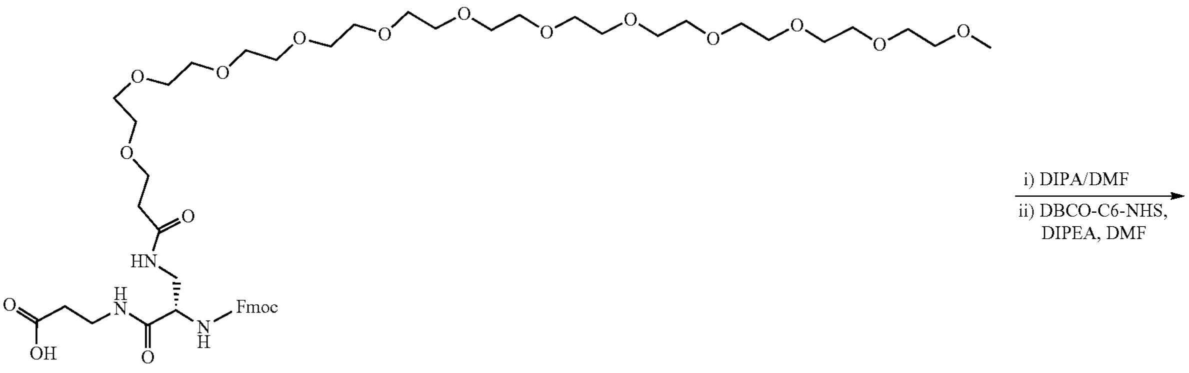
14
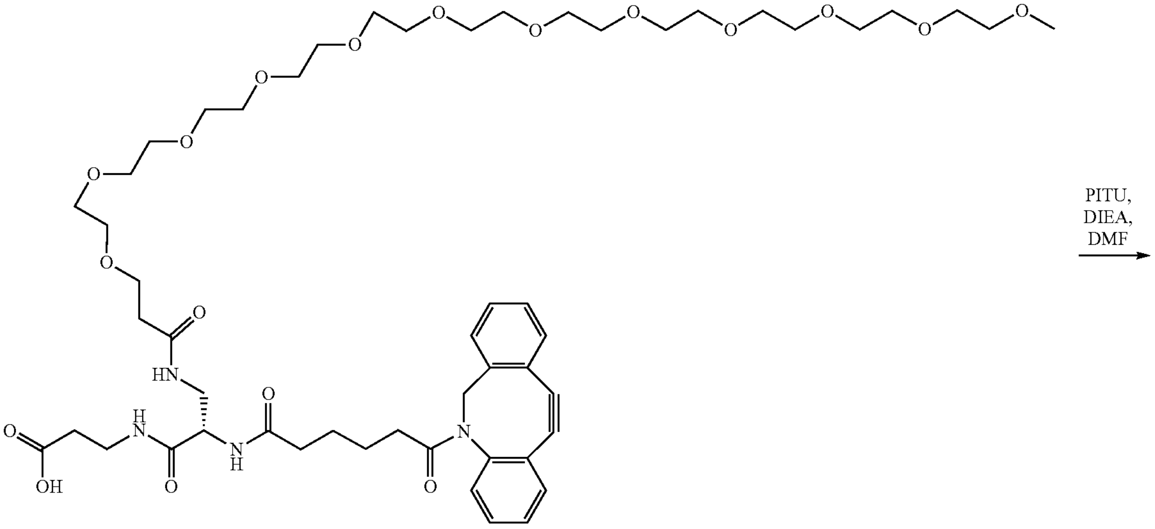
15
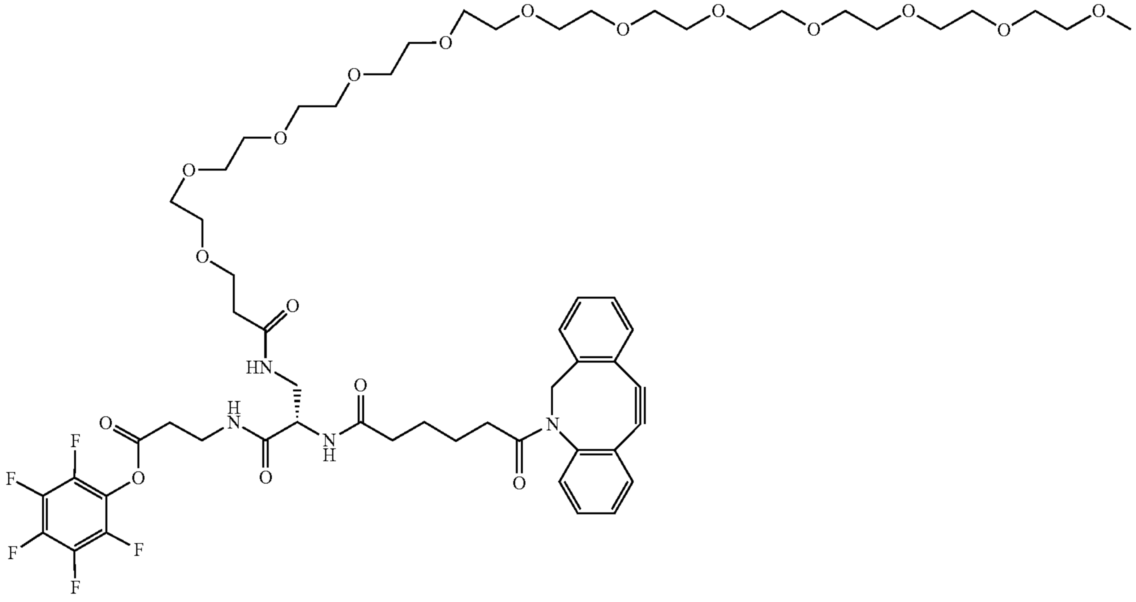
16 (m-PEG12-DBCO-PFP linker)

Scheme 5: Synthetic Scheme for Compound (LP2) PEGylated-DBCO-β-Glucuronidase cleavable Exatecan Linker payload
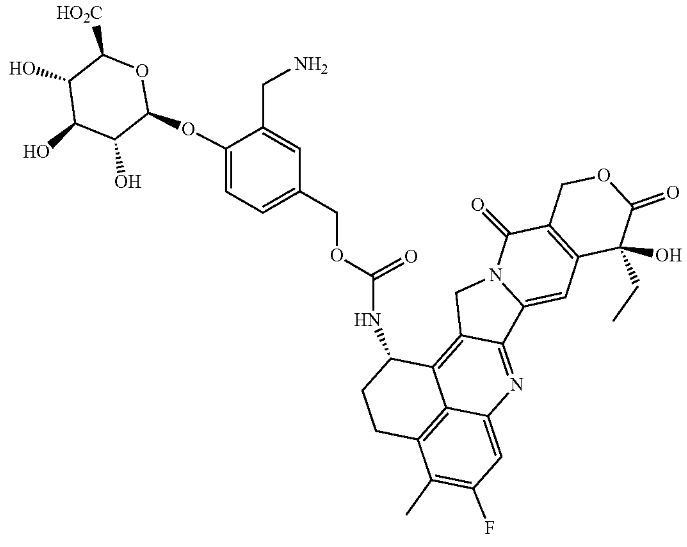
19
+
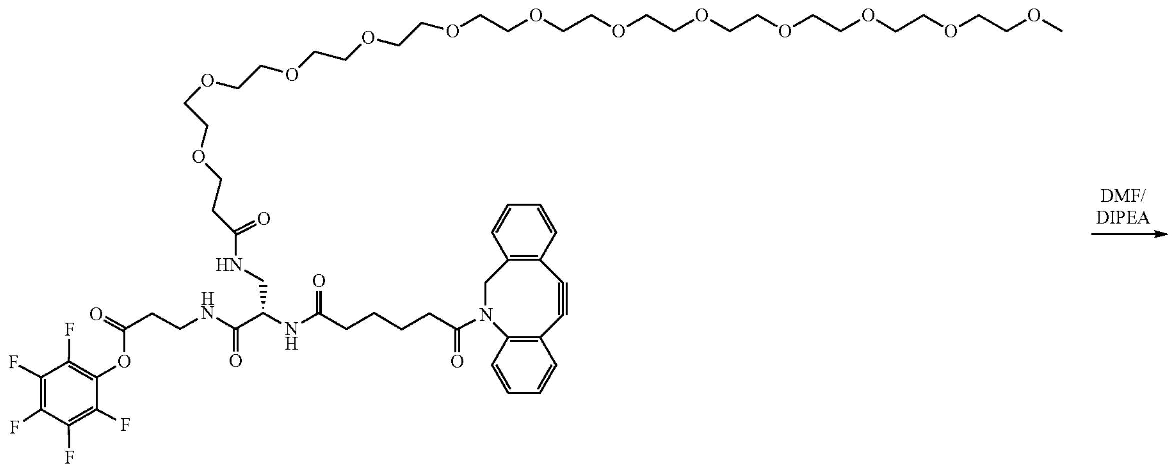
16

-continued

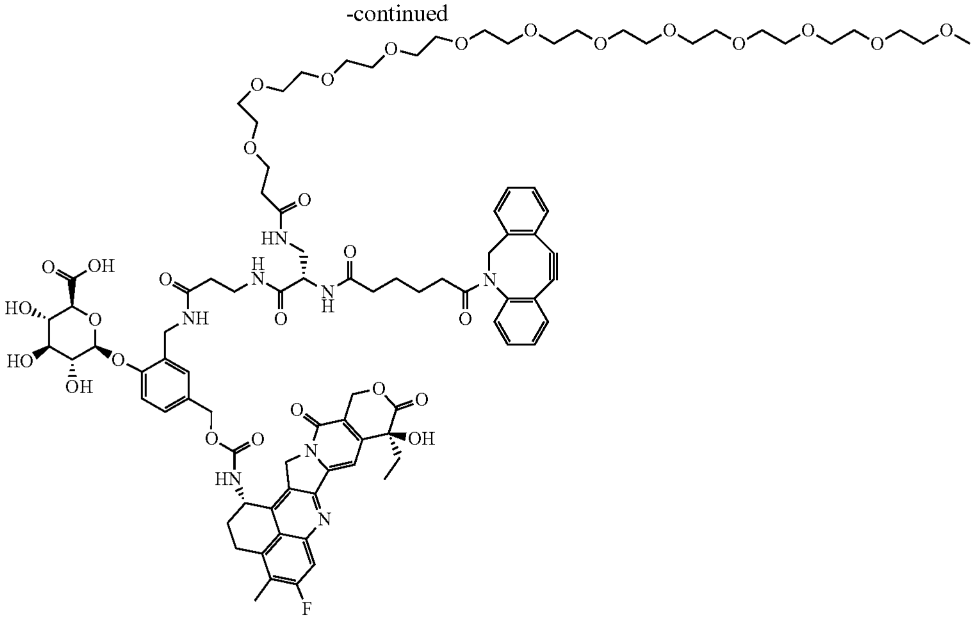

LP2

Synthesis of β-Glu PNP Linker Fragment (8)

Synthesis of Compound (4)

4

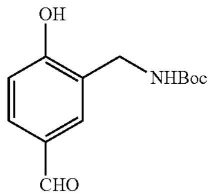

To a suspension of 4-hydroxybenzaldehyde (1) (5.3 g, 43.4 mmol) and 2-Chloro-N-(hydroxymethyl) acetamide (2) (5 g, 40.6 mmol) in AcOH (20 mL) was slowly added concentrated $H_2SO_4$ (32 mL). The mixture was stirred at room temperature (22° C.) for 16 h. The resulting viscous liquid was poured into ice water (300 mL) and extracted with EtOAc (100 mL×5). The organic layer was dried over $Na_2SO_4$ and concentrated under reduced pressure to give crude compound (3), which was dissolved in 1,4-dioxane (40 mL). To this solution was added concentrated hydrochloric acid (40 mL). The mixture was heated under reflux for one hour and then concentrated in vacuo to give a residue. The residue was dissolved in dioxane:$H_2O$ (1:1, 50 mL). To this mixture was added $Et_3N$ (9 mL), followed by $Boc_2O$ (10 g, 46 mmol). The reaction mixture was stirred at room temperature for 16 h and partitioned between EtOAc (300 mL) and water (100 mL). The organic layer was dried over $Na_2SO_4$ and concentrated to dryness under reduced pressure. The residue was purified by silica gel chromatography (220 g column, 20-30% EtOAc:hexane in 30 mins, flow rate: 40 mL/min) to furnish compound (4) as an off-white solid (5.3 g). MS calculated for $C_{13}H_{17}NO_4$, 251.3; found 252.2 $[M+H]^+$; $^1H$ NMR (500 MHz, DMSO-$d_6$) δ 10.75 (s, 1H), 9.77 (s, 1H), 7.69-7.62 (m, 2H), 7.31 (t, J=6.2 Hz, 1H), 6.96 (d, J=8.1 Hz, 1H), 4.11 (d, J=6.1 Hz, 2H), 1.41 (s, 9H).

Synthesis of Compound 7

7

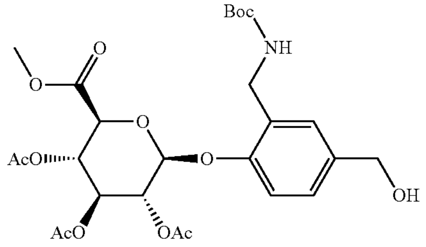

To a solution of compound (4) (2.2 g, 8.8 mmol) and (2R,3R,4S,5S,6S)-2-bromo-6-(methoxycarbonyl)tetrahydro-2H-pyran-3,4,5-triyl triacetate (5) (3.2 g, 8.1 mmol) in anhydrous acetonitrile (50 mL) was added $Ag_2O$ (3.7 g, 16 mmol). The suspension was stirred under argon atmosphere for 16 h. The solids were filtered off and washed with acetonitrile (10 mL). To the combined acetonitrile solution was added i-PrOH (10 mL) and $NaBH_4$ (300 mg, 8.1 mmol), and the mixture was stirred at room temperature. After 30 min, the reaction was quenched with water (100 mL) and extracted with EtOAc (3×100 mL). The organic layer was dried over $Na_2SO_4$ and concentrated to dryness under reduced pressure. The residue was purified by silica gel chromatography (220 g column, 40-70% EtOAc:hexane in 30 min, flow rate: 40 mL/min) to furnish compound (7) as a white foam (3.0 g, 5.2 mmol). MS calculated for $C_{26}H_{35}NO_{13}$, 569.2; found 570.4 $[M+H]^+$; $^1H$ NMR (500 MHZ, DMSO-$d_6$) δ 7.15 (q, J=6.0 Hz, 3H), 6.98 (d, J=8.7 Hz, 1H), 5.61-5.41 (m, 2H), 5.25-5.03 (m, 3H), 4.73 (d, J=9.9 Hz, 1H), 4.42 (d, J=5.3 Hz, 2H), 4.03 (tt, J=16.4, 8.3 Hz, 2H), 3.65 (s, 3H), 2.14-1.92 (m, 10H), 1.41 (s, 9H), 1.33-1.14 (m, 2H).

Synthesis of Compound (8)

8

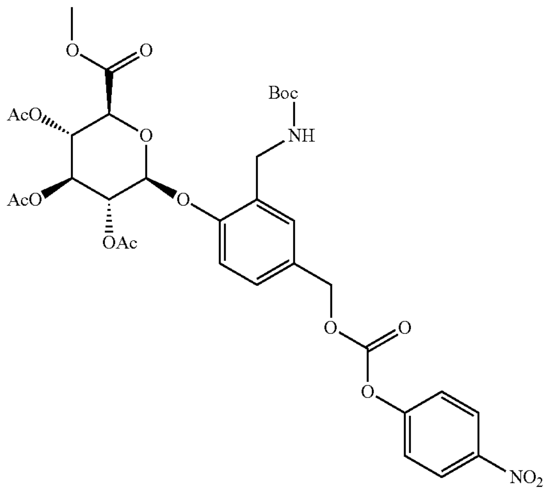

To a solution of compound (7) (2.6 g, 4.56 mmol) in anhydrous DMF (15 mL) was added DIEA (1.1 mL) and bis-PNP carbonate (2 g, 6.57 mmol). The mixture was stirred at room temperature for 16 h and purified directly by reverse phase HPLC (Phenomenex Gemini NX 5μ, C18, 110Å, 150×50 mm, Mobile phase: A: 0.1% TFA in water, B: acetonitrile, Gradient: 20-90% B over 20 min, flow 50 mL/min) to give compound (8) (1.8 g) as a white solid after lyophilization. MS calculated for $C_{33}H_{38}N_2O_{17}$, 734.2; found 735.5 $[M+H]^+$; $^1H$ NMR (500 MHz, DMSO-$d_6$) δ 8.35-8.29 (m, 2H), 7.60-7.53 (m, 2H), 7.36 (dd, J=8.4, 2.2 Hz, 1H), 7.29 (d, J=2.3 Hz, 1H), 7.22 (t, J=6.2 Hz, 1H), 7.09 (d, J=8.4 Hz, 1H), 5.65 (d, J=7.9 Hz, 1H), 5.52 (t, J=9.6 Hz, 1H), 5.26 (s, 2H), 5.19 (dd, J=9.8, 7.9 Hz, 1H), 5.10 (t, J=9.7 Hz, 1H), 4.76 (d, J=9.9 Hz, 1H), 4.03 (qd, J=16.7, 6.2 Hz, 3H), 3.66 (s, 3H), 2.06 (s, 3H), 2.02 (d, J=2.6 Hz, 6H), 1.39 (s, 8H), 1.30 (s, 1H).

Synthesis of m-PEG12-DBCO-PFP

Synthesis of Compound 11

11

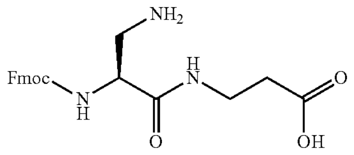

To a solution of Fmoc-Dap (Boc)-COOH (9) (853 mg, 2 mmol) in anhydrous DMF (10 mL) was added N,N,N',N'-Tetramethyl-O—(N-succinimidyl) uronium tetrafluoroborate (TSTU) (608 mg, 2 mmol), followed by DIPEA (0.7 mL). The mixture was stirred at room temperature for 10 min. A solution of beta-alanine (0.2 g) in acetonitrile:water (1:1, 3 mL) was added, followed by DIPEA (0.4 mL). The reaction mixture was stirred at room temperature for 30 min, and then acidified with 0.5 N hydrochloric acid (50 mL). The mixture was extracted with EtOAc (200 mL) and the organic layer was dried over $Na_2SO_4$ and concentrated to dryness under reduced pressure to give crude compound (10) as white powder. Crude compound (10) was treated with TFA: DCM (1:4, v/v, 20 mL) at room temperature for one hour. The mixture was evaporated to dryness under reduced pressure to give crude compound (11) which was used directly in the next step. MS calculated for $C_{21}H_{23}N_3O_5$, 397.16; found 398.2 $[M+H]^+$.

Synthesis of Compound (14)

14

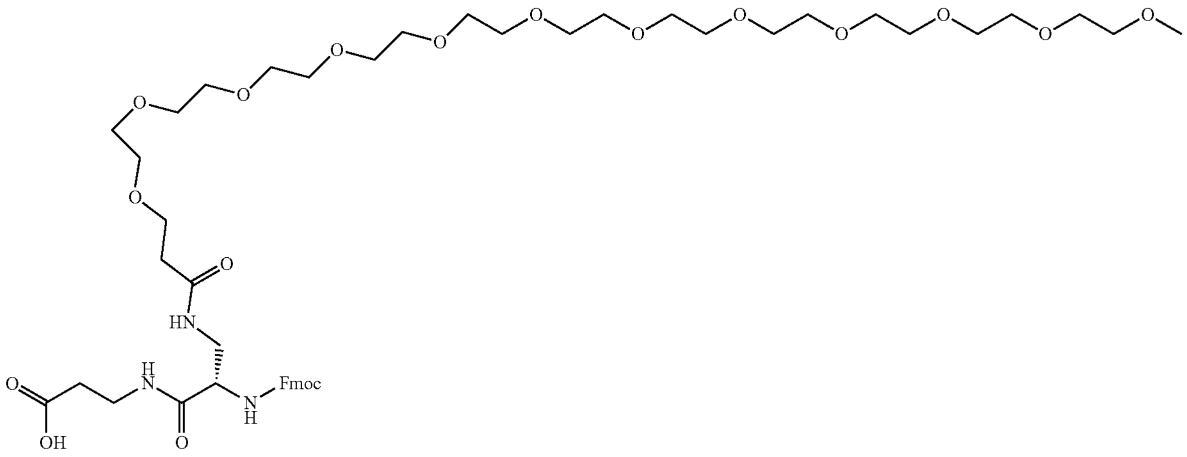

m-PEG12-acid (12) (1.18 g, 2 mmol) was dissolved in DMF (10 mL) and TSTU (610 mg, 2 mmol) was added, followed by DIPEA (700 μL). After 5 min, a solution of compound (11) in DMF (10 mL) with DIPEA (0.7 mL) was added. The reaction mixture was stirred at room temperature for 30 mins and purified directly by reverse phase HPLC to give compound (14) as a viscous foam (1.27 g). MS calculated for $C_{47}H_{73}N_3O_{18}$, 967.5; found 968.8 $[M+H]^+$; $^1H$ NMR (500 MHz, DMSO-$d_6$) δ 8.35-8.29 (m, 2H), 7.60-7.53 (m, 2H), 7.36 (dd, J=8.4, 2.2 Hz, 1H), 7.29 (d, J=2.3 Hz, 1H), 7.22 (t, J=6.2 Hz, 1H), 7.09 (d, J=8.4 Hz, 1H), 5.65 (d, J=7.9 Hz, 1H), 5.52 (t, J=9.6 Hz, 1H), 5.26 (s, 2H), 5.19 (dd, J=9.8, 7.9 Hz, 1H), 5.10 (t, J=9.7 Hz, 1H), 4.76 (d, J=9.9 Hz, 1H), 4.03 (qd, J=16.7, 6.2 Hz, 3H), 3.66 (s, 3H), 2.06 (s, 3H), 2.02 (d, J=2.6 Hz, 6H), 1.39 (s, 8H), 1.30 (s, 1H).

Synthesis of Compound (15)

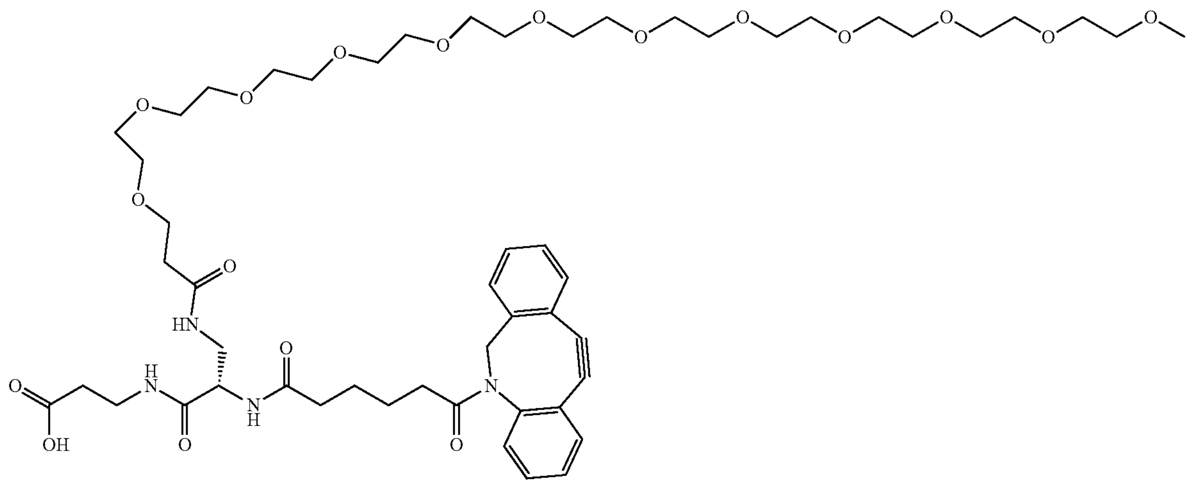

15

To a solution of compound (14) (1.24 g) in DMF (10 mL) was added i-$Pr_2NH$ (DIPEA) (10 mL) and the reaction mixture was stirred at room temperature for 2 h. The mixture was then concentrated under reduced pressure to about 9 mL. To this solution, DBCO-C6-NHS (0.55 g) was added followed by DIPEA (0.23 mL). The mixture was stirred at room temperature for 2 h and then purified directly by reverse phase HPLC to give compound (15) as a colorless syrup (1.17 g). MS calculated for $C_{53}H_{80}N_4O_{18}$, 1060.6; found 1061.9 $[M+H]^+$.

Synthesis of Compound (16)

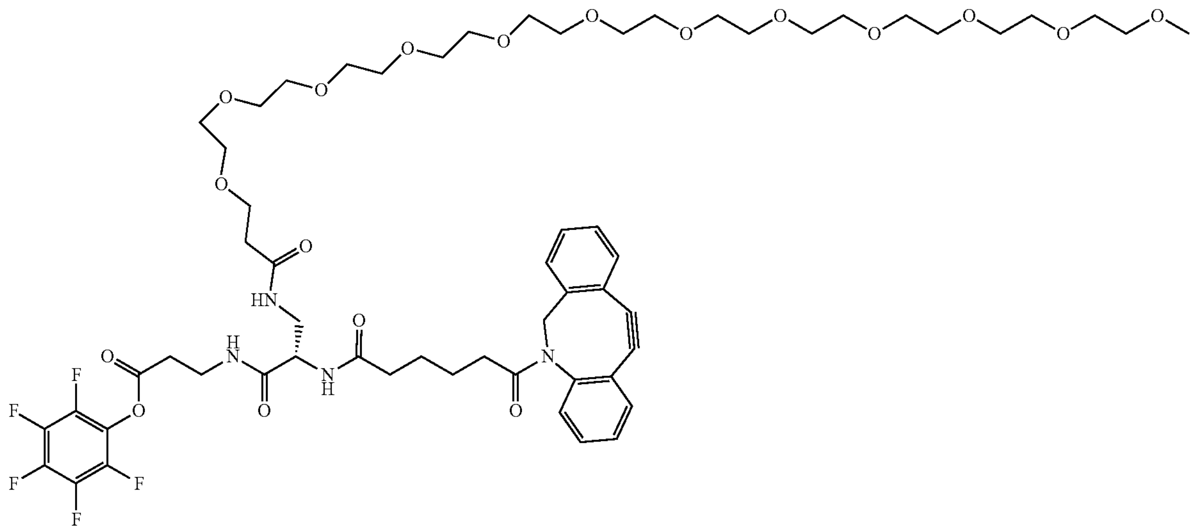

16

(m-PEG12-DBCO-PFP linker)

To a solution of compound (15) (1.1 g) in DMF (8 mL) was added Pentafluorophenol-tetramethyluronium hexafluorophosphate (PfTU) (0.5 g) followed by DIEA (0.4 mL) and the reaction mixture was stirred at room temperature for 10 min. The mixture was purified directly by RP-HPLC to give compound (16) as a colorless syrup (1.0 g). MS calculated for $C_{59}H_{79}F_5N_4O_{18}$, 1226.5; found 1227.8 $[M+H]^+$. Compound (16) was used in the next reaction.

Synthesis of Compound (19)

19

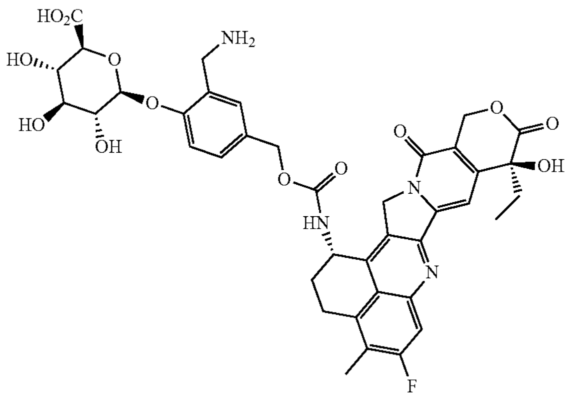

20 mL) at room temperature for one hour. The mixture was diluted with toluene (30 mL) and then evaporated to dryness under reduced pressure. The residue was purified by reverse phase HPLC to give compound (19) as a yellow solid (745 mg). MS calculated for $C_{39}H_{39}FN_4O_{13}$, 790.3; found 791.6 $[M+H]^+$; $^1H$ NMR (500 MHZ, DMSO-$d_6$) δ 8.09 (d, J=8.0 Hz, 4H), 7.73 (dd, J=10.7, 3.2 Hz, 1H), 7.54 (d, J=2.1 Hz, 1H), 7.49 (dd, J=8.5, 2.2 Hz, 1H), 7.32 (s, 1H), 7.22 (d, J=8.5 Hz, 1H), 6.55 (s, 1H), 5.75 (s, 1H), 5.48 (d, J=16.3 Hz, 1H), 5.46-5.37 (m, 3H), 5.31-5.13 (m, 4H), 5.08-5.02 (m, 2H), 4.19-4.07 (m, 2H), 3.95 (d, J=9.5 Hz, 1H), 3.44 (dd, J=8.8, 2.6 Hz, 1H), 3.28-3.19 (m, 2H), 3.14-3.04 (m, 1H), 2.34 (s, 3H), 2.26 (dd, J=12.5, 6.4 Hz, 1H), 2.12 (qd, J=9.0, 4.6 Hz, 1H), 1.87 (dh, J=21.5, 7.2 Hz, 2H), 0.89 (t, J=7.2 Hz, 3H).

Final Coupling of Synthesis LP2:

LP2

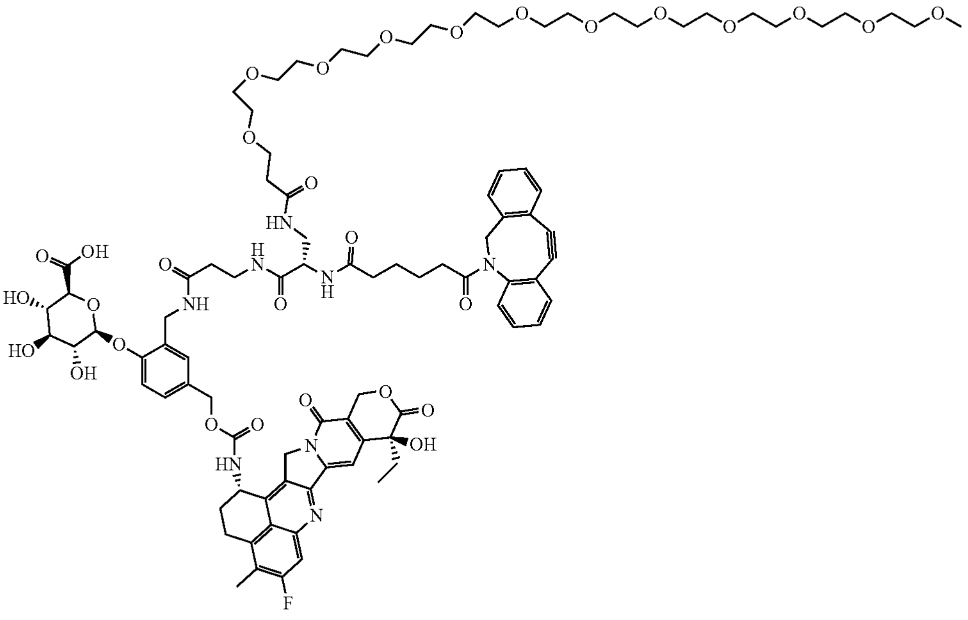

To a solution of compound (8) (735 mg, 1 mmol) and Exatecan mesylate 1, 531 mg, 1 mmol) in DMF (10 mL) was added DIPEA (350 μL). The reaction mixture was stirred at room temperature (22° C.) for 5 hours and then diluted with EtOAc (200 mL). The mixture was washed with 0.5 N hydrochloric acid (100 mL), water (100 mL), and brine (50 mL). The organic layer was dried over $Na_2SO_4$ and concentrated to dryness under reduced pressure to give crude compound (18) which was suspended in acetonitrile:water (2:1, 50 mL). To this mixture, 1 N aq. NaOH (7 mL) was added and the reaction was stirred at room temperature. After 3 h, 1 N hydrochloric acid (7 mL) was added and the mixture was evaporated to dryness under reduced pressure. The resulting residue was treated with TFA:DCM (1:4, v/v, The compound b-Glu-Exatecan benzyl amine (19) (540 mg, 0.68 mmol) was dissolved in DMF (4 mL) and compound m-PEG12-DBCO-PFP (16) (750 mg, 0.6 mmol) was added, followed by DIPEA (0.32 mL). The reaction mixture was stirred at room temperature for 30 min and purified directly by reverse phase HPLC (Phenomenex Gemini NX 5μ, C18, 110Å, 150×50 mm, Mobile phase: A: 0.1% TFA in water, B: acetonitrile, Gradient: 20-90% B over 20 min, flow 50 mL/min) to give compound LP2 as a pale-yellow solid (704 mg). HRMS m/z ($ESI^+$): calculated for $C_{92}H_{117}FN_8O_{30}$, 1832.78; found 1833.79 $[M+H]^+$; $^1H$ NMR (500 MHZ, DMSO-$d_6$) δ 12.84 (s, 1H), 8.20 (t, J=6.2 Hz, 1H), 8.02 (d, J=8.8 Hz, 1H), 7.75 (td, J=6.1, 3.4 Hz, 2H), 7.62-7.52 (m, 1H), 7.50-7.39 (m, 2H), 7.32-7.25 (m, 2H), 6.52 (s, 1H), 5.50-5.39 (m, 2H), 5.27 (d, J=13.6 Hz, 3H), 5.01-4.94 (m, 1H), 4.29 (t, J=6.3 Hz, 2H), 3.57 (d, J=14.0 Hz, 1H), 3.56-3.46 (m, 35H), 3.48-3.40 (m, 5H), 3.35 (td, J=12.8, 6.5 Hz, 5H), 3.24 (s, 2H), 3.22 (s, 3H), 2.36 (d, J=1.8 Hz, 3H), 2.27 (dq, J=13.4, 6.3 Hz, 3H), 2.16 (ddd, J=21.5, 11.0, 6.0 Hz, 2H), 1.87 (dp, J=21.0, 7.2 Hz, 4H), 1.17 (s, 3H), 0.88 (t, J=7.3 Hz, 3H).

Example 11: Synthetic Example LP3 (DBCO-NNAA-PEG13-VKG-Exatecan)
LP3
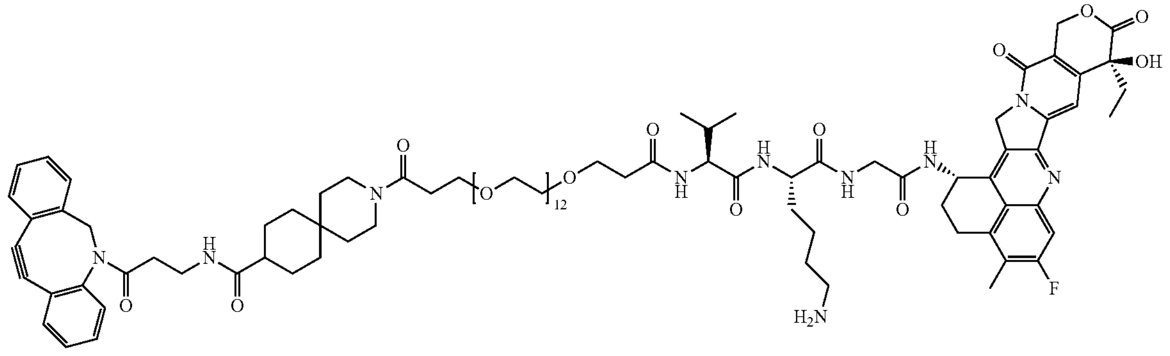
Scheme 6: Synthesis of VK(Fmoc)G-Exatecan (10)
-continued
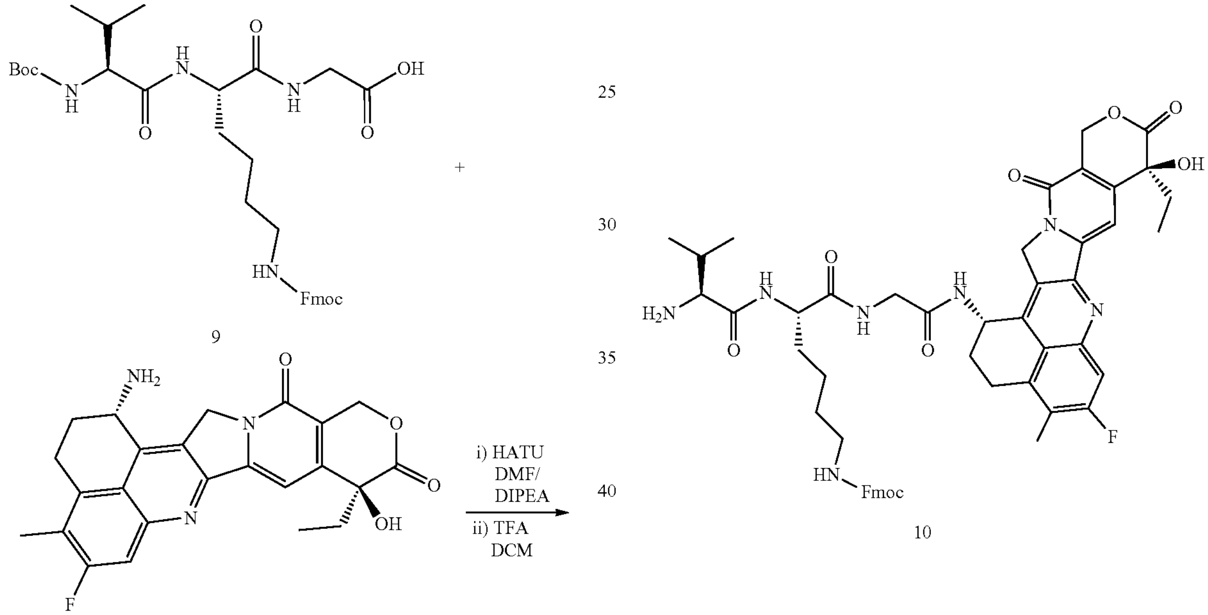
9
1
10
Scheme 7: Final couplings and deprotection of the synthesis of LP3
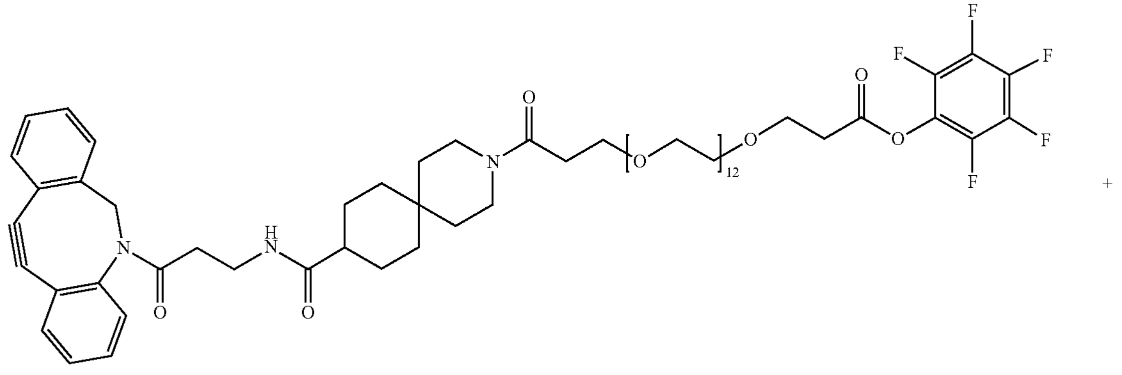
4

-continued

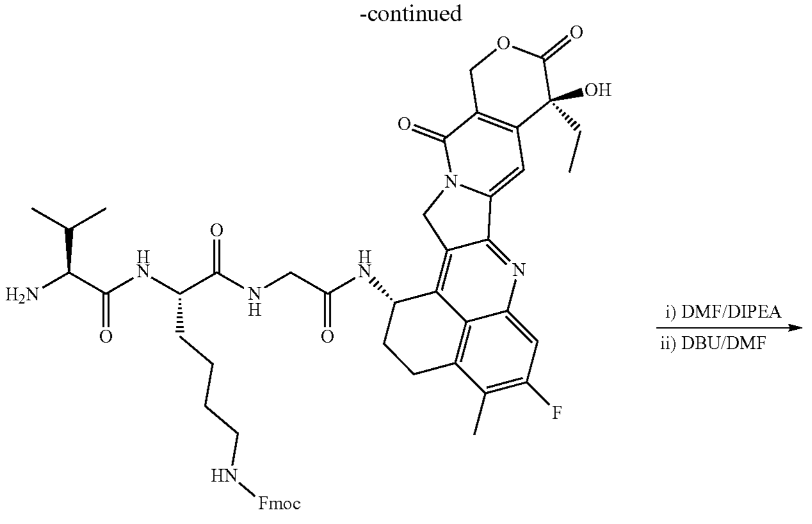

16

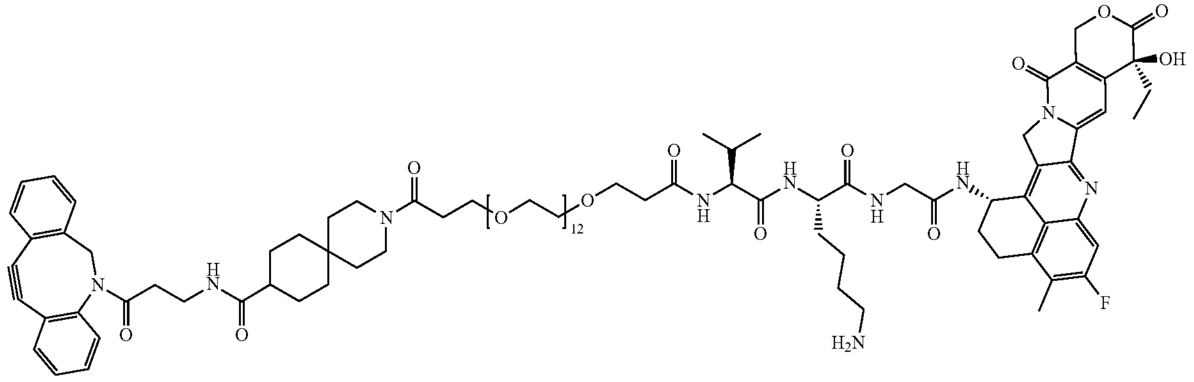

LP3

Synthesis of Compound 10

10

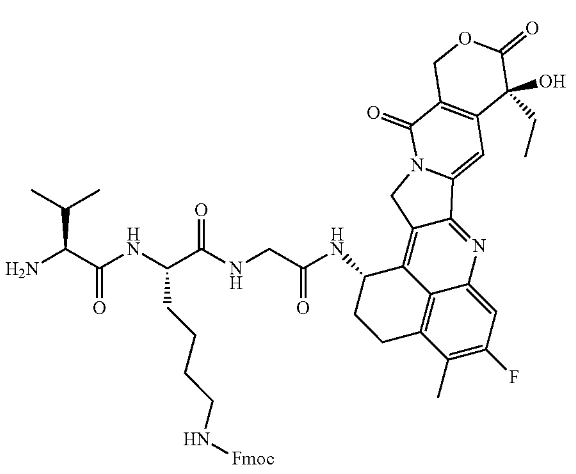

To a solution of compound Boc-VK(Fmoc)-G-OH 9 (562 mg, 0.9 mmol) in anhydrous DMF (10 mL) was added Exatecan mesylate (1) (478 mg, 0.9 mmol) and DIPEA (470 μL). After all components dissolved, HATU (342 mg, 0.9 mmol) was added, and the mixture was stirred at room temperature for 10 min. The reaction was then diluted with water (80 mL) and extracted with EtOAc (150 mL). The organic layer was washed with hydrochloric acid (0.2 M, 50 mL) and brine (50 mL), dried over $Na_2SO_4$ and evaporated to dryness under reduced pressure. The residue obtained was treated with TFA/DCM (1/4, 20 mL) at room temperature for 30 min and the reaction was evaporated to dryness under reduced pressure. The crude mixture was dissolved in 5 mL of DMF and purified by reverse phase HPLC to give compound 10 as a yellowish solid (771 mg). MS calculated for $C_{52}H_{56}FN_7O_9$, 941.4; found 942.9 $[M+H]^+$.

Synthesis of LP3

LP3

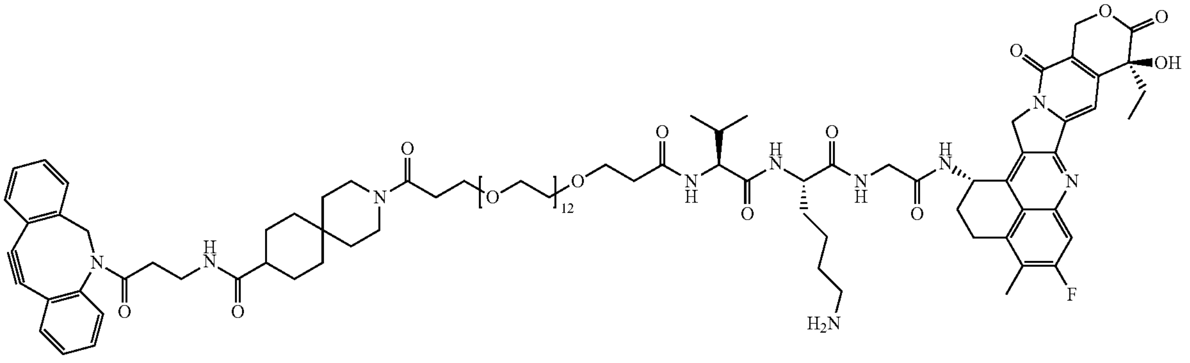

To a solution of compound 4 (426 mg, 0.33 mmol) in anhydrous DMF (3 mL) was added compound 10 (TFA salt, 347 mg, 0.33 mmol) and DIPEA (130 μL). The mixture was stirred at room temperature for 15 min, the LCMS showed the desired product formation. Then DBU (366 μL) was added dropwise, and the mixture was stirred at room temperature for additional 10 min. LCMS showed completion of the reaction. Then the mixture was purified directly by reverse phase HPLC to give LP3 as a yellowish solid (350 mg); HRMS m/z (ESI$^+$): calculated for $C_{96}H_{133}FN_{10}O_{24}$, 1828.94; found 1829.95 $[M+H]^+$; $^1H$ NMR (500 MHZ, DMSO) δ 8.43 (d, J=8.5 Hz, 1H), 8.14 (t, J=5.6 Hz, 1H), 7.98 (d, J=7.4 Hz, 1H), 7.81 (d, J=10.9 Hz, 1H), 7.77-7.53 (m, 7H), 7.54-7.23 (m, 10H), 5.57 (dt, J=8.7, 4.4 Hz, 1H), 5.47-5.38 (m, 2H), 5.25 (d, J=3.3 Hz, 2H), 5.04 (d, J=14.1 Hz, 2H), 4.16 (td, J=8.1, 5.9 Hz, 3H), 4.08 (dd, J=8.5, 6.8 Hz, 3H), 3.88-3.68 (m, 13H), 3.50 (d, J=3.6 Hz, 71H), 3.25-3.13 (m, 4H), 3.13-3.03 (m, 2H), 2.92 (dq, J=13.4, 6.8 Hz, 2H), 2.78 (q, J=6.8 Hz, 3H), 2.60-2.26 (m, 18H), 2.26-2.03 (m, 3H), 1.98-1.74 (m, 6H), 1.74-1.46 (m, 8H), 1.46-1.09 (m, 12H), 0.97 (s, 2H), 0.88 (t, J=7.3 Hz, 3H), 0.78 (dd, J=14.1, 6.7 Hz, 7H).

Example 12: Synthetic Example LP4 (DBCO-NNAA-PEG13-AAN-Exatecan) Legumain Cleavable Exatecan Linker Payload

LP4

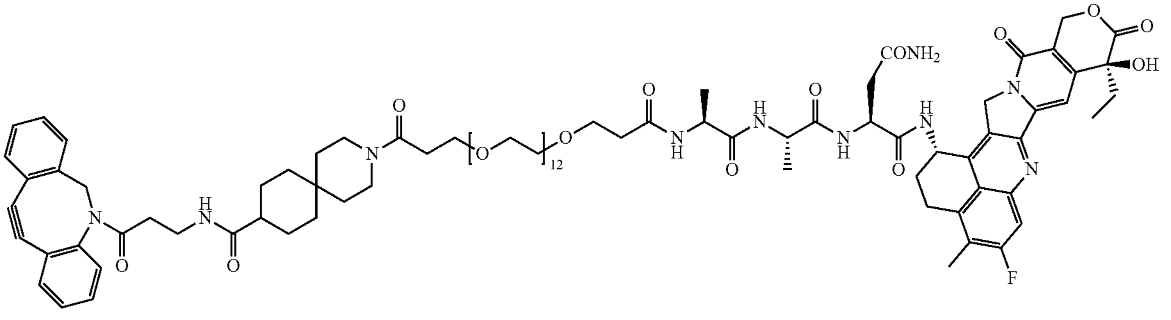

Scheme 8: Synthesis of AAN-Exatecan (3)

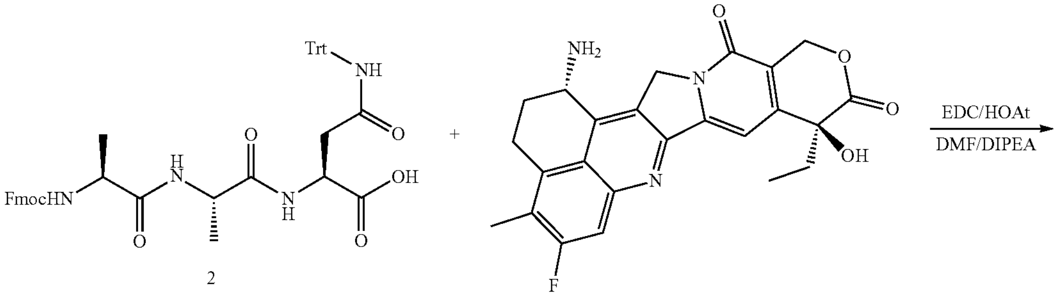

2

1

-continued
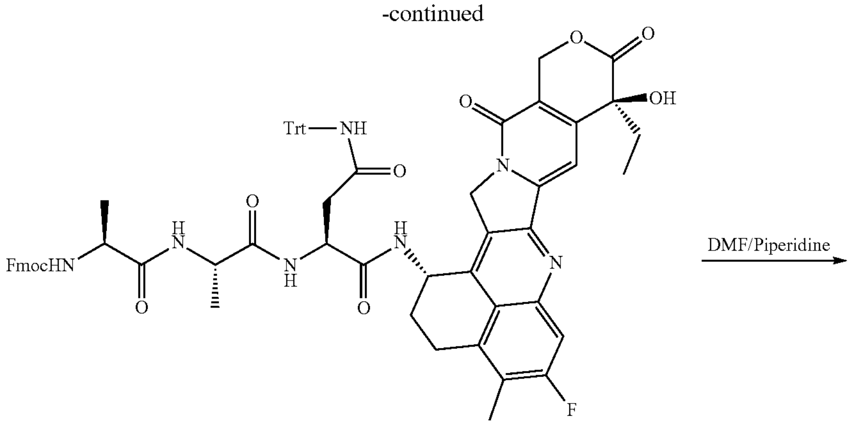
2a
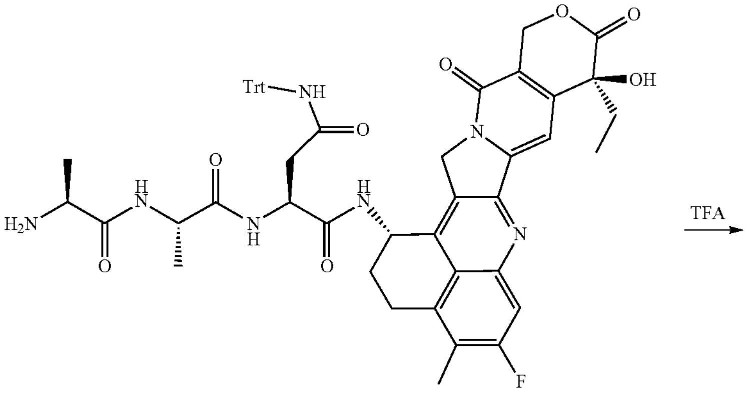
2b
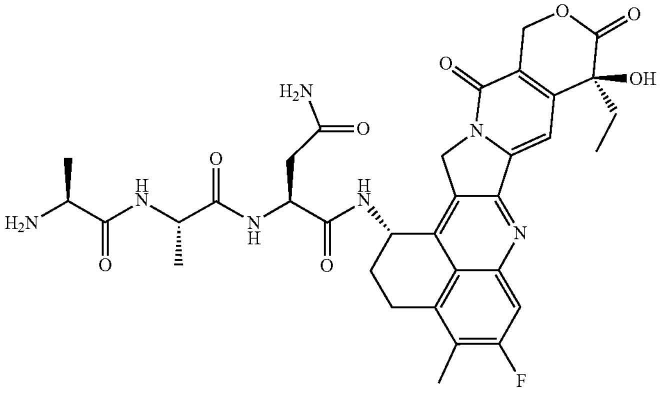
3

Scheme 9: Synthesis of DBCO-nnAA-PEG13-PFP linker (4)
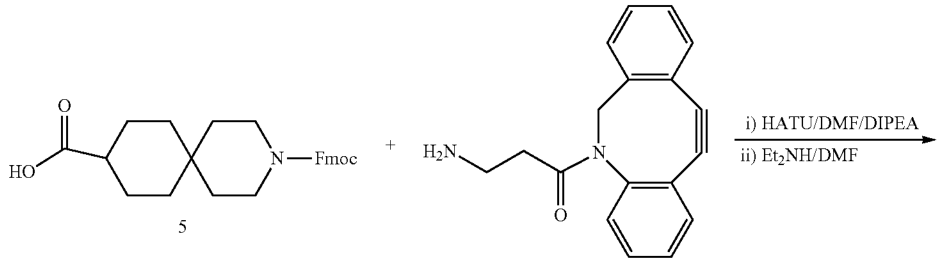
5
6
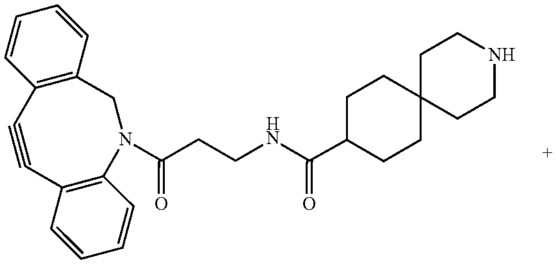
7
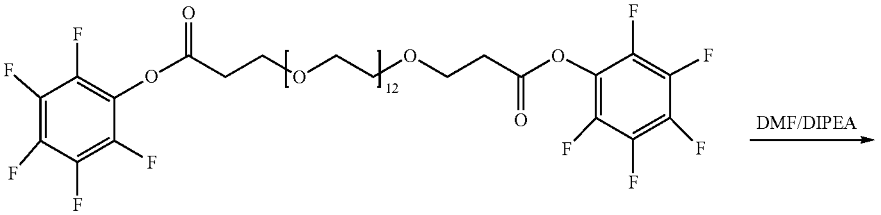
8
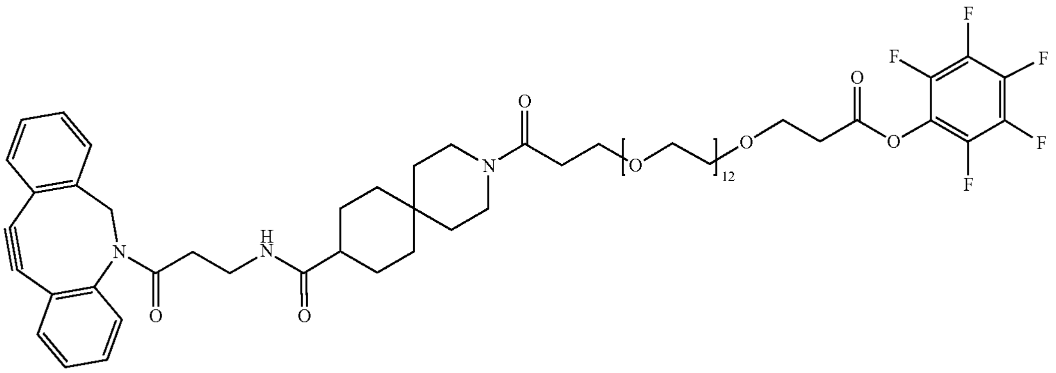
4

Scheme 10: Final coupling for the synthesis of LP4

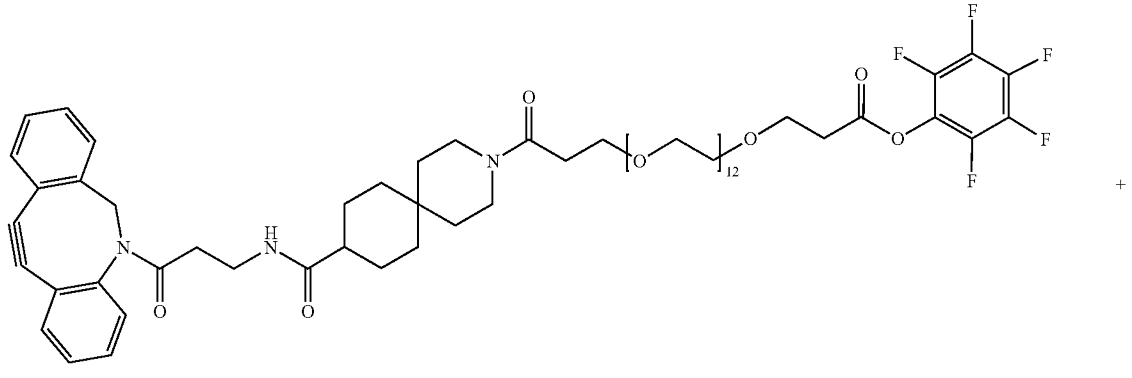

4

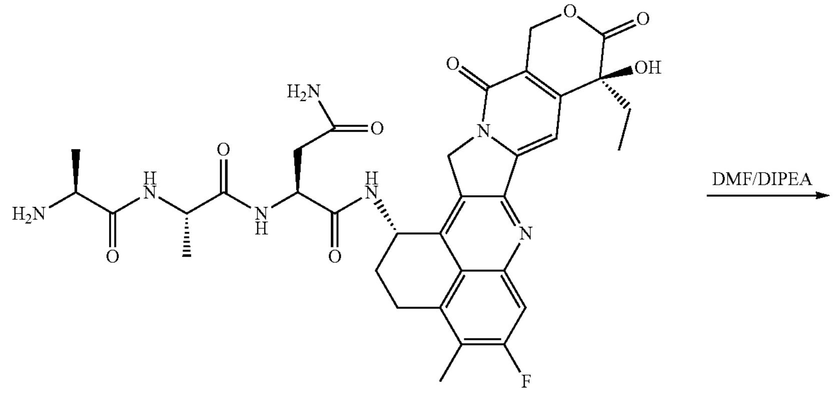

3

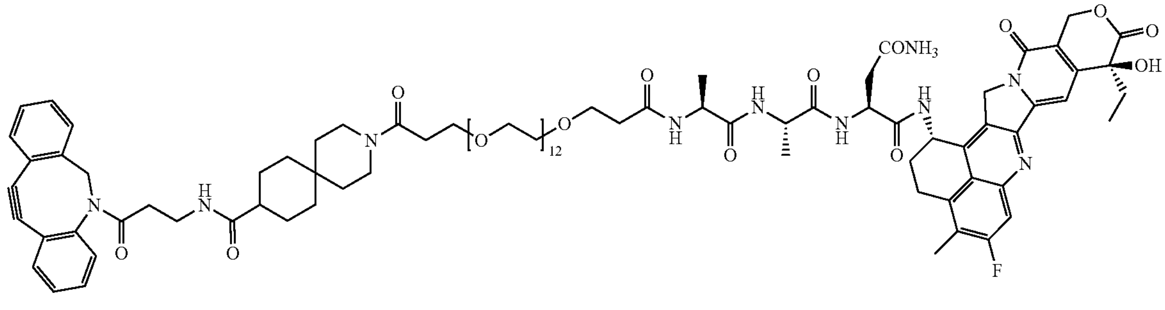

LP4

Synthesis of Compound 3:

3

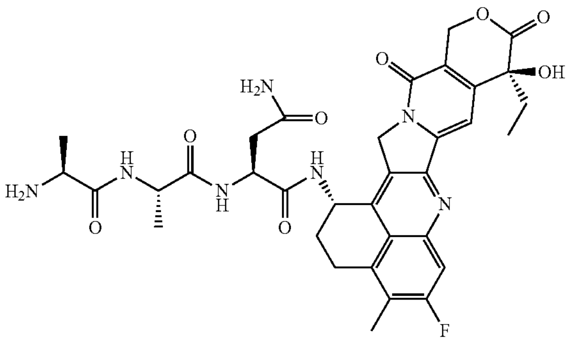

To a suspension of exatecan mesylate 1 (MsOH salt, 150 mg, 0.28 mmol) in anhydrous DMF (3 mL) at room temperature was added Fmoc-AAN (Trt)-OH 2 (250 mg, 0.33 mmol), EDC (65 mg, 0.34 mmol), HOAt (46 mg, 0.34 mmol), and DIPEA (53 μL). The reaction was stirred at RT for 1 h, LCMS showed the desired product, then 0.3 mL of piperidine was added. The mixture was stirred for 5 min, and then added to a 1/1 mixture of hexane/diethyl ether (45 mL). The precipitate was collected by centrifugation and the solvent was removed by decantation to give the compound 2b. The residue 2b was dissolved in 3 mL of TFA and the mixture was stirred for 10 min at RT. Then the TFA was removed under reduced pressure, the crude mixture was purified by reverse phase HPLC. Pure Fractions were lyophilized to give compound 3 as a TFA salt (63 mg); LCMS m/z ($ESI^+$): calculated for $C_{34}H_{38}FN_7O_8$, 691.28; found 692.4 (M+H).

Synthesis of Compound 7:

7

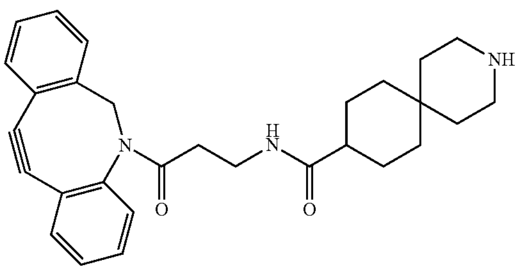

Compound 5 (1.4 g, 3.34 mmol) was dissolved in DMF (10 mL). To the clear solution was added HATU (1.2 g, 3.34 mmol) and DIPEA (861 mg, 6.68 mmol). The solution was stirred at room temperature for about 30 sec. followed by the addition of DBCO-amine 7 (922 mg, 3.34 mmol) in DMF (2 mL). After the mixture was stirred at room temperature for 20 minutes, diethyl amine (2 mL) was added into and allowed to stir for another 30 minutes, LCMS showed completion of the reaction. The reaction solution was concentrated under reduced pressure and purified by reverse phase HPLC to afford compound 7 (790 mg); LCMS m/z (ESI+): calculated for $C_{29}H_{33}N_3O_2$, 455.26; found 456.4 (M+H).

Synthesis of Compound 4:

4

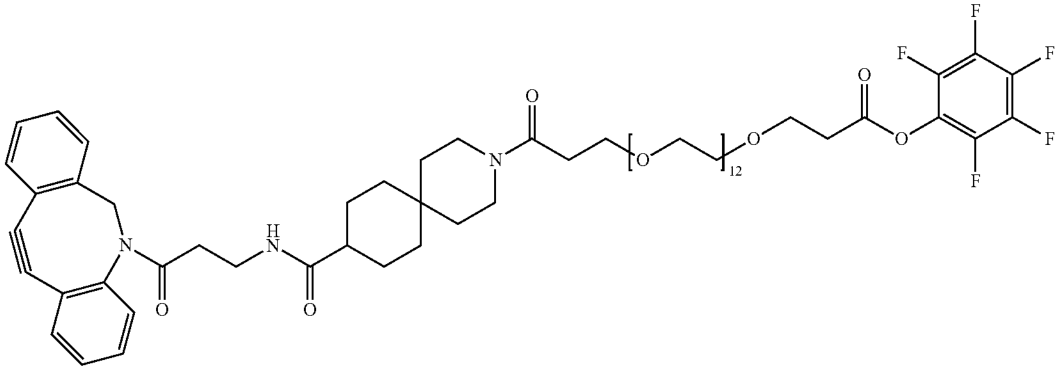

A solution of compound 8 (3 g, 2.9 mmol), compound 7 (780 mg, 1.37 mmol) and DIPEA (353 mg, 2.74 mmol) in DMF (20 mL) was stirred for 20 minutes, LCMS showed completion of the reaction. The reaction mixture was directly purified by reverse phase HPLC to give compound 4 (1.52 g); LCMS m/z (ESI+): calculated for $C_{65}H_{88}F_5N_3O_{18}$, 1293.60; found 1293.7 (M+H).

Synthesis of LP4:

LP4

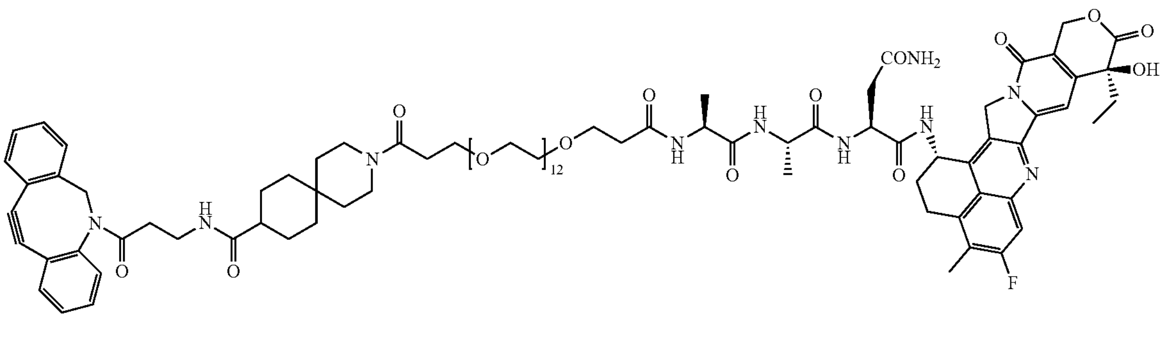

To a solution of compound 4 (770 mg, 0.6 mmol) in anhydrous DMF (3 mL) was added compound 3 (TFA salt, 478 mg, 0.6 mmol) and DIPEA (206 μL). The mixture was stirred at room temperature for 10 min, LCMS showed completion of the reaction. Then the mixture was purified directly by reverse phase HPLC to give LP4 as a light yellowish solid (710 mg); $^1$H NMR (500 MHz, DMSO-d6) δ 11.41 (s, 1H), 8.25 (d, J=8.5 Hz, 1H), 8.07-7.91 (m, 3H), 7.77 (d, J=10.9 Hz, 1H), 7.68-7.54 (m, 2H), 7.47 (dddd, J=13.4, 7.6, 4.9, 2.8 Hz, 4H), 7.43-7.22 (m, 5H), 6.98-6.83 (m, 1H), 5.51 (dt, J=8.8, 4.5 Hz, 1H), 5.43 (s, 2H), 5.22 (s, 2H), 5.04 (d, J=14.0 Hz, 1H), 4.47 (q, J=6.8 Hz, 1H), 4.09 (dp, J=18.0, 7.1 Hz, 3H), 3.73 (s, 10H), 3.67-3.27 (m, 61H), 3.22-3.01 (m, 3H), 2.92 (dq, J=13.3, 6.7 Hz, 1H), 2.68-2.45 (m, 8H), 2.45-2.28 (m, 6H), 2.19 (dq, J=9.3, 4.8 Hz, 1H), 1.87 (qd, J=13.8, 7.1 Hz, 4H), 1.61 (d, J=13.1 Hz, 2H), 1.49-1.21 (m, 7H), 1.13 (dd, J=26.8, 7.1 Hz, 7H), 0.97 (ddd, J=16.1, 11.6, 6.4 Hz, 2H), 0.88 (t, J=7.3 Hz, 3H); LCMS m/z (ESI$^+$): calculated for $C_{93}H_{125}FN_{10}O_{25}$, 1801.9; found 1802.9 $[M+H]^+$.

Example 13: Synthetic Example LP5 (DBCO-NNAA-PEG13-AAA-Exatecan)

LP5

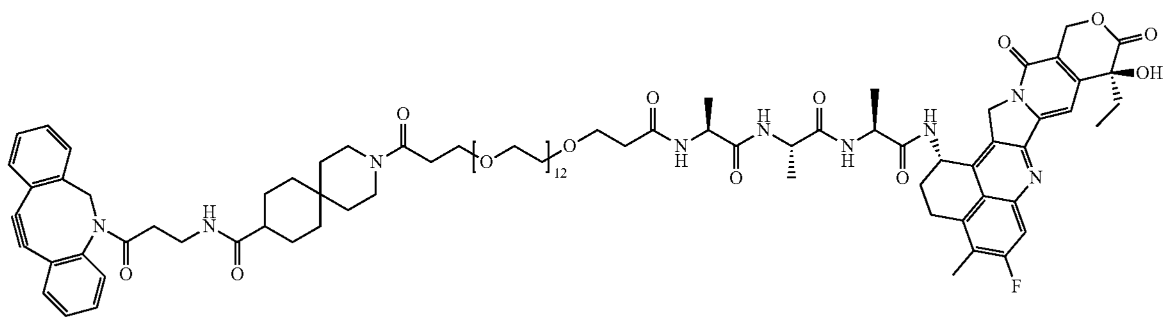

Scheme 11: Synthesis of AAA-Exatecan

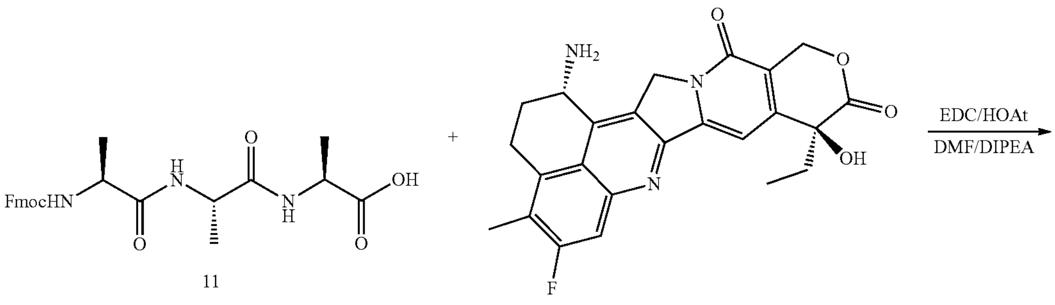

11

1

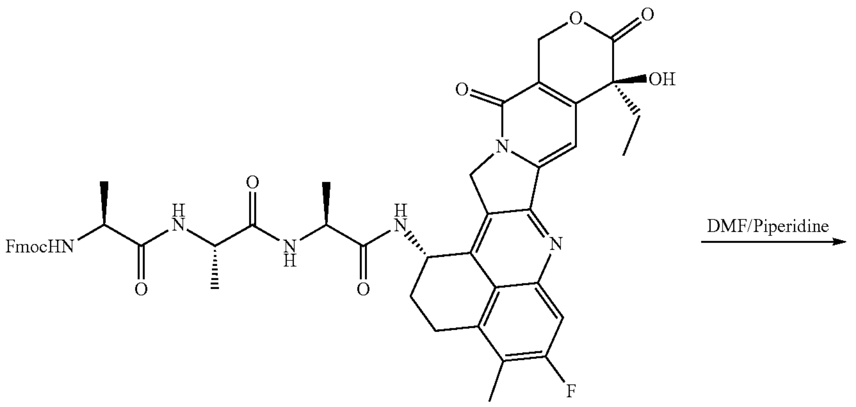

12

-continued
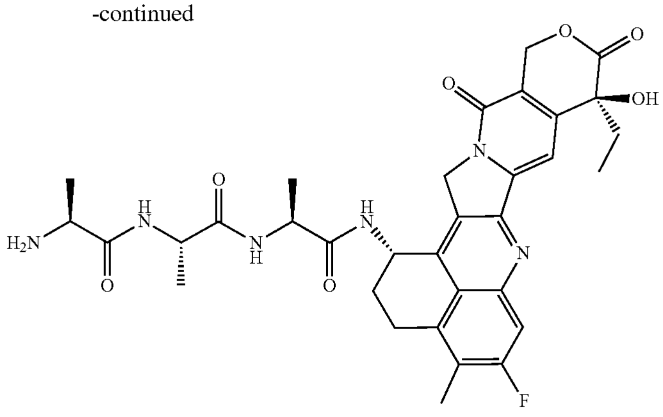
13
Scheme 12: Synthesis of DBCO-nnAA-PEG-13-AAA-Exatecan (LP5)
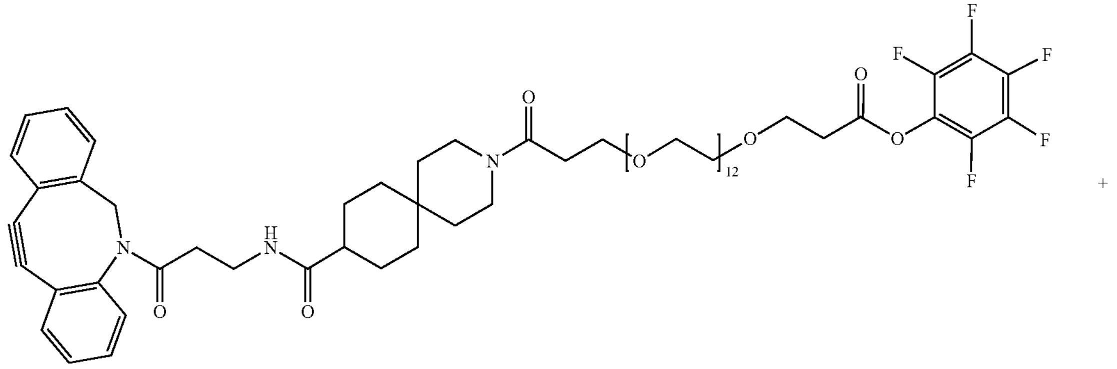
4
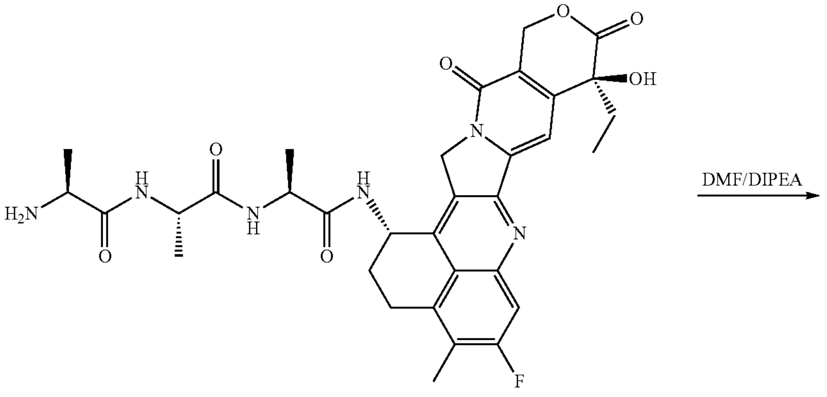
13

-continued

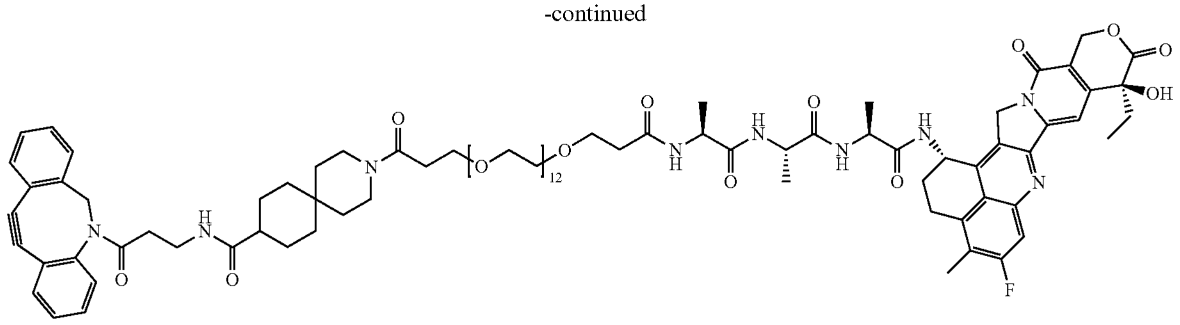

LP5

LP5 was synthesized in an analogous fashion using the same methods as described above. LCMS m/z ($ESI^+$): calculated for $C_{92}H_{124}FN_9O_{24}$, 1757.87; found 1759.1 $[M+H]^+$.

Example 14: Para-Azidomethylphenylalanine (pAMF) Incorporation

Non-natural para-azidomethylphenylalanine (pAMF) residues were incorporated in monoclonal antibodies (mAbs) in place of specific residues using XpressCF+® cell-free expression platform (Yin et al., 2017, Sci Rep 7 (1): 3026). Sites were chosen for pAMF incorporation to enable the conjugation of cytotoxin moieties via copper-catalyzed azide-alkyne cycloaddition (CuAAC) or a copper-free conjugation method, e.g., strain-promoted azide-alkyne cycloaddition (SPAAC) through dibenzocyclooctyne (DBCO or DIBO). mAbs were purified through affinity chromatography column followed by ion exchange chromatography columns.

The CFPS reaction mix included 37.5% (v/v) S30 *E. coli* cell extract, 3 mg/L plasmid DNA, and 2 mM pAMF as well as the 20 natural amino acids, NMPs, polyamines, and small molecules for energy generation (Cai et al. *Biotechnol. Prog.* 2015, 31, 823-831). *M. jannaschii* pAMF tRNA synthetase, *M. jannaschii* amber suppressor tRNA, and T7 RNA polymerase were individually over-expressed in intact *E. coli* cells and added to the CF reaction as a crude lysate at a final concentration of 1-2% each. Reactions were conducted in a stirred tank bioreactor for 14 hrs at 25° C. at pH 7.0 and 20% DO followed by 3 hrs at pH 8.0 80% DO. mAbs were captured by Protein A affinity chromatography eluted with eluted with 100 mM Glycine at pH 3.2. The neutralized Protein A eluate was concentrated and further polished by preparative SEC preparative SEC (Superdex 200) in phosphate-buffered saline (1×PBS).

Example 15: General Methods for Conjugation of Compounds to Antibodies

Method #1: Dibenzocylcooctyne (DBCO) compound was dissolved in dimethylsulfoxide (DMSO) to a final concentration of 5 mM. The conjugation was carried out in 1×PBS at antibody concentration of 1-30 mg/mL, DBCO compound to pAMF ratio of 1.5-3, and with 25% DMSO. The reaction mixture was incubated at room temperature for overnight. The conjugation efficiency was measured by LC/MS. Unconjugated DBCO compound was removed by cation exchange. The conjugate was formulated in formulation buffer supplemented with 9% sucrose. The drug to antibody ratio (DAR) was measured by LC/MS.

Method #2: Linker payloads were dissolved in DMSO to a final concentration of 5 mM. The conjugation was carried out in 1×PBS at antibody concentration of 1 mg/mL, drug linker to pAMF ratio of 3, and with 15% of DMSO. The reaction mixture was incubated at room temperature for overnight. The conjugation efficiency was measured by MALDI. Unconjugated drug linker was removed by desalting and formulated in 1×PBS. Purity of the conjugate was measured by Sepax SEC-300.

Example 16: Differential Scanning Fluorimetry

A protein thermal shift assay was carried out by mixing the protein to be assayed with an environmentally sensitive dye (SYPRO Orange, Life Technologies #S-6650) and monitoring the fluorescence of the mixture in real time as it underwent controlled thermal denaturation. Protein solutions at 1 mg/mL were mixed at a 1-1 volumetric ratio with a solution of SYPRO Orange solution diluted 250-fold in PBS+10% sucrose. 5 μL aliquots of the protein-dye mixture were dispensed in quadruplicate in a 384-well microplate (Bio-Rad #MSP-3852). The plate was sealed with an optically clear sealing film (Bio-Rad #MSB-1001) and placed in a 384-well plate real-time thermocycler (Bio-Rad CFX384 Real Time System). The protein-dye mixture was heated from 25° C. to 95° C., at increments of 0.2° C. per cycle, allowing 3 seconds of equilibration at each temperature before taking a fluorescence measurement. At the end of the experiment, the transition melting temperatures (TM1 and TM2) were determined using the Bio-Rad CFX manager software. TM1 represents the melting temperature of the Fc domain. TM2 represents the melting temperature of the Fab domain.

TABLE 21

DSF Melting temperatures for parent antibody and ADC.

| | | DSF | |
|---|---|---|---|
| Conjugate/mAB # | Description | TM1 (° C.) | TM2 (° C.) |
| mAb 41 | 2900-A02 F241/F404TAG | 61.6 | 82.6 |
| Conjugate 7 | 2900-A02 F241/F404 LP2 | 72.5 | 81.2 |

Example 17: Biacore Kinetic Analysis

Anti-Fc polyclonal antibodies were immobilized onto a CM4 chip (Cytiva #BR100534) using amine coupling chemistry (Human Antibody Capture Kit, Cytiva #BR100839). The immobilization steps were carried out at a flow rate of 25 μL/min in 1×HBS-EP+buffer (Cytiva #BR100669). The sensor surfaces were activated for 7 min with a mixture of NHS (0.05 M) and EDC (0.2 M). The Anti-Fc antibodies were injected over all 4 flow cells at a concentration of 25 ug/ml in 10 mM sodium acetate, pH 4.5, for 7 min. Ethanolamine (1 M, pH 8.5) was injected for 7 min to block any remaining activated groups. Approximately 6,000 response units (RU) of capture antibody was immobilized on each flow cell. Off-rate and kinetic binding experiments were performed at 25° C. using 1×HBS-EP+buffer. Antibodies or ADCs were injected over the anti-Fc surface at a concentration of 3 μg/mL for 12 seconds at a flow rate of 10 μL/min on flow cells 2, 3 and 4, followed by a buffer wash for 30 seconds at the same flow rate. Kinetic characterization of antibody or ADC samples was carried out with a range of antigen concentrations from about 1-100 nM and 1 injection of 0 nM antigen (for example, 100, 50, 12.5, 3.125, 0.781 and 0 nM). After capturing ligand (antibody) on the anti-Fc surface, the analyte (human TF, Lake Pharma; cynomolgus TF, Sino Bio #90885-C08H; mouse TF, R&D Systems #3178-PA) was bound for 180 seconds, followed by a 420 second dissociation phase at a flow rate of 50 μL/min. Between each ligand capture and analyte binding cycle, regeneration was carried out using 2 injections of 10 mM Glycine pH 2.0 for 30 seconds at 30 μL/min, followed by a 30 second buffer wash step. The data was fit with the Biacore T200 Evaluation software, using a 1-1 Langmuir binding model. KD (affinity, nM) was determined as a ratio of the kinetic rate constants calculated from the fits of the association and dissociation phases.

C., and 37° C. and evaluated over a 3-week period with sample collected at 3 days, 7 days, 14 days and 21 days. Study 2: Freeze/thaw stability was evaluated over five freeze/thaw cycles. Samples were evaluated by HPLC-SEC. The formulations used in the study include:

Buffer #1:10 mM citrate, 9% sucrose, pH 6.0 .

Buffer #2:10 mM citrate, 0.01% PS20, 9% sucrose, pH 6.0

Buffer #3:10 mM histidine, 9% sucrose, pH 7.0

Figure 3A:
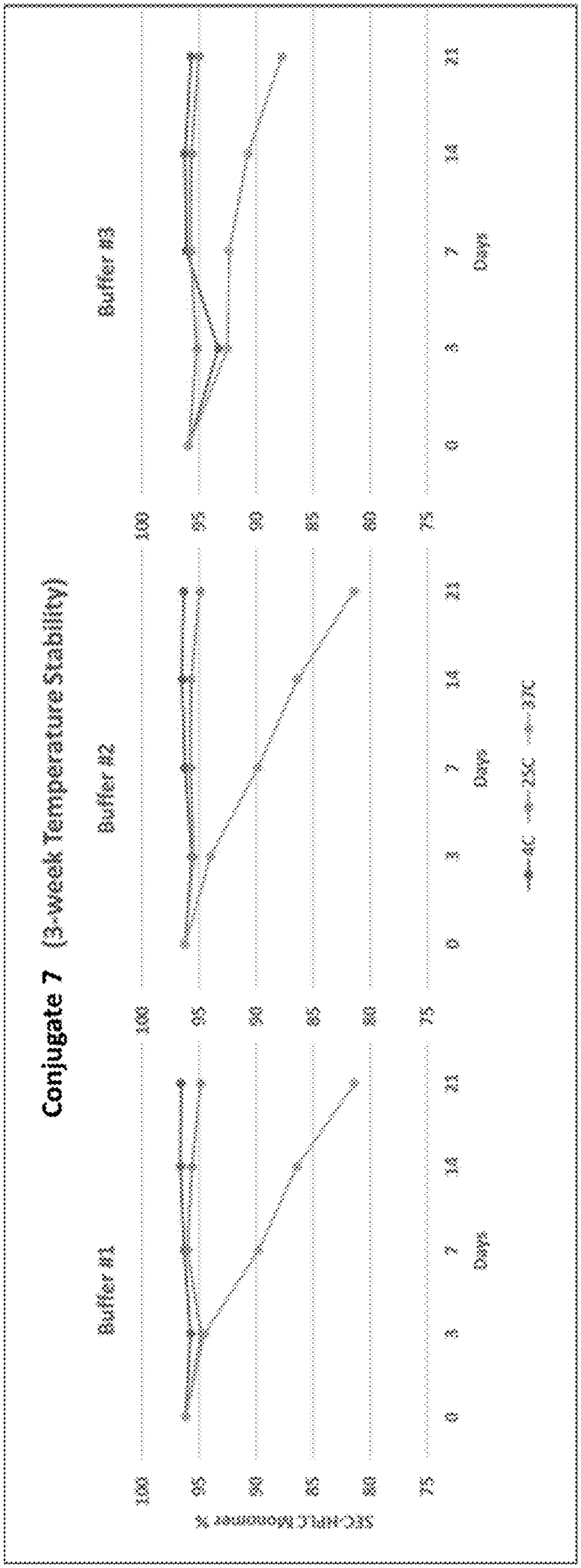
FIG. 3A provides HPLC-SEC results for formulation buffer comparison for Conjugate 7 at 4° C., 25° C. and 37° C. conditions.
Figure 3B:
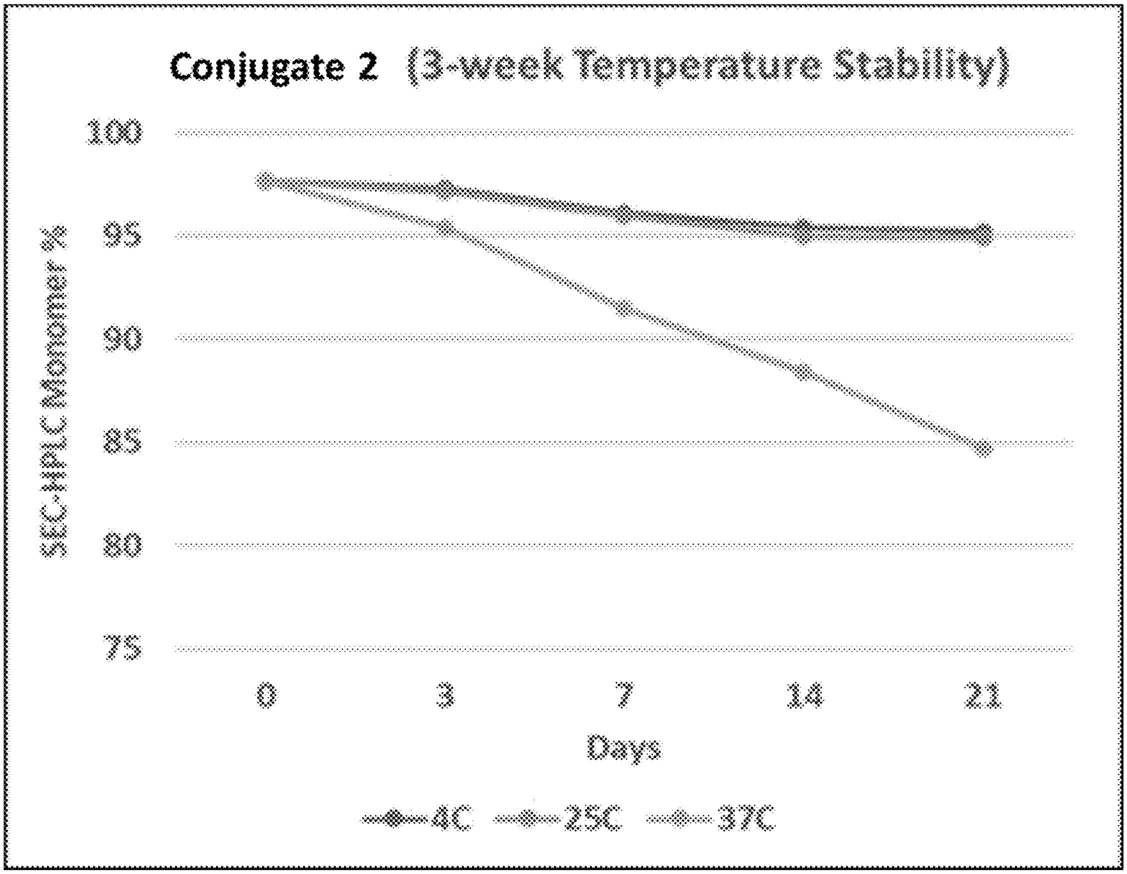
FIG. 3B provides HPLC-SEC results for Conjugate 2 at 4° C., 25° C. and 37° C. conditions.

As shown in FIG. 3A, Conjugate 7 at 4° C. and 25° C. did not show significant biophysical changes in any of the formulation buffers, however at 37° C. Conjugate 7 was aggregated which resulted in a decrease of monomer percentage. Buffer #3 which was formulated into histidine did mitigate some monomer % loss at 37° C., while for the other two formulation buffers, there was no impact. Conjugate 2 showed comparable results in FIG. 3B, no significant changes in overall product quality at 4° C. and 25° C., but significantly impacted over the 3-week hold at 37° C.

Figure 4:
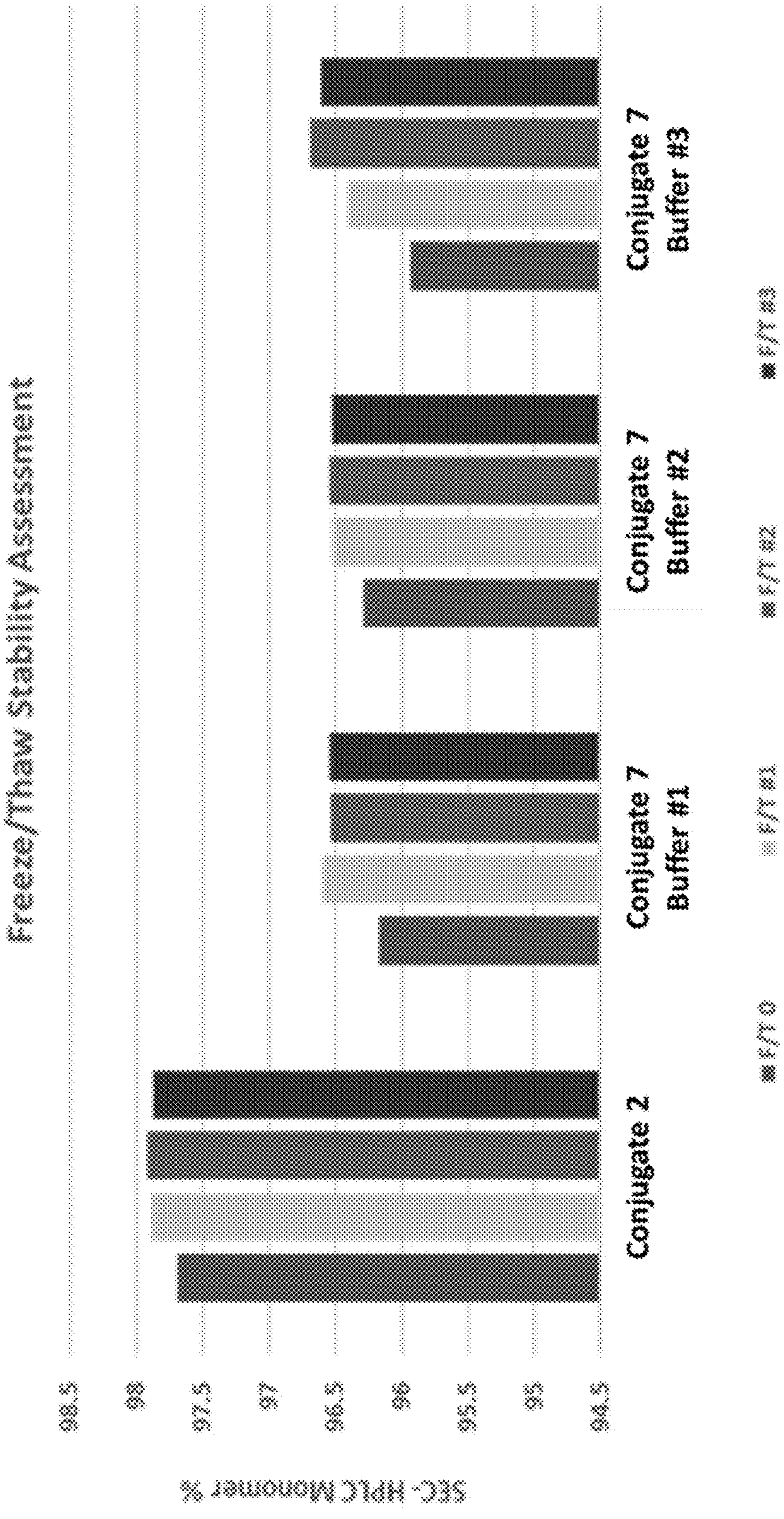
FIG. 4 provides HPLC-SEC results over 5× freeze/thaw cycles for Conjugate 2 in one formulation buffer and for Conjugate 7 in three different formulation buffers.

Five freeze/thaw cycles (each aliquot being placed in liquid nitrogen for 10 seconds and then left at ambient temperature until completely thawed) were performed on Conjugate 2 and Conjugate 7. After one, three, and five freeze/thaw cycles, an aliquot from both samples was assayed by HPLC-SEC. HPLC-SEC (FIG. 4) results were consistent across all five freeze/thaw cycles for each sample in all formulation buffers.

Example 19: Conjugates 2, 3 and 6 Neutrophil Viability Assessment

To evaluate the possible toxicity of the ADCs on Neutrophil precursor cells $CD34^+$ hematopoietic stem cells were

TABLE 22

Biacore Kinetics for parent antibody and ADCs.

| Conjugate/ mAb # | Description | Biacore human TF kinetics ka (1/Ms) | kd (1/s) | KD (M) | Biacore cynomolgus TF kinetics ka (1/Ms) | kd (1/s) | KD (M) |
|---|---|---|---|---|---|---|---|
| mAb 41 | 2900-A02 F241/F404TAG | 4.03E+05 | 1.82E−03 | 4.52E−09 | 4.57E+05 | 8.40E−04 | 1.84E−09 |
| Conjugate 2 | 2900-A02 F241/F404 LP1 | 5.08E+05 | 1.89E−03 | 3.71E−09 | 7.47E+05 | 8.92E−04 | 1.19E−09 |
| Conjugate 7 | 2900-A02 F241/F404 LP2 | 5.08E+05 | 2.09E−03 | 4.11E−09 | 5.82E+05 | 1.03E−03 | 1.77E−09 |

Example 18: Conjugates 2 and 7 Developability and Thermostability Testing

Figure 5:
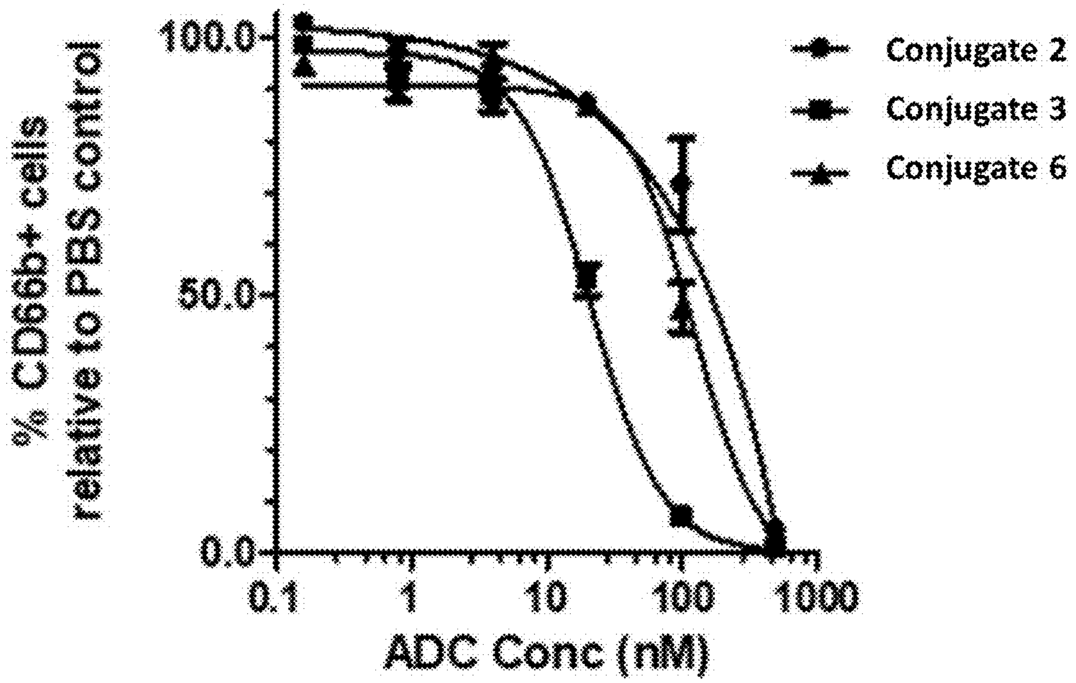
FIG. 5 provides the viability of CD66b+ cells as a percentage relative to PBS control for Neutrophil precursor cells treated with Conjugates 2, 3 and 6.

Thermal stability assessment for Conjugate 2 (HC 2900-A02 F241/F404TAG SEQ ID NO: 3178; LC SEQ ID NO: 3179; conjugated to LP1; aTF_2900-A02_HC_F241/F404TAG_SerOpt pAzMeF+LP1/Trastuzumab LC SerOpt) was evaluated under various stress conditions in one formulation buffer (10 mM citrate, 9% sucrose, pH 6.0). Thermal stability assessment for Conjugate 7 (HC 2900-A02 F241/F404TAG SEQ ID NO: 3178; LC SEQ ID NO: 3179; conjugated to LP2; aTF_2900-A02_HC_F241/F404TAG_SerOpt pAzMeF+LP2; Trastuzumab LC SerOpt) was evaluated under various stress conditions in several different formulation buffers at 10 mg/mL protein concentration. Study 1: Accelerated short term temperature stability was tested for signs of aggregation/degradation at 4° C., 25° differentiated into Neutrophil precursor cells and treated with the ADCs for 6 days followed by detection with flow cytometry using the CD66b granulocyte marker (Zhao et al., *Mol. Cancer Ther.* 16, 1866-1876 (2017)). $CD34^+$ cells derived from normal human bone marrow were prepared in media containing X-Vivo-15, rhIL-3 (20 ng/mL), rhIL-6 (20 ng/mL), rhSCF (100 ng/mL) and rhFlt-3L (100 ng/mL). 10,000 cells per well were plated in round-bottom 96-well plates and cultured in a humidified incubator at 37° C., 5% CO2 for 3 days. Cells were then washed twice with X-Vivo medium and incubated in X-Vivo-15 medium supplemented with rhSCF (50 ng/mL), rhFlt-3L (100 ng/ml), rh IL3 (5 ng/ml), rhGM-CSF (5 ng/mL) rhG-CSF (5 ng/mL) for 4 days. The cells were washed again (×2) and incubated in X-Vivo-15 medium supplemented with rhIL-3 (5 ng/ml) and rhG-CSF (30 ng/mL) for another 4 days. On day 11, the cells were washed twice and placed in the final media formulation containing X-Vivo-15 supplemented with just rhG-CSF (30 ng/mL) for the final 6 days. Cells were then treated with ADCs or PBS for a further 6 days. For flow analysis, cells were blocked with 10% FBS and 20 μg/mL human IgG at 4° C. for 10 minutes. Following blocking, the surface markers of the cells were stained with a PE-conjugated anti-CD66b antibody (Biolegend, catalog number 392904) and DAPI (viability) at 4° C. for 20 minutes. The cells were then washed and resuspended in 200 μL per well of PBS+2% FBS, and then analyzed by flow cytometry using a Beckman Coulter cytoFlex cytometer. The viability of Neutrophil precursor cells based on % CD66b+ cell numbers relative to a PBS treated control were tested for Conjugates 2, 3 and 6 (FIG. 5)

Example 20: In Vitro Cell Killing of TF Lead Antibodies Conjugated to LP1

Anti-TF antibodies were conjugated to LP1 at Y180/F404 sites to make ADCs of DAR=4 and the cell killing activity of the ADCs was evaluated on TF positive BxPC3, NCI-H292, NCI-H1975, NCI-H441, NCI-H1954, JIMT1, and MDA-MB-468 cells as well as TF negative NCI-H1703 cells.

BxPC3, NCI-H292, NCI-H1975, NCI-H441, NCI-H1954, JIMT1, MDA-MB-468 and NCI-H1703 cells were purchased from ATCC (American Type Culture Collection). All the other cell lines were maintained in DMEM/F12 (1:1), high glucose (Corning) supplemented with 10% heat-inactivated fetal bovine serum (Sigma), 2 mM glutamax (Thermo Scientific), and 1× Penicillin/Streptomycin (Corning). Cytotoxicity effects of the ADC on the cancer cell lines were measured with a cell proliferation assay. A total of 625 cells in a volume of 25 microliters were seeded in a 384-well flat bottom white polystyrene plate the day before the assay. ADC and free drugs were formulated at 2× starting concentration in cell culture medium and filtered through SpinX 0.22 micron cellulose acetate filtered 2 mL centrituge tubes (Corning Costar). Filter sterilized samples were serial diluted (1:3) under sterile conditions and added onto cells in triplicates. Plates were cultured at 37° C. in a CO2 incubator for 120 hours. For cell viability measurement, 30 microliters of Cell Titer-Glo® reagent (Promega Corp, Madison, WI) was added into each well, and plates processed as per product instructions. Relative luminescence was measured on an ENVISION® plate reader (Perkin-Elmer; Waltham, MA). Relative luminescence readings were converted to % viability using untreated cells as controls. Data was fitted with non-linear regression analysis, using log (inhibitor) vs. response, variable slope, 4-parameter fit equation using GraphPad Prism. Data was expressed as % relative cell viability vs. dose of free linker-warhead or ADC in nanomolar with error bars indicating the Standard Deviation (SD) of the triplicates.

The cell killing activity of ADCs for the antibody leads from SRP2799 and SRP2767 on BxPC3 cells were summarized in Table 23. All of the tested ADCs showed similar high potency cell killing on BxPC3 cells.

TABLE 23

Cell killing activity for different TF antibodies conjugated to LP1 on BxPC3.

| Conjugate # | Sample | DAR | EC50 (nM) | Span (%) |
|---|---|---|---|---|
| 30 | 2799-A05 Y180/F404-LP1 | 3.9 | 0.025 | 99 |
| 31 | 2799-B03 Y180/F404-LP1 | 3.9 | 0.023 | 99 |
| 32 | 2799-B06 Y180/F404-LP1 | 3.9 | 0.061 | 99 |

The cell killing activity of the ADCs for antibody leads from SRP2900 and SRP2842 were summarized in Table 24. All of the tested ADCs showed potent cell killing on TF positive NCI-H292, NCI-H441, NCI-H1954 and MDA-MB-468, some cell killing on NCI-H1975 and JIMT1 cells, but not much cell killing on TF negative NCI-H1703 cells.

TABLE 24

Cell killing activity of different TF antibodies conjugated to LP1.

| | | NCI-H292 (TF++++) | | NCI-H1975 (TF++) | | NCI-H441 (TF+) | | NCI-H703 (TF±) | |
|---|---|---|---|---|---|---|---|---|---|
| Conjugate # | DAR | EC50 (nM) | Span (%) | EC50 (nM) | Span (%) | EC50 (nM) | Span (%) | EC50 (nM) | Span (%) |
| 1 | 3.8 | 0.06 | 83 | >100 | NC | 0.511 | 53 | >100 | NC |
| 21 | 3.74 | 0.022 | 86 | 0.234 | 66 | 0.116 | 56 | >100 | NC |
| 22 | 3.71 | 0.106 | 82 | >100 | NC | >100 | NC | >100 | NC |
| 23 | 3.71 | 0.048 | 79 | >101 | NC | 1.54 | 42 | >100 | NC |
| 24 | 3.61 | 0.057 | 78 | >102 | NC | 0.803 | 43 | >100 | NC |
| 25 | 3.73 | 0.048 | 78 | >103 | NC | 0.805 | 43 | >100 | NC |
| 26 | 3.71 | 0.177 | 84 | >104 | NC | 0.708 | 55 | >100 | NC |
| 27 | 3.71 | 0.115 | 83 | >105 | NC | 0.738 | 56 | >100 | NC |
| 28 | 3.67 | 0.201 | 81 | >106 | NC | 0.733 | 51 | >100 | NC |
| 29 | 3.73 | 0.066 | 77 | >107 | NC | 0.389 | 45 | >100 | NC |

| | | NCI-H1954 (TF+++) | | JIMT1 (TF++) | | MDA-MB-468 (TF++) | |
|---|---|---|---|---|---|---|---|
| Conjugate # | DAR | EC50 (nM) | Span (%) | EC50 (nM) | Span (%) | EC50 (nM) | Span (%) |
| 1 | 3.8 | 0.133 | 92 | >100 | NC | 0.361 | 88 |
| 21 | 3.74 | 0.022 | 94 | 0.3 | 60 | 0.054 | 87 |
| 22 | 3.71 | 0.966 | 90 | >100 | NC | 3.51 | 93 |
| 23 | 3.71 | 0.186 | 87 | >100 | NC | 0.536 | 84 |

TABLE 24-continued

| Cell killing activity of different TF antibodies conjugated to LP1. | | | | | | | |
|---|---|---|---|---|---|---|---|
| 24 | 3.61 | 0.165 | 90 | >100 | NC | 0.485 | 85 |
| 25 | 3.73 | 0.149 | 88 | >100 | NC | 0.602 | 81 |
| 26 | 3.71 | 0.172 | 92 | >100 | NC | 0.505 | 85 |
| 27 | 3.71 | 0.151 | 91 | 5.31 | 54 | 0.475 | 86 |
| 28 | 3.67 | 0.222 | 88 | >100 | NC | 0.941 | 86 |
| 29 | 3.73 | 0.175 | 89 | >100 | NC | 1 | 85 |

Example 21: In Vitro Cell Killing of TF ADCs Conjugated to LP1 at Different Conjugation Sites and DARs Anti-TF antibody 2900-A02 was conjugated to LP1 at different conjugation sites with different DARs. The cell killing activity of the ADCs was evaluated on TF positive NCI-H292, NCI-H1975, HCC1954, as well as TF negative NCI-H1703 cells.

The cell killing EC50 the ADCs were summarized in Table 25. TF ADCs with different DARs showed similar high potency cell killing on TF positive NCI-H292 and HCC1954, relatively lower cell killing activity on TF low NCI-H1975, and not much cell killing on TF negative NCI-H1703 cells.

TABLE 25

Cell killing activity of TF ADCs conjugated to LP1 at different sites and DARs.

| | | NCI-H292 (TF++++) | | HCC1954 (TF+++) | | NCI-H1975(TF++) | | NCI-H1703 (TF±) | |
|---|---|---|---|---|---|---|---|---|---|
| Conjugate # | DAR | EC50 (nM) | Span (%) | EC50 (nM) | Span (%) | EC50 (nM) | Span (%) | EC50 (nM) | Span (%) |
| 2 | 3.98 | 0.056 | 86 | 0.094 | 93 | 9.1 | 82 | >100 | NC |
| 4 | 5.91 | 0.038 | 89 | 0.083 | 94 | 6.2 | 91 | >100 | NC |
| 1 | 3.96 | 0.064 | 85 | 0.15 | 93 | 13 | 84 | >100 | NC |
| 3 | 5.97 | 0.042 | 87 | 0.13 | 94 | 6.5 | 79 | >100 | NC |

To evaluate if the cell killing observed on these cells are specific to TF expression on the positive cells, unconjugated antibodies were included at 0.5 uM to compete with the cell killing of the ADCs.

The cell killing activity of the ADCs in the presence and absence of the unconjugated antibodies were summarized in Table 26. TF ADCs with different DARs showed similar high potency cell killing on TF positive NCI-H292 and HCC1954, relatively lower cell killing activity on TF low NCI-H1975. The cell killing activity of the ADCs on TF positive cells was greatly reduced in the presence of 0.5 uM of un-conjugated antibodies, which indicated that the cell killing of TF ADCs was depended on the binding of antibodies to the TF on the cell surface. Very weak cell killing activity was observed for TF ADCs on TF negative NCI-H1703 cells and this weak cell killing was not affected by the presence of un-conjugated antibodies, which indicated that the weak killing on TF negative cells might be not specific to TF expression.

TABLE 26

Competition cell killing activity of TF ADCs conjugated to LP1 at different sites and DARs.

| | | NCI-H292 (TF++++) | | HCC1954 (TF+++) | | NCI-H1975(TF++) | | NCI-H1703 (TF±) | |
|---|---|---|---|---|---|---|---|---|---|
| Conjugate # | DAR | EC50 (nM) | Span (%) | EC50 (nM) | Span (%) | EC50 (nM) | Span (%) | EC50 (nM) | Span (%) |
| 1 | 3.96 | 0.055 | 85 | 0.064 | 95 | ~25 | 62 | >100 | NC |
| 3 | 5.97 | 0.048 | 82 | 0.073 | 93 | ~7 | 68 | >100 | NC |
| 5 | 7.5 | 0.045 | 87 | 0.08 | 91 | ~4.4 | 72 | >100 | NC |
| 6 | 7.94 | 0.044 | 86 | 0.085 | 93 | ~5 | 71 | >100 | NC |
| 1 + 0.5 uM mAb 36 | 3.96 | >100 | NC | >100 | NC | >100 | NC | >100 | NC |
| 3 + 0.5 uM mAb 39 | 5.97 | >100 | NC | >100 | NC | >100 | NC | >100 | NC |

TABLE 26-continued

Competition cell killing activity of TF ADCs conjugated to LP1 at different sites and DARs.

| | | NCI-H292 (TF++++) | | HCC1954 (TF+++) | | NCI-H1975(TF++) | | NCI-H1703 (TF±) | |
|---|---|---|---|---|---|---|---|---|---|
| Conjugate # | DAR | EC50 (nM) | Span (%) | EC50 (nM) | Span (%) | EC50 (nM) | Span (%) | EC50 (nM) | Span (%) |
| 5 + 0.5 uM mAb 38 | 7.5 | >100 | NC | >100 | NC | >100 | NC | >100 | NC |
| 6 + 0.5 uM mAb 40 | 7.94 | >100 | NC | >100 | NC | >100 | NC | >100 | NC |

Example 22: In Vitro Cell Killing of TF ADCs Conjugated to Different Exatecan Linker Payloads Anti-TF antibody 2900-A02 and 2842-B01 were conjugated to exatecan payload with different linkers and the cell killing activity of the ADCs was evaluated on TF positive NCI-H292, NCI-H1975, HCC1954, as well as TF negative NCI-H1703 cells. 2900-A02 conjugated to exatecan linkers (LP2, LP3, LP4, LP5) showed various cell killing activity on TF positive NCI-H292 and HCC1954, not much cell killing on TF relative low NCI-H1975 and TF negative NCI-H1703 cells. 2842-B01 conjugated to LP3, LP4 and LP5 showed potent cell killing activity on NCI-H292 cells, but no cell killing on other cells tested. The cell killing activity of the ADCs were summarized in Table 27.

TABLE 27

Cell killing activity of TF ADCs conjugated to Exatecan linker payloads.

| | | NCI-H292 (TF++++) | | HCC1954 (TF+++) | | NCI-H1975(TF++) | | NCI-H1703 (TF±) | |
|---|---|---|---|---|---|---|---|---|---|
| Conjugate or mAb # | DAR | EC50 (nM) | Span (%) | EC50 (nM) | Span (%) | EC50 (nM) | Span (%) | EC50 (nM) | Span (%) |
| 9 | 3.63 | 0.3 | 74 | >100 | NC | >100 | NC | >100 | NC |
| 10 | 3.72 | 0.049 | 91 | 0.28 | 40 | >100 | NC | >100 | NC |
| 11 | 3.74 | 0.086 | 90 | 0.49 | 38 | >100 | NC | >100 | NC |
| 12 | 3.81 | 0.16 | 88 | 2.1 | 39 | >100 | NC | >100 | NC |
| 18 | 3.99 | 0.23 | 90 | >100 | NC | >100 | NC | >100 | NC |
| 19 | 3.99 | 0.41 | 89 | >100 | NC | >100 | NC | >100 | NC |
| 20 | 3.99 | 0.67 | 86 | >100 | NC | >100 | NC | >100 | NC |

The TF antibody 2900-A02 was also conjugated to exatecan linker payload LP2 at DAR=4 (Conjugate 7) and DAR=8 (Conjugate 8) and the cell killing activities were compared to LP1 ADC at DAR=4 (Conjugate 2) on TF positive MDA-MB-231, BxPC3, NCI-H292, A431, NCI-H1975 and NCI-H441 cells, as well as TF negative NCI-H1703 cells.

The hemiasterlin ADC at DAR4 (Conjugate 2) showed potent cell killing on TF positive MDA-MB-231, BxPC3, NCI-H292 and A431. Some cell killing was observed on NCI-H441 cells, but not much cell killing on NCI-H1975 and NCI-H1703 cells. The exatecan ADCs showed potent cell killing on BxPC3, NCI-H292 and A431 cells, but not much cell killing on other cells tested. In general, the exatecan ADCs showed lower cell killing activity on TF positive cells compared to Hemiasterlin ADC at DAR=4. Exatecan ADC at DAR8 showed slightly better cell killing than exatecan ADC at DAR4 on TF positive cells. The cell killing activities were summarized in Table 28.

TABLE 28

Cell killing activity of TF ADCs conjugated to LP2 at DAR4 and DAR8.

| | Conjugate #2 | | Conjugate #7 | | Conjugate #8 | |
|---|---|---|---|---|---|---|
| Cell Line Tested | $EC_{50}$ (nM) | Span (%) | $EC_{50}$ (nM) | Span (%) | $EC_{50}$ (nM) | Span (%) |
| MDA-MB-231 | 0.159 | 66 | 6.363 | 33 | 3.808 | 35 |
| BxPC3 | 0.64 | 96 | 0.469 | 58 | 0.735 | 61 |
| NCI-H292 | 0.639 | 82 | 0.509 | 72 | 0.326 | 75 |

TABLE 28-continued

Cell killing activity of TF ADCs conjugated to LP2 at DAR4 and DAR8.

| | Conjugate #2 | | Conjugate #7 | | Conjugate #8 | |
|---|---|---|---|---|---|---|
| Cell Line Tested | $EC_{50}$ (nM) | Span (%) | $EC_{50}$ (nM) | Span (%) | $EC_{50}$ (nM) | Span (%) |
| A431 | 0.711 | 97 | 0.697 | 82 | 0.589 | 80 |
| NCI-H1975 | >100 | NC | >100 | NC | >100 | NC |
| NCI-H441 | 1 | 40 | >100 | NC | >100 | NC |
| NCI-H1703 | >100 | NC | >100 | NC | >100 | NC |

Example 23: In Vitro Cell Binding of TF Antibodies on Primary Keratinocytes

Since TF is expressed in human skin, anti-TF antibody 2900-A02 and 2842-B01-Hc3/Lc2 were tested in cell binding assay on primary adult human keratinocyte cells purchased from Thermo Fisher Scientific. Keratinocytes were cultured in defined keratinocyte culture medium (EpiLife Medium, Thermo Fisher Scientific) supplemented with growth supplement S7 (S0175 from Thermo Fisher Scientific) and Penicillin/Streptomycin on plates coated with keratinocyte coating matrix (Thermo Fisher Scientific).

To evaluate antibody binding activity of the anti-TF antibodies on the adult primary keratinocytes, a total of 100,000 keratinocytes per well were incubated on ice with serial dilutions of anti-TF antibodies in FACS buffer (PBS buffer supplemented with 1% bovine serum albumin, 0.05% sodium azide) for 60 minutes. Cells were washed twice with ice-cold FACS buffer and then incubated with 5 microgram/mL Alexa 647 labeled donkey anti-human Fc antibody (Jackson ImmunoResearch, West Grove, PA) on ice for another 60 minutes. Unstained cells and cells stained with secondary antibodies alone were used as controls. Samples were then washed twice using FACS buffer and analyzed using an Attune flow cytometer (Thermo Fisher). Geometric mean fluorescence intensities were fitted using non-linear regression analysis with one site specific binding equation on GraphPad Prism.

The TF antibody 2900-A02 (mAb 36) bound to human primary keratinocytes with high affinity, while the TF antibody lead 2842-B01-HC3/LC2 (mAb 37) showed reduced affinity to human primary keratinocytes. The cell binding activity of the antibodies on human primary keratinocytes was summarized in Table 29.

TABLE 29

TF antibodies cell binding activity on primary human keratinocytes.

| | | Keratinocyte Binding | |
|---|---|---|---|
| mAb# | Name | Bmax | Kd (nM) |
| 36 | 2900-A02 Y180/F404 | 164743 | 3.1 |
| 37 | 2842-B01-HC3/LC2 Y180/F404 | 151831 | 24 |

Example 24: In Vitro Cell Killing of TF ADCs on Primary Keratinocytes

Anti-TF antibody 2900-A02 ADCs conjugated to LP1 at different conjugation sites with different DARs, as well as TF antibody 2842-B01-HC3/Lc2 conjugated to LP1 at DAR4, were tested in cell killing assay on primary adult human keratinocyte cells.

To evaluate the cytotoxicity effects of the ADC on the adult primary keratinocytes, a total of 2000 keratinocytes in a volume of 50 microliters were seeded in a 96-well flat bottom cell culture plate coated with keratinocyte coating matrix (Thermo Fisher Scientific) the day before the actual assay starts. ADCs were formulated at 2× starting concentration in cell culture medium and filtered through SpinX 0.22 micron cellulose acetate filtered 2 mL centrifuge tubes (Corning Costar). Filter sterilized samples were serial diluted (1:3) under sterile conditions and added onto cells in triplicates. Plates were cultured at 37° C. in a CO2 incubator for 120 hours. For cell viability measurement, 10 microliters of WST-8 reagent (VWR) were added into each well and plates were incubated at 37° C. in a CO2 incubator for 4 hours. The absorbance at 450 nm was measured using a microplate reader (M5, Molecular Devices) and readings were converted to % viability using untreated cells as controls. Data was fitted with non-linear regression analysis, using log (inhibitor) vs. response, variable slope, 4-parameter fit equation using GraphPad Prism. Data was expressed as % relative cell viability vs. dose of free linker-warhead or ADC in nanomolar with error bars indicating the Standard Deviation (SD) of the triplicates.

ADCs for the TF antibody 2900-A02 showed similar potent cell killing on human primary keratinocytes, while the ADC for the lower affinity TF antibody 2842-B01-HC3/Lc2 showed reduced cell killing activity compared to 2900-A2 ADCs. The cell killing activity of the ADCs on human primary keratinocytes were summarized in Table 30.

TABLE 30

TF ADCs cell killing and binding activity on primary human keratinocytes.

| | | | Keratinocyte Killing | |
|---|---|---|---|---|
| Conjugate or mAb# | Name | DAR | EC50 (nM) | Span (%) |
| 36 | 2900-A02 Y180/F404 | — | >100 | NC |
| 1 | 2900-A02 Y180/F404-LP1 | 4 | 0.0055 | 73 |
| 3 | 2900-A02 Y180/F404/k42-LP1 | 6 | 0.0091 | 74 |
| 5 | 2900-A02 Y180/F404/k42/E161-LP1 | 7.5 | 0.0062 | 72 |
| 6 | 2900-A02 Y180/F241/F404/k42-LP1 | 7.9 | 0.0048 | 74 |
| 37 | 2842-B01-HC3/LC2 Y180/F404 | — | >100 | NC |
| 26 | 2842-B01-HC3/LC2 Y180/F404-LP1 | 3.9 | 0.038 | 73 |
| 7 | 2900-A02_HC_F241/F404-LP2 | 3.96 | 14.2 | 60 |
| 35 | 2900-A02_Y180/F241/Y391/F404-LP2 | 7.83 | 0.781 | 74 |

Example 25: In Vitro Cell Killing of TF ADCs on Primary Human Corneal Epithelial Cells Anti-TF antibody 2900-A02 ADCs conjugated to LP2 at different DARs (Conjugate 7 and conjugate 35) were tested in cell killing assay on primary human corneal epithelial cells to evaluate potential eye toxicity.

Primary human corneal epithelial cells (HCECs) were purchased from ATCC and maintained in corneal epithelial cell growth medium (corneal epithelial cell basal medium supplied with corneal epithelial cell growth kit from ATCC that contains apo-transferrin, epinephrine, Extract P, hydrocortisone hemisuccinate, L-Glutamine, recombinant human insulin and CE Growth Factor). To evaluate the cytotoxicity effects of the ADCs on HCECs, a total of 625 cells in a volume of 25 microliters of corneal epithelial cell growth medium were seeded in a 384-well white bottom cell culture plate the day before the actual assay starts. ADCs were formulated at 2× starting concentration in cell culture medium and filtered through SpinX 0.22 micron cellulose acetate filtered 2 mL centrifuge tubes (Corning Costar). Filter sterilized samples were serial diluted (1:3) under sterile conditions and 25 microliters were added onto cells in quadroplicates. Plates were cultured at 37° C. in a CO2 incubator for 7 days. For cell viability measurement, 10 microliters of PrestoBlue reagent were added into each well and plates were incubated at 37° C. in a CO2 incubator for 3 hours. The fluorescence was measured using a microplate reader (M5, Molecular Devices) and readings were converted to % viability using untreated cells as controls. Data was fitted with non-linear regression analysis, using log (inhibitor) vs. response, variable slope, 4-parameter fit equation using GraphPad Prism. Data was expressed as % relative cell viability vs. dose of ADC in nanomolar with error bars indicating the Standard Deviation (SD) of the quadroplicates.

ADCs for the TF antibody 2900-A02 showed weak cell killing on human primary corneal epithelial, while DAR8 ADC conjugate 35 showed slightly more activity compared to DAR4 ADC (conjugate 7). The cell killing activity of the ADCs were summarized in Table 31.

TABLE 31

TF ADCs cell killing on primary human corneal epithelial cells.

| HCEC | Conjugate 7 | | Conjugate 35 | |
|---|---|---|---|---|
| Lot# | EC50 (nM) | Span (%) | EC50 (nM) | Span (%) |
| 8120122 | 0.33 | 63.6 | 0.11 | 62.5 |
| 1001654 | 0.79 | 52 | 0.29 | 65 |
| 70036737 | 0.41 | 60.1 | 0.25 | 67.5 |

Example 26: DAR Stability

Figure 6A:
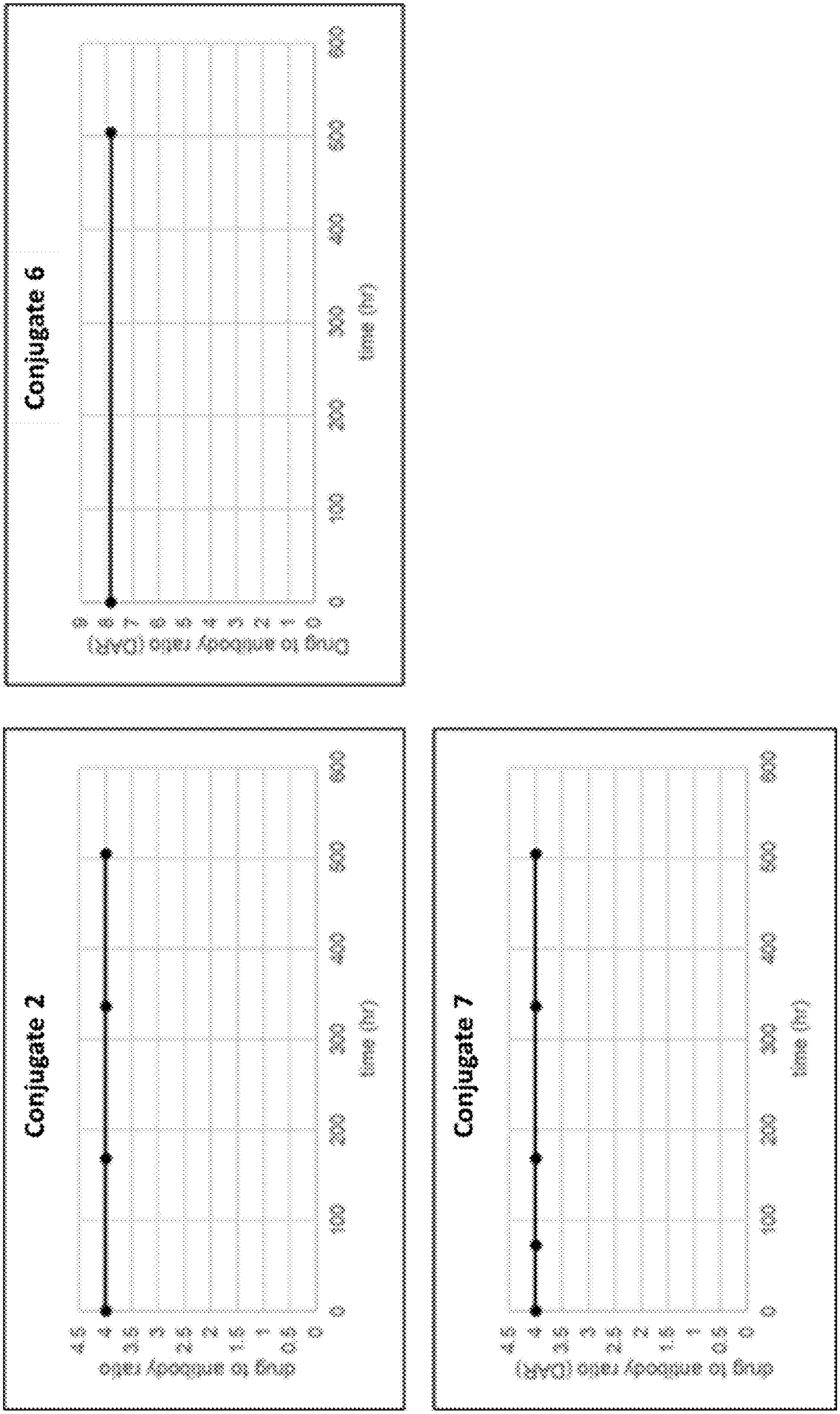
FIG. 6A provides measured DAR of Conjugates 2, 6 and 7 over 21 days.
Figure 6B:
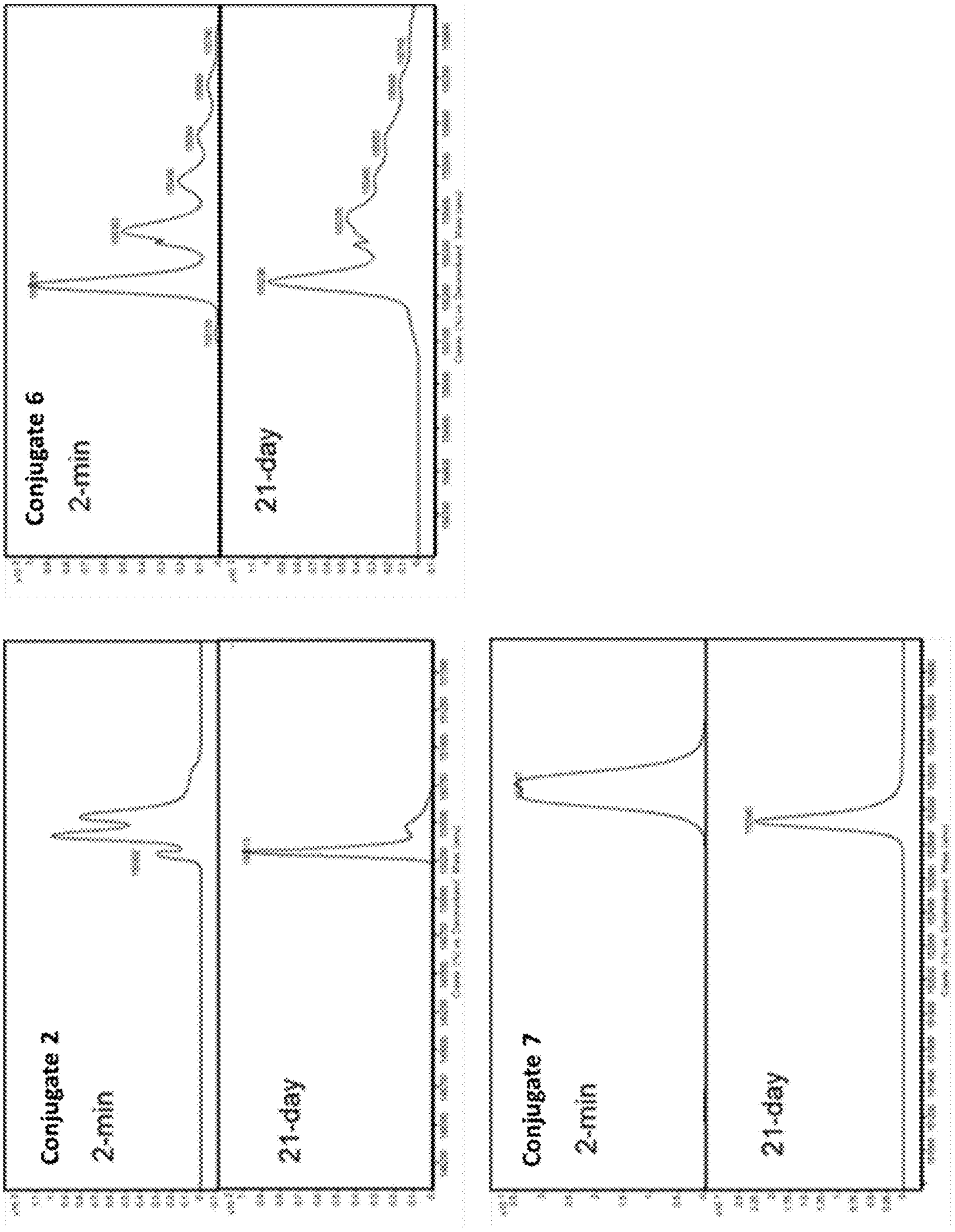
FIG. 6B provides deconvoluted mass spectra of anti-TF ADC samples from in vivo linker payload stability study for Conjugates 2, 6 and 7.

In vivo linker payload stability of Conjugates 2, 6 and 7 was investigated in rats or cynomolgus monkeys. Briefly, Conjugates 2, 6 and 7 were injected through IV. Plasma samples were collected from 2-5 animals at 15 min, 3 days, 7 days, 14 days and 21 days after dosing and were kept frozen until ready to be analyzed. aTF ADC was pulled down from plasma using anti-hFc and then injected on to Agilent QToF for intact mass analysis. DAR was calculated based on deconvoluted peak area. The three ADCs tested were all stable over 21 days (FIG. 6A). Comparison of 15-min sample and day 21 sample demonstrated that there was no degradation products observed over 21 days (FIG. 6B). Multiple peaks detected in 15-min samples were due to HC C-terminal lysine clipping that was common from in vivo samples.

Example 27: In Vivo Efficacy in the HCC1954 Breast Cancer Xenograft Model

The activity of different TF-targeted ADCs was examined in the HCC1954 breast cancer xenograft model. Briefly, BALB/c nude mice were implanted subcutaneously with $5\times10^6$ HCC1954 tumor cells in the right flank and randomized and enrolled into the study 13 days post implant, with tumor sizes around 140 $mm^3$. Tumor-bearing mice were administered a single dose of the test articles i.v. at 0.5 mg/kg and 5 mg/kg. All treatments were well tolerated, and mice exhibited normal body weight gain throughout the course of the study.

Figure 7A:
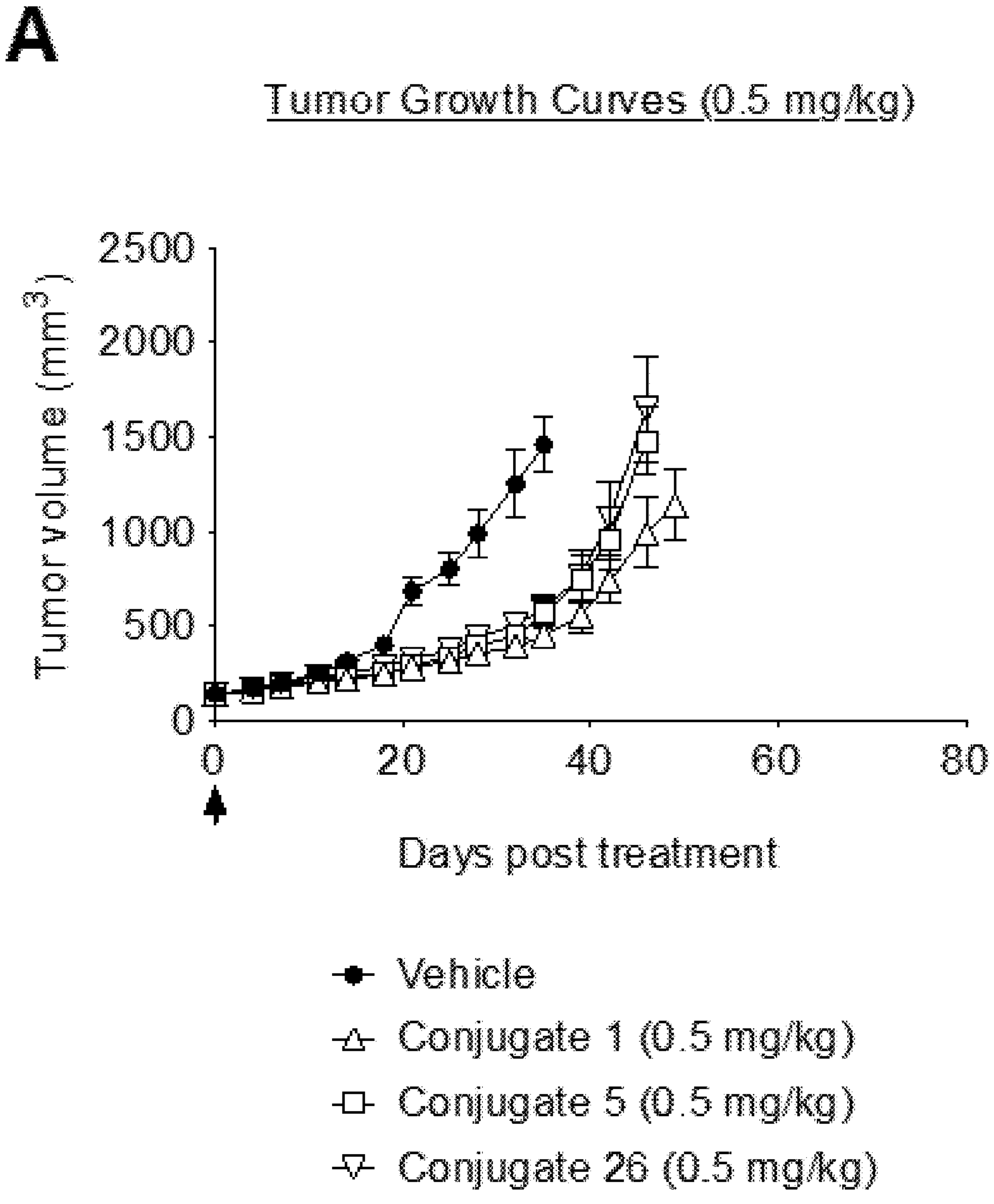
FIGS. 7A-C provide HCC1954 tumor growth curves in response to treatment with a single i.v. dose of TF-targeted ADCs, with doses (FIG. 7A) 0.5 mg/kg or (FIG. 7B) 5 mg/kg.
Figure 7B:
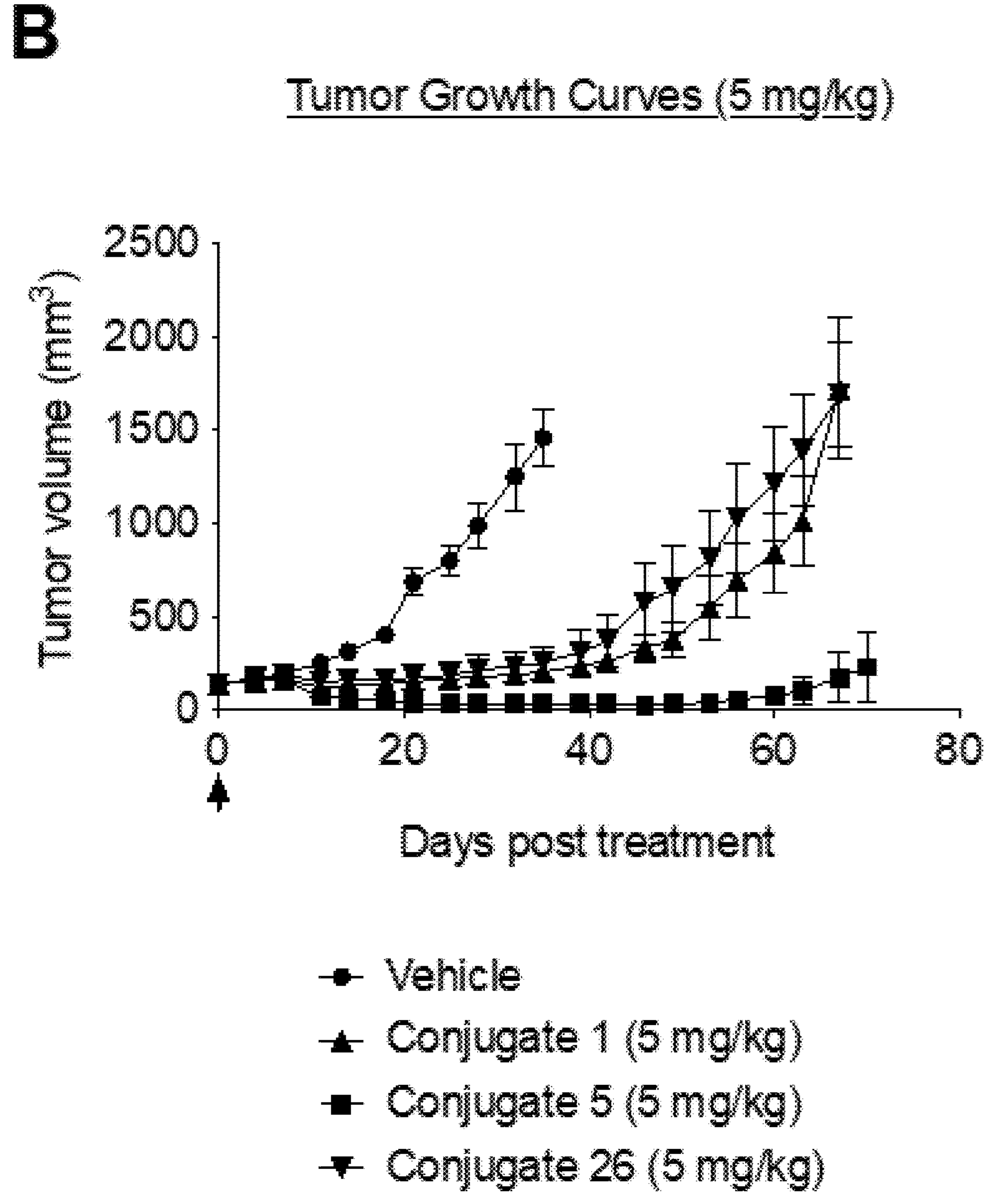
Figure 7C:
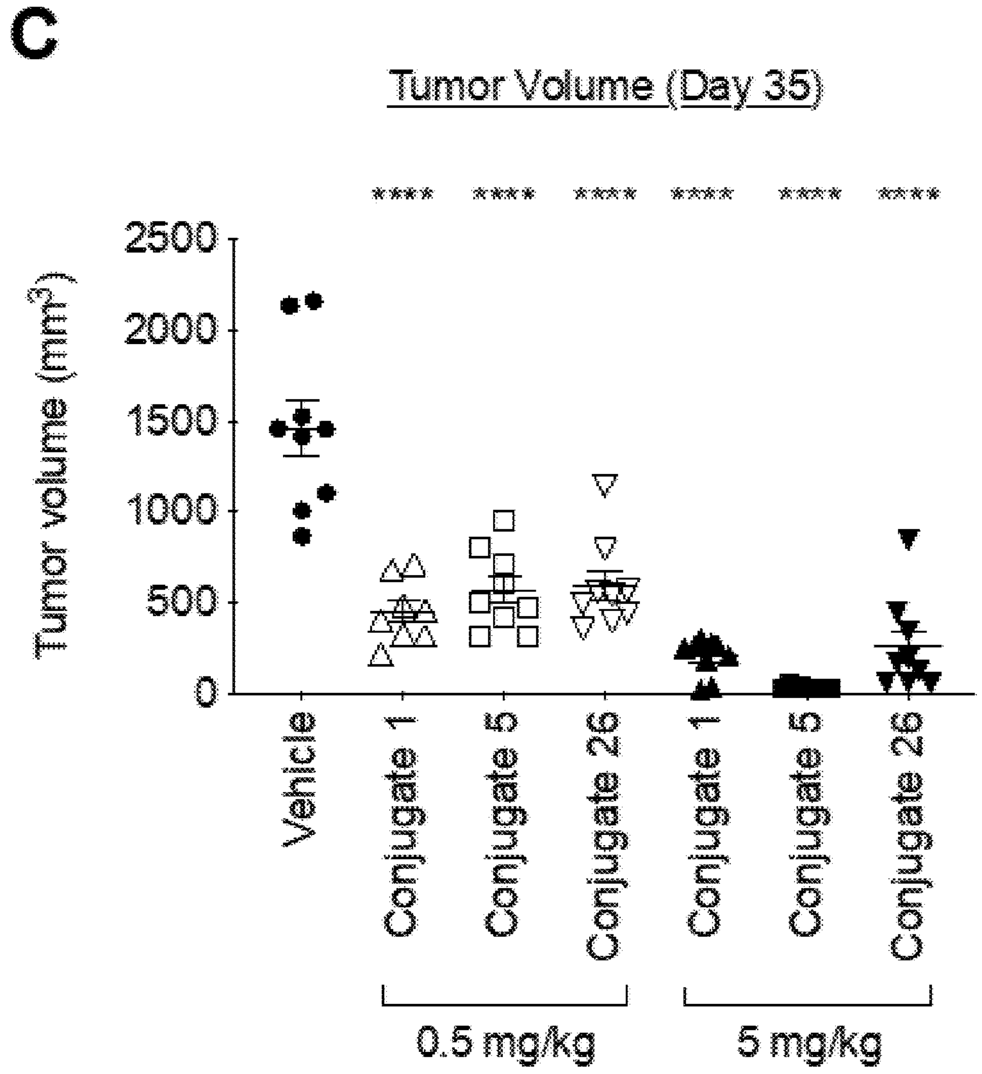

FIGS. 7A and 7B illustrate the effects of the different test articles on HCC1954 tumor growth up until the end of the study at day 70 post treatment. Analysis of tumor sizes on day 35, when the mean of vehicle-treated tumors reached the study endpoint (~1,500 $mm^3$), revealed that all test articles demonstrated significant anti-tumor activity, with efficacy ranging from approximately 60% to 110% TGI (FIG. 7C). At 0.5 mg/kg, Conjugate 1, Conjugate 5, and Conjugate 26 exhibited moderate and roughly equivalent tumor growth suppression (73%, 62%, and 60% TGI, respectively). At 5 mg/kg, Conjugate 1, Conjugate 5, and Conjugate 26 all demonstrated robust tumor growth inhibition (94%, 110%, and 90% TGI, respectively), with Conjugate 5 exhibiting the greatest potency. Notably, Conjugate 5 was the only test article to achieve sustained tumor regression, with no evidence of tumor outgrowth until day 53 post treatment (FIG. 7B).

Example 28: In Vivo Efficacy in the H1975 Lung Cancer Xenograft Model

The activity of different TF-targeted ADCs was examined in the H1975 lung cancer xenograft model. Briefly, SCID Beige mice were implanted subcutaneously with $5\times10^6$ H1975 tumor cells in the right flank and randomized and enrolled into the study 10 days post implant, with tumor sizes around 130 $mm^3$. Tumor-bearing mice were administered a single dose of the test articles i.v. at 1 mg/kg or 2 mg/kg. All treatments were well tolerated, and mice exhibited normal body weight gain throughout the course of the study.

Figure 8A:
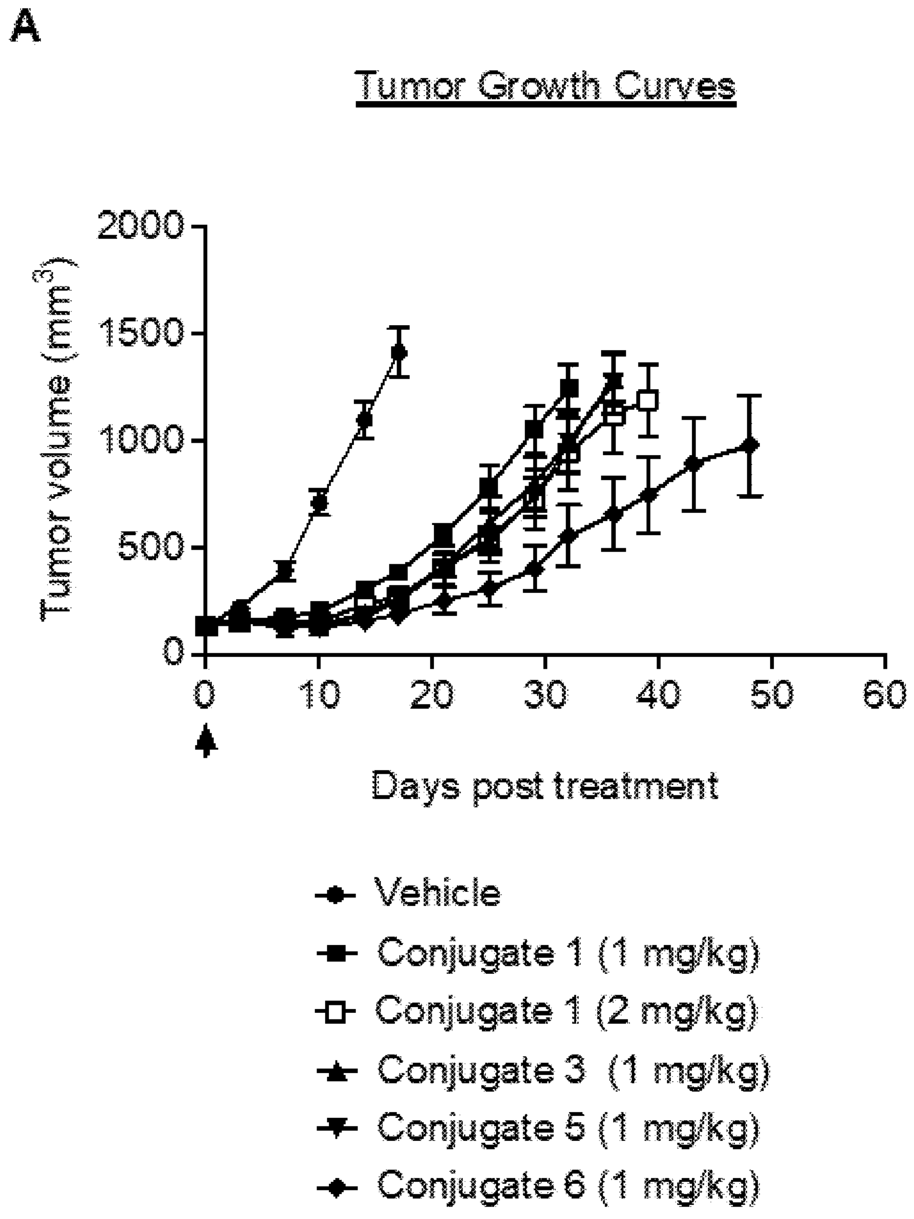
FIGS. 8A-B provide (FIG. 8A) H1975 tumor growth curves in response to treatment with a single i.v. dose of TF-targeted ADCs at 1 mg/kg or 2 mg/kg.
Figure 8B:
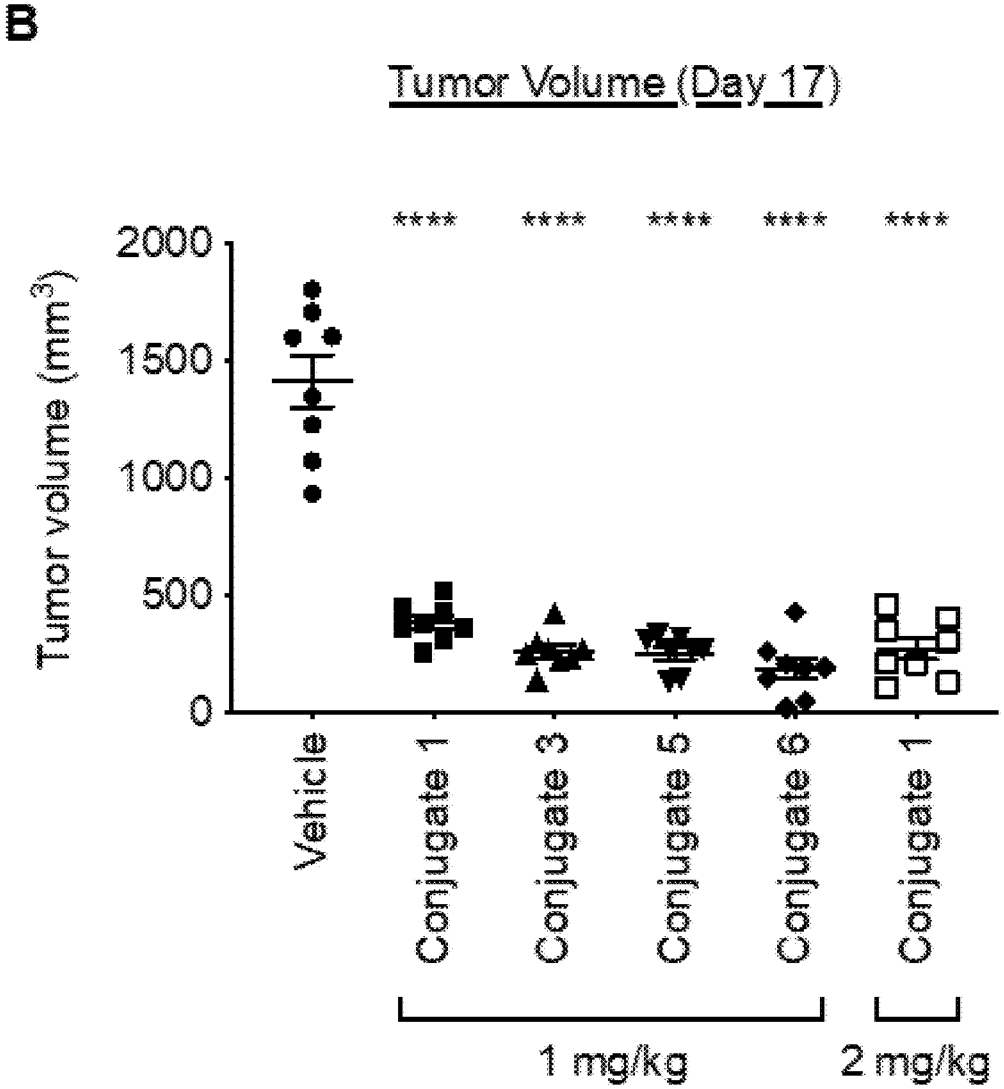

FIG. 8A illustrates the effects of the different test articles on H1975 tumor growth up until the end of the study at day 48 post treatment. Analysis of tumor sizes on day 17, when the mean of vehicle-treated tumors reached the study endpoint (~1,500 $mm^3$), revealed that all test articles demonstrated significant anti-tumor activity, with efficacy ranging from approximately 80% to 96% TGI (FIG. 8B). At 1 mg/kg, Conjugate 1, Conjugate 3, Conjugate 5, and Conjugate 6 all showed potent and roughly equivalent tumor growth suppression (80%, 90%, 91%, and 96% TGI, respectively).

Example 29: In Vivo Efficacy in the H1975 Lung Cancer Xenograft Model

The activity of different TF-targeted ADCs was examined in the H1975 lung cancer xenograft model. Briefly, SCID Beige mice were implanted subcutaneously with $5\times10^6$ H1975 tumor cells in the right flank and randomized and enrolled into the study 10 days post implant, with tumor sizes around 120 $mm^3$. Tumor-bearing mice were administered a single dose of the test articles i.v. at doses ranging from 0.5 mg/kg to 2 mg/kg. All treatments were well tolerated, and mice exhibited normal body weight gain throughout the course of the study.

Figure 9A:
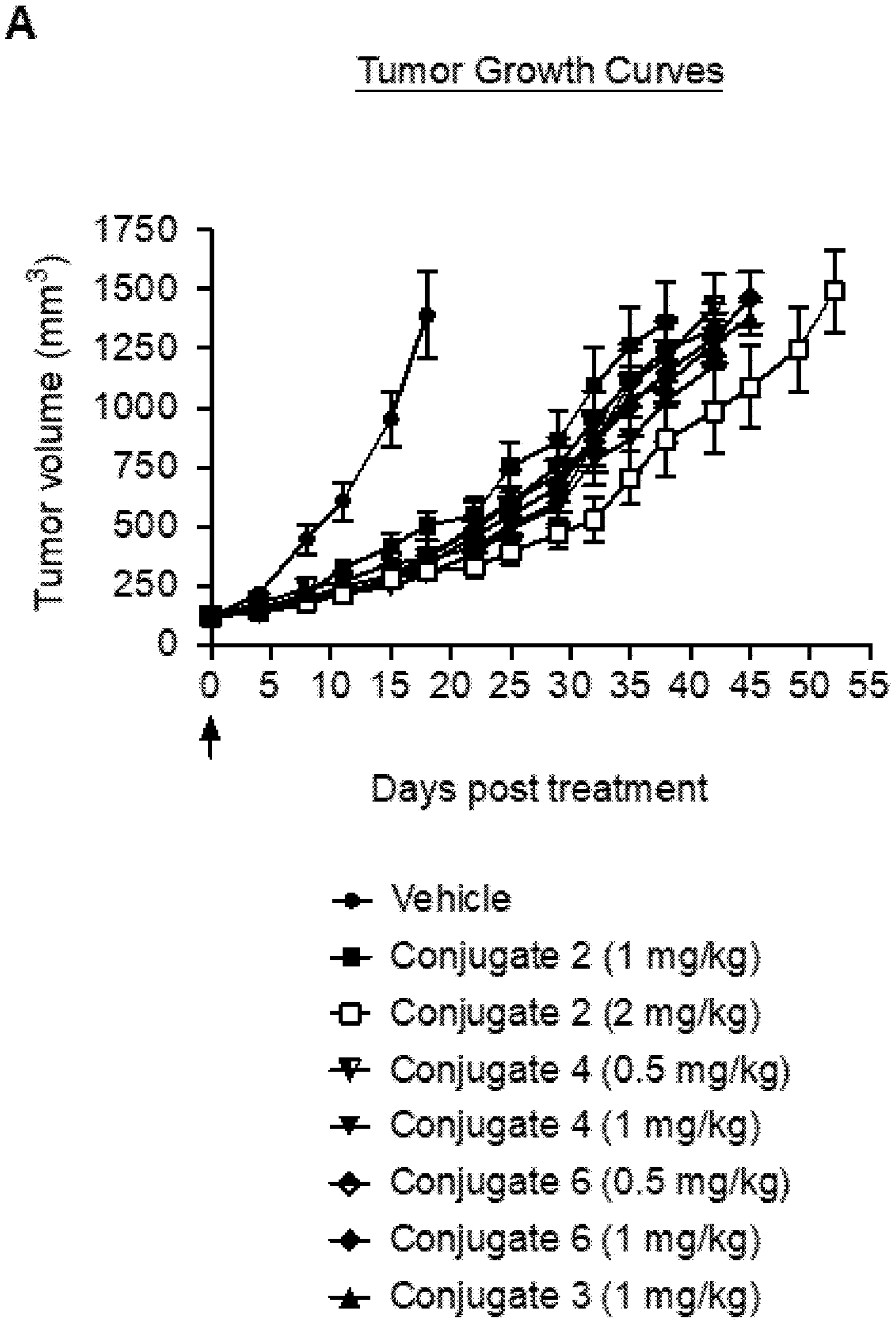
FIGS. 9A-B provide (FIG. 9A) H1975 tumor growth curves in response to treatment with a single i.v. dose of TF-targeted ADCs at doses ranging from 0.5 mg/kg to 2 mg/kg.
Figure 9B:
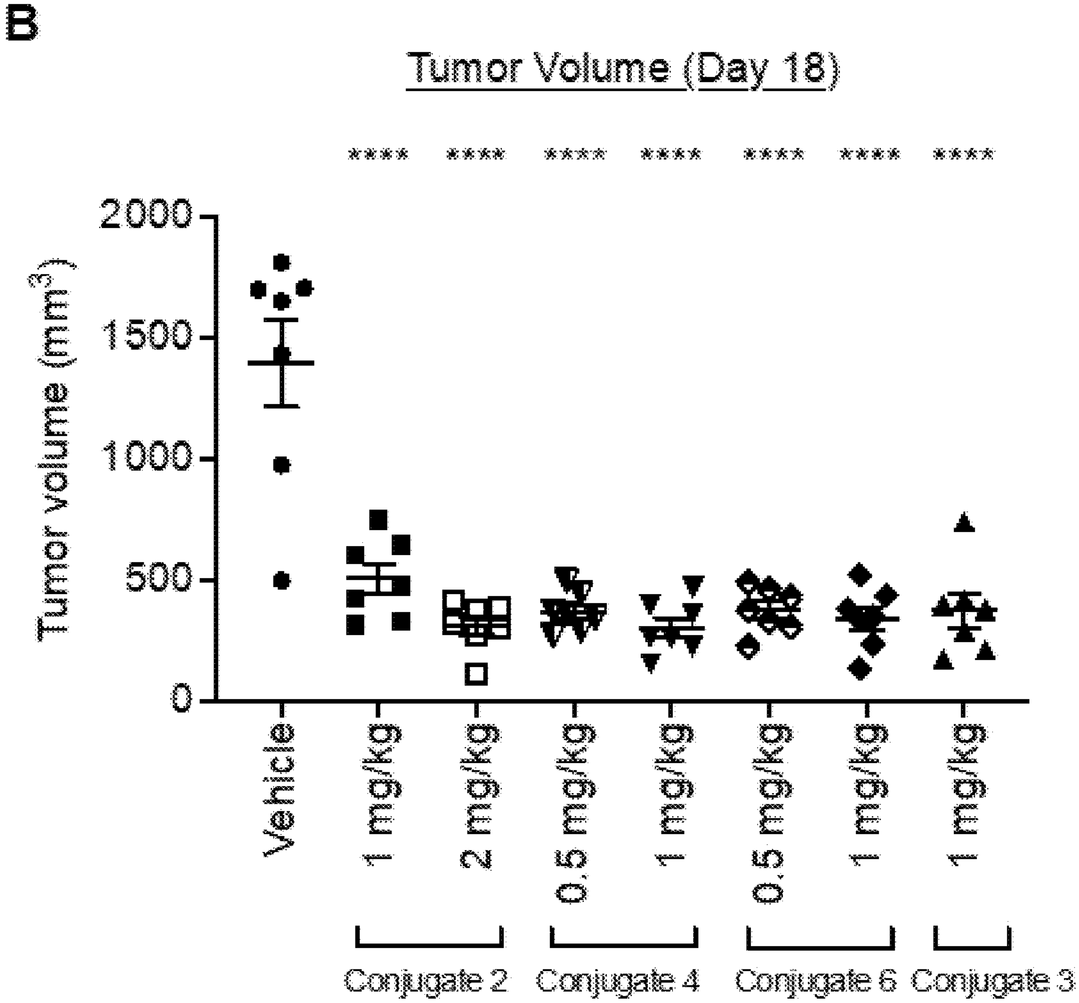

FIG. 9A illustrates the effects of the different test articles on H1975 tumor growth up until the end of the study at day 52 post treatment. Analysis of tumor sizes on day 18, when the mean of vehicle-treated tumors reached the study endpoint (~1,400 $mm^3$), revealed that all test articles demonstrated significant anti-tumor activity, with efficacy ranging from approximately 70% to 86% TGI (FIG. 9B). At 1 mg/kg, Conjugate 2, Conjugate 4, Conjugate 6, and Conjugate 3 all showed potent and roughly equivalent tumor growth suppression (70%, 80%, 86%, and 83% TGI, respectively). Conjugate 4 and Conjugate 6 dosed at 0.5 mg/kg and Conjugate 2 dosed at 2 mg/kg also exhibited similar levels of tumor growth inhibition (81%, 80%, and 85% TGI, respectively).

Example 30: In Vivo Efficacy in the MDA-MB-231 TNBC Xenograft Model

The activity of different TF-targeted ADCs was examined in the MDA-MB-231 TNBC xenograft model. Briefly, SCID Beige mice were implanted subcutaneously with $5\times10^6$ MDA-MB-231 tumor cells in the mammary fat pad and randomized and enrolled into the study with an average tumor volume of 110-120 $mm^3$. Tumor-bearing mice were administered two weekly doses (qwx2) of the test articles i.v. at doses ranging from 0.25 mg/kg to 2 mg/kg. All treatments were well tolerated, and mice exhibited normal body weight gain throughout the course of the study.

Figure 10A:
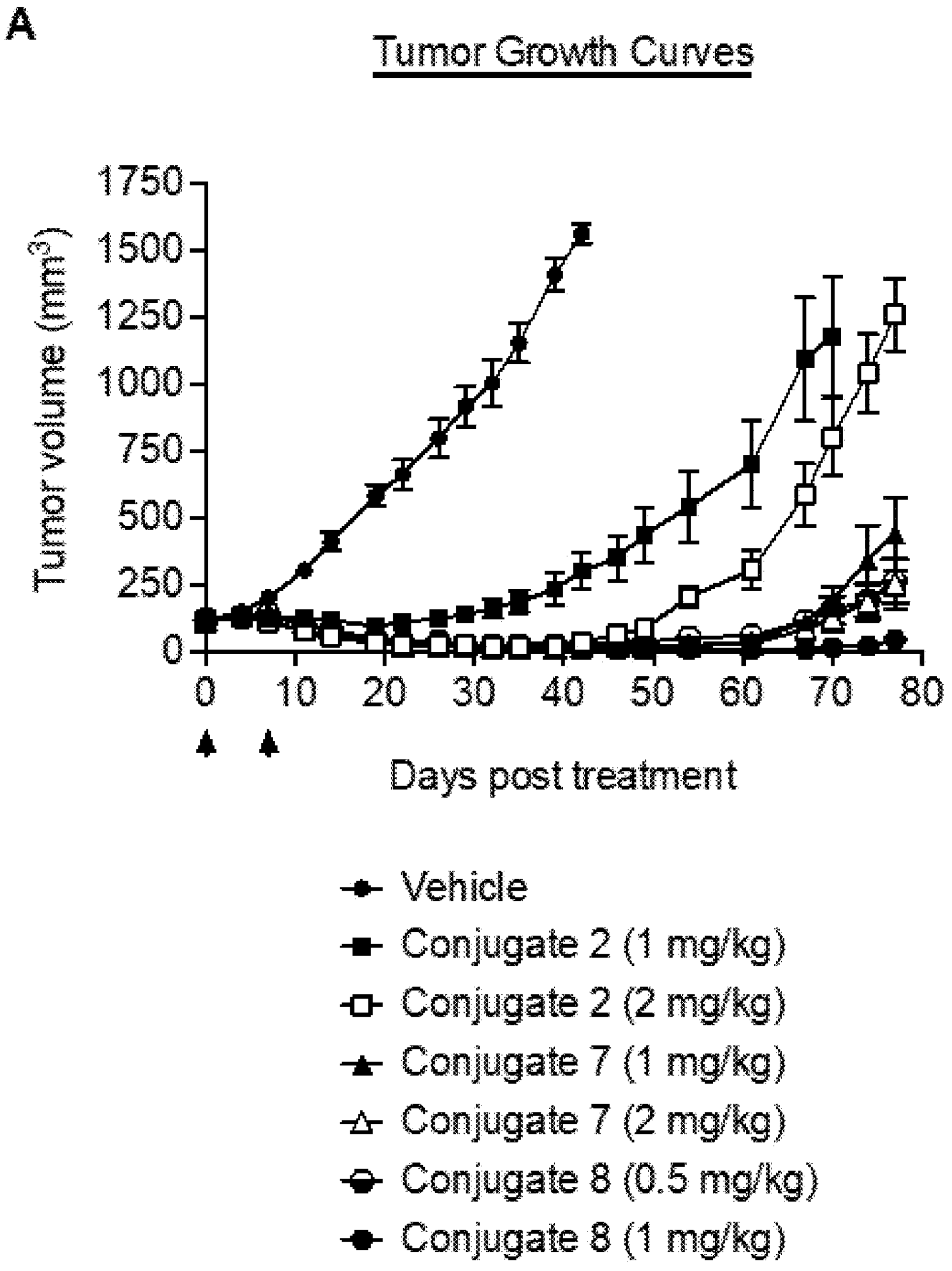
FIGS. 10A-D provide (FIG. 10A) MDA-MB-231 tumor growth curves in response to treatment with two weekly i.v. doses (qwx2) of TF-targeted ADCs at doses ranging from 0.5 mg/kg to 2 mg/kg.
Figure 10B:
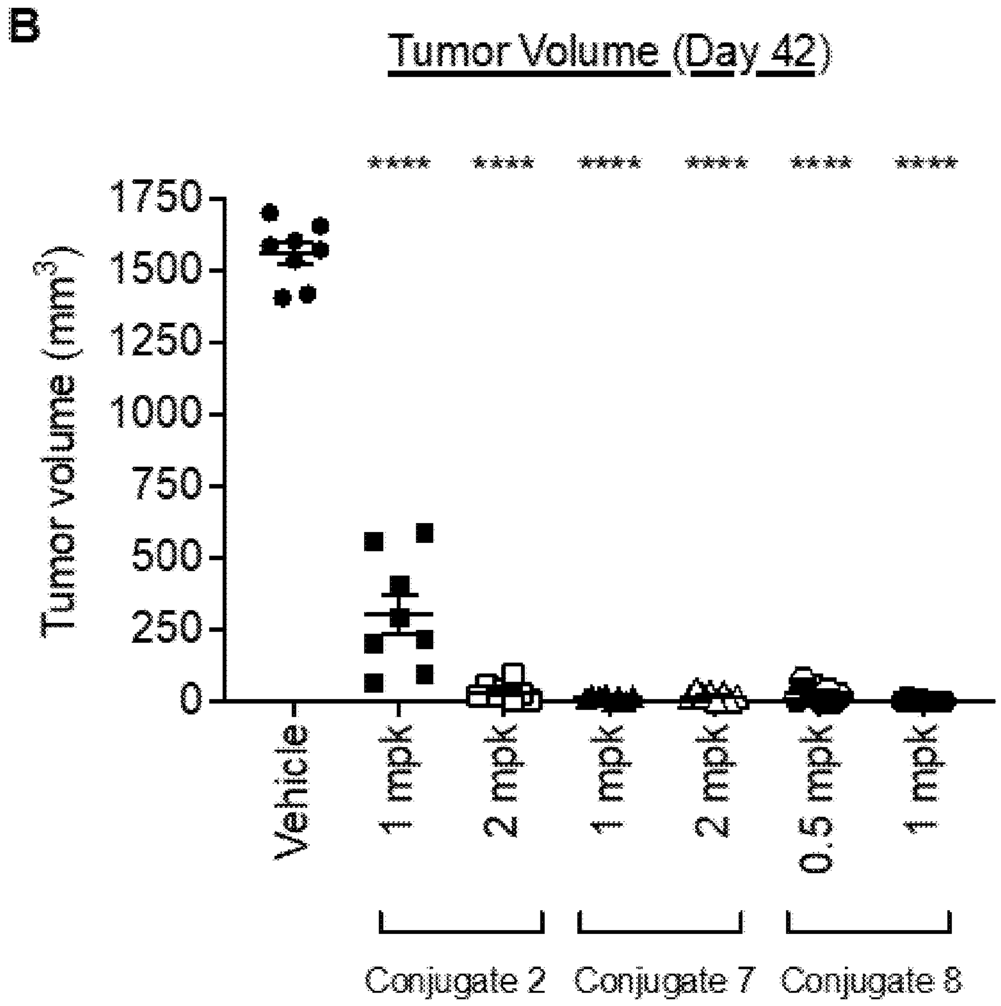
Figure 10C:
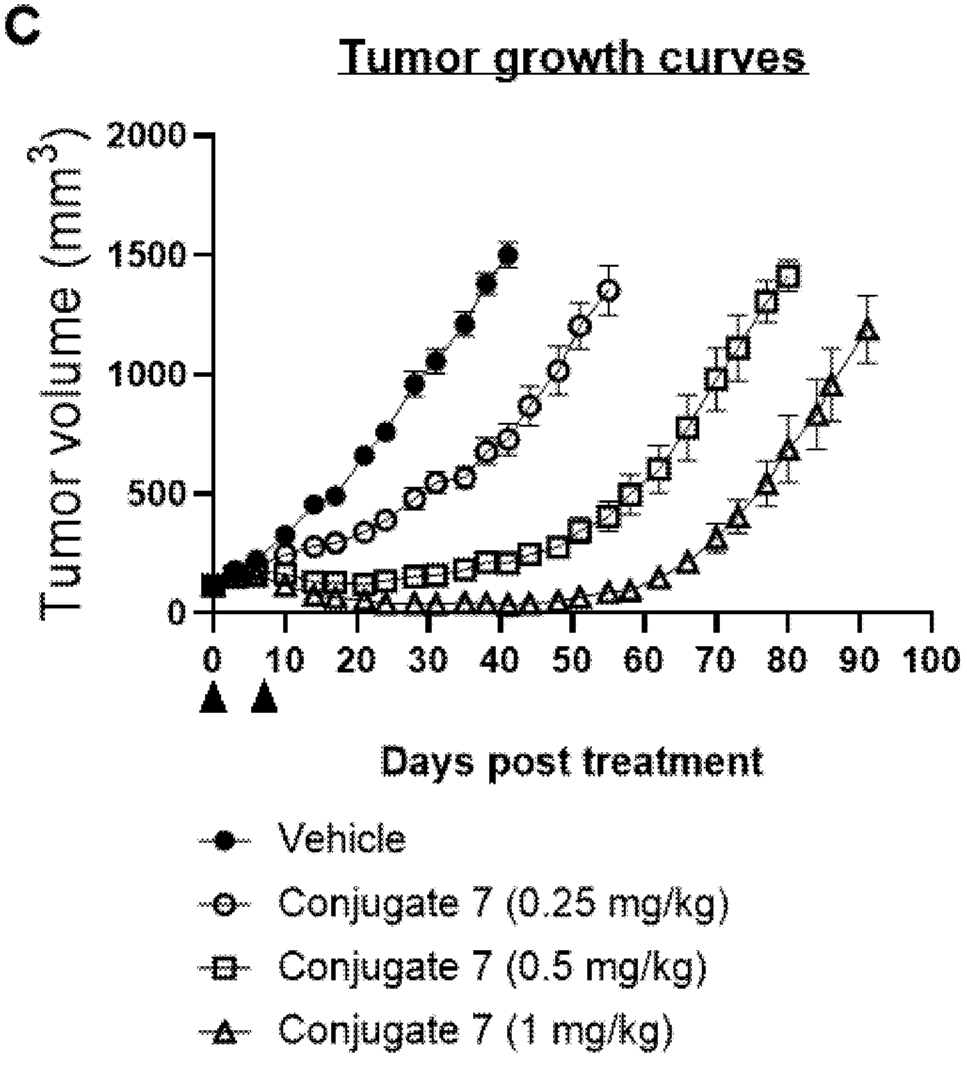
Figure 10D:
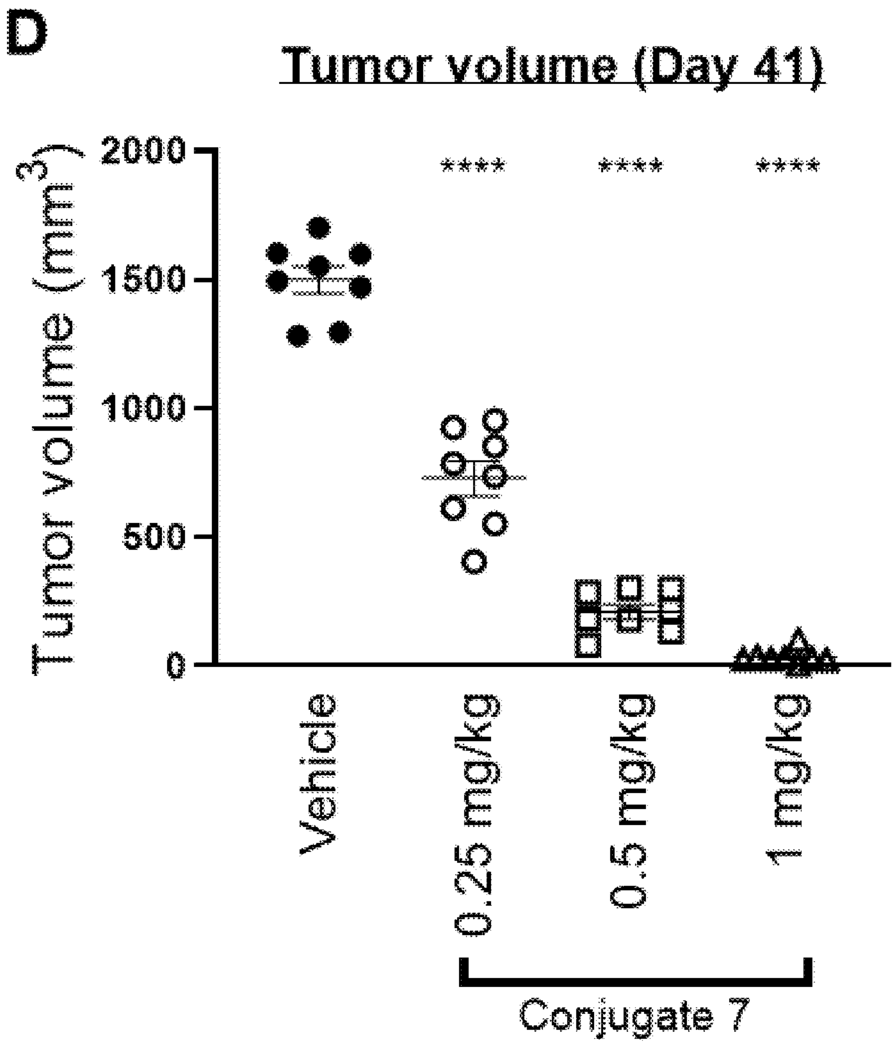

FIG. 10A illustrates the effects of the different test articles on MDA-MB-231 tumor growth up until the end of the study at day 77 post treatment. Analysis of tumor sizes on day 42, when the mean of vehicle-treated tumors reached the study endpoint (~1,500 $mm^3$), revealed that all test articles demonstrated significant anti-tumor activity, with efficacy ranging from approximately 87% to 108% TGI (FIG. 10B). At 1 mg/kg, Conjugate 2, Conjugate 7, and Conjugate 8 all exhibited potent anti-tumor efficacy (87%, 107%, and 108% TGI, respectively), achieving prolonged tumor stasis or tumor regression following treatment. Dose-dependent activity was observed for Conjugate 2, with 1 mg/kg and 2 mg/kg treatments achieving 87% and 106% TGI, respectively, while Conjugate 7 and Conjugate 8 did not appear to exhibit clear dose-dependent activity at these doses (Conjugate 7 1 mg/kg and 2 mg/kg both achieved 107% TGI, and Conjugate 8 0.5 mg/kg and 1 mg/kg achieved 106% and 108% TGI, respectively). Notably, Conjugate 7 and Conjugate 8 demonstrated similar activity when compared to each other but improved activity compared to Conjugate 2. Furthermore, only Conjugate 7 and Conjugate 8 were able to achieve complete responses. FIG. 10C illustrates the effects of the different test articles on MDA-MB-231 tumor growth up until the end of the study at day 91 post treatment. Analysis of tumor sizes on day 41, when the mean of vehicle-treated tumors reached the study endpoint (~1,500 $mm^3$), revealed that Conjugate 7 demonstrated significant anti-tumor activity, with efficacy ranging from approximately 56% to 106% TGI (FIG. 10D). Dose-dependent activity was observed for Conjugate 7, with 0.5 mg/kg and 1 mg/kg treatments achieving potent anti-tumor efficacy (93% and 106% TGI, respectively) and prolonged tumor stasis or tumor regression following treatment.

Example 31: In Vivo Efficacy in the H1975 Lung Cancer Xenograft Model

The activity of different TF-targeted ADCs was examined in the H1975 lung cancer xenograft model. Briefly, SCID Beige mice were implanted subcutaneously with $5\times10^6$ H1975 tumor cells in the right flank and randomized and enrolled into the study with tumor sizes around 110 $mm^3$. Tumor-bearing mice were administered a single dose of the test articles i.v. at doses ranging from 0.25 mg/kg to 2 mg/kg. All treatments were well tolerated, and mice exhibited normal body weight gain throughout the course of the study.

Figure 11A:
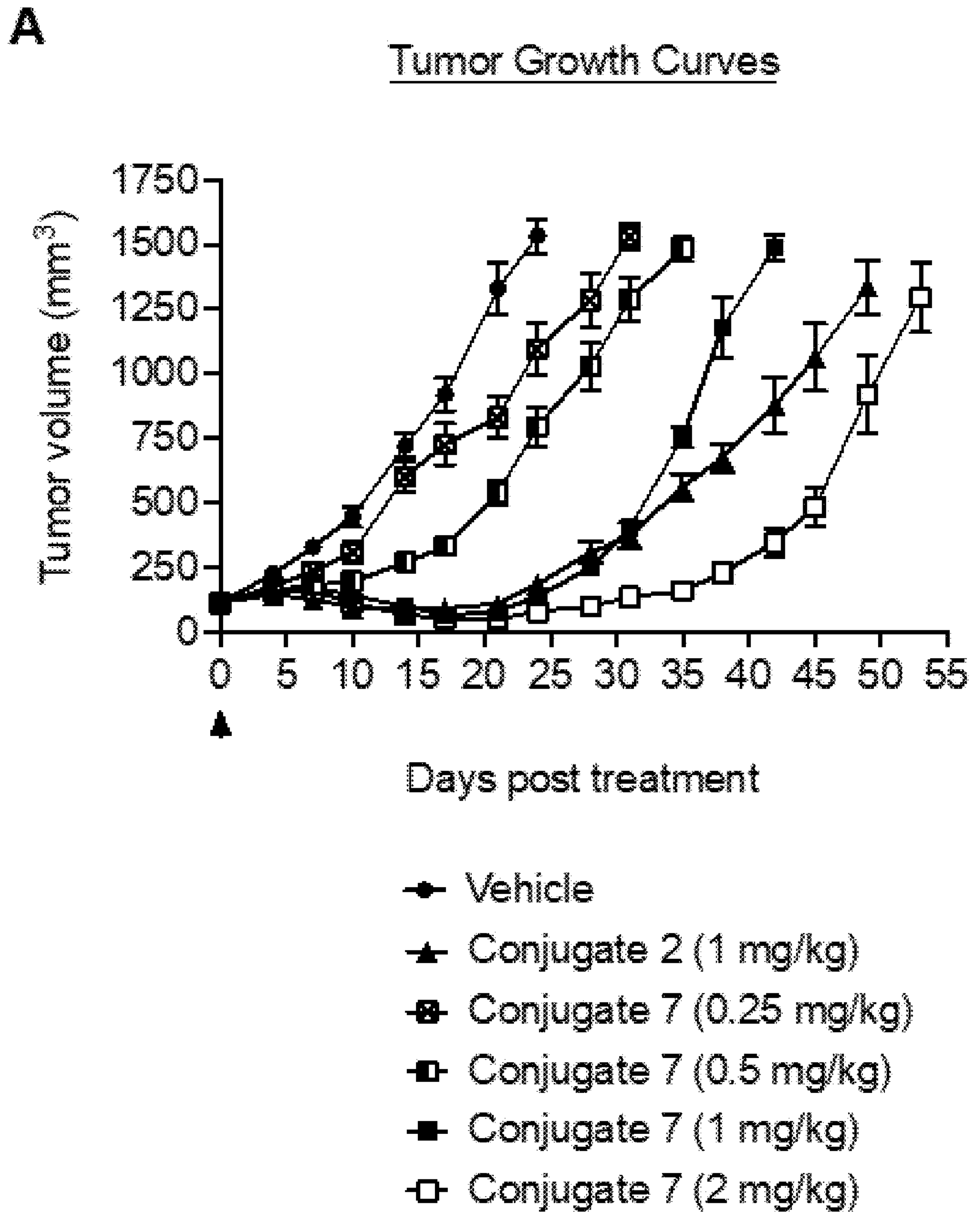
FIGS. 11A-D provide (FIG. 11A) H1975 tumor growth curves in response to treatment with a single i.v. dose of TF-targeted ADCs at doses ranging from 0.25 mg/kg to 2 mg/kg.
Figure 11B:
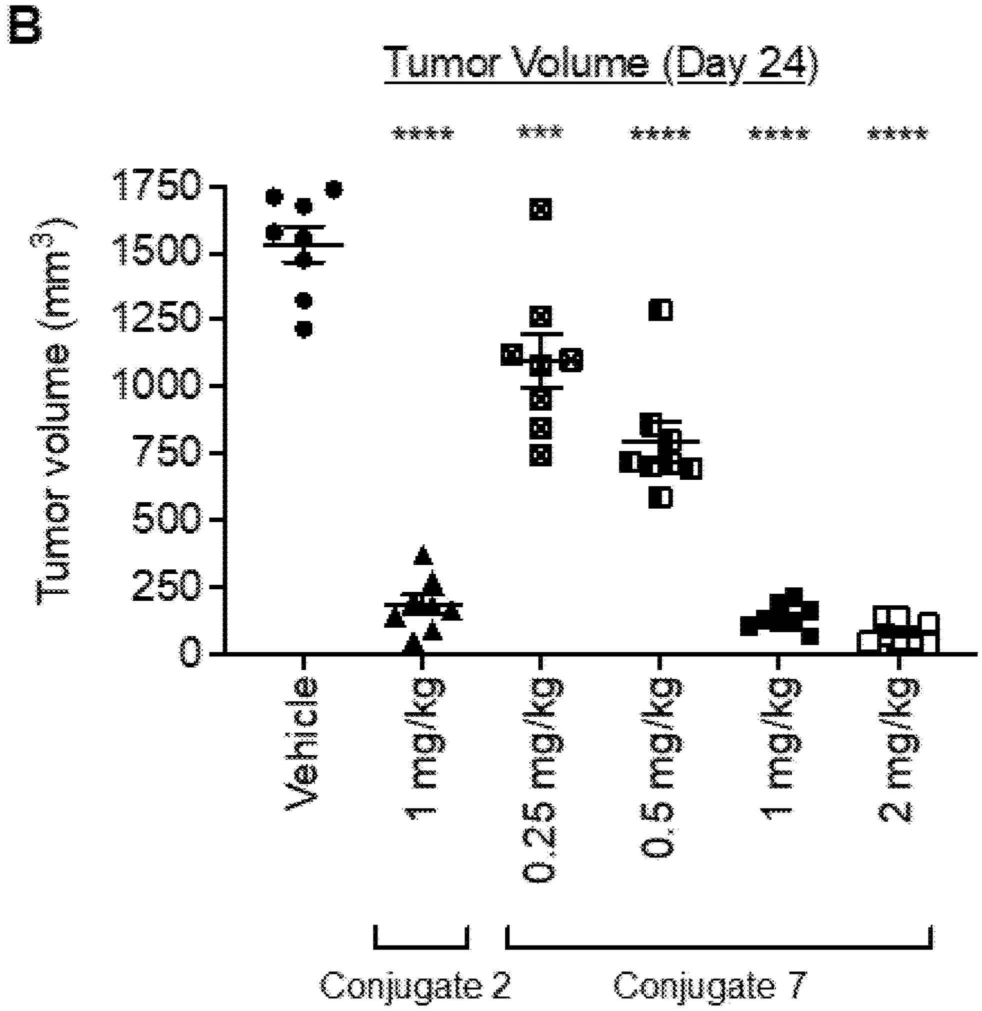
Figure 11C:
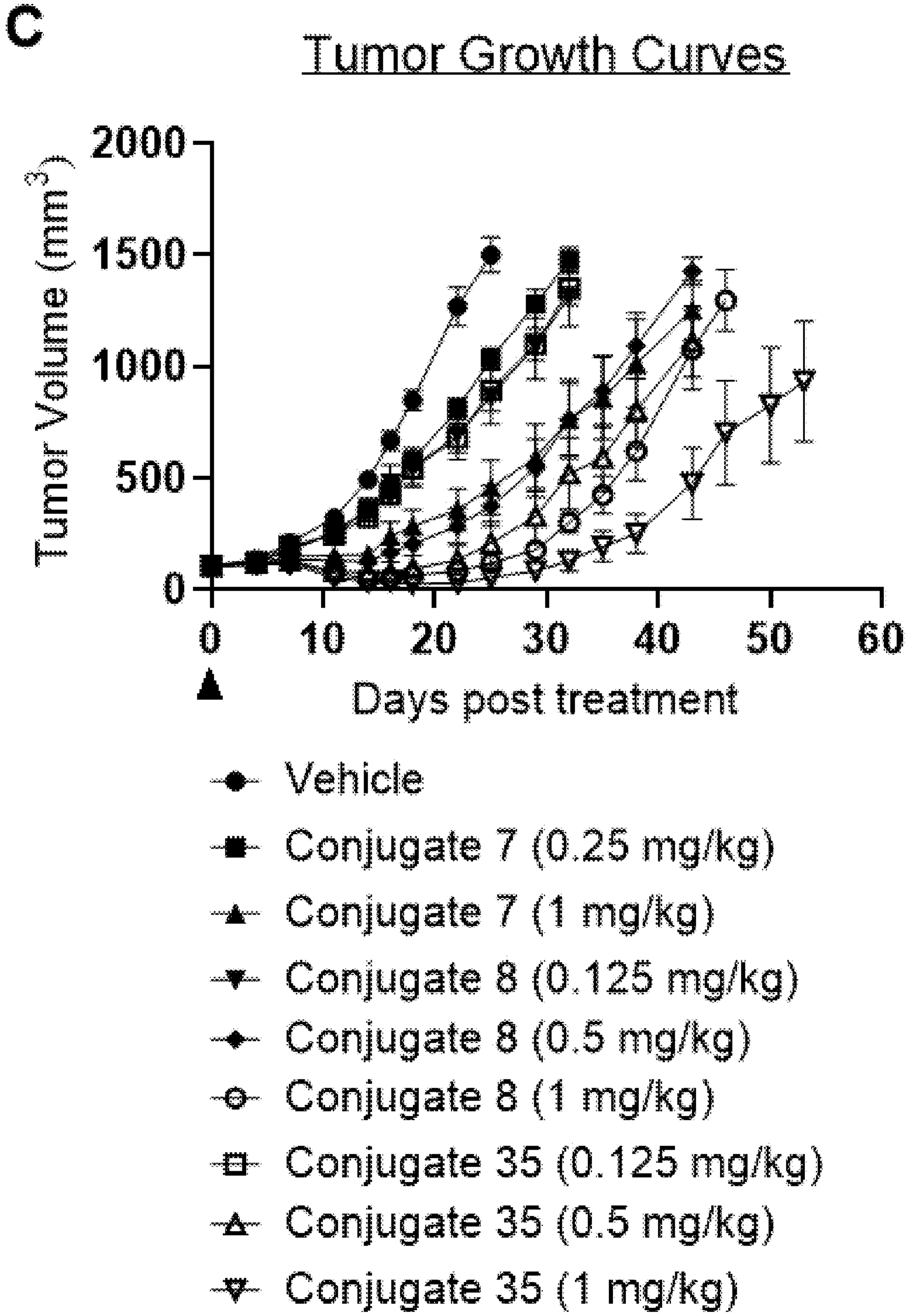
Figure 11D:
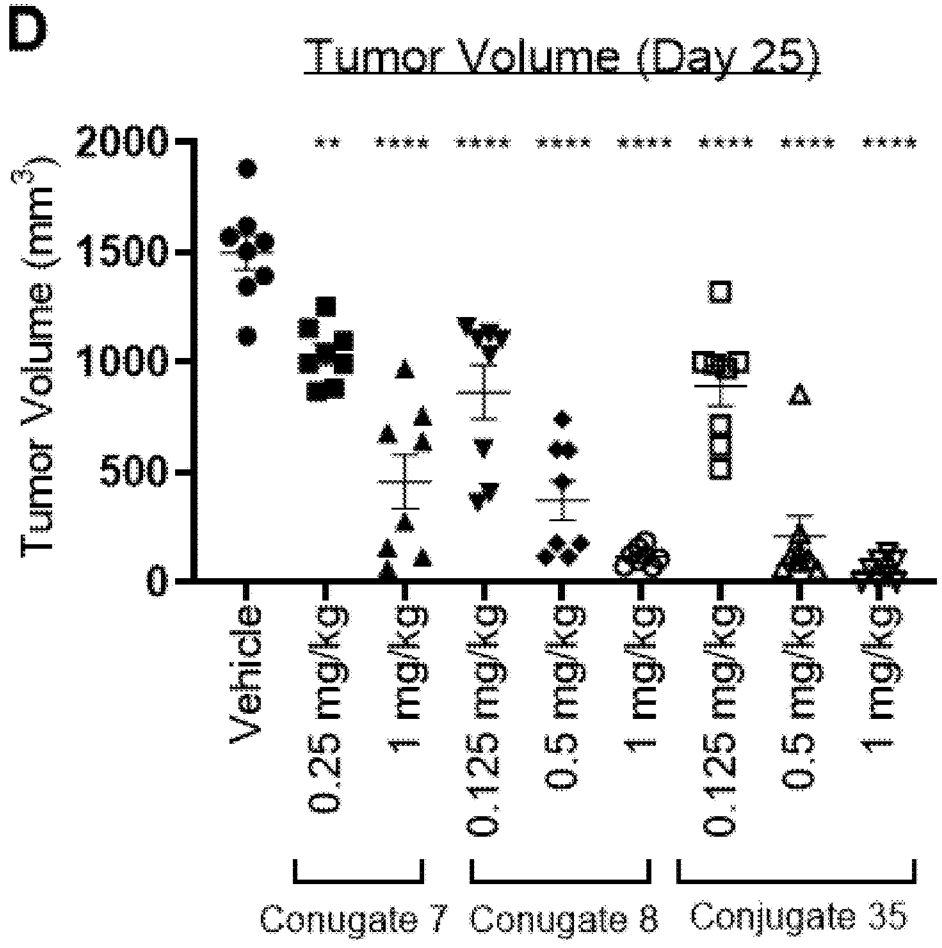

FIG. 11A illustrates the effects of the two test articles on H1975 tumor growth up until the end of the study at day 53 post treatment. Analysis of tumor sizes on day 24, when the mean of vehicle-treated tumors reached the study endpoint (~1,500 $mm^3$), revealed that both test articles demonstrated significant anti-tumor activity, with efficacy ranging from approximately 31% to 102% TGI (FIG. 11B). Conjugate 7 demonstrated robust dose-dependent activity, with a single 0.25, 0.5, 1, and 2 mg/kg dose achieving 31%, 52%, 98%, and 102% TGI, respectively. Conjugate 7 and Conjugate 2 dosed at 1 mg/kg exhibited similar efficacies at day 24 post treatment (both achieved 98% TGI). FIG. 11C illustrates the effects of the different test articles on H1975 tumor growth up until the end of the study at day 53 post treatment. Analysis of tumor sizes on day 25, when the mean of vehicle-treated tumors reached the study endpoint (~1,500 $mm^3$), revealed that all test articles demonstrated dose dependent anti-tumor activity, with efficacy ranging from approximately 33% to 104% TGI (FIG. 11D). Conjugate 8 at 1 mg/kg, and Conjugate 35 at 0.5 mg/kg and 1 mg/kg exhibited potent anti-tumor efficacy (99%, 99%, and 104% TGI, respectively), achieving prolonged tumor stasis or tumor regression following treatment.

Example 32: In Vivo Efficacy in the Detroit562 Pharyngeal Xenograft Model

The activity of different TF-targeted ADCs was examined in the Detroit562 pharyngeal cancer xenograft model. Briefly, SCID Beige mice were implanted subcutaneously with $5\times10^6$ Detroit562 tumor cells in the hind flank and randomized and enrolled into the study with an average tumor volume of 115 to 120 $mm^3$. Tumor-bearing mice were administered a single dose of Conjugate 7 i.v. at 1 mg/kg or 2 mg/kg. All treatments were well tolerated, with mice exhibiting normal body weight gain throughout the course of the study.

Figure 12A:
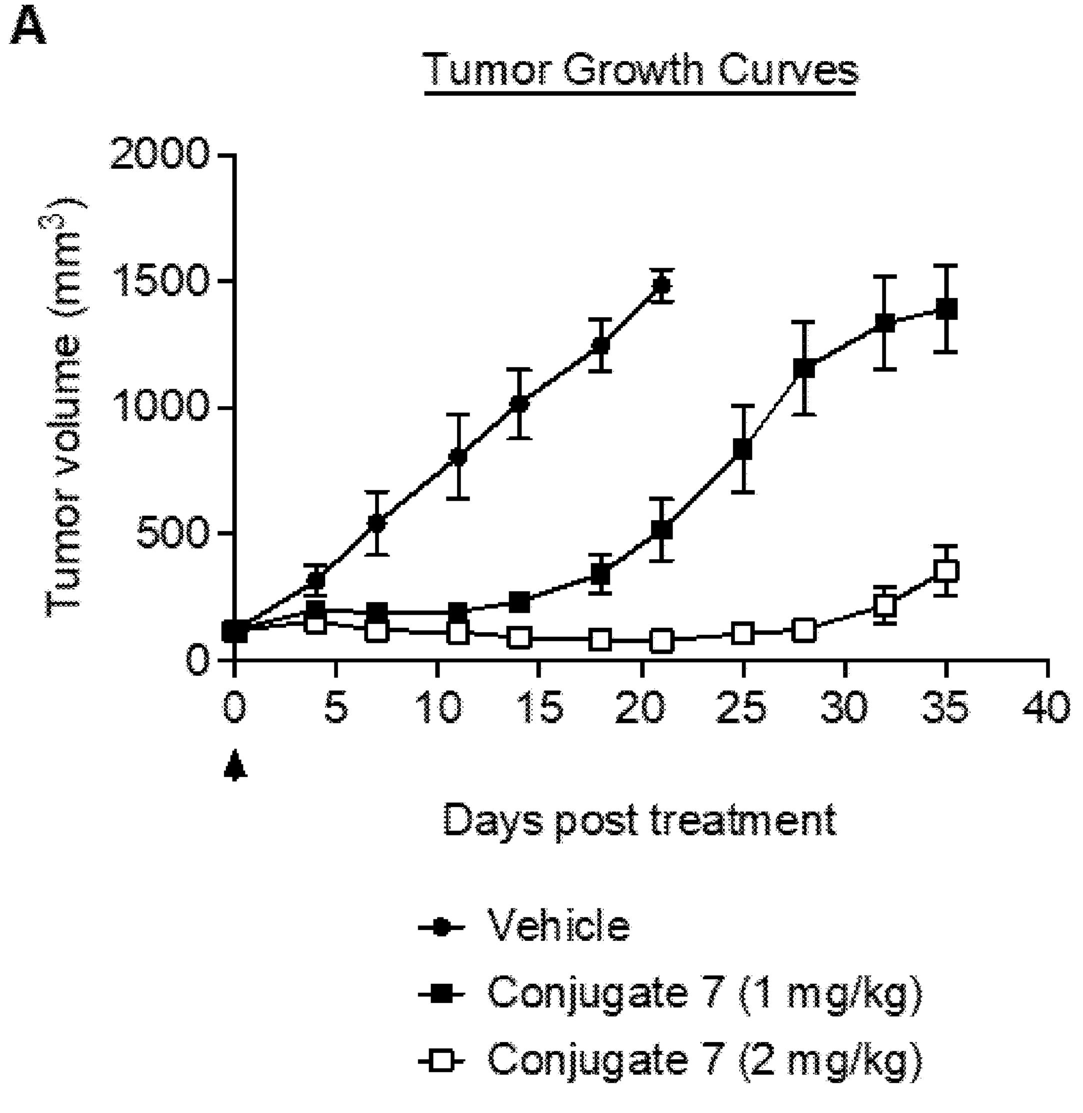
FIGS. 12A-D provide (FIG. 12A) Detroit562 tumor growth curves in response to treatment with a single i.v. dose of Conjugate 7 at 1 mg/kg or 2 mg/kg.
Figure 12B:
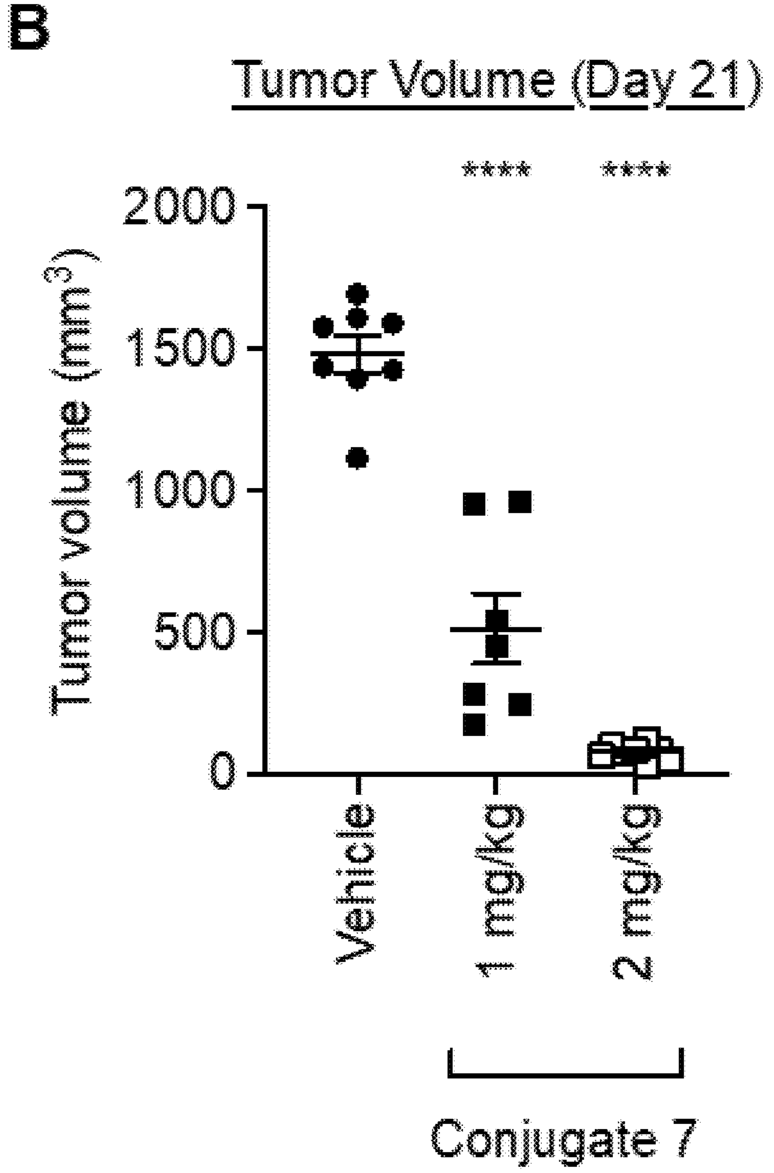
Figure 12C:
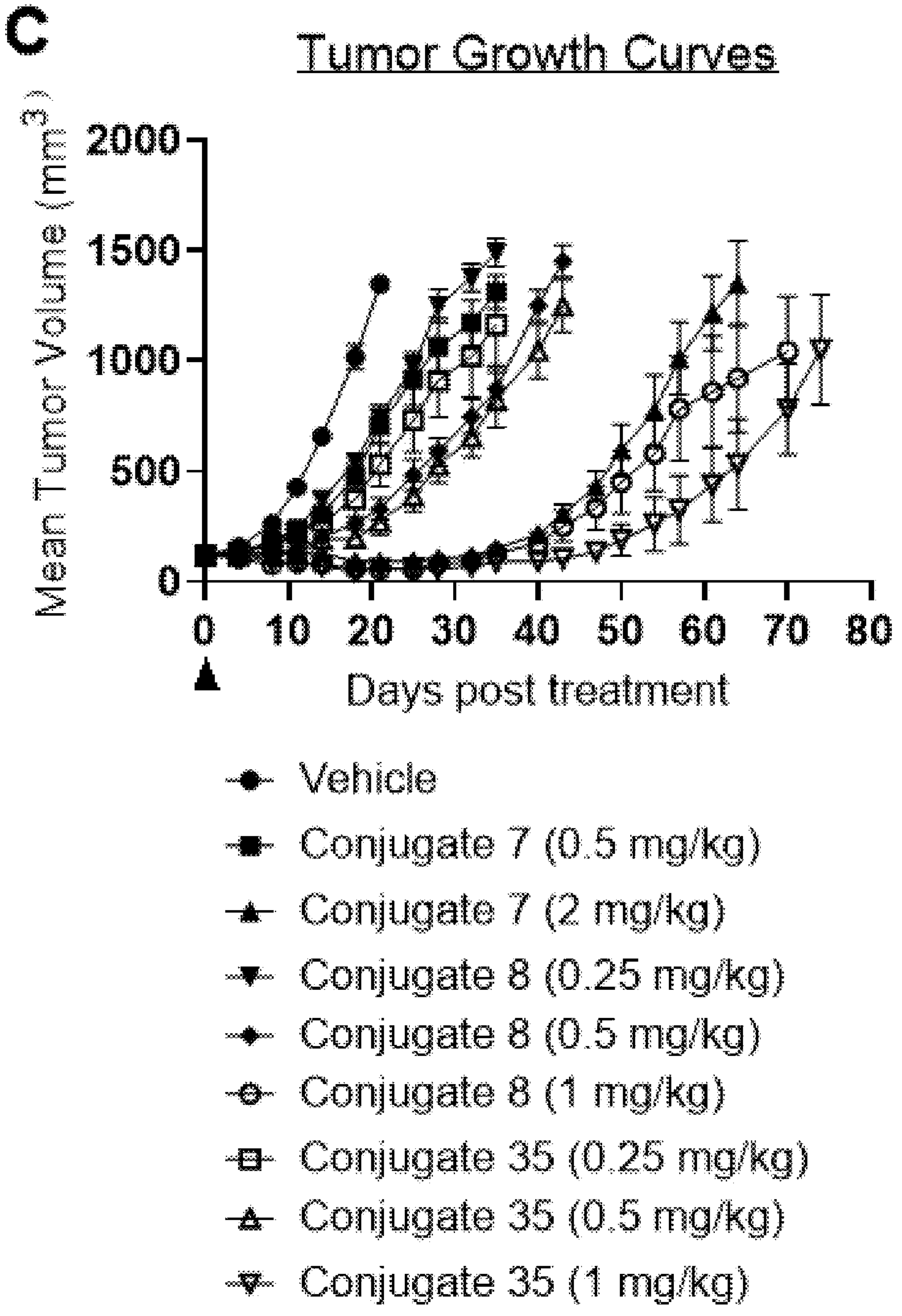
Figure 12D:
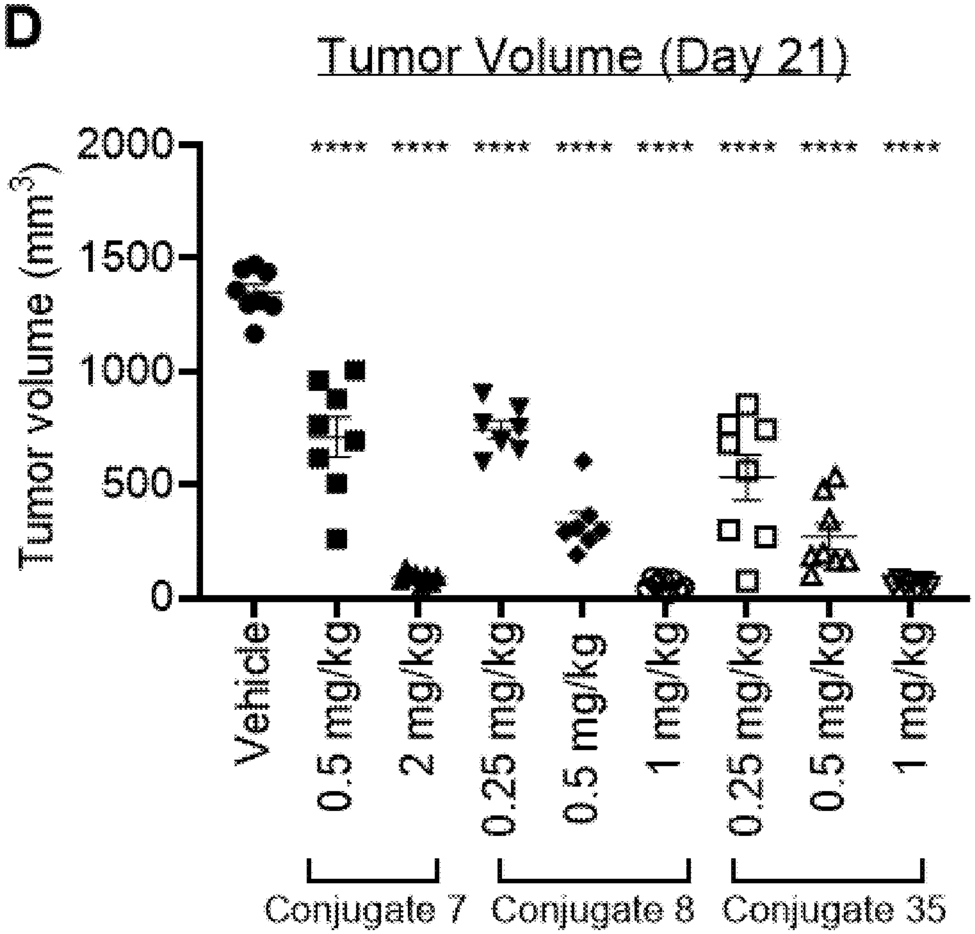

FIG. 12A illustrates the effects of Conjugate 7 on Detroit562 tumor growth up until the end of the study at day 35 post treatment. Analysis of tumor sizes on day 21, when the mean of vehicle-treated tumors reached the study endpoint (~1,500 $mm^3$), revealed that Conjugate 7 demonstrated significant dose-dependent anti-tumor activity. A single dose of Conjugate 7 at 1 mg/kg and 2 mg/kg achieved 72% and 103% TGI, respectively (FIG. 12B). While Conjugate 7 dosed at 1 mg/kg only slowed tumor growth, Conjugate 7 dosed at 2 mg/kg achieved sustained tumor regression, with no evidence of tumor outgrowth until day 25 post treatment (FIG. 12A). FIG. 12C illustrates the effects of the different test articles on Detroit562 tumor growth up until the end of the study at day 53 post treatment. Analysis of tumor sizes on day 21, when the mean of vehicle-treated tumors reached the study endpoint (~1,300 $mm^3$), revealed that all test articles demonstrated dose dependent anti-tumor activity, with efficacy ranging from approximately 49% to 105% TGI (FIG. 12D). Conjugate 7 at 2 mg/kg and Conjugate 8 and Conjugate 35 at 1 mg/kg exhibited potent anti-tumor efficacy (102%, 105%, and 105% TGI, respectively), achieving prolonged tumor stasis or tumor regression following treatment.

Example 33: In Vivo Efficacy in the HCT-116 Colon Xenograft Model

The activity of different TF-targeted ADCs was examined in the HCT-116 colon cancer xenograft model. Briefly, athymic nude mice were implanted subcutaneously with $4\times10^6$ HCT-116 tumor cells in the hind flank and randomized and enrolled into the study with tumor sizes around 150 $mm^3$. Tumor-bearing mice were administered a single dose of the test articles i.v. at doses ranging from 2.5 mg/kg to 7.5 mg/kg. All treatments were well tolerated, with mice exhibiting normal body weight gain throughout the course of the study.

Figure 13A:
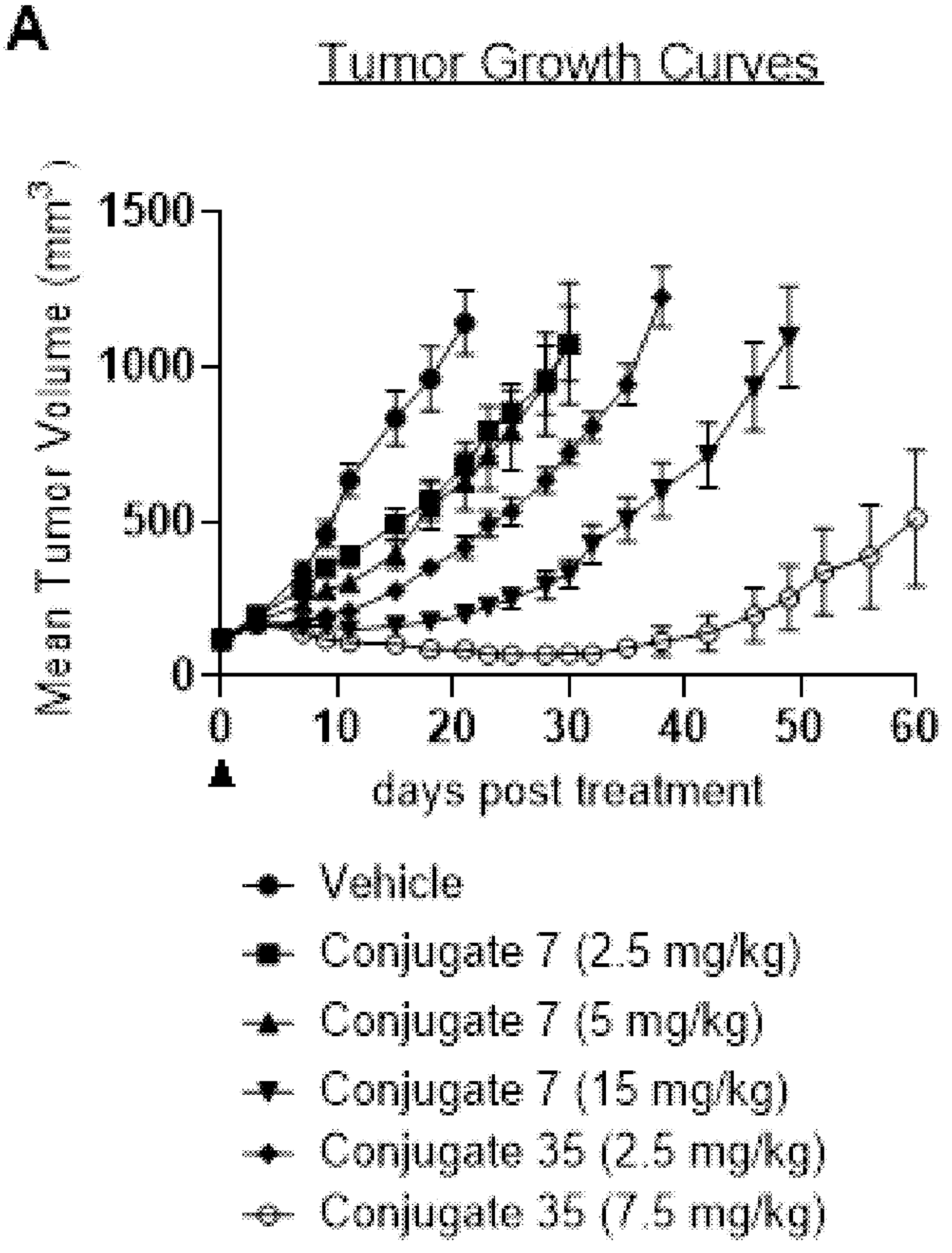
FIGS. 13A-B provide (FIG. 13A) HCT-116 tumor growth curves in response to treatment with a single i.v. dose of TF-targeted ADCs at doses ranging from 2.5 mg/kg to 15 mg/kg.
Figure 13B:
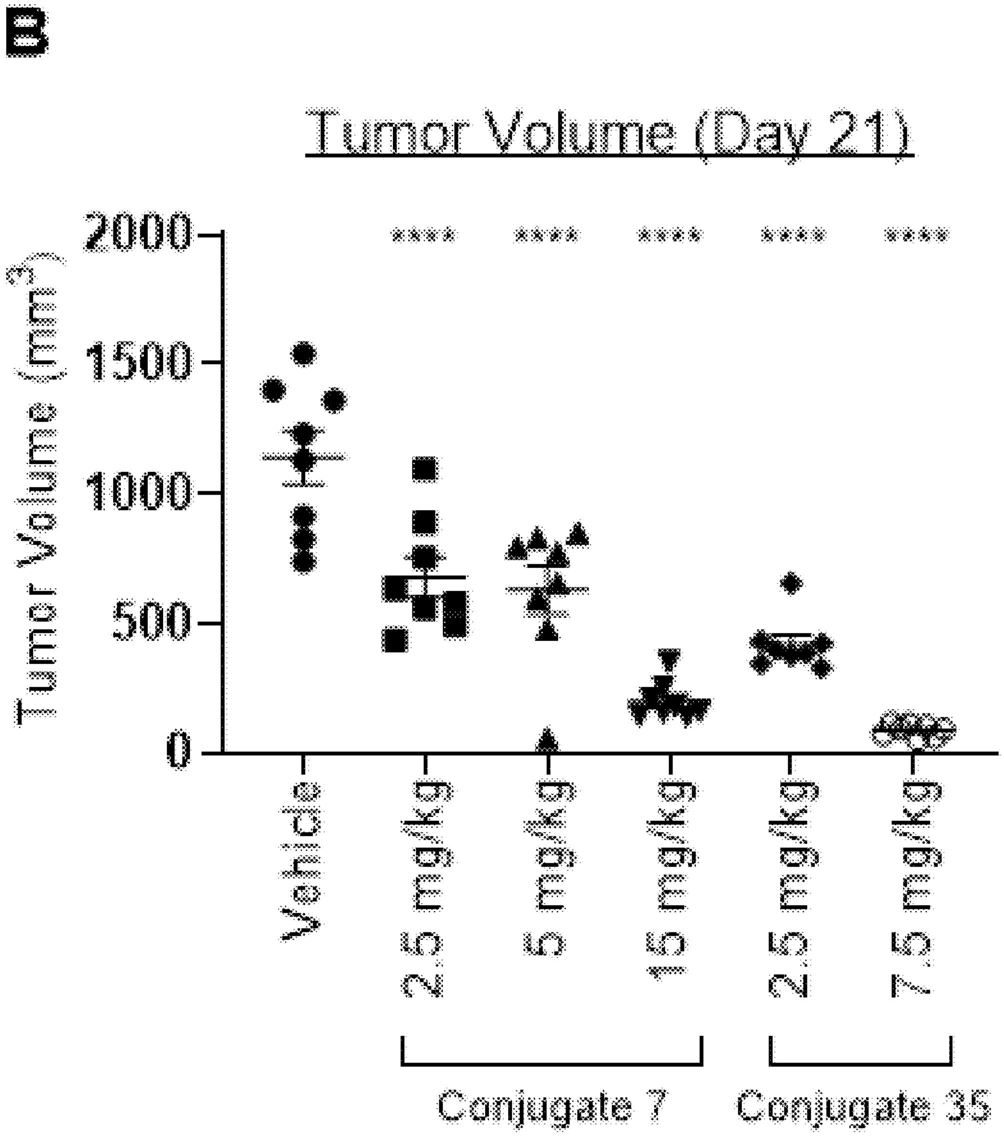

FIG. 13A illustrates the effects of the different test articles on HCT-116 tumor growth up until the end of the study at day 60 post treatment. Analysis of tumor sizes on day 21, when the mean of vehicle-treated tumors reached the study endpoint (~1,200 $mm^3$), revealed that both test articles demonstrated dose dependent anti-tumor activity, with efficacy ranging from approximately 45% to 103% TGI (FIG. 13B). Conjugate 35 at 7.5 mg/kg exhibited potent anti-tumor efficacy achieving prolonged tumor regression following treatment.

Example 34: Combination with Immune Checkpoint Blockcade

The activity of TF-targeted conjugates as a single agent or in combination with anti-PD-1 was assessed in a syngeneic model using a mouse colorectal cancer line engineered to express human TF, MC38-hTF. Briefly, $C_{57}$BL/6 mice were implanted subcutaneously with $1\times10^6$ MC38-hTF tumor cells in the hind flank and randomized and enrolled with tumor sizes around 400 $mm^3$. Tumor-bearing mice were administered a single dose of TF-targeted conjugates i.v. at the indicated doses with or without anti-PD-1 (q3d-q4dx3-4) i.p. at 10 mg/kg. All treatments were well tolerated, with mice exhibiting normal body weight gain throughout the course of the study.

Figure 14A:
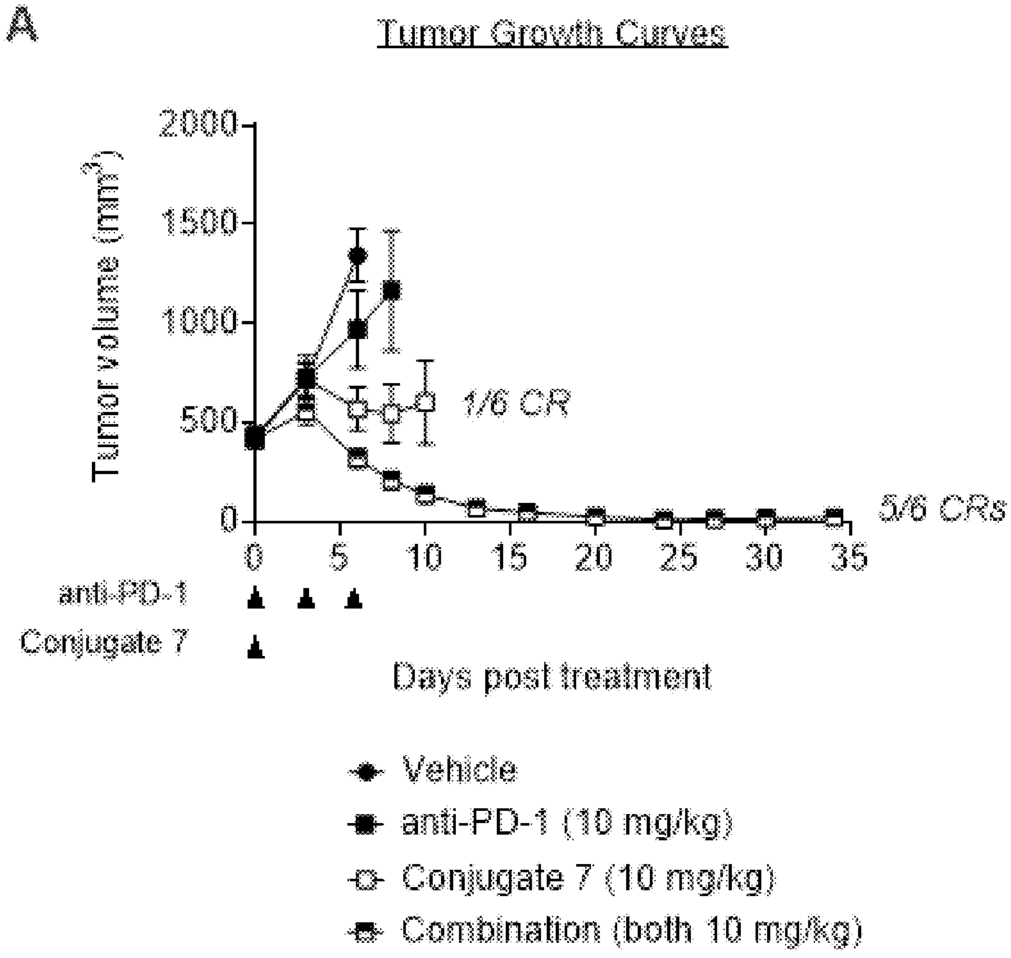
FIGS. 14A-D provide (FIG. 14A) MC38-hTF tumor growth curves in response to treatment with a single i.v. dose of Conjugate 7 at 10 mg/kg, multiple i.p. doses of anti-PD-1 at 10 mg/kg, or combination treatment. Number of complete responses (CRs) are designated to the right of the tumor growth curves.
Figure 14B:
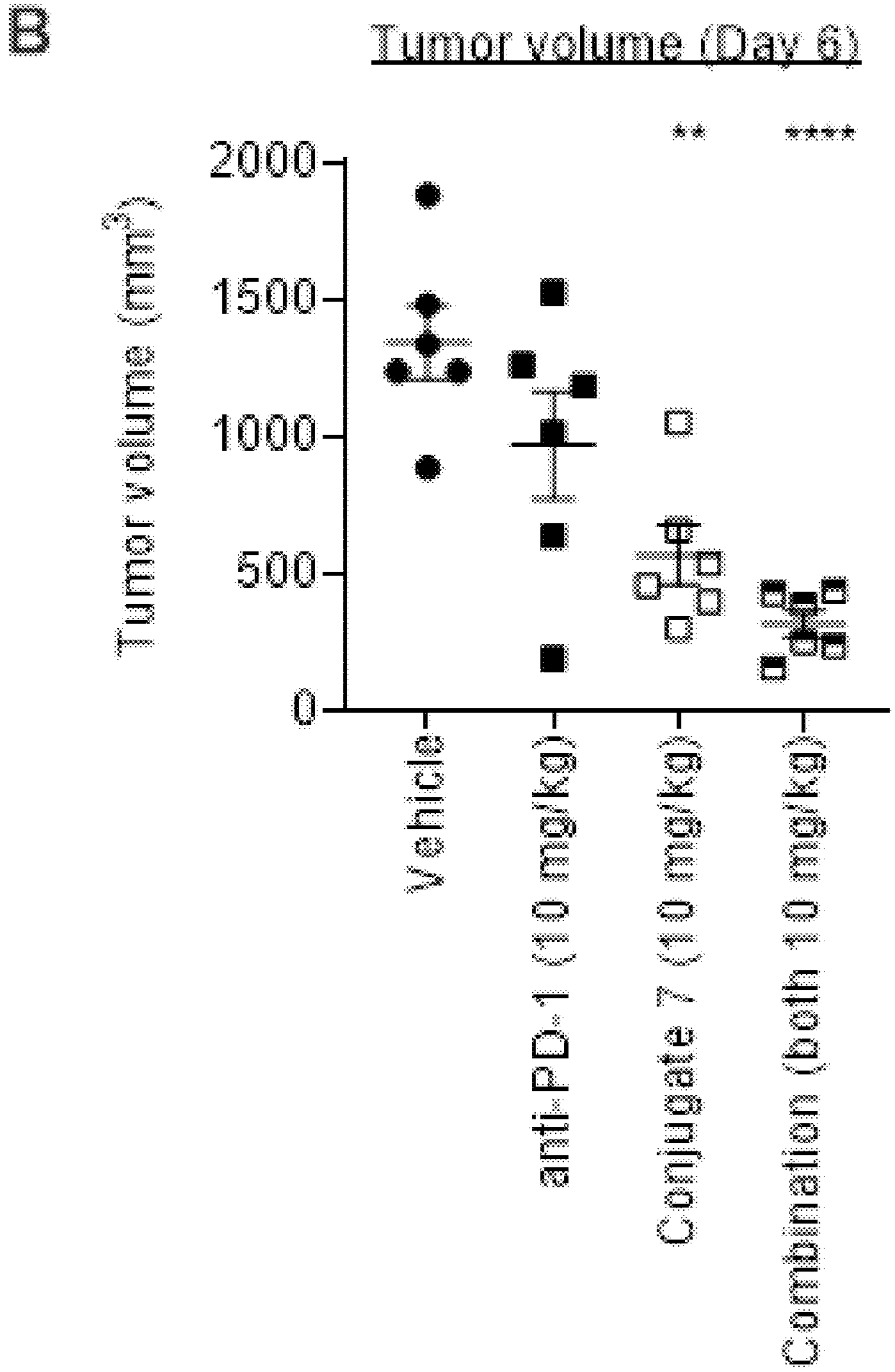
Figure 14C:
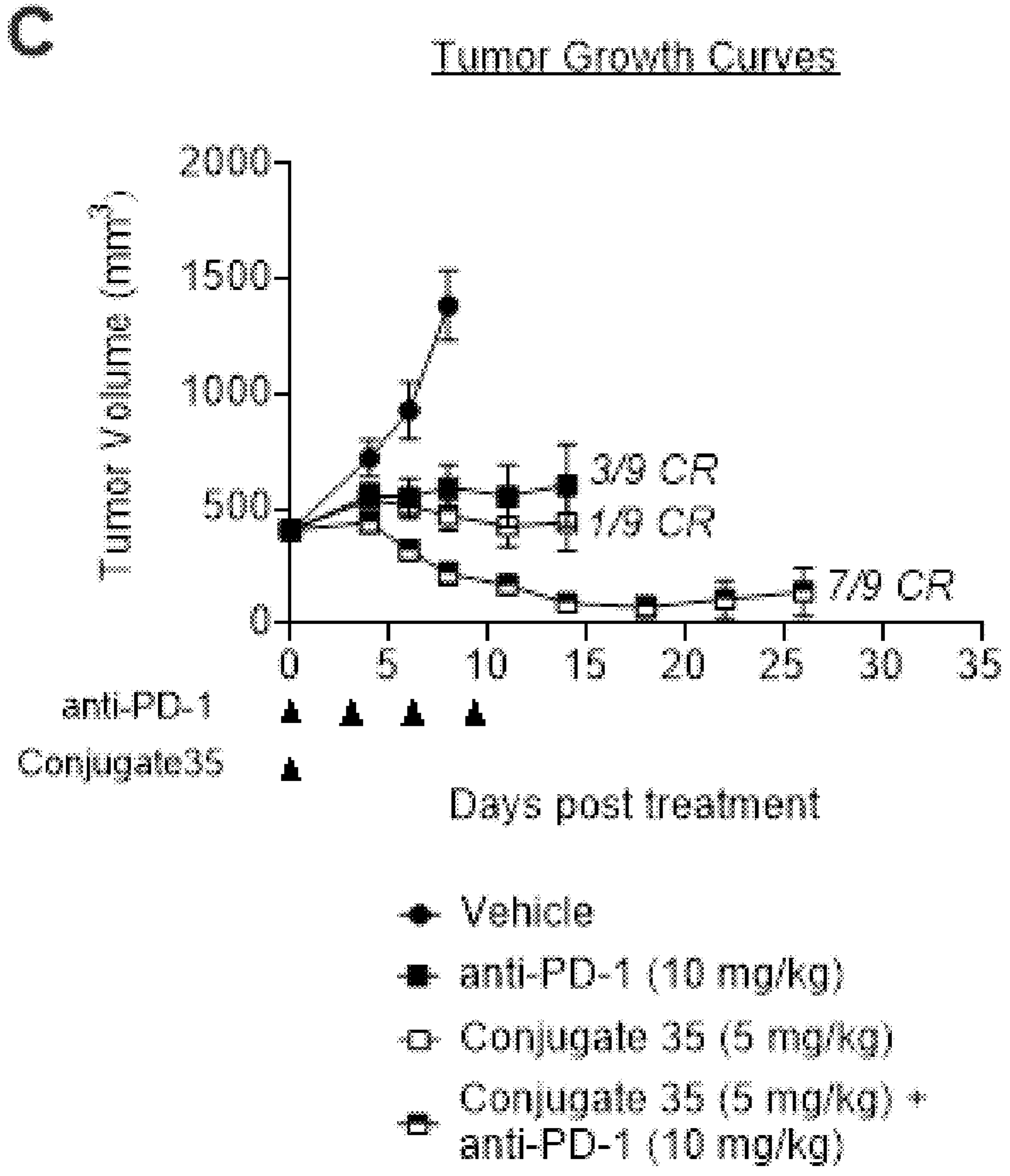
Figure 14D:
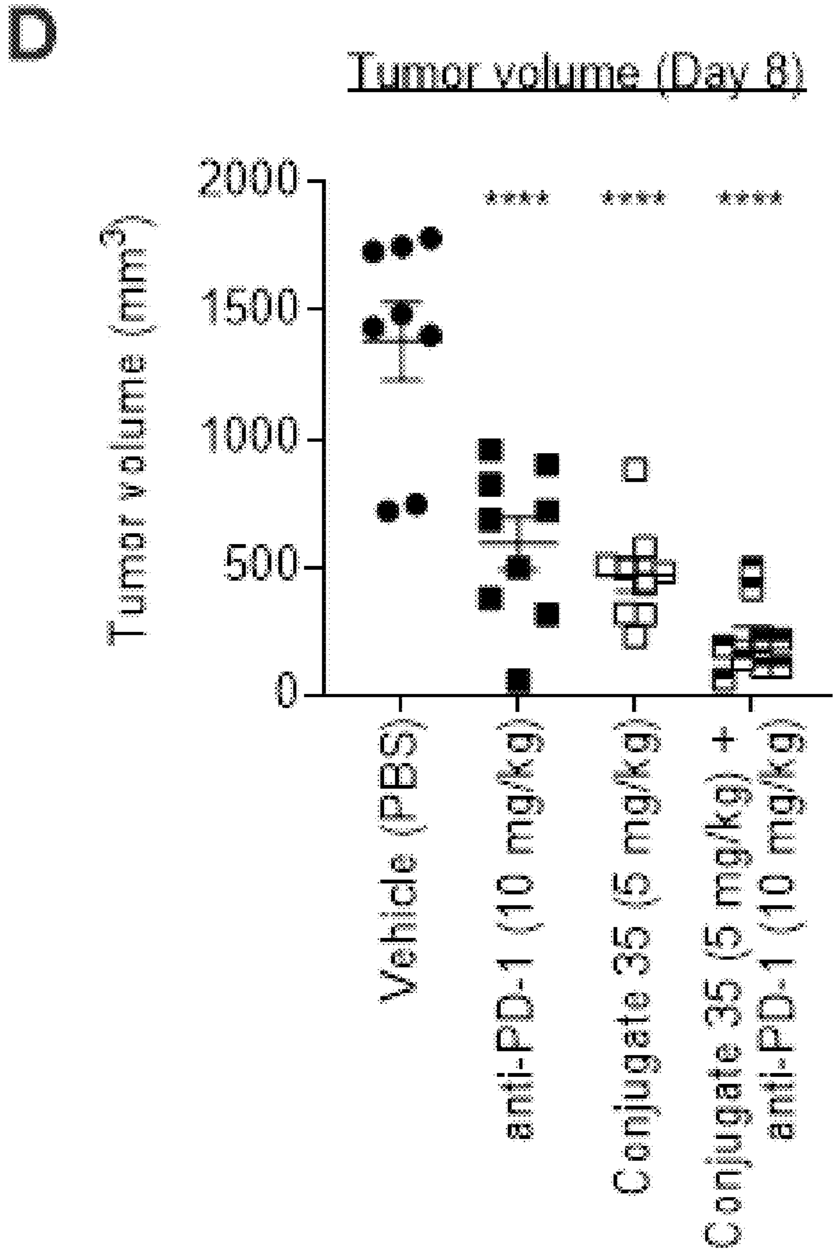

FIG. 14A illustrates the effects of Conjugate 7 monotherapy, anti-PD-1 monotherapy, and combination treatment on MC38-hTF tumor growth up until the end of the study at day 34 post treatment. Analysis of tumor sizes on day 6, when the mean of vehicle-treated tumors reached the study endpoint (>1,300 $mm^3$), revealed that Conjugate 7 and the combination treatment demonstrated significant anti-tumor activity, and treatment with anti-PD-1 monotherapy was not found to be significantly different from the vehicle-treated group (FIG. 14B). Notably, combination treatment demonstrated lasting tumor regression and achieved a greater number of complete responses (CRs) (1/6 and 5/6 mice in the Conjugate 7 monotherapy and combination treatment groups, respectively) (FIG. 14A). FIG. 14C illustrates the effects of Conjugate 35 monotherapy, anti-PD-1 monotherapy, and combination treatment on MC38-hTF tumor growth up until the end of the study at day 26 post treatment. Analysis of tumor sizes on day 8, when the mean of vehicle-treated tumors reached the study endpoint (>1,300 $mm^3$), revealed that Conjugate 35, anti-PD-1 monotherapy, and the combination treatment demonstrated significant anti-tumor activity (FIG. 14D). Notably, combination treatment demonstrated lasting tumor regression and achieved a greater number of complete responses (CRs) (1/6, 3/9, and 5/9 mice in the Conjugate 35, anti-PD-1 monotherapy, and combination treatment groups, respectively) (FIG. 14C).

Example 35: Efficacy of TF-Targeted Conjugates in PDX Models

The activity of different TF-targeted conjugates was examined in NSCLC, head and neck cancer, and esophageal patient-derived xenograft (PDX) models. Briefly, PDX tumors, spanning varying levels of TF expression, are passaged in athymic nude $Foxl^{nu}$ mice before being processed into tumor fragments for subcutaneous implantation into the hind flank of mice for study initiation. When tumors reach a volume of around 150-300 $mm^3$, the mice are randomized and enrolled into the study. Tumor-bearing mice are administered a single dose of the test articles i.v. at the indicated dose levels.

Figure 15A:
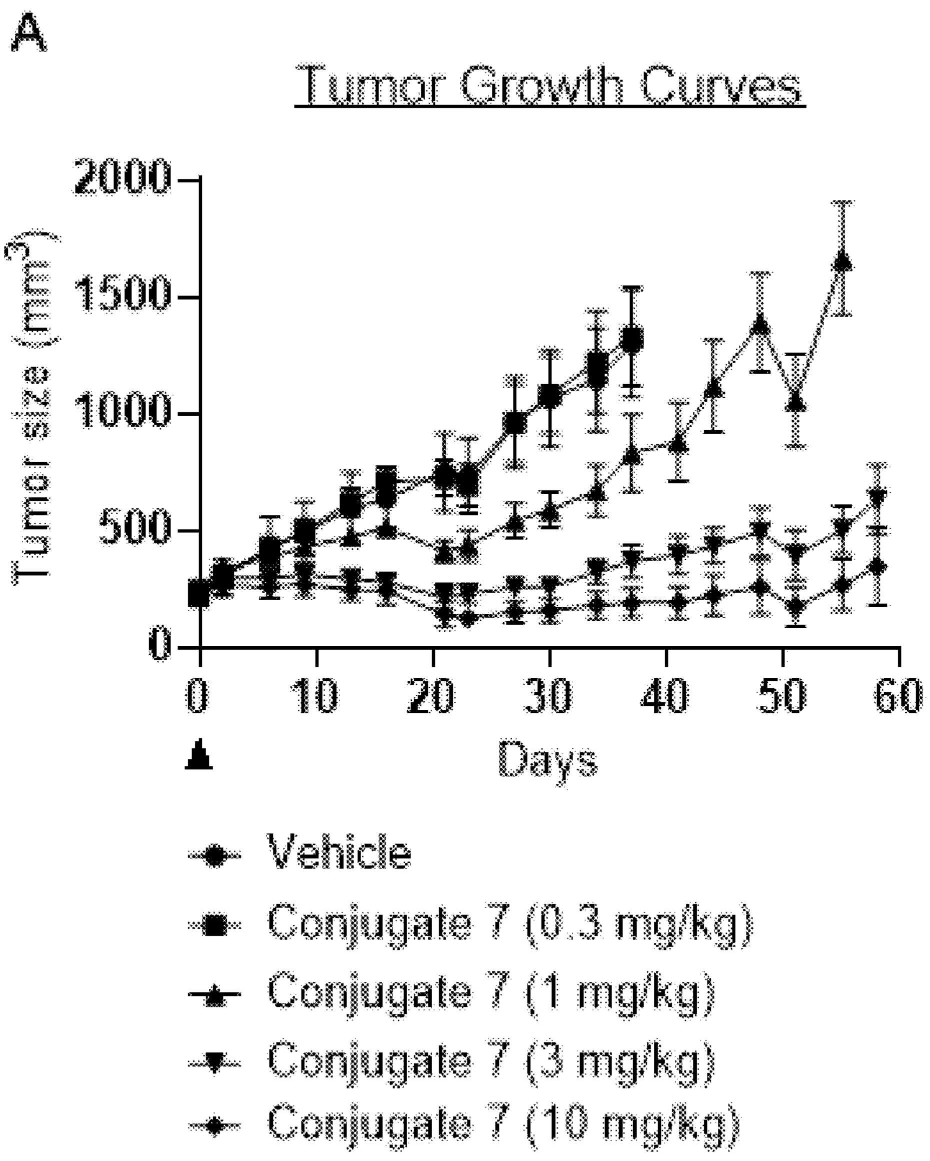
FIGS. 15A-B provide (FIG. 15A) Tumor growth curves of a NSCLC PDX model in response to treatment with a single i.v. dose of Conjugate 7 at doses ranging from 0.3 mg/kg to 10 mg/kg.
Figure 15B:
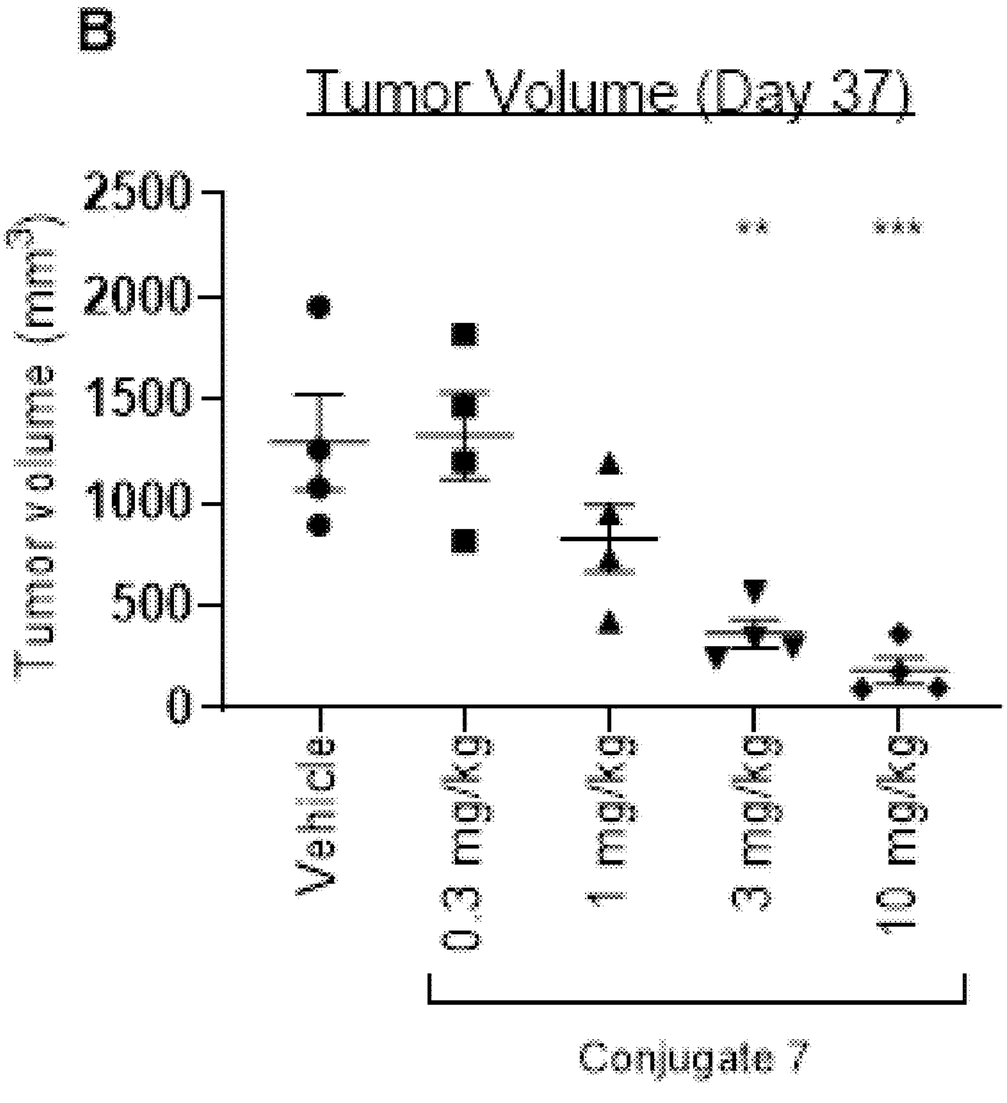

FIG. 15A illustrates the effects of Conjugate 7 on tumor growth of a NSCLC PDX model at doses ranging from 0.1 mg/kg to 10 mg/kg model up until the end of the study at day 58 post treatment. Analysis of tumor sizes on day 37 revealed that Conjugate 7 demonstrated dose-dependent anti-tumor activity. A single dose of Conjugate 7 at 3 mg/kg and 10 mg/kg achieved significant tumor growth inhibition compared to the vehicle group. (FIG. 15B).

Example 36: Safety Evaluation of Tissue Factor-Targeted Therapies

It is suspected that Tissue Factor-targeted therapies could present the potential for systemic toxicity (myelosuppression) and on-target toxicity potential because TF is widely expressed in the skin, eye, and gastrointestinal tissues with key risks being bleeding, skin toxicity, and eye toxicity.

A study was designed in Non-Human Primate (NHP) using Tissue Factor antibody drug conjugates. TF were characterized by TMDD with a conjugate of the present disclosure administered between 5 and 100 mg/kg q3w×2 for lower DAR variants or at 25-50 mg/kg q3w×2 for higher DAR variants. Pharmacokinetics was assessed for significant exposure with TMDD.

Example 37: Preclinical Testing

An antibody conjugate of the present disclosure was assessed for tolerance in NHP up to 100 mg/kg with dose-dependent exposures achieved. Safety was monitored for whether MTD/HNSTD was not reached at 100 mg/kg. Myelosuppression was monitored based on changes in neutrophiles, platelets and WBCs. Liver enzymes were observed and safety concerns were also monitored by histopathology.

The data demonstrates that a potent and specific antibody that does not interfere with the coagulation cascade can provide a potent and clinically validated exatecan payload with broad activity in solid tumors, incorporating a β-glucuronidase linker for improved stability and hydrophilicity. The antibody conjugate can be optimized for the linker-payload for stability. The antibody conjugate demonstrates potent, dose dependent anti-tumor activity in models of lung, breast, head and neck cancer, as well as checkpoint refractory tumors. The antibody conjugate was also well-tolerated in NHPs without reaching MTD at 100 mg/kg. Any toxicities observed were mild to minimal and ADCs were generally well-tolerated with minimal body weight loss. Thus, it is believed, without being bound to theory that the antibody conjugate has a widened therapeutic index.

Example 38: Sequences

Table 32 provides sequences referred to herein. Note an N-terminal methionine has been introduced to accommodate translation in a bacterially-derived expression system for each distinct protein chain for the illustrative antibodies (e.g. $V_H$ and $V_L$ sequences). * indicates the position of TAG codons for non-natural amino acids (in certain embodiments of the sequences, the non-natural amino acid is pAzMeF). It should be understood that sequences recited and claimed in this disclosure can be with or without an N-terminal methionine, with or without an N-terminal methionine-alanine, or with or without an N-terminal MSKNK.

TABLE 32

Sequences.

| SEQ ID NO: | Molecule | Region | Scheme | Sequence |
|---|---|---|---|---|
| 1 | Human Tissue Factor | | | METPAWPRVPRPETAVARTLLLGWVFAQ VAGASGTTNTVAAYNLTWKSTNFKTILE WEPKPVNQVYTVQISTKSGDWKSKCFYT TDTECDLTDEIVKDVKQTYLARVFSYPA GNVESTGSAGEPLYENSPEFTPYLETNL GQPTIQSFEQVGTKVNVTVEDERTLVRR NNTFLSLRDVFGKDLIYTLYYWKSSSSG KKTAKTNTNEFLIDVDKGENYCFSVQAV IPSRTVNRKSTDSPVECMGQEKGEFREI FYIIGAVVFVVIILVIILAISLHKCRKA GVGQSWKENSPLNVS |
| 2 | Cynomolgus Tissue Factor | | | METPAWPRVPRPETAVARTLLLGWVFAQVAG ASGTTNTVAAYNLTWKSTNFKTILEWEPKPI NQVYTVQISTKSGDWKSKCFYTADTECDLTD EIVKDVKQTYLARVESYPAGHVESTGSTEEP PYENSPEFTPYLETNLGQPTIQSFEQVGTKV NVTVQDEWTLVRRNDTFLSLRDVFGKDLIYT LYYWKSSSSGKKTAKTNTNEFLIDVDKGENY CFSVQAVIPSRRTANRKSTDSPVECMGHEKG ESREIFYIIGAVVFVVIILVIILAISLHKCK KARVGRSWKENSPLNVA |
| 105 | SRP2799-A05 | CDR-H1 | Chothia | GFNISSY |
| 114 | SRP2799-B03 | CDR-H1 | Chothia | GFNISDY |
| 117 | SRP2799-B06 | CDR-H1 | Chothia | GFNISDY |
| 129 | SRP2900-A01 | CDR-H1 | Chothia | GFTISSY |
| 130 | SRP2900-A02 | CDR-H1 | Chothia | GFTISGY |
| 131 | SRP2900-A03 | CDR-H1 | Chothia | GFTIPSY |
| 132 | SRP2900-A04 | CDR-H1 | Chothia | GFTISGY |
| 133 | SRP2900-A05 | CDR-H1 | Chothia | GFTIPDY |
| 134 | SRP2900-A06 | CDR-H1 | Chothia | GFTISSY |
| 135 | SRP2900-A07 | CDR-H1 | Chothia | GFTISSY |
| 136 | SRP2900-A08 | CDR-H1 | Chothia | GFTLTGY |
| 137 | SRP2900-A09 | CDR-H1 | Chothia | GFTIADY |
| 138 | SRP2900-A10 | CDR-H1 | Chothia | GFTISSY |
| 139 | SRP2900-A11 | CDR-H1 | Chothia | GFTITDY |
| 140 | SRP2900-B01 | CDR-H1 | Chothia | GFTISGY |
| 141 | SRP2900-B02 | CDR-H1 | Chothia | GFTISDY |
| 142 | SRP2900-B03 | CDR-H1 | Chothia | GFTIADY |
| 143 | SRP2900-B04 | CDR-H1 | Chothia | GFTISEY |
| 144 | SRP2900-B05 | CDR-H1 | Chothia | GFTISGY |

TABLE 32-continued

| Sequences. | | | | |
|---|---|---|---|---|
| SEQ ID NO: | Molecule | Region | Scheme | Sequence |
| 145 | SRP2900-B06 | CDR-H1 | Chothia | GFTIPSY |
| 146 | SRP2900-B07 | CDR-H1 | Chothia | GFTIADY |
| 147 | SRP2900-B08 | CDR-H1 | Chothia | GFTIPSY |
| 148 | SRP2900-B09 | CDR-H1 | Chothia | GFTISQY |
| 149 | SRP2900-B10 | CDR-H1 | Chothia | GFTIPAY |
| 150 | SRP2900-B11 | CDR-H1 | Chothia | GFTIPAY |
| 151 | SRP2900-C01 | CDR-H1 | Chothia | GFTIGSY |
| 152 | SRP2900-C02 | CDR-H1 | Chothia | GFTISSY |
| 153 | SRP2900-C03 | CDR-H1 | Chothia | GFTISGY |
| 154 | SRP2900-C04 | CDR-H1 | Chothia | GFTIVSY |
| 155 | SRP2900-C05 | CDR-H1 | Chothia | GFTISGY |
| 156 | SRP2900-C06 | CDR-H1 | Chothia | GFTISGY |
| 157 | SRP2900-C07 | CDR-H1 | Chothia | GFTISGY |
| 158 | SRP2900-C08 | CDR-H1 | Chothia | GFTIPAY |
| 159 | SRP2900-C09 | CDR-H1 | Chothia | GFTISDY |
| 160 | SRP2900-C10 | CDR-H1 | Chothia | GFTISDY |
| 161 | SRP2900-C11 | CDR-H1 | Chothia | GFTISQY |
| 162 | SRP2900-D01 | CDR-H1 | Chothia | GFTIHEY |
| 163 | SRP2900-D02 | CDR-H1 | Chothia | GFTISDY |
| 164 | SRP2900-D03 | CDR-H1 | Chothia | GFTISQY |
| 165 | SRP2900-D04 | CDR-H1 | Chothia | GFTISDY |
| 166 | SRP2900-D05 | CDR-H1 | Chothia | GFAIANY |
| 167 | SRP2900-D06 | CDR-H1 | Chothia | GFTISDY |
| 168 | SRP2900-D07 | CDR-H1 | Chothia | GFTISDY |
| 169 | SRP2900-D08 | CDR-H1 | Chothia | GFTISDY |
| 170 | SRP2900-D09 | CDR-H1 | Chothia | GFTISGY |
| 171 | SRP2900-D10 | CDR-H1 | Chothia | GFTISDY |
| 172 | SRP2900-D11 | CDR-H1 | Chothia | GFTISDY |
| 173 | SRP2900-E01 | CDR-H1 | Chothia | GFTISDY |
| 174 | SRP2900-E02 | CDR-H1 | Chothia | GFTISDY |
| 175 | SRP2900-E03 | CDR-H1 | Chothia | GFTISDY |
| 176 | SRP2900-E04 | CDR-H1 | Chothia | GFTIPDY |
| 177 | SRP2900-E05 | CDR-H1 | Chothia | GFTISGY |
| 178 | SRP2900-E06 | CDR-H1 | Chothia | GFTISGY |
| 179 | SRP2900-E07 | CDR-H1 | Chothia | GFTISQY |
| 180 | SRP2900-E08 | CDR-H1 | Chothia | GFTITDY |
| 181 | SRP2900-E09 | CDR-H1 | Chothia | GFTISQY |
| 182 | SRP2900-E10 | CDR-H1 | Chothia | GFTISDY |

TABLE 32-continued

| Sequences. | | | | |
|---|---|---|---|---|
| SEQ ID NO: | Molecule | Region | Scheme | Sequence |
| 183 | SRP2900-E11 | CDR-H1 | Chothia | GFTISYY |
| 184 | SRP2900-F01 | CDR-H1 | Chothia | GFTISDY |
| 185 | SRP2900-F02 | CDR-H1 | Chothia | GFTIGVY |
| 186 | SRP2900-F03 | CDR-H1 | Chothia | GFTISDY |
| 187 | SRP2900-F04 | CDR-H1 | Chothia | GFTISDY |
| 188 | SRP2900-F05 | CDR-H1 | Chothia | GFTINDY |
| 189 | SRP2900-F06 | CDR-H1 | Chothia | GFTISIY |
| 190 | SRP2900-F07 | CDR-H1 | Chothia | GFTISDY |
| 191 | SRP2900-F08 | CDR-H1 | Chothia | GFTIAYY |
| 192 | SRP2900-F09 | CDR-H1 | Chothia | GFTIHDY |
| 193 | SRP2900-F10 | CDR-H1 | Chothia | GFTISDY |
| 194 | SRP2900-F11 | CDR-H1 | Chothia | GFTISGY |
| 195 | SRP2900-G01 | CDR-H1 | Chothia | GFTIFDY |
| 196 | SRP2900-G02 | CDR-H1 | Chothia | GFTISYY |
| 197 | SRP2900-G03 | CDR-H1 | Chothia | GFTINNY |
| 198 | SRP2900-G04 | CDR-H1 | Chothia | GFTTRDY |
| 199 | SRP2900-G05 | CDR-H1 | Chothia | GFTIAYY |
| 200 | SRP2900-G06 | CDR-H1 | Chothia | GFTISDY |
| 201 | SRP2900-G07 | CDR-H1 | Chothia | GFTISDY |
| 202 | SRP2900-G08 | CDR-H1 | Chothia | GFTIGGY |
| 203 | SRP2900-G09 | CDR-H1 | Chothia | GFTISDY |
| 204 | SRP2900-G10 | CDR-H1 | Chothia | GFTIPDY |
| 205 | SRP2900-G11 | CDR-H1 | Chothia | GFTIYDY |
| 206 | SRP2900-H01 | CDR-H1 | Chothia | GFTIFDY |
| 207 | SRP2900-H02 | CDR-H1 | Chothia | GFTIFDY |
| 208 | SRP2900-H03 | CDR-H1 | Chothia | GFTIYDY |
| 209 | SRP2900-H04 | CDR-H1 | Chothia | GFTISHY |
| 210 | SRP2900-H05 | CDR-H1 | Chothia | GFTISDY |
| 211 | SRP2900-H06 | CDR-H1 | Chothia | GFTIAAY |
| 212 | SRP2900-H07 | CDR-H1 | Chothia | GFNIAYY |
| 213 | SRP2900-H08 | CDR-H1 | Chothia | GFTISDY |
| 214 | SRP2900-H09 | CDR-H1 | Chothia | GFTISDY |
| 215 | SRP2900-H10 | CDR-H1 | Chothia | GFTISDY |
| 216 | SRP2900-H11 | CDR-H1 | Chothia | GFTISSY |
| 218 | SRP2842-B01 | CDR-H1 | Chothia | GFSISSY |
| 224 | SRP2842-G04 | CDR-H1 | Chothia | GFSLSYY |
| 229 | SRP2901-B05_ 2842-G04_HC2 | CDR-H1 | Chothia | GFSLSYY |

TABLE 32-continued

| Sequences. | | | | |
|---|---|---|---|---|
| SEQ ID NO: | Molecule | Region | Scheme | Sequence |
| 235 | SRP2901-D03_ 2842-B01_HC-3 | CDR-H1 | Chothia | GFSISSY |
| 237 | SRP2901-E03_ 2842-B01_HC-3 | CDR-H1 | Chothia | GFSISSY |
| 238 | SRP2901-F01_ 2842-B01_HC-1 | CDR-H1 | Chothia | GFSISSY |
| 430 | SRP2799-A05 | CDR-H1 | Kabat | SYWIH |
| 439 | SRP2799-B03 | CDR-H1 | Kabat | DYWIH |
| 442 | SRP2799-B06 | CDR-H1 | Kabat | DYNIH |
| 454 | SRP2900-A01 | CDR-H1 | Kabat | SYWIH |
| 455 | SRP2900-A02 | CDR-H1 | Kabat | GYIIH |
| 456 | SRP2900-A03 | CDR-H1 | Kabat | SYWIH |
| 457 | SRP2900-A04 | CDR-H1 | Kabat | GYWIH |
| 458 | SRP2900-A05 | CDR-H1 | Kabat | DYWIH |
| 459 | SRP2900-A06 | CDR-H1 | Kabat | SYWIH |
| 460 | SRP2900-A07 | CDR-H1 | Kabat | SYWIH |
| 461 | SRP2900-A08 | CDR-H1 | Kabat | GYWIH |
| 462 | SRP2900-A09 | CDR-H1 | Kabat | DYWIH |
| 463 | SRP2900-A10 | CDR-H1 | Kabat | SYWIH |
| 464 | SRP2900-A11 | CDR-H1 | Kabat | DYVIH |
| 465 | SRP2900-B01 | CDR-H1 | Kabat | GYWIH |
| 466 | SRP2900-B02 | CDR-H1 | Kabat | DYWIH |
| 467 | SRP2900-B03 | CDR-H1 | Kabat | DYWIH |
| 468 | SRP2900-B04 | CDR-H1 | Kabat | EYWIH |
| 469 | SRP2900-B05 | CDR-H1 | Kabat | GYWIH |
| 470 | SRP2900-B06 | CDR-H1 | Kabat | SYWIH |
| 471 | SRP2900-B07 | CDR-H1 | Kabat | DYWIH |
| 472 | SRP2900-B08 | CDR-H1 | Kabat | SYWIH |
| 473 | SRP2900-B09 | CDR-H1 | Kabat | QYWIH |
| 474 | SRP2900-B10 | CDR-H1 | Kabat | AYWIH |
| 475 | SRP2900-B11 | CDR-H1 | Kabat | AYWIH |
| 476 | SRP2900-C01 | CDR-H1 | Kabat | SYWIH |
| 477 | SRP2900-C02 | CDR-H1 | Kabat | SYWIH |
| 478 | SRP2900-C03 | CDR-H1 | Kabat | GYWIH |
| 479 | SRP2900-C04 | CDR-H1 | Kabat | SYWIH |
| 480 | SRP2900-C05 | CDR-H1 | Kabat | GYWIH |
| 481 | SRP2900-C06 | CDR-H1 | Kabat | GYWIH |
| 482 | SRP2900-C07 | CDR-H1 | Kabat | GYWIH |
| 483 | SRP2900-C08 | CDR-H1 | Kabat | AYWIH |

TABLE 32-continued

| Sequences. | | | | |
|---|---|---|---|---|
| SEQ ID NO: | Molecule | Region | Scheme | Sequence |
| 484 | SRP2900-C09 | CDR-H1 | Kabat | DYIIH |
| 485 | SRP2900-C10 | CDR-H1 | Kabat | DYWIH |
| 486 | SRP2900-C11 | CDR-H1 | Kabat | QYWIH |
| 487 | SRP2900-D01 | CDR-H1 | Kabat | EYWIH |
| 488 | SRP2900-D02 | CDR-H1 | Kabat | DYWIH |
| 489 | SRP2900-D03 | CDR-H1 | Kabat | QYWIH |
| 490 | SRP2900-D04 | CDR-H1 | Kabat | DYWIH |
| 491 | SRP2900-D05 | CDR-H1 | Kabat | NYWIH |
| 492 | SRP2900-D06 | CDR-H1 | Kabat | DYWIH |
| 493 | SRP2900-D07 | CDR-H1 | Kabat | DYWIH |
| 494 | SRP2900-D08 | CDR-H1 | Kabat | DYWIH |
| 495 | SRP2900-D09 | CDR-H1 | Kabat | GYWIH |
| 496 | SRP2900-D10 | CDR-H1 | Kabat | DYWIH |
| 497 | SRP2900-D11 | CDR-H1 | Kabat | DYWIH |
| 498 | SRP2900-E01 | CDR-H1 | Kabat | DYWIH |
| 499 | SRP2900-E02 | CDR-H1 | Kabat | DYVIH |
| 500 | SRP2900-E03 | CDR-H1 | Kabat | DYWIH |
| 501 | SRP2900-E04 | CDR-H1 | Kabat | DYWIH |
| 502 | SRP2900-E05 | CDR-H1 | Kabat | GYWIH |
| 503 | SRP2900-E06 | CDR-H1 | Kabat | GYIIH |
| 504 | SRP2900-E07 | CDR-H1 | Kabat | QYWIH |
| 505 | SRP2900-E08 | CDR-H1 | Kabat | DYWIH |
| 506 | SRP2900-E09 | CDR-H1 | Kabat | QYWIH |
| 507 | SRP2900-E10 | CDR-H1 | Kabat | DYWIH |
| 508 | SRP2900-E11 | CDR-H1 | Kabat | YYIIH |
| 509 | SRP2900-F01 | CDR-H1 | Kabat | DYWIH |
| 510 | SRP2900-F02 | CDR-H1 | Kabat | VYIIH |
| 511 | SRP2900-F03 | CDR-H1 | Kabat | DYWIH |
| 512 | SRP2900-F04 | CDR-H1 | Kabat | DYWIH |
| 513 | SRP2900-F05 | CDR-H1 | Kabat | DYVIH |
| 514 | SRP2900-F06 | CDR-H1 | Kabat | IYTIH |
| 515 | SRP2900-F07 | CDR-H1 | Kabat | DYTIH |
| 516 | SRP2900-F08 | CDR-H1 | Kabat | YYIIH |
| 517 | SRP2900-F09 | CDR-H1 | Kabat | DYVIH |
| 518 | SRP2900-F10 | CDR-H1 | Kabat | DYVIH |
| 519 | SRP2900-F11 | CDR-H1 | Kabat | GYIIH |
| 520 | SRP2900-G01 | CDR-H1 | Kabat | DYTIH |

TABLE 32-continued

| Sequences. | | | | |
|---|---|---|---|---|
| SEQ ID NO: | Molecule | Region | Scheme | Sequence |
| 521 | SRP2900-G02 | CDR-H1 | Kabat | YYIIH |
| 522 | SRP2900-G03 | CDR-H1 | Kabat | NYIIH |
| 523 | SRP2900-G04 | CDR-H1 | Kabat | DYVIH |
| 524 | SRP2900-G05 | CDR-H1 | Kabat | YYVIH |
| 525 | SRP2900-G06 | CDR-H1 | Kabat | DYIIH |
| 526 | SRP2900-G07 | CDR-H1 | Kabat | DYVIH |
| 527 | SRP2900-G08 | CDR-H1 | Kabat | GYIIH |
| 528 | SRP2900-G09 | CDR-H1 | Kabat | DYIIH |
| 529 | SRP2900-G10 | CDR-H1 | Kabat | DYIIH |
| 530 | SRP2900-G11 | CDR-H1 | Kabat | DYIIH |
| 531 | SRP2900-H01 | CDR-H1 | Kabat | DYIIH |
| 532 | SRP2900-H02 | CDR-H1 | Kabat | DYIIH |
| 533 | SRP2900-H03 | CDR-H1 | Kabat | DYIIH |
| 534 | SRP2900-H04 | CDR-H1 | Kabat | HYIIH |
| 535 | SRP2900-H05 | CDR-H1 | Kabat | DYTIH |
| 536 | SRP2900-H06 | CDR-H1 | Kabat | AYIIH |
| 537 | SRP2900-H07 | CDR-H1 | Kabat | YYTIH |
| 538 | SRP2900-H08 | CDR-H1 | Kabat | DYVIH |
| 539 | SRP2900-H09 | CDR-H1 | Kabat | DYVIH |
| 540 | SRP2900-H10 | CDR-H1 | Kabat | DYVIH |
| 541 | SRP2900-H11 | CDR-H1 | Kabat | SYIIH |
| 543 | SRP2842-B01 | CDR-H1 | Kabat | SYDMS |
| 549 | SRP2842-G04 | CDR-H1 | Kabat | YYGVS |
| 554 | SRP2901-B05_ 2842-G04_HC2 | CDR-H1 | Kabat | YYGVS |
| 560 | SRP2901-D03_ 2842-B01_HC-3 | CDR-H1 | Kabat | SYDMS |
| 562 | SRP2901-E03_ 2842-B01_HC-3 | CDR-H1 | Kabat | SYDMS |
| 563 | SRP2901-F01_ 2842-B01_HC-1 | CDR-H1 | Kabat | SYDMS |
| 755 | SRP2799-A05 | CDR-H2 | Chothia | DPYSGS |
| 764 | SRP2799-B03 | CDR-H2 | Chothia | DPYNGY |
| 767 | SRP2799-B06 | CDR-H2 | Chothia | DPSNGY |
| 779 | SRP2900-A01 | CDR-H2 | Chothia | DPYNGA |
| 780 | SRP2900-A02 | CDR-H2 | Chothia | DPSNGY |

TABLE 32-continued

Sequences.

| SEQ ID NO: | Molecule | Region | Scheme | Sequence |
|---|---|---|---|---|
| 781 | SRP2900-A03 | CDR-H2 | Chothia | DPANGA |
| 782 | SRP2900-A04 | CDR-H2 | Chothia | DPYNGA |
| 783 | SRP2900-A05 | CDR-H2 | Chothia | DPYNGY |
| 784 | SRP2900-A06 | CDR-H2 | Chothia | DPFNGA |
| 785 | SRP2900-A07 | CDR-H2 | Chothia | DPYNGA |
| 786 | SRP2900-A08 | CDR-H2 | Chothia | DPYNGA |
| 787 | SRP2900-A09 | CDR-H2 | Chothia | DPYNGA |
| 788 | SRP2900-A10 | CDR-H2 | Chothia | DPYNGA |
| 789 | SRP2900-A11 | CDR-H2 | Chothia | DPSNGY |
| 790 | SRP2900-B01 | CDR-H2 | Chothia | DPYNGA |
| 791 | SRP2900-B02 | CDR-H2 | Chothia | DPYNGA |
| 792 | SRP2900-B03 | CDR-H2 | Chothia | DPYNGA |
| 793 | SRP2900-B04 | CDR-H2 | Chothia | DPYNGY |
| 794 | SRP2900-B05 | CDR-H2 | Chothia | DPYNGA |
| 795 | SRP2900-B06 | CDR-H2 | Chothia | DPYNGA |
| 796 | SRP2900-B07 | CDR-H2 | Chothia | DPYNGY |
| 797 | SRP2900-B08 | CDR-H2 | Chothia | DPYNGY |
| 798 | SRP2900-B09 | CDR-H2 | Chothia | DPYNGY |
| 799 | SRP2900-B10 | CDR-H2 | Chothia | DPYNGS |
| 800 | SRP2900-B11 | CDR-H2 | Chothia | DPSNGY |
| 801 | SRP2900-C01 | CDR-H2 | Chothia | DPSNGY |
| 802 | SRP2900-C02 | CDR-H2 | Chothia | DPYNGA |
| 803 | SRP2900-C03 | CDR-H2 | Chothia | DPYNGA |
| 804 | SRP2900-C04 | CDR-H2 | Chothia | DPYNGA |
| 805 | SRP2900-C05 | CDR-H2 | Chothia | DPYNGA |
| 806 | SRP2900-C06 | CDR-H2 | Chothia | DPYNGA |
| 807 | SRP2900-C07 | CDR-H2 | Chothia | DPYNGA |
| 808 | SRP2900-C08 | CDR-H2 | Chothia | DPYNGS |
| 809 | SRP2900-C09 | CDR-H2 | Chothia | DPSNGY |
| 810 | SRP2900-C10 | CDR-H2 | Chothia | DPYNGY |
| 811 | SRP2900-C11 | CDR-H2 | Chothia | DPYNGY |
| 812 | SRP2900-D01 | CDR-H2 | Chothia | DPANGF |
| 813 | SRP2900-D02 | CDR-H2 | Chothia | DPYNGY |
| 814 | SRP2900-D03 | CDR-H2 | Chothia | DPYNGY |
| 815 | SRP2900-D04 | CDR-H2 | Chothia | DPYNGY |
| 816 | SRP2900-D05 | CDR-H2 | Chothia | DPYNGY |
| 817 | SRP2900-D06 | CDR-H2 | Chothia | DPQNGW |
| 818 | SRP2900-D07 | CDR-H2 | Chothia | DPSNGY |

TABLE 32-continued

| Sequences. | | | | |
|---|---|---|---|---|
| SEQ ID NO: | Molecule | Region | Scheme | Sequence |
| 819 | SRP2900-D08 | CDR-H2 | Chothia | DPYNGY |
| 820 | SRP2900-D09 | CDR-H2 | Chothia | DPANGF |
| 821 | SRP2900-D10 | CDR-H2 | Chothia | DPKNGY |
| 822 | SRP2900-D11 | CDR-H2 | Chothia | DPYNGY |
| 823 | SRP2900-E01 | CDR-H2 | Chothia | DPSNGY |
| 824 | SRP2900-E02 | CDR-H2 | Chothia | DPSNGY |
| 825 | SRP2900-E03 | CDR-H2 | Chothia | DPQNGW |
| 826 | SRP2900-E04 | CDR-H2 | Chothia | DPYSGS |
| 827 | SRP2900-E05 | CDR-H2 | Chothia | DPANGF |
| 828 | SRP2900-E06 | CDR-H2 | Chothia | DPSNGY |
| 829 | SRP2900-E07 | CDR-H2 | Chothia | DPYNGY |
| 830 | SRP2900-E08 | CDR-H2 | Chothia | DPYNGY |
| 831 | SRP2900-E09 | CDR-H2 | Chothia | DPYNGY |
| 832 | SRP2900-E10 | CDR-H2 | Chothia | DPANGY |
| 833 | SRP2900-E11 | CDR-H2 | Chothia | DPSNGY |
| 834 | SRP2900-F01 | CDR-H2 | Chothia | DPYNGY |
| 835 | SRP2900-F02 | CDR-H2 | Chothia | DPSNGY |
| 836 | SRP2900-F03 | CDR-H2 | Chothia | DPYNGY |
| 837 | SRP2900-F04 | CDR-H2 | Chothia | DPYNGF |
| 838 | SRP2900-F05 | CDR-H2 | Chothia | DPSNGY |
| 839 | SRP2900-F06 | CDR-H2 | Chothia | DPSNGY |
| 840 | SRP2900-F07 | CDR-H2 | Chothia | DPSNGY |
| 841 | SRP2900-F08 | CDR-H2 | Chothia | DPSNGY |
| 842 | SRP2900-F09 | CDR-H2 | Chothia | DPSNGY |
| 843 | SRP2900-F10 | CDR-H2 | Chothia | DPSNGY |
| 844 | SRP2900-F11 | CDR-H2 | Chothia | DPSNGY |
| 845 | SRP2900-G01 | CDR-H2 | Chothia | DPSNGY |
| 846 | SRP2900-G02 | CDR-H2 | Chothia | DPSNGY |
| 847 | SRP2900-G03 | CDR-H2 | Chothia | DPSNGY |
| 848 | SRP2900-G04 | CDR-H2 | Chothia | DPSNGY |
| 849 | SRP2900-G05 | CDR-H2 | Chothia | DPSNGY |
| 850 | SRP2900-G06 | CDR-H2 | Chothia | DPSNGY |
| 851 | SRP2900-G07 | CDR-H2 | Chothia | DPSNGY |
| 852 | SRP2900-G08 | CDR-H2 | Chothia | DPSNGY |
| 853 | SRP2900-G09 | CDR-H2 | Chothia | DPSNGY |
| 854 | SRP2900-G10 | CDR-H2 | Chothia | DPSNGY |
| 855 | SRP2900-G11 | CDR-H2 | Chothia | DPSNGY |

TABLE 32-continued

| Sequences. | | | | |
|---|---|---|---|---|
| SEQ ID NO: | Molecule | Region | Scheme | Sequence |
| 856 | SRP2900-H01 | CDR-H2 | Chothia | DPSNGY |
| 857 | SRP2900-H02 | CDR-H2 | Chothia | DPSNGY |
| 858 | SRP2900-H03 | CDR-H2 | Chothia | DPSNGY |
| 859 | SRP2900-H04 | CDR-H2 | Chothia | DPSNGY |
| 860 | SRP2900-H05 | CDR-H2 | Chothia | DPSNGY |
| 861 | SRP2900-H06 | CDR-H2 | Chothia | DPSNGY |
| 862 | SRP2900-H07 | CDR-H2 | Chothia | DPSNGY |
| 863 | SRP2900-H08 | CDR-H2 | Chothia | DPSNGY |
| 864 | SRP2900-H09 | CDR-H2 | Chothia | DPSNGY |
| 865 | SRP2900-H10 | CDR-H2 | Chothia | DPSNGF |
| 866 | SRP2900-H11 | CDR-H2 | Chothia | DPSNGY |
| 868 | SRP2842-B01 | CDR-H2 | Chothia | IGSNGR |
| 874 | SRP2842-G04 | CDR-H2 | Chothia | DSSGR |
| 879 | SRP2901-B05_ 2842-G04_HC2 | CDR-H2 | Chothia | DSSGR |
| 885 | SRP2901-D03_ 2842-B01_HC-3 | CDR-H2 | Chothia | IGSNGR |
| 887 | SRP2901-E03_ 2842-B01_HC-3 | CDR-H2 | Chothia | IGSNGR |
| 888 | SRP2901-F01_ 2842-B01_HC-1 | CDR-H2 | Chothia | IGSNGR |
| 1080 | SRP2799-A05 | CDR-H2 | Kabat | YIDPYSGSTYYADSVKG |
| 1089 | SRP2799-B03 | CDR-H2 | Kabat | FIDPYNGYTNYADSVKG |
| 1092 | SRP2799-B06 | CDR-H2 | Kabat | YIDPSNGYTYYADSVKG |
| 1104 | SRP2900-A01 | CDR-H2 | Kabat | YIDPYNGATYYADSVKG |
| 1105 | SRP2900-A02 | CDR-H2 | Kabat | YIDPSNGYTYYADSVKG |
| 1106 | SRP2900-A03 | CDR-H2 | Kabat | YIDPANGATYYADSVKG |
| 1107 | SRP2900-A04 | CDR-H2 | Kabat | YIDPYNGATYYADSVKG |
| 1108 | SRP2900-A05 | CDR-H2 | Kabat | FIDPYNGYTNYADPVKS |
| 1109 | SRP2900-A06 | CDR-H2 | Kabat | YIDPFNGATYYADSVKG |
| 1110 | SRP2900-A07 | CDR-H2 | Kabat | YIDPYNGATYYADSVKG |
| 1111 | SRP2900-A08 | CDR-H2 | Kabat | YIDPYNGATYYADSVKG |
| 1112 | SRP2900-A09 | CDR-H2 | Kabat | YIDPYNGATYYADSVKG |
| 1113 | SRP2900-A10 | CDR-H2 | Kabat | YIDPYNGATYYADSVKG |
| 1114 | SRP2900-A11 | CDR-H2 | Kabat | YIDPSNGYTYYADSVKG |
| 1115 | SRP2900-B01 | CDR-H2 | Kabat | YIDPYNGATYYADSVKG |
| 1116 | SRP2900-B02 | CDR-H2 | Kabat | YIDPYNGATYYADSVKG |
| 1117 | SRP2900-B03 | CDR-H2 | Kabat | YIDPYNGATYYADSVKG |
| 1118 | SRP2900-B04 | CDR-H2 | Kabat | FIDPYNGYTGYADSVRG |
| 1119 | SRP2900-B05 | CDR-H2 | Kabat | YIDPYNGATYYADSVKG |

TABLE 32-continued

| Sequences. | | | | |
|---|---|---|---|---|
| SEQ ID NO: | Molecule | Region | Scheme | Sequence |
| 1120 | SRP2900-B06 | CDR-H2 | Kabat | YIDPYNGATYYADSVKG |
| 1121 | SRP2900-B07 | CDR-H2 | Kabat | FIDPYNGYTGYADSVKG |
| 1122 | SRP2900-B08 | CDR-H2 | Kabat | YIDPYNGYTYYADSVKG |
| 1123 | SRP2900-B09 | CDR-H2 | Kabat | FIDPYNGYTNYADSVKG |
| 1124 | SRP2900-B10 | CDR-H2 | Kabat | YIDPYNGSTYYADSVKG |
| 1125 | SRP2900-B11 | CDR-H2 | Kabat | YIDPSNGYTYYADSVKG |
| 1126 | SRP2900-C01 | CDR-H2 | Kabat | YIDPSNGYTYYADSVKG |
| 1127 | SRP2900-C02 | CDR-H2 | Kabat | YIDPYNGATYYADSVKG |
| 1128 | SRP2900-C03 | CDR-H2 | Kabat | YIDPYNGATYYADSVKG |
| 1129 | SRP2900-C04 | CDR-H2 | Kabat | YIDPYNGATYYADSVKG |
| 1130 | SRP2900-C05 | CDR-H2 | Kabat | YIDPYNGATYYADSVKG |
| 1131 | SRP2900-C06 | CDR-H2 | Kabat | YIDPYNGATFYADSVKG |
| 1132 | SRP2900-C07 | CDR-H2 | Kabat | YIDPYNGATYYADSVKG |
| 1133 | SRP2900-C08 | CDR-H2 | Kabat | YIDPYNGSTYHADSVKG |
| 1134 | SRP2900-C09 | CDR-H2 | Kabat | YIDPSNGYTYHADSVKG |
| 1135 | SRP2900-C10 | CDR-H2 | Kabat | YIDPYNGYTYYADSVNG |
| 1136 | SRP2900-C11 | CDR-H2 | Kabat | YIDPYNGYTYYADSVKG |
| 1137 | SRP2900-D01 | CDR-H2 | Kabat | YIDPANGFTYYADSVKG |
| 1138 | SRP2900-D02 | CDR-H2 | Kabat | YIDPYNGYTYYADSVKG |
| 1139 | SRP2900-D03 | CDR-H2 | Kabat | YIDPYNGYTYYADSVKG |
| 1140 | SRP2900-D04 | CDR-H2 | Kabat | FIDPYNGYTYHADSVEG |
| 1141 | SRP2900-D05 | CDR-H2 | Kabat | YIDPYNGYTYYADSVKG |
| 1142 | SRP2900-D06 | CDR-H2 | Kabat | YIDPQNGWTYYADSVKG |
| 1143 | SRP2900-D07 | CDR-H2 | Kabat | YIDPSNGYTYYADSVKG |
| 1144 | SRP2900-D08 | CDR-H2 | Kabat | YIDPYNGYTYYADSVKG |
| 1145 | SRP2900-D09 | CDR-H2 | Kabat | YIDPANGFTYYADSVKG |
| 1146 | SRP2900-D10 | CDR-H2 | Kabat | FIDPKNGYTYYADSVKG |
| 1147 | SRP2900-D11 | CDR-H2 | Kabat | YIDPYNGYTYYADSVKG |
| 1148 | SRP2900-E01 | CDR-H2 | Kabat | YIDPSNGYTYYADSVKG |
| 1149 | SRP2900-E02 | CDR-H2 | Kabat | YIDPSNGYTYYADPVKG |
| 1150 | SRP2900-E03 | CDR-H2 | Kabat | YIDPQNGWTYYADSVKG |
| 1151 | SRP2900-E04 | CDR-H2 | Kabat | YIDPYSGSTFYADSVKG |
| 1152 | SRP2900-E05 | CDR-H2 | Kabat | YIDPANGFTYYADSVKG |
| 1153 | SRP2900-E06 | CDR-H2 | Kabat | YIDPSNGYTYHADSVKG |
| 1154 | SRP2900-E07 | CDR-H2 | Kabat | YIDPYNGYTYYADSVKG |
| 1155 | SRP2900-E08 | CDR-H2 | Kabat | YIDPYNGYTYYADSVKG |
| 1156 | SRP2900-E09 | CDR-H2 | Kabat | YIDPYNGYTYYADSVKG |

TABLE 32-continued

Sequences.

| SEQ ID NO: | Molecule | Region | Scheme | Sequence |
|---|---|---|---|---|
| 1157 | SRP2900-E10 | CDR-H2 | Kabat | YIDPANGYTYYADSVKG |
| 1158 | SRP2900-E11 | CDR-H2 | Kabat | YIDPSNGYTYYADSVKG |
| 1159 | SRP2900-F01 | CDR-H2 | Kabat | YIDPYNGYTYYADSVRG |
| 1160 | SRP2900-F02 | CDR-H2 | Kabat | YIDPSNGYTYYADSVKG |
| 1161 | SRP2900-F03 | CDR-H2 | Kabat | YIDPYNGYTYYADSVKG |
| 1162 | SRP2900-F04 | CDR-H2 | Kabat | YIDPYNGFTYYADSVKG |
| 1163 | SRP2900-F05 | CDR-H2 | Kabat | YIDPSNGYTYYADSVKG |
| 1164 | SRP2900-F06 | CDR-H2 | Kabat | YIDPSNGYTYYADSVKG |
| 1165 | SRP2900-F07 | CDR-H2 | Kabat | YIDPSNGYTYHADSVKG |
| 1166 | SRP2900-F08 | CDR-H2 | Kabat | YIDPSNGYTYYADSVKG |
| 1167 | SRP2900-F09 | CDR-H2 | Kabat | YIDPSNGYTYYADSVKG |
| 1168 | SRP2900-F10 | CDR-H2 | Kabat | YIDPSNGYTYYADSVKG |
| 1169 | SRP2900-F11 | CDR-H2 | Kabat | YIDPSNGYTFYADSVKG |
| 1170 | SRP2900-G01 | CDR-H2 | Kabat | YIDPSNGYTFYADSVKG |
| 1171 | SRP2900-G02 | CDR-H2 | Kabat | YIDPSNGYTYYADSVKG |
| 1172 | SRP2900-G03 | CDR-H2 | Kabat | YIDPSNGYTYYADSVKG |
| 1173 | SRP2900-G04 | CDR-H2 | Kabat | YIDPSNGYTYYADSVKG |
| 1174 | SRP2900-G05 | CDR-H2 | Kabat | YIDPSNGYTYYADSVKG |
| 1175 | SRP2900-G06 | CDR-H2 | Kabat | YIDPSNGYTYYADSVKG |
| 1176 | SRP2900-G07 | CDR-H2 | Kabat | YIDPSNGYTYYADSVKG |
| 1177 | SRP2900-G08 | CDR-H2 | Kabat | YIDPSNGYTYYADSVKG |
| 1178 | SRP2900-G09 | CDR-H2 | Kabat | YIDPSNGYTYYADSVKG |
| 1179 | SRP2900-G10 | CDR-H2 | Kabat | YIDPSNGYTYYADSVKG |
| 1180 | SRP2900-G11 | CDR-H2 | Kabat | YIDPSNGYTDYADSVKG |
| 1181 | SRP2900-H01 | CDR-H2 | Kabat | YIDPSNGYTYYADSVKG |
| 1182 | SRP2900-H02 | CDR-H2 | Kabat | YIDPSNGYTYYADSVKG |
| 1183 | SRP2900-H03 | CDR-H2 | Kabat | YIDPSNGYTYHADSVKG |
| 1184 | SRP2900-H04 | CDR-H2 | Kabat | YIDPSNGYTYYADSVKG |
| 1185 | SRP2900-H05 | CDR-H2 | Kabat | YIDPSNGYTYYADSVKG |
| 1186 | SRP2900-H06 | CDR-H2 | Kabat | YIDPSNGYTYYADSVKG |
| 1187 | SRP2900-H07 | CDR-H2 | Kabat | YIDPSNGYTYYADSVKG |
| 1188 | SRP2900-H08 | CDR-H2 | Kabat | YIDPSNGYTFYADSVKG |
| 1189 | SRP2900-H09 | CDR-H2 | Kabat | YIDPSNGYTYYADSVKG |
| 1190 | SRP2900-H10 | CDR-H2 | Kabat | YIDPSNGFTYYADSVKG |
| 1191 | SRP2900-H11 | CDR-H2 | Kabat | YIDPSNGYTYYADSVKG |
| 1193 | SRP2842-B01 | CDR-H2 | Kabat | IIGSNGRTYYPNWAKS |
| 1199 | SRP2842-G04 | CDR-H2 | Kabat | TIDSSGRTYYASWANG |

TABLE 32-continued

| SEQ ID NO: | Molecule | Region | Scheme | Sequence |
|---|---|---|---|---|
| 1204 | SRP2901-B05_ 2842-G04_HC2 | CDR-H2 | Kabat | TIDSSGRTYYNPSLKS |
| 1210 | SRP2901-D03_ 2842-B01_HC-3 | CDR-H2 | Kabat | IIGSNGRTYYPDSVKG |
| 1212 | SRP2901-E03_ 2842-B01_HC-3 | CDR-H2 | Kabat | IIGSNGRTYYPDSVKG |
| 1213 | SRP2901-F01_ 2842-B01_HC-1 | CDR-H2 | Kabat | IIGSNGRTYYADSVKG |
| 1405 | SRP2799-A05 | CDR-H3 | Chothia | SDYYYVDEY |
| 1414 | SRP2799-B03 | CDR-H3 | Chothia | GYGSWPDY |
| 1417 | SRP2799-B06 | CDR-H3 | Chothia | DDQSVSSP |
| 1429 | SRP2900-A01 | CDR-H3 | Chothia | ADYYYVDEYFDY |
| 1430 | SRP2900-A02 | CDR-H3 | Chothia | DDQSLSSPFDY |
| 1431 | SRP2900-A03 | CDR-H3 | Chothia | ADYFYVDEYLDY |
| 1432 | SRP2900-A04 | CDR-H3 | Chothia | ADYFYIDEYWDY |
| 1433 | SRP2900-A05 | CDR-H3 | Chothia | ADYYYVDEYWDY |
| 1434 | SRP2900-A06 | CDR-H3 | Chothia | ADYYYVDEYWDY |
| 1435 | SRP2900-A07 | CDR-H3 | Chothia | SDYYYVDEFFDY |
| 1436 | SRP2900-A08 | CDR-H3 | Chothia | ADYYYVDEYWDY |
| 1437 | SRP2900-A09 | CDR-H3 | Chothia | ADYYYVDEYWDY |
| 1438 | SRP2900-A10 | CDR-H3 | Chothia | ADYYYVDEYLDY |
| 1439 | SRP2900-A11 | CDR-H3 | Chothia | DDQSFTSPFDY |
| 1440 | SRP2900-B01 | CDR-H3 | Chothia | ADYYYVDEYLDY |
| 1441 | SRP2900-B02 | CDR-H3 | Chothia | ADYYYVDEYWDY |
| 1442 | SRP2900-B03 | CDR-H3 | Chothia | ADYYYVDEYWDY |
| 1443 | SRP2900-B04 | CDR-H3 | Chothia | ADYYYVDEYWDY |
| 1444 | SRP2900-B05 | CDR-H3 | Chothia | ADYYGVDEFLDY |
| 1445 | SRP2900-B06 | CDR-H3 | Chothia | ADYHGVDEYWDY |
| 1446 | SRP2900-B07 | CDR-H3 | Chothia | ADYHGVDEYWDY |
| 1447 | SRP2900-B08 | CDR-H3 | Chothia | ADYYYVDEYFDY |
| 1448 | SRP2900-B09 | CDR-H3 | Chothia | ADYYYVDEYWDY |
| 1449 | SRP2900-B10 | CDR-H3 | Chothia | ADYYYVDEYWDY |
| 1450 | SRP2900-B11 | CDR-H3 | Chothia | ADYHGVDEYWDY |
| 1451 | SRP2900-C01 | CDR-H3 | Chothia | ADYYYVDEYWDY |
| 1452 | SRP2900-C02 | CDR-H3 | Chothia | ADYYYVDEYWDY |
| 1453 | SRP2900-C03 | CDR-H3 | Chothia | ADYYYVDEYWDY |
| 1454 | SRP2900-C04 | CDR-H3 | Chothia | ADYYYVDEYWDY |
| 1455 | SRP2900-C05 | CDR-H3 | Chothia | ADYHGVDEYWDY |
| 1456 | SRP2900-C06 | CDR-H3 | Chothia | ADYYYVDEYWDY |
| 1457 | SRP2900-C07 | CDR-H3 | Chothia | ADYYYVDEYFDY |

TABLE 32-continued

Sequences.

| SEQ ID NO: | Molecule | Region | Scheme | Sequence |
|---|---|---|---|---|
| 1458 | SRP2900-C08 | CDR-H3 | Chothia | ADYYYVDEYWDY |
| 1459 | SRP2900-C09 | CDR-H3 | Chothia | DDQSFSSPFDY |
| 1460 | SRP2900-C10 | CDR-H3 | Chothia | DYGSYLVSLDY |
| 1461 | SRP2900-C11 | CDR-H3 | Chothia | DYGSWRIRLDY |
| 1462 | SRP2900-D01 | CDR-H3 | Chothia | DYGSLQVFLDY |
| 1463 | SRP2900-D02 | CDR-H3 | Chothia | DYGSLQVFIDH |
| 1464 | SRP2900-D03 | CDR-H3 | Chothia | DYGSLQVQLDY |
| 1465 | SRP2900-D04 | CDR-H3 | Chothia | DYGSLQVQLDY |
| 1466 | SRP2900-D05 | CDR-H3 | Chothia | DYGSLEVSLDY |
| 1467 | SRP2900-D06 | CDR-H3 | Chothia | DYGSLTINLDY |
| 1468 | SRP2900-D07 | CDR-H3 | Chothia | DYGSLEVSLDY |
| 1469 | SRP2900-D08 | CDR-H3 | Chothia | DYGSLEVSLDY |
| 1470 | SRP2900-D09 | CDR-H3 | Chothia | DYGSIQVFLDY |
| 1471 | SRP2900-D10 | CDR-H3 | Chothia | DYGSLQVFIDY |
| 1472 | SRP2900-D11 | CDR-H3 | Chothia | DYGSLQVQLDY |
| 1473 | SRP2900-E01 | CDR-H3 | Chothia | DYGSLQVFIDY |
| 1474 | SRP2900-E02 | CDR-H3 | Chothia | DPQSFYIAFDY |
| 1475 | SRP2900-E03 | CDR-H3 | Chothia | DYGSLEVSLDY |
| 1476 | SRP2900-E04 | CDR-H3 | Chothia | ADYYYVDEYLDY |
| 1477 | SRP2900-E05 | CDR-H3 | Chothia | DYGSVRVFLDY |
| 1478 | SRP2900-E06 | CDR-H3 | Chothia | DDQSVSSPFDY |
| 1479 | SRP2900-E07 | CDR-H3 | Chothia | DYGSLRVSLDY |
| 1480 | SRP2900-E08 | CDR-H3 | Chothia | DYGSLQVFIDY |
| 1481 | SRP2900-E09 | CDR-H3 | Chothia | DYGSFRVQLDY |
| 1482 | SRP2900-E10 | CDR-H3 | Chothia | DYGSLHVQLDY |
| 1483 | SRP2900-E11 | CDR-H3 | Chothia | DVQSVSGEFDY |
| 1484 | SRP2900-F01 | CDR-H3 | Chothia | DYGSLQVFIDY |
| 1485 | SRP2900-F02 | CDR-H3 | Chothia | DDQSVSSPFDY |
| 1486 | SRP2900-F03 | CDR-H3 | Chothia | DYGSLQVFIDY |
| 1487 | SRP2900-F04 | CDR-H3 | Chothia | DYGSLQVFIDY |
| 1488 | SRP2900-F05 | CDR-H3 | Chothia | DDQSLSSPFDY |
| 1489 | SRP2900-F06 | CDR-H3 | Chothia | DPQSISSPFDY |
| 1490 | SRP2900-F07 | CDR-H3 | Chothia | DPQSVSSPFDY |
| 1491 | SRP2900-F08 | CDR-H3 | Chothia | DDQSLSSPFDY |
| 1492 | SRP2900-F09 | CDR-H3 | Chothia | DDQSISSPLDY |
| 1493 | SRP2900-F10 | CDR-H3 | Chothia | DPQSLFYPFDY |
| 1494 | SRP2900-F11 | CDR-H3 | Chothia | DDQSLSSPFDY |

TABLE 32-continued

| Sequences. | | | | |
|---|---|---|---|---|
| SEQ ID NO: | Molecule | Region | Scheme | Sequence |
| 1495 | SRP2900-G01 | CDR-H3 | Chothia | DIQSVSGEFDY |
| 1496 | SRP2900-G02 | CDR-H3 | Chothia | DDQSVSSPFEY |
| 1497 | SRP2900-G03 | CDR-H3 | Chothia | DPQSLSSPFDY |
| 1498 | SRP2900-G04 | CDR-H3 | Chothia | DPQSLSSPFDY |
| 1499 | SRP2900-G05 | CDR-H3 | Chothia | DDQSLSSPFDY |
| 1500 | SRP2900-G06 | CDR-H3 | Chothia | DDQSLSSPFDY |
| 1501 | SRP2900-G07 | CDR-H3 | Chothia | DPQSLTSPFDY |
| 1502 | SRP2900-G08 | CDR-H3 | Chothia | DIQSVSGEFDY |
| 1503 | SRP2900-G09 | CDR-H3 | Chothia | DPQSLTSPFDY |
| 1504 | SRP2900-G10 | CDR-H3 | Chothia | DIQSVSGEFDY |
| 1505 | SRP2900-G11 | CDR-H3 | Chothia | DIQSVSGEFDY |
| 1506 | SRP2900-H01 | CDR-H3 | Chothia | DPQSVGSEFDY |
| 1507 | SRP2900-H02 | CDR-H3 | Chothia | DIQSVSGEFDY |
| 1508 | SRP2900-H03 | CDR-H3 | Chothia | DPQSLSSPFDY |
| 1509 | SRP2900-H04 | CDR-H3 | Chothia | DIQSVSGEFDY |
| 1510 | SRP2900-H05 | CDR-H3 | Chothia | DIQSVSGEFDY |
| 1511 | SRP2900-H06 | CDR-H3 | Chothia | DDQSFSSPFDY |
| 1512 | SRP2900-H07 | CDR-H3 | Chothia | DPQSFSSPFDY |
| 1513 | SRP2900-H08 | CDR-H3 | Chothia | DPQSLSSPFDY |
| 1514 | SRP2900-H09 | CDR-H3 | Chothia | DDQSISSPLDY |
| 1515 | SRP2900-H10 | CDR-H3 | Chothia | DIQSVSGEFDY |
| 1516 | SRP2900-H11 | CDR-H3 | Chothia | DPQTLTSPFDY |
| 1518 | SRP2842-B01 | CDR-H3 | Chothia | GLYDGTGNI |
| 1524 | SRP2842-G04 | CDR-H3 | Chothia | DFYGWNSGALDI |
| 1529 | SRP2901-B05_ 2842-G04_HC2 | CDR-H3 | Chothia | DFYGWNSGALDI |
| 1535 | SRP2901-D03_ 2842-B01_HC-3 | CDR-H3 | Chothia | GLYDGTGNI |
| 1537 | SRP2901-E03_ 2842-B01_HC-3 | CDR-H3 | Chothia | GLYDGTGNI |
| 1538 | SRP2901-F01_ 2842-B01_HC-1 | CDR-H3 | Chothia | GLYDGTGNI |
| 1730 | SRP2799-A05 | CDR-H3 | Kabat | SDYYYVDEYMDY |
| 1739 | SRP2799-B03 | CDR-H3 | Kabat | GYGSWPDYLDY |
| 1742 | SRP2799-B06 | CDR-H3 | Kabat | DDQSVSSPFDY |
| 1754 | SRP2900-A01 | CDR-H3 | Kabat | ADYYYVDEYFDY |
| 1755 | SRP2900-A02 | CDR-H3 | Kabat | DDQSLSSPFDY |
| 1756 | SRP2900-A03 | CDR-H3 | Kabat | ADYFYVDEYLDY |
| 1757 | SRP2900-A04 | CDR-H3 | Kabat | ADYFYIDEYWDY |
| 1758 | SRP2900-A05 | CDR-H3 | Kabat | ADYYYVDEYWDY |

TABLE 32-continued

| Sequences. | | | | |
|---|---|---|---|---|
| SEQ ID NO: | Molecule | Region | Scheme | Sequence |
| 1759 | SRP2900-A06 | CDR-H3 | Kabat | ADYYYVDEYWDY |
| 1760 | SRP2900-A07 | CDR-H3 | Kabat | SDYYYVDEFFDY |
| 1761 | SRP2900-A08 | CDR-H3 | Kabat | ADYYYVDEYWDY |
| 1762 | SRP2900-A09 | CDR-H3 | Kabat | ADYYYVDEYWDY |
| 1763 | SRP2900-A10 | CDR-H3 | Kabat | ADYYYVDEYLDY |
| 1764 | SRP2900-A11 | CDR-H3 | Kabat | DDQSFTSPFDY |
| 1765 | SRP2900-B01 | CDR-H3 | Kabat | ADYYYVDEYLDY |
| 1766 | SRP2900-B02 | CDR-H3 | Kabat | ADYYYVDEYWDY |
| 1767 | SRP2900-B03 | CDR-H3 | Kabat | ADYYYVDEYWDY |
| 1768 | SRP2900-B04 | CDR-H3 | Kabat | ADYYYVDEYWDY |
| 1769 | SRP2900-B05 | CDR-H3 | Kabat | ADYYGVDEFLDY |
| 1770 | SRP2900-B06 | CDR-H3 | Kabat | ADYHGVDEYWDY |
| 1771 | SRP2900-B07 | CDR-H3 | Kabat | ADYHGVDEYWDY |
| 1772 | SRP2900-B08 | CDR-H3 | Kabat | ADYYYVDEYFDY |
| 1773 | SRP2900-B09 | CDR-H3 | Kabat | ADYYYVDEYWDY |
| 1774 | SRP2900-B10 | CDR-H3 | Kabat | ADYYYVDEYWDY |
| 1775 | SRP2900-B11 | CDR-H3 | Kabat | ADYHGVDEYWDY |
| 1776 | SRP2900-C01 | CDR-H3 | Kabat | ADYYYVDEYWDY |
| 1777 | SRP2900-C02 | CDR-H3 | Kabat | ADYYYVDEYWDY |
| 1778 | SRP2900-C03 | CDR-H3 | Kabat | ADYYYVDEYWDY |
| 1779 | SRP2900-C04 | CDR-H3 | Kabat | ADYYYVDEYWDY |
| 1780 | SRP2900-C05 | CDR-H3 | Kabat | ADYHGVDEYWDY |
| 1781 | SRP2900-C06 | CDR-H3 | Kabat | ADYYYVDEYWDY |
| 1782 | SRP2900-C07 | CDR-H3 | Kabat | ADYYYVDEYFDY |
| 1783 | SRP2900-C08 | CDR-H3 | Kabat | ADYYYVDEYWDY |
| 1784 | SRP2900-C09 | CDR-H3 | Kabat | DDQSFSSPFDY |
| 1785 | SRP2900-C10 | CDR-H3 | Kabat | DYGSYLVSLDY |
| 1786 | SRP2900-C11 | CDR-H3 | Kabat | DYGSWRIRLDY |
| 1787 | SRP2900-D01 | CDR-H3 | Kabat | DYGSLQVFLDY |
| 1788 | SRP2900-D02 | CDR-H3 | Kabat | DYGSLQVFIDH |
| 1789 | SRP2900-D03 | CDR-H3 | Kabat | DYGSLQVQLDY |
| 1790 | SRP2900-D04 | CDR-H3 | Kabat | DYGSLQVQLDY |
| 1791 | SRP2900-D05 | CDR-H3 | Kabat | DYGSLEVSLDY |
| 1792 | SRP2900-D06 | CDR-H3 | Kabat | DYGSLTINLDY |
| 1793 | SRP2900-D07 | CDR-H3 | Kabat | DYGSLEVSLDY |
| 1794 | SRP2900-D08 | CDR-H3 | Kabat | DYGSLEVSLDY |
| 1795 | SRP2900-D09 | CDR-H3 | Kabat | DYGSIQVFLDY |

TABLE 32-continued

| Sequences. | | | | |
|---|---|---|---|---|
| SEQ ID NO: | Molecule | Region | Scheme | Sequence |
| 1796 | SRP2900-D10 | CDR-H3 | Kabat | DYGSLQVFIDY |
| 1797 | SRP2900-D11 | CDR-H3 | Kabat | DYGSLQVQLDY |
| 1798 | SRP2900-E01 | CDR-H3 | Kabat | DYGSLQVFIDY |
| 1799 | SRP2900-E02 | CDR-H3 | Kabat | DPQSFYIAFDY |
| 1800 | SRP2900-E03 | CDR-H3 | Kabat | DYGSLEVSLDY |
| 1801 | SRP2900-E04 | CDR-H3 | Kabat | ADYYYVDEYLDY |
| 1802 | SRP2900-E05 | CDR-H3 | Kabat | DYGSVRVFLDY |
| 1803 | SRP2900-E06 | CDR-H3 | Kabat | DDQSVSSPFDY |
| 1804 | SRP2900-E07 | CDR-H3 | Kabat | DYGSLRVSLDY |
| 1805 | SRP2900-E08 | CDR-H3 | Kabat | DYGSLQVFIDY |
| 1806 | SRP2900-E09 | CDR-H3 | Kabat | DYGSFRVQLDY |
| 1807 | SRP2900-E10 | CDR-H3 | Kabat | DYGSLHVQLDY |
| 1808 | SRP2900-E11 | CDR-H3 | Kabat | DVQSVSGEFDY |
| 1809 | SRP2900-F01 | CDR-H3 | Kabat | DYGSLQVFIDY |
| 1810 | SRP2900-F02 | CDR-H3 | Kabat | DDQSVSSPFDY |
| 1811 | SRP2900-F03 | CDR-H3 | Kabat | DYGSLQVFIDY |
| 1812 | SRP2900-F04 | CDR-H3 | Kabat | DYGSLQVFIDY |
| 1813 | SRP2900-F05 | CDR-H3 | Kabat | DDQSLSSPFDY |
| 1814 | SRP2900-F06 | CDR-H3 | Kabat | DPQSISSPFDY |
| 1815 | SRP2900-F07 | CDR-H3 | Kabat | DPQSVSSPFDY |
| 1816 | SRP2900-F08 | CDR-H3 | Kabat | DDQSLSSPFDY |
| 1817 | SRP2900-F09 | CDR-H3 | Kabat | DDQSISSPLDY |
| 1818 | SRP2900-F10 | CDR-H3 | Kabat | DPQSLFYPFDY |
| 1819 | SRP2900-F11 | CDR-H3 | Kabat | DDQSLSSPFDY |
| 1820 | SRP2900-G01 | CDR-H3 | Kabat | DIQSVSGEFDY |
| 1821 | SRP2900-G02 | CDR-H3 | Kabat | DDQSVSSPFEY |
| 1822 | SRP2900-G03 | CDR-H3 | Kabat | DPQSLSSPFDY |
| 1823 | SRP2900-G04 | CDR-H3 | Kabat | DPQSLSSPFDY |
| 1824 | SRP2900-G05 | CDR-H3 | Kabat | DDQSLSSPFDY |
| 1825 | SRP2900-G06 | CDR-H3 | Kabat | DDQSLSSPFDY |
| 1826 | SRP2900-G07 | CDR-H3 | Kabat | DPQSLTSPFDY |
| 1827 | SRP2900-G08 | CDR-H3 | Kabat | DIQSVSGEFDY |
| 1828 | SRP2900-G09 | CDR-H3 | Kabat | DPQSLTSPFDY |
| 1829 | SRP2900-G10 | CDR-H3 | Kabat | DIQSVSGEFDY |
| 1830 | SRP2900-G11 | CDR-H3 | Kabat | DIQSVSGEFDY |
| 1831 | SRP2900-H01 | CDR-H3 | Kabat | DPQSVGSEFDY |
| 1832 | SRP2900-H02 | CDR-H3 | Kabat | DIQSVSGEFDY |
| 1833 | SRP2900-H03 | CDR-H3 | Kabat | DPQSLSSPFDY |

TABLE 32-continued

| Sequences. | | | | |
|---|---|---|---|---|
| SEQ ID NO: | Molecule | Region | Scheme | Sequence |
| 1834 | SRP2900-H04 | CDR-H3 | Kabat | DIQSVSGEFDY |
| 1835 | SRP2900-H05 | CDR-H3 | Kabat | DIQSVSGEFDY |
| 1836 | SRP2900-H06 | CDR-H3 | Kabat | DDQSFSSPFDY |
| 1837 | SRP2900-H07 | CDR-H3 | Kabat | DPQSFSSPFDY |
| 1838 | SRP2900-H08 | CDR-H3 | Kabat | DPQSLSSPFDY |
| 1839 | SRP2900-H09 | CDR-H3 | Kabat | DDQSISSPLDY |
| 1840 | SRP2900-H10 | CDR-H3 | Kabat | DIQSVSGEFDY |
| 1841 | SRP2900-H11 | CDR-H3 | Kabat | DPQTLTSPFDY |
| 1843 | SRP2842-B01 | CDR-H3 | Kabat | GLYDGTGNI |
| 1849 | SRP2842-G04 | CDR-H3 | Kabat | DFYG |
| 1854 | SRP2901-B05_ 2842-G04_HC2 | CDR-H3 | Kabat | DFYGWNSGALDI |
| 1860 | SRP2901-D03_ 2842-B01_HC-3 | CDR-H3 | Kabat | GLYDGTGNI |
| 1862 | SRP2901-E03_ 2842-B01_HC-3 | CDR-H3 | Kabat | GLYDGTGNI |
| 1863 | SRP2901-F01_ 2842-B01_HC-1 | CDR-H3 | Kabat | GLYDGTGNI |
| 1954 | SRP2842-B01 | CDR-L1 | Chothia | QASQSVYGNNWLS |
| 1960 | SRP2842-G04 | CDR-L1 | Chothia | QASQSVYSNKYLS |
| 1965 | SRP2901-B05_ 2842-G04_LC2 | CDR-L1 | Chothia | RASQSVYSNKYLS |
| 1971 | SRP2901-D03_ 2842-B01_LC3 | CDR-L1 | Chothia | RASQSVYGNNWLS |
| 1973 | SRP2901-E03_ 2842-B01_LC3 | CDR-L1 | Chothia | RASQSVYGNNWLS |
| 1974 | SRP2901-F01_ 2842-B01_LC1 | CDR-L1 | Chothia | QASQSVYGNNWLS |
| 2064 | trastuzumab | CDR-L1 | Chothia | RASQDVNTAVA |
| 2066 | SRP2842-B01 | CDR-L1 | Kabat | QASQSVYGNNWLS |
| 2072 | SRP2842-G04 | CDR-L1 | Kabat | QASQSVYSNKYLS |
| 2077 | SRP2901-B05_ 2842-G04_LC2 | CDR-L1 | Kabat | RASQSVYSNKYLS |
| 2083 | SRP2901-D03_ 2842-B01_LC3 | CDR-L1 | Kabat | RASQSVYGNNWLS |
| 2085 | SRP2901-E03_ 2842-B01_LC3 | CDR-L1 | Kabat | RASQSVYGNNWLS |
| 2086 | SRP2901-F01_ 2842-B01_LC1 | CDR-L1 | Kabat | QASQSVYGNNWLS |
| 2176 | trastuzumab | CDR-L1 | Kabat | RASQDVNTAVA |
| 2178 | SRP2842-B01 | CDR-L2 | Chothia | GASKLAS |
| 2184 | SRP2842-G04 | CDR-L2 | Chothia | KASTLAS |
| 2189 | SRP2901-B05_ 2842-G04_LC2 | CDR-L2 | Chothia | KASTLAS |

TABLE 32-continued

| Sequences. | | | | |
|---|---|---|---|---|
| SEQ ID NO: | Molecule | Region | Scheme | Sequence |
| 2195 | SRP2901-D03_ 2842-B01_LC3 | CDR-L2 | Chothia | GASKLAS |
| 2197 | SRP2901-E03_ 2842-B01_LC3 | CDR-L2 | Chothia | GASKLAT |
| 2198 | SRP2901-F01_ 2842-B01_LC1 | CDR-L2 | Chothia | GASKLAS |
| 2288 | trastuzumab | CDR-L2 | Chothia | SASFLYS |
| 2290 | SRP2842-B01 | CDR-L2 | Kabat | GASKLAS |
| 2296 | SRP2842-G04 | CDR-L2 | Kabat | KASTLAS |
| 2301 | SRP2901-B05_ 2842-G04_LC2 | CDR-L2 | Kabat | KASTLAS |
| 2307 | SRP2901-D03_ 2842-B01_LC3 | CDR-L2 | Kabat | GASKLAS |
| 2309 | SRP2901-E03_ 2842-B01_LC3 | CDR-L2 | Kabat | GASKLAT |
| 2310 | SRP2901-F01_ 2842-B01_LC1 | CDR-L2 | Kabat | GASKLAS |
| 2400 | trastuzumab | CDR-L2 | Kabat | SASFLYS |
| 2402 | SRP2842-B01 | CDR-L3 | Chothia | QGTYYSGDWYFA |
| 2408 | SRP2842-G04 | CDR-L3 | Chothia | AAAYSDDSDTA |
| 2413 | SRP2901-B05_ 2842-G04_LC2 | CDR-L3 | Chothia | AAAYSDDSDTA |
| 2419 | SRP2901-D03_ 2842-B01_LC3 | CDR-L3 | Chothia | QGTYYSGDWYFA |
| 2421 | SRP2901-E03_ 2842-B01_LC3 | CDR-L3 | Chothia | QGTYYSGDWYFA |
| 2422 | SRP2901-F01_ 2842-B01_LC1 | CDR-L3 | Chothia | QGTYYSGDWYFA |
| 2512 | trastuzumab | CDR-L3 | Chothia | QQHYTTPPT |
| 2514 | SRP2842-B01 | CDR-L3 | Kabat | QGTYYSGDWYFA |
| 2520 | SRP2842-G04 | CDR-L3 | Kabat | AAAYSDDSDTA |
| 2525 | SRP2901-B05_ 2842-G04_LC2 | CDR-L3 | Kabat | AAAYSDDSDTA |
| 2531 | SRP2901-D03_ 2842-B01_LC3 | CDR-L3 | Kabat | QGTYYSGDWYFA |
| 2533 | SRP2901-E03_ 2842-B01_LC3 | CDR-L3 | Kabat | QGTYYSGDWYFA |
| 2534 | SRP2901-F01_ 2842-B01_LC1 | CDR-L3 | Kabat | QGTYYSGDWYFA |
| 2624 | Trastuzumab | CDR-L3 | Kabat | QQHYTTPPT |
| 2727 | SRP2799-A05 | $V_H$ | | MAEVQLVESGGGLVQPGGSLRLSCAA SGFNISSYWIHWVRQAPGKGLEWVGY IDPYSGSTYYADSVKGRFTISADTSK NTAYLQMNSLRAEDTAVYYCARSDYY YVDEYMDYWGQGTLVTVSS |
| 2736 | SRP2799-B03 | $V_H$ | | MAEVQLVESGGGLVQPGGSLRLSCAA SGFNISDYWIHWVRQAPGKGLEWVGF IDPYNGYTNYADSVKGRFTISADTSK |

TABLE 32-continued

| SEQ ID NO: | Molecule | Region | Scheme | Sequence |
|---|---|---|---|---|
| | | | | NTAYLQMNSLRAEDTAVYYCARGYGS WPDYLDYWGQGTLVTVSS |
| 2739 | SRP2799-B06 | $V_H$ | | MAEVQLVESGGGLVQPGGSLRLSCAA SGFNISDYNIHWVRQAPGKGLEWVGY IDPSNGYTYYADSVKGRFTISADTSK NTAYLQMNSLRAEDTAVYYCARDDQS VSSPFDYWGQGTLVTVSS |
| 2751 | SRP2900-A01 | $V_H$ | | MEVQLVESGGGLVQPGGSLRLSCAAS GFTISSYWIHWVRQAPGKGLKWVGYI DPYNGATYYADSVKGRFTISADTSKN TAYLQMNSLRAEDTAVYYCARADYYY VDEYFDYWGQGTLVTVSS |
| 2752 | SRP2900-A02 | $V_H$ | | MEVQLVESGGGLVQPGGSLRLSCAAS GFTISGYIIHWVRQAPGKGLEWVGYI DPSNGYTYYADSVKGRFTISADTSKN TAYLQMNSLRAEDTAVYYCARDDQSL SSPFDYWGQGTLVTVSS |
| 2753 | SRP2900-A03 | $V_H$ | | MEVQLVESGGGLVQPGGSLRLSCAAS GFTIPSYWIHWVRQAPGKGLEWVGYI DPANGATYYADSVKGRFTISADTSKN TAYLQMNSLRAEDTAVYYCARADYFY VDEYLDYWGQGTLVTVSS |
| 2754 | SRP2900-A04 | $V_H$ | | MEVQLVESGGGLVQPGGSLRLSCAAS GFTISGYWIHWVRQAPGKGLEWVGYI DPYNGATYYADSVKGRFTISADTSKN AAYLQMNSLRAEDTAVYYCARADYFY IDEYWDYWGQGTLVTVSS |
| 2755 | SRP2900-A05 | $V_H$ | | MEVQLVESGGGLVQPGGSLRLSCAAS GFTIPDYWIHWVRQAPGKGLEWVGFI DPYNGYTNYADPVKSRFTISADTSKN TAYLQMNSLRAEDTAVYYCARADYYY VDEYWDYWGQGTLVTVSS |
| 2756 | SRP2900-A06 | $V_H$ | | MEVQLVESGGGLVQPGGSLRLSCAAS GFTISSYWIHWVRQAPGKGLEWVGYI DPFNGATYYADSVKGRFTISADTSKN TAYLQMNSLRAEDTAVYYCARADYYY VDEYWDYWGQGTLVTVSS |
| 2757 | SRP2900-A07 | $V_H$ | | MEVQLVESGGGLVQPGGSLRLSCAAS GFTISSYWIHWVRQAPGKGLEWVGYI DPYNGATYYADSVKGRFTISADTSKN TAYLQMNSLRAEDTAVYYCARSDYYY VDEFFDYWGQGTLVTVSS |
| 2758 | SRP2900-A08 | $V_H$ | | MEVQLVESGGGLVQPGGSLRLSCAAS GFTLIGYWIHWVRQAPGKGLEWVGYI DPYNGATYYADSVKGRFTISADTSKN TAYLQMNSLRAEDTAVYYCARADYYY VDEYWDYWGQGTLVTVSS |
| 2759 | SRP2900-A09 | $V_H$ | | MEVQLVESGGGLVQPGGSLRLSCAAS GFTIADYWIHWVRQAPGKGLEWVGYI DPYNGATYYADSVKGRFTISADTSKN TAYLQMNSLRAEDTAVYYCARADYYY VDEYWDYWGQGTLVTVSS |
| 2760 | SRP2900-A10 | $V_H$ | | MEVQLVESGGGLVQPGGALRLSCAAS GFTISSYWIHWVRQAPGKGLEWVGYI DPYNGATYYADSVKGRFTISADTSKN TAYLQMNSLRAEDTAVYYCARADYYY VDEYLDYWGQGTLVTVSS |
| 2761 | SRP2900-A11 | $V_H$ | | MEVQLVESGGGLVQPGGSLRLSCAAS GFTITDYVIHWVRQAPGKGLEWVGYI DPSNGYTYYADSVKGRFTISADTSKN TAYLQMNSLRAEDTAVYYCARDDQSF TSPFDYWGQGTLVTVSS |

TABLE 32-continued

| Sequences. | | | | |
|---|---|---|---|---|
| SEQ ID NO: | Molecule | Region | Scheme | Sequence |
| 2762 | SRP2900-B01 | $V_H$ | | MEVQLVESGGGLVQPGGSLRLSCAAS GFTISGYWIHWVRQAPGKGLEWVGYI DPYNGATYYADSVKGRFTISADTSKN TAYLQMNSLRAEDTAVYYCARADYYY VDEYLDYWGQGTLVTVSS |
| 2763 | SRP2900-B02 | $V_H$ | | MEVQLVESGGGSVQPGGSLRLSCAAS GFTISDYWIHWVRQAPGKGLEWVGYI DPYNGATYYADSVKGRFTISADTSKN TAYLQMNSLRAEDTAVYYCARADYYY VDEYWDYWGQGTLVTVSS |
| 2764 | SRP2900-B03 | $V_H$ | | MEVQLVESGGGLVQPGGSLRLSCSAS GFTIADYWIHWVRQAPGKGLEWVGYI DPYNGATYYADSVKGRFTISADTSKN TAYLQMNSLRAEDTAVYYCARADYYY VDEYWDYWGQGTLVTVSS |
| 2765 | SRP2900-B04 | $V_H$ | | MEVQLVESGGGLVQPGGSLRLSCAAS GFTISEYWIHWVRQAPGKGLEWVGFI DPYNGYTGYADSVRGRFTISADTSKN TAYLQMNSLRAEDTAVYYCARADYYY VDEYWDYWGQGTLVTVSS |
| 2766 | SRP2900-B05 | $V_H$ | | MEVQLVESGGGLVQPGGSLRLSCAAS GFTISGYWIHWVRQAPGKGLEWVGYI DPYNGATYYADSVKGRFTISADTSKN TAYLQMNSLRAEDTAVYYCARADYYG VDEFLDYWGQGTLVTVSS |
| 2767 | SRP2900-B06 | $V_H$ | | MEVQLVESGGGLVQPGGSLRLSCAAS GFTIPSYWIHWVRQAPGKGLEWVGYI DPYNGATYYADSVKGRFTISADTSKN TAYLQMNSLRAEDTAVYYCARADYHG VDEYWDYWGQGTLVTVSS |
| 2768 | SRP2900-B07 | $V_H$ | | MEVQLVESGGGLVQPGGSLRLSCAAS GFTIADYWIHWVRQAPGKGLEWVGFI DPYNGYTGYADSVKGRFTISADNSKN TAYLQMNSLRAEDTAVYYCARADYHG VDEYWDYWGQGTLVTVSS |
| 2769 | SRP2900-B08 | $V_H$ | | MEVQLVESGGGLVQPGGSLRLSCAAS GFTIPSYWIHWVRQAPGKGLEWVGYI DPYNGYTYYADSVKGRFTISADTSKN TAYLQMNSLRAEDTAVYYCARADYYY VDEYFDYWGQGTLVTVSS |
| 2770 | SRP2900-B09 | $V_H$ | | MEVQLVESGGGLVQPGGSLRLSCAAS GFTISQYWIHWVRQAPGKGLEWVGFI DPYNGYTNYADSVKGRFTISADTSEN TAYLQMNSLRAEDTAVYYCARADYYY VDEYWDYWGQGTLVTVSS |
| 2771 | SRP2900-B10 | $V_H$ | | MEVQLVESGGGLVQPGGSLRLSCAAS GFTIPAYWIHWVRQAPGKGLEWVGYI DPYNGSTYYADSVKGRFTISADTSKN TAYLQMNSLRAEDTAVYYCARADYYY VDEYWDYWGQGTLVTVSS |
| 2772 | SRP2900-B11 | $V_H$ | | MEVQLVESGGGLVQPGGSLRLSCAAS GFTIPAYWIHWVRQAPGKGLEWVGYI DPSNGYTYYADSVKGRFTISADASKN TAYLQMNSLRAEDTAAYYCARADYHG VDEYWDYWGQGTLVTVSS |
| 2773 | SRP2900-C01 | $V_H$ | | MEVQLVESGGGLVQPGGSLRLSCAAS GFTIGSYWIHWVRQAPGKGLEWVGYI DPSNGYTYYADSVKGRFTISADTSKN TAYLQMNSLRAEDTAVYYCARADYYY VDEYWDYWGQGTLVTVSS |
| 2774 | SRP2900-C02 | $V_H$ | | MEVQLVESGGGLVQPGGSLRLSCAAS GFTISSYWIHWVRQAPGKGLEWVGYI |

TABLE 32-continued

| Sequences. | | | | |
|---|---|---|---|---|
| SEQ ID NO: | Molecule | Region | Scheme | Sequence |
| | | | | DPYNGATYYADSVKGRFTISADTSKN TAYLQMNSLRAEDTAVYYCARADYYY VDEYWDYWGQGTLVTVSS |
| 2775 | SRP2900-C03 | $V_H$ | | MEVQLVESGGGLVQPGGSLRLSCAAS GFTISGYWIHWVRQAPGKGLEWVGYI DPYNGATYYADSVKGRFTISADTSKN TAYLQMNSLRAEDTAVYYCARADYYY VDEYWDYWGQGTLVTVSS |
| 2776 | SRP2900-C04 | $V_H$ | | MEVQLVESGGGLVQPGGSLRLSCAAS GFTIVSYWIHWVRQAPGKGLEWVGYI DPYNGATYYADSVKGRFTISADTSKN TAYLQMNSLRAEDTAVYYCARADYYY VDEYWDYWGQGTLVTVSS |
| 2777 | SRP2900-C05 | $V_H$ | | MEVQLVESGGGLVQPGGSLRLSCAAS GFTISGYWIHWVRQAPGKGLEWVGYI DPYNGATYYADSVKGRFTISADTPKN TAYLQMNSLRAEDTAVYYCARADYHG VDEYWDYWGQGTLVTVSS |
| 2778 | SRP2900-C06 | $V_H$ | | MEVQLVESGGGLVQPGGSLRLSCAAS GFTISGYWIHWVRQAPGKGLEWVGYI DPYNGATFYADSVKGRFTISADTSKN TAYLQMNSLRAEDTAVYYCARADYYY VDEYWDYWGQGTLVTVSS |
| 2779 | SRP2900-C07 | $V_H$ | | MEVQLVESGGGLVQPGGSLRLSCAAS GFTISGYWIHWVRQAPGKGLEWVGYI DPYNGATYYADSVKGRFTISADTSKN TAYLQMNSLRAEDTAVYYCARADYYY VDEYFDYWGQGTLVTVSS |
| 2780 | SRP2900-C08 | $V_H$ | | MEVQLVESGGGLVQPGGSLRLSCAAS GFTIPAYWIHWVRQAPGKGLEWVGYI DPYNGSTYHADSVKGRFTISADTSKN TAYLQMNSLRAEDTAVYYCARADYYY VDEYWDYWGQGTLVTVSS |
| 2781 | SRP2900-C09 | $V_H$ | | MEVQLVESGGGLVQPGGSLRLSCAAS GFTISDYIIHWVRQAPGKGLEWVGYI DPSNGYTYHADSVKGRFTISADTSKN TAYLQMNSLRAEDTAVYYCARDDQSF SSPFDYWGQGTLVTVSS |
| 2782 | SRP2900-C10 | $V_H$ | | MEVQLVESGGGLVQPGGSLRLSCAAS GFTISDYWIHWVRQAPGKGLEWVGYI DPYNGYTYYADSVNGRFTISADTSKN TAYLQMNSLRAEDTAVYYCARDYGSY LVSLDYWGQGTLVTVSS |
| 2783 | SRP2900-C11 | $V_H$ | | MEVQLVESGGGLVQPGGSLRLSCAAS GFTISQYWIHWVRQAPGKGLEWVGYI DPYNGYTYYADSVKGRFTISADTSKN TAYLQMNSLRAEDTAVYYCARDYGSW RIRLDYWGQGTLVTVSS |
| 2784 | SRP2900-D01 | $V_H$ | | MEVQLVESGGGLVQPGGSLRLSCAAS GFTIHEYWIHWVRQAPGKGLEWVGYI DPANGFTYYADSVKGRFTISADTSKN TAYLQMNSLRAEDTAVYYCARDYGSL QVFLDYWGQGTLVTVSS |
| 2785 | SRP2900-D02 | $V_H$ | | MEVQLVESGGGLVQPGGSLRLSCAAS GFTISDYWIHWVRQAPGKGLEWVGYI DPYNGYTYYADSVKGRFTISADTSKN TAYLQMNSLRAEDTAVYYCARDYGSL QVFIDHWGQGTLVTVSS |
| 2786 | SRP2900-D03 | $V_H$ | | MEVQLVESGGGLVQPGGSLRLSCAAS GFTISQYWIHWVRQAPGKGLEWVGYI DPYNGYTYYADSVKGRFTISADTSKN TAYLQMNSLRAEDTAVYYCARDYGSL QVQLDYWGQGTLVTVSS |

TABLE 32-continued

| Sequences. | | | | |
|---|---|---|---|---|
| SEQ ID NO: | Molecule | Region | Scheme | Sequence |
| 2787 | SRP2900-D04 | $V_H$ | | MEVQLVESGGGLVQPGGSLRLSCAAS GFTISDYWIHWVRQAPGKGLEWVGFI DPYNGYTYHADSVEGRFTISADTSKN TAYLQMNSLRAEDTAVYYCARDYGSL QVQLDYWGQGTLVTVSS |
| 2788 | SRP2900-D05 | $V_H$ | | MEVQLVESGGGLVQPGGSLRLSCAAS GFAIANYWIHWVRQAPGKGLEWVGYI DPYNGYTYYADSVKGRFTISADTSKN TAYLQMNSLRAEDTAVYYCARDYGSL EVSLDYWGQGTLVTVSS |
| 2789 | SRP2900-D06 | $V_H$ | | MEVQLVESGGGLVQPGGSLRLSCAAS GFTISDYWIHWVRQAPGKGLEWVGYI DPQNGWTYYADSVKGRFTISADTSKN TAYLQMNSLRAEDTAVYYCARDYGSL TINLDYWGQGTLVTVSS |
| 2790 | SRP2900-D07 | $V_H$ | | MEVQLVESGGGLVQPGGSLRLSCAAS GFTISDYWIHWVRQAPGKGLEWVGYI DPSNGYTYYADSVKGRFTISADTSRN TAYLQMNSLRAEDTAVYYCARDYGSL EVSLDYWGQGTLVTVSS |
| 2791 | SRP2900-D08 | $V_H$ | | MEVQLVESGGGLVQPGGSLRLSCAAS GFTISDYWIHWVRQAPGKGLEWVGYI DPYNGYTYYADSVKGRFTISADTSKN TAYLQMNSLRAEDTAVYYCARDYGSL EVSLDYWGQGTLVTVSS |
| 2792 | SRP2900-D09 | $V_H$ | | MEVQLVESGGGLVQPGGSLRLSCAAS GFTISGYWIHWVRQAPGKGLEWVGYI DPANGFTYYADSVKGRFTISADTSKN TAYLQMNSLRAEDTAVYYCARDYGSI QVFLDYWGQGTLVTVSS |
| 2793 | SRP2900-D10 | $V_H$ | | MEVQLVESGGGLVQPGGSLRLSCAAS GFTISDYWIHWVRQAPGKGLEWVGFI DPKNGYTYYADSVKGRFTISAGTSKN TAYLQMNSLRAEDTAVYYCARDYGSL QVFIDYWGQGTLVTVSS |
| 2794 | SRP2900-D11 | $V_H$ | | MEVQLVESGGGLVQPGGSLRLSCAAS GFTISDYWIHWVRQAPGKGLEWVGYI DPYNGYTYYADSVKGRFTISADTSKN TAYLQMNPLRAEDTAVYYCARDYGSL QVQLDYWGQGTLVTVSS |
| 2795 | SRP2900-E01 | $V_H$ | | MEVQLVESGGGLVQPGGSLRLSCAAS GFTISDYWIHWVRQAPGKGLEWVGYI DPSNGYTYYADSVKGRFTISADTSKN TAYLQMNSLRAEDTAVYYCARDYGSL QVFIDYWGQGTLVTVSS |
| 2796 | SRP2900-E02 | $V_H$ | | MEVQLVESGGGLVQPGGSLRLSCAAS GFTISDYVIHWVRQAPGKGLEWVGYI DPSNGYTYYADPVKGRFTISADTSKN TAYLQMNSLRAEDTAVYYCARDPQSF YIAFDYWGQGTLVTVSS |
| 2797 | SRP2900-E03 | $V_H$ | | MEVQLVESGGGLVQPGGSLRLSCAAS GFTISDYWIHWVRQAPGKGLEWVGYI DPQNGWTYYADSVKGRFTISADTSKN TAYLQMNSLRAEDTAVYYCARDYGSL EVSLDYWGQGTLVTVSS |
| 2798 | SRP2900-E04 | $V_H$ | | MEVQLVESGGGLVQPGGSLRLSCAAS GFTIPDYWIHWVRQAPGKGLEWVGYI DPYSGSTFYADSVKGRFTISADTSKN TAYLQMNSLRAEDTAVYYCARADYYY VDEYLDYWGQGTLVTVSS |
| 2799 | SRP2900-E05 | $V_H$ | | MEVQLVESGGGLVQPGGSLRLSCAAS GFTISGYWIHWVRQAPGKGLEWVGYI |

TABLE 32-continued

| Sequences. | | | | |
|---|---|---|---|---|
| SEQ ID NO: | Molecule | Region | Scheme | Sequence |
| | | | | DPANGFTYYADSVKGRFTISADTSKN TAYLQMNSLRAEDTAVYYCARDYGSV RVFLDYWGQGTLVTVSS |
| 2800 | SRP2900-E06 | $V_H$ | | MEVQLVESGGGLVQPGGSLRLSCAAS GFTISGYIIHWVRQAPGKGLEWVGYI DPSNGYTYHADSVKGRFTISADTSKN TAYLQMNSLRAEDTAVYYCARDDQSV SSPFDYWGQGTLVTVSS |
| 2801 | SRP2900-E07 | $V_H$ | | MEVQLVESGGGLVQPGGSLRLSCAAS GFTISQYWIHWVRQAPGKGLEWVGYI DPYNGYTYYADSVKGRFTISADTSKN TAYLQMNSLRAEDTAVYYCARDYGSL RVSLDYWGQGTLVTVSS |
| 2802 | SRP2900-E08 | $V_H$ | | MEVQLVESGGGLVQPGGSLRLSCAAS GFTITDYWIHWVRQAPGKGLEWVGYI DPYNGYTYYADSVKGRFTISADTSKN TAYLQMNSLRAEDTAVYYCARDYGSL QVFIDYWGQGTLVTVSS |
| 2803 | SRP2900-E09 | $V_H$ | | MEVQLVESGGGLVQPGGSLRLSCAAS GFTISQYWIHWVRQAPGKGLEWVGYI DPYNGYTYYADSVKGRFTISADTSKN TAHLQMNSLRAEDTAVYYCARDYGSF RVQLDYWGQGTLVTVSS |
| 2804 | SRP2900-E10 | $V_H$ | | MEVQLVESGGGLVQPGGSLRLSCAAS GFTISDYWIHWVRQAPGKGLEWVGYI DPANGYTYYADSVKGRFTISADTSKN TAYLQMNSLRAEDTAVYYCARDYGSL HVQLDYWGQGTLVTVSS |
| 2805 | SRP2900-E11 | $V_H$ | | MEVQLVESGGGLVQPGGSLRLSCAAS GFTISYYIIHWVRQAPGKGLEWVGYI DPSNGYTYYADSVKGRFTISADTSKN TAYLQMNSLRAEDTAVYYCARDVQSV SGEFDYWGQGTLVTVSS |
| 2806 | SRP2900-F01 | $V_H$ | | MEVQLVESGGGLVQPGGSLRLSCAAS GFTISDYWIHWVRQAPGKGLEWVGYI DPYNGYTYYADSVRGRFTISADTSKN TAYLQMNSLRAEDTAVYYCARDYGSL QVFIDYWGQGTLVTVSS |
| 2807 | SRP2900-F02 | $V_H$ | | MEVQLVESGGGLVQPGGSLRLACAAS GFTIGVYIIHWVRQAPGKGLEWVGYI DPSNGYTYYADSVKGRFTISADTSKN TAYLQMNSLRAEDTAVYYCARDDQSV SSPFDYWGQGTLVTVSS |
| 2808 | SRP2900-F03 | $V_H$ | | MEVQLVESGGGLVQPGGSLRLSCAAS GFTISDYWIHWVRQAPGKGLEWVGYI DPYNGYTYYADSVKGRFTISAGTSKN TAYLQMNSLRAEDTAVYYCARDYGSL QVFIDYWGQGTLVTVSS |
| 2809 | SRP2900-F04 | $V_H$ | | MEVQLVESGGGLVQPGGSLRLSCAAS GFTISDYWIHWVRQAPGKGLEWVGYI DPYNGFTYYADSVKGRFTISADTSKN TAYLQMNSLRAEDTAVYYCARDYGSL QVFIDYWGQGTLVTVSS |
| 2810 | SRP2900-F05 | $V_H$ | | MEVQLVESGGGLVQPGGSLRLSCAAS GFTINDYVIHWVRQAPGKGLEWVGYI DPSNGYTYYADSVKGRFTISADTSKN TAYLQMNSLRAEDTAVYYCARDDQSL SSPFDYWGQGTLVTVSS |
| 2811 | SRP2900-F06 | $V_H$ | | MEVQLVESGGGLVQPGGSLRLSCAAS GFTISIYTIHWVRQAPGKGLEWVGYI DPSNGYTYYADSVKGRLTISADTSKN TAYLQMNSLRAEDTAVYYCARDPQSI SSPFDYWGQGTLVTVSS |

TABLE 32-continued

| Sequences. | | | | |
|---|---|---|---|---|
| SEQ ID NO: | Molecule | Region | Scheme | Sequence |
| 2812 | SRP2900-F07 | $V_H$ | | MEVQLVESGGGLVQPGGSLRLSCAASGFTISDYTIHWVRQAPGKGLEWVGYIDPSNGYTYHADSVKGRFTISADTSKNTAYLQMNSLRAEDTAVYYCARDPQSVSSPFDYWGQGTLVTVSS |
| 2813 | SRP2900-F08 | $V_H$ | | MEVQLVESGGGLVQPGGSLRLSCAASGFTIAYYIIHWVRQAPGKGLEWVGYIDPSNGYTYYADSVKGRFTISADTSKNTAYLQMNSLRAEDTAVYYCARDDQSLSSPFDYWGQGTLVTVSS |
| 2814 | SRP2900-F09 | $V_H$ | | MEVQLVESGGGLVQPGGSLRLSCAASGFTIHDYVIHWVRQAPGKGLEWVGYIDPSNGYTYYADSVKGRFTISADTSKNTAYLQMNSLRAEDTAVYYCARDDQSISSPLDYWGQGTLVTVSS |
| 2815 | SRP2900-F10 | $V_H$ | | MEVQLVESGGGLVQPGGSLRLSCAASGFTISDYVIHWVRQAPGKGLEWVGYIDPSNGYTYYADSVKGRFTISADTSKNTAYLQMNSLRAEDTAVYYCARDPQSLFYPFDYWGQGTLVTVSS |
| 2816 | SRP2900-F11 | $V_H$ | | MEVQLVESGGGLVQPGGSLRLSCAASGFTISGYIIHWVRQAPGKGLEWVGYIDPSNGYTFYADSVKGRFTISADTSKNTAYLRMNSLRAEDTAVYYCARDDQSLSSPFDYWGQGTLVTVSS |
| 2817 | SRP2900-G01 | $V_H$ | | MEVQLVESGGGLVQPGGSLRLSCAASGFTIFDYTIHWVRQAPGKGLEWVGYIDPSNGYTFYADSVKGRFTISADTSKNTAYLQVNSLRAEDTAVYYCARDIQSVSGEFDYWGQGTLVTVSS |
| 2818 | SRP2900-G02 | $V_H$ | | MEVQLVESGGDLVRPGGSLRLSCAASGFTISYYIIHWVRQAPGKGLEWVGYIDPSNGYTYYADSVKGRFTISADTSKNTAYLQMNSLRAEDTAVYYCARDDQSVSSPFEYWGQGTLVTVSS |
| 2819 | SRP2900-G03 | $V_H$ | | MEVQLVESGGGLVQPGGSLRLSCAASGFTINNYIIHWVRQAPGKGLEWVGYIDPSNGYTYYADSVKGRFTISADTSKNTAYLQMNSLRAEDTAVYYCARDPQSLSSPFDYWGQGTLVTVSS |
| 2820 | SRP2900-G04 | $V_H$ | | MEVQLVESGGGLVQPGGSLRLSCAASGFTTRDYVIHWVRQAPGKGLEWVGYIDPSNGYTYYADSVKGRFTISADTSKNTAYLQMNSLRAEDTAVYYCARDPQSLSSPFDYWGQGTLVTVSS |
| 2821 | SRP2900-G05 | $V_H$ | | MEVQLVESGGGLVQPGGLLRLSCAASGFTIAYYVIHWVRQAPGKGLEWVGYIDPSNGYTYYADSVKGRFTISADTSKNTAYLQMNSLRAEDTAVYYCARDDQSLSSPFDYWGQGTLVTVSS |
| 2822 | SRP2900-G06 | $V_H$ | | MEVQLVESGGGLVQPGGSLRLSCAASGFTISDYIIHWVRQAPGKGLEWVGYIDPSNGYTYYADSVKGRFTISADTSKNTAYLQMNSLRAEDTAVYYCARDDQSLSSPFDYWGQGTLVTVSS |
| 2823 | SRP2900-G07 | $V_H$ | | MEVQLVESGGGLVQPGGSLRLSCAASGFTISDYVIHWVRQAPGKGLEWVGYIDPSNGYTYYADSVKGRFTISADTSKNTAYLQMNSLRAEDTAVYYCARDPQSLTSPFDYWGQGTLVTVSS |
| 2824 | SRP2900-G08 | $V_H$ | | MEVQLVESGGGLVQLGGSLRLSCAASGFTIGGYIIHWVRQAPGKGLEWVGYI |

TABLE 32-continued

| SEQ ID NO: | Molecule | Region | Scheme | Sequence |
|---|---|---|---|---|
| Sequences. | | | | |
| | | | | DPSNGYTYYADSVKGRFTISADTSKN TAYLQMNSLRAEDTAVYYCARDIQSV SGEFDYWGQGTLVTVSS |
| 2825 | SRP2900-G09 | $V_H$ | | MEVQLVESGGGLVQPGGSLRLSCAAS GFTISDYIIHWVRQAPGKGLEWVGYI DPSNGYTYYADSVKGRFTISADTSKN TAYLQMNSLRAEDTAVYYCARDPQSL TSPFDYWGQGTLVTVSS |
| 2826 | SRP2900-G10 | $V_H$ | | MEVQLVESGGGLVQPGGSLRLSCAAS GFTIPDYIIHWVRQAPGKGLEWVGYI DPSNGYTYYADSVKGRFTISADTSKN TAYLQMNSLRAEDTAVYYCARDIQSV SGEFDYWGQGTLVTVSS |
| 2827 | SRP2900-G11 | $V_H$ | | MEVQLVESGGGLVQPGGSSRLSCAAS GFTIYDYIIHWVRQAPGKGLEWVGYI DPSNGYTDYADSVKGRFTISADTSKN TAYLQMNSLRAEDTAVYYCARDIQSV SGEFDYWGQGTLVTVSS |
| 2828 | SRP2900-H01 | $V_H$ | | MEVQLVESGGGLVQPGGSLRLSCAAS GFTIFDYIIHWVRQAPGKGLEWVGYI DPSNGYTYYADSVKGRFTISADTSKN TAYLQMNSLRAEDTAVYYCARDPQSV GSEFDYWGQGTLVTVSS |
| 2829 | SRP2900-H02 | $V_H$ | | MEVQLVESGGGLVQPGGSLRLSCAAS GFTIFDYIIHWVRQAPGKGLEWVGYI DPSNGYTYYADSVKGRFTISADTSKN TAYLQMNSLRAEDTAVYYCARDIQSV SGEFDYWGQGTLVTVSS |
| 2830 | SRP2900-H03 | $V_H$ | | MEVQLVESGGGLVQPGGSLRLSCAAS GFTIYDYIIHWVRQAPGKGLEWVGYI DPSNGYTYHADSVKGRFTISADTSKN TAYLQMNSLRAEDTAVYYCARDPQSL SSPFDYWGQGTLVTVSS |
| 2831 | SRP2900-H04 | $V_H$ | | MEVQLVESGGGLVQPGGSLRLSCAAS GFTISHYIIHWVRQAPGKGLEWVGYI DPSNGYTYYADSVKGRFTISADTSKN TAYLQMNSLRAEDTAVYYCARDIQSV SGEFDYWGQGTLVTVSS |
| 2832 | SRP2900-H05 | $V_H$ | | MEVQLVESGGGLVQPGGSLRLSCAAS GFTISDYTIHWVRQAPGKGLEWVGYI DPSNGYTYYADSVKGRFTISADTSKN TAYLQMNSLRAEDTAVYYCARDIQSV SGEFDYWGQGTLVTVSS |
| 2833 | SRP2900-H06 | $V_H$ | | MEVQLVESGGGLVQPGGSLRLSCAAS GFTIAAYIIHWVRQAPGKGLEWVGYI DPSNGYTYYADSVKGRFTISADTSKN TAYLQMNSLRAEDTAVYYCARDDQSF SSPFDYWGQGTLVTVSS |
| 2834 | SRP2900-H07 | $V_H$ | | MEVQLVESGGGLVQPGGSLRLSCAAS GFNIAYYTIHWVRQAPGKGLEWVGYI DPSNGYTYYADSVKGRFTISADTSKN TAYLQMNSLRAEDTAVYYCARDPQSF SSPFDYWGQGTLVTVSS |
| 2835 | SRP2900-H08 | $V_H$ | | MEVQLVESGGGLVQPGGSLRLSCAAS GFTISDYVIHWVRQAPGKGLEWVGYI DPSNGYTFYADSVKGRFTISADTPKN TAYLQMNSLRAKDTAVYYCARDPQSL SSPFDYWGQGTLVTVSS |
| 2836 | SRP2900-H09 | $V_H$ | | MEVQLVESGGGLVQPGGSLRLSCAAS GFTISDYVIHWVRQAPGKGLEWVGYI DPSNGYTYYADSVKGRFTISADTSKN TAYLQMNSLRAEDTAVYYCARDDQSI SSPLDYWGQGTLVTVSS |

TABLE 32-continued

| Sequences. | | | | |
|---|---|---|---|---|
| SEQ ID NO: | Molecule | Region | Scheme | Sequence |
| 2837 | SRP2900-H10 | $V_H$ | | MEVQLVESGGGLVQPGGSLRLSCAAS GFTISDYVIHWVRQAPGKGLEWVGYI DPSNGFTYYADSVKGRFTISADTSKN TAYLQTNSLRAEDTAVYYCARDIQSV SGEFDYWGQGTLVTVSS |
| 2838 | SRP2900-H11 | $V_H$ | | MEVQLVESGGGLVQPGGSLRLSCAAS GFTISSYIIHWVRQAPGKGPEWVGYI DPSNGYTYYADSVKGRFTISADTSKN TAYLQMNSLRAEDTAVYYCARDPQTL TSPFDYWGQGTLVTVSS |
| 2840 | SRP2842-B01 | $V_H$ | | QSVEESEGGLFKPADTLTLTCTASGF SISSYDMSWVRQAPGNGLEWIGIIGS NGRTYYPNWAKSRSTITRNTNENTVT LKMTSLTAADTATYFCARGLYDGTGN IWGPGTLVTVSS |
| 2846 | SRP2842-G04 | $V_H$ | | QSVEESEGGLFKPTDTLTLTCTVSGF SLSYYGVSWVRQAPGNGLEWIGTIDS SGRTYYASWANGRFTISNDNAPNTVS LQVNSLAAADTATYFCARDFYGWNSG ALDIWGPGTLVTVSS |
| 2851 | SRP2901-B05_ 2842-G04_HC2 | $V_H$ | | MQVQVQESGPGLVKPPGTLSLTCAVS GFSLSYYGVSWVRQPPGKGLEWIGTI DSSGRTYYNPSLKSRVTISNDNAPNT VSLKLSSVTAADTAVYYCARDFYGWN SGALDIWGQGTLVTVSS |
| 2857 | SRP2901-D03_ 2842-B01_HC-3 | $V_H$ | | MEVQLVESGGGLVQPGGSLRLSCAAS GFSISSYDMSWVRQAPGKGLEWIGII GSNGRTYYPDSVKGRFTISRDNSKNT VTLQMNSLRAEDTAVYYCARGLYDGT GNIWGQGTLVTVSS |
| 2859 | SRP2901-E03_ 2842-B01_HC-3 | $V_H$ | | MEVQLVESGGGLVQPGGSLRLSCAAS GFSISSYDMSWVRQAPGKGLEWIGII GSNGRTYYPDSVKGRFTISRDNSKNT VTLQMNSLRAEDTAVYYCARGLYDGT GNIWGQGTLVTVSS |
| 2860 | SRP2901-F01_ 2842-B01_HC-1 | $V_H$ | | MQVQVVESGGGLVKPGGSLRLSCAAS GFSISSYDMSWIRQAPGKGLEWIGII GSNGRTYYADSVKGRFTISRNTNENT VYLQMNSLRAEDTAVYYCARGLYDGT GNIWGQGTLVTVSS |
| 2951 | SRP2842-B01 | $V_L$ | | ELVMTQTPSPVSAAVGSTVTISCQAS QSVYGNNWLSWFQQKPGQPPKLLIYG ASKLASGVSSRFKGSGSGTQFTLTIS GVQCDDAATYYCQGTYYSGDWYFAFG GGTELEIL |
| 2957 | SRP2842-G04 | $V_L$ | | ELDLTQTASPVSAAVGGTVTINCQAS QSVYSNKYLSWYQQKPGQPPKLLIYK ASTLASGVPSRESGSGFGTEFTLTIS DVQCDDAATYYCAAAYSDDSDTAFGG GTKVVVE |
| 2962 | SRP2901-B05_ 2842-G04_LC2 | $V_L$ | | MDLQLTQSPSTLSASVGDRVTITCRA SQSVYSNKYLSWYQQKPGKAPKLLIY KASTLASGVPSRFSGSGSGTEFTLTI SSLQPDDFATYYCAAAYSDDSDTAFG QGTKVEIK |
| 2968 | SRP2901-D03_ 2842-B01_LC1 | $V_L$ | | MDLQMTQSPSSLSASVGDRVTITCRA SQSVYGNNWLSWYQQKPGKAPKLLIY GASKLASGVPSRFSGSGSGTQFTLTI SSLQPEDFATYYCQGTYYSGDWYFAF GQGTKVEIK |
| 2970 | SRP2901-E03_ 2842-B01_LC2 | $V_L$ | | MELVMTQSPPTLSLSPGERVTLSCRA SQSVYGNNWLSWYQQKPGQAPRLLIY |

TABLE 32-continued

| Sequences. | | | | |
|---|---|---|---|---|
| SEQ ID NO: | Molecule | Region | Scheme | Sequence |
| | | | | GASKLATSIPARFSGSGSGTQFTLTI SSLQPEDFAVYYCQGTYYSGDWYFAF GQGTKVEIK |
| 2971 | SRP2901-F01_ 2842-B01_LC3 | $V_L$ | | MDIQMTQSPSSLSASVGDRVTITCQA SQSVYGNNWLSWYQQKPGKAPKLLIY GASKLASGVPSRFSGSGSGTDFTLTI SSLQPEDFATYYCQGTYYSGDWYFAF GGGTKVEIK |
| 3061 | trastuzumab VL | $V_L$ | | DIQMTQSPSSLSASVGDRVTITCRAS QDVNTAVAWYQQKPGKAPKLLIYSAS FLYSGVPSRFSGSRSGTDFTLTISSL QPEDFATYYCQQHYTTPPTFGQGTKV EIK |
| 3062 | Human IgG1 HC Constant | | | ASTKGPSVFPLAPSSKSTSGGTAALG CLVKDYFPEPVTVSWNSGALTSGVHT FPAVLQSSGLYSLSSVVTVPSSSLGT QTYICNVNHKPSNTKVDKKVEPKSCD KTHTCPPCPAPELLGGPSVFLFPPKP KDTLMISRTPEVTCVVVDVSHEDPEV KFNWYVDGVEVHNAKTKPREEQYNST YRVVSVLTVLHQDWLNGKEYKCKVSN KALPAPIEKTISKAKGQPREPQVYTL PPSREEMTKNQVSLTCLVKGFYPSDI AVEWESNGQPENNYKTTPPVLDSDGS FFLYSKLTVDKSRWQQGNVFSCSVMH EALHNHYTQKSLSLSPGK |
| 3063 | Human IgG LC Constant Ckappa | | | RTVAAPSVFIFPPSDEQLKSGTASVV CLLNNFYPREAKVQWKVDNALQSGNS QESVTEQDSKDSTYSLSSTLTLSKAD YEKHKVYACEVTHQGLSSPVTKSFNR GEC |
| 3064 | Mouse IgG1 HC Constant | | | AKTTPPSVYPLAPGSAAQTNSMVTLG CLVKGYFPEPVTVTWNSGSLSSGVHT FPAVLQSDLYTLSSSVTVPSSTWPSE TVTCNVAHPASSTKVDKKIVPRDCGC KPCICTVPEVSSVFIFPPKPKDVLTI TLTPKVTCVVVDISKDDPEVQFSWFV DDVEVHTAQTQPREEQFNSTERSVSE LPIMHQDWLNGKEFKCRVNSAAFPAP IEKTISKTKGRPKAPQVYTIPPPKEQ MAKDKVSLTCMITDFFPEDITVEWQW NGQPAENYKNTQPIMDTDGSYFVYSK LNVQKSNWEAGNTFTCSVLHEGLHNH HTEKSLSHSPG |
| 3065 | Mouse IgG LC Constant Ckappa | | | RADAAPTVSIFPPSSEQLTSGGASVV CFLNNFYPKDINVKWKIDGSERQNGV LNSWTDQDSKDSTYSMSSTLTLTKDE YERHNSYTCEATHKTSTSPIVKSFNR NEC |
| 3066 | Kappa LC | | | HMTVAAPSVFIFPPSDEQLKSGTASV VCLLNNFYPREAKVQWKVDNALQSGN SQESVTEQDSKDSTYSLSSTLTLSKA DYEKHKVYACEVTHQGLSSPVTKSFN RGEC |
| 3067 | Lambda LD | | | GQPKAAPSVTLFPPSSEELQANKATL VCLISDFYPGAVTVAWKADSSPVKAG VETTTPSKQSNNKYAASSYLSLTPEQ WKSHRSYSCQVTHEGSTVEKTVAPTE CS |
| 3068 | IgG1 Fc from scFv-Fc | | | DKTHTCPPCSAPELLGGSSVFLFPPK PKDTLMISRTPEVTCVVVDVSHEDPE VKFNWYVDGVEVHNAKTKPREEQYNS TYRVVSVLTVLHQDWLNGKEYKCKVS NKALPAPIEKTISKAKGQPREPQVYT LPPSRDELTKNQVSLTCLVKGFYPSD IAVEWESNGQPENNYKTTPPVLDSDG |

TABLE 32-continued

Sequences.

| SEQ ID NO: | Molecule | Region | Scheme | Sequence |
|---|---|---|---|---|
| | | | | SFFLYSKLTVDKSRWQQGNVFSCSVM HEALHNHYTQKSLSLSPGKGSGDYKD DDDKGSG |
| 3069 | FlagHis Tag | | | GSGDYKDDDDKGSGHHHHHH |
| 3070 | Linker | | | GGGGSGGGGSGGGGS |
| 3071 | Linker | | | AAGSDQEPKSS |
| 3073 | SRP2842-B01 (scFv (SKNK-$V_H$-linker-VL)) | | | MSKNKQSVEESEGGLFKPADTLTLTC TASGFSISSYDMSWVRQAPGNGLEWI GIIGSNGRTYYPNWAKSRSTITRNTN ENTVTLKMTSLTAADTATYFCARGLY DGTGNIWGPGTLVTVSSGGGGSGGGG SGGGGSELVMTQTPSPVSAAVGSTVT ISCQASQSVYGNNWLSWFQQKPGQPP KLLIYGASKLASGVSSRFKGSGSGTQ FTLTISGVQCDDAATYYCQGTYYSGD WYFAFGGGTELEILA |
| 3079 | SRP2842-G04 (scFv (SKNK-$V_H$-linker-VL)) | | | MSKNKQSVEESEGGLFKPTDTLTLTC TVSGFSLSYYGVSWVRQAPGNGLEWI GTIDSSGRTYYASWANGRFTISNDNA PNTVSLQVNSLAAADTATYFCARDFY GWNSGALDIWGPGTLVTVSSGGGGSG GGGSGGGGSELDLTQTASPVSAAVGG TVTINCQASQSVYSNKYLSWYQQKPG QPPKLLIYKASTLASGVPSRFSGSGF GTEFTLTISDVQCDDAATYYCAAAYS DDSDTAFGGGTKVVVEA |
| 3160 | Murine Tissue Factor | | | MAILVRPRLLAALAPTFLGCLLLQVIAGAGI PEKAFNLTWISTDFKTILEWQPKPTNYTYTV QISDRSRNWKNKCFSTTDTECDLTDEIVKDV TWAYEAKVLSVPRRNSVHGDGDQLVIHGEEP PFTNAPKFLPYRDTNLGQPVIQQFEQDGRKL NVVVKDSLTLVRKNGTFLTLRQVFGKDLGYI ITYRKGSSTGKKTNITNTNEFSIDVEEGVSY CFFVQAMIFSRKTNQNSPGSSTVCTEQWKSF LGETLIIVGAVVLLATIFIILLSISLCKRRK NRAGQKGKNTPSRLA |
| 3161 | Human Tissue Factor Isoform 2 Precursor | | | METPAWPRVPRPETAVARTLLLGWVFAQVAG ASGTTNTVAAYNLTWKSTNFKTILEWEPKPV NQVYTVQISTKSGDWKSKCFYTTDTECDLTD EIVKDVKQTYLARVFSYPAGNVESTGSAGEP LYENSPEFTPYLETNLGQPTIQSFEQVGTKV NVTVEDERTLVRRNNTFLSLRDVFGKDLIYT LYYWKSSSSGKKYSTSLELWYLWSSSLSSSW LYLYTSVERQEWGRAGRRTPH |
| 3162 | Murine Tissue Factor Precursor | | | MAILVRPRLLAALAPTFLGCLLLQVTAGAGI PEKAFNLTWISTDFKTILEWQPKPTNYTYTV QISDRSRNWKNKCFSTTDTECDLTDEIVKDV TWAYEAKVLSVPRRNSVHGDGDQLVIHGEEP PFTNAPKFLPYRDTNLGQPVIQQFEQDGRKL NVVVKDSLTLVRKNGTFLTLRQVFGKDLGYI ITYRKGSSTGKKTNITNTNEFSIDVEEGVSY CFFVQAMIFSRKTNQNSPGSSTVCTEQWKSF LGETLIIVGAVVLLATIFIILLSISLCKRRK NRAGQKGKNTPSRLA |
| 3163 | aTF 2799-A05 HC Y180/F404TAG | Heavy Chain | | MEVQLVESGGGLVQPGGSLRLSCAASGF NISSYWIHWVRQAPGKGLEWVGYIDPYS GSTYYADSVKGRFTISADTSKNTAYLQM NSLRAEDTAVYYCARSDYYYVDEYMDYW GQGTLVTVSSASTKGPSVFPLAPSSKST SGGTAALGCLVKDYFPEPVTVSWNSGAL TSGVHTFPAVLQSSGL*SLSSVVTVPSS SLGTQTYICNVNHKPSNTKVDKKVEPKS CDKTHTCPPCPAPELLGGPSVFLFPPKP KDTLMISRTPEVTCVVVDVSHEDPEVKF NWYVDGVEVHNAKTKPREEQYNSTYRVV SVLTVLHQDWLNGKEYKCKVSNKALPAP |

TABLE 32-continued

| Sequences. | | | | |
|---|---|---|---|---|
| SEQ ID NO: | Molecule | Region | Scheme | Sequence |
| | | | | IEKTISKAKGQPREPQVYTLPPSREEMT KNQVSLTCLVKGFYPSDIAVEWESNGQP ENNYKTTPPVLDSDGS*FLYSKLTVDKS RWQQGNVFSCSVMHEALHNHYTQKSLSL SPGK |
| 3164 | aTF 2799-B03 HC Y180/F404TAG | Heavy Chain | | MEVQLVESGGGLVQPGGSLRLSCAASGF NISDYWIHWVRQAPGKGLEWVGFIDPYN GYTNYADSVKGRFTISADTSKNTAYLQM NSLRAEDTAVYYCARGYGSWPDYLDYWG QGTLVTVSSASTKGPSVFPLAPSSKSTS GGTAALGCLVKDYFPEPVTVSWNSGALT SGVHTFPAVLQSSGL*SLSSVVTVPSSS LGTQTYICNVNHKPSNTKVDKKVEPKSC DKTHTCPPCPAPELLGGPSVFLFPPKPK DTLMISRTPEVTCVVVDVSHEDPEVKFN WYVDGVEVHNAKTKPREEQYNSTYRVVS VLTVLHQDWLNGKEYKCKVSNKALPAPI EKTISKAKGQPREPQVYTLPPSREEMTK NQVSLTCLVKGFYPSDIAVEWESNGQPE NNYKTTPPVLDSDGS*FLYSKLTVDKSR WQQGNVFSCSVMHEALHNHYTQKSLSLS PGK |
| 3165 | aTF 2799-B06 HC Y180/F404TAG | Heavy Chain | | MEVQLVESGGGLVQPGGSLRLSCAASGF NISDYNIHWVRQAPGKGLEWVGYIDPSN GYTYYADSVKGRFTISADTSKNTAYLQM NSLRAEDTAVYYCARDDQSVSSPFDYWG QGTLVTVSSASTKGPSVFPLAPSSKSTS GGTAALGCLVKDYFPEPVTVSWNSGALT SGVHTFPAVLQSSGL*SLSSVVTVPSSS LGTQTYICNVNHKPSNTKVDKKVEPKSC DKTHTCPPCPAPELLGGPSVFLFPPKPK DTLMISRTPEVTCVVVDVSHEDPEVKFN WYVDGVEVHNAKTKPREEQYNSTYRVVS VLTVLHQDWLNGKEYKCKVSNKALPAPI EKTISKAKGQPREPQVYTLPPSREEMTK NQVSLTCLVKGFYPSDIAVEWESNGQPE NNYKTTPPVLDSDGS*FLYSKLTVDKSR WQQGNVFSCSVMHEALHNHYTQKSLSLS PGK |
| 3168 | aTF_2900-A02_HC_Y180/F404TAG_SerOpt | Heavy Chain | | MEVQLVESGGGLVQPGGSLRLSCAASGF TISGYIIHWVRQAPGKGLEWVGYIDPSN GYTYYADSVKGRFTISADTSKNTAYLQM NSLRAEDTAVYYCARDDQSLSSPFDYWG QGTLVTVSSASTKGPSVFPLAPSSKSTS GGTAALGCLVKDYFPEPVTVSWNSGALT SGVHTFPAVLQSSGL*SLSSVVTVPSSS LGTQTYICNVNHKPSNTKVDKKVEPKSC DKTHTCPPCPAPELLGGPSVFLFPPKPK DTLMISRTPEVTCVVVDVSHEDPEVKFN WYVDGVEVHNAKTKPREEQYNSTYRVVS VLTVLHQDWLNGKEYKCKVSNKALPAPI EKTISKAKGQPREPQVYTLPPSREEMTK NQVSLTCLVKGFYPSDIAVEWESNGQPE NNYKTTPPVLDSDGS*FLYSKLTVDKSR WQQGNVFSCSVMHEALHNHYTQKSLSLS PGK |
| 3169 | aTF_2842-B01_Hc3_Y180/F404TAG | Heavy Chain | | MEVQLVESGGGLVQPGGSLRLSCAASGF SISSYDMSWVRQAPGKGLEWIGIIGSNG RTYYPDSVKGRFTISRDNSKNTVTLQMN SLRAEDTAVYYCARGLYDGTGNIWGQGT LVTVSSASTKGPSVFPLAPSSKSTSGGT AALGCLVKDYFPEPVTVSWNSGALTSGV HTFPAVLQSSGL*SLSSVVTVPSSSLGT QTYICNVNHKPSNTKVDKKVEPKSCDKT HTCPPCPAPELLGGPSVFLFPPKPKDTL MISRTPEVTCVVVDVSHEDPEVKFNWYV DGVEVHNAKTKPREEQYNSTYRVVSVLT VLHQDWLNGKEYKCKVSNKALPAPIEKT ISKAKGQPREPQVYTLPPSREEMTKNQV SLTCLVKGFYPSDIAVEWESNGQPENNY |

TABLE 32-continued

| Sequences. | | | | |
|---|---|---|---|---|
| SEQ ID NO: | Molecule | Region | Scheme | Sequence |
| | | | | KTTPPVLDSDGS*FLYSKLTVDKSRWQQ GNVFSCSVMHEALHNHYTQKSLSLSPGK |
| 3170 | aTF_2900-C11_HC_Y180/F404TAG_SerOpt | Heavy Chain | | MEVQLVESGGGLVQPGGSLRLSCAASGF TISQYWIHWVRQAPGKGLEWVGYIDPYN GYTYYADSVKGRFTISADTSKNTAYLQM NSLRAEDTAVYYCARDYGSWRIRLDYWG QGTLVTVSSASTKGPSVFPLAPSSKSTS GGTAALGCLVKDYFPEPVTVSWNSGALT SGVHTFPAVLQSSGL*SLSSVVTVPSSS LGTQTYICNVNHKPSNTKVDKKVEPKSC DKTHTCPPCPAPELLGGPSVFLFPPKPK DTLMISRTPEVTCVVVDVSHEDPEVKFN WYVDGVEVHNAKTKPREEQYNSTYRVVS VLTVLHQDWLNGKEYKCKVSNKALPAPI EKTISKAKGQPREPQVYTLPPSREEMTK NQVSLTCLVKGFYPSDIAVEWESNGQPE NNYKTTPPVLDSDGS*FLYSKLTVDKSR WQQGNVFSCSVMHEALHNHYTQKSLSLS PGK |
| 3171 | aTF_2900-F06_HC_Y180/F404TAG_SerOpt | Heavy Chain | | MEVQLVESGGGLVQPGGSLRLSCAASGE TISIYTIHWVRQAPGKGLEWVGYIDPSN GYTYYADSVKGRLTISADTSKNTAYLQM NSLRAEDTAVYYCARDPQSISSPFDYWG QGTLVTVSSASTKGPSVFPLAPSSKSTS GGTAALGCLVKDYFPEPVTVSWNSGALT SGVHTFPAVLQSSGL*SLSSVVTVPSSS LGTQTYICNVNHKPSNTKVDKKVEPKSC DKTHTCPPCPAPELLGGPSVFLFPPKPK DTLMISRTPEVTCVVVDVSHEDPEVKFN WYVDGVEVHNAKTKPREEQYNSTYRVVS VLTVLHQDWLNGKEYKCKVSNKALPAPI EKTISKAKGQPREPQVYTLPPSREEMTK NQVSLTCLVKGFYPSDIAVEWESNGQPE NNYKTTPPVLDSDGS*FLYSKLTVDKSR WQQGNVFSCSVMHEALHNHYTQKSLSLS PGK |
| 3172 | aTF_2900-F09_HC_Y180/F404TAG_SerOpt | Heavy Chain | | MEVQLVESGGGLVQPGGSLRLSCAASGF TIHDYVIHWVRQAPGKGLEWVGYIDPSN GYTYYADSVKGRFTISADTSKNTAYLQM NSLRAEDTAVYYCARDDQSISSPLDYWG QGTLVTVSSASTKGPSVFPLAPSSKSTS GGTAALGCLVKDYFPEPVTVSWNSGALT SGVHTFPAVLQSSGL*SLSSVVTVPSSS LGTQTYICNVNHKPSNTKVDKKVEPKSC DKTHTCPPCPAPELLGGPSVFLFPPKPK DTLMISRTPEVTCVVVDVSHEDPEVKFN WYVDGVEVHNAKTKPREEQYNSTYRVVS VLTVLHQDWLNGKEYKCKVSNKALPAPI EKTISKAKGQPREPQVYTLPPSREEMTK NQVSLTCLVKGFYPSDIAVEWESNGQPE NNYKTTPPVLDSDGS*FLYSKLTVDKSR WQQGNVFSCSVMHEALHNHYTQKSLSLS PGK |
| 3173 | aTF_2900-H06_HC_Y180/F404TAG_SerOpt | Heavy Chain | | MEVQLVESGGGLVQPGGSLRLSCAASGF TIAAYIIHWVRQAPGKGLEWVGYIDPSN GYTYYADSVKGRFTISADTSKNTAYLQM NSLRAEDTAVYYCARDDQSFSSPFDYWG QGTLVTVSSASTKGPSVFPLAPSSKSTS GGTAALGCLVKDYFPEPVTVSWNSGALT SGVHTFPAVLQSSGL*SLSSVVTVPSSS LGTQTYICNVNHKPSNTKVDKKVEPKSC DKTHTCPPCPAPELLGGPSVFLFPPKPK DTLMISRTPEVTCVVVDVSHEDPEVKFN WYVDGVEVHNAKTKPREEQYNSTYRVVS VLTVLHQDWLNGKEYKCKVSNKALPAPI EKTISKAKGQPREPQVYTLPPSREEMTK NQVSLTCLVKGFYPSDIAVEWESNGQPE NNYKTTPPVLDSDGS*FLYSKLTVDKSR WQQGNVFSCSVMHEALHNHYTQKSLSLS PGK |

TABLE 32-continued

| SEQ ID NO: | Molecule | Region | Scheme | Sequence |
|---|---|---|---|---|
| Sequences. | | | | |
| 3174 | aTF_2900-H09_HC_Y180/F404TAG_SerOpt | Heavy Chain | | MEVQLVESGGGLVQPGGSLRLSCAASGFTISDYVIHWVRQAPGKGLEWVGYIDPSNGYTYYADSVKGRFTISADTSKNTAYLQMNSLRAEDTAVYYCARDDQSISSPLDYWGQGTLVTVSSASTKGPSVFPLAPSSKSTSGGTAALGCLVKDYFPEPVTVSWNSGALTSGVHTFPAVLQSSGL*SLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGS*FLYSKLTVDKSRWQQGNVFSCSVMHEALHNHYTQKSLSLSPGK |
| 3175 | aTF_2842-B01_Hc1_Y180/F404TAG | Heavy Chain | | MQVQVVESGGGLVKPGGSLRLSCAASGFSISSYDMSWIRQAPGKGLEWIGIIGSNGRTYYADSVKGRFTISRNTNENTVYLQMNSLRAEDTAVYYCARGLYDGTGNIWGQGTLVTVSSASTKGPSVFPLAPSSKSTSGGTAALGCLVKDYFPEPVTVSWNSGALTSGVHTFPAVLQSSGL*SLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGS*FLYSKLTVDKSRWQQGNVFSCSVMHEALHNHYTQKSLSLSPGK |
| 3176 | aTF_2842-G04_Hc2 Y180/F404TAG | Heavy Chain | | MQVQVQESGPGLVKPPGTLSLTCAVSGFSLSYYGVSWVRQPPGKGLEWIGTIDSSGRTYYNPSLKSRVTISNDNAPNTVSLKLSSVTAADTAVYYCARDFYGWNSGALDIWGQGTLVTVSSASTKGPSVFPLAPSSKSTSGGTAALGCLVKDYFPEPVTVSWNSGALTSGVHTFPAVLQSSGL*SLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGS*FLYSKLTVDKSRWQQGNVFSCSVMHEALHNHYTQKSLSLSPGK |
| 3177 | aTF_2900-A02_HC_Y180/F241/F404TAG_SerOpt | Heavy Chain | | MEVQLVESGGGLVQPGGSLRLSCAASGFTISGYIIHWVRQAPGKGLEWVGYIDPSNGYTYYADSVKGRFTISADTSKNTAYLQMNSLRAEDTAVYYCARDDQSLSSPFDYWGQGTLVTVSSASTKGPSVFPLAPSSKSTSGGTAALGCLVKDYFPEPVTVSWNSGALTSGVHTFPAVLQSSGL*SLSSVVTVPSSSLGTQTYICNVNHKPSNTKVDKKVEPKSCDKTHTCPPCPAPELLGGPSV*LFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGS*FLYSKLTVDKSRWQQGNVFSCSVMHEALHNHYTQKSLSLSPGK |
| 3178 | aTF_2900-A02_HC_F241/F404TAG_SerOpt | Heavy Chain | | MEVQLVESGGGLVQPGGSLRLSCAASGFTISGYIIHWVRQAPGKGLEWVGYIDPSNGYTYYADSVKGRFTISADTSKNTAYLQM |

TABLE 32-continued

| Sequences. | | | | |
|---|---|---|---|---|
| SEQ ID NO: | Molecule | Region | Scheme | Sequence |
| | | | | NSLRAEDTAVYYCARDDQSLSSPFDYWG QGTLVTVSSASTKGPSVFPLAPSSKSTS GGTAALGCLVKDYFPEPVTVSWNSGALT SGVHTFPAVLQSSGLYSLSSVVTVPSSS LGTQTYICNVNHKPSNTKVDKKVEPKSC DKTHTCPPCPAPELLGGPSV*LFPPKPK DTLMISRTPEVTCVVVDVSHEDPEVKFN WYVDGVEVHNAKTKPREEQYNSTYRVVS VLTVLHQDWLNGKEYKCKVSNKALPAPI EKTISKAKGQPREPQVYTLPPSREEMTK NQVSLTCLVKGFYPSDIAVEWESNGQPE NNYKTTPPVLDSDGS*FLYSKLTVDKSR WQQGNVFSCSVMHEALHNHYTQKSLSLS PGK |
| 3179 | Trastuzumab LC SerOpt | Light Chain | | MDIQMTQSPSSLSASVGDRVTITCRASQ DVNTAVAWYQQKPGKAPKLLIYSASFLY SGVPSRFSGSRSGTDFTLTISSLQPEDF ATYYCQQHYTTPPTFGQGTKVEIKRTVA APSVFIFPPSDEQLKSGTASVVCLLNNF YPREAKVQWKVDNALQSGNSQESVTEQD SKDSTYSLSSTLTLSKADYEKHKVYACE VTHQGLSSPVTKSFNRGEC |
| 3180 | aTF_2842-B01_Lc2 | Light Chain | | MELVMTQSPPTLSLSPGERVTLSCRASQ SVYGNNWLSWYQQKPGQAPRLLIYGASK LATSIPARFSGSGSGTQFTLTISSLQPE DFAVYYCQGTYYSGDWYFAFGQGTKVEI KRTVAAPSVFIFPPSDEQLKSGTASVVC LLNNFYPREAKVQWKVDNALQSGNSQES VTEQDSKDSTYSLSSTLTLSKADYEKHK VYACEVTHQGLSSPVTKSFNRGEC |
| 3181 | aTF_2842-B01_Lc1 | Light Chain | | MDLQMTQSPSSLSASVGDRVTITCRASQ SVYGNNWLSWYQQKPGKAPKLLIYGASK LASGVPSRFSGSGSGTQFTLTISSLQPE DEATYYCQGTYYSGDWYFAFGQGTKVEI KRTVAAPSVFIFPPSDEQLKSGTASVVC LLNNFYPREAKVQWKVDNALQSGNSQES VTEQDSKDSTYSLSSTLTLSKADYEKHK VYACEVTHQGLSSPVTKSFNRGEC |
| 3182 | aTF_2842-B01_Lc3 | Light Chain | | MDIQMTQSPSSLSASVGDRVTITCQASQ SVYGNNWLSWYQQKPGKAPKLLIYGASK LASGVPSRFSGSGSGTDFTLTISSLQPE DFATYYCQGTYYSGDWYFAFGGGTKVEI KRTVAAPSVFIFPPSDEQLKSGTASVVC LLNNFYPREAKVQWKVDNALQSGNSQES VTEQDSKDSTYSLSSTLTLSKADYEKHK VYACEVTHQGLSSPVTKSFNRGEC |
| 3183 | aTF_2842-G04_Lc2 | Light Chain | | MDLQLTQSPSTLSASVGDRVTITCRASQ SVYSNKYLSWYQQKPGKAPKLLIYKAST LASGVPSRFSGSGSGTEFTLTISSLQPD DFATYYCAAAYSDDSDTAFGQGTKVEIK RTVAAPSVFIFPPSDEQLKSGTASVVCL LNNFYPREAKVQWKVDNALQSGNSQESV TEQDSKDSTYSLSSTLTLSKADYEKHKV YACEVTHQGLSSPVTKSFNRGEC |
| 3184 | trastuzumab LC SerOpt K42TAG/ E161TAG/ TCT162AGC | Light Chain | | MDIQMTQSPSSLSASVGDRVTITCRASQ DVNTAVAWYQQKPG*APKLLIYSASFLY SGVPSRESGSRSGTDFTLTISSLQPEDF ATYYCQQHYTTPPTFGQGTKVEIKRTVA APSVEIFPPSDEQLKSGTASVVCLLNNF YPREAKVQWKVDNALQSGNSQ*SVTEQD SKDSTYSLSSTLTLSKADYEKHKVYACE VTHQGLSSPVTKSFNRGEC |
| 3185 | trastuzumab LC SerOpt K42TAG | Light Chain | | MDIQMTQSPSSLSASVGDRVTITCRASQ DVNTAVAWYQQKPG*APKLLIYSASFLY SGVPSRESGSRSGTDFTLTISSLQPEDF ATYYCQQHYTTPPTFGQGTKVEIKRTVA APSVFIFPPSDEQLKSGTASVVCLLNNF YPREAKVQWKVDNALQSGNSQESVTEQD |

TABLE 32-continued

| SEQ ID NO: | Molecule | Region | Scheme | Sequence |
|---|---|---|---|---|
| | | | | SKDSTYSLSSTLTLSKADYEKHKVYACE VTHQGLSSPVTKSENRGEC |
| 3186 | aTF_2900-C11_HC_Y180/F404TAG_SerOpt | Heavy Chain | | MEVQLVESGGGLVQPGGSLRLSCAASGF TISQYWIHWVRQAPGKGLEWVGYIDPYN GYTY YADSVKGRFTISADTSKNTAYLQMNSLR AEDTAVYYCARDYGSWRIRLDYWGQGTL VTVS SASTKGPSVFPLAPSSKSTSGGTAALGC LVKDYFPEPVTVSWNSGALTSGVHTFPA VLQSSGL*SLSSVVTVPSSSLGTQTYIC NVNHKPSNTKVDKKVEPKSCDKTHTCPP CPAPELLGGPSVFLFPPKPKDTLMISRT PEVTCVVVDVSHEDPEVKFNWYVDGVEV HNAKTKPREEQYNSTYRVVSVLTVLHQD WLNGKEYKCKVSNKALPAPIEKTISKAK GQPREPQVYTLPPSREEMTKNQVSLTCL VKGFYPSDIAVEWESNGQPENNYKTTPP VLDSDGS*FLYSKLTVDKSRWQQGNVES CSVMHEALHNHYTQKSLSLSPGK |
| 3187 | aTF_2900-F06_HC_Y180/F404TAG_SerOpt | Heavy Chain | | MEVQLVESGGGLVQPGGSLRLSCAASGF TISIYTIHWVRQAPGKGLEWVGYIDPSN GYTYYADSVKGRLTISADTSKNTAYLQM NSLRAEDTAVYYCARDPQSISSPFDYWG QGTLVTVSSASTKGPSVFPLAPSSKSTS GGTAALGCLVKDYFPEPVTVSWNSGALT SGVHTFPAVLQSSGL*SLSSVVTVPSSS LGTQTYICNVNHKPSNTKVDKKVEPKSC DKTHTCPPCPAPELLGGPSVFLFPPKPK DTLMISRTPEVTCVVVDVSHEDPEVKFN WYVDGVEVHNAKTKPREEQYNSTYRVVS VLTVLHQDWLNGKEYKCKVSNKALPAPI EKTISKAKGQPREPQVYTLPPSREEMTK NQVSLTCLVKGFYPSDIAVEWESNGQPE NNYKTTPPVLDSDGS*FLYSKLTVDKSR WQQGNVFSCSVMHEALHNHYTQKSLSLS PGK |
| 3188 | aTF_2900-F09_HC_Y180/F404TAG_SerOpt | Heavy Chain | | MEVQLVESGGGLVQPGGSLRLSCAASGF TIHDYVIHWVRQAPGKGLEWVGYIDPSN GYTYYADSVKGRFTISADTSKNTAYLQM NSLRAEDTAVYYCARDDQSISSPLDYWG QGTLVTVSSASTKGPSVFPLAPSSKSTS GGTAALGCLVKDYFPEPVTVSWNSGALT SGVHTFPAVLQSSGL*SLSSVVTVPSSS LGTQTYICNVNHKPSNTKVDKKVEPKSC DKTHTCPPCPAPELLGGPSVFLFPPKPK DTLMISRTPEVTCVVVDVSHEDPEVKFN WYVDGVEVHNAKTKPREEQYNSTYRVVS VLTVLHQDWLNGKEYKCKVSNKALPAPI EKTISKAKGQPREPQVYTLPPSREEMTK NQVSLTCLVKGFYPSDIAVEWESNGQPE NNYKTTPPVLDSDGS*FLYSKLTVDKSR WQQGNVFSCSVMHEALHNHYTQKSLSLS PGK |
| 3189 | aTF_2900-H06_HC_Y180/F404TAG_SerOpt | Heavy Chain | | MEVQLVESGGGLVQPGGSLRLSCAASGF TIAAYIIHWVRQAPGKGLEWVGYIDPSN GYTYYADSVKGRFTISADTSKNTAYLQM NSLRAEDTAVYYCARDDQSFSSPFDYWG QGTLVTVSSASTKGPSVFPLAPSSKSTS GGTAALGCLVKDYFPEPVTVSWNSGALT SGVHTFPAVLQSSGL*SLSSVVTVPSSS LGTQTYICNVNHKPSNTKVDKKVEPKSC DKTHTCPPCPAPELLGGPSVFLFPPKPK DTLMISRTPEVTCVVVDVSHEDPEVKFN WYVDGVEVHNAKTKPREEQYNSTYRVVS VLTVLHQDWLNGKEYKCKVSNKALPAPI EKTISKAKGQPREPQVYTLPPSREEMTK NQVSLTCLVKGFYPSDIAVEWESNGQPE NNYKTTPPVLDSDGS*FLYSKLTVDKSR WQQGNVFSCSVMHEALHNHYTQKSLSLS PGK |

TABLE 32-continued

Sequences.

| SEQ ID NO: | Molecule | Region | Scheme | Sequence |
|---|---|---|---|---|
| 3190 | aTF_2900-H09_HC_Y180/F404TAG_SerOpt | Heavy Chain | | MEVQLVESGGGLVQPGGSLRLSCAASGF TISDYVIHWVRQAPGKGLEWVGYIDPSN GYTYYADSVKGRFTISADTSKNTAYLQM NSLRAEDTAVYYCARDDQSISSPLDYWG QGTLVTVSSASTKGPSVFPLAPSSKSTS GGTAALGCLVKDYFPEPVTVSWNSGALT SGVHTFPAVLQSSGL*SLSSVVTVPSSS LGTQTYICNVNHKPSNTKVDKKVEPKSC DKTHTCPPCPAPELLGGPSVFLFPPKPK DTLMISRTPEVTCVVVDVSHEDPEVKFN WYVDGVEVHNAKTKPREEQYNSTYRVVS VLTVLHQDWLNGKEYKCKVSNKALPAPI EKTISKAKGQPREPQVYTLPPSREEMTK NQVSLTCLVKGFYPSDIAVEWESNGQPE NNYKTTPPVLDSDGS*FLYSKLTVDKSR WQQGNVFSCSVMHEALHNHYTQKSLSLS PGK |
| 3191 | aTF_2900-A02_HC_Y180/F241/Y391/F404TAG | Heavy Chain | | MEVQLVESGGGLVQPGGSLRLSCAASGF TISGYIIHWVRQAPGKGLEWVGYIDPSN GYTYYADSVKGRFTISADTSKNTAYLQM NSLRAEDTAVYYCARDDQSLSSPFDYWG QGTLVTVSSASTKGPSVFPLAPSSKSTS GGTAALGCLVKDYFPEPVTVSWNSGALT SGVHTFPAVLQSSGL*SLSSVVTVPSSS LGTQTYICNVNHKPSNTKVDKKVEPKSC DKTHTCPPCPAPELLGGPSV*LFPPKPK DTLMISRTPEVTCVVVDVSHEDPEVKFN WYVDGVEVHNAKTKPREEQYNSTYRVVS VLTVLHQDWLNGKEYKCKVSNKALPAPI EKTISKAKGQPREPQVYTLPPSREEMTK NQVSLTCLVKGFYPSDIAVEWESNGQPE NN*KTTPPVLDSDGS*FLYSKLTVDKSR WQQGNVFSCSVMHEALHNHYTQKSLSLS PGK |

EQUIVALENTS

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in this application, in applications claiming priority from this application, or in related applications. Such claims, whether directed to a different invention or to the same invention, and whether broader, narrower, equal, or different in scope in comparison to the original claims, also are regarded as included within the subject matter of the inventions of the present disclosure.

One or more features from any embodiments described herein or in the figures may be combined with one or more features of any other embodiments described herein or in the figures without departing from the scope of the invention.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An antibody conjugate comprising an antibody that specifically binds to tissue factor (TF) linked site-specifically to at least one payload moiety, wherein the antibody comprises one or more non-natural amino acids, and wherein the antibody comprises (a) a $V_H$ comprising: a CDR-H1 comprising SEQ ID NO: 130; a CDR-H2 comprising SEQ ID NO: 780; and a CDR-H3 comprising SEQ ID NO: 1430; and a $V_L$ comprising: a CDR-L1 comprising SEQ ID NO: 2064; a CDR-L2 comprising SEQ ID NO: 2288; and a CDR-L3 comprising SEQ ID NO: 2512;

(b) a $V_H$ comprising: a CDR-H1 comprising SEQ ID NO: 455; a CDR-H2 comprising SEQ ID NO: 1105; and a CDR-H3 comprising SEQ ID NO: 1755; and a $V_L$ comprising: a CDR-L1 comprising SEQ ID NO: 2176; a CDR-L2 comprising SEQ ID NO: 2400; and a CDR-L3 comprising SEQ ID NO: 2624;

(c) a $V_H$ comprising: a CDR-H1 comprising SEQ ID NO: 214; a CDR-H2 comprising SEQ ID NO: 864; and a CDR-H3 comprising SEQ ID NO: 1514; and a $V_L$ comprising: a CDR-L1 comprising SEQ ID NO: 2064; a CDR-L2 comprising SEQ ID NO: 2288; and a CDR-L3 comprising SEQ ID NO: 2512;

(d) a $V_H$ comprising: a CDR-H1 comprising SEQ ID NO: 539; a CDR-H2 comprising SEQ ID NO: 1189; and a CDR-H3 comprising SEQ ID NO: 1839; and a $V_L$ comprising: a CDR-L1 comprising SEQ ID NO: 2176; a CDR-L2 comprising SEQ ID NO: 2400; and a CDR-L3 comprising SEQ ID NO: 2624;

(e) a $V_H$ comprising: a CDR-H1 comprising SEQ ID NO: 192; a CDR-12 comprising SEQ ID NO: 842; and a CDR-H3 comprising SEQ ID NO: 1492; and a $V_L$ comprising: a CDR-L1 comprising SEQ ID NO: 2064; a CDR-L2 comprising SEQ ID NO: 2288; and a CDR-L3 comprising SEQ ID NO: 2512; or (f) a $V_H$ comprising: a CDR-H1 comprising SEQ ID NO: 517; a CDR-H2 comprising SEQ ID NO: 1167; and a CDR-H3 comprising SEQ ID NO: 1817; and a $V_L$ comprising: a CDR-L1 comprising SEQ ID NO: 2176; a CDR-L2 comprising SEQ ID NO: 2400; and a CDR-L3 comprising SEQ ID NO: 2624.

2. A kit comprising the antibody conjugate of claim 1 and instructions for use of the antibody conjugate.

3. A polynucleotide encoding the antibody of the antibody conjugate of claim 1.

4. A vector comprising the polynucleotide of claim 3.

5. A recombinant host cell comprising the vector of claim 4.

6. A pharmaceutical composition comprising the antibody conjugate of claim 1 and a pharmaceutically acceptable carrier.

7. A pharmaceutical composition comprising the antibody conjugate of claim 1, (b) one or more additional active agents, and (c) a pharmaceutically acceptable carrier.

8. A method for reducing cell proliferation in a subject in need thereof, comprising administering to the subject an effective amount of an antibody conjugate of claim 1.

9. A method for treating cancer in a subject in need thereof, comprising administering to the subject an effective amount of an antibody conjugate of claim 1.

10. The method of claim 9, further comprising administering to the subject one or more additional active agents.

11. A method of diagnosing and treating cancer in subject in need thereof, comprising (a) detecting the expression of tissue factor in a cell or tissue of the subject to diagnose the cancer; and (b) administering to the subject an effective amount of a pharmaceutical composition of claim 6.

12. The antibody conjugate of claim 1, wherein the antibody comprises one or more non-natural amino acid selected from the group consisting of: HC-F404, HC-K121, HC-Y180, HC-F241, HC-221, HC-Y391, LC-T22, LC-S7, LC-N152, LC-K42, LC-E161, LC-D170, HC-S136, HC-S25, HC-A40, HC-S119, HC-S190, HC-K222, HC-R19, HC-Y52, and HC-S70, according to the Kabat, Chothia, or EU numbering scheme.

13. The antibody conjugate of claim 1, wherein a residue of the one or more non-natural amino acids is linked to the payload moiety via a linker that is cleavable.

14. The antibody conjugate of claim 1, wherein the one or more non-natural amino acids is selected from the group consisting of p-acetyl-L-phenylalanine, O-methyl-L-tyrosine, an -3-(2-naphthyl) alanine, 3-methyl-phenylalanine, O-4-allyl-L-tyrosine, 4-propyl-L-tyrosine, a tri-O-acetyl-GlcNAcβ-serine, L-Dopa, fluorinated phenylalanine, isopropyl-L-phenylalanine, p-azido-L-phenylalanine, p-azidomethyl-L-phenylalanine, compound 56, p-acyl-L-phenylalanine, p-benzoyl-L-phenylalanine, L-phosphoserine, phosphonoserine, phosphonotyrosine, p-iodo-phenylalanine, p-bromophenylalanine, p-amino-L-phenylalanine, isopropyl-L-phenylalanine, and p-propargyloxy-phenylalanine.

15. The antibody conjugate of claim 1, wherein the payload moiety is selected from the group consisting of maytansines, hemiasterlins, amanitins, camptothecins, exatecans, anthracyclines, pyrrolobenzodiazepines, and auristatins.

16. The antibody conjugate of claim 1, wherein the antibody comprises a $V_H$ comprising: a CDR-H1 comprising SEQ ID NO: 130; a CDR-H2 comprising SEQ ID NO: 780; and a CDR-H3 comprising SEQ ID NO: 1430; and a $V_L$ comprising: a CDR-L1 comprising SEQ ID NO: 2064; a CDR-L2 comprising SEQ ID NO: 2288; and a CDR-L3 comprising SEQ ID NO: 2512.

17. The antibody conjugate of claim 1, wherein the antibody comprises three heavy chain CDRs and three light chain CDRs from a $V_H/V_L$ pair, selected from the group consisting of SEQ ID NOs: 2752/3061, 2814/3061, and 2836/3061.

18. The antibody conjugate of claim 1, wherein the antibody comprises a $V_H/V_L$ pair, selected from the group consisting of SEQ ID NOs: 2752/3061, and 2836/3061.

19. The antibody conjugate of claim 1, wherein the antibody conjugate comprises:

(a) an antibody comprising a $V_H$ comprising: a CDR-H1 comprising SEQ ID NO: 130; a CDR-H2 comprising SEQ ID NO: 780; and a CDR-H3 comprising SEQ ID NO: 1430; and a $V_L$ comprising: a CDR-L1 comprising SEQ ID NO: 2064; a CDR-L2 comprising SEQ ID NO: 2288; and a CDR-L3 comprising SEQ ID NO: 2512;

(b) para-azidomethylphenylalanine residues at antibody sites HC241, HC404, HC180, and HC391; and (c) the following linker-payload, wherein n2 is 8 and each linker-payload is bonded to one of the para-azidomethylphenylalanine residue side chains:

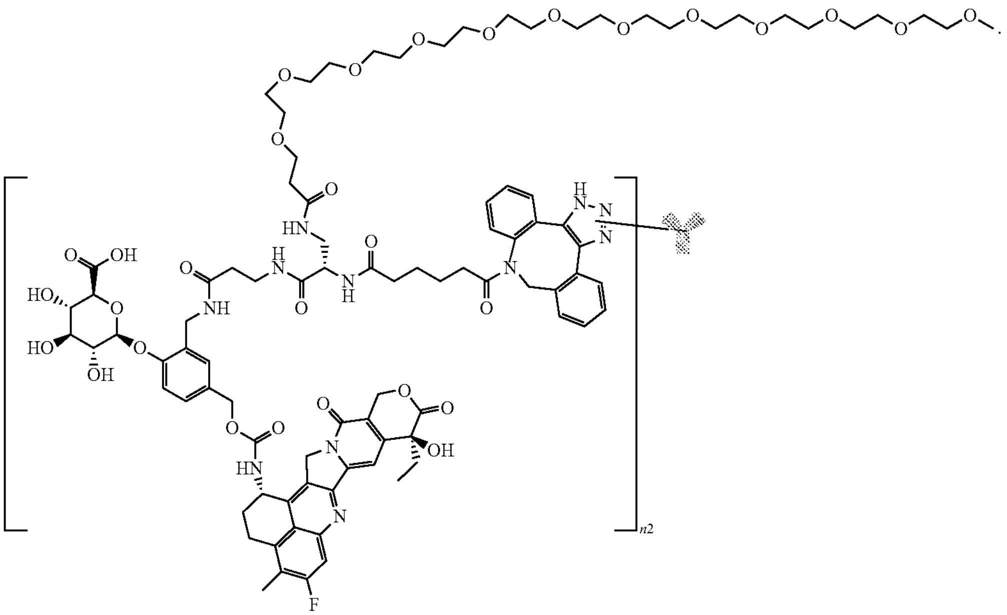

20. The antibody conjugate of claim 1, wherein the antibody comprises a $V_H$ comprising: a CDR-H1 comprising SEQ ID NO: 455; a CDR-H2 comprising SEQ ID NO: 1105; and a CDR-H3 comprising SEQ ID NO: 1755; and a $V_L$ comprising: a CDR-L1 comprising SEQ ID NO: 2176; a CDR-L2 comprising SEQ ID NO: 2400; and a CDR-L3 comprising SEQ ID NO: 2624.

21. The antibody conjugate of claim 1, wherein the antibody comprises a $V_H$ comprising: a CDR-H1 comprising SEQ ID NO: 214; a CDR-H2 comprising SEQ ID NO: 864; and a CDR-H3 comprising SEQ ID NO: 1514; and a $V_L$ comprising: a CDR-L1 comprising SEQ ID NO: 2064; a CDR-L2 comprising SEQ ID NO: 2288; and a CDR-L3 comprising SEQ ID NO: 2512.

22. The antibody conjugate of claim 1, wherein the antibody comprises a $V_H$ comprising: a CDR-H1 comprising SEQ ID NO: 539; a CDR-H2 comprising SEQ ID NO: 1189; and a CDR-H3 comprising SEQ ID NO: 1839; and a $V_L$ comprising: a CDR-L1 comprising SEQ ID NO: 2176; a CDR-L2 comprising SEQ ID NO: 2400; and a CDR-L3 comprising SEQ ID NO: 2624.

23. The antibody conjugate of claim 1, wherein the antibody comprises a $V_H$ comprising: a CDR-H1 comprising SEQ ID NO: 192; a CDR-H2 comprising SEQ ID NO: 842; and a CDR-H3 comprising SEQ ID NO: 1492; and a $V_L$ comprising: a CDR-L1 comprising SEQ ID NO: 2064; a CDR-L2 comprising SEQ ID NO: 2288; and a CDR-L3 comprising SEQ ID NO: 2512.

24. The antibody conjugate of claim 1, wherein the antibody comprises a $V_H$ comprising: a CDR-H1 comprising SEQ ID NO: 517; a CDR-H2 comprising SEQ ID NO: 1167; and a CDR-H3 comprising SEQ ID NO: 1817; and a $V_L$ comprising: a CDR-L1 comprising SEQ ID NO: 2176; a CDR-L2 comprising SEQ ID NO: 2400; and a CDR-L3 comprising SEQ ID NO: 2624.

25. The antibody conjugate of claim 1, wherein the antibody conjugate comprises:

(a) an antibody comprising a $V_H$ comprising: a CDR-H1 comprising SEQ ID NO: 455; a CDR-H2 comprising SEQ ID NO: 1105; and a CDR-H3 comprising SEQ ID NO: 1755; and a $V_L$ comprising: a CDR-L1 comprising SEQ ID NO: 2176; a CDR-L2 comprising SEQ ID NO: 2400; and a CDR-L3 comprising SEQ ID NO: 2624;

(b) para-azidomethylphenylalanine residues at antibody sites HC241, HC404, HC180, and HC391; and (c) the following linker-payload, wherein n2 is 8 and each linker-payload is bonded to one of the para-azidomethylphenylalanine residue side chains:

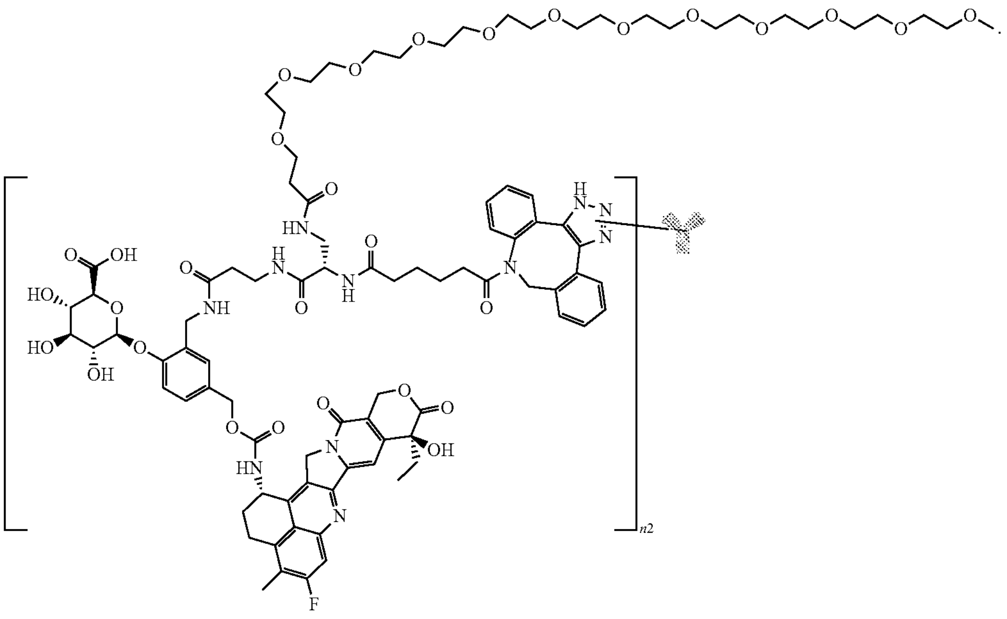

26. The antibody conjugate of claim 17, wherein the antibody comprises three heavy chain CDRs and three light chain CDRs from the $V_H/V_L$ pair according to SEQ ID NOS: 2752/3061.

27. The antibody conjugate of claim 17, wherein the antibody comprises three heavy chain CDRs and three light chain CDRs from the $V_H/V_L$ pair according to SEQ ID NOS: 2814/3061.

28. The antibody conjugate of claim 17, wherein the antibody comprises three heavy chain CDRs and three light chain CDRs from the $V_H/V_L$ pair according to SEQ ID NOS: 2836/3061.

29. The antibody conjugate of claim 17, wherein the antibody comprises the $V_H/V_L$ pair according to SEQ ID NOS: 2752/3061.

30. The antibody conjugate of claim 17, wherein the antibody comprises the $V_H/V_L$ pair according to SEQ ID NOS: 2814/3061.

31. The antibody conjugate of claim 17, wherein the antibody comprises the $V_H/V_L$ pair according to SEQ ID NOS: 2836/3061.

32. The antibody conjugate of claim 17, wherein the antibody conjugate comprises:

(a) para-azidomethylphenylalanine residues at antibody sites HC241, HC404, HC180, and HC391; and (b the following linker-payload, wherein n2 is 8 and each linker-payload is bonded to one of the para-azidomethylphenylalanine residue side chains:

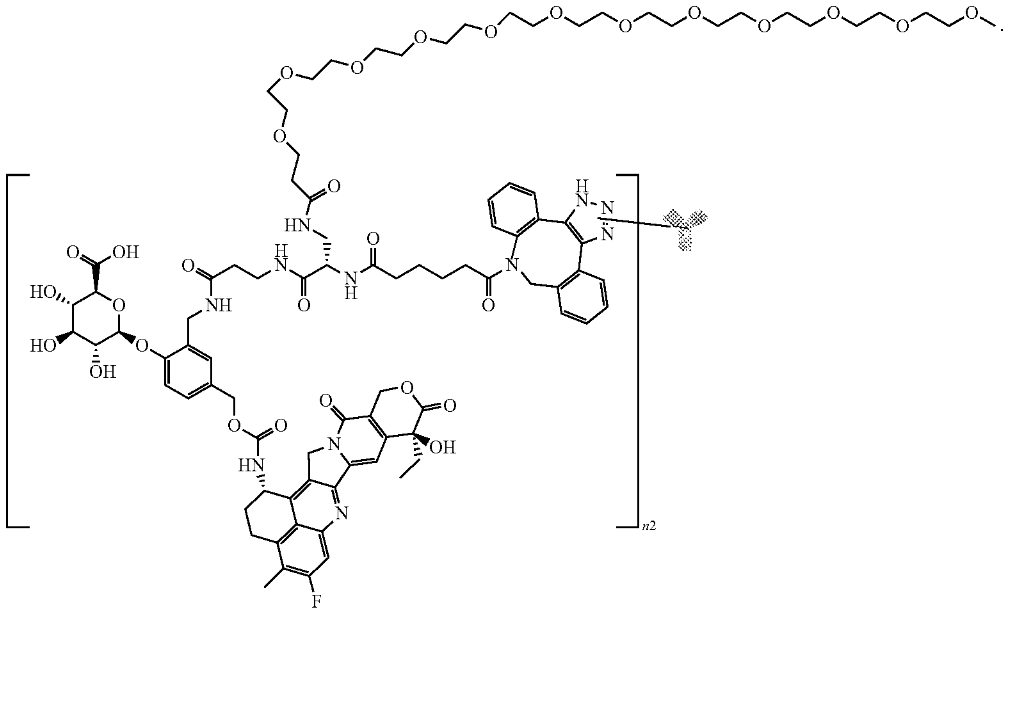

33. The antibody conjugate of claim 32, wherein the antibody comprises three heavy chain CDRs and three light chain CDRs from the $V_H/V_L$ pair according to SEQ ID NOS: 2752/3061.

34. The antibody conjugate of claim 32, wherein the antibody comprises three heavy chain CDRs and three light chain CDRs from the $V_H/V_L$ pair according to SEQ ID NOS: 2814/3061.

NO: 1430; and a $V_L$ comprising: a CDR-L1 comprising SEQ ID NO: 2064; a CDR-L2 comprising SEQ ID NO: 2288; and a CDR-L3 comprising SEQ ID NO: 2512;

(b) para-azidomethylphenylalanine residues at antibody sites HC241 and HC404; and (c) the following linker-payload, wherein n2 is 4 and each linker-payload is bonded to one of the para-azidomethylphenylalanine residue side chains:

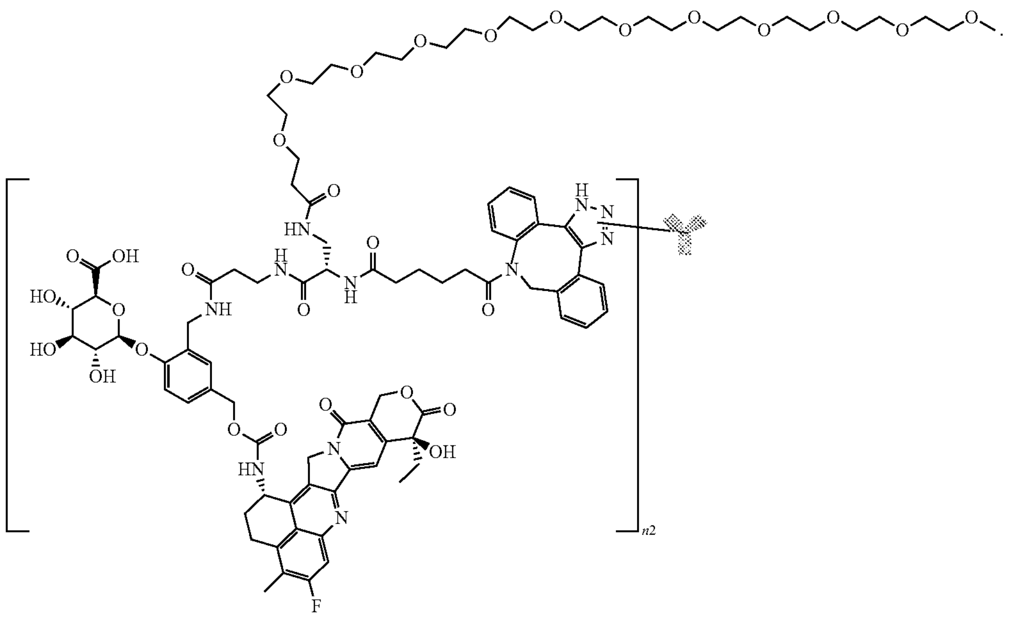

35. The antibody conjugate of claim 32, wherein the antibody comprises three heavy chain CDRs and three light chain CDRs from the $V_H/V_L$ pair according to SEQ ID NOS: 2836/3061.

36. The antibody conjugate of claim 32, wherein the antibody comprises the $V_H/V_L$ pair according to SEQ ID NOS: 2752/3061.

37. The antibody conjugate of claim 32, wherein the antibody comprises the $V_H/V_L$ pair according to SEQ ID NOS: 2814/3061.

38. The antibody conjugate of claim 32, wherein the antibody comprises the $V_H/V_L$ pair according to SEQ ID NOS: 2836/3061.

39. The antibody conjugate of claim 1, wherein the antibody conjugate comprises:

(a) an antibody comprising a $V_H$ comprising: a CDR-H1 comprising SEQ ID NO: 130; a CDR-H2 comprising SEQ ID NO: 780; and a CDR-H3 comprising SEQ ID 40. The antibody conjugate of claim 1, wherein the antibody conjugate comprises:

(a) an antibody comprising a $V_H$ comprising: a CDR-H1 comprising SEQ ID NO: 455; a CDR-H2 comprising SEQ ID NO: 1105; and a CDR-H3 comprising SEQ ID NO: 1755; and a $V_L$ comprising: a CDR-L1 comprising SEQ ID NO: 2176; a CDR-L2 comprising SEQ ID NO: 2400; and a CDR-L3 comprising SEQ ID NO: 2624;

(b) para-azidomethylphenylalanine residues at antibody sites HC241 and HC404; and (c) the following linker-payload, wherein n2 is 4 and each linker-payload is bonded to one of the para-azidomethylphenylalanine residue side chains:

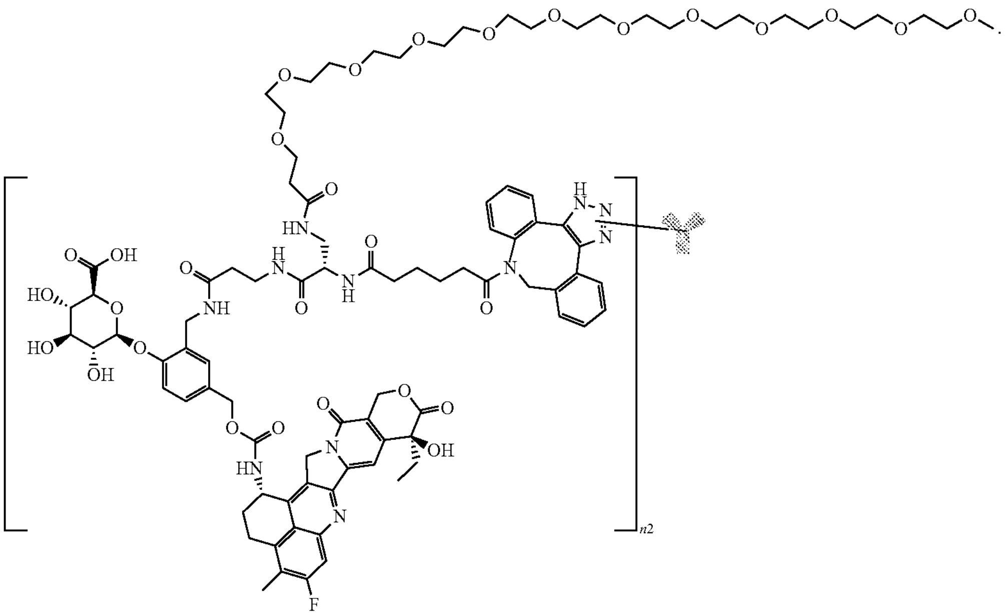
* * * * *